(12) United States Patent
Ohta et al.

(10) Patent No.: US 7,576,135 B2
(45) Date of Patent: *Aug. 18, 2009

(54) DIAMINE DERIVATIVES

(75) Inventors: Toshiharu Ohta, Tokyo (JP); Satoshi Komoriya, Tokyo (JP); Toshiharu Yoshino, Tokyo (JP); Kouichi Uoto, Tokyo (JP); Yumi Nakamoto, Tokyo (JP); Hiroyuki Naito, Tokyo (JP); Akiyoshi Mochizuki, Tokyo (JP); Tsutomu Nagata, Tokyo (JP); Hideyuki Kanno, Tokyo (JP); Noriyasu Haginoya, Tokyo (JP); Kenji Yoshikawa, Tokyo (JP); Masatoshi Nagamochi, Tokyo (JP); Syozo Kobayashi, Tokyo (JP); Makoto Ono, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 86 days.

This patent is subject to a terminal disclaimer.

(21) Appl. No.: 10/540,259

(22) PCT Filed: Dec. 25, 2003

(86) PCT No.: PCT/JP03/16783

§ 371 (c)(1),
(2), (4) Date: Jun. 5, 2006

(87) PCT Pub. No.: WO2004/058715

PCT Pub. Date: Jul. 15, 2004

(65) Prior Publication Data

US 2006/0252837 A1 Nov. 9, 2006

(30) Foreign Application Priority Data

Dec. 25, 2002 (JP) ............................ 2002-373787
Nov. 7, 2003 (JP) ............................ 2003-379163

(51) Int. Cl.
*A61K 31/13* (2006.01)
(52) U.S. Cl. .................................................. 514/673
(58) Field of Classification Search ................. 514/673
See application file for complete search history.

(56) References Cited

U.S. PATENT DOCUMENTS

| | | |
|---|---|---|
| 6,525,042 B1 | 2/2003 | Kobayashi et al. |
| 6,747,023 B1 | 6/2004 | Kobayashi et al. |
| 2004/0082611 A1 | 4/2004 | Kobayashi et al. |
| 2004/0122063 A1 | 6/2004 | Yoshino et al. |
| 2005/0020645 A1 | 1/2005 | Ohta et al. |
| 2005/0119486 A1 | 6/2005 | Ohta et al. |
| 2006/0252837 A1 | 11/2006 | Ohta et al. |

FOREIGN PATENT DOCUMENTS

| | | |
|---|---|---|
| EP | 0 947 510 | 10/1999 |
| JP | 06-174919 | 6/1994 |
| JP | 2003-183286 | 7/2003 |
| WO | 97/10853 | 3/1997 |
| WO | 99/32225 | 7/1999 |
| WO | 00/64902 | 11/2000 |
| WO | 01/58588 | 8/2001 |
| WO | 01/74774 | 10/2001 |
| WO | WO 01/74774 A1 * | 10/2001 |
| WO | 03/000657 | 1/2003 |
| WO | 03/026652 | 4/2003 |
| WO | 03/048081 | 6/2003 |
| WO | 03/048158 | 6/2003 |
| WO | 03/074531 | 9/2003 |
| WO | 03/099276 | 12/2003 |
| WO | 03/101927 | 12/2003 |

OTHER PUBLICATIONS

U.S. Appl. No. 12/259,496, filed Oct. 28, 2008, Ohta, et al.
U.S. Appl. No. 12/250,586, filed Oct. 14, 2008, Ohta, et al.
U.S. Appl. No. 10/539,995, filed Jun. 22, 2005, Nakamoto, et al.
U.S. Appl. No. 10/540,259, filed Jun. 23, 2005, Ohta, et al.
U.S. Appl. No. 10/481,629, filed Jun. 1, 2004, Ohta, et al.

(Continued)

*Primary Examiner*—D. Margaret Seaman
*Assistant Examiner*—Nizal S Chandrakumar
(74) *Attorney, Agent, or Firm*—Oblon, Spivak, McClelland, Maier & Neustadt, P.C.

(57) ABSTRACT

A compound represented by formula (1):

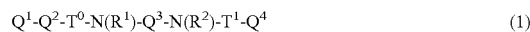

[wherein $R^1$ and $R^2$ are hydrogen atoms or the like; $Q^1$ is a saturated or unsaturated, 5- or 6-membered cyclic hydrocarbon group which may be substituted, or the like; $Q^2$ is a single bond or the like; $Q^3$ represents the following group:

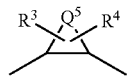

(wherein $Q^5$ is an alkylene group having 1 to 8 carbon atoms, or the like); and $T^0$ and $T^1$ are carbonyl groups or the like], a salt thereof, a solvate thereof, or an N-oxide thereof.

The compound is useful as an agent for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

37 Claims, No Drawings

OTHER PUBLICATIONS

Kim, Kyung-Jun et al., "Chiral, Metallomacrocycles", Bull. Korean Chem. Soc., vol. 20, No. 12, p. 1387 to 1387 to 1388, 1999.

Iorio, Edward James et al., "Highly sequence selective nonmacrocylic two-armed receptors from peptides", Bioorganic & Medicinal Chemistry Letters, vol. 9, No. 15, pp. 2145-2150, 1999.

Pandey, Bhagwan R. et al., Interrelationship between anticonvulsant and enzyme inhibitory properties of N-Methyl-N-2-[1-(1-Arylthiocarbamido)] Cyclopentyl Nitrobenzamides, Pharmacological Research Communications, vol. 13, No. 1, pp. 65 to 74, 1981.

U.S. Appl. No. 11/217,837, filed Sep. 2, 2005, Yoshino, et al.

* cited by examiner

DIAMINE DERIVATIVES

TECHNICAL FIELD

The present invention relates to novel compounds which inhibit activated blood coagulation factor X (hereinafter abbreviated as "FXa") to exhibit a potent anticoagulant effect and can be orally administered, and anticoagulants or agents for preventing and/or treating thrombosis or embolism, which comprise such a novel compound as an active ingredient.

BACKGROUND ART

Hypercoagulable state is one of the pivotal factors that account for unstable angina, cerebral infarction, cerebral embolism, myocardial infarction, pulmonary infarction, pulmonary embolism, Buerger's disease, deep venous thrombosis, disseminated intravascular coagulation syndrome, thrombus formation after artificial valve replacement, reocclusion after angioplasty and thrombus formation during extracorporeal circulation. Therefore, there is a demand for development of excellent anticoagulants which have good dose responsiveness, long duration, low risk of hemorrhage and little side effects and fast onset of sufficient effects even by oral administration (Thrombosis Research, Vol. 68, pp. 507-512, 1992).

Based on the research of anticoagulants worked through various mechanism of action, it is suggested that FXa inhibitors are promising anticoagulants. A blood coagulation system comprises a series of reactions in which a great amount of thrombin is produced through an amplification process by multi-stage enzyme reactions to form insoluble fibrin. In an endogenous system, activated factor IX activates factor X on a phospholipid membrane in the presence of activated factor VIII and calcium ions after multi-stage reactions subsequent to activation of a contact factor. In an exogenous system, activated factor VII activates factor X in the presence of a tissue factor. More specifically, the activation of the factor X into FXa in the coagulation system is a crucial reaction in the formation of thrombin. The activated factor X (FXa) limitedly decomposes prothrombin to produce thrombin in the both systems. Since the produced thrombin activates coagulation factors in the upper stream, the formation of thrombin is further amplified. As described above, the coagulation system in the upper stream of FXa is divided into the endogenous system and the exogenous system, thus production of FXa cannot be sufficiently suppressed by inhibiting the enzymes involved in the coagulation system in the upper stream of FXa, leading to production of thrombin. Since the coagulation system comprises self-amplification reactions, inhibition of the coagulation system can be more efficiently achieved by inhibiting FXa in the upper stream of thrombin than the inhibition of the product; namely, thrombin (Thrombosis Research, Vol. 15, pp. 617-629, 1979). Another excellent point of FXa inhibitors is a great difference between an effective dose in a thrombosis model and a dose which allows elongation of bleeding time in an experimental hemorrhagic model. From this experimental result, FXa inhibitors are considered to be anticoagulants having low risk of hemorrhage.

Various compounds have been reported as FXa inhibitors. It is generally known that antithrombin III and antithrombin III dependent pentasaccharides can not inhibit prothrombinase complexes which play a practical role in the thrombus formation in a living body (Thrombosis Research, Vol. 68, pp. 507-512, 1992; Journal of Clinical Investigation, Vol. 71, pp. 1383-1389, 1983; Mebio, Vol. 14, the August number, pp. 92-97). In addition, they do not exhibit effectiveness by oral administration. Tick anticoagulant peptide (TAP) (Science, Vol. 248, pp. 593-596, 1990) and antistasin (AST) (Journal of Biological Chemistry, Vol. 263, pp. 10162-10167, 1988) isolated from mites or leeches, which are bloodsuckers, also inhibit Fxa and exhibit anti-thrombotic effects against venous thrombosis and arterial thrombosis. However, these compounds are high-molecular weight peptides and are not effective by oral administration. As described above, development of antithrombin III independent low-molecular weight FXa inhibitors which directly inhibit coagulation factors and which can be orally administered has been conducted.

DISCLOSURE OF THE INVENTION

It is therefore an object of the present invention to provide a novel compound which has a potent FXa-inhibiting effect and exhibits an anti-thrombotic effect quickly, sufficiently and persistently by oral administration.

The present inventors have investigated synthesis and pharmacological effects of novel FXa inhibitors. As a result, diamine derivatives, salts thereof, and solvates and N-oxides thereof, which exhibit potent FXa-inhibiting effect and anticoagulant effect, have been found. It has also been found that these compounds promptly, persistently and potently inhibit FXa and exhibit potent anticoagulant effect and anti-thrombotic effect by oral administration, and are hence useful as prophylactics and remedies for various diseases based on thromboembolism, thus leading to completion of the present invention.

This invention provides a compound represented by the general formula (1):

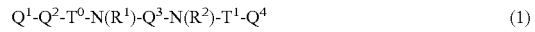

wherein $R^1$ and $R^2$ each independently represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$Q^3$ represents the following group:

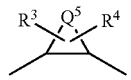

in which $Q^5$ represents an alkylene group having 1 to 8 carbon atoms, an alkenylene group having 2 to 8 carbon atoms, or a group —$(CH_2)_m$—$CH_2$-A-$CH_2$-$(CH_2)_n$— (in which m and n are each independently 0 or an integer of 1-3, and A represents an oxygen atom, nitrogen atom, sulfur atom, —SO—, —SO₂—, —NH—, —O—NH—, —NH—NH—, —S—NH—, —SO—NH— or —SO₂—NH—), and;

R³ and R⁴ are substituents on carbon atom(s), nitrogen atom(s) or a sulfur atoms of a ring comprising Q⁵ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, 3- to 6-membered heterocyclic group which may be substituted, 3- to 6-membered heterocyclic alkyl group which may be substituted, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, alkoxycarbonylalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, 3- to 6-membered heterocyclic oxy group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s), alkylsulfonylacyl group, N-arylcarbamoyl group, N-(3- to 6-membered heterocyclic) carbamoyl group, N-alkyl-N-arylcarbamoyl group, N-alkyl-N-(3- to 6-membered heterocyclic) carbamoyl group, N-arylcarbamoylalkyl group, N-(3- to 6-membered heterocyclic) carbamoylalkyl group, N-alkyl-N-arylcarbamoylalkyl group, N-alkyl-N-(3- to 6-membered heterocyclic) carbamoylalkyl group, aminocarbothioyl group, N-alkylaminocarbothioyl group, N,N-dialkylaminocarbothioyl group, alkoxyalkyl(thiocarbonyl) group, alkylthioalkyl group or N-acyl-N-alkylaminoalkyl group, or R³ and R⁴ together form an alkylene group having 1 to 5 carbon atoms, alkenylene group having 2 to 5 carbon atoms, alkylenedioxy group having 1 to 5 carbon atoms or carbonyldioxy group;

Q⁴ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

T⁰ represents a carbonyl or thiocarbonyl group; and

T¹ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-A¹-N(R")— (in which A¹ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-A²-C(=O)— (in which A² represents a single bond or alkylene group having 1 to 5 carbon atoms), group —C(=O)-A³-C(=O)—NH— (in which A³ represents an alkylene group having 1 to 5 carbon atoms), group —C(=O)—C(=NORᵃ)—N(Rᵇ)—, group —C(=S)—C(=NORᵃ)—N(Rᵇ)— (in which Rᵃ represents a hydrogen atom, alkyl group or alkanoyl group, and Rᵇ represents a hydrogen atom, hydroxyl group, alkyl group or alkoxy group), group —C(=O)—N=N—, group —C(=S)—N=N—, group —C(=NORᶜ)—C(=O)—N(Rᵈ)— (in which Rᶜ represents a hydrogen atom, alkyl group, alkanoyl group, aryl group or aralkyl group, and Rᵈ represents a hydrogen atom, hydroxyl group, alkyl group or alkoxy group), group —C(=N—N(Rᵉ)(Rᶠ))—C(=O)—N(Rᵍ)— (in which Rᵉ and Rᶠ each independently represent a hydrogen atom, alkyl group, alkanoyl or alkyl(thiocarbonyl) group, and Rᵍ represents a hydrogen atom, hydroxyl group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO₂—, group —SO₂—NH—, group —C(=NCN)—NH—C(=O)—, group —C(=S)—C(=O)—, or thiocarbonyl group;

a salt thereof, a solvate thereof, or an N-oxide thereof.

This invention also provides a drug, an activated blood coagulation factor X inhibitor, an anticoagulant, an agent for preventing and/or treating thrombosis or embolism and an agent for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood gathering, which each comprises the compound represented by the general formula (1), a salt thereof, a solvate thereof, or an N-oxide thereof.

This invention further provides an intermediate for preparing the compound represented by the general formula (1).

This invention still further provides use of the compound represented by the general formula (1), a salt thereof, a solvate thereof, or an N-oxide thereof for preparation of a drug.

This invention yet still further provides a method for treating thrombosis or embolism, which comprises administering an effective amount of the compound represented by the general formula (1), a salt thereof, a solvate thereof, or an N-oxide thereof.

The cyclic diamine derivatives of the present invention exhibit a potent inhibitory effect on activated blood coagulation factor X. Therefore, the derivatives are useful as a drug, an activated blood coagulation factor X inhibitor, an anticoagulant, an agent for preventing and/or treating thrombosis or embolism, an agent for preventing and/or treating thrombotic diseases, and an agent for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood gathering.

BEST MODE FOR CARRYING OUT THE INVENTION

Substituents in the diamine derivatives according to the present invention represented by the general formula (1) will hereinafter be described.

<On Group $Q^4$>

The group $Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted.

In the group $Q^4$, the aryl group may include aryl groups having 6 to 14 carbon atoms, for example, phenyl, naphthyl, anthryl and phenanthryl groups. The arylalkenyl group means a group formed by an aryl group having 6 to 14 carbon atoms and an alkenylene group having 2 to 6 carbon atoms, and examples thereof may include a styryl group. The arylalkynyl group means a group formed by an aryl group having 6 to 14 carbon atoms and an alkynylene group having 2 to 6 carbon atoms, and examples thereof may include a phenylethynyl group.

The heteroaryl group means a monovalent aromatic group having at least one hetero atom selected from oxygen, sulfur and nitrogen atoms, and examples thereof may include 5- or 6-membered heteroaryl groups, for example, pyridyl, pyridazinyl, pyrazinyl, furyl, thienyl, pyrrolyl, thiazolyl, oxazolyl, pyrimidinyl and tetrazolyl groups. The heteroarylalkenyl group means a group formed by the above-described heteroaryl group and an alkenylene group having 2 to 6 carbon atoms, and examples thereof may include thienylethenyl and pyridylethenyl groups.

The saturated or unsaturated, bicyclic or tricyclic condensed hydrocarbon group means a monovalent group derived from a saturated or unsaturated, bicyclic or tricyclic condensed hydrocarbon. The saturated or unsaturated, bicyclic or tricyclic condensed hydrocarbon denotes a bicyclic or tricyclic condensed hydrocarbon formed by condensing 2 or 3 saturated or unsaturated, 5- or 6-membered cyclic hydrocarbons which are the same or different from each other. In this case, examples of the saturated or unsaturated, 5- or 6-membered cyclic hydrocarbons may include cyclopentane, cyclopentene, cyclohexane, cyclohexene, cyclohexadiene and benzene. Specific examples of the saturated or unsaturated, bicyclic or tricyclic condensed hydrocarbon group may include indenyl, indanyl, tetrahydronaphthyl and naphthyl groups. Incidentally, the position of the saturated or unsaturated, bicyclic or tricyclic condensed hydrocarbon group bonded to $T^1$ in the general formula (1) is not particularly limited.

The saturated or unsaturated, bicyclic or tricyclic condensed heterocyclic group means a monovalent group derived from a saturated or unsaturated, bicyclic or tricyclic condensed heterocyclic ring. The saturated or unsaturated, bicyclic or tricyclic condensed heterocyclic ring denotes the following heterocyclic ring 1), 2), or 3):

1) a bicyclic or tricyclic condensed heterocyclic ring formed by condensing 2 or 3 saturated or unsaturated, 5- to 7-membered heterocyclic rings which are the same or different from each other;

2) a bicyclic or tricyclic condensed heterocyclic ring formed by condensing a saturated or unsaturated, 5- to 7-membered heterocyclic ring with 1 or 2 saturated or unsaturated, 5- or 6-membered cyclic hydrocarbons; or 3) a tricyclic condensed heterocyclic ring formed by condensing 2 saturated or unsaturated, 5- to 7-membered heterocyclic rings with a saturated or unsaturated, 5- or 6-membered cyclic hydrocarbon.

The position of the saturated or unsaturated, bicyclic or tricyclic condensed heterocyclic group bonded to $T^1$ in the general formula (1) is not particularly limited.

The saturated or unsaturated, 5- to 7-membered heterocyclic ring denotes a heterocyclic ring having at least one hetero atom selected from oxygen, sulfur and nitrogen atoms, and specific examples thereof may include furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, thiadiazine, oxadiazine, azepine, diazepine, triazepine, thiazepine and oxazepine. The saturated or unsaturated, 5- or 6-membered cyclic hydrocarbon denotes the same saturated or unsaturated, 5- or 6-membered cyclic hydrocarbon as shown in the description of the saturated or unsaturated, bicyclic or tricyclic condensed hydrocarbon group. Specific examples of the saturated or unsaturated, bicyclic or tricyclic condensed heterocyclic group may include benzofuryl, isobenzofuryl, benzothienyl, indolyl, indolinyl, isoindolyl, isoindolinyl, indazolyl, quinolyl, dihydroquinolyl, 4-oxodihydroquinolyl (dihydroquinolin-4-one), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzoisothiazolyl, benzoisoxazolyl, benzimidazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thienopyrrolyl, thiazolopyrimidinyl, 4-oxotetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzoisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzoazepinyl, tetrahydrobenzoazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups.

No particular limitation is imposed on the condensing form of the condensed heterocyclic group. For example, the naphthyridinyl group may be any of 1,5-, 1,6-, 1,7-, 1,8-, 2,6- and 2,7-naphthyridinyl groups, the thienopyridyl group may be any of thieno[2,3-b]pyridyl, thieno[2,3-c]pyridyl, thieno[3,2-b]pyridyl, thieno[3,2-c]pyridyl, thieno[3,4-b]pyridyl and thieno[3,4-c]pyridyl groups, the thienopyrrolyl group may be any of thieno[2,3-b]pyrrolyl and thieno[2,3-b]pyrrolyl groups, the thiazolopyridyl group may be any of thiazolo[4,5-b]pyridyl, thiazolo[4,5-c]pyridyl, thiazolo[5,4-b]pyridyl, thiazolo[5,4-c]pyridyl, thiazolo[3,4-a]pyridyl and thiazolo[3,2-a]pyridyl groups, the thiazolopyridazinyl group may be any of thiazolo[4,5-c]pyridazinyl, thiazolo[4,5-d]pyridazinyl, thiazolo[5,4-c]pyridazinyl and thiazolo[3,2-b]pyridazinyl groups, the pyrrolopyridyl group may be any of pyrrolo[2,3-b]pyridyl, pyrrolo[2,3-c]pyridyl, pyrrolo[3,2-b]pyridyl, pyrrolo[3,2-c]pyridyl, pyrrolo[3,4-b]pyridyl and pyrrolo[3,4-c]pyridyl group, the pyridopyrimidinyl group may be any of pyrido[2,3-d]pyrimidinyl, pyrido[3,2-d]pyrimidinyl, pyrido[3,4-d]pyrimidinyl, pyrido[4,3-d]pyrimidinyl, pyrido[1,2-c]pyrimidinyl and pyrido[1,2-a]pyrimidinyl groups, the pyranothiazolyl group may be any of pyrano[2,3-d]thiazolyl, pyrano[4,3-d]thiazolyl, pyrano[3,4-d]thiazolyl and pyrano[3,2-d]thiazolyl groups, the furopyridyl group may be any of furo[2,3-b]pyridyl, furo[2,3-c]pyridyl, furo[3,2-b]pyridyl, furo[3,2-c]pyridyl, furo[3,4-b]pyridyl and furo[3,4-c]pyridyl groups, the oxazolopyridyl group may be any of oxazolo[4,5-b]pyridyl, oxazolo[4,5-c]pyridyl, oxazolo[5,4-b]pyridyl, oxazolo[5,4-c]pyridyl, oxazolo[3,4-a]pyridyl and oxazolo[3,2-a]pyridyl groups, the oxazolopyridazinyl group may be any of oxazolo[4,5-c]pyridazinyl, oxazolo[4,5-d]pyridazinyl, oxazolo[5,4-c]pyridazinyl and oxazolo[3,4-b]pyridazinyl groups, the pyrrolothiazolyl group may be any of pyrrolo[2,1-b]thiazolyl, pyrrolo[1,2-c]thiazolyl, pyrrolo[2,3-d]thiazolyl, pyrrolo[3,2-d]thiazolyl and pyrrolo[3,4-d]thiazolyl groups, the pyrrolooxazolyl group may be any of pyrrolo[2,1-b]oxazolyl, pyrrolo[1,2-c]oxazolyl, pyrrolo[2,3-d]oxazolyl, pyrrolo[3,2-d]oxazolyl and pyrrolo[3,4-d]oxazolyl groups, the benzoazepinyl group may be any of 1H-1-benzoazepinyl, 1H-2-benzoazepinyl and 1H-3-benzoazepinyl groups, or may be a dihydro-oxo derivative type benzoazepinyl group such as 4,5-dihydro-1-oxo-1H-2-benzoazepinyl group, the benzodiazepinyl group may be any of 1H-1,3-benzodiazepinyl, 1H-1,4-benzodiazepinyl and 1H-1,5-benzodiazepinyl groups, or may be a dihydro-oxo derivative type benzodiazepinyl group such as 4,5-dihydro-4-oxo-1H-1,3-benzodiazepinyl group, the benzotriazepinyl group may be any of 1H-1,3,4-benzotriazepinyl and 1H-1,3,5-benzotriazepinyl groups, or may be a dihydro-oxo derivative type benzotriazepinyl group such as 4,5-dihydro-5-oxo-1H-1,3,4-benzotriazepinyl group, and the thienoazepinyl group may be any of thieno[2,3-b]azepinyl, thieno[2,3-c]azepinyl, thieno[2,3-d]azepinyl, thieno[3,2-c]azepinyl and thieno[3,2-b]azepinyl groups, or may be a dihydro-oxo derivative type thienoazepinyl group such as 5,6,7,8-tetrahydro-4-oxo-4H-thieno[3,2-c]azepinyl group. Thienodiazepinyl and thienotriazepinyl groups may also be any condensing forms, or may be those of the dihydro-oxo derivative type. The benzothiazepinyl group may be any of 1H-1-benzothiazepinyl, 1H-2-benzothiazepinyl and 1H-3-benzothiazepinyl groups, or may be a dihydro-oxo derivative type benzothiazepinyl group such as 4,5-dihydro-1-oxo-1H-2-benzothiazepinyl group, and the benzoxazepinyl group may be any of 1H-1-benzoxazepinyl, 1H-2-benzoxazepinyl and 1H-3-benzoxazepinyl groups, or may be a dihydro-oxo derivative type benzoxazepinyl group such as 4,5-dihydro-1-oxo-1H-2-benzoxazepinyl group. Other condensing forms than these may be allowed.

The above-described aryl groups, heteroaryl groups, arylalkenyl group, heteroarylalkenyl groups, saturated or unsaturated, bicyclic or tricyclic condensed hydrocarbon groups and saturated or unsaturated, bicyclic or tricyclic condensed heterocyclic groups may each have 1 to 3 substituents. Examples of the substituents may include a hydroxyl group, halogen atoms such as fluorine atom, chlorine atom, bromine atom and iodine atom, halogenoalkyl groups having 1 to 6 carbon atoms substituted by 1 to 3 halogen atoms, an amino group, a cyano group, aminoalkyl groups, a nitro group, hydroxyalkyl groups (for example, hydroxymethyl group, 2-hydroxyethyl group, etc.), alkoxyalkyl groups (for example, methoxymethyl group, 2-methoxyethyl group, etc.), a carboxyl group, carboxyalkyl groups (for example, carboxymethyl group, 2-carboxyethyl group, etc.), alkoxycarbonylalkyl groups (for example, methoxycarbonylmethyl group, ethoxycarbonylmethyl group, etc.), acyl groups (for example, alkanoyl groups such as formyl group, acetyl group and propionyl group), an amidino group, a hydroxyamidino group (amino(hydroxyimino)methyl group), linear, branched or cyclic alkyl groups having 1 to 6 carbon atoms (for example, methyl group, ethyl group, etc.), linear, branched or cyclic alkoxy groups having 1 to 6 carbon atom (for example, methoxy group, ethoxy group, etc.), amidino groups substituted by a linear, branched or cyclic alkyl group having 1 to 6 carbon atoms (for example, imino(methylamino)methyl group), amidino groups substituted by a linear, branched or cyclic alkoxy group having 1 to 6 carbon atoms (for example, amino(methoxyimino)methyl group), amidino groups substituted by a linear, branched or cyclic alkoxycarbonyl group having 2 to 7 carbon atoms (for example, amino(methoxycarbonylimino)methyl group and amino(ethoxycarbonylimino)methyl group), linear, branched or cyclic alkenyl groups having 2 to 6 carbon atoms (for example, vinyl group, allyl group, etc.), linear or branched alkynyl groups having 2 to 6 carbon atoms (for example, ethynyl group, propynyl group, etc.), linear, branched or cyclic alkoxycarbonyl groups having 2 to 6 carbon atoms (for example, methoxycarbonyl group, ethoxycarbonyl group, etc.), a carbamoyl group, mono- or di-alkylcarbamoyl groups having on the nitrogen atom one or two linear, branched or cyclic alkyl group havings 1 to 6 carbon atoms (for example, methylcarbamoyl group, ethylcarbamoyl group, dimethylcarbamoyl group, ethylmethylcarbamoyl group, etc.), mono- or di-alkylamino groups substituted by a linear, branched or cyclic alkyl group having 1 to 6 carbon atoms (for example, ethylamino, dimethylamino and methylethylamino groups), and 5- or 6-membered nitrogen-containing heterocyclic groups (for example, pyrrolidino group, piperidino group, piperazino group, morpholino group, etc.).

As the group $Q^4$, the following 12 groups (a) to (l) among the above-described groups are preferred. Namely, (a)

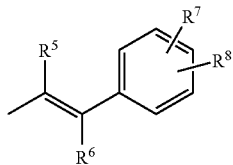

wherein $R^5$ and $R^6$ each independently represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^7$ and $R^8$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(b)

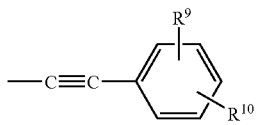

wherein $R^9$ and $R^{10}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(c)

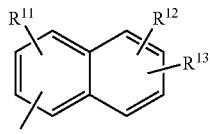

wherein $R^{11}$, $R^{12}$ and $R^{13}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(d)

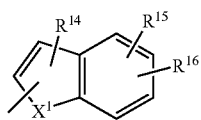

wherein $X^1$ represents $CH_2$, CH, NH, NOH, N, O or S, and $R^{14}$, $R^{15}$ and $R^{16}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(e)

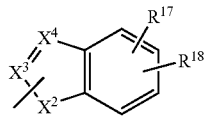

wherein $X^2$ represents NH, N, O or S, $X^3$ represents N, C or CH, $X^4$ represents N, C or CH, and $R^{17}$ and $R^{18}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, excluding the cases where $X^3$ and $X^4$ are combinations of C and CH, and are both C or CH;

(f)

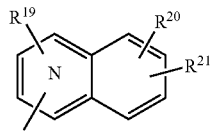

wherein N indicates that 1 or 2 carbon atoms of the ring substituted by $R^{19}$ have been substituted by a nitrogen atom, and $R^{19}$, $R^{20}$ and $R^{21}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(g)

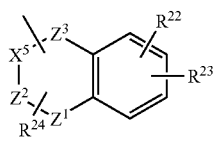

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ and $R^{23}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, and $R^{24}$ represents a hydrogen atom or alkyl group;

(h)

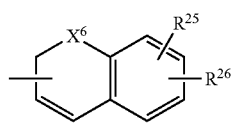

wherein $X^6$ represents O or S, and $R^{25}$ and $R^{26}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

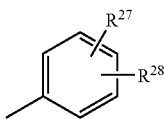

(i)

wherein $R^{27}$ and $R^{28}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

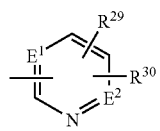

(j)

wherein $E^1$ and $E^2$ each independently represent N or CH, and $R^{29}$ and $R^{30}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

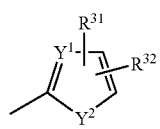

(k)

wherein $Y^1$ represents CH or N, $Y^2$ represents —N($R^{33}$)— (in which $R^{33}$ represents a hydrogen atom or alkyl group having 1 to 6 carbon atoms), O or S, and $R^{31}$ and $R^{32}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group; and

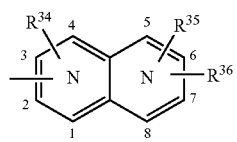

(l)

wherein numerals 1 to 8 indicate positions, each N indicates that any one of carbon atoms of positions 1 to 4 and any one of carbon atoms of positions 5 to 8 has been substituted by a nitrogen atom, and $R^{34}$, $R^{35}$ and $R^{36}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group.

These groups will hereinafter be described.

In the description of $R^5$ to $R^{36}$, the halogen atom is a fluorine, chlorine, bromine or iodine atom, the alkyl group is a linear, branched or cyclic alkyl group having 1 to 6 carbon atoms, the alkenyl group is a linear, branched or cyclic alkenyl group having 2 to 6 carbon atoms, the alkynyl group is a linear or branched alkynyl group having 2 to 6 carbon atoms, the hydroxyalkyl group means the above-described $C_1$-$C_6$ alkyl group substituted by one hydroxyl group, the alkoxy group is a linear, branched or cyclic alkoxy group having 1 to 6 carbon atoms, the alkoxyalkyl group means the above-described $C_1$-$C_6$ alkyl group substituted by one $C_1$-$C_6$ alkoxy group, the carboxyalkyl group means the above-described $C_1$-$C_6$ alkyl group substituted by one carboxyl group, the acyl group is an alkanoyl group (including formyl) having 1 to 6 carbon atoms, an aroyl group such as a benzoyl or naphthoyl group, or an arylalkanoyl group with the above-described $C_6$-$C_{14}$ aryl group substituted on the above-described $C_1$-$C_6$ alkanoyl group, the N-alkylcarbamoyl group means a carbamoyl group with the above-described $C_1$-$C_6$ alkyl group substituted on the nitrogen atom, the N,N-dialkylcarbamoyl group means a carbamoyl group with two $C_1$-$C_6$ alkyl groups substituted on the nitrogen atom, the alkoxycarbonyl group is a group composed of the above-described $C_1$-$C_6$ alkoxy group and a carbonyl group, the alkoxycarbonylalkyl group means the above-described $C_1$-$C_6$ alkyl group substituted by one $C_1$-$C_6$ alkoxycarbonyl group, and the halogenoalkyl group means the above-described $C_1$-$C_6$ alkyl group substituted by 1 to 3 halogen atoms. Incidentally, in the above description, no particular limitation is imposed on the substituting position.

In the following group:

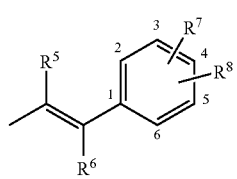

(a)

wherein $R^5$, $R^6$, $R^7$ and $R^8$ have the same meanings as defined above, and numerals 1 to 6 indicate positions, $R^5$ and $R^6$ are each independently preferably a hydrogen atom, cyano group, halogen atom, alkyl group, alkenyl group, alkynyl group or halogenoalkyl group. $R^5$ and $R^6$ are more preferably hydrogen atoms or alkyl groups. In the case of the alkyl group, a methyl group is preferred. It is preferable that one of $R^7$ and $R^8$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorostyryl, fluorostyryl, bromostyryl and ethynylstyryl groups. The position substituted by the halogen atom, alkyl group or alkynyl group is particularly preferably a 4-position in the above formula though it should not be particularly limited. As specific preferable examples thereof, may be mentioned 4-chlorostyryl, 4-fluorostyryl, 4-bromostyryl and 4-ethynylstyryl groups.

In the following group:

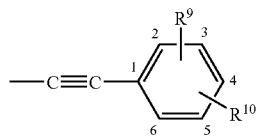

(b)

wherein $R^9$ and $R^{10}$ have the same meanings as defined above, and numerals 1 to 6 indicate positions, $R^9$ and $R^{10}$ are each independently preferably a hydrogen atom, halogen atom, alkyl group or alkynyl group. It is further preferable that $R^9$ is a hydrogen atom, and $R^{10}$ is a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorophenylethynyl, fluorophenylethynyl, bromophenylethynyl and ethynylphenylethynyl groups. The position substituted by the halogen atom, alkyl group or alkynyl group is particularly preferably a 4-position in the above formula though it should not be particularly limited. As specific preferable examples thereof, may be mentioned 4-chlorophenylethynyl, 4-fluorophenylethynyl, 4-bromophenylethynyl and 4-ethynylphenylethynyl groups.

In the following group:

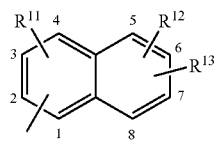

(c)

wherein $R^{11}$, $R^{12}$ and $R^{13}$ have the same meanings as defined above, and numerals 1 to 8 indicate positions, $R^{11}$, $R^{12}$ and $R^{13}$ are each independently preferably a hydrogen atom, cyano group, halogen atom, alkyl group, alkenyl group, alkynyl group or halogenoalkyl group. $R^{11}$ is preferably a hydrogen atom, alkyl group, halogen atom or hydroxyl group, with a hydrogen atom being particularly preferred. It is preferable that one of $R^{12}$ and $R^{13}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. In the naphthyl group, a 2-naphthyl group is preferred to a 1-naphthyl group. In the case of the 2-naphthyl group, the position substituted by a halogen atom, alkyl group or alkynyl group is preferably a 6- or 7-position in the above formula though it should not be particularly limited, with a 6-position being most preferred. These naphthyl groups are preferably substituted by a chlorine, fluorine or bromine atom, an alkynyl group, or the like, with a group having a substituent such as a chlorine, fluorine or bromine atom, an alkynyl group, or the like at the above-described position in the above formula being particularly preferred. As specific preferable examples thereof, may be mentioned 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl and 7-ethynyl-2-naphthyl groups.

In the following group:

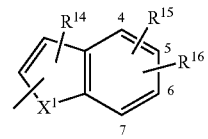

(d)

wherein $X^1$, $R^{14}$, $R^{15}$ and $R^{16}$ have the same meanings as defined above, and numerals 4 to 7 indicate positions, $X^1$ is preferably NH, NOH, N, O or S, with NH, O or S being particularly preferred. $R^{14}$ is preferably a hydrogen atom, halogen atom, acyl group, N-alkylcarbamoyl group, N,N-dialkylcarbamoyl group or alkyl group, and $R^{15}$ and $R^{16}$ are each independently preferably a hydrogen atom, cyano group, halogen atom, alkyl group, alkenyl group, alkynyl group or halogenoalkyl group. It is preferable that one of $R^{15}$ and $R^{16}$ is a hydrogen or a halogen atom, preferably fluorine atom or chlorine atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 4-, 5- or 6-position in the above formula though it should be not particularly limited. As specific preferable examples of the group represented by the above formula, may be mentioned 5-chloroindolyl, 5-fluoroindolyl, 5-bromoindolyl, 5-ethynylindolyl, 5-methylindolyl, 5-chloro-4-fluoroindolyl, 5-chloro-3-fluoroindolyl, 5-fluoro-3-chloroindolyl, 5-ethynyl-3-fluoroindolyl, 5-chloro-3-(N,N-dimethylcarbamoyl)indolyl, 5-fluoro-3-(N,N-dimethylcarbamoyl)indolyl, 5-chloro-3-formylindolyl, 5-fluoro-3-formylindolyl, 6-chloroindolyl, 6-fluoroindolyl, 6-bromoindolyl, 6-ethynylindolyl, 6-methylindolyl, 5-chlorobenzothienyl, 5-fluorobenzothienyl, 5-bromobenzothienyl, 5-ethynylbenzothienyl, 5-methylbenzothienyl, 5-chloro-4-fluorobenzothienyl, 6-chlorobenzothienyl, 6-fluorobenzothienyl, 6-bromobenzothienyl, 6-ethynylbenzothienyl, 6-methylbenzothienyl, 5-chlorobenzofuryl, 5-fluorobenzofuryl, 5-bromobenzofuryl, 5-ethynylbenzofuryl, 5-methylbenzofuryl, 5-chloro-4-fluorobenzofuryl, 6-chlorobenzofuryl, 6-fluorobenzofuryl, 6-bromobenzofuryl, 6-ethynylbenzofuryl and 6-methylbenzofuryl groups. The position of the above-described substituent group bonded to $T^1$ is not particularly limited, but is preferably a 2-position or 3-position in the formula (d). Specifically, more preferred are 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N- dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chloroindol-3-yl, 5-fluoroindol-3-yl, 5-bromoindol-3-yl, 5-ethynylindol-3-yl, 5-methylindol-3-yl, 5-chloro-4-fluoroindol-3-yl, 6-chloroindol-3-yl, 6-fluoroindol-3-yl, 6-bromoindol-3-yl, 6-ethynylindol-3-yl, 6-methylindol-3-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzothiophen-3-yl, 5-fluorobenzothiophen-3-yl, 5-bromobenzothiophen-3-yl, 5-ethynylbenzothiophen-3-yl, 5-methylbenzothiophen-3-yl, 5-chloro-4-fluorobenzothiophen-3-yl, 6-chlorobenzothiophen-3-yl, 6-fluorobenzothiophen-3-yl, 6-bromobenzothiophen-3-yl, 6-ethynylbenzothiophen-3-yl, 6-methylbenzothiophen-3-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzofuran-3-yl, 5-fluorobenzofuran-3-yl, 5-bromobenzofuran-3-yl, 5-ethynylbenzofuran-3-yl, 5-methylbenzofuran-3-yl, 5-chloro-4-fluorobenzofuran-3-yl, 6-chlorobenzofuran-3-yl, 6-fluorobenzofuran-3-yl, 6-bromobenzofuran-3-yl, 6-ethynylbenzofuran-3-yl and 6-methylbenzofuran-3-yl groups, with 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl and 6-methylbenzofuran-2-yl groups being particularly preferred.

In the following group:

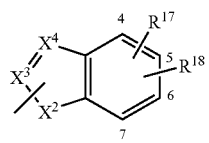

(e)

wherein $X^2$, $X^3$, $X^4$, $R^{17}$ and $R^{18}$ have the same meanings as defined above, and numerals 4 to 7 indicate positions, $X^2$ is preferably NH, O or S, any one of $X^3$ and $X^4$ is preferably CH or C, particularly preferably C. $R^{17}$ and $R^{16}$ are each independently preferably a hydrogen atom, cyano group, halogen atom, alkyl group, alkenyl group, alkynyl group or halogenoalkyl group. It is preferable that one of $R^{17}$ and $R^{18}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 5- or 6-position in the above formula though it should not be particularly limited. As specific preferable examples of the group represented by the above formula, may be mentioned 5-chloroindazolyl, 5-fluoroindazolyl, 5-bromoindazolyl, 5-ethynylindazolyl, 6-chloroindazolyl, 6-fluoroindazolyl, 6-bromoindazolyl, 6-ethynylindazolyl, 5-chlorobenzimidazolyl, 5-fluorobenzimidazolyl, 5-bromobenzimidazolyl, 5-ethynylbenzimidazolyl, 6-chlorobenzimidazolyl, 6-fluorobenzimidazolyl, 6-bromobenzimidazolyl, 6-ethynylbenzimidazolyl, 5-chlorobenzothiazolyl, 5-fluorobenzothiazolyl, 5-bromobenzothiazolyl, 5-ethynylbenzothiazolyl, 6-chlorobenzothiazolyl, 6-fluorobenzothiazolyl, 6-bromobenzothiazolyl, 6-ethynylbenzothiazolyl, 5-chlorobenzoxazolyl, 5-fluorobenzoxazolyl, 5-bromobenzoxazolyl, 5-ethynylbenzoxazolyl, 6-chlorobenzoxazolyl, 6-fluorobenzoxazolyl, 6-bromobenzoxazolyl, 6-ethynylbenzoxazolyl, 5-chlorobenzoisothiazolyl, 5-fluorobenzoisothiazolyl, 5-bromobenzoisothiazolyl, 5-ethynylbenzoisothiazolyl, 6-chlorobenzoisothiazolyl, 6-fluorobenzoisothiazolyl, 6-bromobenzoisothiazolyl, 6-ethynylbenzoisothiazolyl, 5-chlorobenzoisoxazolyl, 5-fluorobenzoisoxazolyl, 5-bromobenzoisoxazolyl, 5-ethynylbenzoisoxazolyl, 6-chlorobenzoisoxazolyl, 6-fluorobenzoisoxazolyl, 6-bromobenzoisoxazolyl and 6-ethynylbenzoisoxazolyl groups. The position of the above-described substituent group bonded to $T^1$ is not particularly limited. More preferred are 5-chloroindazol-3-yl, 5-fluoroindazol-3-yl, 5-bromoindazol-3-yl, 5-ethynylindazol-3-yl, 6-chloroindazol-3-yl, 6-fluoroindazol-3-yl, 6-bromoindazol-3-yl, 6-ethynylindazol-3-yl, 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, 6-ethynylbenzoxazol-2-yl, 5-chlorobenzoisothiazol-3-yl, 5-fluorobenzoisothiazol-3-yl, 5-bromobenzoisothiazol-3-yl, 5-ethynylbenzoisothiazol-3-yl, 6-chlorobenzoisothiazol-3-yl, 6-fluorobenzoisothiazol-3-yl, 6-bromobenzoisothiazol-3-yl, 6-ethynylbenzoisothiazol-3-yl, 5-chlorobenzoisoxazol-3-yl, 5-fluorobenzoisoxazol-3-yl, 5-bromobenzoisoxazol-3-yl, 5-ethynylbenzoisoxazol-3-yl, 6-chlorobenzoisoxazol-3-yl, 6-fluorobenzoisoxazol-3-yl, 6-bromobenzoisoxazol-3-yl and 6-ethynylbenzoisoxazol-3-yl groups, with 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl and 6-ethynylbenzoxazol-2-yl groups being particularly preferred. Among these, 5-chlorobenzimidazol-2-yl, 5-fluorobenzimidazol-2-yl, 5-bromobenzimidazol-2-yl and 5-ethynylbenzimidazol-2-yl groups are further preferred.

In the following group:

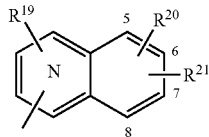

(f)

wherein N indicates that 1 or 2 carbon atoms of the ring substituted by $R^{19}$ have been substituted by a nitrogen atom, $R^{19}$, $R^{20}$ and $R^{21}$ have the same meanings as defined above, and numerals 5 to 8 indicate positions, $R^{19}$, $R^{20}$ and $R^{21}$ are each independently preferably a hydrogen atom, cyano group, halogen atom, alkyl group, alkenyl group, alkynyl group or halogenoalkyl group. $R^{19}$ is particularly preferably a hydrogen atom. It is preferable that one of $R^{20}$ and $R^{21}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should not be particularly limited. As specific preferable examples thereof, may be mentioned quinolinyl, isoquinolinyl and cinnolinyl groups. More preferred are 6-chloroquinolinyl, 6-fluoroquinolinyl, 6-bromoquinolinyl, 6-ethynylquinolinyl, 6-chloroisoquinolinyl, 6-fluoroisoquinolinyl, 6-bromoisoquinolinyl, 6-ethynylisoquinolinyl, 7-chlorocinnolinyl, 7-fluorocinnolinyl, 7-bromocinnolinyl and 7-ethynylcinnolinyl groups, with 6-chloroquinolin-2-yl, 6-fluoroquinolin-2-yl, 6-bromoquinolin-2-yl, 6-ethynylquinolin-2-yl, 6-chloroquinolin-3-yl, 6-fluoroquinolin-3-yl, 6-bromoquinolin-3-yl, 6-ethynylquinolin-3-yl, 7-chloroquinolin-2-yl, 7-fluoroquinolin-2-yl, 7-bromoquinolin-2-yl, 7-ethynylquinolin-2-yl, 7-chloroquinolin-3-yl, 7-fluoroquinolin-3-yl, 7-bromoquinolin-3-yl, 7-ethynylquinolin-3-yl, 6-chloroisoquinolin-3-yl, 6-fluoroisoquinolin-3-yl, 6-bromoisoquinolin-3-yl, 6-ethynylisoquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl and 7-ethynylcinnolin-3-yl groups being particularly preferred. Among these, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl and 7-ethynylcinnolin-3-yl groups are further preferred.

In the following group:

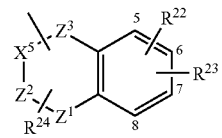

(g)

wherein numerals 5 to 8 indicate positions, $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, and $R^{22}$, $R^{23}$ and $R^{24}$ have the same meanings as defined above, $R^{22}$ and $R^{23}$ are each independently preferably a hydrogen atom, cyano group, halogen atom, alkyl group, alkenyl group, alkynyl group or halogenoalkyl group. It is preferable that one of $R^{22}$ and $R^{23}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should be not particularly limited. $R^{24}$ is preferably a hydrogen atom or alkyl group, and a methyl group is preferred as the alkyl group. As $R^{24}$, is particularly preferred a hydrogen atom. As specific preferable examples of the group represented by the above formula, may be mentioned 4-oxodihydroquinolinyl, tetrahydroquinolinyl, 4-oxodihydroquinazolin-2-yl, 4-oxotetrahydrocinnolinyl, 4-oxobenzopyranyl, 4-oxobenzothiadiazinyl, 1,1-dioxy-4-oxobenzothiadiazinyl and benzoxadiazinyl groups. As specific preferable examples thereof, may be mentioned 6-chloro-4-oxodihydroquinolinyl, 6-fluoro-4-oxodihydroquinolinyl, 6-bromo-4-oxodihydroquinolinyl, 6-ethynyl-4-oxodihydroquinolinyl, 7-chloro-4-oxodihydroquinolinyl, 7-fluoro-4-oxodihydroquinolinyl, 7-bromo-4-oxodihydroquinolinyl, 7-ethynyl-4-oxodihydroquinolinyl, 6-chloro-4-oxo-1,4-dihydroquinazolinyl, 6-fluoro-4-oxo-1,4-dihydroquinazolinyl, 6-bromo-4-oxo-1,4-dihydroquinazolinyl, 6-ethynyl-4-oxo-1,4-dihydroquinazolinyl, 7-chloro-4-oxo-1,4-dihydroquinazolinyl, 7-fluoro-4-oxo-1,4-dihydroquinazolinyl, 7-bromo-4-oxo-1,4-dihydroquinazolinyl, 7-ethynyl-4-oxo-1,4-dihydroquinazolinyl, 6-chloro-1,2,3,4-tetrahydroquinolinyl, 6-fluoro-1,2,3,4-tetrahydroquinolinyl, 6-bromo-1,2,3,4-tetrahydroquinolinyl, 6-ethynyl-1,2,3,4-tetrahydroquinolinyl, 7-chloro-1,2,3,4-tetrahydroquinolinyl, 7-fluoro-1,2,3,4-tetrahydroquinolinyl, 7-bromo-1,2,3,4-tetrahydroquinolinyl, 7-ethynyl-1,2,3,4-tetrahydroquinolinyl, 6-chloro-1,2,3,4-tetrahydro-4-oxocinnolinyl, 6-fluoro-1,2,3,4-tetrahydro-4-oxocinnolinyl, 6-bromo-1,2,3,4-tetrahydro-4-oxocinnolinyl, 6-ethynyl-1,2,3,4-tetrahydro-4-oxocinnolinyl, 7-chloro-1,2,3,4-tetrahydro-4-oxocinnolinyl, 7-fluoro-1,2,3,4-tetrahydro-4-oxocinnolinyl, 7-bromo-1,2,3,4-tetrahydro-4-oxocinnolinyl, 7-ethynyl-1,2,3,4-tetrahydro-4-oxocinnolinyl, 6-chloro-4H-4-oxobenzopyranyl, 6-fluoro-4H-4-oxobenzopyranyl, 6-bromo-4H-4-oxobenzopyranyl, 6-ethynyl-4H-4-oxobenzopyranyl, 7-chloro-4H-4-oxobenzopyranyl, 7-fluoro-4H-4-oxobenzopyranyl, 7-bromo-4H-4-oxobenzopyranyl, 7-ethynyl-4H-4-oxobenzopyranyl, 6-chloro-1,1-dioxy-2H-1,2,4- benzothiadiazinyl, 6-fluoro-1,1-dioxy-2H-1,2,4-benzothiadiazinyl, 6-bromo-1,1-dioxy-2H-1,2,4-benzothiadiazinyl, 6-ethynyl-1,1-dioxy-2H-1,2,4-benzothiadiazinyl, 7-chloro-1,1-dioxy-2H-1,2,4-benzothiadiazinyl, 7-fluoro-1,1-dioxy-2H-1,2,4-benzothiadiazinyl, 7-bromo-1,1-dioxy-2H-1,2,4-benzothiadiazinyl, 7-ethynyl-1,1-dioxy-2H-1,2,4-benzothiadiazinyl, 6-chloro-2H-1,2,4-benzoxadiazinyl, 6-fluoro-2H-1,2,4-benzoxadiazinyl, 6-bromo-2H-1,2,4-benzoxadiazinyl, 6-ethynyl-2H-1,2,4-benzoxadiazinyl, 7-chloro-2H-1,2,4-benzoxadiazinyl, 7-fluoro-2H-1,2,4-benzoxadiazinyl, 7-bromo-2H-1,2,4-benzoxadiazinyl and 7-ethynyl-2H-1,2,4-benzoxadiazinyl groups; with 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 7-chloro-4-oxo-1,4-dihydroquinolin-2-yl, 7-fluoro-4-oxo-1,4-dihydroquinolin-2-yl, 7-bromo-4-oxo-1,4-dihydroquinolin-2-yl, 7-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, 6-ethynyl-4-oxo-1,4-dihydroquinazolin-2-yl, 7-chloro-4-oxo-1,4-dihydroquinazolin-2-yl, 7-fluoro-4-oxo-1,4-dihydroquinazolin-2-yl, 7-bromo-4-oxo-1,4-dihydroquinazolin-2-yl, 7-ethynyl-4-oxo-1,4-dihydroquinazolin-2-yl, 6-chloro-1,2,3,4-tetrahydroquinolin-2-yl, 6-fluoro-1,2,3,4-tetrahydroquinolin-2-yl, 6-bromo-1,2,3,4-tetrahydroquinolin-2-yl, 6-ethynyl-1,2,3,4-tetrahydroquinolin-2-yl, 6-chloro-1,2,3,4-tetrahydro-4-oxocinnolin-2-yl, 6-fluoro-1,2,3,4-tetrahydro-4-oxocinnolin-2-yl, 6-bromo-1,2,3,4-tetrahydro-4-oxocinnolin-2-yl, 6-ethynyl-1,2,3,4-tetrahydro-4-oxocinnolin-2-yl, 7-chloro-1,2,3,4-tetrahydro-4-oxocinnolin-2-yl, 7-fluoro-1,2,3,4-tetrahydro-4-oxocinnolin-2-yl, 7-bromo-1,2,3,4-tetrahydro-4-oxocinnolin-2-yl, 7-ethynyl-1,2,3,4-tetrahydro-4-oxocinnolin-2-yl, 6-chloro-4H-4-oxobenzopyran-2-yl, 6-fluoro-4H-4-oxobenzopyran-2-yl, 6-bromo-4H-4-oxobenzopyran-2-yl, 6-ethynyl-4H-4-oxobenzopyran-2-yl, 7-chloro-4H-4-oxobenzopyran-2-yl, 7-fluoro-4H-4-oxobenzopyran-2-yl, 7-bromo-4H-4-oxobenzopyran-2-yl, 7-ethynyl-4H-4-oxobenzopyran-2-yl, 6-chloro-1,1-dioxy-2H-1,2,4-benzothiadiazin-3-yl, 6-fluoro-1,1-dioxy-2H-1,2,4-benzothiadiazin-3-yl, 6-bromo-1,1-dioxy-2H-1,2,4-benzothiadiazin-3-yl, 6-ethynyl-1,1-dioxy-2H-1,2,4-benzothiadiazin-3-yl, 7-chloro-1,1-dioxy-2H-1,2,4-benzothiadiazin-3-yl, 7-fluoro-1,1-dioxy-2H-1,2,4-benzothiadiazin-3-yl, 7-bromo-1,1-dioxy-2H-1,2,4-benzothiadiazin-3-yl, 7-ethynyl-1,1-dioxy-2H-1,2,4-benzothiadiazin-3-yl, 6-chloro-2H-1,2,4-benzoxadiazin-3-yl, 6-fluoro-2H-1,2,4-benzoxadiazin-3-yl, 6-bromo-2H-1,2,4-benzoxadiazin-3-yl, 6-ethynyl-2H-1,2,4-benzoxadiazin-3-yl, 7-chloro-2H-1,2,4-benzoxadiazin-3-yl, 7-fluoro-2H-1,2,4-benzoxadiazin-3-yl, 7-bromo-2H-1,2,4-benzoxadiazin-3-yl and 7-ethynyl-2H-1,2,4-benzoxadiazin-3-yl groups being preferred. Among these, 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl and 6-ethynyl-4-oxo-1,4-dihydroquinazolin-2-yl are particularly preferred.

In the following group:

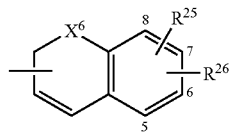

(h)

wherein $X^6$ represents O or S, $R^{25}$ and $R^{26}$ have the same meanings as defined above, and numerals 5 to 8 indicate positions, $X^6$ is preferably O, and $R^{25}$ and $R^{26}$ are each independently preferably a hydrogen atom, cyano group, halogen atom, alkyl group, alkenyl group, alkynyl group or halogenoalkyl group. It is preferable that one of $R^{25}$ and $R^{26}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should be not particularly limited. As specific preferable examples thereof, may be mentioned 6-chloro-2H-chromen-3-yl, 6-fluoro-2H-chromen-3-yl, 6-bromo-2H-chromen-3-yl, 6-ethynyl-2H-chromen-3-yl, 7-chloro-2H-chromen-3-yl, 7-fluoro-2H-chromen-3-yl, 7-bromo-2H-chromen-3-yl and 7-ethynyl-2H-chromen-3-yl groups, with 7-chloro-2H-chromen-3-yl, 7-fluoro-2H-chromen-3-yl, 7-bromo-2H-chromen-3-yl and 7-ethynyl-2H-chromen-3-yl groups being particularly preferred.

In the following group:

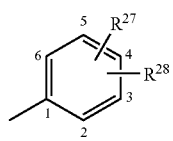

(i)

wherein $R^{27}$ and $R^{28}$ have the same meanings as defined above, and numerals 1 to 6 indicate positions, it is preferable that one of $R^{27}$ and $R^{28}$ is a hydrogen atom or halogen atom, and the other is a hydrogen atom, cyano group, nitro group, amino group, halogen atom, alkyl group, alkenyl group, alkynyl group, halogenoalkyl group or N,N-dialkylcarbamoyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned phenyl, chlorophenyl, fluorophenyl, bromophenyl, ethynylphenyl and chlorofluorophenyl groups. The position substituted by the halogen atom, alkyl group or alkynyl group in these groups is particularly preferably a 3- or 4-position in the above formula in the case of one substituent or a combination of a 4-position and a 2- or 3-position in the above formula in the case of two substituents though it should be not particularly limited. As specific preferable examples thereof, may be mentioned phenyl, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl and 3,4-dibromophenyl groups.

In the following group:

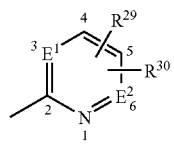

wherein $E^1$, $E^2$, $R^{29}$ and $R^{30}$ have the same meanings as defined above, and numerals 1 to 6 indicate positions, it is preferable that one of $R^{29}$ and $R^{30}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned pyridyl, pyrimidyl and pyridazinyl groups. The position substituted by the halogen atom, alkyl group or alkynyl group in these groups is particularly preferably a 4- or 5-position in the above formula in the case where its bonding to the group $T^1$ is at a 2-position in the above formula though it should be not particularly limited. As specific preferable examples thereof, may be mentioned 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 5-chloro-2-pyrimidyl, 5-fluoro-2-pyrimidyl, 5-bromo-2-pyrimidyl, 5-ethynyl-2-pyrimidyl, 4-chloro-3-pyridazinyl, 4-fluoro-3-pyridazinyl, 4-bromo-3-pyridazinyl, 4-ethynyl-3-pyridazinyl, 6-chloro-3-pyridazinyl, 6-fluoro-3-pyridazinyl, 6-bromo-3-pyridazinyl and 6-ethynyl-3-pyridazinyl groups. Particularly preferred are 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 6-chloro-3-pyridazinyl, 6-fluoro-3-pyridazinyl, 6-bromo-3-pyridazinyl, 6-ethynyl-3-pyridazinyl, 4-chloro-3-pyridazinyl, 4-fluoro-3-pyridazinyl, 4-bromo-3-pyridazinyl and 4-ethynyl-3-pyridazinyl groups. Among these, 2-pyridyl, 3-pyridyl, 4-pyridyl, 5-chloro-2-pyridyl, 5-fluoro-2-pyridyl, 5-bromo-2-pyridyl, 5-ethynyl-2-pyridyl, 5-chloro-4-fluoro-2-pyridyl, 4-chloro-5-fluoro-2-pyridyl, 4-chloro-3-pyridazinyl, 4-fluoro-3-pyridazinyl, 4-bromo-3-pyridazinyl and 4-ethynyl-3-pyridazinyl groups are further preferred.

In the following group:

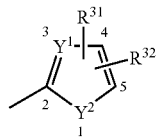

wherein $Y^1$, $Y^2$, $R^{31}$ and $R^{32}$ have the same meanings as defined above, and numerals 1 to 5 indicate positions, it is preferable that one of $R^{31}$ and $R^{32}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned thienyl, pyrrolyl, furyl, oxazolyl and thiazolyl groups. The position substituted by the halogen atom, alkyl group or alkynyl group in these groups is particularly preferably a 4- or 5-position in the above formula though it should be not particularly limited. As specific preferable examples thereof, may be mentioned 4-chloro-2-thienyl, 4-fluoro-2-thienyl, 4-bromo-2-thienyl, 4-ethynyl-2-thienyl, 4-chloro-2-pyrrolyl, 4-fluoro-2-pyrrolyl, 4-bromo-2-pyrrolyl, 4-ethynyl-2-pyrrolyl, 4-chloro-2-furyl, 4-fluoro-2-furyl, 4-bromo-2-furyl, 4-ethynyl-2-furyl, 5-chloro-2-thienyl, 5-fluoro-2-thienyl, 5-bromo-2-thienyl, 5-ethynyl-2-thienyl, 5-chloro-2-thiazolyl, 5-fluoro-2-thiazolyl, 5-bromo-2-thiazolyl, 5-ethynyl-2-thiazolyl, 5-chloro-2-oxazolyl, 5-fluoro-2-oxazolyl, 5-bromo-2-oxazolyl and 5-ethynyl-2-oxazolyl groups. Paticularly preferred are 5-chloro-2-thiazolyl, 5-fluoro-2-thiazolyl, 5-bromo-2-thiazolyl and 5-ethynyl-2-thiazolyl groups.

In the following group:

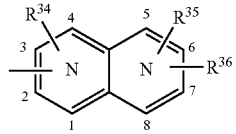

wherein numerals 1 to 8 indicate positions, each N indicates that any one of 4 carbon atoms at positions 1 to 4 and any one of 4 carbon atoms at positions 5 to 8 have been substituted by a nitrogen atom, and $R^{34}$ to $R^{36}$ have the same meanings as defined above, the position of each nitrogen atom may be in any positional relation, and $R^{34}$ is preferably a hydrogen atom or halogen atom. It is preferable that one of $R^{35}$ and $R^{36}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. The position substituted by the halogen atom, alkyl group or alkynyl group should not be particularly limited. As preferable examples of specific groups represented by the above formula, may be mentioned 6-chloro-1,5-naphthyridin-2-yl, 6-fluoro-1,5-naphthyridin-2-yl, 6-bromo-1,5-naphthyridin-2-yl, 6-ethynyl-1,5-naphthyridin-2-yl, 7-chloro-1,5-naphthyridin-2-yl, 7-fluoro-1,5-naphthyridin-2-yl, 7-bromo-1,5-naphthyridin-2-yl, 7-ethynyl-1,5-naphthyridin-2-yl, 6-chloro-1,5-naphthyridin-3-yl, 6-fluoro-1,5-naphthyridin-3-yl, 6-bromo-1,5-naphthyridin-3-yl, 6-ethynyl-1,5-naphthyridin-3-yl, 7-chloro-1,5-naphthyridin-3-yl, 7-fluoro-1,5-naphthyridin-3-yl, 7-bromo-1,5-naphthyridin-3-yl, 7-ethynyl-1,5-naphthyridin-3-yl, 6-chloro-1,7-naphthyridin-2-yl, 6-fluoro-1,7-naphthyridin-2-yl, 6-bromo-1,7-naphthyridin-2-yl, 6-ethynyl-1,7-naphthyridin-2-yl, 6-chloro-1,7-naphthyridin-3-yl, 6-fluoro-1,7-naphthyridin-3-yl, 6-bromo-1,7-naphthyridin-3-yl, 6-ethynyl-1,7-naphthyridin-3-yl, 6-chloro-1,8-naphthyridin-2-yl, 6-fluoro-1,8-naphthyridin-2-yl, 6-bromo-1,8-naphthyridin-2-yl, 6-ethynyl-1,8-naphthyridin-2-yl, 7-chloro-1,8-naphthyridin-2-yl, 7-fluoro-1,8-naphthyridin-2-yl, 7-bromo-1,8-naphthyridin-2-yl, 7-ethynyl-1,8-naphthyridin-2-yl, 6-chloro-1,8-naphthyridin-3-yl, 6-fluoro-1,8-naphthyridin-3-yl, 6-bromo-1,8-naphthyridin-3-yl, 6-ethynyl-1,8-naphthyridin-3-yl, 7-chloro-1,8-naphthyridin-3-yl, 7-fluoro-1,8-naphthyridin-3-yl, 7-bromo-1,8-naphthyridin-3-yl, 7-ethynyl-1,8-naphthyridin-3-yl, 6-chloro-2,5-naphthyridin-3-yl, 6-fluoro-2,5-naphthyridin-3-yl, 6-bromo-2,5-naphthyridin-3-yl, 6-ethynyl-2,5-naphthyridin-3-yl, 7-chloro-2,5-naphthyridin-3-yl, 7-fluoro-2,5-naphthyridin-3-yl, 7-bromo-2,5-naphthyridin-3-yl, 7-ethynyl-2,5-naphthyridin-3-yl, 7-chloro-2,6-naphthyridin-3-yl, 7-fluoro-2,6-naphthyridin-3-yl, 7-bromo-2,6-naphthyridin-3-yl, 7-ethynyl-2,6-naphthyridin-3-yl, 6-chloro-2,8-naphthyridin-3-yl, 6-fluoro-2,8-naphthyridin-3-yl, 6-bromo-2,8-naphthyridin-3-yl, 6-ethynyl-2,8-naphthyridin-3-yl, 7-chloro-2,8-naphthyridin-3-yl, 7-fluoro-2,8-naphthyridin-3-yl, 7-bromo-2,8-naphthyridin-3-yl and 7-ethynyl-2,8-naphthyridin-3-yl groups. Particularly preferable examples thereof include 7-chloro-2,5-naphthyridin-3-yl, 7-fluoro-2,5-naphthyridin-3-yl, 7-bromo-2,5-naphthyridin-3-yl and 7-ethynyl-2,5-naphthyridin-3-yl groups.

In addition to the above-mentioned 12 groups (a) to (l), a thienopyrrolyl group which may be substituted is preferred. This group may have 1 to 3 substituents, and examples of the substituents include a hydroxyl group, a nitro group, an amino group, a cyano group, halogen atoms, alkyl groups, alkenyl groups, alkynyl groups, halagenoalkyl groups, hydroxyalkyl groups, alkoxy groups, alkoxyalkyl groups, a carboxyl group, carboxyalkyl groups, acyl groups, a carbamoyl group, N-alkylcarbamoyl groups, N,N-dialkylcarbamoyl groups, alkoxycarbonyl groups, an amidino group and alkoxycarbonylalkyl groups. Among these, a cyano group, halogen atoms, alkyl groups, alkenyl groups, alkynyl groups and halogenoalkyl groups are preferred. As specific preferable examples thereof, may be mentioned 2-chlorothieno[2,3-b]pyrrol-5-yl, 2-fluorothieno[2,3-b]pyrrol-5-yl, 2-bromothieno[2,3-b]pyrrol-5-yl, and 2-ethynylthieno[2,3-b]pyrrol-5-yl groups.

<On Group $Q^1$>

In the present invention, $Q^1$ means a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted.

As examples of the saturated or unsaturated, 5- or 6-membered cyclic hydrocarbon group, may be mentioned cyclopentyl, cyclopentenyl, cyclohexyl, cyclohexenyl and phenyl groups. Cyclopentyl, cyclohexyl and phenyl groups are preferred, with a phenyl group being more preferred.

The saturated or unsaturated, 5- to 7-membered heterocyclic group means a monovalent heterocyclic group having at least one hetero atom selected from among oxygen, sulfur and nitrogen atoms, and examples thereof may include furyl, pyrrolyl, thienyl, pyrazolyl, imidazolyl, pyrazolinyl, oxazolyl, oxazolinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl, triazinyl, azepinyl, diazepinyl and triazepinyl groups. Of these, thienyl, pyrazolyl, imidazolyl, oxazolyl, thiazolyl, thiadiazolyl, furazanyl, pyridyl, pyrimidyl, pyridazinyl, pyrrolidinyl, piperazinyl, piperidinyl, morpholinyl, thiadiazinyl and triazolyl groups are preferred, with thienyl, thiazolyl, pyrazolyl, imidazolyl, pyridyl, pyrimidyl, pyridazinyl, pyrrolidinyl, piperazinyl and piperidinyl groups being more preferred. Of these heterocyclic groups, the nitrogen-containing heterocyclic groups may be in the form of an N-oxide.

The saturated or unsaturated, bicyclic or tricyclic condensed hydrocarbon group means the same saturated or unsaturated, bicyclic or tricyclic condensed hydrocarbon group as described in the description of $Q^4$ in the general formula (1). As specific examples thereof, may be mentioned indenyl, indanyl, naphthyl, tetrahydronaphthyl, anthryl and phenanthryl groups, with indenyl, indanyl, naphthyl and tetrahydronaphthyl groups being preferred.

The saturated or unsaturated, bicyclic or tricyclic condensed heterocyclic group means the same saturated or unsaturated, bicyclic or tricyclic condensed heterocyclic group as described in the description of $Q^4$ in the general formula (1). As specific examples thereof, may be mentioned benzofuryl, isobenzofuryl, benzothienyl, indolyl, indolinyl, isoindolyl, isoindolinyl, indazolyl, quinolyl, dihydroquinolyl, 4-oxo-dihydroquinolyl (dihydroquinolin-4-one), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzoisothiazolyl, benzoisoxazolyl, benzimidazoyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydrooxazolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thienopyrrolyl, thiazolopyrimidinyl, dihydrothiazolopyrimidinyl, 4-oxo-tetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzoazepinyl, tetrahydrobenzoazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups. Preferred are benzothiazolyl, tetrahydrobenzothiazolyl, thienopyridyl, tetrahydrothienopyridyl, thienopyrrolyl, thiazolopyridyl, tetrahydrothiazolopyridyl, thiazolopyridazinyl, tetrahydrothiazolopyridazinyl, pyrrolopyrimidinyl, dihydropyrrolopyrimidinyl, pyranothiazolyl, dihydropyranothiazolyl, furopyridyl, tetrahydrofuropyridyl, oxazolopyridyl, tetrahydrooxazolopyridyl, pyrrolopyridyl, dihydropyrrolopyridyl, tetrahydropyrrolopyridyl, oxazolopyridazinyl, tetrahydrooxazolopyridazinyl, pyrrolothiazolyl, dihydropyrrolothiazolyl, pyrrolooxazolyl, dihydropyrrolooxazolyl, thiazolopyrimidinyl, dihydrothiazolopyrimidinyl, benzoazepinyl, tetrahydrobenzoazepinyl, thiazoloazepinyl, tetrahydrothiazoloazepinyl, thienoazepinyl, tetrahydrothienoazepinyl, 4,5,6,7-tetrahydro-5,6-tetramethylenethiazolopyridazinyl and 5,6-trimethylene-4,5,6,7-tetrahydrothiazolopyridazinyl groups, with tetrahydrobenzothiazolyl, tetrahydrothienopyridyl, tetrahydrothiazolopyridyl, tetrahydrothiazolopyridazinyl, dihydropyrrolopyrimidinyl, dihydropyranothiazolyl, tetrahydrooxazolopyridyl, dihydropyrrolothiazolyl, 4,5,6,7-tetrahydro-5,6-tetramethylenethiazolopyridazinyl and 5,6-trimethylene-4,5,6,7-tetrahydrothiazolopyridazinyl groups being particularly preferred.

No particular limitation is imposed on the condensing form of the condensed heterocyclic groups. For example, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, with thieno[2,3-c]pyridine and thieno[3,2-c]-pyridine being preferred. Thienopyrrolyl may be any of thieno[2,3-b]pyrrolyl and thieno[3,2-b]pyrrolyl. Thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, with thiazolo[4,5-c]pyridine and thiazolo[5,4-c]pyridine being preferred. Thiazolopyridazine may be any of thiazolo[4,5-c]pyridazine, thiazolo[4,5-d]pyridazine, thiazolo[5,4-c]pyridazine and thiazolo[3,2-b]pyridazine, with thiazolo[4,5-d]pyridazine being preferred. Pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, with pyrrolo[2,3-c]pyridine and pyrrolo[3,2-c]pyridine being preferred. Pyrrolopyrimidine may be any of pyrrolo[3,4-d]pyrimidine, pyrrolo[3,2-d]pyrimidine and pyrrolo[2,3-d]pyrimidine, with pyrrolo[3,4-d]pyrimidine being preferred. Pyridopyrimidine may be any of pyrido[2,3-d]pyrimidine, pyrido[3,2-d]pyrimidine, pyrido[3,4-d]pyrimidine, pyrido[4,3-d]pyrimidine, pyrido[1,2-c]pyrimidine and pyrido[1,2-a]pyrimidine, with pyrido[3,4-d]pyrimidine and pyrido[4,3-d]pyrimidine being preferred. Pyranothiazole may be any of pyrano[2,3-d]thiazole, pyrano[4,3-d]thiazole, pyrano[3,4-d]thiazole and pyrano[3,2-d]thiazole, with pyrano[4,3-d]thiazole and pyrano[3,4-d]thiazole being preferred. Furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine, with furo[2,3-c]pyridine and furo[3,2-c]pyridine being preferred. Oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, with oxazolo[4,5-c]pyridine and oxazolo[5,4-c]pyridine being preferred. Oxazolopyridazine may be any of oxazolo[4,5-c]pyridazine, oxazolo[4,5-d]pyridazine, oxazolo[5,4-c]pyridazine and oxazolo[3,4-b]pyridazine, with oxazolo[4,5-d]pyridazine being preferred. Pyrrolothiazole may be any of pyrrolo[2,1-b]thiazole, pyrrolo[1,2-c]thiazole, pyrrolo[2,3-d]thiazole, pyrrolo[3,2-d]thiazole and pyrrolo[3,4-d]thiazole, with pyrrolo[3,4-d]thiazole being preferred. Pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole, with pyrrolo[3,4-d]oxazole being preferred. Benzoazepine may be any of 1H-1-benzoazepine, 1H-2-benzoazepine and 1H-3-benzoazepine, with 1H-3-benzoazepine being preferred. Thiazolo[4,5-c]azepine may be any of 4H-thiazolo[4,5-c]azepine, 4H-thiazolo[4,5-d]azepine and 4H-thiazolo[5,4-c]azepine, with 4H-thiazolo[4,5-d]azepine being preferred. Thieno[2,3-c]azepine may be any of 4H-thieno[2,3-d]azepine and 4H-thieno[3,2-c]azepine, with 4H-thieno[2,3-d]azepine being preferred.

Of these heterocyclic groups, the nitrogen-containing heterocyclic groups may be in the form of an N-oxide. Incidentally, the position of the above substituent group bonded to $Q^2$ is not particularly limited.

The above-described saturated or unsaturated, 5- or 6-membered cyclic hydrocarbon groups, saturated or unsaturated, 5- to 7-membered heterocyclic groups, saturated or unsaturated, bicyclic or tricyclic condensed hydrocarbon groups and saturated or unsaturated, bicyclic or tricyclic condensed heterocyclic groups may each have 1 to 3 substituents. Examples of the substituents may include a hydroxyl group; halogen atoms such as fluorine atom, chlorine atom, bromine atom and iodine atom; halogenoalkyl groups having 1 to 3 halogen atoms; an amino group; a cyano group; an amidino group; a hydroxyamidino group; linear, branched or cyclic alkyl groups having 1 to 6 carbon atoms (hereinafter referred to as $C_1$-$C_6$ alkyl groups which mean linear, branched and cyclic alkyl groups; for example, linear or branched $C_1$-$C_6$ alkyl groups such as methyl group, ethyl group, isopropyl group and tert-butyl group; $C_3$-$C_6$ cycloalkyl groups such as cyclopropyl group, cyclobutyl group, cyclopentyl group and 1-methylcyclopropyl group; and $C_3$-$C_6$ cycloalkyl-$C_1$-$C_6$ alkyl groups such as cyclopropylmethyl group); hydroxy-$C_1$-$C_6$ alkyl groups (such as hydroxyethyl and 1,1-dimethyl-2-hydroxyethyl groups); $C_1$-$C_6$ alkoxy groups (for example, methoxy group, ethoxy group and the like); $C_1$-$C_6$ alkoxy-$C_1$-$C_6$ alkyl groups; a carboxyl group; $C_2$-$C_6$ carboxyalkyl groups (for example, carboxymethyl group and the like); $C_2$-$C_6$ alkoxycarbonyl-$C_1$-$C_6$ alkyl groups (for example, methoxycarbonylmethyl group, tert-butoxycarbonylmethyl group and the like); amidino groups substituted by a $C_2$-$C_6$ alkoxycarbonyl group; $C_2$-$C_6$ alkenyl groups (for example, vinyl group, allyl group and the like); $C_2$-$C_6$ alkynyl groups (for example, ethynyl group, propynyl group and the like); $C_2$-$C_6$ alkoxycarbonyl groups (for example, methoxycarbonyl group, ethoxycarbonyl group, tert-butoxycarbonyl group and the like); amino $C_1$-$C_6$ alkyl groups (for example, aminomethyl group, aminoethyl group and the like); $C_1$-$C_6$ alkylamino-$C_1$-$C_6$ alkyl groups (for example, N-methylaminomethyl group, N-ethylaminomethyl group and the like); di($C_1$-$C_6$ alkyl)amino-$C_1$-$C_6$ alkyl groups (for example, N,N-dimethylaminomethyl group, N,N-diethylaminomethyl group, N-ethyl-N-methylaminomethyl group and the like); $C_2$-$C_6$ alkoxycarbonylamino-$C_1$-$C_6$ alkyl groups (for example, methoxycarbonylaminoethyl group, tert-butoxycarbonylaminoethyl group and the like); $C_1$-$C_6$ alkanoyl groups (for example, formyl group, acetyl group, methylpropionyl group, cyclopentanecarbonyl group and the like); $C_1$-$C_6$ alkanoylamino-$C_1$-$C_6$ alkyl groups (for example, acetylaminomethyl group and the like); $C_1$-$C_6$ alkylsulfonyl groups (for example, methanesulfonyl group and the like); $C_1$-$C_6$ alkylsulfonylamino-$C_1$-$C_6$ alkyl groups (for example, methanesulfonylaminomethyl group and the like); a carbamoyl group; $C_1$-$C_6$ alkylcarbamoyl groups (for example, methylcarbamoyl group, ethylcarbamoyl group, isopropylcarbamoyl group, tert-butylcarbamoyl group and the like); N,N-di($C_1$-$C_6$ alkyl)carbamoyl groups (for example, dimethylcarbamoyl group, diethylcarbamoyl group, methylethylcarbamoyl group and the like); $C_1$-$C_6$ alkylamino groups (for example, N-methylamino group, N-ethylamino group and the like); di($C_1$-$C_6$ alkyl)amino groups (for example, N,N-dimethylamino group, N,N-diethylamino group, N-ethyl-N-methylamino group and the like); an aminosulfonyl group; arylsulfonyl groups (for example, phenylsulfonyl group and the like); arylcarbonyl groups which may be substituted by, for example, a halogen atom (for example, benzoyl group, 4-fluoro-benzoyl group and the like); $C_2$-$C_6$ alkoxycarbonyl ($C_1$-$C_6$ alkyl)amino $C_1$-$C_6$ alkyl groups (for example, methoxycarbonyl(methyl)aminomethyl group, tert-butoxycarbonyl(methyl)aminomethyl group and the like); $C_1$-$C_6$ alkylsulfonyl $C_1$-$C_6$ alkyl groups (for example, methylsulfonylmethyl group and the like); 5- or 6-membered heterocyclic groups containing one of nitrogen, oxygen and sulfur or the same or different two atoms thereof (for example, pyrrolidinyl group, piperidinyl group, piperazinyl group, morpholinyl group, pyridyl group, pyrimidinyl group, tetrahydropyranyl group and the like); the above 5- or 6-membered heterocyclic-$C_1$-$C_4$ alkyl groups (for example, morpholinomethyl group and the like); the above 5- or 6-membered heterocyclic-carbonyl groups (for example, pyrrolidinocarbonyl group and the like); the above 5- or 6-membered heterocyclic-amino-$C_1$-$C_4$ alkyl groups (for example, N-(oxazol-2-yl)aminomethyl group and the like); the above 5- or 6-membered heterocyclic-amino groups (for example, pyridylamino group and the like); the above 5- or 6-membered heterocyclic-oxy groups (for example, 4-pyridinyloxy group, (1-methyliminopiperidin-4-yl)oxy group and the like); 3- to 6-membered heterocyclic-carbonyl-$C_1$-$C_4$ alkyl groups (for example, 4,4-dioxothiomorpholin-1-yl)carbonylmethyl group and the like); and the above 5- or 6-membered heterocyclic ($C_1$-$C_6$ alkyl)amino-$C_1$-$C_4$ alkyl groups (for example, N-(4,5-dihydro-1,3-oxazol-2-yl)-N-methylaminomethyl group and the like).

As specific examples of $Q^1$, may be mentioned 5- or 6-membered cyclic hydrocarbon groups such as 2-aminosulfonylphenyl group; bicyclic heterocyclic groups such as 5-methyl-4,5,6,7-tetrahydrothiazolo[5,4-c]pyridin-2-yl, 4,5,6,7-tetrahydrothiazolo[5,4-c]pyridin-2-yl, 5-cyclopropyl-4,5,6,7-tetrahydrothiazolo[5,4-c]pyridin-2-yl, 5-carboxymethyl-4,5,6,7-tetrahydrothiazolo[5,4-c]pyridin-2-yl, 5-butyl-4,5,6,7-tetrahydrothiazolo[5,4-c]pyridin-2-yl, 5-(4-pyridyl)-4,5,6,7-tetrahydrothiazolo[5,4-c]pyridin-2-yl, 5-methyl-4,5,6,7-tetrahydrothiazolo[4,5-c]pyridin-2-yl, 6-methyl-4,5,6,7-tetrahydrothieno[2,3-c]pyridin-2-yl, 5-methyl-4,5,6,7-tetrahydrooxazolo[5,4-c]pyridin-2-yl, 5-methyl-4,6-dihydro-5H-pyrrolo[3,4-d]thiazol-2-yl, 5,7-dihydro-6-methylpyrrolo[3,4-d]pyrimidin-2-yl, 5,6-dimethyl-4,5,6,7-tetrahydrothiazolo[4,5-d]pyridazin-2-yl, 5,6-dimethyl-4,5,6,7-tetrahydrooxazolo[4,5-d]pyridazin-2-yl, 5-dimethylamino-4,5,6,7-tetrahydrobenzo[d]thiazol-2-yl, 5-(4-pyridyl)-4,5,6,7-tetrahydrothiazolo[5,4-c]pyridin-2-yl and 6,7-dihydro-4H-pyrano[4,3-d]thiazol-2-yl groups; and 5- or 6-membered heterocyclic groups such as pyridyl groups such as 4-pyridyl and 2-pyridyl; dihydrooxazolyl groups such as 4,5-dihydrooxazol-2-yl; 4-[N-(4,5-dihydrooxazol-2-yl)-N-methylaminomethyl]thiophen-2-yl, 4-[N-(4,5-dihydrooxazol-2-yl)-N-methylaminomethyl]-3-chlorothiophen-2-yl, 5-(N-methylaminomethyl)thiazol-2-yl, 5-(N-methylaminomethyl)thiophen-2-yl, 5-(N,N-dimethylaminomethyl) thiazol-2-yl, 5-(N,N-dimethylaminomethyl)thiophen-2-yl and 5-(N,N-dimethylaminomethyl)pyridin-2-yl groups. Incidentally, $Q^1$ is not limited by these examples at all.

<On Group $Q^2$>

The group $Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted.

In the group $Q^2$, examples of the linear or branched alkylene group having 1 to 6 carbon atoms include methylene, ethylene, trimethylene, propylene, tetramethylene, pentamethylene and hexamethylene groups.

Examples of the linear or branched alkenylene group having 2 to 6 carbon atoms include vinylene, propenylene, butenylene and pentenylene groups. No particular limitation is imposed on the position of a carbon-carbon double bond.

Examples of the linear or branched alkynylene group having 2 to 6 carbon atoms include ethynylene, propynylene, butynylene, pentynylene and hexynylene groups. No particular limitation is imposed on the position of a carbon-carbon triple bond.

The saturated or unsaturated, 5- or 6-membered divalent cyclic hydrocarbon group means a divalent group derived from the saturated or unsaturated, 5- or 6-membered cyclic hydrocarbon described in the description of $Q^4$ in the general formula (1). As specific examples thereof, may be mentioned cyclohexylene, cyclohexenylene and phenylene groups, with cyclohexylene and phenylene groups being preferred.

The saturated or unsaturated, 5- to 7-membered divalent heterocyclic group means a divalent group derived from the saturated or unsaturated, 5- to 7-membered heterocyclic ring described in the description of $Q^4$ in the general formula (1). As specific examples thereof, may be mentioned divalent groups derived from furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, azepien, diazepine and triazepine. Among these, preferable examples thereof include divalent groups derived from pyrazole, imidazole, oxazole, thiazole, thiadiazole, furazane, pyridine, pyrimidine, pyridazine, pyrrolidine, piperazine, piperidine, triazole, triazine, azepien, diazepine and triazepine.

The saturated or unsaturated, divalent bicyclic or tricyclic condensed hydrocarbon means a divalent group derived from the saturated or unsaturated, bicyclic or tricyclic condensed hydrocarbon group described in the description of $Q^4$ in the general formula (1). As specific examples thereof, may be mentioned divalent groups derived from indene, indane, naphthalene, tetrahydronaphthalene, anthracene, phenanthrene and the like. As preferable examples thereof, may be mentioned divalent groups derived from indane and naphthalene.

The saturated or unsaturated, divalent bicyclic or tricyclic condensed heterocyclic group means a divalent group derived from the saturated or unsaturated, bicyclic or tricyclic condensed heterocyclic ring described in the description of $Q^4$ in the general formula (1). As specific examples thereof, may be mentioned divalent groups derived from benzofuran, benzothiophene, indole, isoindole, indazole, quinoline, tetrahydroquinoline, isoquinoline, tetrahydroisoquinoline, quinazoline, dihydroquinazoline, tetrahydroquinazoline, quinoxaline, tetrahydroquinoxaline, cinnoline, tetrahydrocinnoline, indolizine, tetrahydroindolizine, benzothiazole, tetrahydrobenzothiazole, naphthyridine, tetrahydronaphthyridine, thienopyridine, tetrahydrothienopyridine, thiazolopyridine, tetrahydrothiazolopyridine, thiazolopyridazine, tetrahydrothiazolopyridazine, pyrrolopyridine, dihydropyrrolopyridine, tetrahydropyrrolopyridine, pyrrolopyrimidine, dihydropyrrolopyrimidine, dihydropyridoquinazoline, pyranothiazole, dihydropyranothiazole, furopyridine, tetrahydrofuropyridine, oxazolopyridine, tetrahydrooxazolopyridine, oxazolopyridazine, tetrahydrooxazolopyridazine, pyrrolothiazole, dihydropyrrolothiazole, pyrrolooxazole, dihydropyrrolooxazole and benzoazepine. As preferable examples thereof, may be mentioned divalent groups derived from benzofuran, benzothiophene, indole, indazole, quinoline, isoquinoline, tetrahydroisoquinoline, benzothiazole, naphthyridine, thienopyridine, thiazolopyridine, tetrahydrothiazolopyridine, thiazolopyridazine, pyrrolopyridine, tetrahydropyrrolopyridine, pyridopyrimidine, pyranothiazole, dihydropyranothiazole, furopyridine, oxazolopyridine, oxazolopyridazine, pyrrolothiazole, dihydropyrrolothiazole, pyrrolooxazole and dihydropyrrolooxazole. No particular limitation is imposed on the condensing form of the condensed heterocyclic group. For example, naphthyridine may be any of 1,5-, 1,6-, 1,7-, 1,8-, 2,6- and 2,7-naphthyridine, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, thiazolopyridazine may be any of thiazolo[4,5-c]pyridazine, thiazolo[4,5-d]pyridazine, thiazolo[5,4-c]pyridazine and thiazolo[3,2-b]pyridazine, pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, pyrrolopyrimidine may be any of pyrrolo[3,4-d]pyrimidine, pyrrolo[3,2-d]pyrimidine and pyrrolo[2,3-d]pyrimidine, pyridopyrimidine may be any of pyrido[2,3-d]pyrimidine, pyrido[3,2-d]pyrimidine and pyrido[3,4-d]pyrimidine, pyranothiazole may be any of pyrano[2,3-d]thiazole, pyrano[4,3-d]thiazole, pyrano[3,4-d]thiazole and pyrano[3,2-d]thiazole, furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine, oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, oxazolopyridazine may be any of oxazolo[4,5-c]pyridazine, oxazolo[4,5-d]pyridazine, oxazolo[5,4-c]pyridazine and oxazolo[3,4-b]pyridazine, pyrrolothiazole may be any of pyrrolo[2,1-b]thiazole, pyrrolo[1,2-c]thiazole, pyrrolo[3,2-d]thiazole and pyrrolo[3,4-d]thiazole, and pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole. Other condensing forms than these may be allowed.

The above-described saturated or unsaturated, 5- or 6-membered divalent cyclic hydrocarbon groups, saturated or unsaturated, 5- to 7-membered divalent heterocyclic groups, saturated or unsaturated, divalent bicyclic or tricyclic condensed hydrocarbon groups and saturated or unsaturated, divalent bicyclic or tricyclic condensed heterocyclic groups may each have 1 to 3 substituents. Examples of the substituents may include a hydroxyl group, halogen atoms such as a fluorine, chlorine, bromine and iodine atoms, halogenoalkyl groups having 1 to 3 halogen atoms, an amino group, a cyano group, aminoalkyl groups, an amidino group, a hydroxyamidino group, linear, branched or cyclic alkyl groups having 1 to 6 carbon atoms (for example, methyl group, ethyl group, etc.), linear, branched or cyclic alkoxy groups having 1 to 6 carbon atoms (for example, methoxy group, ethoxy group, etc.), an amidino group substituted by a linear, branched or cyclic alkoxycarbonyl groups having 2 to 7 carbon atoms (for example, methoxycarbonylamidino group, ethoxycarbonylamidino group, etc.), linear, branched or cyclic alkenyl groups having 2 to 6 carbon atoms (for example, vinyl group, allyl group, etc.), linear or branched alkynyl groups having 2 to 6 carbon atoms (for example, ethynyl group, propynyl group, etc.), linear, branched or cyclic alkoxycarbonyl group having 2 to 6 carbon atoms (for example, methoxycarbonyl group, ethoxycarbonyl group, etc.), and a carbamoyl group.

Preferable groups in $Q^2$ described above are a single bond, saturated or unsaturated, 5- or 6-membered divalent cyclic hydrocarbon groups which may be substituted, saturated or unsaturated, 5- to 7-membered divalent heterocyclic groups which may be substituted, and saturated or unsaturated, divalent bicyclic or tricyclic condensed heterocyclic groups which may be substituted. Of these, a single bond, saturated or unsaturated, divalent 5- or 6-membered cyclic hydrocarbon groups, saturated or unsaturated, 5- to 7-membered divalent heterocyclic groups are preferred.

When $Q^1$ is a saturated or unsaturated, bicyclic or tricyclic condensed hydrocarbon group which may be substituted, or a saturated or unsaturated, bicyclic or tricyclic condensed heterocyclic group which may be substituted, the group $Q^2$ is preferably a single bond. The case where $Q^2$ is a single bond in the above-described combination means that the general formula (1):

$$Q^1\text{-}Q^2\text{-}T^0\text{-}N(R^1)\text{-}Q^3\text{-}N(R^2)\text{-}T^1\text{-}Q^4 \qquad (1)$$

wherein $R^1$, $R^2$, $Q^1$, $Q^2$, $Q^3$, $Q^4$, $T^0$ and $T^1$ have the same meanings as defined above, comes to the following general formula (1'):

$$Q^1\text{-}T^0\text{-}N(R^1)\text{-}Q^3\text{-}N(R^2)\text{-}T^1\text{-}Q^4 \qquad (1')$$

wherein $Q^1$ represents the above bicyclic or tricyclic condensed hydrocarbon group or bicyclic or tricyclic condensed heterocyclic group, and $R^1$, $R^2$, $Q^3$, $Q^4$, $T^1$ and $T^1$ have the same meanings as defined above.

Specifically, are preferred those in which the group $Q^1$ is a thienopyridyl group which may be substituted; a tetrahydrothienopyridyl group which may be substituted; a thiazolopyridyl group which may be substituted; a tetrahydrothiazolopyridyl group which may be substituted; a thiazolopyridazinyl group which may be substituted; a tetrahydrothiazolopyridazinyl group which may be substituted; a pyranothiazolyl group which may be substituted; a dihydropyranothiazolyl group which may be substituted; a furopyridyl group which may be substituted; a tetrahydrofuropyridyl group which may be substituted; an oxazolopyridyl group which may be substituted; a tetrahydrooxazolopyridyl group which may be substituted; a pyrrolopyridyl group which may be substituted; a dihydropyrrolopyridyl group which may be substituted; a tetrahydropyrrolopyridyl group which may be substituted; a pyrrolopyrimidinyl group which may be substituted; a dihydropyrrolopyrimidinyl group which may be substituted; an oxazolopyridazinyl group which may be substituted; a tetrahydrooxazolopyridazinyl group which may be substituted; a pyrrolothiazolyl group which may be substituted; a dihydropyrrolothiazolyl group which may be substituted; a pyrroloooxazolyl group which may be substituted; a dihydropyrroloooxazolyl group which may be substituted; a benzothiazolyl group which may be substituted; a tetrahydrobenzothiazolyl group which may be substituted; a thiazolopyrimidinyl which may be substituted; a dihydrothiazolopyrimidinyl which may be substituted; a benzoazepinyl which may be substituted; a tetrahydrobenzoazepinyl which may be substituted; a thiazoloazepinyl which may be substituted; a tetrahydrothiazoloazepinyl which may be substituted; a thienoazepinyl which may be substituted; a tetrahydrothienoazepinyl which may be substituted; a 4,5,6,7-tetrahydro-5,6-tetramethylenethiazolopyridazinyl group which may be substituted; or a 5,6-trimethylene-4,5,6,7-tetrahydrothiazolopyridazinyl group which may be substituted, and $Q^2$ is a single bond.

When $Q^1$ is a saturated or unsaturated, 5- or 6-membered cyclic hydrocarbon group which may be substituted, or a saturated or unsaturated, 5- to 7-membered heterocyclic group which may be substituted, the group $Q^2$ is preferably a saturated or unsaturated, 5- or 6-membered divalent cyclic hydrocarbon group which may be substituted, or a saturated or unsaturated, 5- to 7-membered divalent heterocyclic group which may be substituted. As preferable examples of the group $Q^1$-$Q^2$, may be mentioned 4-(4-pyridyl)phenyl, 4-(2-pyridyl)phenyl, 5-(4-pyridyl)thiazolyl, 1-(4-pyridyl)piperidyl, 4-(4-pyridyl)piperidyl, 4-hydroxy-1-(4-pyridyl)piperidin-4-yl, biphenylyl, 4-(2-aminosulfonylphenyl)phenyl, 4-(2-amidinophenyl)phenyl, 4-(2-methylsulfonylphenyl)phenyl, 4-(2-aminomethylphenyl)phenyl, 4-(2-carbamoylphenyl)phenyl, 4-(2-imidazolyl)phenyl, 4-(1-methyl-2-imidazolyl)phenyl, 4-(2,3,4,5-tetrahydropyrimidin-2-yl)phenyl, 4-(1-methyl-2,3,4,5-tetrahydropyrimidin-2-yl)phenyl, 4-(5-tetrazolyl)phenyl, 1-(4-pyridyl)piperidin-4-yl, 3-(4-piperidyl)isoxazolin-5-yl, 3-(4-amidinophenyl)isoxazolin-5-yl, 3-(4-piperidyl)isoxazolidin-5-yl, 3-(4-amidinophenyl)isoxazolidin-5-yl, 2-(4-piperidyl)-1,3,4-thiadiazol-5-yl, 2-(4-aminophenyl)-1,3,4-oxadiazol-5-yl, 4-(4-piperidyl)piperidin-1-yl, 4-(4-piperidyl)piperazin-1-yl, 4-(4-piperazinyl)piperazin-1-yl, 1-(4-pyrimidinyl)piperidin-1-yl, 1-(2-methylpyrimidin-4-yl)piperidin-4-yl, 1-(4-pyrimidinyl)pyrrolidin-3-yl, 1-(4-methylpyrimidin-6-yl)piperazin-4-yl, 1-(2-methylpyrimidin-4-yl)pyrrolidin-4-yl, 1-(6-chloropyrimidin-4-yl)piperidin-4-yl, 5-(4-chlorophenyl)thiophen-2-yl, 2-(4-chlorophenyl)thiazol-4-yl, 3-(4-chlorophenyl)-1H-pyrrol-2-yl, 4-(4-pyrimidinyl)phenyl, 4-(4-imidazolyl)phenyl, 5-(pyridin-4-yl)pyrimidin-2-yl, 2'-[(dimethylamino)methyl][1,1'-biphenyl]-4-yl, 4-[2-(hydroxymethyl)pyridin-4-yl]phenyl, 4-[2-(aminomethyl)pyridin-4-yl]phenyl, 2'-(aminosulfonyl)[1,1'-biphenyl]-4-yl and 4-(3-oxomorpholin-4-yl)phenyl groups.

<On Group $Q^3$>

The group $Q^3$ represents the following group:

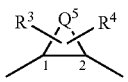

wherein $Q^5$ represents an alkylene group having 1 to 8 carbon atoms, an alkenylene group having 2 to 8 carbon atoms, or a group —$(CH_2)_m$—$CH_2$-A-$CH_2$—$(CH_2)_n$— (in which m and n are each independently 0 or an integer of 1-3, and A represents an oxygen atom, nitrogen atom, sulfur atom, —SO—, —SO$_2$—, —NH—, —O—NH—, —NH—NH—, —S—NH—, —SO—NH— or —SO$_2$—NH—, numerals 1 and 2 indicate positions) and;

$R^3$ and $R^4$ are substituents on carbon atom(s), nitrogen atom(s) or sulfur atom(s) of a ring comprising $Q^5$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, 3- to 6-membered heterocyclic group which may be substituted, 3- to 6-membered heterocyclic alkyl group which may be substituted, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, alkoxycarbonylalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, 3- to 6-membered heterocyclic oxy group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s), alkylsulfonylacyl group, N-arylcarbamoyl group, N-(3- to 6-membered heterocyclic) carbamoyl group, N-alkyl-N-arylcarbamoyl group, N-alkyl-N-(3- to 6-membered heterocyclic) carbamoyl group, N-arylcarbamoylalkyl group, N-(3- to 6-membered heterocyclic) carbamoylalkyl group, N-alkyl-N-arylcarbamoylalkyl group, N-alkyl-N-(3- to 6-membered heterocyclic) carbamoylalkyl group, aminocarbothioyl group, N-alkylaminocarbothioyl group, N,N-dialkylaminocarbothioyl group, alkoxyalkyl(thiocarbonyl) group, alkylthioalkyl group or N-acyl-N-alkylaminoalkyl group, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group.

The following group will be described in detail.

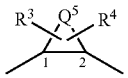

wherein $Q^5$, $R^3$ and $R^4$ have the same meanings as defined above, and numerals 1 and 2 indicate positions.

A portion of the cyclic structure having the group $Q^5$ is a 3- to 10-membered divalent cyclic hydrocarbon group which may have a double bond, or a 5- to 12-membered divalent heterocyclic group containing 1 or 2 hetero atoms, preferably a 3- to 8-membered divalent cyclic hydrocarbon group or a 5- to 8-membered divalent heterocyclic group, more preferably a 5- to 7-membered divalent cyclic hydrocarbon group or a 5- to 7-membered divalent heterocyclic group. Among others, a group in which $Q^5$ is an alkylene group having 3 to 6 carbon atoms or a group —$(CH_2)_m$—$CH_2$-A-$CH_2$—$(CH_2)_n$— (in which m and n are each independently 0 or 1, and A has the same meaning as defined above) is preferred. In particular, a group in which $Q^5$ is an alkylene group having 4 carbon atoms is preferred.

This cyclic hydrocarbon group or heterocyclic group may have both cis and trans structures in the relation between position 1 and position 2. However, the trans-form is preferred in the case of the 5-membered ring, while both cis-form and trans-form are preferred in the 6- or 7-membered ring.

The substituents $R^3$ and $R^4$ will now be described in detail. The halogen atom means a fluorine, chlorine, bromine or iodine atom. Examples of the alkyl group include linear, branched or cyclic $C_1$-$C_6$ alkyl groups (for example, methyl group, cyclopropyl group, isobutyl group and the like). Examples of the halogenoalkyl group include the 1 to 3 halogen-substituted alkyl groups (for example, chloromethyl group, 1-bromoethyl group, trifluoromethyl group and the like). Examples of the cyanoalkyl group include the $C_1$-$C_6$ alkyl groups substituted with one cyano group (for example, cyanomethyl group, 1-cyanoethyl group and the like). Examples of the alkenyl group include linear or branched alkenyl groups having 2 to 6 carbon atoms and a double bond (for example, vinyl group, allyl group and the like). Examples of the alkynyl group include linear or branched alkynyl groups having 2 to 6 carbon atoms and a triple bond (for example, ethynyl group, propynyl group and the like). Examples of the acyl group include $C_1$-$C_6$ alkanoyl groups (for example, formyl group, acetyl group and the like), $C_7$-$C_{15}$ aroyl groups such as a benzoyl group and a naphthoyl group, and arylalkanoyl groups that are the $C_1$-$C_6$ alkanoyl groups substituted with one $C_6$-$C_{14}$ aryl group (for example, phenacetyl group and the like). Examples of the acylalkyl group include the $C_1$-$C_6$ alkyl groups substituted with one acyl group (for example, acethylmethyl group and the like). Examples of the alkoxy group include linear, branched or cyclic $C_1$-$C_6$ alkoxy groups (for example, methoxy group, cyclopropoxy group, an isopropoxy group and the like). Examples of the alkoxyalkyl group include the $C_1$-$C_6$ alkyl groups substituted with one $C_1$-$C_6$ alkoxy group (for example, methoxymethyl group, ethoxymethyl group and the like). Examples of the hydroxyalkyl group include the $C_1$-$C_6$ alkyl groups substituted with one hydroxyl group (for example, hydroxymethyl group, 1-hydroxyethyl group and the like). Examples of the carboxyalkyl group include the $C_1$-$C_6$ alkyl groups substituted with one carboxyl group (for example, carboxymethyl group, 1-carboxyethyl group and the like). Examples of the alkoxycarbonyl group include groups composed of the $C_1$-$C_6$ alkoxy group and a carbonyl group (for example, methoxycarbonyl group, ethoxycarbonyl group and the like). Examples of the alkoxycarbonylalkyl group include the $C_1$-$C_6$ alkyl groups substituted with one alkoxycarbonyl group (for example, methoxycarbonylethyl group, ethoxycarbonylethyl group and the like). Examples of the carbamoylalkyl group include the $C_1$-$C_6$ alkyl groups substituted a carbamoyl group (for example, carbamoylmethyl group, carbamoylethyl group and the like).

The 3- to 6-membered heterocyclic group which may be substituted means a saturated or unsaturated 3- to 6-membered heterocyclic group which may contain 1 to 3 hetero atoms (nitrogen atom, oxygen atom, sulfur atom, etc.). The heterocyclic group may have a substituent such as a hydroxy group, halogen atom, amino group, $C_1$-$C_6$ alkyl group, oxo group, or halogenoalkyl group. Examples of the 3- to 6-membered heterocyclic group include pyrrolyl, thienyl, pyrazolyl, imidazolyl, pyrazolinyl, oxazolyl, oxazolinyl, oxadiazolyl, oxazolidinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl, and triazinyl groups. Specific examples include thiazolyl, 4,5-dihydrothiazolyl, oxazolyl, 4,5-dihydrooxazolyl, 5-methyloxazolyl, imidazolyl, pyrrolidinyl, 3-hydroxypyrrolidinyl, piperidyl, piperazinyl, morpholinyl, thiomorpholinyl, 1,1-dioxothiomorpholinyl, tetrahydropyranyl, pyridyl, 1,2,4-oxadiazolyl, 3-methyl-1,2,4-oxadiazolyl, 5-methyl-1,2,4-oxadiazolyl, 1,3,4-oxadiazolyl, 5-methyl-1,3,4-oxadiazolyl, 5-(trifluoromethyl)-1,3,4-oxadiazolyl, 1,3-oxazolyl, 1,3,4-thiadiazolyl, 5-methyl-1,3,4-thiadiazolyl, and 1,3-oxazolidinyl groups. Examples of the 3- to 6-membered heterocyclic alkyl group which may be substituted include groups obtained by substituting one of the above-described 3- to 6-membered heterocyclic group which may be substituted by an alkyl group (for example, thiazolylmethyl, 4,5-dihydrothiazolylmethyl, morpholinylmethyl, and 1,1-dioxothiomorpholinylmethyl groups). Examples of the aryl group include aryl groups having 6 to 14 carbon atoms, such as phenyl group and naphthyl group. The aryl groups may have 1 to 3 substituents selected from among the $C_1$-$C_6$ alkyl groups, the $C_1$-$C_6$ alkanoyl groups, a hydroxyl group, a nitro group, a cyano group, halogen atoms, the $C_2$-$C_6$ alkenyl groups, the $C_2$-$C_6$ alkynyl groups, the $C_1$-$C_6$ halogenoalkyl groups, the $C_1$-$C_6$ alkoxy groups, a carboxy group, a carbamoyl group, the $C_1$-$C_6$ alkoxycarbonyl groups and the like. Examples of the aralkyl group include the $C_1$-$C_6$ alkyl groups substituted with one $C_6$-$C_{14}$ aryl group (for example, benzyl group, phenethyl group and the like). Incidentally, in the above description, no particular limitation is imposed on the substituting position. Examples of the acylamino group which may be substituted include the amino groups substituted with the $C_1$-$C_6$ acyl group (for example, formylamino group, acetylamino group and the like) and besides acyl groups having 1 to several substituents selected from among halogen atoms, a hydroxyl group, $C_1$-$C_6$ alkoxy groups, a amino group, N-$C_1$-$C_6$ alkylamino groups, N,N-di-$C_1$-$C_6$ alkylamino groups, a carboxyl group, $C_2$-$C_6$ alkoxycarbonyl groups and the like (for example, 2-methoxyacetylamino group, 3-aminopropionylamino group and the like). Examples of the acylaminoalkyl group include the $C_1$-$C_6$ alkyl groups substituted with the $C_1$-$C_6$ acylamino group (for example, formylaminomethyl group, acetylaminomethyl group and the like). Examples of the aminoalkyl group include the $C_1$-$C_6$ alkyl groups substituted with one amino group (for example, aminomethyl group, 1-aminoethyl group and the like). Examples of the N-alkylaminoalkyl group include the amino-$C_1$-$C_6$ alkyl groups substituted with one $C_1$-$C_6$ alkyl group on the nitrogen atom (for example, N-methylaminomethyl group, N-methylaminoethyl group and the like). Examples of N,N-dialkylaminoalkyl group include the amino-$C_1$-$C_6$ alkyl groups respectively substituted with two $C_1$-$C_6$ alkyl groups on the nitrogen atom (for example, N,N-dimethylaminomethyl group, N-ethyl-N-methylaminoethyl group and the like). Examples of the N-alkenylcarbamoyl group include carbamoyl groups substituted with a linear or branched $C_2$-$C_6$ alkenyl group (for example, allylcarbamoyl group and the like). Examples of the N-alkenylcarbamoylalkyl group include the $C_1$-$C_6$ alkyl groups substituted with the N-$C_2$-$C_6$ alkenylcarbamoyl group (for example, allylcarbamoylethyl group and the like). Examples of the N-alkenyl-N-alkylcarbamoyl group include the N-$C_2$-$C_6$ alkenylcarbamoyl groups substituted with a linear or branched $C_1$-$C_6$ alkyl group on the nitrogen atom (for example, N-allyl-N-methylcarbamoyl group and the like). Examples of the N-alkenyl-N-alkylcarbamoylalkyl group include the N-$C_2$-$C_6$ alkenylcarbamoylalkyl groups substituted with a linear or branched $C_1$-$C_6$ alkyl group on the nitrogen atom (for example, N-allyl-N-methylcarbamoylmethyl group and the like). Example of the N-alkoxycarbamoyl group include carbamoyl groups substituted with a linear or branched $C_1$-$C_6$ alkoxy group (for example, methoxycarbamoyl group and the like). Examples of the N-alkoxycarbamoylalkyl group include linear or branched $C_1$-$C_6$ alkyl groups substituted with the N-$C_1$-$C_6$ alkoxycarbamoyl group (for example, methoxycarbamoylmethyl group and the like). Examples of the N-alkyl-N-alkoxycarbamoyl group include carbamoyl groups substituted with linear or branched $C_1$-$C_6$ alkoxy group and $C_1$-$C_6$ alkyl group (for example, N-ethyl-N-methoxycarbamoyl group and the like). Examples of the N-alkyl-N-alkoxycarbamoylalkyl group include linear or branched $C_1$-$C_6$ alkyl groups substituted with the N-$C_1$-$C_6$ alkyl-N-$C_1$-$C_6$ alkoxycarbamoyl group (for example, N-ethyl-N-methoxycarbamoylmethyl group and the like). Examples of the carbazolyl group which may be substituted by 1 to 3 alkyl groups include a carbazolyl group, and besides carbazolyl groups substituted with 1 to 3 linear or branched $C_1$-$C_6$ alkyl groups (for example, 1-methylcarbazolyl group, 1,2-dimethylcarbazolyl group and the like). Examples of the alkylsulfonyl group include linear, branched or cyclic $C_1$-$C_6$ alkylsulfonyl groups (for example, methanesulfonyl group and the like). Examples of the alkylsulfonylalkyl group include linear or branched $C_1$-$C_6$ alkyl groups substituted with the $C_1$-$C_6$ alkylsulfonyl group (for example, methanesulfonylmethyl group and the like). Examples of the alkoxyimino group include $C_1$-$C_6$ alkoxyimino groups (for example, methoxyimino group, ethoxyimino group and the like). Examples of the alkoxycarbonylalkylamino group include amino groups substituted with one $C_1$-$C_6$ alkoxycarbonylalkyl group (for example, methoxycarbonylmethylamino group, ethoxycarbonylpropylamino group and the like). Examples of the carboxyalkylamino group include amino groups substituted with one carboxy-$C_1$-$C_6$ alkyl group (for example, carboxymethylamino group, carboxyethylamino group and the like). Examples of the alkoxycarbonylamino group include amino groups substituted with one $C_1$-$C_6$ alkoxycarbonyl group (for example, methoxycarbonylamino group, tert-butoxycarbonylamino group and the like). Examples of the alkoxycarbonylaminoalkyl group include the alkyl groups substituted with one $C_1$-$C_6$ alkoxycarbonylamino group (for example, methoxycarbonylaminomethyl group, tert-butoxycarbonylaminoethyl group and the like). The N-alkylcarbamoyl group which may have a substituent on the alkyl group means a carbamoyl group substituted with a linear, branched or cyclic $C_1$-$C_6$ alkyl group which may be substituted with a hydroxyl group, amino group, N-$C_1$-$C_6$ alkylamino group, amidino group, halogen atom, carboxyl group, cyano group, carbamoyl group, $C_1$-$C_6$ alkoxy group, $C_1$-$C_6$ alkanoyl group, $C_1$-$C_6$ alkanoylamino group, $C_1$-$C_6$ alkylsulfonylamino group or the like, and examples thereof include N-methylcarbamoyl group, N-ethylcarbamoyl group, N-isopropylcarbamoyl group, N-cyclopropylcarbamoyl group, N-(2-hydroxyethyl)carbamoyl group, N-(2-fluoroethyl)carbamoyl group, N-(2-cyanoethyl)carbamoyl group, N-(2-methoxyethyl)carbamoyl group, N-carboxymethylcarbamoyl group, N-(2-aminoethyl)carbamoyl group, N-(2-amidinoethyl)carbamoyl group and the like. Examples of the N,N-dialkylcarbamoyl group which may have a substituent on the alkyl group(s) means a carbamoyl group substituted with 2 linear, branched or cyclic $C_1$-$C_6$ alkyl groups which may be substituted with a hydroxyl group, amino group, N-$C_1$-$C_6$ alkylamino group, amidino group, halogen atom, carboxyl group, cyano group, carbamoyl group, $C_1$-$C_6$ alkoxy group, $C_1$-$C_6$ alkanoyl group, $C_1$-$C_6$ alkanoylamino group, $C_1$-$C_6$ alkylsulfonylamino group or the like, and examples thereof include N,N-dimethylcarbamoyl group, N,N-diethylcarbamoyl group, N-ethyl-N-methylcarbamoyl group, N-isopropyl-N-methylcarbamoyl group, N-(2-hydroxyethyl)-N-methylcarbamoyl group, N,N-bis(2-hydroxyethyl)carbamoyl group, N,N-bis(2-fluoroethyl)carbamoyl group, N-(2-cyanoethyl)-N-methylcarbamoyl group, N-(2-methoxyethyl)-N-methylcarbamoyl group, N-carboxymethyl-N-methylcarbamoyl group, N,N-bis(2-aminoethyl)carbamoyl group and the like. Examples of the N-alkylcarbamoylalkyl group which may have a substituent on the alkyl group(s) include linear or branched $C_1$-$C_6$ alkyl groups substituted with the N-alkylcarbamoyl group which may have a substituent on the $C_1$-$C_6$ alkyl group (for example, N-methylcarbamoylmethyl group, N-(2-hydroxyethyl)carbamoylmethyl group and the like). Examples of the N,N-dialkylcarbamoylalkyl group which may have a substituent on the alkyl group(s) include linear or branched $C_1$-$C_6$ alkyl groups substituted with the N,N-dialkylcarbamoyl group which may have a substituent on the $C_1$-$C_6$ alkyl group(s) (for example, N,N-dimethylcarbamoylmethyl group, N-(2-hydroxyethyl)-N-methylcarbamoylmethyl group and the like). Examples of the 3- to 6-membered heterocyclic carbonyl group which may be substituted include groups composed of the 3- to 6-membered heterocyclic group which may be substituted and a carbonyl group (for example, aziridinylcarbonyl group, azetidinylcarbonyl group, 3-hydroxyazetidinylcarbonyl group, 3-methoxyazetidinylcarbonyl group, pyrrolidinylcarbonyl group, 3-hydroxypyrrolidinylcarbonyl group, 3-fluoropyrrolidinylcarbonyl group, piperidylcarbonyl group, piperazinylcarbonyl group, morpholinylcarbonyl group, thiomorpholinylcarbonyl group, 1,1-dioxothiomorpholinylcarbonyl group, tetrahydropyranylcarbonyl group, pyridylcarbonyl group, furoyl group, and thiophenecarbonyl group). Examples of the 3- to 6-membered heterocyclic carbonylalkyl group which may be substituted include the $C_1$-$C_6$ alkyl groups substituted with one 3- to 6-membered heterocyclic carbonyl group which may be substituted (for example, azetidinylcarbonylmethyl group, pyrrolidinylcarbonylethyl group and the like) Examples of the 3- to 6-membered heterocyclic carbonyloxyalkyl group which may be substituted include the $C_1$-$C_6$ alkyl groups substituted with one 3- to 6-membered heterocyclic carbonyloxy group which is composed of the 3- to 6-membered heterocyclic carbonyl group and an oxygen atom (for example, piperidinylcarbonyloxyethyl group, morpholinylcarbonyloxymethyl group and the like). Examples of the carbamoyloxyalkyl group include the $C_1$-$C_6$ alkyl groups substituted with one carbamoyloxy group which is composed of a carbamoyl group and an oxygen atom (for example, carbamoyloxymethyl group, carbamoyloxyethyl group and the like). Examples of the N-alkylcarbamoyloxyalkyl group include the $C_1$-$C_6$ alkyl groups substituted with one N-alkylcarbamoyloxy group which is composed of the N-alkylcarbamoyl group, which may have a substituent on the $C_1$-$C_6$ alkyl group, and an oxygen atom (for example, N-methylcarbamoyloxymethyl group, N-methylcarbamoyloxyethyl group and the like). Examples of the N,N-dialkylcarbamoyloxyalkyl group include the $C_1$-$C_6$ alkyl groups substituted with one N,N-dialkylcarbamoyloxy group which is composed of the N,N-dialkylcarbamoyl group, which may have a substituent on the alkyl group(s), and an oxygen atom (for example, N,N-dimethylcarbamoyloxymethyl group, N-ethyl-N-methylcarbamoyloxyethyl group and the like). Examples of the alkylsulfonylamino group include amino groups substituted with one alkylsulfonyl group having the $C_1$-$C_6$ alkyl group (for example, methylsulfonylamino group, isopropylsulfonylamino group and the like). Examples of the arylsulfonylamino group include amino groups substituted with one arylsulfonyl group having the aryl group (for example, phenylsulfonylamino group, naphthylsulfonylamino group and the like). Examples of the alkylsulfonylaminoalkyl group include the $C_1$-$C_6$ alkyl groups substituted with one $C_1$-$C_6$ alkylsulfonylamino group (for example, methylsulfonylaminomethyl group, methylsulfonylaminoethyl group and the like). Examples of the arylsulfonylaminoalkyl group include the $C_1$-$C_6$ alkyl groups substituted with one arylsulfonylamino group (for example, phenylsulfonylaminomethyl group, naphthylsulfonylaminoethyl group and the like). Examples of the alkylsulfonylaminocarbonyl group include groups composed of the $C_1$-$C_6$ alkylsulfonylamino group and a carbonyl group (for example, methylsulfonylaminocarbonyl group, isopropylsulfonylaminocarbonyl group and the like). Examples of the arylsulfonylaminocarbonyl group include groups composed of the arylsulfonylamino group and a carbonyl group (for example, phenylsulfonylaminocarbonyl group, naphthylsulfonylaminocarbonyl group and the like). Examples of the alkylsulfonylaminocarbonylalkyl group include the $C_1$-$C_6$ alkyl groups substituted with the $C_1$-$C_6$ alkylsulfonylaminocarbonyl group (for example, methylsulfonylaminocarbonylmethyl group, isopropylsulfonylaminocarbonylmethyl group and the like). Examples of the arylsulfonylaminocarbonylalkyl group include the $C_1$-$C_6$ alkyl groups substituted with the arylsulfonylaminocarbonyl group (for example, phenylsulfonylaminocarbonylmethyl group, naphthylsulfonylaminocarbonylmethyl group and the like). Examples of the alkoxycarbonylalkyloxy group include the $C_1$-$C_6$ alkoxy groups substituted with the alkoxycarbonyl group (for example, methoxycarbonylmethyloxy group). The acyloxy group means a group composed of the acyl group and an oxygen atom (for example, formyloxy group, acetyloxy group and the like). Examples of the acyloxyalkyl group include the $C_1$-$C_6$ alkyl groups substituted with the acyloxy group (for example, formyloxymethyl group, acetyloxymethyl group and the like). Examples of the aralkyloxy group include the $C_1$-$C_6$ alkoxy groups substituted with the aryl group (for example, benzyloxy group, naphthylmethoxy group and the like). Examples of the carboxyalkyloxy group include the alkoxy groups substituted with a carboxyl group (for example, carboxymethoxy group, carboxyethoxy group and the like).

Examples of the arylsulfonyl group include $C_6$-$C_{14}$ arylsulfonyl groups (for example, phenylsulfonyl group, naphthylsulfonyl group and the like). Examples of the alkoxycarbonylalkylsulfonyl group include groups composed of the $C_1$-$C_6$ alkoxycarbonylalkyl group and a sulfonyl group (for example, methoxycarbonylethylsulfonyl group, ethoxycarbonylethylsulfonyl group and the like). Examples of the carboxyalkylsulfonyl group include groups composed of the carboxyalkyl group and a sulfonyl group (for example, carboxymethylsulfonyl group, carboxyethylsulfonyl group and the like). Examples of the alkoxycarbonylacyl group include groups composed of the alkoxycarbonylalkyl group and a carbonyl group (for example, methoxycarbonylmethylcarbonyl group, ethoxycarbonylmethylcarbonyl group and the like). Examples of the alkoxyalkyloxycarbonyl group include the alkoxycarbonyl groups substituted with one $C_1$-$C_6$ alkoxy group (for examples, methoxymethyloxycarbonyl group, methoxyethyloxycarbonyl group and the like). Examples of the hydroxyacyl group include the acyl groups (including $C_1$-$C_6$ alkanoyl and aroyl) substituted with one hydroxyl group (for example, glycoloyl group, lactoyl group, benziloyl group and the like). Examples of the alkoxyacyl group include the acyl groups substituted with one $C_1$-$C_6$ alkoxy group (for example, methoxyacetyl group, ethoxyacetyl group and the like). Examples of the halogenoacyl group include groups composed of the halogenoalkyl group and a carbonyl group (for example, chloromethylcarbonyl group, trifluoromethylcarbonyl group and the like). Examples of the carboxyacyl group include the acyl groups sucstituted with one carboxyl group (for example, carboxyacetyl group, 2-carboxypropionyl group and the like). Examples of the aminoacyl group include the acyl groups (including $C_1$-$C_6$ alkanoyl and aroyl) substituted with one amino group (for example, aminomethylcarbonyl group, 1-aminoethylcarbonyl group and the like). Examples of the acyloxyacyl group include groups composed of the acyloxyalkyl and a carbonyl group (for example, formyloxymethylcarbonyl group, acetyloxymethylcarbonyl group and the like). Examples of the acyloxyalkylsulfonyl group include groups composed of the acyloxyalkyl and a sulfonyl group (for example, formyloxymethylsulfonyl group, acetyloxymethylsulfonyl group and the like). Examples of the hydroxyalkylsulfonyl group include groups composed of the $C_1$-$C_6$ hydroxyalkyl group and a sulfonyl group (for example, hydroxymethylsulfonyl group, 1-hydroxyethylsulfonyl group and the like). Examples of the alkoxyalkylsulfonyl group include the groups composed of $C_1$-$C_6$ alkoxyalkyl group and a sulfonyl group (for example, methoxymethylsulfonyl group, ethoxyethylsulfonyl group and the like). Examples of the 3- to 6-membered heterocyclic sulfonyl group which may be substituted include groups composed of the 3- to 6-membered heterocyclic group which may be substituted and a sulfonyl group (for example, aziridinylsulfonyl group, azetidinylsulfonyl group, pyrrolidinylsulfonyl group, piperidylsulfonyl group, piperazinylsulfonyl group, morpholinylsulfonyl group, tetrahydropyranylsulfonyl group and the like). Examples of the 3- to 6-membered heterocyclic oxy group which may be substituted include groups composed of the 3- to 6-membered heterocyclic group which may be substituted and an oxygen atom (for example, tetrahydrofuranyloxy group). Examples of the N-alkylaminoacyl group include the aminoacyl groups substituted with one $C_1$-$C_6$ alkyl group on the nitrogen atom (for example, N-methylaminoacetyl group, N-ethylaminoacetyl group and the like). Examples of the N,N-dialkylaminoacyl group include the aminoacyl groups substituted with two $C_1$-$C_6$ alkyl groups on the nitrogen atoms (for example, N,N-dimethylaminoacetyl group, N-ethyl-N-methylaminoacetyl group and the like). Examples of the N,N-dialkylcarbamoylacyl group which may have a substituent on the alkyl group(s) include the acyl groups substituted with the N,N-dialkylcarbamoyl group which may have a substituent on the $C_1$-$C_6$ alkyl group(s) (for example, N,N-dimethylcarbamoylacetyl group, N,N-diethylcarbamoylacyl group, N-ethyl-N-methylcarbamoylacetyl group and the like). Examples of the N,N-dialkylcarbamoylalkylsulfonyl group which may have a substituent on the alkyl group(s) include groups composed of the N,N-dialkylcarbamoyl group which may have a substituent on the $C_1$-$C_6$ alkyl group(s) and a sulfonyl group (for example, N,N-dimethylcarbamoylmethylsulfonyl group, N-(2-hydroxyethyl)-N-methylcarbamoylmethylsulfonyl group and the like). Examples of the alkylsulfonylacyl group include the acyl groups substituted with one alkylsulfonyl group having the $C_1$-$C_6$ alkyl group (for example, methylsulfonylacetyl group, isopropylsulfonylacetyl group and the like).

Examples of the N-arylcarbamoyl group include groups obtained through substitution of the above-described aryl group with a carbamoyl group (for example, phenylcarbamoyl group and naphthylcarbamoyl group). Examples of the N-(3- to 6-membered heterocyclic) carbamoyl group include groups obtained through substitution of the above-described 3- to 6-membered heterocyclic group which may be substituted with a carbamoyl group (for example, pyridylcarbamoyl group and thienylcarbamoyl group). Examples of the N-alkyl-N-arylcarbamoyl group include groups obtained through substitution of the hydrogen atom on the nitrogen atom of the above-described N-arylcarbamoyl group with a linear or branched $C_1$-$C_6$ alkyl group (for example, N-methyl-N-phenylcarbamoyl group). Examples of the N-alkyl-N-(3- to 6-membered heterocyclic) carbamoyl group include groups obtained through substitution of the hydrogen atom on the nitrogen atom of the above-described N-(3- to 6-membered heterocyclic) carbamoyl group with a linear or branched $C_1$-$C_6$ alkyl group (for example, N-methyl-N-thienylcarbamoyl group). Examples of the N-arylcarbamoylalkyl group include groups obtained through substitution of the above-described N-arylcarbamoyl with a linear or branched $C_1$-$C_6$ alkyl group (for example, phenylcarbamoylmethyl group). Examples of the N-(3- to 6-membered heterocyclic) carbamoylalkyl group include groups obtained through substitution of the above-described N-(3- to 6-membered heterocyclic) carbamoyl group with a linear or branched $C_1$-$C_6$ alkyl group (for example, pyridylcarbamoylmethyl group). Examples of the N-alkyl-N-arylcarbamoylalkyl group include groups obtained through substitution of the hydrogen atom on the nitrogen atom of the above-described N-arylcarbamoylalkyl group with a linear or branched $C_1$-$C_6$ alkyl group (for example, N-methyl-N-phenylcarbamoylmethyl group). Examples of the N-alkyl-N-(3- to 6-membered heterocyclic) carbamoylalkyl group include groups obtained through substitution of the hydrogen atom on the nitrogen atom of the above-described N-(3- to 6-membered heterocyclic) carbamoylalkyl group with a linear or branched $C_1$-$C_6$ alkyl group (for example, N-methyl-N-thienylcarbamoylmethyl group).

The aminocarbothioyl group is a group represented by —C(=S)—NH$_2$, and the N-alkylaminocarbothioyl group means an aminothiocarbonyl group substituted by one of the above-described alkyl groups, and examples thereof include (methylamino)carbothioyl group, (ethylamino)carbothioyl group and the like. The N,N-dialkylaminocarbothioyl group means an aminothiocarbonyl group substituted by two of the above-described alkyl groups, and examples thereof include (dimethylamino)carbothioyl group, (diethylamino)carbothioyl group and (ethylmethylamino)carbothioyl group. The alkoxyalkyl(thiocarbonyl) group means a group composed of the above-described alkoxyalkyl group and a thiocarbonyl group, and examples thereof include 2-ethoxyethanethioyl group and the like. Examples of the alkylthioalkyl group include groups obtained through substitution of a linear, branched, or cyclic $C_1$-$C_6$ alkylthio group with a linear, branched, or cyclic $C_1$-$C_6$ alkyl group (for example, methylthiomethyl group and 1-methylthioethyl group). Examples of the N-acyl-N-alkylaminoalkyl group include groups obtained through substitution of the hydrogen atoms on the nitrogen atom of an amino-$C_1$-$C_6$ alkyl group with a $C_1$-$C_6$ alkyl group and an acyl group (for example, N-acetyl-N-methylaminomethyl group).

The alkylene group means a linear or branched alkylene group having 1 to 5 carbon atoms, and examples thereof include methylene group, ethylene group, propylene group and the like. The alkenylene group is an alkenylene group having 2 to 5 carbon atoms and a double bond, and examples thereof include vinylene group, propenylene group and the like. Examples of the alkylenedioxy group include those having 1 to carbon atoms, such as methylenedioxy group, ethylenedioxy group and propylenedioxy group. The carbonyldioxy group is a group represented by —O—C(=O)—O—. Incidentally, no particular limitation is imposed on the substituting position in the above description.

Among these substituents represented by $R^3$ and $R^4$, the hydrogen atom, hydroxyl group, alkyl group, alkenyl group, alkynyl group, halogen atom, halogenoalkyl group, amino group, hydroxyimino group, alkoxyimino group, aminoalkyl group, N-alkylaminoalkyl group, N,N-dialkylaminoalkyl group, acyl group, acylalkyl group, acylamino group which may be substituted, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, 3- to 6-membered heterocyclic carbonyloxyalkyl group which may be substituted, 3- to 6-membered heterocyclic group which may be substituted, carbamoylalkyl group, carbamoyloxyalkyl group, N-alkylcarbamoyloxyalkyl group, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, oxo group, acyloxy group, acyloxyalkyl group, arylsulfonyl group, alkoxycarbonylalkylsulfonyl group, carboxyalkylsulfonyl group, alkoxycarbonylacyl group, carboxyacyl group, alkoxyalkyloxycarbonyl group, halogenoacyl group, N,N-dialkylaminoacyl group, acyloxyacyl group, hydroxyacyl group, alkoxyacyl group, alkoxyalkylsulfonyl group, N,N-dialkylcarbamoylacyl group, N,N-dialkylcarbamoylalkylsulfonyl group, alkylsulfonylacyl group, aminocarbothioyl group, N-alkylaminocarbothioyl group, N,N-dialkylaminocarbothioyl group, alkoxyalkyl(thiocarbonyl) group and the like are preferred. The alkylene group, alkenylene group, alkylenedioxy group, carbonyldioxy group and the like which are formed by $R^3$ and $R^4$ together are also preferred.

It is preferred that $R^3$ be a hydrogen atom, and $R^4$ be one of the substituents mentioned above as preferable groups. In this case, examples of a group more preferred as $R^4$ include the hydrogen atom, hydroxyl group, alkyl group, halogen atom, hydroxyimino group, N-alkylaminoalkyl group, N,N-dialkylaminoalkyl group, acyl group, acylamino group which may be substituted, acylaminoalkyl group, alkoxy group, alkoxyalkyl group, hydroxyalkyl group, carboxyl group, alkoxycarbonyl group, alkoxycarbonylalkyl group, alkoxycarbonylamino group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, 3- to 6-membered heterocyclic carbonyloxyalkyl group which may be substituted, 3- to 6-membered heterocyclic group which may be substituted, carbamoylalkyl group, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, acyloxy group, arylsulfonyl group, alkoxycarbonylalkylsulfonyl group, carboxyalkylsulfonyl group, alkoxycarbonylacyl group, carboxyacyl group, alkoxyalkyloxycarbonyl group, halogenoacyl group, N,N-dialkylaminoacyl group, acyloxyacyl group, hydroxyacyl group, alkoxyacyl group, alkoxyalkylsulfonyl group, N,N-dialkylcarbamoylacyl group, N,N-dialkylcarbamoylalkylsulfonyl group, alkylsulfonylacyl group, aminocarbothioyl group, N-alkylaminocarbothioyl group, N,N-dialkylaminocarbothioyl group, alkoxyalkyl(thiocarbonyl) group and the like.

Of these, as examples of $R^4$, are particularly preferred the hydrogen atom, hydroxyl group, alkyl group, N,N-dialkylaminoalkyl group, acylamino group which may be substituted, acylaminoalkyl group, alkoxy group, alkoxyalkyl group, hydroxyalkyl group, alkoxycarbonyl group, alkoxycarbonylamino group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkyl-N-alkoxycarbamoyl group, carbazolyl group which may be substituted by 1 to 3 alkyl groups, alkylsulfonyl group, alkylsulfonylalkyl group, 3- to 6-membered heterocyclic carbonyl group which may be substituted, 3- to 6-membered heterocyclic group which may be substituted, N,N-dialkylcarbamoyloxyalkyl group, N-alkylcarbamoylalkyl group which may have a substituent on the alkyl group(s), N,N-dialkylcarbamoylalkyl group which may have a substituent on the alkyl group(s), alkylsulfonylamino group, alkylsulfonylaminoalkyl group, acyloxy group, acyl group, alkoxyalkyloxycarbonyl group, halogenoacyl group, N,N-dialkylaminoacyl group, hydroxyacyl group, alkoxyacyl group, aminocarbothioyl group, N-alkylaminocarbothioyl group, N,N-dialkylaminocarbothioyl group, alkoxyalkyl(thiocarbonyl) group and the like.

As specific preferable examples of $R^3$ and $R^4$, may be mentioned a hydrogen atom, hydroxyl group, methyl group, ethyl group, isopropyl group, N,N-dimethylaminomethyl group, N,N-dimethylaminoethyl group, N,N-diethylaminomethyl group, acetylamino group, methoxyacetylamino group, acetylaminomethyl group, acetylaminoethyl group, methoxy group, ethoxy group, methoxymethyl group, methoxyethyl group, hydroxymethyl group, 2-hydroxyethyl group, 1-hydroxy-1-methylethyl group, methoxycarbonyl group, ethoxycarbonyl group, methoxycarbonylamino group, ethoxycarbonylamino group, N-allylcarbamoyl group, N-allylcarbamoylmethyl group, N-allyl-N-methylcarbamoyl group, N-allyl-N-methylcarbamoylmethyl group, N-methoxy-N-methylcarbamoyl group, N,N-dimethylcarbazolyl group, N; N,N'-trimethylcarbazolyl group, methanesulfonyl group, methanesulfonylmethyl group, ethanesulfonylmethyl group, N-methylcarbamoyl group, N-ethylcarbamoyl group, N-propylcarbamoyl group, N-isopropylcarbamoyl group, N-tert-butylcarbamoyl group, N-cyclopropylcarbamoyl group, N-cyclopropylmethylcarbamoyl group, N-(1-ethoxycarbonylcyclopropyl)carbamoyl group, N-(2-hydroxyethyl)carbamoyl group, N-(2-fluoroethyl)carbamoyl group, N-(2-methoxyethyl)carbamoyl group, N-(carboxymethyl)carbamoyl group, N-(2-aminoethyl)carbamoyl group, N-(2-amidinoethyl)carbamoyl group, N,N-dimethylcarbamoyl group, N,N-diethylcarbamoyl group, N-ethyl-N-methylcarbamoyl group, N-isopropyl-N-methylcarbamoyl group, N-methyl-N-propylcarbamoyl group, N-(2-hydroxyethyl)-N-methylcarbamoyl group, N-(2-fluoroethyl)-N-methylcarbamoyl group, N,N-bis(2-hydroxyethyl)carbamoyl group, N,N-bis(2-fluoroethyl)carbamoyl group, N-(2-methoxyethyl)-N-methylcarbamoyl group, N-carboxymethyl-N-methylcarbamoyl group, N,N-bis(2-aminoethyl)carbamoyl group, azetidinocarbonyl group, 3-methoxyazetidinocarbonyl group, 3-hydroxyazetidinocarbonyl group, pyrrolidinocarbonyl group, 3-hydroxypyrrolidinocarbonyl group, 3-fluoropyrrolidinocarbonyl group, 3,4-dimethoxypyrrolidinocarbonyl group, piperidinocarbonyl group, piperazinocarbonyl group, morpholinocarbonyl group, (tetrahydropyran-4-yl)carbonyl group, benzoyl group, pyridylcarbonyl group, thiazolyl group, 4,5-dihydrothiazolyl group, oxazolyl group, 4,5-dihydrooxazolyl group, 5-methyloxazolyl group, imidazolyl group, pyrrolidinyl group, 3-hydroxypyrrolidinyl group, piperidyl group, piperazinyl group, morpholinyl group, thiomorpholinyl group, 1,1-dioxothiomorpholinyl group, tetrahydropyranyl group, pyridyl group, 1,2,4-oxadiazolyl group, 3-methyl-1,2,4-oxadiazolyl group, 5-methyl-1,2,4-oxadiazolyl group, 1,3,4-oxadiazolyl group, 5-methyl-1,3,4-oxadiazolyl group, 5-(trifluoromethyl)-1,3,4-oxadiazolyl group, 1,3-oxazolyl group, 1,3,4-thiadiazolyl group, 5-methyl-1,3,4-thiadiazolyl group, 1,3-oxazolidinyl group, N-methylcarbamoylmethyl group, N-methylcarbamoylethyl group, N-ethylcarbamoylmethyl group, N-(2-fluoroethyl)carbamoylmethyl group, N-(2-methoxyethyl)carbamoylmethyl group, N,N-dimethylcarbamoylmethyl group, N,N-dimethylcarbamoylethyl group, N-(2-fluoroethyl)-N-methylcarbamoylmethyl group, N-(2-methoxyethyl)-N-methylcarbamoylmethyl group, N,N-dimethylcarbamoyloxymethyl group, 2-(N-ethyl-N-methylcarbamoyloxy)ethyl group, methylsulfonylamino group, ethylsulfonylamino group, methylsulfonylaminomethyl group, methylsulfonylaminoethyl group, acetyl group, propionyl group, isobutyryl group, 2-methoxyethoxycarbonyl group, trifluoroacetyl group, N,N-dimethylaminoacetyl group, N-ethyl-N-methylaminoacetyl group, hydroxyacetyl group, 1,1-dimethyl-2-hydroxyethylcarbonyl group, methoxyacetyl group, 1,1-dimethyl-2-methoxyethylcarbonyl group, aminocarbothioyl group, (dimethylamino)carbothioyl group, 2-methoxyethanethioyl group and the like.

As described above, it is preferred that $R^3$ be a hydrogen atom, and $R^4$ be one of these specified substituents, preferably, an N,N-dialkylcarbamoyl group which may have a substituent on the alkyl group(s), particularly preferably, an N,N- dimethylcarbamoyl group. However, $R^3$ and $R^4$ are not limited to these specific substituents at all.

<On Group $T^0$>

The group $T^0$ represents a carbonyl group or thiocarbonyl group, with the carbonyl group being preferred.

<On Group $T^1$>

The group $T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-$A^1$-N(R")— (in which $A^1$ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-$A^2$-C(=O)— (in which $A^2$ represents a single bond or alkylene group having 1 to 5 carbon atoms), group —C(=O)-$A^3$-C(=O)—NH— (in which $A^3$ represents an alkylene group having 1 to 5 carbon atoms), group —C(=O)—C(=NOR$^a$)—N(R$^b$)—, group —C(=S)—C(=NOR$^a$)—N(R$^b$)— (in which R$^a$ represents a hydrogen atom, alkyl group or alkanoyl group, and R$^b$ represents a hydrogen atom, hydroxyl group, alkyl group or alkoxy group), group —C(=O)—N=N—, group —C(=S)—N=N—, group —C(=NOR$^c$)—C(=O)—N(R$^d$)— (in which R$^c$ represents a hydrogen atom, alkyl group, alkanoyl group, aryl group or aralkyl group, and R$^d$ represents a hydrogen atom, hydroxyl group, alkyl group or alkoxy group), group —C(=N—N(R$^e$)(R$^f$))—C(=O)—N(R$^g$)— (in which R$^e$ and R$^f$ each independently represent a hydrogen atom, alkyl group, alkanoyl group or alkyl(thiocarbonyl) group, and R$^g$ represents a hydrogen atom, hydroxyl group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)—, or thiocarbonyl group.

In the above group, the alkylene group having 1 to 5 carbon atoms in $A^1$, $A^2$ and $A^3$ represents a linear, branched or cyclic alkylene group having 1 to 5 carbon atoms, and examples thereof include methylene, ethylene, propylene, cyclopropylene, 1,3-cyclopentylene groups and the like. The alkyl group in R', R", R$^a$, R$^b$, R$^c$, R$^d$, R$^e$, R$^f$ and R$^g$ represents a linear, branched or cyclic alkyl group having 1 to 6 carbon atoms, and examples thereof include methyl, ethyl groups and the like. The alkoxy group means a linear, branched or cyclic alkoxy group having 1 to 6 carbon atoms, and examples thereof include methoxy, ethoxy groups and the like.

In R$^a$, R$^c$, R$^e$ and R$^f$, the alkanoyl group means a group composed of a linear, branched or cyclic alkyl group having 1 to 6 carbon atoms and a carbonyl group, and examples thereof include acetyl, propionyl groups and the like.

In R$^c$, the aryl group means an aryl group having 6 to 14 carbon atoms, and examples thereof include phenyl, naphthyl groups and the like. The aralkyl group means a linear, branched or cyclic alkyl group having 1 to 6 carbon atoms substituted with the aryl group having 6 to 14 carbon atoms, and examples thereof include benzyl, phenethyl groups and the like.

As $T^1$, is preferred a carbonyl group, group —C(=O)—C(=O)—N(R')—, group —C(=S)—C(=O)—N(R')—, group —C(=O)—C(=S)—N(R')—, group —C(=S)—C(=S)—N(R')— and group —C(=O)—CH$_2$—N(R")—, with a carbonyl group, group —C(=O)—C(=O)—N(R')—, group —C(=S)—C(=O)—N(R')—, group —C(=O)—C(=S)—N(R')— and group —C(=S)—C(=S)—N(R')— being particularly preferred.

<On Group $R^1$ and Group $R^2$>

$R^1$ and $R^2$ are each independently a hydrogen atom, hydroxyl group, alkyl group or alkoxy group, preferably a hydrogen atom or alkyl group, more preferably a hydrogen atom.

In $R^1$ and $R^2$, the alkyl group means a linear, branched or cyclic alkyl group having 1 to 6 carbon atoms, and examples thereof include methyl, ethyl groups and the like. The alkoxy group means a linear, branched or cyclic alkoxy group having 1 to 6 carbon atoms, and examples thereof include methoxy, ethoxy groups and the like. $R^1$ and $R^2$ are preferably each independently a hydrogen atom or alkyl group, more preferably both hydrogen atoms.

When $T^1$ is a carbonyl or sulfonyl group, and $Q^5$ in the group $Q^3$ is an alkylene group having 1 to 8 carbon atoms or an alkenylene group having 2 to 8 carbon atoms, $Q^4$ is preferably a group (b), (f), (g), (h), (i), (j), (k) and (l) of the above-described 12 groups, with the proviso that N in the group (f) indicates that 2 carbon atoms of the ring substituted by $R^{19}$ have been substituted by a nitrogen atom.

When $T^1$ is a carbonyl or sulfonyl group, and $Q^5$ in the group $Q^3$ is an alkylene group having 1 to 8 carbon atoms or an alkenylene group having 2 to 8 carbon atoms, the substituent on the group $Q^5$ is preferably an N-alkylcarbamoyl or N,N-dialkylcarbamoyl group.

When $T^1$ is a group —C(=O)—C(=O)—N(R')—, group —C(=S)—C(=O)—N(R')—, group —C(=O)—C(=S)—N(R')— or group —C(=S)—C(=S)—N(R')—, and $Q^5$ in the group $Q^3$ is an alkylene group having 1 to 8 carbon atoms or an alkenylene group having 2 to 8 carbon atoms, $Q^4$ is preferably a group (i), (j) or (k) of the above-described 12 groups.

When $T^1$ is a group —C(=O)—C(=O)—N(R')—, group —C(=S)—C(=O)—N(R')—, group —C(=O)—C(=S)—N(R')— or group —C(=S)—C(=S)—N(R')—, and $Q^5$ in the group $Q^3$ is an alkylene group having 1 to 8 carbon atoms or an alkenylene group having 2 to 8 carbon atoms, the substituent on the group $Q^5$ is preferably an N-alkylcarbamoyl or N,N-dialkylcarbamoyl group.

A feature of the compounds of the present invention represented by the general formula (1), the salts thereof, the solvates thereof, or the N-oxides thereof resides in a combination of the group $T^1$ and the group $Q^3$. The combination is roughly divided into the following two cases (I) and (II):

(I) A case where $T^1$ is a carbonyl, sulfonyl, group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)— or thiocarbonyl group, and $Q^3$ is the following group:

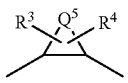

wherein $Q^5$ represents a group —(CH$_2$)$_m$—CH$_2$-A-CH$_2$—(CH$_2$)$_n$— (in which m and n are each independently 0 or an integer of 1-3, and A represents an oxygen atom, nitrogen atom, sulfur atom, —SO—, —SO₂—, —NH—, —O—NH—, —NH—NH—, —S—NH—, —SO—NH— or —SO₂—NH—); and (II) a case where T¹ is a group —C(=O)—C(=O)—N(R')—, group —C(=S)—C(=O)—N(R')—, group —C(=O)—C(=S)—N(R')— or group —C(=S)—C(=S)—N(R')— (in which R' represents a hydrogen atom, hydroxyl group, alkyl group or alkoxy group), group —C(=O)-A¹-N(R")— (in which A¹ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-A²-C(=O)— (in which A² represents a single bond or alkylene group having 1 to 5 carbon atoms), group —C(=O)-A³-C(=O)—NH— (in which A³ represents an alkylene group having 1 to 5 carbon atoms), group —C(=O)—C(=NORᵃ)—N(Rᵇ)—, group —C(=S)—C(=NORᵃ)—N(Rᵇ)— (in which Rᵃ represents a hydrogen atom, alkyl group or alkanoyl group, and Rᵇ represents a hydrogen atom, hydroxyl group, alkyl group or alkoxy group), group —C(=O)—N=N—, group —C(=S)—N=N—, group —C(=NORᶜ)—C(=O)—N(Rᵈ)— (in which Rᶜ represents a hydrogen atom, alkyl group, alkanoyl group, aryl group or aralkyl group, and Rᵈ represents a hydrogen atom, hydroxy group, alkyl group or alkoxy group), group —C(=N—N(Rᵉ)(Rᶠ))—C(=O)—N(Rᵍ)— (in which Rᵉ and Rᶠ are each independently a hydrogen atom, alkyl group, alkanoyl group or alkyl(thiocarbonyl)group, and Rᵍ represents a hydrogen atom, hydroxy group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO₂—, group —SO₂—NH—, group —C(=NCN)—NH—C(=O)—, group —C(=S)—C(=O)—, or thiocarbonyl group, and Q³ is the following group:

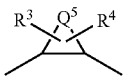

wherein Q⁵ represents an alkylene group having 1 to 8 carbon atoms, an alkenylene group having 2 to 8 carbon atoms or a group —(CH₂)ₘ—CH₂-A-CH₂—(CH₂)ₙ— (in which m and n are each independently 0 or an integer of 1-3, and A represents an oxygen atom, nitrogen atom, sulfur atom, —SO—, —SO₂—, —NH—, —O—NH—, —NH—NH—, —S—NH—, —SO—NH— or —SO₂—NH—).

In the cases (I) and (II), the following (i) and (ii) are mentioned as preferred examples, respectively.

(i) An example where the group R¹ and the group R² are each independently a hydrogen atom or alkyl group, the group Q¹ is a saturated or unsaturated, bicyclic or tricyclic condensed hydrocarbon group which may be substituted, or a saturated or unsaturated, bicyclic or tricyclic condensed heterocyclic group which may be substituted, the group Q² is a single bond, the group Q⁵ in the group Q³ is a group —(CH₂)ₙ—CH₂-A-CH₂—(CH₂)ₙ— (in which m and n are each independently 0 or 1, and A has the same meaning as defined above), the group Q⁴ is selected from 9 groups (a) to (h) and (l) of the above-described 12 groups, the group T⁰ is a carbonyl group or thiocarbonyl group, and the group T¹ is a carbonyl group or sulfonyl group; and (ii) An example where in the generaly formula (1), the groups R¹ and R² are each independently a hydrogen atom or alkyl group, the group Q¹ is a saturated or unsaturated, bicyclic or tricyclic condensed hydrocarbon group which may be substituted, or a saturated or unsaturated, bicyclic or tricyclic condensed heterocyclic group which may be substituted, the group Q² is a single bond, the group Q⁵ in the group Q³ is an alkylene group having 3 to 6 carbon atoms or a group —(CH₂)ₘ—CH₂-A-CH₂—(CH₂)ₙ— (in which m and n are each independently 0 or 1, and A has the same meaning as defined above), the group Q⁴ is selected from 3 groups (i), (j) and (k) of the above-described 12 groups, the group T⁰ is a carbonyl group or thiocarbonyl group, and the group T¹ is a group —C(=O)—C(=O)—N(R')—, group —C(=S)—C(=O)—N(R')—, group —C(=O)—C(=S)—N(R')— or group —C(=S)—C(=S)—N(R')—.

Stereoisomers or optical isomers derived from an asymmetric carbon atom may be present in the compounds of the present invention represented by the general formula (1). However, these stereoisomers, optical isomers and mixtures thereof are all included in the present invention.

No particular limitation is imposed on salts of the compounds of the present invention represented by the general formula (1) so far as they are pharmaceutically acceptable salts. However, specific examples thereof include mineral acid salts such as hydrochlorides, hydrobromides, hydriodides, phosphates, nitrates and sulfates; benzoates; organic sulfonates such as methanesulfonates, 2-hydroxyethanesulfonates and p-toluenesulfonates; and organic carboxylates such as acetates, propanoates, oxalates, malonates, succinates, glutarates, adipates, tartrates, maleates, malates and mandelates. In the case where the compounds represented by the general formula (1) have an acidic group, they may be salts of alkali metal ions or alkaline earth metal ions. No particular limitation is imposed on the solvates thereof so far as they are pharmaceutically acceptable solvates. As specific examples thereof, however, may be mentioned hydrates and solvates with ethanol. When a nitrogen atom is present in the general formula (1), such a compound may be converted to an N-oxide thereof.

As the compounds according to the present invention, are preferred the compounds described in the following Examples and salts thereof as well as the following compounds and salts thereof.

1) 3-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)[1,6]naphthyridine-7-carboxamide;

2) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-fluorocinnoline-3-carboxamide;

3) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4a,8a-dihydro-4H-1,2,4-benzoxadiazine-3-carboxamide;

4) N-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-6-fluoro-4-oxo-1,4-dihydroquinoline-2-carboxamide;

5) 7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-5-oxo-4,5-dihydro-1H-1,3,4-benzotriazepine-2-carboxamide;

6) 6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-3,4-dihydro-2(1H)-cinnolinecarboxamide;

7) 6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-1,2,3,4-tetrahydroquinoline-2-carboxamide;

8) N-{(1R,2S,5S)-2-{[3-(3-chlorophenyl)-2-propinoyl]amino}-5-[(dimethylamino)carbonyl]cyclohexyl}-5-methyl-4,5,6,7-tetrahydrothiazolo[5,4-c]pyridin-2-carboxamide;

9) N-{(1R,2S,5S)-2-[(4-chlorobenzoyl)amino]-5-[(dimethylamino)carbonyl]cyclohexyl}-5-methyl-4,5,6,7-tetrahydrothiazolo[5,4-c]pyridin-2-carboxamide;

10) N-{(1R,2S,5S)-2-{[(5-chloroindol-2-yl)carbonyl]amino}-5-[(dimethylamino)carbonyl]cyclohexyl}-6-methyl-5,6,7,8-tetrahydro-4H-thiazolo[4,5-d]azepin-2-carboxamide;

11) 5-Chloro-N-[(1S,2R,4S)-4-[(dimethylamino)carbonyl]-2-({[5-(3-pyrrolidinyloxy)thiazol-2-yl]carbonyl}amino)cyclohexyl]indole-2-carboxamide;

12) $N^1$-(4-Chlorophenyl)-$N^2$-((1S,2R)-2-{[(5-methyl-4,5,6,7-tetrahydrothiazolo[5,4-c]pyridin-2-yl)carbonyl]amino}cyclohexyl)ethanediamide;

13) $N^1$-(5-Chloropyridin-2-yl)-$N^2$-((1S,2R)-2-{[(5-methyl-4,5,6,7-tetrahydrothiazolo[5,4-c]pyridin-2-yl)carbonyl]amino}cyclohexyl)ethanediamide;

14) $N^1$-(5-Chloropyridin-2-yl)-$N^2$-((1S,2R)-2-{[(5-methyl-5,6-dihydro-4H-pyrrolo[3,4-d]thiazol-2-yl)carbonyl]amino}cyclohexyl)ethanediamide;

15) $N^1$-(4-Chlorophenyl)-$N^2$-((1S,2R)-2-{[(5-methyl-5,6-dihydro-4H-pyrrolo[3,4-d]thiazol-2-yl)carbonyl]amino}cyclohexyl)ethanediamide;

16) $N^1$-(5-Chloropyridin-2-yl)-$N^2$-((1R,2R)-2-{[(5-methyl-5,6-dihydro-4H-pyrrolo[3,4-d]thiazol-2-yl)carbonyl]amino}cyclopentyl)ethanediamide;

17) $N^1$-(4-Chlorophenyl)-$N^2$-((1R,2R)-2-{[(5-methyl-5,6-dihydro-4H-pyrrolo[3,4-d]thiazol-2-yl)carbonyl]amino}cyclopentyl)ethanediamide;

18) $N^1$-(4-Chlorophenyl)-$N^2$-((1R,2R)-2-{[(5-methyl-4,5,6,7-tetrahydrothiazolo[5,4-c]pyridin-2-yl)carbonyl]amino}cycloheptyl)ethanediamide;

19) $N^1$-(5-Chloropyridin-2-yl)-$N^2$-((1R,2R)-2-{[(5-methyl-4,5,6,7-tetrahydrothiazolo[5,4-c]pyridin-2-yl)carbonyl]amino}cycloheptyl)ethanediamide;

20) $N^1$-(5-Chloropyridin-2-yl)-$N^2$-((1R,2R)-2-{[(5-methyl-5,6-dihydro-4H-pyrrolo[3,4-d]thiazol-2-yl)carbonyl]amino}cycloheptyl)ethanediamide;

21) $N^1$-(4-Chlorophenyl)-$N^2$-((1R,2R)-2-{[(5-methyl-5,6-dihydro-4H-pyrrolo[3,4-d]thiazol-2-yl)carbonyl]amino}cycloheptyl)ethanediamide;

22) $N^1$-(5-Chloro-6-methylpyridin-2-yl)-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

23) $N^1$-(5-Chloro-3-methylpyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

24) $N^1$-(5-Chloro-4-methylpyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

25) $N^1$-(4-Chloro-3-hydroxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

26) $N^1$-(4-Chloro-2-hydroxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

27) $N^1$-[4-Chloro-2-(fluoromethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

28) $N^1$-[4-Chloro-2-(methoxymethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

29) N-{(1R,2S,5S)-2-({[1-(4-Chloroanilino)cyclopropyl]carbonyl}amino)-5-[(dimethylamino)carbonyl]cyclohexyl}-5-methyl-4,5,6,7-tetrahydrothiazolo[5,4-c]pyridin-2-carboxamide;

30) $N^1$-(5-Chloropyridin-2-yl)-$N^2$-((1R,2R,4R)-4-(hydroxymethyl)-2-{[(5-methyl-4,5,6,7-tetrahydrothiazolo[5,4-c]pyridin-2-yl)carbonyl]amino}cyclopentyl)ethanediamide;

31) $N^1$-(5-Chloropyridin-2-yl)-$N^2$-((1R,2R,4S)-4-(hydroxymethyl)-2-{[(5-methyl-4,5,6,7-tetrahydrothiazolo[5,4-c]pyridin-2-yl)carbonyl]amino}cyclopentyl)ethanediamide;

32) $N^1$-((3R,4S)-1-Acetyl-3-{[(5-methyl-4,5,6,7-tetrahydrothiazolo[5,4-c]pyridin-2-yl)carbonyl]amino}piperidin-4-yl)-$N^2$-(5-chloropyridin-2-yl)ethanediamide;

33) $N^1$-(5-Chloropyridin-2-yl)-$N^2$-((3R,4S)-1-(methylsulfonyl)-3-{[(5-methyl-4,5,6,7-tetrahydrothiazolo[5,4-c]pyridin-2-yl)carbonyl]amino}piperidin-4-yl)ethanediamide;

34) $N^1$-{(1S,2R,4S)-2-{[(3-Chlorobenzothiophen-2-yl)carbonyl]amino}-4-[(dimethylamino)carbonyl]cyclohexyl}-$N^2$-(5-chloropyridin-2-yl)ethanediamide;

35) $N^1$-(5-Chloropyridin-2-yl)-$N^2$-((1S,2R,4S)-4-[(dimethylamino)carbothioyl]-2-{[(5-methyl-4,5,6,7-tetrahydrothiazolo[5,4-c]pyridin-2-yl)carbonyl]amino}cyclohexyl)ethanediamide;

36) $N^1$-(5-Chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbothioyl]amino}cyclohexyl)ethanediamide;

37) $N^1$-(5-Chloropyridin-2-yl)-$N^2$-((3R,4S)-1-(2-methoxyethanethioyl)-3-{[(5-methyl-4,5,6,7-tetrahydrothiazolo[5,4-c]pyridin-2-yl)carbonyl]amino}piperidin-4-yl)ethanediamide;

38) $N^1$-(5-Chloropyridin-2-yl)-$N^2$-((3R,4S)-1-(2-methoxyacetyl)-3-{[(5-methyl-4,5,6,7-tetrahydrothiazolo[5,4-c]pyridin-2-yl)carbothioyl]amino}piperidin-4-yl)ethanediamide;

39) N-[(3R,4S)-4-({2-[(5-Chloropyridin-2-yl)amino]-2-oxoethanethioyl}amino)-1-(2-methoxyacetyl)piperidin-3-yl]-5-methyl-4,5,6,7-tetrahydrothiazolo[5,4-c]pyridine-2-carboxamide;

40) N-[(3R,4S)-4-({2-[(5-Chloropyridin-2-yl)amino]-2-thioxoacetyl}amino)-1-(2-methoxyacetyl)piperidin-3-yl]-5-methyl-4,5,6,7-tetrahydrothiazolo[5,4-c]pyridine-2-carboxamide;

41) $N^1$-(4-Chlorophenyl)-$N^2$-((3R,4S)-1-(2-methoxyethanethioyl)-3-{[(5-methyl-4,5,6,7-tetrahydrothiazolo[5,4-c]pyridin-2-yl)carbonyl]amino}piperidin-4-yl)ethanediamide;

42) $N^1$-(4-Chlorophenyl)-$N^2$-((3R,4S)-1-(2-methoxyacetyl)-3-{[(5-methyl-4,5,6,7-tetrahydrothiazolo[5,4-c]pyridin-2-yl)carbothioyl]amino}piperidin-4-yl)ethanediamide;

43) N-[(3R,4S)-4-{[2-[(4-Chloroanilino)-2-oxoethanethioyl]amino}-1-(2-methoxyacetyl)piperidin-3-yl]-5-methyl-4,5,6,7-tetrahydrothiazolo[5,4-c]pyridine-2-carboxamide;

44) N-[(3R,4S)-4-({2-[(4-Chlorophenyl)amino]-2-thioxoacetyl}amino)-1-(2-methoxyacetyl)piperidin-3-yl]-5-methyl-4,5,6,7-tetrahydrothiazolo[5,4-c]pyridine-2-carboxamide;

45) $N^1$-((1S,2R,4S)-4-(1-azetidinylcarbonyl)-2-{[(5-methyl-4,5,6,7-tetrahydrothiazolo[5,4-c]pyridin-2-yl)carbonyl]amino}cyclohexyl)-$N^2$-(5-chloropyridin-2-yl)ethanediamide;

46) $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1-pyrrolidinylcarbonyl)cyclohexyl]ethanediamide; 47-Y $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1-piperidinylcarbonyl)cyclohexyl]ethanediamide;

48) $N^1$-(5-Chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(4-morpholinylcarbonyl)cyclohexyl]ethanediamide;

49) $N^1$-(5-Chloropyridin-2-yl)-$N^2$-((1S,2R,4S)-4-[(methylamino)carbonyl]-2-{[(5-methyl-4,5,6,7-tetrahydrothiazolo[5,4-c]pyridin-2-yl)carbonyl]amino}cyclohexyl)ethanediamide;

50) $N^1$-{(1R,2S,5S)-2-({2-[(6-Chloropyridazin-3-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide;

51) $N^1$-(4-Bromophenyl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide;

52) $N^1$-(5-Chloropyridin-2-yl)-$N^2$-((3R,4S)-1-(2-methoxyacetyl)-3-{[4-(pyridin-4-yl)benzoyl]amino}piperidin-4-yl)ethanediamide;

53) $N^1$-(5-Chloropyridin-2-yl)-$N^2$-[(3R,4S)-1-(2-methoxyacetyl)-3-({[2-(pyridin-4-yl)pyrimidin-5-yl]carbonyl}amino)piperidin-4-yl]ethanediamide;

54) $N^1$-(5-Chloropyridin-2-yl)-$N^2$-[(1S,2R,4S)-4-[(dimethylamino)carbonyl]-2-({[2-(pyridin-4-yl)pyrimidin-5-yl]carbonyl}amino)cyclohexyl]ethanediamide;

55) N-{(1R,2S,5S)-2-{[2-(4-Chloroanilino)-2-oxoethane(methoxy)imidoyl]amino}-5-[(dimethylamino)carbonyl]cyclohexyl}-5-methyl-4,5,6,7-tetrahydrothiazolo[5,4-c]pyridine-2-carboxamide;

56) N-{(1R,2S,5S)-2-{[2-(4-Chloroanilino)-2-(methoxyimino)acetyl]amino}-5-[(dimethylamino)carbonyl]cyclohexyl}-5-methyl-4,5,6,7-tetrahydrothiazolo[5,4-c]pyridine-2-carboxamide;

57) $N^1$-(5-Chloropyridin-2-yl)-$N^2$-((1S,2R,4S)-4-[(dimethylamino)carbonyl]-2-{[(4,4,5-trimethyl-5,6-dihydro-4H-pyrrolo[3,4-d]thiazol-2-yl)carbonyl]amino}cyclohexyl)ethanediamide;

58) $N^1$-(5-Chloropyridin-2-yl)-N-((1S,2R,4S)-4-[(dimethylamino)carbonyl]-2-{[(4,4-ethylene-5-methyl-5,6-dihydro-4H-pyrrolo[3,4-d]thiazol-2-yl)carbonyl]amino}cyclohexyl)ethanediamide;

59) N-{(1R,2S,5S)-2-({[(E)-2-(4-Chlorophenyl)ethenyl]sulfonyl}amino)-5-[(dimethylamino)carbonyl]cyclohexyl}-5-methyl-4,5,6,7-tetrahydrothiazolo[5,4-c]pyridine-2-carboxamide;

60) N-{(1R,2S,5S)-2-{[(4-Chlorobenzyl)sulfonyl]amino}-5-[(dimethylamino)carbonyl]cyclohexyl}-5-methyl-4,5,6,7-tetrahydrothiazolo[5,4-c]pyridine-2-carboxamide;

61) N-{(1R,2S,5S)-2-[(2-{[(4-Chlorophenyl)sulfonyl]amino}acetyl)amino]-5-[(dimethylamino)carbonyl]cyclohexyl}-5-methyl-4,5,6,7-tetrahydrothiazolo[5,4-c]pyridine-2-carboxamide;

62) N-{(1R,2S,5S)-2-({2-[(5-Chloropymiridin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide;

63) N-{(1R,2S,5S)-2-({2-[(5-Chloropyrazin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide;

64) N-[(1R,2S,5S)-5-[(Dimethylamino)carbonyl]-2-({2-[(5-fluoro-2-thienyl)amino]-2-oxoethanethioyl}amino)cyclohexyl]-5-methyl-4,5,6,7-tetrahydrothiazolo[5,4-c]pyridine-2-carboxamide;

65) N-{(1R,2S,5S)-2-{[2-(3-Amino-4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide;

66) $N^1$-(4-Chlorothiazol-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

67) $N^1$-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-$N^2$-(3-fluorophenyl)ethanediamide;

68) $N^1$-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-$N^2$-phenylethanediamide;

69) $N^1$-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-$N^2$-(pyridin-2-yl)ethanediamide;

70) $N^1$-(5-Chloropyridin-2-yl)-$N^2$-((1S,2R,4S)-4-[(dimethylamino)carbonyl]-2-{[(5,6,6-trimethyl-5,6-dihydro-4H-pyrrolo[3,4-d]thiazol-2-yl)carbonyl]amino}cyclohexyl)ethanediamide;

71) $N^1$-(5-Chloropyridin-2-yl)-$N^2$-((1S,2R,4S)-4-[(dimethylamino)carbonyl]-2-{[(4,4,5,6,6-pentamethyl-5,6-dihydro-4H-pyrrolo[3,4-d]thiazol-2-yl)carbonyl]amino}cyclohexyl)ethanediamide;

72) $N^1$-(5-Chloropyridin-2-yl)-$N^2$-((1S,2R,4S)-4-[(dimethylamino)carbonyl]-2-{[(2-methyl-2,3-dihydrothiazolo[5,4-d]isooxazol-5-yl)carbonyl]amino}cyclohexyl)ethanediamide;

73) $N^1$-(5-Chloropyridin-2-yl)-$N^2$-((1S,2R,4S)-4-[(dimethylamino)carbonyl]-2-{[(2-methyl-2,3-dihydrothiazolo[4,5-d]isooxazol-5-yl)carbonyl]amino}cyclohexyl)ethanediamide;

74) $N^1$-(5-Chloro-2-furyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

75) $N^1$-(5-Chloroxazol-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

76) N$^1$-(5-Chloro-1H-imidazol-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

77) N-{(1R,2S,5S)-2-{[2-(4-Chloroanilino)-1-ethoxyimino-2-oxoethyl]amino}-5-[(dimethylamino)carbonyl]cyclohexyl}-5-methyl-4,5,6,7-tetrahydrothiazolo[5,4-c]pyridine-2-carboxamide;

78) N-{(1R,2S,5S)-2-{[2-(4-Chloroanilino)-1-phenoxyimino-2-oxoethyl]amino}-5-[(dimethylamino)carbonyl]cyclohexyl}-5-methyl-4,5,6,7-tetrahydrothiazolo[5,4-c]pyridine-2-carboxamide;

79) N-{(1R,2S,5S)-2-{[1-Benzyloxyimino-2-(4-chloroanilino)-2-oxoethyl]amino}-5-[(dimethylamino)carbonyl]cyclohexyl}-5-methyl-4,5,6,7-tetrahydrothiazolo[5,4-c]pyridine-2-carboxamide;

80) N-{(1R,2S,5S)-2-({2-(4-Chloroanilino)-1-hydrazono-2-oxoethyl}amino)-5-[(dimethylamino)carbonyl]cyclohexyl}-5-methyl-4,5,6,7-tetrahydrothiazolo[5,4-c]pyridine-2-carboxamide;

81) N-{(1R,2S,5S)-2-({2-(4-Chloroanilino)-1-(2-methylhydrazono)-2-oxoethyl}amino)-5-[(dimethylamino)carbonyl]cyclohexyl}-5-methyl-4,5,6,7-tetrahydrothiazolo[5,4-c]pyridine-2-carboxamide;

82) N-{(1R,2S,5S)-2-({2-[(5-Chloropyridin-2-yl)amino]-1-(2,2-dimethylhydrazono)-2-oxoethyl}amino)-5-[(dimethylamino)carbonyl]cyclohexyl}-5-methyl-4,5,6,7-tetrahydrothiazolo[5,4-c]pyridine-2-carboxamide;

83) N-{(1R,2S,5S)-2-{[2-(4-Chloroanilino)-1-methylimino-2-oxoethyl]amino}-5-[(dimethylamino)carbonyl]cyclohexyl}-5-methyl-4,5,6,7-tetrahydrothiazolo[5,4-c]pyridine-2-carboxamide;

84) N-{(1R,2S,5S)-2-{[1-(2-Acetylhydrazono)-2-(4-chloroanilino)-2-oxoethyl]amino}-5-[(dimethylamino)carbonyl]cyclohexyl}-5-methyl-4,5,6,7-tetrahydrothiazolo[5,4-c]pyridine-2-carboxamide;

85) N-{(1R,2S,5S)-2-({2-(4-Chloroanilino)-1-[(2-ethanethioyl)hydrazono]-2-oxoethyl}amino)-5-[(dimethylamino)carbonyl]cyclohexyl)-5-methyl-4,5,6,7-tetrahydrothiazolo[5,4-c]pyridine-2-carboxamide; and 86) N-{(1R,2S,5S)-2-{[(E)-3-(5-Chloropyridin-2-yl)-2-propenoyl]amino}-5-[(dimethylamino)carbonyl]cyclohexyl}-5-methyl-4,5,6,7-tetrahydrothiazolo[5,4-c]pyridine-2-carboxamide.

The preparation process of the diamine derivatives (1) according to the present invention will hereinafter be described.

[Preparation Process 1]

A compound represented by the general formula (1), a salt thereof, a solvate thereof, or an N-oxide thereof can be prepared in accordance with, for example, the following process:

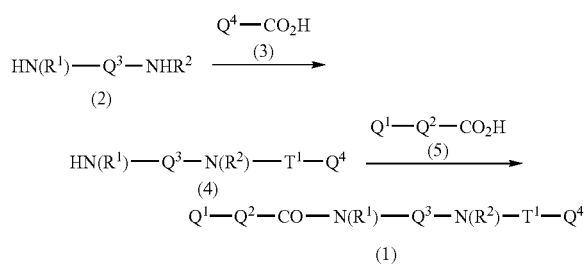

wherein $Q^1$, $Q^2$, $Q^3$, $Q^4$, $R^1$ and $R^2$ have the same meanings as defined above, and $T^1$ represents a carbonyl group.

A mixed acid anhydride, acid halide, activated ester or the like, which is derived from carboxylic acid (3), may react with diamine (2), giving compound (4). The resultant compound (4) may react with carboxylic acid (5) under the same conditions, giving compound (1) according to the present invention. In the above reaction steps, reagents and conditions, which are generally used in peptide synthesis, may be applied. The mixed acid anhydride can be prepared by, for example, reaction of a chloroformate such as ethyl chloroformate or isobutyl chloroformate with carboxylic acid (3) in the presence of a base. The acid halide can be prepared by treating carboxylic acid (3) with an acid halide such as thionyl chloride or oxalyl chloride. The activated ester includes various kinds of esters. Such an ester can be prepared by, for example, reaction of a phenol such as p-nitrophenol, N-hydroxybenzotriazole, or N-hydroxysuccinimide with carboxylic acid (3) using a condensing agent such as N,N'-dicyclohexylcarbodiimide or 1-ethyl-3-(3-dimethylaminopropyl)carbodiimide hydrochloride. The activated ester can also be prepared by reaction of carboxylic acid (3) with pentafluorophenyl trifluoroacetate or the like, reaction of carboxylic acid (3) with 1-benzotriazolyloxytripyrrolidinophosphonium hexafluorophosphite, reaction of carboxylic acid (3) with diethyl cyanophosphonate (Shioiri method), reaction of carboxylic acid (3) with triphenylphosphine and 2,2'-dipyridyl disulfide (Mukaiyama method) or the like. The thus-obtained mixed acid anhydride, acid halide or activated ester of carboxylic acid (3) may react with diamine (2) at −78° C. to 150° C. in the presence of a proper base in an inert solvent, giving compound (4). Thus-obtained compound (4) may react with a mixed acid anhydride, acid halide or activated ester of carboxylic acid (5) under the same conditions, giving compound (1) according to the present invention. The reagents and reaction conditions in the reaction of compound (4) with carboxylic acid (5) are the same as those in the reaction of diamine (2) with carboxylic acid (3).

As specific examples of the base used in each of the above mentioned steps, may be carbonates of alkali metals or alkaline earth metals, such as sodium carbonate and potassium carbonate, alkali metal alkoxides such as sodium ethoxide and potassium butoxide, alkali metal hydroxides such as sodium hydroxide and potassium hydroxide, and hydrides of alkali metals or alkaline earth metals, such as sodium hydride and potassium hydride; organic metal bases exemplified by alkyllithium such as n-butyllithium, and dialkylaminolithium such as lithium diisopropylamide; organic metal bases exemplified by bis(silyl)amine, such as lithium bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent used in this reaction include alkyl halide type solvents such as dichloromethane, chloroform and carbon tetrachloride, etheric solvents such as tetrahydrofuran, 1,2-dimethoxyethane and dioxane, aromatic solvents such as benzene and toluene, and amide solvents such as N,N-dimethylformamide, N,N-dimethylacetamide and N-methylpyrrolidin-2-one. In addition to these solvent, a sulfoxide solvent such as dimethyl sulfoxide or sulfolane, a ketone solvent such as acetone or methyl ethyl ketone, or the like may be used in some cases.

[Preparation Process 2]

Compound (1) according to the present invention can also be prepared in accordance with the following process:

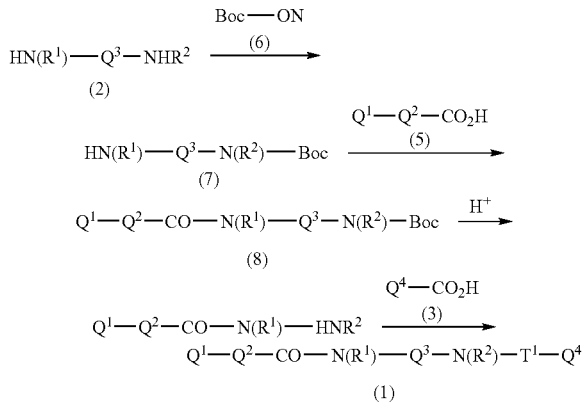

wherein $Q^1$, $Q^2$, $Q^3$, $Q^4$, $R^1$ and $R^2$ have the same meanings as defined above, $T^1$ represents a carbonyl group, Boc represents a tert-butoxycarbonyl group, and Boc-ON represents 2-(tert-butoxycarbonyloxyimino)-2-phenylacetonitrile.

As described above, diamine (2) is treated with Boc-ON (6) to prepare compound (7) in which one of 2 amino groups has been protected with tert-butoxycarbonyl group. The resultant compound (7) reacts with carboxylic acid (5) and affords compound (8). Compound (8) is successively treated with an acid to give compound (9). Compound (9) then reacts with the carboxylic acid (3), giving compound (1) according to the present invention. Compound (7) can be prepared by a reaction at −10° C. to 40° C. in the presence of triethylamine in a solvent such as dichloromethane. Reaction of compound (7) with the mixed acid anhydride, acid halide or activated ester of the carboxylic acid (5) is carried out using the same reagents and reaction conditions as those described in Preparation Process 1, whereby compound (8) can be prepared. The resultant compound (8) is treated with trifluoroacetic acid or the like at −20° C. to 70° C., whereby amine (9) can be prepared. In the reaction of the resultant amine (9) with carboxylic acid (3), the same reagents and conditions as those described in Preparation Process 1 may be used.

By the way, the tert-butoxycarbonyl group of compound (7) may be replaced by other amino-protecting groups. In this case, reagent (6) is also changed to other reagents, and reaction conditions and the like according to the reagents must be used. As examples of other protecting groups for amino groups, may be mentioned alkanoyl groups such as an acetyl group, alkoxycarbonyl groups such as methoxycarbonyl and ethoxycarbonyl groups, arylmethoxycarbonyl groups such as benzyloxycarbonyl, p-methoxybenzyloxycarbonyl and p- or o-nitrobenzyloxycarbonyl groups, arylmethyl groups such as benzyl and triphenylmethyl groups, aroyl groups such as a benzoyl group, and arylsulfonyl groups such as 2,4-dinitrobenzenesulfonyl and o-nitrobenzenesulfonyl groups. These protecting groups may be chosen for use according to the nature and the like of the compound of which amino group is to be protected. Upon leaving such a protecting group, reagents and conditions may be employed according to the protecting group.

[Preparation Process 3]

Compound (1) according to the present invention can be prepared by reacting diamine (2) with sulfonyl halide (10) and then condensing the reaction product with carboxylic acid (5).

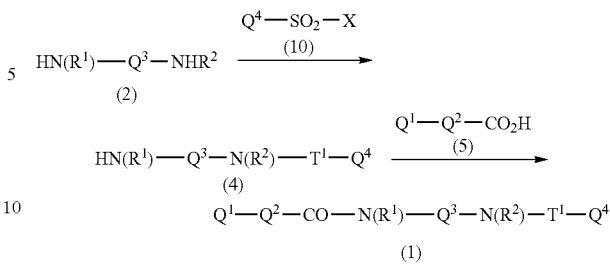

wherein $Q^1$, $Q^2$, $Q^3$, $Q^4$, $R^1$ and $R^2$ have the same meanings as defined above, $T^1$ represents a sulfonyl group, and X represents a halogen atom.

Diamine (2) reacts with sulfonyl halide (10) at −10° C. to 30° C. in the presence of a base such as triethylamine in an inert solvent, giving compound (4). The inert solvent and base may be suitably chosen for use from those described in Preparation Process 1. The resultant compound (4) is condensed with carboxylic acid (5) using the reagents and conditions described in Preparation Process 1, whereby compound (1) according to the present invention can be prepared. Sulfonyl halide (10) may be synthesized in the presence of a proper base in accordance with the publicly known process (WO96/10022, WO00/09480) or a process according to it.

[Preparation Process 4]

Compound (1) according to the present invention can also be prepared in accordance with the following process:

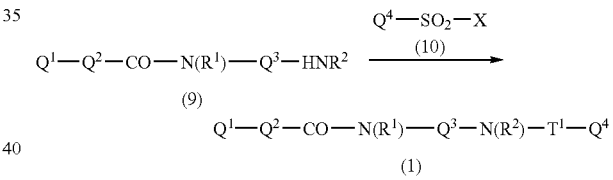

wherein $Q^1$, $Q^2$, $Q^3$, $Q^4$, $R^1$, $R^2$ and X have the same meanings as defined above, and $T^1$ represents a sulfonyl group.

More specifically, amine (9) may react with sulfonyl halide (10) at −10° C. to 30° C. in the presence of a base in an inert solvent, giving compound (1). The inert solvent and base may be suitably chosen for use from those described in Preparation Process 1.

[Preparation Process 5]

In the compounds (1) according to the present invention, geometrical isomers of trans-form and cis-form in the relation between position 1 and position 2 are present when $Q^3$ is the following group:

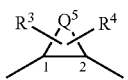

wherein $R^3$, $R^4$ and $Q^5$ have the same meanings as defined above, and numerals 1 and 2 indicate positions. The preparation processes of such compounds (1) having the trans-form and the cis-form will hereinafter be described.

<Preparation Process of Trans-Form>

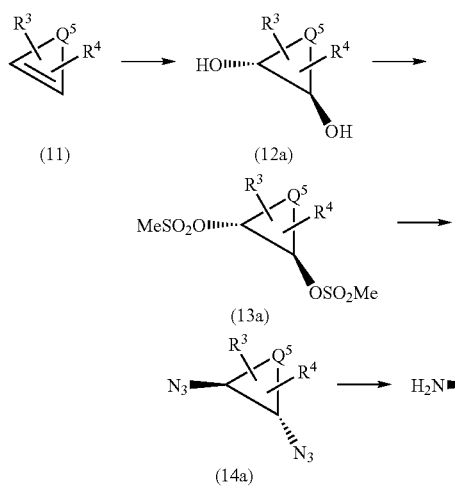

wherein $Q^5$, $R^3$ and $R^4$ have the same meanings as defined above.

As an example of preparation of trans-diol (12a) from cyclic alkene (11), conversion from, for example, cyclohexene to trans-cyclohexanediol (Organic Synthesis, 1955, Vol. III, p. 217) is known. As an example of preparation of trans-diamine (2a) from trans-diol (12a), conversion from trans-cyclopentanediol to trans-cyclopentanediamine (WO98/30574) is reported. Trans-diamine (2a) can be prepared from the cyclic alkene (11) according to these reports.

Trans-diamine (2a) prepared in accordance with the above-described process can be converted into trans-compound (1) by any of the above-described Preparation Processes 1 to 4.

<Preparation Process of Cis-Form>

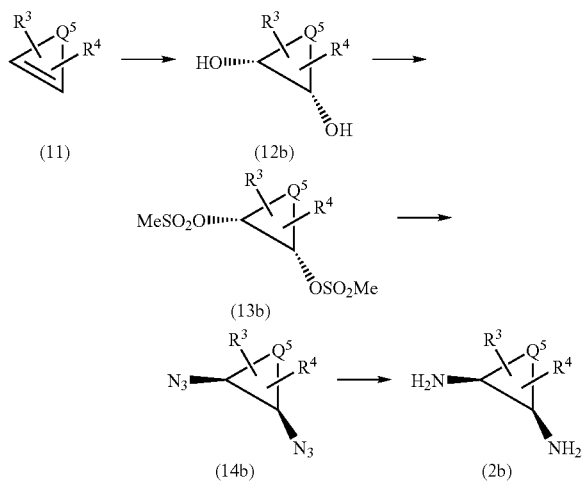

wherein $Q^5$, $R^3$ and $R^4$ have the same meanings as defined above.

As an example of preparation of cis-diol (12b) from cyclic alkene (11), conversion from cyclohexene to cis-cyclohexanediol (J. Org. Chem., 1998, Vol. 63, p. 6094) and the like is known. As an example of preparation of cis-diamine (2b) from cis-diol (12b), conversion from cis-cyclopentanediol to cis-cyclopentanediamine (WO98/30574) and the like is reported. Cis-diamine (2b) can be prepared from cyclic alkene (11) according to these reports.

Cis-diamine (2b) prepared in accordance with the above-described process can be converted into the cis-compound (1) by any of the above-described Preparation Processes 1 to 4.

[Preparation Process 6]

As described above, either cis-form or trans-form generated in $Q^3$ may be present in the compounds (1) according to the present invention, and so geometrical isomers are present. Further, optical isomers may be present in the respective geometrical isomers. The preparation process of an optically active substance will hereinafter be described.

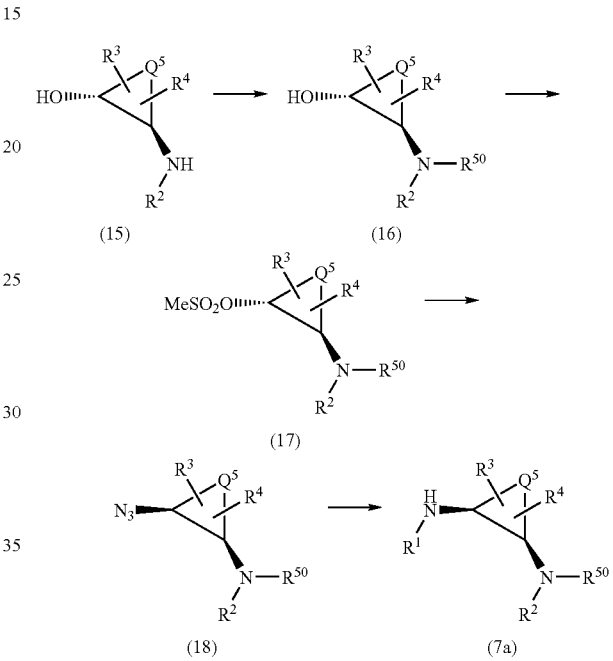

wherein $Q^5$, $R^1$, $R^2$, $R^3$ and $R^4$ have the same meanings as defined above, and $R^{50}$ represents a protecting group for amino group.

With respect to the preparation process of optically active aminoalcohol derivative (15) of 1,2-trans-form, for example, the preparation process of optically active 1,2-trans-2-aminocyclopentanol from cyclopentene oxide or the preparation process of optically active 1,2-trans-2-aminocyclohexanol from cyclohexene oxide is known (Tetrahedron: Asymmetry, 1996, Vol. 7, p. 843; J. Org. Chem., 1985, Vol. 50, p. 4154; J. Med. Chem., 1998, Vol. 41, p. 38). When the amino group of optically active aminoalcohol derivative (15) prepared by such an already known process or by applying such a process reacts with a proper protecting reagent, compound (16) can be produced. As a protecting group corresponding to $R^{50}$ in compound (16), is preferred, among the ordinary acyl type protecting groups, an alkoxycarbonyl group such as methoxycarbonyl, ethoxycarbonyl, tert-butoxycarbonyl group and the like, an arylmethoxycarbonyl group such as benzyloxycarbonyl, p-methoxybenzyloxycarbonyl, p- or o-nitrobenzyloxycarbonyl group and the like, or an arylsulfonyl group such as 2,4-dinitrobenzenesulfonyl, o-nitrobenzenesulfonyl group and the like. When the amino group is protected with, for example, a tert-butoxycarbonyl group, aminoalcohol derivative (15) may react with di-tert-butyl dicarbonate at −78° C. to 50° C. in an inert solvent, giving compound (16).

The inert solvent may be suitably chosen for use from those described in Preparation Process 1.

Compound (16) may react with methanesulfonyl chloride at −78° C. to 50° C. in the presence of a base in an inert solvent, giving compound (17). The inert solvent may be suitably chosen for use from those described in Preparation Process 1. As the base, is preferred an organic base such as pyridine, 2,6-lutidine, collidine, 4-dimethylaminopyridine, triethylamine, N-methylmorpholine, diisopropylethylamine and diazabicyclo[5.4.0]undec-7-ene (DBU) and the like.

Compound (17) may react with sodium azide at −10° C. to 150° C. in a proper solvent, giving compound (18). As the solvent, an amide solvent such as N,N-dimethylformamide, N,N-dimethylacetamide or N-methylpyrrolidin-2-one, an alcoholic solvent such as methanol or ethanol, an etheric solvent such as tetrahydrofuran, 1,2-dimethoxyethane or dioxane, benzenoid solvent such as toluene, a carbon halogenide such as dichloromethane, chloroform or carbon tetrachloride, acetone, dimethyl sulfoxide, or a mixed solvent of such a solvent with water is suitable.

As a process for converting azide derivative (18) into compound (7a), there are many processes such as a process of conducting hydrogenation with a palladium catalyst, Raney nickel catalyst or platinum catalyst, a reaction using a reducing agent such as lithium aluminum hydride, sodium borohydride or zinc borohydride, a reaction using zinc in the presence of nickel chloride or cobalt chloride, a reaction using triphenylphosphine and the like. Suitable reaction conditions may be selected according to the nature of the compound. For example, azide derivative (18) is hydrogenated at a temperature of −10° C. to 70° C. using 1 to 20% palladium carbon as a catalyst in a proper solvent, whereby compound (7a) can be prepared. The hydrogen pressure may be raised higher than atmospheric pressure. As the solvent, an alcoholic solvent such as methanol or ethanol, an etheric solvent such as tetrahydrofuran, 1,2-dimethoxyethane or dioxane, an amide solvent such as N,N-dimethylformamide, N,N-dimethylacetamide or N-methylpyrrolidin-2-one, an ester solvent such as ethyl acetate, acetic acid, hydrochloric acid, water, a mixed solvent thereof and the like is suitable.

Optically active amine (7a) prepared in accordance with the above-described process can be converted to optically active compound (1) in accordance with the above-described Preparation Process 2. Antipode (1) of optically active substance (1) obtained from optically active amine (7a) may also be prepared in accordance with a similar process.

Optically active compound (1) may be prepared by separating racemic compound (1) through a column composed of an optically active carrier. It is also possible to separate intermediate (2), (4), (7), (8) or (9) for preparing racemic compound (1) through a column composed of an optically active carrier to isolate optically active intermediate (2), (4), (7), (8) or (9), and then prepare optically active compound (1) in accordance with any of Preparation Processes 1 to 4. As a process for isolating optically active compound (1), optically active intermediate (2), (4), (7) or (9), a process of fractionally crystallizing a salt with an optically active carboxylic acid, or a process of fractionally crystallizing a salt with an optically active base on the contrary may be used.

[Preparation Process 7]

Among the compounds (1) according to the present invention, a preparation process of compound (1c) containing heteroatom(s) in the group $Q^3$ will hereinafter be described in detail.

A compound represented by the general formula (1c), a salt thereof, a solvate thereof, or an N-oxide thereof can be prepared in accordance with, for example, the following process:

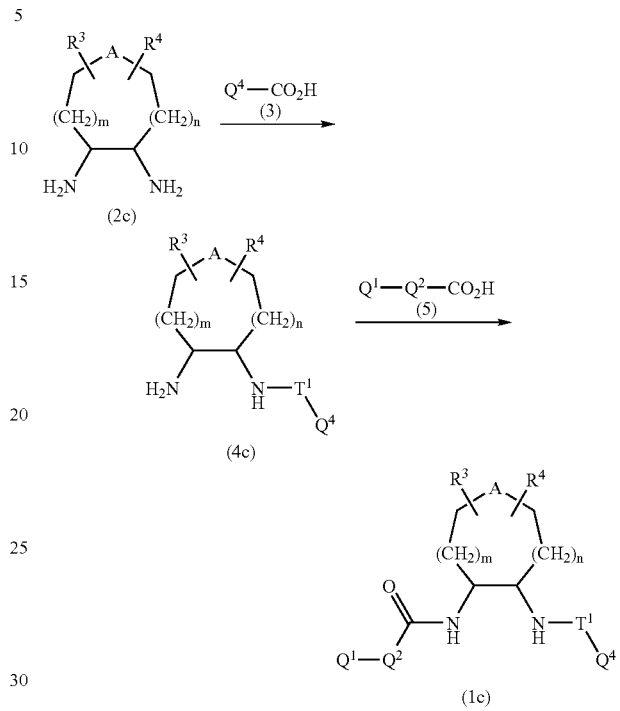

wherein $Q^1$, $Q^2$, $Q^4$, $R^3$, $R^4$, A, m and n have the same meanings as defined above, and $T^1$ represents a carbonyl group.

A mixed acid anhydride, acid halide, activated ester or the like, which is derived from carboxylic acid (3), may react with compound (2c), giving compound (4c). The resultant compound (4c) may react with carboxylic acid (5) under the same conditions, giving compound (1c) according to the present invention.

In the above reaction steps, reagents and conditions, which are generally used in peptide synthesis, may be applied. The mixed acid anhydride can be prepared by, for example, reaction of a chloroformate such as ethyl chloroformate or isobutyl chloroformate with carboxylic acid (3) in the presence of a base. The acid halide can be prepared by treating carboxylic acid (3) with an acid halide such as thionyl chloride or oxalyl chloride. The activated ester includes various kinds of esters. Such an ester can be prepared by, for example, reaction of a phenol such as p-nitrophenol, N-hydroxybenzotriazole, or N-hydroxysuccinimide with carboxylic acid (3) using a condensing agent such as N,N'-dicyclohexylcarbodiimide (DCC) or 1-ethyl-3-(3-dimethylaminopropyl)carbodiimide hydrochloride. The activated ester can also be prepared by reaction of carboxylic acid (3) with pentafluorophenyl trifluoroacetate or the like, reaction of carboxylic acid (3) with 1-benzotriazolyloxytripyrrolidinophosphonium hexafluorophosphite, reaction of carboxylic acid (3) with diethyl cyanophosphonate (Shioiri method), reaction of carboxylic acid (3) with triphenylphosphine and 2,2'-dipyridyl disulfide (Mukaiyama method) or the like. The thus-obtained mixed acid anhydride, acid halide or activated ester of carboxylic acid (3) may react with diamine (2c) at a temperature under cooling to a temperature under heating in the presence of a proper base in an inert solvent, giving compound (4c). Thus-obtained compound (4c) may react with a mixed acid anhydride, acid halide or activated ester of carboxylic acid (5) under the same conditions, giving compound (1c) according to the present invention. The reagents and reaction conditions in the reaction of compound (4c) with carboxylic acid (5) are the same as those in the reaction of diamine (2c) with carboxylic acid (3).

As specific examples of the base used in each step, may be mentioned carbonates of alkali metals or alkaline earth metals, such as sodium carbonate and potassium carbonate, alkali metal alkoxides such as sodium ethoxide and potassium butoxide, alkali metal hydroxides such as sodium hydroxide and potassium hydroxide, and hydrides of alkali metals, such as sodium hydride and potassium hydride; organic metal bases exemplified by alkyllithium such as n-butyllithium, and dialkylaminolithium such as lithium diisopropylamide; organic metal bases exemplified by bis(silyl)amine, such as lithium-bis(trimethylsilyl)amide; and organic bases such as pyridine, 2,6-lutidine, 4-dimethylaminopyridine, triethylamine, N-methylmorpholine, diisopropylethylamine and diazabicyclo[5.4.0]undec-7-ene (DBU).

Examples of the inert solvent used in this reaction include alkyl halide type solvents such as dichloromethane and chloroform, etheric solvents such as tetrahydrofuran and 1,4-dioxane, aromatic solvents such as benzene and toluene, and amide solvents such as N,N-dimethylformamide. In addition to these solvent, a sulfoxide solvent such as dimethyl sulfoxide, a ketone solvent such as acetone, or the like may be used in some cases.

In the above-described preparation steps, processes such as attaching and leaving of a protecting group, and conversion of a functional group can be suitably applied, thereby preparing compound (1c) of the present invention.

As the protecting group for amino group, it is only necessary to use a protecting group, which is generally used as a protecting group for amino group in syntheses of organic compounds, particularly, peptide synthesis. As examples thereof, may be mentioned alkoxycarbonyl groups such as tert-butoxycarbonyl, methoxycarbonyl and ethoxycarbonyl groups, arylmethoxycarbonyl groups such as benzyloxycarbonyl, p-methoxybenzyloxycarbonyl and p- or o-nitrobenzyloxycarbonyl groups, arylmethyl groups such as benzyl, 4-methoxybenzyl and triphenylmethyl groups, alkanoyl groups such as formyl and acetyl groups, aroyl groups such as a benzoyl group, and arylsulfonyl groups such as 2,4-dinitrobenzenesulfonyl and o-nitrobenzenesulfonyl groups.

As the protecting group for hydroxyl group, it is only necessary to use a protecting group for hydroxyl group, which is generally used in syntheses of organic compounds. As examples thereof, may be mentioned alkoxymethyl groups such as a methoxymethyl group, arylmethyl groups such as benzyl, 4-methoxybenzyl and triphenylmethyl groups, alkanoyl groups such as an acetyl group, aroyl groups such as a benzoyl group, and a tert-butyldiphenylsilyloxy group. A carboxyl group can be protected as an ester with an alkyl group such as a methyl, ethyl or tert-butyl group or an arylmethyl group such as a benzyl group. The attaching and leaving of the protecting group may be conducted in accordance with a method known per se in the art.

Compound (1c) according to the present invention can be converted into various derivatives by converting its functional group. For example, a compound in which A is a nitrogen atom having no substituent can be converted into an amide compound by acylation using a mixed acid anhydride, acid halide, activated ester or the like in accordance with ordinary organic chemical methods, a sulfonamide compound by reaction with a sulfonyl halide, an N-alkyl compound by reaction with an alkyl halide, an N-aryl compound by reaction with an aryl halide or a carbamate compound by reaction with an isocyanate. Incidentally, the compound in which A is a nitrogen atom having no substituent can be prepared by, for example, treating compound (1c) prepared from diamine (2c), in which A has been protected with tert-butoxycarbonyl group, in accordance with Preparation Process 7 with an acid.

The compounds according to the present invention thus prepared can be isolated and purified by publicly known methods, for example, extraction, precipitation, fractional chromatography, fractional crystallization, recrystallization, etc. The compounds according to the present invention can be converted into desired salts in accordance with ordinary salt-forming reactions.

Optical isomers derived from an asymmetric carbon atom are present in the compounds of the present invention. Such an optically active isomer can be prepared by the process of preparing from optically active diamine (2c), and besides, a process of forming an optically active amine or acid and a salt from racemic compound (1c) and fractionally crystallizing it, a process of separating it by column chromatography using an optically active carrier.

Compound (1c), in which $T^1$ is a sulfonyl group, can be prepared by changing carboxylic acid (3) to sulfonyl halide (10) in the reaction of compound (2c) with carboxylic acid (3).

[Preparation Process 8]

Compound (1c) according to the present invention can also be prepared in accordance with the following process:

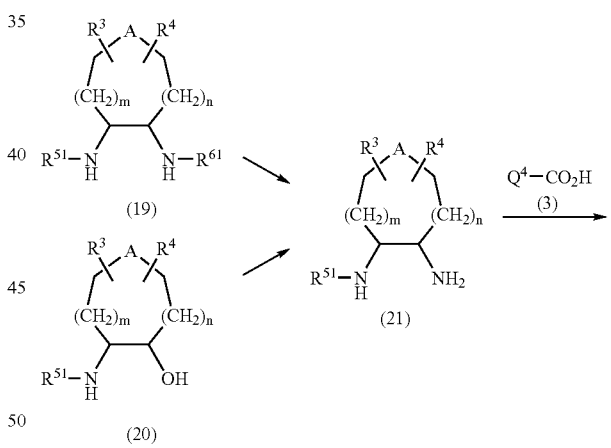

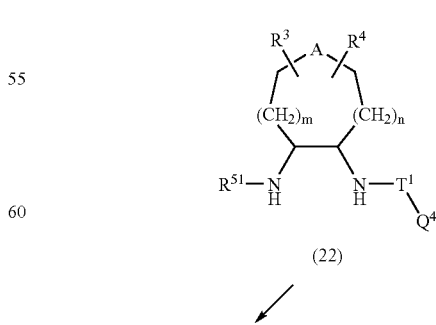

-continued

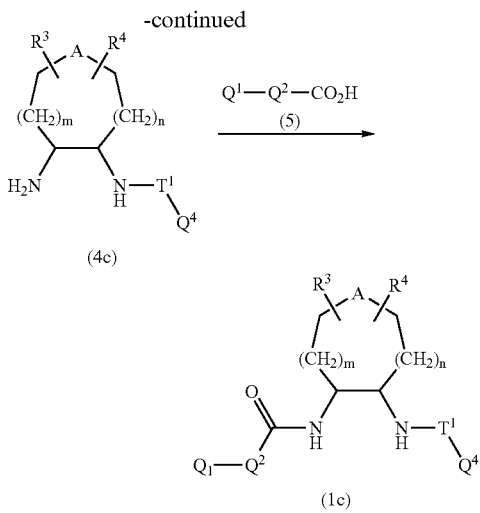

wherein $Q^1$, $Q^2$, $Q^4$, $R^3$, $R^4$, A, m and n have the same meanings as defined above, $T^1$ represents a carbonyl group, and $R^{51}$ and $R^{61}$ represent protecting groups for amino group.

Compound (21) can be prepared by removing the protecting group $R^{61}$ of compound (19) obtained by protecting the amino groups of compound (2c). No particular limitation is imposed on the protecting groups for amino acid illustrated as $R^{51}$ and $R^{61}$ so far as they are groups generally used in protection of the amino group. However, as typical examples thereof, may be mentioned the protecting groups for amino group described in Preparation Process 7. In this case, $R^{51}$ and $R^{61}$ are required to be protecting groups capable of leaving by different methods or conditions from each other. As typical examples thereof, may be mentioned a combination that $R^{51}$ is a tert-butoxycarbonyl group, and $R^{61}$ is a benzyloxycarbonyl group. These protecting groups may be chosen for use according to the nature and the like of the compound of which amino groups are to be protected. Upon leaving such a protecting group, reagents and conditions may be employed according to the protecting group.

Compound (21) can also be prepared by converting the hydroxyl group in aminoalcohol derivative (20) into an amino group. As an example of the preparation of aminoalcohol derivative (20), is known conversion of methionine into 3-hydroxy-4-aminothiopyrane-1,1-dioxide (Tetrahedron Lett., Vol. 37, p. 7457, 1996).

As a process for converting the hydroxyl group in aminoalcohol derivative (20) into an amino group, may be mentioned a process in which aminoalcohol derivative (20) may react with methanesulfonyl chloride, p-toluenesulfonyl chloride, trifluoromethanesulfonic anhydride or the like, the resultant product may then react with ammonia, a primary arylalkylamine such as benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine, and benzyl group or the like is then removed as needed, thereby preparing diamine (21). Aminoalcohol derivative (20) can also be converted into diamine (21) by reacting it with phthalimide or succinimide in accordance with the reaction with triphenylphosphine and ethyl azodicarboxylate (Mukaiyama method) or the like, and then treating the reaction product with hydrazine or N-methylhydrazine. When A in the formula is $SO_2$, and n is 0, diamine (21) can be prepared by adding ammonia, a primary arylalkylamine such as benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine to an α,β-unsaturated cyclic sulfone formed by reacting aminoalcohol derivative (20) with methanesulfonyl chloride, p-toluenesulfonyl chloride, trifluoromethanesulfonic anhydride or the like and then treating the reaction product with a proper base or directly reacting aminoalcohol derivative (20) with triphenylphosphine and ethyl azodicarboxylate, and removing the benzyl group or the like as needed.

The resultant diamine (21) may react with carboxylic acid (3), giving compound (22). The protecting group $R^{51}$ is successively removed, giving compound (4c). Compound (4c) may react with carboxylic acid (5), giving compound (1c) according to the present invention. The reagents and reaction conditions in the reaction of compound (21) with carboxylic acid (3) and the reaction of compound (4c) with carboxylic acid (5) may be the same as those described in Preparation Process 7.

Similarly, compound (1c) in which $T^1$ is a sulfonyl group can be prepared by changing carboxylic acid (3) to sulfonyl halide (10) in the reaction of compound (21) with carboxylic acid (3).

[Preparation Process 9]

A typical preparation process of intermediate (2c) for preparation described in Preparation Process 7 will be described.

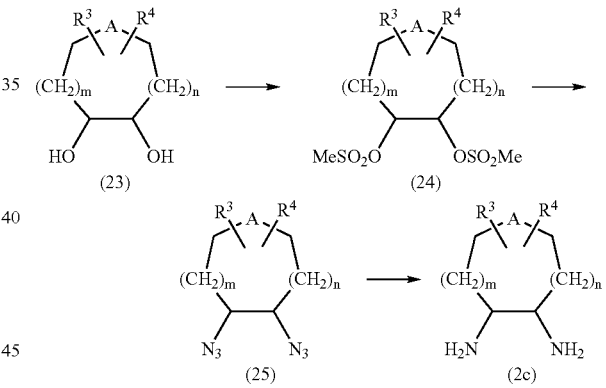

wherein $R^3$, $R^4$, A, m and n have the same meanings as defined above.

As preparation processes of diol derivative (23), are known, for example, conversion of 1,2,3,6-tetrahydropyridine into 1-benzyloxycarbonyl-3,4-cis-dihydroxypyrrolidine (Japanese Patent Application Laid-Open (kokai) No. 138264/1995), conversion of L-tartaric acid into (R,R)-tetrahydrofurandiol or (R,R)-N-benzylpyrrolidinediol (Tetrahedron: Asymmetry, Vol. 8, p. 1861, 1997). Diol derivative (23) can be prepared by using such an already known process or applying such a process and removing a protecting group or converting a functional group as needed.

Diol derivative (23) may react with methanesulfonyl chloride at a temperature under cooling to room temperature in the presence of a base in an inert solvent, giving compound (24). The inert solvent may be suitably chosen for use from those described in Preparation Process 7. However, particularly preferred are alkyl halide type solvents such as dichloromethane and chloroform, and etheric solvents such as tetrahydrofuran and 1,4-dioxane. As the base, is preferred an organic base such as pyridine, 2,6-lutidine, 4-dimethylaminopyridine, triethylamine, N-methylmorpholine, diisopropylethylamine or diazabicyclo[5.4.0]undec-7-ene (DBU).

Compound (24) may react with sodium azide at a temperature under cooling to a temperature under heating in a proper solvent, giving azide derivative (25). As the solvent, an amide solvent such as N,N-dimethylformamide or N-methylpyrrolidin-2-one, an alcoholic solvent such as methanol or ethanol, an etheric solvent such as tetrahydrofuran or 1,4-dioxane, an aromatic solvent such as benzene or toluene, an alkyl halogenide such as dichloromethane or chloroform, dimethyl sulfoxide, acetone, or the like is suitable. Such a solvent may be a mixed solvent with water.

When diol derivative (23) is trans-3,4-dihydroxytetrahydrofuran or trans-1-substituted 3,4-dihydroxypyrrolidine, optically active substances are present. These optically active diol derivatives (23) can be converted into optically active diamine derivatives (2c), and further into optically active compounds (1c) according to the present invention in accordance with Preparation Process 7.

[Preparation Process 10]

A typical preparation process of optically active compounds (30), (31) and (32) included in compound (19) described in Preparation Process 8 will be described. Incidentally, the position of an asymmetric carbon atom shown in the following preparation scheme is indicated as an example.

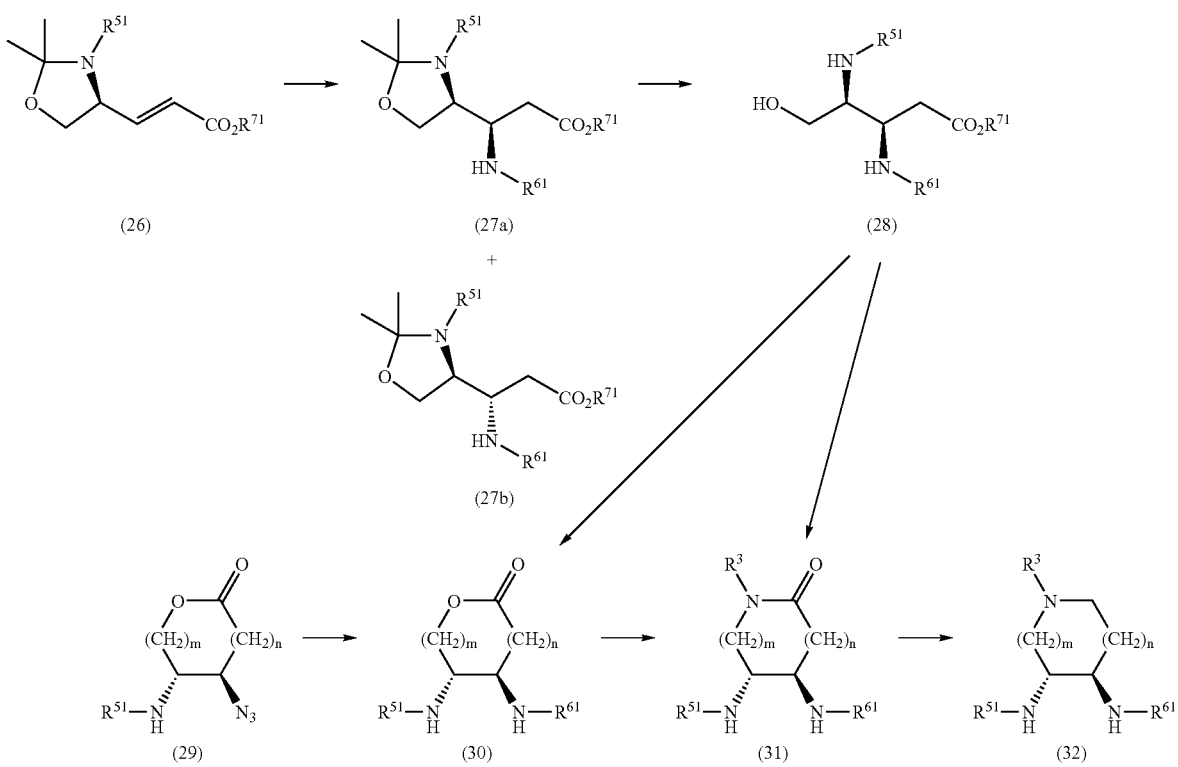

As a process for converting azide derivative (25) into compound (2c), there are many processes such as a process of conducting hydrogenation with a palladium catalyst, Raney nickel catalyst or platinum catalyst, a reaction using a reducing agent such as lithium aluminum hydride or sodium borohydride, a reaction using zinc in the presence of nickel chloride or cobalt chloride, and a reaction using triphenylphosphine. Suitable reagents and reaction conditions may be selected according to the nature of the compound. The hydrogen pressure may be raised higher than atmospheric pressure. As the solvent, an alcoholic solvent such as methanol or ethanol, an etheric solvent such as tetrahydrofuran or 1,4-dioxane, an amide solvent such as N,N-dimethylformamide or N-methylpyrrolidin-2-one, an ester solvent such as ethyl acetate, acetic acid, hydrochloric acid, water, or a mixed solvent thereof is suitable. Compound (1c) according to the present invention can be derived from diamine derivative (2c) prepared in accordance with the above-described process in accordance with Preparation Process 7.

wherein m, n, $R^3$, $R^{51}$ and $R^{61}$ have the same meanings as defined above, and $R^{71}$ represents a protecting group for carboxyl group.

Optically active α,β-unsaturated ester derivative (26) can be prepared in accordance with the process described in literature (J. Org. Chem., Vol. 61, p. 581, 1996; J. Org. Chem., Vol. 57, p. 6279, 1992, etc.) or by applying such a process. Optically active α,β-unsaturated ester derivative (26) may react with an amine at a temperature under cooling to a temperature under heating in a proper solvent, giving diastereomers (27a) and (27b). The amine may be suitably chosen for use from those described in Preparation Process 8. The solvent is desirably an organic solvent unreactive to a substrate, product or reagent, particularly, an alcoholic solvent such as methanol or ethanol, or an etheric solvent such as tetrahydrofuran, 1,2-dimethoxyethane or 1,4-dioxane. Diastereomers (27a) and (27b) can also be prepared by reaction of α,β-unsaturated ester derivative (26) with an organometallic base such as lithium N-benzyl-(trimethylsilyl)amide by applying the process described in literature (J. Org. Chem., Vol. 63, p. 7263, 1998). The diastereomers may be separated to use, for example, diastereomer (27a) in the next reaction.

Compound (27a) is treated with an acid at a temperature under cooling to a temperature under heating in a proper solvent, giving compound (28). Examples of the acid used include hydrochloric acid, sulfuric acid, Lewis acids such as boron trifluoride, trifluoroacetic acid and p-toluenesulfonic acid. As the solvent, is used water or an alcoholic solvent such as methanol or ethanol. Such a solvent may be a mixed solvent with water. In this reaction, the protecting group $R^{61}$ may be left in some cases. In such a case, such a compound is required to react with a proper protecting reagent for amino group as needed.

Compound (28) may be treated with an acid at a temperature under cooling to a temperature under heating in a solvent, giving optically active compound (30). The acid used may be suitably chosen for use from the acids mentioned above, with a Lewis acid such as boron trifluoride, or p-toluenesulfonic acid being particularly preferred. As the solvent used in the reaction, is used an etheric solvent such as 1,4-dioxane or tetrahydrofuran, or an aromatic solvent such as benzene or toluene. Compound (30) can also be prepared from azide derivative (29). As examples of the preparation of optically active azide derivative (29), are known conversion of L-aspartic acid into (R,R)-(3S,4S)-3-amino-4-azide-5-oxotetrahydrofuran (Can. J. Chem., Vol. 71, p. 1407, 1993) and the like. Optically active azide derivative (29) can be prepared by using such an already known process or applying such a process and removing a protecting group or converting a functional group as needed. The azide in azide derivative (29) may be reduced into an amino group, and the resultant product may react with a proper protecting reagent for amino group, giving compound (30). The reagents and reaction conditions used in the reduction of azide (29) may be the same as those described in the process of converting azide derivative (25) into compound (2c) in Preparation Process 9.

The hydroxyl group portion of compound (28) may be converted into an amino group and then treated with a base, giving compound (31). The conversion of the hydroxyl group in compound (28) into the amino group can be performed in accordance with, for example, Preparation Process 8. Compound (31) can also be prepared by treating alcohol derivative (28) with an oxidizing agent and then reductively aminating the resultant aldehyde derivative. Specific preferable examples of the oxidizing agent used in the above reaction include pyridinium chlorochromate (PCC), pyridinium dichromate (PDC) and sulfur trioxide pyridine complexes. Example of the amine include ammonia, primary alkylamines such as methylamine and ethylamine, and primary arylalkylamine such as benzylamine, p-methoxybenzylamine and 2,4-dimethoxybenzylamine. As the reducing process, there are a process of conducting hydrogenation with a palladium catalyst, Raney nickel catalyst or platinum catalyst, a reaction using a reducing agent such as sodium borohydride, sodium triacetoxyborohydride or sodium cyanoborohydride, and suitable reagents and reaction conditions may be selected according to the nature of the compound. The base used in the above process may be suitably chosen for use from those described in Preparation Process 7. Compound (31) can also be prepared by using compound (30) and an amine in accordance with the process described in the literature (Tetrahedron Lett., Vol. 41, p. 1141, 2000; Heterocycles, Vol. 53, p. 173, 2000) or by applying such a process. Examples of the amine used include ammonia, primary alkylamines such as methylamine and ethylamine, primary arylalkylamine such as benzylamine and p-methoxybenzylamine, and aniline.

Compound (31) may be treated with a reducing agent at a temperature under cooling to a temperature under heating in a solvent, giving compound (32). Examples of the reducing agent include borane•tetrahydrofuran complexes, borane•methyl sulfide complexes and lithium aluminum hydride. However, suitable reagents and reaction conditions may be selected according to the nature of the compound. The solvent is desirably an organic solvent unreactive to a substrate, product or reagent, particularly, an etheric solvent such as tetrahydrofuran or 1,4-dioxane.

In accordance with the above-described Preparation Process 8, optically active substances (1c) of the compounds according to the present invention can be derived from the compounds (30), (31) and (32) prepared by the processes described above.

In the above-described preparation scheme, one of optically active substances has been described by way of example. However, other optically active substances different in conformation from each other may also be prepared in accordance with similar preparation schemes by respectively using starting materials different in conformation from each other.

[Preparation Process 11]

Compound (1) in which $T^1$ is a group —CO—CO—N(R')— (in which R' has the same meaning as defined above) can be prepared in accordance with the following scheme:

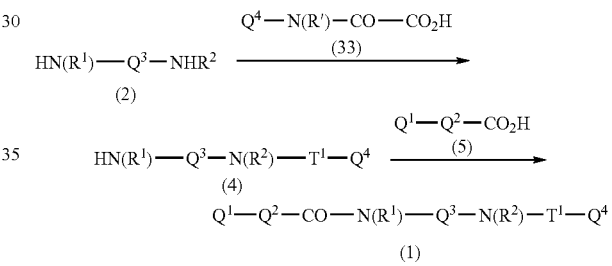

wherein $Q^1$, $Q^2$, $Q^3$, $Q^4$, $R^1$, $R^2$ and R' have the same meanings as defined above, and $T^1$ represents a group —CO—CO—N(R')— (in which R' has the same meaning as defined above).

An acid halide, activated ester or the like, which is derived from carboxylic acid (33), may react with diamine (2), giving compound (4). The resultant compound (4) may react with carboxylic acid (5) under the same conditions, giving compound (1) according to the present invention. In the above reaction steps, reagents and conditions, which are generally used in peptide synthesis, may be applied. The acid halide can be prepared by treating carboxylic acid (33) with an acid halide such as thionyl chloride or oxalyl chloride. The activated ester includes various kinds of esters. Such an ester can be prepared by, for example, reaction of a phenol such as p-nitrophenol, N-hydroxybenzotriazole, or N-hydroxysuccinimide with carboxylic acid (33) using a condensing agent such as N,N'-dicyclohexylcarbodiimide or 1-ethyl-3-(3-dimethylaminopropyl)carbodiimide hydrochloride. The activated ester can also be prepared by reaction of carboxylic acid (33) with pentafluorophenyl trifluoroacetate or the like, reaction of carboxylic acid (33) with 1-benzotriazolyloxytripyrrolidinophosphonium hexafluorophosphite, reaction of carboxylic acid (33) with diethyl cyanophosphonate (Shioiri method), reaction of carboxylic acid (33) with triphenylphosphine and 2,2'-dipyridyl disulfide (Mukaiyama method) or the like. The thus-obtained mixed acid anhydride, acid halide or activated ester of carboxylic acid (33) may react with diamine (2) at −78° C. to 150° C. in the presence of a proper base in an inert solvent, giving compound (4). Thus-obtained compound (4) may react with a mixed acid anhydride, acid halide or activated ester of carboxylic acid (5) under the same conditions, giving compound (1) according to the present invention. The reagents and reaction conditions in the reaction of compound (4) with carboxylic acid (5) are the same as those in the reaction of diamine (2) with carboxylic acid (33). The bases and solvents used in the above respective steps may be suitably chosen from those described in Preparation Process 1.

When compound (1) in which $Q^3$ is the following group:

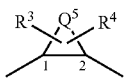

wherein $R^3$, $R^4$ and $Q^5$ have the same meanings as defined above, and numerals 1 and 2 indicate positions, and the relation between position 1 and position 2 is a trans-form or cis-form is prepared, it is only necessary to use diamine (2a) or (2b) described in Preparation Process 5.

When compound (1) in which a heteroatom such as a nitrogen atom, oxygen atom or sulfur atom is contained in $Q^5$ is prepared, it is only necessary to change carboxylic acid (3) to carboxylic acid (33) in the reaction of compound (2c) with carboxylic acid (3) as described in Preparation Process 7. Namely, compound (1) in which a heteroatom is contained in $Q^5$; i.e., compound (1c) can be prepared through the following reaction scheme.

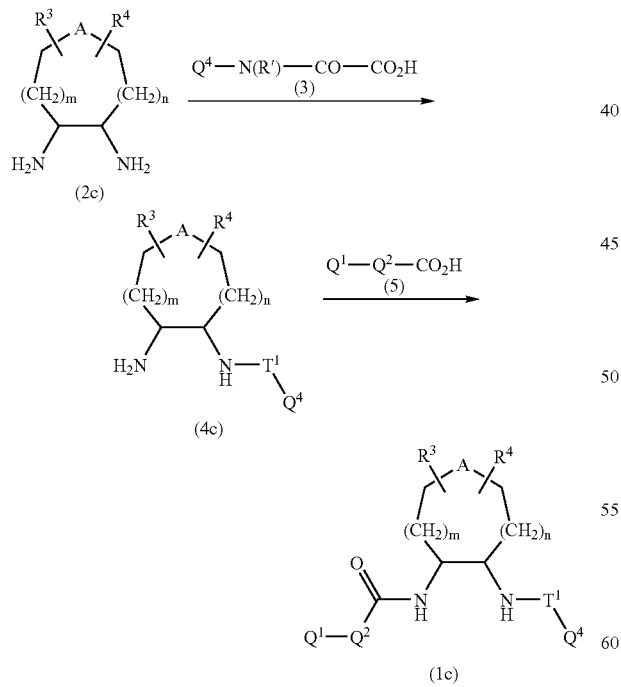

wherein $Q^1$, $Q^2$, $Q^4$, $R^3$, $R^4$, $R^1$, A, m and n have the same meanings as defined above, and $T^1$ represents a group —CO—CO—N(R')— (in which R' has the same meaning as defined above).

[Preparation Process 12]

Compound (1) in which $T^1$ is a group —CO—CO—N (R')— (in which R' has the same meaning as defined above) can also be prepared in accordance with the following scheme:

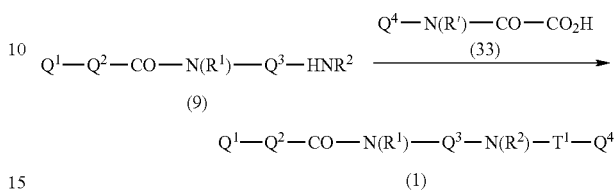

wherein $Q^1$, $Q^2$, $Q^3$, $Q^4$, $R^1$, $R^2$ and R' have the same meanings as defined above, and $T^1$ represents a group —CO—CO—N(R')— (in which R' has the same meaning as defined above).

In the reaction of amine (9) with carboxylic acid (33), the same reagents and conditions as those described in Preparation Process 1 may be used.

Amine (9) used herein can also be prepared in accordance with the following scheme shown as a preparation scheme of amine (41) in addition to the scheme described in Preparation Process 2.

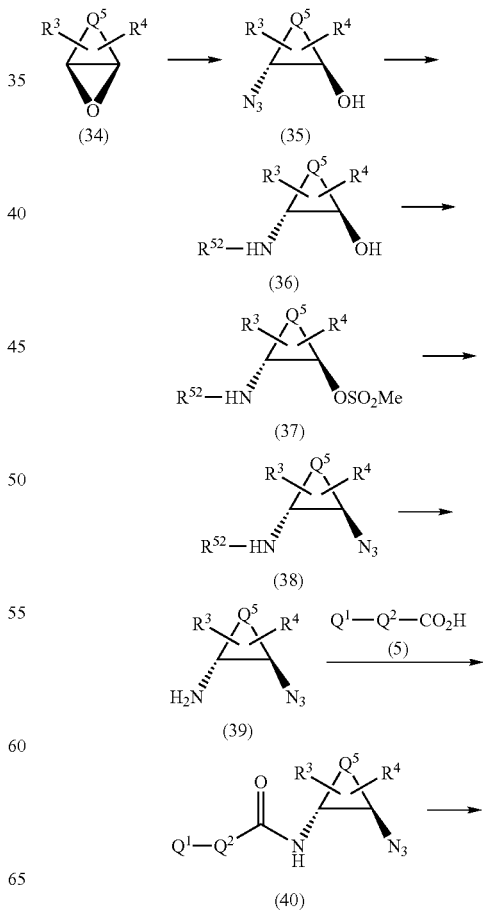

-continued

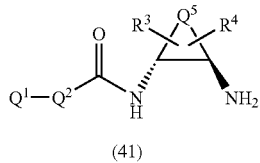

(41)

wherein $R^3$, $R^4$, $Q^1$, $Q^2$ and $Q^5$ have the same meanings as defined above, and $R^{52}$ represents a protecting group for amino group.

Compound (34) in the above preparation scheme can be prepared by treating a cycloalkene with perbenzoic acid or a derivative thereof in a solvent such as dichloromethane to epoxidate it. Ordinary conditions for epoxidation of an alkene may be applied to the conditions of this reaction. Compound (34) can also be prepared in accordance with the process described in J. Org. Chem., Vol. 61, pp. 8687-8691 (1996) or a process corresponding thereto.

Compound (34) may react with sodium azide in accordance with a method known per se in the art, giving azide (35). Azide (35) may be catalytically reduced, and the amino group of the resultant compound may be protected, giving compound (36). As examples of the protecting group for amino group in this reaction, may be mentioned those described in Preparation Process 2. Compound (36) may be converted into azide (38) in a manner similar to the process described Preparation Process 5, and the protecting group for the amino group thereof may be left, giving compound (39). Compound (39) may react with carboxylic acid (5), giving compound (40).

The compound (40) may then be catalytically reduced, giving compound (41).

[Preparation Process 13]

Compound (1) in which $T^1$ is a group —CO—CO—N(R')— (in which R' has the same meaning as defined above) can also be prepared by changing the reaction of compound (9) with carboxylic acid (3) in the scheme described in Preparation Process 2 to a reaction of compound (9) with carboxylic acid (33).

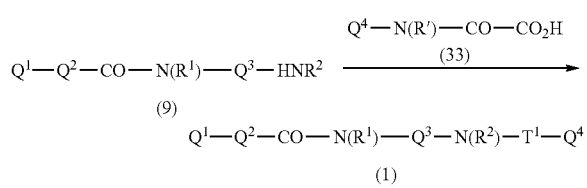

wherein $Q^1$, $Q^2$, $Q^3$, $Q^4$, $R^1$, $R^2$ and R' have the same meanings as defined above, and $T^1$ represents a group —CO—CO—N(R')— (in which R' has the same meaning as defined above).

As the reaction conditions, may be applied those described in Preparation Process 2.

When compound (1) in which $Q^3$ is the following group:

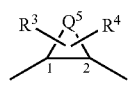

wherein $R^3$, $R^4$ and $Q^5$ have the same meanings as defined above, and numerals 1 and 2 indicate positions, and a heteroatom such as a nitrogen atom, oxygen atom or sulfur atom is contained in $Q^5$ is prepared, it is only necessary to change carboxylic acid (3) to carboxylic acid (33) in the reaction of compound (21) with carboxylic acid (3) as described in Preparation Process 8. Namely, compound (1) in which a heteroatom is contained in $Q^5$; i.e., compound (1c) can be prepared through the following reaction scheme.

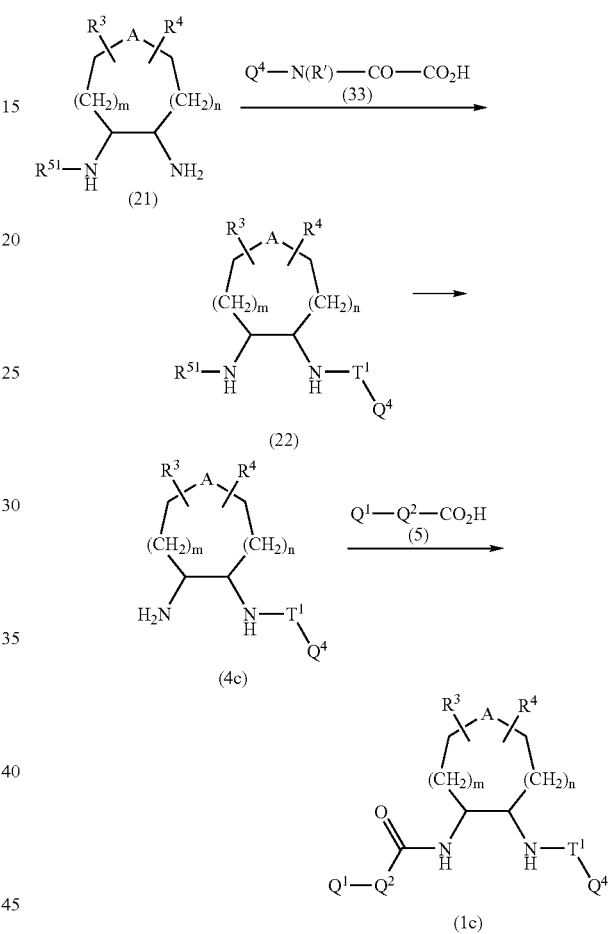

wherein $Q^1$, $Q^2$, $Q^4$, $R^3$, $R^4$, $R^1$, A, m and n have the same meanings as defined above, and $T^1$ represents a group —CO—CO—N(R')— (in which R' has the same meaning as defined above), and $R^{51}$ represents a protecting group for amino group.

[Preparation Process 14]

Compound (1) in which $T^1$ is a group —CO-$A^1$-N(R")— (in which R" represents a hydrogen atom, hydroxyl group, alkyl group or alkoxy group, and $A^1$ represents an alkylene group having 1 to 5 carbon atoms, which may be substituted) can be prepared by reaction of compound (9) described in Preparation Process 2 with $Q^4$-N(R")-$A^1$-$CO_2H$ (42) at −50 to 50° C. using a condensing agent in an inert solvent. As examples of the condensing agent, may be mentioned N,N'-dicyclohexylcarbodiimide and 1-ethyl-3-(3-dimethylaminopropyl)carbodiimide hydrochloride. As examples of the inert solvent, may be mentioned alkyl halide type solvents such as dichloromethane, chloroform and carbon tetrachloride, etheric solvents such as tetrahydrofuran, 1,2-dimethoxyethane and dioxane, aromatic solvents such as benzene and toluene, and amide solvents such as N,N-dimethylformamide.

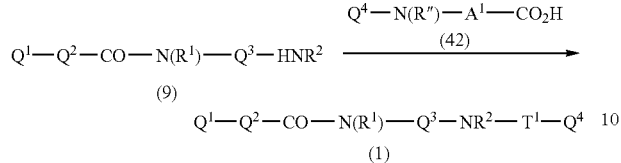

wherein $Q^1$, $Q^2$, $Q^3$, $Q^4$, $R^1$, $R^2$ and R" have the same meanings as defined above, and $T^1$ represents a group —CO-$A^1$-N(R")— (in which R" represents a hydrogen atom, hydroxyl group, alkyl group or alkoxy group, and $A^1$ represents an alkylene group having 1 to 5 carbon atoms, which may be substituted).

Compound (42) described in the preparation process described above can be prepared by, for example, reacting an arylamine such as 4-chloroaniline with an ester of a bromoalkanoic acid at 40 to 120° C. in the presence of a base such as potassium carbonate in a solvent such as acetonitrile or N,N-dimethylformamide and then hydrolyzing the ester with an alkali such as lithium hydroxide, potassium hydroxide or sodium hydroxide. Compound (42) may be used in reaction in the form of a salt such as a potassium salt as it is.

[Preparation Process 15]

Compound (1) in which $T^1$ is a group —C(=O)—NH— or a group —C(=S)—NH— can be prepared by reaction of compound (9) described in Preparation Process 2 with isocyanate ($Q^4$-N=C=O) or isothiocyanate ($Q^4$-N=C=S) at −20 to 50° C. in an inert solvent. A typical example of the inert solvent is described in Preparation Process 14. When an isocyanate or isothiocyanate to be used is not commercialized, the isocyanate or isothiocyanate can be prepared through methods generally used for preparation of isocyanate or isothiocyanate.

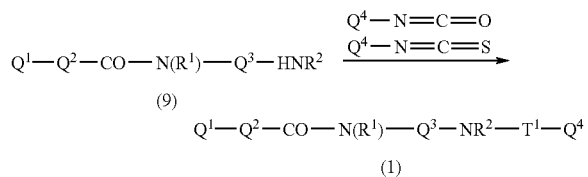

wherein $Q^1$, $Q^2$, $Q^3$, $Q^4$, $R^1$ and $R^2$ have the same meanings as defined above, and $T^1$ represents a group —C(=O)—NH— or —C(=S)—NH—.

[Preparation Process 16]

Compound (1) in which $T^1$ is a group —CO—NH—NH— can be prepared by reaction of compound (9) described in Preparation Process 2 with $Q^4$-NH—NH—$CO_2$Ph (43) at room temperature to 150° C. in an inert solvent in the presence of a base if necessary. As typical examples of the inert solvent, may be mentioned acetonitrile and N,N-dimethylformamide, and besides those described in Preparation Process 14. As examples of the base, may be mentioned pyridine, 2,6-lutidine, collidine, 4-dimethylaminopyridine, triethylamine, N-methylmorpholine, diisopropylethylamine and diazabicyclo[5.4.0]undec-7-ene (DBU).

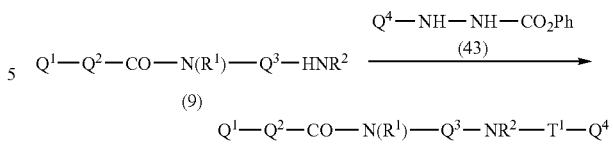

wherein $Q^1$, $Q^2$, $Q^3$, $Q^1$, $R^1$ and $R^2$ have the same meanings as defined above, $T^1$ represents a group —CO—NH—NH—, and Ph represents a phenyl group.

Compound (43) described in the preparation process described above can be prepared by, for example, reacting an arylhydrazine such as 4-chlorophenylhydrazine with diphenyl carbonate at room temperature to 120° C. in a solvent such as acetonitrile, N,N-dimethylformamide, dichloromethane, chloroform, tetrahydrofuran, 1,2-dimethoxyethane, dioxane, benzene or toluene.

[Preparation Process 17]

Compound (1) in which $T^1$ is a group —CO-$A^2$-CO— (in which $A^2$ represents a single bond or alkylene group having 1 to 5 carbon atoms) can be prepared by reaction of compound (9) described in Preparation Process 2 with $Q^1$-CO-$A^2$-$CO_2$H (44) at −50 to 50° C. using a condensing agent in an inert solvent. As examples of the condensing agent, may be mentioned N,N'-dicyclohexylcarbodiimide and 1-ethyl-3-(3-dimethylaminopropyl)carbodiimide hydrochloride. As examples of the solvent, may be mentioned those described in Preparation Process 16.

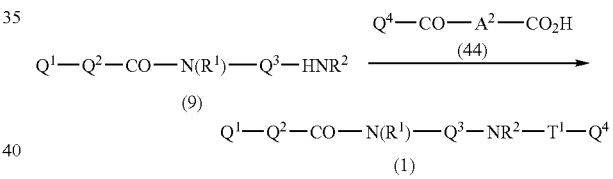

wherein $Q^1$, $Q^2$, $Q^3$, $Q^4$, $R^1$ and $R^2$ have the same meanings as defined above, and $T^1$ represents a group —CO-$A^2$-CO— (in which $A^2$ represents a single bond or alkylene group having 1 to 5 carbon atoms).

When A is a single bond, compound (44) described in the preparation process described above can be prepared by, for example, hydrolyzing a compound (for example, $Q^4$-CO—$CO_2$Et) prepared by the Friedel-Crafts reaction of an aromatic hydrocarbon such as chlorobenzene or an aromatic heterocyclic compound such as thiophene with a chloroxoacetate (for example, ClCO—$CO_2$Et) using an alkali such as lithium hydroxide, potassium hydroxide or sodium hydroxide.

When $A^2$ is a methylene group, compound (44) can be prepared by, for example, hydrolyzing a ketoester derivative (for example, $Q^4$-CO—$CH_2$—$CO_2$Et) obtained by reaction of an arylcarbonyl chloride such as 4-chlorobenzoyl chloride or a heteroarylcarbonyl chloride such as thiophenecarbonyl chloride with potassium malonic monoester monocarboxylate in the presence of magnesium chloride and triethylamine with an alkali such as lithium hydroxide, potassium hydroxide or sodium hydroxide. The ketoester derivative may be used in the reaction with compound (9) in the form of a carboxylic acid obtained by hydrolysis after conversion of its carbonyl group into ethyleneketal. When $A^2$ is an alkylene group having 2 or more carbon atoms, compound (44) can be prepared by, for example, hydrolyzing a ketoester derivative (for example, $Q^4$-CO-$A^2$-$CO_2$Et) obtained by the Friedel-Crafts reaction of an aromatic hydrocarbon such as benzene or an aromatic heterocyclic compound such as thiophene with an alkylenedicarboxylic monoester monochloride using an alkali such as lithium hydroxide, potassium hydroxide or sodium hydroxide.

[Preparation Process 18]

Compound (1) in which $T^1$ is a group —CO-$A^3$-CO—NH— (in which $A^3$ represents an alkylene group having 1 to 5 carbon atoms) can be prepared by reaction of compound (9) described in Preparation Process 2 with $Q^4$-NH—CO-$A^3$-$CO_2$H (45) at −50 to 50° C. using a condensing agent in an inert solvent. As examples of the condensing agent, may be mentioned N,N'-dicyclohexylcarbodiimide and 1-ethyl-3-(3-dimethylaminopropyl)carbodiimide hydrochloride. Examples of the inert solvent include alkyl halide type solvents such as dichloromethane, chloroform, and carbon tetrachloride; etheric solvents such as tetrahydrofuran, 1,2-dimethoxyethane and dioxane; aromatic solvents such as benzene and toluene; and amide solvents such as N,N-dimethylformamide.

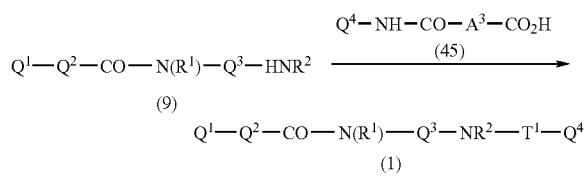

wherein $Q^1$, $Q^2$, $Q^3$, $Q^4$, $R^1$ and $R^2$ have the same meanings as defined above, and $T^1$ represents a group —CO-$A^3$-CO— (in which $A^3$ represents an alkylene group having 1 to 5 carbon atoms).

Compound (45) can be prepared by hydrolyzing a compound (for example, $Q^4$-NH—CO-$A^3$-$CO_2$Et) obtained by reaction of an arylamine such as 4-chloroaniline or a heteroarylamine such as aminopyridine corresponding to $Q^4$-$NH_2$ with potassium alkylenedicarboxylic monoester monocarboxylate at −50 to 50° C. using a condensing agent in an inert solvent with an alkali such as lithium hydroxide, potassium hydroxide or sodium hydroxide.

[Preparation Process 19]

Compound (1) in which $T^1$ is a group —CS—CO—N(R')— (in which R' has the same meaning as defined above) can be prepared in accordance with the following scheme:

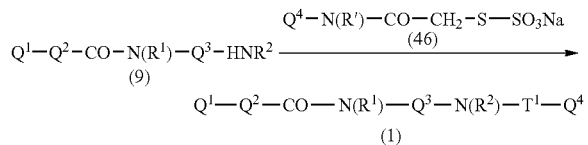

wherein $Q^1$, $Q^2$, $Q^3$, $Q^4$, $R^1$, $R^2$ and R' have the same meanings as defined above, and $T^1$ represents a group —CS—CO—N(R')— (in which R' has the same meaning as defined above).

More specifically, sodium thiosulfate (46) and compound (9) may be dissolved or suspended in a solvent and heated, giving compound (1) according to the present invention. The reaction temperature is preferably 80 to 200° C., particularly preferably about 150° C. As the solvents used in this reaction, may be mentioned water, alcohols such as methanol and ethanol, basic solvents such as pyridine and N-methylmorpholine, alkyl halide type solvents such as dichloromethane and chloroform, etheric solvents such as tetrahydrofuran, 1,2-dimethoxyethane and dioxane, and amide solvents such as N,N-dimethylformamide. These solvents may be suitably mixed for use. As examples of mixed solvents, may be mentioned a mixed solvent of methanol and dichloromethane. In this reaction, the solvent is not necessarily refluxed. For example, when the mixed solvent of methanol and dichloromethane is used, a reaction solution (or a reaction mixture) is heated at an external temperature of 150° C. to distill off the solvent, and the residue is then heated at the same temperature.

[Preparation Process 20]

Compound (1) in which $T^1$ is a group —CO—CS—N(R')— (in which R' has the same meaning as defined above) can be prepared in accordance with the following scheme:

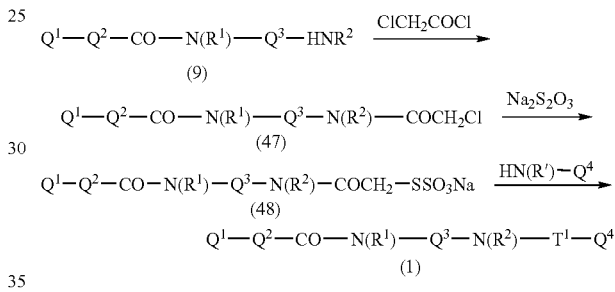

wherein $Q^1$, $Q^2$, $Q^3$, $Q^4$, $R^1$, $R^2$ and R' have the same meanings as defined above, and $T^1$ represents a group —CO—CS—N(R')— (in which R' has the same meaning as defined above).

More specifically, compound (9) may react with chloroacetyl chloride in the presence of a base, giving compound (47). Compound (47) may be heated together with sodium thiosulfate in a solvent, giving sodium thiosulfate derivative (48). The thus-obtained sodium thiosulfate derivative (48) may be heated with an amine (i.e., HN(R')-$Q^4$), giving compound (1) according to the present invention.

As conditions, solvent and the like for preparing compound (47) from compound (9), may be applied those commonly used in reaction of an amine with acid chloride. In order to prepare compound (48) from compound (47), it is only necessary to heat compound (47) together with sodium thiosulfate under reflux for about 1 hour in a solvent such as ethanol. When compound (47) is a salt with hydrochloric acid or the like, the reaction may be performed in the presence of a base such as sodium hydrogencarbonate. The preparation conditions of compound (48) are not limited to those described herein, and the temperature and the kinds of the solvent and base may be suitably changed. The conditions for the reaction of compound (48) with HN(R')-$Q^4$ are the same as those described in Preparation Process 19.

[Preparation Process 21]

Compound (1) in which $T^0$ is a thiocarbonyl group (—CS—) can be prepared in accordance with the following scheme:

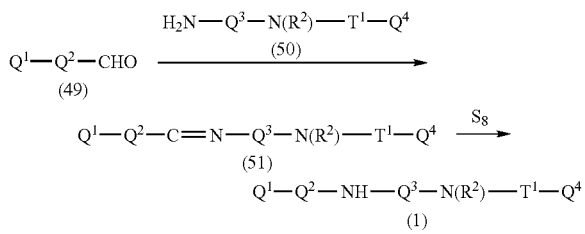

wherein $Q^1$, $Q^2$, $Q^3$, $Q^4$ and $R^2$ have the same meanings as defined above, and $T^1$ represents a group —$SO_2$—, —CO—, —CO—NH—, —CS—NH—, —CO—NH—NH—, —CO—CO—N(R')— (in which R' has the same meaning as defined above), —CO—CS—N(R')— (in which R' has the same meaning as defined above), —CS—CO—N(R')— (in which R' has the same meaning as defined above), —CS—CS—N(R')— (in which R' has the same meaning as defined above), —CO-$A^1$-N(R″)— (in which $A^1$ and R″ have the same meanings as defined above), —CO-$A^2$-CO— (in which $A^2$ has the same meaning as defined above), —CO-$A^3$-CO—NH— (in which $A^3$ has the same meanings as defined above), or —CO-$A^3$-CO— (in which $A^3$ has the same meaning as defined above).

More specifically, compound (49) may be subjected to dehydration reaction with amine (50) in the presence of an acid catalyst such as p-toluenesulfonic acid, giving compound (51). Compound (51) may be heated together with sulfur powder in a solvent such as a mixed solvent of methanol/dichloromethane, giving compound (1) according to the present invention. As conditions for preparing compound (51) from compound (49) and amine (50), may be applied those commonly used in preparation of a Schiff base. Specifically, heating under reflux may be conducted in the presence of an acid catalyst in benzene or toluene under conditions that water is removed from the reaction system by, for example, using a Dean-Stark trap. Molecular sieve may also be used in removing water from the reaction system.

[Preparation Process 22]

Compound (1) in which $T^1$ is a group —CS—CO—N(R')— (in which R' has the same meaning as defined above) can be prepared in accordance with the following scheme:

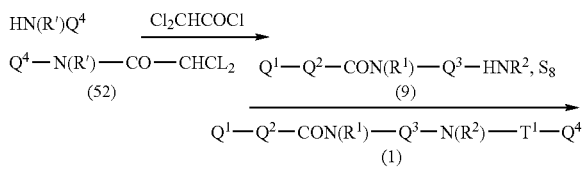

wherein $Q^1$, $Q^2$, $Q^3$, $Q^4$, $R^1$, $R^2$ and R' have the same meanings as defined above, and $T^1$ represents a group —CS—CO—N(R')— (in which R' has the same meaning as defined above).

Compound (52) can be prepared by reacting an arylamine (e.g., 4-chloroaniline) or a heteroarylamine (e.g., aminopyridine), which corresponds to $HN(R')Q^4$, with dichloroacetyl chloride in an inert solvent such as N,N-dimethylformamide or in a basic solvent such as pyridine at −78° C. to 150° C. Compound (52) can also be prepared through reaction of dichloroacetic acid with an amine corresponding to $HN(R')Q^4$ by use of the reagents and conditions described in Preparation Process 1.

Compound (1) can be more efficiently prepared through the following procedure: compound (52) and sulfur powder are suspended in a solvent, and a base (e.g., diisopropylethylamine or triethylamine) and diamine (9) are added to the resultant suspension, followed by reaction at a reaction temperature of 0° C. to 200° C. The amount of the sulfur powder to be used in the reaction is preferably 1 equivalent. The reaction temperature is preferably 60° C. to 160° C., particularly preferably 90° C. to 140° C. Examples of the solvent to be used in this reaction include amide solvents such as N,N-dimethylformamide; basic solvents such as N-methylmorpholine and pyridine; alcohols such as ethanol and butanol; etheric solvents such as dioxane; acetonitrile; and water.

[Preparation Process 23]

Compound (1) in which $T^1$ is a group —CS—CO—N(R')— (in which R' has the same meaning as defined above) can be prepared in accordance with the following scheme:

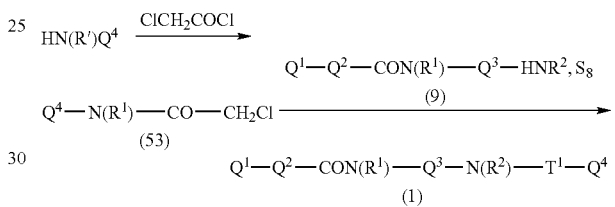

wherein $Q^1$, $Q^2$, $Q^3$, $Q^4$, $R^1$, $R^2$ and R' have the same meanings as defined above, and $T^1$ represents a group —CS—CO—N(R')— (in which R' has the same meaning as defined above).

Compound (53) can be prepared by reacting an arylamine (e.g., 4-chloroaniline) or a heteroarylamine (e.g., aminopyridine), which corresponds to $HN(R')Q^4$, with chloroacetyl chloride in an inert solvent such as N,N-dimethylformamide or in a basic solvent such as pyridine at −78° C. to 150° C. Compound (53) can also be prepared through reaction of chloroacetic acid with an amine corresponding to $HN(R')Q^4$ by use of the reagents and conditions described in Preparation Process 1.

Compound (1) can be prepared through the following procedure: compound (53) and sulfur powder are suspended in a solvent, a base (e.g., diisopropylethylamine or triethylamine) is added to the resultant suspension, followed by stirring for five minutes to eight hours, and then diamine (9) and a condensing agent added to the resultant mixture, followed by reaction. The amount of the sulfur powder to be used in the reaction is preferably 2 equivalents or more. The reaction temperature is preferably 0° C. to 80° C. Examples of the condensing agent to be used include 1-ethyl-3-(3-dimethylaminopropyl)carbodiimide hydrochloride and N,N'-dicyclohexylcarbodiimide. Examples of the solvent to be used in this reaction include amide solvents such as N,N-dimethylformamide; basic solvents such as N-methylmorpholine and pyridine; alkyl halide solvents such as dichloromethane and chloroform; etheric solvents such as dioxane; and acetonitrile. This reaction may proceed in the absence of a condensing agent, yielding compound (1). In such a case, in addition to the above-described solvents, for example, an alcohol such as methanol or ethanol, or water may be used.

[Preparation Process 24]

Compound (1) in which $T^1$ is a group —CS—CO—N(R')— (in which R' has the same meaning as defined above) can be prepared in accordance with the following scheme via preparation of compound (4) in which $T^1$ is a group —CS—CO—N(R')— (in which R' has the same meaning as defined above):

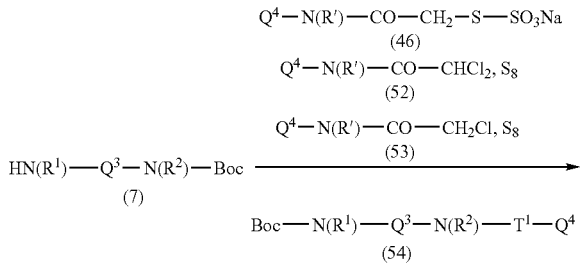

wherein $Q^1$, $Q^2$, $Q^3$, $Q^4$, $R^1$, $R^2$ and R' have the same meanings as defined above, and $T^1$ represents a group —CS—CO—N(R')— (in which R' has the same meaning as defined above).

Specifically, dichloroacetamide derivative (52) or chloroacetamide derivative (53), sulfur powder, and amine (7) are reacted together in a solvent in the presence of a base; a protective group is removed from the resultant reaction product, thereby yielding compound (4); and the resultant compound (4) is condensed with carboxylic acid (5), thereby yielding compound (1) of the present invention. Compound (54) can be more efficiently prepared through the following procedure: compound (52) and sulfur powder are suspended in a solvent, and a base (e.g., diisopropylethylamine or triethylamine) and amine (7) are added to the resultant suspension, followed by reaction at a reaction temperature of 0° C. to 200° C. The amount of the sulfur powder to be used in the reaction is preferably 1 equivalent. The reaction temperature is preferably 60° C. to 160° C., particularly preferably 90° C. to 140° C. Examples of the solvent to be used in this reaction include amide solvents such as N,N-dimethylformamide; basic solvents such as N-methylmorpholine and pyridine; alcohols such as ethanol and butanol; etheric solvents such as dioxane; acetonitrile; and water. Compound (54) can also be prepared through the following procedure: compound (53) and sulfur powder are suspended in a solvent, a base (e.g., diisopropylethylamine or triethylamine) is added to the resultant suspension, followed by stirring for five minutes to five hours, and then amine (7) and a condensing agent added to the resultant mixture, followed by reaction. The amount of the sulfur powder to be used in the reaction is preferably 2 equivalents or more. The reaction temperature is preferably 0° C. to 80° C. Examples of the condensing agent to be used include 1-ethyl-3-(3-dimethylaminopropyl)carbodiimide hydrochloride and N,N'-dicyclohexylcarbodiimide. Examples of the solvent to be used in this reaction include amide solvents such as N,N-dimethylformamide; basic solvents such as N-methylmorpholine and pyridine; alkyl halide solvents such as dichloromethane and chloroform; etheric solvents such as dioxane; and acetonitrile. This reaction may proceed in the absence of a condensing agent, yielding compound (54). In such a case, in addition to the above-described solvents, for example, an alcohol such as methanol or ethanol, or water may be used. Compound (54) can also be prepared by reacting sodium thiosulfate (46) with amine (7) under the reaction conditions described in Preparation Process 19.

Compound (4) can be prepared by treating compound (54) with trifluoroacetic acid or the like at −20° C. to 70° C.

The thus-prepared compound (4) in which $T^1$ is a group —CS—CO—N(R')— (in which R' has the same meaning as defined above) is reacted with carboxylic acid (5) through the method described in Preparation Process 1, thereby yielding compound (1) of the present invention.

The tert-butoxycarbonyl group of compound (7) may be replaced by another protecting group for amino group as described in Preparation Process 2. The type of the protecting group may be selected in accordance with the nature and the like of the compound. Upon leaving such a protecting group, reagents and conditions may be selected in accordance with the protecting group.

[Preparation Process 25]

Compound (1) in which $T^1$ is a group —CO—N(R')—CO— (in which R' has the same meaning as defined above) can be prepared in accordance with the following scheme:

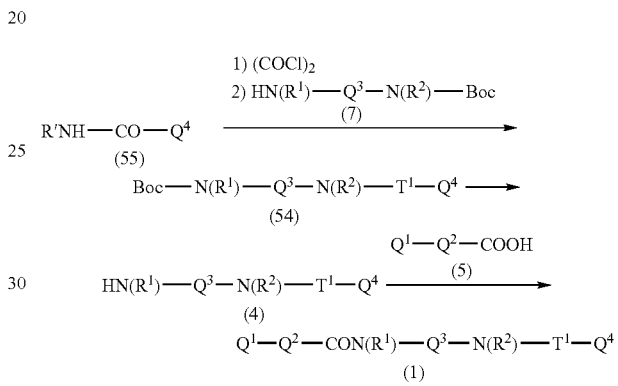

wherein $Q^1$, $Q^2$, $Q^3$, $Q^4$, $R^1$, $R^2$ and R' have the same meanings as defined above, and $T^1$ represents a group —CO—N(R')—CO— (in which R' has the same meaning as defined above).

Specifically, compound (1) of the present invention can be prepared through the following procedure: an arylamide (e.g., 4-chlorobenzamide) or a heteroarylamide (e.g., picolinamide), which corresponds to $HN(R')COQ^4$ (55), is formed into an acyl isocyanate intermediate, and the intermediate is reacted with amine (7), thereby yielding compound (54); the protective group of the compound (54) is removed to yield compound (4); and the resultant compound (4) is condensed with carboxylic acid (5).

For example, amide (55) is reacted with oxalyl chloride at a reaction temperature of 20° C. to 100° C. in an inert solvent, thereby yielding an acyl isocyanate derivative, and the resultant derivative is reacted with amine (7) at a reaction temperature of 0° C. to 100° C., to thereby yield compound (54). Examples of the inert solvent to be used in this reaction include alkyl halide solvents such as dichloromethane, chloroform, and dichloroethane; etheric solvents such as tetrahydrofuran and dioxane; aromatic solvents such as benzene and toluene; amide solvents such as N,N-dimethylformamide and N,N-dimethylacetamide; and acetonitrile.

Compound (4) can be prepared by treating compound (54) with trifluoroacetic acid or the like at −20° C. to 70° C.

The thus-prepared compound (4) in which $T^1$ is a group —CO—N(R')—CO— (in which R' has the same meaning as defined above) is reacted with carboxylic acid (5) through the method described in Preparation Process 1, thereby yielding compound (1) of the present invention.

The tert-butoxycarbonyl group of compound (7) may be replaced by another protecting group for amino group as described in Preparation Process 2. The type of the protecting group may be selected in accordance with the nature and the like of the compound. Upon leaving such a protecting group, reagents and conditions may be selected in accordance with the protecting group.

[Preparation Process 26]

Compound (1) in which $T^1$ is a group $-SO_2-N(R')-$ (in which R' has the same meaning as defined above) can be prepared in accordance with the following scheme:

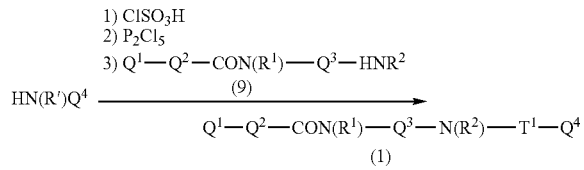

wherein $Q^1$, $Q^2$, $Q^3$, $Q^4$, $R^1$, $R^2$ and R' have the same meanings as defined above, and $T^1$ represents a group $-SO_2-N(R')-$ (in which R' has the same meaning as defined above).

Compound (1) can be prepared through the following procedure: an amine (e.g., 4-chloroaniline) corresponding to $HN(R')Q^4$ is reacted with chlorosulfuric acid in an inert solvent at a reaction temperature of −78° C. to 30° C., thereby yielding an amidosulfate derivative; the derivative is activated with a reagent such as phosphorus pentachloride; and the thus-activated derivative is reacted with amine (9). The reagent for activating the amidosulfate derivative may be a halogenating reagent such as phosphorus pentachloride or phosphorus oxychloride, or a condensing agent such as 1,1'-carbonyldiimidazole. When the amidosulfate derivative is activated with a halogenating agent (e.g., phosphorus pentachloride or phosphorus oxychloride) in this reaction, preferably, the derivative is heated at 50° C. to 120° C. Examples of the inert solvent to be used in this reaction include alkyl halide solvents such as dichloromethane, chloroform, and dichloroethane; etheric solvents such as tetrahydrofuran and dioxane; aromatic solvents such as benzene and toluene; amide solvents such as N,N-dimethylformamide and N,N-dimethylacetamide; and acetonitrile.

The important intermediates described in Preparation Processes 1 to 21 of the compounds (1) according to the present invention will hereinafter be described.

1) The compounds described in Preparation Process 1, 3 and 11 and represented by the following general formula (4):

$$HN(R^1)-Q^3-N(R^2)-T^1-Q^4 \quad (4)$$

wherein $R^1$, $R^2$, $Q^3$ and $Q^4$ have the same meanings as defined above, and $T^1$ represents a carbonyl group, sulfonyl group or group $-CO-CO-N(R')$ (in which R' has the same meaning as defined above) are important as intermediates for preparing compounds (1) according to the present invention.

Among the above-described intermediates, are preferred compounds in which $T^1$ is a group $-C(=O)-C(=O)-N(R')$ (in which R' means a hydrogen atom, hydroxyl group, alkyl group or alkoxy group), and compounds in which $T^1$ in the above formula is a carbonyl group, and $Q^3$ is the following group:

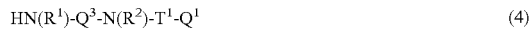

in which $R^3$ and $R^4$ have the same meanings as defined above, and $Q^5$ represents a group $-(CH_2)_m-CH_2-A-CH_2-(CH_2)_n-$ (in which m and n are each independently 0 or an integer of 1-3, and A represents an oxygen atom, nitrogen atom, sulfur atom, $-SO-$, $-SO_2-$, $-NH-$, $-O-NH-$, $-NH-NH-$, $-S-NH-$, $-SO-NH-$ or $-SO_2-NH-$)

2) The compounds described in Preparation Processes 2, 4 and 12 and represented by the following general formula (9):

$$Q^1-Q^2-C(=O)-N(R^1)-Q^3-NHR^2 \quad (9)$$

wherein $R^1$, $R^2$, $Q^1$, $Q^2$ and $Q^3$ have the same meanings as defined above, are important as intermediates for preparing compounds (1) according to the present invention.

Among the above-described intermediates, are preferred compounds in which $Q^3$ is the following group:

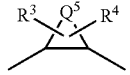

in which $R^3$ and $R^4$ have the same meanings as defined above, and $Q^5$ represents a group $-(CH_2)_m-CH_2-A-CH_2-(CH_2)_n-$ (in which m and n are each independently 0 or an integer of 1-3, and A represents an oxygen atom, nitrogen atom, sulfur atom, $-SO-$, $-SO_2-$, $-NH-$, $-O-NH-$, $-NH-NH-$, $-S-NH-$, $-SO-NH-$ or $-SO_2-NH-$).

3) The following compounds (4c) described in Preparation Processes 7, 11 and 13 are important as intermediates for preparing compounds (1) according to the present invention.

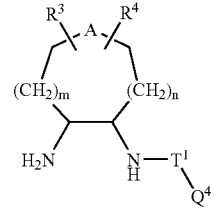

(4c)

wherein $Q^4$, $R^3$, $R^4$, A, m and n have the same meanings as defined above, and $T^1$ represents a carbonyl group, sulfonyl group or group $-CO-CO-N(R')$ (in which R' has the same meaning as defined above).

Among the above-described intermediates, are preferred compounds in which $T^1$ in the above formula is a group $-CO-CO-N(R')-$ (in which R' has the same meaning as defined above), and compounds in which $T^1$ is a carbonyl group, and A is an oxygen atom, nitrogen atom, sulfur atom, $-SO-$, $-SO_2-$, $-NH-$, $-O-NH-$, $-NH-NH-$, $-S-NH-$, $-SO-NH-$ or $-SO_2-NH-$. 4) The following compounds (22) described in Preparation Process 8 and 13 are important as intermediates for preparing compounds (1) according to the present invention.

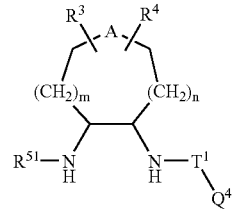

(22)

wherein $Q^4$, $R^3$, $R^4$, A, m and n have the same meanings as defined above, $T^1$ represents a carbonyl group, sulfonyl group or group $-CO-CO-N(R')-$ (in which R' has the same meaning as defined above), and $R^{51}$ represents a protecting group for amino group.

Among the above-described intermediates, are preferred compounds in which $T^1$ in the above formula is a group —CO—CO—N(R')— (in which R' has the same meaning as defined above), and compounds in which $T^1$ is a carbonyl group, and A is an oxygen atom, nitrogen atom, sulfur atom, —SO—, —SO$_2$—, —NH—, —O—NH—, —NH—NH—, —S—NH—, —SO—NH— or —SO$_2$—NH—.

5) The following optically active compounds (7a) described in Preparation Process 6 are important as intermediates for preparing compounds (1) according to the present invention.

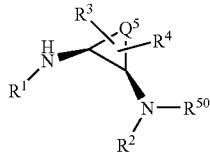
(7a)

wherein $Q^5$, $R^1$, $R^2$, $R^3$ and $R^4$ have the same meanings as defined above, and $R^{50}$ represents a protecting group for amino group.

Among the above-described intermediates, are preferred compounds in which $Q^5$ in the above formula is a group —(CH$_2$)$_m$—CH$_2$-A-CH$_2$—(CH$_2$)$_n$— (in which m and n are each independently 0 or an integer of 1-3, and A represents an oxygen atom, nitrogen atom, sulfur atom, —SO—, —SO$_2$—, —NH—, —O—NH—, —NH—NH—, —S—NH—, —SO—NH— or —SO$_2$—NH—).

6) The following compounds (21) described in Preparation Process 8 are important as intermediates for preparing compounds (1) according to the present invention.

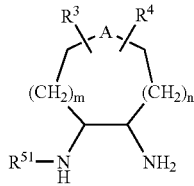
(21)

wherein $R^3$, $R^4$, A, m and n have the same meanings as defined above, and $R^{51}$ represents a protecting group for amino group.

Among the above-described intermediates, are preferred compounds in which A in the above formula is an oxygen atom, nitrogen atom, sulfur atom, —SO—, —SO$_2$—, —NH—, —O—NH—, —NH—NH—, —S—NH—, —SO—NH— or —SO$_2$—NH—.

7) The following compounds described in Preparation Process 10 are important as intermediates for preparing compounds (1) according to the present invention.

More specifically, the following optically active trans-form compounds (30), (31) and (32):

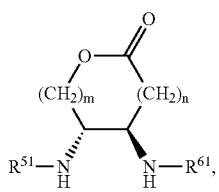
(30)

-continued

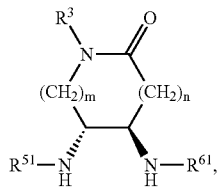
(31)

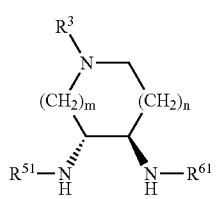
(32)

wherein $R^3$, m and n have the same meanings as defined above, and $R^{51}$ and $R^{61}$ represent protecting groups for amino group;

enantiomers (30a), (31a) and (32a) of the above compounds prepared in a similar manner:

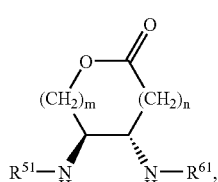
(30a)

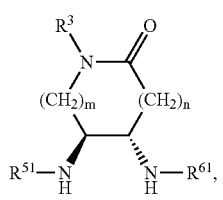
(31a)

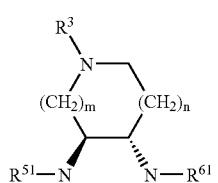
(32a)

wherein $R^3$, m and n have the same meanings as defined above, and $R^{51}$ and $R^{61}$ represent protecting groups for amino group;

cis-form compounds (30b), (31b) and (32b):

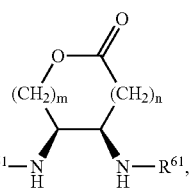
(30b)

-continued

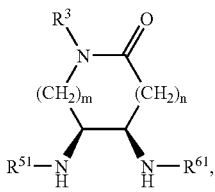
(31b)

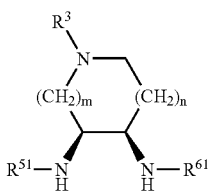
(32b)

wherein $R^3$, m and n have the same meanings as defined above, and $R^{51}$ and $R^{61}$ represent protecting groups for amino group; and enantiomers (30c), (31c) and (32c) thereof:

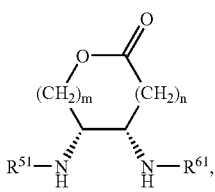
(30c)

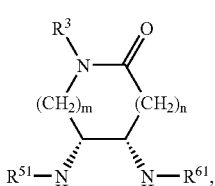
(31c)

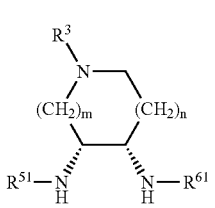
(32c)

wherein $R^3$, m and n have the same meanings as defined above, and $R^{51}$ and $R^{61}$ represent protecting groups for amino group, are important as intermediates for preparing compounds (1) according to the present invention.

The diamine derivatives according to the present invention exhibit strong inhibitory effects on activated blood coagulation factor X and are thus useful for drugs for mammal including human, in particular, activated blood coagulation factor X inhibitors, anticoagulants, agents for preventing and/or treating thrombosis or embolism, agents for preventing and/or treating thrombtic diseases, and agents for preventing and/or treating cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory reaction syndrome (SIRS), multiple organ disease syndrome (MODS), thrombus formation during extracorporeal circulation, or blood clotting upon blood gathering.

When a compound according to the present invention is used as a drug for human body, the dose is within a range of 1 mg to 1 g, preferably 10 mg to 300 mg, per day for an adult. The dose for animal varies according to the object (treatment or prevention) of the administration, the kind and size of an animal to be treated, the kind of a contagium, and the condition of a disease attacked. However, it is generally within a range of 0.1 mg to 200 mg, preferably 0.5 mg to 100 mg, per kg of weight a day. Meanwhile, the administration may be once per day, or may be divided into 2 to 4 times per day. The dose per day may exceed the above range if necessary.

Drug compositions comprising the compound according to the present invention can be prepared by selecting a suitable preparation form according to an administration method in accordance with a preparation method for the preparation form used. As examples of the preparation forms of the drug compositions comprising the compound according to the present invention as a main component, may be mentioned tablets, powder, granules, capsules, solutions, syrups, elixirs, oil or aqueous suspensions for oral preparations.

In the case of an injection, a stabilizer, a preservative and a dissolution aid may be used in a preparation. A solution which may contain these auxiliaries in some cases may also be provided as a solid form for preparing upon use by storing the solution in a container and then drying the solution by lyophilization or the like. A dose or doses of the injection may also be contained in a container.

As examples of preparation forms for external application, may be mentioned solutions, suspensions, emulsions, ointments, gel, creams, lotions, sprays and plasters.

A solid preparation may contain pharmaceutically acceptable additives in addition to the compound according to the present invention. For example, fillers, extenders, binders, disintegrators, dissolution accelerators, humectants, lubricants, etc. may be suitably selected and mixed, giving a preparation.

As examples of liquid preparations, may be mentioned solutions, suspensions and emulsions. They may contain a suspending agent, an emulsifier or the like in some cases.

The compounds of the present invention include the following compounds (A) to (E).

(A) A compound represented by the general formula (1):

$$Q^1-C(=O)-N(R^1)-Q^2-N(R^2)-T^1-Q^3 \qquad (1)$$

wherein $R^1$ and $R^2$ each independently represent a hydrogen atom, hydroxyl group, alkyl group or an alkoxy group;

$Q^1$ represents a saturated or unsaturated, 5- or 6-membered cyclic hydrocarbon group which may be substituted, a saturated or unsaturated, 5- or 6-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents the following group:

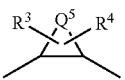

in which $Q^4$ represents an alkylene group having 1 to 8 carbon atoms, an alkenylene group having 2 to 8 carbon atoms or a group —$(CH_2)_m$—$CH_2$-A-$CH_2$—$(CH_2)_n$— (in which m and n are each independently 0 or an integer of 1-3, and A represents an oxygen atom, a sulfur atom, —SO—, —$SO_2$—, —NH—, —O—NH—, —NH—NH—, —S—NH—, —SO—NH— or —$SO_2$—NH—, and numbers 1 and 2 indicate positions); and $R^3$ and $R^4$ are substituents on carbon atom(s), nitrogen atom(s) or sulfur atom(s) of a ring comprising $Q^4$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s), alkylsulfonylacyl group, or the like, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group;

$Q^3$ represents an aryl group which may be substituted, an arylalkenyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted; and $T^1$ represents a carbonyl or sulfonyl group;

a salt thereof, a solvate thereof, or an N-oxide thereof.

(B) A compound represented by the general formula (1):

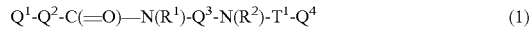

$$Q^1\text{-}Q^2\text{-}C(=O)\text{—}N(R^1)\text{-}Q^3\text{-}N(R^2)\text{-}T^1\text{-}Q^4 \qquad (1)$$

wherein $R^1$ and $R^2$ each independently represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- or 6-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a saturated or unsaturated, 5- or 6-membered divalent cyclic hydrocarbon group which may be substituted, a saturated or unsaturated, 5- or 6-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$Q^3$ represents the following group:

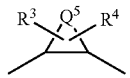

in which $Q^5$ represents an alkylene group having 1 to 8 carbon atoms, an alkenylene group having 2 to 8 carbon atoms or a group —$(CH_2)_n$—$CH_2$-A-$CH_2$—$(CH_2)_n$— (in which m and n are each independently 0 or an integer of 1-3, and A represents an oxygen atom, nitrogen atom, sulfur atom, —SO—, —$SO_2$—, —NH—, —O—NH—, —NH—NH—, —S—NH—, —SO—NH— or —$SO_2$—NH—); and $R^3$ and $R^4$ are substituents on carbon atom(s), nitrogen atom(s) or sulfur atom(s) of a ring comprising $Q^5$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s), alkylsulfonylacyl group, or the like, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group;

$Q^4$ represents an aryl group which may be substituted, an arylalkenyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted; and $T^1$ represents a carbonyl group, sulfonyl group, or group —C(=O)—C(=O)—N(R')— (in which R' represents a hydrogen atom, hydroxyl group, alkyl group or alkoxy group);

a salt thereof, a solvate thereof, or an N-oxide thereof.

(C) A compound represented by the general formula (1):

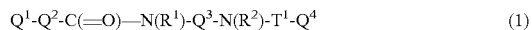

wherein $R^1$ and $R^2$ each independently represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic con densed heterocyclic group which may be substituted; $Q^3$ represents the following group:

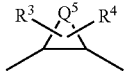

in which $Q^5$ represents an alkylene group having 1 to 8 carbon atoms, an alkenylene group having 2 to 8 carbon atoms or a group —$(CH_2)_n$—$CH_2$-A-$CH_2$—$(CH_2)_n$— (in which m and n are each independently 0 or an integer of 1-3, and A represents an oxygen atom, nitrogen atom, sulfur atom, —SO—, —$SO_2$—, —NH—, —O—NH—, —NH—NH—, —S—NH—, —SO—NH— or —$SO_2$—NH—); and $R^3$ and $R^4$ are substituents on carbon atom(s), nitrogen atom(s) or sulfur atom(s) of a ring comprising $Q^5$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s), alkylsulfonylacyl group, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted; and $T^1$ represents a carbonyl group, sulfonyl group, group —C(=O)—C(=O)—N(R')— (in which R' represents a hydrogen atom, hydroxyl group, alkyl group or alkoxy group), group —C(=O)-$A^1$-N(R")— (in which $A^1$ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-$A^2$-C(=O)— (in which $A^2$ represents a single bond or alkylene group having 1 to 5 carbon atoms), group —C(=O)-$A^3$-C(=O)—NH— (in which $A^3$ represents an alkylene group having 1 to 5 carbon atoms), or thiocarbonyl group;

a salt thereof, a solvate thereof, or an N-oxide thereof.

(D) A compound represented by the general formula (1):

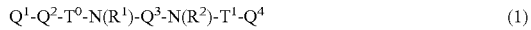

(1)

wherein $R^1$ and $R^2$ each independently represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$Q^3$ represents the following group:

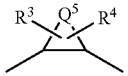

in which $Q^5$ represents an alkylene group having 1 to 8 carbon atoms, an alkenylene group having 2 to 8 carbon atoms, or a group —$(CH_2)_m$—$CH_2$-A-$CH_2$—$(CH_2)_n$— (in which m and n are each independently 0 or an integer of 1-3, and A represents an oxygen atom, nitrogen atom, sulfur atom, —SO—, —$SO_2$—, —NH—, —O—NH—, —NH—NH—, —S—NH—, —SO—NH— or —$SO_2$—NH—), and;

$R^3$ and $R^4$ are substituents on carbon atom(s), nitrogen atom(s) or sulfur atom(s) of a ring comprising $Q^5$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s) or alkylsulfonylacyl group, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^0$ represents a carbonyl or thiocarbonyl group; and $T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-$A^1$-N(R")— (in which $A^1$ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-A²-C(=O)— (in which A² represents a single bond or alkylene group having 1 to 5 carbon atoms), group —C(=O)-A³-C(=O)—NH— (in which A³ represents an alkylene group having 1 to 5 carbon atoms), group —C(=O)—C(=NOR^a)—N(R^b)—, group —C(=S)—C(=NOR^a)—N(R^b)— (in which R^a represents a hydrogen atom, alkyl group or alkanoyl group, and R^b represents a hydrogen atom, hydroxyl group, alkyl group or alkoxy group), group —C(=O)—N=N—, group —C(=S)—N=N—, or thiocarbonyl group;

a salt thereof, a solvate thereof, or an N-oxide thereof.

(E) A compound represented by the general formula (1):

$$Q^1\text{-}Q^2\text{-}T^0\text{-}N(R^1)\text{-}Q^3\text{-}N(R^2)\text{-}T^1\text{-}Q^4 \qquad (1)$$

wherein $R^1$ and $R^2$ each independently represent a hydrogen atom, hydroxyl group, alkyl group or alkoxy group;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$Q^3$ represents the following group:

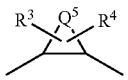

in which $Q^5$ represents an alkylene group having 1 to 8 carbon atoms, an alkenylene group having 2 to 8 carbon atoms, or a group —(CH₂)_m—CH₂A-CH₂—(CH₂)_n— (in which m and n are each independently 0 or an integer of 1-3, and A represents an oxygen atom, nitrogen atom, sulfur atom, —SO—, —SO₂—, —NH—, —O—NH—, —NH—NH—, —S—NH—, —SO—NH— or —SO₂—NH—), and;

$R^3$ and $R^4$ are substituents on carbon atom(s), nitrogen atom(s) or sulfur atom(s) of a ring comprising $Q^5$ and are each independently a hydrogen atom, hydroxyl group, alkyl group, alkenyl group, alkynyl group, halogen atom, halogenoalkyl group, cyano group, cyanoalkyl group, amino group, aminoalkyl group, N-alkylaminoalkyl group, N,N-dialkylaminoalkyl group, acyl group, acylalkyl group, acylamino group which may be substituted, alkoxyimino group, hydroxyimino group, acylaminoalkyl group, alkoxy group, alkoxyalkyl group, hydroxyalkyl group, carboxyl group, carboxyalkyl group, alkoxycarbonyl group, alkoxycarbonylalkyl group, alkoxycarbonylalkylamino group, carboxyalkylamino group, alkoxycarbonylamino group, alkoxycarbonylaminoalkyl group, carbamoyl group, N-alkylcarbamoyl group which may have a substituent on the alkyl group, N,N-dialkylcarbamoyl group which may have a substituent on the alkyl group(s), N-alkenylcarbamoyl group, N-alkenylcarbamoylalkyl group, N-alkenyl-N-alkylcarbamoyl group, N-alkenyl-N-alkylcarbamoylalkyl group, N-alkoxycarbamoyl group, N-alkyl-N-alkoxycarbamoyl group, N-alkoxycarbamoylalkyl group, N-alkyl-N-alkoxycarbamoylalkyl group, carbazolyl group which may be substituted by 1 to 3 alkyl groups, alkylsulfonyl group, alkylsulfonylalkyl group, 3- to 6-membered heterocyclic carbonyl group which may be substituted, carbamoylalkyl group, N-alkylcarbamoylalkyl group which may have a substituent on the alkyl group(s), N,N-dialkylcarbamoylalkyl group which may have a substituent on the alkyl group(s), carbamoyloxyalkyl group, N-alkylcarbamoyloxyalkyl group, N,N-dialkylcarbamoyloxyalkyl group, 3- to 6-membered heterocyclic carbonylalkyl group which may be substituted, 3- to 6-membered heterocyclic carbonyloxyalkyl group which may be substituted, aryl group, aralkyl group, heteroaryl group, heteroarylalkyl group, alkylsulfonylamino group, arylsulfonylamino group, alkylsulfonylaminoalkyl group, arylsulfonylaminoalkyl group, alkylsulfonylaminocarbonyl group, arylsulfonylaminocarbonyl group, alkylsulfonylaminocarbonylalkyl group, arylsulfonylaminocarbonylalkyl group, oxo group, carbamoyloxy group, aralkyloxy group, carboxyalkyloxy group, acyloxy group, acyloxyalkyl group, arylsulfonyl group, alkoxycarbonylalkylsulfonyl group, carboxyalkylsulfonyl group, alkoxycarbonylacyl group, alkoxyalkyloxycarbonyl group, hydroxyacyl group, alkoxyacyl group, halogenoacyl group, carboxyacyl group, aminoacyl group, acyloxyacyl group, acyloxyalkylsulfonyl group, hydroxyalkylsulfonyl group, alkoxyalkylsulfonyl group, 3- to 6-membered heterocyclic sulfonyl group which may be substituted, N-alkylaminoacyl group, N,N-dialkylaminoacyl group, N,N-dialkylcarbamoylacyl group which may have a substituent on the alkyl group(s), N,N-dialkylcarbamoylalkylsulfonyl group which may have a substituent on the alkyl group(s) or alkylsulfonylacyl group, or $R^3$ and $R^4$ together form an alkylene group having 1 to 5 carbon atoms, alkenylene group having 2 to 5 carbon atoms, alkylenedioxy group having 1 to 5 carbon atoms or carbonyldioxy group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^0$ represents a carbonyl or thiocarbonyl group; and $T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-A¹-N(R")— (in which A¹ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-A²-C(=O)— (in which A² represents a single bond or alkylene group having 1 to 5 carbon atoms), group —C(=O)-A³-C(=O)—NH— (in which A³ represents an alkylene group having 1 to 5 carbon atoms), group —C(=O)—)—C(=NOR^a)—N(R^b)—, group —C(=S)—C(=NOR^a)—N(R^b)— (in which R^a represents a hydrogen atom, alkyl group or alkanoyl group, and R^b represents a hydrogen atom, hydroxyl group, alkyl group or alkoxy group), group —C(=O)—N=N—, group —C(=S)—N=N—, or thiocarbonyl group;

a salt thereof, a solvate thereof, or an N-oxide thereof.

EXAMPLES

The present invention will next be described by way of Examples.

Referential Example 1 pyridin-4-ylcarbamic acid tert-butyl ester

4-Aminopyridine (10 g) was dissolved in tetrahydrofuran (500 mL), and di-tert-butyl dicarbonate (25.5 g) was added thereto. The mixture was stirred at room temperature for 10 minutes. The reaction mixture was concentrated under reduced pressure, and the resultant solid was washed with hexane, to thereby give the title compound (16.9 g).

$^1$H-NMR(CDCl$_3$)δ: 1.53(9H, s), 6.86(1H, br.s), 7.30(2H, dd, J=1.5, 4.9 Hz), 8.44(2H, dd, J=1.5, 4.9 Hz).

MS(FAB)m/z: 195(M+H)$^+$.

Referential Example 2

3-sulfanylpyridin-4-ylcarbamic acid tert-butyl ester

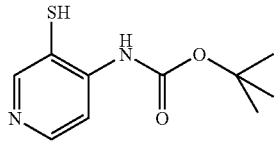

The compound obtained in Referential Example 1 (61.6 g) was dissolved in tetrahydrofuran (2000 mL), and the solution was stirred at −78° C. for 10 minutes. n-Butyllithium (as 1.59N hexane solution, 500 mL) was added dropwise to the reaction mixture, followed by stirring for 10 minutes. The mixture was further stirred for 2 hours under ice cooling. The reaction mixture was cooled to −78° C., and after sulfur powder (12.2 g) was added thereto, the mixture was heated to room temperature, followed by stirring for 1 hour. Water (1000 mL) was added to the reaction mixture to partition the mixture. 3N HCl was added to the aqueous phase, to thereby adjust pH to 3 to 4. Methylene chloride was added for partitioning the mixture. The organic layer was dried over sodium sulfate anhydrate, and the solvent was distilled away under reduced pressure. The residue was purified by silica gel column chromatography (methylene chloride:methanol=50:1), to thereby give the title compound (33.2 g).

$^1$H-NMR(DMSO-d$_6$)δ: 1.52(9H, s), 7.89(1H, d, J=6.4 Hz), 7.99(1H, d, J=6.4 Hz), 8.20(1H, s), 9.91(1H, br.s).

MS(FAB)m/z: 227(M+H)$^+$.

Referential Example 3 thiazolo[5,4-c]pyridine

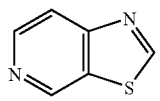

The compound obtained in Referential Example 2 (33.2 g) was dissolved in formic acid (250 mL), and the solution was heated under reflux for 3 days. The reaction mixture was concentrated under reduced pressure, and to the residue were added 5N aqueous potassium hydroxide (100 mL) and diethyl ether to partition the residue. The organic layer was dried over sodium sulfate anhydrate, and the solvent was distilled away under reduced pressure. The residue was purified by silica gel column chromatography (methylene chloride:methanol=25:1), to thereby give the title compound (9.03 g).

$^1$H-NMR(CDCl$_3$)δ: 8.05(1H, d, J=5.4 Hz), 8.70(1H, d, J=5.4 Hz), 9.23(1H, s), 9.34(1H, s).

MS(FAB)m/z: 137(M+H)$^+$.

Referential Example 4

5-methyl-4,5,6,7-tetrahydrothiazolo[5,4-c]pyridine

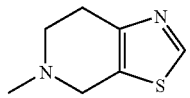

The compound obtained in Referential Example 3 (1.61 g) was dissolved in N,N-dimethylformamide (50 mL), and methyl iodide (1.50 mL) was added thereto, followed by stirring at 80° C. for 4 hours. The reaction mixture was concentrated under reduced pressure. The residue was dissolved in methanol (100 mL), and sodium borohydride (1.53 g) was added thereto, followed by stirring at room temperature for 1 hour. The reaction mixture was concentrated under reduced pressure, and to the residue were added saturated aqueous potassium carbonate and diethyl ether to partition the residue. The organic layer was dried over sodium sulfate anhydrate, and the solvent was distilled away under reduced pressure. The residue was purified by silica gel column chromatography (methylene chloride:methanol=25:1), to thereby give the title compound (1.28 g).

$^1$H-NMR(CDCl$_3$)δ: 2.52(3H, s), 2.83(2H, t, J=5.9 Hz), 2.98(2H, t, J=5.9 Hz), 3.70(2H, s), 8.63(1H, s).

MS(FAB)m/z: 155(M+H)$^+$.

Referential Example 5

5-methyl-4,5,6,7-tetrahydrothiazolo[5,4-c]pyridine-2-carboxylic acid lithium salt

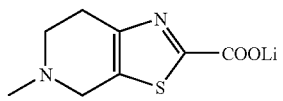

The compound obtained in Referential Example 4 (6.43 g) was dissolved in anhydrous tetrahydrofuran (200 mL), and n-butyllithium (as 1.47N hexane solution, 34.0 mL) was added dropwise to the solution at −78° C., followed by stirring for 40 minutes. After carbon dioxide gas was introduced into the reaction mixture at −78° C. for 1 hour, the reaction mixture was heated to room temperature, and was concentrated under reduced pressure, to thereby give the title compound (9.42 g).

$^1$H-NMR(DMSO-d$_6$)δ: 2.37(3H, s), 2.64-2.77(4H, m), 3.54(2H, s).

MS(FAB)m/z: 199(M+H)$^+$.

Referential Example 6

2-amino-6,7-dihydrothiazolo[5,4-c]pyridine-5[4H]-carboxylic acid tert-butyl ester

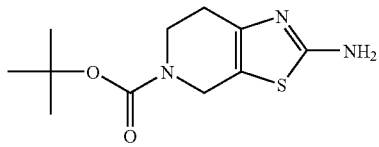

1-tert-Butoxycarbonyl-4-piperidone (40.0 g) was dissolved in cyclohexane (80 mL), and to the solution were added p-toluenesulfonic acid monohydrate (191 mg) and pyrrolidine (17.6 mL). The reaction mixture was heated under reflux for 2 hours while water was removed with Dean-Stark apparatus. The resultant mixture was concentrated under reduced pressure, and the residue was dissolved in methanol (60 mL). After sulfur powder (6.42 g) was added to the solution, a solution of cyanamide (8.44 g) in methanol (10 mL) was slowly added dropwise to the mixture under ice cooling, followed by stirring at room temperature for 5 hours. The resultant precipitated solid was collected by filtration, to thereby give the title compound (31.0 g).

$^1$H-NMR(DMSO-$d_6$)δ: 1.41(9H, s), 2.44(2H, t, J=5.6 Hz), 3.57(2H, t, J=5.6 Hz), 4.29(2H, s), 6.79(2H, s).

MS(EI)m/z: 255(M$^+$).

Referential Example 7

2-bromo-6,7-dihydrothiazolo[5,4-c]pyridine-5[4H]-carboxylic acid tert-butyl ester

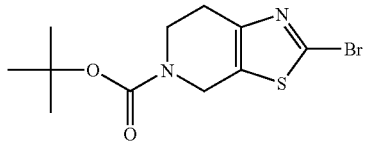

Cupric bromide (1.05 g) was suspended in N,N-dimethylformamide (20 mL), and to the suspension were added tert-butyl nitrite (0.696 mL) and the compound obtained in Referential Example 6 (1.00 g) under ice cooling, followed by stirring at 40° C. for 30 minutes. The reaction mixture was concentrated under reduced pressure, and the residue was purified by silica gel column chromatography (ethyl acetate hexane=1:5), to thereby give the title compound (568 mg).

$^1$H-NMR(CDCl$_3$)δ: 1.48(9H, s), 2.85(2H, br.s), 3.72(2H, br.s), 4.56(2H, br.s).

MS(FAB)m/z: 319(M+H)$^+$.

Referential Example 8

2-bromo-4,5,6,7-tetrahydrothiazolo[5,4-c]pyridine trifluoroacetic acid salt

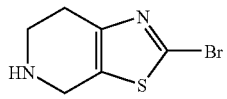

The compound obtained in Referential Example 7 (890 mg) was dissolved in methylene chloride (2 mL), and trifluoroacetic acid (15 mL) was added thereto, followed by stirring at room temperature for 30 seconds. The reaction mixture was concentrated under reduced pressure, and diethyl ether was added to the residue. The resultant precipitated solid was collected by filtration, to thereby give the title compound (867 mg).

$^1$H-NMR(DMSO-$d_6$)δ: 2.98(2H, t, J=6.1 Hz), 3.45(2H, t, J=6.1 Hz), 4.35(2H, s), 9.53(2H, br.s).

MS(FAB)m/z: 219 (M+H)$^+$.

Referential Example 9

2-bromo-5-methyl-4,5,6,7-tetrahydrothiazolo[5,4-c]pyridine

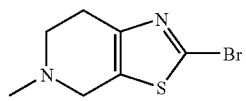

The compound obtained in Referential Example 8 (422 mg) was suspended in methylene chloride (10 mL), and triethylamine (0.356 mL) was dissolved therein. To the thus-obtained mixture were sequentially added acetic acid (0.216 mL), aqueous formaldehyde (as 35% solution, 0.202 mL), and sodium triacetoxyborohydride (428 mg), followed by stirring at room temperature for 1 hour. To the reaction mixture were added saturated aqueous sodium hydrogencarbonate (100 mL), methylene chloride (100 mL), and 3N aqueous sodium hydroxide (3 mL) to partition the mixture. The organic layer was dried over sodium sulfate anhydrate, and the solvent was distilled away under reduced pressure. The residue was purified by silica gel column chromatography (methylene chloride:methanol=100:3), to thereby give the title compound (286 mg).

$^1$H-NMR(CDCl$_3$)δ: 2.49(3H, s), 2.79(2H, t, J=5.7 Hz), 2.85-2.93(2H, m), 3.58(2H, t, J=1.8 Hz).

MS(FAB)m/z: 233(M+H)$^+$.

Referential Example 10

5-methyl-4,5,6,7-tetrahydrothiazolo[5,4-c]pyridine-2-carboxylic acid lithium salt

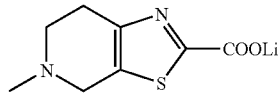

The compound obtained in Referential Example 9 (531 mg) was dissolved in anhydrous diethyl ether (20 mL), and n-butyllithium (as 1.54N hexane solution, 1.63 mL) was added dropwise thereto at −78° C., followed by stirring for 30 minutes under ice cooling. After carbon dioxide gas was introduced into the reaction mixture at −78° C. for 10 minutes, the mixture was heated to room temperature, and the reaction mixture was concentrated under reduced pressure, to thereby give the title compound (523 mg).

$^1$H-NMR(DMSO-$d_6$)δ: 2.37(3H, s), 2.64-2.85(4H, m), 3.54(2H, s).

Referential Example 11

2-[(E)-2-phenylethenyl]oxazole-4-carboxylic acid ethyl ester

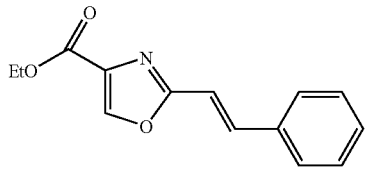

Synthesis was performed as described by Panek et al. (J. Org. Chem., vol. 61, p. 6496 (1996)). Sodium hydrogencarbonate (22.8 g) and ethyl bromopyruvate (10.5 mL) were added to a solution of cinnamamide (10.0 g) in tetrahydrofuran (250 mL) at room temperature, and the mixture was heated under reflux for 48 hours. After the reaction mixture was left to cool to room temperature, the mixture was filtered through Celite, and the filtrate was concentrated under reduced pressure. The residue was dissolved in tetrahydrofuran (30 mL), and trifluoroacetic acid anhydride (30 mL) was added to the solution at 0° C. The mixture was gradually heated to room temperature, and was stirred for 63 hours. Saturated aqueous sodium hydrogencarbonate (500 mL) and ethyl acetate (150 mL) were added to the reaction mixture to partition the mixture. The aqueous layer was extracted with ethyl acetate (150 mL), and the organic layers were combined. The combined organic layer was washed with saturated brine (150 mL), dried over sodium sulfate anhydrate, and concentrated under reduced pressure. The residue was purified by silica gel column chromatography (hexane:ethyl acetate=5:1→3:1), to thereby give the title compound (10.9 g).

$^1$H-NMR(CDCl$_3$)δ: 1.41(3H, t, J=7.0 Hz), 4.42(2H, q, J=7.0 Hz), 6.96(1H, d, J=16.6 Hz), 7.30-7.40(3H, m), 7.53 (2H, d, J=6.8 Hz), 7.63(1H, d, J=16.6 Hz), 8.20(1H, s).

Referential Example 12

2-[(E)-2-phenylethenyl]oxazole-4-carbaldehyde

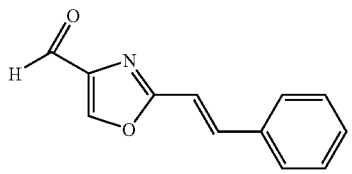

The compound obtained in Referential Example 11 (8.57 g) was dissolved in methylene chloride (80 mL), and diisobutylaluminium hydride (as 1.0N hexane solution, 66 mL) was added dropwise to the solution at −78° C., followed by stirring for 15 minutes. Subsequently, methanol (11 mL) was added dropwise to the resultant mixture, and the mixture was heated to room temperature over 1 hour. The reaction mixture was filtered through Celite, and the resultant paste matter was partitioned between ethyl acetate (200 mL) and saturated aqueous ammonium chloride (200 mL). The aqueous layer was extracted with methylene chloride (2×100 mL), and the organic layers were combined. The combined organic layer was washed with saturated aqueous sodium hydrogencarbonate (100 mL) and saturated brine (100 mL). The washed organic layer was combined with the filtrate from the above-described Celite filtration, and the thus-obtained mixture was dried over sodium sulfate anhydrate. The solvent was distilled away under reduced pressure, and the residue was purified by silica gel column chromatography (methylene chloride:ethyl acetate=5:1-+methylene chloride:methanol=10:1), to thereby give the title compound (5.86 g).

$^1$H-NMR(CDCl$_3$)δ: 6.96(1H, d, J=16.6 Hz), 7.35-7.45 (3H, m), 7.56(2H, d, J=6.4 Hz), 7.67(1H, d, J=16.6 Hz), 8.26(1H, s), 9.98(1H, s).

MS(FAB)m/z: 200 (M+H)$^+$.

Referential Example 13

2-[(E)-2-phenylethenyl]-4-vinyloxazole

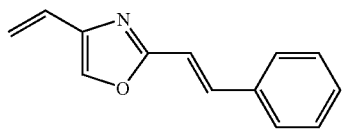

n-Butyllithium (as 1.54N hexane solution, 14.2 mL) was added dropwise to a solution of (methyl)triphenylphosphonium bromide (8.16 g) in tetrahydrofuran (80 mL) at 0° C., and the mixture was stirred at room temperature for 30 minutes. After the reaction mixture was cooled back to 0° C., a solution of the compound obtained in Referential Example 12 (3.64 g) in tetrahydrofuran (20 mL) was added to the mixture, and the thus-obtained mixture was heated to room temperature. After the mixture was stirred for 2 hours, water (200 mL) and ethyl acetate (100 mL) were added thereto to partition the mixture. The aqueous layer was extracted with ethyl acetate (50 mL), and the organic layers were combined. The combined organic layer was washed with saturated brine (100 mL), and dried over sodium sulfate anhydrate. The solvent was distilled away under reduced pressure, and the residue was purified by silica gel column chromatography (hexane: ethyl acetate 4:1→3:1), to thereby give the title compound (2.84 g).

$^1$H-NMR(CDCl$_3$)δ: 5.33(1H, dd, J=1.5, 10.7 Hz), 5.98 (1H, dd, J=1.5, 17.6 Hz), 6.56(1H, dd, J=10.7, 17.6 Hz), 6.95(1H, d, J=16.6 Hz), 7.31-7.42(3H, m), 7.49-7.56(4H, m).

MS(FAB)m/z: 198(M+H)$^+$.

Referential Example 14

2-{2-[(E)-2-phenylethenyl]oxazol-4-yl}-1-ethanol

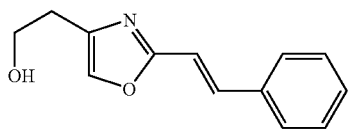

9-Borabicyclo[3.3.1]nonane (as 0.5N tetrahydrofuran solution, 158 mL) was added to a solution of the compound obtained in Referential Example 13 (13.0 g) in tetrahydrofuran (500 mL) at 0° C., and the mixture was stirred at room temperature for 15 hours. To the reaction mixture were sequentially added dropwise water (10 mL), 3N aqueous sodium hydroxide (80 mL), and aqueous hydrogen peroxide (80 mL) at 0° C., and the mixture was stirred at room temperature for 6 hours. Water (600 mL) and ethyl acetate (200 mL) were added to the reaction mixture to partition the mixture, and the aqueous layer was extracted with ethyl acetate (200 mL). The organic layers were combined, and the combined organic layer was washed with saturated brine (200 mL), and dried over sodium sulfate anhydrate. The solvent was distilled away under reduced pressure, and the residue was purified by silica gel column chromatography (hexane: ethyl acetate=2:1→pure ethyl acetate), to thereby give the title compound (14.1 g).

$^1$H-NMR(CDCl$_3$)δ: 2.69(1H, br.s), 2.80(2H, t, J=5.6 Hz), 3.90-3.97(2H, m), 6.91(1H, d, J=16.6 Hz), 7.30-7.42(4H, m), 7.43-7.56(3H, m).

MS(FAB)m/z: 216(M+H)$^+$.

Referential Example 15

2-(2-[2-[(E)-2-phenylethenyl]oxazol-4-yl}ethyl)-1H-isoindole-1,3(2H)-dione

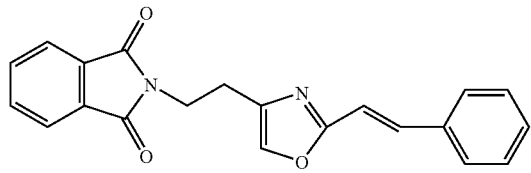

To a solution of the compound obtained in Referential Example 14 (292 mg) in tetrahydrofuran (15 mL) were added phthalimide (200 mg), triphenylphosphine (357 mg), and diethyl azodicarboxylate (0.214 mL) at room temperature, and the mixture was stirred for 4 hours. The solvent was distilled away from the reaction mixture under reduced pressure, and the residue was purified by silica gel column chromatography (hexane:ethyl acetate=3:1), to thereby give the title compound (447 mg).

$^1$H-NMR(CDCl$_3$)δ: 2.98(2H, t, J=7.2 Hz), 4.03(2H, t, J=7.2 Hz), 6.88(1H, d, J=16.6 Hz), 7.28-7.45(5H, m), 7.48 (2H, d, J=7.3 Hz), 7.71(2H, dd, J=2.9, 5.4 Hz), 7.84(2H, dd, J=2.9, 5.4 Hz).

MS(FAB)m/z: 345 (M+H)$^+$.

Referential Example 16

2-{2-[(E)-2-phenylethenyl]oxazol-4-yl}ethylcarbamic acid tert-butyl ester

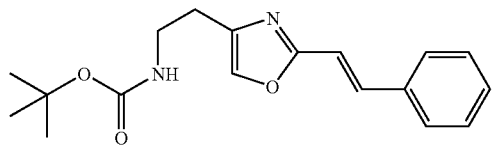

Hydrazine monohydrate (1.50 mL) was added to a solution of the compound obtained in Referential Example 15 (6.40 g) in ethanol (150 mL) at room temperature, and the mixture was stirred for 1 hour. Subsequently, an additional hydrazine monohydrate (0.500 mL) was added thereto at room temperature, and the mixture was stirred for 2 hours. To the reaction mixture were added methylene chloride (150 mL), saturated aqueous sodium hydrogencarbonate (150 mL), and di-tert-butyl dicarbonate (13.4 g) at room temperature, and the mixture was stirred for 30 minutes. After the mixture was partitioned, the aqueous layer was extracted with methylene chloride (50 mL). The organic layers were combined, and the combined organic layer was dried over sodium sulfate anhydrate. The solvent was distilled away under reduced pressure, and the residue was purified by silica gel column chromatography (hexane:ethyl acetate=2:1→1:1), to thereby give the title compound (5.06 g).

$^1$H-NMR(CDCl$_3$)δ: 1.45(9H, s), 2.75(2H, t, J=6.6 Hz), 3.46(2H, dt, J=5.9, 6.6 Hz), 4.92(1H, br.s), 6.91(1H, d, J=16.6 Hz), 7.29-7.45(4H, m), 7.48(1H, d, J=16.6 Hz), 7.52(2H, d, J=7.3 Hz).

MS(FAB)m/z: 315(M+H)$^+$, 259(M-isobutene+H)$^+$, 315 (M-Boc+H)$^+$.

Referential Example 17

2-[(E)-2-phenylethenyl]-6,7-dihydroxazolo[5,4-c]pyridine-5(4H)-carboxylic acid tert-butyl ester

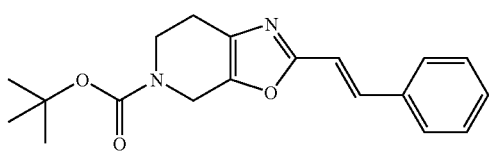

To a solution of the compound obtained in Referential Example 16 (190 mg) in toluene (15 mL) were added paraformaldehyde (54.5 mg) and p-toluenesulfonic acid (7.2 mg) at room temperature. The mixture was heated under reflux for 1 hour, and was left to cool. To the reaction mixture were added ethyl acetate (15 mL) and saturated aqueous sodium hydrogencarbonate (15 mL) to partition the mixture, and the aqueous layer was extracted with ethyl acetate (10 mL). The organic layers were combined, and the combined organic layer was dried over sodium sulfate anhydrate. The solvent was distilled away under reduced pressure, and the residue was purified by silica gel column chromatography (hexane:ethyl acetate=3:1→2:1), to thereby give the title compound (153 mg).

$^1$H-NMR(CDCl$_3$)δ: 1.50(9H, s), 2.67(2H, br.s), 3.73(2H, br.s), 4.55(2H, s), 6.90(1H, d, J=16.1 Hz), 7.29-7.42(3H, m), 7.46(1H, d, J=16.1 Hz), 7.52(2H, d, J=7.3 Hz).

MS(FAB)m/z: 327(M+H)$^+$, 271(M-isobutene+H)$^+$, 227 (M-Boc+H)$^+$.

Referential Example 18

2-formyl-6,7-dihydroxazolo[5,4-c]pyridine-5(4H)-carboxylic acid tert-butyl ester

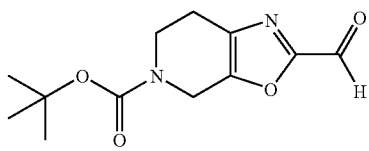

To a solution of the compound obtained in Referential Example 17 (803 mg) in tetrahydrofuran (16 mL) were added acetone (8.0 mL), water (4.0 mL), N-methylmorpholine N-oxide (577 mg), and 0.039M aqueous osmium tetraoxide (3.20 mL) at room temperature, and the mixture was stirred overnight. Ethyl acetate (50 mL) and 10% aqueous sodium thiosulfate (50 mL) were added to the reaction mixture to partition the mixture. The aqueous layer was extracted with ethyl acetate (30 mL). The organic layers were combined, and the combined organic layer was dried over sodium sulfate anhydrate. The solvent was distilled away under reduced pressure, and the residue was dissolved in tetrahydrofuran (16 mL). To the solution were added methanol (8.0 mL), water (8.0 mL), and sodium metaperiodate (790 mg) at room temperature, and the mixture was stirred for 3 hours. Subsequently, ethyl acetate (30 mL) and water (50 mL) were added to the reaction mixture to partition the mixture, and the aqueous layer was extracted with ethyl acetate (20 mL). The organic layers were combined, and the combined organic layer was washed with saturated aqueous sodium hydrogencarbonate (50 mL), and dried over sodium sulfate anhydrate. The solvent was distilled away under reduced pressure, and the residue was purified by silica gel column chromatography (hexane:ethyl acetate=4:1->2:1), to thereby give the title compound (234 mg). This aldehyde was unstable and thus was immediately used for subsequent reaction.

$^1$H-NMR(CDCl$_3$)δ: 1.49(9H, s), 2.77(2H, br.s), 3.77(2H, br.s), 4.62(2H, s), 9.70(1H, s).

Referential Example 19

6,7-dihydroxazolo[5,4-c]pyridine-2,5(4H)-dicarboxylic acid 5-(tert-butyl) 2-methyl ester

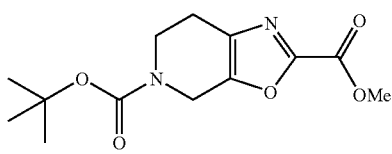

To a solution of the compound obtained in Referential Example 18 (225 mg) in methanol (9.0 mL) were added sodium cyanide (220 mg) and manganese dioxide (780 mg) at room temperature, and the mixture was stirred for 30 minutes. Subsequently, the mixture was filtered through Celite by use of ethyl acetate, and the filtrate was washed with water (50 mL) and saturated brine (50 mL), and dried over sodium sulfate anhydrate. The solvent was distilled away under reduced pressure, and the residue was purified by silica gel column chromatography (hexane:ethyl acetate=3:2→1:1), to thereby give the title compound (120 mg).

$^1$H-NMR(CDCl$_3$)δ: 1.49(9H, s), 2.73(2H, br.s), 3.74(2H, br.s), 4.01(3H, s), 4.59(2H, s).
MS(FAB)m/z: 283 (M+H)$^+$.

Referential Example 20

5-methyl-4,5,6,7-tetrahydroxazolo[5,4-c]pyridine-2-carboxylic acid methyl ester

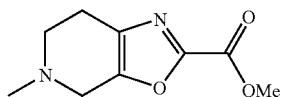

Trifluoroacetic acid (15 mL) was added to a solution of the compound obtained in Referential Example 19 (500 mg) in methylene chloride (15 mL) at room temperature, and the mixture was stirred for 10 minutes. The reaction mixture was concentrated under reduced pressure, and to the resulting residue were added methylene chloride (20 mL), triethylamine (0.495 mL), acetic acid (205 mL), formalin (0.230 mL), and sodium triacetoxyborohydride (570 mg) at room temperature, followed by stirring for 15 minutes. Subsequently, methylene chloride (20 mL) and saturated aqueous sodium hydrogencarbonate (50 mL) were added to the reaction mixture to partition the mixture, and the aqueous layer was extracted with methylene chloride (3×20 mL). The organic layers were combined, and the combined organic layer was dried over sodium sulfate anhydrate. The solvent was distilled away under reduced pressure, and the residue was purified by silica gel column chromatography (chloroform:methanol=20:1→10:1), to thereby give the title compound (257 mg).

$^1$H-NMR(CDCl$_3$)δ: 2.52(3H, s), 2.72-2.78(2H, m), 2.78-2.83(2H, m), 3.61(2H, t, J=1.7 Hz), 4.00(3H, s).
MS(FAB)m/z: 197(M+H)$^+$, 165(M-OCH$_3$)$^+$.

Referential Example 21

5-methyl-4,5,6,7-tetrahydroxazolo[5,4-c]pyridine-2-carboxylic acid lithium salt

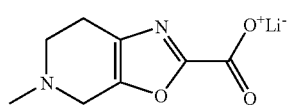

To a solution of the compound obtained in Referential Example 20 (800 mg) in tetrahydrofuran (24 mL) were added water (6.0 mL) and lithium hydroxide (99.7 mg) at room temperature, and the mixture was stirred for 10 minutes. The reaction mixture was concentrated under reduced pressure, to thereby give the title compound (825 mg).

$^1$H-NMR(DMSO-d$_6$)δ: 2.37(3H, s), 2.47(2H, t, J=5.6 Hz), 2.64(2H, t, J=5.6 Hz), 3.43(2H, s).

Referential Example 22

5-chloro-6-fluoroindole-2-carboxylic acid methyl ester

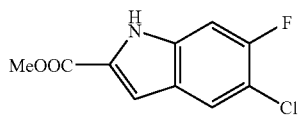

A mixture of 3-chloro-4-fluoro-α-azidocinnamic acid methyl ester (Japanese Patent Application Laid-Open (kokai). No. 7-149723) (1.85 g) and xylene (140 mL) was heated under reflux for 1 hour, and the solvent was distilled away. The residue was purified by silica gel column chromatography (methylene chloride), to thereby give the title compound (491 mg).

$^1$H-NMR(CDCl$_3$)δ: 3.95(3H, s), 7.13-7.15(1H, m), 7.20 (1H, dd, J=9.3, 0.49 Hz), 7.71(1H, d, J=7.3 Hz), 8.93(1H, br.s).
MS(FAB)m/z: 227(M$^+$).

Referential Example 23

5-chloro-6-fluoroindole-2-carboxylic acid

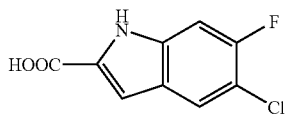

The compound obtained in Referential Example 22 (461 mg) was dissolved in a solvent mixture of tetrahydrofuran (15 mL), methanol (10 mL), and water (10 mL), and lithium hydroxide (283 mg) was added to the solution at room temperature, followed by stirring for 4 hours. The solvent was distilled away under reduced pressure, and to the residue was added 1N HCl, to thereby make the mixture slightly acidic. The resultant powder was collected by filtration, and the powder was dried, to thereby give the title compound (422 mg).

$^1$H-NMR(CDCl$_3$)δ: 7.08-7.10(1H, m), 7.34(1H, d, J=9.5 Hz), 7.88(1H, d, J=7.6 Hz), 12.04(1H, s), 13.16(1H, s).

MS(FAB)m/z: 213(M$^+$).

Referential Example 24

5-(pyridin-4-yl)-4,5,6,7-tetrahydrothiazolo[5,4-c]pyridine

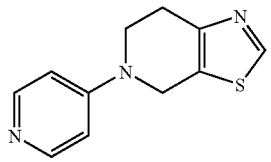

1) Diphosphorus pentasulfide (500 g) was suspended in formamide (3000 mL) under ice cooling, and the suspension was stirred overnight. The reaction mixture was partitioned by adding water and diethyl ether. The organic layer was dried over anhydrous magnesium sulfate, and the solvent was distilled away, to thereby give an oily matter. The oily matter was dissolved in n-butanol (350 mL), and to the solution was added 3-chloro-4-oxo-1-piperidinecarboxylic acid ethyl ester (150 g) which had been synthesized in accordance with the method described in Tetrahedron, vol. 39, p. 3767 (1983), followed by stirring at 100° C. for 2.5 hours. The reaction mixture was filtered through Celite, and the filtrate was washed sequentially with saturated aqueous sodium hydrogencarbonate and saturated brine. The washed filtrate was dried over sodium sulfate anhydrate, and the solvent was distilled away. The residue was purified by silica gel column chromatography (methylene chloride→ethyl acetate:hexane=1:2), to thereby give 6,7-dihydrothiazolo[5,4-c]pyridine-5(4H)-carboxylic acid ethyl ester (79.0 g).

$^1$H-NMR(CDCl$_3$)δ: 1.30(3H, t, J=7.3 Hz), 2.96(2H, br.s), 3.82(2H, br.s), 4.19(2H, q, J=7.3 Hz), 4.73(2H, br.s)8.68(1H, s).

MS(FAB)m/z: 213(M+H)$^+$.

2) To the above product (33.5 g) was added 3.5N aqueous sodium hydroxide (250 mL), and the mixture was heated under reflux overnight. After the reaction mixture was cooled to room temperature, di-tert-butyl dicarbonate (103 g) was added to the mixture under ice cooling, followed by stirring overnight at room temperature. 3N HCl was added to the reaction mixture, to thereby adjust pH to 1 to 2. Methylene chloride was added to the mixture to partition the mixture. The organic layer was sequentially washed with saturated aqueous sodium hydrogencarbonate and saturated brine, and dried over sodium sulfate anhydrate. The mixture was concentrated under reduced pressure, and the resulting residue was purified by silica gel column chromatography (ethyl acetate:hexane=1:2), to thereby give 6,7-dihydrothiazolo[5,4-c]pyridine-5(4H)-carboxylic acid tert-butyl ester (21.1 g).

$^1$H-NMR(CDCl$_3$)δ: 1.49(9H, s), 2.94(2H, br.s), 3.76(2H, br.s), 4.68(2H, s), 8.67(1H, s).

MS(FAB)m/z: 241(M+H)$^+$.

3) Trifluoroacetic acid (25 mL) was added to the solution of the compound obtained in the above-described step 2) (5.00 g) in methylene chloride (25 mL) at room temperature, and the mixture was stirred for 10 minutes. The reaction mixture was concentrated under reduced pressure, and to the resulting residue were added 4-bromopyridine (5.20 g), N,N-dimethylformamide (30 mL), and triethylamine (15.5 mL) at room temperature, followed by stirring at 150° C. for 2 days. The resultant mixture was left to cool to room temperature, and the resultant colorless precipitate was separated by filtration. The filtrate was concentrated under reduced pressure, and methylene chloride (50 mL) and saturated aqueous sodium hydrogencarbonate (100 mL) were added thereto. The aqueous layer was saturated with sodium chloride. After the resultant mixture was partitioned, the aqueous layer was extracted with methylene chloride (5×30 mL), and the organic layers were combined. The combined organic layer was dried over sodium sulfate anhydrate. The solvent was distilled away under reduced pressure, and the residue was purified by silica gel column chromatography (methylene chloride:methanol=20:1->8:1), to thereby give the title compound (2.97 g).

$^1$H-NMR(CDCl$_3$)δ: 3.07(2H, t, J=5.9 Hz), 3.81(2H, t, J=5.9 Hz), 4.61(2H, s), 6.74(2H, t, J=6.5 Hz), 8.30(2H, t, J=6.5 Hz), 8.70(1H, s).

MS(ESI)m/z: 218(M+H)$^+$.

Referential Example 25

2-chloro-6,7-dihydro-4H-pyrano[4,3-d]thiazole

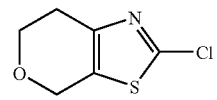

1) Tetrahydro-4H-pyran-4-one (5.0 g) was dissolved in cyclohexane (20 mL), and to the solution were added pyrrolidine (4.35 mL) and p-toluenesulfonic acid monohydrate (48 mg). The mixture was heated under reflux for 70 minutes while water was removed with Dean-Stark apparatus. The reaction mixture was cooled to room temperature, and the supernatant was separated and concentrated under reduced pressure. The residue was dissolved in methanol (15 mL), and sulfur powder (1.60 g) was added thereto under water cooling. After an additional 15 minutes, a solution of cyanamide (2.10 g) in methanol (10 mL) was added dropwise thereto over 20 minutes, and the thus-obtained mixture was stirred for 3 days. The solvent was distilled away under reduced pressure, and the residue was separated by silica gel column chromatography (methylene chloride:methanol=20:1→10:1→4:1), to thereby give 6,7-dihydro-4H-pyrano[4,3-d]thiazol-2-ylamine (3.97 g).

$^1$H-NMR(CDCl$_3$)δ: 2.66-2.70(2H, m), 3.97(2H, t, J=5.6 Hz), 4.63(2H, s), 4.94(2H, br.s).

MS(FAB)m/z: 157(M+H)$^+$.

2) Cupric chloride (4.10 g) was dissolved in acetonitrile (50 mL), and tert-butyl nitrite (3.93 g) was added thereto all at once under water cooling. After 10 minutes, to the mixture was added the compound obtained by the above-described reaction (3.97 g) over approximately 1 hour, and the thus-obtained mixture was stirred at room temperature for 1 hour. Subsequently, the reaction mixture was heated to 65° C. and stirring was continued for 2 hours. After silica gel (20 g) was added to the reaction mixture, the solvent was distilled away under reduced pressure, and the residue was subjected to silica gel column chromatography (hexane:ethyl acetate=3:1), to thereby give the title compound (1.78 g).
$^1$H-NMR(CDCl$_3$)δ: 2.85-2.89(2H, m), 4.02(2H, t, J=5.6 Hz), 4.73(2H, s).
MS(FAB)m/z: 175 (M+H)$^+$.

Referential Example 26

6,7-dihydro-4H-pyrano[4,3-d]thiazole-2-carboxylic acid lithium salt

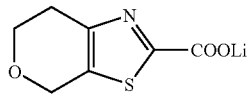

1) The compound obtained in Referential Example 25 (1.78 g) was dissolved in methanol (30 mL), and to the solution were added 10% palladium on carbon (300 mg) and sodium acetate (830 mg), followed by stirring for 5 days under hydrogen stream at a pressure of 5 atm. After the catalyst was filtered off, the solvent was concentrated, and the residue was subjected to silica gel column chromatography (hexane ethyl acetate=2:1), to thereby give 6,7-dihydro-4H-pyrano[4,3-d]thiazole (1.14 g).
$^1$H-NMR(CDCl$_3$)δ: 2.97-3.01(2H, m), 4.04(2H, t, J=5.6 Hz), 4.87(2H, s), 8.69(1H, s).
MS(FAB)m/z: 142 (M+H)$^+$.

2) The above-prepared product (1.14 g) was dissolved in diethyl ether (30 mL), and after the solution was cooled to −78° C., 1.6N butyllithium (6.6 mL) was added thereto, followed by stirring. After 20 minutes, carbon dioxide gas was introduced into the mixture for 15 minutes. The reaction mixture was brought back to room temperature, and the mixture was concentrated under reduced pressure, to thereby give the title compound (1.65 g).
$^1$H-NMR(DMSO-d$_6$)δ: 2.83(2H, t, J=5.6 Hz), 3.92(2H, t, J=5.6 Hz), 4.73(2H, s).

Referential Example 27 thiazolo[4,5-c]pyridine

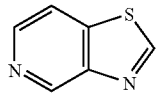

3-(tert-Butoxycarbonylamino)-4-mercaptopyridine (Japanese Patent Application Laid-Open (kokai) No. 4-321691) (9.20 g) was dissolved in formic acid (60 mL), and the solution was heated under reflux for 4 hours. The reaction mixture was concentrated under reduced pressure, and to the residue were added 5N aqueous potassium hydroxide (100 mL) and diethyl ether to partition the residue. The organic layer was dried over sodium sulfate anhydrate, and the solvent was distilled away under reduced pressure. Diethyl ether was added to the residue, and the resultant precipitated solid was collected by filtration, to thereby give the title compound (3.97 g).
$^1$H-NMR(CDCl$_3$)δ: 7.93(1H, d, J=5.4 Hz), 8.60(1H, d, J=5.4 Hz), 9.07(1H, s), 9.46(1H, s).

Referential Example 28

5-methyl-4,5,6,7-tetrahydrothiazolo[4,5-c]pyridine

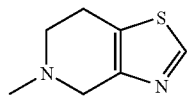

In a manner similar to that employed in Referential Example 4, the title compound was prepared from the compound obtained in Referential Example 27.
$^1$H-NMR(CDCl$_3$)δ: 2.52(3H, s), 2.77(2H, t, J=5.4 Hz), 2.92-3.00(2H, m), 3.69(2H, t, J=2.0 Hz), 8.61(1H, s).
MS(FAB)m/z: 155(M+H)$^+$.

Referential Example 29

5-methyl-4,5,6,7-tetrahydrothiazolo[4,5-c]pyridine-2-carboxylic acid lithium salt

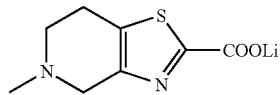

In a manner similar to that employed in Referential Example 5, the title compound was prepared from the compound obtained in Referential Example 28.
$^1$H-NMR(DMSO-d$_6$)δ: 2.38(3H, s), 2.64(2H, br.s), 2.80 (2H, br.s), 3.44(2H, br.s).

Referential Example 30

2-chloro-N,N-dimethyl-4,5,6,7-tetrahydro-benzothiazol-6-amine

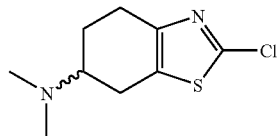

2-Chloro-4,7-dihydro-1,3-benzothiazol-6(5H)-one (Helv. Cim. Acta., vol. 77, p. 1256 (1994)) (2.0 g) was dissolved in methanol (100 mL), and to the solution were added ammonium acetate (8.2 g) and sodium cyanoborohydride (4.0 g), followed by heating under reflux for 20 hours. Hydrochloric acid was added to the reaction mixture, to thereby decompose excess sodium cyanoborohydride, and the solvent was distilled away under reduced pressure. A 1N sodium hydroxide solution was added to the residue, to thereby make the mixture alkaline. The mixture was extracted with methylene chloride. The organic layer was dried over anhydrous magnesium sulfate, and the solvent was distilled away under reduced pressure, to thereby give a pale-yellow oily matter. This oily matter was dissolved in methanol (50 mL), and to the solution were added aqueous formaldehyde (4.29 g) and sodium cyanoborohydride (3.49 g), followed by stirring at room temperature for 12 hours. The solvent was distilled away under reduced pressure, and methylene chloride was added to the residue. The thus-obtained mixture was washed with saturated sodium hydrogencarbonate, and the organic layer was dried over anhydrous magnesium sulfate. The solvent was distilled away under reduced pressure, and the residue was purified by silica gel column chromatography (methylene chloride:methanol=10:1), to thereby give the title compound (740 mg).

$^1$H-NMR(CDCl$_3$)δ: 1.71-1.78(1H, m), 2.10-2.19(1H, m), 2.35(6H, s), 2.66-2.94(5H, m).

MS(FAB)m/z: 217 (M+H)$^+$.

Referential Example 31

6-(dimethylamino)-4,5,6,7-tetrahydrobenzothiazole-2-carboxylic acid lithium salt

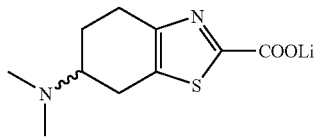

The compound obtained in Referential Example 30 (750 mg) was dissolved in diethyl ether (15 mL), and after the solution was cooled to −78° C., 1.5N tert-butyllithium (3.5 mL) was added thereto, followed by stirring for 20 minutes. After carbon dioxide gas was introduced into the resultant mixture for approximately 15 minutes, the reaction mixture was brought back to room temperature, and was concentrated under reduced pressure, to thereby give the title compound.

$^1$H-NMR(DMSO-d$_6$)δ: 1.75-1.78(1H, m), 1.98-2.07(1H, m), 2.50(6H, s), 2.64-2.88(5H, m).

Referential Example 32

2-amino-4,6-dihydro-5H-pyrrolo[3,4-d]thiazole-5-carboxylic acid tert-butyl ester

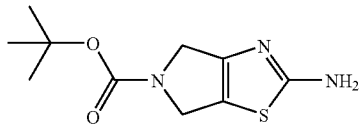

1-tert-Butoxycarbonyl-3-pyrrolidone (1.58 g) was dissolved in cyclohexane (10 mL), and to the solution were added p-toluenesulfonic acid monohydrate (8.12 mg) and pyrrolidine (607 mg). The thus-obtained mixture was heated under reflux for 1.5 hours while water was removed with Dean-Stark apparatus. The supernatant was separated, and was concentrated under reduced pressure. The residue was dissolved in methanol (5 mL), and after sulfur powder (274 mg) was added thereto, the thus-obtained mixture was stirred for 15 minutes under ice cooling. A solution of cyanamide (377 mg) in methanol (2 mL) was slowly added dropwise to the reaction mixture. The thus-obtained mixture was stirred at room temperature overnight, and was further heated under reflux for an additional 2 hours. The reaction mixture was concentrated, and methylene chloride and saturated aqueous sodium hydrogencarbonate were added thereto. The organic layer was dried over sodium sulfate anhydrate, and the solvent was distilled away under reduced pressure. The residue was purified by silica gel column chromatography (methanol:methylene chloride=1:39), to thereby give the title compound (248 mg).

$^1$H-NMR(CDCl$_3$)δ1.50(9H, s), 4.34-4.37(1H, m), 4.40-4.45(1H, m), 4.49-4.55(2H, m), 4.99(2H, m).

Referential Example 33

2-bromo-4,6-dihydro-5H-pyrrolo[3,4-d]thiazole-5-carboxylic acid tert-butyl ester

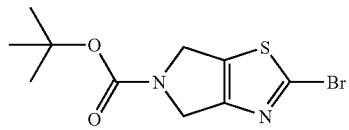

Cupric bromide (445 mg) was suspended in N,N-dimethylformamide, and tert-butyl nitrite (256 mg) was added dropwise thereto at room temperature. To the thus-obtained mixture was added a solution of the compound obtained in Referential Example 32 (400 mg) in N,N-dimethylformamide (1 mL) under ice cooling, and the reaction mixture was stirred at 60° C. for 1.5 hours. Diethyl ether and saturated brine were added to the reaction mixture. The organic layer was dried over anhydrous magnesium sulfate, and was concentrated under reduced pressure. The residue was purified by silica gel column chromatography (ethyl acetate:hexane=1:4), to thereby give the title compound (174 mg).

$^1$H-NMR(CDCl$_3$)δ: 1.51(9H, s), 4.52-4.55(1H, m), 4.57-4.67(3H, m).

MS(FAB)m/z: 305 (M+H)$^+$.

Referential Example 34

5-(tert-butoxycarbonyl)-4,5,6,7-tetrahydrothiazolo[5,4-c]pyridine-2-carboxylic acid lithium salt

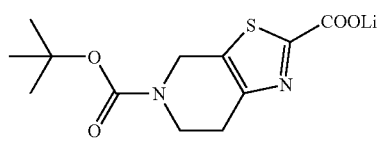

In a manner similar to that employed in Referential Example 10, the title compound was prepared from the compound obtained in Referential Example 7.

$^1$H-NMR(DMSO-d$_6$)δ: 1.42(9H, s), 2.69-2.77(2H, m), 3.60-3.68(2H, m), 4.51-4.58(2H, m).

Referential Example 35

2-bromo-4-(2-methoxy-2-oxoethyl)thiazole-5-carboxylic acid methyl ester

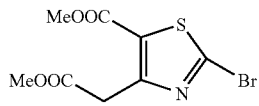

Cupric bromide (26.8 g) was added all at once to a solution of tert-butyl nitrite (15.5 g) in acetonitrile (500 mL) under ice cooling. To the reaction mixture was added dropwise a solution of 2-amino-5-methoxycarbonyl-4-thiazoleacetic acid methyl ester (Yakugaku Zasshi (Journal of the Pharmaceutical Society of Japan), vol. 86, p. 300 (1966)) (23.0 g) in acetonitrile (500 mL) over 45 minutes, and the thus-obtained mixture was stirred for 1 hour under ice cooling, and then at room temperature for 30 minutes. The reaction mixture was concentrated, and 10% hydrochloric acid and diethyl ether were added to the residue. The organic layer was separated, and was dried over anhydrous magnesium sulfate. The solvent was distilled away under reduced pressure, and the residue was purified by silica gel column chromatography (ethyl acetate:hexane=1:4), to thereby give the title compound (25.9 g).

$^1$H-NMR(CDCl$_3$)δ: 3.73(3H, s), 3.87(3H, s), 4.21(2H, s).

Referential Example 36

2-[5-(hydroxymethyl)thiazol-4-yl]-1-ethanol

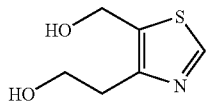

A solution of the compound obtained in Referential Example 35 (23.4 g) in tetrahydrofuran (500 mL) was added dropwise to a suspension of lithium aluminium hydride (9.03 g) in tetrahydrofuran (500 mL) under ice cooling over 1 hour. The thus-obtained mixture was stirred for an additional 1 hour under ice cooling, and to the resultant mixture were sequentially added water (9 mL), 35% aqueous sodium hydroxide (9 mL), and water (27 mL), followed by stirring at room temperature for 1 hour. Anhydrous magnesium sulfate was added to the reaction mixture, and after the thus-obtained mixture was stirred, any insoluble matter was removed by filtration through Celite, and the filtrate was concentrated. The residue was purified by silica gel column chromatography (methanol:methylene chloride=7:93), to thereby give the title compound (8.64 g).

$^1$H-NMR(CDCl$_3$)δ: 3.01(2H, t, J=5.5 Hz), 3.30(1H, br.s), 3.57(1H, br.s), 3.90(2H, br.s), 4.75(2H, br.s), 8.66(1H, s).

MS(ESI)m/z: 160(M+H)$^+$.

Referential Example 37 methanesulfonic acid 2-(5-{[(methylsulfonyl)oxy]methyl}thiazol-4-yl)ethyl ester

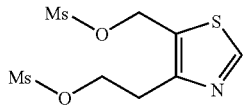

To a solution of the compound obtained in Referential Example 36 (8.64 g) and triethylamine (45.4 mL) in methylene chloride (500 mL) was added dropwise a solution of methanesulfonyl chloride (12.6 mL) in methylene chloride at −78° C. over 20 minutes. The thus-obtained mixture was stirred at −78° C. for 15 minutes, and then at 0° C. for 1 hour. Water was added to the resultant mixture. The organic layer was separated, and was dried over sodium sulfate anhydrate. The solvent was distilled away under reduced pressure, to thereby give the title compound (13.4 g).

$^1$H-NMR(CDCl$_3$)δ: 2.93(3H, s), 3.03(3H, s), 3.28(2H, t, J=6.3 Hz), 4.61(2H, t, J=6.3 Hz), 5.44(2H, s), 8.84(1H, s).

Referential Example 38

5-(1-methylcyclopropyl)-4,5,6,7-tetrahydrothiazolo[5,4-c]pyridine

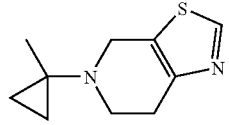

To the compound obtained in Referential Example 37 (4.46 g) in methylene chloride (20 mL) was added 1-methylcyclopropylamine hydrochloride (J. Org. Chem., vol. 54, p. 1815 (1989)) (1.89 g) under ice cooling, and the thus-obtained mixture was stirred at room temperature overnight. Additional 1-methylcyclopropylamine hydrochloride (1.89 g) was added thereto, and the thus-obtained mixture was stirred at room temperature for 20 hours, followed by heating under reflux for 5 hours with stirring. After methylene chloride and water were added to the reaction mixture, the organic layer was separated, and was dried over sodium sulfate anhydrate. The solvent was distilled away under reduced pressure, and the residue was purified by silica gel column chromatography (methanol:methylene chloride=1:49), to thereby give the title compound (944 mg).

$^1$H-NMR(CDCl$_3$)δ: 0.40-0.50(2H, m), 0.68-0.73(2H, m), 1.16(3H, s), 2.88-2.94(2H, m), 3.03(2H, t, J=5.7 Hz), 3.89 (2H, br.s), 8.60(1H, s).

MS(ESI)m/z: 195(M+H)$^+$.

Referential Example 39

5-(1-methylcyclopropyl)-4,5,6,7-tetrahydrothiazolo[5,4-c]pyridine-2-carboxylic acid lithium salt

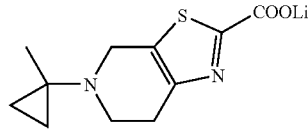

In a manner similar to that employed in Referential Example 5, the title compound was prepared from the compound obtained in Referential Example 38.

$^1$H-NMR(DMSO-d$_6$)δ: 0.39(2H, br.s), 0.56(2H, br.s), 1.10 (3H, br.s), 2.66(2H, br.s), 2.89(2H, br.s), 3.75(2H, br.s).

Referential Example 40

2-[6,7-dihydrothiazolo[5,4-c]pyridin-5(4H)-yl]-2-methyl-1-propanol

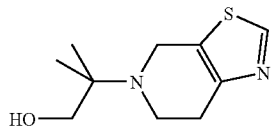

In a manner similar to that employed in Referential Example 38, the title compound was prepared from the compound obtained in Referential Example 37 and 2-amino-2-methyl-1-propanol.

$^1$H-NMR(CDCl$_3$)δ: 1.15(6H, s), 2.91(4H, s), 3.45(2H, s), 3.87(2H, s), 8.63(1H, s).

Referential Example 41

5-(2-{[tert-butyl(diphenyl)silyl]oxy}-1,1-dimethyl-ethyl)-4,5,6,7-tetrahydrothiazolo[5,4-c]pyridine

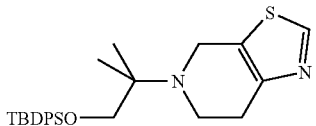

To a solution of the compound obtained in Referential Example 40 (1.24 g) in N,N-dimethylformamide (5 mL) were added tert-butylchlorodiphenylsilane (1.93 g) and imidazole (994 mg) at room temperature, and the thus-obtained mixture was stirred overnight. Water and diethyl ether were added to the reaction mixture. The organic layer was separated, and was dried over anhydrous magnesium sulfate. The solvent was distilled away under reduced pressure, and the residue was purified by silica gel column chromatography (hexane:ethyl acetate=1:2), to thereby give the title compound (2.46 g).

$^1$H-NMR(CDCl$_3$)δ: 1.07(9H, s), 1.15(6H, s), 2.83-2.90 (2H, m), 2.93-3.00(2H, m), 3.63(2H, s), 3.97(2H, s), 7.35-7.48(6H, m), 7.63-7.70(4H, m), 8.58(1H, s).

MS(ESI)m/z: 451 (M+H)$^+$.

Referential Example 42

5-(2-{[tert-butyl(diphenyl)silyl]oxy}-1,1-dimethyl-ethyl)-4,5,6,7-tetrahydrothiazolo[5,4-c]pyridine-2-carboxylic acid lithium salt

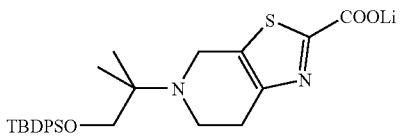

In a manner similar to that employed in Referential Example 5, the title compound was prepared from the compound obtained in Referential Example 41.

$^1$H-NMR(DMSO-d$_6$)δ: 1.01(9H, s), 1.11(6H, s), 2.55-2.65 (2H, m), 2.80-2.90(2H, m), 3.57(2H, s), 3.80(2H, br.s), 7.40-7.52(6H, m), 7.60-7.65(4H, m).

Referential Example 43

4, 7, 8, 10-tetrahydro-6H-pyrazolo[1,2-a]thiazolo[4,5-d]pyridazine

1) 4,5-Dimethylthiazole (5.00 g), N-bromosuccinimide (15.7 g), and α,α'-azobisisobutyronitrile (362 mg) were dissolved in ethylene dichloride (500 mL) at room temperature, and the solution was heated under reflux for 1 hour. The solvent was distilled away, and the residue was purified by silica gel column chromatography (hexane:diethyl ether=1:4), to thereby give 4,5-bis(bromomethyl)thiazole (5.24 g).

$^1$H-NMR(CDCl$_3$)δ: 4.64(2H, s), 4.74(2H, s), 8.75(1H, s).

2) 4,5-Bis(bromomethyl)thiazole (1.37 g) and 1,2-trimethylenehydrazine hydrochloride (WO9532965) (732 mg) were suspended in ethanol (15 mL) under ice cooling, and triethylamine (2.82 mL) was added dropwise thereto over 5 minutes, followed by stirring at room temperature for 2 hours. The solvent was distilled away, and methylene chloride (50 mL) and saturated aqueous sodium hydrogencarbonate were added to the residue. The organic layer was separated, and was dried over sodium sulfate anhydrate. The solvent was distilled away under reduced pressure, and the residue was purified by silica gel column chromatography (methanol methylene chloride=3:47), to thereby give the title compound (358 mg).

$^1$H-NMR(CDCl$_3$)δ: 2.10-2.25(2H, m), 3.01(4H, br.s), 3.95 (2H, s), 3.99(2H, br.s), 8.64(1H, s). MS(FAB)m/z: 182(M+H)$^+$.

Referential Example 44

4, 7, 8, 10-tetrahydro-6H-pyrazolo[1,2-a]thiazolo[4,5-d]pyridazine-2-carboxylic acid lithium salt

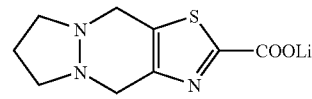

In a manner similar to that employed in Referential Example 5, the title compound was prepared from the compound obtained in Referential Example 43.

$^1$H-NMR(DMSO-d$_6$)δ: 1.90-2.10(2H, m), 2.60-3.10(4H, br.s), 3.65-4.00(4H, m).

Referential Example 45

4,6,7,8,9,11-hexahydropyridazino[1,2-a]thiazolo[4,5-d]pyridazine

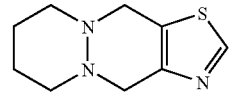

In a manner similar to that employed in Referential Example 43, the title compound was prepared from 4,5-bis(bromomethyl)thiazole (2.20 g) obtained in the step 1) of Referential Example 43 and 1,2-tetramethylenehydrazine hydrochloride (U.S. Pat. No. 5,726,126).

$^1$H-NMR(CDCl$_3$)δ: 1.77(4H, br.s), 2.20-3.50(4H, br), 3.92 (4H, br.s), 8.65(1H, s).

MS(FAB)m/z: 196 (M+H)$^+$.

Referential Example 46

4,6,7,8,9,11-hexahydropyridazino[1,2-a]thiazolo[4,5-d]pyridazine-2-carboxylic acid lithium salt

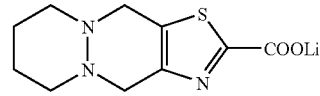

In a manner similar to that employed in Referential Example 5, the title compound was prepared from the compound obtained in Referential Example 45.

Referential Example 47

2-(methylsulfanyl)-5,7-dihydro-6H-pyrolo[3,4-d]pyrimidine-6-carboxylic acid tert-butyl ester

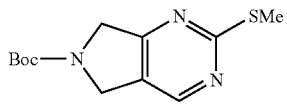

1-(tert-Butoxycarbonyl)-3-pyrrolidone (4.57 g) was added to N,N-dimethylformamide dimethylacetal (30 mL) at room temperature, and the mixture was heated at 140° C. for 1 hour. After the reaction mixture was left to cool to room temperature, the mixture was concentrated under reduced pressure, and hexane was added to the residue. The resultant precipitated yellow powder was collected by filtration. The powder was dissolved in ethanol (100 mL), and to the solution were added methylisothiourea sulfate (9.24 g) and sodium ethoxide (4.52 g) at room temperature, followed by heating under reflux for 24 hours. The reaction mixture was partitioned by adding saturated brine and diethyl ether. The organic layer was dried over sodium sulfate anhydrate, and was concentrated under reduced pressure. The residue was purified by silica gel column chromatography (methanol methylene chloride=1:99), to thereby give the title compound (1.10 g).

$^1$H-NMR(CDCl$_3$)δ: 1.51(9H, s), 2.57(3H, m), 4.15-4.45 (4H, m), 8.39(½H, s), 8.43(½H, s).
MS(FAB)m/z: 268(M+H)$^+$.

Referential Example 48

2-(methylsulfonyl)-5,7-dihydro-6H-pyrolo[3,4-d]pyrimidine-6-carboxylic acid tert-butyl ester

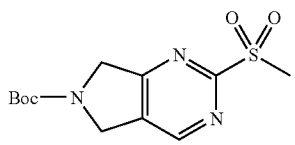

To a solution of the compound obtained in Referential Example 47 (1.08 g) in methylene chloride (20 mL) was added m-chloroperbenzoic acid (1.99 g) under ice cooling, and the mixture was stirred for 5 hours. To the reaction mixture were added saturated aqueous sodium sulfite, saturated aqueous sodium hydrogencarbonate, and methylene chloride, to thereby partition the mixture. The organic layer was dried over sodium sulfate anhydrate, and the solvent was distilled away under reduced pressure. Hexane was added to the residue, and the resultant precipitated powder was collected by filtration, to thereby give the title compound (1.09 g).

$^1$H-NMR(CDCl$_3$)δ: 1.53(9H, s), 3.36(3H, m), 4.77-4.90 (4H, m), 8.77(½H, s), 8.81(½H, s).
MS(FAB)m/z: 300 (M+H)$^+$.

Referential Example 49

2-cyano-5,7-dihydro-6H-pyrolo[3,4-d]pyrimidine-6-carboxylic acid tert-butyl ester

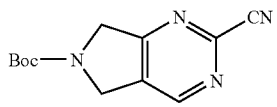

To a solution of the compound obtained in Referential Example 48 (1.05 g) in methylene chloride (30 mL) was added tetrabutylammonium cyanide (1.04 g) at room temperature, and the mixture was stirred at room temperature for 1 hour. To the reaction mixture was added 1N sodium hydroxide. The organic layer was separated, and was dried over sodium sulfate anhydrate. The solvent was distilled away under reduced pressure, and the residue was purified by silica gel column chromatography (methylene chloride:acetone=20:1), to thereby give the title compound (776 mg).

$^1$H-NMR(CDCl$_3$)δ: 1.52(9H, s), 4.70-4.85(4H, m), 8.68-8.77(1H, m).
MS(FAB)m/z: 247 (M+H)$^+$.

Referential Example 50

5,7-dihydro-6H-pyrolo[3,4-d]pyrimidine-2,6-dicarboxylic acid 6-(tert-butyl) 2-methyl ester

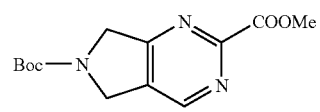

To a solution of the compound obtained in Referential Example 49 (776 mg) in methanol (10 mL) was added concentrated hydrochloric acid (5 mL) at room temperature, and the mixture was stirred at 100° C. for 1 hour. The reaction mixture was left to cool, and was concentrated under reduced pressure. The residue was dissolved in methanol (10 mL), and to the solution were added triethylamine (2.20 mL) and di-tert-butyl dicarbonate (1.37 g) at room temperature, followed by stirring for 1 hour. The resultant mixture was concentrated under reduced pressure, and was partitioned by adding methylene chloride and saturated brine. The organic layer was dried over sodium sulfate anhydrate, and the solvent was distilled away. The residue was purified by silica gel column chromatography (methanol:methylene chloride=3:97), to thereby give the title compound (317 mg).

$^1$H-NMR(CDCl$_3$)δ: 1.53(9H, s), 4.09(3H, s), 4.75-4.85 (4H, m), 8.81(½H, s), 8.85(½H, s).
MS(FAB)m/z: 280 (M+H)$^+$.

Referential Example 51

5,6-dimethyl-4,5,6,7-tetrahydrothiazolo[4,5-d]pyridazine-2-carboxylic acid lithium salt

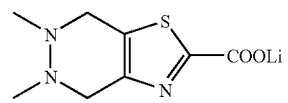

1) 4,5-Bis(bromomethyl)thiazole (600 mg) obtained in the step 1) of Referential Example 43 was dissolved in ethanol (20 mL), and 1,2-dimethylhydrazine hydrochloride (294 mg) was added to the solution under ice cooling, followed by addition of triethylamine (1.23 mL) all at once. The thus-obtained mixture was stirred at room temperature for 30 minutes, and then at 50° C. for 30 minutes. The solvent was distilled away, and the residue was purified by silica gel column chromatography (methanol:methylene chloride=1:19), to thereby give 5,6-dimethyl-4,5,6,7-tetrahydrothiazolo[4,5-d]pyridazine (90 mg).

$^1$H-NMR(CDCl$_3$)δ: 2.43(3H, s), 2.56(3H, s), 3.92(2H, s), 4.06(2H, br.s), 8.68(1H, s). MS(FAB)m/z: 170(M+H)$^+$.

2) In a manner similar to that employed in Referential Example 5, the title compound was prepared from 5,6-dimethyl-4,5,6,7-tetrahydrothiazolo[4,5-d]pyridazine.

$^1$H-NMR(DMSO-d$_6$)δ: 2.28(3H, s), 2.39(3H, s), 3.66(2H, br.s), 3.88(2H, br.s).

Referential Example 52

5-chloroindole-2-carboxylic acid 4-nitrophenyl ester

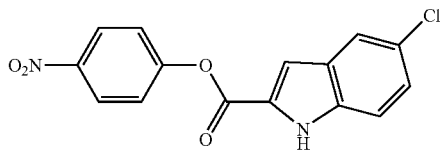

5-Chloroindole-2-carboxylic acid (20 g) was suspended in methylene chloride (1500 mL), and N,N-dimethylformamide (2 mL) was added thereto, followed by dropwise addition of thionyl chloride (11 mL) at room temperature. The reaction mixture was heated under reflux overnight, and the resultant mixture was concentrated under reduced pressure. The residue was dissolved in methylene chloride (1000 mL). Triethylamine (84.7 mL) was added to the solution under ice cooling, and p-nitrophenol (14.2 g) was added thereto, followed by stirring at room temperature for 1 hour. The reaction mixture was concentrated under reduced pressure, and the residue was partitioned by adding ethyl acetate and 0.2N hydrochloric acid. The organic layer was sequentially washed with saturated aqueous sodium hydrogencarbonate and saturated brine, and was dried over sodium sulfate anhydrate. The solvent was distilled away under reduced pressure, to thereby give the title compound (29.9 g).

$^1$H-NMR(CDCl$_3$)δ: 7.35(1H, dd, J=9.0, 1.7 Hz), 7.39-7.42 (2H, m), 7.45(2H, dd, J=7.3, 1.7 Hz), 7.73(1H, d, J=1.0 Hz), 8.35(2H, dd, J=7.3, 1.7 Hz), 9.09(1H, br.s).

MS(FD)m/z: 316(M$^+$).

Referential Example 53

6-chloro-2-quinolinecarbonitrile

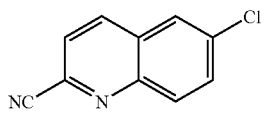

6-Chloroquinoline (2.50 g) was dissolved in methylene chloride (25 mL), and m-chloroperbenzoic acid (3.71 g) was added to the solution under ice cooling, followed by stirring at room temperature for 1 hour. The thus-obtained mixture was diluted with methylene chloride, and the diluted mixture was washed with aqueous sodium thiosulfate and aqueous sodium hydroxide, followed by drying over sodium sulfate anhydrate. The solvent was distilled away under reduced pressure, and the residue was dissolved in methylene chloride (40 mL). To the solution were added trimethylsilyl cyanide (2.0 mL) and N,N-dimethylcarbamoyl chloride (1.50 mL), and the thus-obtained mixture was heated under reflux for 9 hours. To the resultant mixture were added additional trimethylsilyl cyanide (1.0 mL) and N,N-dimethylcarbamoyl chloride (0.80 mL), and the thus-obtained mixture was heated under reflux for 16 hours. The resultant mixture was diluted with methylene chloride, and 10% aqueous potassium carbonate (40 mL) was added thereto, followed by stirring for 30 minutes. The organic layer was separated, and was dried over sodium sulfate anhydrate. The solvent was distilled away under reduced pressure, and methylene chloride was added to the residue. The resultant precipitated crystals were collected by filtration, to thereby give the title compound (1.77 g). Furthermore, the filtrate was concentrated, and was purified by silica gel column chromatography (methylene chloride), to thereby give the title compound (0.80 g).

$^1$H-NMR(DMSO-d$_6$)δ: 7.94(1H, dd, J=9.0, 2.2 Hz), 8.09 (1H, d, J=8.5 Hz), 8.15(1H, d, J=9.0 Hz), 8.29(1H, d, J=2.2 Hz), 8.63(1H, d, J=8.5 Hz).

MS(FAB)m/z: 189(M+H)$^+$.

Referential Example 54

6-chloro-2-quinolinecarboxylic acid

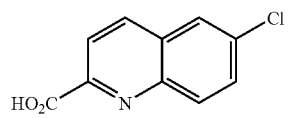

The compound obtained in Referential Example 53 (1.73 g) was dissolved in concentrated hydrochloric acid (40 mL), and the solution was heated under reflux for 19 hours. After the resultant mixture was cooled to room temperature, the precipitate was collected by filtration, and was washed with water, to thereby give the title compound (1.81 g).

$^1$H-NMR(DMSO-d$_6$)δ: 7.87(1H, dd, J=9.0, 2.4 Hz), 8.10-8.20(2H, m), 8.24(1H, d, J=2.2 Hz), 8.52(1H, d, J=8.5 Hz).

MS(FAB)m/z: 208 (M+H)$^+$.

Referential Example 55

3-(4-chlorophenyl)-2-(formylamino)propionic acid methyl ester

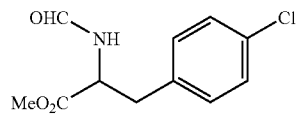

(±)-(4-Chlorophenyl)alanine methyl ester hydrochloride (2.00 g) was suspended in methylene chloride (20 mL), and to the suspension were added 1-(3-dimethylaminopropyl)-3-ethylcarbodiimide hydrochloride (1.60 g), 1-hydroxybenzotriazole monohydrate (1.23 g), N-methylmorpholine (1.90 mL), and formic acid (0.30 mL), followed by stirring for 15 minutes. Subsequently, formic acid (0.30 mL) addition and subsequent stirring for 15 minutes were repeated 3 times. The reaction mixture was diluted with methylene chloride. The organic layer was washed with water, and was dried over sodium sulfate anhydrate. The solvent was distilled away under reduced pressure, and the residue was purified by silica gel column chromatography (methylene chloride:methanol=40:1), to thereby give the title compound (1.21 g).

$^1$H-NMR(CDCl$_3$)δ: 3.10(1H, dd, J=13.9, 5.6 Hz), 3.18 (1H, dd, J=13.9, 5.9 Hz), 3.75(3H, s), 4.95(1H, m), 6.07(1H, br), 7.05(2H, d, J=8.3 Hz), 7.27(2H, d, J=8.3 Hz), 8.18(1H, s).

MS(FAB)m/z: 242(M+H)$^+$.

Referential Example 56

7-chloro-3-isoquinolinecarboxylic acid methyl ester

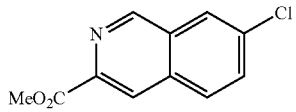

The compound obtained in Referential Example 55 (1.45 g) was dissolved in methylene chloride (40 mL), and oxalyl chloride (0.57 mL) was added dropwise thereto, followed by stirring at room temperature for 30 minutes. Ferric chloride (1.17 g) was added to the resultant mixture at an external temperature of −10° C., and the mixture was stirred at room temperature for 4 days. To the resultant mixture was added 1N hydrochloric acid, and the mixture was diluted with methylene chloride. The organic layer was separated, and was dried over sodium sulfate anhydrate. The solvent was distilled away under reduced pressure, and the residue was dissolved in methanol (38 mL). Concentrated sulfuric acid (2 mL) was added to the solution, and the thus-obtained mixture was heated under reflux for 20 hours. Aqueous sodium hydrogencarbonate was added to the reaction mixture, and the mixture was extracted with methylene chloride, followed by drying over sodium sulfate anhydrate. The solvent was distilled away under reduced pressure, and the residue was purified by silica gel column chromatography (hexane:ethyl acetate=2:1→ethyl acetate), to thereby give the title compound (0.25 g).

$^1$H-NMR(CDCl$_3$)δ: 4.07(3H, s), 7.74(1H, dd, J=8.8, 2.0 Hz), 7.94(1H, d, J=8.8 Hz), 8.06(1H, d, J=2.0 Hz), 8.59(1H, s), 9.28(1H, s).

Referential Example 57

7-chloro-3-isoquinolinecarboxylic acid hydrochloride

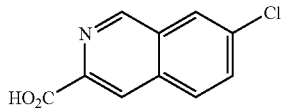

The compound obtained in Referential Example 56 (0.23 g) was dissolved in concentrated hydrochloric acid (10 mL), and the solution was heated under reflux for 18 hours. After the reaction mixture was cooled to room temperature, the precipitate was collected by filtration, and was washed with water, to thereby give the title compound (0.21 g).

$^1$H-NMR(DMSO-d$_6$)δ: 7.96(1H, m), 8.29(1H, d, J=8.5 Hz), 8.44(1H, s), 8.72(1H, s), 9.45(1H, d, J=6.6 Hz).

MS(FAB)m/z: 208 (M+H)$^+$.

Referential Example 58

(3R)-1-benzyl-3-{[tert-butyl(diphenyl)silyl]oxy}pyrrolidine

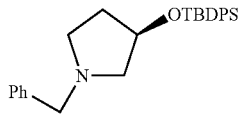

(3R)-1-Benzyl-3-hydroxypyrrolidine (500 μL) and imidazole (466 mg) were dissolved in N,N-dimethylformamide (15 mL), and tert-butyldiphenylsilyl chloride (1.57 mL) was added to the solution under ice cooling, followed by stirring at room temperature for 9 days. The solvent was distilled away under reduced pressure, and the residue was partitioned by adding methylene chloride and water. The organic layer was dried over sodium sulfate anhydrate, and the solvent was distilled away under reduced pressure. The residue was subjected to silica gel flash column chromatography (hexane:ethyl acetate=3:1), to thereby give the title compound (1.27 g).

$^1$H-NMR(CDCl$_3$)δ: 1.05(9H, s), 1.70-1.85(1H, m), 1.90-2.00(1H, m), 2.45-2.65(3H, m), 2.70-2.80(1H, m), 3.50-3.70(2H, m), 4.35-4.45(1H, m), 7.20-7.45(11H, m), 7.60-7.70(4H, m).

MS(ESI)m/z: 416(M+H)$^+$.

Referential Example 59

N-[(1R*,2S*)-2-aminocyclopropyl]-5-chloroindole-2-carboxamide

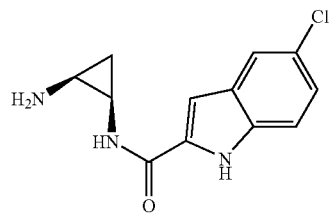

To a solution of cis-1,2-cyclopropanediamine hydrochloride (J. Med. Chem., vol. 41, pp. 4723-4732 (1998)) (405 mg) and 5-chloroindole-2-carboxylic acid (546 mg) in N,N-dimethylformamide (10 mL) were added 1-hydroxybenzotriazole monohydrate (377 mg), 1-(3-dimethylaminopropyl)-3-ethylcarbodiimide hydrochloride (642 mg), and diisopropylethylamine (1.95 mL) at room temperature, followed by stirring for 50 hours. The reaction mixture was concentrated under reduced pressure, and thereto were added methylene chloride (50 mL) and saturated aqueous sodium hydrogencarbonate (200 mL). The precipitated colorless solid was filtered off. The filtrate was partitioned, and aqueous layer was extracted with methylene chloride. The organic layers were combined, and the combined organic layer was dried over sodium sulfate anhydrate. The solvent was distilled away under reduced pressure, and the resultant residue was purified by silica gel flash column chromatography (methylene chloride:methanol=100:7→10:1), to thereby give the title compound (110 mg).

$^1$H-NMR(DMSO-d$_6$)δ: 0.44(1H, dd, J=10.7, 4.4 Hz), 1.11 (1H, dd, J=14.0, 7.4 Hz), 2.63-2.70(1H, m), 3.07-3.16(1H, m), 6.77(1H, s), 6.97(1H, br.s), 7.23(1H, dd, J=8.9, 1.8 Hz), 7.36(1H, d, J=8.9 Hz), 7.60(1H, s), 9.32(1H, s).

MS(FAB)m/z: 250(M+H)$^+$.

Referential Example 60

N-[(1R*,2S*)-2-aminocyclobutyl]-5-chloroindole-2-carboxamide

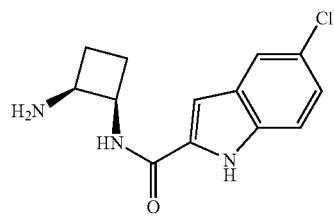

In a manner similar to that employed in Referential Example 59, the title compound was prepared from cis-1,2-cyclobutanediamine hydrochloride (J, Am. Chem. Soc., vol. 64, pp. 2696-2700 (1942)).

¹H-NMR(DMSO-d₆)δ: 1.55-2.20(4H, m), 3.52-3.62(1H, m), 4.35-4.50(1H, m), 7.16(1H, dd, J=8.7, 2.1 Hz), 7.19(1H, s), 7.42(1H, d, J=8.7 Hz), 7.70(1H, d, J=2.1 Hz), 8.36(1H, d, J=7.8 Hz), 11.77(1H, br.s).

MS(ESI)m/z: 264(M+H)⁺.

Referential Example 61

(1R*,2R*)-2-aminocyclopentylcarbamic acid tert-butyl ester

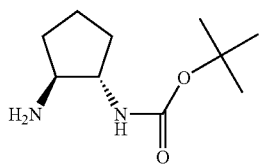

(±)-trans-1,2-Cyclopentanediamine (WO98/30574) (692 mg) was dissolved in methylene chloride (10 mL), and to the solution were added triethylamine (1.1 mL) and 2-(tert-butoxycarbonyloxyimino)-2-phenylacetonitrile (493 mg) at 0° C., followed by stirring at 0° C. for 1 hour. Subsequently, additional 2-(tert-butoxycarbonyloxyimino)-2-phenylacetonitrile (493 mg) was added thereto, and the thus-obtained mixture was stirred at room temperature for 7 hours. Water was added to the reaction mixture to partition the mixture. The organic layer was washed with saturated brine, and was dried over sodium sulfate anhydrate. The residue was purified by silica gel flash column chromatography (methylene chloride:methanol=9:1), to thereby give the title compound (395 mg).

¹H-NMR(CDCl₃)δ: 1.25-1.40(2H, m), 1.49(9H, s), 1.59-1.77(2H, m), 1.92-2.08(1H, m), 2.10-2.17(1H, m), 2.98(1H, q, J=7.2 Hz), 3.48-3.53(1H, m), 4.49(1H, br.s).

MS(ESI)m/z: 201 (M+H)⁺.

Referential Example 62

N-[(1R*,2R*)-2-aminocyclopentyl]-5-methyl-4,5,6,7-tetrahydrothiazolo[5,4-c]pyridine-2-carboxamide hydrochloride

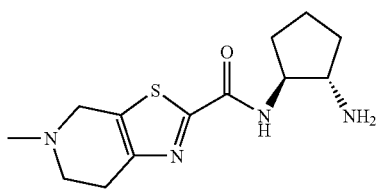

The compound obtained in Referential Example 61 (175 mg) was dissolved in N,N-dimethylformamide (3 mL), and to the solution were added 5-methyl-4,5,6,7-tetrahydrothiazolo[5,4-c]pyridine-2-carboxylic acid lithium salt (90% purity, 258 mg), 1-(3-dimethylaminopropyl)-3-ethylcarbodiimide hydrochloride (252 mg), 1-hydroxybenzotriazole monohydrate (60 mg), followed by stirring at room temperature for 2 days. The solvent was distilled away under reduced pressure by means of a pump, and the residue was partitioned by adding methylene chloride and saturated aqueous sodium hydrogencarbonate. The organic layer was washed with saturated brine, and was dried over sodium sulfate anhydrate. The solvent was distilled away under reduced pressure, and the residue was purified by silica gel flash column chromatography (methylene chloride:methanol=47:3). The resultant pale-yellow oily matter was dissolved in hydrochloric acid-ethanol (5 mL), and the solution was stirred at room temperature for 1 hour. Ethyl acetate was added thereto, and the solvent was removed under reduced pressure. Ethyl acetate was added to the residue, and the resultant precipitate was collected by filtration, to thereby give the title compound (120 mg).

¹H-NMR(DMSO-d₆)δ: 1.63-1.73(4H, m), 1.99-2.06(2H, m), 2.91(3H, s), 3.09-3.14(1H, m), 3.25-3.70(4H, m), 4.27-4.32(1H, m), 4.42-4.46(1H, m), 4.68-4.71(1H, m), 8.20-8.23 (3H, m), 9.09(1H, d, J=8.3 Hz), 11.82-12.01(1H, m).

MS(ESI)m/z: 281(M+H)⁺.

Referential Example 63

N-[(1R*,2R*)-2-aminocyclopentyl]-5-chloro-1H-indole-2-carboxamide hydrochloride

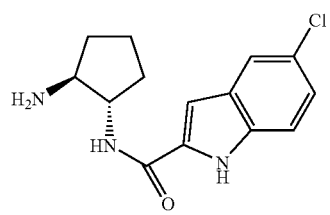

The compound obtained in Referential Example 61 (1.40 g) was dissolved in N,N-dimethylformamide (15 mL), and to the solution were added 5-chloroindole-2-carboxylic acid (1.64 g), 1-(3-dimethylaminopropyl)-3-ethylcarbodiimide hydrochloride (2.68 g), and 1-hydroxybenzotriazole monohydrate (473 mg), followed by stirring at room temperature for 23 hours. The solvent was distilled away under reduced pressure, and to the residue were added methylene chloride and saturated aqueous sodium hydrogencarbonate. The resultant precipitate was collected by filtration, and the precipitate was washed with ethyl acetate, methylene chloride, and methanol. Aside from this, the filtrate was partitioned, and the organic layer was separated, followed by drying over sodium sulfate anhydrate. The solvent was distilled away under reduced pressure, and the residue was purified by silica gel flash column chromatography (methylene chloride:methanol=19:1), to thereby give a pale-yellow solid. This pale-yellow solid was combined with the precipitate collected by the above-described filtration, and this mixture was dissolved in methylene chloride (10 mL). Trifluoroacetic acid (10 mL) was added thereto, and the thus-obtained mixture was stirred at room temperature for 3 hours. The solvent was distilled away under reduced pressure, and to the residue were added methylene chloride and 1N aqueous sodium hydroxide. The resultant precipitate was collected by filtration. The organic layer of the filtrate was separated, and was dried over sodium sulfate anhydrate. To the solution was added the precipitate collected by the above-described filtration, and a 4N HCl-dioxane solution (20 mL) was added thereto. The solvent was distilled away under reduced pressure, and after methylene chloride (10 mL) and a 4N HCl-dioxane solution (10 mL) were added to the residue, the solvent was distilled away again under reduced pressure. Ethyl acetate was added to the residue, and the resultant precipitate was collected by filtration, to thereby give the title compound (1.83 g).

¹H-NMR(DMSO-d₆)δ: 1.60-1.75(4H, m), 2.05-2.10(2H, m), 3.49(1H, q, J=7.6 Hz), 4.27(4H, quintet, J=7.6 Hz), 7.17 (1H, d, J=8.6 Hz), 7.19(1H, s), 7.42(1H, d, J=8.6 Hz), 7.70 (1H, s), 8.24(3H, br.s), 8.85(1H, d, J=7.3 Hz), 11.91(1H, s).

MS(ESI)m/z: 278(M+H)⁺.

Referential Example 64

(1R*,2R*)-2-aminocyclohexylcarbamic acid tert-butyl ester

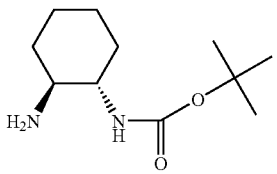

In a manner similar to that employed in Referential Example 61, the title compound was prepared from (±)-trans-1,2-cyclohexanediamine.

m.p. 79-81° C.

$^1$H-NMR(CDCl$_3$)δ: 1.05-1.34(4H, m), 1.45(9H, s), 1.68-1.75(2H, m), 1.92-2.02(2H, m), 2.32(1H, dt, J=10.3, 3.9 Hz), 3.08-3.20(1H, m), 4.50(1H, br.s).

MS(FAB)m/z: 215(M+H)$^+$.

Referential Example 65

N-[(1R*,2R*)-2-aminocyclohexyl]-5-methyl-4,5,6,7-tetrahydrothiazolo[5,4-c]pyridine-2-carboxamide trifluoroacetic acid salt (and hydrochloride)

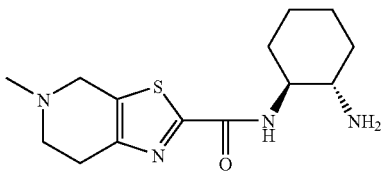

In a manner similar to that employed in Referential Example 62, the title compound was prepared from the compound obtained in Referential Example 64.

$^1$H-NMR(DMSO-d$_6$)δ: 1.10-1.80(7H, m), 1.95-2.05(1H, m), 2.97(3H, s), 3.00-3.20(3H, m), 3.63(2H, br.s), 3.72-3.88(1H, m), 4.61(2H, br.s), 7.98(3H, s), 8.89(1H, d, J=9.2 Hz).

MS(FAB)m/z: 295(M+H)$^+$.

In a manner similar to that described above, the hydrochloride was also prepared.

Referential Example 66

(1R*,2S*)-2-aminocyclohexylcarbamic acid tert-butyl ester

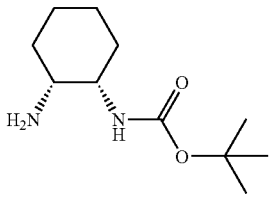

In a manner similar to that employed in Referential Example 61, the title compound was prepared from cis-1,2-cyclohexanediamine.

$^1$H-NMR(CDCl$_3$)δ: 1.30-1.70(17H, m), 2.98-3.05(1H, m), 3.60(1H, br.s), 4.98(1H, br.s).

MS(FAB)m/z: 215(M+H)$^+$.

Referential Example 67

N-[(1R*,2S*)-2-aminocyclohexyl]-5-methyl-4,5,6,7-tetrahydrothiazolo[5,4-c]pyridine-2-carboxamide hydrochloride (and trifluoroacetic acid salt)

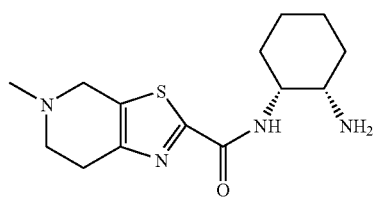

In a manner similar to that employed in Referential Example 62, the title compound was prepared from the compound obtained in Referential Example 66.

$^1$H-NMR(DMSO-d$_6$)δ: 1.30-1.90(8H, m), 2.92(3H, s), 3.05-3.79(5H, m), 4.23(1H, br.s), 4.34-4.79(2H, m), 8.01-8.34(3H, m), 8.30-8.49(1H, m), 11.90-12.30(1H, m).

MS(FAB)m/z: 295(M+H)$^+$.

In a manner similar to that described above, trifluoroacetic acid salt was also prepared.

Referential Example 68

(1R*,2R*)-2-{[(5-chloroindol-2-yl)carbonyl]amino}cyclohexylcarbamic acid tert-butyl ester

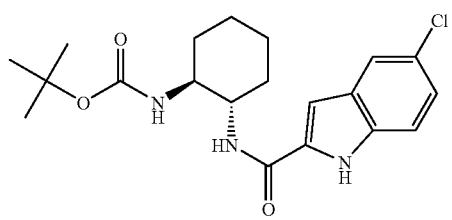

To a solution of the compound obtained in Referential Example 64 (3.00 g) in N,N-dimethylformamide (10 mL) were added 5-chloroindole-2-carboxylic acid (2.88 g), 1-hydroxybenzotriazole monohydrate (2.08 g), and 1-(3-dimethylaminopropyl)-3-ethylcarbodiimide hydrochloride (2.95 g) at room temperature, and the thus-obtained mixture was stirred for 3 days. The reaction mixture was concentrated under reduced pressure, and to the resultant residue were added methylene chloride (30 mL), saturated aqueous sodium hydrogencarbonate (150 mL), and water (150 mL). The resultant colorless precipitate was collected by filtration, and was dried, to thereby give the title compound (5.21 g).

$^1$H-NMR(DMSO-d$_6$)δ: 1.10-1.45(4H, m), 1.21(9H, s), 1.68(2H, d, J=8.1 Hz), 1.86(2H, t, J=16.2 Hz), 3.22-3.42(1H, m), 3.69(1H, br.s), 6.66(1H, d, J=8.5 Hz), 7.02(1H, s), 7.15(1H, dd, J=8.5, 2.0 Hz), 7.41(1H, d, J=8.5 Hz), 7.67(1H, d, J=2.0 Hz), 8.15(1H, d, J=8.1 Hz), 11.73(1H, br.s).

MS(ESI)m/z: 392 (M+H)$^+$.

Referential Example 69

N-[(1R*,2R*)-2-aminocyclohexyl]-5-chloroindole-2-carboxamide hydrochloride

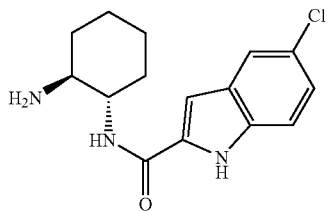

To a solution of the compound obtained in Referential Example 68 (5.18 g) in methylene chloride (100 mL) was added a HCl-ethanol solution (100 mL) at room temperature, and the mixture was stirred for 2 days. The reaction mixture was concentrated under reduced pressure, and diethyl ether (300 mL) was added to the resultant residue. The resultant colorless precipitate was collected by filtration, and was dried, to thereby give the title compound (4.30 g).

$^1$H-NMR(DMSO-d$_6$)δ: 1.20-1.36(2H, m), 1.36-1.50(2H, m), 1.60(2H, br.s), 1.90(1H, d, J=13.0 Hz), 2.07(1H, d, J=13.7 Hz), 3.06(1H, br.s), 3.83-3.96(1H, m), 7.15-7.24(2H, m), 7.45(1H, d, J=8.6 Hz), 7.73(1H, s), 8.00(3H, br.s), 8.60 (1H, d, J=8.3 Hz), 11.86(1H, s).

MS(ESI)m/z: 292(M+H)$^+$.

Referential Example 70

(1R*,2S*)-2-{[(5-chloroindol-2-yl)carbonyl]amino}cyclohexylcarbamic acid tert-butyl ester

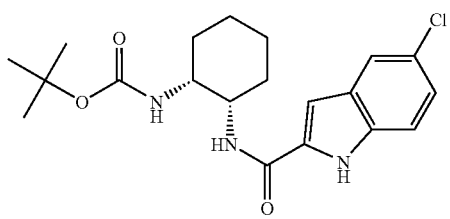

In a manner similar to that employed in Referential Example 68, the title compound was prepared from the compound obtained in Referential Example 66.

$^1$H-NMR(DMSO-d$_6$)δ: 1.20-1.45(11H, m), 1.45-1.70(4H, m), 1.70-1.85(2H, m), 3.76(1H, br.s), 4.08(1H, br.s), 6.64 (1H, d, J=7.6 Hz), 7.12(1H, s), 7.16(1H, dd, J=8.8, 2.0 Hz), 7.43(1H, d, J=8.8 Hz), 7.69(1H, d, J=2.0 Hz), 7.85(1H, d, J=6.9 Hz), 11.80(1H, br.s).

MS(ESI)m/z: 392(M+H)$^+$.

Referential Example 71

N-[(1R*,2S*)-2-aminocyclohexyl-5-chloroindole-2-carboxamide hydrochloride

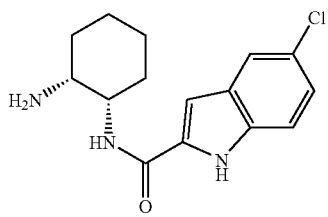

In a manner similar to that employed in Referential Example 69, the title compound was prepared from the compound obtained in Referential Example 70.

$^1$H-NMR(DMSO-d$_6$)δ: 1.30-1.50(2H, m), 1.55-1.95(6H, m), 3.41(1H, br.s), 4.32(1H, br.s), 7.19(1H, dd, J=8.7, 2.0 Hz), 7.33(1H, s), 7.45(1H, d, J=8.7 Hz), 7.60-7.90(4H, m), 8.17(1H, d, J=7.1 Hz), 11.91(1H, s).

MS(FAB)m/z: 292 (M+H)$^+$.

Referential Example 72

(1R*,2R*)-1,2-cycloheptanediol

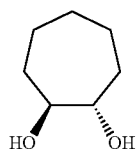

Cycloheptene (3.85 g) was added in small portions to 30% hydrogen peroxide (45 mL) and 88% formic acid (180 mL), and the thus-obtained mixture was stirred for 1 hour at 40-50° C., and then at room temperature overnight. The solvent was distilled away under reduced pressure, and to the residue was added 35% aqueous sodium hydroxide, to thereby make the mixture basic. The resultant mixture was stirred at 40-50° C. for 10 minutes, and ethyl acetate was added to the mixture to partition the mixture. The aqueous layer was extracted with ethyl acetate 4 times. The organic layers were combined, and the combined organic layer was dried over sodium sulfate anhydrate. The solvent was distilled away under reduced pressure, to thereby give the title compound (4.56 g).

$^1$H-NMR(CDCl$_3$)δ: 1.44-1.56(6H, m), 1.63-1.70(2H, m), 1.83-1.91(2H, m), 2.91(2H, br.s), 3.40-3.44(2H, m).

MS(FAB)m/z: 131 (M+H)$^+$.

Referential Example 73

(1R*,2R*)-1,2-cycloheptanediamine hydrochloride

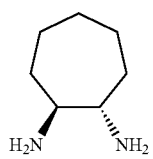

The compound obtained in Referential Example 72 (4.56 g) was dissolved in methylene chloride (35 mL), and triethylamine (29 mL) was added thereto, followed by cooling to −78° C. To the mixture was added dropwise methanesulfonyl chloride (8.13 mL), and additional methylene chloride (10 mL) was added thereto. The reaction mixture was stirred at the same temperature for 20 minutes, and then at 0° C. for 1.5 hours. Water was added to the reaction mixture to partition the mixture. The organic layer was washed with saturated aqueous sodium hydrogencarbonate, and was dried over sodium sulfate anhydrate. The solvent was distilled away under reduced pressure, to thereby give an oily matter. This oily matter was dissolved in N,N-dimethylformamide (90 mL), and sodium azide (13.65 g) was added thereto, followed by stirring at 65° C. for 18 hours. The resultant mixture was partitioned by adding diethyl ether and water. The diethyl ether layer was washed with saturated aqueous sodium hydrogencarbonate and saturated brine, and was dried over sodium sulfate anhydrate. The solvent was distilled away under reduced pressure, to thereby give an oily matter.

This oily matter was dissolved in ethanol (70 mL), and 10% palladium on carbon (50% water content, 4 g) was added thereto, followed by stirring for 4 days under hydrogen atmosphere (3.5 atm). The 10% palladium on carbon was filtered off, and a 1N HCl-ethanol solution (70 mL) was added to the filtrate. The solvent was distilled away under reduced pressure, and the residue was dissolved in methanol. Ethyl acetate was added to the solution, and the solvent was distilled away again under reduced pressure. The resultant precipitate was collected by filtration, to thereby give the title compound (3.57 g).

$^1$H-NMR(DMSO)δ: 1.44(4H, br.s), 1.73-1.81(6H, m), 3.43(2H, br.s), 8.63(6H, br.s). MS(ESI)m/z: 129(M+H)$^+$.

Referential Example 74

N-[(1R*,2R*)-2-aminocycloheptyl]-5-chloroindole-2-carboxamide

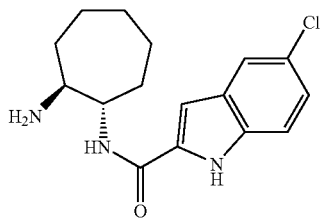

In a manner similar to that employed in Referential Example 59, the title compound was prepared from the compound obtained in Referential Example 73.

$^1$H-NMR(DMSO-d$_6$)δ: 1.49-1.52(4H, m), 1.72-1.91(6H, m), 4.04-4.10(1H, m), 7.17-7.23(2H, m), 7.44(1H, d, J=8.8 Hz), 7.72(1H, d, J=2.0 Hz), 7.96(2H, br.s), 8.75(1H, d, J=8.5 Hz), 11.89(1H, br.s).

MS(ESI)m/z: 306(M+H)$^+$.

Referential Example 75

(1R*,2S*)-1,2-cyclooctanediol

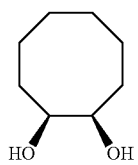

Cyclooctene (4.41 g) was dissolved in acetonitrile (45 mL) and water (15 mL), and to the solution were added N-methylmorpholine N-oxide (5.15 g), microencapsulated osmium tetraoxide (1 g, 10% osmium tetraoxide content), followed by stirring at 40-50° C. for 21 hours. Any insoluble microencapsulated osmium was filtered off, and was washed with acetonitrile. The filtrate was concentrated under reduced pressure, and the residue was purified by silica gel flash column chromatography (hexane:ethyl acetate=1:1), to thereby give the title compound (4.97 g).

$^1$H-NMR(CDCl$_3$)δ: 1.48-1.58(6H, m), 1.64-1.75(4H, m), 1.86-1.96(2H, m), 2.28(2H, d, J=2.9 Hz), 3.90(2H, d, J=8.3 Hz).

MS(FAB)m/z: 145(M+H)$^+$.

Referential Example 76

(1R*,2S*)-1,2-diazidocyclooctane

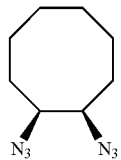

cis-1,2-Cyclooctanediol (4.82 g) was dissolved in methylene chloride (60 mL), and triethylamine (27.7 mL) was added thereto. After the reaction container was purged with argon, the reaction mixture was cooled to −78° C., and methanesulfonyl chloride (7.7 mL, 100 mmol) was added dropwise thereto. The mixture was stirred at the same temperature for 1 hour in total, and then at 0° C. for 1 hour. Water was added to the reaction mixture to partition the mixture. The organic layer was washed with water, 0.5N aqueous hydrochloric acid, water, and saturated aqueous sodium hydrogencarbonate, and was dried over sodium sulfate anhydrate. The solvent was distilled away under reduced pressure. The residue was dissolved in N,N-dimethylformamide (80 mL), and sodium azide (13.0 g) was added thereto, followed by stirring at 65° C. for 19 hours. The reaction mixture was partitioned by adding diethyl ether and water. The diethyl ether layer was washed with saturated aqueous sodium hydrogencarbonate and saturated brine, and was dried over sodium sulfate anhydrate. The solvent was distilled away under reduced pressure, and the residue was purified by silica gel flash column chromatography (hexane:ethyl acetate=6:1), to thereby give the title compound (4.85 g).

$^1$H-NMR(CDCl$_3$)δ: 1.49-1.64(6H, m), 1.67-1.78(2H, m), 1.81-1.97(4H, m), 3.74-3.76(2H, m).

Referential Example 77

(1R*,2S*)-1,2-cyclooctanediamine hydrochloride

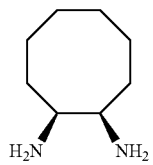

The compound obtained in Referential Example 76 (4.85 g) was dissolved in ethanol (55 mL), and 10% palladium on carbon (50% water content, 3.0 g) was added thereto, followed by stirring for 21 hours under hydrogen atmosphere (4.5 atm). The catalyst was filtered off, and to the filtrate was added a 1N HCl-ethanol solution (50 mL). The solvent was distilled away under reduced pressure, and ethyl acetate was added to the residue. The resultant precipitate was collected by filtration, to thereby give the title compound (4.14 g).

$^1$H-NMR(DMSO)δ: 1.51(6H, br.s), 1.69(2H, br.s), 1.79-1.99(4H, m), 3.68-3.70(2H, m), 8.66(6H, br.s).

MS(ESI)m/z: 143(M+H)$^+$.

Referential Example 78

N-[(1R*,2S*)-2-aminocyclooctyl]-5-chloroindole-2-carboxamide

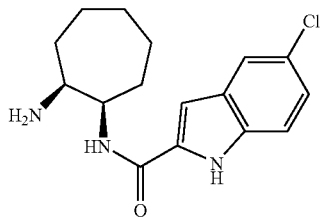

In a manner similar to that employed in Referential Example 59, the title compound was prepared from the compound obtained in Referential Example 77.

MS(ESI)m/z: 320(M+H)$^+$.

Referential Example 79

(1R*,2R*)-4-methoxy-1,2-cyclopentanediol (mixture of 4-position stereoisomers)

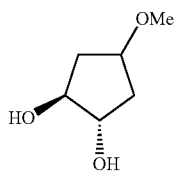

To a solution of 3-cyclopenten-1-ol (1.68 g) and methyl iodide (1.25 mL) in tetrahydrofuran (20 mL), 60% sodium hydride (800 mg) was added in small portions under ice cooling, and the thus-obtained mixture was stirred at room temperature overnight. The reaction mixture was partitioned by adding water and diethyl ether, and the organic layer was dried over anhydrous magnesium sulfate. The solvent was distilled away under reduced pressure under ice cooling, to thereby give crude 4-methoxy-1-cyclopentene.

To the thus-obtained 4-methoxy-1-cyclopentene were added 88% formic acid (90 mL) and 30% hydrogen peroxide (3.17 mL) at room temperature, and the mixture was stirred at room temperature overnight. The reaction mixture was concentrated under reduced pressure, and 35% aqueous sodium hydroxide was added to the residue, to thereby make the reaction mixture basic, followed by stirring at 50° C. for 10 minutes. The resultant mixture was cooled to room temperature, and was extracted with ethyl acetate. The organic layer was dried over anhydrous magnesium sulfate, and the solvent was distilled away. The residue was purified by silica gel column chromatography (methanol:methylene chloride=1:19), to thereby give the title compound (1.21 g).

$^1$H-NMR(CDCl$_3$)δ: 1.65-1.85(2H, m), 2.15-2.30(2H, m), 3.28(3H, s), 3.90-4.00(2H, m), 4.26(1H, br.s).

Referential Example 80

(1R*,2R*)-1,2-diazido-4-methoxycyclopentane (mixture of 4-position stereoisomers)

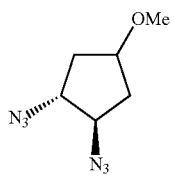

The compound obtained in Referential Example 79 (1.21 g) and triethylamine (7.66 mL) were dissolved in methylene chloride (20 mL), and methanesulfonyl chloride (2.13 mL) was added dropwise thereto at −78° C. over 20 minutes. After completion of the addition, the reaction mixture was heated to 0° C., and was stirred for 80 minutes, to thereby give crude (1R*,2R*)-1,2-bis(methanesulfonyloxy)-4-methoxycyclopentane. This crude product was dissolved in N,N-dimethylformamide (20 mL), and sodium azide (3.57 g) was added thereto, followed by stirring at 65° C. for 22 hours, and additional sodium azide (3.57 g) was added thereto, followed by stirring at 70° C. for 2 days. After the reaction mixture was left to cool, the mixture was partitioned by adding water and diethyl ether, and the organic layer was dried over anhydrous magnesium sulfate. The solvent was distilled away, and the residue was purified by silica gel column chromatography (hexane:ethyl acetate=2:1), to thereby give the title compound (584 mg).

$^1$H-NMR(CDCl$_3$)δ: 1.65-1.80(2H, m), 2.05-2.18(1H, m), 2.25-2.40(1H, m), 3.21(3H, s), 3.55-3.65(1H, m), 3.75-3.90 (2H, m).

Referential Example 81

(1R*,2R*)-4-methoxy-1,2-cyclopentanediamine hydrochloride (mixture of 4-position stereoisomers)

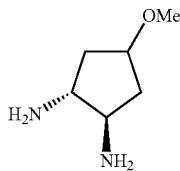

The compound obtained in Referential Example 80 (584 mg) was dissolved in ethanol, and 10% palladium on carbon (321 mg) was added thereto. The reaction mixture was subjected to hydrogenation at ambient temperature and at atmospheric pressure for 2 days. The catalyst was filtered off, and the filtrate was concentrated. To the residue were added a 1N HCl-ethanol solution and ethyl acetate, and the mixture was concentrated, to thereby give the title compound (488 mg).

$^1$H-NMR(CDCl$_3$)δ: 1.72-1.83(1H, m), 1.91-2.03(1H, m), 2.07-2.18(1H, m), 2.37-2.50(1H, m), 3.19(3H, s), 3.55-3.75 (2H, br), 3.85-3.95(1H, m), 8.60-8.90(6H, br).

MS(ESI)m/z: 261(2M+H)$^+$.

Referential Example 82

N-[(1R*,2R*)-2-amino-4-methoxycyclopentyl]-5-chloroindole-2-carboxamide (mixture of 4-position stereoisomers)

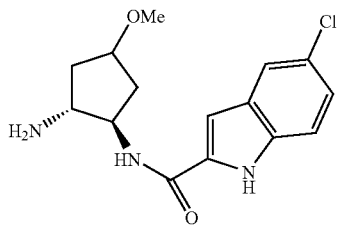

The compound obtained in Referential Example 81 (470 mg) was suspended in N,N-dimethylformamide (5 mL), and to the suspension were added triethylamine (0.966 mL) and 5-chloroindole-2-carboxylic acid p-nitrophenyl ester (805 mg), followed by stirring at room temperature for 4 days. The solvent was distilled away under reduced pressure, and the residue was partitioned by adding methylene chloride and saturated aqueous sodium hydrogencarbonate. The organic layer was dried over sodium sulfate anhydrate, and the solvent was distilled away under reduced pressure. The residue was purified by silica gel column chromatography (methanol:methylene chloride=1:9), to thereby give the title compound (268 mg).

Referential Example 83

(1R*,2R*)-4-[(benzyloxy)methyl-1,2-cyclopentanediol (mixture of 4-position stereoisomers)

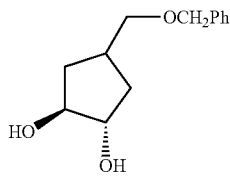

In a manner similar to that employed in Referential Example 79, 4-hydroxymethyl-1-cyclopentene (J. Heterocycl. Chem., vol. 26, p. 451 (1989)) was benzylated with benzyl bromide, and the benzylated compound was reacted with formic acid-hydrogen peroxide, to thereby give the title compound.

$^1$H-NMR(CDCl$_3$)δ: 1.44-1.52(1H, m), 1.77-1.85(1H, m), 1.89-1.97(1H, m), 2.25-2.35(1H, m), 2.46-2.58(1H, m), 3.40-3.50(2H, m), 3.89(1H, br.s), 4.08(1H, br.s), 4.54(2H, s), 7.27-7.39(5H, m).

MS(FAB)m/z: 223(M+H)$^+$.

Referential Example 84

(1R*,2R*)-4-[(benzyloxy)methyl]-1,2-cyclopentanediamine (mixture of 4-position stereoisomers)

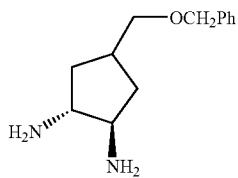

In a manner similar to that employed in Referential Example 80, (1R*,2R*)-4-benzyloxymethyl-1,2-diazidocyclopentane was prepared from the compound obtained in Referential Example 83. This compound was used in the next step without further purification, and in a manner similar to that employed in Referential Example 81, the title compound was prepared from the compound described above.

Referential Example 85

N-{(1R*,2R*)-2-amino-4-[(benzyloxy)methyl]cyclopentyl}-5-chloroindole-2-carboxamide (mixture of 4-position stereoisomers)

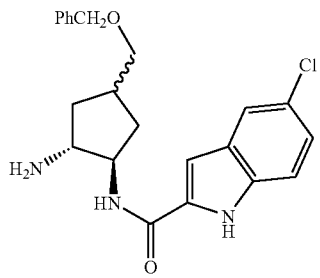

In a manner similar to that employed in Referential Example 59, the title compound was prepared from the compound obtained in Referential Example 84.

$^1$H-NMR(DMSO-d$_6$)δ: 1.07-1.15(0.5H, m), 1.26-1.35 (0.5H, m), 1.47-1.55(0.5H, m), 1.61-1.79(1H, m), 1.83-1.92 (0.5H, m), 1.99-2.10(0.5H, m), 2.12-2.20(0.5H, m), 2.27-2.40(1H, m), 3.10-3.20(1H, m), 3.33-3.39(2H, m), 3.81-3.92 (1H, m), 4.48(2H, s), 7.13-7.20(2H, m), 7.22-7.39(5H, m), 7.43(1H, d, J=8.5 Hz), 7.69(1H, d, J=2.2 Hz), 8.34(1H, t, J=7.1 Hz).

MS(FAB)m/z: 398(M+H)$^+$.

Referential Example 86

(1R*,3R,6S*)-7-oxabicyclo[4.1.0]heptane-3-carboxylic acid ethyl ester

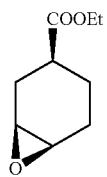

(1R*,4R*,5R*)-4-Iodo-6-oxabicyclo[3.2.1]octan-7-one (J. Org. Chem., vol. 61, p. 8687 (1996)) (14.3 g) was dissolved in ethanol (130 mL), and 2N aqueous sodium hydroxide (34.5 mL) was added to the solution under ice cooling, followed by stirring at room temperature for 7 hours. The solvent was distilled away under reduced pressure, and water was added to the residue. The mixture was extracted with methylene chloride, and the extract was dried over sodium sulfate anhydrate. The solvent was distilled away under reduced pressure, and the residue was purified by silica gel column chromatography (hexane:ethyl acetate=83:17), to thereby give the title compound (6.54 g).

$^1$H-NMR(CDCl$_3$)δ: 1.25(3H, t, J=7.1 Hz), 1.50-1.70(2H, m), 1.71-1.82(1H, m), 2.08-2.28(4H, m), 3.16(2H, s), 4.12 (2H, q, J=7.1 Hz).

Referential Example 87

(1R*,3S*,4S*)-3-azido-4-hydroxycyclohexanecarboxylic acid ethyl ester

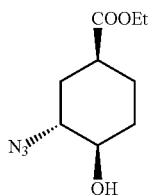

The compound obtained in Referential Example 86 (13.6 g) was dissolved in N,N-dimethylformamide (100 mL), and to the solution were sequentially added ammonium chloride (6.45 g) and sodium azide (7.8 g) at room temperature, followed by stirring at 75° C. for 12 hours. The resultant mixture was concentrated to about one-third of its original volume, and the resultant mixture was diluted with water and ethyl acetate, followed by stirring for 3 minutes. The organic layer was washed with water and saturated brine, and was dried over anhydrous magnesium sulfate. The solvent was distilled away under reduced pressure, and the residue was purified by silica gel column chromatography (ethyl acetate hexane=1:4), to thereby give the title compound (15.8 g).

$^1$H-NMR(CDCl$_3$)δ: 1.28(3H, t, J=7.1 Hz), 1.37-1.67(2H, m), 1.86-1.95(1H, m), 2.04-2.18(2H, m), 2.32-2.43(1H, m), 2.68-2.78(1H, m), 3.40-3.60(2H, m), 4.17(2H, q, J=7.1 Hz).

Referential Example 88

(1R*,3S*,4S*)-3-[(tert-butoxycarbonyl)amino]-4-hydroxycyclohexanecarboxylic acid ethyl ester

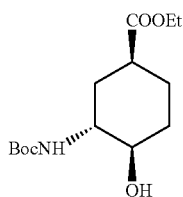

The compound obtained in Referential Example 87 (100 mg) and di-tert-butyl dicarbonate (133 mg) were dissolved in ethyl acetate (12 mL), and a catalytic amount of 10% palladium on carbon was added thereto, followed by stirring at room temperature for 12 hours under hydrogen flow. After any insoluble matter was filtered off, the solvent was distilled away under reduced pressure, and the residue was purified by silica gel column chromatography (hexane:ethyl acetate=3:1), to thereby give the title compound (145 mg).

$^1$H-NMR(CDCl$_3$)δ: 1.28(3H, t, J=7.1 Hz), 1.45(9H, s), 1.38-1.57(2H, m), 1.86-1.95(1H, m), 2.05-2.17(1H, m), 2.29-2.39(2H, m), 2.61-2.68(1H, m), 3.25-3.66(3H, m), 4.17(2H, q, J=7.1 Hz), 4.53(1H, br.s).

Referential Example 89

(1R*,3S*,4R*)-4-azido-3-[(tert-butoxycarbonyl)amino]cyclohexanecarboxylic acid ethyl ester and (1R*,3S*,4S*)-4-azido-3-[(tert-butoxycarbonyl)amino]cyclohexanecarboxylic acid ethyl ester

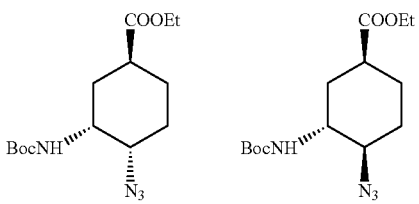

The compound obtained in Referential Example 88 (16 g) and triethylamine (38 mL) were dissolved in methylene chloride (150 mL), and after the solution was cooled to −78° C., methanesulfonyl chloride (13 mL) was added dropwise thereto at the same temperature, followed by stirring at the same temperature for 15 minutes. The resultant mixture was heated to 0° C., and was stirred for 30 minutes and then at room temperature for 2 hours. To the thus-obtained mixture was added 0.1N HCl, and the mixture was diluted with methylene chloride. The organic layer was separated, and was washed with saturated aqueous sodium hydrogencarbonate and saturated brine, followed by drying over anhydrous magnesium sulfate. The solvent was distilled away under reduced pressure, to thereby give crude (1R*,3S*,4S*)-3-[(tert-butoxycarbonyl)amino]-4-[(methylsulfonyl)oxy]cyclohexanecarboxylic acid ethyl ester.

The thus-obtained product was dissolved in N,N-dimethylformamide (100 mL), and sodium azide (18 g) was added thereto at room temperature. The mixture was heated to 75° C., and was stirred for 12 hours. The resultant mixture was concentrated to about one-third of its original volume, and the resultant mixture was diluted with water and ethyl acetate, followed by stirring for 3 minutes. The organic layer was separated, and was washed with saturated brine, followed by drying over anhydrous magnesium sulfate. The solvent was distilled away under reduced pressure, and the residue was purified by silica gel column chromatography (ethyl acetate:hexane=1:4), to thereby give the (1R*,3S*,4R*)-isomer (6.74 g) and the (1R*,3S*,4S*)-isomer (1.32 g) of the title compound.

(1R*,3S*,4R*)-isomer:

$^1$H-NMR(CDCl$_3$)δ: 1.26(3H, t, J=7.1 Hz), 1.45(9H, s), 1.38-2.33(6H, m), 2.57-2.68(1H, m), 3.77-4.20(4H, m), 4.63(1H, br.s).

(1R*,3S*,4S*)-isomer:

$^1$H-NMR(CDCl$_3$)δ: 1.27(3H, t, J=7.1 Hz), 1.46(9H, s), 1.53-2.30(6H, m), 2.50-2.65(1H, m), 3.42-3.72(2H, m), 4.15(2H, q.J=7.1 Hz), 4.67(1H, br.s).

Referential Example 90

(1R*,3S*,4R*)-4-amino-3-[(tert-butoxycarbonyl) amino]cyclohexanecarboxylic acid ethyl ester

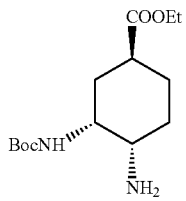

(1R*,3S*,4R*)-4-Azido-3-[(tert-butoxycarbonyl)amino] cyclohexanecarboxylic acid ethyl ester (5.4 g) obtained in Referential Example 89 was dissolved in a solvent mixture of ethanol (10 mL) and ethyl acetate (10 mL), and a catalytic amount of 10% palladium on carbon was added thereto, followed by stirring at room temperature for 20 hours under hydrogen flow. After any insoluble matter was filtered off, the solvent was distilled away under reduced pressure, to thereby give the title compound (4.7 g).

Referential Example 91

(1R*,3S*,4R*)-3-[(tert-butoxycarbonyl)amino]-4-{ [(5-chloroindol-2-yl)carbonyl] amino}cyclohexanecarboxylic acid ethyl ester

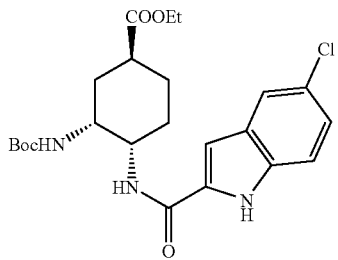

The compound obtained in Referential Example 90 (4.62 g) was dissolved in methylene chloride (50 mL), and to the solution were added 5-chloroindole-2-carboxylic acid (3.63 g), 1-hydroxybenzotriazole monohydrate (2.43 g), and 1-(3-dimethylaminopropyl)-3-ethylcarbodiimide hydrochloride (3.45 g) at room temperature, followed by stirring for 12 hours. To the reaction mixture was added 0.1N aqueous HCl, and the mixture was extracted with methylene chloride. The organic layer was washed with saturated aqueous sodium hydrogencarbonate and saturated brine, and was dried over anhydrous magnesium sulfate. The solvent was distilled away under reduced pressure, and the residue was purified by silica gel column chromatography (ethyl acetate:hexane=2:3), to thereby give the title compound (5.3 g).

$^1$H-NMR(CDCl$_3$)δ: 1.26(3H, t, J=7.1 Hz), 1.43(9H, s), 1.35-2.46(7H, m), 3.91-4.02(1H, m), 4.10-4.22(2H, m), 4.79 (1H, br.s), 6.79(1H, s), 7.18-7.40(2H, m), 7.59(1H, s), 8.00 (1H, br.s), 9.13(1H, br.s).

Referential Example 92

(1S,3S,6R)-7-oxabicyclo[4.1.0]heptane-3-carboxylic acid ethyl ester (1S,4S,5S)-4-Iodo-6-oxabicyclo[3.2.1]octan-7-one (J. Org. Chem., vol. 61, p. 8687 (1996)) (89.3 g) was suspended in ethanol (810 mL), and 2N aqueous sodium hydroxide (213 mL) was added thereto, followed by stirring at room temperature for 3 hours. The solvent was distilled away under reduced pressure, and water was added to the residue. The thus-obtained mixture was extracted with methylene chloride, and the extract was dried over anhydrous magnesium sulfate. The solvent was distilled away under reduced pressure, and the residue was purified by silica gel column chromatography (hexane:ethyl acetate=17:3), to thereby give the title compound (41.3 g).

$[α]_D^{25}$=−58° (c=1.0, chloroform).

Referential Example 93

(1S,3R,4R)-3-azido-4-hydroxycyclohexanecarboxylic acid ethyl ester

The compound obtained in Referential Example 92 (41 g) was dissolved in N,N-dimethylformamide (300 mL), and to the solution were sequentially added ammonium chloride (19.3 g) and sodium azide (23.5 g) at room temperature, followed by stirring at 76° C. for 13 hours. The reaction mixture was filtered, and the filtrate was concentrated. The residue was combined with the solid matter obtained from the above-described filtration, and the thus-obtained mixture was dissolved in water. The solution was extracted with ethyl acetate. The organic layer was washed with water and saturated brine, and was dried over anhydrous magnesium sulfate. The solvent was distilled away under reduced pressure, to thereby give the title compound (51.5 g).

$[α]_D^{25}$=+8° (c=1.0, chloroform)

Referential Example 94

(1S,3R,4R)-3-[(tert-butoxycarbonyl)amino]-4-hydroxycyclohexanecarboxylic acid ethyl ester The compound obtained in Referential Example 93 (51.2 g) and di-tert-butyl dicarbonate (68.1 g) were dissolved in ethyl acetate (1000 mL), and 5% palladium on carbon (5.0 g) was added thereto, followed by stirring at room temperature overnight under hydrogen at a pressure of 7 kg/cm$^2$. After any insoluble matter was filtered off, the solvent was removed under reduced pressure, and the residue was purified by silica gel column chromatography (hexane:ethyl acetate=4:1→3: 1), followed by precipitation by addition of hexane, to thereby give the title compound (46.9 g).

$[α]_D^{25}$=+25° (c=1.0, chloroform).

Referential Example 95

(1S,3R,4S)-4-azido-3-[(tert-butoxycarbonyl)amino] cyclohexanecarboxylic acid ethyl ester and (1S,3R, 4R)-4-azido-3-[(tert-butoxycarbonyl)amino]cyclohexanecarboxylic acid ethyl ester The compound obtained in Referential Example 94 (53.5 g) and triethylamine (130 mL) were dissolved in methylene chloride (500 mL), and methanesulfonyl chloride (42 mL) was added dropwise thereto at −10 to −15° C. over 20 minutes, followed by stirring at the same temperature for 20 minutes, and the resultant mixture was heated to room temperature over 2 hours. The reaction mixture was cooled to 0° C., and 0.5N HCl (800 mL) was added dropwise thereto, followed by extraction with methylene chloride. The organic layer was washed with saturated aqueous sodium hydrogencarbonate and saturated brine, and was dried over anhydrous magnesium sulfate. The solvent was distilled away under reduced pressure, to thereby give crude (1S,3R,4R)-3-[(tert-butoxycarbonyl)amino]-4-[(methylsulfonyl)oxy]cyclohexanecarboxylic acid ethyl ester.

The crude product was dissolved in N,N-dimethylformamide (335 mL), and sodium azide (60.5 g) was added thereto, followed by stirring at 67 to 75° C. for 16 hours. The reaction mixture was filtered, and the filtrate was concentrated, to thereby evaporate 250 mL of the solvent. The residue was combined with the solid matter collected by the above-described filtration, and the thus-obtained mixture was dissolved in water, followed by extraction with ethyl acetate. The organic layer was washed with saturated brine, and was dried over anhydrous magnesium sulfate. The solvent was distilled away under reduced pressure. The residue was purified by silica gel column chromatography (ethyl acetate hexane=1:4), to thereby give the (1S,3R,4S)-isomer (18.4 g) of the title compound and the (1S,3R,4R)-isomer (3.3 g) of the title compound.

(1S,3R,4S)-isomer: $[\alpha]_D^{25}=+62°$ (c=1.0, chloroform).
(1S,3R,4R)-isomer: $[\alpha]_D^{25}=-19°$ (c=1.0, chloroform).

Referential Example 96

(1S,3R,4S)-4-amino-3-[(tert-butoxycarbonyl)amino]cyclohexanecarboxylic acid ethyl ester The compound obtained in Referential Example 95 (4.0 g) was dissolved in a solvent mixture of ethanol (150 mL) and ethyl acetate (150 mL), and 5% palladium on carbon (0.5 g) was added thereto, followed by stirring at room temperature for 17 hours under hydrogen atmosphere (5 kg/cm$^2$). After any insoluble matter was filtered off, the solvent was distilled away under reduced pressure, to thereby give the title compound (4.2 g).

Referential Example 97

(1S,3R,4S)-3-[(tert-butoxycarbonyl)amino]-4-{[(5-chloroindol-2-yl)carbonyl]amino}cyclohexanecarboxylic acid ethyl ester

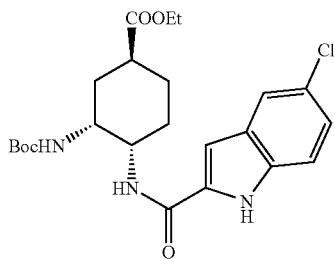

The compound obtained in Referential Example 96 (4.2 g) was dissolved in methylene chloride (50 mL), and to the solution were added 5-chloroindole-2-carboxylic acid (3.33 g), 1-hydroxybenzotriazole monohydrate (2.52 g), and 1-(3-dimethylaminopropyl)-3-ethylcarbodiimide hydrochloride (3.15 g) at room temperature, followed by stirring for 12 hours. To the reaction mixture was added 0.1N aqueous HCl, and the mixture was extracted with methylene chloride. The organic layer was washed with saturated aqueous sodium hydrogencarbonate and saturated brine, and was dried over anhydrous magnesium sulfate. The solvent was distilled away under reduced pressure, and the residue was purified by silica gel column chromatography (ethyl acetate:hexane=1:1), to thereby give the title compound (4.36 g).

$[\alpha]_D=-27°$ (c=1.0, chloroform).

Referential Example 98

(1R*,3S*,4R*)-3-[(tert-butoxycarbonyl)amino]-4-{[(5-methyl-4,5,6,7-tetrahydrothiazolo[5,4-c]pyridin-2-yl)carbonyl]amino}cyclohexanecarboxylic acid ethyl ester

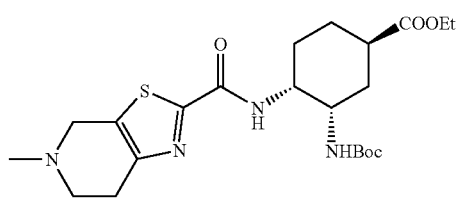

In a manner similar to that employed in Referential Example 91, the title compound was prepared from the compound obtained in Referential Example 90 and the compound obtained in Referential Example 10.

Referential Example 99

3-cyclohexene-1-carboxylic acid benzyl ester

(±)-3-Cyclohexene-1-carboxylic acid (50 g) was dissolved in N,N-dimethylformamide (550 mL), and to the solution were added triethylamine (170 mL) and benzyl bromide (61 mL) under ice cooling, followed by stirring at room temperature for 12 hours. Water was added to the resultant mixture, and the mixture was extracted with ethyl acetate. The organic layer was washed with saturated brine, and was dried over anhydrous magnesium sulfate. The solvent was distilled away under reduced pressure, and the residue was purified by silica gel column chromatography (hexane:ethyl acetate=3:1), to thereby give the title compound (70.8 g).

$^1$H-NMR(CDCl$_3$)δ: 1.66-1.76(1H, m), 2.00-2.13(3H, m), 2.27-2.29(2H, m), 2.58-2.65(1H, m), 5.13(2H, s), 5.66(2H, br.s), 7.29-7.38(5H, m).

Referential Example 100

(1R*,3S*,6S*)-7-oxabicyclo[4.1.0]heptane-3-carboxylic acid benzyl ester

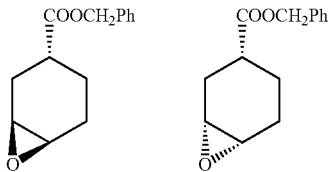

The compound obtained in Referential Example 99 (40 g) was dissolved in methylene chloride (500 mL), and m-chloroperbenzoic acid (86 g) was added thereto under ice cooling, followed by stirring for 2 hours. To the resultant mixture was added 10% aqueous sodium thiosulfate, and the mixture was stirred for 20 minutes. The organic layer was separated, and was washed with saturated sodium hydrogencarbonate and saturated brine, followed by drying over anhydrous magnesium sulfate. The solvent was distilled away under reduced pressure, and the residue was purified by silica gel column chromatography (ethyl acetate:hexane=1:9), to thereby give the title compound (23.4 g) and (1R*,3R*,6S*)-7-oxabicyclo[4.1.0]heptane-3-carboxylic acid benzyl ester (12.1 g).

$^1$H-NMR(CDCl$_3$)δ: 1.39-1.49(1H, m), 1.75-1.82(1H, m), 1.90-2.04(3H, m), 2.30(1H, dd, J=14.9, 4.9 Hz), 2.54-2.61 (1H, m), 3.12-3.14(1H, m), 3.22-3.24(1H, m), 5.12(2H, s), 7.30-7.39(5H, m).

MS(FAB)m/z: 233(M+H)$^+$.

Referential Example 101

(1R*,3S*,4S*)-4-azido-3-hydroxycyclohexanecarboxylic acid benzyl ester

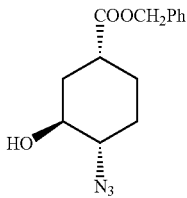

The compound obtained in Referential Example 100 (52.3 g) was dissolved in N,N-dimethylformamide (1000 mL), and to the solution were added ammonium chloride (21.9 g) and sodium azide (18.1 g), followed by stirring at 70° C. for 24 hours. The solvent was distilled away under reduced pressure, and water was added to the residue, followed by extraction with ethyl acetate. The organic layer was washed with saturated brine, and was dried over anhydrous magnesium sulfate. The solvent was distilled away under reduced pressure, to thereby give the title compound (61.8 g).

$^1$H-NMR(CDCl$_3$)δ: 1.51-1.66(2H, m), 1.91-1.98(1H, m), 2.07-2.10(1H, m), 2.27-2.32(1H, m), 2.51-2.52(1H, m), 2.81-2.86(1H, m), 3.30-3.36(1H, m), 3.70-3.75(1H, m), 5.13(2H, s), 7.30-7.39(5H, m).

Referential Example 102

(1R*,3S*,4S*)-4-[(tert-butoxycarbonyl)amino]-3-hydroxycyclohexanecarboxylic acid benzyl ester

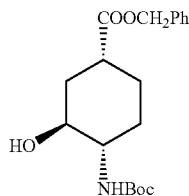

The compound obtained in Referential Example 101 (5.27 g) was dissolved in tetrahydrofuran (25 mL), and triphenylphosphine (5.53 g) and water (0.55 mL) were added to the solution, followed by stirring at room temperature for 20 hours. To the reaction mixture was added di-tert-butyl dicarbonate (4.82 g), and the mixture was stirred for an additional 2 hours. The solvent was distilled away under reduced pressure, and the residue was purified by silica gel column chromatography (hexane:ethyl acetate=2:1), to thereby give the title compound (6.22 g).

$^1$H-NMR(CDCl$_3$)δ: 1.44(9H, s), 1.59-1.66(2H, m), 1.88-2.00(2H, m), 2.29-2.32(1H, m), 2.80-2.85(1H, m), 3.02(1H, br.s), 3.42(1H, br.s), 3.59-3.65(1H, m), 4.56(1H, br.s), 5.12 (2H, q, J=12.5 Hz), 7.30-7.38(5H, m).

MS(FAB)m/z: 350(M+H)$^+$.

Referential Example 103

(1R*,3S*,4S*)-4-[(tert-butoxycarbonyl)amino]-3-hydroxycyclohexanecarboxylic acid methyl ester

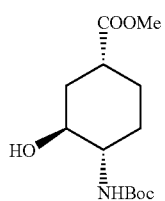

The compound obtained in Referential Example 102 (2.54 g) was dissolved in ethyl acetate (15 mL), and a catalytic amount of 10% palladium on carbon was added thereto, followed by stirring at room temperature for 20 hours under hydrogen flow. The catalyst was filtered off, and the filtrate was concentrated under reduced pressure, to thereby give (1R*,3S*,4S*)-4-[(tert-butoxycarbonyl)amino]-3-hydroxycyclohexanecarboxylic acid as a colorless oily matter. This oily matter was dissolved in a solvent mixture of methanol (8 mL) and toluene (15 mL), and a 2N solution of trimethylsilyldiazomethane in hexane (10 mL) was added to the solution under ice cooling, followed by stirring at room temperature for 30 minutes. The solvent was distilled away under reduced pressure, and was purified by silica gel column chromatography (hexane:ethyl acetate=1:1), to thereby give the title compound (1.82 g).

$^1$H-NMR(CDCl$_3$)δ: 1.44(9H, s), 1.36-2.32(7H, m), 2.74-2.82(1H, m), 3.04(1H, br.s), 3.33-3.47(1H, m), 3.55-3.65 (1H, m), 3.68(3H, s), 4.56(1H, br.s).

MS(FAB)m/z: 274 (M+H)$^+$.

Referential Example 104

(1R*,3R*,4S*)-3-azido-4-[(tert-butoxycarbonyl)amino]cyclohexanecarboxylic acid methyl ester and (1R*,3S*,4S*)-3-azido-4-[(tert-butoxycarbonyl)amino]cyclohexanecarboxylic acid methyl ester

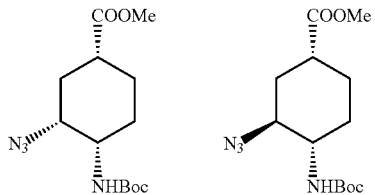

The compound obtained in Referential Example 103 (1.81 g) was dissolved in methylene chloride (36 mL), and to the solution were added triethylamine (4.6 mL) and methanesulfonyl chloride (1.63 mL) at −78° C. After 30 minutes, the reaction mixture was heated to 0° C., and was further stirred for an additional 30 minutes. To the resultant mixture was added 1N HCl, and the mixture was extracted with methylene chloride. The organic layer was washed with saturated brine, and was dried over anhydrous magnesium sulfate. The solvent was distilled away under reduced pressure, to thereby give crude (1R*,3S*,4S*)-4-[(tert-butoxycarbonyl)amino]-3-[(methylsulfonyl)oxy]cyclohexanecarboxylic acid methyl ester.

This crude product was dissolved in N,N-dimethylformamide (23 mL), and sodium azide (1.29 g) was added thereto, followed by stirring at 70° C. for 12 hours. Water was added to the reaction mixture, and the mixture was extracted with ethyl acetate. The organic layer was washed with saturated brine, and was dried over anhydrous magnesium sulfate. The solvent was distilled away under reduced pressure, and the residue was purified by silica gel column chromatography (ethyl acetate:hexane=3:17), to thereby give (1R*,3S*,4S*)-3-azido-4-[(tert-butoxycarbonyl)amino]cyclohexanecarboxylic acid methyl ester (85 mg) and (1R*,3R*,4S*)-3-azido-4-[(tert-butoxycarbonyl)amino]cyclohexanecarboxylic acid methyl ester (590 mg).

(1R*,3R*,4S*)-isomer: $^1$H-NMR(CDCl$_3$)δ: 1.45(9H, s), 1.35-2.35(7H, m), 2.45-2.55(1H, m), 3.73(3H, s), 3.67-3.84 (2H, m), 4.70(1H, br.s).

MS(FAB)m/z: 299(M+H)$^+$.

(1R*,3S*,4S*)-isomer: $^1$H-NMR(CDCl$_3$)δ: 1.45(9H, s), 1.56-2.25(7H, m), 2.68-2.80(1H, m), 3.70(3H, s), 3.48-3.68 (2H, m), 4.56(1H, br.s).

MS(FAB)m/z: 299(M+H)$^+$.

Referential Example 105

(1R*,3R*,4S*)-3-amino-4-[(tert-butoxycarbonyl)amino]cyclohexanecarboxylic acid methyl ester

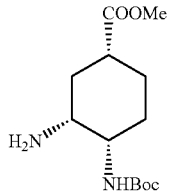

The (1R*,3R*,4S*)-compound (230 mg) obtained in Referential Example 104 was dissolved in ethyl acetate (8 mL), and a catalytic amount of 10% palladium on carbon was added thereto, followed by stirring for 20 hours under hydrogen flow. Any insoluble matter was filtered off, and the filtrate was concentrated under reduced pressure, to thereby give the title compound (220 mg).

Referential Example 106

(1R*,3R*,4S*)-4-[(tert-butoxycarbonyl)amino]-3-{[(5-methyl-4,5,6,7-tetrahydrothiazolo[5,4-c]pyridin-2-yl)carbonyl]amino}cyclohexanecarboxylic acid methyl ester

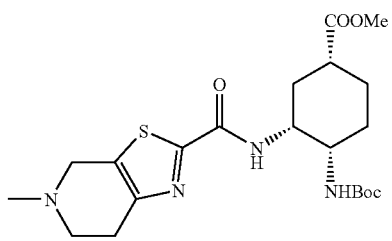

In a manner similar to that employed in Referential Example 91, the title compound was prepared from the compound obtained in Referential Example 105 and the compound obtained in Referential Example 10.

$^1$H-NMR(CDCl$_3$)δ: 1.46(9H, s), 1.53-1.95(5H, m), 2.17-2.24(1H, m), 2.50(3H, s), 2.50-2.53(1H, m), 2.80-2.96(4H, m), 3.67(3H, s), 3.69-3.74(1H, m), 4.10(2H, br.s), 4.88(1H, br.s).

MS(FAB)m/z: 453(M+H)$^+$.

Referential Example 107

(1R*,3R*,4S*)-4-[(tert-butoxycarbonyl)amino]-3-{[(5-chloroindol-2-yl)carbonyl]amino}cyclohexanecarboxylic acid methyl ester

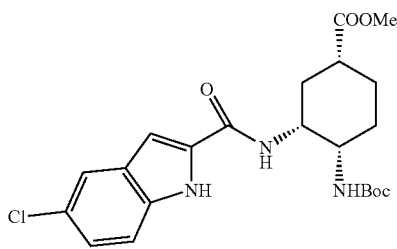

In a manner similar to that employed in Referential Example 91, the title compound was prepared from the compound obtained in Referential Example 105.

$^1$H-NMR(CDCl$_3$)δ: 1.33(9H, s), 1.42-2.47(6H, m), 2.78-2.88(1H, m), 3.70(3H, s), 3.86-4.15(2H, m), 4.65-4.75(1H, m), 6.86(1H, br.s), 7.18-7.38(2H, m), 7.57-7.61(1H, m), 8.32 (1H, br.s). MS(ESI)m/z: 450(M+H)$^+$.

Referential Example 108

(1S,3R,6R)-7-oxabicyclo[4.1.0]heptane-3-carboxylic acid benzyl ester

1) In a manner similar to that employed in Referential Example 99, (1R)-3-cyclohexene-1-carboxylic acid benzyl ester was prepared from (1R)-3-cyclohexene-1-carboxylic acid (J. Am. Chem. Soc, vol. 100, p. 5199 (1978)).

2) In a manner similar to that employed in Referential Example 100, the title compound was prepared from the thus-obtained product.
MS(FAB)m/z: 233(M+H)⁺.

Referential Example 109

(1R,3S,4S)-4-[(tert-butoxycarbonyl)amino]-3-hydroxycyclohexanecarboxylic acid benzyl ester 1) In a manner similar to that employed in Referential Example 101, (1R,3S,4S)-4-azido-3-hydroxycyclohexanecarboxylic acid benzyl ester was prepared from the compound obtained in Referential Example 108.

2) In a manner similar to that employed in Referential Example 102, the title compound was prepared from the thus-obtained product.
MS(FAB)m/z: 350(M+H)⁺.

Referential Example 110

(1R,3R,4S)-3-azido-4-[(tert-butoxycarbonyl)amino] cyclohexanecarboxylic acid benzyl ester

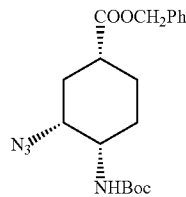

In a manner similar to that employed in Referential Example 104, the title compound was prepared from the compound obtained in Referential Example 109.
¹H-NMR(CDCl₃)δ: 1.45(9H, s), 1.52-1.66(2H, m), 1.83-2.01(3H, m), 2.20-2.28(1H, m), 2.51-2.54(1H, m), 3.77(2H, br.s), 4.70(1H, br.s), 5.15(2H, ABq, J=12.2 Hz), 7.33-7.38 (5H, m).
MS(FAB)m/z: 375(M+H)⁺.

Referential Example 111

(1R,3R,4S)-3-azido-4-[(tert-butoxycarbonyl)amino] cyclohexanecarboxylic acid methyl ester

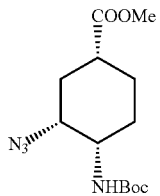

The compound obtained in Referential Example 110 (3.5 g) was dissolved in tetrahydrofuran (130 mL) and water (16 mL), and lithium hydroxide (291 mg) was added to the solution under ice cooling. After 10 minutes, the reaction mixture was brought back to room temperature, and was stirred for 20 hours. The solvent was distilled away under reduced pressure, and the residue was subjected to silica gel column chromatography (methanol:methylene chloride=1:20), to thereby give (1R,3R,4S)-3-azido-4-[(tert-butoxycarbonyl)amino]cyclohexanecarboxylic acid (3.34 g) as a pale-yellow oily matter. This oily matter was dissolved in methanol (18 mL) and toluene (64 mL), and to the solution was added a 2M solution of trimethylsilyldiazomethane in hexane (6.1 mL) under ice cooling. After 10 minutes, the reaction mixture was brought back to room temperature, and was stirred for 2 hours. The solvent was distilled away under reduced pressure, and the residue was purified by silica gel column chromatography (ethyl acetate:hexane=1:4), to thereby give the title compound (3.35 g).
¹H-NMR(CDCl₃)δ: 1.45(9H, s), 1.57-1.63(2H, m), 1.82-1.85(1H, m), 1.95-1.99(2H, m), 2.20-2.28(1H, m), 2.48-2.51 (1H, m), 3.73(3H, s), 3.78(2H, br.s), 4.70-4.72(1H, m).
MS(FAB)m/z: 299 (M+H)⁺.

Referential Example 112

(1R,3R,4S)-4-[(tert-butoxycarbonyl)amino]-3-{[(5-methyl-4,5,6,7-tetrahydrothiazolo[5,4-c]pyridin-2-yl)carbonyl]amino}cyclohexanecarboxylic acid methyl ester

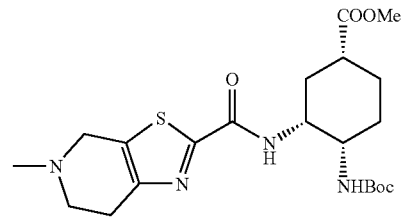

1) In a manner similar to that employed in Referential Example 105, (1R,3R,4S)-3-amino-4-[(tert-butoxycarbonyl) amino]cyclohexanecarboxylic acid methyl ester was prepared from the compound obtained in Referential Example 111.

2) In a manner similar to that employed in Referential Example 106, the title compound was prepared from the thus-obtained product and the compound obtained in Referential Example 10.
MS(FAB)m/z: 453(M+H)⁺.

Referential Example 113

(1R*,2S*,5S*)-5-aminocarbonyl-2-{[(5-chloroindol-2-yl)carbonyl]amino}cyclohexylcarbamic acid tert-butyl ester

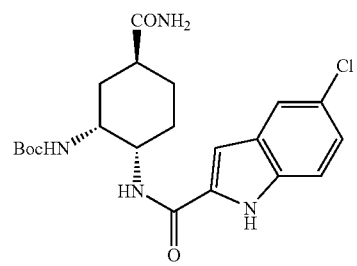

The compound obtained in Referential Example 91 (590 mg) was dissolved in a solvent mixture of ethanol (3 mL) and tetrahydrofuran (6 mL), and 1N aqueous sodium hydroxide (2.5 mL) was added thereto at room temperature, followed by stirring for 12 hours. The solvent was distilled away, to thereby give (1R*,3S*,4R*)-3-[(tert-butoxycarbonyl)amino]-4-{[(5-chloroindol-2-yl)carbonyl]amino}cyclohexanecarboxylic acid sodium salt. This compound was suspended in N,N-dimethylformamide (4 mL), and to the suspension were added di-tert-butyl dicarbonate (654 mg) and ammonium hydrogencarbonate (1 g) at room temperature, followed by stirring for 18 hours. The solvent was distilled away under reduced pressure, and water was added thereto; The resultant mixture was extracted with chloroform. The organic layer was washed with saturated brine, and was dried over anhydrous magnesium sulfate. The solvent was distilled away under reduced pressure, and the residue was purified by silica gel column chromatography (methylene chloride:methanol=47:3), to thereby give the title compound (82 mg).

MS(ESI)m/z: 435(M+H)$^+$.

Referential Example 114

(1R,6S)-6-{[(benzyloxy)carbonyl]amino}-3-cyclohexen-1-ylcarbamic acid benzyl ester

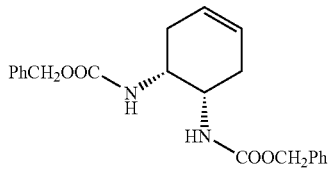

4-Cyclohexene-1,2-diamine hydrochloride (4.0 g) was dissolved in a solvent mixture of water (20 mL) and acetonitrile (20 mL), and to the solution were added benzyl chloroformate (7.66 mL) and potassium carbonate (14.9 g), followed by stirring at room temperature for 3 days. The reaction mixture was poured into water, and the thus-obtained mixture was extracted with methylene chloride. The organic layer was washed with saturated brine, and was dried over sodium sulfate anhydrate. The solvent was distilled away under reduced pressure, and the residue was purified by silica gel column chromatography (methylene chloride), to thereby give the title compound (8.22 g).

$^1$H-NMR(CDCl$_3$)δ: 2.03(2H, m), 2.53(2H, d, J=17.1 Hz), 3.77(2H, m), 5.03(2H, q, J=12.3 Hz), 5.09(2H, q, J=12.3 Hz), 5.59(2H, s), 7.32(10H, m).

MS(ESI)m/z: 381(M+H)$^+$.

Referential Example 115

(1R*,2S*)-2-{[(benzyloxy)carbonyl]amino}-5-hydroxycyclohexylcarbamic acid benzyl ester

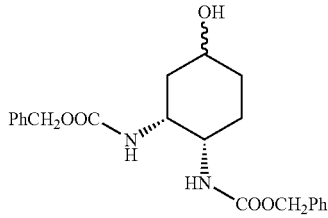

The compound obtained in Referential Example 114 (10 g) was dissolved in anhydrous tetrahydrofuran (70 mL), and borane-dimethyl sulfide complex (7.4 mL) was added thereto at 0° C. The thus-obtained mixture was gradually heated to room temperature, followed by stirring for 14 hours, and ice was added to the reaction mixture, to thereby decompose excess borane. To the resultant mixture were added 1N aqueous sodium hydroxide (80 mL) and 30% hydrogen peroxide (80 mL), and the thus-obtained mixture was stirred for 1 hour. The resultant mixture was extracted with ethyl acetate. The organic layer was washed with saturated brine, and was dried over sodium sulfate anhydrate. The solvent was distilled away under reduced pressure, and the residue was purified by silica gel column chromatography (ethyl acetate:hexane=2:1), to thereby give the title compound (9.2 g).

$^1$H-NMR(CDCl$_3$)δ: 1.98(1H, m), 2.08(1H, m), 2.30(1H, m), 3.43(2H, m), 3.73(1H, m), 5.06(6H, m), 7.32(10H, s).

MS(ESI)m/z: 399(M+H)$^+$.

Referential Example 116

(1R*,2S*)-2-{[(benzyloxy)carbonyl]amino}-5-oxo-cyclohexylcarbamic acid benzyl ester

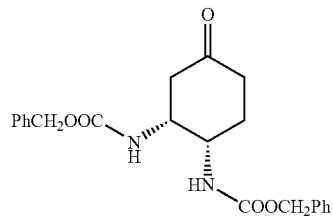

Dimethyl sulfoxide (8.2 mL) was added to a solution of oxalyl chloride (9.9 mL) in methylene chloride (90 mL) while being stirred at −60° C. Subsequently, a solution of the compound obtained in Referential Example 115 (9.2 g) in tetrahydrofuran (90 mL) was added thereto all at once. After 1 hour, the resultant mixture was heated to −40° C., and triethylamine (26 mL) was added thereto all at once. The thus-obtained mixture was heated to room temperature, and was stirred for 3 hours. The reaction mixture was poured into water, and the mixture was extracted with methylene chloride. The organic layer was washed with saturated brine, and was dried over sodium sulfate anhydrate. The solvent was distilled away under reduced pressure, and the residue was purified by silica gel column chromatography (ethyl acetate hexane=1:1), to thereby give the title compound (8.0 g).

$^1$H-NMR(CDCl$_3$)δ: 2.27-2.43(4H, m), 2.78(1H, dd, J=14.4, 3.9 Hz), 3.86(2H, m), 5.08(4H, m), 5.22(2H, m), 7.32(10H, m).

MS(ESI)m/z: 397(M+H)$^+$.

Referential Example 117

(1R*,2S*)-2-{[(benzyloxy)carbonyl]amino}-5,5-dimethoxycyclohexylcarbamic acid benzyl ester

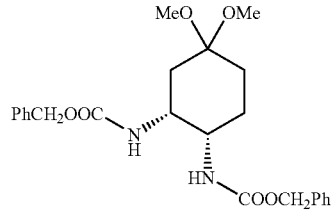

The compound obtained in Referential Example 116 (3.89 g) was dissolved in a solvent mixture of methanol (15 mL) and tetrahydrofuran (15 mL), and to the solution were added 2,2-dimethoxypropane (10.7 mL) and p-toluenesulfonic acid (187 mg), followed by stirring at room temperature for 3 hours. The solution was concentrated, and saturated aqueous sodium hydrogencarbonate was added thereto, followed by extraction with ethyl acetate. The organic layer was washed with saturated brine, and was dried over sodium sulfate anhydrate. The solvent was distilled away under reduced pressure, and the residue was purified by silica gel column chromatography (ethyl acetate:hexane=1:2), to thereby give the title compound (3.54 g).

$^1$H-NMR(CDCl$_3$)δ: 1.30-1.41(4H, m), 1.93(1H, m), 2.38 (1H, m), 3.19(6H, s), 3.46(1H, m), 3.59(1H, m), 5.03(2H, q, J=12.5 Hz), 5.09(2H, q, J=12.5 Hz), 7.32(10H, s).

Referential Example 118

N-[(1R*,2S*)-2-amino-4,4-dimethoxycyclohexyl]-5-chloroindole-2-carboxamide and N-[(1R*,2S*)-2-amino-5,5-dimethoxycyclohexyl]-5-chloroindole-2-carboxamide

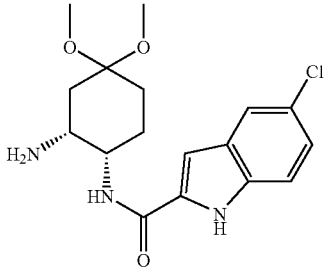

The compound obtained in Referential Example 117 (1.45 g) was dissolved in methanol (12 mL), and 10% palladium on carbon (290 mg) was added thereto, followed by stirring at room temperature for 20 hours under hydrogen atmosphere. Additional 10% palladium on carbon (290 mg) and methanol (10 mL) were added thereto, and the thus-obtained mixture was stirred for 8 hours. The reaction mixture was filtered through Celite, and the filtrate was concentrated. The residue was dissolved in N,N-dimethylformamide (10 mL), and to the solution were added 5-chloroindole-2-carboxylic acid (320 mg), 1-(3-dimethylaminopropyl)-3-ethylcarbodiimide hydrochloride (377 mg), 1-hydroxybenzotriazole monohydrate (301 mg), and N-methylmorpholine (360 mL), followed by stirring at room temperature for 14 hours. The reaction mixture was poured into aqueous sodium hydrogencarbonate, and the mixture was extracted with ethyl acetate. The organic layer was washed with saturated brine, and was dried over sodium sulfate anhydrate. The solvent was distilled away under reduced pressure, and the residue was purified by silica gel thin layer chromatography (methylene chloride:methanol=93:7), to thereby isolate N-[(1R*,2S*)-2-amino-4,4-dimethoxycyclohexyl]-5-chloroindole-2-carboxamide (or N-[(1R*,2S*)-2-amino-5,5-dimethoxycyclohexyl]-5-chloroindole-2-carboxamide) (98 mg) and N-[(1R*,2S*)-2-amino-5,5-dimethoxycyclohexyl]-5-chloroindole-2-carboxamide (or N-[(1R*,2S*)-2-amino-4,4-dimethoxycyclohexyl]-5-chloroindole-2-carboxamide) (105 mg).

N-[(1R*,2S*)-2-amino-4,4-dimethoxycyclohexyl]-5-chloroindole-2-carboxamide $^1$H-NMR(CDCl$_3$)δ: 1.45-1.50(2H, m), 2.06-2.10(2H, m), 2.34(1H, d, J=13.1 Hz), 2.78(1H, dt, J=2.9, 13.1 Hz), 3.18 (3H, s), 3.23(3H, s), 3.75-3.77(1H, m), 6.24(1H, d, J=8.3 Hz), 6.79(1H, s), 7.23(1H, dd, J=8.8, 2.0 Hz), 7.35(1H, d, J=8.8 Hz), 7.60(1H, d, J=8.8 Hz), 9.53(1H, br.s).

MS(ESI)m/z: 352(M+H)$^+$.

N-[(1R*,2S*)-2-amino-5,5-dimethoxycyclohexyl]-5-chloroindole-2-carboxamide $^1$H-NMR(CDCl$_3$)δ: 1.83-1.87(1H, m), 1.97-2.01(1H, m), 2.39(1H, br, J=13.2 Hz), 2.86-2.90(1H, m), 3.22-3.28(10H, m), 4.00-4.02(1H, m), 6.77(1H, s), 7.23(1H, d, J=8.5 Hz), 7.37(1H, d, J=8.5 Hz), 7.61(1H, s), 9.49(1H, br.s).

MS(ESI)m/z: 352 (M+H)$^+$.

Referential Example 119

(7R*,8S*)-7-{[(benzyloxy)carbonyl]amino}-1,4-dioxaspiro[4.5]dec-8-ylcarbamic acid benzyl ester

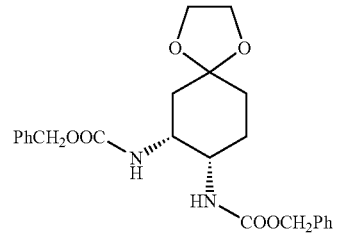

The compound obtained in Referential Example 116 (4.0 g) was dissolved in anhydrous tetrahydrofuran (30 mL), and to the solution were added ethylene glycol (5.6 mL) and p-toluenesulfonic acid (192 mg), followed by stirring at room temperature for 17 hours. The reaction mixture was poured into saturated aqueous sodium hydrogencarbonate, and the mixture was extracted with ethyl acetate. The organic layer was washed with saturated brine, and was dried over sodium sulfate anhydrate. The solvent was distilled away under reduced pressure, and the residue was purified by silica gel column chromatography (ethyl acetate:hexane=1:1), to thereby give the title compound (4.23 g).

$^1$H-NMR(CDCl$_3$)δ: 1.65-1.71(4H, m), 2.00(1H, m), 2.11 (1H, m), 3.49(1H, m), 3.73(1H, m), 3.93(4H, s), 5.03(2H, q, J=12.2 Hz), 5.08(2H, q, J=12.2 Hz), 7.32(10H, s).

MS(ESI)m/z: 441(M+H)$^+$.

Referential Example 120

N-[(7R*,8S*)-7-amino-1,4-dioxaspiro[4.5]dec-8-yl]-5-chloroindole-2-carboxamide and N-[(7R*,8S*)-8-amino-1,4-dioxaspiro[4.5]dec-7-yl]-5-chloroindole-2-carboxamide

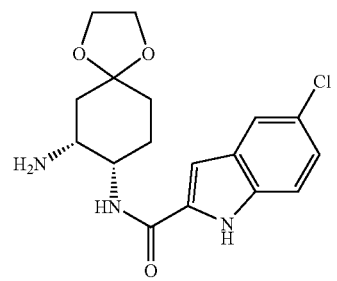

In a manner similar to that employed in Referential Example 118, N-[(7R*,8S*)-7-amino-1,4-dioxaspiro[4.5] dec-8-yl]-5-chloroindole-2-carboxamide (or N-[(7R*,8S*)-8-amino-1,4-dioxaspiro[4.5]dec-7-yl]-5-chloroindole-2-carboxamide) and N-[(7R*,8S*)-8-amino-1,4-dioxaspiro[4.5] dec-7-yl]-5-chloroindole-2-carboxamide (or N-((7R*,8S*)-7-amino-1,4-dioxaspiro[4.5]dec-8-yl]-5-chloroindole-2-carboxamide) were prepared from the compound obtained in Referential Example 119.

N-[(7R*,8S*)-8-amino-1,4-dioxaspiro[4.5]dec-7-yl]-5-chloroindole-2-carboxamide (or N-[(7R*,8S*)-7-amino-1,4-dioxaspiro[4.5]dec-8-yl]-5-chloroindole-2-carboxamide)

$^1$H-NMR(CDCl$_3$)δ: 1.68-1.81(4H, m), 2.11(2H, m), 2.87 (1H, td, J=3.9, 11.2 Hz), 3.77(1H, m), 3.97(4H, s), 6.27(1H, d, J=7.6 Hz), 6.80(1H, s), 7.24(1H, d, J=9.0 Hz), 7.35(1H, d, J=9.0 Hz), 7.61(1H, s), 9.47(br.s, 1H).
MS(ESI)m/z: 350(M+H)$^+$.

N-[(7R*,8S*)-8-amino-1,4-dioxaspiro[4.5]dec-7-yl]-5-chloroindole-2-carboxamide (or N-[(7R*,8S*)-7-amino-1,4-dioxaspiro[4.5]dec-8-yl]-5-chloroindole-2-carboxamide)

$^1$H-NMR(CDCl$_3$)δ: 1.65(2H, m), 1.88(1H, m), 1.96(1H, m), 2.31(1H, dd, J=12.9, 3.2 Hz), 2.96(1H, m), 3.98(1H, m), 4.02(4H, s), 4.12(1H, m), 6.77(1H, s), 7.06(1H, br.s), 7.23 (1H, dd, J=8.8, 2.0 Hz), 7.37(1H, d, J=8.8 Hz), 7.62(1H, d, J=2.0 Hz), 9.49(1H, br.s).
MS(ESI)m/z: 350(M+H)$^+$.

Referential Example 121

(1R,6S)-6-[(tert-butoxycarbonyl)amino]-3-cyclohexen-1-ylcarbamic acid tert-butyl ester

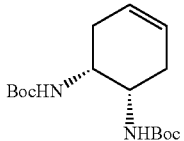

cis-4-Cyclohexene-1,2-diamine hydrochloride (4.0 g) was dissolved in water (40 mL) and acetonitrile (40 mL), and to the solution were added di-tert-butoxycarbonate (11.8 g) and triethylamine (12 mL), followed by stirring at room temperature for 4.5 hours. The reaction mixture was poured into water, and the mixture was extracted with methylene chloride. The methylene chloride layer was washed with saturated brine, and was dried over sodium sulfate anhydrate. The solvent was distilled away under reduced pressure, and the residue was purified by silica gel column chromatography (ethyl acetate:hexane=1:4), to thereby give the title compound (6.12 g).
$^1$H-NMR(CDCl$_3$)δ: 1.44(18H, s), 1.98(2H, dd, J=9.3, 15.9 Hz), 2.48(2H, br.d, J=15.9 Hz), 3.66(2H, br.s), 4.88(2H, br.s), 5.58(2H, d, J=2.7 Hz).

Referential Example 122

(1R*,2S*)-2-[(tert-butoxycarbonyl)amino]-5-hydroxycyclohexylcarbamic acid tert-butyl ester (stereoisomeric mixture)

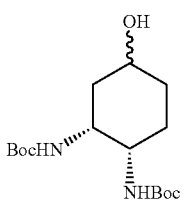

The compound obtained in Referential Example 121 (6.1 g) was dissolved in anhydrous tetrahydrofuran (40 mL), and borane-dimethyl sulfide complex (2.22 mL) was added to the solution under ice cooling. The reaction mixture was gradually heated to room temperature while being stirred for 16 hours. Ice was added to the reaction mixture, and to the mixture were added 1N aqueous sodium hydroxide and 30% hydrogen peroxide (50 mL). The thus-obtained mixture was stirred at room temperature for 2 hours. The resultant mixture was extracted with ethyl acetate. The organic layer was washed with saturated brine, and was dried over sodium sulfate anhydrate. The solvent was distilled away under reduced pressure, and the residue was purified by silica gel column chromatography (ethyl acetate:hexane=1:2->2:1), to thereby give the title compound (6.1 g).
$^1$H-NMR(CDCl$_3$)δ: 1.42(9H, s), 1.43(9H, s), 1.83-1.67 (5H, m), 2.15(1H, m), 2.22(1H, s), 3.34(1H, m), 3.78(1H, m), 4.15(1H, s), 4.98(1H, q, J=9.0 Hz), 5.02(1H, q, J=9.0 Hz).
MS(ESI)m/z: 331(M+H)$^+$.

Referential Example 123

(1R*,2S*)-2-[(tert-butoxycarbonyl)amino]-5-oxocyclohexylcarbamic acid tert-butyl ester

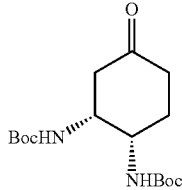

Oxalyl chloride (8.2 mL) and dimethyl sulfoxide (6.8 mL) were dissolved in methylene chloride (100 mL), and the solution was cooled to −60° C. Subsequently, a solution of the compound obtained in Referential Example 122 (stereoisomeric mixture) (6.32 g) in tetrahydrofuran (80 mL) was added thereto all at once, followed by stirring for 1 hour. The resultant mixture was heated to −40° C., and triethylamine (21 mL) was added thereto, followed by heating to room temperature. After 3 hours, the mixture was poured into water, and the thus-obtained mixture was extracted with methylene chloride. The organic layer was washed with saturated brine, and was dried over sodium sulfate anhydrate. The solvent was distilled away under reduced pressure, and the residue was purified by silica gel column chromatography (ethyl acetate:hexane=1:1), to thereby give the title compound (3.8 g).
$^1$H-NMR(CDCl$_3$)δ: 1.43(9H, s), 1.44(9H, s), 2.24-2.36 (3H, m), 2.39-2.44(2H, m), 2.75(1H, dd, J=14.6, 2.9 Hz), 3.66-3.81(2H, m), 4.95-4.90(1H, m), 4.97-5.03(1H, m).
MS(ESI)m/z: 329(M+H)$^+$.

Referential Example 124

(1R*,2S*)-2-[(tert-butoxycarbonyl)amino]-5-(methoxyimino)cyclohexylcarbamic acid tert-butyl ester

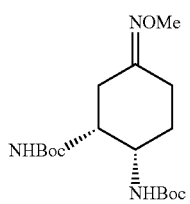

The compound obtained in Referential Example 123 (1.5 g) was dissolved in methanol (30 mL), and to the solution were added o-methylhydroxylamine hydrochloride (572 mg) and pyridine (737 mL), followed by stirring at room temperature for 17 hours. After the reaction mixture was concentrated, water was added to the residue, and the mixture was extracted with ethyl acetate. The organic layer was washed with saturated brine, and was dried over sodium sulfate anhydrate. The solvent was distilled away under reduced pressure, and the residue was purified by silica gel column chromatography (ethyl acetate:hexane=1:4), to thereby give the title compound (1.52 g).

$^1$H-NMR(CDCl$_3$)δ: 1.44(18H, s), 1.64(1H, m), 2.16(2H, m), 2.44(1H, m), 3.45-3.63(3H, m), 3.82(3H, s), 4.93(1H, m).
MS(ESI)m/z: 358(M+H)$^+$.

Referential Example 125

(1R*,2S*)-2-[(tert-butoxycarbonyl)amino]-5-{[tert-butyl(diphenyl)silyl]oxy}cyclohexylcarbamic acid tert-butyl ester (stereoisomer A)

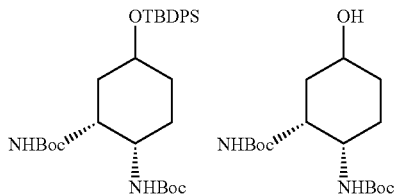

In a manner similar to that employed in Referential Example 58, the title compound was prepared from the compound obtained in Referential Example 122 (stereoisomeric mixture). At the same time, (1R*,2S*)-2-[(tert-Butoxycarbonyl)amino]-5-hydroxycyclohexylcarbamic acid tert-butyl ester (stereoisomer B) was also recovered.

$^1$H-NMR(CDCl$_3$)δ: 1.03(9H, s), 1.39(9H, s), 1.40(9H, s), 1.72(1H, m), 1.86(1H, m), 2.13(1H, m), 3.24(2H, m), 3.65 (1H, m), 4.83(1H, m), 7.37(10H, m).

Referential Example 126

(1R*,2S*)-2-{[(benzyloxy)carbonyl]amino}-5-hydroxy-5-methylcyclohexylcarbamic acid benzyl ester

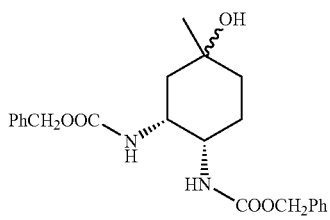

Anhydrous cerium chloride (6.4 g) was suspended in tetrahydrofuran (50 mL), and the suspension was cooled to −78° C. under argon flow. Methyllithium solution (as 1.14N diethyl ether solution, 22.5 mL) was added to the suspension, and the thus-obtained mixture was stirred at −78° C. for 30 minutes. To the resultant mixture was added dropwise a solution of the compound obtained in Referential Example 116 (3.0 g) in tetrahydrofuran (50 mL) at −78° C., followed by stirring for 30 minutes. The reaction mixture was poured into 3% aqueous acetic acid (100 mL), and diethyl ether (50 mL) was added thereto, followed by stirring at room temperature for 10 minutes. The reaction mixture was extracted with ethyl acetate. The organic layer was sequentially washed with saturated aqueous sodium hydrogencarbonate and saturated brine, and was dried over sodium sulfate anhydrate. The solvent was distilled away under reduced pressure, and the residue was purified by silica gel column chromatography (methanol:chloroform=0:100 to 1:19) twice, to thereby give the title compound (stereoisomer A) (780 mg) and the title compound (stereoisomer B) (1.1 g).

Stereoisomer A:
$^1$H-NMR(CDCl$_3$)δ: 1.26(3H, s), 1.27-2.08(6H, m), 3.48 (1H, br.s), 3.59(1H, br.s), 5.02-5.09(5H, m), 5.33(1H, br.s), 7.30-7.32(10H, s).
MS(FAB)m/z: 413(M+H)$^+$.

Stereoisomer B:
$^1$H-NMR(CDCl$_3$)δ: 1.25(3H, s), 1.29-2.07(6H, m), 3.39 (1H, br.s), 3.82(1H, br.s), 5.02-5.23(6H, m), 7.30(10H, s).
MS(FAB)m/z: 413(M+H)$^+$.

Referential Example 127

(3R*,4S*)-3,4-diamino-1-methylcyclohexanol (stereoisomer A)

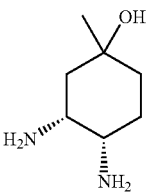

In a solution of the compound obtained in Referential Example 126 (stereoisomer A) (780 mg) in methanol (100 mL) was suspended 10% palladium on carbon (350 mg), and the suspension was stirred for 5 hours under hydrogen flow. The catalyst was filtered off, and the filtrate was concentrated under reduced pressure. The residue was dissolved in methylene chloride (100 mL), and the solution was dried over sodium sulfate anhydrate. The solvent was distilled away, to thereby give the title compound (stereoisomer A) (190 mg).

$^1$H-NMR(CDCl$_3$)δ: 1.22(3H, s), 1.25-2.48(11H, m), 2.62 (1H, br.s), 2.78(1H, br.s).

Referential Example 128 mixture of N-[(1R*,2S*)-2-amino-4-hydroxy-4-methylcyclohexyl]-5-chloroindole-2-carboxamide (stereoisomer A) and N-[(1R*,2S*)-2-amino-5-hydroxy-5-methylcyclohexyl]-5-chloroindole-2-carboxamide (stereoisomer A)

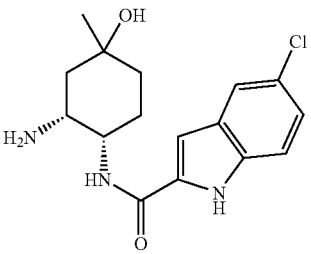

In a manner similar to that employed in Referential Example 59, the title compound was prepared from the compound obtained in Referential Example 127 (stereoisomer A) and 5-chloroindole-2-carboxylic acid.

$^1$H-NMR(CDCl$_3$)δ: 1.32(3H, s), 1.34-2.29(6H, m), 4.42-4.70(4H, br), 7.13(2H, s), 7.50(2H, s), 8.00(1H, s), 11.0(1H, br).

Referential Example 129

(1R*,2R*,5S*)-2-{[(5-chloroindol-2-yl)carbonyl]amino}-5-(hydroxymethyl)cyclohexylcarbamic acid tert-butyl ester

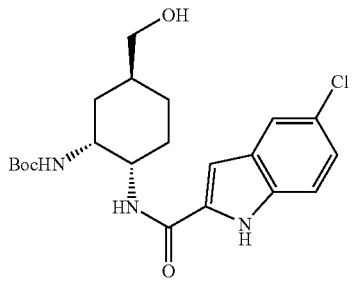

1) In a manner similar to that employed in Referential Examples 90 to 91, (1R*,3S*,4S*)-3-[(tert-butoxycarbonyl)amino]-4-{[(5-chloroindol-2-yl)carbonyl]amino}cyclohexanecarboxylic acid ethyl ester was prepared from the (1R*,3S*,4S*)-isomer obtained in Referential Example 89.

$^1$H-NMR(CDCl$_3$)δ: 1.22-1.72(6H, m), 2.15-2.28(2H, m), 2.41-2.49(1H, m), 2.85(1H, brs), 3.62-3.75(1H, m), 3.78-3.92(1H, m), 4.12-4.28(2H, m), 4.56-4.63(1H, m), 6.88(1H, brs), 7.20(1H, dd, J=8.8 and 2.0 Hz), 7.33(1H, d, J=8.8 Hz), 7.52-7.57(1H, m), 7.59(1H, d, J=2.0 Hz), 9.24(1H, s).

MS(ESI)m/z: 464(M+H)$^+$.

2) The thus-obtained product (735 mg) was dissolved in methylene chloride (10 mL), and to the solution was added a 1N solution of diisobutylaluminium hydride in hexane (5 mL) at −78° C., followed by stirring for 3 hours, and then at 0° C. for 30 minutes. Saturated aqueous ammonium chloride was added to the reaction mixture at −78° C., and the thus-obtained mixture was extracted with methylene chloride. The organic layer was washed with saturated aqueous sodium hydrogencarbonate and saturated brine, and was dried over anhydrous magnesium sulfate. The solvent was distilled away under reduced pressure, and the residue was purified by silica gel column chromatography (methylene chloride:methanol=19:1), to thereby give the title compound (480 mg).

$^1$H-NMR(CDCl$_3$)δ: 1.20-2.30(7H, m), 3.60-3.86(4H, m), 4.64(1H, br.s), 6.87(1H, s), 7.20-7.48(3H, m), 9.15(1H, br.s).

MS(ESI)m/z: 422(M+H)$^+$.

Referential Example 130

(1R*,3R*,6S*)-3-(methoxymethyl)oxabicyclo[4.1.0]heptane

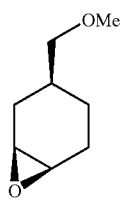

1) (1R*,4R*,5R*)-4-Iodo-6-oxabicyclo[3.2.1]octan-7-one (2.8 g) was dissolved in a solvent mixture of tetrahydrofuran (27 mL) and water (3 mL), and concentrated HCl (0.1 mL) was added thereto, followed by heating under reflux for 1 hour. The solvent was distilled away under reduced pressure, to thereby give (1R*,3R*,4R*)-3-hydroxy-4-iodocyclohexanecarboxylic acid (3.23 g) as a colorless solid.

2) The product obtained from the above-described reaction (3.22 g) was dissolved in tetrahydrofuran (50 mL), and borane-dimethyl sulfide complex (as 2M tetrahydrofuran solution, 47 mL) was added to the solution under ice cooling, followed by stirring at room temperature for 12 hours. The solvent was distilled away under reduced pressure, and the residue was dissolved in isopropanol (10 mL). To the solution was added 1N aqueous sodium hydroxide (12 mL) at room temperature, and the mixture was stirred for 12 hours. After the mixture was concentrated to about one-fifth of its original volume, the resultant mixture was diluted with water and methylene chloride, followed by stirring for 10 minutes. The organic layer was separated, and was sequentially washed with saturated aqueous ammonium chloride and saturated brine, followed by drying over anhydrous magnesium sulfate. The solvent was distilled away under reduced pressure, and the residue was purified by silica gel column chromatography (ethyl acetate:hexane=1:2), to thereby give (1R*,3R*,6S*)-7-oxabicyclo[4.1.0]hept-3-ylmethanol (1.25 g) as a colorless oily matter.

3) The product obtained from the reaction in the above step 2) (4.63 g) was dissolved in tetrahydrofuran (50 mL), and to the solution was added potassium bis(trimethylsilyl)amide (as 0.5N toluene solution, 80 mL) at −78° C., followed by stirring at the same temperature for 10 minutes, and methyl iodide (2.93 mL) was added thereto. The resultant mixture was heated to 0° C., and was stirred for 1 hour. Saturated aqueous ammonium chloride was added to the thus-obtained mixture, and the mixture was diluted with diethyl ether. The organic layer was separated, and was washed with saturated brine, followed by drying over anhydrous magnesium sulfate. The solvent was distilled away under reduced pressure, and the residue was purified by silica gel column chromatography (ethyl acetate:hexane=1:4), to thereby give the title compound (3.7 g).

$^1$H-NMR(CDCl$_3$)δ: 0.89-1.63(5H, m), 1.80-2.05(2H, m), 1.89-3.06(4H, m), 3.16(3H, s).

Referential Example 131

(1R*,2R*,4S*)-2-azido-4-(methoxymethyl)cyclohexanol

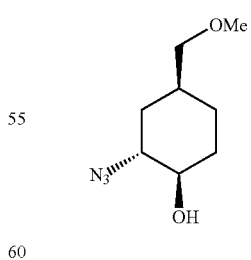

In a manner similar to that employed in Referential Example 87, the title compound was prepared from the compound obtained in Referential Example 130.

$^1$H-NMR(CDCl$_3$)δ: 1.45-1.70(5H, m), 1.77-1.95(2H, m), 1.98-2.08(1H, m), 3.30(2H, d, J=6.8 Hz), 3.35(3H, s), 3.45-3.65(2H, m).

Referential Example 132

(1R*,2R*,5S*)-2-hydroxy-5-(methoxymethyl)cyclohexylcarbamic acid tert-butyl ester

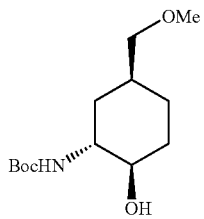

In a manner similar to that employed in Referential Example 88, the title compound was prepared from the compound obtained in Referential Example 131.
¹H-NMR(CDCl₃)δ: 1.35-2.01(16H, m), 3.05(1H, br.s), 3.32(2H, d, J=7.1 Hz), 3.34(3H, s), 3.44-3.62(2H, m), 4.59 (1H, br.s).

Referential Example 133

(1R*,2S*,5S*)-2-azido-5-(methoxymethyl)cyclohexylcarbamic acid tert-butyl ester

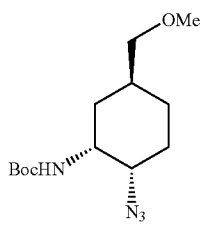

In a manner similar to that employed in Referential Example 89, a methanesulfonic acid ester was prepared from the compound obtained in Referential Example 132, and the title compound was prepared from the methanesulfonic acid ester.
¹H-NMR(CDCl₃)δ: 1.31-1.93(16H, m), 3.27(2H, d, J=6.4 Hz), 3.32(3H, s), 3.57-3.70(1H, m), 3.67(1H, br.s), 3.95(1H, br.s).

Referential Example 134

(1R*,2S*,5S*)-2-amino-5-(methoxymethyl)cyclohexylcarbamic acid tert-butyl ester

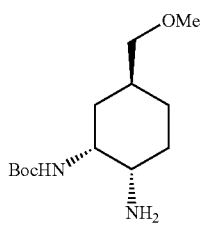

In a manner similar to that employed in Referential Example 90, the title compound was prepared from the compound obtained in Referential Example 133.

Referential Example 135

(1R*,2S*,5S*)-2-{[(5-chloroindol-2-yl)carbonyl]amino}-5-(methoxymethyl)cyclohexylcarbamic acid tert-butyl ester

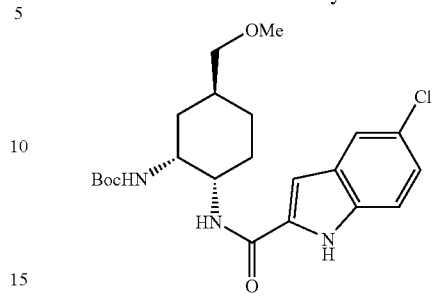

In a manner similar to that employed in Referential Example 91, the title compound was prepared from the compound obtained in Referential Example 134 and 5-chloroindole-2-carboxylic acid.
¹H-NMR(CDCl₃)δ: 1.12-2.31(16H, m), 3.14-3.30(2H, m), 3.34(3H, s), 3.92(1H, br.s), 4.13(1H, br.s), 4.88(1H, br.s), 6.82(1H, s), 7.21(1H, br.d, J=8.8 Hz), 7.33(1H, d, J=8.8 Hz), 7.60(1H, s), 8.09(1H, br.s), 9.42(1H, br.s).
MS(ESI)m/z: 436(M+H)⁺.

Referential Example 136

(1R*,2S*,5S*)-2-{[(5-chloroindol-2-yl)carbonyl]amino}-5-(hydroxymethyl)cyclohexylcarbamic acid tert-butyl ester

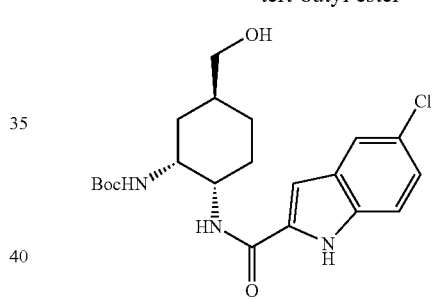

In a manner similar to that employed in Referential Example 129, the title compound was prepared from the compound obtained in Referential Example 91.
¹H-NMR(CDCl₃)δ: 0.78-2.30(16H, m), 3.41-3.59(3H, m), 3.86-3.95(1H, m), 4.12-4.20(1H, m), 4.82-4.91(1H, m), 6.81 (1H, s), 7.17-7.40(2H, m), 7.60(1H, s), 8.03(1H, br.s), 9.18 (1H, br.s).
MS(ESI)m/z: 422 (M+H)⁺.

Referential Example 137

(1R*,2S*,5S*)-5-(azidomethyl)-2-{[(5-chloroindol-2-yl)carbonyl]amino}cyclohexylcarbamic acid tert-butyl ester

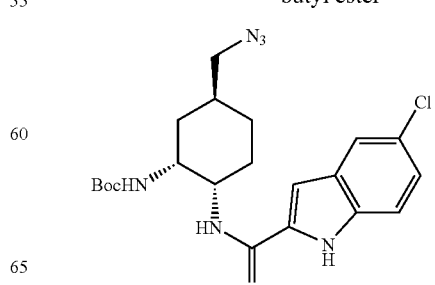

In a manner similar to that employed in Referential Example 80, the title compound was prepared from the compound obtained in Referential Example 136.

Referential Example 138

3-cyclohexen-1-ylcarbamic acid tert-butyl ester

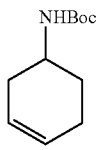

3-Cyclohexene-1-carboxylic acid (25.3 g) was dissolved in tert-butanol (250 mL), and to the solution were added triethylamine (28 mL) and diphenylphosphoryl azide (43.0 mL), followed by stirring at room temperature for 1 hour, and then at 90° C. for 2 days. The solvent was distilled away under reduced pressure, and the residue was purified by silica gel column chromatography (methylene chloride). The purified product was further purified by silica gel column chromatography (hexane:ethyl acetate=20:1) to thereby give the title compound (24.9 g).

$^1$H-NMR(CDCl$_3$)δ: 1.45(9H, s), 1.45-1.60(1H, m), 1.80-1.90(2H, m), 2.05-2.20(2H, m), 2.35-2.45(1H, m), 3.78(1H, br), 4.56(1H, br), 5.55-5.65(1H, m), 5.65-5.75(1H, m).

Referential Example 139

(3R*,4S*)-3,4-dihydroxycyclohexylcarbamic acid tert-butyl ester

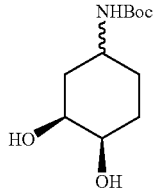

The compound obtained in Referential Example 138 (1.24 g) was dissolved in a solvent mixture of acetonitrile (15 mL) and water (5 mL), and to the solution were added N-methylmorpholine N-oxide (0.90 g) and microencapsulated 10% osmium tetraoxide (1 g), followed by stirring at about 80° C. for 1 day. Any insoluble matter was filtered off, and the filtrate was concentrated under reduced pressure. The residue was purified by silica gel column chromatography (methylene chloride:methanol=20:1), to thereby give the title compound (1.28 g).

$^1$H-NMR(CDCl$_3$)δ: 1.15-1.30(½H, m), 1.35-2.00(15H, m), 2.15-2.30(³⁄₂H, m), 2.40-2.60(1H, m), 3.64(1H, br), 3.75-3.90(³⁄₂H, m), 4.00(½H, br).

MS(FAB)m/z: 232(M+H)$^+$.

Referential Example 140

(3R*,4S*)-3,4-diazidocyclohexylcarbamic acid tert-butyl ester (stereoisomer A and stereoisomer B)

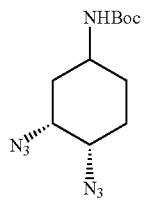

In a manner similar to that employed in Referential Example 80, the title compounds (stereoisomer A and stereoisomer B) were prepared from the compound obtained in Referential Example 139.

Stereoisomer A:
$^1$H-NMR(CDCl$_3$)δ: 1.45(9H, s), 1.40-1.55(1H, m), 1.55-1.80(3H, m), 1.95-2.15(2H, m), 3.53(1H, m), 3.59(1H, br), 3.80(1H, m), 4.70(1H, br).

Stereoisomer B:
$^1$H-NMR(CDCl$_3$)δ: 1.27(1H, m), 1.44(9H, s), 1.40-1.55(1H, m), 1.80-2.00(2H, m), 2.00-2.15(1H, m), 2.21(1H, m), 3.48(1H, m), 3.77(1H, br), 3.89(1H, br), 4.34(1H, br).

Referential Example 141

(1S,3R,4S)-4-{[(benzyloxy)carbonyl]amino}-3-[(tert-butoxycarbonyl)amino]cyclohexanecarboxylic acid ethyl ester

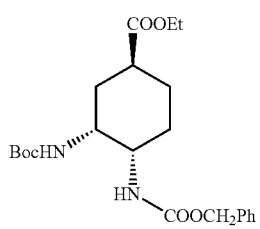

The compound obtained in Referential Example 96 (3.10 g) was dissolved in tetrahydrofuran (50 mL), and saturated aqueous sodium hydrogencarbonate (50 mL) was added thereto. Benzyloxycarbonyl chloride (1.71 mL) was added dropwise to the reaction mixture under ice cooling, and the thus-obtained mixture was stirred at room temperature for 4 days. The reaction mixture was partitioned between ethyl acetate (200 mL) and water (200 mL). The organic layer was dried over sodium sulfate anhydrate, and the solvent was distilled away under reduced pressure. The resultant solid was collected by filtration, to thereby give the title compound (3.24 g).

$^1$H-NMR(CDCl$_3$)δ: 1.24(3H, t, J=7.1 Hz), 1.29-1.44(1H, m), 1.44(9H, s), 1.51-1.64(1H, m), 1.72-2.10(4H, m), 2.27-2.43(1H, m), 3.60-3.73(1H, m), 4.00-4.18(3H, m), 4.62(1H, br.s), 5.01-5.13(2H, m), 5.26(1H, br.s), 7.27-7.38(5H, m).

Referential Example 142

(1S,3R,4S)-4-{[(benzyloxy)carbonyl]amino}-3-[(tert-butoxycarbonyl)amino]cyclohexanecarboxylic acid

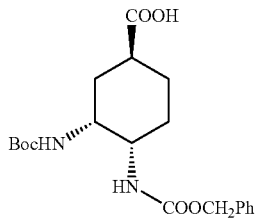

The compound obtained in Referential Example 141 (620 mg) was dissolved in tetrahydrofuran (20 mL), and an aqueous solution (10 mL) of lithium hydroxide monohydrate (93 mg) was added thereto, followed by stirring at room temperature for 16 hours. Additional lithium hydroxide monohydrate (217 mg) was added to the reaction mixture, and the thus-obtained mixture was stirred at room temperature for 2 hours. Subsequently, the resultant mixture was neutralized with 1N aqueous HCl, and was extracted with methylene chloride. The organic layer was washed with saturated brine, and was dried over sodium sulfate anhydrate. The solvent was distilled away, to thereby give the title compound (600 mg).

$^1$H-NMR(CDCl$_3$)δ: 1.22-2.20(6H, m), 1.44(9H, s), 2.45 (1H, br.s), 3.60-3.80(1H, br), 4.09(1H, br.s), 4.66(1H, br.s), 5.00-5.20(2H, m), 5.26(1H, br.s), 7.20-7.40(5H, m).

MS(ESI)m/z: 393(M+H)$^+$.

Referential Example 143

(1S,2R,4S)-2-[(tert-butoxycarbonyl)amino]-4-[(dimethylamino)carbonyl]cyclohexylcarbamic acid benzyl ester

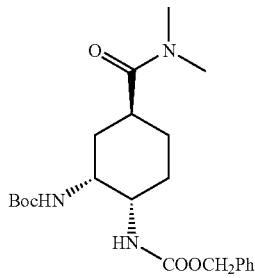

The compound obtained in Referential Example 142 (600 mg) and dimethylamine hydrochloride (240 mg) were suspended in methylene chloride (50 mL), and a proper amount of tetrahydrofuran was added thereto, to thereby dissolve any solid matter. To the solution were added triethylamine (0.41 mL), 1-(3-dimethylaminopropyl)-3-ethylcarbodiimide hydrochloride (422 mg), and 1-hydroxybenzotriazole monohydrate (338 mg), and the thus-obtained mixture was stirred at room temperature for 1 hour. To the reaction mixture were further added dimethylamine hydrochloride (480 mg) and triethylamine (0.82 mL), and the thus-obtained mixture was stirred at room temperature for an additional 18 hours. The reaction mixture was poured into water. The organic layer was separated, and was washed with 1N HCl and saturated brine, followed by drying over sodium sulfate anhydrate. The solvent was distilled away under reduced pressure, and the residue was purified by silica gel column chromatography (methanol:methylene chloride=3:47→2:23), to thereby give the title compound (620 mg).

$^1$H-NMR(CDCl$_3$)δ: 1.20-1.50(2H, m), 1.44(9H, s), 1.50-2.10(4H, m), 2.60(1H, br.t, J=11.6 Hz), 2.93(3H, s), 3.02(3H, s), 3.70(1H, br.s), 4.14(1H, br.s), 4.65(1H, br.s), 5.00-5.30 (3H, m), 7.26-7.40(5H, m).

MS(ESI)m/z=420 (M+H)$^+$.

Referential Example 144

(1R,2S,5S)-2-amino-5-[(dimethylamino)carbonyl]cyclohexylcarbamic acid tert-butyl ester

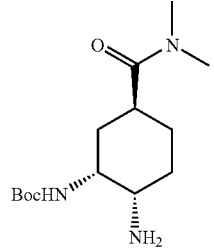

To a solution of the compound obtained in Referential Example 143 (190 g) in methanol (8000 mL) was added 10% palladium on carbon (57 g), and the thus-obtained mixture was stirred for 3 hours under hydrogen at a pressure of 7 atm. After the catalyst was filtered off, the filtrate was concentrated under reduced pressure. Toluene was added to the residue, and the thus-obtained mixture was concentrated under reduced pressure, followed by precipitation by addition of hexane (2500 mL) The resultant solid was collected by filtration, and was dried, to thereby give the title compound (121 g).

$^1$H-NMR(CDCl$_3$)δ: 1.20-1.77(6H, m), 1.45(9H, s), 2.20-2.35(1H, br), 2.63-2.74(1H, m), 2.92(3H, s), 3.02(3H, s), 3.02-3.11(2H, m), 3.74-3.82(1H, m), 4.88-5.00(1H, br)MS (ESI)m/z: 286(M+H)$^+$.

Referential Example 145

(1R,2S,5S)-2-{[(6-chloroquinolin-2-yl)carbonyl]amino}-5-[(dimethylamino)carbonyl]cyclohexylcarbamic acid tert-butyl ester

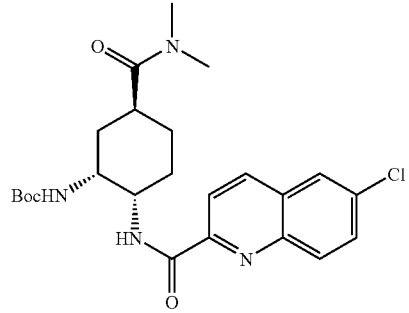

In a manner similar to that employed in Referential Example 91, the title compound was prepared from the compound obtained in Referential Example 144 and the compound obtained in Referential Example 54.

$^1$H-NMR(CDCl$_3$)δ: 1.41(9H, br), 1.50-1.70(1H, m), 1.75-1.95(2H, m), 1.95-2.25(3H, m), 2.65-2.80(1H, m), 2.96(3H, s), 3.07(3H, s), 4.15-4.30(1H, m), 4.30-4.40(1H, m), 4.95

Referential Example 146

(1R,2S,5S)-2-{[(7-chloroquinolin-3-yl)carbonyl]amino}-5-[(dimethylamino)carbonyl]cyclohexylcarbamic acid tert-butyl ester

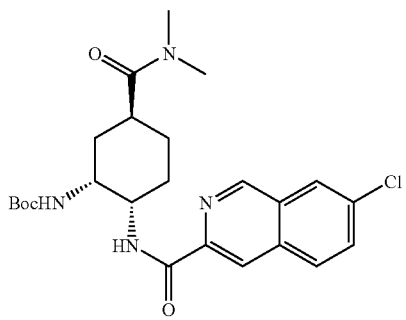

In a manner similar to that employed in Referential Example 91, the title compound was prepared from the compound obtained in Referential Example 144 and the compound obtained in Referential Example 57.

$^1$H-NMR(CDCl$_3$)δ: 1.30-1.65(10H, br), 1.75-1.90(2H, m), 1.90-2.25(3H, m), 2.65-2.90(1H, br), 2.96(3H, s), 3.08 (3H, s), 4.20-4.30(1H, m), 4.30-4.40(1H, m), 4.93(1H, br), 7.68(1H, m), 7.90(1H, br), 7.99(1H, s), 8.35-8.70(2H, m), 9.01(1H, br).
MS(FAB)m/z: 475 (M+H)$^+$.

Referential Example 147

2-bromo-5-isopropyl-4,5,6,7-tetrahydrothiazolo[5,4-c]pyridine

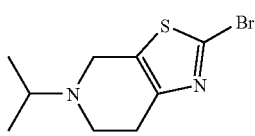

In a manner similar to that employed in Referential Example 9, the title compound was prepared from the compound obtained in Referential Example 8.

$^1$H-NMR(CDCl$_3$)δ: 1.13(6H, d, J=6.5 Hz), 2.86(4H, s), 2.89-3.00(1H, m), 3.70(2H, s).

Referential Example 148

5-ispopropyl-4,5,6,7-tetrahydrothiazolo[5,4-c]pyridine-2-carboxylic acid lithium salt

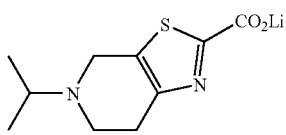

In a manner similar to that employed in Referential Example 10, the title compound was prepared from the compound obtained in Referential Example 147.

$^1$H-NMR(DMSO-d$_6$)δ: 1.05(6H, d, J=6.4 Hz), 2.68-2.70 (2H, m), 2.75-2.77(2H, m), 2.87-2.93(1H, m), 3.66(2H, s).

Referential Example 149

5-methyl-4,5,6,7-tetrahydrothiazolo[5,4-c]pyridine-2-carboxylic acid 4-nitrophenyl ester

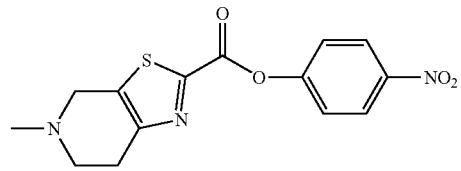

In a manner similar to that employed in Referential Example 52, the title compound was prepared from the compound obtained in Referential Example 10 and p-nitrophenol.

$^1$H-NMR(CDCl$_3$)δ: 2.55(3H, s), 2.88(2H, t, J=5.7 Hz), 3.06-3.12(2H, m), 3.80(2H, s), 7.46(2H, d J=9.3 Hz), 8.32 (2H, d, J=9.3 Hz).
MS(ESI)m/z: 320(M+H$^+$).

Referential Example 150

3-oxocyclobutanecarboxylic acid benzyl ester

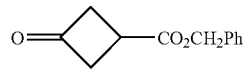

Triethylamine (2.0 mL) and benzyl bromide (1.2 mL) were added to a solution of 3-oxocyclobutanecarboxylic acid (J. Org. Chem., vol. 53, pp. 3841-3843 (1981)) (995 mg) in tetrahydrofuran (5.0 mL), and the mixture was stirred at room temperature for 2 hours. The reaction mixture was diluted with ethyl acetate, and was sequentially washed with 1N aqueous HCl, saturated aqueous sodium hydrogencarbonate, and saturated brine, followed by drying over sodium sulfate anhydrate. The solvent was distilled away under reduced pressure, and the residue was purified by silica gel column chromatography (ethyl acetate:hexane=1:6), to thereby give the title compound (886 mg).

$^1$H-NMR(CDCl$_3$)δ: 3.22-3.33(3H, m), 3.37-3.48(2H, m), 5.19(2H, s), 7.31-7.42(5H, m). MS(FAB)m/z: 205(M+H$^+$).

Referential Example 151

3-hydroxycyclobutanecarboxylic acid benzyl ester

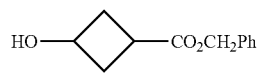

To a mixture of the compound obtained in Referential Example 150 (781 mg), tetrahydrofuran (10 mL), and methanol (0.5 mL) was added sodium borohydride (76 mg) at 0° C., and the thus-obtained mixture was stirred at the same temperature for 30 minutes. The reaction mixture was diluted with ethyl acetate, and the diluted mixture was sequentially washed with saturated aqueous sodium hydrogencarbonate and saturated brine, followed by drying over sodium sulfate anhydrate. The solvent was distilled away under reduced pressure, and the residue was purified by silica gel column chromatography (ethyl acetate:hexane=1:2), to thereby give the title compound (770 mg).

$^1$H-NMR(CDCl$_3$)δ: 2.13-2.27(3H, m), 2.55-2.71(3H, m), 4.14-4.23(1H, m), 5.12(2H, s), 7.28-7.39(5H, m).

MS(FAB)m/z: 207(M+H$^+$).

Referential Example 152

3-hydroxycyclobutanecarboxylic acid

To a solution of the compound obtained in Referential Example 151 (706 mg) in ethanol (10 mL) was added 10% palladium on carbon (108 mg), and the mixture was stirred at room temperature for 2 hours under hydrogen atmosphere. The catalyst was removed by filtration through Celite, and the filtrate was concentrated under reduced pressure, to thereby give the title compound (399 mg).

$^1$H-NMR(CD$_3$OD)δ: 2.00-2.21(2H, m), 2.41-2.61(3H, m), 4.01-4.13(1H, m).

Referential Example 153

3-methoxycyclobutanecarboxylic acid benzyl ester

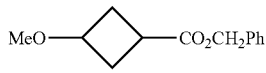

To a solution of the compound obtained in Referential Example 151 (317 mg) in N,N-dimethylformamide (3.0 mL) were added methyl iodide (194 μL) and silver oxide (237 mg), followed by stirring at 45° C. for 1 hour. To the reaction mixture were added additional methyl iodide (194 μL) and silver oxide (226 mg), followed by stirring at 45° C. for 16 hours. The catalyst was filtered off, and the filtrate was concentrated under reduced pressure. The residue was purified by silica gel column chromatography (ethyl acetate hexane=1:10), to thereby give the title compound (152 mg).

$^1$H-NMR(CDCl$_3$)δ: 2.14-2.24(2H, m), 2.44-2.54(2H, m), 2.59-2.72(1H, m), 3.21(3H, s), 3.73-3.81(1H, m), 5.11(2H, s), 7.22-7.39(5H, m).

MS(ESI)m/z: 221(M+H$^+$).

Referential Example 154

3-methoxycyclobutanecarboxylic acid

In a manner similar to that employed in Referential Example 152, the title compound was prepared from the compound obtained in Referential Example 153.

$^1$H-NMR(CDCl$_3$)δ: 2.17-2.27(2H, m), 2.48-2.58(2H, m), 2.62-2.73(1H, m), 3.25(3H, s), 3.76-3.86(1H, m), 8.60-9.30 (1H, br).

Referential Example 155

3-methoxy-2-(methoxymethyl)propionic acid methyl ester

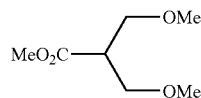

Sodium methoxide (1.21 g) was added to a solution of 2-(bromomethyl)acrylic acid methyl ester (1.0 mL) in methanol (10 mL), and the mixture was heated under reflux for 26 hours. The reaction mixture was cooled, and was diluted with diethyl ether. The precipitate was filtered off, and the filtrate was concentrated under reduced pressure. The residue was purified by silica gel column chromatography (ethyl acetate hexane=1:4), to thereby give the title compound (726 mg).

$^1$H-NMR(CDCl$_3$)δ: 2.90-2.96(1H, m), 3.34(6H, s), 3.57 (2H, dd, J=9.3, 5.9 Hz), 3.64(2H, dd, J=9.3, 6.6 Hz), 3.73(3H, s).

$^{13}$C-NMR(CDCl$_3$)δ: 172.71, 70.31, 59.91, 46.49.

MS(ESI)m/z: 163(M+H$^+$).

Referential Example 156 tetrahydro-2H-pyran-4-carboxylic acid

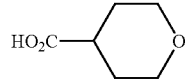

To tetrahydro-4H-pyran-4,4-dicarboxylic acid dimethyl ester (4.04 g) was added 20% HCl (20 mL), and the mixture was heated under reflux for 19 hours. Water was added to the reaction mixture, and the thus-obtained mixture was extracted with diethyl ether. The organic layer was washed with saturated brine, and was dried over sodium sulfate anhydrate. The solvent was distilled away under reduced pressure, and hexane was added to the residue. The resultant solid was collected by filtration, and was washed, to thereby give the title compound (2.63 g).

$^1$H-NMR(CDCl$_3$)δ: 1.75-1.95(4H, m), 2.55-2.65(1H, m), 3.40-3.52(2H, m), 3.93-4.05(2H, m).

Referential Example 157

3-{[tert-butyl(diphenyl)silyl]oxy}-2,2-dimethylpropionic acid methyl ester

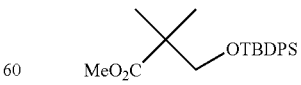

In a manner similar to that employed in Referential Example 41, the title compound was prepared from 2,2-dimethyl-3-hydroxypropionic acid methyl ester.

$^1$H-NMR(CDCl$_3$)δ: 1.03(9H, s), 1.20(6H, s), 3.64-3.68 (5H, m), 7.38-7.44(6H, m), 7.63-7.65(4H, m).

Referential Example 158

3-{[tert-butyl(diphenyl)silyl]oxy}-2,2-dimethylpropionic acid

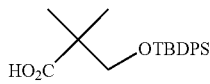

Water (0.24 mL) was added to a suspension comprising potassium tert-butoxide (5.32 g) and diethyl ether (100 mL) under ice cooling. After the thus-obtained mixture was stirred for 5 minutes, the compound obtained in Referential Example 157 (2.22 g) was added thereto, followed by stirring at room temperature overnight. Water was added to the reaction mixture, and 1N aqueous HCl was added thereto, to thereby make the mixture acidic. The resultant mixture was extracted with diethyl ether 3 times, and the organic layer was dried over sodium sulfate anhydrate. The solvent was distilled away under reduced pressure, and the residue was purified by silica gel column chromatography (ethyl acetate hexane=1:6), to thereby give the title compound (735 mg).

$^1$H-NMR(CDCl$_3$)δ: 1.04(9H, d, J=0.7 Hz), 1.22(6H, s), 3.65(2H, s), 7.36-7.45(6H, m), 7.64-7.66(4H, m).

Referential Example 159

3-methoxy-2,2-dimethylpropionic acid methyl ester

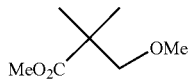

A solution of 3-hydroxy-2,2-dimethyl-propionic acid methyl ester (25.0 g) in tetrahydrofuran (300 mL) was added dropwise to a suspension comprising sodium hydride (as 60% oil suspension, 8.32 g) and tetrahydrofuran (100 mL) under ice cooling, followed by stirring at 60° C. for 1 hour. Methyl iodide (53.7 g) was added to the reaction mixture, and the thus-obtained mixture was stirred at room temperature for an additional 2 hours. After water was carefully added thereto, the reaction mixture was extracted with methylene chloride twice. The organic layer was washed with saturated brine, and was dried over sodium sulfate anhydrate. The solvent was distilled away under reduced pressure, and the resultant oily matter was subjected to distillation, to thereby give the title compound (12.8 g).

b.p.: 140-142° C. (atmospheric pressure)

$^1$H-NMR(CDCl$_3$)δ: 1.19(6H, d, J=1.0 Hz), 3.33(3H, d, J=1.0 Hz), 3.38(2H, d, J=1.0 Hz), 3.69(3H, d, J=1.0 Hz).

Referential Example 160

3-methoxy-2,2-dimethylpropionic acid

In a manner similar to that employed in Referential Example 158, the title compound was prepared from the compound obtained in Referential Example 159.

$^1$H-NMR(CDCl$_3$)δ: 1.22(6H, d, J=0.7 Hz), 3.38(3H, d, J=0.7 Hz), 3.40(2H, d, J=0.7 Hz).

Referential Example 161

1-(methoxycarbonyl)cyclopropanecarboxylic acid

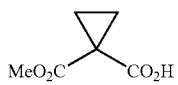

1,1-Cyclopropanedicarboxylic acid dimethyl ester (25 g) was dissolved in methanol (250 mL). The solution was cooled under ice cooling, and 1N aqueous sodium hydroxide (158 mL) was added dropwise thereto. The thus-obtained mixture was brought back to room temperature, and was stirred overnight. Methanol was distilled away, and the residue was washed with chloroform. The aqueous layer was cooled under ice cooling, and concentrated aqueous HCl was added thereto, to thereby adjust to pH 2. The resultant mixture was extracted with ethyl acetate, and the extract was dried over sodium sulfate anhydrate. The solvent was distilled away under reduced pressure, to thereby give the title compound (16.8 g).

$^1$H-NMR(CDCl$_3$)δ: 1.76-1.80(2H, m), 1.82-1.88(2H, m), 3.79(3H, s), 12.73(1H, br).

Referential Example 162

1-(hydroxymethyl)cyclopropanecarboxylic acid methyl ester

The compound obtained in Referential Example 161 (9.0 g) and triethylamine (9.7 mL) were dissolved in tetrahydrofuran (180 mL). After the solution was cooled to 10° C., isobutyl chloroformate (9.1 mL) was added dropwise thereto, followed by stirring for 1 hour. Sodium borohydride (7.1 g) was dissolved in a mixture of tetrahydrofuran (100 mL) and water (25 mL). After this solution was cooled under ice cooling, the previously prepared solution was added dropwise thereto while insoluble matter was removed by filtration, and the thus-obtained mixture was stirred at the same temperature for 1 hour. The reaction mixture was poured into a chilled 10% aqueous citric acid, and the thus-obtained mixture was extracted with ethyl acetate. The extract was washed with saturated brine, and was dried over sodium sulfate anhydrate. The solvent was distilled away under reduced pressure, and the residue was purified by silica gel column chromatography (ethyl acetate:hexane=1:9 to 2:1), to thereby give the title compound (4.25 g).

$^1$H-NMR(CDCl$_3$)δ: 0.87-0.93(2H, m), 1.28-1.30(2H, m), 3.63(2H, s), 3.70(3H, s).

Referential Example 163

1-(bromomethyl)cyclopropanecarboxylic acid methyl ester

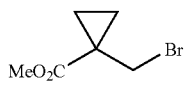

To a solution of the compound obtained in Referential Example 162 (4.20 g) in methylene chloride (168 mL) were added triphenylphosphine (10 g) and carbon tetrabromide (16 g) at room temperature under nitrogen atmosphere, and after 2 minutes, saturated aqueous sodium hydrogencarbonate was added thereto. The organic layer was washed with saturated brine, and was dried over sodium sulfate anhydrate. The solvent was distilled away under reduced pressure, and the residue was purified by silica gel column chromatography (ethyl acetate hexane=1:19), to thereby give the title compound (2.15 g).

$^1$H-NMR(CDCl$_3$)δ: 1.00-1.05(2H, m), 1.52-1.59(2H, m), 3.61(2H, s), 3.73(3H, s).

Referential Example 164

(4S)-4-[(E)-3-ethoxy-3-oxo-1-propenyl]-2,2-dimethyl-1,3-oxazolidine-3-carboxylic acid tert-butyl ester

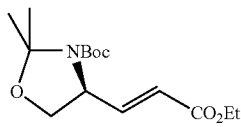

A mixture comprising (4R)-4-formyl-2,2-dimethyl-1,3-oxazolidine-3-carboxylic acid tert-butyl ester (11.7 g), (carbethoxymethylene)triphenylphosphorane (20.7 g), and toluene (100 mL) was stirred at 100° C. for 18 hours. The reaction mixture was concentrated, and the residue was purified by silica gel column chromatography (hexane:ethyl acetate=8:1), to thereby give the title compound (17 g).

$^1$H-NMR(CDCl$_3$)δ: 1.29(3H, t, J=6.6 Hz), 1.43-1.56(15H, m), 3.80(1H, dd, J=9.0, 2.4 Hz), 4.09(1H, dd, J=9.0, 6.6 Hz), 4.11-4.23(2H, m), 4.30-4.61(1H, m), 5.83-6.02(1H, m), 6.74-6.89(1H, m).

Referential Example 165

(4S)-4-[1-(benzylamino)-3-ethoxy-3-oxopropyl]-2,2-dimethyl-1,3-oxazolidine-3-carboxylic acid tert-butyl ester

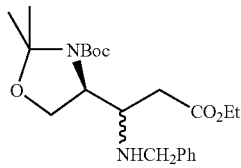

A mixture comprising the compound obtained in Referential Example 164 (22.2 g), benzylamine (16 g) and ethanol (100 mL) was heated under reflux for 2 days. The reaction mixture was concentrated, and the residue was purified by silica gel column chromatography (hexane:ethyl acetate=8:1), to thereby give the title compound (26 g).

$^1$H-NMR(CDCl$_3$)δ: 1.25(3H, t, J=6.6 Hz), 1.42-1.63(15H, m), 2.24-2.33(0.5H, m), 2.40-2.50(1H, m), 2.63-2.74(0.5H, m), 3.41-3.52(1H, m), 3.67-3.80(1H, m), 3.83(2H, s), 3.89-4.00(1H, m), 4.03-4.22(4H, m), 7.23-7.45(5H, m).

Referential Example 166

(4S)-4-(1-amino-3-ethoxy-3-oxopropyl)-2,2-dimethyl-1,3-oxazolidine-3-carboxylic acid tert-butyl ester

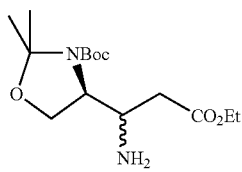

To a solution of the compound obtained in Referential Example 165 (13.6 g) in ethanol (200 mL) was added 10% palladium on carbon (10 g), and the thus-obtained mixture was stirred for 2 days under hydrogen atmosphere. Any insoluble matter was filtered off through a Celite pad, and the filtrate was concentrated under reduced pressure, to thereby give the title compound (10.5 g).

$^1$H-NMR(DMSO-d$_6$)δ: 1.19(1.5H, t, J=6.6 Hz), 1.20(1.5H, t, J=6.6 Hz), 1.32-1.50(15H, m), 2.63-2.81(2H, m), 3.22-3.34(2H, m), 3.93(1H, dd, J=10.0, 6.8 Hz), 4.08(2H, q, J=6.6 Hz), 4.20-4.30(1H, m).

Referential Example 167

(4S)-4-(1-{[(benzyloxy)carbonyl]amino}-3-ethoxy-3-oxopropyl)-2,2-dimethyl-1,3-oxazolidine-3-carboxylic acid tert-butyl ester

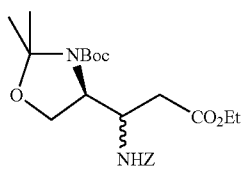

The compound obtained in Referential Example 166 (3.0 g) was suspended in 9% aqueous sodium hydrogencarbonate (56 mL), and to the suspension was added dropwise a solution of N-(benzyloxycarbonyloxy)succinimide (2.3 g) in dioxane (12 mL) under ice cooling. The thus-obtained mixture was gradually brought back to room temperature while being stirred. After the reaction mixture was stirred for 3 hours, the mixture was diluted with ethyl acetate. The diluted mixture was washed with water, 10% aqueous citric acid, and saturated brine, and was dried over sodium sulfate anhydrate. The solvent was distilled away under reduced pressure, and the residue was purified by silica gel column chromatography (chloroform), to thereby give the title compound (3.8 g).

$^1$H-NMR(CDCl$_3$)δ: 1.23(3H, t, J=6.6 Hz), 1.48(9H, s), 1.56(6H, s), 2.40-2.51(2H, m), 2.63-2.70(2H, m), 3.92-4.04 (1H, m), 4.06-4.10(2H, m), 4.14-4.22(1H, m), 5.09(2H, s), 7.30-7.43(5H, m).

Referential Example 168

(3S,4S)-3-{[(benzyloxy)carbonyl]amino}-4-[(tert-butoxycarbonyl)amino]-5-hydroxyvaleric acid ethyl ester (low-polar compound) and (3R,4S)-3-{[(benzyloxy)carbonyl]amino}-4-[(tert-butoxycarbonyl)amino]-5-hydroxyvaleric acid ethyl ester (high-polar compound)

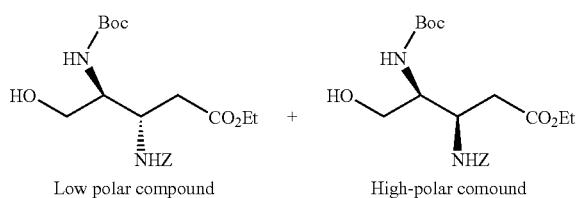

Low polar compound      High-polar comound

To a solution of the compound obtained in Referential Example 167 (30 g) in methylene chloride (100 mL) was added dropwise trifluoroacetic acid (100 mL) under ice cooling, and the thus-obtained mixture was gradually brought back to room temperature while being stirred. After the reaction mixture was stirred for 3 hours, the mixture was concentrated under reduced pressure, and the residue was dissolved in methylene chloride (100 mL). To the solution were sequentially added dropwise triethylamine (20 mL) and a solution of di-tert-butyl dicarbonate (19 g) in methylene chloride (100 mL) under ice cooling, and the thus-obtained mixture was gradually brought back to room temperature while being stirred. After the reaction mixture was stirred for 4 hours, the mixture was concentrated under reduced pressure, and the residue was purified by silica gel column chromatography (hexane:ethyl acetate=2:1), to thereby give the title low-polar compound (7.6 g) and the title high-polar compound (10 g).

Low-Polar Compound:
$^1$H-NMR(CDCl$_3$)δ: 1.24(3H, t, J=6.6 Hz), 1.42(9H, s), 2.63(2H, d, J=4.4 Hz), 3.30-3.41(1H, m), 3.50(1H, t, J=9.7 Hz), 3.65(1H, t, J=9.7 Hz), 3.75(1H, d, J=11.7 Hz), 3.90-4.00 (1H, m), 4.03-4.23(2H, m), 5.12(2H, s), 5.13-5.25(1H, m), 5.79-6.02(1H, m), 7.32-7.41(5H, m).

High-Polar Compound:
$^1$H-NMR(CDCl$_3$)δ: 1.22(3H, t, J=6.6 Hz), 1.41(9H, s), 2.50-2.70(2H, m), 3.20-3.31(1H, m), 3.43-3.51(1H, m), 3.56-3.70(1H, m), 3.74-3.78(1H, m), 4.00-4.19(2H, m), 4.23-4.30 (1H, m), 4.78-4.89(1H, m), 5.10(2H, s), 5.56-5.67(1H, m), 7.31-7.40(5H, m).

Referential Example 169 methanesulfonic acid (3R,4S)-4-[(methylsulfonyl)oxy]tetrahydro-3-furanyl ester

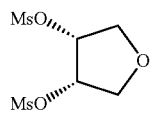

Triethylamine (12.0 mL) and methanesulfonyl chloride (3.6 mL) were sequentially added dropwise to a solution of 1,4-anhydroerythritol (5.0 g) in methylene chloride (50 mL) under ice cooling, followed by stirring for 10 minutes under ice cooling. The reaction mixture was diluted with methylene chloride, and the diluted mixture was washed with 10% aqueous HCl, saturated aqueous sodium hydrogencarbonate, and saturated brine. The organic layer was dried over sodium sulfate anhydrate, and the solvent was distilled away under reduced pressure, to thereby give the title compound (9.2 g).

$^1$H-NMR(CDCl$_3$)δ: 3.15(6H, s), 3.99(2H, dd, J=11.2, 2.5 Hz), 4.16(2H, dd, J=11.2, 4.6 Hz), 5.10-5.20(2H, m).

Referential Example 170

(3R,4S)-3,4-diazidotetrahydrofuran

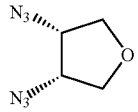

The compound obtained in Referential Example 169 (9.2 g) was dissolved in N,N-dimethylformamide (50 mL), and sodium azide (18 g) was added thereto, followed by stirring at 100° C. for 18 hours. The reaction mixture was diluted with ethyl acetate, and the diluted mixture was washed with water and saturated brine. The organic layer was dried over sodium sulfate anhydrate, and the solvent was distilled away under reduced pressure, to thereby give the title compound (3.8 g).

$^1$H-NMR(CDCl$_3$)δ: 3.83(2H, dd, J=8.6, 2.0 Hz), 3.96-4.12 (4H, m).

Referential Example 171

(3R,4S)-tetrahydro-3,4-furandiamine dihydrochloride

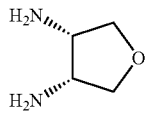

The compound obtained in Referential Example 170 (3.8 g) was dissolved in ethanol (50 mL), and 10% palladium on carbon (1.0 g) was added thereto, followed by stirring for 18 hours under hydrogen atmosphere. After any insoluble matter was removed by filtration through a Celite pad, the filtrate was concentrated under reduced pressure. To the residue was added 1N HCl-ethanol, to thereby give an hydrochloride salt, and this compound was recrystallized from a solvent mixture of ethanol and diethyl ether, to thereby give the title compound (2.0 g).

$^1$H-NMR(CDCl$_3$)δ: 3.90(2H, dd, J=9.0, 3.7 Hz), 4.01-4.13 (4H, m), 8.84(6H, s).

Referential Example 172

N-[(3R*,4S*)-4-aminotetrahydro-3-furanyl]-5-chloroindole-2-carboxamide

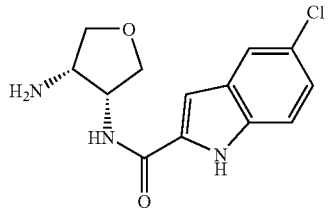

To a solution of the compound obtained in Referential Example 171 (0.5 g) in N,N-dimethylformamide (10 mL) were sequentially added 5-chloroindole-2-carboxylic acid (0.29 g), 1-hydroxybenzotriazole (0.2 g), and 1-(3-dimethylaminopropyl)-3-ethylcarbodiimide hydrochloride (0.6 g) at room temperature, followed by stirring at 50° C. for 1 day. The reaction mixture was concentrated, and the residue was diluted with a solvent mixture comprising chloroform and methanol (9:1). The diluted mixture was washed with saturated aqueous sodium hydrogencarbonate and saturated brine, and the organic layer was dried over sodium sulfate anhydrate. The solvent was distilled away under reduced pressure, and the residue was purified by silica gel column chromatography (chloroform:methanol=95:5), to thereby give the title compound (0.2 g).

$^1$H-NMR(CDCl$_3$)δ: 1.80-1.92(1H, m), 3.62(1H, dd, J=9.3, 4.2 Hz), 3.68-3.80(2H, m), 4.06(1H, dd, J=9.3, 5.6 Hz), 4.21 (1H, dd, J=9.3, 6.8 Hz), 4.36-4.52(2H, m), 6.87(1H, s), 7.24 (1H, dd, J=8.8, 2.0 Hz), 7.36(1H, d, J=8.8 Hz), 7.44-7.56(1H, m), 7.62(1H, d, J=2.0 Hz), 9.41(1H, s).

Referential Example 173

(4R)-4-[(E)-3-ethoxy-3-oxo-1-propenyl]-2,2-dimethyl-1,3-oxazolidine-3-carboxylic acid tert-butyl ester

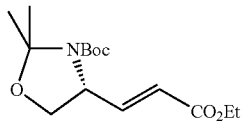

In a manner similar to that employed in Referential Example 164, the title compound was prepared from (4S)-4-formyl-2,2-dimethyl-1,3-oxazolidine-3-carboxylic acid tert-butyl ester.

$^1$H-NMR(CDCl$_3$)δ: 1.29(3H, t, J=6.6 Hz), 1.40-1.60(15H, m), 3.80(1H, dd, J=9.0, 2.4 Hz), 4.09(1H, dd, J=9.0, 6.6 Hz), 4.11-4.21(2H, m), 4.32-4.64(1H, m), 5.78-6.01(1H, m), 6.67-6.89(1H, m).

Referential Example 174

(4R)-4-[1-(benzylamino)-3-ethoxy-3-oxopropyl]-2,2-dimethyl-1,3-oxazolidine-3-carboxylic acid tert-butyl ester

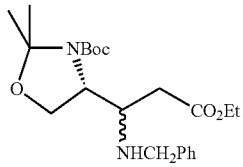

In a manner similar to that employed in Referential Example 165, the title compound was prepared from the compound obtained in Referential Example 173.

$^1$H-NMR(CDCl$_3$)δ: 1.25(3H, t, J=6.6 Hz), 1.40-1.61(15H, m), 2.21-2.32(0.5H, m), 2.40-2.51(1H, m), 2.61-2.72(0.5H, m), 3.43-3.50(1H, m), 3.67-3.80(1H, m), 3.83(2H, s), 3.90-4.03(1H, m), 4.04-4.22(4H, m), 7.20-7.40(5H, m).

Referential Example 175

(4R)-4-(1-{[(5-chloroindol-2-yl)carbonyl]amino}-3-ethoxy-3-oxopropyl)-2,2-dimethyl-1,3-oxazolidine-3-carboxylic acid tert-butyl ester

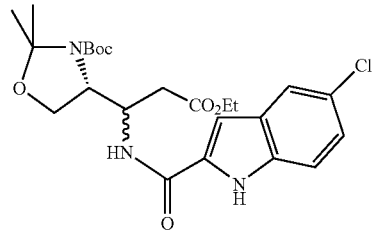

In a manner similar to that employed in Referential Example 166, the compound obtained in Referential Example 174 was subjected to catalytic reduction, to thereby eliminate the benzyl group. Subsequently the thus-obtained compound was subjected to condensation reaction with 5-chloroindole-2-carboxylic acid in a manner similar to that employed in Referential Example 172, to thereby give the title compound.

$^1$H-NMR(CDCl$_3$)δ: 1.23(1.5H, t, J=6.6 Hz), 1.25(1.5H, t, J=6.6 Hz), 1.50(4.5H, s), 1.54(4.5H, s), 1.62(6H, s), 2.50-2.70(1.5H, m), 2.86(0.5H, dd, J=16.4, 5.5 Hz), 3.80-3.90 (0.5H, m), 4.00-4.31(5H, m), 4.41-4.67(0.5H, m), 6.85(0.5H, s), 6.87(0.5H, s), 7.10-7.20(1H, m), 7.34(0.5H, d, J=8.8 Hz), 7.38(0.5H, d, J=8.8 Hz), 7.57(0.5H, s), 7.63(0.5H, s), 7.88 (0.5H, d, J=7.6 Hz), 8.54(0.5H, d, J=7.6 Hz), 9.40(0.5H, s), 9.54(0.5H, s).

Referential Example 176

(3R,4R)-4-{[(5-chloroindol-2-yl)carbonyl]amino}-6-oxotetrahydro-2H-pyran-3-ylcarbamic acid tert-butyl ester (low-polar compound) and (3R,4S)-4-{[(5-chloroindol-2-yl)carbonyl]amino}-6-oxotetrahydro-2H-pyran-3-ylcarbamic acid tert-butyl ester (high-polar compound)

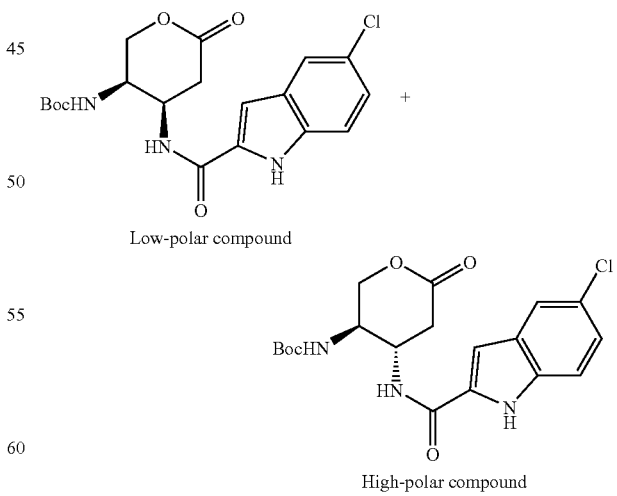

To a solution of the compound obtained in Referential Example 175 (1.0 g) in ethanol (20 mL) was added 1N aqueous sodium hydroxide (4.0 mL), and after the thus-obtained mixture was stirred for 4 hours, citric acid was added to the reaction mixture, to thereby adjust pH to 4.0. The resultant mixture was extracted with ethyl acetate. The organic layer was washed with saturated brine, and was dried over sodium sulfate anhydrate. The solvent was distilled away under reduced pressure. The residue was dissolved in methanol (50 mL), and toluenesulfonic acid monohydrate (0.1 g) was added thereto, followed by stirring for 18 hours. The reaction mixture was diluted with ethyl acetate, and the diluted mixture was washed with saturated aqueous sodium hydrogencarbonate and saturated brine. The organic layer was dried over sodium sulfate anhydrate, and the solvent was distilled away under reduced pressure. The residue was purified by silica gel column chromatography (chloroform:methanol=99:1), to thereby give the title low-polar compound (0.3 g) and the title high-polar compound (0.3 g).

Low-Polar Compound:
$^1$H-NMR(CDCl$_3$)δ: 1.45(9H, s), 2.70(1H, dd, J=16.5, 4.9 Hz), 2.85(1H, dd, J=16.5, 4.6 Hz), 3.50-3.61(1H, m), 3.71-3.81(2H, m), 4.30-4.40(1H, m), 5.30(1H, d, J=9.5 Hz), 6.89 (1H, s), 7.23(1H, dd, J=8.8, 2.0 Hz), 7.38(1H, d, J=8.8 Hz), 7.62(1H, d, J=2.0 Hz), 7.93(1H, d, J=9.5 Hz), 9.30(1H, s).

High-Polar Compound:
$^1$H-NMR(CDCl$_3$)δ: 1.39(9H, s), 2.75(1H, dd, J=16.5, 4.9 Hz), 2.82(1H, dd, J=16.5, 4.6 Hz), 3.41-3.52(2H, m), 3.71-3.82(1H, m), 3.85-3.94(1H, m), 5.03(1H, d, J=9.3 Hz), 6.99 (1H, s), 7.22-7.31(1H, m), 7.34(1H, d, J=8.8 Hz), 7.61(1H, d, J=2.0 Hz), 7.83(1H, d, J=9.3 Hz), 9.28(1H, s).

Referential Example 177

1,1,3,-trioxohexahydro-1-thiopyran-4-ylcarbamic acid tert-butyl ester

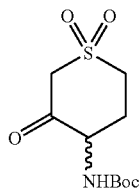

A solution of N-tert-butoxycarbonyl-L-methionine sulfone methyl ester (60.2 g) in tetrahydrofuran (900 mL) was cooled to −78° C., and potassium bis(trimethylsilyl)amide (as 0.5M toluene solution, 900 mL) was added dropwise thereto, followed by stirring at −78° C. for 2 hours, and then at room temperature for 4.5 hours. To the resultant mixture was added 1M aqueous ammonium chloride, and the thus-obtained mixture was stirred. The reaction mixture was separated, and the organic layer was washed with water and saturated brine, followed by drying over anhydrous magnesium sulfate. The solvent was distilled away under reduced pressure, and the resultant solid was collected by filtration, to thereby give the title compound (12.4 g). The aqueous layer previously separated was extracted with ethyl acetate twice, and the organic layers were combined. The combined organic layer was washed with water and saturated brine, and was dried over anhydrous magnesium sulfate. Furthermore, the aqueous layers used for the washing of the organic layer were combined, and the mixture was futher extracted with ethyl acetate. The extract was washed with saturated brine, and was dried over anhydrous magnesium sulfate. The ethyl acetate extracts were combined. The mixture was concentrated under reduced pressure, to thereby give the title compound (27.7 g) (total amount of the title compound: 40.1 g).
$^1$H-NMR(CDCl$_3$)δ: 1.45(9H, s), 1.85-1.96(1H, m), 2.76-2.78(1H, m), 3.34-3.46(2H, m), 4.05(1H, dd, J=13.5, 3.7 Hz), 4.14(1H, d, J=13.5 Hz), 4.38-4.44(1H, m), 5.46(1H, br).
MS(ESI)m/z: 262(M−H).

Referential Example 178

(3R*,4R*)-3-hydroxy-1,1-dioxohexahydro-1-thiopyran-4-ylcarbamic acid tert-butyl ester

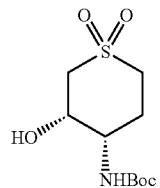

To a suspension of the compound obtained in Referential Example 177 (10.1 g) in methanol (200 mL) was added sodium borohydride (2.17 g), and the thus-obtained mixture was stirred at room temperature for 2 hours. The reaction mixture was concentrated under reduced pressure, and ethyl acetate and saturated aqueous sodium hydrogencarbonate were added to the residue. The aqueous layer was separated, and was extracted with ethyl acetate twice. The organic layers were combined. The combined organic layer was dried over magnesium sulfate, and was concentrated under reduced pressure, to thereby give the title compound (9.96 g).
$^1$H-NMR(CDCl$_3$)δ: 1.44(9H, s), 2.21-2.36(2H, m), 3.03-3.17(2H, m), 3.26-3.28(2H, m), 3.77-3.80(2H, m), 4.26-4.28 (1H, m), 5.05-5.07(1H, m).
MS(ESI)m/z: 264[(M−H).

Referential Example 179

(3R*,4R*)-3-amino-1,1-dioxohexahydro-1-thiopyran-4-ylcarbamic acid tert-butyl ester (low-polar compound) and (3R*,4S*)-3-amino-1,1-dioxohexahydro-1-thiopyran-4-ylcarbamic acid tert-butyl ester (high-polar compound)

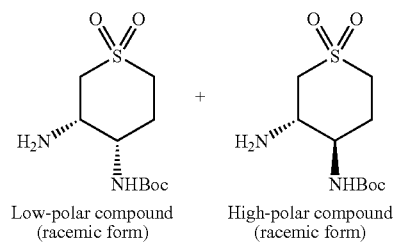

Low-polar compound (racemic form)  High-polar compound (racemic form)

To a solution of the compound obtained in Referential Example 178 (9.66 g) and triphenylphosphine (10.5 g) in tetrahydrofuran (150 mL) was added diethyl azodicarboxylate (6.96 g), and the thus-obtained mixture was stirred at room temperature for 4.5 hours. The reaction mixture was concentrated under reduced pressure, and diethyl ether was added to the residue. The resultant solid was collected by filtration, and the thus-obtained solid was purified by silica gel column chromatography (hexane:ethyl acetate=7:3), to thereby give a mixture (7.25 g) containing 1,1-dioxo-1,2,3,4-tetrahydrothiopyran-4-ylcarbamic acid tert-butyl ester as a colorless solid. Furthermore, the filtrate was concentrated under reduced pressure, and the residue was purified by silica gel column chromatography (hexane:ethyl acetate=7:3), to thereby give a mixture (9.18 g) containing 1,1-dioxo-1,2,3,4-tetrahydrothiopyran-4-ylcarbamic acid tert-butyl ester as a colorless solid (total amount: 16.4 g). The thus-obtained mixture was dissolved in dioxane (60 mL), and 28% aqueous ammonia (60 mL) was added thereto, followed by stirring at 60° C. for 4.5 hours in a sealed tube. After the reaction mixture was left to cool, the mixture was concentrated under reduced pressure. After dioxane was distilled away, the residue was extracted with methylene chloride five times. The organic layers were combined, and the mixture was concentrated under reduced pressure. The residue was separated and purified by silica gel column chromatography (methylene chloride:methanol=96:4), to thereby give the title low-polar compound (2.31 g) and the title high-polar compound (4.31 g).

Low-Polar Compound:
$^1$H-NMR(CDCl$_3$)δ: 1.44(9H, s), 2.14-2.28(2H, m), 3.01-3.08(3H, m), 3.23(1H, dd, J=13.8, 3.9 Hz), 3.47-3.49(1H, m), 3.71-3.76(1H, m), 5.32(1H, d, J=7.3 Hz).
MS(ESI)m/z: 265(M+H$^+$).

High-Polar Compound:
$^1$H-NMR(CDCl$_3$)δ: 1.45(9H, s), 1.94-2.01(1H, m), 2.37-2.44(1H, m), 2.91(1H, dd, J=11.2, 14.1 Hz), 3.04-3.07(2H, m), 3.12-3.19(1H, m), 3.26-3.30(1H, m), 3.39-3.42(1H, m), 4.62(1H, br).
MS(ESI)m/z: 265(M+H$^+$).

Referential Example 180

(2S,3S)-2,3-bis(methoxymethoxy)-1,4-butanediol

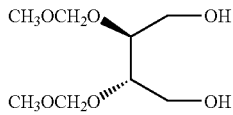

Chloromethyl methyl ether (4.8 mL) was added dropwise to a mixture comprising diethyl L-tartrate (8.6 g), diisopropylethylamine (40 mL), and methylene chloride (40 mL) under ice cooling, and the thus-obtained mixture was gradually brought back to room temperature while being stirred. After the mixture was stirred for 18 hours, the reaction mixture was concentrated, and the residue was diluted with ethyl acetate. The diluted mixture was washed with 10% aqueous HCl, saturated aqueous sodium hydrogencarbonate, and saturated brine. The organic layer was dried over sodium sulfate anhydrate, and the solvent was distilled away under reduced pressure. The residue was dissolved in tetrahydrofuran, and the thus-obtained solution was added dropwise to a suspension of lithium aluminium hydride (2.2 g) in tetrahydrofuran under ice cooling, followed by stirring for 2 hours under ice cooling. Subsequently, 10% aqueous sodium hydrogen sulfate was carefully added to the reaction mixture under ice cooling, and the thus-obtained mixture was stirred for 1 hour. The resultant mixture was diluted with saturated brine, and the diluted mixture was extracted with ethyl acetate. The organic layer was dried over sodium sulfate anhydrate, and the solvent was distilled away under reduced pressure, to thereby give the title compound (3.0 g).

$^1$H-NMR(CDCl$_3$)δ: 1.55-1.64(2H, m), 3.44(6H, s), 3.70-3.81(6H, m), 4.70(2H, d, J=6.9 Hz), 4.76(2H, d, J=6.9 Hz).

Referential Example 181

(3S,4S)-3,4-bis(methoxymethoxy)tetrahydrofuran

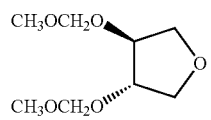

To a mixture comprising the compound obtained in Referential Example 180 (3.0 g), triphenylphosphine (4.5 g), tetrahydrofuran (10 mL), and toluene (40 mL) was added dropwise diethyl azodicarboxylate (2.64 mL), and the thus-obtained mixture was stirred at room temperature for 4 days. The reaction mixture was concentrated, and to the residue was added a solvent mixture (160 mL) comprising hexane and diethyl ether (1:1), followed by stirring for 3 hours. The resultant insoluble matter was removed by filtration, and the filtrate was concentrated. The residue was purified by silica gel column chromatography (hexane:ethyl acetate=4:1), to thereby give the title compound (1.95 g).

$^1$H-NMR(CDCl$_3$)δ: 3.38(6H, s), 3.80(2H, dd, J=9.2, 1.7 Hz), 4.00(2H, dd, J=9.2, 4.4 Hz), 4.23(2H, dd, J=4.4, 1.7 Hz), 4.67(2H, d, J=6.9 Hz), 4.71(2H, d, J=6.9 Hz).

Referential Example 182

(3S,4S)tetrahydro-3,4-furandiol

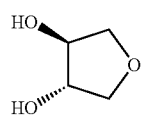

To a solution of the compound obtained in Referential Example 181 (1.95 g) in methanol (6.0 mL) was added concentrated HCl (2.1 mL), and the thus-obtained mixture was stirred for 18 hours. The reaction mixture was concentrated, and the residue was diluted with chloroform, followed by drying over potassium carbonate. The solvent was distilled away under reduced pressure, to thereby give the title compound (0.52 g).

$^1$H-NMR(CDCl$_3$)δ: 1.77(2H, d, J=4.7 Hz), 3.73(2H, d, J=10.2 Hz), 4.08(2H, dd, J=10.2, 3.7 Hz), 4.18-4.34(2H, m).

Referential Example 183

(3S,4S)tetrahydro-3,4-furandiamine

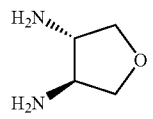

In a manner similar to that employed in Referential Examples 169 to 171, the title compound was prepared from the compound obtained in Referential Example 182.

$^1$H-NMR(CDCl$_3$)δ: 1.35-1.46(4H, m), 3.19(2H, dd, J=5.6, 4.1 Hz), 3.50(2H, dd, J=9.0, 4.1 Hz), 4.09(2H, dd, J=9.0, 5.6 Hz).

Referential Example 184

(2R,3R)-2,3-bis(methoxymethoxy)-1,4-butanediol

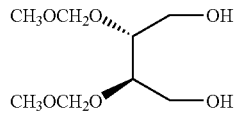

In a manner similar to that employed in Referential Example 180, the title compound was prepared from diethyl D-tartrate.

¹H-NMR: The data was coincided with that of its enantiomer in Referential Example 180.

Referential Example 185

(3R,4R)-3,4-bis(methoxymethoxy)tetrahydrofuran

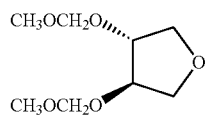

In a manner similar to that employed in Referential Example 181, the title compound was prepared from the compound obtained in Referential Example 184.

¹H-NMR: The data was coincided with that of its enantiomer in Referential Example 181.

Referential Example 186

(3R,4R)tetrahydro-3,4-furandiol

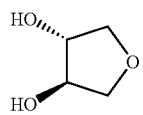

In a manner similar to that employed in Referential Example 182, the title compound was prepared from the compound obtained in Referential Example 185.

¹H-NMR: The data was coincided with that of its enantiomer in Referential Example 182.

Referential Example 187

(3R,4R)tetrahydro-3,4-furandiamine

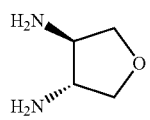

In a manner similar to that employed in Referential Example 183, the title compound was prepared from the compound obtained in Referential Example 186.

¹H-NMR: The data was coincided with that of its enantiomer in Referential Example 183.

Referential Example 188

(3R,4R)-1-benzyl-3,4-dihydroxy-2,5-pyrrolidinedione

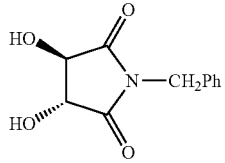

L-Tartaric acid (30 g) and benzylamine (22 mL) were added to xylene (150 mL), and the mixture was heated under reflux at 150° C. for 3 hours while water was removed with Dean-Stark apparatus. After the reaction mixture was left to cool overnight, the resultant crystals were collected by filtration, and were washed with acetone. The thus-obtained crude product was recrystallized from ethanol, to thereby give the title compound (23.2 g).

¹H-NMR(DMSO-$d_6$)δ: 4.36-4.40(2H, m), 4.55(each 1H, AB type d, J=15 Hz), 6.26-6.30(2H, m), 7.25-7.35(5H, m).

Referential Example 189

(3S,4S)-1-benzyl-3,4-pyrrolidinediol

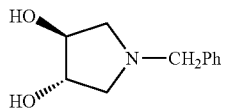

The compound obtained in Referential Example 188 (11 g) was dissolved in tetrahydrofuran (110 mL), and lithium aluminium hydride (5.69 g) was added thereto in small portions under ice cooling. The thus-obtained mixture was heated to room temperature, and after 1 hour, the mixture was heated under reflux overnight. The resultant mixture was left to cool, and to the mixture were sequentially added water (5.7 mL), 15% aqueous sodium hydroxide (5.7 mL), water (17.1 mL) under ice cooling. The reaction mixture was brought back to room temperature, and was stirred for 1 hour. The resultant precipitate was filtered through Celite, and the filtrate was concentrated. The residue was recrystallized from ethyl acetate, to thereby give the title compound (6.35 g).

¹H-NMR(CDCl₃)δ: 2.40-2.44(2H, m), 2.88-2.92(2H, m), 3.58(each 1H, AB type d, J=7.8 Hz), 4.04(2H, t, J=4.2 Hz), 7.25-7.34(5H, m).

Referential Example 190 methanesulfonic acid (3S,4S)-1-benzyl-4-[(methylsulfonyl)oxy]pyrrolidinyl ester

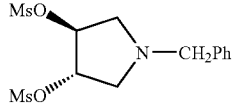

In a manner similar to that employed in Referential Example 169, the title compound was prepared from the compound obtained in Referential Example 189.

$^1$H-NMR(CDCl$_3$)δ: 2.76(2H, dd, J=11, 4.6 Hz), 3.08(6H, s), 3.64(2H, d, J=2.5 Hz), 3.68-3.75(2H, m), 5.12-5.15(2H, m), 7.27-7.35(5H, m).

Referential Example 191

(3S,4S)-3,4-bis[(methylsulfonyl)oxy]-1-pyrrolidin-ecarboxylic acid tert-butyl ester

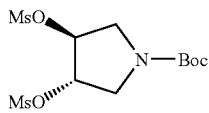

The compound obtained in Referential Example 190 (1.57 g) was dissolved in 1,2-dichloroethane (16 mL), and 1-chloroethyl chloroformate (0.73 mL) was added thereto at room temperature, followed by heating under reflux for 4 hours. The solvent was distilled away under reduced pressure, and methanol (16 mL) was added to the residue, followed by heating under reflux for 1 hour. The resultant mixture was left to cool, and was concentrated. The residue was crystallized from ethyl acetate, and the crystals were collected by filtration, to thereby give (3S,4S)-3,4-bis-[(methylsulfonyl)oxy] pyrrolidine hydrochloride (1.30 g) as colorless crystals. To a solution of the thus-obtained hydrochloride salt and triethylamine (1.40 mL) in methylene chloride (26 mL) was added di-tert-butyl dicarbonate (1.15 mL), and the thus-obtained mixture was stirred at room temperature overnight. The resultant mixture was concentrated, and the residue was diluted with ethyl acetate. The diluted mixture was washed with water and saturated brine, and was dried over sodium sulfate anhydrate. The solvent was distilled away under reduced pressure, and the residue was purified by silica gel column chromatography (ethyl acetate hexane=1:9 to 1:1), to thereby give the title compound (1.40 g).

$^1$H-NMR(CDCl$_3$)δ: 1.47(9H, s), 3.12(6H, s), 3.70-3.73 (2H, m), 3.79(1H, d, J=4.5 Hz), 3.82(1H, d, J=4.5 Hz), 5.19 (2H, br).

Referential Example 192

(3R,4R)-3,4-diazido-1-pyrrolidinecarboxylic acid tert-butyl ester

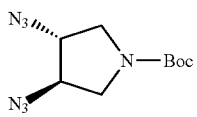

In a manner similar to that employed in Referential Example 170, the title compound was prepared from the compound obtained in Referential Example 191.

$^1$H-NMR(CDCl$_3$)δ: 1.47(9H, s), 3.37-3.46(2H, m), 3.64-3.71(2H, m), 3.96(2H, t, J=3.2 Hz).

Referential Example 193

(3R,4R)-3-amino-4-{[(5-chloroindol-2-yl)carbonyl] amino}pyrrolidine-1-carboxylic acid tert-butyl ester

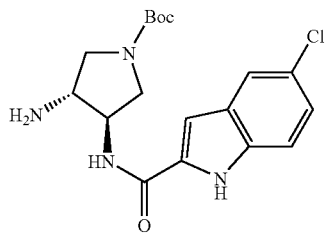

In a manner similar to that employed in Referential Examples 171 and 172, the title compound was prepared from the compound obtained in Referential Example 192.

$^1$H-NMR(DMSO-d$_6$)δ: 1.39(9H, s), 2.95-3.00(1H, m), 3.09-3.13(1H, m), 3.52(1H, dd, J=10, 6.5 Hz), 3.68(1H, dd, J=10, 7.8 Hz), 4.04-4.09(2H, m), 7.16(1H, s), 7.18(1H, s), 7.42(1H, d, J=8.5 Hz), 7.69(1H, d, J=1.5 Hz), 8.50(1H, d, J=6.5 Hz), 11.77(1H, br).

Referential Example 194

(3S)-5-oxotetrahydro-3-furanylcarbamic acid tert-butyl ester

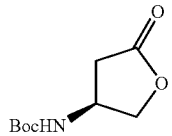

To a solution of (3S)-(−)-tetrahydro-5-oxo-3-furanylcarbamic acid benzyl ester (3.3 g) in tetrahydrofuran (20 mL) were added di-tert-butyl dicarbonate (4.1 g) and 10% palladium on carbon (0.4 g), followed by stirring for 1 day under hydrogen atmosphere. Any insoluble matter was removed by filtration through a Celite pad, and the filtrate was concentrated under reduced pressure. The residue was purified by silica gel column chromatography (hexane:ethyl acetate=4:1), to thereby give the title compound (1.5 g).

$^1$H-NMR(CDCl$_3$)δ: 1.45(9H, s), 2.45(1H, dd, J=17.8, 2.7 Hz), 2.86(1H, dd, J=17.8, 7.3 Hz), 4.12-4.23(1H, m), 4.54-4.62(2H, m), 4.85-4.95(1H, m).

Referential Example 195

(3S,4S)-4-azido-5-oxotetrahydro-3-furanylcarbamic acid tert-butyl ester

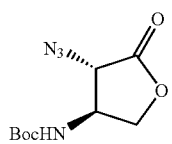

To a solution of the compound obtained in Referential Example 194 (0.87 g) in tetrahydrofuran (20 mL) was added dropwise lithium bis(trimethylsilyl)amide (as 1M tetrahydrofuran solution, 8.65 mL) at −78° C., and the thus-obtained mixture was stirred for 30 minutes. Subsequently, a solution of p-toluenesulfonyl azide (1.02 g) in tetrahydrofuran (10 mL) was added thereto, followed by stirring for 5 minutes, and after trimethylchlorosilane (1.7 mL) was added thereto, the thus-obtained mixture was gradually brought back to room temperature while being stirred. After the reaction mixture was stirred for 2 hours, the mixture was diluted with diethyl ether, and the diluted mixture was washed with 10% aqueous HCl, 5% saturated aqueous sodium hydrogencarbonate, and saturated brine, followed by drying over sodium sulfate anhydrate. The solvent was distilled away under reduced pressure, and the residue was purified by silica gel column chromatography (hexane:ethyl acetate=4:1), to thereby give the title compound (0.62 g).

$^1$H-NMR(CDCl$_3$)δ: 1.46(9H, s), 4.09(1H, dt, J=15.3, 7.6 Hz), 4.12-4.23(1H, m), 4.37-4.50(1H, m), 4.54(1H, dd, J=9.0, 7.6 Hz), 4.81-4.90(1H, m).

Referential Example 196

(3S,4S)-4-{[(5-chloroindol-2-yl)carbonyl]amino}-5-oxotetrahydro-3-furanylcarbamic acid tert-butyl ester

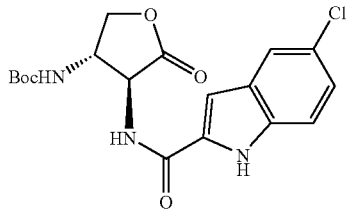

In a manner similar to that employed in Referential Examples 90 and 91, the title compound was prepared from the compound obtained in Referential Example 195.

$^1$H-NMR(CDCl$_3$)δ: 1.44(9H, s), 4.01-4.13(1H, m), 4.20-4.36(1H, m), 4.78-4.93(2H, m), 6.15(1H, s), 6.93(1H, s), 7.03-7.11(1H, m), 7.20-7.28(1H, m), 7.30(1H, d, J=8.8 Hz), 7.61(1H, s), 9.27(1H, s).

Referential Example 197

(3S,4S)-4-{[(5-methyl-4,5,6,7-tetrahydrothiazolo[5,4-c]pyridin-2-yl)carbonyl]amino}-5-oxotetrahydro-3-furanylcarbamic acid tert-butyl ester

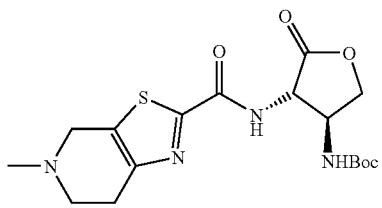

In a manner similar to that employed in Referential Example 90, (3S,4S)-4-amino-5-oxotetrahydro-3-furanylcarbamic acid tert-butyl ester was prepared from the compound obtained in Referential Example 195. Subsequently, the thus-obtained compound was reacted with the compound obtained in Referential Example 10 in accordance with the reaction conditions described in Referential Example 91, to thereby give the title compound.

$^1$H-NMR(CDCl$_3$)δ: 1.44(9H, s), 2.52(3H, s), 2.83(2H, t, J=5.9 Hz), 2.79-3.02(2H, m), 3.74(2H, s), 4.03-4.12(1H, m), 4.21-4.36(1H, m), 4.80-4.95(2H, m), 6.14-6.24(1H, m), 7.76-7.85(1H, m).

Referential Example 198

2-[((3S)-3-[(tert-butoxycarbonyl)amino]-2-{[(5-chloroindol-2-yl)carbonyl]amino}-4-hydroxybutanoyl)amino]acetic acid ethyl ester

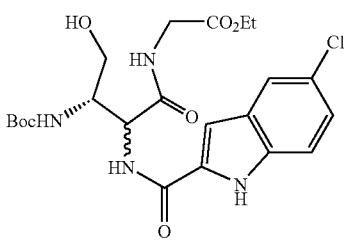

The compound obtained in Referential Example 196 (0.4 g), glycine ethyl ester hydrochloride (1.0 g), and triethylamine (1.0 mL) were added to ethanol (20 mL), and the mixture was stirred at 60° C. for 18 hours. The reaction mixture was diluted with chloroform, and the diluted mixture was washed with 10% aqueous citric acid and saturated brine. The organic layer was dried over sodium sulfate anhydrate, and the solvent was distilled away under reduced pressure. The residue was purified by silica gel column chromatography (chloroform:methanol=98:2), to thereby give the title compound (0.31 g).

$^1$H-NMR(DMSO-d$_6$)δ: 1.17(3H, t, J=7.0 Hz), 1.34(6H, s), 1.36(3H, s), 3.51-3.63(0.6H, m), 3.72-3.80(2H, m), 4.06(2H, q, J=7.0 Hz), 4.11-4.23(1.4H, m), 4.67-4.82(1H, m), 4.85-4.91(1H, m), 6.48(0.4H, d, J=9.5 Hz), 6.80(0.6H, d, J=9.5 Hz), 7.10-7.22(2H, m), 7.42(1H, d, J=8.8 Hz), 7.72(0.4H, d, J=2.0 Hz), 7.73(0.6H, d, J=2.0 Hz), 8.23-8.31(0.6H, m), 8.34-8.41(0.4H, m), 8.43-8.50(1H, m), 11.83(1H, s).

Referential Example 199

2-((4R)-4-amino-3-{[(5-chloroindol-2-yl)carbonyl]amino}-2-oxopyrrolidin-1-yl)acetic acid ethyl ester hydrochloride

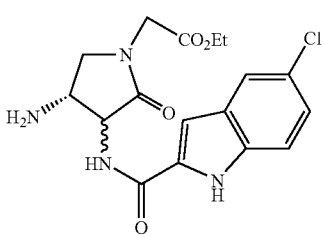

In accordance with the reaction conditions described in Referential Example 181, the compound obtained in Referential Example 198 was converted to a pyrrolidone derivative. Subsequently, the tert-butoxycarbonyl group was eliminated in a manner similar to that employed in Referential Example 69, to thereby give the title compound.

¹H-NMR(DMSO-d₆)δ: 1.17(2H, t, J=7.0 Hz), 1.23(1H, t, J=7.0 Hz), 3.31-3.40(0.6H, m), 3.57(0.4H, d, J=11.2 Hz), 3.90-4.23(4H, m), 4.42(0.6H, dd, J=12.0, 6.1 Hz), 4.50-4.60 (0.4H, m), 4.62(0.6H, dd, J=12.0, 3.9 Hz), 5.12-5.23(0.4H, m), 7.17(0.4H, s), 7.20(0.4H, dd, J=8.8, 2.0 Hz), 7.28(0.6H, dd, J=8.8, 2.0 Hz), 7.30(0.6H, s), 7.44(0.4H, d, J=8.8 Hz), 7.50(0.6H, d, J=8.8 Hz), 7.75(1H, d, J=2.0 Hz), 8.20-8.33 (1H, m), 8.71-8.94(3.6H, m), 9.22-9.35(0.4H, m), 11.97(0.4H, s), 12.44(0.6H, s).

Referential Example 200

(3R,4S)-4-{[(5-chloroindol-2-yl)carbonyl]amino}-1-methyl-5-oxopyrrolidin-3-ylcarbamic acid tert-butyl ester

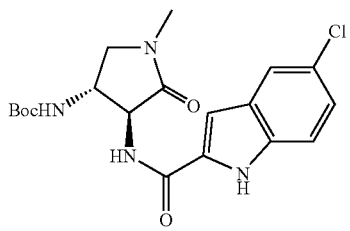

In a manner similar to that employed in Referential Example 198, the compound obtained in Referential Example 196 was reacted with methylamine (as 40% methanol solution). Subsequently, the title compound was prepared from the thus-obtained compound in a manner similar to that employed in Referential Example 181.

¹H-NMR(CDCl₃)δ: 1.43(9H, s), 2.90(3H, s), 4.26(1H, br.s), 4.36(2H, m), 4.51-4.52(1H, m), 5.35(1H, br.s), 6.95-6.99(2H, m), 7.22-7.32(3H, m), 7.63(1H, s), 8.95(1H, br.s)

Referential Example 201

N-[(3S,4R)-4-amino-1-methyl-2-oxopyrrolidin-3-yl]-5-chloroindole-2-carboxamide

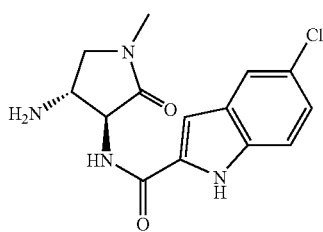

In a manner similar to that employed in Referential Example 69, the title compound was prepared from the compound obtained in Referential Example 200.

¹H-NMR(CDCl₃)δ: 2.95(3H, d, J=5.1 Hz), 3.91-3.93(1H, m), 4.19(1H, d, J=3.7 Hz), 4.36(1H, dd, J=11, 1.7 Hz), 4.48 (1H, dd, J=11, 2.0 Hz), 6.90-6.97(2H, m), 7.21-7.33(2H, m), 7.62(1H, d, J=2.0 Hz), 8.90(1H, s)

Referential Example 202

3,6-dihydro-[(2H)-pyridinecarboxylic acid tert-butyl ester

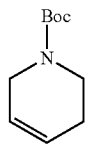

di-tert-Butyl dicarbonate (6.55 g) was added to a mixture of 1,2,3,6-tetrahydropyridine (2.50 g) and 10% aqueous sodium carbonate (3.0 mL), and the thus-obtained mixture was stirred at room temperature for 20 hours. Water was added to the reaction mixture, and the mixture was extracted with ethyl acetate. The organic layer was sequentially washed with 0.5N HCl, water, saturated aqueous sodium hydrogencarbonate, and saturated brine, and was dried over sodium sulfate anhydrate. The solvent was distilled away under reduced pressure, to thereby give the title compound (5.08 g).

¹H-NMR(CDCl₃)δ: 1.47(9H, s), 2.12(2H, br.s), 3.48(2H, t, J=5.6 Hz), 3.88(2H, br.s), 5.60(1H, br.s), 5.78-5.90(1H, m).

Referential Example 203

(3R*,4S*)-3,4-dihydroxy-1-piperidinecarboxylic acid tert-butyl ester

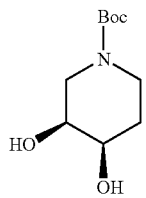

The compound obtained in Referential Example 202 (18.45 g) was dissolved in acetonitrile (200 mL), and to the solution were added water (38 mL), 0.039M aqueous osmium tetraoxide (82 mL), and N-methylmorpholine N-oxide (23.13 g), followed by stirring at room temperature for 17 hours. After any excess oxidizing agent was treated with saturated aqueous sodium sulfite, the thus-obtained mixture was extracted with ethyl acetate. The organic layer was sequentially washed with water, 0.5N HCl, water, saturated aqueous sodium hydrogencarbonate, and saturated brine, and was dried over sodium sulfate anhydrate, followed by concentration under reduced pressure. The residue was purified by silica gel column chromatography (hexane:ethyl acetate=1: 3), to thereby give the title compound (15.0 g).

¹H-NMR(CDCl₃)δ: 1.46(9H, s), 1.60-1.73(1H, m), 1.77-1.90(1H, m), 2.68(1H, br.s), 2.80-3.20(1H, br), 3.22-3.32

(1H, m), 3.42(1H, dd, J=14.3, 3.4 Hz), 3.50-3.62(2H, m), 3.77(1H, brs), 3.81-3.92(1H, m).

Referential Example 204

(3R*,4S*)-3,4-bis[(methylsulfonyl)oxy]-1-piperidinecarboxylic acid tert-butyl ester

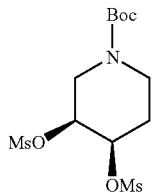

In a manner similar to that employed in Referential Example 169, the title compound was prepared from the compound obtained in Referential Example 203.
$^1$H-NMR(CDCl$_3$)δ: 1.47(9H, s), 1.85-1.97(1H, m), 2.08-2.20(1H, m), 3.00-4.20(4H, m), 3.12(6H, s), 4.85(1H, br.s), 4.94(1H, br.s).

Referential Example 205

(3R*,4S*)-3,4-diazido-1-piperidinecarboxylic acid tert-butyl ester

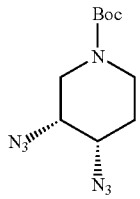

In a manner similar to that employed in Referential Example 170, the title compound was prepared from the compound obtained in Referential Example 204.
$^1$H-NMR(CDCl$_3$)δ: 1.47(9H, s), 1.70-1.80(1H, m), 1.90-2.00(1H, m), 3.05-4.00(6H, m).

Referential Example 206

(3R*,4S*)-3,4-diamino-1-piperidinecarboxylic acid tert-butyl ester

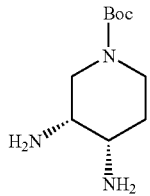

In a manner similar to that employed in Referential Example 171, the title compound was prepared from the compound obtained in Referential Example 205.
$^1$H-NMR(CDCl$_3$)δ: 1.46(9H, s), 1.48-1.60(2H, m), 1.80-2.10(4H, br), 2.85-2.91(2H, m), 2.97(1H, br.s), 3.09(1H, dd, J=13.6, 2.7 Hz), 3.74(1H, dd, J=13.6, 4.2 Hz), 3.81(1H, s).

Referential Example 207

(3R*,4S*)-3-amino-4-{[(5-chloroindol-2-yl)carbonyl]amino}-1-piperidinecarboxylic acid tert-butyl ester

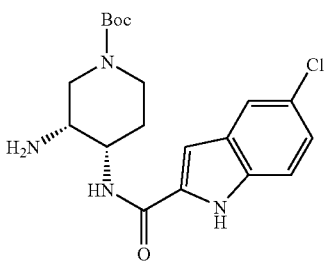

The compound obtained in Referential Example 206 (3.23 g) was dissolved in N,N-dimethylformamide (100 mL), and to the solution were added triethylamine (2.08 mL) and the compound obtained in Referential Example 52 (3.80 g), followed by stirring at room temperature for 3 days. The reaction mixture was concentrated under reduced pressure, and water was added to the residue. The thus-obtained mixture was extracted with methylene chloride. The organic layer was washed with saturated aqueous sodium hydrogencarbonate and saturated brine, and was dried over sodium sulfate anhydrate, followed by concentration under reduced pressure. The residue was purified by silica gel column chromatography (methylene chloride:methanol=20:1 to 10:1), to thereby give the title compound (2.70 g).
$^1$H-NMR(DMSO-d$_6$)δ: 1.40-1.58(3H, m), 1.41(9H, s), 1.75-1.90(1H, m), 2.95(1H, br.s), 2.98-3.05(1H, m), 3.19-3.28(1H, m), 3.74(1H, dd, J=19.5, 15.4 Hz), 3.79(1H, br.s), 4.04-4.12(1H, m), 7.17(1H, dd, J=8.7, 1.9 Hz), 7.21(1H, s), 7.42(1H, d, J=8.7 Hz), 7.68(1H, d, J=1.9 Hz), 8.00(1H, br.d, J=7.6 Hz), 11.80(1H, s).

Referential Example 208

(3R*,4S*)-3-amino-4-{[(5-methyl-4,5,6,7-tetrahydrothiazolo[5,4-c]pyridin-2-yl)carbonyl]amino}-1-piperidinecarboxylic acid tert-butyl ester

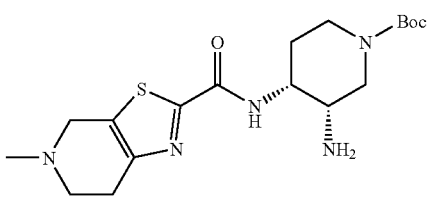

The compound obtained in Referential Example 206 (3.23 g) was dissolved in N,N-dimethylformamide (100 mL), and triethylamine (2.08 mL) was added thereto. Subsequently, the compound obtained in Referential Example 149 (3.83 g) was added thereto, and the thus-obtained mixture was stirred at room temperature for 3 days. The reaction mixture was concentrated under reduced pressure, and water was added to the residue. The thus-obtained mixture was extracted with methylene chloride. The organic layer was washed with saturated aqueous sodium hydrogencarbonate and saturated brine, and was dried over sodium sulfate anhydrate. The solvent was distilled away under reduced pressure, and the residue was separated by silica gel column chromatography (methylene chloride:methanol=10:1 to 5:1), to thereby give the title compound (2.27 g).

$^1$H-NMR(CDCl$_3$)δ: 1.30-1.62(3H, m), 1.47(9H, s), 1.78-1.88(1H, m), 2.51(3H, s), 2.81(2H, t, J=5.9 Hz), 2.85-2.98 (3H, m), 3.00-3.15(2H, m), 3.71(2H, s), 3.80-4.15(3H, m), 7.79(1H, br.s).

Referential Example 209

(3R*,4S*)-3-amino-4-{[(5-fluoroindol-2-yl)carbonyl]amino}-1-piperidinecarboxylic acid tert-butyl ester

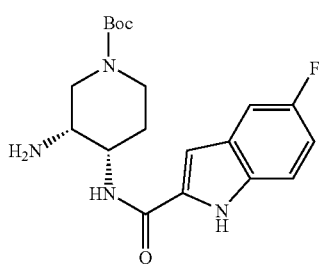

In a manner similar to that employed in Referential Example 172, the title compound was prepared from the compound obtained in Referential Example 206 and 5-fluoroindole-2-carboxylic acid.

$^1$H-NMR(CDCl$_3$)δ: 1.40-1.70(3H, m), 1.48(9H, s), 2.79-2.92(1H, m), 2.99-3.14(1H, m), 4.00-4.23(3H, m), 6.85(1H, s), 7.04(1H, td, J=9.0, 2.4 Hz), 7.07-7.20(1H, br), 7.27(1H, dd, J=9.0, 2.4 Hz), 7.35(1H, d, J=9.0, 4.4 Hz), 9.25-9.50(1H, br).

MS(ESI)m/z: 377(M+H)$^+$.

Referential Example 210

(3S,4R)-5-azido-3-{[(benzyloxy)carbonyl]amino}-4-[(tert-butoxycarbonyl)amino]valeric acid ethyl ester

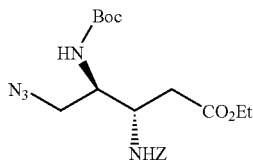

To a solution of the (3S,4S)-isomer (low-polar compound) obtained in Referential Example 168 (7.1 g) in methylene chloride (100 mL) were sequentially added dropwise triethylamine (4.80 mL) and methanesulfonyl chloride (1.55 mL) under ice cooling, followed by stirring for 30 minutes under ice cooling. The reaction mixture was diluted with chloroform, and the diluted mixture was washed with 10% aqueous citric acid, saturated aqueous sodium hydrogencarbonate, and saturated brine. The organic layer was dried over sodium sulfate anhydrate, and the solvent was distilled away under reduced pressure, to thereby give a methanesulfonyl compound (9.20 g). A mixture comprising the thus-obtained methanesulfonyl compound, sodium azide (5.64 g), and N,N-dimethylformamide (100 mL) was stirred at 80° C. for 20 hours. Subsequently, the reaction mixture was diluted with ethyl acetate, and the diluted mixture was washed with water and saturated brine. The organic layer was dried over sodium sulfate anhydrate, and the solvent was distilled away under reduced pressure. The residue was purified by silica gel column chromatography (chloroform), to thereby give the title compound (5.42 g).

$^1$H-NMR(CDCl$_3$)δ: 1.24(3H, t, J=7.1 Hz), 1.43(9H, s), 2.56-2.68(2H, m), 3.48-3.60(2H, m), 3.88-3.97(1H, m), 4.04-4.20(3H, m), 4.88-4.97(1H, br), 5.10(2H, s), 5.60-5.75(1H, br), 7.30-7.40(5H, m).

MS(ESI)m/z: 436(M+H)$^+$.

Referential Example 211

(4S,5R)-5-[(tert-butoxycarbonyl)amino]-2-oxopiperidin-4-ylcarbamic acid benzyl ester

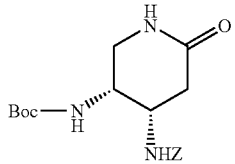

To a mixture of the compound obtained in Referential Example 210 (5.42 g), ethanol (150 mL)., and tetrahydrofuran (10.0 mL) was added Lindlar catalyst (2.71 g), and the thus-obtained mixture was stirred for 3 hours under hydrogen atmosphere, and then for 14 hours under nitrogen conditions. Any insoluble matter was removed by filtration through a Celite pad, and the filtrate was concentrated under reduced pressure. The residue was dissolved in tetrahydrofuran (30 mL), and triethylamine (3.0 mL) was added thereto, followed by stirring at room temperature for 1.5 hours. The reaction mixture was diluted with ethyl acetate, and the diluted mixture was washed with 10% aqueous citric acid, saturated aqueous sodium hydrogencarbonate and saturated brine. The organic layer was dried over sodium sulfate anhydrate, and the solvent was distilled away under reduced pressure. The residue was purified by silica gel column chromatography (chloroform:methanol=25:1), to thereby give the title compound (2.50 g).

$^1$H-NMR(CDCl$_3$)δ: 1.44(9H, s), 2.30-2.50(1H, br), 2.65-2.90(1H, br), 3.15-3.30(1H, br), 3.35-3.65(1H, br), 4.00-4.25 (2H, br), 5.11(2H, s), 5.55-5.60(1H, br), 5.65-5.90(1H, br), 6.25-6.55(1H, br), 7.28-7.40(5H, m).

MS(ESI)m/z: 364(M+H)$^+$.

Referential Example 212

(3R,4S)-3-[(tert-butoxycarbonyl)amino]piperidin-4-ylcarbamic acid benzyl ester

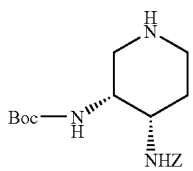

To a solution of the compound obtained in Referential Example 211 (2.49 g) in tetrahydrofuran (70 mL) was added dropwise borane-tetrahydrofuran complex (as 1M tetrahydrofuran solution, 34.0 mL) under ice cooling, and the thus-obtained mixture was gradually brought back to room temperature while being stirred. After the mixture was stirred for 20 hours, methanol (100 mL) was added to the reaction mixture, and the solvent was distilled away under reduced pressure. To the residue were added ethanol (45 mL), water (5 mL), and triethylamine (10 mL), and the thus-obtained mixture was heated under reflux for 24 hours. The reaction mixture was concentrated, and the residue was purified by silica gel column chromatography (chloroform methanol:water=7: 3:1, lower layer), to thereby give the title compound (1.61 g).

$^1$H-NMR(CDCl$_3$)δ: 1.44(9H, s), 1.65-1.72(2H, m), 2.67 (1H, t, J=12.0 Hz), 2.82(12H, d, J=12.0 Hz), 2.90-3.10(1H, br), 3.60-3.80(2H, m), 3.90-4.00(1H, m), 5.00-5.20(2H, m), 5.40-5.60(2H, br), 7.25-7.74(5H, m). MS(FAB)m/z: 350(M+H)$^+$.

Referential Example 213

(3R,4S)-1-acetyl-4-{[(benzyloxy)carbonyl] amino}piperidin-3-ylcarbamic acid tert-butyl ester

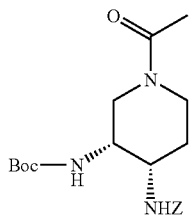

The compound obtained in Referential Example 212 was reacted with acetyl chloride in the presence of triethylamine in methylene chloride, to thereby give the title compound.

$^1$H-NMR(CDCl$_3$)δ: 1.44(9H, s), 1.85-2.15(2H, m), 2.07 (1.5H, s), 2.14(1.5H, s), 2.75-2.90(1H, m), 3.10-3.20(0.5H, m), 3.25-3.35(0.5H, br.d, J=14.2 Hz), 3.65-4.05(3H, m), 4.38-4.47(0.5H, br.d, J=13.0 Hz), 4.5, 4-4.63(0.5H, m), 4.69-4.83(1H, br), 4.98-5.20(2.5H, m), 5.90-6.05(0.5H, br), 7.30-7.40(5H, m).

MS(ESI)m/z: 392(M+H$^+$).

Referential Example 214

(3R,4S)-1-acetyl-4-{[(5-chloroindol-2-yl)carbonyl] amino}piperidin-3-ylcarbamic acid tert-butyl ester

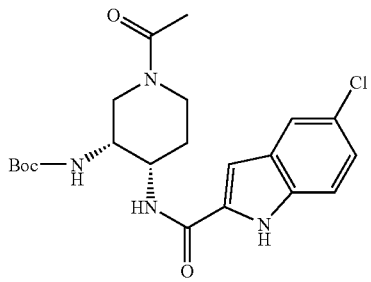

To a solution of the compound obtained in Referential Example 213 (745 mg) in ethanol (50 mL) was added 10% palladium on carbon (532 mg), and the thus-obtained mixture was stirred at room temperature for 16 hours under hydrogen atmosphere. Any insoluble matter was removed by filtration through Celite, and the filtrate was concentrated under reduced pressure. The residue was reacted with 5-chloroindole-2-carboxylic acid (467 mg) in a manner similar to that employed in Referential Example 68, to thereby give the title compound (650 mg).

$^1$H-NMR(CDCl$_3$)δ: 1.52(9H, s), 1.60-1.80(2H, m), 2.12 (1H, s), 2.16(2H, s), 2.30-2.45(0.5H, m), 2.67-2.82(0.3H, m), 2.89(0.7H, d, J=13.7 Hz), 3.23(0.7H, t, J=12.9 Hz), 3.37 (0.3H, d, J=13.7 Hz), 3.81-3.95(1H, m), 4.05-4.33(2H, m), 4.62-4.72(0.3H, br), 4.77(0.7H, d, J=13.7 Hz), 5.10-5.27(1H, m), 6.81(0.3H, br.s), 6.85(0.7H, s), 7.21(1H, br.d, J=8.8 Hz), 7.34(1H, d, J=8.8 Hz), 7.57(0.3H, br.s), 7.61(0.7H, s), 8.55-8.65(0.5H, br), 9.43-9.53(0.7H, br), 9.60-9.70(0.3H, br).

MS(ESI)m/z: 435(M+H$^+$).

Referential Example 215

(3R,4R)-5-azido-3-{[(benzyloxy)carbonyl]amino}-4-[(tert-butoxycarbonyl)amino]valeric acid ethyl ester

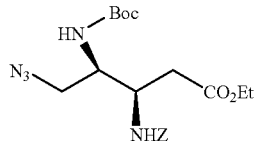

In a manner similar to that employed in Referential Example 210, the title compound was prepared from the (3R,4S)-isomer (high-polar compound) obtained in Referential Example 168.

$^1$H-NMR(CDCl$_3$)δ: 1.23(3H, t, J=6.6 Hz), 1.42(9H, s), 2.51-2.63(2H, m), 3.43-3.50(2H, m), 3.84-3.92(1H, m), 4.03-4.23(3H, m), 5.10(2H, s), 5.11-5.24(1H, m), 5.54-5.60(1H, m), 7.32-7.44(5H, m).

Referential Example 216

(4R,5R)-5-[(tert-butoxycarbonyl)amino]-2-oxopiperidin-4-ylcarbamic acid benzyl ester

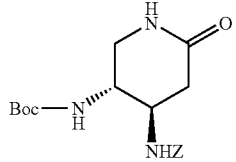

In a manner similar to that employed in Referential Example 211, the title compound was prepared from the compound obtained in Referential Example 215.

$^1$H-NMR(DMSO-d$_6$)δ: 1.35(9H, s), 2.19(1H, dd, J=17.4, 9.1 Hz), 2.41-2.51(1H, m), 2.97(1H, t, J=9.1 Hz), 3.00-3.11 (1H, m), 3.51-3.64(1H, m), 3.67-3.73(1H, m), 5.00(2H, s), 6.71-6.80(1H, m), 7.20-7.30(5H, m), 7.44-7.52(1H, m), 8.30 (1H, s).

Referential Example 217

(3R,4R)-3-[(tert-butoxycarbonyl)amino]piperidin-4-ylcarbamic acid benzyl ester

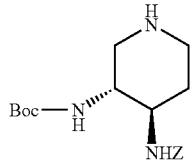

In a manner similar to that employed in Referential Example 212, the title compound was prepared from the compound obtained in Referential Example 216.

$^1$H-NMR(CDCl$_3$)δ: 1.39(9H, s), 2.05(2H, d, J=12.9 Hz), 2.40(1H, t, J=11.0 Hz), 2.63(1H, t, J=12.0 Hz), 3.09(1H, d, J=12.0 Hz), 3.31(1H, d, J=11.0 Hz), 3.42-3.53(2H, m), 4.80-4.91(1H, m), 5.09(2H, s), 5.23-5.32(1H, m), 7.34-7.41(5H, m).

Referential Example 218

(3R,4R)-1-acetyl-4-{[(benzyloxy)carbonyl]amino}piperidin-3-ylcarbamic acid tert-butyl ester

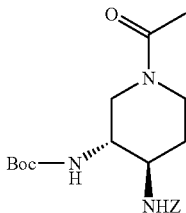

In a manner similar to that employed in Referential Example 213, the title compound was prepared from the compound obtained in Referential Example 217.

$^1$H-NMR(CDCl$_3$)δ: 1.42(9H, s), 1.53-1.67(1H, m), 1.89-2.00(1H, m), 2.09(1.5H, s), 2.15(1.5H, s), 2.57(1H, t, J=12.0 Hz), 2.78(1H, t, J=12.0 Hz), 3.20-3.30(1H, m), 3.40-3.56(2H, m), 4.23-4.31(1H, m), 4.45-4.56(1H, m), 5.01-5.08(1H, m), 5.10(2H, s), 7.32-7.44(5H, m).

Referential Example 219

(3R,4R)-1-acetyl-4-{[(5-chloroindol-2-yl)carbonyl]amino}piperidin-3-ylcarbamic acid tert-butyl ester

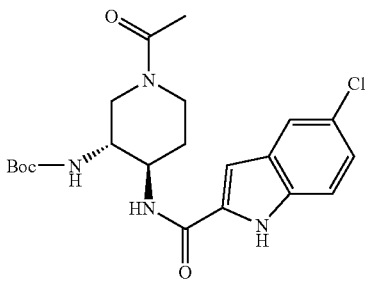

In a manner similar to that employed in Referential Example 214, the title compound was prepared from the compound obtained in Referential Example 218.

$^1$H-NMR(CDCl$_3$)δ: 1.35(9H, s), 1.42-1.56(2H, m), 2.00-2.10(1H, m), 2.12(1.5H, s), 2.17(1.5H, s), 2.31-2.43(1H, m), 2.67-3.00(1H, m), 3.55-3.63(1H, m), 3.78-4.00(1H, m), 4.03-4.21(1H, m), 4.78-5.24(2H, m), 6.91(0.5H, s), 6.92(0.5H, s), 7.22-7.32(1H, m), 7.33(1H, d, J=8.8 Hz), 7.58(1H, s), 9.45 (0.5H, s), 9.51(0.5H, s).

Referential Example 220

(3R,4S)-3-[(tert-butoxycarbonyl)amino]-1-(2-methoxyacetyl)piperidin-4-ylcarbamic acid benzyl ester

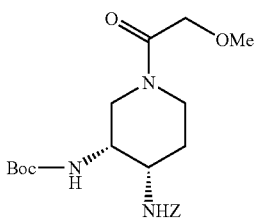

In a manner similar to that employed in Referential Example 213, the title compound was prepared from the compound obtained in Referential Example 212 and methoxyacetyl chloride.

$^1$H-NMR(CDCl$_3$)δ: 1.44(9H, s), 1.70-2.15(2H, m), 2.70-2.85(1H, m), 2.90-3.30(1H.m), 3.35-3.70(1H, m), 3.43(3H, s), 3.75-3.90(2H, m), 3.90-4.25(3H, m), 4.40-4.80(1H, m), 5.05-5.09(1H, m), 5.10(2H, br.s), 7.30-7.40(5H, m).

MS(ESI)m/z: 322(M+H$^+$).

Referential Example 221

(3R,4S)-4-{[(5-chloroindol-2-yl)carbonyl]amino}-1-(2-methoxyacetyl)piperidin-3-ylcarbamic acid tert-butyl ester

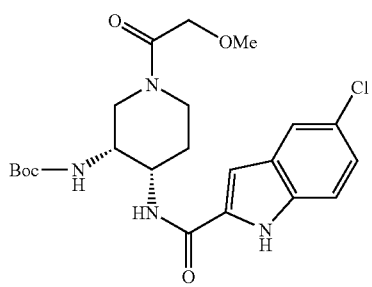

In a manner similar to that employed in Referential Example 214, the title compound was prepared from the compound obtained in Referential Example 220.

$^1$H-NMR(CDCl$_3$)δ: 1.52(9H, s), 1.60-1.80(1H, m), 2.20-2.40(1H, m), 2.70-2.80(0.6H, m), 2.90-3.00(0.4H, m), 3.15-3.30(0.4H, m), 3.32-3.40(0.6H, m), 3.46, 3.49(total 3H, each s), 3.85-4.30(5H, m), 4.55-4.80(1H, m), 5.11(0.4H, br.s), 6.05(0.6H, br.s), 6.86(1H, s), 7.20(1H, dd, J=8.7, 2.0 Hz), 7.33(1H, d, J=8.7 Hz), 7.61(1H, s), 8.40-8.60(1H, m), 9.41 (1H, br.s).

MS(FAB)m/z: 465(M+H$^+$).

Referential Example 222

(3R,4R)-3-[(tert-butoxycarbonyl)amino]-1-(2-methoxyacetyl)piperidin-4-ylcarbamic acid benzyl ester

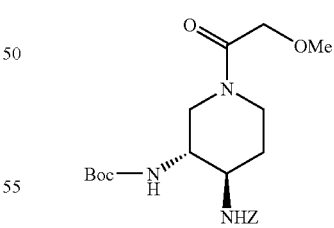

In a manner similar to that employed in Referential Example 213, the title compound was prepared from the compound obtained in Referential Example 217 and methoxyacetyl chloride.

$^1$H-NMR(CDCl$_3$)δ: 1.41(9H, s), 1.45-1.67(1H, m), 2.01-2.14(1H, m), 2.63(1H, t, J=12.0 Hz), 2.75(1H, t, J=12.0 Hz), 3.20-3.30(1H, m), 3.32-3.41(5H, m), 3.44-3.56(2H, m), 4.21-4.32(1H, m), 4.50-4.63(1H, m), 5.03-5.08(1H, m), 5.09(2H, s), 7.32-7.40(5H, m).

Referential Example 223

(3R,4R)-4-{[(5-chloroindol-2-yl)carbonyl]amino}-1-(2-methoxyacetyl)piperidin-3-ylcarbamic acid tert-butyl ester

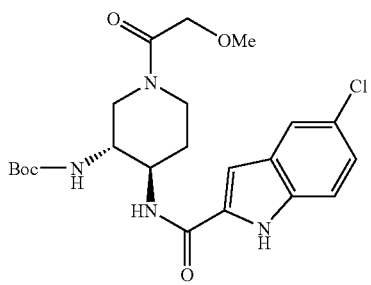

In a manner similar to that employed in Referential Example 214, the title compound was prepared from the compound obtained in Referential Example 222 and 5-chloroindole-2-carboxylic acid.

$^1$H-NMR(CDCl$_3$)δ: 1.35(9H, s), 1.41-1.56(2H, m), 2.11-2.23(0.5H, m), 2.34-2.50(0.5H, m), 2.78-2.89(0.5H, m), 3.01-3.12(0.5H, m), 3.42(5H, s), 3.45-3.56(1H, m), 3.78-3.89(1H, m), 4.00-4.21(2H, m), 4.78-5.21(2H, m), 6.91(0.5H, s), 6.93(0.5H, s), 7.23(1H, dd, J=8.8, 2.0 Hz), 7.33(1H, d, J=8.8 Hz), 7.59(1H, s), 9.37(0.5H, s), 9.54(0.5H, s).

Referential Example 224

(3R,4S)-3-{[(benzyloxy)carbonyl]amino}-4-[(tert-butoxycarbonyl)amino]-5-{[tert-butyl(diphenyl)silyl]oxy}valeric acid ethyl ester

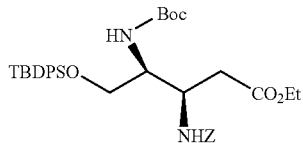

To a solution of the (3R,4S)-isomer (high-polar compound) obtained in Referential Example 168 (0.74 g) in N,N-dimethylformamide (30 mL) were sequentially added triethylamine (0.47 mL), imidazole (0.19 g), and tert-butylchlorodiphenylsilane (0.7 mL) under ice cooling, and the thus-obtained mixture was gradually brought back to room temperature while being stirred. After the mixture was stirred for 4 days, the reaction mixture was diluted with ethyl acetate, and the diluted mixture was washed with 10% aqueous citric acid and saturated brine. The organic layer was dried over sodium sulfate anhydrate, and the solvent was distilled away under reduced pressure. The residue was purified by silica gel column chromatography (hexane:ethyl acetate=8:1), to thereby give the title compound (0.85 g).

$^1$H-NMR(CDCl$_3$)δ: 1.07(9H, s), 1.19(3H, t, J=7.4 Hz), 1.40(9H, s), 2.40-2.50(1H, m), 2.60(1H, dd, J=15.9, 4.5 Hz), 3.56-3.67(1H, m), 3.74(1H, dd, J=11.2, 4.5 Hz), 3.78-3.89 (1H, m), 4.08(2H, q, J=7.4 Hz), 4.21-4.30(1H, m), 4.99-5.13 (3H, m), 5.41-5.52(1H, m), 7.40-7.53(6H, m), 7.60-7.72(4H, m).

Referential Example 225

(3R,4S)-4-[(tert-butoxycarbonyl)amino]-5-{[tert-butyl(diphenyl)silyl]oxy}-3-({(5-chloroindol-2-yl)carbonyl]amino}valeric acid ethyl ester

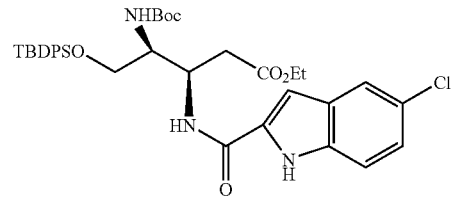

In a manner similar to that employed in Referential Example 214, the benzyloxycarbonyl group was eliminated from the compound obtained in Referential Example 224, and the thus-obtained compound was subjected to condensation reaction with 5-chloroindole-2-carboxylic acid, to thereby give the title compound.

$^1$H-NMR(CDCl$_3$)δ: 1.10(9H, s), 1.20(3H, t, J=7.4 Hz), 1.32(9H, s), 2.40-2.52(1H, m), 2.71(1H, dd, J=15.9, 4.5 Hz), 3.67-3.81(2H, m), 4.00-4.20(2H, m), 4.56-4.74(1H, m), 5.00-5.11(1H, m), 6.81(1H, s), 7.21(1H, dd, J=8.8, 2.0 Hz), 7.32 (1H, d, J=8.8 Hz), 7.40-7.50(6H, m), 7.58(1H, d, J=8.5 Hz), 7.63-7.74(5H, m), 9.01-9.14(1H, m).

Referential Example 226

(3R*,4R*)-3-{[(5-methyl-4,5,6,7-tetrahydrothiazolo[5,4-c]pyridin-2-yl)carbonyl]amino}-1,1-dioxohexahydro-1-thiopyran-4-ylcarbamic acid tert-butyl ester

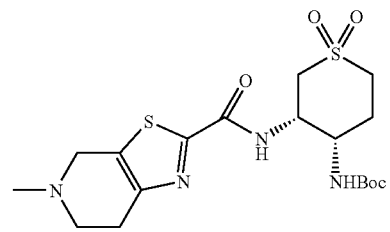

In a manner similar to that employed in Referential Example 68, the title compound was prepared from the (3R*,4R*)-isomer (low-polar compound) obtained in Referential Example 179 and the compound obtained in Referential Example 10.

$^1$H-NMR(CDCl$_3$)δ: 1.43(9H, s), 2.30-2.37(2H, m), 2.51 (3H, s), 2.82-2.85(2H, m), 2.92-2.95(2H, m), 3.17-3.20(4H, m), 3.40-3.43(1H, m), 3.69-3.77(2H, m), 3.97-3.98(1H, m), 4.98(1H, br), 5.25(1H, br).

Referential Example 227

N-(3R*,4R*)-4-amino-1,1-dioxohexahydro-1-thiopyran-3-yl]-5-methyl-4,5,6,7-tetrahydrothiazolo[5,4-c]pyridine-2-carboxamide hydrochloride

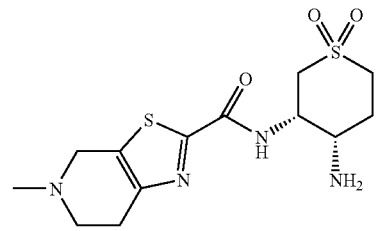

In a manner similar to that employed in Referential Example 69, the title compound was prepared from the compound obtained in Referential Example 226.

¹H-NMR(DMSO-d₆)δ: 2.29-2.33(2H, m), 2.93(3H, s), 3.16(2H, br), 3.40(2H, br), 3.52(2H, br), 3.69-3.76(3H, m), 4.48(1H, br), 4.71-4.82(2H, m), 8.34(2H, br), 8.82(1H, br).
MS(ESI)m/z: 345(M+H)⁺.

Referential Example 228

(3R*,4R*)-3-{[(5-chloroindol-2-yl)carbonyl]amino}-1,1-dioxohexahydro-1-thiopyran-4-ylcarbamic acid tert-butyl ester

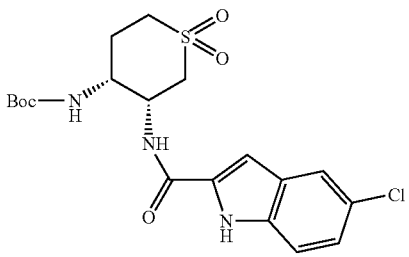

In a manner similar to that employed in Referential Example 68, the title compound was prepared from the (3R*, 4R*)-isomer (low-polar compound) obtained in Referential Example 179 and 5-chloroindole-2-carboxylic acid.
¹H-NMR(DMSO-d₆)δ: 1.34(9H, s), 2.09(2H, br), 3.07(1H, d, J=12.6 Hz), 3.24-3.28(1H, m), 3.48(2H, br), 4.12 (1H, br), 4.53(1H, br), 7.04(1H, s), 7.16-7.18(2H, m), 7.44 (1H, d, J=8.7 Hz), 7.67(1H, s), 8.37(1H, br), 11.81(1H, s).
MS(ESI)m/z: 442(M+H)⁺.

Referential Example 229

N-[(3R*,4R*)-4-amino-1,1-dioxohexahydro-1-thiopyran-3-yl]-5-chloroindole-2-carboxamide hydrochloride

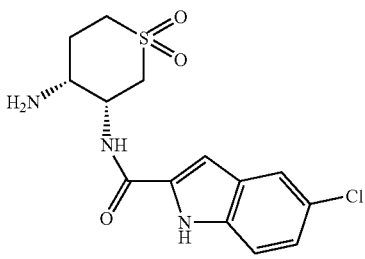

In a manner similar to that employed in Referential Example 69, the title compound was prepared from the compound obtained in Referential Example 228.
¹H-NMR(DMSO-d₆)δ: 2.24-2.33(2H, m), 3.43-3.55(3H, m), 3.60-3.66(1H, m), 3.77(1H, br), 4.75-4.79(1H, m), 7.18-7.21(2H, m), 7.46(1H, d, J=8.8 Hz), 7.72(1H, d, J=1.7 Hz), 8.39(2H, br), 8.58(1H, d, J=6.8 Hz), 11.93(1H, s).
MS(ESI)m/z: 342(M+H⁺).

Referential Example 230

(3R*,4S*)-3-{[(5-methyl-4,5,6,7-tetrahydrothiazolo[5,4-c]pyridin-2-yl)carbonyl]amino}-1,1-dioxohexahydro-1-thiopyran-4-ylcarbamic acid tert-butyl ester

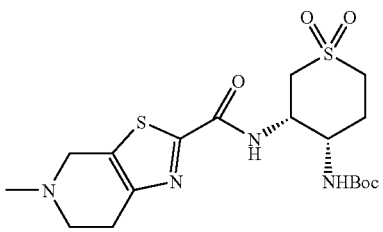

In a manner similar to that employed in Referential Example 98, the title compound was prepared from the (3R*, 4S*)-isomer (high-polar compound) obtained in Referential Example 179 and the compound obtained in Referential Example 10.
¹H-NMR(CDCl₃)δ: 1.32(9H, s), 2.14-2.24(1H, m), 2.33-2.38(1H, m), 2.50(3H, s), 2.78-2.83(2H, m), 2.86-2.95(2H, m), 3.08-3.14(3H, m), 3.55(1H, d, J=13.4 Hz), 3.68(1H, d, J=15.5 Hz), 3.72(1H, d, J=15.5 Hz), 3.86-3.88(1H, m), 4.45-4.53(1H, m), 4.75(1H, d, J=8.5 Hz), 7.76(1H, d, J=8.3 Hz).
MS(ESI)m/z: 445(M+H)⁺.

Referential Example 231

N-[(3R*,4S*)-4-amino-1,1-dioxohexahydro-1-thiopyran-3-yl]-5-methyl-4,5,6,7-tetrahydrothiazolo[5,4-c]pyridine-2-carboxamide hydrochloride

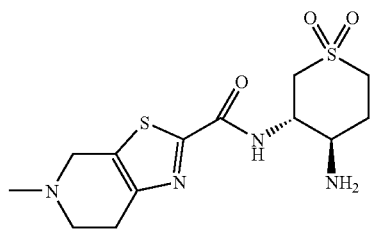

In a manner similar to that employed in Referential Example 69, the title compound was prepared from the compound obtained in Referential Example 230.
¹H-NMR(DMSO-d₆)δ: 2.03-2.12(1H, m), 2.51(1H, br), 2.93(3H, s), 3.14(2H, d, J=12.2 Hz), 3.28(2H, br), 3.33(2H, br), 3.48(3H, br), 3.72(2H, br), 4.49(2H, br), 4.71-4.74(1H, m), 8.38(2H, br), 9.21-9.24(1H, m).
MS(ESI)m/z: 345(M+H⁺).

Referential Example 232

(3R*,4R*)-3-{[(5-fluoroindol-2-yl)carbonyl]amino}-1,1-dioxohexahydro-1-thiopyran-4-ylcarbamic acid tert-butyl ester

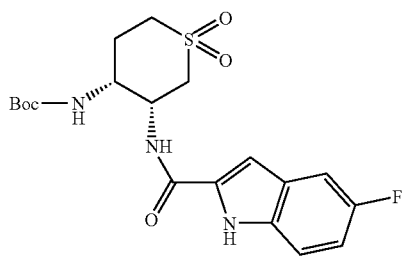

In a manner similar to that employed in Referential Example 68, the title compound was prepared from the (3R*, 4R*)-isomer (low-polar compound) obtained in Referential Example 179 and 5-fluoroindole-2-carboxylic acid.
¹H-NMR(DMSO-d₆)δ: 1.37(9H, s), 2.10-2.13(2H, m), 3.06(1H, br), 3.37-3.49(3H, m), 4.13(1H, br), 4.57(1H, br), 6.95-7.01(2H, m), 7.14(1H, br), 7.30(1H, d, J=8.5 Hz), 7.41 (1H, dd, J=8.8, 4.5 Hz), 8.28(1H, br), 11.68(1H, s).
MS(ESI)m/z: 426(M+H⁺).

Referential Example 233

N-[(3R*,4R*)-4-amino-1,1-dioxohexahydro-1-thiopyran-3-yl]-5-fluoroindole-2-carboxamide hydrochloride

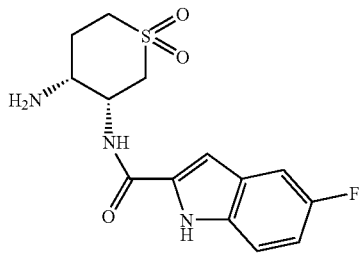

In a manner similar to that employed in Referential Example 69, the title compound was prepared from the compound obtained in Referential Example 232.

$^1$H-NMR(DMSO-d$_6$)δ: 2.25-2.31(1H, m), 2.47(1H, br), 3.30(1H, br), 3.49-3.53(2H, m), 3.60-3.66(1H, m), 3.78(1H, br), 4.79(1H, br), 7.01-7.05(1H, m), 7.21(1H, s), 7.38(1H, d, J=9.0 Hz), 7.44(1H, dd, J=8.8, 4.4 Hz), 8.40(2H, br), 8.56(1H, br), 11.81(1H, s).

MS(ESI)m/z: 326(M+H$^+$).

Referential Example 234

(3R)-3-{[(benzyloxy)carbonyl]amino}-4-[(tert-butoxycarbonyl)amino]-5-oxovaleric acid ethyl ester

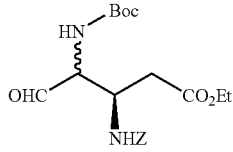

To a mixture comprising the (3R,4S)-isomer (high-polar compound) obtained in Referential Example 168 (0.5 g), dimethyl sulfoxide (6.8 mL), and triethylamine (2.6 mL) was gradually added sulfur trioxide-pyridine complex (1.5 g) at room temperature, and the thus-obtained mixture was stirred for 20 minutes. The reaction mixture was poured into water, and the thus-obtained mixture was extracted with ethyl acetate. The organic layer was washed with saturated aqueous ammonium chloride, saturated aqueous sodium hydrogencarbonate, and saturated brine, and was dried over sodium sulfate anhydrate. The solvent was distilled away under reduced pressure, and the residue was purified by silica gel column chromatography (hexane:ethyl acetate=3:1), to thereby give the title compound (0.51 g).

$^1$H-NMR(CDCl$_3$)δ: 1.25(3H, t, J=7.4 Hz), 1.44(9H, s), 2.51-2.70(2H, m), 4.01-4.23(2H, m), 4.45-4.67(1H, m), 5.00-5.23(2H, s), 5.24-5.42(1H, m), 7.23-7.43(5H, m), 9.63(0.5H, s), 9.67(0.5H, s).

Referential Example 235

(4R)-5-[(tert-butoxycarbonyl)amino]-1-methyl-2-oxopiperidin-4-ylcarbamic acid benzyl ester

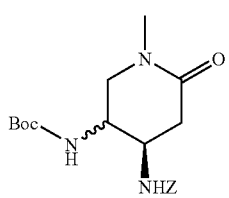

To a solution of the compound obtained in Referential Example 234 (0.51 g) in ethanol (10 mL) were sequentially added acetic acid (0.27 mL) and methylamine (as 2M tetrahydrofuran solution, 1.0 mL) under ice cooling, and the thus-obtained mixture was gradually brought back to room temperature while being stirred. After the mixture was stirred for 1 hour, sodium cyanoborohydride (0.15 g) was added thereto, and the thus-obtained mixture was stirred for 18 hours. The reaction mixture was diluted with chloroform, and the diluted mixture was washed with saturated aqueous sodium hydrogencarbonate and saturated brine. The organic layer was dried over sodium sulfate anhydrate, and the solvent was distilled away under reduced pressure. The residue was dissolved in toluene (20 mL), and triethylamine (2 mL) was added to the solution, followed by heating under reflux for 2 hours. The reaction mixture was concentrated under reduced pressure, and the residue was purified by silica gel column chromatography (chloroform:methanol=98:2), to thereby give the title compound (0.28 g).

$^1$H-NMR(DMSO-d$_6$)δ: 1.36(3.6H, s), 1.38(5.4H, s), 2.22-2.43(1H, m), 2.44-2.61(1H, m), 2.72(1.2H.s), 2.80(1.8H.s), 3.10(0.5H, dd, J=12.5, 8.3 Hz), 3.21-3.30(0.5H, m), 3.33-3.45(1H, m), 3.56-3.82(1H, m), 3.89-4.00(1H, m), 4.94(1H, d, J=8.1 Hz), 5.00(1.2H.s), 5.01(0.8H, s), 6.89-7.02(0.5H, m), 7.23-7.44(5.5H, m).

Referential Example 236

(4R)-4-{[(5-chloroindol-2-yl)carbonyl]amino}-1-methyl-6-oxopiperidin-3-ylcarbamic acid tert-butyl ester

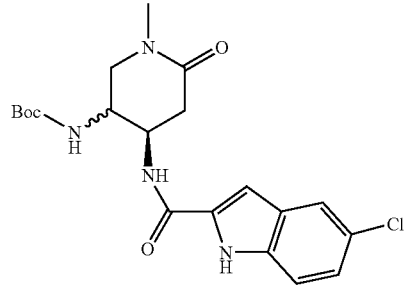

In a manner similar to that employed in Referential Example 214, the title compound was prepared from the compound obtained in Referential Example 235 and 5-chloroindole-2-carboxylic acid.

$^1$H-NMR(DMSO-d$_6$)δ: 1.24(5.4H, s), 1.35(3.6H, s), 2.43-2.56(2H, m), 2.80(3H, s), 3.10-3.20(1H, m), 3.30-3.52(1H, m), 3.83-3.91(0.4H, m), 4.02-4.10(0.6H, m), 4.20-4.31(0.6H, m), 4.43-4.54(0.4H, m), 6.94(0.6H, d, J=8.1 Hz), 7.08(1H, s), 7.16(1H, dd, J=8.8, 2.0 Hz), 7.42(1H, d, J=8.8 Hz), 7.69(1H, d, J=2.0 Hz), 8.30(0.4H, s), 8.36(0.4H, d, J=7.3 Hz), 8.43 (0.6H, d, J=8.3 Hz), 11.75(0.6H, s), 11.78(0.4H, s).

Referential Example 237

4-(pyridin-4-yl)benzoic acid hydrochloride

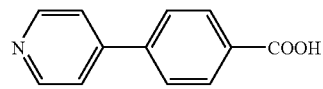

4-Bromopyridine hydrochloride (11.7 g) and 4-carboxyphenylboronic acid (10.0 g) were dissolved in a solvent mixture of toluene (250 mL) and water (250 mL), and to the solution were sequentially added tetrakis(triphenylphosphine)palladium(0) (5.0 g) and anhydrous sodium carbonate (25.4 g), followed by heating under reflux at 120° C. for 19 hours. After the resultant mixture was cooled to room temperature, ethyl acetate was added thereto, and the thus-obtained mixture was extracted with water. Concentrated HCl was added to the aqueous layer, to thereby make the mixture acidic. The aqueous layer was washed with ethyl acetate, and was concentrated. The resultant solid was collected by filtration, to thereby give the title compound (8.37 g).
$^1$H-NMR(DMSO-d$_6$)δ: 8.11(2H, d, J=8.8 Hz), 8.14(2H, dJ=8.8 Hz), 8.35(2H, d, J=6.6 Hz), 8.97(2H, d, J=6.6 Hz).
MS(FAB)m/z: 200 (M+H)$^+$.

Referential Example 238

4-(pyridin-4-yl)benzoic acid methyl ester

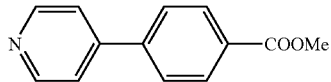

The compound obtained in Referential Example 237 (12.4 g) was dissolved in methanol (200 mL), and concentrated sulfuric acid (5 mL) was added thereto at room temperature, followed by heating under reflux for 3 hours. After completion of the reaction, the solvent was distilled away, and saturated aqueous sodium hydrogencarbonate was added to the residue. The thus-obtained mixture was extracted with ethyl acetate, and the extract was dried over sodium sulfate anhydrate. The solvent was distilled away, and hexane was added to the residue, to thereby precipitate the title compound (9.86 g).
$^1$H-NMR(CDCl$_3$)δ: 3.96(3H, s), 7.54(2H, d, J=5.9 Hz), 7.71(2H, d,J=8.3 Hz), 8.16(2H, d, J=8.3 Hz), 8.71(2H, d, J=5.9 Hz).

Referential Example 239

4-[4-(methoxycarbonyl)phenyl]pyridine N-oxide

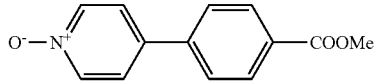

The compound obtained in Referential Example 238 (1.49 g) was dissolved in methylene chloride (30 mL), and 70% m-chloroperbenzoic acid (3.46 g) was added thereto, followed by stirring at room temperature for 1 hour. Aqueous sodium sulfite was added to the resultant mixture to partition the mixture. The organic layer was washed with saturated aqueous sodium hydrogencarbonate, and was dried over sodium sulfate anhydrate. The solvent was distilled away under reduced pressure, to thereby give the title compound (1.33 g).
$^1$H-NMR(DMSO)δ: 3.88(3H, s), 7.86(2H, d, J=7.2 Hz), 7.94(2H, d, J=8.3 Hz), 8.05(2H, d, J=8.3 Hz), 8.30(2H, d, J=7.2 Hz).
MS(FAB)m/z: 230 (M+H)$^+$.

Referential Example 240

4-(4-carboxyphenyl)pyridine N-oxide

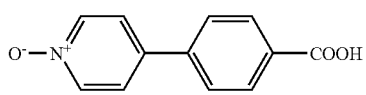

The compound obtained in Referential Example 239 (802 mg) was dissolved in dioxane (20 mL), and 1N aqueous sodium hydroxide (5 mL) was added thereto. The reaction mixture was refluxed for 1 hour, and was stirred at room temperature for 2 hours. The resultant mixture was neutralized with 1N aqueous HCl (5 mL), and water (5 mL) was added thereto. The resultant precipitate was collected by filtration, to thereby give the title compound (627 mg).
$^1$H-NMR(DMSO)δ: 7.85(2H, d, J=7.2 Hz), 7.91(2H, d, J=8.3 Hz), 8.03(2H, d, J=8.3 Hz), 8.30(2H, d, J=7.2 Hz).

Referential Example 241

2-(4-carboxylphenyl)-1-pyridine N-oxide

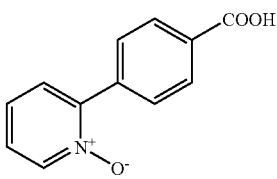

In a manner similar to that employed in Referential Examples 237, 238, 239, and 240, the title compound was prepared from 2-bromopyridine.
$^1$H-NMR(DMSO-d$_6$)δ: 7.41-7.45(2H, m), 7.65-7.69(1H, m), 7.94(2H, d, J=8.3 Hz), 8.02(2H, d, J=8.3 Hz), 8.34-8.38 (1H, m), 13.09(1H, s).
MS(FAB)m/z: 216 (M+H)$^+$.

Referential Example 242

2-(4-chloroanilino)-2-oxoacetic acid ethyl ester

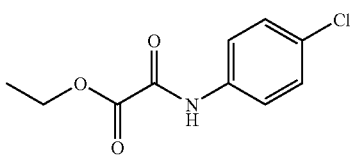

To a solution of 4-chloroaniline (1.16 g) in methylene chloride (26 mL) were sequentially added triethylamine (1.52 mL) and ethyl chlorooxoacetate (1.11 mL) under ice cooling, and the thus-obtained mixture was stirred at room temperature for 14 hours. Saturated aqueous sodium hydrogencarbonate was added to the reaction mixture to partition the mixture. The organic layer was sequentially washed with 10% aqueous citric acid and saturated brine, and was dried over sodium sulfate anhydrate. The solvent was concentrated under reduced pressure, and hexane was added to the residue. The precipitated crystals were collected by filtration, and were dried, to thereby give the title compound (1.89 g).
$^1$H-NMR(CDCl$_3$)δ: 1.43(3H, t, J=7.1 Hz), 4.42(2H, q, J=7.1 Hz), 7.34(2H, d, J=8.8 Hz), 7.60(2H, d, J=8.8 Hz), 8.86(1H, br.s).
MS(ESI)m/z: 228(M+H)$^+$.

Referential Example 243

2-[(5-chloropyridin-2-yl)amino]-2-oxoacetic acid methyl ester

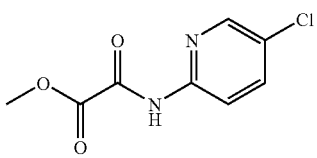

2-Amino-5-chloropyridine (1.16 g) and triethylamine (1.51 mL) were dissolved in methylene chloride (26 mL), and ethyl chlorooxoacetate (1.10 mL) was added thereto under ice cooling, followed by stirring at room temperature for 14 hours. Saturated aqueous sodium hydrogencarbonate was added to the reaction mixture to partition the mixture, and the organic layer was dried over sodium sulfate anhydrate. The solvent was distilled away under reduced pressure, and the residue was purified by silica gel column chromatography (hexane:ethyl acetate=3:1). The resultant pale-yellow solid was dissolved in methanol (20 mL), and the solution was stirred at 50° C. for 11 hours. The reaction mixture was concentrated under reduced pressure. The precipitated crystals were collected by filtration, and were dried, to thereby give the title compound (0.43 g).

$^1$H-NMR(CDCl$_3$)δ: 3.99(3H, s), 7.73(1H, dd, J=8.8, 2.2 Hz), 8.24(1H, d, J=8.8 Hz), 8.31(1H, d, J=2.2 Hz), 9.39(1H, br.s).

MS(ESI)m/z: 215(M+H)$^+$.

Referential Example 244

(1S)-3-cyclohexene-1-carboxylic acid

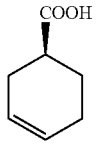

(R)-(+)-α-Methylbenzylamine salt of (1S)-3-cyclohexene-1-carboxylic acid (J. Am. Chem. Soc., vol. 100, pp. 5199-5203 (1978)) (95.0 g) was dissolved in ethyl acetate (1.6 L) and 2N HCl (1.6 L). After the organic layer was separated, the aqueous layer was extracted with ethyl acetate (500 mL×2). The organic layers were combined, and the combined organic layer was washed with saturated brine (300 mL×2). After the organic layer was separated, the aqueous layer was extracted with ethyl acetate (200 mL), and the organic layer was washed with saturated brine (100 mL). All organic layers were combined, and the combined organic layer was dried over sodium sulfate anhydrate, followed by concentration under reduced pressure, to thereby give the title compound (48.3 g).

$[α]^{25}_D$=−104° (c=1, chloroform).

$^1$H-NMR(CDCl$_3$)δ: 1.66-1.77(1H, m), 2.00-2.20(3H, m), 2.20-2.38(2H, m), 2.57-2.65(1H, m), 5.65-5.75(2H, m).

Referential Example 245

(1S,4S,5S)-4-iodo-6-oxabicyclo[3.2.1]octan-7-one

To a mixture of the compound obtained in Referential Example 244 (48.0 g), methylene chloride (580 mL), potassium iodide (82.1 g), sodium hydrogencarbonate (42.0 g), and water (530 mL) was added iodine (125.4 g) at an internal temperature of 5° C., followed by stirring at room temperature for 3 hours. To the reaction mixture was added 1N aqueous sodium thiosulfate (800 mL), and the thus-obtained mixture was extracted with methylene chloride (1 L, 500 mL). The organic layer was washed with aqueous sodium hydrogencarbonate (300 mL), water (500 mL), and saturated brine (300 mL), and was dried over anhydrous magnesium sulfate, followed by concentration. The precipitated crystals were collected by filtration, and were washed with hexane, followed by drying, to thereby give the title compound (89.5 g).

m.p.: 130-131° C.

$[α]^{25}_D$=−41° (c=1, chloroform)

$^1$H-NMR(CDCl$_3$)δ: 1.78-1.96(2H, m), 2.12(1H, dd, J=16.5 Hz, 5.2 Hz), 2.35-2.50(2H, m), 2.65-2.70(1H, m), 2.80(1H, d, J=12.2 Hz), 4.45-4.55(1H, m), 4.77-4.87(1H, m).

Referential Example 246

(1S,3S,6R)-7-oxabicyclo[4.1.0]heptane-3-carboxylic acid ethyl ester

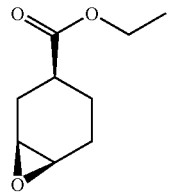

To a suspension of the compound obtained in Referential Example 245 (89.3 g) in ethanol (810 mL) was added 2N aqueous sodium hydroxide (213 mL) at room temperature while being stirred, and the thus-obtained mixture was stirred for 3 hours. The reaction mixture was concentrated in a bath at a temperature of 35° C. under reduced pressure. Water (500 mL) was added to the resultant oily matter, and the thus-obtained mixture was extracted with methylene chloride (500 mL and 300 mL). The organic layer was washed with water (300 mL), and was dried over anhydrous magnesium sulfate, followed by concentration under reduced pressure. The resultant oily matter was purified by silica gel column chromatography (hexane:ethyl acetate=85:15), to thereby give the title compound (41.3 g).

$[α]^{25}_D$=−58° (c=1, chloroform).

$^1$H-NMR(CDCl$_3$)δ: 1.25(3H, t, J=7.2 Hz), 1.50-1.70(2H, m), 1.71-1.82(1H, m), 2.08-2.28(4H, m), 3.16(2H, s), 4.12(2H, q, J=7.2 Hz).

Referential Example 247

(1S,3R,4R)-3-azido-4-hydroxycyclohexanecarboxylic acid ethyl ester

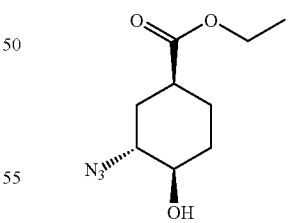

A mixture of the compound obtained in Referential Example 246 (41.0 g), N,N-dimethylformamide (300 mL), ammonium chloride (19.3 g), and sodium azide (23.5 g) was stirred at 76° C. for 13 hours. After any insoluble matter was collected by filtration, the filtrate was concentrated under reduced pressure while not allowing the solvent to evaporate to dryness. The residue was combined with the solid matter collected by the previous filtration, and the thus-obtained mixture was dissolved in water (500 mL). The solution was extracted with ethyl acetate (500 mL, 300 mL). The extract was washed with water and saturated brine, and was dried over anhydrous magnesium sulfate, followed by concentration, to thereby give the title compound (51.5 g).

$[\alpha]^{25}_D$=+8° (c=1, chloroform)

¹H-NMR(CDCl₃)δ: 1.28(3H, t, J=7.1 Hz), 1.37-1.64(3H, m), 1.86-1.95(1H, m), 2.04-2.16(1H, m), 2.32-2.41(1H, m), 2.44(1H, br.s), 2.68-2.78(1H, m), 3.45-3.60(2H, m), 4.17(2H, q, J=7.1 Hz).

Referential Example 248

(1S,3R,4R)-3-[(tert-butoxycarbonyl)amino]-4-hydroxycyclohexanecarboxylic acid ethyl ester

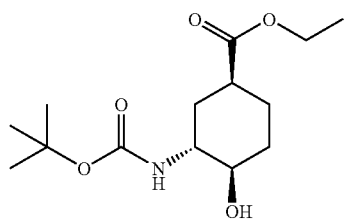

A mixture of the compound obtained in Referential Example 247 (51.2 g), di-tert-butyl dicarbonate (68.1 g), 5% palladium on carbon (5.0 g), and ethyl acetate (1000 mL) was stirred at room temperature overnight at a hydrogen pressure of 7 kg/cm². After the reaction mixture was filtered, the filtrate was concentrated, and the thus-obtained oily matter was purified by silica gel column chromatography (hexane ethyl acetate=4:1→3:1). The thus-obtained compound was crystallized from hexane, to thereby give the title compound (46.9 g). Furthermore, the mother liquor was purified by silica gel column chromatography (chloroform:methanol=100:1), to thereby give the title compound (6.74 g).

$[\alpha]^{25}_D$=+25° (c=1, chloroform).

¹H-NMR(CDCl₃)δ: 1.28(3H, t, J=7.1 Hz), 1.38-1.57(3H, m), 1.45(9H, s), 1.86-1.95(1H, m), 2.05-2.17(1H, m), 2.29-2.39(1H, m), 2.61-2.68(1H, m), 3.34(1H, br.s), 3.39-3.48 (1H, m), 3.53-3.64(1H, m), 4.10-4.24(2H, m), 4.54(1H, br.s).

Referential Example 249

(1S,3R,4S)-4-azido-3-[(tert-butoxycarbonyl)amino] cyclohexanecarboxylic acid ethyl ester

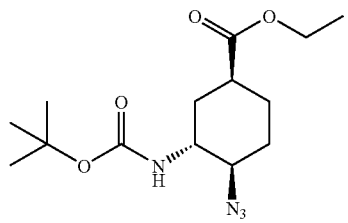

To a solution of the compound obtained in Referential Example 248 (53.5 g) in methylene chloride (500 mL) and triethylamine (130 mL) was added dropwise methanesulfonyl chloride (42 mL) at −10° C. to −15° C. over 20 minutes. The thus-obtained mixture was heated to room temperature over 2 hours, and was stirred for an additional 2 hours. To the reaction mixture was added dropwise 0.5N HCl (800 mL) at 0° C., to thereby make the mixture acidic, and the resultant mixture was extracted with methylene chloride (500 mL, 300 mL). The organic layer was washed with saturated aqueous sodium hydrogencarbonate and saturated brine, and was dried over anhydrous magnesium sulfate, followed by concentration. The resultant crystals were dissolved in N,N-dimethylformamide (335 mL), and sodium azide (60.5 g) was added thereto, followed by stirring at 67 to 75° C. for 16 hours. The reaction mixture was filtrated, and the filtrate was concentrated under reduced pressure, to thereby evaporate 250 mL of the solvent. The residue was combined with the solid matter collected by the previous filtration, and the thus-obtained mixture was dissolved in water (500 mL). The solution was extracted with ethyl acetate (1 L and 300 mL). The organic layer was washed with saturated brine (400 mL, 200 mL), and was dried over anhydrous magnesium sulfate, followed by concentration. The resultant crystals were purified by silica gel column chromatography (hexane:ethyl acetate=4:1), to thereby give the title compound (18.4 g).

$[\alpha]^{25}_D$=+62° (c=1, chloroform)

¹H-NMR(CDCl₃)δ: 1.26(3H, t, J=7.1 Hz), 1.35-2.00(15H, s), 2.60-2.68(1H, m), 3.80-3.96(2H, m), 4.15(2H, q, J-7.1 Hz), 4.61(1H, br.s).

Referential Example 250

(1S,3R,4S)-4-azido-3-[(tert-butoxycarbonyl)amino] cyclohexanecarboxylic acid

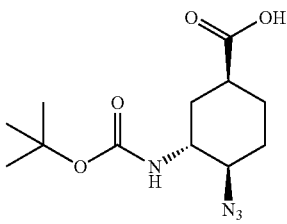

To a solution of the compound obtained in Referential Example 249 (1.0 g) in tetrahydrofuran (25 mL) were added lithium hydroxide (102 mg) and water (5 mL), and after the thus-obtained mixture was stirred for 17 hours, additional lithium hydroxide (50 mg) was added thereto, followed by stirring for 4 hours. To the reaction mixture was added 1N aqueous HCl (6.3 mL), and the thus-obtained mixture was extracted with ethyl acetate. The organic layer was dried, and the solvent was distilled away under reduced pressure, to thereby give the title compound (980 mg).

¹H-NMR(CDCl₃)δ: 1.30-2.20(6H, m), 1.45(9H, s), 2.70-2.80(1H, m), 3.94(2H, br.s), 4.73(1H, br.s).

Referential Example 251

(1R,2S,5S)-2-azido-5-[(dimethylamino)carbonyl] cyclohexylcarbamic acid tert-butyl ester

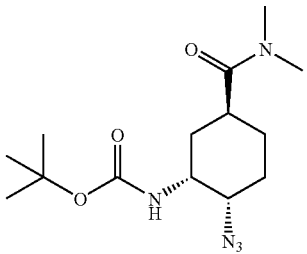

The compound obtained in Referential Example 250 (4.77 g) was dissolved in methylene chloride (150 mL), and to the solution were added dimethylamine hydrochloride (3.26 g), 1-ethyl-3-(3-dimethylaminopropyl)carbodiimide hydrochloride (4.60 g), 1-hydroxybenzotriazole monohydrate (3.24 g),

Referential Example 252

N-{(1R,2S,5S)-2-azido-5-[(dimethylamino)carbonyl]cyclohexyl}-5-methyl-4,5,6,7-tetrahydrothiazolo[5,4-c]pyridine-2-carboxamide

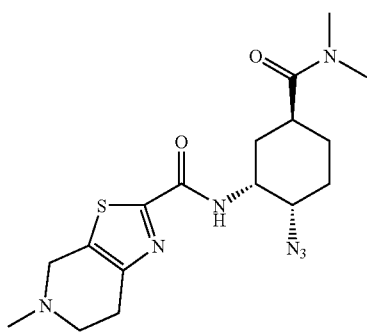

The compound obtained in Referential Example 251 (9.13 g) was dissolved in methylene chloride (100 mL), and HCl-ethanol (100 mL) was added thereto, followed by stirring at room temperature for 1 minute. The reaction mixture was concentrated under reduced pressure, and the residue was dissolved in N,N-dimethylformamide (200 mL). To the solution were added the compound obtained in Referential Example 10 (7.75 g), 1-hydroxybenzotriazole monohydrate (4.47 g), 1-(3-dimethylaminopropyl)-3-ethylcarbodiimide hydrochloride (11.2 g), and triethylamine (2.02 mL), followed by stirring at room temperature overnight. To the resultant mixture were further added the compound obtained in Referential Example 10 (2.38 g) and 1-(3-dimethylaminopropyl)-3-ethylcarbodiimide hydrochloride (5.60 g), followed by stirring for 3 days. The reaction mixture was concentrated under reduced pressure, and the residue was partitioned between methylene chloride and saturated aqueous sodium hydrogencarbonate. The organic layer was dried over sodium sulfate anhydrate, and the solvent was distilled away under reduced pressure. The residue was purified by silica gel column chromatography (methylene chloride:methanol=47:3), to thereby give the title compound (7.38 g).

$^1$H-NMR(CDCl$_3$)δ: 1.72-1.97(4H, m), 2.10-2.27(2H, m), 2.51(3H, s), 2.77-3.05(11H, m), 3.68(1H, d, J=15.4 Hz), 3.74 (1H, d, J=15.4 Hz), 3.86-3.93(1H, m), 4.54-4.60(1H, m), 7.25(1H, d, J=7.6 Hz).

Referential Example 253

N-{(1R,2S,5S)-2-amino-5-[(dimethylamino)carbonyl]cyclohexyl}-5-methyl-4,5,6,7-tetrahydrothiazolo[5,4-c]pyridine-2-carboxamide

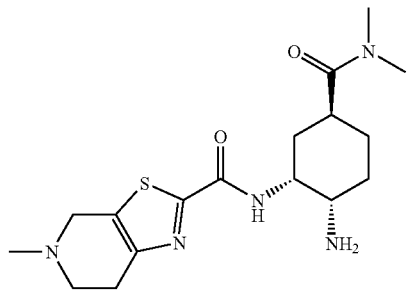

To a solution of the compound obtained in Referential Example 252 (9.0 g) in methanol (300 mL) was added 10% palladium on carbon (6.0 g), and the thus-obtained mixture was vigorously stirred at room temperature for 11 hours at a hydrogen pressure of 4 atm. The catalyst was filtered off, and the filtrate was concentrated, to thereby give the title compound (7.67 g).

$^1$H-NMR(CDCl$_3$)δ: 1.42-1.54(1H, m), 1.66-1.89(5H, m), 2.30-2.40(1H, m), 2.51(3H, s), 2.68-3.05(6H, m), 2.92(3H, s), 3.00(3H, s), 3.10-3.18(1H, m), 3.65-3.77(2H, m), 4.21-4.28(1H, m), 7.52(1H, d, J=6.1 Hz).

Referential Example 254

2-(4-fluoroanilino)-2-oxoacetic acid methyl ester

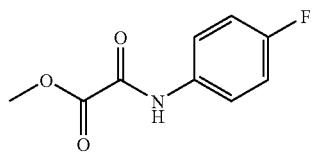

In a manner similar to that employed in Referential Example 242, the title compound was prepared from 4-fluoroaniline and methyl chlorooxoacetate.

$^1$H-NMR(CDCl$_3$)δ: 3.98(3H, s), 7.00-7.14(2H, m), 7.55-7.68(2H, m), 8.85(1H, br.s).

MS(ESI)m/z: 198(M+H)$^+$.

Referential Example 255

2-(4-bromoanilino)-2-oxoacetic acid methyl ester

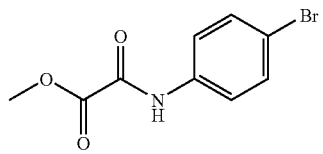

In a manner similar to that employed in Referential Example 242, the title compound was prepared from 4-bromoaniline and methyl chlorooxoacetate.

$^1$H-NMR(CDCl$_3$)δ: 3.98(3H, s), 7.49(2H, d, J=9.0 Hz), 7.55(2H, d, J=9.0 Hz), 8.85(1H, br.s).

MS(FAB)m/z: 258M$^+$.

Referential Example 256

2-(4-chloro-2-methylanilino)-2-oxoacetic acid methyl ester

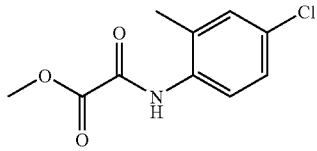

In a manner similar to that employed in Referential Example 242, the title compound was prepared from 4-chloro-2-methylaniline and methyl chlorooxoacetate.
$^1$H-NMR(CDCl$_3$)δ: 2.31(3H, s), 3.99(3H, s), 7.15-7.30 (2H, m), 7.98(1H, d, J=8.8 Hz), 8.77(1H, br).
MS(FAB)m/z: 228 (M+H)$^+$.

Referential Example 257

2-[(4-chloro-3-methylanilino)-2-oxoacetic acid methyl ester

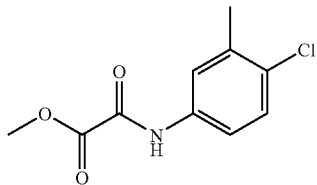

In a manner similar to that employed in Referential Example 242, the title compound was prepared from 4-chloro-3-methylaniline and methyl chlorooxoacetate.
$^1$H-NMR(CDCl$_3$)δ: 2.39(3H, s), 3.98(3H, s), 7.33(1H, d, J=12.5 Hz), 7.44(1H, dd, J=12.5, 2.5 Hz), 7.53(1H, d, J=2.5 Hz), 8.81(1H, br.s).
MS(ESI)m/z: 228(M+H)$^+$.

Referential Example 258

2-(4-chloro-2-fluoroanilino)-2-oxoacetic acid methyl ester

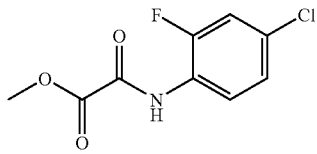

In a manner similar to that employed in Referential Example 242, the title compound was prepared from 4-chloro-2-fluoroaniline and methyl chlorooxoacetate.
$^1$H-NMR(CDCl$_3$)δ: 3.99(3H, s), 7.15-7.24(2H, m), 8.33 (1H, t, J=8.4 Hz), 9.05(1H, br.s).
MS(ESI)m/z: 232(M+H)$^+$.

Referential Example 259

2-(2,4-difluoroanilino)-2-oxoacetic acid methyl ester

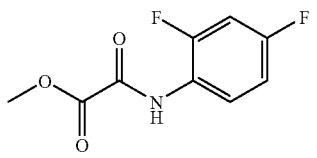

In a manner similar to that employed in Referential Example 242, the title compound was prepared from 2,4-difluoroaniline and methyl chlorooxoacetate.
$^1$H-NMR(CDCl$_3$)δ: 3.99(3H, s), 6.87-7.00(2H, m), 8.29-8.38(1H, m), 8.99(1H, br.s).
MS(ESI)m/z: 215M$^+$.

Referential Example 260

2-(3,4-difluoroanilino)-2-oxoacetic acid methyl ester

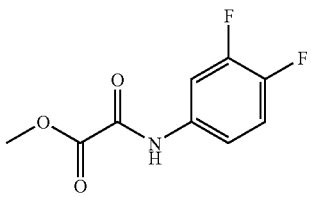

In a manner similar to that employed in Referential Example 242, the title compound was prepared from 3,4-difluoroaniline and methyl chlorooxoacetate.
$^1$H-NMR(CDCl$_3$)δ: 3.98(3H, s), 7.10-7.28(2H, m), 7.67-7.78(1H, m), 8.83(1H, br.s).
MS(ESI)m/z: 215M$^+$.

Referential Example 261

2-oxo-2-(pyridin-4-ylamino)acetic acid methyl ester

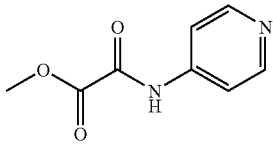

In a manner similar to that employed in Referential Example 242, the title compound was prepared from 4-aminopyridine and methyl chlorooxoacetate.
$^1$H-NMR(CDCl$_3$)δ: 3.99(3H, s), 7.58(2H, dd, J=4.8, 1.6 Hz), 8.60(2H, dd, J=4.8, 1.6 Hz), 9.04(1H, br.s).
MS(ESI)m/z: 181 (M+H)$^+$.

Referential Example 262

2-[(5-bromopyridin-2-yl)amino]-2-oxoacetic acid methyl ester

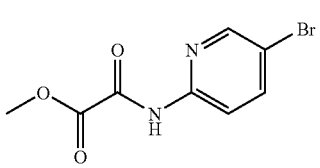

In a manner similar to that employed in Referential Example 242, the title compound was prepared from 2-amino-5-bromopyridine and methyl chlorooxoacetate.
$^1$H-NMR(CDCl$_3$)δ: 3.99(3H, s), 7.87(1H, dd, J=8.8, 2.4 Hz), 8.19(1H, d, J=8.8 Hz), 8.41(1H, d, J=2.4 Hz), 9.38(1H, br.s).
MS(FAB)m/z: 259 M$^+$.

Referential Example 263

2-[(6-chloropyridin-3-yl)amino]-2-oxoacetic acid ethyl ester

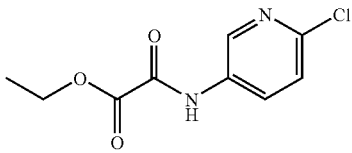

5-Amino-2-chloropyridine (386 mg) was dissolved in N,N-dimethylformamide (8 mL), and to the solution were added potassium 2-ethoxy-2-oxoacetate (469 mg), 1-(3-dimethylaminopropyl)-3-ethylcarbodiimide hydrochloride (863 mg), and 1-hydroxybenzotriazole monohydrate (203 mg), followed by stirring at room temperature for 2 days. The solvent was distilled away under reduced pressure, and the residue was partitioned between methylene chloride and saturated aqueous sodium hydrogencarbonate. The organic layer was dried over sodium sulfate anhydrate, and the solvent was removed under reduced pressure. The residue was purified by silica gel flash column chromatography (hexane ethyl acetate=2:1), to thereby give the residue (200 mg) containing the title compound.
$^1$H-NMR(CDCl$_3$)δ: 1.43(3H, t, J=7.2 Hz), 4.44(2H, q, J=7.2 Hz), 7.36(1H, d, J=8.7 Hz), 8.24(1H, dd, J=8.7, 2.7 Hz), 8.55(1H, d, J=2.7 Hz), 9.03(1H, br.s).

Referential Example 264

2-[(6-chloropyridazin-3-yl)amino]-2-oxoacetic acid methyl ester

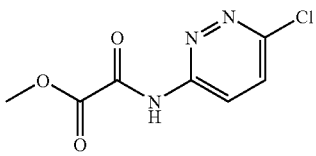

3-Amino-6-chloropyridazine (516 mg) was dissolved in pyridine (26 mL), and to the solution were sequentially added triethylamine (665 mL) and methyl chlorooxoacetate (441 μL) under ice cooling, followed by stirring at room temperature for 14 hours. Water was added to the reaction mixture to partition the mixture, and the organic layer was dried over sodium sulfate anhydrate. The solvent was distilled away under reduced pressure, to thereby give the title compound (748 mg).
$^1$H-NMR(CDCl$_3$)δ: 4.03(3H, s), 7.59(1H, d, J=9.3 Hz), 8.52(1H, d, J=9.3 Hz), 9.88(1H, br.s).
MS(FAB)m/z: 215M$^+$.

Referential Example 265

2-[(5-chlorothiazol-2-yl)amino]-2-oxoacetic acid methyl ester

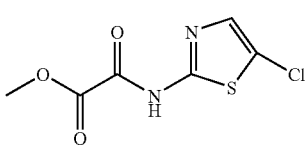

In a manner similar to that employed in Referential Example 242, the title compound was prepared from 2-amino-5-chlorothiazole and methyl chlorooxoacetate.

$^1$H-NMR(CDCl$_3$)δ: 4.02(3H, s), 7.48(1H, s), 11.03(1H, br.s).
MS(ESI)m/z: 221(M+H)$^+$.

Referential Example 266

2-[(5-chloropyridin-2-yl)amino]-2-oxoacetic acid lithium salt

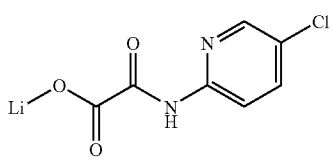

To a solution of the compound obtained in Referential Example 243 (1.12 g) in tetrahydrofuran (20 mL) were added water (5.0 mL) and lithium hydroxide (128 mg) at room temperature, and the thus-obtained mixture was stirred for 5 hours. The solvent was distilled away under reduced pressure, and to the resultant white solid was added hexane (30 mL), followed by stirring for 30 minutes. The resultant solid matter was collected by filtration, and was dried, to thereby give the title compound (1.02 g).
$^1$H-NMR(DMSO-d$_6$)δ: 7.90(1H, dd, J=8.9, 2.6 Hz), 8.12(1H, d, J=8.9 Hz), 8.34(1H, d, J=2.6 Hz), 10.18(1H, s).

Referential Example 267

2-(4-chloroanilino)acetic acid ethyl ester

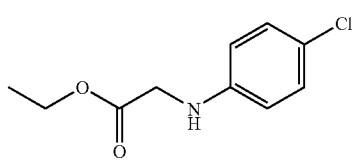

4-Chloroaniline (2.0 g) was dissolved in acetonitrile (20 mL), and bromoethyl acetate (2.1 g) and potassium carbonate (2.2 g) were added thereto, followed by stirring at 60° C. for 2 days. The reaction mixture was filtered through a Celite pad, and the filtrate was concentrated under reduced pressure. The residue was purified by silica gel column chromatography (hexane:chloroform=2:1), to thereby give the title compound (2.3 g).
$^1$H-NMR(CDCl$_3$)δ: 1.30(3H, t, J=7.3 Hz), 3.86(2H, s), 4.24(2H, q, J=7.3 Hz), 4.26-4.35(1H, m), 6.53(2H, dd, J=6.6, 2.2 Hz), 7.14(2H, dd, J=6.6, 2.2 Hz).

Referential Example 268

2-(4-chloro-2-fluoroanilino)acetic acid ethyl ester

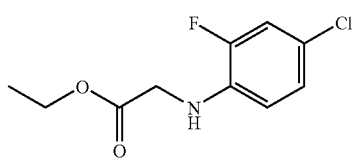

In a manner similar to that employed in Referential Example 267, the title compound was prepared from 4-chloro-2-fluoroaniline and bromoethyl acetate.

¹H-NMR(CDCl₃)δ: 1.29(3H, t, J=7.3 Hz), 3.91(2H, s), 4.22(2H, q, J=7.3 Hz), 4.42-4.51(1H, m), 6.49(1H, t, J=8.8 Hz), 6.98(1H, dt, J=8.8, 2.5 Hz), 7.01(1H, dd, J=11.3, 2.5 Hz).

Referential Example 269

2-[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]-2-oxoacetic acid ethyl ester

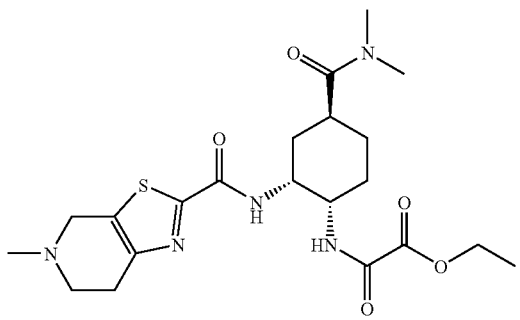

The compound obtained in Referential Example 253 (1.5 g) was dissolved in N,N-dimethylformamide (15 mL), and to the solution were added potassium 2-ethoxy-2-oxoacetate (962 mg), 1-(3-dimethylaminopropyl)-3-ethylcarbodiimide hydrochloride (1.18 g), and 1-hydroxybenzotriazole monohydrate (277 mg), followed by stirring at room temperature for 14 hours. The solvent was distilled away under reduced pressure, and the residue was partitioned between saturated aqueous sodium hydrogencarbonate and methylene chloride. The organic layer was dried over sodium sulfate anhydrate, and the solvent was distilled away under reduced pressure. The residue was purified by silica gel flash column chromatography (methylene chloride:methanol=47:3), to thereby give the title compound (1.13 g).

¹H-NMR(CDCl₃)δ: 1.37(3H, t, J=7.1 Hz), 1.55-2.15(6H, m), 2.52(3H, s), 2.77-2.89(3H, m), 2.94(5H, br.s), 3.06(3H, s), 3.71(1H, d, J=15.5 Hz), 3.73(1H, d, J=15.5 Hz), 4.06-4.13 (1H, m), 4.32(2H, q, J=7.1 Hz), 4.60-4.63(1H, m), 7.39(1H, d, J=8.3 Hz), 7.83(1H, d, J=7.6 Hz).

MS(ESI)m/z: 466(M+H)⁺.

Referential Example 270

2-[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]-2-oxoacetic acid lithium salt

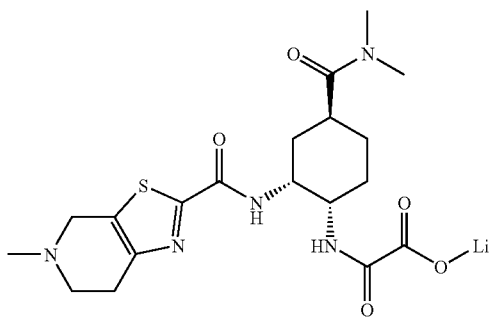

The compound obtained in Referential Example 269 (1.13 g) was dissolved in tetrahydrofuran (20 mL), methanol (10 mL), and water (10 mL), and lithium hydroxide (58 mg) was added thereto, followed by stirring at room temperature for 30 minutes. The solvent was distilled away under reduced pressure, to thereby give the title compound (1.10 g).

¹H-NMR(DMSO-d₆)δ: 1.41-1.73(4H, m), 2.00-2.07(2H, m), 2.39(3H, s), 2.74-2.99(11H, m), 3.67(2H, s), 3.82-3.88 (1H, m), 4.28-4.30(1H, m), 8.66-8.70(2H, m).

Referential Example 271

N-{(1R,2S,5S)-2-azido-5-[(dimethylamino)carbonyl]cyclohexyl}-5-methyl-5,6-dihydro-4H-pyrolo[3,4-d]thiazole-2-carboxamide

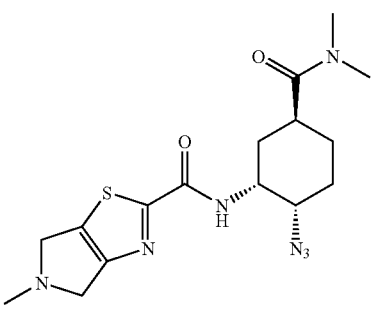

In a manner similar to that employed in Referential Example 252, the title compound was prepared from the compound obtained in Referential Example 293 and the compound obtained in Referential Example 251.

¹H-NMR(CDCl₃)δ: 1.73-1.87(4H, m), 2.11-2.20(2H, m), 2.67(3H, s), 2.85-2.90(1H, m), 2.93(3H, s), 3.00(3H, s), 3.90-4.10(5H, m), 4.57-4.62(1H, m), 7.20-7.22(1H, m).

MS(FAB)m/z: 378(M+H)⁺.

Referential Example 272

N-{(1R,2S,5S)-2-amino-5-[(dimethylamino)carbonyl]cyclohexyl}-5-methyl-5,6-dihydro-4H-pyrolo[3,4-d]thiazole-2-carboxamide

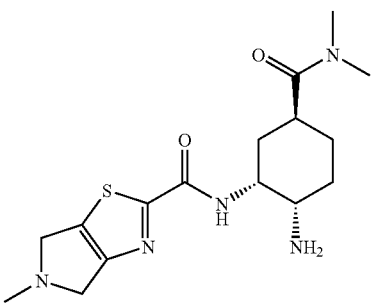

In a manner similar to that employed in Referential Example 253, the title compound was prepared from the compound obtained in Referential Example 271.

¹H-NMR(CDCl₃)δ: 1.67-1.97(6H, m), 2.36-2.40(1H, m), 2.67(3H, s), 2.92(3H, s), 3.00(3H, s), 3.07-3.18(1H, m), 3.92-3.95(2H, m), 4.02-4.06(2H, m), 4.23-4.26(1H, m), 7.50-7.52 (1H, m).

Referential Example 273

5-chloro-4-fluoroindole-2-carboxylic acid methyl ester

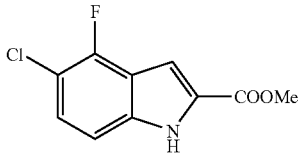

Ethanol (100 mL) was added to sodium hydride (60% sodium hydride content, 4.7 g) at 0° C. under argon atmosphere, and the mixture was stirred for 10 minutes. 2-Nitropropane (11 mL) was added to the reaction mixture, and after the thus-obtained mixture was stirred for 10 minutes, 1-(bromomethyl)-3-chloro-2-fluorobenzene (10 g) was added thereto, followed by stirring at room temperature for 3.5 hours. The precipitate was filtered off, and the filtrate was concentrated under reduced pressure. The residue was partitioned between diethyl ether and water. The organic layer was sequentially washed with 1N aqueous sodium hydroxide, water, and saturated brine, and was dried over sodium sulfate anhydrate. The solvent was distilled away, and the residue was purified by silica gel column chromatography (ethyl acetate:hexane=3:7), to thereby give crude 3-chloro-2-fluorobenzaldehyde (5.5 g) as a pale-yellow oily compound. Methanol (20 mL) was added to sodium hydride (60% sodium hydride content, 1.6 g) under argon atmosphere at 0° C., and the thus-obtained mixture was stirred for 10 minutes. After the reaction mixture was cooled to −20° C., a solution of the crude 3-chloro-2-fluorobenzaldehyde (5.5 g) and methyl 2-azidoacetate (5.0 g) in methanol (10 mL) was added thereto within 20 minutes. After the reaction mixture was heated to 0° C., the mixture was stirred for 2.5 hours, and water (40 mL) was added thereto. The reaction mixture was concentrated under reduced pressure, and the residue was extracted with a mixture of methylene chloride and ethyl acetate. The extract was washed with saturated brine, and was dried over sodium sulfate anhydrate. The solvent was distilled away, and the residue was purified by silica gel column chromatography (toluene:hexane=3:17), to thereby give crude 2-azido-3-[(3-chloro-2-fluoro)phenyl]acrylic acid methyl ester (2.6 g). This compound was dissolved in xylene (50 mL), and the solution was stirred at 130-140° C. for 3 hours. The reaction mixture was concentrated, and the residue was purified by silica gel column chromatography (methylene chloride). The thus-obtained compound was crystallized from diethyl ether-hexane, to thereby give the title compound (440 mg).

$^1$H-NMR(DMSO-$d_6$)δ: 4.08(3H, s), 7.20(1H, s), 7.31-7.38 (2H, m).
MS(FAB)m/z: 228(M+H)$^+$.

Referential Example 274

5-chloro-4-fluoroindole-2-carboxylic acid

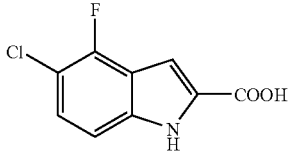

The compound obtained in Referential Example 273 (440 mg) was dissolved in tetrahydrofuran (10 mL), and an aqueous solution (5 mL) of lithium hydroxide (160 mg) was added thereto, followed by stirring at room temperature for 3 hours. To the reaction mixture was further added an aqueous solution (5 mL) of lithium hydroxide (240 mg), and the thus-obtained mixture was stirred at room temperature for an additional 1 hour. The reaction mixture was concentrated under reduced pressure, and the residue was neutralized with 1N aqueous HCl. The thus-obtained mixture was extracted with ethyl acetate 3 times, and the organic layers were combined. The combined organic layer was washed with saturated brine, and was dried over sodium sulfate anhydrate. The solvent was distilled away under reduced pressure, to thereby give the title compound (390 mg).

$^1$H-NMR(DMSO-$d_6$)δ: 6.79(1H, s), 7.16-7.26(2H, m)
MS(FAB)m/z: 214(M+H)$^+$.

Referential Example 275

1-benzyl-5-chloroindole-2-carboxylic acid ethyl ester

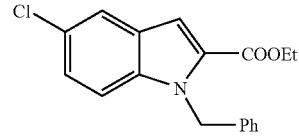

5-Chloroindole-2-carboxylic acid ethyl ester (1.4 g) was dissolved in N,N-dimethylformamide (30 mL), and to the solution were added potassium carbonate (2.9 g) and benzyl chloride (2.4 mL), followed by stirring in a bath at a temperature of 100° C. for 1.5 hours. The reaction mixture was concentrated, and the residue was poured into ice water. The thus-obtained mixture was extracted with ethyl acetate. The organic layer was washed with saturated brine, and was dried over sodium sulfate anhydrate. The solvent was distilled away, and the residue was purified by silica gel column chromatography (ethyl acetate:hexane=1:19). The thus-obtained compound was crystallized from diethyl ether-hexane, to thereby give the title compound (1.6 g).

$^1$H-NMR(CDCl$_3$)δ: 1.36(3H, t, J=7.1 Hz), 4.33(2H, q, J=7.1 Hz), 5.83(2H, s), 7.00-7.02(2H, d), 7.20-7.38(6H, m), 7.67(1H, d, J=1.7 Hz).

Referential Example 276

1-benzyl-5-chloro-3-fluoroindole-2-carboxylic acid ethyl ester

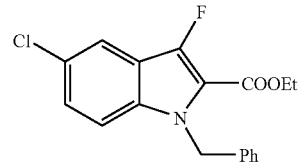

To a solution of the compound obtained in Referential Example 275 (2.2 g) in methylene chloride (30 mL) was added 1-fluoro-2,6-dichloropyridinium triflate (4.4 g), and the thus-obtained mixture was heated under reflux for 3 days. The reaction mixture was partitioned between ethyl acetate and water. The aqueous layer was extracted with ethyl acetate, and the organic layers were combined. The combined organic layer was sequentially washed with 1N HCl, water, and saturated brine, and was dried over sodium sulfate anhydrate. The solvent was distilled away, and the residue was purified by silica gel column chromatography (ethyl acetate:hexane=1:24), to thereby give the crude title compound (2.8 g). A portion of the thus-obtained compound was purified by silica gel thin layer chromatography, to thereby give the title compound.

$^1$H-NMR (DMSO-d$_6$)δ: 1.25(3H, t, J=7.1 Hz), 4.29(2H, q, J=7.1 Hz), 5.77(2H, s), 6.97-6.99(2H, m), 7.18-7.28(3H, m), 7.39(1H, dd, J=9.0, 2.1 Hz), 7.69(1H, dd, J=9.0, 2.1 Hz), 7.78(1H, d, J=2.1 Hz)

Referential Example 277

5-chloro-3-fluoroindole-2-carboxylic acid ethyl ester

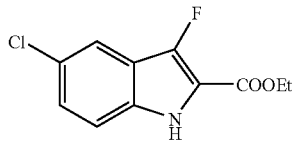

The crude compound obtained in Referential Example 276 (1.4 g) was dissolved in anisole (30 mL), and aluminium chloride (2.9 g) was added thereto in small portions under ice cooling, followed by stirring at room temperature for 30 minutes. Additional aluminium chloride (2.9 g) was added thereto, and the thus-obtained mixture was stirred for 18 hours. To the reaction mixture was added aluminium chloride (8.0 g), and the mixture was stirred for 5 hours. After water was added thereto, the reaction mixture was extracted with ethyl acetate, and the organic layers were combined. The combined organic layer was sequentially washed with saturated aqueous sodium hydrogencarbonate and saturated brine, and was dried over sodium sulfate anhydrate. The solvent was distilled away under reduced pressure, and the residue was purified by silica gel column chromatography (methylene chloride), to thereby give the title compound (470 mg).

$^1$H-NMR(CDCl$_3$)δ: 1.43(3H, t, J=7.2 Hz), 4.45(2H, q, J=7.2 Hz), 7.25-7.31(2H, m), 7.66(1H, d, J=0.73 Hz), 8.53 (1H, br.s).

MS(FAB)m/z: 242 (M+H)$^+$.

Referential Example 278

5-chloro-3-fluoroindole-2-carboxylic acid

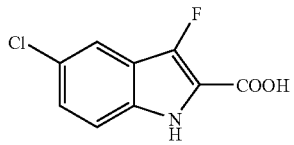

In a manner similar to that employed in Referential Example 274, the title compound was prepared from the compound obtained in Referential Example 277.

$^1$H-NMR(DMSO-d$_6$)δ: 7.31(1H, dd, J=8.8, 1.9 Hz), 7.42 (1H, dd, J=8.8, 1.9 Hz), 7.70(1H, d, J=1.9 Hz), 11.78(1H, s)

MS(FAB)m/z: 214(M+H)$^+$.

Referential Example 279

(1R,2S,5S)-{[(5-chloro-3-fluoroindol-2-yl)carbonyl]amino}-5-[(dimethylamino)carbonyl]cyclohexylcarbamic acid tert-butyl ester

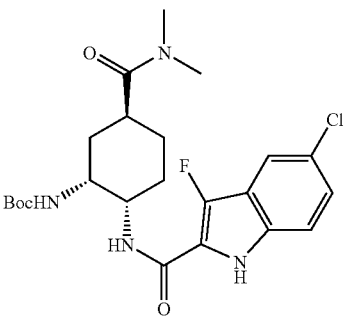

In a manner similar to that employed in Referential Example 97, the title compound was prepared from the compound obtained in Referential Example 144 and the compound obtained in Referential Example 278.

$^1$H-NMR(CDCl$_3$)δ: 1.45(9H, s), 1.73-2.11(6H, m), 2.65 (1H, br.s), 2.96(3H, s), 3.07(3H, s), 4.20(1H, br.s), 4.28(1H, br.s), 4.78(1H, br), 7.23-7.30(3H, m), 7.58(1H, s), 9.03(1H, s).

MS(FAB)m/z: 481(M+H)$^+$.

Referential Example 280

3-bromo-5-chloroindole-2-carboxylic acid ethyl ester

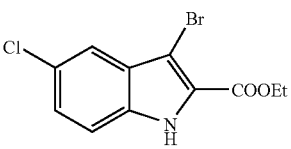

N-Bromosuccinimide (440 mg) was added to a solution of 5-chloroindole-2-carboxylic acid ethyl ester (500 mg) in N,N-dimethylformamide (10 mL) under ice cooling. The reaction mixture was stirred at room temperature for 18 hours, and the solvent was distilled away under reduced pressure. The residue was partitioned between ethyl acetate and water. The aqueous layer was extracted with ethyl acetate, and the organic layers were combined. The combined organic layer was washed with saturated brine, and was dried over sodium sulfate anhydrate. The solvent was distilled away, and the residue was purified by silica gel column chromatography (ethyl acetate:hexane=1:9). The thus-obtained white powder was washed with hexane, to thereby give the title compound (680 mg).

$^1$H-NMR(CDCl$_3$)δ: 1.42-1.48(3H, m), 4.43-4.49(2H, m), 7.30-7.32(2H, m), 7.65(1H, d, J=0.74 Hz), 9.11(1H, s)

MS(FAB)m/z: 303(M+H)$^+$.

Referential Example 281

3-bromo-5-chloroindole-2-carboxylic acid

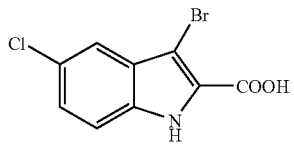

In a manner similar to that employed in Referential Example 274, the title compound was prepared from the compound obtained in Referential Example 280.

$^1$H-NMR(DMSO-d$_6$)δ: 7.35(1H, dd, J=8.8, 2.0 Hz), 7.48-7.53(2H, m), 12.33(1H, s)

MS(FAB)m/z: 275 (M+H)$^+$.

Referential Example 282

(1R,2S,5S)-2-{[(3-bromo-5-chloroindol-2-yl)carbonyl]amino}-5-[(dimethylamino)carbonyl]cyclohexylcarbamic acid tert-butyl ester

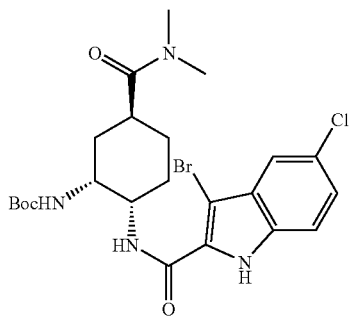

In a manner similar to that employed in Referential Example 97, the title compound was prepared from the compound obtained in Referential Example 144 and the compound obtained in Referential Example 281.

$^1$H-NMR(CDCl$_3$)δ: 1.42(9H, s), 1.58-2.17(6H, m), 2.70 (1H, br.s), 2.96(3H, s), 3.07(3H, s), 4.23-4.28(2H, m), 4.83 (1H, br), 7.34-7.41(3H, m), 7.52(1H, s), 9.76(1H, s).

MS(FAB)m/z: 542(M+H)$^+$.

Referential Example 283

3-chloro-5-fluoroindole-2-carboxylic acid ethyl ester

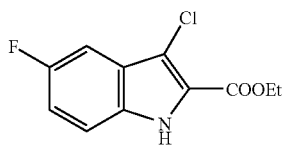

5-Fluoroindole-2-carboxylic acid ethyl ester (2.0 g) was dissolved in N,N-dimethylformamide (20 mL), and a solution of N-chlorosuccinimide (1.4 g) in N,N-dimethylformamide (10 mL) was added dropwise thereto under ice cooling, followed by stirring at room temperature for 18 hours. The reaction mixture was diluted with ethyl acetate, and the diluted mixture was sequentially washed with saturated aqueous sodium hydrogencarbonate and saturated brine. The organic layer was dried over sodium sulfate anhydrate, and the solvent was distilled away under reduced pressure. The residue was purified by silica gel column chromatography (hexane:ethyl acetate=5:1), to thereby give the title compound (1.9 g).

$^1$H-NMR(CDCl$_3$)δ: 1.45(3H, t, J=7.4 Hz), 4.46(2H, q, J=7.4 Hz), 7.14(1H, dt, J=8.0, 2.7 Hz), 7.32-7.36(2H, m), 8.91(1H, br).

Referential Example 284

3-chloro-5-fluoroindole-2-carboxylic acid

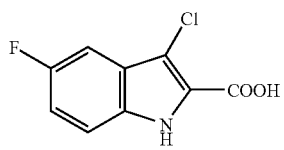

In a manner similar to that employed in Referential Example 274, the title compound was prepared from the compound obtained in Referential Example 283.

$^1$H-NMR(DMSO-d$_6$)δ: 7.20(1H, dt, J=8.8, 2.4 Hz), 7.31 (1H, dd, J=8.8, 2.4 Hz), 7.46(1H, dd, J=8.8, 4.4 Hz), 12.12 (1H, br).

Referential Example 285

5-chloro-3-formylindole-2-carboxylic acid ethyl ester

Phosphorus oxychloride (2.0 mL) was added to N-methylformanilide (2.9 g), and after the mixture was stirred for 15 minutes, 1,2-dichloroethane (50 mL) and 5-chloroindole-2-carboxylic acid ethyl ester (4.0 g) were added thereto, followed by heating under reflux for 1 hour. The reaction mixture was poured into an aqueous solution (28 mL) of sodium acetate (14 g) under ice cooling, and the thus-obtained mixture was stirred for 18 hours. Insoluble matter was collected by filtration, and was sequentially washed with water and diethyl ether, to thereby give the title compound (3.56 g).

$^1$H-NMR(DMSO-d$_6$)δ: 1.38(3H, t, J=7.1 Hz), 4.44(2H, q, J=7.1 Hz), 7.38(1H, dd, J=8.0, 1.4 Hz), 7.56(1H, d, J=8.0 Hz), 8.19(1H, d, J=1.4 Hz), 10.53(1H, s).

Referential Example 286

5-chloro-3-formylindole-2-carboxylic acid

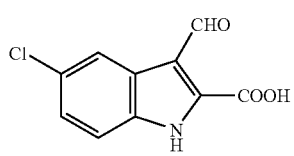

The compound obtained in Referential Example 285 (1.0 g) was dissolved in ethanol (10 mL), and 1N aqueous sodium hydroxide (10 mL) was added dropwise thereto, followed by stirring at 50° C. for 2 hours. To the reaction mixture was added 1N aqueous HCl (11 mL), and the thus-obtained mixture was stirred. The resultant insoluble matter was collected by filtration, to thereby give the title compound (0.86 g).

$^1$H-NMR(DMSO-d$_6$)δ: 7.39(1H, d, J=8.0 Hz), 7.55(1H, d, J=8.0 Hz), 8.20(1H, s), 10.58(1H, s), 12.90(1H, br).

Referential Example 287

5-chloro-2-ethoxycarbonylindole-3-carboxylic acid

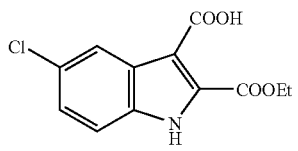

The compound obtained in Referential Example 286 (1.5 g) and sulfamic acid (1.7 g) were dissolved in tert-butanol (30 mL) and water (30 mL), and sodium chlorite (1.6 g) was added thereto, followed by stirring for 8 hours. The reaction mixture was diluted with water, and the diluted mixture was extracted with ethyl acetate. The extract was sequentially washed with 1N aqueous HCl and saturated brine, and was dried over sodium sulfate anhydrate. The solvent was distilled away under reduced pressure, and the residue was recrystallized from a solvent mixture comprising isopropyl ether and hexane, to thereby give the title compound (0.7 g).

$^1$H-NMR(DMSO-$d_6$)δ: 1.34(3H, t, J=7.1 Hz), 4.38(2H, q, J=7.1 Hz), 7.33(1H, dd, J=8.0, 1.4 Hz), 7.52(1H, d, J=8.0 Hz), 7.97(1H, d, J=1.4 Hz), 12.75(1H, br).

Referential Example 288

5-chloro-3-[(dimethylamino)carbonyl]indole-2-carboxylic acid ethyl ester

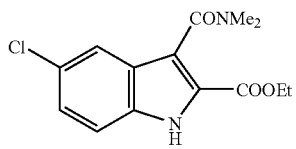

The compound obtained in Referential Example 287 (0.7 g) was dissolved in N,N-dimethylformamide (10 mL), and to the solution were added dimethylamine hydrochloride (0.26 g), 1-hydroxybenzotriazole monohydrate (0.43 g), and 1-(3-dimethylaminopropyl)-3-ethylcarbodiimide hydrochloride (1.0 g), followed by stirring at room temperature for 2 days. The reaction mixture was diluted with ethyl acetate, and the diluted mixture was sequentially washed with 1N aqueous HCl, saturated aqueous sodium hydrogencarbonate, and saturated brine. The organic layer was dried over sodium sulfate anhydrate. The solvent was distilled away under reduced pressure, and the residue was recrystallized from a solvent mixture comprising isopropyl ether and hexane, to thereby give the title compound (0.6 g).

$^1$H-NMR(DMSO-$d_6$)δ: 1.29(3H, t, J=7.1 Hz), 2.78(3H, s), 3.04(3H, s), 4.30(2H, q, J=7.1 Hz), 7.31(1H, dd, J=8.0, 1.4 Hz), 7.45(1H, d, J=1.4 Hz), 7.48(1H, d, J=8.0 Hz), 12.29(1H, s).

Referential Example 289

5-chloro-3-[(dimethylamino)carbonyl]indole-2-carboxylic acid

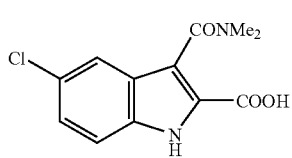

In a manner similar to that employed in Referential Example 286, the title compound was prepared from the compound obtained in Referential Example 288.

$^1$H-NMR(DMSO-$d_6$)δ: 2.91(6H, s), 7.29(1H, d, J=8.0 Hz), 7.44(1H, d, J=8.0 Hz), 7.47(1H, s), 12.16(1H, s).

Referential Example 290

5-(phenylsulfonyl)-5,6-dihydro-4H-pyrolo[3,4-d]thiazole

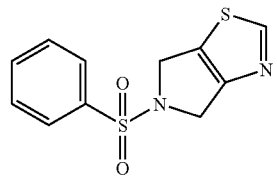

Benzenesulfonamide (638 mg) and 4,5-bis(bromomethyl)thiazole (M. Al. Hariri, O. Galley, F. Pautet, H. Fillion, Eur. J. Org. Chem., pp. 593-594 (1998)) (1.10 g) were dissolved in N,N-dimethylformamide (10 mL) under ice cooling, and sodium hydride (60% in oil, 357 mg) was added thereto at a time, followed by stirring at room temperature for 3 hours. The resultant mixture was partitioned between water and methylene chloride, and the organic layer was dried over sodium sulfate anhydrate. The solvent was distilled away, and the residue was purified by silica gel column chromatography (methylene chloride:ethyl acetate=9:1), to thereby give the title compound (137 mg).

$^1$H-NMR(CDCl$_3$)δ: 4.60-4.63(2H, m), 4.70-4.73(2H, m), 7.52-7.64(3H, m), 7.88-7.92(2H, m), 8.71(1H, s).

MS(FAB)m/z: 267 (M+H)$^+$.

Referential Example 291

5,6-dihydro-4H-pyrolo[3,4-d]thiazole dihydrobromide

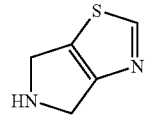

A mixture of the compound obtained in Referential Example 290 (800 mg), phenol (800 μL), and 47% aqueous hydrobromic acid (5.00 mL) was heated under reflux for 2 hours. After the resultant mixture was cooled to room temperature, the mixture was partitioned between ethyl acetate and water. The solvent of the aqueous layer was distilled away under reduced pressure. After ethyl acetate was added to the residue, the resultant precipitate was collected by filtration, and was dried, to thereby give the title compound (521 mg).

$^1$H-NMR(DMSO-$d_6$)δ: 4.42(2H, br s), 4.56(2H, br s), 9.14 (1H, s).

MS(FAB)m/z: 127(M+H)$^+$.

Referential Example 292

5-methyl-5,6-dihydro-4H-pyrolo[3,4-d]thiazole

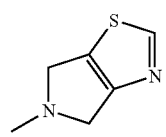

In a manner similar to that employed in Referential Example 9, the title compound was prepared from the compound obtained in Referential Example 291.

$^1$H-NMR(CDCl$_3$)δ: 2.67(3H, s), 3.95-3.99(2H, m), 4.01-4.05(2H, m), 8.69(1H, s).

MS(ESI)m/z: 141(M+H)$^+$.

Referential Example 293

5-methyl-5,6-dihydro-4H-pyrolo[3,4-d]thiazole-2-carboxylic acid lithium salt

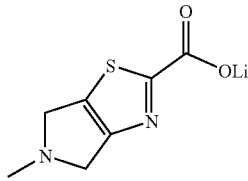

In a manner similar to that employed in Referential Example 5, the title compound was prepared from the compound obtained in Referential Example 292.

¹H-NMR(DMSO-d₆)δ: 2.52(3H, s), 3.73(2H, t, J=3.2 Hz), 3.87(2H, t, J=3.2 Hz).

Referential Example 294

(1R,2S,5S)-2-[(6-chloro-2-naphthoyl)amino]-5-[(dimethylamino)carbonyl]cyclohexylcarbamic acid tert-butyl ester

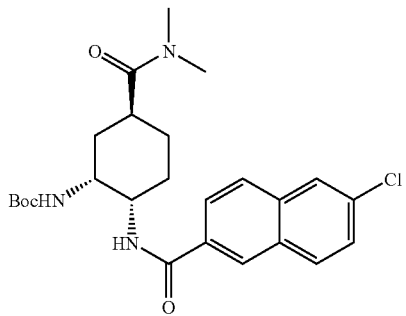

In a manner similar to that employed in Referential Example 97, the title compound was prepared from the compound obtained in Referential Example 144 and 6-chloronaphthalene-2-carboxylic acid (Eur. J. Chem-Chim. Ther., vol. 19, pp. 205-214 (1984)).

¹H-NMR(CDCl₃)δ: 1.30-2.00(15H, m), 2.60-2.80(1H, m), 2.96(3H, s), 3.09(3H, s), 4.00-4.20(1H, m), 4.20-4.30(1H, m), 4.75-4.95(1H, m), 7.44(1H, d, J=9.0 Hz), 7.70-7.95(5H, m), 8.31(1H, s).

MS(FAB)m/z: 474 (M+H)⁺.

Referential Example 295

(E)-3-(morpholin-4-yl)-2-acrylic acid ethyl ester

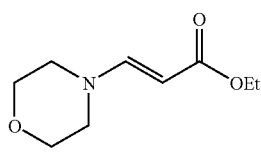

Propionic acid ethyl ester (2.0 mL) was dissolved in methylene chloride (20 mL), and morpholine (1.70 mL) was added dropwise thereto under ice cooling, followed by stirring at room temperature for 1 hour. The resultant mixture was concentrated under reduced pressure, and the residue was purified by silica gel column chromatography (methylene chloride:methanol=20:1), to thereby give the title compound (3.72 g).

¹H-NMR(CDCl₃)δ: 1.26(3H, t, J=7.1 Hz), 3.21(4H, t, J=5.1 Hz), 3.71(4H, t, J=5.1 Hz), 4.14(2H, q, J=7.1 Hz), 4.70(1H, d, J=13.4 Hz), 7.36(1H, d, J=13.4 Hz).

MS(FAB)m/z: 186 (M+H)⁺.

Referential Example 296

3-chlorobenzenediazonium tetrafluoroborate

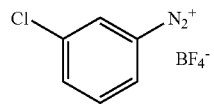

3-Chloroaniline (2.0 g) was dissolved in a solvent mixture of water (30 mL) and concentrated HCl (3.5 mL), and sodium nitrite (1.30 g) was added thereto under ice cooling, followed by stirring for 10 minutes. To the resultant mixture were added concentrated HCl (5.3 mL) and sodium tetrafluoroborate (6.90 g), followed by stirring for 30 minutes under ice cooling. The precipitate was collected by filtration, and was washed with water, methanol, and diethyl ether, to thereby give the title compound (2.63 g). The compound was directly used for the next reaction.

Referential Example 297

7-chlorocinnoline-3-carboxylic acid ethyl ester

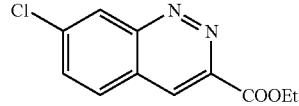

The compound obtained in Referential Example 295 (1.45 g) was dissolved in acetonitrile (100 mL), and the compound obtained in Referential Example 296 (1.73 g) was added thereto. The thus-obtained mixture was stirred at room temperature for 1 hour, and was heated under reflux for 7 days. The solvent was distilled away under reduced pressure, and the residue was purified by silica gel column chromatography (methylene chloride→methylene chloride ethyl acetate=10:1, followed by hexane:ethyl acetate 4:1→1:1), to thereby give the title compound (0.25 g).

¹H-NMR(CDCl₃)δ: 1.53(3H, t, J=7.1 Hz), 4.62(2H, q, J=7.1 Hz), 7.80(1H, dd, J=8.8, 2.0 Hz), 7.95(1H, d, J=8.8 Hz), 8.64(1H, s), 8.68(1H, d, J=2.0 Hz).

Referential Example 298

7-chlorocinnoline-3-carboxylic acid

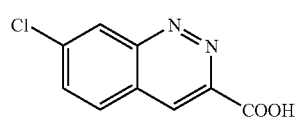

In a manner similar to that employed in Referential Example 286, the title compound was prepared from the compound obtained in Referential Example 297.

¹H-NMR(DMSO-d₆)δ: 8.02(1H, dd, J=8.8, 2.0 Hz), 8.34 (1H, d, J=8.8 Hz), 8.70(1H, s), 8.90(1H, s).

MS(FAB)m/z: 209(M+H)⁺.

Referential Example 299

(1R,2S,5S)-2-{[(7-chlorocinnolin-3-yl)carbonyl]amino}-5-[(dimethylamino)carbonyl]cyclohexylcarbamic acid tert-butyl ester

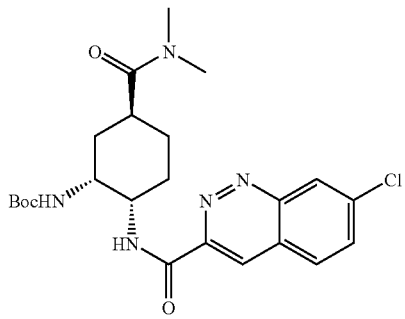

In a manner similar to that employed in Referential Example 97, the title compound was prepared from the compound obtained in Referential Example 144 and the compound obtained in Referential Example 298.

$^1$H-NMR(CDCl$_3$)δ: 1.36(9H, s), 1.80-2.20(5H, m), 2.72 (1H, m), 2.96(3H, s), 3.07(3H, s), 3.49(1H, d, J=3.7 Hz), 4.30-4.45(2H, m), 4.87(1H, br), 7.77(1H, dd, J=8.8, 2.0 Hz), 7.96(1H, d, J=8.8 Hz), 8.59(2H, br), 8.72(1H, s).

MS(FAB)m/z: 476(M+H)$^+$.

Referential Example 300

(1R,2S,5S)-2-{[(5-chloro-1H-benzimidazol-2-yl)carbonyl]amino}-5-[(dimethylamino)carbonyl]cyclohexylcarbamic acid tert-butyl ester

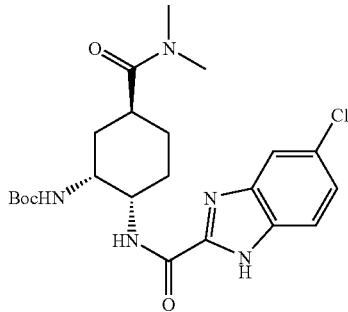

To a solution of the compound obtained in Referential Example 143 (235 mg) in tetrahydrofuran (5.0 mL) was added 10% palladium on carbon (50 mg), and the thus-obtained mixture was stirred at room temperature overnight under hydrogen atmosphere. The reaction mixture was filtered, and the filtrate was concentrated. The residue and 5-chlorobenzimidazole-2-carboxylic acid (Bull. Chem. Soc. Jpn., vol. 62, p. 2668 (1989)) (165 mg) were dissolved in N,N-dimethylformamide (5.0 mL), and to the solution were added 1-hydroxybenzotriazole monohydrate (100 mg) and 1-(3-dimethylaminopropyl)-3-ethylcarbodiimide hydrochloride (171 mg) at room temperature, followed by stirring for 4 days. The reaction mixture was concentrated, and to the residue were added methylene chloride, aqueous sodium hydrogencarbonate, and water to partition the residue. The aqueous layer was extracted with methylene chloride, and the organic layers were combined. The combined organic layer was dried over sodium sulfate anhydrate, and the solvent was distilled away under reduced pressure. The residue was purified by silica gel flash column chromatography (methylene chloride:methanol=10:1), to thereby give the title compound (250 mg).

$^1$H-NMR(DMSO-d$_6$)δ: 1.01-2.00(6H, m), 1.34(9H, s), 2.79(3H, s), 2.80-2.95(1H, m), 2.98(3H, s), 3.89-4.06(2H, m), 7.08(1H, d, J=6.6 Hz), 7.31(1H, d, J=8.5 Hz), 7.62(2H, br.s), 8.47(1H, d, J=8.5 Hz), 13.46(1H, br.s).

MS(ESI)m/z: 466(M+H)$^+$.

Referential Example 301

3-(4-fluorophenyl)-2-{[(4-methylphenyl)sulfonyl]amino}propionic acid methyl ester

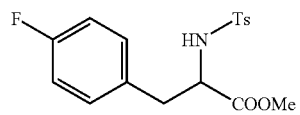

2-Amino-3-(4-fluorophenyl)propionic acid methyl ester (2.01 g), p-toluenesulfonyl chloride (2.25 g), and 4-dimethylaminopyridine (309 mg) were dissolved in chloroform (30 mL), and pyridine (3.0 mL) was added thereto, followed by heating under reflux for 4.5 hours. Additional p-toluenesulfonyl chloride (2.20 g) was added thereto, and the thus-obtained mixture was heated under reflux for 3.5 hours. The reaction mixture was poured into ice and 1N HCl (17 mL) to partition the mixture. The organic layer was sequentially washed with saturated aqueous sodium hydrogencarbonate and saturated brine, and was dried over sodium sulfate anhydrate. The solvent was distilled away under reduced pressure, and the residue was purified by silica gel column chromatography (hexane:ethyl acetate=9:1->2:1), to thereby give the title compound (2.89 g).

$^1$H-NMR(CDCl$_3$)δ: 2.41(3H, s), 2.90-3.10(2H, m), 3.51 (3H, s), 4.10-4.20(1H, m), 5.04(1H, d, J=9.0 Hz), 6.85-6.95 (2H, m), 7.00-7.10(2H, m), 7.20-7.30(2H, m), 7.60-7.70(2H, m).

MS(ESI)m/z: 352(M+H)$^+$.

Referential Example 302

7-fluoro-2-[(4-methylphenyl)sulfonyl]-1,2,3,4-tetrahydroisoquinoline-3-carboxylic acid methyl ester

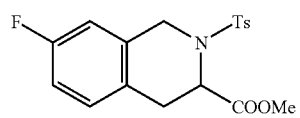

The compound obtained in Referential Example 301 (1.50 g) and paraformaldehyde (207 mg) were dissolved in chloroform (40 mL), and after the reaction vessel was purged with argon, trifluoroborane-diethyl ether complex (1.20 mL) was added thereto, followed by stirring at room temperature for 7.5 hours. The reaction mixture was poured into ice and saturated aqueous sodium hydrogencarbonate to partition the mixture, and the organic layer was dried over sodium sulfate anhydrate. The solvent was distilled away under reduced pressure, and the residue was purified by silica gel column chromatography (hexane:ethyl acetate=3:1), to thereby give the title compound (1.45 g).

$^1$H-NMR(CDCl$_3$)δ: 2.42(3H, s), 3.15(2H, d, J=3.9 Hz), 3.46(3H, s), 4.45(1H, d, J=15.9 Hz), 4.69(1H, d, J=15.9 Hz), 5.01(1H, t, J=4.4 Hz), 6.70-6.80 (1H, m), 6.80-6.90(1H, m), 7.00-7.10(1H, m), 7.29(2H, d, J=8.1 Hz), 7.72(2H, d, J=8.3 Hz).

MS(ESI)m/z: 364(M+H)⁺.

Referential Example 303

7-fluoroisoquinoline-3-carboxylic acid methyl ester

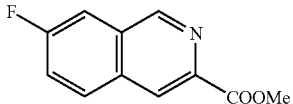

The compound obtained in Referential Example 302 (1.45 g) was dissolved in N,N-dimethylformamide (40 mL), and oxygen gas was introduced into the reaction mixture, followed by stirring at 100° C. for 3.5 hours. The reaction mixture was concentrated under reduced pressure, and the residue was partitioned between saturated aqueous sodium hydrogencarbonate and methylene chloride. The organic layer was sequentially washed with 10% aqueous citric acid and saturated brine, and was dried over sodium sulfate anhydrate. The solvent was distilled away under reduced pressure, and the residue was purified by silica gel column chromatography (hexane:ethyl acetate=1:1), to thereby give the title compound (0.59 g).

¹H-NMR(CDCl₃)δ: 4.07(3H, s), 7.55-7.65(1H, m), 7.65-7.75(1H, m), 8.00-8.05(1H, m), 8.61(1H, s), 9.30(1H, s).

MS(ESI)m/z: 206(M+H)⁺.

Referential Example 304

7-fluoroisoquinoline-3-carboxylic acid hydrochloride

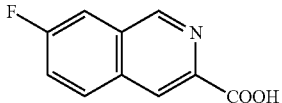

The compound obtained in Referential Example 303 (1.45 g) was dissolved in concentrated HCl (18 mL), and the solution was heated under reflux for 2.5 hours. The reaction mixture was cooled, and the precipitated crystals were collected by filtration. The crystals were washed with water, and was dried, to thereby give the title compound (0.46 g).

¹H-NMR(DMSO-d₆)δ: 7.90-8.00(1H, m), 8.15-8.25(1H, m), 8.40-8.50(1H, m), 8.82(1H, s), 9.55(1H, s).

MS(FAB)m/z: 192 (M+H)⁺.

Referential Example 305

7-chloro-2H-chromene-3-carboxylic acid ethyl ester

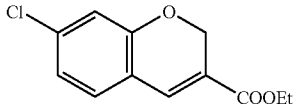

4-Chloro-2-hydroxybenzaldehyde (Acta. Chem. Scand., vol. 53, p. 258 (1999)) (510 mg) was dissolved in tetrahydrofuran (40 mL), and sodium hydride (60% in oil, 157 mg) was added thereto, followed by stirring at room temperature for 2 hours. To the reaction mixture was added a solution of 2-diethylphosphonoacrylic acid ethyl ester (J. Org. Chem., vol. 43, p. 1256 (1978)) (769 mg) in tetrahydrofuran (10 mL), and the thus-obtained mixture was stirred at room temperature for 2 hours, followed by heating under reflux overnight. After the reaction mixture was cooled to room temperature, the mixture was partitioned between water and diethyl ether. The organic layer was dried over sodium sulfate anhydrate, and the solvent was distilled away under reduced pressure. The residue was purified by silica gel column chromatography (hexane:ethyl acetate=10:1), to thereby give the title compound (247 mg).

¹H-NMR(DMSO-d₆)δ: 1.33(3H, t, J=7.1 Hz), 4.27(2H, q, J=7.1 Hz), 4.99(2H, d, J=1.2 Hz), 6.85(1H, d, J=1.2 Hz), 6.89(1H, dd, J=8.1, 2.0 Hz), 7.04(1H, d, J=8.1 Hz), 7.38(1H, d, J=1.0 Hz).

MS(EI)m/z: 238(M⁺).

Referential Example 306

7-chloro-2H-chromene-3-carboxylic acid

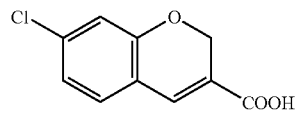

In a manner similar to that employed in Referential Example 274, the title compound was prepared from the compound obtained in Referential Example 305.

¹H-NMR(DMSO-d₆)δ: 4.92(1H, d, J=2.0 Hz), 6.95(1H, d, J=2.0 Hz), 7.01(1H, dd, J=8.1, 2.2 Hz), 7.35(1H, d, J=8.1 Hz), 7.44(1H, s). MS(EI)m/z: 210(M⁺).

Referential Example 307

(1R,2S,5S)-2-{[(E)-3-(4-chlorophenyl)-2-propenoyl] amino}-5-[(dimethylamino)carbonyl]cyclohexylcarbamic acid tert-butyl ester

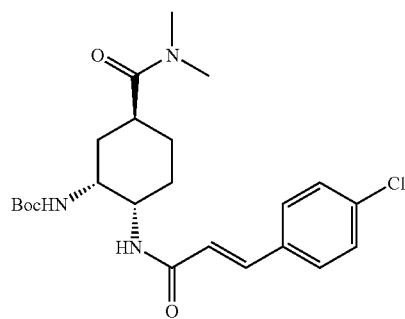

In a manner similar to that employed in Referential Example 97, the title compound was prepared from the compound obtained in Referential Example 144 and 4-chlorocinnamic acid.

¹H-NMR(CDCl₃)δ: 1.30-1.55(3H, m), 1.48(9H, s), 1.60-2.30(4H, m), 2.57-2.70(1H, m), 2.95(3H, s), 3.06(3H, s), 4.01(1H, br s), 4.10-4.20(1H, m), 4.78(1H, br.s), 6.30(1H, d, J=15.6 Hz), 7.02(1H, s), 7.31(2H, d, J=8.5 Hz), 7.40(2H, d, J=8.5 Hz), 7.52(1H, d, J=15.6 Hz).

MS(ESI)m/z: 450(M+H)⁺.

Referential Example 308

6-chloro-4-oxo-1,4-dihydroquinoline-2-carboxylic acid methyl ester

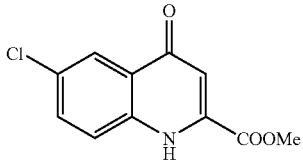

Dimethyl acetylenedicarboxylate (13.5 mL) was added to a solution of 4-chloroaniline (12.76 g) in methanol (150 mL), and the thus-obtained mixture was heated under reflux for 8 hours. The reaction mixture was concentrated under reduced pressure, and the residue was dissolved in diphenyl ether (70 mL), followed by stirring at 240° C. for 4 hours. After the reaction mixture was cooled, a solvent mixture of hexane and diethyl ether was added thereto. The precipitated crystals were collected by filtration, and were washed, to thereby give the title compound (11.09 g).

$^1$H-NMR(DMSO-$d_6$)δ: 3.97(3H, s), 7.76(1H, dd, J=9.0, 2.5 Hz), 7.90-8.05(2H, m), 12.28(1H, br.s).
MS(ESI)m/z: 238(M+H)$^+$.

Referential Example 309

6-chloro-4-oxo-1,4-dihydroquinoline-2-carboxylic acid

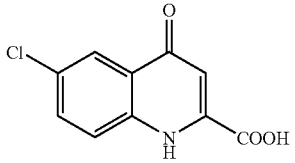

In a manner similar to that employed in Referential Example 286, the title compound was prepared from the compound obtained in Referential Example 308.

$^1$H-NMR(DMSO-$d_6$)δ: 6.90-7.05(1H, m), 7.90-8.05(2H, m), 10.10-10.30(1H, m), 12.13(1H, br.s).
MS(ESI)m/z: 224(M+H)$^+$.

Referential Example 310

(1R,2S,5S)-2-{[(5-chloroindol-2-yl)carbonyl]amino}-5-[(dimethylamino)carbonyl]cyclohexylcarbamic acid tert-butyl ester

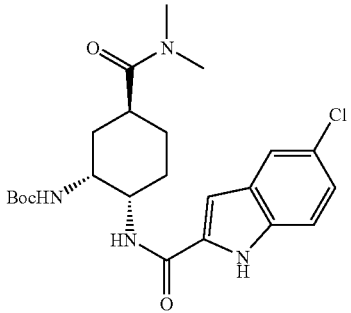

To a solution of the compound obtained in Referential Example 97 (5.00 g) in tetrahydrofuran (40 mL) were added water (10 mL) and lithium hydroxide (263 mg), and the thus-obtained mixture was stirred at room temperature overnight. The reaction mixture was filtered, and the filtrate was concentrated. The residue and dimethylamine hydrochloride (1.85 g) were dissolved in N,N-dimethylformamide (100 mL), and to the solution were added 1-hydroxybenzotriazole monohydrate (1.75 g), 1-(3-dimethylaminopropyl)-3-ethylcarbodiimide hydrochloride (3.32 g), and diisopropylethylamine (11.3 mL) at room temperature, followed by stirring for 2 days. The reaction mixture was concentrated, and to the residue were added methylene chloride, aqueous sodium hydrogencarbonate, and water to partition the residue. The aqueous layer was extracted with methylene chloride, and the organic layers were combined. The combined organic layer was dried over sodium sulfate anhydrate, and the solvent was distilled away under reduced pressure. The residue was purified by silica gel column chromatography (methylene chloride:acetone=2:1→1:1), to thereby give the title compound (4.59 g).

$^1$H-NMR(CDCl$_3$)δ: 1.60-1.76(2H, m), 1.73(9H, s), 1.76-1.87(1H, m), 1.93(1H, br.s), 2.14(1H, br.s), 2.28(1H, br.s), 2.65(1H, br.s), 2.95(3H, s), 3.05(3H, s), 4.01(1H, br.s), 4.21(1H, br.s), 4.84(1H, br.s), 6.81(1H, br.s), 7.20(1H, dd, J=8.8, 1.9 Hz), 7.36(1H, d, J=8.8 Hz), 7.59(1H, br.s), 8.02(1H, br.s), 10.06(1H, br.s).
MS(FAB)m/z: 465(M+H)$^+$.

Referential Example 311

(1R,2S,5S)-2-{[(5-fluoroindol-2-yl)carbonyl]amino}-5-[(dimethylamino)carbonyl]cyclohexylcarbamic acid tert-butyl ester

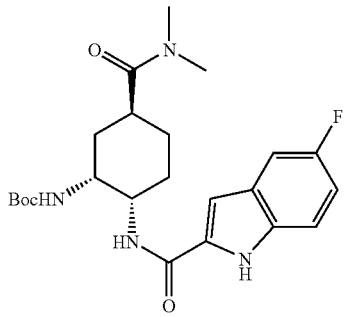

1) In a manner similar to that employed in Referential Example 91, (1S,3R,4S)-3-[(tert-butoxycarbonyl)amino]-4-{[(5-fluoroindol-2-yl)carbonyl]amino}cyclohexanecarboxylic acid ethyl ester was prepared from the compound obtained in Referential Example 96 and 5-fluoroindole-2-carboxylic acid.

$^1$H-NMR(CDCl$_3$)δ: 1.26(3H, t, J=7.1 Hz), 1.52(9H, s), 1.67-2.41(7H, m), 3.97(1H, br.s), 4.15(2H, q, J=7.1 Hz), 4.08-4.22(1H, m), 6.83(1H, s), 7.00-7.05(1H, m), 7.32-7.36(1H, m), 8.02(1H, s), 9.51(1H, s).
MS(FAB)m/z: 448 (M+H)$^+$.

2) In a manner similar to that employed in Referential Example 310, the title compound was prepared from the above-described compound.

$^1$H-NMR(CDCl$_3$)δ: 1.52(9H, s), 1.57-1.79(2H, m), 1.79-2.00(2H, m), 2.14(1H, br.s), 2.31(1H, br.s), 2.65(1H, br.s), 2.95(3H, s), 3.07(3H, s), 4.02(1H, br.s), 4.17-4.25(1H, m), 4.80(1H, br.s), 6.82(1H, br.s), 7.02(1H, dt, J=2.3, 9.0 Hz), 7.24(1H, br.s), 7.35(1H, dd, J=9.0, 4.3 Hz), 7.91(1H, br.s), 9.49(1H, br.s).
MS(FAB)m/z: 447(M+H)$^+$.

Referential Example 312

2-amino-6,6-dimethyl-6,7-dihydrothiazolo[4,5-c]pyridine-5(4H)-carboxylic acid ethyl ester

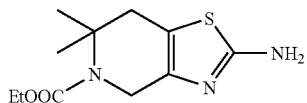

Cuprous cyanide (918 mg) was suspended in tetrahydrofuran (50 mL) under argon flow, and after the suspension was cooled to −20° C., n-butyllithium (as 1.56N hexane solution, 6.41 mL) was added dropwise thereto over 5 minutes, followed by stirring at −20° C. for 30 minutes. The reaction mixture was cooled to −50° C., and diisobutylaluminium hydride (as 1.00M hexane solution) was added dropwise thereto over 20 minutes, followed by stirring at −50° C. for 1 hour. To the reaction mixture was added dropwise a solution of 2,2-dimethyl-5-oxo-5,6-dihydro-2H-pyridine-1-carboxylic acid ethyl ester (Helv. Chim. Acta, vol. 81, p. 303 (1998)) (986 mg) in tetrahydrofuran (5 mL) over 5 minutes, followed by stirring at −50° C. for 2 hours. The resultant mixture was heated to −20° C., and bromine (4.90 mL) was added thereto at a time, followed by stirring at −20° C. for 30 minutes. The reaction mixture was partitioned between water and ethyl acetate. The organic layer was washed with saturated aqueous sodium sulfite, and was dried over anhydrous magnesium sulfate. The solvent was distilled away, and the residue was dissolved in N,N-dimethylformamide (10 mL). Thiourea (760 mg) was added thereto, and the thus-obtained mixture was stirred at 50° C. overnight. The solvent was distilled away, and the residue was partitioned between methylene chloride and saturated aqueous sodium hydrogencarbonate. The organic layer was dried over sodium sulfate anhydrate, and the solvent was distilled away. The residue was purified by silica gel column chromatography (ethyl acetate:hexane=4:1), to thereby give the title compound (412 mg).

$^1$H-NMR(CDCl$_3$)δ: 1.25(3H, t, J=7.1 Hz), 1.54(6H, s), 2.65-2.67(2H, m), 4.09(2H, q, J=7.1 Hz), 4.44-4.46(2H, m), 4.78(2H, br.s).

Referential Example 313

2-bromo-6,6-dimethyl-6,7-dihydrothiazolo[4,5-c]pyridine-5(4H)-carboxylic acid ethyl ester

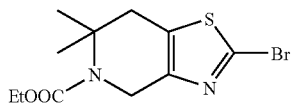

Cupric bromide (431 mg) was suspended in acetonitrile (8 mL), and tert-butyl nitrite (249 mg) was added dropwise thereto at room temperature. To the reaction mixture was added a solution of the compound obtained in Referential Example 312 (412 mg) in acetonitrile (8 mL) under ice cooling, and the thus-obtained mixture was heated to 50° C., followed by stirring for 15 minutes. The solvent was distilled away, and the residue was partitioned between diethyl ether and 10% HCl. The organic layer was dried over anhydrous magnesium sulfate, and was concentrated under reduced pressure. The residue was purified by silica gel column chromatography (hexane:ethyl acetate=6:1), to thereby give the title compound (151 mg).

$^1$H-NMR(CDCl$_3$)δ: 1.26(3H, t, J=7.1 Hz), 1.55(6H, s), 2.79-2.81(2H, m), 4.10(2H, q, J=7.1 Hz), 4.65-4.67(2H, m). MS(ESI)m/z: 319(M+H)$^+$.

Referential Example 314

6,6-dimethyl-6,7-dihydrothiazolo[4,5-c]pyridine-5(4H)-carboxylic acid ethyl ester

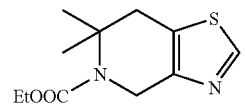

To a solution of the compound obtained in Referential Example 313 (432 mg) in diethyl ether (5 mL) was added n-butyllithium (as 1.56N hexane solution, 1.04 mL) at −78° C., and the thus-obtained mixture was stirred at −78° C. for 30 minutes. The reaction mixture was partitioned between water and diethyl ether, and the organic layer was dried over anhydrous magnesium sulfate. The solvent was distilled away, to thereby give the title compound (307 mg).

$^1$H-NMR(CDCl$_3$)δ: 1.28(3H, t, J=7.1 Hz), 1.55(6H, s), 2.90(2H, s), 4.12(2H, q, J=7.1 Hz), 4.75(2H, m), 8.63(1H, s).

Referential Example 315

6,6-dimethyl-4,5,6,7-tetrahydrothiazolo[4,5-c]pyridine

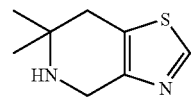

The compound obtained in Referential Example 314 (307 mg) was dissolved in a solvent mixture of water (5 mL), ethanol (5 mL), and dioxane (5 mL), and lithium hydroxide (598 mg) was added to the reaction mixture, followed by heating under reflux for 7 days. The resultant mixture was left to cool to room temperature, and was partitioned between water and methylene chloride. The aqueous layer was extracted with methylene chloride 6 times, and the organic layer was dried over sodium sulfate anhydrate. The solvent was distilled away, to thereby give the title compound (207 mg).

$^1$H-NMR(CDCl$_3$)δ: 1.23(6H, s), 2.71-2.73(2H, m), 4.09-4.11(2H, m), 8.61(1H, s).
MS(ESI)m/z: 168(M$^+$).

Referential Example 316

6,6-dimethyl-6,7-dihydrothiazolo[4,5-c]pyridine-5(4H)-carboxylic acid tert-butyl ester

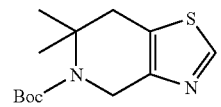

The compound obtained in Referential Example 315 (207 mg) was dissolved in methylene chloride (5 mL), and to the solution were added di-tert-butyl dicarbonate (404 mg) and 4-(N,N-dimethylamino)pyridine (151 mg), followed by stirring at room temperature for 2 hours. After additional di-tert-butyl dicarbonate (404 mg) was added thereto, the thus-obtained mixture was stirred at room temperature overnight, and additional di-tert-butyl dicarbonate (1.00 g) was further added thereto, followed by stirring for 1 hour. The resultant mixture was partitioned between methylene chloride and 10% aqueous HCl, and the organic layer was dried over sodium sulfate anhydrate. The solvent was distilled away, and the residue was purified by silica gel column chromatography (hexane:ethyl acetate=4:1), to thereby give the title compound (95.4 mg).

$^1$H-NMR(CDCl$_3$)δ: 1.47(9H, s), 1.52(6H, s), 2.87(2H, s), 4.69(2H, s), 8.62(1H, s).

MS(ESI)m/z: 269(M+H)$^+$.

Referential Example 317

4-chloro-5-(1,3-dioxolan-2-yl)thiazole-2-carboxylic acid lithium salt

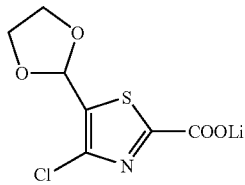

2,4-Dichlorothiazole-5-carbaldehyde ethylene acetal (J. Chem. Soc. Perkin Trans. 1, p. 973 (1992)) (2.26 g) was dissolved in tetrahydrofuran (15 mL), and n-butyllithium (as 1.5N hexane solution, 6.8 mL) was added thereto while being cooled with dry ice-acetone. After the reaction mixture was stirred for 20 minutes, carbon dioxide gas was introduced into the mixture at the same temperature. The reaction mixture was gradually heated to room temperature over 1.5 hours, and the mixture was concentrated under reduced pressure. Hexane was added to the residue, and the resultant powder was collected by filtration. The powder was suspended in ethyl acetate, and the powder was collected by filtration again, to thereby give the title compound (1.65 g).

Referential Example 318

4-chloro-5-(1,3-dioxolan-2-yl)thiazole-2-carboxylic acid ethyl ester

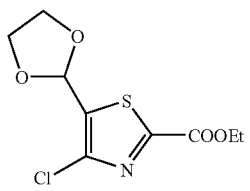

The compound obtained in Referential Example 317 (242 mg) and ethanol (0.2 mL) were dissolved in N,N-dimethylformamide (2 mL), and to the solution were added 1-hydroxybenzotriazole monohydrate (136 mg) and 1-(3-dimethylaminopropyl)-3-ethylcarbodiimide hydrochloride (250 mg), followed by stirring at room temperature overnight. The solvent was concentrated under reduced pressure, and diethyl ether and diluted HCl were added thereto. The organic layer was separated, and was washed with water and saturated aqueous sodium hydrogencarbonate, followed by drying over anhydrous magnesium sulfate. The solvent was distilled away under reduced pressure, to thereby give the title compound (170 mg).

$^1$H-NMR(CDCl$_3$)δ: 1.43(3H, t, J=7.3 Hz), 4.00-4.10(2H, m), 4.10-4.20(2H, m), 4.48(2H, q, J=7.3 Hz), 6.15(1H, s).

MS(ESI)m/z: 264(M+H)$^+$.

Referential Example 319

4-chloro-5-formylthiazole-2-carboxylic acid ethyl ester

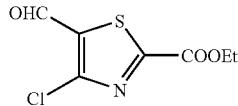

The compound obtained in Referential Example 318 (132 mg) was dissolved in diethyl ether (5 mL), and 20% aqueous HCl (0.3 mL) was added thereto, followed by stirring at room temperature for 7 hours. Saturated aqueous sodium hydrogencarbonate was added to the reaction mixture, and the thus-obtained mixture was extracted with diethyl ether, followed by drying over anhydrous magnesium sulfate. The solvent was distilled away under reduced pressure, to thereby give the title compound (110 mg).

$^1$H-NMR(CDCl$_3$)δ: 1.46(3H, t, J=7.1 Hz), 4.52(2H, q, J=7.1 Hz), 10.12(1H, s).

Referential Example 320

4-azido-5-formylthiazole-2-carboxylic acid ethyl ester

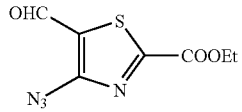

The compound obtained in Referential Example 319 (5.15 g) was dissolved in dimethyl sulfoxide (30 mL), and sodium azide (1.52 g) was added thereto, followed by stirring at room temperature for 2.5 hours. Ice water was added to the reaction mixture, and the thus-obtained mixture was extracted with diethyl ether. The extract was washed with water twice, and was dried over anhydrous magnesium sulfate. The solvent was distilled away under reduced pressure, and the residue was purified by silica gel column chromatography (methylene chloride:methanol=24:1), to thereby give the title compound (1.78 g).

$^1$H-NMR(CDCl$_3$)δ: 1.45(3H, t, J=7.1 Hz), 4.50(2H, q, J=7.1 Hz), 9.95(1H, s).

Referential Example 321

Ethyl 6-methyl-6,7-dihydrothiazolo[4,5-d]pyrimidine-2-carboxylate

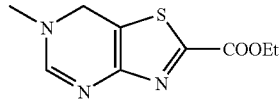

The compound (1.56 g) obtained in Referential Example 320 was dissolved in methylene chloride (20 mL), and acetic acid (2 mL), methylamine (2N tetrahydrofuran solution, 21 mL), and sodium triacetoxyborohydride (2.98 g) were added to the solution, followed by stirring. After 1 hour, sodium triacetoxyborohydride (2.98 g) was additionally added to the mixture, and the stirring was continued for additional 4.5 hours. 0.5N Aqueous sodium hydroxide (100 mL) was added to the reaction mixture to alkalify it. After the reaction mixture was extracted with methylene chloride, the extract was dried over magnesium sulfate anhydrate. The solvent was distilled away under reduced pressure, to thereby give a brown oil (1.43 g). This oil was dissolved in ethanol (50 mL), and 10% palladium on carbon (2.0 g) was added to the solution, followed by hydrogenation at normal temperature and normal pressure. After 2.5 hours, the catalyst was removed by filtration, and the filtrate was concentrated. The residue was dissolved in methylene chloride (30 mL), and trimethyl orthoformate (0.7 mL) and boron trifluoride-diethyl ether complex (0.3 mL) were added to the solution, followed by stirring at room temperature for 15 hours. Saturated aqueous sodium hydrogencarbonate was added to the reaction mixture, and the resultant mixture was extracted with methylene chloride. The extract was dried over sodium sulfate anhydrate. The solvent was distilled away under reduced pressure, and the residue was purified by silica gel column chromatography (methylene chloride:methanol=97:3), to thereby give the title compound (100 mg).

$^1$H-NMR (CDCl$_3$) δ: 1.41(3H,t,J=7.1 Hz), 2.95(3H,s), 4.44(2H,q,J=7.1 Hz), 4.87(2H,s), 7.06(1H,s).

MS(ESI)m/z: 226(M+H)$^+$.

Referential Example 322

Lithium 6-methyl-6,7-dihydrothiazolo[4,5-d]pyrimidine-2-carboxylate

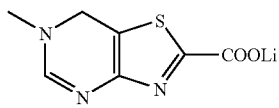

The compound (463 mg) obtained in Referential Example 321 was dissolved in tetrahydrofuran (20 mL), and lithium hydroxide (54.1 mg) and water (4 mL) were added to the solution, followed by stirring at room temperature for 4.5 hours. The solvent was distilled away under reduced pressure, and the residue was dried by means of a vacuum pump, to thereby give the title compound (460 mg).

$^1$H-NMR (DMSO-d$_6$) δ: 2.86(3H,s), 4.71(2H,s), 7.03(1H, s).

Referential Example 323 tert-Butyl (1R,2S,5S)-2-azido-5-{[ethyl(methyl) amino]carbonyl}cyclohexylcarbamate

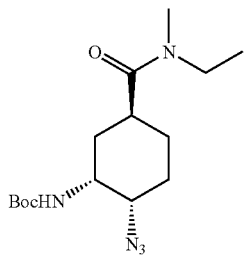

The title compound was obtained by condensing the compound obtained in Referential Example 250 with ethylmethylamine.

$^1$H-NMR (CDCl$_3$) δ: 1.08, 1.18(total 3H, each t,J=7.1 Hz), 1.46(9H,s), 1.52-1.80(4H,m), 2.04-2.08(2H,m), 2.71-2.77 (1H,m), 2.89, 2.98(total 3H, each s), 3.32, 3.39(total 2H, each q,J=7.1 Hz), 3.74-3.76(1H,m), 4.09-4.11(1H,m), 4.60(1H, br.s).

MS(EI)m/z: 326(M+H)$^+$.

Referential Example 324 tert-Butyl (1R,2S,5S)-2-{[(7-chloroisoquinolin-3-yl) carbonyl]amino}-5-{[ethyl(methyl)amino] carbonyl}cyclohexylcarbamate

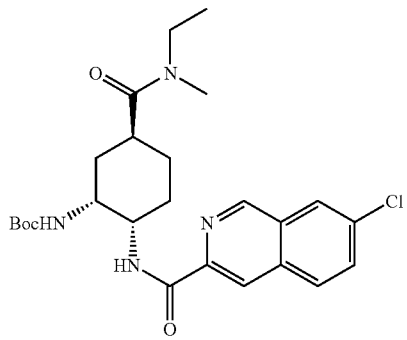

The compound (1.44 g) obtained in Referential Example 323 was dissolved in methanol (20 mL), 10% palladium on carbon (150 mg) was added, and the mixture was stirred under a hydrogen atmosphere. After 24 hours, the catalyst was removed by filtration, and the solvent was then concentrated under reduced pressure, to thereby give a colorless oil. This oil as such was used in the next reaction.

The above-obtained oil was dissolved in methylene chloride (30 mL), and the compound (850 mg) obtained in Referential Example 57, 1-ethyl-3-(3-dimethylaminopropyl)carbodiimide hydrochloride (1.27 g), 1-hydroxybenzotriazole monohydrate (900 mg), and N-methylmorpholine (1.34 g) were added to the solution, followed by stirring at room temperature. After 17 hours had elapsed, methylene chloride and saturated aqueous sodium hydrogencarbonate were added to the reaction mixture for partitioning the mixture, and the resultant organic layer was dried over magnesium sulfate anhydrate. The solvent was distilled away under reduced pressure, and the residue was subjected to silica gel column chromatography (methanol methylene chloride=1:50), to thereby give the title compound (1.61 g).

$^1$H-NMR (CDCl$_3$) δ: 1.10, 1.22(total 3H, each t, J=7.1 Hz), 1.43(9H,s), 1.84-2.17(6H,m), 2.66(1H,br.s), 2.92, 3.03(total 3H, each s), 3.35-3.44(2H,m), 4.20-4.30(2H,m), 5.30(1H, br.s), 7.70(1H,d,J=8.6 Hz), 7.92(1H,d,J=8.6 Hz), 8.00(1H,s), 8.40(1H,br.s), 8.56(1H,s), 9.03(1H,s).

MS(FAB)m/z: 489(M+H)$^+$.

Referential Example 325

N-((1S,2R,4S)-2-Amino-4-[(7-chloroisoquinolin-3-yl)-carbonyl]-4-{[ethyl(methyl)amino] carbonyl}cyclohexyl)-7-chloroisoquinoline-3-carboxamide

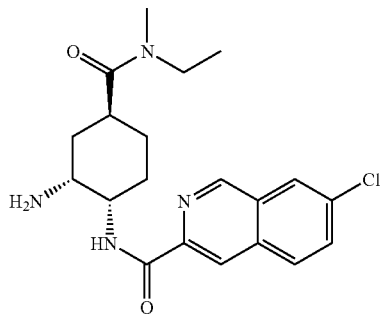

The compound (1.60 g) obtained in Referential Example 324 was dissolved in HCL-ethanol (25 mL), and the solution was stirred at room temperature for 30 minutes. The solvent was distilled away under reduced pressure, and methylene chloride and 1N aqueous sodium hydroxide were added to the residue for partitioning the mixture. The resultant aqueous layer was extracted with methylene chloride, and the organic layers were combined and dried over potassium carbonate. The solvent was distilled away under reduced pressure, hexane was added to the residue, and precipitate was collected by filtration, to thereby give the title compound (1.22 g).

$^1$H-NMR (DMSO-$d_6$) δ: 1.10, 1.23(total 3H, each t,J=7.1 Hz), 1.26(2H,br.s), 1.69-2.11(6H,m), 2.89(1H,br.s), 2.93, 3.05(total 3H, each s), 3.38-3.45(2H,m), 3.52(1H,s), 4.18 (1H,br.s), 7.70(1H,dd,J=8.8, 2.0 Hz), 7.94(1H,d,J=8.8 Hz), 8.02(1H,d,J=2.0 Hz), 8.50(1H,br.s), 8.59(1H,s), 9.11(1H,s).

MS(FAB)m/z: 389(M+H)$^+$.

Referential Example 326

Ethyl (1R*,3S*,4S*)-3-[(tert-butoxycarbonyl) amino]-4-{[tert-butyl(diphenyl)silyl] oxy}cyclohexanecarboxylate

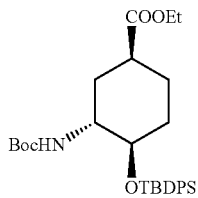

The compound (28.0 g) obtained in Referential Example 88 was dissolved in N,N-dimethylformamide (500 mL), and tert-butyldiphenylsilyl chloride (63.5 mL) and imidazole (19.9 g) were added. After the mixture was stirred at room temperature for 10 hours, ethyl acetate and water were added to the reaction mixture for partitioning the mixture. The resultant aqueous layer was extracted with ethyl acetate, and the organic layers were combined, washed twice with water and dried over sodium sulfate anhydrate. After the solvent was distilled away under reduced pressure, the residue was purified by silica gel column chromatography (methylene chloride:methanol=1:0→47:3), to thereby give the title compound (52.5 g) containing 0.4 molecules of N,N-dimethylformamide.

$^1$H-NMR (CDCl$_3$) δ: 1.07(9H,s), 1.27(3H,t,J=7.1 Hz), 1.38(9H,s), 1.43-1.59(3H,m), 1.63-1.67(1H,m), 1.92-1.98 (1H,m), 2.25-2.32(1H,m), 2.37-2.42(1H,m), 3.66(1H,br.s), 3.80(1H,br.s), 4.16(2H,q,J=7.1 Hz), 4.32(1H,d,J=8.1 Hz), 7.34-7.46(6H,m), 7.65-7.73(4H,m).

Referential Example 327 tert-Butyl (1R*,2R*,5S*)-2-{[tert-butyl(diphenyl) silyl]oxy}-5-(hydroxymethyl)cyclohexanecarbmate

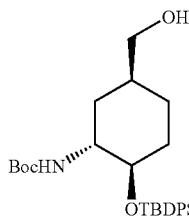

Lithium aluminum hydride (7.11 g) was suspended in absolute diethyl ether (100 mL) at 0° C. while purging with argon, and a diethyl ether solution (500 mL) of the compound (52.5 g) obtained in Referential Example 326 was added dropwise over 30 minutes. After stirring at 0° C. for 30 minutes, methanol (100 mL) was added dropwise to the reaction mixture. The resultant slurry was removed by filtration through Celite, and the filtrate was concentrated. The residue was purified by silica gel column chromatography (hexane: ethyl acetate=3:1), to thereby give the title compound (29.6 g).

$^1$H-NMR (CDCl$_3$) δ: 1.07(9H,s), 1.32-1.74(16H,m), 1.87 (1H,t,J=10.4 Hz), 3.35-3.55(2H,m), 3.71(1H,br.s), 3.79(1H, br.s), 4.36(1H,br.s), 7.34-7.44(6H,m), 7.65-7.72(4H,m).

Referential Example 328

((1R*,3S*,4S*)-3-[(tert-Butoxycarbonyl)amino]-4-{ [tert-butyl(diphenyl)silyl]oxy}cyclohexyl)methyl methane-sulfonate

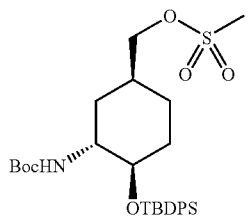

The compound (29.5 g) obtained in Referential Example 327 was dissolved in methylene chloride (200 mL) and pyridine (20 mL). To the solution, methanesulfonyl chloride (9.5 mL) was added, and the mixture was stirred at room temperature for 6 hours. The solvent was distilled away under reduced pressure, and ethyl acetate and water were added to the residue for partitioning the mixture. The resultant aqueous layer was extracted with ethyl acetate, and the organic layers were combined, washed twice with water and then dried over sodium sulfate anhydrate. The solvent was distilled away under reduced pressure, and the residue was purified by silica gel column chromatography (hexane:ethyl acetate 2:1), to thereby give the title compound (29.8 g).

$^1$H-NMR (CDCl$_3$) δ: 1.08(9H,s), 1.38(9H,s), 1.43-1.61 (5H,m), 1.86-1.89(2H,m), 3.02(3H,s), 3.77(1H,br.s), 3.81(1H,br.s), 4.10(2H,d,J=5.4 Hz), 4.32(1H,br.s), 7.35-7.45 (6H,m), 7.64-7.68(4H,m).

MS(ESI)m/z: 562(M+H)$^+$.

Referential Example 329 tert-Butyl (1R*,2R*,5S*)-2-{[tert-butyl(diphenyl) silyl]oxy}-5-(cyanomethyl)cyclohexanecarbamate

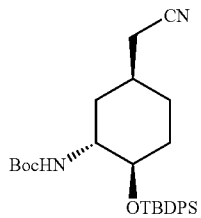

The compound (29.8 g) obtained in Referential Example 328 was dissolved in N,N-dimethylformamide (400 mL), and sodium cyanide (3.64 g) was added to the solution, followed by stirring at 80° C. for 11 hours. Ethyl acetate and saturated aqueous sodium hydrogencarbonate were added to the reaction mixture for partitioning the mixture. The resultant aqueous layer was extracted twice with ethyl acetate, and the organic layers were combined, washed with saturated aqueous sodium hydrogencarbonate and saturated brine and then dried over sodium sulfate anhydrate. The solvent was distilled away under reduced pressure, and the residue was purified by silica gel column chromatography (hexane:ethyl acetate=5:1), to thereby give the title compound (20.6 g).

¹H-NMR (CDCl₃) δ: 1.08(9H,s), 1.38(9H,s), 1.43-1.68 (5H,m), 1.79-1.85(1H,m), 1.88-1.95(1H,m), 2.32(2H,d, J=7.1 Hz), 3.77(1H,br.s), 3.82(1H,br.s), 4.32(1H,br.d,J=6.8 Hz), 7.35-7.45(6H,m), 7.65-7.71(4H,m).

Referential Example 330 tert-Butyl (1R*,2R*,5S*)-2-{[tert-butyl(diphenyl)silyl]oxy}-5-(2-oxoethyl)cyclohexanecarbamate

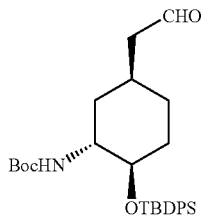

The compound (2.00 g) obtained in Referential Example 329 was dissolved in absolute methylene chloride (20 mL), and the system was purged with argon and then cooled to −78° C. To the solution, was added dropwise diisobutylaluminum hydride (0.95 M hexane solution, 8.55 mL). The temperature of the mixture was then allowed to elevate to room temperature, and the mixture was stirred for 3 hours. The reaction mixture was cooled to 0° C., and methanol (10 mL) was added dropwise. The resultant slurry was removed by filtration through Celite, and the filtrate was removed under reduced pressure. The residue was purified by silica gel column chromatography (methylene chloride:methanol=1:0→49:1), to thereby give the title compound (1.45 g).

¹H-NMR (CDCl₃) δ: 1.07(9H,s), 1.38(9H,s), 1.43-1.54 (5H,m), 1.82-1.88(1H,m), 2.06(1H,br.s), 2.42-2.43(2H,m), 3.72(1H,br.s), 3.77(1H,br.s), 4.38(1H,br.s), 7.34-7.44(6H,m), 7.65-7.68(4H,m), 9.77(1H,t,J=1.7 Hz).

MS(FAB)m/z: 496(M+H)⁺.

Referential Example 331

2-((1R*,3S*,4S*)-3-[(tert-Butoxycarbonyl)amino]-4-{[tert-butyl(diphenyl)silyl]oxy]cyclohexyl)acetic acid

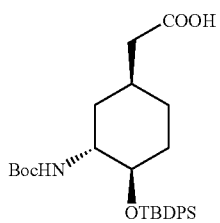

The compound (8.40 g) obtained in Referential Example 330 was dissolved in a solvent mixture of water (33 mL) and tert-butanol (120 mL). To the solution, 2-methyl-2-butene (8.08 mL), sodium dihydrogenphosphate dihydrate (2.64 g), and sodium chlorite (3.45 g) were added, and the mixture was stirred at room temperature for 1.5 hours. Methylene chloride and water were added to the reaction mixture for dilution. The resultant aqueous layer was adjusted to pH of about 4 with 1N hydrochloric acid. The mixture was partitioned, and the resultant aqueous layer was extracted twice with methylene chloride. The organic layers were combined and dried over magnesium sulfate anhydrate, and the solvent was distilled away under reduced pressure. The residue was purified by silica gel column chromatography (hexane:ethyl acetate=2:1→1:1), to thereby give the title compound (7.62 g).

¹H-NMR (CDCl₃) δ: 1.07(9H,s), 1.22-1.63(15H,m), 1.82 (1H,br.s), 2.17(1H,br.s), 2.27-2.33(1H,m), 3.69(1H,br.s), 3.84(1H,br.s), 7.00(1H,br.s), 7.33-7.42(6H,m), 7.63-7.65 (4H,m).

MS(ESI)m/z: 512(M+H)⁺.

Referential Example 332 tert-Butyl (1R*,2R*,5S*)-2-{[tert-butyl(diphenyl)silyl]oxy}-5-[2-(dimethylamino)-2-oxoethyl]cyclohexanecarbamate

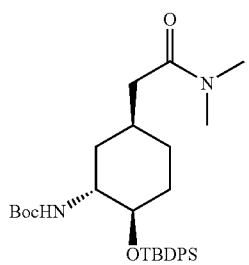

The compound (7.62 g) obtained in Referential Example 331 was dissolved in N,N-dimethylformamide (150 mL). To the solution, dimethylamine hydrochloride (6.07 g), 1-(3-dimethylaminopropyl)-3-ethylcarbodiimide hydrochloride (8.56 g), 1-hydroxybenzotriazole monohydrate (1.01 g), and triethylamine (10.3 mL) were added, and the mixture was stirred at room temperature for 4 days. The solvent was distilled away under reduced pressure, and methylene chloride and saturated aqueous sodium hydrogencarbonate were added to the residue for partitioning the mixture. The resultant aqueous layer was extracted with methylene chloride, and the organic layers were combined and dried over sodium sulfate anhydrate. The solvent was distilled away under reduced pressure, and the residue was purified by silica gel column chromatography (hexane:ethyl acetate=1:1). The solvent was distilled away, hexane was added to the residue, and formed white precipitate was collected by filtration, to thereby give the title compound (6.42 g).

¹H-NMR (CDCl₃) δ: 1.08(9H,s), 1.38(9H,br.s), 1.43-1.55 (5H,m), 1.79-1.86(1H,m), 2.03(1H,br.s), 2.21-2.32(2H,s), 2.94(3H,s), 3.03(3H,s), 3.74(1H,br.s), 3.80(1H,br.s), 4.49(1H,br.s), 7.33-7.44(6H,m), 7.64-7.69(4H,m).

MS(ESI)m/z: 539(M+H)⁺.

Referential Example 333 tert-Butyl (1R*,2R*,5S*)-5-[2-(dimethylamino)-2-oxoethyl]-2-hydroxycyclohexanecarbamate

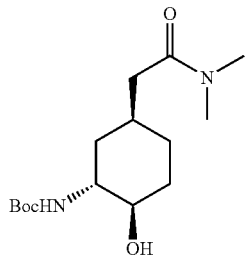

The compound (6.36 g) obtained in Referential Example 332 was dissolved in tetrahydrofuran (50 mL), and tetrabutylammonium fluoride (1N tetrahydrofuran solution, 17.85 mL) was added to the solution, followed by stirring at room temperature for 13 hours. The solvent was distilled away under reduced pressure, and the residue was purified by flash silica gel column chromatography (methylene chloride methanol=24:1), to thereby give the title compound (3.49 g).

$^1$H-NMR (CDCl$_3$) δ: 1.44(9H,s), 1.46-1.60(4H,m), 1.79-1.84(2H,m), 2.28-2.35(3H,s), 2.82(1H,br.s), 2.95(3H,s), 3.01(3H,s), 3.56(2H,br.s), 4.67(1H,br.s).

MS(ESI)m/z: 301(M+H)$^+$.

Referential Example 334

(1R*,2R*,4S*)-2-[(tert-Butoxycarbonyl)amino]-4-[2-(dimethylamino)-2-oxoethyl]cyclohexyl methanesulfonate

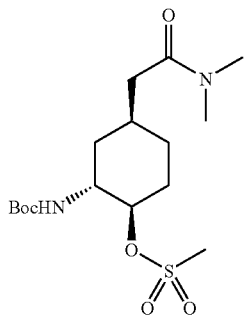

The compound (8.05 mg) obtained in Referential Example 333 was dissolved in methylene chloride (50 mL), and the solution was cooled to −78° C. under an argon atmosphere to add dropwise methanesulfonyl chloride (2.70 mL). After the temperature of the mixture was allowed to elevate to 0° C., the mixture was stirred for 30 minutes and then stirred for 2 hours at room temperature. Water was added to the reaction mixture for partitioning the mixture, and the resultant aqueous layer was extracted with methylene chloride. The organic layers were combined, washed with water and dried over sodium sulfate anhydrate. The solvent was distilled away under reduced pressure, and the residue was purified by flash silica gel column chromatography (hexane:ethyl acetate=1:1-+0:1), to thereby give the title compound (3.63 g).

$^1$H-NMR (CDCl$_3$) δ: 1.43(9H,s), 1.59-1.74(4H,m), 1.85-2.30(5H,m), 2.95(3H,s), 3.00(3H,s), 3.10(3H,s), 3.79-3.83(1H,m), 4.72(1H,br.s), 4.91(1H,br.s).

MS(ESI)m/z: 379(M+H)$^+$.

Referential Example 335 tert-Butyl (1R*,2S*,5S*)-2-azido-5-[2-(dimethylamino)-2-oxoethyl]cyclohexanecarbamate

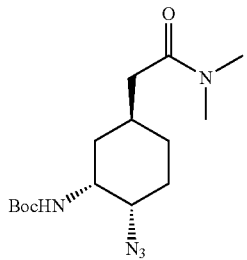

The compound (3.62 g) obtained in Referential Example 334 was dissolved in N,N-dimethylformamide (20 mL), and sodium azide (3.11 g) was added to the solution, followed by stirring at 75° C. for 17 hours. The reaction mixture was poured into a solvent mixture of water and ethyl acetate for partitioning the mixture. The resultant aqueous layer was extracted twice with ethyl acetate, and the organic layers were combined, washed with water, saturated aqueous sodium hydrogencarbonate and saturated brine and dried over sodium sulfate anhydrate. The solvent was distilled away under reduced pressure, and the residue was purified by flash silica gel column chromatography (ethyl acetate), to thereby give the title compound (1.30 g).

$^1$H-NMR (CDCl$_3$) δ: 1.14-1.21(1H,m), 1.33-1.40(1H,m), 1.45(9H,s), 1.61-1.71(1H,m), 1.78-1.91(3H,m), 2.22-2.27(3H,m), 2.94(3H,s), 3.00(3H,s), 3.60-3.62(1H,m), 3.97(1H,br.s), 4.76(1H,br.s).

MS(ESI)m/z: 326(M+H)$^+$.

Referential Example 336

N-{(1R*,2S*,4R*)-2-Amino-4-[2-(dimethylamino)-2-oxoethyl]cyclohexyl}-5-chloroindole-2-carboxamide hydrochloride

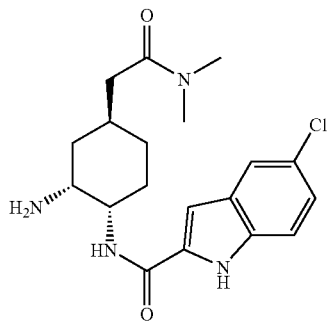

In a manner similar to that employed in Referential Example 324, the compound obtained in Referential Example 335 was catalytically reduced, and the product was condensed with 5-chloroindole-2-carboxylic acid, followed by treatment in a manner similar to that employed in Referential Example 69, to thereby give the title compound.

$^1$H-NMR (DMSO-d$_6$) δ: 1.16-1.19(1H,m), 1.51-1.56(1H,m), 1.70-1.73(1H,m), 1.81-1.91(2H,m), 1.99-2.03(1H,m), 2.19-2.30(3H,m), 2.83(3H,s), 2.99(3H,s), 3.63(1H,br.s), 4.08(1H,br.s), 7.19(1H,dd,J=8.7, 1.7 Hz), 7.35(1H,s), 7.44(1H,d,J=8.7 Hz), 7.69(1H,d,J=1.7 Hz), 8.22(3H,br.s), 8.62(1H,d,J=7.1 Hz), 11.91(1H,s).

MS(ESI)m/z: 377(M+H)$^+$.

Referential Example 337 tert-Butyl (1R,2S,5S)-2-{[(5-chloroindol-2-yl)carbonyl]amino}-5-(hydroxymethyl)cyclohexanecarbamate

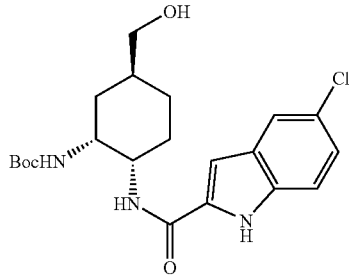

In a manner similar to that employed in step 2) of Referential Example 129, the title compound was obtained from the compound obtained in Referential Example 97.

Referential Example 338

((1S,3R,4S)-3-[(tert-butoxycarbonyl)amino]-4-{[(5-chloroindol-2-yl)carbonyl]amino}cyclohexyl)methyl methanesulfonate

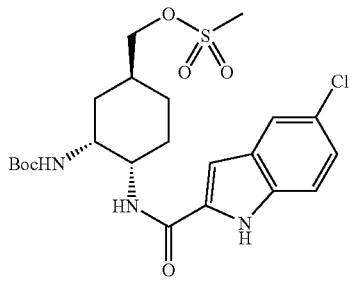

The compound (500 mg) obtained in Referential Example 337 and triethylamine (329 mL) were suspended in tetrahydrofuran (8 mL)-methylene chloride (8 mL), and the suspension was cooled to −78° C. After methanesulfonyl chloride (138 mL) was added dropwise to the suspension, the temperature of the suspension was gradually elevated to −5° C., and the suspension was stirred for 15 hours at the same temperature. After the reaction mixture was concentrated, water was added to the residue, and the mixture was extracted 3 times with methylene chloride. The resultant organic layers were washed with saturated brine and dried over sodium sulfate anhydrate, and the solvent was then distilled away under reduced pressure, to thereby give the title compound (654 mg).

$^1$H-NMR (CDCl$_3$) δ: 1.57(9H,s), 1.84-2.01(4H,m), 2.28-2.31(1H,m), 3.04(3H,s), 3.68(1H,s), 3.74-3.75(1H, m), 3.91-3.93(1H,m), 4.02-4.12(2H,m), 4.18-4.20(1H,m), 4.85(1H,br.s), 6.81(1H,s), 7.21(1H,dd,J=2.0, 8.8 Hz), 7.34 (1H,d,J=8.8 Hz), 7.60(1H,s), 8.02(1H,br.s), 9.27(1H,br.s).

MS(ESI)m/z: 500(M+H)$^+$.

Referential Example 339 tert-Butyl (1R,2S,5S)-2-{[(5-chloroindol-2-yl)carbonyl]amino}-5-[(methylsulfanyl)methyl]cyclohexanecarbamate

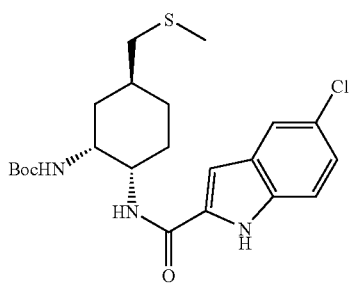

The compound (654 mg) obtained in Referential Example 338 was dissolved in N,N-dimethylformamide (8 mL), and 15% aqueous sodium thiomethoxide (1.8 mL) was added to the solution, followed by stirring at room temperature for 4 hours. The reaction mixture was poured into water and extracted 3 times with ethyl acetate. The resultant organic layers were washed with saturated brine, dried over sodium sulfate anhydrate and then concentrated. The residue was purified by silica gel column chromatography (methylene chloride:methanol=24:1), to thereby give the title compound (492 mg).

$^1$H-NMR (CDCl$_3$) δ: 1.52(9H,s), 1.87-3.04(13H,m), 3.91-3.94(1H,m), 4.12-4.15(1H,m), 4.95(1H,br.s), 6.81(1H,s), 7.19(1H,dd,J=8.8, 1.2 Hz), 7.35(1H,d,J=8.8 Hz), 7.57(1H,s), 9.82(1H,br.s).

MS(ESI)m/z: 452(M+H)$^+$.

Referential Example 340 tert-Butyl (1R,2S,5S)-2-{[(5-chloroindol-2-yl)carbonyl]amino}-5-[(methylsulfonyl)methyl]cyclohexanecarbamate

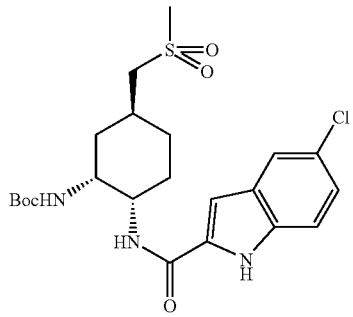

The compound (300 mg) obtained in Referential Example 339 was dissolved in methylene chloride (10 mL), and m-chloroperbenzoic acid (70%, 400 mg) was added to the solution under stirring at 0° C. After the mixture was stirred for 1 hour, the reaction mixture was poured into water and extracted 3 times with methylene chloride. The resultant organic layers were washed with saturated brine, dried over sodium sulfate anhydrate and then concentrated under reduced pressure. The residue was purified by silica gel column chromatography (methylene chloride:methanol=24:1), and then subjected to partition between saturated aqueous sodium hydrogencarbonate and ethyl acetate, and the resultant organic layer was concentrated, to thereby give the title compound (254 mg).

$^1$H-NMR (CDCl$_3$) δ: 1.44-2.19(13H,m), 2.22-2.30(2H,m), 2.89-3.25(7H,m), 3.93-4.15(2H,m), 4.98(1H,br.s), 6.82(1H, s), 7.21(1H,dd,J=8.8, 2.0 Hz), 7.34(1H,d,J=8.8 Hz), 7.60(1H, br.s), 9.54(1H,br.s).

Referential Example 341

(5-Chlorothien-3-yl)methanol

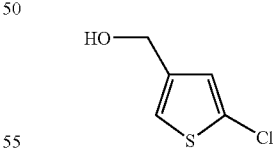

5-Chlorothiophene-3-carboxylic acid (Monatsh. Chem., Vol. 120, p. 53, 1989) (6.93 g) was dissolved in tetrahydrofuran (750 mL), and triethylamine (27.3 mL) and ethyl chloroformate (18.7 mL) were added to the solution, followed by stirring at room temperature for 2.5 hours. An aqueous solution (41 mL) of sodium borohydride (19.3 g) was added dropwise over 10 minutes, and the mixture was stirred at room temperature for 18.5 hours. After acetic acid was added to the reaction mixture to acidify it, the solvent was distilled away under reduced pressure. Water and methylene chloride were added to the residue for partitioning the mixture. The resultant organic layer was washed with water and saturated aqueous sodium hydrogencarbonate. The organic layer was dried over magnesium sulfate anhydrate, the solvent was distilled away under reduced pressure. The residue was purified by flash silica gel column chromatography (ethyl acetate: hexane=1:4), to thereby give the title compound (5.17 g).

$^1$H-NMR (CDCl$_3$) δ: 1.63(1H,t,J=5.8 Hz), 4.59(2H,d, J=5.3 Hz), 6.91(1H,d,J=1.7 Hz), 6.98-6.99(1H,m).

Referential Example 342

5-Chlorothiophene-3-carbaldehyde

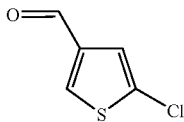

The compound (5.17 g) obtained in Referential Example 341 was dissolved in methylene chloride (400 mL), and manganese dioxide (51.3 g) was added to the solution, followed by stirring at room temperature for 15 hours. After the reaction mixture was filtered, the solvent was distilled away under reduced pressure, to thereby give the title compound (2.84 g).

$^1$H-NMR (CDCl$_3$) δ: 7.35(1H,d,J=1.7 Hz), 7.88(1H,d, J=1.7 Hz), 9.75(1H,s).

Referential Example 343

Ethyl 2-azido-3-(5-chlorothien-3-yl)acrylate

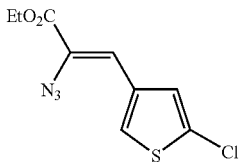

After ethanol (15 mL) was added to a 20% ethanol solution (10.7 mL) of sodium ethoxide, and the mixture was cooled to 0° C., a mixture of the compound (1.01 g) obtained in Referential Example 342 and ethyl azidoacetate (3.55 g) was added dropwise over 30 minutes, and the resultant mixture was stirred at 0° C. for 3 hours. A cooled aqueous ammonium chloride was added to the reaction mixture, and the resultant mixture was extracted 3 times with diethyl ether. The organic layers were combined, and the solvent was distilled away under reduced pressure. The residue was purified by flash silica gel column chromatography (ethyl acetate hexane=1: 49), to thereby give the title compound (1.04 g).

$^1$H-NMR (CDCl$_3$) δ: 1.38(3H,t,J=7.1 Hz), 4.34(2H,q, J=7.1 Hz), 6.75(1H,s), 7.39(1H,d,J=1.7 Hz), 7.54(1H,d,J=1.7 Hz).

Referential Example 344

Ethyl 2-chloro-6H-thieno[2,3-b]pyrrole-5-carboxylate

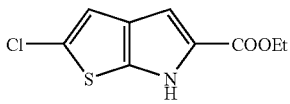

The compound (0.97 g) obtained in Referential Example 343 was dissolved in xylene (20 mL), and the solution was heated under reflux for 30 minutes. After allowing the reaction mixture to cool, the solvent was distilled away under reduced pressure. Hexane was added to the residue, solids formed were collected by filtration, to thereby give the title compound (0.608 g).

$^1$H-NMR (CDCl$_3$) δ: 1.38(3H,t,J=7.0 Hz), 4.35(2H,q, J=7.0 Hz), 6.90(1H,s), 7.00(1H,d,J=1.9 Hz), 9.32(1H,br).

Referential Example 345

2-Chloro-6H-thieno[2,3-b]pyrrole-5-carboxylic acid

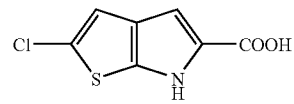

In a manner similar to that employed in Referential Example 274, the title compound was obtained from the compound obtained in Referential Example 344.

$^1$H-NMR (CD$_3$OD) δ: 3.35(1H,s), 6.94(1H,s), 6.96(1H,s). MS(ESI)m/z: 200(M−H)−.

Referential Example 346

1-Chloro-4-(2,2-dibromovinyl)benzene

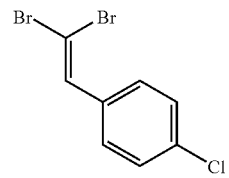

4-Chlorobenzaldehyde (2.81 g) was dissolved in methylene chloride (300 mL), and carbon tetrabromide (13.3 g) and triphenylphosphine (21.0 g) were added to the solution, followed by stirring at room temperature for 90 minutes. After insoluble matter precipitated was removed by filtration, the filtrate was concentrated under reduced pressure. The residue was purified by silica gel column chromatography (hexane: ethyl acetate=20:1), to thereby give the title compound (5.54 g).

$^1$H-NMR (CDCl$_3$) δ: 7.33(2H,d,J=8.5 Hz), 7.43(1H,s), 7.47(2H,d,J=8.5 Hz).

MS(EI)m/z: 296(M$^+$).

Referential Example 347

3-(4-Chlorophenyl)-2-propiolic acid

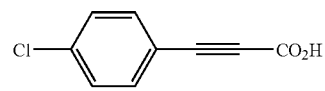

The compound (1.0 g) obtained in Referential Example 346 was dissolved in tetrahydrofuran (30 mL), and n-butyllithium (1.59 N hexane solution, 4.46 mL) was added dropwise at −78° C. under an argon atmosphere. The temperature of the reaction mixture was allowed to elevate to room temperature and stirred for 1 hour. The reaction mixture was cooled again to −78° C., stirred for 2 minutes under a carbon dioxide atmosphere and then warmed to room temperature. After the reaction mixture was concentrated under reduced pressure, saturated brine and ethyl acetate were added to the residue for partitioning the mixture. The aqueous layer was acidified with 3N Hydrochloric acid and extracted with ethyl acetate. The resultant organic layer was dried over sodium sulfate anhydrate and concentrated under reduced pressure, to thereby give the title compound (453 mg).

$^1$H-NMR (DMSO-$d_6$) δ: 7.55(2H,d,J=8.5 Hz), 7.66(2H,d, J=8.5 Hz), 13.90(1H,br.s).

MS(EI)m/z: 180(M$^+$).

Referential Example 348

Ethyl 6-chloro-4-oxo-1,4-dihydroquinazoline-2-carboxylate

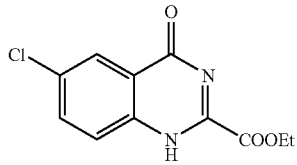

Ethyl chlorooxoacetate (2.0 mL) was added to a solution of 2-amino-5-chlorobenzamide (2.50 g) in pyridine (15 mL), and the mixture was stirred at room temperature for 18 hours. The reaction mixture was concentrated under reduced pressure, and the resultant residue was dissolved in acetic acid (50 mL). Acetic anhydride (5.0 mL) was added to the solution, and the mixture was heated under reflux for 16 hours. The solvent was distilled away under reduced pressure, and ethanol was added to the residue. Crystals precipitated were collected by filtration and washed, to thereby give the title compound (2.71 g).

$^1$H-NMR (DMSO-$d_6$) δ: 1.35(3H,t,J=7.1 Hz), 4.38(2H,q, J=7.1 Hz), 7.85(1H,d,J=8.6 Hz), 7.91(1H,dd,J=8.6, 2.3 Hz), 8.10(1H,d,J=2.3 Hz), 12.85(1H,br.s).

MS(ESI)m/z: 253(M+H)$^+$.

Referential Example 349

6-Chloro-4-oxo-1,4-dihydroquinazoline-2-carboxylic acid

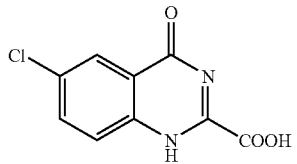

Lithium hydroxide (263 mg) was added to a solution of the compound (1.26 g) obtained in Referential Example 348 in a solvent mixture of water (5 mL) and tetrahydrofuran (15 mL), and the mixture was stirred at room temperature for 18 hours. The reaction mixture was neutralized with 1N hydrochloric acid (11 mL) under ice cooling and stirred for 1 hour. Crystals precipitated were collected by filtration and washed with water, to thereby give the title compound (0.96 g).

$^1$H-NMR (DMSO-$d_6$) δ: 7.50-8.20(3H,m), 12.44(1H,br.s).

MS(ESI)m/z: 265(M+H+CH$_3$CN)$^+$.

Referential Example 350

2-Chloro-N-(4-chlorophenyl)acetamide

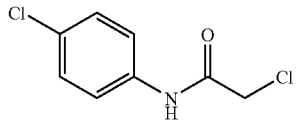

p-Chloroaniline (3.82 g) was dissolved in ethyl acetate (30 mL), and, at room temperature, chloroacetyl chloride (2.39 mL) was added to the solution, followed by stirring for 1 hour. After the reaction mixture was heated and stirred at 60° C. for 3.5 hours, crystals precipitated were collected by filtration, to thereby give the title compound (4.78 g). The filtrate was concentrated to about ¼, and crystals precipitated were collected by filtration, to thereby give the title compound (1.01 g).

$^1$H-NMR (CDCl$_3$) δ: 4.19(2H,s), 7.33(2H,d,J=9.0 Hz), 7.51(2H,d,J=9.0 Hz), 8.22(1H,br.s).

Referential Example 351

Sodium S-[2-(4-chloroanilino)-2-oxoethyl]thiosulfate

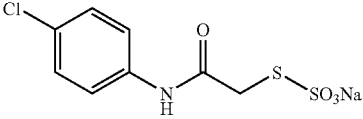

The compound (5.79 g) obtained in Referential Example 350 was dissolved in ethanol (140 mL), and an aqueous solution (140 mL) of sodium thiosulfate pentahydrate (7.04 g) was added to the solution at a time under stirring at 70° C., followed by heating under reflux for 1.5 hours. The reaction mixture was concentrated to about ⅒, and crystals precipitated were collected by filtration, to thereby give the title compound (8.20 g).

$^1$H-NMR (DMSO-$d_6$) δ: 3.73(2H,s), 7.35(2H,d,J=8.8 Hz), 7.57(2H,d,J=8.8 Hz), 10.30(1H,s).

Referential Example 352

2-Chloro-N-(5-chloropyridin-2-yl)acetamide hydrochloride

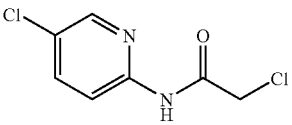

2-Amino-5-chloropyridine (3.85 g) was dissolved in ethyl acetate (60 mL), and, at room temperature, chloroacetyl chloride (2.39 mL) was added to the solution, followed by stirring for 1 hour. After the reaction mixture was heated and stirred at 60° C. for 30 minutes, chloroacetyl chloride (0.5 mL) was additionally added, and the mixture was stirred at 60° C. for additional 1 hour. Powder precipitated was collected by filtration, to thereby give the title compound (6.18 g).

$^1$H-NMR (DMSO-$d_6$) δ: 4.36(2H,s), 7.94(1H,dd,J=8.8, 2.7 Hz), 8.09(1H,d,J=8.8 Hz), 8.40(1H,d,J=2.7 Hz), 11.03 (1H,s).

Referential Example 353

Sodium S-{2-[(5-chloropyridin-2-yl)amino]-2-oxoethyl}thiosulfate

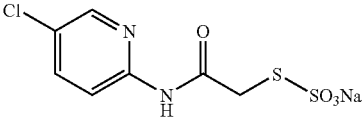

The compound (6.18 g) obtained in Referential Example 352 was dissolved in ethanol (130 mL), and an aqueous solution (130 mL) of sodium thiosulfate pentahydrate (6.35 g) and sodium hydrogencarbonate (2.15 g) dissolved therein was added to the solution at a time at 80° C. under stirring, and the mixture was heated under reflux for 2 hours at an exterior temperature of 110° C. The reaction mixture was concentrated to solids under reduced pressure, and ethanol (500 mL) was added to the residue. The resultant mixture was heated and extracted twice. The extract was concentrated to about ½₀, and diethyl ether was added. Insoluble matter precipitated was collected by filtration, to thereby give the title compound (6.65 g).

$^1$H-NMR (DMSO-$d_6$) δ: 3.77(2H,s), 7.89(1H,dd,J=9.0, 2.7 Hz), 8.09(1H,d,J=9.0 Hz), 8.34(1H,d,J=2.7 Hz), 10.57 (1H,s).

Referential Example 354

N-{(1R,2S,5S)-2-[(2-chloroacetyl)amino]-5-[(dimethylamino)carbonyl]cyclohexyl}-5-methyl-4,5,6,7-tetrahydrothiazolo[5,4-c]pyridin-2-carboxamide hydrochloride

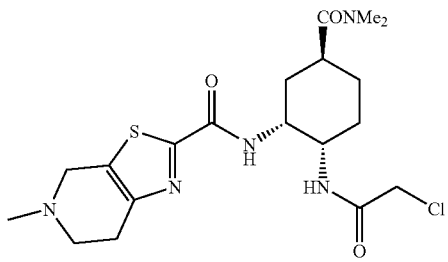

The compound (100 mg) obtained in Referential Example 253 was disslved in ethyl acetate (10 mL), and chloroacetyl chloride (21.6 μl) was added to heat and stir the mixture at 60° C. for 30 minutes. After allowing the reaction mixture to cool, insoluble matter was collected by filtration and dissolved in methylene chloride-methanol, and the solvent was distilled away under reduced pressure, to thereby give the title compound (112 mg) as a non-purified form.

$^1$H-NMR (DMSO-$d_6$) δ: 1.35-1.50(1H,m), 1.55-2.00(5H, m), 2.78(3H,s), 2.98(3H,s), 3.00-3.25(5H,m), 3.17(3H,s), 3.80-3.90(1H, m), 3.96(1H,d,J=12.9 Hz), 4.00-4.15(1H,m), 4.02(1H,d,J=12.9 Hz), 4.45-4.70(2H,m), 7.85-8.00(1H,br), 8.12(1H,d,J=7.3 Hz), 8.35(1H,d,J=8.3 Hz).

MS(ESI)m/z: 442(M+H)$^+$.

Referential Example 355

Sodium S-{2-[((1S,2R,4S)-4-[(dimethylamino)carbonyl]-2-{[(5-methyl-4,5,6,7-tetrathiazolo[5,4-c]pyridine-2-yl)carbonyl]amino}cyclohexyl)amino]-2-oxoethyl}thiosulfate

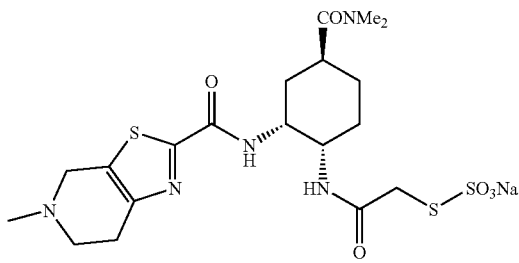

The compound (106 mg) obtained in Referential Example 354 was dissolved in ethanol (1.5 mL), and an aqueous solution (1.5 mL) of sodium thiosulfate pentahydrate (55 mg) and sodium hydrogencarbonate (18.6 mg) dissolved therein was added to the solution at a time at 90° C. under stirring. The resultant mixture was heated under reflux for 1 hour. The reaction mixture was concentrated to solids under reduced pressure, and ethanol (10 mL) was added to the residue. The resultant mixture was extracted under heating. The extract was concentrated to about ½, and isopropyl ether (10 mL) was added. Insoluble matter precipitated was collected by filtration, to thereby give the title compound (72 mg).

$^1$H-NMR (DMSO-$d_6$) δ: 1.35-1.50(1H,m), 1.55-1.90(5H, m), 2.40(3H,s), 2.78(3H,s), 2.80-3.10(5H,m), 2.96(3H,s), 3.44(1H,d,J=14.2 Hz), 3.50(1H,d,J=14.2 Hz), 3.68(2H,s), 3.75-3.90(1H,m), 4.45-4.50(1H,m), 8.01(1H,d,J=7.4 Hz), 8.15(1H,d,J=8.3 Hz).

Referential Example 356

Methyl 2-[(5-chlorothien-2-yl)amino]-2-oxoacetate

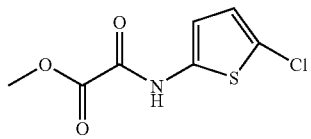

Triethylamine (1.25 mL) and diphenylphosphoryl azide (1.55 mL) were added to a suspension of 5-chlorothiophene-2-carboxylic acid (0.99 g) in toluene (20 mL), and the mixture was stirred at 80° C. for 1 hour. After the reaction mixture was cooled to room temperature, tert-butanol (2 mL) was added, and the mixture was heated under reflux for 19 hours. The reaction mixture was concentrated under reduced pressure, and methylene chloride (200 mL) was added to the resultant residue. The resultant mixture was successively washed with distilled water, 10% aqueous citric acid, distilled water, saturated aqueous sodium hydrogencarbonate and saturated brine and then dried over sodium sulfate anhydrate. The solvent was distilled away under reduced pressure, and the residue was subjected to silica gel column chromatography (hexane:ethyl acetate=4:1), to thereby give tert-butyl 5-chloro-2-thienylcarbamate (1.05 g).

$^1$H-NMR (CDCl$_3$) δ: 1.51(9H,s), 6.21(1H,d,J=3.1 Hz), 6.60(1H,d,J=3.1 Hz), 6.91(1H,br.s).

MS(ESI)m/z: 234(M+H)$^+$. The product (1.87 g) obtained above was added to a 4N HCl-dioxane (40 mL), and the mixture was stirred at room temperature for 4 hours. The solvent was distilled away under reduced pressure, and the residue was suspended in tetrahydrofuran (50 mL). Sodium hydrogencarbonate (2.02 g) and methyl chlorooxoacetate (0.883 mL) were added to the suspension under ice cooling, and the mixture was stirred at room temperature for 18 hours. After the solvent was distilled away under reduced pressure, and water and methylene chloride were added to the residue for partitioning the mixture, the resultant organic layer was washed with saturated brine and dried over sodium sulfate anhydrate and then concentrated under reduced pressure. The residue was purified by silica gel column chromatography (hexane:ethyl acetate=3:1), and the solvent was distilled away, to thereby give the title compound (1.44 g).

$^1$H-NMR (CDCl$_3$) δ: 3.98(3H,s), 6.61(1H,d,J=4.2 Hz), 6.75(1H,d,J=4.2 Hz), 9.42(1H,br.s).

MS(FAB)m/z: 220(M+H)$^+$.

Referential Example 357

Methyl 2-[(5-fluoropyridin-2-yl)amino]-2-oxoacetate

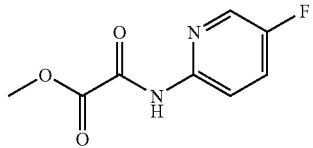

The title compound was obtained from 2-amino-5-fluoropyridine and methyl chlorooxoacetate in a manner similar to the process described in Referential Example 242.

¹H-NMR (CDCl₃) δ: 3.99(3H,s), 7.48-7.53(1H,m), 8.21 (1H,d,J=2.9 Hz), 8.27-8.31(1H,m), 9.41(1H,br.s).
MS(FAB)m/z: 198(M+H)⁺.

Referential Example 358

Methyl 2-(4-chloro-2-(trifluoromethyl)anilino]-2-oxoacetate

The title compound was obtained from 4-chloro-2-trifluoroaniline and methyl chlorooxoacetate in a manner similar to the process described in Referential Example 242.
¹H-NMR (CDCl₃) δ: 4.01(3H,s), 7.58(1H,dd, J=8.8, 2.2 Hz), 7.65(1H,d,J=2.2 Hz), 8.34(1H,d,J=8.8 Hz), 9.30(1H, br.s).
MS(EI)m/z: 281(M+H)⁺.

Referential Example 359

2-[4-Chloro-2-(trifluoromethyl)anilino]-2-oxoacetic acid

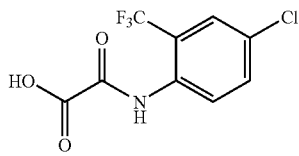

Lithium hydroxide (28 mg) was added to a solution of the compound (297 mg) obtained in Referential Example 358 in a solvent mixture of tetrahydrofuran (7 mL) and water (3 mL), and the mixture was stirred at room temperature for 2 hours. 1N Hydrochloric acid (8 mL) and methylene chloride (20 mL) were added to the reaction mixture for partitioning the mixture. After the resultant organic layer was dried over sodium sulfate anhydrate, the solvent was distilled away under reduced pressure, and the residue was dried, to thereby give the title compound (291 mg).
¹H-NMR (CDCl₃) δ: 7.61(1H,dd,J=8.8, 2.5 Hz), 7.68(1H, d,J=2.5 Hz), 8.26(1H,d,J=8.8 Hz), 9.36(1H,br.s).
MS(ESI, anion)m/z: 267(M−H).

Referential Example 360

5-Chloro-N,N-dimethyl-2-nitrobenzamide

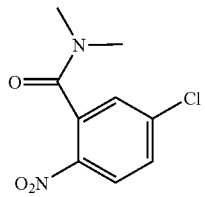

The title compound was obtained by condensing 5-chloro-2-nitrobenzoic acid with dimethylamine in a manner similar to the process described in Referential Example 143.

¹H-NMR (CDCl₃) δ: 2.86(3H,s), 3.16(3H,s), 7.38(1H,d, J=2.2 Hz), 7.51(1H,dd,J=8.8, 2.2 Hz), 8.15(1H,d,J=8.8 Hz).

Referential Example 361

2-Amino-5-chloro-N,N-dimethylbenzamide

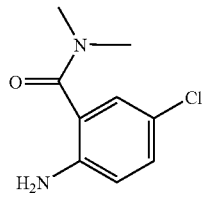

Iron (III) chloride hexahydrate (9.93 g) and zinc powder (8.01 g) were added to absolution of the compound (2.8 g) obtained in Referential Example 360 in a solvent mixture of N,N-dimethylformamide (80 mL) and water (40 mL), and the mixture was heated under reflux for 20 minutes. The reaction mixture was filtered through Celite 545, and ethyl acetate (200 mL) was added to the filtrate for partitioning the mixture. The resultant aqueous layer was washed with ethyl acetate (100 ml×2), and the organic layers were combined, washed with distilled water (100 mL) and dried over sodium sulfate anhydrate. The solvent was distilled away under reduced pressure, and the resultant residue was subjected to silica gel column chromatography (methylene chloride:hexane=1:1→1:0→methanol:methylene chloride=1:100), to thereby give the title compound (2.41 g).
¹H-NMR (CDCl₃) δ: 3.13(6H,s), 4.33(2H,br), 6.65(1H,d, J=8.5 Hz), 7.07(1H,d,J=2.2 Hz), 7.11(1H,dd,J=8.5, 2.2 Hz).
MS(ESI)m/z: 240(M+MeCN)⁺.

Referential Example 362

Methyl 2-{4-chloro-2-[(dimethylamino)carbonyl]anilino}-2-oxoacetate

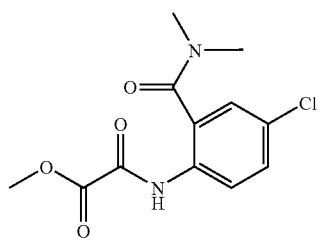

In a manner similar to that employed in Referential Example 242, the title compound was produced from the compound obtained in Referential Example 361 and methyl chlorooxoacetate.
¹H-NMR (CDCl₃) δ: 3.09(6H,br), 3.96(3H,s), 7.30(1H,d, J=2.4 Hz), 7.41(1H,d,J=8.8, 2.4 Hz), 8.34(1H,d,J=8.8 Hz), 10.46(1H,br).
MS(ESI)m/z: 285(M+H)⁺.

Referential Example 363

4-Chloro-2-methoxyaniline

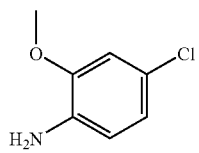

In a manner similar to that employed in Referential Example 361, the title compound was obtained from 5-chloro-2-nitroanisole.

$^1$H-NMR (CDCl$_3$) δ: 3.65-3.95(2H,br), 3.87(3H,s), 6.61 (1H,d,J=8.8 Hz), 6.74-6.78(2H,m).

MS(ESI)m/z: 199(M+MeCN+H)$^+$.

Referential Example 364

Methyl 2-(4-chloro-2-methoxyanilino)-2-oxoacetate

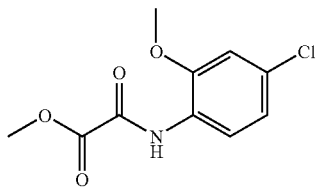

The title compound was obtained from the compound obtained in Referential Example 363 and methyl chlorooxoacetate in a manner similar to the process described in Referential Example 242.

$^1$H-NMR (CDCl$_3$) δ: 3.92(3H,s), 3.97(3H,s), 6.90(1H,d, J=2.2 Hz), 6.98(1H,dd,J=8.8, 2.2 Hz), 8.35(1H,d,J=8.8 Hz), 9.33-9.44(1H,br).

MS(ESI)m/z: 244(M+H)$^+$.

Referential Example 365

Ethyl 2-(4-chloroanilino)-2-(hydroxyimino)-acetate

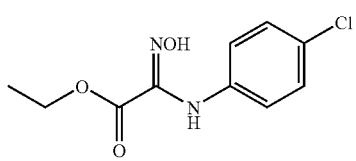

The title compound was obtained from 4-chloroaniline (3.03 g) and ethyl 2-chloro-2-hydroxyiminoacetate in a manner similar to the process described in literature (Gilchrist, T. L.; Peek, M. E.; Rees, C. W.; J. Chem. Soc. Chem. Commun., 1975, 913).

$^1$H-NMR (CDCl$_3$) δ: 1.26(3H,t,J=7.1 Hz), 1.60-1.80(1H, br), 4.28(2H,q,J=7.1 Hz), 6.85(2H,d,J=8.6 Hz), 7.24(2H,d, J=8.6 Hz), 8.15-8.45(1H,br).

MS(ESI)m/z: 243(M+H)$^+$.

Referential Example 366 tert-Butyl (1R,2S,5S)-2-{[2-(4-chloroanilino)-2-(hydroxyimino)acetyl]amino}-5-[(dimethylamino) carbonyl]-cyclohexylcarbamate

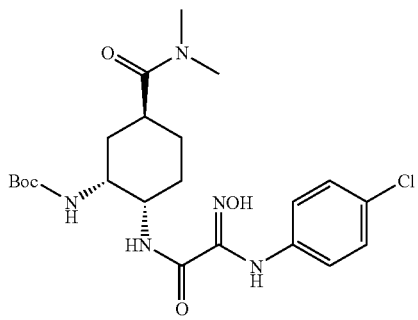

The compound (597 mg) obtained in Referential Example 144 was added to a solution of the compound (350 mg) obtained in Referential Example 365 in ethanol (5.0 mL), and the mixture was stirred at 70° C. for 3 days. After the reaction mixture was concentrated under reduced pressure, the residue was purified by silica gel column chromatography (methylene chloride:methanol=30:1), to thereby give the title compound (180 mg).

$^1$H-NMR (CD$_3$OD) δ: 1.46(9H,s), 1.47-1.84(6H,m), 1.88-1.95(1H,m), 2.90(3H,s), 3.08(3H,s), 3.90-3.97(1H,m), 4.11-4.17(1H,m), 6.84(2H,d,J=8.8 Hz), 7.18(2H,d,J=8.8 Hz).

MS(ESI)m/z: 504(M+Na)$^+$.

Referential Example 367

(3R,4S)-4-{[2-(4-chloroanilino)-2-oxoacetyl] amino}-1-(2-methoxyacetyl)piperidin-3-ylcarbamic acid tert-butyl ester

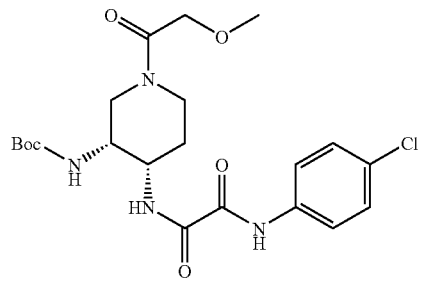

The method described in Referential Example 214 was performed by use of the compound obtained in Referential Example 374 and the compound obtained in Referential Example 220, whereby the title compound was obtained.

$^1$H-NMR(CDCl$_3$)δ: 1.45(9H, s), 1.55-1.75(1H, br), 1.94-2.07(1H, br), 2.70-3.00(1H, m), 3.10-3.37(1H, m), 3.44(3H, s), 3.88-4.22(4H, m), 4.55-4.69(1H, br), 4.80-4.90(0.5H, br), 5.36-5.48(0.5H, br), 7.20-7.30(1H, br), 7.32(2H, d, J=8.8 Hz), 7.62(2H, d, J=8.8 Hz), 8.20-8.40(1H, br), 9.15-9.25(1H, br).

MS(ESI)m/z: 469(M+H)$^+$.

Referential Example 368

(3R,4S)-4-({2-[(5-chloropyridin-2-yl)amino]-2-oxoacetyl}amino)-1-(2-methoxyacetyl)piperidin-3-ylcarbamic acid tert-butyl ester

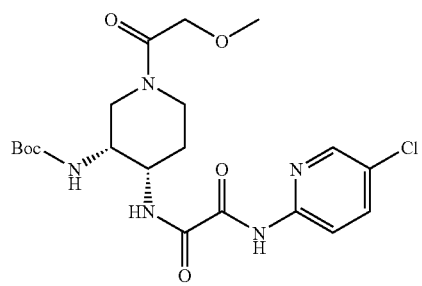

The method described in Referential Example 214 was performed by use of the compound obtained in Referential Example 266 and the compound obtained in Referential Example 220, whereby the title compound was obtained.

$^1$H-NMR(CDCl$_3$)δ: 1.45(9H, s), 1.65-2.30(2H, br), 2.68-3.02(1H, m), 3.10-3.35(1H, m), 3.44(3H, s), 3.80-4.25(4H, m), 4.45-4.70(1H, m), 5.05-5.20(0.5H, m), 5.80-5.93(0.5H, m), 7.30-7.40(1H, br), 7.71(1H, br d, J=8.7 Hz), 7.95-8.05 (0.3H, br), 8.19(1H, br d, J=8.8 Hz), 8.31(1H, br.s), 8.38-8.53 (0.7H, br), 9.74-9.84(1H, br).

MS(ESI)m/z: 470 (M+H)$^+$.

Referential Example 369

(3R,4S)-4-({2-[(5-bromopyridin-2-yl)amino]-2-oxoacetyl}amino)-1-(2-methoxyacetyl)piperidin-3-ylcarbamic acid tert-butyl ester

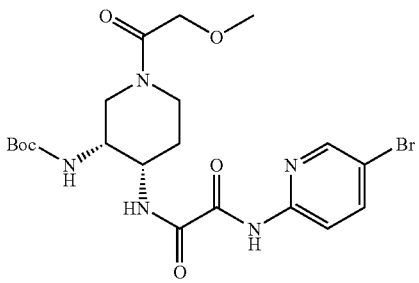

The method described in Referential Example 214 was performed by use of the compound obtained in Referential Example 375 and the compound obtained in Referential Example 220, whereby the title compound was obtained.

$^1$H-NMR(CDCl$_3$)δ: 1.47(9H, s), 1.50-1.75(1H, m), 1.95-2.13(1H, br), 2.70-2.98(1H, m), 3.05-3.36(1H, m), 3.45(3H, s), 3.80-4.24(4H, m), 4.57-4.73(1H, br), 4.85-4.95(0.25H, br), 5.10-5.15(0.25H, br), 5.45-5.58(0.5H, br), 7.30-7.38(1H, m), 7.84(1H, dd, J=8.8, 2.2 Hz), 8.16(1H, d, J=8.8 Hz), 8.30-8.55(1H, br), 8.40(1H, d, J=2.2 Hz), 9.68(1H, br.s).

Referential Example 370

3-(4-chloroanilino)-3-oxopropionic acid ethyl ester

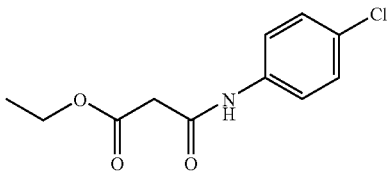

To a solution of 4-chloroaniline (2.0 g) in N,N-dimethylformamide (20 mL) were sequentially added at room temperature potassium ethyl malonate (3.2 g), 1-hydroxybenzotriazole (2.1 g), and 1-(3-dimethylaminopropyl)-3-ethylcarbodiimide hydrochloride (4.5 g), followed by stirring at room temperature for 2 hours. The reaction mixture was diluted with ethyl acetate and washed with saturated aqueous sodium hydrogencarbonate, 10% aqueous citric acid, and saturated brine. The organic layer was dried over sodium sulfate anhydrate, and the solvent was distilled away under reduced pressure, to thereby give the title compound (4.0 g).

$^1$H-NMR(CDCl$_3$)δ: 1.33(3H, t, J=7.3 Hz), 3.47(2H, s), 4.26(2H, q, J=7.3 Hz), 7.29(2H, d, J=8.8 Hz), 7.51(2H, d, J=8.8 Hz), 9.32(1H, br.s).

Referential Example 371

3-(4-chloroanilino)-3-oxopropionic acid

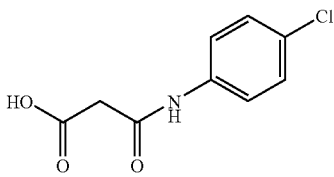

To a solution of the compound (1.0 g) obtained in Referential Example 370 in ethanol (10 mL), 1N aqueous sodium hydroxide (10 mL) was added dropwise at room temperature, followed by stirring for 2 hours. 1N Aqueous hydrochloric acid (10 mL) was added to the reaction mixture, followed by stirring, and the precipitated insoluble material was recovered by filtration, to thereby give the title compound (0.5 g).

$^1$H-NMR(DMSO-d$_6$)δ: 3.34(2H, s), 7.35(2H, d, J=8.8 Hz), 7.59(2H, d, J=8.8 Hz), 10.26(1H, s), 12.66(1H, br.s).

Referential Example 372

3-(3-chloroanilino)-3-oxopropionic acid ethyl ester

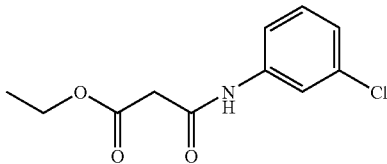

In a manner similar to that described in Referential Example 370, 3-chloroaniline was condensed with potassium ethyl malonate, whereby the title compound was obtained.

$^1$H-NMR(CDCl$_3$)δ: 1.33(3H, t, J=7.3 Hz), 3.47(2H, s), 4.26(2H, q, J=7.3 Hz), 7.09(1H, d, J=8.8 Hz), 7.22-7.26(1H, m), 7.39(1H, d, J=8.8 Hz), 7.69(1H, s), 9.35(1H, br.s).

Referential Example 373

3-(3-chloroanilino)-3-oxopropionic acid

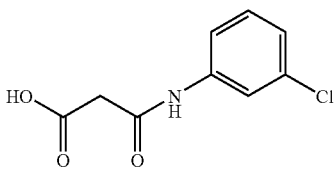

The method described in Referential Example 371 was performed by use of the compound obtained in Referential Example 372, whereby the title compound was obtained.

$^1$H-NMR(DMSO-d$_6$)δ: 3.35(2H, s), 7.11(1H, d, J=8.8 Hz), 7.33(1H, t, J=8.8 Hz), 7.39(1H, d, J=8.8 Hz), 7.78(1H, s), 10.31(1H, s), 12.67(1H, br.s).

Referential Example 374

2-(4-chloroanilino)-2-oxoacetic acid

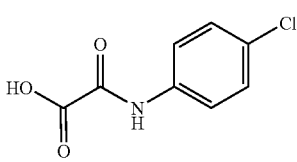

The method described in Referential Example 359 was performed by use of the compound obtained in Referential Example 242, whereby the title compound was obtained.

$^1$H-NMR(DMSO-d$_6$)δ: 7.37(2H, d, J=8.8 Hz), 7.79(2H, d, J=8.8 Hz), 10.66(1H, s).

Referential Example 375

2-[(5-bromopyridin-2-yl)amino]-2-oxoacetic acid

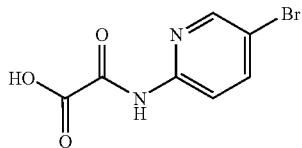

The method described in Referential Example 359 was performed by use of the compound obtained in Referential Example 262, whereby the title compound was obtained.

$^1$H-NMR(DMSO-d$_6$)δ: 7.95-8.00(1H, m), 8.08(1H, dd, J=8.8, 2.0 Hz), 8.50(1H, d, J=2.0 Hz), 10.74(1H, s).

Referential Example 376

4-chloro-3-fluorobenzoic acid

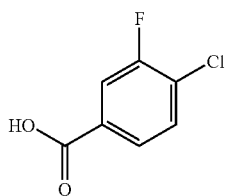

Sodium chlorite (17 g) was added dropwise to a mixture of 4-chloro-3-fluorobenzaldehyde (10 g), amidesulfuric acid (18 g), tert-butyl alcohol (50 mL), and water (50 mL) under ice cooling. The temperature of the mixture was returned gradually to room temperature, and the mixture was stirred for 4 days. The reaction mixture was diluted with ethyl acetate, and the resultant mixture was washed with water, 1N hydrochloric acid, and saturated brine. The organic layer was dried over sodium sulfate anhydrate, and the solvent was distilled away under reduced pressure. The residue was recrystallized from a solvent mixture of diisopropyl ether and hexane, to thereby give the title compound (11.2 g).

$^1$H-NMR(DMSO-d$_6$)δ: 7.72(1H, dt, J=8.3, 1.5 Hz), 7.77 (1H, dt, J=8.3, 1.6 Hz), 7.82(1H, dt, J=9.7, 1.5 Hz), 13.45(1H, s).

Referential Example 377

2-(4-chloro-3-fluoroanilino)-2-oxoacetic acid methyl ester

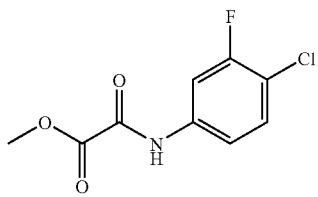

In a manner similar to that described in Referential Example 356, the compound obtained in Referential Example 376 was subjected to Curtius transition reaction. The resultant compound was condensed with methyl chlorooxoacetate, whereby the title compound was obtained.

$^1$H-NMR(CDCl$_3$)δ: 3.99(3H, s), 7.25-7.27(1H, m), 7.39 (1H, t, J=8.5 Hz), 7.72(1H, dd, J=10.4, 2.4 Hz), 8.90(1H, br.s).

Referential Example 378

2-(4-chloro-3-fluoroanilino)-2-oxoacetic acid

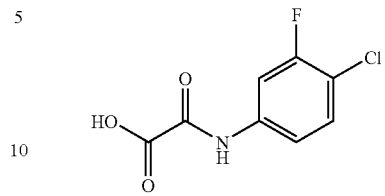

The method described in Referential Example 359 was performed by use of the compound obtained in Referential Example 377, whereby the title compound was obtained.

$^1$H-NMR(DMSO-d$_6$)δ: 7.52(1H, t, J=8.8 Hz), 7.63(1H, dd, J=8.8, 2.2 Hz), 7.88(1H, dd, J=12.0, 2.2 Hz), 10.83(1H, br.s).

Referential Example 379

3-(4-chlorophenyl)-3-oxopropionic acid ethyl ester

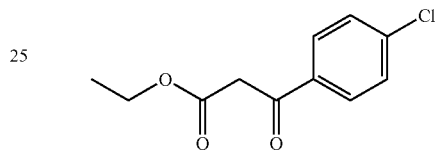

To a suspension of potassium ethyl malonate (8.2 g) in ethyl acetate (100 mL), triethylamine (17 mL) and magnesium chloride (5.5 g) were added under ice cooling. The temperature of the resultant mixture was returned gradually to room temperature, and the mixture was stirred for 18 hours. In addition, a suspension of 4-chlorobenzoic acid (5.0 g), thionyl chloride (12 mL), N,N-dimethylformamide (1 drop), and toluene (100 mL) was heated under reflux for 1 hour, and the reaction mixture was concentrated. The residue was dissolved in ethyl acetate, and the solution was added dropwise to the above mixture under ice cooling. The temperature of the mixture was gradually returned to room temperature, and the mixture was stirred for 18 hours. 10% Aqueous citric acid was added to the reaction mixture, and the mixture was stirred for 30 minutes, and the organic layer was partitioned. The resultant organic layer was washed with saturated brine, followed by drying over sodium sulfate anhydrate. The solvent was distilled away under reduced pressure. The residue was separated and purified by silica gel column chromatography (chloroform), to thereby give the title compound (6.4 g).

$^1$H-NMR(CDCl$_3$)δ: 1.26(3H, t, J=7.3 Hz), 3.96(2H, s), 4.21(2H, q, J=7.3 Hz), 7.46(2H, d, J=8.8 Hz), 7.89(2H, d, J=8.8 Hz).

Referential Example 380

3-(4-chlorophenyl)-3-hydroxypropionic acid ethyl ester

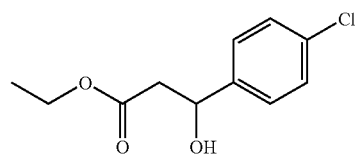

To the compound (1.0 g) obtained in Referential Example 379 dissolved in tetrahydrofuran (10 mL), sodium borohydride (0.2 g) was added dropwise under ice cooling. The temperature of the mixture was gradually returned to room temperature, and the mixture was stirred for 2 hours. 10% Aqueous citric acid was added to the reaction mixture, and the resultant mixture was extracted with ethyl acetate. The organic layer was washed with saturated brine, followed by drying over sodium sulfate anhydrate. The solvent was distilled away under reduced pressure. The residue was separated and purified by silica gel column chromatography (chloroform), to thereby give the title compound (0.56 g).

$^1$H-NMR(CDCl$_3$)δ: 1.27(3H, t, J=7.3 Hz), 2.70(1H, d, J=7.8 Hz), 2.71(1H, d, J=3.4 Hz), 3.37(1H, d, J=3.4 Hz), 4.18(2H, q, J=7.3 Hz), 5.09-5.13(1H, m), 7.30-7.35(5H, m).

Referential Example 381

3-(4-chlorophenyl)-3-hydroxypropionic acid

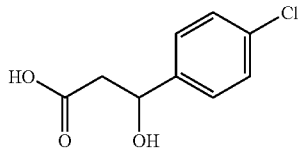

The method described in Referential Example 359 was performed by use of the compound obtained in Referential Example 380, whereby the title compound was obtained.

$^1$H-NMR(DMSO-d$_6$)δ: 3.25-3.32(1H, m), 4.89-4.95(1H, m), 5.45-5.53(1H, m), 7.35-7.36(5H, m), 12.11-12.18(1H, m).

MS(ESI, anion)m/z: 198(M−H)$^-$.

Referential Example 382

(1R,2S,5S)-2-{[3-(4-chlorophenyl)-3-hydroxypropanoyl]amino}-5-[(dimethylamino)carbonyl]cyclohexylcarbamic acid tert-butyl ester

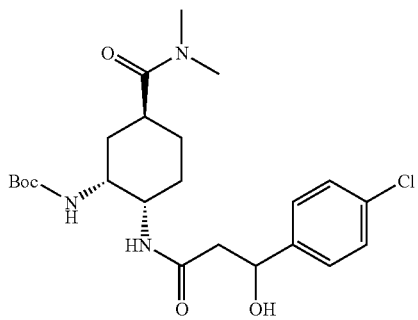

In a manner similar to that described in Referential Example 91, the compound obtained in Referential Example 144 was condensed with the compound obtained in Referential Example 381, whereby the title compound was obtained.

$^1$H-NMR(CDCl$_3$)δ: 1.21-1.44(2H, m), 1.46(9H, s), 1.76-1.92(2H, m), 1.95-2.10(2H, m), 2.40-2.55(2H, m), 2.55-2.68 (1H, m), 2.94(3H, s), 3.05(3H, s), 3.82-3.96(1H, m), 4.02-4.17(1H, m), 4.65-4.80(2H, m), 5.03-5.13(1H, m), 7.28-7.33 (5H, m).

MS(ESI)m/z: 468(M+H)$^+$.

Referential Example 383

(1R,2S,5S)-2-{[3-(4-chlorophenyl)-3-oxopropanoyl]amino}-5-[(dimethylamino)carbonyl]cyclohexylcarbamic acid tert-butyl ester

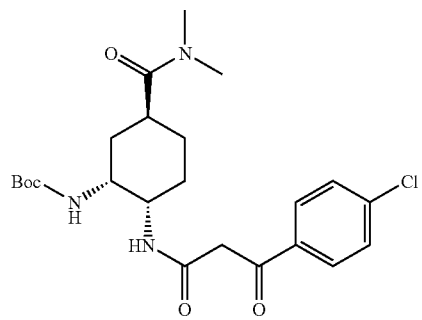

To a solution of the compound (0.5 g) obtained in Referential Example 382 in 1,4-dioxane (20 mL), manganese dioxide (0.47 g) was added at room temperature, followed by stirring for 4 days. The insoluble material was removed through filtration through a celite pad. The resultant filtrate was concentrated under reduced pressure, to thereby give the title compound (0.46 g).

$^1$H-NMR(DMSO-d$_6$)δ: 1.28-1.39(1H, m), 1.40(9H, s), 1.41-1.63(3H, m), 2.25-2.42(2H, m), 2.76(3H, s), 2.90-2.97 (1H, m), 2.98(3H, s), 3.56(2H, s), 3.89-3.97(1H, m), 4.88-4.98(1H, m), 6.65-6.70(1H, m), 7.30-7.35(4H, m), 7.33(1H, dd, J=2.9, 1.7 Hz).

MS(ESI, anion)m/z: 464(M−H)$^-$.

Referential Example 384

(1S,3R,4R)-4-azido-3-[(tert-butoxycarbonyl)amino]cyclohexanecarboxylic acid ethyl ester

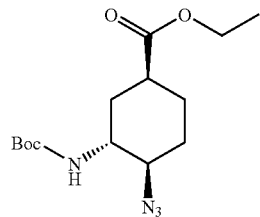

The method described in Referential Example 249 was performed by use of the compound obtained in Referential Example 248, whereby the title compound was obtained.

$[α]_D^{25}$+62° (c=1, chloroform)

$^1$H-NMR(CDCl$_3$)δ: 1.27(3H, t, J=7.1 Hz), 1.46(9H, s), 1.61(1H, s), 1.61-1.71(2H, m), 1.81-1.90(1H, m), 1.97-2.03 (1H, m), 2.22-2.28(1H, m), 2.56-2.60(1H, m), 3.54(1H, br.s), 3.63-3.68(1H, m), 4.16(2H, q, J=7.1 Hz), 4.58(1H, br.s),

Referential Example 385

(1R,2R,5S)-2-azido-5-[(dimethylamino)carbonyl]cyclohexylcarbamic acid tert-butyl ester

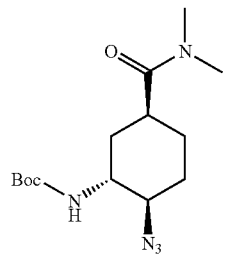

The methods described in Referential Example 250 and Referential Example 251 were performed by use of the compound obtained in Referential Example 384, whereby the title compound was obtained.

$^1$H-NMR(CDCl$_3$)δ: 1.46(9H, s), 1.40-2.20(6H, m), 2.70-2.80(1H, m), 2.93(3H, s), 3.03(3H, s), 3.60-3.78(1H, m), 3.83-3.95(1H, m), 4.65(1H, d, J=7.2 Hz).

Referential Example 386

(1R,2R,5S)-2-({2-[(5-chloropyridin-2-yl)amino]-2-oxoacetyl}amino)-5-[(dimethylamino)carbonyl]cyclohexylcarbamic acid tert-butyl ester

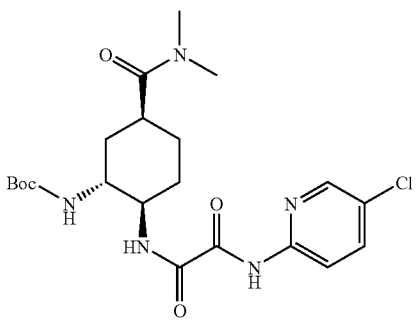

In a manner similar to that described in Referential Example 90, the azido group of the compound obtained in Referential Example 385 was converted to an amino group. In a manner similar to that described in Referential Example 91, the converted compound was condensed with the compound obtained in Referential Example 266, whereby the title compound was obtained.

$^1$H-NMR(CDCl$_3$)δ: 1.13-2.25(16H, m), 2.94(3H, s), 3.03(3H, s), 3.60-3.78(1H, m), 4.13-4.31(1H, m), 4.45-4.65(1H, m), 7.80(1H, dd, J=8.8, 2.4 Hz), 8.03(1H, br.s), 8.21(1H, d, J=8.8 Hz), 8.29(1H, d, J=2.4 Hz), 9.71(1H, s).

MS(ESI)m/z: 468(M+H)$^+$.

Referential Example 387

N-{(1R,2R,5S)-2-azido-5-[(dimethylamino)carbonyl]cyclohexyl}-5-methyl-4,5,6,7-tetrahydrothiazolo[5,4-c]pyridine-2-carboxamide

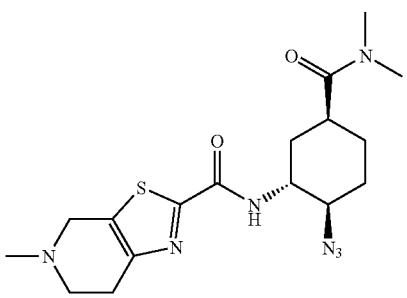

The method described in Referential Example 252 was performed by use of the compound obtained in Referential Example 385 and the compound obtained in Referential Example 10, whereby the title compound was obtained.

$^1$H-NMR(CDCl$_3$)δ: 1.75-2.08(6H, m), 2.20-2.32(1H, m), 2.51(3H, s), 2.75-2.97(4H, m), 2.95(3H, s), 3.04(3H, s), 3.65-3.80(3H, m), 4.27-4.39(1H, m), 7.17-7.28(1H, m).

MS(ESI)m/z: 392(M+H)$^+$.

Referential Example 388

4-[(2-methoxy-2-oxoacetyl)amino]piperidine-1-carboxylic acid tert-butyl ester

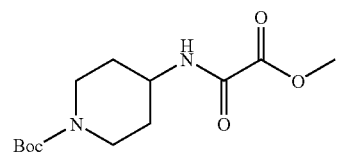

The method described in Referential Example 242 was performed by use of (4-amino-N-tert-butoxycarbonyl)piperidine and methyl chlorooxoacetate, whereby the title compound was obtained.

$^1$H-NMR(DMSO-d$_6$)δ: 1.46(9H, s), 1.34-1.51(2H, m), 1.89-1.98(2H, m), 2.82-2.96(2H, m), 3.91(3H, s), 3.88-4.14(3H, m), 6.96-7.07(1H, m).

MS(FAB)m/z: 287(M+H)$^+$.

Referential Example 389

4-{[2-({(1R,2S,5S)-2-{[(5-chloroindol-2-yl)carbonyl]amino}-5-[(dimethylamino)carbonyl]cyclohexyl}amino)-2-oxoacetyl]amino}piperidine-1-carboxylic acid tert-butyl ester

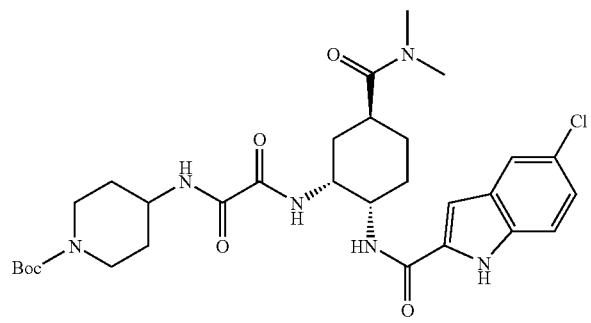

The method described in Example 191 was performed by use of the compound obtained in Referential Example 310 and the compound obtained in Referential Example 388, whereby the title compound was obtained.

$^1$H-NMR(DMSO-d$_6$)δ: 1.46(9H, s), 1.35-2.28(11H, m), 2.70-3.18(9H, m), 3.80-4.57(4H, m), 6.78(1H, s), 7.15-8.12(6H, m), 9.45(1H, s).

MS(FAB)m/z: 617(M+H)$^+$.

Referential Example 390

2-[(5-chloropyridin-2-yl)(methyl)amino]-2-oxoacetic acid methyl ester

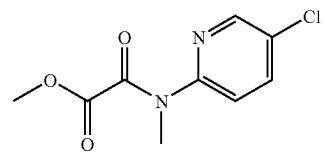

The method described in Referential Example 242 was performed by use of 5-chloro-N-methyl-2-pyridinamine and methyl chlorooxoacetate, whereby the title compound was obtained. $^1$H-NMR(CDCl$_3$)δ: 3.43(3H, s), 3.81(3H, s), 7.08(1H, br.s), 7.68-7.78(1H, m), 8.27(1H, br.s).

MS(ESI)m/z: 229(M+H)$^+$.

Referential Example 391

2-[(5-chloro-pyrimidin-2-yl)amino]-2-oxoacetic acid methyl ester

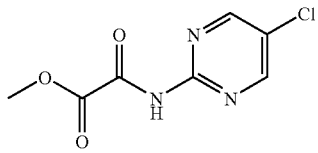

The method described in Referential Example 242 was performed by use of 2-amino-5-chloropyrimidine and methyl chlorooxoacetate, whereby the title compound was obtained.

$^1$H-NMR(CDCl$_3$)δ: 4.00(3H, s), 8.63(2H, s), 9.58(1H, br.s).
MS(ESI)m/z: 215 (M+H)$^+$.

Referential Example 392

N-((1R,2S,5S)-2-azido-5-{[ethyl(methyl)amino]carbonyl}cyclohexyl)-5-methyl-5,6-dihydro-4H-pyrrolo[3,4-d]thiazole-2-carboxamide

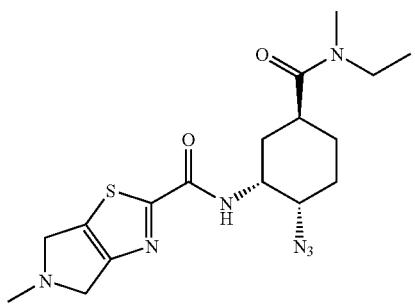

The method described in Referential Example 252 was performed by use of the compound obtained in Referential Example 323 and the compound obtained in Referential Example 293, whereby the title compound was obtained.

$^1$H-NMR(CDCl$_3$)δ: 1.08, 1.15(3H, each t, J=7.1 Hz), 1.74-1.88(4H, m), 2.12-2.22(2H, m), 2.67(3H, s), 2.81-2.86(1H, m), 2.89, 2.96(3H, each s), 3.28-3.43(2H, m), 3.91-4.10(5H, m), 4.60-4.62(1H, m), 7.21(1H, d, J=7.6 Hz).
MS(ESI)m/z: 392(M+H)$^+$.

Referential Example 393

2-(4-chloro-3-methoxyanilino)-2-oxoacetic acid methyl ester

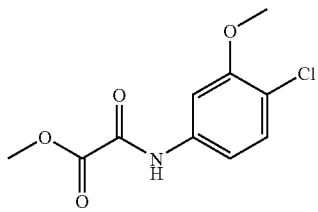

In a manner similar to that described in Referential Example 361, 2-chloro-5-nitroanisole was reduced to the corresponding amino compound. In a manner similar to that described in Referential Example 242, the amino compound was condensed with methyl chlorooxoacetate, whereby the title compound was obtained.

$^1$H-NMR(CDCl$_3$)δ: 3.93(3H, s), 3.98(3H, s), 7.00(1H, dd, J=8.5, 2.4 Hz), 7.33(1H, d, J=8.5 Hz), 7.57(1H, d, J=2.4 Hz), 8.89(1H, br.s).

Referential Example 394

2-(4-chloro-3-methoxyanilino)-2-oxoacetic acid

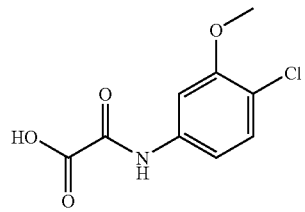

In a manner similar to that described in Referential Example 359, the compound obtained in Referential Example 393 was hydrolyzed, whereby the title compound was obtained.

$^1$H-NMR(DMSO-d$_6$)δ: 3.81(3H, s), 7.36(1H, d, J=8.7 Hz), 7.43(1H, d, J=8.7 Hz), 7.65(1H, d, J=2.2 Hz), 10.79(1H, s).
MS(ESI, anion)m/z: 228(M−H)$^-$.

Referential Example 395

N$^1$-{(1S,2R,4S)-2-amino-4-[(dimethylamino)carbonyl]cyclohexyl}-N$^2$-(4-chloro-3-methoxyphenyl)ethanediamide

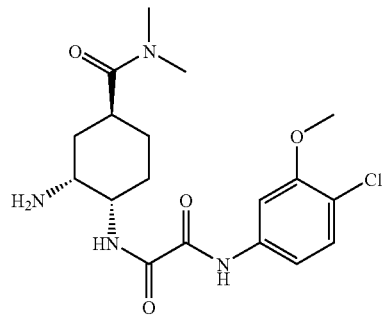

In a manner similar to that described in Referential Example 97, the compound obtained in Referential Example 144 was condensed with the compound obtained in Referential Example 394. In a manner similar to that described in Referential Example 69, the condensed compound was treated with hydrochloric acid and neutralized with 1N aqueous sodium hydroxide, whereby the title compound was obtained.

$^1$H-NMR(CDCl$_3$)δ: 1.48-2.00(8H, m), 2.84-2.93(1H, m), 2.95(3H, s), 3.08(3H, s), 3.33-3.35(1H, m), 3.89-3.94(4H, m), 7.06(1H, dd, J=8.5, 2.2 Hz), 7.32(1H, d, J=8.5 Hz), 7.56(1H, d, J=2.2 Hz), 8.05(1H, d, J=8.5 Hz), 9.43(1H, br.s).
MS(ESI)m/z: 397(M$^+$).

Referential Example 396

2-(4-ethynylanilino)-2-oxoacetic acid methyl ester

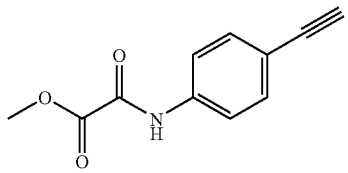

The method described in Referential Example 242 was performed by use of 4-ethynylaniline and methyl chlorooxoacetate, whereby the title compound was obtained.

$^1$H-NMR(CDCl$_3$)δ: 3.09(1H, s), 3.98(3H, s), 7.50(2H, d, J=8.4 Hz), 7.62(2H, d, J=8.4 Hz), 8.89(1H, br.s).

Referential Example 397

2-(4-ethynylanilino)-2-oxoacetic acid sodium salt

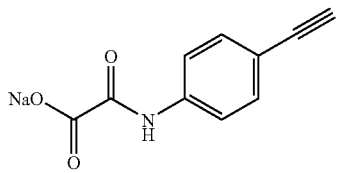

In a manner similar to that described in Referential Example 266, the compound obtained in Referential Example 396 was hydrolyzed with sodium hydroxide, whereby the title compound was obtained.

$^1$H-NMR(DMSO-d$_6$)δ: 4.06(1H, s), 7.39(2H, d, J=8.4 Hz), 7.80(2H, d, J=8.4 Hz), 10.33(1H, br.s).

Referential Example 398

2-[(5-chloropyrazin-2-yl)amino]-2-oxoacetic acid methyl ester

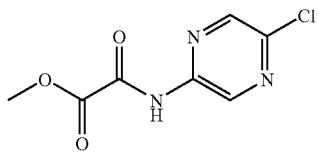

In a manner similar to that employed in Referential Example 242, the title compound was obtained from methyl chlorooxoacetate and 2-amino-5-chloropyrazine which had been synthesized according to the literature (Sato, Nobuhiro et al., J. Heterocycl. Chem. 1982, 19(3), 673-4).

$^1$H-NMR(CDCl$_3$)δ: 4.02(3H, s), 8.35(1H, d, J=1.5 Hz), 9.37(1H, d, J=1.5 Hz), 9.41(1H, br.s).
MS(FAB)m/z: 216(M+H)$^+$.

Referential Example 399

2-[(5-chloropyrazin-2-yl)amino]-2-oxoacetic acid

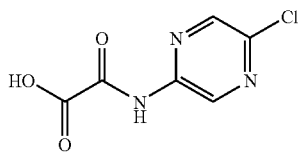

The method described in Referential Example 359 was performed by use of the compound obtained in Referential Example 398, whereby the title compound was obteined.

$^1$H-NMR(DMSO-d$_6$)δ: 8.62(1H, s), 9.02(1H, br.s), 11.30 (1H, s).
MS(EI)m/z: 201 M$^+$.

Referential Example 400

2-(4-chloro-3-nitroanilino)-2-oxoacetic acid

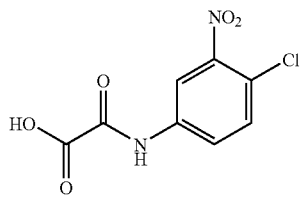

In a manner similar to that described in Referential Example 242, 4-chloro-3-nitroaniline was condensed with methyl chlorooxoacetate. In a manner similar to that described in Referential Example 359, the condensed compound was hydrolyzed, whereby the title compound was obtained.

$^1$H-NMR(DMSO-d$_6$)δ: 7.76(1H, dd, J=8.8 Hz), 8.04(1H, dd, J=8.8, 2.4 Hz), 8.55(1H, d, J=2.4 Hz), 11.24(1H, s). carboxylic acid proton unobserved.
MS(EI)m/z: 244 M$^+$.

Referential Example 401

2-(4-chloro-2-nitroanilino)-2-oxoacetic acid sodium salt

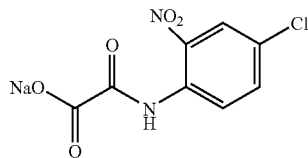

In a manner similar to that described in Referential Example 242, 4-chloro-2-nitroaniline was condensed with methyl chlorooxoacetate. In a manner similar to that described in Referential Example 266, the condensed compound was hydrolyzed. The residue was dissolved in methanol, 1N aqueous sodium hydroxide was added thereto, and the precipitated material was recoverd by filtration, whereby the title compound was obtained.

$^1$H-NMR(DMSO-d$_6$)δ: 7.84(1H, dd, J=9.0, 2.5 Hz), 8.20 (1H, d, J=2.5 Hz), 8.67(1H, d, J=9.0 Hz), 11.89(1H, s).

Referential Example 402

6-chloro-4-methyl-3-pyridineamine

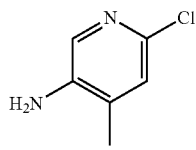

2-Chloro-4-methyl-5-nitropyridine (173 mg) was dissolved in ethanol (5 mL). To the solution, a catalytic amount of Raney nickel was added, and the resultant mixture was stirred in a hydrogen atmosphere at room temperature for 9 hours. The catalyst was removed through filtration, and the solvent was distilled away under reduced pressure. The residue was purified by silica gel column chromatography (hexane:ethyl acetate=3:2), to thereby give the title compound (113 mg).

$^1$H-NMR(CDCl$_3$)δ: 2.13(3H, s), 3.85(2H, br.s), 6.96(1H, s), 7.74(1H, s).

MS(EI)m/z: 142 M$^+$.

Referential Example 403

N$^1$-(2-aminophenyl)-N$^2$-(4-chlorophenyl)ethanediamide

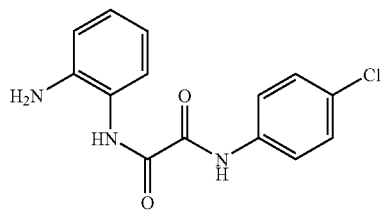

In a manner similar to that described in Referential Example 59, 1,2-benzenediamine was condensed with the compound obtained in Referential Example 374, whereby the title compound was obtained.

$^1$H-NMR(DMSO-d$_6$)δ: 5.00(2H, s), 6.59-6.63(1H, m), 6.78(1H, dd, J=8.1, 1.2 Hz), 6.96-7.01(1H, m), 7.25(1H, dd, J=7.8, 1.2 Hz), 7.44(2H, d, J=8.8 Hz), 7.91(2H, d, J=8.8 Hz), 10.04(1H, s), 10.91(1H, s).

MS(FAB): 290(M+H)$^+$.

Referential Example 404

N-((1R,2S,5S)-2-azido-5-{[ethyl(methyl)amino]carbonyl}cyclohexyl)-5-methyl-4,5,6,7-tetrahydrothiazolo[5,4-c]pyridine-2-carboxamide

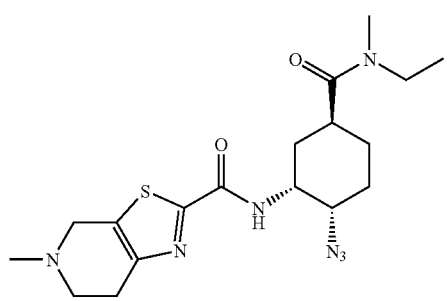

In a manner similar to that described in Referential Example 252, the compound obtained in Referential Example 323 was treated with hydrochloric acid for deprotection. The deprotected compound was condensed with the compound obtained in Referential Example 10, whereby the title compound was obtained.

$^1$H-NMR(CDCl$_3$)δ: 1.08(½ of 3H, t, J=7.2 Hz), 1.14(½ of 3H, t, J=7.2 Hz), 1.70-1.90(4H, m), 2.10-2.25(2H, m), 2.52 (3H, s), 2.78-3.00(8H, m), 3.25-3.45(2H, m), 3.69(1H, d, J=13.4 Hz), 3.73(1H, d, J=13.4 Hz), 3.87-3.95(1H, m), 4.55-4.62(1H, m), 7.26(1H, d, J=7.6 Hz).

Referential Example 405

2-(4-chlorophenyl)-1-hydrazinecarboxylic acid phenyl ester

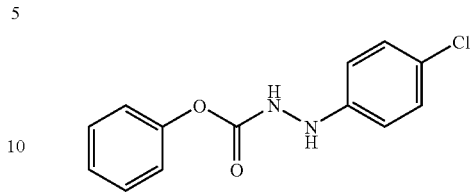

(4-Chlorophenyl)hydrazine hydrochloride (3.00 g) was added to a mixture of tetrahydrofuran (50 mL), diethyl ether (50 mL), and saturated aqueous sodium hydrogencarbonate. The organic layer was separated, followed by drying over sodium sulfate anhydrate and concentrating, to thereby give (4-chlorophenyl)hydrazine as a brown solid. The solid was dissolved in benzene (15 mL), and the solution was heated under reflux. Under refluxing, diphenyl carbonate (5.22 g) dissolved in benzene (8.0 mL) was added dropwise thereto over 30 minutes or more. The mixture was refluxed for 19 hours, allowed to cool to room temperature, and concentrated. Benzene (15 mL) was added thereto, and the mixture was slurried by ultrasonic wave. Hexane (50 mL) was added thereto, and the resultant mixture was stirred for 30 minutes. The insoluble material was recoverd by filtration, followed by drying, to thereby give the title compound (1.05 g).

$^1$H-NMR(CDCl$_3$)δ: 5.86(1H, br.s), 6.83-6.92(3H, m), 7.17 (1H, br.s), 7.20-7.32(4H, m), 7.37(2H, t, J=7.7 Hz).

MS(ESI)m/z: 263(M+H)$^+$.

Referential Example 406

5-tert-butoxycarbonyl-5,6-dihydro-4H-pyrrolo[3,4-d]thiazole-2-carboxylic acid lithium salt

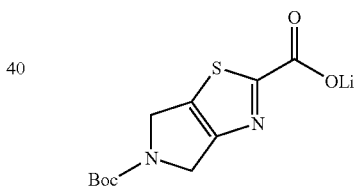

The method described in Referential Example 10 was performed by use of the compound obtained in Referential Example 33, whereby the title compound was obtained.

$^1$H-NMR(DMSO-d$_6$)δ: 1.46(9H, s), 4.30-4.70(4H, m).

Referential Example 407

1-hydroxycyclopropanecarboxylic acid benzyl ester

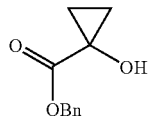

Triethylamine (1.0 mL) and benzyl bromide (650 μL) were added to a solution of 1-hydroxycyclopropanecarboxylic acid (409 mg) in tetrahydrofuran (3.0 mL), and the mixture was stirred at room temperature for 23 hours. To the reaction mixture were added methylene chloride and 1N aqueous hydrochloric acid to thereby give two layers. The organic layer was washed with saturated aqueous sodium hydrogencarbonate and saturated brine, followed by drying over sodium sulfate, to thereby give a crude product. The crude product was subjected to purification through silica gel column chromatography (hexane:ethyl acetate=4:1), to thereby give the title compound (607 mg).

¹H-NMR(CDCl₃)δ: 1.16(2H, dd, J=7.9, 4.9 Hz), 1.32(2H, dd, J=7.9, 4.9 Hz), 3.09(0.5H, s), 3.11(0.5H, s), 5.17(2H, s), 7.30-7.39(5H, m).

MS(FAB)m/z: 192 (M+H)⁺.

Referential Example 408

1-methoxycyclopropanecarboxylic acid benzyl ester

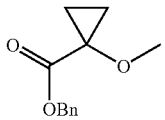

The compound (600 mg) obtained in Referential Example 407 was dissolved in tetrahydrofuran (5.0 mL). To the solution, 60% oily sodium hydride (345 mg) and methyl iodide (900 µL) were added, and the mixture was refluxed for 28 hours. Ethyl acetate and saturated aqueous ammonium chloride were added to the reaction mixture to thereby give two layers. The organc layer was washed with saturated brine, followed by drying over sodium sulfate, to thereby give a crude product. The crude product was subjected to purification through silica gel column chromatography (hexane:ethyl acetate=10:1), to thereby give the title compound (340 mg).

¹H-NMR(CDCl₃)δ: 1.16(2H, dd, J=7.9, 4.8 Hz), 1.31(2H, dd, J=7.9, 4.8 Hz), 3.42(3H, s), 5.18(2H, s), 7.30-7.39(5H, m).

MS(FAB)m/z: 207 (M+H)⁺.

Referential Example 409

1-methoxycyclopropanecarboxylic acid

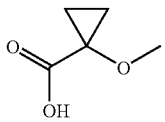

The method described in Referential Example 152 was performed by use of the compound obtained in Referential Example 408, whereby the title compound was obtained.

¹H-NMR(CDCl₃)δ: 1.23(2H, dd, J=8.0, 4.9 Hz), 1.38(2H, dd, J=8.0, 4.9 Hz), 3.45(3H, s), 8.80-9.00(1H, br).

Referential Example 410

(3R,4S)-4-{[(7-chloroisoquinolin-3-yl)carbonyl]amino}-1-(2-methoxyacetyl)piperidin-3-ylcarbamic acid tert-butyl ester

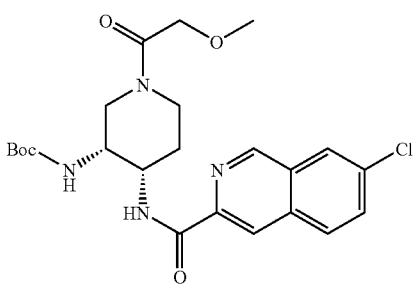

The method described in Referential Example 214 was performed by use of the compound obtained in Referential Example 220 and the compound obtained in Referential Example 57, whereby the title compound was obtained.

¹H-NMR(CDCl₃)δ: 1.46(9H, br s), 1.62-1.80(1H, m), 2.04-2.22(1H, m), 2.95-3.32(1H, m), 3.38-3.53(1H, m), 3.46 (3H, s), 3.84-3.95(1H, m), 4.02-4.27(3H, m), 4.30-4.65(2H, m), 4.87-4.98(0.5H, br), 5.32-5.43(0.5H, br), 7.71(1H, dd, J=8.8, 2.0 Hz), 7.94(1H, d, J=8.8 Hz), 8.02(1H, s), 8.55-8.66 (0.7H, br), 8.58(1H, s), 8.73-8.85(0.3H, br), 9.14(1H, br s).

MS(ESI)m/z: 477(M+H)⁺.

Referential Example 411

(3R,4S)-4-{[2-(4-chloro-3-fluoroanilino)-2-oxoacetyl]amino}-1-(2-methoxyacetyl)piperidin-3-ylcarbamic acid tert-butyl ester

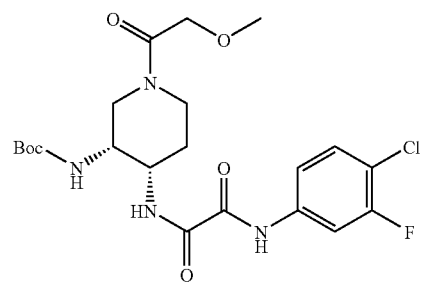

In a manner similar to that described in Referential Example 214, the compound obtained in Referential Example 220 was condensed with the compound obtained in Referential Example 377, whereby the title compound was obtained.

¹H-NMR(CDCl₃)δ: 1.46(9H, s), 1.60-1.75(1H, m), 1.92-2.08(1H, m), 2.68-2.80(0.5H, m), 2.88-3.03(0.5H, m), 3.06-3.24(0.5H, m), 3.27-3.36(0.5H, m), 3.45(3H, s), 3.90-4.22 (5H, m), 4.56-4.71(1H, m), 4.80-4.92(0.3H, br), 5.44-5.54 (0.7H, br), 7.24(1H, d, J=12.9 Hz), 7.35(1H, t, J=8.3 Hz), 7.72(1H, dd, J=8.3, 2.3 Hz), 8.20-8.42(1H, br), 9.18-9.28(1H, br).

MS(ESI)m/z: 487 (M+H)⁺.

Referential Example 412

(3R,4S)-4-({2-[(5-chloro-2-thienyl)amino]-2-oxoacetyl}amino)-1-(2-methoxyacetyl)piperidin-3-ylcarbamic acid tert-butyl ester

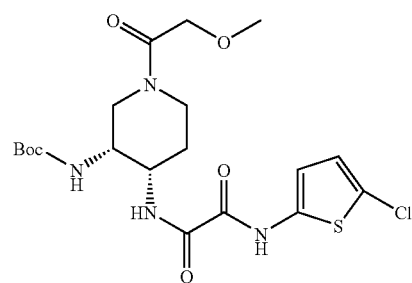

The method described in Referential Example 214 was performed by use of the compound obtained in Referential Example 220 and a lithium salt of carboxylic acid prepared by hydrolysis of the compound obtained in Referential Example 356, whereby the title compound was obtained.

¹H-NMR(CDCl₃)δ: 1.45(9H, s), 1.55-1.75(1H, br), 1.90-2.10(1H, br), 2.68-2.80(0.7H, m), 2.90-3.03(0.3H, br), 3.07-3.22(0.3H, br), 3.25-3.35(0.7H, br), 3.45(3H, s), 3.83-4.22 (5H, m), 4.55-4.70(1H, br), 4.80-4.90(0.2H, br), 5.07-5.14 (0.2H, br), 5.44-5.55(0.6H, br), 6.58-6.64(1H, br), 6.73(1H, d, J=3.9 Hz), 8.05-8.27(1H, br), 9.65-9.88(1H, br).

MS(FAB)m/z: 475 (M+H)⁺.

Referential Example 413

5-methyl-5H-pyrrolo[3,4-d]thiazolo-2-carboxylic acid ethyl ester

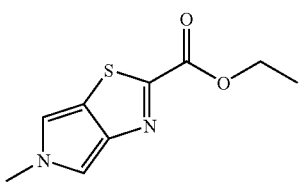

1) To a solution of 3-bromo-2-butanone (26.36 g) in ethanol (250 mL), was added ethyl 2-thioxoacetate (26.75 g), and the mixture was refluxed for 14 hours. The reaction mixture was cooled, and concentrated under reduced pressure. Ethyl acetate and saturated brine were added to the residue to thereby give two layers. The organic layer was washed with saturated aqueous sodium hydrogencarbonate and saturated brine, followed by drying over sodium sulfate anhydrate. The solvent was concentrated under reduced pressure, and the residue was purified by silica gel column chromatography (hexane:ethyl acetate=6:1), to thereby give ethyl 4,5-dimethylthiazole-2-carboxylate (19.53 g).

¹H-NMR(CDCl₃)δ: 1.42(3H, t, J=7.1 Hz), 2.42(3H, s), 2.44(3H, s), 4.45(2H, q, J=7.1 Hz).

2) The above product (19.53 g) was dissolved in 1,2-dichloroethane (500 mL). To the solution were added N-bromosuccinimide (62.42 g) and 2,2'-azobisisobutyronitrile (227 mg), and the mixture was refluxed for 42 hours. The reaction mixture was cooled, and water and methylene chloride were added thereto to thereby give two layers. The organic layer was washed with saturated brine, followed by concentrating under reduced pressure, thereby yielding a crude product (40.54 g) as dark brown oil. The crude product (8.41 g) was dissolved in acetonitrile (400 mL). To the solution, triethylamine (8.0 mL) and a solution (11.0 mL) of methylamine (2 mol) in tetrahydrofuran were added at 0° C., and the mixture was stirred at room temperature for 3 days. The reaction mixture was concentrated under reduced pressure. Methylene chloride and saturated brine were added to the residue to thereby give two layers. The organic layer was washed with saturated brine, followed by drying over sodium sulfate anhydrate. The solvent was concentrated under reduced pressure. The residue was purified by silica gel column chromatography (hexane:ethyl acetate=3:1), to thereby give the title compound (270 mg).

¹H-NMR(CDCl₃)δ: 1.45(3H, t, J=7.1 Hz), 3.91(3H, s), 4.48(2H, q, J=7.1 Hz), 6.73(1H, d, J=1.7 Hz), 7.30(1H, d, J=1.7 Hz).

MS(ESI)m/z: 211(M+H)⁺.

Referential Example 414

6-chloro-4-oxo-4H-chromene-2-carboxylic acid ethyl ester

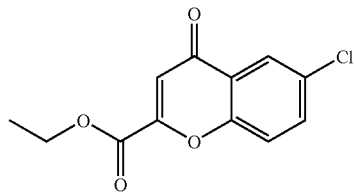

In an argon atmosphere, ca. 60% oily sodium hydride (1.68 g) was added to ethanol (10 mL). The mixture was stirred at room temperature for 10 minutes. Diethyl oxalate (3.36 mL) was added thereto, 5'-chloro-2'-hydroxyacetophenone (2.82 g) dissolved in ethanol (20 mL) was added dropwise to the resultant mixture, and ethanol (40 mL) was further added, followed by refluxing for 1.5 hours and stirring at 50° C. for 14 hours. To the reaction mixture, concentrated sulfuric acid (1.5 mL) and ethanol (10 mL) were added, and the mixture was refluxed for 4 hours. The resultant mixteure was cooled, concentrated under reduced pressure to reduce the solvent by half, and toluene and 1N aqueous sodium hydroxide (15 mL) were added to the concentrated mixture. The resultant mixture was extracted with ethyl acetate, and the organic layer was washed with saturated brine, followed by drying over sodium sulfate anhydrate. The solvent was concentrated under reduced pressure, and the residue was purified by silica gel column chromatography (hexane:ethyl acetate=7:1). The resultant solid was washed with hexane, to thereby give the title compound (1.20 g).

¹H-NMR(CDCl₃)δ: 1.44(3H, t, J=7.1 Hz), 4.47(2H, q, J=7.1 Hz), 7.12(1H, s), 7.58(1H, d, J=9.0 Hz), 7.69(1H, dd, J=9.0, 2.7 Hz), 8.16(1H, d, J=2.7 Hz).

MS(ESI)m/z: 293(M+MeCN+H)⁺.

Referential Example 415

6-chloro-4-oxo-4H-chromene-2-carboxylic acid

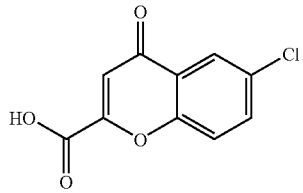

The method described in Referential Example 359 was performed by use of the compound obtained in Referential Example 414, whereby the title compound was obtained.

¹H-NMR(CDCl₃)δ: 7.12(1H, s), 7.60(1H, d, J=8.8 Hz), 7.69(1H, dd, J=8.8, 2.7 Hz), 8.15(1H, d, J=2.7 Hz).

MS(FAB)m/z: 225 (M+H)⁺.

Referential Example 416

(1S,3R,4S)-4-amino-3-[(tert-butoxycarbonyl)amino] cyclohexanecarboxylic acid ethyl ester

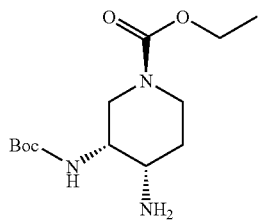

The method described in Referential Example 90 was performed by use of the compound obtained in Referential Example 249, whereby the title compound was obtained.

$^1$H-NMR(CDCl$_3$)δ: 1.20-1.80(4H, m), 1.25(3H, t, J=7.3 Hz), 1.46(9H, s), 1.85-2.00(1H, m), 2.10-2.20(1H, m), 2.30-2.45(1H, m), 2.90-3.00(1H, m), 3.84(1H, br s), 4.12(2H, q, J=7.3 Hz), 4.75(1H, br s).

Referential Example 417

(1R,2S,5S)-2-{[(6-chloro-4-oxo-4H-chromen-2-yl)carbonyl]amino}-5-[(dimethylamino)carbonyl]cyclohexylcarbamic acid tert-butyl ester

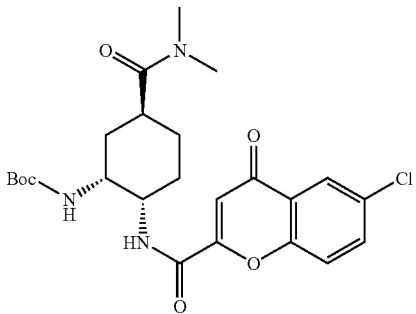

The compound (213 mg) obtained in Referential Example 415 was dissolved in thionyl chloride (2.0 mL). N,N-Dimethylformamide (0.02 mL) was added thereto, and the mixture was refluxed for 15 minutes. The reaction mixture was concentrated under reduced pressure, and the residue was dissolved in tetrahydrofuran (4.0 mL). To the solution, triethylamine (500 µL) and the compound (294 mg) obtained in Referential Example 144 were added, followed by stirring at room temperature for 15 minutes. To the reaction mixture, ethyl acetate and 10% aqueous citric acid were added to thereby give two layers. The organic layer was washed with saturated aqueous sodium hydrogencarbonate and saturated brine, followed by drying over sodium sulfate anhydrate and concentrating under reduced pressure. The residue was purified by silica gel column chromatography (methylene chloride:methanol=30:1), to thereby give the title compound (230 mg).

$^1$H-NMR(CDCl$_3$)δ: 1.33-1.77(3H, m), 1.50(9H, s), 1.81-2.34(3H, m), 2.63-2.80(1H, m), 2.95(3H, s), 3.10(3H, s), 3.90-4.04(1H, br), 4.18-4.31(1H, br), 4.93-5.12(1H, br), 7.13(1H, s), 7.55(1H, d, J=8.8 Hz), 7.66(1H, dd, J=8.8, 2.4 Hz), 8.14(1H, d, J=2.4 Hz), 8.77-8.92(1H, br).

MS(ESI)m/z: 492(M+H)$^+$.

Referential Example 418

(3R,4S)-4-{[(7-chlorocinnolin-3-yl)carbonyl]amino}-1-(2-methoxyacetyl)piperidin-3-ylcarbamic acid tert-butyl ester

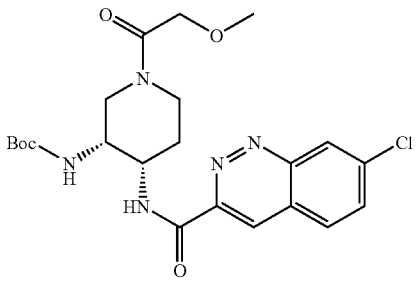

The method described in Referential Example 214 was performed by use of the compound obtained in Referential Example 220 and a lithium salt of carboxylic acid obtained by hydrolysis of the ester described in Referential Example 297, whereby the title compound was obtained.

$^1$H-NMR(CDCl$_3$)δ: 1.38(9H, s), 1.65-1.90(1H, m), 1.90-2.15(1H, m), 2.80-3.00(0.6H, m), 3.00-3.15(0.4H, m), 3.20-3.50(1H, m), 3.46(3H, s), 3.80-4.70(6H, m), 4.87(0.4H, br s), 5.30(0.6H, br s), 7.78(1H, d, J=8.8 Hz), 7.97(1H, d, J=8.8 Hz), 8.61(1H, s), 8.62-8.90(1H, br), 8.73(1H, s).

MS(ESI)m/z: 478 (M+H)$^+$.

Referential Example 419

(1R,2S,5S)-2-({2-[(5-chloropyridin-2-yl)amino]-2-oxoacetyl}amino)-5-[(dimethylamino)carbonyl]cyclohexylcarbamic acid tert-butyl ester

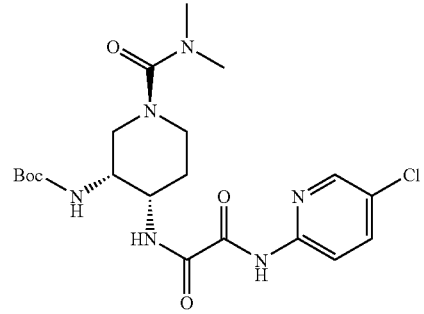

In a manner similar to that described in Referential Example 68, the compound obtained in Referential Example 144 was condensed with the compound obtained in Referential Example 266, whereby the title compound was obtained.

$^1$H-NMR(CDCl$_3$)δ: 1.35-1.65(1H, m), 1.45(9H, s), 1.65-1.89(2H, m), 1.90-2.10(3H, m), 2.56-2.74(1H, br), 2.95(3H, s), 3.06(3H, s), 3.94-4.01(1H, m), 4.18-4.27(1H, m), 4.70-4.90(0.7H, br), 5.80-6.20(0.3H, br), 7.68(1H, dd, J=8.9, 2.6 Hz), 7.83(1H, br s), 8.14(1H, br d, J=7.8 Hz), 8.30(1H, s), 9.72(1H, s).

MS(ESI)m/z: 468(M+H)$^+$.

Referential Example 420

N$^1$-{(1S,2R,4S)-2-amino-4-[(dimethylamino)carbonyl]cyclohexyl}-N$^2$-(5-chloropyridin-2-yl)ethanediamide hydrochloride

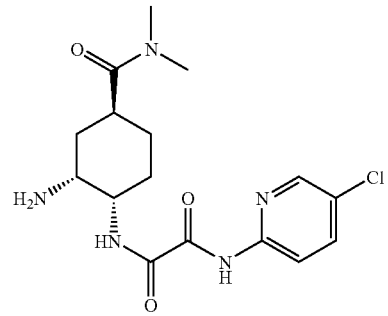

The method described in Referential Example 69 was performed by use of the compound obtained in Referential Example 419, whereby the title compound was obtained.

$^1$H-NMR(DMSO-d$_6$)δ: 1.38-1.51(1H, m), 1.65-1.85(3H, m), 1.96-2.10(2H, m), 2.81(3H, s), 3.07(3H, s), 3.23-3.33(1H, m), 3.74(1H, br s), 3.84-3.92(1H, m), 8.02(1H, dd, J=9.0, 2.5 Hz), 8.07(1H, d, J=9.0 Hz), 8.34(3H, br s), 8.46(1H, d, J=2.5 Hz), 8.96(1H, d, J=6.6 Hz), 10.34(1H, s).

MS(ESI)m/z: 368(M+H)$^+$.

Referential Example 421

2-[({(1R,2S,5S)-2-({2-[(5-chloropyridin-2-yl)amino]-2-oxoacetyl}amino)-5-[(dimethylamino)carbonyl]cyclohexyl}amino)carbonyl]-6,7-dihydrothieno[3,2-c]pyridine-5(4H)-carboxylic acid tert-butyl ester

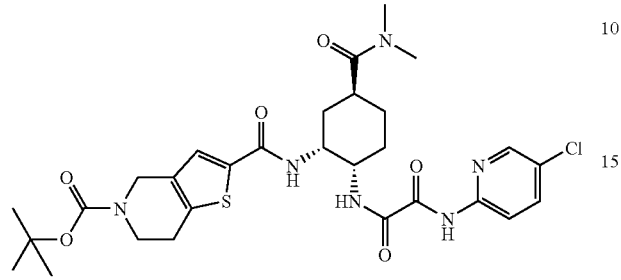

The compound obtained in Referential Example 420 was condensed with 5-(tert-butoxycarbonyl)-4,5,6,7-tetrahydrothieno[3,2-c]pyridine-2-carboxylic acid (WO94/21599), whereby the title compound was obtained.

$^1$H-NMR(CDCl$_3$)δ: 1.50(9H, s), 1.73-1.95(3H, m), 1.95-2.06(1H, m), 2.08-2.20(2H, m), 2.82(3H, br s), 2.94(3H, s), 3.03(3H, s), 3.60-3.80(2H, m), 3.96-4.08(1H, m), 4.44(2H, br s), 4.66(1H, br s), 6.74(1H, br s), 7.20-7.32(1H, m), 7.66(1H, dd, J=9.0, 2.4 Hz), 8.13(1H, d, J=9.0 Hz), 8.13-8.25(1H, m), 8.28(1H, d, J=2.4 Hz), 9.75(1H, s).

MS(ESI)m/z: 633(M+H)$^+$.

Referential Example 422

2-chloro-N-(4-fluorophenyl)acetamide

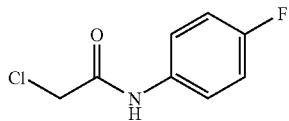

The method described in Referential Example 350 was performed by use of p-fluoroaniline, whereby the title compound was obtained.

$^1$H-NMR(CDCl$_3$)δ: 4.19(2H, s), 7.05(2H, t, J=8.6 Hz), 7.51(2H, dd, J=9.1, 4.7 Hz), 8.19(1H, br s).

Referential Example 423

S-[2-(4-fluoroanilino)-2-oxoethyl]thiosulfuric acid sodium salt

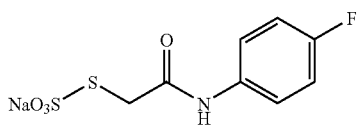

The method described in Referential Example 351 was performed by use of the compound obtained in Referential Example 422, whereby the title compound was obtained.

$^1$H-NMR(DMSO-d$_6$)δ: 3.72(2H, s), 7.14(2H, t, J=9.0 Hz), 7.56(2H, dd, J=9.0, 5.1 Hz), 10.21(1H, s).

Referential Example 424

(1R,2S,5S)-5-[(dimethylamino)carbonyl]-2-{[2-(4-fluoroanilino)-2-oxoethanethioyl]amino}cyclohexylcarbamic acid tert-butyl ester

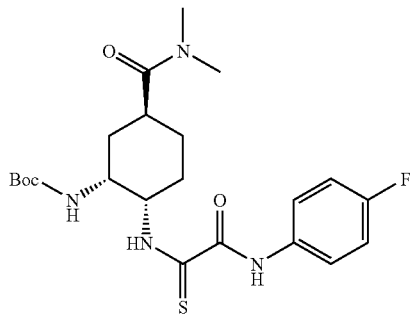

The compound (1.1 g) obtained in Referential Example 144 and the compound (1.24 g) obtained in Referential Example 423 were dissolved in N-methylmorpholine (20 mL). The solution was heated from room temperature to 140° C. on a bath over 15 minutes and stirred at 140° C. for 15 minutes. The reaction mixture was allowed to cool to room temperature, a mixture of ice and water was added thereto, and the insoluble material was recovered by filtration. The material was purified by silica gel column chromatography (methylene chloride:methanol=200:1→197:3), to thereby give the title compound (1.43 g).

$^1$-NMR(CDCl$_3$)δ: 1.45(9H, s), 1.70-2.10(5H, m), 2.10-2.30(1H, m), 2.60-2.80(1H, m), 2.96(3H, s), 3.07(3H, s), 4.30-4.50(2H, m), 4.65-4.85(1H, m), 7.06(2H, t, J=8.5 Hz), 7.50-7.70(2H, m), 9.75-9.95(1H, m), 10.13(1H, s).

MS(ESI)m/z: 467(M+H)$^+$.

Referential Example 425

2-chloro-N-(5-fluoropyridin-2-acetamide hydrochloride

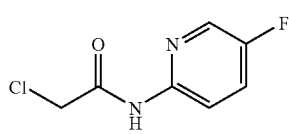

The method described in Referential Example 352 was performed by use of 2-amino-5-fluoropyridine, whereby the title compound was obtained.

$^1$H-NMR(DMSO-d$_6$)δ: 4.35(2H, s), 7.74-7.82(1H, m), 8.10(1H, dd, J=9.0, 4.2 Hz), 8.36(1H, d, J=2.9 Hz), (1H, br s).

MS(ESI)m/z: 188(M+H)$^+$.

Referential Example 426

S-{2-[(5-fluoropyridin-2-yl)amino]-2-oxoethyl}thiosulfuric acid sodium salt

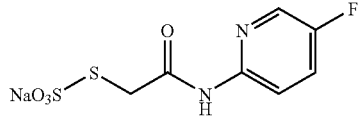

The method described in Referential Example 353 was performed by use of the compound obtained in Referential Example 425, whereby the title compound was obtained.

¹H-NMR(DMSO-d₆)δ: 3.75(2H, s), 7.67-7.77(1H, m), 8.07(1H, dd, J=9.2, 4.2 Hz), 8.28(1H, d, J=2.9 Hz), 10.48(1H, s).

Referential Example 427

(1R,2S,5S)-5-[(dimethylamino)carbonyl]-2-({2-[(5-fluoropyridin-2-yl)amino]-2-oxoethanethioyl}amino)cyclohexylcarbamic acid tert-butyl ester

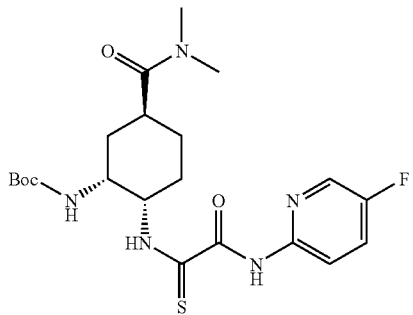

The compound (1.20 g) obtained in Referential Example 144 was dissolved in pyridine (70 mL). The resultant solution was heated at 120° C., and the compound (2.42 g) obtained in Referential Example 426 was added thereto. The resultant mixture was stirred for 30 minutes and then allowed to cool to room temperature, and the solvent was distilled away under reduced pressure. Methylene chloride (100 mL), saturated aqueous sodium hydrogencarbonate (100 mL), and water (50 mL) were added to the residue for partitioning the mixture. The aqueous layer was extracted with methylene chloride. The organic layers were combined, followed by drying over sodium sulfate anhydrate. The solvent was distilled away under reduced pressure, and the residue was purified by silica gel column chromatography (hexane tetrahydrofuran=1:1). The resultant solid was slurried in isopropyl ether (40 mL) for 1 hour, and the solid was recovered by filtration, followed by dring, to thereby give the title compound (920 mg).
¹H-NMR(CDCl₃)δ: 1.47(9H, s), 1.70-2.10(5H, m), 2.27 (1H, br s), 2.70(1H, br s), 2.96(3H, s), 3.08(3H, s), 4.34-4.44 (2H, m), 4.77(1H, br s), 7.44-7.51(1H, m), 8.18-8.27(2H, m), 9.90(1H, br s), 10.57(1H, s).
MS(ESI)m/z: 468 (M+H)⁺.

Referential Example 428

(1R,2S,5S)-2-({2-[(5-chloropyridin-2-yl)amino]-2-oxoethanethioyl}amino)-5-[(dimethylamino)carbonyl]cyclohexylcarbamic acid tert-butyl ester

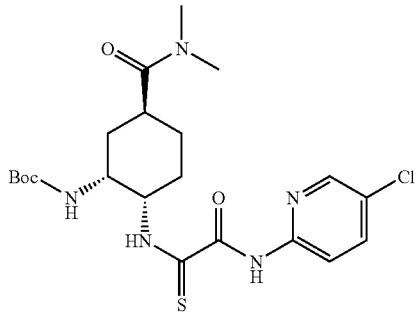

The method described in Referential Example 427 was performed by use of the compound obtained in Referential Example 144 and the compound obtained in Referential Example 353, whereby the title compound was obtained.
¹H-NMR(CDCl₃)δ: 1.43(9H, s), 1.65-2.35(6H, m), 2.70 (1H, br s), 2.95(3H, s), 3.09(3H, s), 4.30-4.60(2H, m), 4.87 (½H, br s), 6.92(½H, br s), 7.69(1H, dd, J=8.9, 2.6 Hz), 7.95-8.20(1H, br), 8.29(1H, s), 9.67(½H, br s), 9.93(½H, br s), 10.54(1H, br s).

Referential Example 429

2-chloro-4,5,6,7-tetrahydrobenzothiazol-6-ylformamide

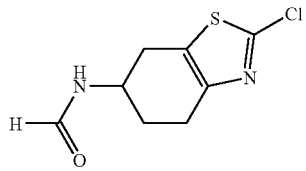

To a solution of 2-chloro-5-oxo-4,5,6,7-tetrahydrobenzo[d]thiazole (Helv. Cim. Acta., 1994, Vol. 77, 1256) (4.53 g) in methanol (200 mL), were added ammonium acetate (18.58 g) and sodium cyanoborohydride (10.68 g), and the mixture was heated under reflux. After 19 hours had elapsed, hydrochloric acid was added thereto to decompose excess reagents. The reaction mixture was concentrated under reduced pressure, alkalized with 1N aqueous sodium hydroxide, and methylene chloride was added thereto for partitioning the mixture. The organic layer was dried over magnesium sulfate anhydrate, and the solvent was distilled away under reduced pressure. The residue was subjected to silica gel column chromatography (methylene chloride:methanol=20:1), and the solvent was distilled away to thereby give a light yellow oily compound (2.42 g). The oily compound was dissolved in methylene chloride (100 mL). To the resultant solution were added formic acid (530 μL), 1-(3-dimethylaminopropyl)-3-ethylcarbodiimide hydrochloride (3.68 g), 1-hydroxybenzotriazole (2.60 g), and N-methylmorpholine (3.88 g), followed by stirring at room temperature. After 20 hours had elapsed, methylene chloride and saturated aqueous sodium hydrogencarbonate were added to the reation mixture for partitioning the mixture. The organic layer was dried over magnesium sulfate anhydrate, and the solvent was distilled away under reduced pressure. The residue was subjected to silica gel column chromatography (methylene chloride:methanol=20:1), to thereby give the title compound (2.21 g).
¹H-NMR(CDCl₃)δ: 1.93-2.11(2H, m), 2.63-2.69(1H, m), 2.83-2.89(2H, m), 3.13(1H, dd, J=16.2, 4.4 Hz), 4.46-4.48 (1H, m), 5.76(1H, br s), 8.17(1H, s).

Referential Example 430

N-(2-chloro-4,5,6,7-tetrahydrobenzothiazol-6-yl)-N-methylcarbamic acid tert-butyl ester

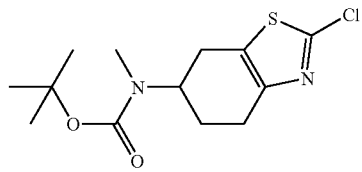

The compound (2.11 g) obtained in Referential Example 429 was dissolved in tetrahydrofuran (50 mL). To the solution, a 1M solution (14.6 mL) of borane-tetrahydrofuran complex in tetrahydrofuran was added, and the resultant mixture was heated under reflux. After 15 hours had elapsed, a 1M solution (6.0 mL) of borane-tetrahydrofuran complex in tetrahydrofuran was further added thereto, followed by refluxing under heat. After 4 hours had elapsed, ethanol (10 mL) and 1N hydrochloric acid (15 mL) were added thereto, and the resultant mixture was heated under reflux. After 3 hours had elapsed, the reaction mixture was concentrated under reduced pressure. 1N Aqueous sodium hydroxide and methylene chloride were added thereto for partitioning the mixture. The organic layer was dried over magnesium sulfate anhydrate, and the solvent was distilled away under reduced pressure. The residue was dissolved in methylene chloride (50 mL), and triethylamine (1.28 g) and di-tert-butyl dicarbonate (2.21 g) were added thereto, followed by stirring at room temperature. After 30 minutes had elapsed, methylene chloride and 1N hydrochloric acid were added to the reaction mixture for partitioning the mixture. The organic layer was dried over magnesium sulfate anhydrate, and the solvent was distilled away under reduced pressure. The residue was subjected to silica gel column chromatography (hexane:ethyl acetate=2:1), to thereby give the title compound (2.26 g).

$^1$H-NMR(CDCl$_3$)δ: 1.47(9H, s), 1.96-1.98(2H, m), 2.80-2.96(7H, m), 4.40-4.50(1H, m).

MS(FAB)m/z: 303 (M+H)$^+$.

Referential Example 431

N-(2-[({(1R,2S,5S)-2-({2-[(5-chloropyridin-2-yl)amino]-2-oxoacetyl}amino)-5-[(dimethylamino)carbonyl]cyclohexyl}amino)carbonyl]-4,5,6,7-tetrahydrobenzothiazol-6-yl)-N-methylcarbamic acid tert-butyl ester

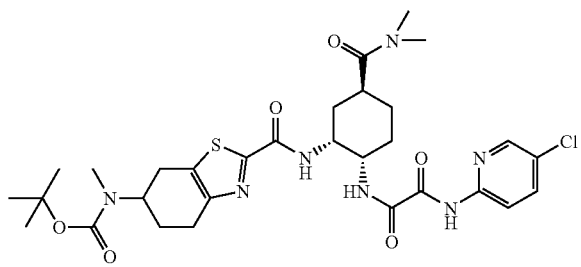

The compound (1.0 g) obtained in Referential Example 430 was dissolved in diethyl ether (10 mL)-tetrahydrofuran (5 mL), and the solution was cooled to −78° C. 1.6N Tert-butyllithium pentane solution (3.1 mL) was added thereto, the resultant mixture was stirred for 20 minutes, and carbon dioxide gas was injected thereto for 20 minutes. The temperature of the reaction mixture was returned to room temperature, and the mixture was concentrated under reduced pressure, to thereby give 6-[(tert-butoxycarbonyl)(methyl)amino]-4,5,6,7-tetrahydrobenzothiazole-2-carboxylic acid lithium salt.

The compound (490.5 mg) obtained in Referential Example 420 was dissolved in N,N-dimethylformamide (20 mL). To the resultant solution were added the above carboxylic acid lithium salt (350.2 mg), 1-(3-dimethylaminopropyl)-3-ethylcarbodiimide hydrochloride (287.6 mg), 1-hydroxybenzotriazole (202.7 mg), and N-methylmorpholine (0.319 mL), followed by stirring at room temperature for 4 days. The solvent was distilled away under reduced pressure. Water and methylene chloride were added to the residue for partitioning the mixture. The organic layer was sequentially washed with saturated aqueous sodium hydrogencarbonate and saturated brine. The resultant mixture was dried over sodium sulfate anhydrate, and concentrated under reduced pressure. The residue was purified by silica gel column chromatography (methylene chloride:methanol=40:1→20:1), to thereby give the title compound (323.9 mg).

$^1$H-NMR(CDCl$_3$)δ: 1.48, 1.49(total 9H, each s), 1.60-1.92 (4H, m), 1.95-2.20(6H, m), 2.78-3.10(3H, m), 2.83 (3H, s), 2.95(3H, s), 3.06, 3.07 (total 3H, each s), 4.05-4.15(1H, m), 4.20-4.60(1H, m), 4.63-4.73(1H, m), 7.39(1H, d, J=8.6 Hz), 7.68(1H, dt, J=8.8, 2.6 Hz), 7.95-8.10(1H, m), 8.13-8.22(1H, m), 8.30-8.35(1H, m), 9.72(1H, brs).

MS(ESI)m/z: 662(M+H)$^+$.

Referential Example 432

N-{(1S,2R,4S)-2-amino-4-[(dimethylamino)carbonyl]cyclohexyl}-5-chloroindole-2-carboxamide hydrochloride

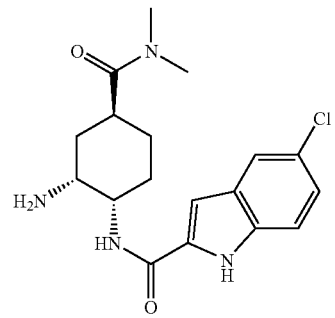

In a manner similar to that described in Referential Example 69, the compound obtained in Referential Example 310 was deprotected, whereby the title compound was obtained.

$^1$H-NMR(DMSO-d$_6$)δ: 1.43-1.56(0.5H, m), 1.72-1.97 (4.5H, m), 2.82(3H, s), 3.06(3H, s), 3.11-3.26(1H, m), 3.75-3.84(1H, m), 4.07-4.14(1H, m), 4.22-4.41(1H, m), 7.19(1H, dd, J=2.0, 8.8 Hz), 7.29(1H, d, J=2.0 Hz), 7.45(1H, d, J=8.8 Hz), 7.72(1H, s), 8.07(3H, br), 8.47(1H, m), 11.85(1H, br).

Referential Example 433

2-[(5-chloropyridin-2-yl)amino]-2-oxoacetic acid lithium salt

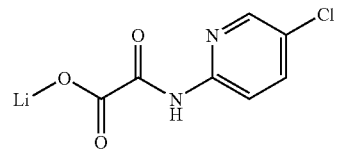

Methyl chlorooxoacetate (78.7 mL) was added dropwise at 0° C. to a suspension of 2-amino-5-chloropyridine (100 g) and sodium hydrogencarbonate (78.4 g) in tetrahydrofuran (2,000 mL), the resultant mixture was stirred at room temperature for 2 hours. Under stirring, the reaction mixture was added to a mixture of diethyl ether (2,000 mL), ammonium chloride (62.4 g), and water (1,000 mL). The resultant mixture was partitioned, and the aqueous layer was extracted with methylene chloride. The organic layers were combined, followed by drying over sodium sulfate anhydrate. The solvent was distilled away under reduced pressure, followed by drying to thereby give 2-[(5-chloropyridin-2-yl)amino]-2-oxoacetic acid methyl ester (162 g). The ester (160 g) was dissolved in tetrahydrofuran (1,800 mL), and water (450 mL) and lithium hydroxide (18.2 g) were added to the solution, followed by stirring at room temperature for 2 hours. The solvent was distilled away under reduced pressure, and hexane (3,000 mL) was added to the residue. The resultant mixture was stirred for 3 hours. The resultant solid was recovered by filtration, followed by drying. Acetonitrile (1,000 mL) was added to the solid (190 g), and the resultant mixture was stirred for 1 hour. The resultant solid was recovered by filtration, followed by washing with diethyl ether (500 mL) and drying, to thereby give the title compound (158 g).

$^1$H-NMR(DMSO-$d_6$)δ: 7.92(1H, dd, J=9.1, 2.7 Hz), 8.13 (1H, dd, J=9.1, 0.5 Hz), 8.36(1H, dd, J=2.7, 0.5 Hz), 10.19 (1H, s).

Referential Example 434

(1R,2S,5S)-2-({2-[(5-chloropyridin-2-yl)amino]-2-oxoacetyl}amino)-5-[(dimethylamino)carbonyl]cyclohexylcarbamic acid tert-butyl ester

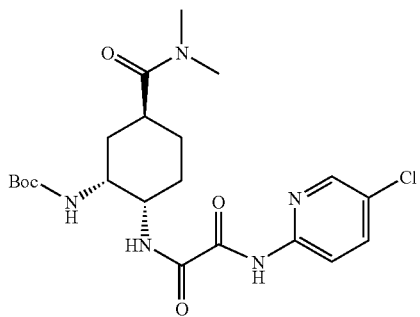

The method described in Referential Example 91 was performed by use of the compound obtained in Referential Example 144 and the compound obtained in Referential Example 433, whereby the title compound was obtained.

$^1$H-NMR(CDCl$_3$)δ: 1.25-1.55(1H, m), 1.45(9H, s), 1.60-2.15(5H, m), 2.56-2.74(1H, br), 2.95(3H, s), 3.06(3H, s), 3.90-4.01(1H, m), 4.18-4.27(1H, m), 4.70-4.85(0.7H, br), 5.70-6.00(0.3H, br), 7.70(1H, dd, J=8.8, 2.4 Hz), 7.75-8.00 (1H, br), 8.16(1H, br d, J=8.8 Hz), 8.30(1H, d, J=2.4 Hz), 9.73(1H, s).

MS(ESI)m/z: 468(M+H)$^+$.

Referential Example 435

N$^1$-{(1S,2R,4S)-2-amino-4-[(dimethylamino)carbonyl]cyclohexyl}-N$^2$-(5-chloropyridin-2-yl)ethanediamide hydrochloride

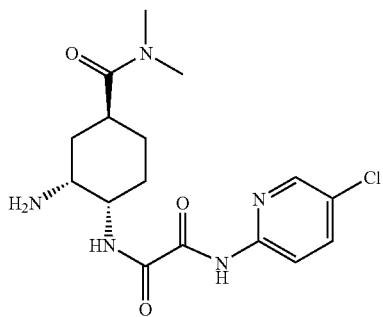

The method described in Referential Example 69 was performed by use of the compound obtained in Referential Example 434, whereby the title compound was obtained.

$^1$H-NMR(DMSO-$d_6$)δ: 1.38-1.51(1H, m), 1.65-1.85(3H, m), 1.92-2.09(2H, m), 2.80(3H, s), 3.06(3H, s), 3.20-3.32 (1H, m), 3.55-4.40(2H, br), 8.02(1H, dd, J=9.1, 2.5 Hz), 8.07(1H, d, J=9.1 Hz), 8.15-8.40(3H, br), 8.45(1H, d, J=2.5 Hz), 8.96(1H, d, J=6.6 Hz), 10.33(1H, s).

Referential Example 436

(1S,2R,4S)-2-[(tert-butoxycarbonyl)amino]-4-[(methylamino)carbonyl]cyclohexylcarbamic acid benzyl ester

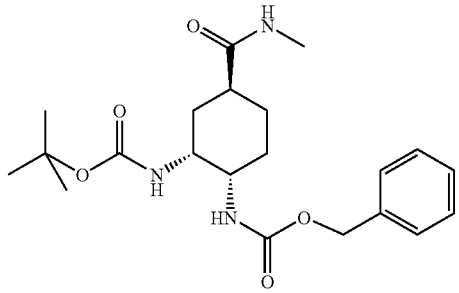

The method described in Referential Example 143 was performed by use of the compound obtained in Referential Example 142 and methylamine hydrochloride, whereby the title compound was obtained.

$^1$H-NMR(DMSO-$d_6$)δ: 1.39(9H, s), 1.40-1.61(4H, m), 1.63-1.73(1H, m), 1.75-1.85(1H, m), 2.23-2.48(1H, m), 2.53 (3H, d, J=4.6 Hz), 3.48(1H, br.s), 3.80-3.91(1H, m), 5.01(1H, ½ABq, J=12.1 Hz), 5.03(1H, ½ABq, J=12.1 Hz), 6.28-6.40 (1H, m), 6.82-6.98(1H, m), 7.25-7.40(5H, m), 7.50-7.60(1H, m).

MS(FAB)m/z: 406(M+H)$^+$.

Referential Example 437

(1R,2S,5S)-2-({2-[(5-chloropyridin-2-yl)amino]-2-oxoacetyl}amino)-5-[(methylamino)carbonyl]cyclohexylcarbamic acid tert-butyl ester

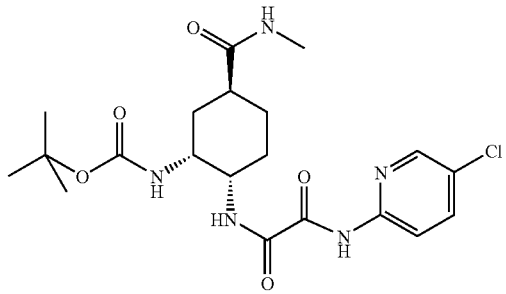

In a manner similar to that described in Referential Example 144, the compound obtained in Referential Example 436 was deprotected to obtain the corresponding amine compound.

In a manner similar to that described in Referential Example 91, the amine compound was condensed with the compound obtained in Referential Example 433, whereby the title compound was obtained.

$^1$H-NMR(DMSO-$d_6$)δ: 1.35-1.75(3H, m), 1.39(9H, s), 1.75-1.86(2H, m), 1.87-1.95(1H, m), 2.30-2.40(1H, m), 2.55 (3H, d, J=4.6 Hz), 3.79-3.90(2H, m), 6.73-6.90(1H, m), 7.58-7.70(1H, m), 8.00-8.13(2H, m), 8.46(1H, dd, J=2.2, 1.0 Hz), 8.67(1H, d, J=7.6 Hz), 10.26(1H, s).

MS(ESI: negative)m/z: 452[(M−H)$^−$, Cl$^{35}$], 454[(M−H)$^−$, Cl$^{37}$].

Referential Example 438

2-chloro-N-(5-methylpyridin-2-yl)acetamide hydrochloride

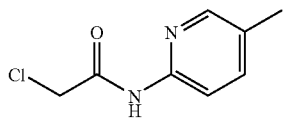

The method described in Referential Example 425 was performed by use of 2-amino-5-picoline, whereby the title compound was obtained.

$^1$H-NMR(DMSO-$d_6$)δ: 2.30(3H, s), 4.40(2H, s), 7.83(1H, d, J=8.8 Hz), 7.91(1H, d, J=8.5 Hz), 8.21(1H, s), 11.40(1H, s).

Referential Example 439

S-{2-[(5-methylpyridin-2-yl)amino]-2-oxoethyl}thiosulfuric acid sodium salt

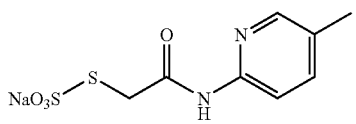

The method described in Referential Example 353 was performed by use of the compound obtained in Referential Example 438, whereby the title compound was obtained.

$^1$H-NMR(DMSO-$d_6$)δ: 2.24(3H, s), 3.74(2H, s), 7.59(1H, d, J=8.5 Hz), 7.94(1H, d, J=8.3 Hz), 8.12(1H, s), 10.26(1H, s).

Referential Example 440

(1R,2S,5S)-5-[(dimethylamino)carbonyl]-2-{[2-[(5-methylpyridin-2-yl)amino]-2-oxoethanethioyl}amino)cyclohexylcarbamic acid tert-butyl ester

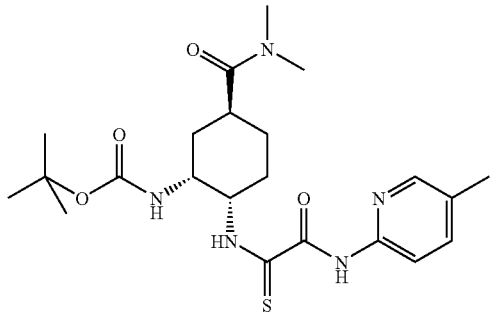

The method described in Referential Example 427 was performed by use of the compound obtained in Referential Example 144 and the compound obtained in Referential Example 439, whereby the title compound was obtained.

$^1$H-NMR(CDCl$_3$)δ: 1.46(9H, s), 1.60-2.10(5H, m), 2.15-2.35(1H, m), 2.31(3H, s), 2.60-2.80(1H, m), 2.95(3H, s), 3.07(3H, s), 4.30-4.45(2H, m), 4.65-4.85(1H, m), 7.54(1H, dd, J=8.5, 2.0 Hz), 8.06(1H, br.d), 8.18(1H, s), 9.70-9.90(1H, m), 10.48(1H, s).

MS(ESI)m/z: 464 (M+H)$^+$.

Referential Example 441

(3R,4S)-4-{[2-(4-chloroanilino)-2-oxoethanethioyl] amino}-1-(2-methoxyacetyl)piperidin-3-ylcarbamic acid tert-butyl ester

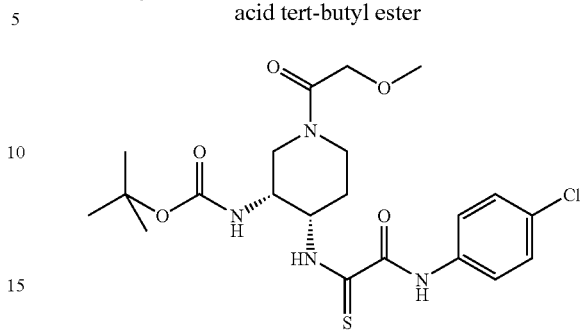

In a manner similar to that described in Referential Example 214, the compound obtained in Referential Example 220 was deprotected by catalytic reduction. In a manner similar to that described in Referential Example 427, the resultant amine was condensed with the compound obtained in Referential Example 351, whereby the title compound was obtained. $^1$H-NMR(CDCl$_3$)δ: 1.46(9H, s), 1.59-1.84(1H, m), 2.10-2.33(1H, m), 2.68-2.81(0.7H, m), 2.94-2.04(0.3H, m), 3.15-3.40(1H, m), 3.44(3H, s), 3.91-4.32(4H, m), 4.45-4.58(1H, m), 4.60-4.77(1H, m), 5.15-5.30(0.3H, br), 5.84-5.94(0.7H, m), 7.32(2H, d, J=8.6 Hz), 7.61(2H, d, J=8.6 Hz), 10.12(1H, s), 10.19-10.33(1H, br).

MS(FAB)m/z: 485[(M+H)$^+$, Cl$^{35}$], 487[(M+H)$^+$, Cl$^{37}$].

Referential Example 442

(1S,2R,4S)-2-[(tert-butoxycarbonyl)amino]-4-[(dimethylamino)carbonyl]cyclohexylcarbamic acid 9H-fluoren-9-ylmethyl ester

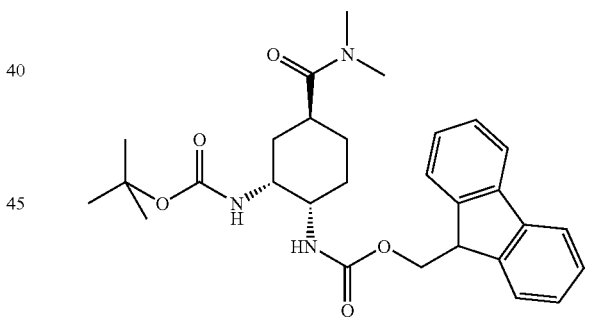

The compound (856 mg) obtained in Referential Example 144 was dissolved in acetone (10 mL). To the solution, pentafluorophenylcarbamic acid 9-fluorenylmethyl ester (1.34 g) and sodium hydrogencarbonate (302 mg) were added, followed by stirring at room temperature for 2.5 hours. Pentafluorophenylcarbamic acid 9-fluorenylmethyl ester (609 mg) and sodium hydrogencarbonate (151 mg) were further added thereto, and the resulting mixture was heated under reflux for 30 minutes. The solvent was distilled away under reduced pressure. The residue was purified by silica gel flash column chromatography (SI-40B, methylene chloride: methanol=93:7), to thereby give the title compound (1.47 g).

$^1$H-NMR(CDCl$_3$)δ: 1.45(9H, s), 1.30-2.05(6H, m), 2.63 (1H, br.s), 2.94(3H, s), 3.04(3H, s), 3.69(1H, br.s), 4.15(1H, br.s), 4.21(1H, br.s), 4.37(2H, br.s), 4.73(1H, br.s), 5.41(1H, br.s), 7.29(2H, t, J=7.3 Hz), 7.39(2H, t, J=7.3 Hz), 7.57(2H, d, J=7.3 Hz), 7.75(2H, d, J=7.3 Hz).

MS(ESI)m/z: 508 (M+H)$^+$.

Referential Example 443

(1S,2R,4S)-2-[(tert-butoxycarbonyl)amino]-4-[(dimethylamino)carbothioyl]cyclohexylcarbamic acid 9H-fluoren-9-ylmethyl ester

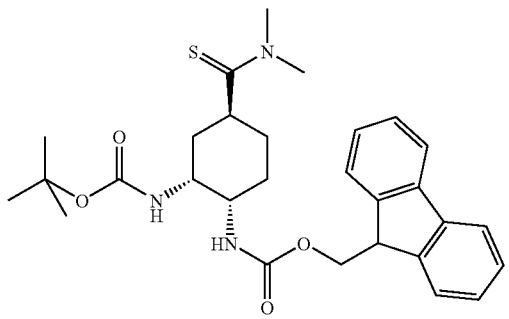

The compound (1.26 g) obtained in Referential Example 442 was dissolved in toluene (50 mL), and Lawson reagent (1.00 g) was added thereto. The resultant mixture was stirred at 60° C. for 1 hour. Insoluble material was removed through filtration, and the solvent was distilled away under reduced pressure. The residue was dissolved in ethanol (50 mL), and di-tert-butyl dicarbonate (541 mg) and sodium hydrogencarbonate (208 mg) were added thereto. The resultant mixture was stirred at room temperature for 1 hour. The solvent was distilled away under reduced pressure. The residue was purified by silica gel flash column chromatography (hexane:ethyl acetate=1:1→methylene chloride:methanol=9:1), whereby the title compound (609 mg) was obtained as a white solid.

$^1$H-NMR(CDCl$_3$)δ: 1.43(9H, s), 1.43-2.10(6H, m), 2.92 (1H, br.s), 3.31(3H, s), 3.47(3H, s), 3.74(1H, br.s), 4.09-4.19 (2H, m), 4.38(2H, br.s), 4.75(1H, br), 5.29(1H, br.s), 7.29(2H, t, J=7.3 Hz), 7.38(2H, t, J=7.3 Hz), 7.55(2H, br.s), 7.75(2H, d, J=7.3 Hz).

Referential Example 444

(1R,2S,5S)-2-({2-[(5-chloropyridin-2-yl)amino]-2-oxoacetyl]amino}-5-[(dimethylamino)carbothioyl] cyclohexylcarbamic acid tert-butyl ester

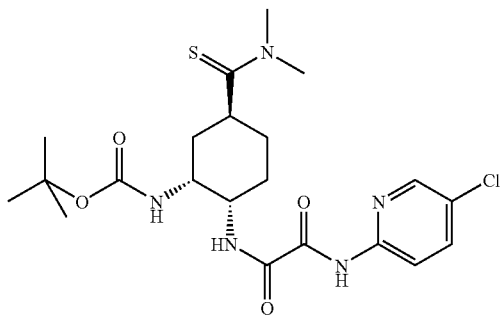

The compound (1.11 g) obtained in Referential Example 443 was dissolved in N,N-dimethylformamide (30 mL), and piperazine (3.0 mL) was added thereto, followed by stirring at room temperature for 15 minutes. The solvent was distilled away under reduced pressure, and ethyl acetate and water were added to the residue for partitioning the mixture.

The aqueous layer was extracted twice with ethyl acetate. The organic layers were combined, followed by drying over sodium sulfate anhydrate. The solvent was distilled away under reduced pressure. In a manner similar to that described in Referential Example 91, the residue was condensed with the compound obtained in Referential Example 433, to thereby give the title compound (629 mg).

$^1$H-NMR(CDCl$_3$)δ: 1.45(9H, s), 1.48-2.23(6H, m), 2.98 (1H, br.s), 3.36(3H, s), 3.49(3H, s), 3.98-4.04(1H, m), 4.22-4.25(1H, m), 4.75(1H, br.s), 7.70(1H, dd, J=8.8, 2.7 Hz), 7.85(1H, br.s), 8.16(1H, d, J=8.8 Hz), 8.30(1H, d, J=2.7 Hz), 9.73(1H, s).

MS(FAB)m/z: 484[(M+H)$^+$, Cl$^{35}$], 486[(M+H)$^+$, Cl$^{37}$].

Referential Example 445

$N^1$-{(1S,2R,4S)-2-amino-4-[(dimethylamino)carbothioyl]cyclohexyl}-$N^2$-(5-chloropyridin-2-yl) ethanediamide dihydrochloride

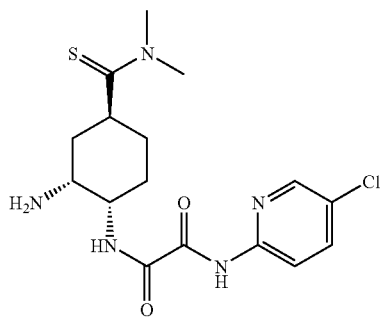

The method described in Referential Example 69 was performed by use of the compound obtained in Referential Example 444, whereby the title compound was obtained.

$^1$H-NMR(DMSO-d$_6$)δ: 1.66-2.11(6H, m), 3.38(3H, s), 3.42(3H, s), 3.52(1H, br.s), 3.75(1H, br.s), 3.88(1H, br.s), 8.03-8.09(2H, m), 8.21(3H, br.s), 8.48(1H, d, J=2.2 Hz), 9.06 (1H, d, J=6.8 Hz), 10.34(1H, s).

MS(FAB)m/z: 384[(M+H)$^+$, Cl$^{35}$], 386[(M+H)$^+$, Cl$^{37}$].

Referential Example 446

(3R,4S)-3-[(tert-butoxycarbonyl)amino]-1-(2-methoxyacetyl)piperidin-4-ylcarbamic acid 9H-fluoren-9-ylmethyl ester

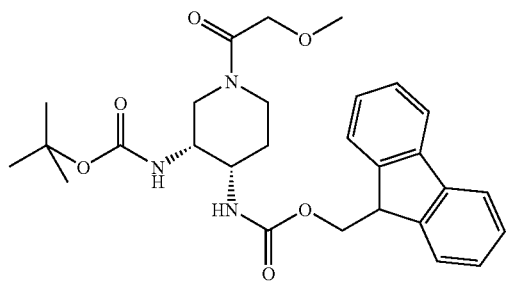

In a manner similar to that described Referential Example 214, the compound obtained in Referential Example 220 was deprotected by catalytic reduction to obtain the corresponding amine. The method described in Referential Example 442 was performed by use of the resultant amine, whereby the title compound was obtained.

$^1$H-NMR(CDCl$_3$)δ: 1.48(9H, s), 1.55-1.80(1H, m), 1.92-2.20(1H, m), 2.70-3.35(2H, m), 3.44(3H, s), 3.77-4.90(10H, m), 5.29-5.45(0.6H, br), 5.75-5.90(0.4H, br), 7.26-7.34(2H, m), 7.39(2H, t, J=7.6 Hz), 7.55-7.65(2H, m), 7.76(2H, d, J=7.6 Hz).

MS(FAB)m/z: 510 (M+H)$^+$.

Referential Example 447

(3R,4S)-3-[(tert-butoxycarbonyl)amino]-1-(2-methoxyethanethioyl)piperidin-4-ylcarbamic acid 9H-fluoren-9-ylmethyl ester

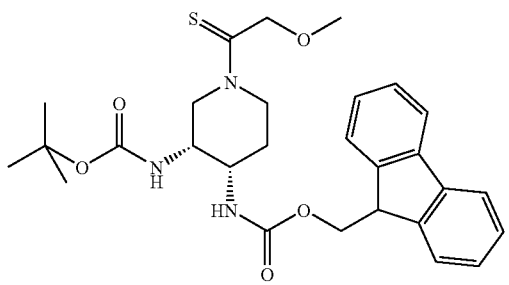

The method described in Referential Example 443 was performed by use of the compound obtained in Referential Example 446, whereby the title compound was obtained.

$^1$H-NMR(CDCl$_3$)δ: 1.48(9H, s), 1.50-1.80(1H, m), 2.07-2.23(1H, m), 3.04-3.18(0.5H, m), 3.25-3.37(0.5H, m), 3.44 (1.5H, s), 3.47(1.5H, s), 3.88-4.75(9H, m), 5.00-5.70(2H, br), 5.98-6.23(1H, br), 7.26-7.29(2H, m), 7.39(2H, t, J=7.3 Hz), 7.55-7.68(2H, m), 7.77(2H, d, J=7.3 Hz).

MS(FAB)m/z: 526 (M+H)$^+$.

Referential Example 448

(3R,4S)-4-({2-[(5-chloropyridin-2-yl)amino]-2-oxoacetyl}amino)-1-(2-methoxyethanethioyl)piperidin-3-ylcarbamic acid tert-butyl ester

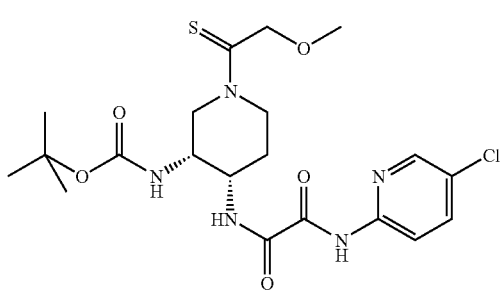

In a manner similar to that described in Referential Example 444, the compound obtained in Referential Example 447 was treated with diethylamine for deprotection. The deprotected compound was condensed with the compound obtained in Referential Example 433, whereby the title compound was obtained.

$^1$H-NMR(CDCl$_3$)δ: 1.47(9H, s), 1.73-1.88(1H, m), 2.07-2.22(1H, m), 3.05-3.15(1H, m), 3.27-3.42(1H, m), 3.45(1H, s), 3.48(2H, s), 4.10-4.54(5H, m), 5.12-5.21(0.3H, br), 5.48-5.56(0.7H, br), 5.61-5.74(1H, br), 7.70(1H, dd, J=8.5, 2.0 Hz), 8.21(1H, d, J=8.5 Hz), 8.31(1H, d, J=2.0 Hz), 8.42-8.60 (1H, br), 9.72(1H, br.s).

MS(ESI)m/z: 486[(M+H)$^+$, Cl$^{35}$], 488[(M+H)$^+$, Cl$^{37}$].

Referential Example 449

(1S,3R,4S)-4-{[(allyloxy)carbonyl]amino}-3-[(tert-butoxycarbonyl)amino]cyclohexanecarboxylic acid ethyl ester

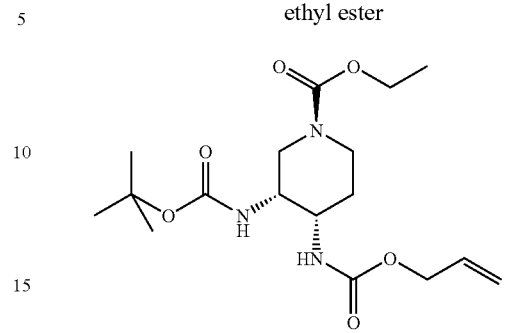

The compound (10.0 g) obtained in Referential Example 141 was dissolved in a mixture of tetrahydrofuran (40 mL) and ethanol (40 mL), and 10% palladium carbon catalyst (10.2 g) was added to the solution. The resultant mixture was stirred in a hydrogen atmosphere at room temperature for 63 hours. The catalyst was removed through filtration through celite, and the filtrate was concentrated under reduced pressure. The resultant colorless oil was dissolved in tetrahydrofuran (25 mL). Pyridine (2.3 mL) was added thereto at room temperature. To the mixture, allyl chloroformate (2.70 mL) was added dropwise at 0° C., followed by stirring for 20 minutes. Ice and ethyl acetate were added to the reaction mixture, followed by stirring for 5 minutes. The resultant mixture was acidified with 10% aqueous citric acid. The organic layer was washed with saturated aqueous sodium hydrogencarbonate and saturated aqueous sodium chloride, followed by drying over sodium sulfate anhydrate. The resultant mixture was concentrated under reduced pressure to obtain the residue. The residue was purified by silica gel column chromatography (methylene chloride:methanol=40:1), to thereby give the title compound (6.03 g).

$^1$H-NMR(CDCl$_3$)δ: 1.25(3H, t, J=7.1 Hz), 1.31-1.40(1H, m), 1.45(9H, s), 1.51-1.65(1H, m), 1.72-1.86(1H, m), 1.89-2.10(3H, m), 2.25-2.50(1H, br), 3.63-3.72(1H, m), 4.03-4.15 (1H, br), 4.13(2H, q, J=7.1 Hz), 4.49-4.59(2H, m), 4.60-4.75 (1H, m), 5.20(1H, d, J=10.5 Hz), 5.22-5.32(1H, br), 5.29(1H, dd, J=17.1, 1.7 Hz), 5.85-5.97(1H, m).

MS(ESI)m/z: 371(M+H)$^+$.

Referential Example 450

(1S,3R,4S)-4-{[(allyloxy)carbonyl]amino}-3-[(tert-butoxycarbonyl)amino]cyclohexanecarboxylic acid

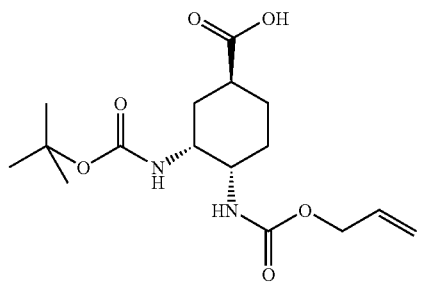

The method described in Referential Example 142 was performed by use of the compound obtained in Referential Example 449, whereby the title compound was obtained.

$^1$H-NMR(CDCl$_3$)δ: 1.35-2.15(6H, br), 1.45(9H, s), 2.35-2.65(1H, br), 3.65-3.75(1H, m), 4.00-4.15(1H, br), 4.48-4.63

(2H, m), 4.63-4.80(1H, br), 5.03-5.33(1H, br), 5.21(1H, d, J=10.3 Hz), 5.29(1H, dd, J=17.1, 1.5 Hz), 5.86-5.97(1H, m).
MS(ESI)m/z: 343(M+H)+.

Referential Example 451

(1S,3R,4S)-4-{[(allyloxy)carbonyl]amino}-3-[(tert-butoxycarbonyl)amino]cyclohexanecarboxylic acid 2,2,2-trichloroethyl ester

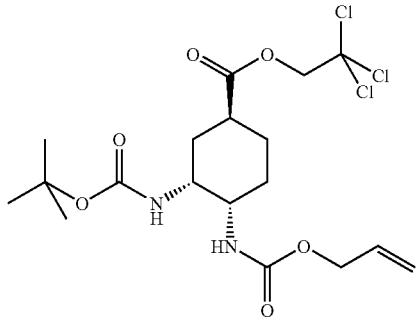

To a solution of the compound (5.93 g) obtained in Referential Example 450 in N,N-dimethylformamide (40 mL), were added 1-(3-dimethylaminopropyl)-3-ethylcarbodiimide hydrochloride (4.99 g), 1-hydroxybenzotriazole (2.81 g), 2,2,2-trichloroethanol (4.15 mL), and 4-dimethylaminopyridine (4.15 g). The resultant mixture was stirred at room temperature for 1.5 hours. The reaction mixture was concentrated under reduced pressure, and ethyl acetate and water were added to the residue. The aqueous layer was extracted with ethyl acetate. The organic layers were combined, followed by washing with 10% aqueous citric acid, saturated aqueous sodium hydrogencarbonate, and saturated aqueous sodium chloride. The resultant mixture was dried over sodium sulfate anhydrate, followed by concentrating under reduced pressure. The residue was purified by silica gel column chromatography (methylene chloride:methanol=40:1), to thereby give the title compound (8.88 g).
$^1$H-NMR(CDCl$_3$)δ: 1.35-1.50(1H, m), 1.46(9H, s), 1.55-1.73(1H, m), 1.77-2.22(4H, m), 2.50-2.65(1H, br), 3.66-3.75(1H, m), 4.05-4.20(1H, m), 4.50-4.60(2H, m), 4.60-4.80(1H, br), 4.71(1H, d, J=11.8 Hz), 4.77(1H, d, J=11.8 Hz), 5.18-5.34(1H, br), 5.20(1H, d, J=10.5 Hz), 5.30(1H, dd, J=17.4, 1.0 Hz), 5.86-5.97(1H, m).
MS(ESI)m/z: 473[(M+H)+, 3×Cl$^{35}$], 475[(M+H)+, 2×Cl$^{35}$, Cl$^{37}$], 477[(M+H)+, Cl$^{35}$, 2×Cl$^{37}$].

Referential Example 452

(1S,3R,4S)-4-amino-3-[(tert-butoxycarbonyl)amino]cyclohexanecarboxylic acid 2,2,2-trichloroethyl ester

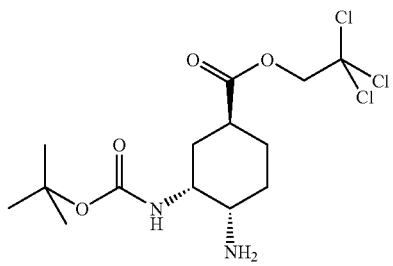

To a solution of the compound (8.83 g) obtained in Referential Example 451 in tetrahydrofuran (35 mL), were added diethylamine (20 mL) and tetrakis(triphenylphosphine)palladium (719 mg). The mixture was stirred in an argon atmosphere at room temperature for 2.5 hours. 10% Aqueous citric acid (250 mL) was added to the reaction mixture to acidify, and diethyl ether was added thereto. The aqueous layer was washed with diethyl ether, and sodium carbonate was added thereto to basify, followed by extracting with methylene chloride. Methylene chloride layer was washed with saturated aqueous sodium chloride. The resultant mixture was dried over sodium sulfate anhydrate, followed by concentrating under reduced pressure to thereby give the title compound (4.35 g).
$^1$H-NMR(CDCl$_3$)δ: 1.20-1.50(3H, m), 1.46(9H, s), 1.58-1.69(1H, m), 1.70-1.81(2H, m), 1.98-2.07(1H, m), 2.22-2.31(1H, m), 2.55-2.66(1H, m), 2.97-3.04(1H, m), 3.79-3.93(1H, br), 4.70(1H, d, J=12.0 Hz), 4.75-4.85(1H, br), 4.78(1H, d, J=12.0 Hz).
MS(ESI)m/z: 389[(M+H)+, 3×Cl$^{35}$], 391[(M+H)+, 2×Cl$^{35}$, Cl$^{37}$], 393[(M+H)+, Cl$^{35}$, 2×Cl$^{37}$].

Referential Example 453

(1S,3R,4S)-3-[(tert-butoxycarbonyl)amino]-4-({2-[(5-chloropyridin-2-yl)amino]-2-oxoacetyl}amino)cyclohexanecarboxylic acid 2,2,2-trichloroethyl ester

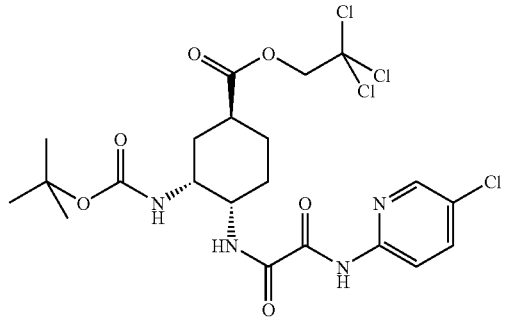

In a manner similar to that described in Referential Example 91, the compound obtained in Referential Example 452 was condensed with the compound obtained in Referential Example 433, whereby the title compound was obtained.
$^1$H-NMR(CDCl$_3$)δ: 1.46(9H, s), 1.50-1.63(1H, m), 1.65-1.79(2H, m), 1.87-2.08(2H, m), 2.10-2.22(2H, m), 2.50-2.70(1H, br), 3.94-4.02(1H, m), 4.17-4.30(1H, br), 4.73(1H, d, J=12.0 Hz), 4.78(1H, d, J=12.0 Hz), 7.70(1H, dd, J=8.8, 2.4 Hz), 7.90-8.07(1H, br), 8.18(1H, d, J=8.8 Hz), 8.31(1H, d, J=2.4 Hz), 9.72(1H, br.s).
MS(ESI)m/z: 571[(M+H)+, 3×Cl$^{35}$], 573[(M+H)+, 2×Cl$^{35}$, Cl$^{37}$], 575[(M+H)+, Cl$^{35}$, 2×Cl$^{37}$].

Referential Example 454

2-[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]-2-(methoxyimino)acetic acid methyl ester

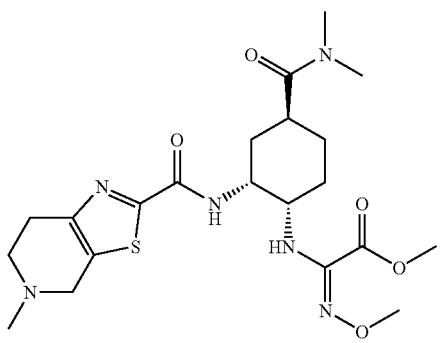

The compound (435 mg) obtained in Referential Example 144 and 2-(methoxyimino)-2-(methylsulfonyl)acetic acid methyl ester (WO99/67209) (233 mg) were dissolved in tetrahydrofuran (5 mL). Triethylamine (332 μL) was added thereto, followed by stirring at 70° C. overnight. The reaction mixture was concentrated under reduced pressure. Methylene chloride and saturated aqueous sodium hydrogencarbonate were added thereto for partitioning the mixture. The oil layer was dried over sodium sulfate anhydrate. After concentration, the residue was purified by silica gel chromatography (methylene chloride:methanol=91:9), to thereby give the title compound (111 mg).

$^1$H-NMR(CDCl$_3$)δ: 1.42-2.10(6H, m), 2.52(3H, s), 2.70-3.10(11H, m), 3.71(2H, br.s), 3.83(3H, s), 3.84(3H, s), 4.22-4.35(1H, m), 4.55-4.65(1H, m), 5.16(1H, d, J=8.8 Hz), 7.25-7.30(1H, m).

MS(ESI)m/z: 481(M+H)$^+$.

Referential Example 455

N$^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N$^2$-{5-[2-(trimethylsilyl)ethynyl]pyridin-2-yl}ethanediamide

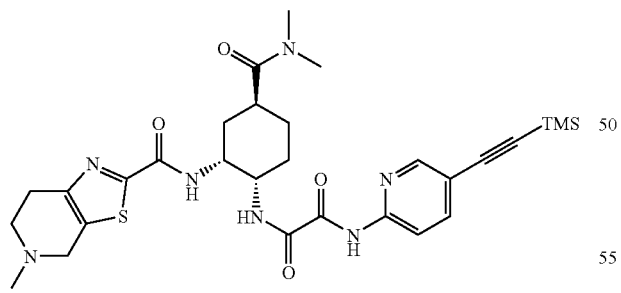

The compound (658 mg) obtained in Example 204 was dissolved in tetrahydrofuran (10 mL), N,N-dimethylformamide (10 mL), and triethylamine (20 mL). Triphenylphosphine (87 mg), trimethylsilylacetylene (471 μL), and palladium acetate (50 mg) were added thereto. The resultant mixture was stirred in an argon atmosphere at 80° C. for 14 hours. The reaction mixture was filtered through celite, followed by washing with methylene chloride throughly. Water was added to the filtrate for partitioning the mixture. The organic layer was decolored with activated carbon (about 3 g), followed by drying over sodium sulfate anhydrate. The resultant mixture was filtered and the solvent was distilled away under reduced pressure. The residue was purified by silica gel column chromatography (methylene chloride:methanol=93:7), to thereby give the title compound (360 mg).

$^1$H-NMR(CDCl$_3$)δ: 0.25(9H, s), 1.66-2.13(6H, m), 2.52(3H, s), 2.78-2.96(8H, m), 3.05(3H, s), 3.70(1H, d, J=15.4 Hz), 3.73(1H, d, J=15.4 Hz), 4.08-4.15(1H, m), 4.66-4.69(1H, m), 7.42(1H, d, J=8.4 Hz), 7.77(1H, dd, J=8.4, 2.1 Hz), 8.03(1H, d, J=8.1 Hz), 8.13(1H, d, J=8.8 Hz), 8.43(1H, d, J=2.1 Hz), 9.74(1H, s).

MS(ESI)m/z: 610 (M+H)$^+$.

Referential Example 456

5-methyl-5,6-dihydro-4H-thieno[2,3-c]pyrrole-2-carboxylic acid methyl ester

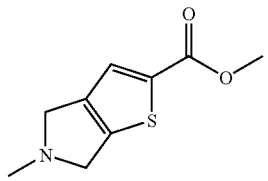

4,5-Bis(chloromethyl)-2-thiophenecarboxylic acid methyl ester (D. J. Zwanenburg and Hans Wynberg, J. Org. Chem., 34, 333-340, (1969)) (520 mg) was dissolved in acetonitrile (600 mL). Methylamine (40% methanol solution, 722 μL) was added thereto, followed by stirring at room temperature for 3 days. The solvent was distilled away under reduced pressure. The residue was purified by silica gel column chromatography (methylene chloride:methanol=1:0→19:1), to thereby give the title compound (176 mg).

$^1$H-NMR(CDCl$_3$)δ: 2.63(3H, s), 3.82-3.83(2H, m), 3.86(3H, s), 3.97-3.99(2H, m), 7.51(1H, s).

MS(ESI)m/z: 198(M+H)$^+$.

Referential Example 457

2-chloro-N-(6-chloropyridazin-3-yl)acetamide

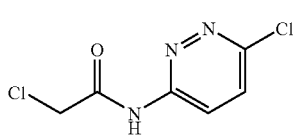

3-Amino-6-chloropyridazine (10.4 g) was dissolved in N,N-dimethylformamide (200 mL). Chloroacetyl chloride (7.48 mL) was added thereto, and the resultant mixture was stirred at room temperature for 1 hour. The solvent was distilled away under reduced pressure, and ethyl acetate and saturated aqueous sodium hydrogencarbonate were added to the residue. The precipitated solid was recoverd by filtration, followed by washing with ethyl acetate and water, to thereby give the title compound (9.39 g).

$^1$H-NMR(CDCl$_3$)δ: 4.30(2H, s), 7.56(1H, d, J=9.3 Hz), 8.51(1H, d, J=9.3 Hz), 9.68(1H, br.s).

Referential Example 458

S-{2-[(6-chloropyridazin-3-yl)amino]-2-oxoethyl}thiosulfuric acid sodium salt

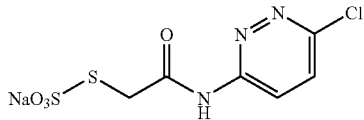

The method described in Referential Example 353 was performed by use of the compound obtained in Referential Example 457, whereby the title compound was obtained.
$^{1}$H-NMR(DMSO-$d_6$)δ: 3.84(2H, s), 7.87(1H, d, J=9.4 Hz), 8.36(1H, d, J=9.4 Hz), 11.21(1H, br.s).

Referential Example 459

(1R,2S,5S)-2-({2-[(6-chloropyridazin-3-yl)amino]-2-oxoethanethioyl}amino)-5-[(dimethylamino)carbonyl]cyclohexylcarbamic acid tert-butyl ester

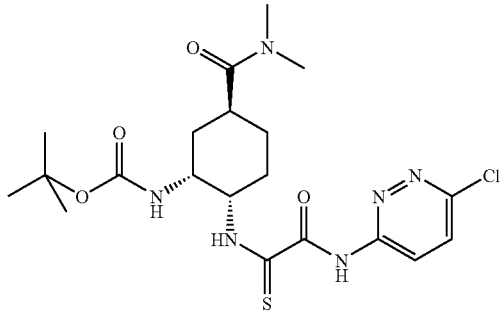

The method described in Referential Example 427 was performed by use of the compound obtained in Referential Example 458 and the compound obtained in Referential Example 144, whereby the title compound was obtained.
$^{1}$H-NMR(CDCl$_3$)δ: 1.35-1.58(10H, m), 1.71-1.80(1H, m), 1.86-1.94(2H, m), 2.09(1H, br.s), 2.30(1H, br.s), 2.96(3H, s), 3.08(3H, s), 4.36(2H, br.s), 4.79(1H, br.s), 5.30(1H, br.s), 7.54(1H, d, J=9.0 Hz), 8.47(1H, d, J=9.0 Hz), 10.03(1H, br.s), 11.03(1H, s).

Referential Example 460

(1S,3R,4S)-3-amino-4-({2-[(6-chloropyridazin-3-yl)amino]-2-oxoethanethioyl}amino)-N,N-dimethylcyclohexanecarboxamide hydrochloride

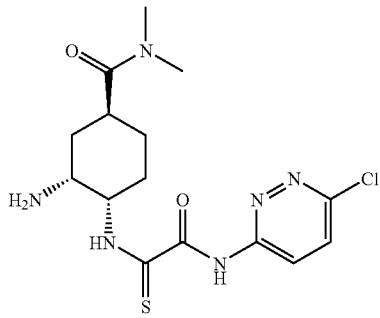

The method described in Referential Example 69 was performed by use of the compound obtained in Referential Example 459, whereby the title compound was obtained.

$^{1}$H-NMR(DMSO-$d_6$)δ: 1.45-1.53(1H, m), 1.73-1.85(3H, m), 2.03-2.07(1H, m), 2.15-2.24(1H, m), 2.82(3H, s), 3.08(3H, s), 3.32-3.37(1H, m), 4.06(1H, br.s), 4.39(1H, br.s), 8.01(1H, d, J=9.3 Hz), 8.37(1H, d, J=9.3 Hz), 8.43(3H, br.s), 11.11(1H, d, J=6.6 Hz), 11.37(1H, s).
MS(FAB)m/z: 385[(M+H)$^+$, Cl$^{35}$], 387[(M+H)$^+$, Cl$^{37}$].

Referential Example 461

2-chloro-N-(6-chloropyridin-3-yl)acetamide

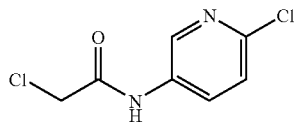

The method described in Referential Example 457 was performed by use of 5-amino-2-chloropyridine, whereby the title compound was obtained.
$^{1}$H-NMR(CDCl$_3$)δ: 4.22(2H, s), 7.34(1H, d, J=8.5 Hz), 8.14(1H, dd, J=8.5, 2.7 Hz), 8.30(1H, br.s), 8.45(1H, d, J=2.7 Hz).

Referential Example 462

S-{2-[(6-chloropyridin-3-yl)amino]-2-oxoethyl}thiosulfuric acid sodium salt

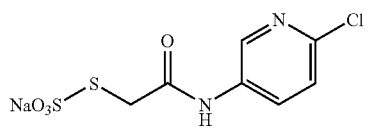

The method described in Referential Example 353 was performed by use of the compound obtained in Referential Example 461, whereby the title compound was obtained.
$^{1}$H-NMR(DMSO-$d_6$)δ: 3.77(2H, s), 7.47(1H, d, J=8.8 Hz), 8.04(1H, dd, J=8.8, 2.7 Hz), 8.57(1H, d, J=2.7 Hz), 10.51(1H, s).

Referential Example 463

(1R,2S,5S)-2-({2-[(6-chloropyridin-3-yl)amino]-2-oxoethanethioyl}amino)-5-[(dimethylamino)carbonyl]cyclohexylcarbamic acid tert-butyl ester

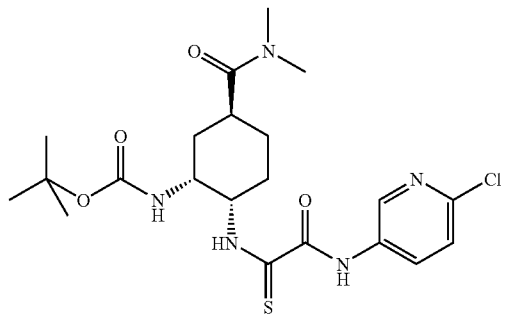

The method described in Referential Example 427 was performed by use of the compound obtained in Referential Example 462 and the compound obtained in Referential Example 144, whereby the title compound was obtained.

¹H-NMR(CDCl₃)δ: 1.46(9H, br.s), 1.60-2.23(6H, m), 2.68 (1H, br.s), 2.96(3H, s), 3.08(3H, s), 4.34-4.38(2H, m), 4.78 (1H, m), 7.33(1H, d, J=8.5 Hz), 8.09(1H, br.s), 8.63(1H, s), 9.91(1H, br.s), 10.24(1H, s).
MS(ESI)m/z: 506[(M+Na)⁺, Cl³⁵], 508[(M+Na)⁺, Cl³⁷].

Referential Example 464

(1S,3R,4S)-3-amino-4-({2-[(6-chloropyridin-3-yl)amino]-2-oxoethanethioyl}amino)-N,N-dimethylcyclohexanecarboxamide hydrochloride

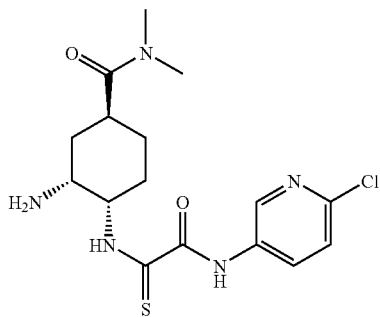

The method described in Referential Example 69 was performed by use of the compound obtained in Referential Example 463, whereby the title compound was obtained.
¹H-NMR(DMSO-d₆)δ: 1.46-1.49(1H, m), 1.79-1.81(3H, m), 1.99-2.03(1H, m), 2.14-2.16(1H, m), 2.82(3H, s), 3.06 (3H, s), 3.25-3.28(1H, m), 3.99(1H, br.s), 4.30-4.60(1H, br), 7.55(1H, d, J=8.7 Hz), 8.26(1H, dd, J=8.7, 2.4 Hz), 8.38(3H, br.s), 8.85(1H, d, J=2.4 Hz), 10.90(1H, d, J=6.8 Hz), 11.07 (1H, s).
MS(FAB)m/z: 384[(M+H)⁺, Cl³⁵], 386[(M+H)⁺, Cl³⁷].

Referential Example 465

2'-aminosulfonyl-1,1'-biphenyl-4-carboxylic acid

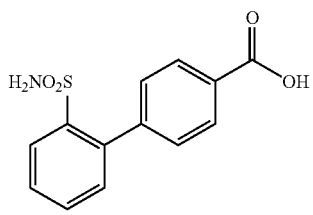

2-Bromobenzenesulfonamide (800 mg) and 4-carboxyphenyl boronic acid (563 mg) were suspended in a solvent mixture of toluene (5 mL) and water (5 mL). To the reaction mixture, tetrakis(triphenylphosphine)palladium (392 mg) and sodium carbonate anhydrate (1.08 g) were sequentially added, and the resultant mixture was heated under reflux overnight. The resultant mixture was cooled to room temperature, and diethyl ether and water were added thereto for partitioning the mixture. The organic layer was extracted twice with water. All the resultant aqueous layers were combined together, and 12N aqueous hydrochloric acid was added thereto to acidfy. The mixture was concentrated to about 20 mL under reduced pressure, and the precipitated colorless powder was recovered by filtration, followed by drying under reduced pressure, to thereby give the title compound (539 mg).
MS(EI)m/z: 277M⁺.

Referential Example 466

2-[(5-methylpyridin-2-yl)amino]-2-oxoacetic acid methyl ester

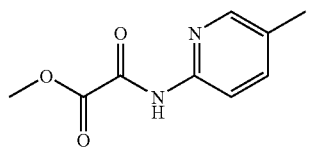

The method described in Referential Example 242 was performed by use of 2-amino-5-methylpyridine and methyl chlorooxoacetate, whereby the title compound was obtained.
¹H-NMR(CDCl₃)δ: 2.33(3H, s), 3.98(3H, s), 7.57(1H, dd, J=8.4, 2.0 Hz), 8.14(1H, d, J=8.4 Hz), 8.17(1H, d, J=2.0 Hz).
MS(ESI)m/z: 195(M+H)⁺.

Referential Example 467

2-[(5-methylpyridin-2-yl)amino]-2-oxoacetic acid lithium salt

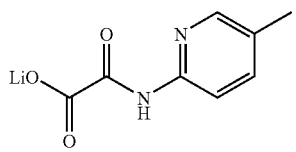

The method described in Referential Example 266 was performed by use of the compound obtained in Referential Example 466, whereby the title compound was obtained.
¹H-NMR(DMSO-d₆)δ: 2.25(3H, s), 7.63(1H, d, J=8.2 Hz), 8.00(1H, d, J=8.2 Hz), 8.15(1H, s), 10.00(1H, br.s).
MS(FAB)m/z: 181(M-Li+2H)⁺.

Referential Example 468

2-oxo-2-(4-toluidino)acetic acid methyl ester

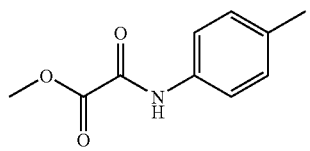

The method described in Referential Example 242 was performed by use of p-toluidine and methyl chlorooxoacetate, whereby the title compound was obtained.
MS(ESI)m/z: 194 (M+H)⁺.

Referential Example 469

(1R,2S,5S)-5-[(dimethylamino)carbonyl]-2-{[2-oxo-2-(4-toluidino)acetyl]amino}cyclohexylcarbamic acid tert-butyl ester

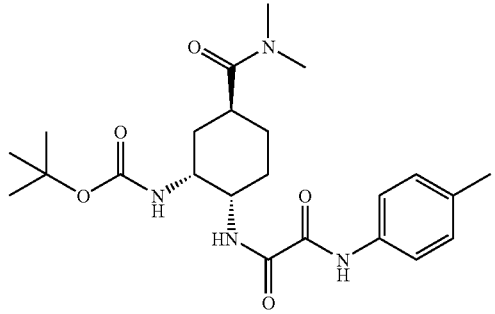

In a manner similar to that described in Referential Example 91, a lithium salt of a carboxylic acid produced by hydrolyzing the ester described in Referential Example 468 was condensed with the compound obtained in Referential Example 144, whereby the title compound was obtained.
MS(ESI)m/z: 447(M+H)+.

Referential Example 470

4-bromomethyl-3-chlorothiophene-2-carboxylic acid methyl ester

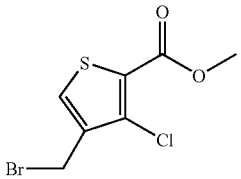

3-Chloro-4-methyl-2-thiophenecarboxylic acid methyl ester (3.81 g) was dissolved in carbon tetrachloride (40 mL). To the solution, N-bromosuccinimide (3.56 g) and α,α'-azobisisobutyronitrile (200 mg) were added, and the mixture was heated under reflux for 2.5 hours. The insoluble material was removed through filtration, and the filtrate was concentrated under reduced pressure. The residue was purified by silica gel column chromatography (ethyl acetate hexane=1:19→1:9), to thereby give the title compound (2.92 g) as a yellow oil.
$^1$H-NMR(CDCl$_3$)δ: 3.91(3H, s), 4.46(2H, s), 7.59(1H, s).
MS(ESI)m/z: 269(M+H)+.

Referential Example 471

4-{[(tert-butoxycarbonyl)(methyl)amino]methyl}-3-chloro-2-thiophenecarboxylic acid

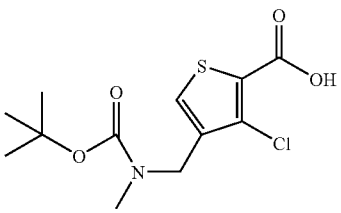

To a solution of methylamine (2 mol/L tetrahydrofuran solution, 27 mL) in tetrahydrofuran (30 mL), a solution of the compound (2.92 g) obtained in Referential Example 470 in tetrahydrofuran (50 mL) was added dropwise over 30 minutes. The resultant mixture was stirred at room temperature for 1 hour. The reaction mixture was concentrated in about half under reduced pressure, and di-tert-butyl dicarbonate (3.0 g) was added thereto, followed by stirring at room temperature for 75 minutes. The reaction mixture was concentrated under reduced pressure, and ethyl acetate was added to the residue. The resultant mixture was allowed to stand overnight. Water was added to the resultant mixture for partitioning the mixture. The resultant organic layer was dried over magnesium sulfate anhydrate. The solvent was distilled away under reduced pressure. The residue was purified by silica gel column chromatography (hexane:ethyl acetate=99:1→19:1), to thereby give a colorless oil (4.0 g). To a solution of the oil (4.0 g) in methanol (35 mL), were added water (5 mL) and sodium hydroxide (1.2 g), followed by stirring at room temperature for 30 minutes. The reaction mixture was concentrated under reduced pressure, ice water was added to the residue, and the resultant mixture was acidified with concentrated hydrochloric acid. The mixture was extracted with ethyl acetate, and the extract was dried over magnesium sulfate anhydrate. The solvent was distilled away under reduced pressure, and the residue was crystallized from hexane, to thereby give the title compound (2.67 g) as a colorless powder.
$^1$H-NMR(CDCl$_3$)δ: 1.48(9H, s), 2.74(3H, br.s), 4.14(2H, br.s), 7.40(0.5H, br.s), 7.48(0.5H, br.s).

Referential Example 472

(1R,2S)-2-({2-[(5-chloropyridin-2-yl)amino]-2-oxoacetyl}amino)cyclohexylcarbamic acid tert-butyl ester

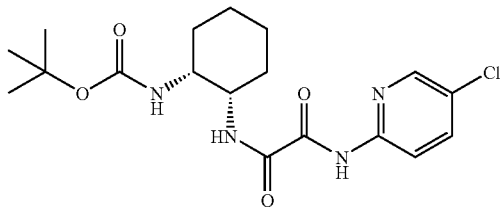

In a manner similar to that described in Referential Example 68, (1R,2S)-2-aminocyclohexylcarbamic acid tert-butyl ester (WO01/74774) was condensed with the compound obtained in Referential 266, whereby the title compound was obtained.
$^1$H-NMR(CDCl$_3$)δ: 1.35-1.90(8H, m), 1.46(9H, s), 3.97 (1H, br.s), 4.00-4.12(1H, m), 4.73-4.82(1H, m), 7.69(1H, dd, J=8.8, 2.5 Hz), 7.90(1H, br. s), 8.17(1H, dd, J=8.8, 0.55 Hz), 8.29(1H, dd, J=2.5, 0.55 Hz), 9.76(1H, br.s).
MS(ESI)m/z: 397(M+H)+.

Referential Example 473

5-[(4-methylphenyl)sulfonyl]-5,6,7,8-tetrahydro-4H-thiazolo[5,4-c]azepin-2-ylamine

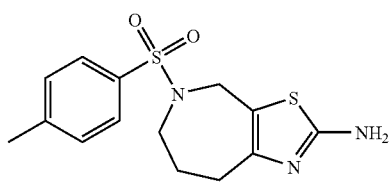

3-Bromo-1-[(4-methylphenyl)sulfonyl]-4-azepanone (6.54 g) (J. Chem. Soc. Perkin Trans., 1995, Vol. 1, 2355) was dissolved in N,N-dimethylformamide (100 mL). Thiourea (1.44 g) was added thereto, followed by stirring at 60° C. overnight. The solvent was distilled away under reduced pressure. To the residue, methylene chloride (100 mL) and saturated aqueous sodium hydrogencarbonate (100 mL) were added for partitioning the mixture. The aqueous layer was extracted with methylene chloride (100 mL). All the organic layers were combined, followd by drying over magnesium sulfate anhydrate. The solvent was distilled away under reduced pressure. Ethyl acetate (100 mL) was added to the residue, and the precipitated light yellow powder was recovered by filtration to thereby give 5-[(4-methylphenyl)sulfonyl]-5,6,7,8-tetrahydro-4H-thiazolo[5,4-c]azepin-2-ylfolmamide (1.86 g) in a crude form. The filtrate was concentrated under reduced pressure. The residue was purified by silica gel chromatography (methanol:methylene chloride=1:19), to thereby give a mixture (4.01 g) of the titile compound and 5-[(4-methylphenyl)sulfonyl]-5,6,7,8-tetrahydro-4H-thiazolo[5,4-c]azepin-2-ylformamide. This mixture and the above crude product were combined. The resultant mixture was suspended in dioxane (50 mL), 3N HCl (50 mL) was added thereto, and the resultant mixture was heated under reflux for 1 hour. The solvent was distilled away under reduced pressure. Methylene chloride (250 mL) and saturated aqueous sodium carbonate (200 mL) were added thereto for partitioning the mixture. The oil layer was dried over magnesium sulfate anhydrate, and the solvent was distilled away. Diisopropyl ether (100 mL) was added to the residue. The precipitated light yellow powder was recovered by filtration, to thereby give the title compound (4.47 g).

$^1$H-NMR(CDCl$_3$)δ: 1.75-1.87(2H, m), 2.40(3H, s), 2.62 (2H, t, J=5.7 Hz), 3.53(2H, t, J=5.7 Hz), 4.37(2H, s), 4.73(2H, br.s), 7.25(2H, d, J=8.5 Hz), 7.61(2H, d, J=8.5 Hz).

MS(ESI)m/z: 324 (M+H)$^+$.

Referential Example 474

5,6,7,8-tetrahydro-4H-thiazolo[5,4-c]azepin-2-ylamine hydrobromic acid salt

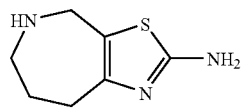

The method described in Referential Example 291 was performed by use of the compound obtained in Referential Example 473, whereby the title compound was obtained.

$^1$H-NMR(DMSO-d$_6$)δ: 1.95(2H, br.s), 2.70-2.90(2H, m), 3.38(2H, br.s), 4.56(2H, br.s), 9.07(3H, br.s).

MS(ESI)m/z: 170(M+H)$^+$.

Referential Example 475

5-methyl-5,6,7,8-tetrahydro-4H-thiazolo[5,4-c]azepin-2-ylamine

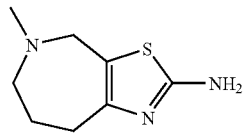

The compound (2.73 g) obtained in Referential Example 474 was suspended in methanol. To the suspension, under ice cooling, were added triethylamine (2.30 mL), acetic acid (453 µL), 37% aqueous formaldehyde (668 µL), and sodium cyanoborohydride (544 mg). The mixture was stirred at room temperature overnight. Saturated aqueous sodium hydrogencarbonate (20 mL) was added thereto, and the resultant mixture was concentrated to dryness. The residue was purified by silica gel chromatography (methanol:methylene chloride=3: 17). To the resultant crude product, methanol (100 mL) and sodium carbonate anhydrate (20 g) were added, followed by stirring at room temperature for 30 minutes. The insoluble material was removed through filtration. The filtrate was concentrated under reduced pressure. Methylene chloride (250 mL) and methanol (50 mL) were added to the residue, and the insoluble materaial was removed through filtration. The filtrate was concentrated under reduced pressure. The resultant pale yellow powder was washed with acetonitrile (100 mL), to thereby give the title compound (1.23 g).

$^1$H-NMR(CDCl$_3$)δ: 1.70-1.85(2H, s), 2.38(3H, s), 2.77 (2H, t, J=5.6 Hz), 2.97(2H, t, J=5.6 Hz), 3.65(2H, s), 4.68(2H, br.s).

MS(ESI)m/z: 184(M+H)$^+$.

Referential Example 476

2-bromo-5-methyl-5,6,7,8-tetrahydro-4H-thiazolo[5,4-c]azepine

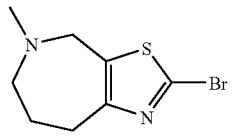

The compound (1.13 g) obtained in Referential Example 475 was suspended in water (10 mL). To the suspension, 48% hydrobromic acid aqueous solution (7.0 mL) was addd, followed by stirring under ice cooling. To the reaction mixture, aqueous solution (3.0 mL) containig sodium nitrite (639 mg) was carefully added dropwise. After dropping, this suspension was stirred at room temperature overnight. Under ice cooling, Methylene chloride (100 mL) was added to the reaction mixture, and under stirring, the resultant mixture was neutralized with saturated aqueous sodium carbonate. After partition, the aqueous layer was extracted with methylene chloride (100 mL). The organic layers were combined, followed by drying over sodium sulfate anhydrate. The residue was purified by silica gel chromatography (methanol:methylene chloride=3:47), to thereby give the title compound (582 mg) as a pale orange oil.

$^1$H-NMR(CDCl$_3$)δ: 1.70-1.85(2H, s), 2.38(3H, s), 2.95-3.05(4H, m), 3.79(2H, s).

MS(ESI)m/z: 247(M+H)$^+$.

Referential Example 477

5-methyl-5,6,7,8-tetrahydro-4H-thiazolo[5,4-c]azepine-2-carboxylic acid lithium salt

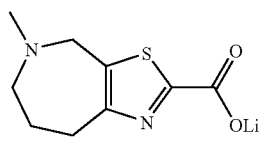

The method described in Referential Example 10 was performed by use of the compound obtained in Referential Example 476, whereby the title compound was obtained.

$^1$H-NMR(DMSO-d$_6$)δ: 1.65(2H, br.s), 2.23(3H, s), 2.80-2.97(4H, m), 3.75(2H, s).

Referential Example 478

4,4,5-trimethyl-5,6-dihydro-4H-pyrrolo[3,4-d]thiazol-2-ylamine

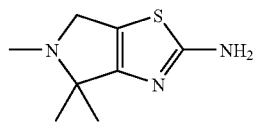

1,2,2-Trimethylpyrrolidin-3-one (1.00 g) was dissolved in cyclohexane (5 mL). Pyrrolidine (1.31 mL) and p-toluenesulfonic acid monohydrate (7.48 mg) were sequentially added thereto, and the mixture was heated under reflux for 3 days, and allowed to cool to room temperature. The resultant mixture was concentrated under reduced pressure to thereby give a crude product of 1,2,2-trimethyl-3-(pyrrolidine-1-yl)-2,5-dihydro-1H-pyrrole (972 mg). To the product dissolved in dimethylformamide (10 mL), formamidine disulfide hydrochloride (1.20 g) was added, followed by stirring at room temperature for 4 days. The resultant mixture was concentrated under reduced pressure. Methanol (50 mL) and sodium carbonate anhydrate (20 g) were added to the residue, and the resultant mixture was stirred at room temperature for 1 hour. The insoluble material was removed through filtration, followed by washing with methanol. The filtrate was concentrated under reduced pressure. The residue was purified by silica gel chromatography (methanol methylene chloride=1:99→1:9), to thereby give the title compound (580 mg).

$^1$H-NMR(CDCl$_3$)δ: 1.25(6H, s), 2.48(3H, s), 3.83(2H, s), 4.83(2H, br.s).
MS(ESI)m/z: 184(M+H)$^+$.

Referential Example 479

2-bromo-4,4,5-trimethyl-5,6-dihydro-4H-pyrrolo[3,4-d]thiazole

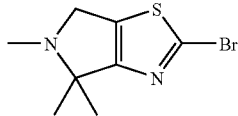

The method described in Referential Example 476 was performed by use of the compound obtained in Referential Example 478, whereby the title compound was obtained.
$^1$H-NMR(CDCl$_3$)δ: 1.30(6H, s), 2.49(3H, s), 3.91(2H, s).
MS(ESI)m/z: 247(M+H)$^+$.

Referential Example 480

2,3-dihydro-1H-pyrrolo[3,4-c]pyridine-6-carboxylic acid

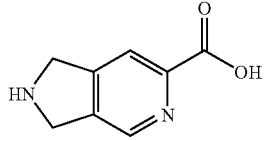

The method described in Referential Example 291 was performed by use of 2-[(4-methylphenyl)sulfonyl]-2,3-dihydro-1H-pyrrolo[3,4-c]pyridine-6-carboxylic acid ethyl ester (Chem. Commun., 2001, 1102), whereby the title compound was obtained.
$^1$H-NMR(CDCl$_3$)δ: 4.60-4.75(4H, m), 8.17(1H, s), 8.78 (1H, s), 9.69(2H, br.s).
MS(ESI)m/z: 165(M+H)$^+$.

Referential Example 481

2-(tert-butoxycarbonyl)-2,3-dihydro-1H-pyrrolo[3,4-c]pyridine-6-carboxylic acid lithium salt

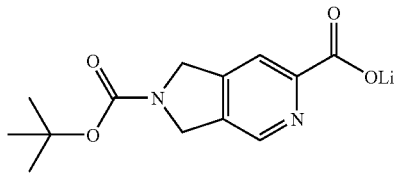

The compound (1.66 g) obtained in Referential Example 480 was dissolved in methanol (100 mL). Thionyl chloride (3.0 mL) was added thereto, and the mixture was heated under reflux overnight, followed by allowing to cool to room temperature. The solvent was distilled away under reduced pressure, and methylene chloride (100 mL) and saturated aqueous sodium hydrogencarbonate (100 mL) were added thereto for partitioning the mixture. To the aqueous layer, methylene chloride (100 mL) and di-tert-butyl dicarbonate (1.40 g) were added. The resultant mixture was sirred at room temperature for 2 hours. After partition, the organic layer was dried over magnesium sulfate anhydrate, and the solvent was distilled away under reduced pressure. Hexane (50 mL) was added to the residue, and the precipitated light yellow powder was recovered by filtration to thereby give a crude product of 2-(tert-butoxycarbonyl)-1,3-dihydro-2H-pyrrolo[3,4-c]pyridine-6-carboxylic acid methyl ester (602 mg). The crude product (564 mg) was dissolved in methanol (10 mL), and 1N aqueous lithium hydroxide (2.20 mL) was added thereto, followed by stirring at room temperature overnight. The resultant mixture was distilled away under reduced pressure, to thereby give the title compound (591 mg) as a light brown solid.

$^1$H-NMR(DMSO-d$_6$)δ: 1.46(9H, br.s), 4.63(2H, br.s), 4.65 (2H, br.s), 7.93(0.5H, br.s), 7.96(0.5H, br.s), 8.40(1H, br.s).
MS(ESI)m/z: 265(M-Li+2H)$^+$.

Referential Example 482

5-(pyridin-4-yl)pyrimidine-2-carboxylic acid methyl ester

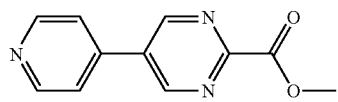

In a manner similar to that described in Referential Example 237, a compound was obtained from pyridin-4-yl boronic acid and 5-bromopyrimidine-2-carboxylic acid, and the resultant compound was esterified with methanol through use of thionyl chloride, whereby the title compound was obtained.
$^1$H-NMR(CDCl$_3$)δ: 4.12(3H, s), 7.57(2H, d, J=6.1 Hz), 8.83(2H, d, J=6.1 Hz), 9.18(2H, s).
MS(ESI)m/z: 216(M+H)$^+$.

Referential Example 483

5-(pyridin-4-yl)pyrimidine-2-carboxylic acid lithium salt

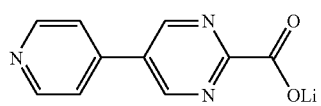

The method described in Referential Example 322 was performed by use of the compound obtained in Referential Example 482, whereby the title compound was obtained.
$^1$H-NMR(DMSO-d$_6$)δ: 7.85(2H, d, J=6.0 Hz), 8.69(2H, d, J=6.0 Hz), 9.12(2H, s).
MS(ESI)m/z: 202(M-Li+2H)$^+$.

Referential Example 484

2'-methyl-[1,1'-biphenyl]-4-carbaldehyde

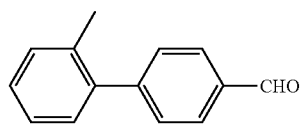

The method described in Referential Example 237 was performed by use of 2-bromotoluene and 4-formylbenzene boronic acid, whereby the title compound was obtained.
$^1$H-NMR(CDCl$_3$)δ: 2.28(3H, s), 7.20-7.33(4H, m), 7.50 (2H, d, J=8.2 Hz), 7.94(2H, d, J=8.2 Hz), 10.07(1H, s).
MS(ESI)m/z: 197(M+H)$^+$.

Referential Example 485

2'-methyl-[1,1'-biphenyl]-4-carboxylic acid

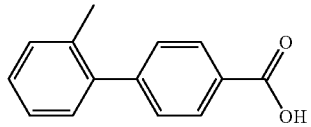

The compound (1.51 g) obtained in Referential Example 484 was suspended in water (100 mL). To the suspension were sequentially added tert-butanol (10 mL), 2-methyl-2-butene (20 mL), sodium chlorite (3.67 g), and sodium dihydrogen phosphate dihydrate (3.62 g). The resultant mixture was stirred at room temperature overnight. To the reaction mixture, diisopropyl ether (200 mL) was added for partitioning the mixture. The organic layer was washed with 3N HCl (50 mL), followed by drying over magnesium sulfate anhydrate. The solvent was distilled away under reduced pressure. The residue was washed with hexane, to thereby give the title compound (1.43 g) as a colorless powder.

$^1$H-NMR(CDCl$_3$)δ: 2.29(3H, s), 7.20-7.35(4H, m), 7.65 (2H, d, J=8.1 Hz), 8.18(2H, d, J=8.1 Hz).

MS(ESI)m/z: 213(M+H)$^+$.

Referential Example 486

2'-methyl-[1,1'-biphenyl]-4-carboxylic acid methyl ester

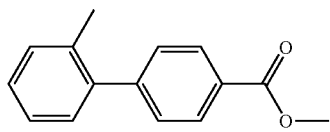

The compound (1.42 g) obtained in Referential Example 485 was suspended in methanol. To the suspension, thionyl chloride (1 mL) was added, and the resultant mixture was heated under reflux for 2 hours, followed by allowing to cool to room temperature. Saturated aqueous sodium hydrogencarbonate (100 mL) and methylene chloride (100 mL) were added to the reaction mixture for partitioning the mixture. The organic layer was dried over sodium sulfate anhydrate, and the solvent was distilled away under reduced pressure, to thereby give the title compound (1.51 g) as a colorless oil.

$^1$H-NMR(CDCl$_3$)δ: 2.26(3H, s), 3.94(3H, s), 7.20-7.35 (4H, m), 7.40(2H, d, J=7.8 Hz), 8.08(2H, d, J=7.8 Hz).

MS(ESI)m/z: 227(M+H)$^+$.

Referential Example 487

2'-[(dimethylamino)methyl]-[1,1'-biphenyl]-4-carboxylic acid methyl ester

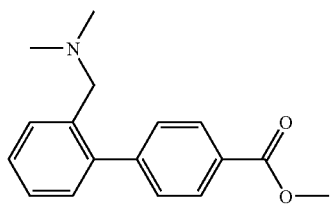

The compound (663 mg) obtained in Referential Example 486 was dissolved in 1,2-dichloroethane (30 mL). To the solution, N-bromosuccinimide (521 mg) and 2,2'-azobisisobutyronitrile (48.1 mg) were added, and the resultant mixture was heated under reflux for 1 hour. After the completion of reaction, the mixture was cooled to 0° C., and dimethylamine (40% aqueous solution, 0.99 mL) was added thereto, followed by stirring at room temperature for 3 days. Water (100 mL) and methylene chloride (100 mL) were added to this mixture for partitioning the mixture. The organic layer was dried over sodium sulfate anhydrate. The solvent was distilled away under reduced pressure. The residue was purified by silica gel chromatography (methanol:methylene chloride=1:25), to thereby give the title compound (607 mg) as a colorless oil.

$^1$H-NMR(CDCl$_3$)δ: 2.13(6H, s), 3.31(2H, s), 3.95(3H, s), 7.23(1H, dd, J=7.4, 1.5 Hz), 7.31(1H, dt, J=1.5, 7.4 Hz), 7.37(1H, dt, J=1.5, 7.4 Hz), 7.46(2H, d, J=8.2 Hz), 7.52(1H, dd, J=7.4, 1.5 Hz), 8.07(2H, d, J=8.2 Hz).

MS(ESI)m/z: 270 (M+H)$^+$.

Referential Example 488

2'-[(dimethylamino)methyl]-[1,1'-biphenyl]-4-carboxylic acid lithium salt

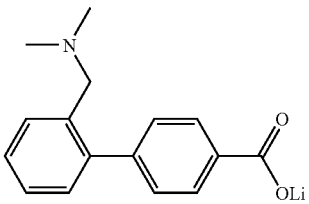

The method described in Referential Example 322 was performed by use of the compound obtained in Referential Example 487, whereby the title compound was obtained.

$^1$H-NMR(DMSO-d$_6$)δ: 2.06(6H, s), 3.29(2H, s), 7.20-7.38 (5H, m), 7.49(1H, d, J=7.3 Hz), 7.88(2H, d, J=8.0).

MS(ESI)m/z: 256(M-Li+2H)$^+$.

Referential Example 489

4-[4-(methoxycarbonyl)phenyl]-2-methyl-1-pyridine N-oxide

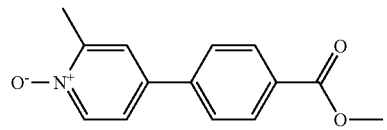

The method described in Referential Example 239 was performed by use of 4-(2-methylpyridin-4-yl)benzoic acid methyl ester (Japanese Patent Application Laid-Open (kokai) No. 2000-143623), whereby the title compound was obtained.

$^1$H-NMR(CDCl$_3$)δ: 2.60(3H, s), 3.96(3H, s), 7.42(1H, dd, J=6.8, 2.7 Hz), 7.53(1H, d, J=2.7 Hz), 7.66(2H, d, J=8.2 Hz), 8.14(2H, d, J=8.2 Hz), 8.33(1H, d, J=6.8 Hz).

MS(FAB)m/z: 244 (M+H)$^+$.

Referential Example 490

4-{2-[(acetyloxy)methyl]pyridin-4-yl}benzoic acid methyl ester

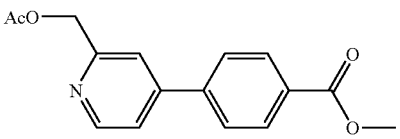

The compound (980 mg) obtained in Referential Example 489 was dissolved in acetic anhydrate (25 mL), and the solution was stirred at 130° C. for 30 minutes. The resultant mixture was cooled to 90° C., and methanol (50 mL) was added thereto, followed by stirring for 1 hour. Methylene chloride (50 mL) and saturated aqueous sodium hydrogencarbonate (150 mL) were added to the reaction mixture. Solid sodium hydrogencarbonate was added thereto till the resultant mixture became basic, followed by stirring for 3 hours and partitioning. The aqueous layer was extracted with methylene chloride (2×50 mL). The organic layers were combined, and dried over sodium sulfate anhydrate. The solvent was distilled away under reduced pressure. The residue was purified by silica gel column chromatography (methylene chloride: methanol=40:1→10:1), and further purified by medium-pressure silica gel column chromatography (hexane ethyl acetate=2:1→1:1), to thereby give the title compound (749 mg) as a white solid.

$^1$H-NMR(CDCl$_3$)δ: 2.19(3H, s), 3.96(3H, s), 5.29(2H, s), 7.47(1H, dd, J=5.1, 1.7 Hz), 7.57-7.60(1H, m), 7.70(2H, d, J=8.5 Hz), 8.15(2H, d, J=8.5 Hz), 8.68(1H, d, J=5.1 Hz).

MS(ESI)m/z: 286(M+H)$^+$.

Referential Example 491

4-(2-{[(tert-butoxycarbonyl)amino]methyl}pyridin-4-yl)benzoic acid methyl ester

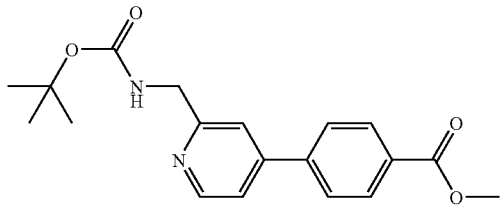

The compound (532 mg) obtained in Referential Example 490 was dissolved in tetrahydrofuran (4.0 mL), and water (1.0 mL) and lithium hydroxide (137 mg) were added to the solution at room temperature, followed by stirring for 24 hours. Tetrahydrofuran was distilled away under reduced pressure, and water (4.0 mL) and 1N hydrochloric acid (5.65 mL) were added thereto. The resultant solid was recovered by filtration, followed by washing with water and drying to thereby give a white solid (400 mg). A portion of the solid (272 mg) was suspended in tetrahydrofuran (10 mL), and methanol (2.0 mL) and trimethylsilyldiazomethane (2.0M hexane solution, 890 μL) were added thereto at room temperature, followed by stirring for 1 hour. The reaction mixture was concentrated under reduced pressure. To a methylene chloride solution (10 mL) of the resultant solid were added ethyl acetate (5.0 mL), trimethylamine hydrochloride (12 mg), methanesulfonyl chloride (140 μL), and triethylamine (252 μL) at room temperature. The resultant mixture was stirred for 3 hours, and saturated aqueous sodium hydrogencarbonate (20 mL) and methylene chloride (20 mL) were added thereto for partitioning the mixture. The aqueous layer was extracted with methylene chloride (2×15 mL). The organic layers were combined, and dried over sodium sulfate anhydrate. The solvent was distilled away under reduced pressure. The resultant red-purple oil was dissolved in N,N-dimethylformamide (5.0 mL). Sodium azide (155 mg) was added thereto at room temperature, followed by stirring for 1 hour. Water (100 mL) and methylene chloride (30 mL) were added to the resultant mixture for partitioning the mixture. The aqueous layer was extracted with methylene chloride (3×20 mL). The organic layers were combined, and dried over sodium sulfate anhydrate, followed by adding dioxane (5.0 mL) thereto. The resultant mixture was concentrated to about 5 mL under redeced pressure. To the resultant brown mixture were added tetrahydrofuran (5.0 mL), di-tert-butyl dicarbonate (400 mg), and 10% palladium-carbon (100 mg). The resultant mixture was stirred in a hydrogen atmosphere at room temperature for 14 hours. The reaction mixture was filtered, and the filtrate was concentrated under reduced pressure. The residue was purified by silica gel column chromatography (methylene chloride:acetone=20:1), to thereby give the title compound (270 mg) as a light yellow oil.

$^1$H-NMR(CDCl$_3$)δ: 1.48(9H, s), 3.96(3H, s), 4.52(2H, d, J=5.4 Hz), 4.94(0.5H, br.s), 5.59(0.5H, br.s), 7.42(1H, dd, J=5.1, 1.7 Hz), 7.51(1H, br.s), 7.69(2H, d, J=8.3 Hz), 8.15 (2H, d, J=8.3 Hz), 8.61(1H, d, J=5.1 Hz).

MS(ESI)m/z: 343 (M+H)$^+$.

Referential Example 492

1-(phenylsulfonyl)pyperidine-4-carboxylic acid ethyl ester

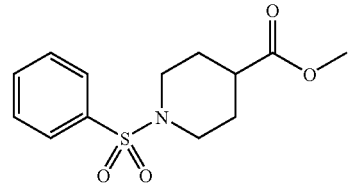

To isonipecotic acid ethyl ester (1.08 mL) dissolved in tetrahydrofuran (10 mL), triethylamine (1.40 mL) was added, and benzenesulfonyl chloride (1.02 mL) was added thereto at 0° C. The resultant mixture was stirred at room temerature for 21 hours. Ice was added to the mixture, followed by stirring for 10 minutes. Ethyl acetate and 0.5N hydrochloric acid were added thereto to thereby give two layers. The organic layer was washed with saturated aqueous sodium hydrogencarbonate and saturated aqueous sodium chloride. The resultant mixture was dried over sodium sulfate anhydrate, and concentrated under reduced pressure. The residue was purified by silica gel column chromatography (hexane:ethyl acetate=4: 1→2:1), to thereby give the title compound (1.66 g) as a white solid.

$^1$H-NMR(CDCl$_3$)δ: 1.21(3H, t, J=7.1 Hz), 1.76-1.87(2H, m), 1.92-2.01(2H, m), 2.20-2.29(1H, m), 2.49(2H, dt, J=2.9, 11.4 Hz), 3.59-3.67(2H, m), 4.10(2H, q, J=7.1 Hz), 7.51-7.63 (3H, m), 7.74-7.78(2H, m).

MS(ESI)m/z: 298 (M+H)$^+$.

Referential Example 493

1-(phenylsulfonyl)pyperidine-4-carboxylic acid

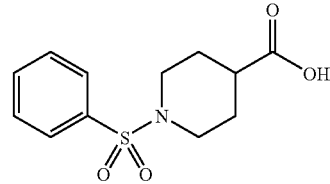

The method described in Referential Example 274 was performed by use of the compound obtained in Referential Example 492, whereby the title compound was obtained.

$^1$H-NMR(CDCl$_3$)δ: 1.74-1.90(2H, m), 1.90-2.04(2H, m), 2.23-2.33(1H, m), 2.39-2.54(2H, m), 3.58-3.72(2H, m), 7.48-7.64(3H, m), 7.67-7.80(2H, m).

MS(ESI)m/z: 270(M+H)$^+$.

Referential Example 494

1-(4-fluorobenzoyl)pyperidine-4-carboxylic acid ethyl ester

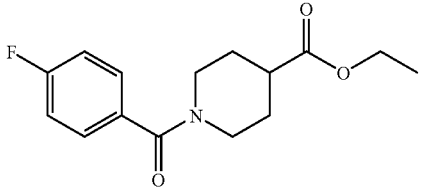

The method described in Referential Example 492 was performed by use of isonipecotic acid ethyl ester and p-fluorobenzoyl chloride, whereby the title compound was obtained.
$^1$H-NMR(CDCl$_3$)δ: 1.27(3H, t, J=7.1 Hz), 1.60-2.10(4H, br), 2.54-2.62(1H, m), 2.95-3.13(2H, m), 3.55-3.90(1H, br), 4.16(2H, q, J=7.1 Hz), 4.30-4.70(1H, br), 7.09(2H, t, J=8.8 Hz), 7.41(2H, dd, J=8.8, 5.4 Hz).
MS(ESI)m/z: 280(M+H)$^+$.

Referential Example 495

1-(4-fluorobenzoyl)piperidine-4-carboxylic acid

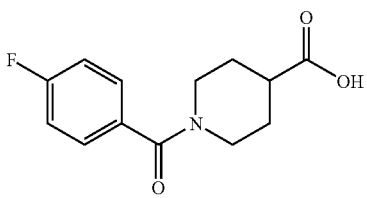

The method described in Referential Example 274 was performed by use of the compound obtained in Referential Example 494, whereby the title compound was obtained.
$^1$H-NMR(CDCl$_3$)δ: 1.60-2.20(4H, br), 2.57-2.68(1H, m), 2.98-3.20(2H, m), 3.55-4.00(1H, br), 4.25-4.65(1H, br), 7.09 (2H, t, J=8.5 Hz), 7.40(2H, dd, J=8.5, 5.4 Hz).
MS(ESI)m/z: 252 (M+H)$^+$.

Referential Example 496

4-(pyrrolidin-1-ylcarbonyl)benzoic acid methyl ester

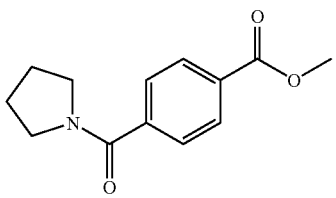

The method described in Referential Example 492 was performed by use of pyrrolidine and terephthalic acid monomethyl chloride, whereby the title compound was obtained.
$^1$H-NMR(CDCl$_3$)δ: 1.85-1.93(2H, m), 1.94-2.01(2H, m), 3.38(2H, t, J=6.6 Hz), 3.66(2H, t, J=6.6 Hz), 3.94(3H, s), 7.57(2H, d, J=8.6 Hz), 8.07(2H, d, J=8.6 Hz).
MS(ESI)m/z: 234(M+H)$^+$.

Referential Example 497

4-(pyrrolidin-1-ylcarbonyl)benzoic acid

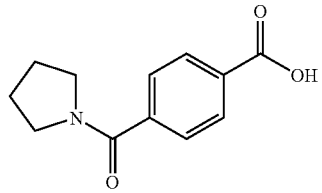

The method described in Referential Example 274 was performed by use of the compound obtained in Referential Example 496, whereby the title compound was obtained.
$^1$H-NMR(CDCl$_3$)δ: 1.85-2.03(4H, m), 3.43(2H, t, J=6.6 Hz), 3.67(2H, t, J=6.6 Hz), 7.61(2H, d, J=8.6 Hz), 8.14(2H, d, J=8.6 Hz).
MS(ESI)m/z: 220(M+H)$^+$.

Referential Example 498

4-(pyrrolidin-1-ylmethyl)benzoic acid methyl ester

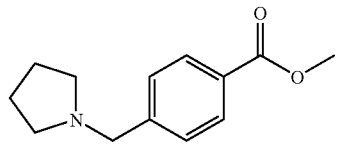

The method described in Referential Example 212 was performed by use of the compound obtained in Referential Example 496, whereby the title compound was obtained.
$^1$H-NMR(CDCl$_3$)δ: 1.75-1.84(4H, m), 2.47-2.56(4H, m), 3.37(2H, s), 3.90(3H, s), 7.41(2H, d, J=8.3 Hz), 7.98(2H, d, J=8.3 Hz).
MS(ESI)m/z: 220(M+H)$^+$.

Referential Example 499

(1S,2R,4S)-2-[(tert-butoxycarbonyl)amino]-4-[(methylamino)carbonyl]cyclohexylcarbamic acid 9H-fluoren-9-ylmethyl ester

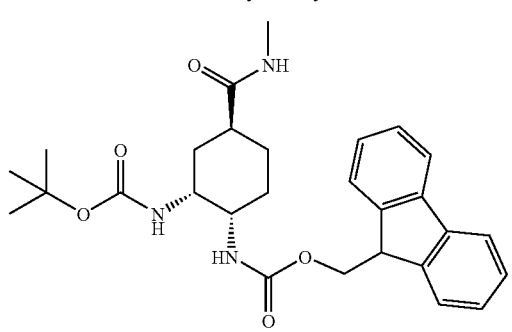

The compound (823 mg) obtained in Referential Example 436 was dissolved in methanol (20 mL), 10% palladium carbon catalyst (117 mg) was added thereto, and the resultant mixture was stirred in a hydrogen atmosphere at room temperature for 3 hours. The catalyst was removed through filtration through a glass filter. The filtrate was concentrated under reduced pressure. To the resultant colorless viscous oil (622 mg) dissolved in 1,2-dimethoxyethane (15 mL) were added saturated aqueous sodium hydrogencarbonate (5 mL), water (2 mL), and fluoren-9-ylmethyl succinimidylcarbonate (867 mg). The resultant mixture was stirred at room temperature for 13 hours. The reaction mixture was diluted with ethyl acetate, followed by adding water thereto to thereby give two layers. The organic layer was washed with saturated aqueous sodium chloride, the resultant mixture was dried over sodium sulfate anhydrate, and concentrated under reduced pressure.

Ethyl acetate was added to the residue, and the mixture was slurry-washed. A white powder was recovered by filtration. The mother liquid was also concentrated under reduced pressure, and was slurry-washed with diethyl ether. A white powder was recovered by filtration. The respective powder was dissolved in ethyl acetate, followed by mixing. The solvent was distilled away under reduced pressure, followed by drying under vacuum pump, to thereby give the title compound (939 mg) as a white powder.

$^1$H-NMR(CDCl$_3$)δ: 1.46(9H, br.s), 1.60-1.74(1H, m), 1.78-1.92(2H, m), 1.92-2.07(2H, m), 2.10-2.26(1H, m), 2.81 (3H, d, J=4.9 Hz), 3.62-3.77(1H, br), 3.85-4.63(5H, m), 5.30-5.67(2H, br), 7.24-7.33(2H, m), 7.39(2H, t, J=7.6 Hz), 7.58 (2H, br.d, J=7.1 Hz), 7.76(2H, d, J=7.6 Hz).

MS(ESI)m/z: 394(M-COOtBu)$^+$.

Referential Example 500

(1S,2R,4S)-2-[(tert-butoxycarbonyl)amino]-4-[(methylamino)carbothioyl]cyclohexylcarbamic acid 9H-fluoren-9-ylmethyl ester

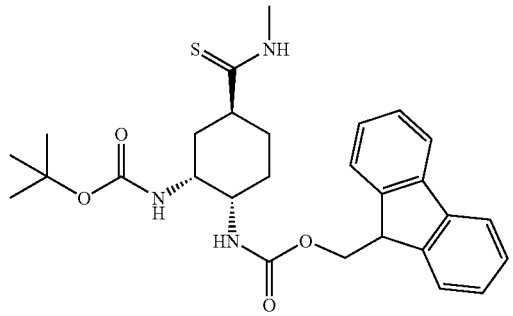

The method described in Referential Example 443 was performed by use of the compound obtained in Referential Example 499, whereby the title compound was obtained.

$^1$H-NMR(CDCl$_3$)δ: 1.46(9H, br.s), 1.55-2.10(6H, m), 2.45-2.72(1H, br), 3.17(3H, d, J=4.4 Hz), 3.65-3.77(1H, br), 3.78-3.88(0.5H, m), 4.00-4.65(4H, br), 4.75-5.25(0.5H, br), 5.30-5.60(0.5H, br), 6.85-7.00(0.5H, br), 7.25-7.34(2H, m), 7.39(2H, t, J=7.6 Hz), 7.42-7.53(0.5H, br), 7.58(2H, br.d, J=6.6 Hz), 7.75(2H, d, J=7.6 Hz), 7.80-7.90(0.5H, br).

MS(ESI)m/z: 410(M-COOtBu)$^+$.

Referential Example 501

(1R,2S,5S)-2-({2-[(5-chloropyridin-2-yl)amino]-2-oxoacetyl}amino)-5-[(methylamino)carbothioyl] cyclohexylcarbamic acid tert-butyl ester

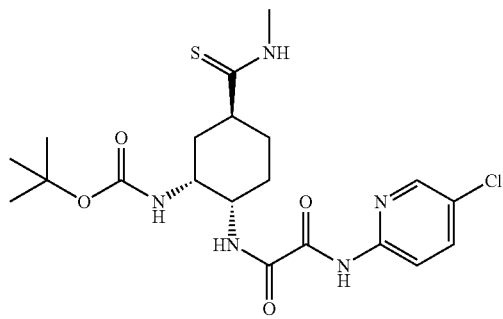

The method described in Referential Example 444 was performed by use of the compound obtained in Referential Example 500, whereby the title compound was obtained.

$^1$H-NMR(CDCl$_3$)δ: 1.45(9H, s), 1.50-1.70(1H, m), 1.80-2.16(5H, m), 2.60-2.75(1H, br), 3.19(3H, d, J=4.9 Hz), 3.94-4.05(1H, br), 4.10-4.28(1H, br), 4.80-5.00(0.8H, br), 5.75-5.90(0.2H, br), 7.40-7.55(1H, br), 7.68(1H, dd, J=8.8, 2.2 Hz), 7.96-8.07(1H, br), 8.17(1H, d, J=8.8 Hz), 8.30(1H, d, J=2.0 Hz), 9.76(1H, s).

MS(ESI)m/z: 414(M-$^t$Bu+H)$^+$.

Referential Example 502

2,2-dichloro-N-(5-chloropyrimidin-2-yl)acetamide

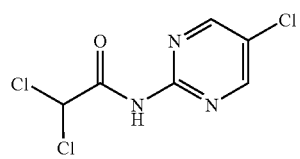

To 2-amino-5-chloropyrimidine (1.30 g) dissolved in N,N-dimethylformamide (30 mL), dichloroacetyl chloride (1.44 mL) and sodium hydrogencarbonate (1.26 g) were added, and the resultant mixture was stirred at room temperature for 1 hour. The solvent was distilled away under reduced pressure. Methylene chloride and water were added to the residue for partitioning the mixture. The aqueous layer was extracted with methylene chloride. The organic layers were combined, and the resultant mixture was washed with water, followed by drying over sodium sulfate anhydrate. The solvent was distilled away under reduced pressure. The residue was purified by silica gel flash column chromatography (hexane ethyl acetate=1:1). The resultant white solid was slurry-washed with a solvent mixture of hexane-diethyl ether (4:1), followed by filtration to recover, to thereby give the title compound (1.24 g) as a white solid.

$^1$H-NMR(CDCl$_3$): 6.43(1H, br.s), 8.65(2H, s), 9.07(1H, br.s).

MS(ESI)m/z: 240 (M+H)$^+$.

Referential Example 503

(1R,2S,5S)-2-({2-[(5-chloropyrimidin-2-yl)amino]-2-oxoethanethioyl}amino)-5-[(dimethylamino)carbonyl]cyclohexylcarbamic acid tert-butyl ester

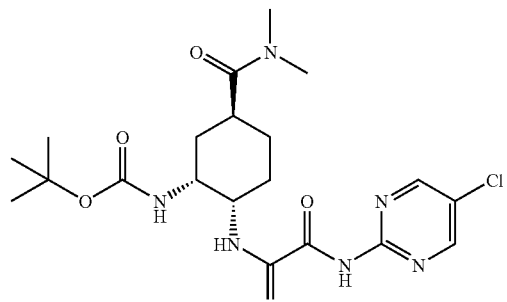

The compound (8.03 g) obtained in Referential Example 144, the compound (6.76 g) obtained in Referential Example 502, and sulfur (947 mg) were added in N,N-dimethylformamide (90 mL). The resultant mixture was heated at 120° C. Diisopropylethylamine (9.57 mL) was added thereto, followed by stirring at 120° C. for 10 minutes. The solvent was distilled away under reduced pressure. Methylene chloride was added to the residue, and the insoluble material was removed through filtration through celite. Water was added to the filtrate for partitioning the mixture, and the organic layer was washed with water and then subjected to silica gel flash column chromatography (methylene chloride:methanol=19:1), thereby yielding a crude product. The crude product was dissolved in methylene chloride, hexane was added thereto, and the resultant solid was recovered by filtration, to thereby give the title compound (940 mg) as a light yellow solid. The filtrate was also purified by silica gel column chromatography, to thereby give the title compound (940 mg) containig N,N-dimethylformamide as a light brown solid.

$^1$H-NMR(DMSO)δ: 1.28-2.22(15H, m), 2.71(1H, br.s), 2.96(3H, s), 3.07(3H, s), 4.25-4.42(2H, m), 8.62(2H, s), 9.88 (1H, br.s), 10.89(1H, s).

Referential Example 504

2-chloro-N-(4-chloro-3-nitrophenyl)acetamide

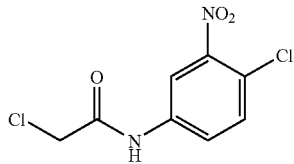

The method described in Referential Example 502 was performed by use of 4-chloro-3-nitroaniline and chloroacetyl chloride, whereby the title compound was obtained.

$^1$H-NMR(CDCl$_3$)δ: 4.23(2H, s), 7.54(1H, d, J=8.8 Hz), 7.74(1H, dd, J=8.8, 2.4 Hz), 8.22(1H, d, J=2.4 Hz), 8.39(1H, br.s).

Referential Example 505

(1R,2S,5S)-2-{[2-(4-chloro-3-nitroanilino)-2-oxoethanethioyl]amino}-5-[(dimethylamino)carbonyl]cyclohexylcarbamic acid tert-butyl ester

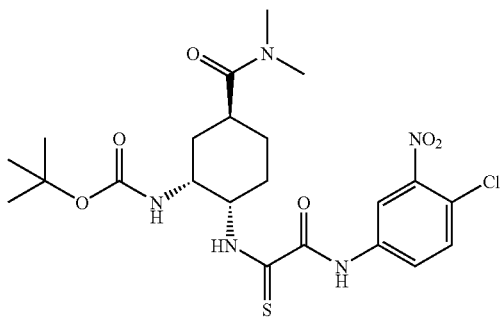

The compound (498 mg) obtained in Referential Example 504 was dissolved in N,N-dimethylformamide (4 mL), and sulfur (128 mg) and triethylamine (833 μL) were added thereto, followed by stirring at room temperature for 1 hour. To the reaction mixture were added the compound (571 mg) obtained in Referential Example 144 and 3-(3-dimethylaminopropyl)-1-ethylcarbodiimide hydrochloride (767 mg). The resultant mixture was stirred at room temperature overnight. The solvent was distilled away under reduced pressure. Methylene chloride and water were added to the residue for partitioning the mixture. The aqueous layer was extracted with methylene chloride. The organic layers were combined. The resultant mixture was washed with water, followed by drying over sodium sulfate anhydrate. The solvent was distilled away under reduced pressure. The residue was purified by silica gel flash column chromatography (ethyl acetate), to thereby give the title compound (688 mg) as a yellow solid.

$^1$H-NMR(CDCl$_3$)δ: 1.47(9H, m), 1.48-1.59(1H, m), 1.72-1.81(1H, m), 1.86-1.95(2H, m), 2.04(1H, br.s), 2.23(1H, br.s), 2.69(1H, br.s), 2.96(3H, s), 3.09(3H, s), 4.34-4.39(2H, m), 4.78(1H, br.s), 7.52(1H, d, J=8.6 Hz), 7.69(1H, d, J=8.6 Hz), 8.39(1H, br.s), 9.95(1H, br.s), 10.37(1H, s).

MS(ESI)m/z: 528(M+H)$^+$.

Referential Example 506

(1S,3R,4S)-3-[(tert-butoxycarbonyl)amino]-4-{[(7-chlorocinnolin-3-yl)carbonyl]amino}cyclohexanecarboxylic acid ethyl ester

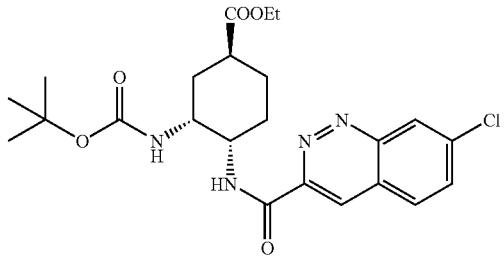

In a manner similar to that described in Referential Example 97, the compound obtained in Referential Example 96 was condensed with the compound obtained in Referential Example 298, whereby the title compound was obtained.

$^1$H-NMR(CDCl$_3$)δ: 1.28(3H, t, J=7.2 Hz), 1.36(9H, s), 1.53-2.16(6H, m), 2.48(1H, br.s), 4.17(2H, q, J=7.2 Hz), 4.30-4.35(2H, m), 4.86(1H, br.s), 7.78(1H, dd, J=8.8, 2.0 Hz), 7.97(1H, d, J=8.8 Hz), 8.59-8.60(1H, m), 8.64(1H, d, J=8.6 Hz), 8.73(1H, s).

MS(ESI)m/z: 477(M+H)$^+$.

Referential Example 507

(1S,3R,4S)-3-[(tert-butoxycarbonyl)amino]-4-{[(7-chlorocinnolin-3-yl)carbothioyl]amino}cyclohexanecarboxylic acid ethyl ester

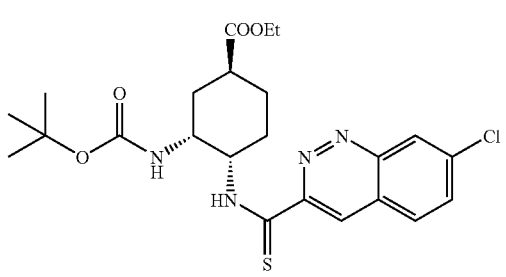

The method described in Referential Example 443 was performed by use of the compound obtained in Referential Example 506, whereby the title compound was obtained.

$^1$H-NMR(CDCl$_3$)δ: 1.28(3H, t, J=7.1 Hz), 1.37(9H, br.s), 1.59-2.26(6H, m), 2.49(1H, br.s), 4.17(2H, q, J=7.1 Hz), 4.54 (1H, br.s), 4.83-4.87(2H, m), 7.76(1H, dd, J=8.7, 1.8 Hz), 7.97(1H, d, J=8.7 Hz), 8.57(1H, s), 9.20(1H, s), 10.64(1H, br.s).

MS(ESI)m/z: 493(M+H)+.

Referential Example 508

(1R,2S,5S)-2-{[(7-chlorocinnolin-3-yl)carbothioyl]amino}-5-[(dimethylamino)carbonyl]cyclohexylcarbamic acid tert-butyl ester

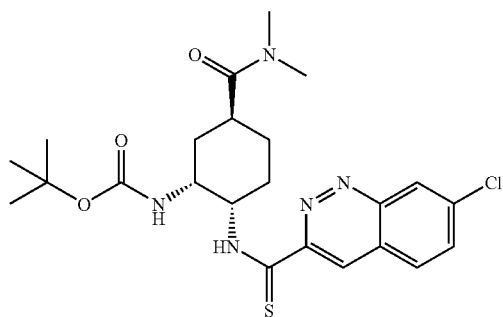

In a manner similar to that described in Referential Example 251, calboxylic acid prepared by hydrolysis of the compound obtained in Referential Example 507 was condensed with dimethylamine hydrochloride, whereby the title compound was obtained.

$^1$H-NMR(CDCl$_3$)δ: 1.37(9H, br.s), 1.66(1H, br.s), 1.82-2.05(4H, m), 2.29-2.32(1H, m), 2.76(1H, br.s), 2.97(3H, s), 3.09(3H, s), 4.56-4.59(1H, m), 4.90(2H, br.s), 7.75(1H, dd, J=8.7, 2.0 Hz), 7.97(1H, d, J=8.7 Hz), 8.56(1H, s), 9.19(1H, br.s), 10.60(1H, d, J=7.8 Hz).

MS(ESI)m/z: 492(M+H)+.

Referential Example 509

(1S,3R,4S)-3-amino-4-{[(7-chlorocinnolin-3-yl)carbothioyl]amino}-N,N-dimethylcyclohexanecarboxamide

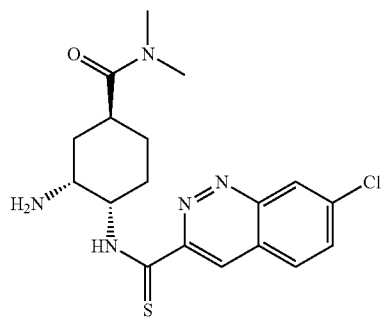

The method described in Referential Example 325 was performed by use of the compound obtained in Referential Example 508, whereby the title compound was obtained.

MS(ESI)m/z: 392 (M+H)+.

Referential Example 510

(1R,2S,5S)-2-({[[(4-chlorobenzoyl)amino]carbonyl}amino)-5-[(dimethylamino)carbonyl]cyclohexylcarbamic acid tert-butyl ester

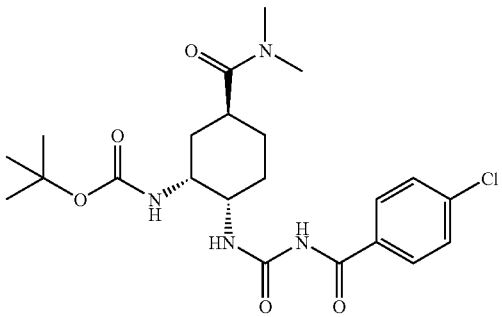

To a dichloroethane (20 mL) solution of p-chlorobenzamide (311 mg), oxalyl chloride (435 μL) was added, and the resultant mixture was heated under reflux for 3 hours. The solvent was distilled away under reduced pressure. Acetonitrile (10 mL) solution of the residue was added dropwise to solution of the compound (571 mg) obtained in Referential Example 144 dissolved in acetonitrile (20 mL), followed by stirring at room temperature for 10 minutes. The solvent was distilled away under reduced pressure. Ether was added to the residue, and the resultant solid was recovered by filtration, to thereby give the title compound (678 mg) as a white solid.

$^1$H-NMR(CDCl$_3$)δ: 1.42(9H, s), 1.52-2.01(6H, m), 2.68 (1H, br.s), 2.95(3H, s), 3.08(3H, s), 3.95(1H, br.s), 4.29(1H, br.s), 4.84(1H, br.s), 7.41(2H, d, J=8.3 Hz), 7.88(2H, br.s), 8.92(1H, d, J=7.6 Hz), 9.78(1H, s).

MS(ESI)m/z: 489(M+Na)+.

Referential Example 511

(1S,3R,4S)-3-amino-4-({[[(4-chlorobenzoyl)amino]carbonyl}amino)-N,N-dimethylcyclohexanecarboxamide

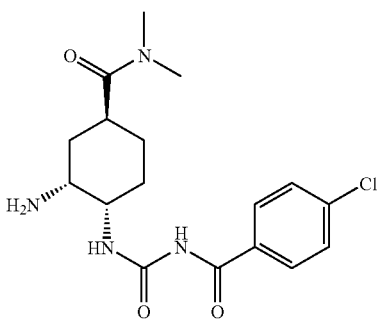

The method described in Referential Example 325 was performed by use of the compound obtained in Referential Example 510, whereby the title compound was obtained.

$^1$H-NMR(CDCl$_3$)δ: 1.51(2H, br.s), 1.67-1.96(6H, m), 2.90 (1H, br.s), 2.95(3H, s), 3.08(3H, s), 3.44(1H, br.s), 3.93(1H, br.s), 7.47(2H, d, J=8.5 Hz), 7.86(2H, d, J=8.5 Hz), 8.85(1H, br.s), 8.93(1H, d, J=7.3 Hz).

MS(ESI)m/z: 367 (M+H)+.

Referential Example 512

(E)-3-(5-chloropyridin-2-yl)-2-acrylic acid methyl ester

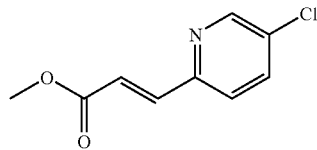

Sodium hydride (60% oil, 580 mg) was suspended in tetrahydrofuran (30 mL). At −30° C., 2-(dimethoxyphosphoryl) acetic acid methyl ester (2.35 mL) dissolved in tetrahydrofuran (30 mL) was added dropwise thereto, followed by stirring at −30° C. for 30 minutes. To the resultant mixture, tetrahydrofuran (10 mL) and 5-chloropyridine-2-carboxyaldehyde (J. Med. Chem. 1970, Vol. 13, 1124) (1.96 g) dissolved in tetrahydrofuran (15 mL) were added, followed by heating gradually to room temperature over 1 hour. Water (100 mL) and diethyl ether (50 mL) were added thereto for partitioning the mixture. The aqueous layer was extracted with diethyl ether (50 mL). The organic layers were combined, and the resultant mixture was washed with saturated brine (50 mL), followed by drying over sodium sulfate anhydrate. The solvent was distilled away under reduced pressure. Hexane (30 mL) was added to the resultant white solid, and the resultant mixture was stirred for 30 minutes, and filtered to recover, to thereby give the title compound (1.89 g) as a white solid.

$^1$H-NMR(CDCl$_3$)δ: 3.82(3H, s), 6.91(1H, dd, J=15.7, 0.9 Hz), 7.36(1H, d, J=8.3 Hz), 7.64(1H, d, J=15.7 Hz), 7.68(1H, ddd, J=8.3, 2.4, 0.9 Hz), 8.59(1H, d, J=2.4 Hz).

MS(ESI)m/z: 197(M$^+$).

Referential Example 513

(1R,2S,5S)-2-{[(E)-3-(5-chloropyridin-2-yl)acryloyl]amino}-5-[(dimethylamino)carbonyl]cyclohexylcarbamic acid tert-butyl ester

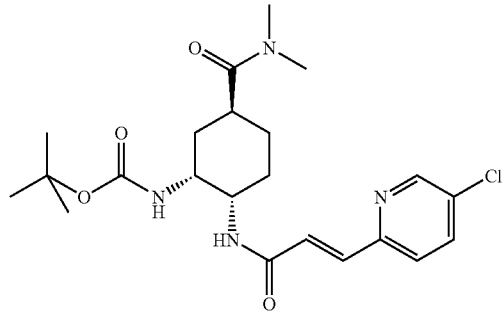

In a manner similar to that described in Referential Example 97, carboxylic acid lithium salt prepared by hydrolysis of the compound obtained in Referential Example 512 was condensed with the compound obtained in Referential Example 144, whereby the title compound was obtained.

$^1$H-NMR(CDCl$_3$)δ: 1.47(9H, s), 1.65-1.88(3H, m), 1.88-2.00(2H, m), 2.05-2.22(1H, m), 2.65(1H, br.s), 2.94(3H, s), 3.05(3H, s), 4.05(1H, br.s), 4.10-4.18(1H, m), 4.78(1H, br.s), 6.71(1H, br.s), 6.89(1H, d, J=15.4 Hz), 7.30(1H, d, J=8.3 Hz), 7.54(1H, d, J=15.4 Hz), 7.65(1H, dd, J=8.3, 2.4 Hz), 8.53(1H, d, J=2.4 Hz).

MS(ESI)m/z: 451 (M+H)$^+$.

Referential Example 514

3-(4-chlorophenyl)-2-fluoro-3-hydroxypropionic acid ethyl ester

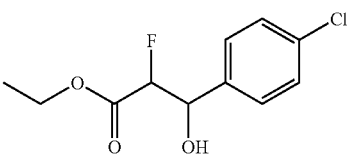

Zinc powder (1.96 g) was added to 4-chlorobenzaldehyde (141 mg) dissolved in benzene (20 mL), and a catalytic amount of iodine was added to the mixture while refluxing by heating. Ethyl bromofluoroacetate (185 mg) in benzene (2.5 mL) was added dropwise thereto, followed by stirring for 2.5 hours. The reaction mixture was cooled by ice, 1N hydrochloric acid (12.5 mL) was added thereto, and the resultant mixture was stirred at room temperature for 1.5 hours. Water and ethyl acetate were added thereto for partiton. The aqueous layer was extracted with ethyl acetate. The organic layers were combined, and dried over sodium sulfate anhydrate. The solvent was distilled away under reduced pressure. The residue was purified by preparative thin layer chromatography (hexane:ethyl acetate=3:1), to thereby give the title compound (diastereomer mixture) (117 mg) as a colorless oil.

$^1$H-NMR(CDCl$_3$)δ: 1.16-1.24(3H, m), 3.35(1H, br.d, J=51.9 Hz), 4.15-4.25(2H, m), 4.89-5.11(2H, m), 7.31-7.33 (4H, m).

MS(EI)m/z: 246(M$^+$).

Referential Example 515

(Z)-3-(4-chlorophenyl)-2-fluoroacrylic acid ethyl ester

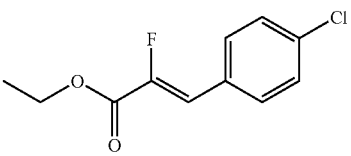

The compound (51 mg) obtained in Referential Example 514 was dissolved in methylene chloride (1.0 mL). Pyridine (100 μL) was added thereto, and the mixture was cooled to 0° C. Thionyl chloride (20 μL) was added to the resultant mixture followed by stirring at 0° C. for 20 minutes. 1N Hydrochloric acid and ethyl acetate were added thereto for partitioning the mixture. The aqueous layer was extracted with ethyl acetate. The organic layers were combined, and dried over sodium sulfate anhydrate. The solvent was distilled away under reduced pressure. The residue was dissolved in methylene chloride (2 mL), and 1,8-diazabicyclo[5.4.0]undec-7-ene (34 μL) was added thereto, followed by stirring at room temperature for 3.5 hours. 1N Hydrochloric acid and methylene chloride were added to the resultant mixture for partitioning the mixture. The aqueous layre was extracted with methylene chloride. The organic layers were combined, and dried over sodium sulfate anhydrate. The solvent was distilled away under reduced pressure. The residue was purified by preparative thin layer chromatography (hexane ethyl acetate=4:1), to thereby give the title compound (22 mg) as a pale yellow solid.

¹H-NMR(CDCl₃)δ: 1.38(3H, t, J=7.2 Hz), 4.35(2H, q, J=7.2 Hz), 6.87(1H, d, J=34.9 Hz), 7.37(2H, d, J=8.3 Hz), 7.57(2H, d, J=8.3 Hz).

Referential Example 516

(Z)-3-(4-chlorophenyl)-2-fluoroacrylic acid

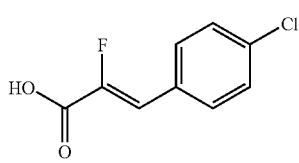

The method described in Referential Example 274 was performed by use of the compound obtained in Referential Example 515, whereby the title compound was obtained.

¹H-NMR(DMSO-d₆)δ: 7.06(1H, d, J=36.4 Hz), 7.52(2H, d, J=8.2 Hz), 7.72(2H, d, J=8.2 Hz).

MS(ESI-negative)m/z: 198(M−H)−.

Referential Example 517

(1S,2R,4S)-2-[(tert-butoxycarbonyl)amino]-4-[(dimethylamino)carbonyl]cyclohexylcarbamic acid 2,2,2-trichloroethyl ester

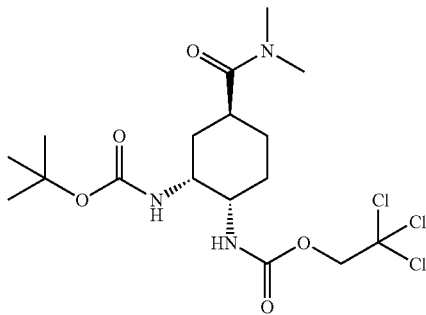

The compound (10.0 g) obtained in Referential Example 144 was dissolved in pyridine (175 mL). To the solution, 2,2,2-trichloroethyl chloroformate (10.6 mL) was added dropwise, followed by stirring at room temperature overnight. The solvent was distilled away under reduced pressure. Methylene chloride and 0.5N hydrochloric acid were added thereto for partitioning the mixture. The resultant organic layer was washed twice with 0.5N hydrochloric acid, and then washed once with saturated brine, followed by drying over sodium sulfate anhydrate. The solvent was distilled away under reduced pressure. The residue was dissolved in a small amount of methylene chloride, and hexane was added thereto. The resultant solid was recoverd by filtration. The solid was slurry-washed with diethyl ether, to thereby give the title compound (13.6 g) as a white solid.

¹H-NMR(CDCl₃)δ: 1.46(9H, s), 1.62-1.97(6H, m), 2.67 (1H, br.s), 2.94(3H, s), 3.05(3H, s), 3.71-3.76(1H, m), 4.16 (1H, br.s), 4.64-4.86(3H, m), 5.62(1H, d, J=7.3 Hz).

MS(ESI)m/z: 460(M+H)⁺.

Referential Example 518

(1S,2R,4S)-4-[(dimethylamino)carbonyl]-2-{[(5-methyl-4,5,6,7-tetrahydro[1,3]thiazolo[5,4-c]pyridin-2-yl)carbonyl]amino}cyclohexylcarbamic acid 2,2,2-trichloroethyl ester

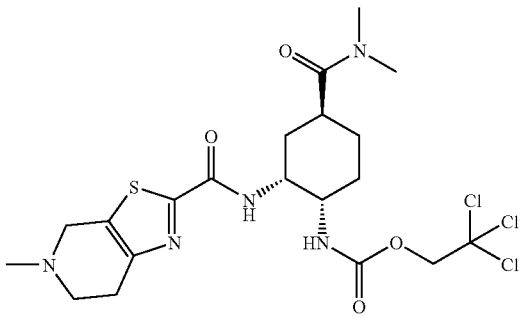

In a manner similar to that described in Referential Example 252, the compound obtained in Referential Example 517 was treated with hydrochloric acid for deprotection. The deprotected compound was condensed with the compound obtained in Referential Example 10, whereby the title compound was obtained.

¹H-NMR(CDCl₃)δ: 1.53-2.17(6H, m), 2.52(3H, s), 2.74-2.93(8H, m), 3.03(3H, s), 3.72(2H, br.s), 3.83-3.90(1H, m), 4.62-4.79(3H, m), 5.65(1H, br.d, J=6.8 Hz), 7.36(1H, br.d, J=8.5 Hz).

MS(ESI)m/z: 540(M+H)⁺.

Referential Example 519

(1S,2R,4S)-4-[(dimethylamino)carbonyl]-2-{[(5-methyl-4,5,6,7-tetrahydro[1,3]thiazolo[5,4-c]pyridin-2-yl)carbonyl]amino}cyclohexylcarbamic acid tert-butyl ester

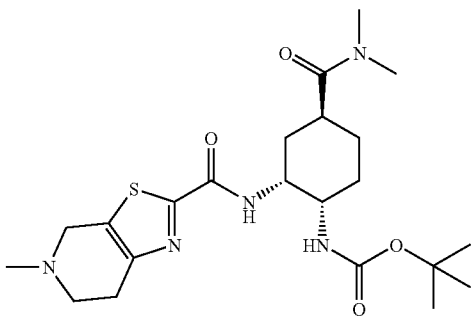

The compound (5.01 g) obtained in Referential Example 518 was dissolved in a mixture of ethanol (100 mL) and water (5 mL). Zinc (6.06 g) and ammonium chloride (2.48 g) were added thereto, followed by stirring at 40° C. for 4.5 hours. Zinc was removed through filtration through celite. Sodium hydrogencarbonate (7.78 g) and di-tert-butyl dicarbonate (6.08 g) were added to the filtrate, and the mixture was stirred at room temperature overnight. The solvent was distilled away under reduced pressure. Methylene chloride and water were added to the residue for partitioning the mixture. The aqueous layer was extracted twice with methylene chloride. The organic layers were combined, and dried over sodium sulfate anhydrate. The solvent was distilled away under reduced pressure. The residue was purified by silica gel flash column chromatography (ethyl acetate:methanol=7:3). The residue was further purified by preparative recycle HPLC (Japan Analytical Industry Co., LC908-C60, column: JAI-GEL 1H-40 and 2H-40, solvent:chloroform), to thereby give the title compound (2.30 g) as a light yellow solid.

$^1$H-NMR(CDCl$_3$)δ: 1.43(9H, s), 1.48-2.07(6H, m), 2.52 (3H, s), 2.70-2.96(8H, m), 3.00(3H, s), 3.68-3.77(3H, m), 4.57-4.60(1H, m), 4.94(1H, br.s), 7.33(1H, br.s).

MS(ESI)m/z: 466(M+H)$^+$.

Referential Example 520

2,2-dichloro-N-(5-chloropyridin-2-yl)acetamide

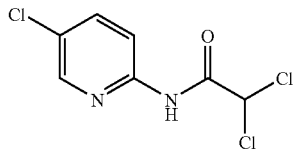

The method described in Referential Example 457 was performed by use of 2-amino-5-chloropyridine, whereby the title compound was obtained.

$^1$H-NMR(CDCl$_3$)δ: 6.06(1H, s), 7.73(1H, dd, J=8.8, 2.4 Hz), 8.15(1H, dd, J=9.0, 0.5 Hz), 8.30(1H, dd, J=2.5, 0.5 Hz), 8.78(1H, s).

MS(ESI)m/z: 239(M+H)$^+$.

Referential Example 521

(1R,2S,5S)-2-({2-[(5-chloropyridin-2-yl)amino]-2-oxoethanethioyl}amino)-5-[(methylamino)carbonyl] cyclohexylcarbamic acid tert-butyl ester

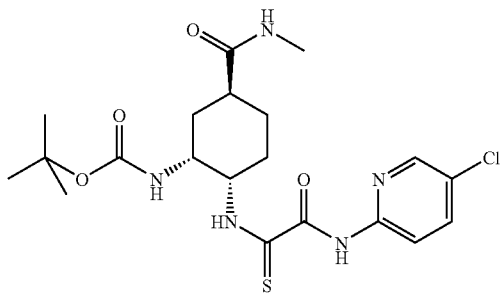

The compound (1.01 g) obtained in Referential Example 436 was dissolved in methanol (50 mL). To the solution, 10% palladium carbon catalyst (0.35 g) was added, and the mixture was stirred in a hydrogen atmosphere at room temperature for 16 hours. The catalyst was removed through filtration, and the filtrate was concentrated under reduced pressure. The residue was dissolved in N,N-dimethylformamide (5.0 mL). To the mixture were added the compound obtained in Referential Example 520 (600 mg), diisopropylethylamine (5.0 mL), and sulfur (80.3 mg), followed by stirring at 120° C. for 2 hours. The reaction mixture was concentrated under reduced pressure. Water was added to the residue, and the resultant mixture was extracted twice with methylene chloride (200 mL). The organic layer was sequentially washed with 10% aqueous citric acid, saturated aqueous sodium hydrogencarbonate, and saturated brine. The resultant mixture was dried over sodium sulfate anhydrate, and concentrated under reduced pressure. The residue was purified by silica gel flash column chromatography (methylene chloride:methanol=50:1→30:1), to thereby give the title compound (812 mg) as a yellow glassy solid.

$^1$H-NMR(CDCl$_3$)δ: 1.25-2.50(7H, m), 1.46(9H, s), 2.82 (3H, d, J=4.9 Hz), 4.23-4.43(2H, m), 4.80-5.10(0.8H, br), 5.50-5.80(1H, br), 580-6.05(0.2H, br), 7.69(1H, dd, J=8.8, 22.4 Hz), 8.02(1H, s), 8.10-8.23(1H, m), 8.31(1H, d, J=2.4 Hz), 9.50-9.85(0.2H, br), 9.85-10.15(0.8H, br), 10.56(1H, s).

MS(ESI)m/z: 470(M+H)$^+$.

Referential Example 522

(1S,3R,4S)-3-amino-4-({2-[(5-fluoropyridin-2-yl) amino]-2-oxoethanethioyl}amino)-N,N-dimethylcyclohexanecarboxamide hydrochloride

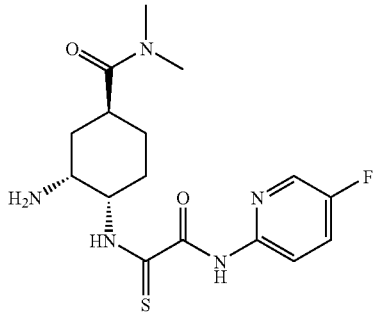

The method described in Referential Example 69 was performed by use of the compound obtained in Referential Example 427, whereby the title compound was obtained.

$^1$H-NMR(DMSO-d$_6$)δ: 1.42-1.55(1H, m), 1.72-1.90(3H, m), 2.00-2.09(1H, m), 2.11-2.28(1H, m), 2.82(3H, s), 3.08 (3H, s), 3.27-3.40(1H, m), 4.03(1H, br.s), 4.35-4.45(1H, m), 7.89(1H, dt, J=2.9, 9.0 Hz), 8.14(1H, dd, J=9.0, 4.2 Hz), 8.33(3H, br.s), 8.44(1H, d, J=2.9 Hz), 10.64(1H, s), 10.97 (1H, d, J=7.1 Hz).

MS(ESI)m/z: 368(M+H)$^+$.

Referential Example 523

3-amidinobenzoic acid ethyl ester hydrochloride

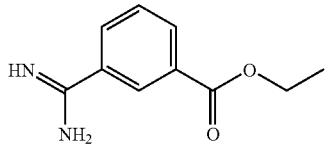

To 3-cyanobenzoic acid (5 g) in ethanol (100 mL), under ice cooling and stirring, Hcl gas was injected to saturation. Ethanol (400 mL) was added to the resultant suspension to dissolve, followed by heating to room temerature. The resultant mixture was sealed, allowed to stand for 18 hours, and concentrated to dryness under reduced pressure. The residue was dissolved in ethanol (100 mL), and under ice cooling and stirring, ammonia gas was injected thereto to saturation. The resultant mixture was heated to room temperature, saeled, and allowed to stand for 18 hours. The solvent was distilled away under reduced pressure. The residue was purified with a synthetic absorbent material HP-20 (water→acetonitrile:water=1:4). The resultant crude product was dissolved in methanol/dichloromethane=1/4, and the insoluble material was removed through filtration. The residue was further purified by silica gel chromatography (methanol:methylene chloride=1:4), to thereby give the title compound (5.53 g) as a colorless powder.

$^1$H-NMR(DMSO-$d_6$)δ: 1.36(3H, t, J=7.0 Hz), 4.38(2H, q, J=7 Hz), 7.78(1H, t, J=7.8 Hz), 8.11(1H, dd, J=7.8, 1.0 Hz), 8.27(1H, d, J=7.8 Hz), 8.38(1H, d, J=1.5 Hz), 9.41(1H, br.s), 9.61(1H, br.s).

MS(FAB)m/z: 193 (M+H)+

Referential Example 524

3-[[(tert-butoxycarbonyl)amino](imino)methyl]benzoic acid ethyl ester

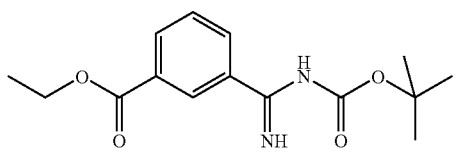

The compound (250 mg) obtained in Referential Example 523 was dissolved in methanol (5.0 mL). To the solution, diisopropylethylamine (952 μL) and di-tert-butoxycarbonate (480 mg) were added, followd by stirring for 3 days. The solvent was distilled away under reduced pressure. The residue was purified by medium-pressure silica gel column chromatography (methylene chloride:methanol=25:1), to thereby the title compound (285 mg) as a white foamed solid.

$^1$H-NMR(CDCl$_3$)δ: 1.41(3H, t, J=7.2 Hz), 1.56(9H, s), 4.41(2H, q, J=7.2 Hz), 7.52(1H, t, J=7.8 Hz), 8.14(1H, d, J=7.8 Hz), 8.19(1H, d, J=7.8 Hz), 8.43(1H, s).

MS(ESI)m/z: 293(M+H)$^+$.

Referential Example 525

(1R,2S,5S)-2-[(3-cyanobenzoyl)amino]-5-[(dimethylamino)carbonyl]cyclohexylcarbamic acid tert-butyl ester

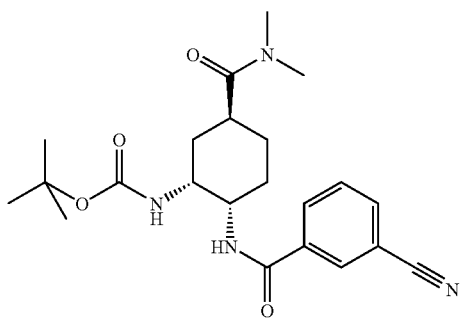

The compound (800 mg) obtained in Referential Example 144 and 3-cyanobenzoyl chloride (560 mg) were dissolved in methylene chloride (30 mL). To the solution, diisopropylethylamine (730 μL) was added at room temperature. The resulting mixture was stirred for 4 hours. Water and saturated aqueous ammonium chloride were added thereto for partitioning the mixture. The aqueous layer was extracted with methylene chloride. The organic layers were combined, and dried over sodium sulfate anhydrate. The solvent was distilled away under reduced pressure. The residue was purified by silica gel column chromatography (methylene chloride:acetone=5:1->1:1), to thereby give the title compound (1.15 g) as a white foamy solid.

$^1$H-NMR(CDCl$_3$)δ: 1.40-1.78(2H, m), 1.47(9H, s), 1.78-1.94(2H, m), 2.08-2.40(2H, m), 2.60-2.70(1H, m), 2.96(3H, s), 3.09(3H, s), 3.94-4.08(1H, m), 4.16-4.34(1H, m), 4.79-4.88(1H, m), 7.55(1H, t, J=7.9 Hz), 7.75(1H, d, J=7.9 Hz), 8.06-8.16(3H, m).

MS(ESI)m/z: 415(M+H)$^+$.

Referential Example 526

3-[[(ethoxycarbonyl)amino](imino)methyl]benzoic acid ethyl ester

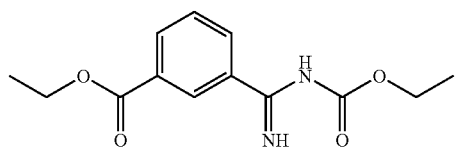

To the compound (250 mg) obtained in Referential Example 523 were added methylene chloride (10 mL), diisopropylethylamine (952 μL)., and chloroformic acid ethyl ester (160 μL). The resultant mixture was stirred for 8 hours. Saturated aqueous sodium hydrogencarbonate and methylene chloride were added thereto for partitioning the mixture. The aqueous layer was extracted with methylene chloride. The organic layers were combined, and dried over sodium sulfate anhydrate. The solvent was distilled away under reduced pressure. The residue was purified by medium-pressure silica gel column chromatography (methylene chloride:methanol=25:1), to thereby give the title compound (270 mg) as a white solid.

$^1$H-NMR(CDCl$_3$)δ: 1.36(3H, t, J=7.1 Hz), 1.40(3H, t, J=7.1 Hz), 4.23(2H, q, J=7.1 Hz), 4.39(2H, q, J=7.1 Hz), 6.84(1H, br.s), 7.51(1H, t, J=7.8 Hz), 8.10-8.25(2H, m), 8.45 (1H, s), 9.63(1H, br.s).

MS(ESI)m/z: 265(M+H)$^+$.

Referential Example 527

2,2-dichloro-N-(5-fluoropyridin-2-yl)acetamide

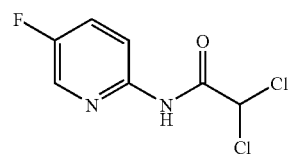

To 2-amino-5-fluoropyridine (250 mg) in ethyl acetate (10 mL), dichloroacetyl chloride (279 μL) was added at room temperature, followed by stirring at 60-70° C. for 2.5 hours. The reaction mixture was cooled, and saturated aqueous sodium hydrogencarbonate was added thereto for partitioning the mixture. The resultant organic layer was dried over magnesium sulfate anhydrate. The solvent was distilled away under reduced pressure, to thereby give the title compound (438 mg) as a crude product.

$^1$H-NMR(CDCl$_3$)δ: 6.05(1H, s), 7.45-7.55(1H, m), 8.15-8.25(2H, m), 8.72(1H, s).

MS(ESI)m/z: 223(M+H)$^+$.

Referential Example 528

(1R,2S,5S)-5-[(dimethylamino)carbonyl]-2-({2-[(5-fluoropyridin-2-yl)amino]-2-oxoethanethioyl}amino)cyclohexylcarbamic acid tert-butyl ester

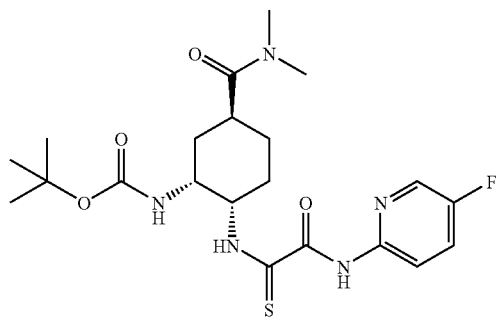

N,N-Dimethylformamide (1.0 mL) and diisopropylethylamine (1.0 mL) were added to the compound (112 mg) obtained in Referential Example 527, the compound (143 mg) obtained in Referential Example 144, and sulfur (17 mg). The resultant mixture was stirred at 130° C. for 20 minutes. The solvent was distilled away under reduced pressure. Saturated aqueous sodium hydrogencarbonate was added to the residue, followed by extracting with methylene chloride. This resultant mixture was purified by silica gel column chromatography (methylene chloride:methanol=99:1), followed by washing with diisopropyl ether, to thereby give the title compound (121 mg). The NMR data were agreed with that of the compound from Referential Example 424.

Referential Example 529

4-morpholinobenzoic acid methyl ester

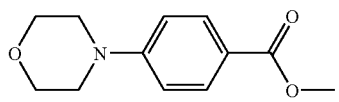

Under ice cooling, thionyl chloride (436 μL) was added dropwise to methanol (10 mL). 4-Morpholinobenzoic acid (207 mg) was added thereto, and the resultant mixture was heated under reflux for 1.5 hours. The solvent was distilled away under reduced pressure. Methylene chloride and water were added to the residue for partitioning the mixture. The organic layer was dried over sodium sulfate anhydrate. The solvent was distilled away under reduced pressure, whereby the title compound was obtained.
$^1$H-NMR(CDCl$_3$)δ: 3.28(4H, t, J=4.9 Hz), 3.84-3.87(7H, m), 6.86(2H, dt, J=9.6, 2.5 Hz), 7.94(2H, dt, J=9.6, 2.4 Hz).
MS(EI)m/z: 222(M+H)$^+$.

Referential Example 530

4-(3-oxomorpholin-4-yl)benzoic acid methyl ester

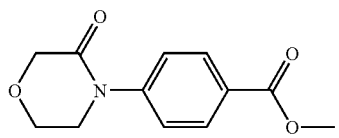

To the compound (207 mg) obtained in Referential Example 529 dissolved in methylene chloride (10 mL), benzyltriethylammonium chloride (639 mg) and potassium permanganate (222 mg) were added, and the resultant mixture was stirred at room temperature for 2 hours. Saturated aqueous sodium hydrogensulfite was added to the reaction mixture for partitioning the mixture. The organic layer was washed with saturated brine, followed by drying over sodium sulfate anhydrate. The solvent was distilled away under reduced pressure. The residue was purified by silica gel flash column chromatography (hexane:ethyl acetate=1:2), to thereby give the title compound (41 mg).
$^1$H-NMR(CDCl$_3$)δ: 3.80-3.83(2H, m), 3.92(3H, s), 4.03-4.07(2H, m), 4.36(2H, s), 7.47(2H, dt, J=9.0, 2.2 Hz), 8.08(2H, dt, J=9.0, 2.2 Hz).
MS(EI)m/z: 236(M+H)$^+$.

Referential Example 531

4-(3-oxomorpholin-4-yl)benzoic acid

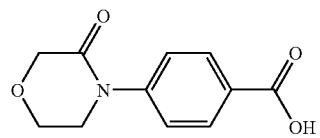

The method described in Referential Example 274 was performed by use of the compound obtained in Referential Example 530, whereby the title compound was obtained.
$^1$H-NMR(DMSO-d$_6$)δ: 3.78-3.82(2H, m), 3.97-4.01(2H, m), 4.23(2H, s), 7.57(2H, dt, J=9.1, 2.2 Hz), 7.96(2H, dt, J=9.1, 2.2 Hz), 12.97(1H, br.s).

Referential Example 532

3-(5-chlorothien-2-yl)-2-fluoro-3-hydroxypropionic acid ethyl ester

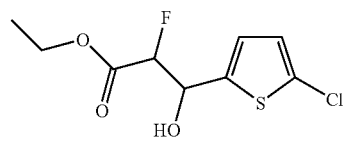

To 5-chlorothiophene-2-carboxyaldehyde (1.07 mL) in benzene (200 mL), zinc powder (19.6 g) was added, and the mixture was heated under reflux. A catalytic amount of iodine was added thereto, and bromofluoroethyl acetate (3.70 g) in benzene (25 mL) was added dropwise thereto. The mixture was heated under reflux for 1.5 hours. A catalytic amount of iodine was further added thereto, and the resultant mixture was heated under reflux for 3.5 hours. The reaction mixture was allowed to cool, and under ice cooling, 1N hydrochloric acid (125 mL) was added thereto, followed by stirring for 1 hour. The insoluble material was filtered through celite, followed by washing with ethyl acetate. The filtrate was partitioned. The organic layer was washed with saturated brine, and dried over sodium sulfate anhydrate. The solvent was distilled away under reduced pressure. The residue was purified by silica gel column chromatography (hexane→hexane:ethyl acetate=4:1), to thereby give the title compound (2.53 g).
$^1$H-NMR(CDCl$_3$)δ: 1.24-1.31(3H, m), 3.09-3.21(1H, m), 4.21-4.31(2H, m), 4.97-5.12(1H, m), 5.21-5.28(1H, m), 6.79-6.86(2H, m).
MS(EI)m/z: 252(M$^+$).

Referential Example 533

(Z)-3-(5-chlorothien-2-yl)-2-fluoroacrylic acid ethyl ester

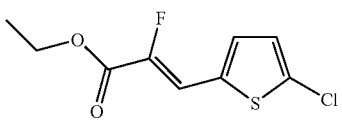

To the compound (2.46 g) obtained in Referential Example 532 dissolved in methylene-chloride (50 mL), under ice cooling, pyridine (4.70 mL) and thionyl chloride (849 μL) were added. The mixture was stirred at 0° C. for 30 minutes, and stirred at room temperature for 1 hour. 1N hydrochloric acid was added to the reaction mixture for partitioning the mixture. The aqueous layer was extracted with methylene chloride. The organic layer was washed with 1N hydrochloric acid, followed by drying over sodium sulfate anhydrate. The solvent was distilled away under reduced pressure. The residue was dissolved in methylene chloride (150 mL). 1,8-Diazabicyclo[5.4.0]undec-7-ene (1.60 mL) was added thereto, and the resultant mixture was stirred at room temperature for 1 hour. The solvent was distilled away under reduced pressure. The residue was purified by silica gel flash column chromatography (hexane:ethyl acetate=7:1), to thereby give the title compound (1.05 g).

$^1$H-NMR(CDCl$_3$)δ: 1.37(3H, t, J=7.1 Hz), 4.34(2H, q, J=7.1 Hz), 6.90(1H, dd, J=3.9, 2.0 Hz), 7.06(1H, d, J=33.7 Hz), 7.08-7.10(1H, m).

MS(FAB)m/z: 235(M+H)$^+$.

Referential Example 534

(Z)-3-(5-chlorothien-2-yl)-2-fluoroacrylic acid

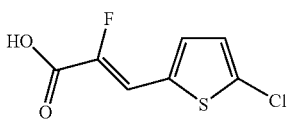

The method described in Referential Example 274 was performed by use of the compound obtained in Referential Example 533, whereby the title compound was obtained.

$^1$H-NMR(DMSO-d$_6$)δ: 7.22(1H, dd, J=3.9, 2.0 Hz), 7.35-7.40(2H, m), 13.76(1H, br.s).

MS(ESI-neg.)m/z: 205(M−H)$^−$.

Referential Example 535

6-methyl-5,6,7,8-tetrahydro-4H-thiazolo[4,5-d]azepin-2-ylamine

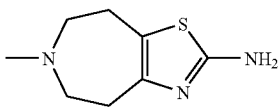

The method described in Referential Example 475 was performed by use of 5,6,7,8-tetrahydro-4H-thiazolo[4,5-d]azepin-2-ylamine (Japanese Patent Application Laid-Open (kokai) No. 2-45489), whereby the title compound was obtained.

$^1$H-NMR(CDCl$_3$)δ: 2.44(3H, s), 2.66-2.69(2H, m), 2.71 (4H, s), 2.80-2.83(2H, m), 4.66(2H, s).

MS(ESI)m/z: 184(M+H)$^+$.

Referential Example 536

2-bromo-6-methyl-5,6,7,8-tetrahydro-4H-thiazolo[4,5-d]azepine

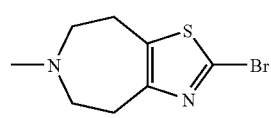

The method described in Referential Example 476 was performed by use of the compound obtained in Referential Example 535, whereby the title compound was obtained.

$^1$H-NMR(CDCl$_3$)δ: 2.45(3H, s), 2.66-2.72(4H, m), 2.85-2.88(2H, m), 3.03-3.06(2H, m).

MS(ESI)m/z: 247 (M+H)$^+$.

Referential Example 537

6-methyl-5,6,7,8-tetrahydro-4H-thiazolo[4,5-d]azepine-2-carboxylic acid lithium salt

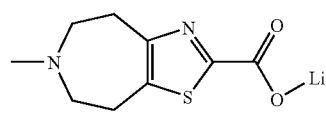

The method described in Referential Example 10 was performed by use of the compound obtained in Referential Example 536, whereby the title compound was obtained.

$^1$H-NMR(DMSO-d$_6$)δ: 2.33(3H, s), 2.56-2.63(4H, m), 2.77-2.93(4H, m).

MS(ESI)m/z: 213(M+H)$^+$.

Referential Example 538

5,6,7,8-tetrahydro[1,6]naphthyridine-2-carbonitrile hydrochloride

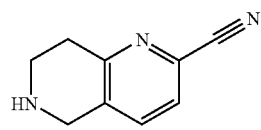

2-Cyano-7,8-dihydro-5H-[1,6]naphthyridine-6-carboxylic acid tert-butyl ester (WO00/09480) (3.74 g) was dissolved in methylene chloride (5.0 mL). 4N HCl-dioxane solution (14 mL) was added thereto. The resultant mixture was stirred at room temperature for 65 minutes, and stirred at 40° C. for 40 minutes. 4N HCl-dioxane solution (8 mL) was further added to the reaction mixture, followed by stirring at 45° C. for 75 minutes. Ethyl acetate was added to the reaction mixture, and the precipitated powder was recovered by filtration, to thereby give the title compound (3.20 g) as a colorless powder.

$^1$H-NMR(DMSO-d$_6$)δ: 3.14(2H, t, J=6.4 Hz), 3.50-3.70 (2H, m), 4.40(2H, s), 7.93(1H, s), 8.30(1H, s), 9.49(1H, br.s).

Referential Example 539

6-methyl-5,6,7,8-tetrahydro[1,6]naphthyridine-2-carbonitrile

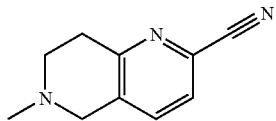

The method described in Referential Example 9 was performed by use of the compound obtained in Referential Example 538, whereby the title compound was obtained.

$^1$H-NMR(CDCl$_3$)δ: 2.49(3H, s), 2.81(2H, q, J=6.0 Hz), 3.10(2H, t, J=6.0 Hz), 3.71(2H, s), 7.44(1H, d, J=8.1 Hz), 7.47(1H, d, J=7.8 Hz).

Referential Example 540

6-methyl-5,6,7,8-tetrahydro[1,6]naphthyridine-2-carboxylic acid hydrochloride

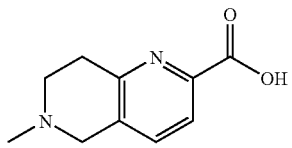

Concentrated hydrochloric acid (12 mL) was added to the compound (2.46 g) obtained in Referential Example 539, and the mixture was heated at 100-110° C. for 5.5 hours. Water was added to the reaction mixture, followed by concentrating under reduced pressure. Water was added thereto, and the mixture was basified with 1N sodium hydroxide. The resultant mixture was concentrated in about half, and neutralized with 1N hydrochloric acid. The solvent was distilled away under reduced pressure. Ethanol was added to the residue, and the resultant mixture was heated at 40-50° C. The insoluble material was removed through filtration through celite. The filtrate was concentrated under reduced pressure. The residue was dissolved in ethanol, and 1N HCl-ethanol (18 mL) was added thereto. The solvent was distilled away under reduced pressure. Ethyl acetate was added to the residue. The insoluble material was recovered by filtration, to thereby give the title compound (2.33 g) as a non-purified form.

$^1$H-NMR(DMSO-d$_6$)δ: 2.93(3H, s), 3.16(1H, d, J=16.4 Hz), 3.37-3.80(3H, m), 4.35-4.47(1H, m), 4.59(1H, d, J=16.8 Hz), 7.83(1H, d, J=8.1 Hz), 7.93(1H, d, J=8.1 Hz).

Referential Example 541

(1S,3R,4S)-4-{[(benzyloxy)carbonyl]amino}-3-[(tert-butoxycarbonyl)amino]cyclohexanecarboxylic acid tert-butyl ester

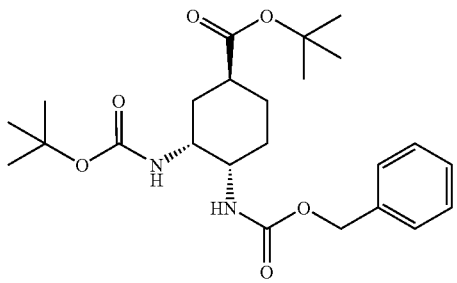

The compound (7.15 g) obtained in Referential Example 142 was dissolved in methylene chloride (100 mL). To the solution were added 2-methyl-2-propanol (4.88 mL), 1-(3-dimethylaminopropyl)-3-ethylcarbodiimide hydrochloride (4.89 g), and 4-dimethylaminopyridine (2.08 g), followed by stirring at room temperature for 19 hours. The reaction mixture was diluted with methylene chloride (200 mL), and washed with 10% aqueous citric acid, saturated aqueous sodium bicarbonate, and saturated brine. The resultant mixture was dried over sodium sulfate anhydrate, followed by concentrating under reduced pressure. The residue was purified by silica gel column chromatography (methylene chloride:acetone=30:1→20:1), to thereby give the title compound (7.07 g).

$^1$H-NMR(CDCl$_3$)δ: 1.20-2.09(6H, m), 1.43(9H, s), 1.44 (9H, s), 2.26(1H, br.s), 3.62-3.72(1H, m), 4.10(1H, br.s), 4.52-5.40(4H, m), 7.27-7.38(5H, m).

MS(FAB)m/z: 449 (M+H)$^+$.

Referential Example 542

(1S,3R,4S)-3-[(tert-butoxycarbonyl)amino]-4-({2-[(5-chloropyridin-2-yl)amino]-2-oxoethanethioyl}amino)cyclohexanecarboxylic acid tert-butyl ester

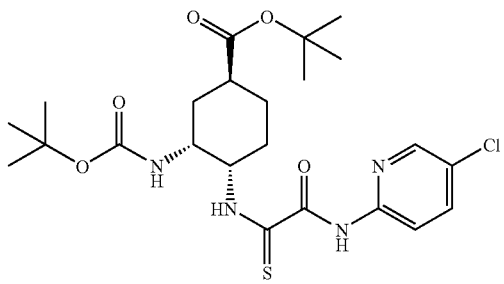

The compound obtained (700 mg) in Referential Example 541 was dissolved in methanol (7.0 mL)-tetrahydrofuran (7.0 mL). 10% Palladium carbon catalyst (wet, 350 mg) was added thereto, and the mixture was stirred under a hydrogen atmosphere at room temperature for 16 hours. The catalyst was removed through filtration, and the filtrate was concentrated under reduced pressure. The residue was dissolved in N,N-dimethylformamide (10 mL). Sulfur (65 mg), the compound (374 mg) obtained in Referential Example 520, and diisopropylethylamine (0.816 mL) were added thereto, and the resultant mixture was stirred at 120° C. for 8 hours. The reaction mixture was concentrated under reduced pressure. Methylene chloride was added to the residue, and the mixture was sequentially washed with 10% aqueous citric acid, saturated aqueous sodium hydrogencarbonate, and saturated brine. The resultant mixture was dried over sodium sulfate anhydrate, followed by concentrating under reduced pressure. The residue was purified by silica gel flash column chromatography (methylene chloride:methanol=100:1→50:1), to thereby give the title compound (373 mg).

$^1$H-NMR(CDCl$_3$)δ: 1.45(9H, s), 1.48(9H, s), 1.49-1.70 (2H, m), 1.80-2.40(5H, m), 4.26-4.39(2H, m), 4.79(1H, br.s), 7.70(1H, dd, J=9.0, 2.4 Hz), 8.19(1H, d, J=9.0 Hz), 8.32(1H, d, J=2.4 Hz), 10.01(1H, br.s), 10.58(1H, s).

MS(ESI)m/z: 513(M+H)$^+$.

Referential Example 543

(1S,3R,4S)-3-amino-4-({2-[(5-chloropyridin-2-yl)amino]-2-oxoethanethioyl}amino)cyclohexanecarboxylic acid tert-butyl ester hydrochloride

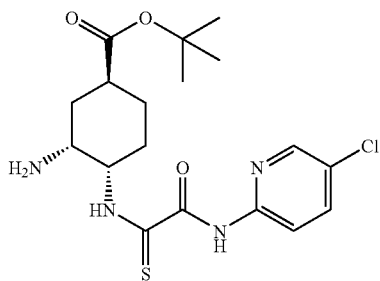

To the compound (530 mg) obtained in Referential Example 542 dissolved in ethyl acetate (3.90 mL), 1N HCl-ethyl acetate solution (1.30 mL) was added. The resultant mixture was stirred at room temperature for 3 hours. Ethyl acetate was added to the reaction mixture. The precipitated solid was recovered by filtration, followed by drying under reduced pressure, to thereby give the title compound (284 mg).

$^1$H-NMR(DMSO-$d_6$)δ: 1.42(9H, s), 1.49-1.61(1H, m), 1.71-1.88(2H, m), 1.88-2.03(1H, m), 2.04-2.26(2H, m), 2.71-2.85(1H, m), 3.84-4.12(1H, m), 4.44(1H, br.s), 8.00-8.29 (5H, m), 8.44-8.51(1H, m), 10.67(1H, s), 10.91(1H, d, J=6.8 Hz).
MS(ESI)m/z: 413(M+H)$^+$.

Referential Example 544

(1S,3R,4S)-3-[(tert-butoxycarbonyl) amino]-4-({2-[(5-chloropyridin-2-yl)amino]-2-oxoacetyl}amino)cyclohexanecarboxylic acid tert-butyl ester

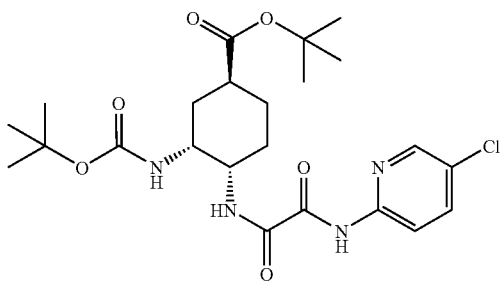

The compound (1.00 g) obtained in Referential Example 541 was dissolved in methanol (20 mL)-tetrahydrofuran (20 mL). 10% Palladium carbon catalyst (wet, 500 mg) was added thereto. The mixture was stirred in a hydrogen atmosphere at room temperature for 4 hours. The catalyst was removed through filtration, and the filtrate was concentrated under reduced pressure. The residue was dissolved in N,N-dimethylformamide (10 mL). To the resultant mixture were sequentially added the compound (231 mg) obtained in Referential Example 266, 1-hydroxybenzotriazole (139 mg), and 1-(dimethylaminopropyl)-3-ethylcarbodiimide hydrochloride (288 mg), followed by stirring at room temperature overnight. The reaction mixture was concentrated under reduced pressure. Ethyl acetate and 10% aqueous citric acid were added to the residue for partitioning the mixture. The oil layer was sequentially washed with saturated brine, aquous sodium hydrogencarbonate, and saturated brine. The oil layer was dried over magnesium sulfate anhydrate, and the solvent was distilled away under reduced pressure, to thereby give the title compound (364 mg).

$^1$H-NMR(CDCl$_3$)δ: 1.44(9H, s), 1.46(9H, s), 1.54-2.09 (6H, m), 2.20-2.38(1H, m), 3.83-3.98(1H, m), 4.08-4.29(1H, m), 4.71(1H, br.s), 7.69(1H, dd, J=8.9, 2.6 Hz), 8.00(1H, br.s), 8.18(1H, d, J=8.9 Hz), 8.31(1H, d, J=2.5 Hz), 9.72(1H, br.s).
MS(ESI)m/z: 441(M-tBu)$^+$.

Referential Example 545

2-methyl-1,2,3,4-tetrahydro-6-isoquinolinecarboxylic acid methyl ester

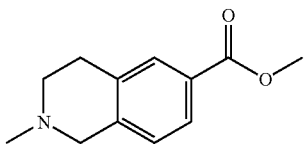

To 3,4-dihydro(1H)isoquinoline-2,6-dicarboxylic acid 2-(tert-butyl) ester 6-methyl ester (WO00/09480) (344 mg) dissolved in methylene chloride (6 mL), under ice cooling, trifluoroacetic acid (3 mL) was added, followed by stirring for 30 minutes. The reaction mixture was concentrated, and diluted with chloroform. The resultant mixture was neutralized with saturated aqueous sodium hydrogencarbonate, followed by extracting with chloroform/methanol (4/1). The resultant organic layer was dried over sodium sulfate anhydrate, and concentrated under reduced pressure. The residue was purified by silica gel chromatography (chloroform:methanol=20:1→1:1), to thereby give 1, 2, 3, 4-tetrahydroisoquinoline-6-carboxylic acid methyl ester (154 mg). This material was dissolved in methylene chloride (5 mL), and formalin (90.6 μL) was added thereto at room temperate, followed by stirring for 10 minutes. Under ice cooling, acetic acid (46 μL) and sodium triacetoxyborohydride (269 mg) were added thereto. The mixture was stirred at room temperature for 105 minutes, and neutralized with saturated aqueous sodium hydrogencarbonate. The resultant mixture was extracted with chloroform. The organic layer was dried over sodium sulfate anhydrate, and concentrated under reduced pressure, to thereby give the title compound (162 mg).

$^1$H-NMR(CDCl$_3$)δ: 2.47(3H, s), 2.70(2H, dd, J=6.0 Hz), 2.96(2H, dd, J=6.0 Hz), 3.62(2H, s), 3.90(3H, s), 7.08(1H, d, J=7.6 Hz), 7.78(1H, d, J=7.6 Hz), 7.80(1H, s).
MS(ESI)m/z: 206 (M+H)$^+$.

Referential Example 546

(1S,2R,4S)-4-(aminocarbonyl)-2-[(tert-butoxycarbonyl)amino]cyclohexylcarbamic acid fluoren-9-ylmethyl ester

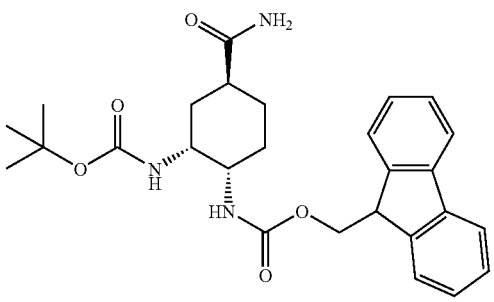

The compound (1.92 g) obtained in Referential Example 142 was dissolved in N,N-dimethylformamide (30 mL) under ice cooling. To the solution were sequentially added ammonium chloride (523 mg), 1-hydroxybenzotriazole (661 mg), 1-(dimethylaminopropyl)-3-ethylcarbodiimide hydrochloride (1.41 g), and diisopropylethylamine (1.70 mL). The temperature of the resultant mixture was returned to room temperature, and the mixture was stirred for 3 days. The reaction mixture was concentrated under reduced pressure. Ethyl acetate and 10% aqueous citric acid were added to the residue for partitioning the mixture. The oil layer was sequentially washed with saturated brine, aqueous sodium hydrogencarbonate, and saturated brine, followed by drying over sodium sulfate anhydrate. The solvent was distilled away under reduced pressure. Hexane was added to the residue to solidify, thereby yielding (1R,2S,5S)-5-(aminocarbonyl)-2-{[(benzyloxy)carbonyl]amino}cyclohexylcarbamic acid tert-butyl ester (1.66 g) as a crude product. A mixture of the crude product (1.65 g), 10% palladium carbon catalyst (400 mg), and methanol (150 mL) was stirred in a hydrogen atmosphere at room temperature overnight. The catalyst was removed through filtration, and the solvent was distilled away under reduced pressure. To the residue were added succinimidylcarboxylic acid 9-fluorenylmethyl ester (2.13 g), 1,2-dimethoxyethane (130 mL), and saturated aqueous sodium hydrogencarbonate (130 mL), followed by stirring at room temperature overnight. Ethyl acetate, saturated brine, and water were added to the reaction mixture for partitioning the mixture. The resultant organic layer was dried over magnesium sulfate anhydrate, and the solvent was distilled away under reduced pressure, to thereby give the title compound (1.99 g).

$^1$H-NMR(CDCl$_3$)δ: 1.45(9H, s), 1.53-2.08(6H, m), 2.30 (1H, br.s), 3.71(1H, br.s), 4.07-4.15(1H, m), 4.21(1H, br.s), 4.37(2H, br.s), 4.70-5.80(4H, m), 7.26-7.33(2H, m), 7.39(2H, t, J=7.3 Hz), 7.53-7.61(2H, m), 7.76(2H, d, J=7.3 Hz).

MS(ESI)m/z: 502 (M+Na)$^+$.

Referential Example 547

(1S,2R,4S)-4-(aminocarbothioyl)-2-[(tert-butoxycarbonyl)amino]cyclohexylcarbamic acid fluoren-9-ylmethyl ester

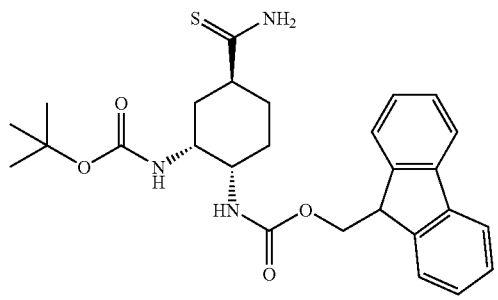

The compound (1.98 g) obtained in Referential Example 546 was dissolved in tetrahydrofuran (200 mL). Lawewson reagent (1.22 g) was added thereto, and the resultant mixture was stirred at room temperature for 4 days. To the reaction mixture, Lawesson reagent (0.50 g) was further added, followed by stirring overnight. Silica gel was added to the reaction mixture, and the solvent was distilled away under reduced pressure. The residue was purified by silica gel chromatography (ethyl acetate:hexane=2:1). Diethyl ether was added to the resultant oil, followed by stirring. The precipitated powder was recovered by filtration, to thereby give the title compound (1.25 g).

$^1$H-NMR(CDCl$_3$)δ: 1.45(9H, br.s), 1.57-2.10(6H, m), 2.69 (1H, br.s), 3.71(1H, br.s), 4.06-4.27(2H, m), 4.36(2H, br.s), 4.89(1H, br.s), 5.46(1H, br.s), 7.1(1H, br.s), 7.26-7.34(2H, m), 7.39(2H, t, J=7.3 Hz), 7.57(3H, br.s), 7.76(2H, d, J=7.1 Hz).

MS(ESI)m/z: 518(M+Na)$^+$.

Referential Example 548

(1R,2S,5S)-5-(aminocarbothioyl)-2-({2-[(5-chloropyridin-2-yl)amino]-2-oxoacetyl}amino)cyclohexylcarbamic acid tert-butyl ester, and (1R,2S,5S)-2-({2-[(5-chloropyridin-2-yl)amino]-2-oxoacetyl}amino)-5-cyanocyclohexylcarbamic acid tert-butyl ester

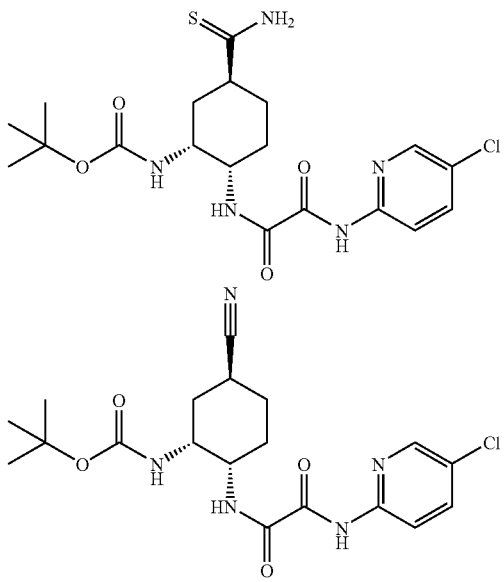

The compound (4.64 g) obtained in Referential Example 547 was dissolved in N,N-dimethylformamide (50 mL). Piperidine (2.78 mL) was added thereto, and the resultant mixture was stirred at room temperature for 30 minutes. The solvent was distilled away under reduced pressure. The residue was purified by silica gel chromatography (methanol methylene chloride=3:47→3:17), to thereby give (1R,2S,5S)-2-amino-5-(aminocarbothioyl)cyclohexylcarbamic acid tert-butyl ester (2.17 g) as a crude product. The crude product was dissolved in N,N-dimethylformamide (100 mL) To this solution were sequentially added the compound (1.78 g) obtained in Referential Example 266, 1-hydroxybenzotriazole (1.07 g), and 1-(dimethylaminopropyl)-3-ethylcarbodiimide hydrochloride (2.28 g), followed by stirring at room temperature overnight. The reaction mixture was concentrated under reduced pressure. Methylene chloride and 10% aqueous citric acid were added to the residue for partitioning the mixture. The oil layer was sequentially washed with saturated brine, sodium hydrogencarbonate aqueous solution, and saturated brine, followed by drying over magnesium sulfate anhydrate. The solvent was distilled away under reduced pressure. The residue was purified by silica gel chromatography (ethyl acetate:hexane=2:1), to thereby give the title cyano compound (427 mg) having a cyano group at 5-position, and the title aminocarbothioyl compound (718 mg) having a aminocarbothioyl group at 5-position.

5-cyano form: $^1$H-NMR(CDCl$_3$)δ: 1.46(9H, s), 1.56-1.66 (1H, m), 1.74-1.87(1H, m), 1.90-2.23(4H, m), 2.72(1H, br.s), 4.02-4.23(2H, m), 4.71(1H, br.s), 7.71(1H, dd, J=8.8, 2.4 Hz), 7.85(1H, br.s), 8.15(1H, d, J=8.8 Hz), 8.31(1H, d, J=2.4 Hz), 9.69(1H, br.s).

5-(aminocarbothioyl) form: $^1$H-NMR(CDCl$_3$)δ: 1.46(9H, s), 1.74-2.17(6H, m), 2.70(1H, s), 3.94-4.04(1H, m), 4.23 (1H, br.s), 4.86(1H, br.s), 6.97(1H, br.s), 7.50(1H, br.s), 7.70 (1H, dd, J=8.8, 2.4 Hz), 7.98(1H, br.s), 8.18(1H, d, J=8.8 Hz), 8.31(1H, d, J=2.4 Hz), 9.72(1H, s).

MS(ESI)m/z: 456(M+H)$^+$.

Referential Example 549

(1R,2S,5RS)-2-({2-[(5-chloropyridin-2-yl)amino]-2-oxoacetyl}amino)-5-(thiazol-2-yl)cyclohexylcarbamic acid tert-butyl ester

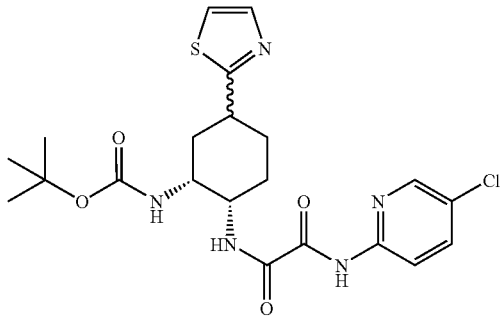

The compound (72 mg) with an aminocarbothioyl group at 5-position obtained in Referential Example 548 and bromoacetoaldehyde dimethyl acetal (20.4 μL) were dissolved in N,N-dimethylformamide (5 mL). The mixture was stirred at 50° C. for 8 hours. Bromoacetoaldehyde dimethyl acetal (80 μL) was further added thereto, followed by stirring for 13 hours. The resultant mixture was allowed to cool to room temperature. To the reaction mixture, di-tert-butyl dicarbonate (34.5 mg) and anhydrous sodium hydrogencarbonate (200 mg) were added. The resultant mixture was stirred at room temperature for 1 hour. Triethylamine (97 μL) was added thereto, followed by stirring for 2 hours. Ethyl acetate and 10% aqueous citric acid were added to the reaction mixture for partitioning the mixture. The organic layer was sequentially washed with saturated brine, saturated aqueous sodium hydrogencarbonate, and saturated brine, followed by drying over magnesium sulfate anhydrate. The solvent was distilled away under reduced pressure. The residue was purified by silica gel chromatography (ethyl acetate:hexane=2:1), to thereby give the title compound (37.5 mg).

$^1$H-NMR(CDCl$_3$)δ: 1.40-1.51(9H, m), 1.75-2.16(5H, m), 2.19-2.39(1H, m), 3.10-3.38(1H, m), 3.91-4.08(1H, m), 4.21-4.40(1H, m), 4.80-4.94(0.5H, m), 5.61-5.90(0.5H, m), 7.24-7.26(1H, m), 7.66-7.74(2H, m), 7.80-7.90(0.5H, m), 8.02-8.11(0.5H, m), 8.16-8.22(1H, m), 8.27-8.33(1H, m), 9.66-9.80(1H, m).

MS(ESI)m/z: 480(M+H)$^+$.

Referential Example 550

(1R,2S,5S)-2-({2-[(5-chloropyridin-2-yl)amino]-2-oxoacetyl}amino)-5-(1,2,4-oxadiazol-3-yl)cyclohexylcarbamic acid tert-butyl ester

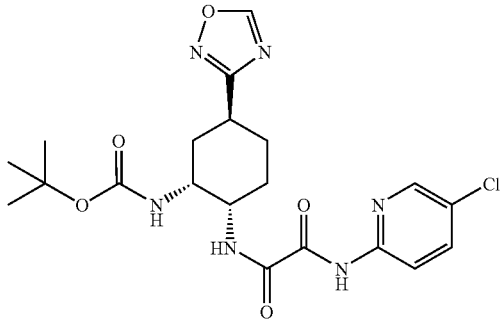

The compound (427 mg) with a cyano group at 5-position obtained in Referential Example 548 and anhydrous sodium hydrogencarbonate (84.9 mg) were suspended in ethanol. To the suspension, hydroxylamine sulfate (82.9 mg) was added, followed by heating at 60° C. and stirring for 6 days. The solvent was distilled away under reduced pressure. The residue was subjected to silica gel chromatography (methanol:methylene chloride=1:9), to thereby give (1R,2S,5S)-5-[amino(hydroxyimino)methyl]-2-({2-[(5-chloropyridin-2-yl)amino]-2-oxoacetyl}amino)cyclohexylcarbamic acid tert-butyl ester (183 mg) as a crude product. To the crude product, methyl orthoformate (5 mL) and boron trifluoride diethyl ether complex (1 drop) were added at room temperature, followed by heating at 55° C. and stirring for 20 minutes. The resultant mixture was allowed to cool to room temperature. The solvent was distilled away under reduced pressure. The residue was purified by silica gel chromatography (methanol:methylene chloride=1:19), to thereby give the title compound (57.6 mg).

$^1$H-NMR(CDCl$_3$)δ: 1.47(9H, s), 1.53-1.70(1H, m), 1.73-1.94(1H, m), 1.95-2.30(4H, m), 3.03(1H, br.s), 4.00-4.11(1H, m), 4.27(1H, br.s), 4.87(1H, br.s), 7.70(1H, dd, J=8.9, 2.4 Hz), 8.04(1H, s), 8.19(1H, d, J=8.8 Hz), 8.31(1H, d, J=2.4 Hz), 8.66(1H, s), 9.74(1H, br.s).

MS(ESI)m/z: 463(M−H)$^-$.

Referential Example 551

(1S,2R,4S)-2-[(tert-butoxycarbonyl)amino]-4-(5-methyl-1,3,4-oxadiazol-2-yl)cyclohexylcarbamic acid benzyl ester

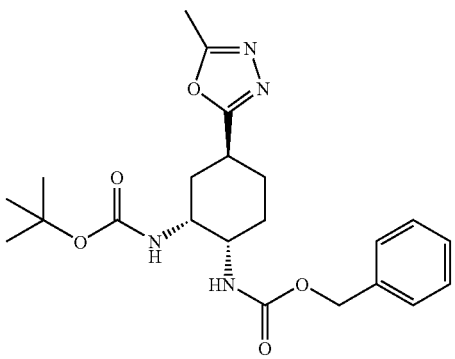

The compound (4.0 g) obtained in Referential Example 142 was dissolved in N,N-dimethylformamide (100 mL). To the solution were added hydrazine monohydrate (765 mg), 1-hydroxybenzotriazole (1.38 g), and 1-(dimethylaminopropyl)-3-ethylcarbodiimide hydrochloride (2.93 g), followed by stirring at room temperature overnight. The reaction mixture was concentrated under reduced pressure. Methylene chloride and sodium hydrogencarbonate aqueous solution were added to the residue for partitioning the mixture. The aqueous layer was extracted with methylene chloride. The resultant organic layers were combined, followed by drying over sodium sulfate anhydrate. Sodium sulfate anhydrate was removed through filtration, and silica gel (25 g) and methanol (15 mL) were added to the filtrate, followed by stirring. The insoluble material was removed through filtration. The solvent was distilled away under reduced pressure, to thereby give (1S,2R,4S)-2-[(tert-butoxycarbonyl)amino]-4-(hydrazinocarbonyl)cyclohexylcarbamic acid benzyl ester (3.71 g) as a crude product. To the crude product (1.73 g), methyl orthoacetate (10 mL) and boron trifluoride diethyl ether complex (2 drops) were added, followed by heating at 70° C. and stirring overnight. The resultant mixture was allowed to cool to room temperature. The solvent was distilled away under reduced pressure. Methylene chloride and sodium hydrogencarbonate aqueous solution were added to the residue for partitioning the mixture. The aqueous layer was extracted with methylene chloride. The resultant organic layers were combined, followed by drying over sodium sulfate anhydrate. The solvent was distilled away under reduced pressure. The residue was purified by silica gel chromatography (methanol:methylene chloride=1:19), to thereby give the title compound (1.10 g).

$^1$H-NMR(CDCl$_3$)δ: 1.44(9H, s), 1.68-2.27(6H, m), 2.50 (3H, s), 2.95-3.09(1H, m), 3.66-3.86(1H, m), 4.08-4.24(1H, m), 4.76(1H, br.s), 5.04-5.16(2H, m), 5.27-5.36(1H, m), 7.29-7.39(5H, m).

MS(ESI)m/z: 431(M+H)$^+$.

Referential Example 552

(1R,2S,5S)-2-({2-[(5-chloropyridin-2-yl)amino]-2-oxoacetyl}amino)-5-(5-methyl-1,3,4-oxadiazol-2-yl)cyclohexylcarbamic acid tert-butyl ester

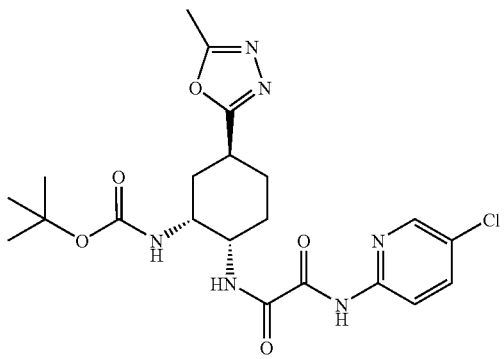

A mixture of the compound (1.10 g) obtained in Referential Example 551, 10% palladium carbon catalyst (300 mg), and methanol (50 mL) was stirred in a hydrogen atmosphere at room tamperature for 1 hour. The catalyst was removed through filtration, and the solvent was distilled away under reduced pressure. The residue was dissolved in N,N-dimethylformamide (50 mL). To the solution were sequentially added the compound (632 mg) obtained in Referential Example 266, 1-hydroxybenzotriazole (381 mg), and 1-(dimethylaminopropyl)-3-ethylcarbodiimide hydrochloride (810 mg), followed by stirring at room temperature overnight. The reaction mixture was concentrated under reduced pressure. Ethyl acetate and 10% aqueous citric acid were added to the residue for partitioning the mixture. The oil layer was sequentially washed with saturated brine, sodium hydrogencarbonate aqueous solution, and saturated brine, followed by drying over magnesium sulfate anhydrate. The solvent was distilled away under reduced pressure, to thereby give the title compound (944 mg). $^1$H-NMR(CDCl$_3$)δ: 1.47(9H, s), 1.58-1.88 (2H, m), 1.92-2.31(4H, m), 2.52(3H, s), 3.04(1H, br.s), 3.98-4.09(1H, m), 4.27(1H, br.s), 4.83(1H, br.s), 7.71(1H, dd, J=8.8, 2.4 Hz), 8.02(1H, br.s), 8.19(1H, d, J=8.8 Hz), 8.32 (1H, d, J=2.4 Hz), 9.72(1H, br.s).

MS(ESI)m/z: 479(M+H)$^+$.

Referential Example 553

(1S,2R,4S)-2-[(tert-butoxycarbonyl)amino]-4-(1,3,4-oxadiazol-2-yl)cyclohexylcarbamic acid benzyl ester

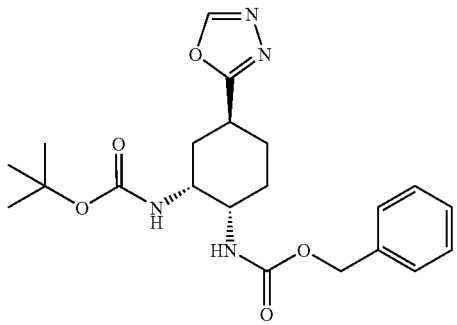

In a manner similar to that described in Referential Example 551, the compound obtained in Referential Example 142 was condensed with hydrazine. By use of methyl orthoformate, the condensed compound was subjected to cyclization reaction, whereby the title compound was obtained.

$^1$H-NMR(CDCl$_3$)δ: 1.45(9H, s), 1.71-2.30(6H, m), 3.04-3.15(1H, m), 3.80(1H, br.s), 4.17(1H, br.s), 4.75(1H, br.s), 5.05-5.15(2H, m), 5.25(1H, s), 7.30-7.38(5H, m), 8.35(1H, s).

MS(ESI)m/z: 417(M+H)$^+$.

Referential Example 554

(1R,2S,5S)-2-({2-[(5-chloropyridin-2-yl)amino]-2-oxoacetyl}amino)-5-(1,3,4-oxadiazol-2-yl)cyclohexylcarbamic acid tert-butyl ester

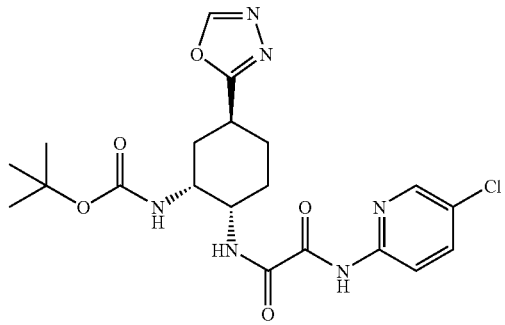

In a manner similar to that described in Referential Example 552, the compound obtained in Referential Example 553 was deprotected. The deprotected compound was condensed with the compound obtained in Referential Example 266, whereby, the title compound was obtained.

$^1$H-NMR(CDCl$_3$)δ: 1.47(9H, s), 1.59-1.92(2H, m), 2.00-2.33(4H, m), 3.02-3.22(1H, m), 3.94-4.10(1H, m), 4.27(1H, br.s), 4.83(1H, br.s), 7.71(1H, dd, J=8.9, 2.6 Hz), 8.00(1H, br.s), 8.19(1H, d, J=8.9 Hz), 8.32(1H, d, J=2.6 Hz), 8.37(1H, br.s), 9.72(1H, s).

MS(ESI)m/z: 465(M+H)$^+$.

Referential Example 555

(1S,2R,4S)-2-[(tert-butoxycarbonyl)amino]-4-{[(2-hydroxyethyl)amino]carbonyl}cyclohexylcarbamic acid benzyl ester

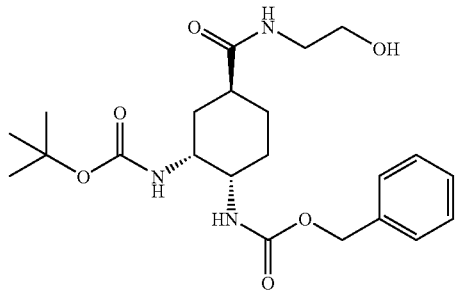

In a manner similar to that described in Referential Example 143, the compound obtained in Referential Example 142 was condensed with 2-aminoethanol, whereby the title compound was obtained.

$^1$H-NMR(CDCl$_3$)δ: 1.44(9H, s), 1.50-2.07(6H, m), 2.28-2.39(1H, m), 3.26-3.49(1H, m), 3.45-3.63(1H, m), 3.65-3.84 (3H, m), 3.90-4.07(1H, m), 5.02-5.28(4H, m), 6.21-6.35(1H, m), 7.28-7.39(5H, m).

MS(ESI)m/z: 436(M+H)$^+$.

Referential Example 556

(1R,2S,5S)-2-({2-[(5-chloropyridin-2-yl)amino]-2-oxoacetyl}amino)-5-(1,3-oxazol-2-yl)cyclohexylcarbamic acid tert-butyl ester

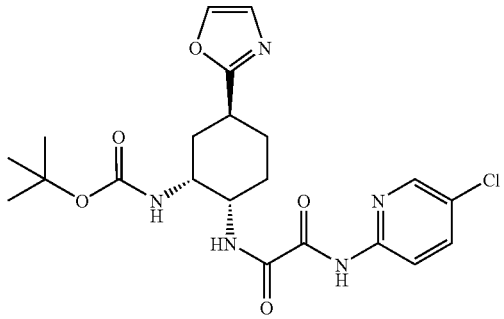

in a nitogen atmosphere and being cooled at −60° C., to oxalyl chloride (2.85 mL) in methylene chloride (50 mL), dimethyl sufoxide (3.47 mL) was added dropwise, and the compound (3.55 g) obtained in Referential Example 555 dissolved in methylene chloride (20 mL) was subsequently added dropwise thereto over 15 minutes. The resultant mixture was stirred at −60° C. for 45 minutes, and triethylamine (11.4 mL) was added dropwise thereto, followed by stirring for 30 minutes. Water was added to the reaction mixture at −60° C., and the temperature of the resultant mixture was returned to room temperature, followed by extracting with chloroform and drying over sodium sulfate anhydrate. The solvent was distilled away under reduced pressure. The residue was purified by silica gel chromatography (chloroform:methanol=50:1→10:1), to thereby give a yellow solid (2.43 g). To triphenylphosphine (4.41 g) in methylene chloride (25 mL) were sequentially added hexachloroethane (3.32 g), triethylamine (4.69 mL), and the yellow solid (2.43 g) dissolved in methylene chloride (35 mL). The resultant mixture was stirred at room temperature for 20 hours. Saturated aqueous sodium hydrogencarbonate was added thereto, followed by stirring for 30 minutes. The reaction mixture was extracted with chloroform. The resultat mixture was dried over sodium sulfate anhydrate, and concentrated under reduced pressure. The residue was purified by silica gel chromatography (chloroform:methanol=50:1), to thereby give oxazole cyclized material as a mixture containig triphenylphosphine oxide. The mixture was dissloved in methanol (30 mL), and 10% palladium carbon catalyst (2.08 g) was added thereto. The resultant mixture was stirred in a hydrogen atmosphere at room temperature for 14 hours. 10% Palladium carbon catalyst (1.02 g) was further added thereto, and the resultant mixture was stirred in a hydrogen atmosphere for 6 hours. The catalyst was removed through filtration, and the filtrate was concentrated under reduced pressure. The residue was purified by silica gel chromatography (chloroform:methanol=50:1→1:1). The resultant compound and the compound (612 mg) obtained in Referential Example 266 were dissolved in N,N-dimethylformamide (15 mL). To the resultant mixture, 1-(dimethylaminopropyl)-3-ethylcarbodiimide hydrochloride (872 mg) and 1-hydroxybenzotriazole monohydrate (461 mg) were added at room temperature. The reaction mixture was stirred for 12 hours, and chloroform was added thereto. The resultant mixture was sequentially washed with water and saturated aqueous sodium hydrogencarbonate, followed by drying over sodium sulfate anhydrate and concentrating under reduced pressure. The residue was purified by silica gel flash column chromatography (methanol:chloroform=50:1), to thereby give the title compound (390 mg).

$^1$H-NMR(CDCl$_3$)δ: 1.46(9H, s), 1.54-2.30(6H, m), 2.90-3.07(1H, m), 3.97-4.08(1H, m), 4.15-4.30(1H, m), 4.91-5.10 (1H, m), 7.03(1H, s), 7.58(1H, s), 7.70(1H, dd, J=8.8, 2.4 Hz), 7.98-8.11(1H, m), 8.25(1H, d, J=8.8 Hz), 8.31(1H, d, J=2.4 Hz), 9.75(1H, s).

MS(ESI)m/z: 464 (M+H)$^+$.

Referential Example 557

(1S,3R,4S)-3-[(tert-butoxycarbonyl)amino]-4-({[2-(trimethylsilyl)ethoxy]carbonyl}amino)cyclohexanecarboxylic acid

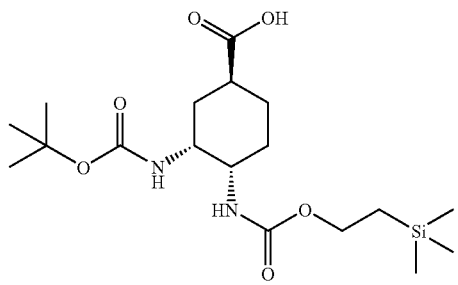

A mixture of the compound (4.20 g) obtained in Referential Example 141, 10% palladium carbon catalyst (1.0 g), and ethanol (100 mL) was stirred in a hydrogen atmosphere at room temperature for 5 hours. The catalyst was removed through filtration, and the solvent was distilled away under reduced pressure. To the residue, dioxane (50 mL), water (50 mL), and triethylamine (2.09 mL) were added, and the mixture was cooled with ice. To the resultant mixture, 1-[2-(trimethylsilyl)ethoxycarbonyloxy]pyrrolidine-2,5-dione (2.85 g) was added, followed by stirring at room temperature for 24 hours. The solvent was distilled away under reduced pressure. Ethyl acetate and 10% aqueous citric acid were added to the residue for partitioning the mixture. The oil layer was sequentially washed by saturated brine, sodium hydrogencarbonate aqueous solution, and saturated brine, followed by drying over magnesium sulfate anhydrate. The solvent was distilled away under reduced pressure to thereby give a light yellow oil (4.46 g). To the oil dissolved in tetrahydrofuran (50 mL), water (10 mL) and lithium hydroxide (479 mg) were added. The resultant mixture was stirred at room temperature overnight. The solvent was distilled away under reduced pressure. Ethyl acetate and 10% aqueous citric acid were added to the residue for partitioning the mixture. The oil layer was washed with saturated brine, followed by drying over magnesium sulfate anhydrate. The solvent was distilled away under reduced pressure. The resultant colorless powder was washed with hexane, to thereby give the title compound (3.51 g).

$^1$H-NMR(CDCl$_3$)δ: 0.06(9H, s), 0.97(2H, t, J=7.8 Hz), 1.46(9H, br.s), 1.52-2.22(6H, m), 2.47(1H, br.s), 3.68(1H, s), 3.97-4.24(3H, m), 4.69(0.5H, br.s), 4.95(0.5H, br.s), 5.18 (0.5H, br.s), 6.42(0.5H, br.s).

MS(ESI)m/z: 401(M−H)$^-$].

Referential Example 558

N-hydroxyacetamidine

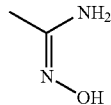

Hydroxyamine (50% aqueous, 661 mg) was dissolved in acetonitrile (10 mL), followed by stirring at 60° C. overnight. The solvent was distilled away under reduced pressure. The resultant colorless powder was washed with diethyl ether, to thereby give the title compound (673 mg).

$^1$H-NMR(DMSO-d$_6$)δ: 1.62(3H, s), 5.33(2H, br.s), 8.66 (1H, br.s).

Referential Example 559

(1S,2R,4S)-2-[(tert-butoxycarbonyl)amino]-4-(3-methyl-1,2,4-oxadiazol-5-yl)cyclohexylcarbamic acid 2-(trimethylsilyl)ethyl ester

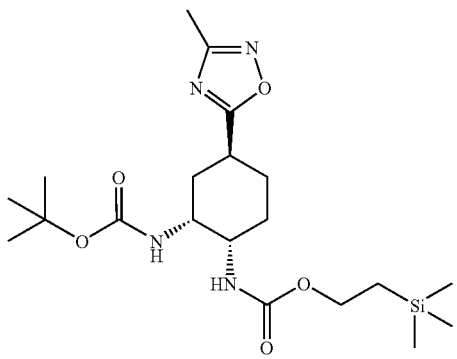

The comound (201 mg) obtained in Referential Example 557 and the compound (37 mg) obtained in Referential Example 558 were suspended in 1,2-dimethoxyethane (5 mL). To the suspension, 1-(dimethylaminopropyl)-3-ethylcarbodiimide hydrochloride (115 mg) was added, followed by stirring at room temperature overnight. Molecular sieve (MS-4A, powder, 1.0 g) was subsequently added to the reaction mixture. The resultant mixture was heated under reflux overnight. The solvent was distilled away under reduced pressure. The residue was purified by silica gel chromatography (hexane ethyl acetate=1:1), to thereby give the title compound (96.5 mg).

$^1$H-NMR(CDCl$_3$)δ: 0.04(9H, s), 0.98(2H, t, J=8.4 Hz), 1.46(9H, s), 1.60-1.83(2H, m), 1.87-2.28(4H, m), 2.38(3H, s), 3.04(1H, br.s), 3.76(1H, br.s), 4.07-4.22(3H, m), 4.72(1H, br.s), 5.14(1H, br.s).

MS(ESI)m/z: 341(M-Boc+2H)$^+$.

Referential Example 560

(1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexylcarbamic acid 2-(trimethylsilyl)ethyl ester

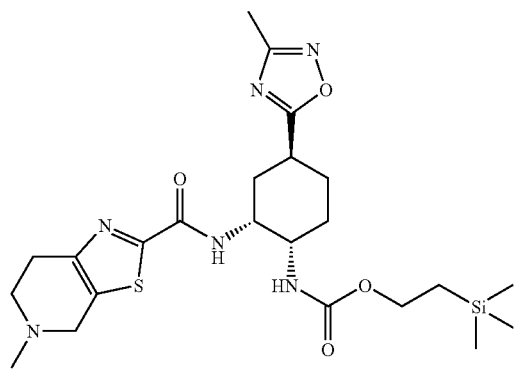

The comound (96.5 mg) obtained in Referential Example 559 was dissolved in ethanol (10 mL). To the solution, p-toluenesulfonic acid (45.8 mg) was added at room temperature. The reaction mixture was heated at 60° C., and stirred overnight. The resultant mixture was allowed to cool to room temperature. The solvent was distilled away under reduced pressure to thereby give a colorless powder. To the powder, the compound (67 mg) obtained in Referential Example 10 and N,N-dimethylformamide (5 mL) were added. 1-Hydroxybenzotriazole (44.5 mg) and 1-(dimethylaminopropyl)-3-ethylcarbodiimide hydrochloride (84 mg) were added thereto, followed by stirring at room temperature overnight. The solvent was distilled away under reduced pressure. Methylene chloride and sodium hydrogencarbonate aqueous solution were added to the residue for partitioning the mixture. The organic layer was dried over sodium sulfate anhydrate, and the solvent was distilled away under reduced pressure. The residue was purified by silica gel chromatography (methanol methylene chloride=3:47), to thereby give the title compound (110 mg).

$^1$H-NMR(CDCl$_3$)δ: 0.02(9H, s), 0.97(2H, dd, J=9.9, 7.0 Hz), 1.57-1.72(1H, m), 1.79-1.92(1H, m), 2.06-2.37(4H, m), 2.38(3H, s), 2.53(3H, s), 2.84-2.89(2H, m), 2.93-2.99(2H, m), 3.12-3.23(1H, m), 3.76(2H, br.s), 3.85-3.94(1H, m), 4.14 (2H, dd, J=9.9, 7.0 Hz), 4.60-4.69(1H, m), 5.23(1H, d, J=7.6 Hz), 7.41(1H, d, J=8.3 Hz).

MS(ESI)m/z: 521(M+H)$^+$.

Referential Example 561

(1S,2R,4S)-2-[(tert-butoxycarbonyl)amino]-4-(1,3,4-thiadiazol-2-yl)cyclohexylcarbamic acid 2-(trimethylsilyl)ethyl ester

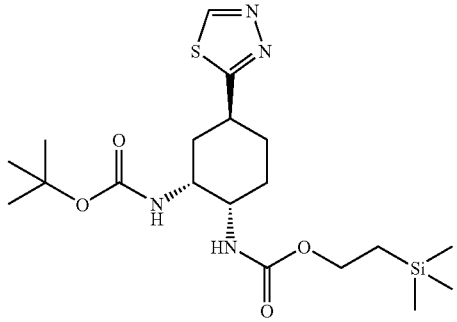

The compound (1.0 g) obtained in Referential Example 557 was dissolved in N,N-dimethylformamide (20 mL). To the solution were sequentially added formic acid hydrazide (149 mg), 1-hydroxybenzotriazole (335 mg), and 1-(dimethylaminopropyl)-3-ethylcarbodiimide hydrochloride (713 mg), followed by stirring at room temperature overnight. The reaction mixture was concentrated under reduced pressure. Ethyl acetate and 10% aqueous citric acid were added to the residue for partitioning the mixture. The oil layer was sequentially washed with saturated brine, sodium hydrogencarbonate aqueous solution, and saturated brine. The organic layer was dried over magnesium sulfate anhydrate. The solvent was distilled away under reduced pressure to thereby give a colorless powder (1.12 g). To the powder, toluene (50 mL) and Lawesson reagent (2.0 g) were added at room temperature, and the resultant mixture was heated under reflux for 1 hour, and allowed to cool to room temperature. Silica gel was added thereto, and the solvent was distilled away under reduced pressure. The residue was purified by silica gel chromatography (hexane:ethyl acetate=1:1→0:1), to thereby give the title compound (511 mg).

$^1$H-NMR(CDCl$_3$)δ: 0.04(9H, s), 0.99(2H, t, J=8.4 Hz), 1.46(9H, s), 1.59-1.85(2H, m), 1.91-2.02(1H, m), 2.05-2.14 (1H, m), 2.18-2.27(1H, m), 2.29-2.40(1H, m), 3.31-3.44(1H, m), 3.69-3.86(1H, m), 4.09-4.23(3H, m), 4.71-4.93(1H, m), 5.07-5.34(1H, m), 9.05(1H, s).

MS(ESI)m/z: 443(M+H)$^+$.

Referential Example 562

(1S,2R,4S)-2-{[(5-methyl-4,5,6,7-tetrahydrothiazolo [5,4-c]pyridin-2-yl)carbonyl]amino}-4-(1,3,4-thiadiazol-2-yl)cyclohexylcarbamic acid 2-(trimethylsilyl)ethyl ester

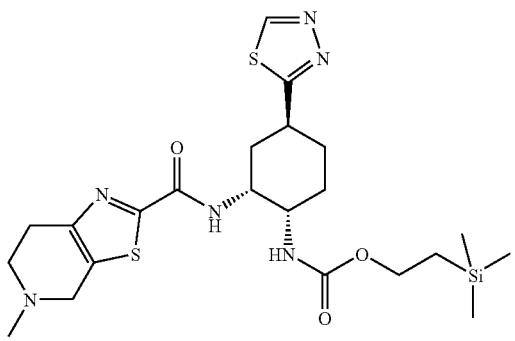

In a manner similar to that described in Referential Example 560, the compound obtained in Referential Example 561 was treated with p-toluenesulfonic acid for deprotection. The deprotected compound was condensed with the compound obtained in Referential Example 10, whereby the title compound was obtained.

$^1$H-NMR(CDCl$_3$)δ: 0.03(9H, s), 0.97(2H, t, J=8.5 Hz), 1.63-1.75(1H, m), 1.81-1.93(1H, m), 2.01-2.22(2H, m), 2.25-2.37(1H, m), 2.42-2.51(1H, m), 2.52(3H, s), 2.81-2.89(2H, m), 2.92-2.99(2H, m), 3.47-3.57(1H, m), 3.73(2H, s), 3.86-3.96(1H, m), 4.14(2H, t, J=8.5 Hz), 4.61-4.69(1H, m), 5.21-5.28(1H, m), 7.41-7.53(1H, m), 9.06(1H, s).

MS(ESI)m/z: 523 (M+H)$^+$.

Referential Example 563

(1S,3R,4S)-3-amino-4-({2-[(5-fluoropyridin-2-yl)amino]-2-oxoethanethioyl}amino)-N,N-dimethylcyclohexanecarboxamide hydrochloride

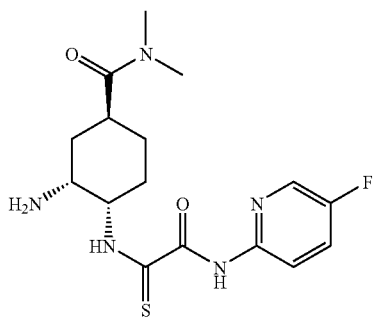

The compound (73.3 g) obtained in Referential Example 427 was suspended in dioxane (350 mL)-methanol (200 mL). To the suspension, 4N HCl-dioxane solution (350 mL) was added dropwise over 5 minutes. The resultant mixture was stirred under ice cooling for 10 minutes, and stirred at room temperature for 2.5 hours. The reaction mixture was concentrated under reduced pressure, and azeotroped with dioxane and tetrahydrofuran, followed by drying, to thereby give the title compound (76.4 g).

$^1$H-NMR(DMSO-d$_6$)δ: 1.34-1.55(1H, m), 1.64-1.84(3H, m), 1.97-2.11(1H, m), 2.11-2.30(1H, m), 2.80(3H, br.s), 3.06 (3H, br.s), 3.20-3.58(1H, m), 3.91-4.07(1H, m), 4.22-4.42 (1H, m), 7.74-7.91(1H, m), 8.00-8.16(1H, m), 8.25-8.60(4H, m), 10.64(1H, d, J=11.9 Hz), 10.89-10.99(1H, m).

MS(ESI)m/z: 367(M+H)$^+$.

Referential Example 564

5-methyl-4,5,6,7-tetrahydrothiazolo[5,4-c]pyridine-2-carboxylic acid hydrochloride

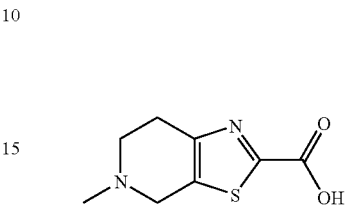

To the compound (3.00 g) obtained in Referential Example 10, 1N HCl in ethanol (36 mL) was added, and the resultant mixture was stirred at room temperature for 1 hour. The precipitated crystal was recovered by filtration, followed by washing with ethanol (9 mL). The wet material was dried at room temperature under reduced pressure, to thereby give the title compound (2.76 g).

$^1$H-NMR(D$_2$O)δ: 4.82-4.88(1H, d, J=16.0 Hz), 4.51-4.57 (1H, d, J=16.0 Hz), 3.88-3.96(1H, m), 3.60-3.70(1H, m), 3.22-3.33(2H, m), 3.15(3H, s).

Referential Example 565

(1S,2R,4S)-2-[(tert-butoxycarbonyl)amino]-4-(5-methyl-1,3,4-thiadiazol-2-yl)cyclohexylcarbamic acid 2-(trimethylsilyl)ethyl ester

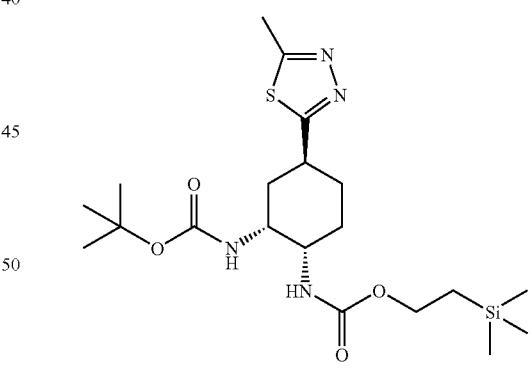

In a manner similar to that described in Referential Example 561, the compound obtained in Referential Example 557 was condensed with acetohydrazide. The condensed compound was reacted with Lawesson reagent, followed by heating, whereby the title compound was obtained.

$^1$H-NMR(CDCl$_3$)δ: 0.04(9H, s), 0.98(2H, t, J=8.5 Hz), 1.46(9H, s), 1.61-1.75(1H, m), 1.80-2.00(3H, m), 2.11-2.20 (1H, m), 2.22-2.31(1H, m), 2.75(3H, s), 3.17-3.32(1H, m), 3.61-3.88(1H, m), 4.07-4.22(3H, m), 4.82(1H, br.s), 5.24(1H, br.s).

MS(ESI)m/z: 457 (M+H)$^+$.

Referential Example 566

(1S,2R,4S)-2-{[(5-methyl-4,5,6,7-tetrahydrothiazolo[5,4-c]pyridin-2-yl)carbonyl]amino}-4-(5-methyl-1,3,4-thiadiazol-2-yl)cyclohexylcarbamic acid 2-(trimethylsilyl)ethyl ester

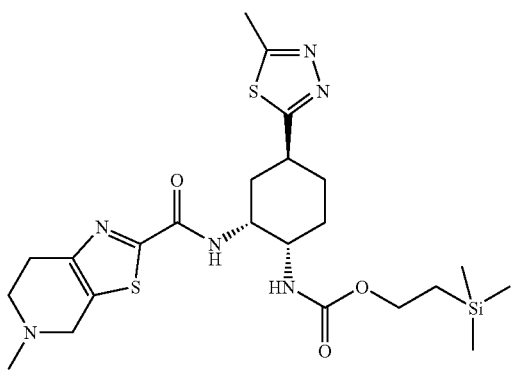

In a manner similar to that described in Referential Example 560, the compound obtained in Referential Example 565 was treated with p-toluenesulfonic acid for deprotection. The deprotected compound was condensed with the compound obtained in Referential Example 564, whereby the title compound was obtained.

$^1$H-NMR (CDCl$_3$)δ: 0.02(9H, s), 0.97(2H, t, J=7.8 Hz), 1.59-1.73(1H, m), 1.74-1.87(1H, m), 1.97-2.08(1H, m), 2.08-2.20(1H, m), 2.20-2.31(1H, m), 2.36-2.45(1H, m), 2.52(3H, s), 2.75(3H, s), 2.84(2H, t, J=5.5 Hz), 2.95(2H, t, J=5.5 Hz), 3.35-3.49(1H, m), 3.73(2H, br.s), 3.89(1H, br.s), 4.14(2H, t, J=7.8 Hz), 4.58-4.69(1H, m), 5.29(1H, br.s), 7.47(1H, d, J=8.1 Hz).
MS(ESI)m/z: 537 (M+H)$^+$.

Referential Example 567

(1S,2R,4S)-2-[(tert-butoxycarbonyl)amino]-4-(1,3-oxazol-5-yl)cyclohexylcarbamic acid benzyl ester

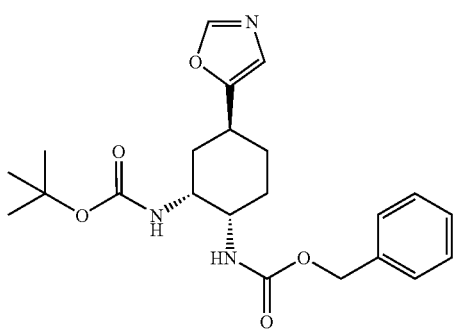

To a mixture of quinoline (8.00 mL) and p-toluenesulfonyl chloride (4.84 g), N-methylformamide (0.99 mL) was added dropwise under reduced pressure at 75° C. The resultant gas was cooled with Liebig condenser to liquefy and recover in an eggplant flask cooled at −78° C., whereby methyl isocyanide (553 mg) was obtained. To methyl isocyanide (349 mg) in tetrahydrofuran (10 mL), n-butyllithium (1.57M hexane solution, 6.95 mL) was added in a nitrogen atmosphere at −78° C., followed by stirring for 15 minutes. To the reaction mixture, the compound (1.02 g) obtained in Referential Example 141 dissolved in tetrahydrofuran (10 mL) was added dropwise at −78° C., followed by stirring for 30 minutes. The reaction mixture was heated to 0° C., and stirred for 15 minutes. The reaction mixture was cooled to −78° C., and acetic acid (0.62 mL) was added thereto, followed by stirring at 0° C. for 45 minutes. The resultant mixture was diluted with diethyl ether, and sequentially washed with water and saturated brine. The resultant mixture was dried over sodium sulfate anhydrate, and concentrated under reduced pressure. The residue was purified by silica gel flash column chromatography (methanol:methylene chloride=1:49-+3:97), to thereby give the title compound (663 mg).

$^1$H-NMR(CDCl$_3$)δ: 1.45(9H, s), 1.50-2.20(6H, m), 2.75-2.88(1H, m), 3.69-3.81(1H, m), 4.19-4.23(1H, m), 4.65-4.84(1H, m), 5.05-5.18(2H, m), 6.78(1H, s), 7.30-7.45(6H, m), 7.77(1H, s).
MS(ESI)m/z: 416(M+H)$^+$.

Referential Example 568

(1R,2S,5S)-2-({2-[(5-chloropyridin-2-yl)amino]-2-oxoacetyl}amino)-5-(1,3-oxazol-5-yl)cyclohexylcarbamic acid tert-butyl ester

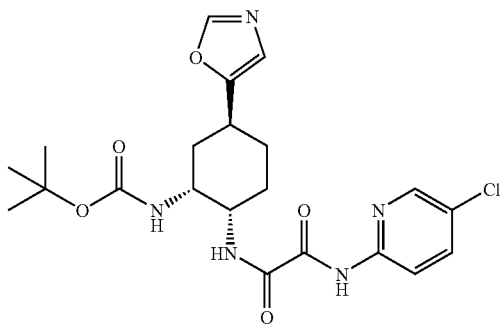

In a manner similar to that described in Referential Example 552, the compound obtained in Referential Example 567 was deprotected. The deprotected compound was condensed with the compound obtained in Referential Example 266, whereby the title compound was obtained.

$^1$H-NMR(CDCl$_3$)δ: 1.45(9H, s), 1.53-1.68(1H, m), 1.70-1.92(2H, m), 1.94-2.24(3H, m), 2.78-2.95(1H, m), 3.94-4.05(1H, m), 4.16-4.30(1H, m), 4.88-5.04(1H, m), 6.78(1H, s), 7.69(1H, dd, J=8.8, 2.4 Hz), 7.78(1H, s), 7.95-8.10(1H, m), 8.17(1H, d, J=8.8 Hz), 8.30(1H, d, J=2.4 Hz), 9.74(1H, s).
MS(ESI)m/z: 464(M+H)$^+$.

Referential Example 569

(1S,2R,4S)-4-(aminocarbonyl)-2-[(tert-butoxycarbonyl)amino]cyclohexylcarbamic acid 2-(trimethylsilyl)ethyl ester

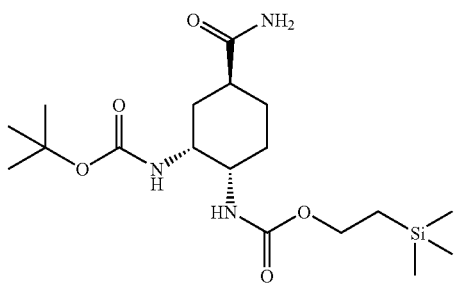

In a manner similar to that described in Referential Example 143, the compound obtained in Referential Example 557 was condensed with ammonium chloride, whereby the title compound was obtained.

¹H-NMR(CDCl₃)δ: 0.04(9H, s), 0.97(2H, t, J=8.3 Hz), 1.45(9H, s), 1.62-2.07(6H, m), 2.33(1H, br.s), 3.69(1H, br.s), 4.00-4.21(3H, m), 4.93(1H, br.s), 5.15(1H, br.s), 5.60(1H, br.s), 5.75(1H, br.s).

MS(ESI)m/z: 302(M-Boc)⁺.

Referential Example 570

(1S,2R,4S)-2-[(tert-butoxycarbonyl)amino]-4-cyano-cyclohexylcarbamic acid 2-(trimethylsilyl)ethyl ester

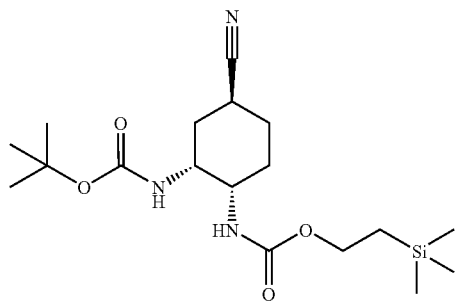

The compound (1.48 g) obtained in Referential Example 569 and triethylamine (1.04 mL) were dissolved in methylene chloride (25 mL). Under ice cooling, trifluoroacetic acid anhydride (0.790 mL) was added thereto, followed by stirring at room temperature for 1 hour. To the resultant mixture, saturated aqueous sodium hydrogencarbonate and methylene chloride were added for partitioning the mixture. The resultant organic layer was dried over sodium sulfate anhydrate, and the solvent was distilled away under reduced pressure. Hexane was added to the residue to solidfy, to thereby give the title compound (1.18 g).

¹H-NMR(DMSO-d₆)δ: 0.01(9H, s), 0.91(2H, dd, J=9.0, 7.1 Hz), 1.38(9H, s), 1.48-1.64(3H, m), 1.65-1.77(1H, m), 1.81(2H, t, J=5.9 Hz), 3.03(1H, br.s), 3.62(1H, br.s), 3.78(1H, br.s), 4.02(2H, dd, J=9.0, 7.1 Hz), 6.54(1H, br.s), 6.74(1H, br.s).

MS(ESI)m/z: 406(M+Na)⁺, 328(M-tBu)⁺, 284(M-Boc)⁺.

Referential Example 571

(1S,2R,4S)-2-[(tert-butoxycarbonyl)amino]-4-(5-methyl-1,2,4-oxadiazol-3-yl)cyclohexylcarbamic acid 2-(trimethylsilyl)ethyl ester

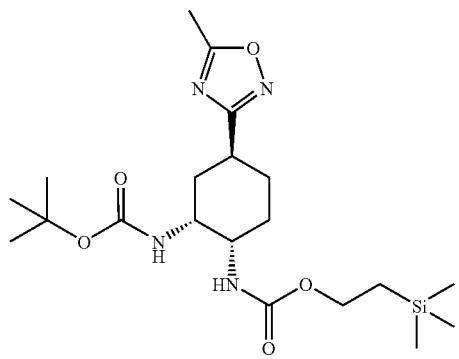

In a manner similar to that described in Referential Example 550, the compound obtained in Referential Example 570 was reacted with hydroxylamine. By use of trimethyl orthoacetate, the resultant compound was subjected to cyclization reaction, whereby the title compound was obtained.

¹H-NMR(CDCl₃)δ: 0.03(9H, s), 0.98(2H, t, J=8.4 Hz), 1.35-2.18(6H, m), 1.45(9H, s), 2.56(3H, s), 2.81-2.96(1H, m), 3.65-3.79(1H, m), 4.05-4.23(3H, m), 4.65-4.83(1H, m), 5.10-5.30(1H, m).

Referential Example 572

(1S,2R,4S)-4-(5-methyl-1,2,4-oxadiazol-3-yl)-2-{[(5-methyl-1-4,5,6,7-tetrahydrothiazolo[5,4-c]pyridin-2-yl)carbonyl]amino}cyclohexylcarbamic acid 2-(trimethylsilyl)ethyl ester

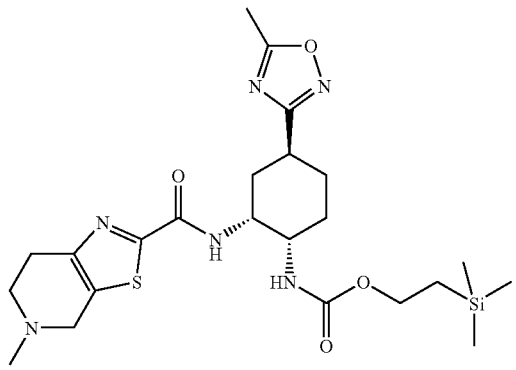

In a manner similar to that described in Referential Example 560, the compound obtained in Referential Example 571 was treated with p-toluenesulfonic acid for deprotection. The deprotected compound was condensed with the compound obtained in Referential Example 10, whereby the title compound was obtained.

¹H-NMR(CDCl₃)δ: 0.02(9H, s), 0.96(2H, t, J=8.4 Hz), 1.52-1.66(1H, m), 1.73-1.90(1H, m), 2.00-2.29(4H, m), 2.56 (3H, s), 2.58(3H, s), 2.85-3.11(5H, m), 3.73-3.93(3H, m), 4.13(2H, t, J=8.4 Hz), 4.59-4.68(1H, m), 5.15-5.26(1H, m), 7.34-7.45(1H, m).

MS(ESI)m/z: 521(M+H)⁺.

Referential Example 573

(1S,2R,4S)-2-[(tert-butoxycarbonyl)amino]-4-({[2-(trimethylsilyl)ethoxy]carbonyl}amino)cyclohexyl-carbamic acid benzyl ester

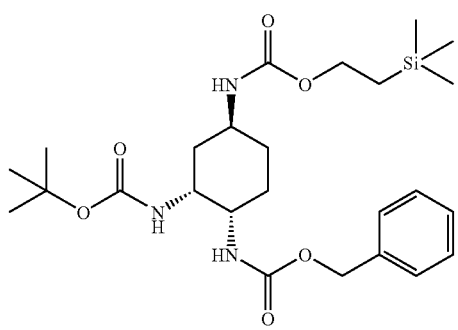

To the compound (3.14 g) obtained in Referential Example 142 in toluene (60 mL) were added triethylamine (1.67 mL) and diphenylphosphoryl azide (2.06 mL), followed by stirring at 80° C. for 2 hours. The mixture was cooled to room temperature, and trimethylsilylethanol (4.59 mL) was added thereto. The resultant mixture was stirred at 90° C. for 16 hours. The reaction mixture was cooled to room temperature, concentrated under reduced pressure, and dissolved in ethyl acetate. The solution was sequentially washed with 10% aqueous citric acid, saturated aqueous solution of sodium hydrogencarbonate, and saturated brine, followed by drying over sodium sulfate anhydrate and concentrating under reduced pressure. The residue was purified by silica gel column chromatography (methylene chloride:methanol=50:1). Hexane was added to the resultant solid, and the mixture was subjected to filtration, to thereby give the title compound (2.72 g).

$^1$H-NMR(CDCl$_3$)δ: 0.03(9H, s), 0.91-1.01(2H, m), 1.23-1.64(3H, m), 1.44(9H, s), 1.90-2.08(3H, m), 3.51-3.75(2H, m), 4.04-4.18(3H, m), 4.49(1H, br.s), 4.78(1H, br.s), 5.03-5.14(2H, m), 5.36(1H, br.s), 7.28-7.38(5H, m).

MS(ESI)m/z: 508(M+H)$^+$.

Referential Example 574

(1S,2R,4S)-4-amino-2-[(tert-butoxycarbonyl)amino]cyclohexylcarbamic acid benzyl ester

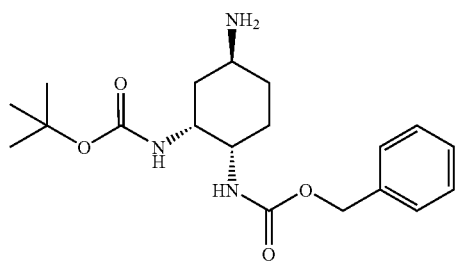

1N Tetrabutylammonium tetrahydrofuran (6.0 mL) was added to the compound (1.02 g) obtained in Referential Example 573 dissolved in tetrahydrofuran (6.0 mL), followed by stirring at room temperature for 3 days. Ethyl acetate was added thereto, and the resultant mixture was sequentially washed with saturated aqueous solution of sodium hydrogencarbonate, water, and saturated brine. The organic layer was dried over sodium sulfate anhydrate, and concentrated under reduced pressure. The residue was purified by silica gel column chromatography (methylene chloride:methanol:concentrated aqueous ammonia=100:10:1), to thereby give the title compound (660 mg).

$^1$H-NMR(CDCl$_3$)δ: 1.19-1.63(3H, m), 1.44(9H, s), 1.80-2.06(3H, m), 2.79-2.91(1H, m), 3.63-3.72(1H, m), 4.11(1H, br.s), 4.68(1H, br.s), 5.03-5.14(2H, m), 5.27(1H, br.s), 7.28-7.38(5H, m).

MS(ESI)m/z: 363(M+H)$^+$.

Referential Example 575

(1S,2R,4S)-2-[(tert-butoxycarbonyl)-4-(4H-1,2,4-triazol-[4-yl)amino]cyclohexylcarbamic acid benzyl ester

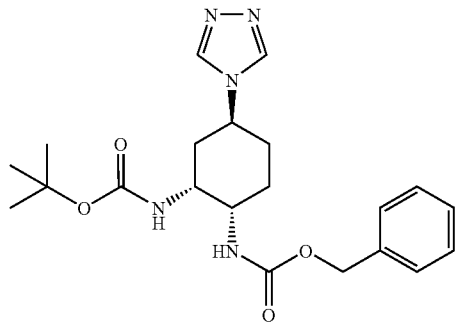

To the compound (182 mg) obtained in Referential Example 574 in pyridine (3.0 mL) were added 1,2-diformylhydrazine (154 mg), triethylamine (0.464 mL), and chlorotrimethylsilane (0.952 mL), followed by stirring at 80° C. for 6 hours. The reaction mixture was cooled to room temperature, and saturated aqueous solution of sodium hydrogencarbonate and methylene chloride were added thereto for partition. The organic layer was washed with saturated brine, followed by drying over sodium sulfate anhydrate and concentrating under reduced pressure. The residue was purified by flash silica gel column chromatography (methylene chloride:methanol=30:1→10:1), to thereby give the title compound (127 mg).

$^1$H-NMR(CDCl$_3$)δ: 1.45(9H, s), 1.54-1.91(3H, m), 1.91-2.15(2H, m), 2.21(1H, d, J=12.5 Hz), 2.37(1H, d, J=12.9 Hz), 3.82(1H, br.s), 4.24(1H, br.s), 4.36(1H, br.s), 5.05-5.16(2H, m), 5.35(1H, d, J=7.6 Hz), 7.30-7.40(5H, m), 8.26(2H, s).

MS(ESI)m/z: 416(M+H)$^+$.

Referential Example 576

(1R,2S,5S)-2-({2-[(5-chloropyridin-2-yl)amino]-2-oxoacetyl}amino)-5-(4H-1,2,4-triazol-4-yl)cyclohexylcarbamic acid tert-butyl ester

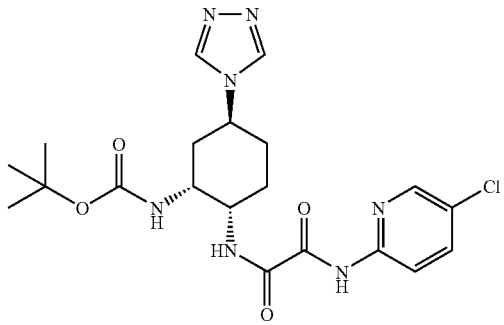

In a manner similar to that described in Referential Example 552, the compound obtained in Referential Example 575 was deprotected. The deprotected compound was condensed with the compound obtained in Referential Example 266, whereby the title compound was obtained.

$^1$H-NMR(CDCl$_3$)δ: 1.47(9H, s), 1.60-1.98(2H, m), 2.05-2.20(2H, m), 2.25-2.35(1H, m), 2.36-2.45(1H, m), 4.03-4.13 (1H, m), 4.37(1H, br.s), 4.47(1H, br.s), 5.42(1H, br.s), 7.71 (1H, dd, J=8.8, 2.4 Hz), 8.04(1H, br.s), 8.17(1H, d, J=8.8 Hz), 8.31-8.33(3H, m), 9.71(1H, s).

MS(ESI)m/z: 464(M+H)$^+$.

Referential Example 577

(1R,2S,5S)-2-amino-5-(5-methyl-1,3,4-oxadiazol-2-yl)cyclohexylcarbamic acid tert-butyl ester

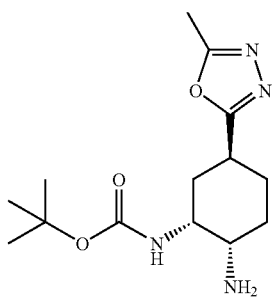

The compound (5.74 g) obtained in Referential Example 551 was dissolved in methanol (110 mL), followed by adding 10% palladium carbon catalyst (1.22 g) thereto and stirring in a hydrogen atmosphere at room temperature for 17 hours. The catalyst was filtered off, and the solvent was distilled away under reduced pressure, to thereby give the title compound (3.95 g).

$^1$H-NMR(CDCl$_3$)δ: 1.47(9H, s), 1.65-2.45(6H, m), 2.51 (3H, s), 3.03-3.60(3H, m), 4.12-4.35(1H, m), 5.45-5.76(1H, m), 6.86-7.17(1H, m).

MS(ESI)m/z: 297 (M+H)$^+$.

Referential Example 578

2-[(5-bromopyridin-2-yl)amino]-2-oxoacetic acid lithium salt

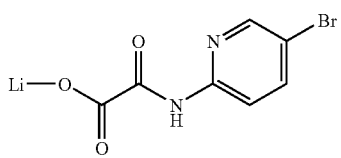

In a manner similar to that described in Referential Example 266, from the compound obtained in Referential Example 262, the title compound was obtained.

$^1$H-NMR(DMSO-d$_6$)δ: 8.03(1H, dd, J=8.8, 2.4 Hz), 8.09 (1H, d, J=8.8 Hz), 8.44(1H, d, J=2.4 Hz), 10.18(1H, s).

Referential Example 579

(1R,2S,5S)-2-({2-[(5-bromopyridin-2-yl)amino]-2-oxoacetyl}amino)-5-(5-methyl-1,3,4-oxadiazol-2-yl)cyclohexylcarbamic acid tert-butyl ester

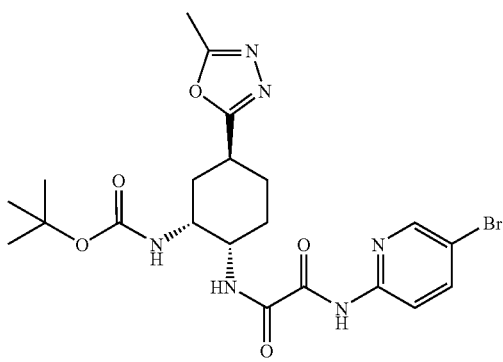

To the compound (900 mg) obtained in Referential Example 577 in N,N-dimethylformamide (40 mL) were added the compound (1.24 g) obtained in Referential Example 578, 3-(3-dimethylaminopropyl)-1-ethylcarbodiimide hydrochloride (1.17 g), and 1-hydroxybenzotriazole (205 mg), followed by stirring at 40° C. for 7 hours. To the reaction mixture were added ethyl acetate and water for partition. The organic layer was washed with water, dried over sodium sulfate anhydrate, and the solvent was distilled away under reduced pressure. The residue was purified by flash silica gel column chromatography (methylene chloride:methanol=19:1), to thereby give the title compound (1.51 g).

$^1$H-NMR(CDCl$_3$)δ: 1.46(9H, s), 1.56-2.31(6H, m), 2.52 (3H, s), 3.01-3.12(1H, m), 4.00-4.08(1H, m), 4.26(1H, br.s), 4.92(1H, br.s), 7.84(1H, dd, J=8.8, 2.5 Hz), 8.03(1H, d, J=2.9 Hz), 8.14(1H, d, J=8.8 Hz), 8.41(1H, d, J=2.5 Hz), 9.72(1H, s).

Referential Example 580

(1R,2S,5S)-2-{[(7-chlorocinnolin-3-yl)carbonyl]amino}-5-(5-methyl-1,3,4-oxadiazol-2-yl)cyclohexylcarbamic acid tert-butyl ester

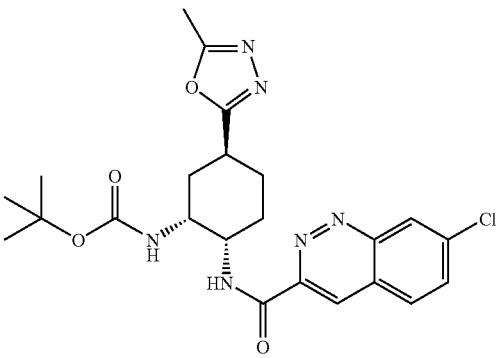

In a manner similar to that described in Referential Example 579, carboxylic acid lithium salt prepared by hydrolysis of the compound obtained in Referential Example 297 was condensed with the compound obtained in Referential Example 577, whereby the title compound was obtained.

$^1$H-NMR(CDCl$_3$)δ: 1.37(9H, s), 1.68-1.82(1H, m), 1.82-1.99(1H, m), 2.01-2.37(4H, m), 2.53(3H, s), 3.12(1H, br.s), 4.40(2H, br.s), 4.96(1H, br.s), 7.79(1H, dd, J=8.8, 1.8 Hz), 7.98(1H, d, J=8.8 Hz), 8.61(1H, s), 8.69(1H, d, J=7.8 Hz), 8.74(1H, s).

MS(ESI)m/z: 487(M+H)$^+$.

Referential Example 581

(1R,2S,5S)-2-{[(7-chloroisoquinolin-3-yl)carbonyl]amino}-5-(5-methyl-1,3,4-oxadiazol-2-yl)cyclohexylcarbamic acid tert-butyl ester

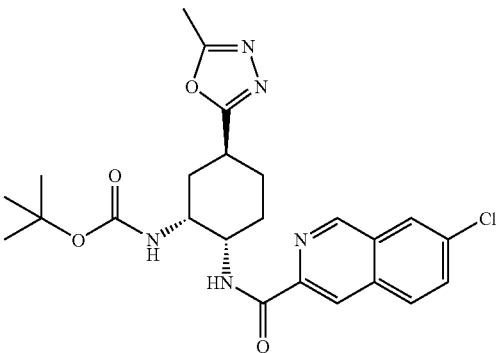

In a manner similar to that described in Referential Example 579, the compound obtained in Referential Example 577 was condensed with the compound obtained in Referential Example 57, whereby the title compound was obtained.

$^1$H-NMR(CDCl$_3$)δ: 1.45(9H, s), 1.57-1.74(1H, m), 1.79-2.49(5H, m), 2.53(3H, s), 3.00-3.16(1H, m), 4.24-4.38(2H, m), 5.00(1H, br.s), 7.71(1H, dd, J=8.8, 1.7 Hz), 7.90-7.97 (1H, m), 8.02(1H, d, J=1.7 Hz), 8.45-8.62(2H, m), 9.05(1H, .s).

MS(ESI)m/z: 486(M+H)$^+$.

Referential Example 582

(1S,2R,4S)-2-[(tert-butoxycarbonyl)amino]-4-(1,2,4-oxadiazol-5-yl)cyclohexylcarbamic acid 2-(trimethylsilyl)ethyl ester

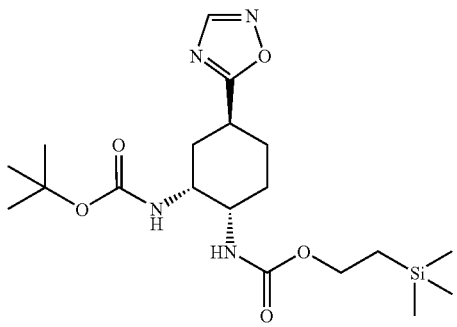

A mixture of the compound (994 mg) obtained in Referential Example 569 and N,N-dimethylformamide dimethylacetal (10 mL) was stirred at 120° C. for 2 hours. The reaction mixture was allowed to cool to room temperature, and concentrated under reduced pressure. Hexane was added to the residue to give colorless powder. To the powder were added 70% aqueous acetic acid (10 mL) and hydroxylamine (50% aqueous solution, 197 mg), followed by stirring at room temperature overnight. The solvent was distilled away under reduced pressure, and to the residue were added ethyl acetate and saturated aqueous solution of sodium hydrogencarbonate for partition. The organic layer was dried over sodium sulfate anhydrate, and the solvent was distilled away under reduced pressure. The residue was purified by silica gel chromatography (hexane:ethyl acetate=2:1), to thereby give the title compound (759 mg).

$^1$H-NMR(CDCl$_3$)δ: 0.04(9H, s), 0.91-1.04(2H, m), 1.46 (9H, s), 1.61-2.44(6H, m), 2.98-3.49(1H, m), 3.73(1H, br.s), 4.03-4.25(2H, m), 4.85(1H, br.s), 5.30(1H, br.s), 6.70(1H, br.s), 8.34(1H, s).

MS(ESI)m/z: 449(M+Na)$^+$, 327(M-Boc)$^+$.

Referential Example 583

(1S,2R,4S)-2-{[(5-methyl-4,5,6,7-tetrahydrothiazolo[5,4-c]pyridin-2-yl)carbonyl]amino}-4-(1,2,4-oxadiazol-5-yl)cyclohexylcarbamic acid 2-(trimethylsilyl)ethyl ester

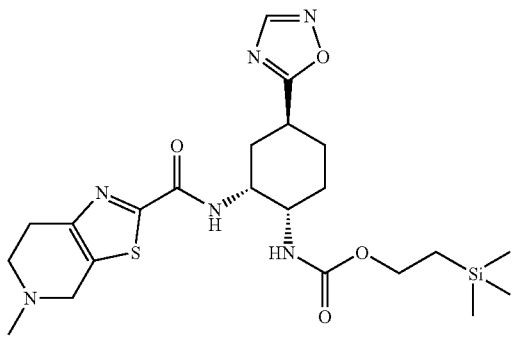

In a manner similar to that described in Referential Example 560, the compound obtained in Referential Example 583 was treated with p-toluenesulfonic acid for deprotection. The deprotected compound was condensed with the compound obtained in Referential Example 564, whereby the title compound was obtained.

$^1$H-NMR(CDCl$_3$)δ: 0.02(9H, s), 0.97(2H, dd, J=9.9, 7.0 Hz), 1.58-1.94(2H, m), 2.07-2.20(2H, m), 2.21-2.30(1H, m), 2.35-2.44(1H, m), 2.53(3H, s), 2.85(2H, t, J=5.6 Hz), 2.95 (2H, t, J=5.6 Hz), 3.20-3.32(1H, m), 3.74(2H, s), 3.90(1H, br.s), 4.14(2H, dd, J=9.9, 7.0 Hz), 4.62-4.69(1H, m), 5.19 (1H, br.s), 7.39(1H, d, J=8.1 Hz), 8.35(1H, s).

MS(ESI)m/z: 507(M+H)$^+$.

Referential Example 584

(1S,2R,4S)-2-[(tert-butoxycarbonyl)amino]-4-{[2-(2,2,2-trifluoroacetyl)hydrazino]carbonyl}cyclohexylcarbamic acid benzyl ester

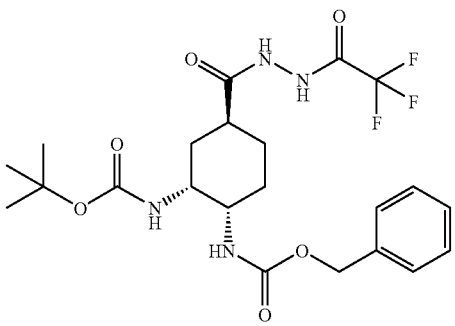

To the compound (4.00 g) obtained in Referential Example 142 in N,N-dimethylformamide (100 mL) were added hydrazine monohydrate (765 mg), 1-hydroxybenzotriazole (1.38 g), and 1-(dimethylaminopropyl)-3-ethylcarbodiimide hydrochloride (2.93 g), followed by stirring at room temperature overnight. The reaction mixture was concentrated under reduced pressure, and to the residue were added methylene chloride and aqueous solution of sodium hydrogencarbonate for partition. The aqueous layer was extracted with methylene chloride, and the obtained organic layers were combined, followed by drying over sodium sulfate anhydrate. The sodium sulfate anhydrate was filtered off, and to the obtained filtrate were added silica gel (25 g) and methanol (15 mL), followed by stirring and filtering to remove insoluble material. The solvent was distilled away under reduced pressure, to thereby give colorless oily crude material of (1S,2R,4S)-2-[(tert-butoxycarbonyl)amino]-4-(hydrazinocarbonyl)cyclohexylcarbamic acid benzyl ester (3.71 g). Methylene chloride (10 mL) and triethylamine (115 μL) were added to the resultant colorless oily material (306 mg). Anhydrous trifluoroacetic acid (116 μl) was added thereto under ice cooling, followed by stirring at room temperature for 5 hours. Moreover, triethylamine (115 μL) and anhydrous trifluoroacetic acid (116 μL) were added, followed by stirring at room temperature for 1 hour. To the reaction mixture were added methylene chloride and water for partition. The aqueous layer was extracted with methylene chloride, and the organic layers were combined, followed by drying over sodium sulfate anhydrate. The solvent was distilled away under reduced pressure, and the residue was purified by silica gel chromatography (methanol:methylene chloride=1:19), to thereby give the title compound (283 mg).

$^1$H-NMR(CDCl$_3$)δ: 1.41(9H, s), 1.52-2.06(6H, m), 2.53 (1H, br.s), 3.73(1H, br.s), 4.09(1H, br.s), 4.99-5.15(3H, m), 5.34(1H, d, J=7.3 Hz), 7.27-7.36(5H, m), 8.92-9.36(1H, m).

MS(ESI)m/z: 525(M+Na)$^+$, 403(M-Boc)$^+$.

Referential Example 585

(1S,2R,4S)-2-[(tert-butoxycarbonyl)amino]-4-[5-(trifluoromethyl)-1,3,4-oxadiazol-2-yl]cyclohexyl-carbamic acid benzyl ester

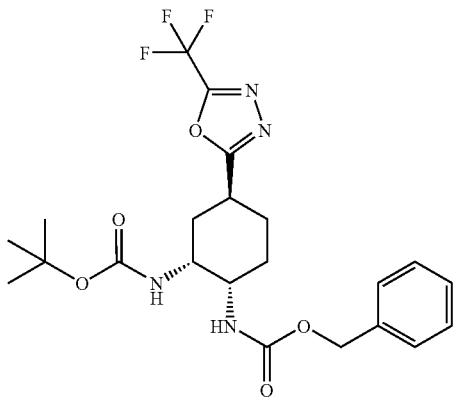

Triphenylphosphine (392 mg) was dissolved in methylene chloride (10 mL). To the resultant solution, hexachloroethane (296 mg), triethylamine (416 µL), and the compound (250 mg) obtained in Referential Example 584 in methylene chloride (5 mL) were sequentially added under ice cooling. The mixture was stirred at room temperature overnight, and to the reaction mixture were added methylene chloride and 10% aqueous citric acid for partition. The organic layer was sequentially washed with saturated brine, aqueous solution of sodium hydrogencarbonate, and saturated brine, followed by drying over sodium sulfate anhydrate. The solvent was distilled away under reduced pressure. The residue was purified by silica gel chromatography (hexane ethyl acetate=1:1), to thereby give the title compound (204 mg).

$^1$H-NMR(CDCl$_3$)δ: 1.44(9H, s), 1.51-1.62(1H, m), 1.71-1.90(1H, m), 1.92-2.16(2H, m), 2.16-2.25(1H, m), 2.28-2.38 (1H, m), 3.16(1H, br.s), 3.81(1H, br.s), 4.20(1H, br.s), 4.56-4.84(1H, m), 5.04-5.16(2H, m), 5.20-5.28(1H, m), 7.29-7.39 (5H, m).

MS(ESI)m/z: 429(M-tBu)$^+$, 385(M-Boc)$^+$.

Referential Example 586

(1R,2S,5S)-2-({2-[(5-chloropyridin-2-yl)amino]-2-oxoacetyl}amino)-5-[5-(trifluoromethyl)-1,3,4-oxadiazol-2-yl]cyclohexylcarbamic acid tert-butyl ester

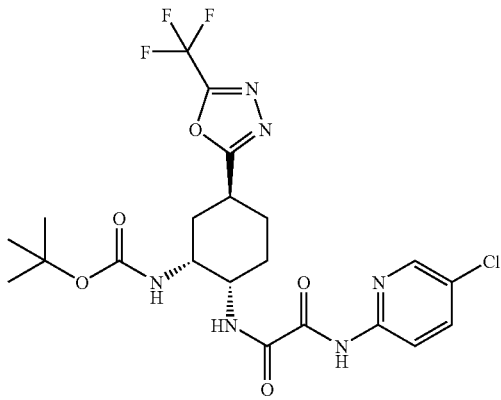

In a manner similar to that described in Referential Example 552, the compound obtained in Referential Example 585 was deprotected. The deprotected compound was condensed with the compound obtained in Referential Example 266, whereby the title compound was obtained.

$^1$H-NMR(CDCl$_3$)δ: 1.46(9H, s), 1.55-1.66(1H, m), 1.79-1.94(1H, m), 1.98-2.19(2H, m), 2.23-2.32(1H, m), 2.32-2.41 (1H, m), 3.18(1H, br.s), 4.00-4.10(1H, m), 4.29(1H, br.s), 4.86(1H, br.s), 7.71(1H, dd, J=8.8, 2.4 Hz), 7.98(1H, br.s), 8.18(1H, d, J=8.8 Hz), 8.32(1H, d, J=2.4 Hz), 9.72(1H, s).

MS(ESI)m/z: 477(M-tBu), 433(M-Boc)$^+$.

Referential Example 587

(1S,2R,4S)-2-[(tert-butoxycarbonyl)amino]-4-{[(2-chloroethoxy)carbonyl]amino}cyclohexylcarbamic acid benzyl ester

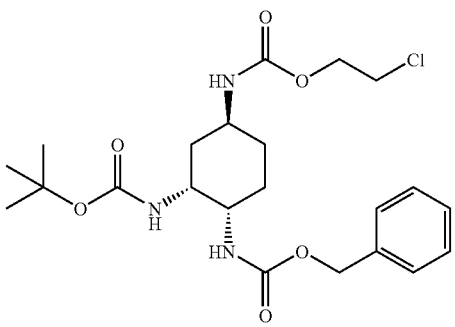

To the compound (872 mg) obtained in Referential Example 574 in methylene chloride (30 mL), under ice cooling were added chloroethyl chloroformate (323 µL) and triethylamine (499 µL), followed by stirring at 0° C. for 1 hour. Water was added to the reaction mixture for partition. The organic layer was washed with water, and dried over sodium sulfate anhydrate. The solvent was distilled away under reduced pressure, and the residue was purified by flash silica gel column chromatography (hexane:ethyl acetate=3:2), to thereby give the title compound (1.03 g).

$^1$H-NMR(CDCl$_3$)δ: 1.24-1.70(12H, m), 1.99-2.03(3H, m), 3.59-3.73(4H, m), 4.06-4.13(1H, m), 4.29(2H, t, J=5.5 Hz), 4.82(1H, br.s), 4.86(1H, br.s), 5.05-5.12(2H, m), 5.41(1H, br.s), 7.28-7.36(5H, m).

MS(ESI)m/z: 492(M+Na)$^+$.

Referential Example 588

(1S,2R,4S)-2-[(tert-butoxycarbonyl)amino]-4-(2-oxo-1,3-oxazolidin-3-yl)cyclohexylcarbamic acid benzyl ester

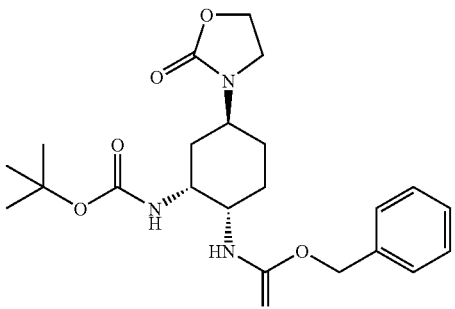

To a suspension of 60% sodium hydride (87 mg) in N,N-dimethylformamide (5.0 mL), the compound (926 mg) obtained in Referential Example 587 in N,N-dimethylformamide (5.0 mL) was added, and the mixture was stirred at room temperature for 1 hour. Water and ethyl acetate were added to the reaction mixture for partition therebetween. The organic layer was washed with water and saturated brine. The organic layer was dried over sodium sulfate anhydrate, and the solvent was distilled away under reduced pressure. The residue was purified by flash silica gel column chromatography (hexane:ethyl acetate=2:3), to thereby give the title compound (680 mg).

¹H-NMR(CDCl₃)δ: 1.44(9H, s), 1.45-2.08(6H, m), 3.44-3.54(2H, m), 3.64(1H, br.s), 3.77-3.87(1H, m), 4.20(1H, br.s), 4.29-4.36(2H, m), 4.84(1H, br.s), 5.05-5.13(2H, m), 5.37(1H, br.s), 7.27-7.36(5H, m).
MS(ESI)m/z: 434(M+H)⁺.

Referential Example 589

(1R,2S,5S)-2-({2-[(5-chloropyridin-2-yl)amino]-2-oxoacetyl}amino)-5-(2-oxo-1,3-oxazolidin-3-yl)cyclohexylcarbamic acid tert-butyl ester

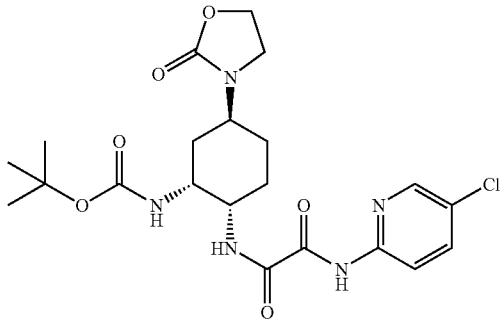

In a manner similar to that described in Referential Example 552, the compound obtained in Referential Example 588 was deprotected. The deprotected compound was condensed with the compound obtained in Referential Example 266, whereby the title compound was obtained.
¹H-NMR(CDCl₃)δ: 1.46(9H, s), 1.58-1.65(2H, m), 1.79-2.05(4H, m), 3.47-3.55(2H, m), 3.84-3.93(2H, m), 4.29(1H, br.s), 4.33-4.39(2H, m), 5.08(1H, br.s), 7.70(1H, dd, J=8.8, 2.5 Hz), 8.10(1H, br.s), 8.19(1H, dd, J=8.8, 0.7 Hz), 8.31(1H, dd, J=2.5, 0.7 Hz), 9.71(1H, s).
MS(ESI)m/z: 504(M+Na)⁺.

Referential Example 590

(1S,2R,4S)-2-[(tert-butoxycarbonyl)amino]-4-(formylamino)cyclohexylcarbamic acid benzyl ester

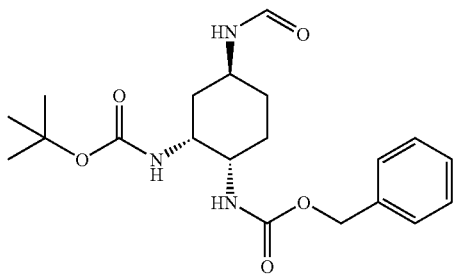

To the compound (200 mg) obtained in Referential Example 574 in methylene chloride (5 mL) were added formic acid (31.1 μL), 1-hydroxybenzotriazole (108 mg), triethylamine (115 μL), and 1-(3-dimethylaminopropyl)-3-ethylcarbodiimide hydrochloride (210 mg), followed by stirring at room temperature for 22 hours. The solvent was distilled away under reduced pressure, and saturated aqueous solution of sodium hydrogencarbonate was added to the residue. The resultant mixture was extracted with methylene chloride, followed by drying over anhydrous magnesium sulfate. The solvent was distilled away under reduced pressure, and the residue was purified by silica gel column chromatography (methylene chloride:methanol=49:1→97:3), to thereby give the title compound (100 mg).
¹H-NMR(CDCl₃)δ: 1.27-1.50(2H, m), 1.44(9H, s), 1.94-2.07(4H, m), 3.66-3.74(1H, m), 3.97-4.07(1H, m), 4.08-4.15 (1H, m), 4.80-4.88(1H, m), 5.05(1H, d, J=12.2 Hz), 5.10(1H, d, J=12.0 Hz), 5.33-5.41(1H, m), 5.43-5.50(1H, m), 7.30-7.37(5H, m), 8.12(1H, s).
MS(ESI)m/z: 392(M+H)⁺.

Referential Example 591

(1R,2S,5S)-2-[(benzyloxycarbonyl)amino]-5-(tetrazol-1-yl)cyclohexylcarbamic acid tert-butyl ester

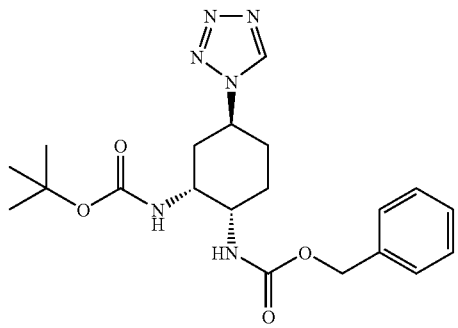

The compound (792 mg) obtained in Referential Example 590 and pyridine (1.63 mL) were dissolved in methylene chloride (10 mL). Under ice cooling, trichloromethyl chloroformate (268 μL) was added thereto, followed by stirring at a constant temperature for 10 minutes. The temperature of the reaction mixture was returned to room temperature, and stirred for 15 minutes. Trimethylsilylazide (295 μL) was added thereto, and the mixture was stirred for 22 hours. The solvent was distilled away under reduced pressure, and aqueous solution of sodium hydrogencarbonate was added to the residue. The insoluble material was recovered by filtration, followed by washing with water. The resultant solid was purified by silica gel column chromatography (methylene chloride:methanol=199:1→49:1), to thereby give the title compound (60 mg).
¹H-NMR(CDCl₃)δ: 1.45(9H, s), 1.55-1.59(1H, m), 2.02-2.14(2H, m), 2.21-2.32(2H, m), 2.41-2.49(1H, m), 3.84-3.92 (1H, m), 4.20-4.25(1H, m), 4.65-4.76(1H, m), 5.07-5.16(3H, m), 5.21-5.28(1H, m), 7.32-7.38(5H, m), 8.68(1H, s).
MS(ESI)m/z: 417 (M+H)⁺.

Referential Example 592

(1R,2S,5S)-2-({2-[(5-chloropyridin-2-yl)amino]-2-oxoacetyl}amino)-5-(tetrazol-1-yl)cyclohexylcarbamic acid tert-butyl ester

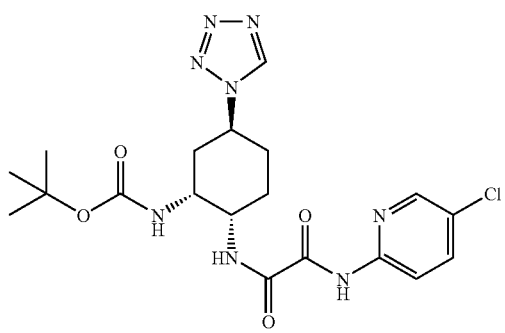

In a manner similar to that described in Referential Example 552, the compound obtained in Referential Example 591 was deprotected. The deprotected compound was condensed with the compound obtained in Referential Example 266, whereby the title compound was obtained.

¹H-NMR(CDCl₃)δ: 1.46(9H, s), 1.73-1.92(1H, m), 2.07-2.21(2H, m), 2.28-2.41(2H, m), 2.45-2.53(1H, m), 4.10-4.19(1H, m), 4.33-4.40(1H, m), 4.71-4.89(1H, m), 4.99-5.14(1H, m), 7.71(1H, dd, J=8.8, 2.4 Hz), 7.96-8.04(1H, m), 8.17(1H, d, J=8.8 Hz), 8.32(1H, d, J=2.4 Hz), 8.69(1H, s), 9.71(1H, s).
MS(ESI)m/z: 465(M+H)⁺.

Referential Example 593

(1S,2R,4S)-2-[(tert-butoxycarbonyl)amino]-4-(1H-pyrrol-1-yl)cyclohexylcarbamic acid benzyl ester

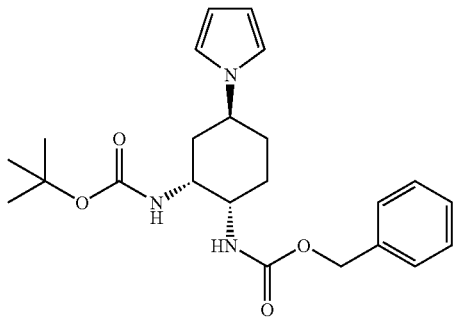

1N Hydrochloric acid (550 μL) was added to a mixture of the compound (200 mg) obtained in Referential Example 574, 2,5-dimethoxytetrahydrofuran (71.3 μL), water (10 mL), and 1,2-dichloroethane (10 mL), followed by stirring at 80° C. for 2.5 hours. The reaction mixture was allowed to cool to room temperature, and saturated aqueous solution of sodium hydrogencarbonate and methylene chloride were added thereto for partition. The organic layer was dried over sodium sulfate anhydrate, and the solvent was distilled away under reduced pressure. The residue was purified by silica gel chromatography (hexane:ethyl acetate=4:1→1:1), to thereby give the title compound (84 mg).
¹H-NMR(CDCl₃)δ: 1.45(9H, s), 1.71-2.20(5H, m), 2.22-2.31(1H, m), 3.78(1H, br.s), 3.99(1H, br.s), 4.22(1H, br.s), 4.73(1H, br.s), 5.04-5.16(2H, m), 5.29(1H, br.s), 6.15(2H, t, J=2.2 Hz), 6.70(2H, t, J=2.2 Hz), 7.29-7.39(5H, m).
MS(ESI)m/z: 436(M+Na)⁺.

Referential Example 594

(1R,2S,5S)-2-({2-[(5-chloropyridin-2-yl)amino]-2-oxoacetyl}amino)-5-(1H-pyrrol-1-yl)cyclohexylcarbamic acid tert-butyl ester

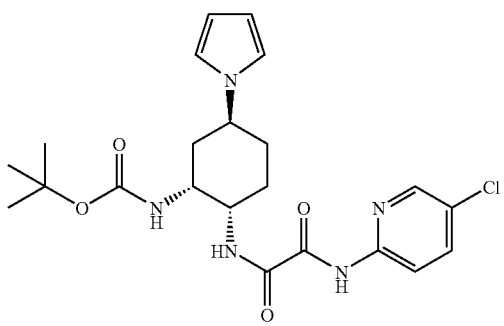

In a manner similar to that described in Referential Example 552, the compound obtained in Referential Example 593 was deprotected. The deprotected compound was condensed with the compound obtained in Referential Example 266, whereby the title compound was obtained.
¹H-NMR(CDCl₃)δ: 1.47(9H, s), 1.80-2.33(6H, m), 3.92-4.08(2H, m), 4.31(1H, br.s), 4.89(1H, br.s), 6.17(2H, t, J=2.0 Hz), 6.71(2H, t, J=2.0 Hz), 7.69(1H, dd, J=8.8, 2.2 Hz), 8.02(1H, br.s), 8.17(1H, d, J=8.8 Hz), 8.31(1H, d, J=2.2 Hz), 9.72(1H, br.s).
MS(ESI)m/z: 462 (M+H)⁺.

Referential Example 595

(1S,2R,4S)-2-[(tert-butoxycarbonyl)amino]-4-({[(dimethylamino)methylidene]amino}carbonyl)cyclohexylcarbamic acid benzyl ester

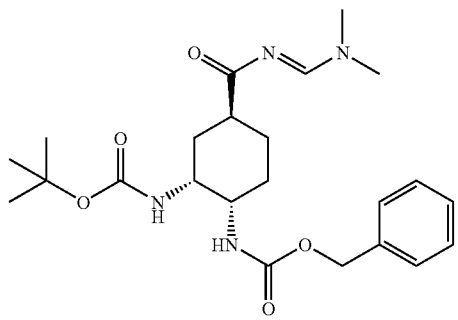

To the compound (1.50 g) obtained in Referential Example 142 in N,N-dimethylformamide (100 mL) were added ammonium chloride (409 mg), 1-hydroxybenzotriazole (516 mg), 1-(dimethylaminopropyl)-3-ethylcarbodiimide hydrochloride (1.03 g), and triethylamine (1.06 mL), followed by stirring at room temperature overnight. The reaction mixture was concentrated under reduced pressure, and ethyl acetate and 10% aqueous citric acid were added to the residue for partition. The organic layer was sequentially washed with saturated brine, aqueous solution of sodium hydrogencarbonate, and saturated brine, followed by drying over anhydrous magnesium sulfate and evaporating the solvent under reduced pressure. The resultant powder was suspended in N,N-dimethylformamide dimethylacetal (30 mL), followed by stirring at 120° C. for 2 hours. The resultant mixture was allowed to cool to room temperature, and precipitated colorless powder was collected by filtration, followed by washing with diethyl ether, to thereby give the title compound (957 mg).
¹H-NMR(CDCl₃)δ: 1.25-1.40(1H, m), 1.44(9H, s), 1.53-1.66(1H, m), 1.73-2.08(4H, m), 2.32-2.46(1H, m), 3.07(3H, s), 3.11(3H, s), 3.63-3.75(1H, m), 4.13(1H, br.s), 4.59-4.75(1H, m), 5.07(1H, d, J=12.2 Hz), 5.12(1H, d, J=12.2 Hz), 5.30-5.45(1H, m), 7.28-7.37(5H, m), 8.40(1H, s).
MS(ESI)m/z: 447 (M+H)⁺.

Referential Example 596

(1S,2R,4S)-2-[(tert-butoxycarbonyl)amino]-4-(1,2,4-triazol-5-yl)cyclohexylcarbamic acid benzyl ester

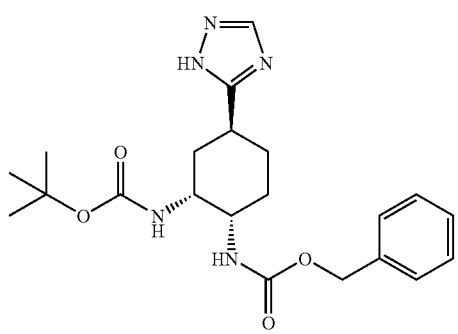

To the compound (400 mg) obtained in Referential Example 595 in acetic acid (10 mL) was added hydrazine monohydrate (51.9 μL), followed by stirring at room temperature for 2 hours. The solvent was distilled away under reduced pressure, and saturated aqueous solution of sodium hydrogencarbonate and ethyl acetate were added to the residue for partition. The organic layer was washed with saturated brine, and dried over anhydrous magnesium sulfate. The solvent was distilled away under reduced pressure, to thereby give the title compound (370 mg).

$^1$H-NMR(DMSO-d$_6$)δ: 1.39(9H, s), 1.48-1.62(2H, m), 1.62-1.75(2H, m), 1.88-2.06(2H, m), 3.06(1H, br.s), 3.56(1H, br.s), 3.95(1H, br.s), 4.95-5.10(2H, m), 6.62(1H, br.s), 7.00(1H, br.s), 7.27-7.38(5H, m), 13.59(1H, br.s).

MS(ESI)m/z: 416(M+H)$^+$.

Referential Example 597

(1R,2S,5S)-2-({2-[(5-chloropyridin-2-yl)amino]-2-oxoacetyl}amino)-5-(1,2,4-triazol-5-yl)cyclohexylcarbamic acid tert-butyl ester

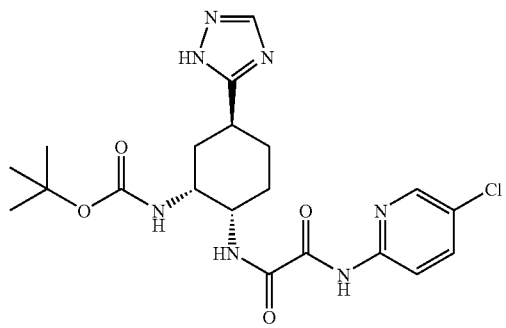

In a manner similar to that described in Referential Example 552, the compound obtained in Referential Example 596 was deprotected. The deprotected compound was condensed with the compound obtained in Referential Example 266, whereby the title compound was obtained.

$^1$H-NMR(DMSO-d$_6$)δ: 1.39(9H, s), 1.50-2.03(5H, m), 2.05-2.17(1H, m), 2.94-3.20(1H, m), 3.85-3.99(2H, m), 7.06(1H, br.s), 7.80(0.5H, br.s), 8.03(1H, dd, J=8.8, 2.2 Hz), 8.06(1H, d, J=8.8 Hz), 8.39(0.5H, s), 8.47(1H, d, J=2.2 Hz), 8.56-8.69(1H, m), 10.27(1H, s), 13.59-13.66(1H, m).

MS(ESI)m/z: 464(M+H)$^+$.

Referential Example 598

(1S,2R,4S)-2-[(tert-butoxycarbonyl)amino]-4-(1-methyl-1H-1,2,4-triazol-5-yl)cyclohexylcarbamic acid benzyl ester

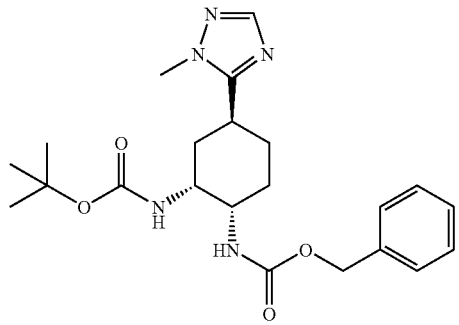

Methylhydrazine (56.9 μL) was added to the compound (400 mg) obtained in Referential Example 595 in acetic acid (10 mL), followed by stirring at room temperature overnight. The solvent was distilled away under reduced pressure, and saturated aqueous solution of sodium hydrogencarbonate and ethyl acetate were added to the residue for partition. The organic layer was washed with saturated brine, and dried over anhydrous magnesium sulfate. The solvent was distilled away under reduced pressure. The residue was purified by silica gel chromatography (methanol:methylene chloride=1:19), to thereby give the title compound (224 mg).

$^1$H-NMR(CDCl$_3$)δ: 1.44(9H, s), 1.53-1.80(2H, m), 1.88-2.18(4H, m), 2.77-2.89(1H, m), 3.71-3.83(1H, m), 3.86(3H, s), 4.17(1H, br.s), 4.74(1H, br.s), 5.08(1H, d, J=12.2 Hz), 5.12(1H, d, J=12.2 Hz), 5.25-5.42(1H, m), 7.29-7.39(5H, m), 7.91(1H, s).

MS(ESI)m/z: 430(M+H)$^+$.

Referential Example 599

(1R,2S,5S)-2-({2-[(5-chloropyridin-2-yl)amino]-2-oxoacetyl}amino)-5-(1-methyl-1H-1,2,4-triazol-5-yl)cyclohexylcarbamic acid tert-butyl ester

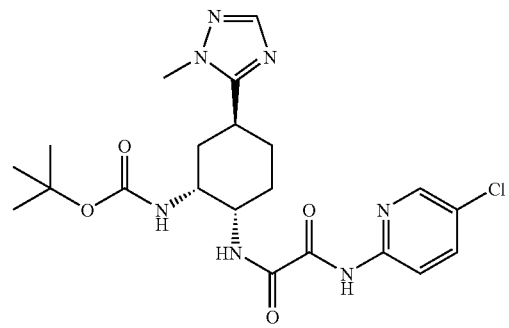

In a manner similar to that described in Referential Example 552, the compound obtained in Referential Example 598 was deprotected. The deprotected compound was condensed with the compound obtained in Referential Example 266, whereby the title compound was obtained.

$^1$H-NMR(CDCl$_3$)δ: 1.47(9H, s), 1.50-1.65(1H, m), 1.72-1.87(1H, m), 1.95-2.22(4H, m), 2.81-2.94(1H, m), 3.87(3H, s), 3.97-4.06(1H, m), 4.25(1H, br.s), 4.91(1H, d, J=8.8 Hz), 7.70(1H, dd, J=8.8, 2.4 Hz), 7.93(1H, s), 8.06(1H, br.s), 8.20(1H, d, J=8.8 Hz), 8.31(1H, d, J=2.4 Hz), 9.74(1H, s).

MS(ESI)m/z: 478(M+H)$^+$.

Referential Example 600

(3R,4S)-4-[(benzyloxycarbonyl)amino]-3-[(tert-butoxycarbonyl)amino]piperidine-1-carbamic acid 2-trimethylsilanylethyl ester

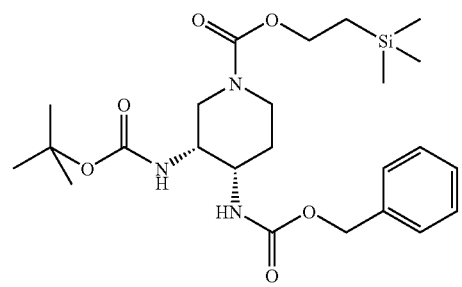

9% Aqueous sodium hydrogencarbonate (150 mL) was added to the compound (5.98 g) obtained in Referential Example 212 in dioxane (50 mL), and the mixture was cooled to 0° C. 1-[(2-Trimethylsilyl)ethoxycarbonyloxy]pyrrolidine-2,5-dione (4.83 g) in dioxane (20 mL) was added thereto, followed by stirring at room temperature for 20 hours. Ethyl acetate and water were added to the reaction mixture, and the organic layer was washed with saturated aqueous solution of sodium hydrogencarbonate, 10% aqueous citric acid, and saturated aqueous sodium chloride, followed by drying over sodium sulfate anhydrate. The solvent was distilled away under reduced pressure, and the residue was purified by silica gel column chromatography (hexane: ethyl acetate=4:1→2:1), to thereby give the title compound (6.75 g).

$^1$H-NMR(CDCl$_3$)δ: 0.00(9H, s), 0.96(2H, t, J=8.3 Hz), 1.36-1.53(1H, m), 1.41(9H, s), 1.82-2.00(1H, m), 2.85(1H, t, J=12.1 Hz), 3.01(1H, d, J=13.4 Hz), 3.66-3.81(1H, m), 3.87-4.25(5H, m), 4.63-4.81(1H, m), 5.06(2H, br.s), 5.22-5.69(1H, br), 7.23-7.40(5H, m). ESI-MSm/z: 394(M-Boc)$^+$.

Referential Example 601

(3R,4S)-4-({2-[(5-chloropyridin-2-yl)amino]-2-oxoacetylamino)-3-[(tert-butoxycarbonyl)amino]piperidine-1-carbamic acid 2-trimethylsilanylethyl ester

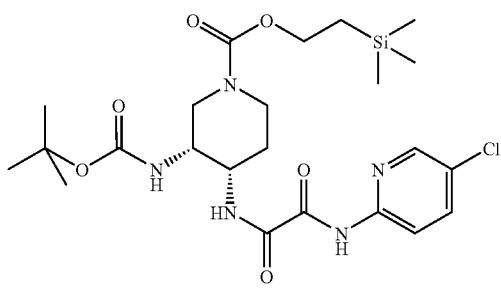

In a manner similar to that described in Referential Example 552, the compound obtained in Referential Example 600 was deprotected. The deprotected compound was condensed with the compound obtained in Referential Example 266, whereby the title compound was obtained.

$^1$H-NMR(CDCl$_3$)δ: 0.05(9H, s), 0.84-0.92(2H, m), 1.47(9H, s), 1.51-1.70(1H, m), 1.98(1H, d, J=11.2 Hz), 2.84-2.98(1H, m), 3.07(1H, d, J=13.9 Hz), 3.94-4.29(6H, m), 4.81-4.95(1H, br), 7.70(1H, d, J=9.0 Hz), 8.09-8.34(1H, br), 8.20(1H, d, J=9.0 Hz), 8.31(1H, s), 9.69(1H, s).

MS(ESI)m/z: 442(M-Boc)$^+$, 486(M-tBu)$^+$.

Referential Example 602

(3R,4S)-[4-({2-[(5-chloropyridin-2-yl)amino]-2-oxoacetyl}amino)piperidin-3-yl]carbamic acid tert-butyl ester

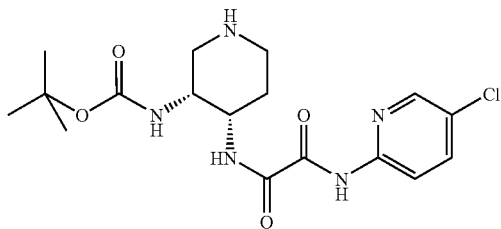

To the compound (6.92 g) obtained in Referential Example 601 in tetrahydrofuran (90 mL) was added 1.0 mmol/l tetrabutylammonium fluoride in tetrahydrofuran (40 mL), followed by stirring at room temperature for 5 days. Ethyl acetate and saturated aqueous sodium chloride were added to the reaction mixture. The aqueous layer was extracted with ethyl acetate and methylene chloride. The organic layers were combined, and washed with saturated aqueous solution of sodium hydrogencarbonate and saturated aqueous sodium chloride, followed by drying over sodium sulfate anhydrate. The solvent was distilled away under reduced pressure, and the residue was purified by silica gel column chromatography (methylene chloride:methanol=30:1→20:1→10:1), to thereby give a crude compound (7.96 g). Ethyl acetate was added to the crude compound, and insoluble material was recovered by filtration, to thereby give the title compound (466 mg). Water was added to the filtrate, and the resultant mixture was extracted with ethyl acetate and methylene chloride. The extract was washed with saturated sodium chloride, followed by drying over sodium sulfate anhydrate. The solvent was distilled away under reduced pressure, to thereby give the title compound (4.86 g) in a mixture form containing about 30% tetrabutylammonium fluoride.

$^1$H-NMR(CDCl$_3$)δ: 1.47(9H, s), 1.55-1.72(2H, m), 1.84-1.99(1H, m), 2.71(1H, t, J=10.7 Hz), 2.85(1H, d, J=11.2 Hz), 3.03(2H, t, J=12.7 Hz), 3.85-3.98(1H, m), 3.98-4.09(1H, m), 5.40-5.71(1H, m), 7.70(1H, dd, J=8.8, 2.4 Hz), 8.13(1H, br.s), 8.21(1H, d, J=8.8 Hz), 8.31(1H, d, J=2.4 Hz), 9.75(1H, s).

MS(ESI)m/z: 398(M+H)$^+$.

Referential Example 603

(3R,4S)-[4-({2-[(5-chloropyridin-2-yl)amino]-2-oxoacetyl}amino)-1-(thiazol-2-yl)piperidin-3-yl]carbamic acid tert-butyl ester

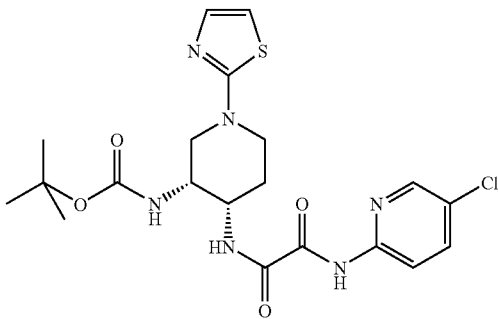

The mixture-form product (401 mg) of Referential Example 602 containing the compound and tetrabutylammonium fluoride was dissolved in toluene (4 mL). To the resultant solution were added 2-bromothiazole (115 μL), sodium tert-butoxide (91 mg), (S)-(−)-2,2'-bis(diphenylphosphino)-1,1'-binaphthyl (65 mg), and tris(dibenzylideneacetone)dipalladium(0) (28 mg), followed by stirring under an argon atmosphere at 80° C. for 3 days. The reaction mixture was cooled, ethyl acetate was added thereto, insoluble material was filtered off through celite, and saturated aqueous sodium chloride was added to the filtrate, and the resultant mixture was extracted with ethyl acetate. The organic layers were combined, and washed with saturated aqueous sodium chloride, followed by drying over sodium sulfate anhydrate and evaporating the solvent under reduced pressure. The residue was purified by silica gel column chromatography (hexane: ethyl acetate=2:1→1:1), to thereby give the title compound (169 mg).

$^1$H-NMR(CDCl$_3$)δ: 1.46(9H, s), 1.78-1.93(1H, m), 2.07-2.18(1H, m), 3.05-3.19(1H, m), 3.27(1H, dd, J=13.2, 1.7 Hz), 3.98(1H, br.d, J=12.9 Hz), 4.04-4.15(2H, m), 4.18-4.29(1H, br), 5.04-5.34(1H, m), 6.65(1H, d, J=3.7 Hz), 7.21(1H, d, J=3.7 Hz), 7.70(1H, dd, J=8.8, 2.4 Hz), 8.21(1H, d, J=8.8 Hz), 8.23-8.33(1H, br), 8.31(1H, d, J=2.4 Hz), 9.73(1H, br.s).
MS(ESI)m/z: 481(M+H)+.

Example 1

N-((1R*,2S*)-2-{[(5-Chloroindol-2-yl)carbonyl]amino}cyclopropyl)-5-methyl-4,5,6,7-tetrahydrothiazolo[5,4-c]pyridine-2-carboxamide hydrochloride

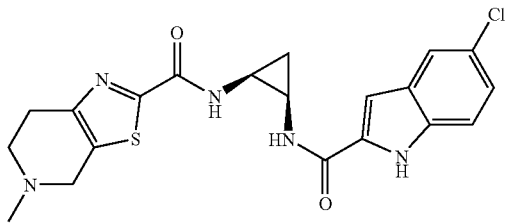

1-Hydroxybenzotriazole monohydrate (71 mg) and 1-(3-dimethylaminopropyl)-3-ethylcarbodiimide hydrochloride (100 mg) were added to a solution with the compound (108 mg) obtained in Referential Example 59 and the compound (124 mg) obtained in Referential Example 10 dissolved in N,N-dimethylformamide (3 mL) at room temperature, and the mixture was stirred for 8 days. After concentrating the reaction mixture under reduced pressure using a vacuum pump, water (50 mL), and saturated aqueous sodium hydrogencarbonate (50 mL) were added to the residue, and the mixture was extracted with methylene chloride. The resultant organic layers were combined and dried over sodium sulfate anhydrate, the solvent was distilled away under reduced pressure, and the residue was purified by silica gel thin layer chromatography (methylene chloride:methanol=10:1). After 1N hydrochloric acid, methylene chloride and methanol were added to the thus-obtained amorphous substance, the mixture was concentrated to give the title compound (72 mg).
¹H-NMR (DMSO-d₆) δ: 1.15-1.35(2H,m), 2.88(3H,s), 2.95-3.25(4H,m), 3.35-3.75(2H,m), 4.32-4.45(1H,m), 4.68 (1H,br,J=15.4 Hz), 7.08(1H,s), 7.17(1H,dd,J=8.6, 2.1 Hz), 7.41(1H,d,J=8.6 Hz), 7.70(1H,s), 8.50(1H,br,J=11.0 Hz), 8.56(1H,br.s), 11.56(1H,br,J=19.3 Hz), 11.86(1H,s).
MS(FAB)m/z: 430(M+H)+.

Example 2

N-((1R*,2S*)-2-{[(5-Chloroindol-2-yl)carbonyl]amino}-cyclobutyl)-5-methyl-4,5,6,7-tetrahydrothiazolo[5,4-c]-pyridine-2-carboxamide hydrochloride

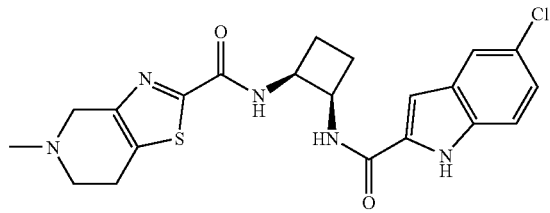

The compound (136 mg) obtained in Referential Example 10, 1-(3-dimethylaminopropyl)-3-ethylcarbodiimide hydrochloride (255 mg) and 1-hydroxybenzotriazole monohydrate (90 mg) were added to a solution with the compound (117 mg) obtained in Referential Example 60 dissolved in N,N-dimethylformamide (5 mL), and the mixture was stirred overnight at room temperature. The solvent was then distilled away under reduced pressure using a vacuum pump, and the residue was partitioned between methylene chloride and saturated aqueous sodium hydrogencarbonate. The resultant organic layer was washed with saturated brine and dried over sodium sulfate anhydrate, the solvent was distilled away under reduced pressure, and the residue was purified by silica gel column chromatography (methanol:methylene chloride=7:93). After ethyl acetate and 1N HCl in ethanol were added to the thus-obtained compound for acidification, and the solvent was distilled away under reduced pressure. Ethyl acetate was added again, and the precipitate formed was collected by filtration and dried to give the title compound (56 mg).
¹H-NMR (DMSO-d₆) δ: 2.00-2.35(4H,m), 2.88(3H,s), 3.10(2H,br.s), 3.20-3.75(3H,m), 4.20-4.85(3H,m), 7.09(1H, s), 7.16(1H,d,J=8.8 Hz), 7.38(1H,d,J=8.8 Hz), 7.71(1H,s), 8.63(1H,d,J=8.3 Hz), 8.85(1H,d,J=8.6 Hz), 10.85-11.20(1H, br), 11.81(1H,s).
MS(FAB)m/z: 444(M+H)+.

Example 3

N-((1R*,2R*)-2-{[(5-Chloroindol-2-yl)carbonyl]amino}-cyclopentyl)-5-methyl-4,5,6,7-tetrahydrothiazolo[5,4-c]-pyridine-2-carboxamide hydrochloride

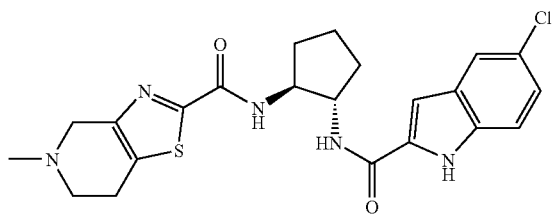

5-Chloroindole-2-carboxylic acid (80 mg), 1-(3-dimethylaminopropyl)-3-ethylcarbodiimide hydrochloride (98 mg), 1-hydroxybenzotriazole monohydrate (23 mg) and triethylamine (141 µl) were added to a solution with the compound (120 mg) obtained in Referential Example 62 dissolved in N,N-dimethylformamide (5 mL), and the mixture was stirred at room temperature for 3 days. The solvent was distilled away under reduced pressure, and methylene chloride and saturated aqueous sodium hydrogencarbonate were added to the residue for partitioning the mixture. The resultant organic layer was dried over sodium sulfate anhydrate, the solvent was distilled away under reduced pressure, and the residue was purified by silica gel column chromatography (methylene chloride:methanol=93:7). After methylene chloride (5 mL) and 1N HCl in ethanol (282 µl) were added to the thus-obtained pale yellow solid, ethyl acetate was added. The solvent was distilled away under reduced pressure, and the precipitate formed was collected by filtration to give the title compound (109 mg).
¹H-NMR (DMSO-d₆) δ: 1.64-1.74(4H,m), 1.98-2.02(2H, m), 2.89(3H,s), 3.14(2H,br.s), 3.47-3.65(2H,m), 4.29-4.63 (4H,m), 7.10(1H,d,J=1.5 Hz), 7.14(1H,dd,J=8.5, 2.0 Hz), 7.38(1H,d,J=8.5 Hz), 7.68(1H,d,J=2.0 Hz), 8.55(1H,d,J=8.5 Hz), 8.91(1H,d,J=8.5 Hz), 11.49(1H,br.s), 11.76(1H,s).
MS(ESI)m/z: 458(M+H)+.

Example 4

N-((1R*,2S*)-2-{[(5-Chloroindol-2-yl)sulfonyl]amino}-cyclohexyl)-5-methyl-4,5,6,7-tetrahydrothiazolo[5,4-c]-pyridine-2-carboxamide hydrochloride

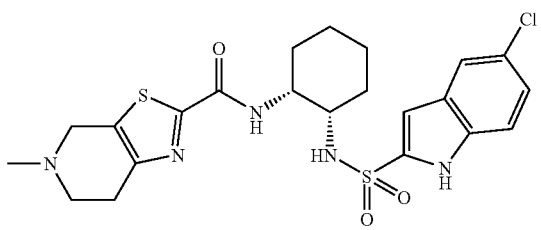

The compound (400 mg) obtained in Referential Example 67 was suspended in methylene chloride (10 mL), triethylamine (0.514 mL) and 5-chloro-1-phenylsulfonylindole-2-sulfonyl chloride (Japanese Patent Application Laid-Open (kokai) No. 2000-119253) (319 mg) were added, and the mixture was stirred at room temperature for 15 minutes. After water was added to the reaction mixture for partitioning the mixture, the resultant organic layer was dried over sodium sulfate anhydrate. The solvent was distilled away under reduced pressure, and the residue was purified by silica gel column chromatography (methylene chloride:methanol=100:3) to give a pale yellow foamy substance. This substance was dissolved in tetrahydrofuran (3 mL), and methanol (2 mL) and 1N aqueous sodium hydroxide (1.5 mL) were added. The mixture was heated under reflux for 2 hours. The reaction mixture was concentrated under reduced pressure, and methylene chloride and 1N hydrochloric acid were added to the residue for partitioning the mixture. After the resultant organic layer was dried over sodium sulfate anhydrate, the solvent was distilled away under reduced pressure, and the residue was purified by silica gel column chromatography (methylene chloride:methanol=100:3). 1N Hydrochloric acid (1 mL) was added to the resultant product, and the mixture was concentrated under reduced pressure to give the title compound (108 mg).

$^1$H-NMR (DMSO-$d_6$) δ: 1.20-1.78(8H,m), 2.94(3H,s), 3.13(2H,br.s), 3.22-3.40(1H,m), 3.44-3.70(3H,m), 3.83-3.95 (1H,m), 4.20-4.70(1H,m), 6.78(1H,s), 7.18-7.30(2H,m), 7.44(1H,s), 7.69(1H,br.s), 8.09(1H,br.s), 11.92(1H,s).
MS(FAB)m/z: 508(M+H)$^+$.

Example 5

N-((1R*,2R*)-2-{[(5-Chloroindol-2-yl)carbonyl]amino}-cyclohexyl)-5-methyl-4,5,6,7-tetrahydrothiazolo[5,4-c]-pyridine-2-carboxamide hydrochloride

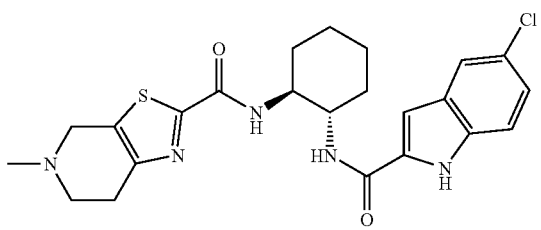

5-Chloroindole-2-carboxylic acid (109 mg), 1-hydroxybenzotriazole monohydrate (9 mg), 1-(3-dimethylaminopropyl)-3-ethylcarbodiimide hydrochloride (321 mg) and triethylamine (0.232 mL) were added to a solution with the compound (300 mg) obtained in Referential Example 65 dissolved in N,N-dimethylformamide (20 mL), and the mixture was stirred overnight at room temperature. The reaction mixture was concentrated under reduced pressure using a vacuum pump, and methylene chloride and water were added to the residue for partitioning the mixture. The resultant organic layer was dried over sodium sulfate anhydrate, the solvent was distilled away under reduced pressure, and the residue was purified by silica gel column chromatography (methylene chloride:methanol=25:1) to give a colorless foamy substance. This substance was suspended in 1N hydrochloric acid (1 mL), and the suspension was concentrated under reduced pressure to give the title compound (203 mg).

$^1$H-NMR (DMSO-$d_6$) δ: 1.25-1.40(2H,m), 1.46-1.81(4H, m), 1.88-1.98(2H,m), 2.89(3H,s), 3.00-3.76(5H,m), 3.86-3.97(1H,m), 4.00-4.10(1H,m), 4.25-4.72(1H,m), 7.03(1H,s), 7.12(1H,dd,J=8.5, 1.2 Hz), 7.38(1H,d,J=8.5 Hz), 7.64(1H,s), 8.28(1H,d,J=8.5 Hz), 8.54(1H,d,J=8.5 Hz), 11.70(1H,s).
MS(FAB)m/z: 472(M+H)$^+$.

Example 6

N-((1R*,2S*)-2-{[(5-Chloroindol-2-yl)carbonyl]amino}-cyclohexyl)-5-methyl-4,5,6,7-tetrahydrothiazolo[5,4-c]pyridine-2-carboxamide hydrochloride

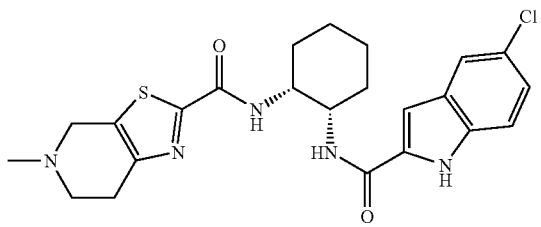

The title compound was obtained from the compound obtained in Referential Example 67 and 5-chloroindole-2-carboxylic acid in a similar manner to Example 5.

$^1$H-NMR (DMSO-$d_6$) δ: 1.35-1.70(6H,m), 1.80-2.06(2H, m), 2.89(3H,s), 3.00-3.27(2H,m), 3.35-3.51(1H,m), 3.57-3.82(1H,m), 4.15-4.30(2H,m), 4.32-4.48(1H,m), 4.60-4.74 (1H,m), 7.15(1H,s), 7.17(1H,dd,J=8.8, 2.0 Hz), 7.41(1H,d, J=8.6 Hz), 7.70(1H,d,J=2.0 Hz), 8.14(1H,br.s), 8.36-8.48 (1H,m), 11.51(1H,br.s), 11.86(1H,s).
MS(FAB)m/z: 472(M+H)$^+$.

Example 7

N-{(1R*,2S*)-2-[(6-Chloro-2-naphthoyl)amino]cyclohexyl}-5-methyl-4,5,6,7-tetrahydrothiazolo[5,4-c]pyridine-2-carboxamide hydrochloride

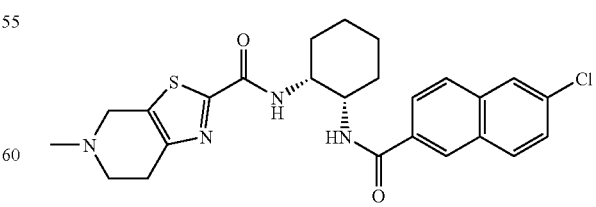

In a manner similar to that employed in Example 5, the title compound was produced. The compound (275 mg) obtained in Referential Example 67, 6-chloronaphthalene-2-carboxylic acid (Eur. J. Chem. Chim. Ther., 1984, Vol. 19, pp. 205-214) (148 mg), triethylamine (0.298 mL), and 1-hydroxybenzotriazole monohydrate (11 mg) were dissolved in N,N-dimethylformamide (20 mL). To the resultant solution, 1-(3-dimethylaminopropyl)-3-ethylcarbodiimide hydrochloride (412 mg) was added, and the mixture was allowed to react, to thereby give the title compound (186 mg).

$^1$H-NMR (DMSO-d$_6$) δ: 1.40-1.56(2H,m), 1.57-1.77(4H,m), 1.90-2.10(2H,m), 2.90(3H,s), 3.13(2H,br.s), 3.28-3.74 (2H,m), 4.26(2H,br.s), 4.30-4.74(2H,m), 7.59(1H,d,J=8.6 Hz), 7.90(1H,d,J=8.6 Hz), 7.98(1H,d,J=8.3 Hz), 8.03-8.11 (2H,m), 8.25-8.58(3H,m), 11.52(1H,br.s).

MS(FAB)m/z: 483(M+H)$^+$.

Example 8

N-((1R*,2R*)-2-{[(6-Chloro-1-benzothiophen-2-yl) carbonyl]amino}cyclohexyl)-5-methyl-4,5,6,7-tetrahydrothiazolo[5,4-c]pyridine-2-carboxamide hydrochloride

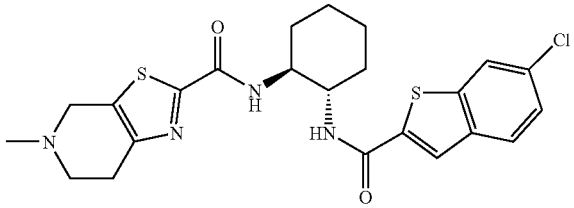

In a manner similar to that employed in Example 5, the title compound was produced. The compound (255 mg) obtained in Referential Example 65, 6-chlorobenzo[b]thiophene-2-carboxylic acid (Japanese Patent Application Laid-Open (kokai) No. 2000-119253) (141 mg), triethylamine (0.276 mL), and 1-hydroxybenzotriazole monohydrate (10 mg) were dissolved in N,N-dimethylformamide (20 mL). To the resultant solution, 1-(3-dimethylaminopropyl)-3-ethylcarbodiimide hydrochloride (382 mg) was added, and the mixture was allowed to react, to thereby give the title compound (239 mg).

$^1$H-NMR (DMSO-d$_6$) δ: 1.20-1.98(8H,m), 2.88(3H,s), 3.00-3.72(4H,m), 3.84-4.09(2H,m), 4.20-4.75(2H,m), 7.41 (1H,dd,J=8.6, 1.7 Hz), 7.91(1H,d,J=8.6 Hz), 7.99(1H,s), 8.12 (1H,s), 8.54-8.67(2H,m), 11.53(1H,br.s).

MS(FAB)m/z: 489(M+H)$^+$.

Example 9

N-((1R*,2R*)-2-{[(5-Fluoroindol-2-yl)carbonyl] amino}-cyclohexyl)-5-methyl-4,5,6,7-tetrahydrothiazolo[5,4-c]-pyridine-2-carboxamide hydrochloride

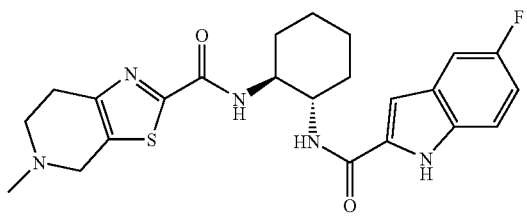

The title compound was obtained from the compound obtained in Referential Example 65 and 5-fluoroindole-2-carboxylic acid in a similar manner to Example 5.

$^1$H-NMR (DMSO-d$_6$) δ: 1.20-1.38(2H,m), 1.40-1.57(1H,m), 1.54-1.68(1H,m), 1.71(2H,d,J=7.3 Hz), 1.88(2H,d, J=12.0 Hz), 2.86(3H,s), 2.95-3.24(2H,m), 3.40(1H,br.s), 3.63(1H,br.s), 3.90(1H,br.s), 3.97-4.10(1H,m), 4.20-4.44 (1H,m), 4.53-4.70(1H,m), 6.98(1H,dd,J=9.2, 2.3 Hz), 7.01 (1H,s), 7.31-7.39(2H,m), 8.26(1H,d,J=8.6 Hz), 8.59(1H,d, J=8.4 Hz), 11.21(½H,br.s), 11.42(½H,br.s), 11.60(1H,s).

MS(ESI)m/z: 456(M+H)$^+$.

Example 10

N-((1R*,2R*)-2-{[(5-Chloro-6-fluoroindol-2-yl) carbonyl]-amino}cyclohexyl)-5-methyl-4,5,6,7-tetrahydrothiazolo-[5,4-c]pyridine-2-carboxamide hydrochloride

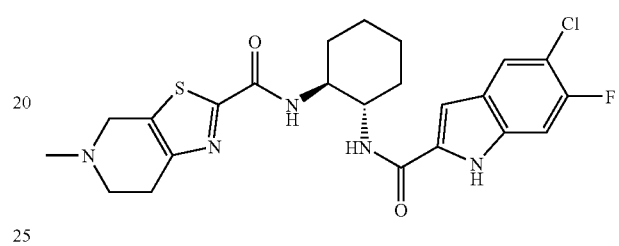

The title compound was obtained from the compound obtained in Referential Example 65 and the compound obtained in Referential Example 23 in a similar manner to Example 5.

$^1$H-NMR (DMSO-d$_6$) δ: 1.20-1.40(2H,m), 1.40-1.80(4H, m), 1.80-2.00(2H,m), 2.87(3H,s), 3.01(2H,br.s), 3.30-3.80 (2H,m), 3.81-3.97(2H,m), 4.20-4.80(2H,m), 7.06(1H,s), 7.28(1H,d,J=10.0 Hz), 7.86(1H,d,J=7.3 Hz), 8.32(1H,d, J=8.5 Hz), 8.59(1H,d,J=8.5 Hz), 11.77(1H,s).

MS(FAB)m/z: 490(M+H)$^+$.

Example 11

N-((1R*,2S*)-2-{[(5-Bromoindol-2-yl)carbonyl] amino}-cyclohexyl)-5-methyl-4,5,6,7-tetrahydrothiazolo[5,4-c]-pyridine-2-carboxamide hydrochloride

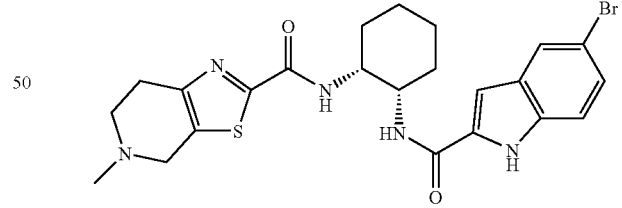

The title compound was obtained from the compound obtained in Referential Example 67 and 5-bromoindole-2-carboxylic acid in a similar manner to Example 5.

$^1$H-NMR (DMSO-d$_6$) δ: 1.43(2H,br.s), 1.61(4H,br.s), 1.80-2.10(2H,m), 2.88(3H,s), 3.00-3.26(2H,m), 3.40(1H,br.s), 3.65(1H,br.s), 4.22(1H,br.s), 4.26(1H,br.s), 4.41(1H,br.s), 4.67(1H,d,J=15.6 Hz), 7.14(1H,s), 7.28(1H,d, J=8.7 Hz), 7.37(1H,d,J=8.7 Hz), 7.84(1H,s), 8.13(1H,br.s), 8.33-8.52(1H,m), 11.51(1H,br.s), 11.86(1H,s).

MS(ESI)m/z: 515(M$^+$).

Example 12

N-((1R*,2S*)-2-{[(5-Ethynylindol-2-yl)carbonyl]amino}-cyclohexyl)-5-methyl-4,5,6,7-tetrahydrothiazolo[5,4-c]-pyridine-2-carboxamide hydrochloride

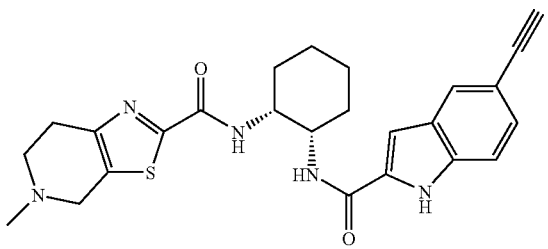

Triethylamine (6 mL), N,N-dimethylformamide (5 mL), trimethylsilylacetylene (0.250 mL) and palladium acetate (20 mg) were added to a tetrahydrofuran solution (2 mL) of the compound (300 mg) obtained in Example 11 and triphenylphosphine (70 mg) at room temperature. After stirring at 90° C. for 2 hours, the reaction mixture was allowed to cool to room temperature, and methylene chloride (20 mL) and saturated aqueous sodium hydrogencarbonate (30 mL) were added for partitioning the mixture. The resultant aqueous layer was extracted with methylene chloride (3×10 mL), the organic layers were combined and dried over sodium sulfate anhydrate, and the solvent was distilled away under reduced pressure to give residue. The resultant residue was purified by silica gel thin layer chromatography (methylene chloride:acetone:methanol=10:10:1) to give colorless solids. This product was dissolved in methanol (6 mL), potassium carbonate (120 mg) was added thereto, and the mixture was stirred for 1 hour. Methylene chloride (20 mL) and water (20 mL) were added to the reaction mixture for partitioning the mixture. The resultant aqueous layer was extracted with methylene chloride (2×15 mL), the organic layers were combined and dried over sodium sulfate anhydrate, and the solvent was distilled away under reduced pressure. The residue was purified by silica gel thin layer chromatography (methylene chloride:acetone:methanol=10:10:1) and dissolved in water-methanol-methylene chloride. The resultant solution was then concentrated to give the title compound (72 mg).

$^1$H-NMR (CDCl$_3$) δ: 1.50-2.25(8H,m), 2.53(3H,s), 2.85(2H,br.s), 2.93(2H,br.s), 3.01(1H,s), 3.74(1H,d,J=14.1 Hz), 3.77(1H,d,J=14.1 Hz), 4.21(1H,br.s), 4.45(1H,br.s), 6.91(1H,s), 7.25-7.42(2H,m), 7.61(1H,br.s), 7.80-7.97(2H, m), 9.72(1H,s).

MS(FAB)m/z: 462(M+H)$^+$.

Example 13

N-((1R*,2S)-2-{[(5-Chloroindol-2-yl)carbonyl]amino}-cyclohexyl)-5,6-dimethyl-4,5,6,7-tetrahydrothiazolo[4,5-d]-pyridazine-2-carboxamide hydrochloride

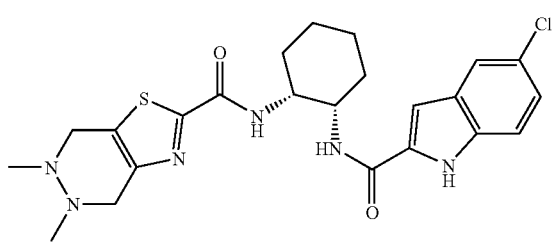

The title compound was obtained from the compound obtained in Referential Example 71 and the compound obtained in Referential Example 51 in a similar manner to Example 2.

$^1$H-NMR (DMSO-d$_6$) δ: 1.35-1.50(2H,m), 1.50-1.75(4H, m), 1.80-2.10(2H,m), 2.70(3H,br.s), 2.79(3H,br.s), 4.10-4.70 (6H,m), 7.10-7.27(2H,m), 7.41(1H,d,J=8.8 Hz), 7.70(1H,s), 8.12(1H,d,J=6.8 Hz), 8.47(1H,d,J=7.6 Hz), 11.85(1H,s).

MS(FAB)m/z: 487(M+H)$^+$.

Example 14

N-((1R*,2S*)-2-{[(5-Chloroindol-2-yl)carbonyl]amino}-cyclohexyl)-6,7-dihydro-4H-pyrano[4,3-d]thiazole-2-carboxamide

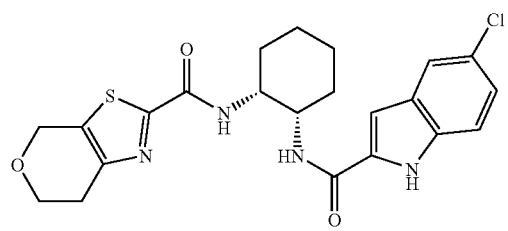

The title compound was obtained from the compound obtained in Referential Example 71 and the compound obtained in Referential Example 26 in a similar manner to Example 2.

$^1$H-NMR (DMSO-d$_6$) δ: 1.36-1.72(6H,m), 1.90-2.10(2H, m), 2.80-2.87(2H,m), 3.93(2H,t,J=5.6 Hz), 4.20-4.32(2H,m), 4.81(2H,s), 7.12(1H,s), 7.15(1H,dd, J=8.8, 2.0 Hz), 7.41(1H, d,J=8.8 Hz), 7.67(1H,d,J=1.7 Hz), 8.11(1H,d,J=6.6 Hz), 8.36 (1H,d,J=8.3 Hz), 11.78(1H,s).

MS(FAB)m/z: 459(M+H)$^+$.

Example 15

N-((1R*,2S*)-2-{[(5-Chloroindol-2-yl)carbonyl]amino}-cyclohexyl)-5-methyl-4,5,6,7-tetrahydrothiazolo[4,5-c]-pyridine-2-carboxamide hydrochloride

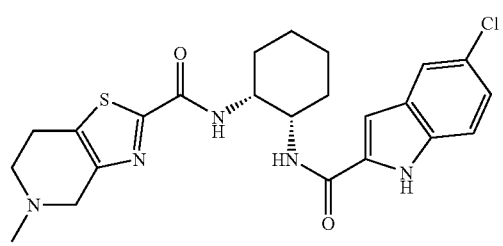

The title compound was obtained from the compound obtained in Referential Example 71 and the compound obtained in Referential Example 29 in a similar manner to Example 2.

$^1$H-NMR (DMSO-d$_6$) δ: 1.32-1.74(6H,m), 1.82-2.10(2H, m), 2.92(3H,s), 3.12-3.50(3H,m), 3.69(1H,br.s), 4.13-4.39 (3H,m), 4.51(1H,br.s), 7.10-7.19(2H,m), 7.41(1H,d,J=8.6 Hz), 7.68(1H,s), 8.10(1H,br.s), 8.40(1H,br.s), 11.41(1H,br.s), 11.87(1H,s).

MS(FAB)m/z: 472(M+H)$^+$.

Example 16

N-((1R*,2R*)-2-{[(5-Chloroindol-2-yl)carbonyl]amino}-cyclohexyl)-5-methyl-4,5,6,7-tetrahydroox-azolo[5,4-c]-pyridine-2-carboxamide hydrochloride

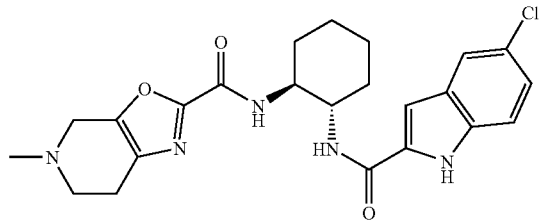

The title compound was obtained from the compound obtained in Referential Example 69 and the compound obtained in Referential Example 21 in a similar manner to Example 2.

$^1$H-NMR (DMSO-$d_6$) δ: 1.23-1.39(2H,m), 1.40-1.81(4H,m), 1.82-1.98(2H,m), 2.60-3.00(5H,m), 3.20-3.70(2H,m), 3.87-3.96(1H,m), 3.98-4.10(1H,m), 4.12-4.70(2H,m), 7.04 (1H,d,J=1.5 Hz), 7.12(1H,dd,J=8.8, 2.0 Hz), 7.38(1H,d, J=8.8 Hz), 7.65(1H,d,J=2.0 Hz), 8.33(1H,d,J=8.6 Hz), 8.72 (1H,d,J=8.6 Hz), 11.61(1H,br.s), 11.72(1H,s).

MS(FAB)m/z: 456(M+H)$^+$.

Example 17

N-((1R*,2S*)-2-{[(5-Chloroindol-2-yl)carbonyl]amino}-cyclohexyl)-4,5,6,7-tetrahydrothieno[3,2-c]pyridine-2-carboxamide hydrochloride

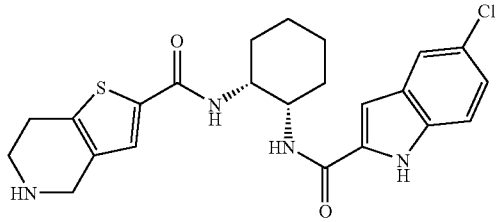

In a manner similar to that employed in Example 2, the title compound was produced. The compound obtained in Referential Example 71 was condensed with 5-(tert-butoxycarbonyl)-4,5,6,7-tetrahydrothieno[3,2-c]pyridin-2-carboxylic acid (WO94/21599), followed by treatment with hydrochloric acid for deprotection, to thereby give the title compound.

$^1$H-NMR (DMSO-$d_6$) δ: 1.42(2H,br.s), 1.56-1.76(4H,m), 1.98-2.11(2H,m), 3.04(2H,br.s), 3.32-3.45(2H,m), 4.15(3H, br.s), 4.26(1H,br.s), 7.14(1H,dd,J=8.8, 2.0 Hz), 7.23(1H,s), 7.41(1H,d,J=8.8 Hz), 7.62(1H,s), 7.77(1H,s), 8.18-8.30(2H, m), 9.42(2H,br.s), 11.92(1H,s).

MS(FAB)m/z: 457(M+H)$^+$.

Example 18

N-((1R*,2S*)-2-{[(5-Chloroindol-2-yl)carbonyl]amino}-cyclohexyl)-5-methyl-4,5,6,7-tetrahydrothieno[3,2-c]-pyridine-2-carboxamide hydrochloride

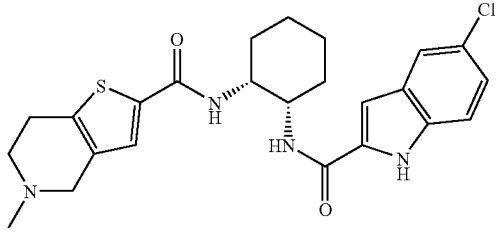

The compound (171 mg) obtained in Example 17 was suspended in methylene chloride (10 mL), and triethylamine (0.104 mL) was added, followed by stirring at room temperature for 10 minutes. After acetic acid (0.059 mL) was added to the reaction mixture, a 35% formalin (0.070 mL) and sodium triacetoxyborohydride (118 mg) were added, and the mixture was stirred at room temperature for 30 minutes. After 1N aqueous sodium hydroxide (3 mL) was added to the reaction mixture, water was added for partitioning the mixture. After the resultant organic layer was dried over sodium sulfate anhydrate, the solvent was then distilled away under reduced pressure, and the residue was purified by silica gel column chromatography (methylene chloride:methanol=50:3) to give a colorless foamy substance. This substance was suspended in 1N hydrochloric acid, and the suspension was concentrated under reduced pressure to give the title compound (85 mg).

$^1$H-NMR (DMSO-$d_6$) δ: 1.40(2H,br.s), 1.50-1.71(4H,m), 1.97-2.05(2H,m), 2.87(3H,s), 2.98-3.20(1H,m), 3.30-3.38 (2H,m), 3.54-3.70(1H,m), 4.05-4.42(4H,m), 7.14(1H,d, J=8.6 Hz), 7.23(1H,s), 7.40(1H,d,J=8.6 Hz), 7.63(1H,s), 7.77 (1H,s), 8.17-8.27(2H,m), 10.83(1H,br.s), 11.92(1H,s).

MS(FAB)m/z: 471(M+H)$^+$.

Example 19

N-((1R*,2S*)-2-[(5-Chloroindol-2-yl)carbonyl]amino}-cyclohexyl)-6-(dimethylamino)-4,5,6,7-tetrahydrobenzothiazole-2-carboxamide hydrochloride

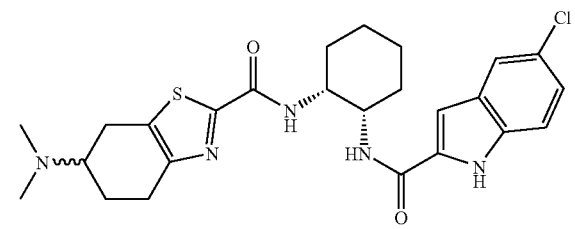

The title compound was obtained from the compound obtained in Referential Example 71 and the compound obtained in Referential Example 31 in a similar manner to Example 2.

$^1$H-NMR (DMSO-$d_6$) δ: 1.44(2H,br.s), 1.52-1.68(4H,m), 1.87-2.08(3H,m), 2.30-2.40(1H,m), 2.65-2.75(1H,m), 2.77 (6H,s), 2.95-3.17(2H,m), 3.30-3.70(2H,m), 4.15-4.30(2H, m), 7.10-7.20(2H,m), 7.41(1H,d,J=8.6 Hz), 7.69(1H,s), 8.11 (1H,d,J=5.1 Hz), 8.34(1H,d,J=8.1 Hz), 10.95(1H,br.s), 11.83 (1H,s).

MS(FAB)m/z: 500(M+H)$^+$.

Example 20

N-((1R*,2S*)-2-{[(5-Chloroindol-2-yl)carbonyl]amino}-cyclohexyl)-5-(pyridin-4-yl)-4,5,6,7-tetrahydrothiazolo-[5,4-c]pyridine-2-carboxamide hydrochloride

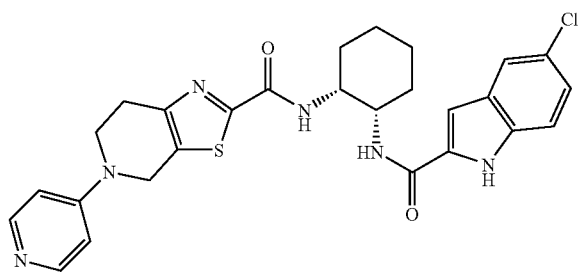

After n-butyllithium (1.60N hexane solution, 0.704 mL) was added dropwise to a solution of the compound (204 mg)

obtained in Referential Example 24 in tetrahydrofuran (3 mL) at −78° C., the mixture was stirred at 0° C. for 30 minutes. After the reaction mixture was cooled to −78° C. again, it was warmed to room temperature in 20 minutes while blowing carbon dioxide, and the reaction mixture was concentrated under reduced pressure. The compound (400 mg) obtained in Referential Example 71, 1-hydroxy-benzotriazole monohydrate (254 mg), 1-(3-dimethylamino-propyl)-3-ethylcarbodiimide hydrochloride (360 mg) and diisopropylamine (0.491 mL) were added to a solution of the resultant residue in N,N-dimethylformamide (6 mL) at room temperature. After stirring for 3 days, the reaction mixture was concentrated under reduced pressure, and methylene chloride (30 mL), saturated aqueous sodium hydrogencarbonate (100 mL), and water (100 mL) were added to the residue for partitioning the mixture. The resultant aqueous layer was extracted with methylene chloride (4×15 mL), the organic layers were combined and dried over sodium sulfate anhydrate, and the solvent was distilled away under reduced pressure. The resultant residue was purified by silica gel column chromatography (methylene chloride:methanol=20:1→10:1). The purified product was dissolved in 1N hydrochloric acid-methanol-methylene chloride. The resultant solution was then concentrated to give the title compound (245 mg).

$^1$H-NMR (DMSO-$d_6$) δ: 1.42(2H,br.s), 1.60(4H,br.s), 1.84-1.94(1H,m), 1.94-2.08(1H,m), 2.97(2H,br.s), 3.97-4.13 (2H,m), 4.19(1H,br.s), 4.27(1H,br.s), 5.03(2H,s), 7.13(1H, br.s), 7.16(1H,dd,J=8.8, 2.0 Hz), 7.32(2H,br.s), 7.40(1H,d, J=8.8 Hz), 7.68(1H,d,J=2.0 Hz), 8.15(1H,br,J=7.3 Hz), 8.31 (2H,d,J=5.9 Hz), 8.39(1H,d,J=8.1 Hz), 11.90(1H,s), 14.03 (1H,br.s).

MS(ESI)m/z: 535(M+H)$^+$.

Example 21

N-((1R*,2R*)-2-{[(5-Chloroindol-2-yl)carbonyl] amino}-cycloheptyl)-5-methyl-4,5,6,7-tetrahydrothiazolo[5,4-c]-pyridine-2-carboxamide hydrochloride

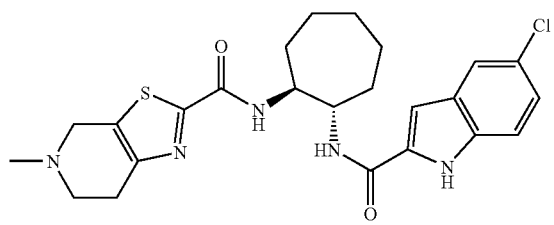

The title compound was obtained from the compound obtained in Referential Example 74 and the compound obtained in Referential Example 10 in a similar manner to Example 2.

$^1$H-NMR (DMSO-$d_6$) δ: 1.51-1.55(4H,m), 1.75-1.80(6H, m), 2.88(3H,s), 3.12(1H,br.s), 3.35-3.63(4H,m), 4.10-4.13 (1H,m), 4.29-4.61(2H,m), 7.06(1H,s), 7.14(1H,dd,J=8.8, 2.0 Hz), 7.39(1H,d,J=8.8 Hz), 7.67(1H,d,J=2.0 Hz), 8.46(1H,d, J=8.3 Hz), 8.77(1H,d,J=8.3 Hz), 11.21-11.35(1H,m), 11.71 (1H,s).

MS(ESI)m/z: 486(M+H)$^+$.

Example 22

N-((1R*,2S*)-2-{[(5-Chloroindol-2-yl)carbonyl] amino}-cyclooctyl)-5-methyl-4,5,6,7-tetrahydrothiazolo[5,4-c]-pyridine-2-carboxamide hydrochloride

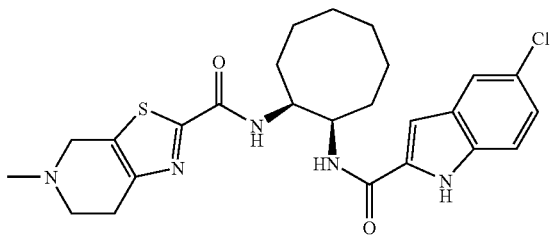

The title compound was obtained from the compound obtained in Referential Example 78 and the compound obtained in Referential Example 10 in a similar manner to Example 2.

$^1$H-NMR (DMSO-$d_6$) δ: 1.61-2.06(12H,m), 2.90(3H,s), 3.08-3.17(2H,m), 3.43-3.45(1H,m), 3.67(1H,br.s), 4.43(3H, br.s), 4.67(1H,br.s), 7.16-7.18(2H,m), 7.42(1H,d,J=8.8 Hz), 7.70(1H,s), 8.24(1H,br.s), 8.58(1H,d,J=8.3 Hz), 11.43, 11.63 (1H, each br.s), 11.80(1H,s).

MS(ESI)m/z: 500(M+H)$^+$.

Example 23

N-((1R*,2R)-2-{[(5-Chloroindol-2-yl)carbonyl] amino}-cyclopentyl)-4,5,6,7-tetrahydrothiazolo[5,4-c]pyridine-2-carboxamide hydrochloride

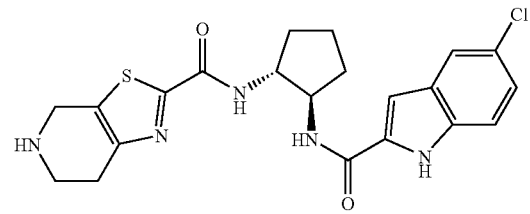

In a manner similar to that employed in Example 2, a product obtained through reaction between the compound obtained in Referential Example 63 and the compound obtained in Referential Example 34 was treated with hydrochloric acid, to thereby give the title compound.

$^1$H-NMR (DMSO-$d_6$) δ: 1.60-1.82(4H,m), 1.91-2.15(2H, m), 3.08(2H,s), 3.37-3.49(2H,m), 4.28-4.56(4H,m), 7.13(1H,s), 7.15(1H,d,J=8.8 Hz), 7.40(1H,d,J=8.8 Hz), 7.69 (1H,s), 8.61(1H,d,J=8.3 Hz), 8.88(1H,d,J=8.3 Hz), 10.05(2H,br.s), 11.82(1H,s).

MS(FAB)m/z: 444(M+H)$^+$.

Example 24

N-((1R*,2R*)-2-{[(5-Chloroindol-2-yl)carbonyl] amino}-cyclopentyl)-5-isopropyl-4,5,6,7-tetrahydrothiazolo-[5,4-c]pyridine-2-carboxamide hydrochloride

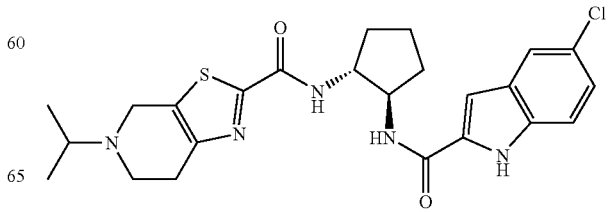

371

The compound (30 mg) obtained in Example 23 was suspended in methylene chloride (20 mL), and triethylamine (260 µl) was added, followed by stirring at room temperature for 15 minutes. Acetic acid (179 µl) and acetone (920 µl) were added to the reaction mixture, and the resultant mixture was stirred at room temperature for 2 minutes. Sodium triacetoxyborohydride (796 mg) was added to the reaction mixture to stir them at room temperature for 5 hours. 1N aqueous sodium hydroxide (10 mL) was added to the reaction mixture for partitioning the mixture. The resultant organic layer was dried over sodium sulfate anhydrate, and the solvent was distilled away under reduced pressure. The residue was purified by silica gel column chromatography (methylene chloride: methanol=100:3) to give a colorless foamy substance. This product was dissolved in methylene chloride, and 1N HCl in ethanol (1 mL) was added. The solution was concentrated under reduced pressure to give the title compound (205 mg).

$^1$H-NMR (DMSO-$d_6$) δ: 1.27-1.39(6H,m), 1.58-1.80(4H, m), 1.95-2.10(2H,m), 3.00-3.12(1H,m), 3.25-3.45(2H,m), 3.59-3.77(2H,m), 4.25-4.39(1H,m), 4.40-4.55(2H,m), 4.57-4.65(1H,m), 7.10(1H,s), 7.14(1H,d,J=8.8 Hz), 7.38(1H,d, J=8.8 Hz), 7.68(1H,s), 8.56(1H,d,J=8.8 Hz), 8.90(1H,d,J=8.8 Hz), 11.39(1H,br.s), 11.76(0.5H,s), 11.80(0.5H,s).

MS(FAB)m/z: 486(M+H)$^+$.

Example 25

N-((1R*,2R*)-2-{[(5-Chloroindol-2-yl)carbonyl] amino}-cyclopentyl)-5-ethyl-4,5,6,7-tetrahydrothiazolo[5,4-c]-pyridine-2-carboxamide hydrochloride

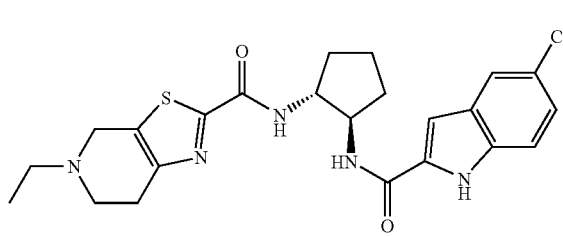

The compound (500 mg) obtained in Example 23 was dissolved in N,N-dimethylformamide (10 mL), and triethylamine (576 µl) and ethyl iodide (329 µl) were added, followed by stirring overnight at room temperature. The reaction mixture was concentrated under reduced pressure, and water was added to the residue to collect insoluble matter by filtration. This product was purified by silica gel column chromatography (methylene chloride:methanol=100:3) to give a pale brown foamy substance. This substance was suspended in 1N hydrochloric acid (2 mL), and the suspension was concentrated under reduced pressure to give the title compound (180 mg).

$^1$H-NMR (DMSO-$d_6$) δ: 1.32(3H,t,J=7.1 Hz), 1.60-1.80 (4H,m), 1.96-2.10(2H,m), 3.20-3.39(5H,m), 3.70-3.80(1H, m), 4.26-4.58(3H,m), 4.68-4.79(1H,m), 7.11(1H,s), 7.15 (1H,dd,J=8.8, 2.0 Hz), 7.39(1H,d,J=8.8 Hz), 7.69(1H,d, J=1.5 Hz), 8.55(1H,d,J=8.5 Hz), 8.92(1H,d,J=8.5 Hz), 11.38 (1H,br.s), 11.70-11.80(1H,m).

MS(FAB)m/z: 472(M+H)$^+$.

372

Example 26

N-((1R*,2R*)-2-{[(5-Chloroindol-2-yl)carbonyl] amino}-cyclopentyl)-5-(1-methylcyclopropyl)-4,5,6,7-tetrahydrothiazolo[5,4-c]pyridine-2-carboxamide hydrochloride

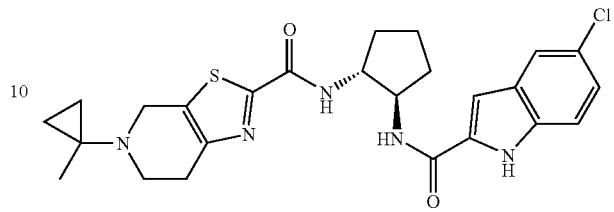

The title compound was obtained from the compound obtained in Referential Example 63 and the compound obtained in Referential Example 39 in a similar manner to Example 2.

$^1$H-NMR (DMSO-$d_6$) δ: 0.81(2H,br.s), 1.20-1.55(5H,br), 1.55-1.80(4H,m), 1.95-2.12(2H,m), 3.05-3.40(2H,br), 3.60-3.80(2H,br), 4.25-4.80(4H,m), 7.10(1H,s), 7.16(1H,d,J=8.8 Hz), 7.39(1H,d,J=8.8 Hz), 7.69(1H,s), 8.53(1H,d,J=8.6 Hz), 8.85-8.95(1H,m), 10.60-10.90(1H,br), 11.73(1H,br.s).

MS(FAB)m/z: 498(M+H)$^+$.

Example 27

N-((1R*,2R*)-2-{[(5-Chloroindol-2-yl)carbonyl] amino}-4-methoxycyclopentyl)-5-methyl-4,5,6,7-tetrahydrothiazolo-[5,4-c]pyridine-2-carboxamide hydrochloride (Stereoisomer A and Stereoisomer B)

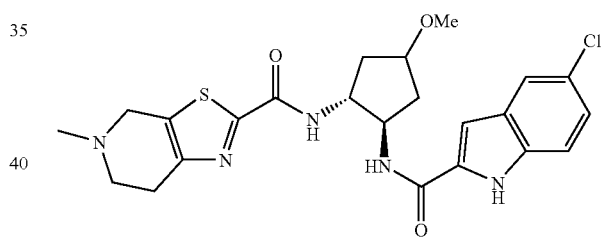

A mixture of the title compounds; i.e., Stereoisomer A and Stereoisomer B, was synthesized by condensing the compound (mixture of 4-position stereoisomers) (268 mg) obtained in Referential Example 82 with the compound obtained in Referential Example 10 in a similar manner to Example 2. The isomers were isolated by silica gel column chromatography and then converted into hydrochlorides to give the title compounds [Stereoisomer A (75 mg) and Stereoisomer B (70 mg)].

Stereoisomer A:

$^1$H-NMR (DMSO-$d_6$) δ: 1.70-2.15(4H,m), 2.90(3H,s), 3.00-3.90(8H,m), 4.10-4.80(4H,m), 7.08(1H,s), 7.16(1H,d, J=8.8 Hz), 7.38(1H,d,J=8.8 Hz), 7.69(1H,s), 8.56(1H,d,J=8.8 Hz), 8.88(1H,d,J=8.3 Hz), 10.96(1H,br.s), 11.75(1H,br.s).

MS(FAB)m/z: 488(M+H)$^+$.

Stereoisomer B:

$^1$H-NMR (DMSO-$d_6$) δ: 1.60-2.10(4H,m), 2.89(3H,s), 3.00-3.70(7H,m), 3.70-3.90(1H,m), 4.20-4.80(4H,m), 7.05-7.20(2H,m), 7.38(1H,d,J=8.8 Hz), 7.68(1H,s), 8.59(1H,d, J=8.3 Hz), 8.90(1H,d,J=8.5 Hz), 11.26(1H,br.s), 11.74(1H, br.s).

MS(FAB)m/z: 488(M+H)$^+$.

Example 28

N-[(1R*,2R*)-2-{[(5-Chloroindol-2-yl)carbonyl]amino}-4-(hydroxymethyl)cyclopentyl]-5-(1,1-dimethyl-2-hydroxyethyl)-4,5,6,7-tetrahydrothiazolo[5,4-c]pyridine-2-carboxamide hydrochloride (Stereoisomer A)

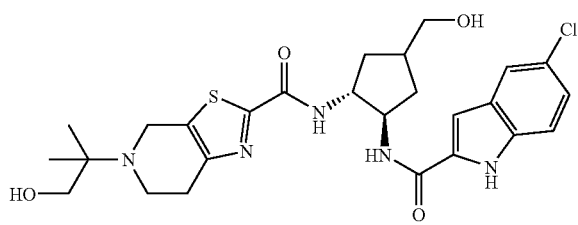

1) Stereoisomers A and B of N-((1R*,2R*)-4-[(benzyloxy)methyl]-2-{(5-chloroindol-2-yl)carbonyl}amino)cyclopentyl)-5-(2-{[tert-butyl(diphenyl)silyl]oxy}-1,1-dimethylethyl)-4,5,6,7-tetrahydrothiazolo[5,4-c]pyridine-2-carboxamide were obtained from the compound obtained in Referential Example 85 and the compound obtained in Referential Example 42 in a similar manner to Example 2.

Stereoisomer A:
$^1$H-NMR (CDCl$_3$) δ: 1.05(9H,s), 1.168, 1.171(6H, each s), 1.53-1.61(1H,m), 1.76-1.88(1H,m), 2.30-2.37(2H,m), 2.78-2.79(2H,m), 2.87-2.90(1H,m), 2.96-3.00(1H,m), 3.37-3.47(2H,m), 3.58(2H,s), 3.96(1H,q,J=13.1 Hz), 4.41-4.45(1H,m), 4.51-4.57(2H,m), 6.88(1H,d,J=1.5 Hz), 7.17(1H,dd,J=8.8, 2.0 Hz), 7.23-7.43(12H,m), 7.52(1H,d,J=7.6 Hz), 9.37(1H,br.s).

Stereoisomer B:
$^1$H-NMR (CDCl$_3$) δ: 1.05(9H,s), 1.17(6H,s), 1.43-1.47(1H,m), 1.85-1.88(1H,m), 2.09-2.14(1H,m), 2.58-2.63(1H,m), 2.78-2.79(2H,m), 2.86-2.90(1H,m), 2.96-3.00(1H,m), 3.38-3.46(2H,m), 3.59(2H,s), 3.95(1H,q,J=13.3 Hz), 4.15-4.20(1H,m), 4.45-4.56(3H,m), 6.74(1H,d,J=2.0 Hz), 7.16(1H,dd,J=8.8, 2.0 Hz), 7.27-7.43(12H,m), 7.57(1H,d,J=2.0 Hz), 9.48(1H,br.s).

2) The above Stereoisomer A (288 mg) was suspended in methylene chloride (20 mL), and dimethyl sulfide (1.15 mL) and anhydrous aluminum chloride (350 mg) were added, followed by stirring at room temperature for 1 hour. 1N aqueous sodium hydroxide (10 mL) was added to the reaction mixture, and the mixture was extracted with methylene chloride. The resultant organic layer was dried over sodium sulfate anhydrate. The solvent was distilled away under reduced pressure, and the residue was purified by silica gel column chromatography (methylene chloride:methanol=9:1) to give 5-(2-{[tert-butyl(diphenyl)silyl]oxy}-1,1-dimethylethyl)-N-[(1R*,2R*)-2-{[(5-Chloroindol-2-yl)carbonyl]amino}-4-(hydroxymethyl)cyclopentyl]-4,5,6,7-tetrahydrothiazolo[5,4-c]pyridine-2-carboxamide (Stereoisomer A) (184 mg).

$^1$H-NMR (CDCl$_3$)δ: 1.04(9H,s), 1.15(6H,s), 1.54-1.62(1H,m), 1.73-1.81(1H,m), 1.99-2.25(2H,m), 2.34-2.38(2H,m), 2.67-2.85(3H,m), 2.92-2.97(1H,m), 3.48-3.62(4H,m), 3.93(1H,q,J=15.6 Hz), 4.20-4.28(1H,m), 4.47-4.56(1H,m), 6.89(1H,s), 7.11-7.18(1H,m), 7.24-7.27(1H,m), 7.32-7.43(6H,m), 7.54(1H,d,J=1.7 Hz), 7.63(4H,dd,J=7.8, 1.5 Hz), 7.90-7.92(2H,m), 10.13(1H,br.s).
MS(FAB)m/z: 784(M+H)$^+$.

3) Stereoisomer A (180 mg) obtained in the step 2) described above was dissolved in a 1N tetrahydrofuran solution (2 mL) of tetrabutylammonium fluoride, and the solution was stirred overnight at room temperature. Methylene chloride, 1N aqueous sodium hydroxide and sodium chloride were added to the reaction mixture for partitioning the mixture. The resultant organic layer was dried over sodium sulfate anhydrate. The solvent was distilled away under reduced pressure, and the residue was purified by silica gel column chromatography (methylene chloride:methanol=19:1). The thus-obtained powder was dissolved in methanol, and 1N HCl in ethanol (229 µl) was added, and then ethyl acetate was added. The solvent was concentrated under reduced pressure to give the title compound (63 mg).

$^1$H-NMR (DMSO-d$_6$) δ: 1.33-1.50(8H,m), 1.70-1.91(2H,m), 2.07-2.14(1H,m), 2.23-2.24(1H,m), 3.04-3.10(1H,m), 3.27-3.44(4H,m), 3.57-3.70(2H,m), 3.92-3.95(1H,m), 4.29-4.72(4H,m), 5.81(1H,br.s), 7.11(1H,s), 7.15(1H,dd,J=8.6, 2.0 Hz), 7.39(1H,d,J=8.6 Hz), 7.68(1H,d,J=2.0 Hz), 8.53-8.56(1H,m), 8.83(1H,d,J=8.3 Hz), 10.36(1H,br.s), 11.75, 11.77(1H, each s).
MS(ESI)m/z: 546(M+H)$^+$.

Example 29

N-((1R*,2S*)-2-{[(5-Chloroindol-2-yl)carbonyl]amino}-cyclohexyl)-4,7,8,10-tetrahydro-6H-pyrazolo[1,2-a]-thiazolo[4,5-d]pyridazine-2-carboxamide hydrochloride

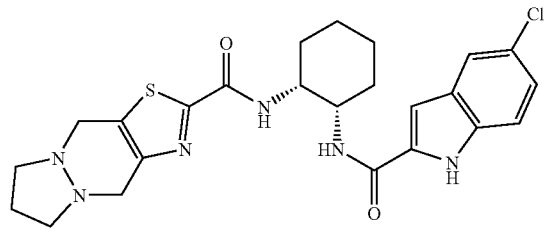

The title compound was obtained from the compound obtained in Referential Example 71 and the compound obtained in Referential Example 44 in a similar manner to Example 2.

$^1$H-NMR (DMSO-d$_6$) δ: 1.35-1.50(2H,m), 1.61(4H,br.s), 1.80-2.00(2H,m), 2.27(2H,br.s), 2.80-4.80(10H,m), 7.14(1H,d,J=1.5 Hz), 7.17(1H,dd,J=8.5, 2.0 Hz), 7.41(1H,d,J=8.5 Hz), 7.70(1H,d,J=2.0 Hz), 8.09(1H,d,J=7.3 Hz), 8.44(1H,br.s), 11.81(1H,br.s).
MS(FAB)m/z: 499(M+H)$^+$.

Example 30

N-((1R*,2S*)-2-{[(5-Chloroindol-2-yl)carbonyl]amino}-cyclohexyl)-4,6,7,8,9,11-hexahydropyridazino[1,2-a]-thiazolo[4,5-d]pyridazine-2-carboxamide hydrochloride

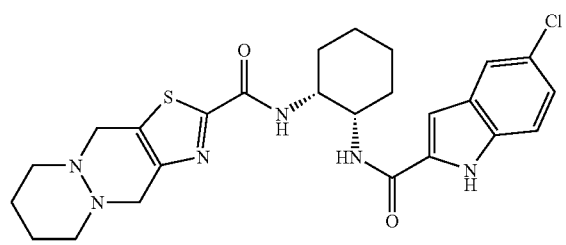

The title compound was obtained from the compound obtained in Referential Example 46 and the compound obtained in Referential Example 71 in a similar manner to Example 2.

$^1$H-NMR (DMSO-d$_6$) δ: 1.35-1.55(2H,m), 1.55-2.10(10H,m), 2.80-4.80(10H,m), 7.10-7.25(2H,m), 7.42(1H,d,J=8.8 Hz), 7.72(1H,d,J=1.7 Hz), 8.12(1H,br.s), 8.41(1H,br.s), 11.83(1H,br.s).
MS(FAB)m/z: 513(M+H)$^+$.

Example 31

5-Chloro-N-{(1R*,2S*)-2-[(5,6-dihydro-4H-pyrrolo[3,4-d]-thiazol-2-ylcarbonyl)amino]cyclohexyl}indole-2-carboxamide hydrochloride

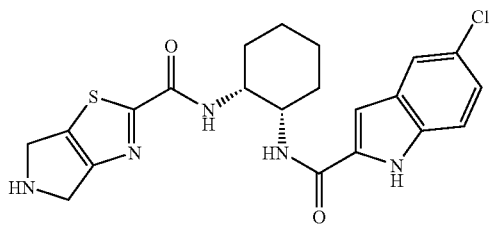

The compound (171 mg) obtained in Referential Example 33 was dissolved in diethyl ether (5 mL) in an argon atmosphere, and the solution was cooled to −78° C., and then n-butyllithium (1.60N hexane solution, 385 μl) was added dropwise. After the reaction mixture was stirred for 10 minutes at −78° C., and carbon dioxide was blown into the reaction mixture for 20 minutes, it was warmed to room temperature. After the reaction mixture was concentrated under reduced pressure, the residue was dissolved in N,N-dimethylformamide (10 mL). To the solution, were added the compound (184 mg) obtained in Referential Example 71, 1-hydroxybenzotriazole monohydrate (76 mg) and 1-(3-dimethylaminopropyl)-3-ethylcarbodiimide hydrochloride (215 mg). The resultant mixture was stirred at room temperature for 3 days. The reaction mixture was concentrated, and methylene chloride and saturated aqueous sodium hydrogencarbonate were added to the residue to separate an organic layer. The organic layer was dried over sodium sulfate anhydrate, and the solvent was then distilled away under reduced pressure. The resultant residue was purified by silica gel column chromatography (methanol:methylene chloride=3:97). After HCl in ethanol (5 mL) was added to the thus-obtained product, the mixture was stirred at room temperature for 1 hour, and the reaction mixture was concentrated. Ethyl acetate was added to the residue for solidification. The resultant powder was collected by filtration to give the title compound (31 mg).

$^1$H-NMR (DMSO-$d_6$) δ: 1.35-1.52(2H,m), 1.55-1.80(4H,m), 1.82-2.05(2H,m), 4.22(1H,br.s), 4.28(1H,br.s), 4.38(2H,s), 4.56(2H,s), 7.14-7.20(2H,m), 7.42(1H,d,J=8.6 Hz), 7.71(1H,d,J=1.7 Hz), 8.10(1H,d,J=7.1 Hz), 8.45(1H,d,J=7.8 Hz), 10.10-10.50(2H,br), 11.83(1H,br.s).

MS(FAB)m/z: 444(M+H)$^+$.

Example 32 tert-Butyl 2-{[(1R*,2S*)-2-{[(5-chloroindol-2-yl)carbonyl]amino}cyclohexyl)amino]carbonyl}-5,7-dihydro-6H-pyrrolo[3,4-d]pyrimidine-6-carboxylate

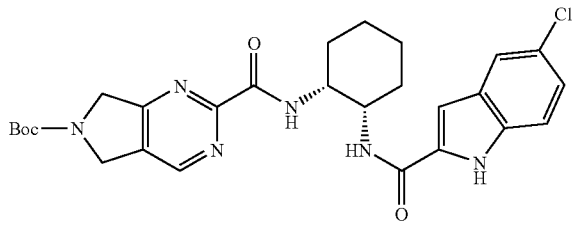

The compound obtained in Referential Example 50 was hydrolyzed with lithium hydroxide. Subsequently, in a manner similar to that employed in Example 2, the resultant product was reacted with the compound obtained in Referential Example 71, to thereby give the title compound.

$^1$H-NMR (CDCl$_3$) δ: 1.54(9H,s), 1.55-2.30(8H,m), 4.23(1H,br.s), 4.53(1H,br.s), 4.74-4.83(4H,m), 6.99(1H,d,J=1.5 Hz), 7.19(1H,dd,J=8.8, 2.1 Hz), 7.34(1H,d,J=8.8 Hz), 7.62(1H,d,J=2.1 Hz), 8.11(1H,br.s), 8.48-8.53(1H,br), 8.70-8.76(1H,br), 9.60-9.70(1H,br).

MS(ESI)m/z: 539(M+H)$^+$.

Example 33

N-((1R*,2S*)-2-{[(5-Chloroindol-2-yl)carbonyl]amino}-cyclohexyl)-6-methyl-6,7-dihydro-5H-pyrrolo[3,4-d]-pyrimidine-2-carboxamide hydrochloride

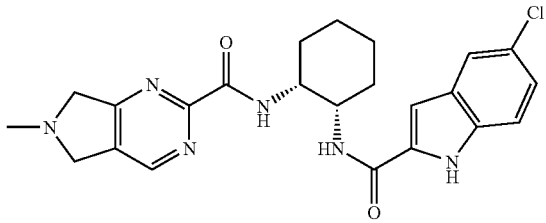

Trifluoroacetic acid (1 mL) was added to a solution of the compound (34.0 mg) obtained in Example 32 dissolved in methylene chloride (1 mL) at room temperature, and the mixture was stirred for 1 hour. The reaction mixture was concentrated under reduced pressure, and the residue was dissolved in methylene chloride (1 mL), and then triethylamine (17.6 μl), acetic acid (7.21 μl), 35% formalin (8.13 μl) and sodium triacetoxyborohydride (20.1 mg) were added at room temperature. The resultant mixture was stirred for 1 hour. Methylene chloride (10 mL) and saturated aqueous sodium hydrogencarbonate were added to the reaction mixture to separate an organic layer. The organic layer was dried over sodium sulfate anhydrate. The solvent was distilled away under reduced pressure, and the residue was purified by silica gel column chromatography (methanol:methylene chloride 7:93). A 1N HCl in ethanol and ethyl acetate were added to the thus-obtained product for solidification, and the resultant solids were collected by filtration to give the title compound (8.00 mg).

$^1$H-NMR (DMSO-$d_6$) δ: 1.40-1.55(2H,m), 1.55-1.75(4H,m), 1.80-2.05(2H,m), 2.98(3H,br.s), 4.28(2H,br.s), 4.65(4H,br.s), 7.14-7.20(2H,m), 7.41(1H,d,J=8.8 Hz), 7.69(1H,d,J=2.0 Hz), 8.17(1H,d,J=6.9 Hz), 8.65(1H,d,J=8.3 Hz), 8.93(1H,s), 11.73(1H,br.s), 11.82(1H,br.s).

MS(FAB)m/z: 453(M+H)$^+$.

Example 34

N-((1R*,2S*)-2-{[(5-Chloroindol-2-yl)carbonyl]amino}-cyclohexyl)-4,5,6,7-tetrahydrothiazolo[5,4-c]pyridine-2-carboxamide hydrochloride

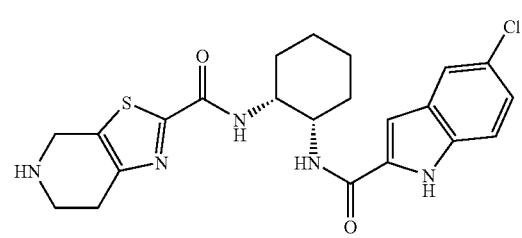

In a manner similar to that employed in Example 2, a product obtained through reaction between the compound obtained in Referential Example 71 and the compound obtained in Referential Example 34 was treated with hydrochloric acid, to thereby give the title compound.

¹H-NMR (DMSO-d₆) δ: 1.39-1.52(2H,m), 1.62(4H,br.s), 1.86-2.09(2H,m), 3.03(2H,br.s), 3.40-3.47(2H,m), 4.17-4.32 (2H,m), 4.44(2H,s), 7.15(1H,s), 7.17(1H,dd,J=8.6, 2.0 Hz), 7.41(1H,d,J=8.6 Hz), 7.71(1H,s), 8.10-8.15(1H,m), 8.40-8.47(1H,m), 9.69(2H,br.s), 11.85(1H,s).

MS(FAB)m/z: 458(M+H)⁺.

Example 35

N-((1R*,2S*)-2-{[(5-Chloroindol-2-yl)carbonyl]amino}-cyclohexyl)-5-(2-methoxyethyl)-4,5,6,7-tetrahydrothiazolo-[5,4-c]pyridine-2-carboxamide hydrochloride

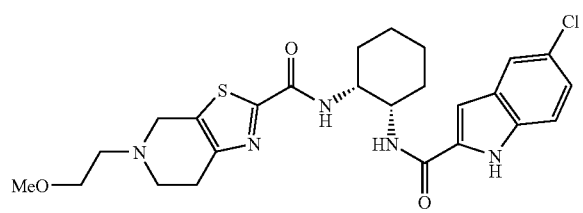

The title compound was obtained from the compound obtained in Example 34 and 2-methoxyethyl bromide in a similar manner to Example 25.

¹H-NMR (DMSO-d₆) δ: 1.44(2H,br.s), 1.62(4H,br.s), 1.85-2.10(2H,m), 2.76-3.21(6H,m), 3.28(3H,s), 3.64(2H,br.s), 4.00-4.52(4H,m), 7.14(1H,s), 7.17(1H,dd, J=8.8, 2.0 Hz), 7.41(1H,d,J=8.8 Hz), 7.70(1H,d,J=2.0 Hz), 8.08-8.20(1H,m), 8.36-8.48(1H,m), 11.84(1H,s).

MS(FAB)m/z: 516(M+H)⁺.

Example 36

Methyl 2-[2-{[(1R*,2S)-2-{[(5-chloroindol-2-yl)-carbonyl]amino}cyclohexyl)amino]carbonyl}-6,7-dihydrothiazolo[5,4-c]pyridin-5(4H)-yl]acetate hydrochloride

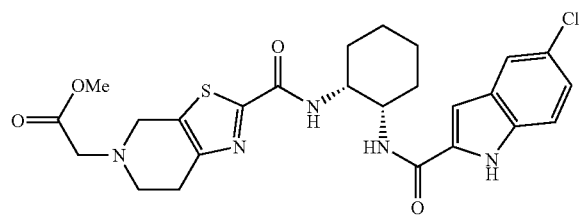

The title compound was obtained from the compound obtained in Example 34 and methyl bromoacetate in a similar manner to Example 25.

¹H-NMR (CDCl₃) δ: 1.52-1.98(7H,m), 2.17(1H,br.s), 2.87-3.10(4H,m), 3.49(2H,s), 3.76(3H,s), 3.93(1H,d,J=15.4 Hz), 3.99(1H,d,J=15.4 Hz), 4.22(1H,br.s), 4.45(1H,br.s), 6.86(1H,d,J=1.2 Hz), 7.18(1H,dd,J=8.8, 2.0 Hz), 7.33(1H,d, J=8.8 Hz), 7.58-7.63(2H,m), 7.87(1H,br.s), 9.88(1H,br.s).

MS(FAB)m/z: 530(M+H)⁺.

Example 37

N-((1R*,2S*)-2-{[(5-Chloroindol-2-yl)carbonyl]amino}-cyclohexyl)-5-isopropyl-4,5,6,7-tetrahydrothiazolo[5,4-c]-pyridine-2-carboxamide hydrochloride

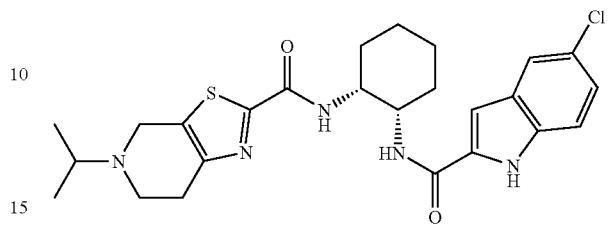

The title compound was obtained from the compound obtained in Example 34 and acetone in a similar manner to Example 24.

¹H-NMR (DMSO-d₆) δ: 1.18-1.73(8H,m), 1.81-2.10(2H, m), 2.97-3.16(1H,m), 3.20-3.41(2H,m), 3.52-3.80(2H,m), 4.19-4.31(2H,m), 4.34-4.77(2H,m), 7.17(1H,s), 7.18(1H,dd, J=8.8, 2.0 Hz), 7.42(1H,d,J=8.8 Hz), 7.71(1H,d,J=2.0 Hz), 8.15(1H,br.s), 8.28-8.51(1H,m), 11.31(1H,br.s), 11.86(1H, s).

MS(FAB)m/z: 500(M+H)⁺.

Example 38

N-((1R*,2S*)-2-{[(5-Chloroindol-2-yl)carbonyl]amino}-cyclohexyl)-5-(tetrahydro-2H-pyran-4-yl)-4,5,6,7-tetrahydrothiazolo[5,4-c]pyridine-2-carboxamide hydrochloride

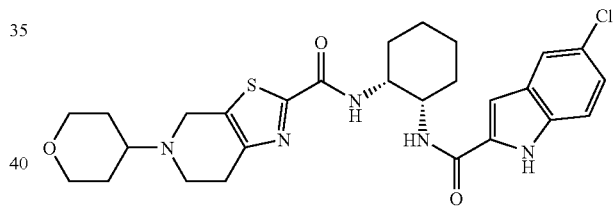

The title compound was obtained from the compound obtained in Example 34 and tetrahydro-4H-pyran-4-one in a similar manner to Example 24.

¹H-NMR (DMSO-d₆) δ: 1.30-3.56(19H,m), 3.70-4.01 (3H,m), 4.17-4.30(2H,m), 4.32-4.80(1H,m), 7.15(1H,s), 7.17(1H,dd,J=8.6, 2.0 Hz), 7.41(1H,d,J=8.6 Hz), 7.71(1H,d, J=2.0 Hz), 8.14(1H,br.s), 8.39(1H,br.s), 11.84(1H,s).

MS(FAB)m/z: 542(M+H)⁺.

Example 39 tert-Butyl 2-[2-{[(1R*,2S*)-2-{[(5-chloroindol-2-yl)carbonyl]amino}cyclohexyl)amino]carbonyl}-6,7-dihydrothiazolo[5,4-c]pyridin-5(4H)-yl]ethylcarbamate

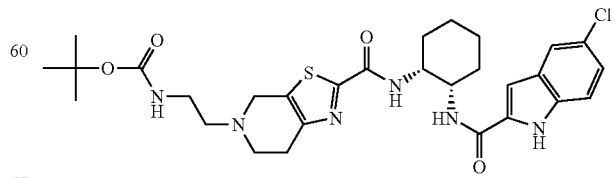

The title compound was obtained from the compound obtained in Example 34 and N-(tert-butoxycarbonyl)aminoacetoaldehyde (J. Org. Chem., 1988, Vol. 53, p. 3457) in a similar manner to Example 24.

$^1$H-NMR (CDCl$_3$) δ: 1.44(9H,s), 1.54-1.98(7H,m), 2.10-2.20(1H,m), 2.74(2H,br.s), 2.92(4H,br.s), 3.34(2H,br.s), 3.84(2H,br.s), 4.21(1H,br.s), 4.45(1H,br.s), 6.86(1H,s), 7.19(1H,dd,J=8.8, 2.0 Hz), 7.33(1H,d,J=8.8 Hz), 7.57-7.63(2H,m), 7.81(1H,br.s), 9.66(1H,br.s).

MS(FAB)m/z: 601(M+H)$^+$.

Example 40

5-(2-Aminoethyl)-N-((1R*,2S*)-2-{[(5-chloroindol-2-yl)carbonyl]amino}cyclohexyl)-4,5,6,7-tetrahydrothiazolo-[5,4-c]pyridine-2-carboxamide hydrochloride

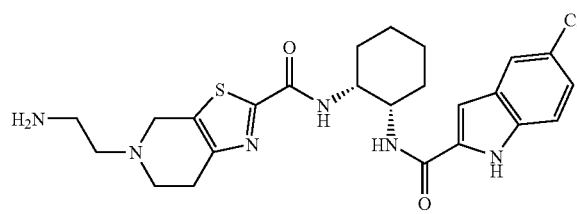

The compound (450 mg) obtained in Example 39 was dissolved in methylene chloride (5 mL), and HCl in ethanol (30 mL) was added, followed by stirring at room temperature for 1 minute. The reaction mixture was concentrated under reduced pressure, ethyl acetate was added to the residue, and solids preciitated were collected by filtration to give the title compound (367 mg).

$^1$H-NMR (DMSO-d$_6$) δ: 1.38-1.50(2H,m), 1.61(4H,br.s), 1.85-2.08(2H,m), 3.00-4.62(12H,m), 7.14(1H,s), 7.16(1H,dd,J=8.8, 2.0 Hz), 7.41(1H,d,J=8.8 Hz), 7.69(1H,d,J=2.0 Hz), 8.12(1H,d,J=6.6 Hz), 8.15-8.68(4H,m), 11.85(1H,s).

MS(FAB)m/z: 501(M+H)$^+$.

Example 41

N-((1R*,2S*)-2-{[(5-Chloroindol-2-yl)carbonyl]amino}-cyclohexyl)-5-{2-[(methylsulfonyl)amino]ethyl}-4,5,6,7-tetrahydrothiazolo[5,4-c]pyridine-2-carboxamide hydrochloride

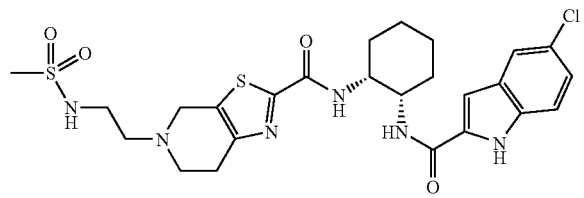

The compound (110 mg) obtained in Example 40 was dissolved in pyridine (3 mL), methanesulfonyl chloride (30 μl) was added, and the mixture was stirred overnight at room temperature. The reaction mixture was concentrated under reduced pressure. To the residue, a 85:15 mixture of methylene chloride and methanol, and water were added for partitioning the mixture. The resultant organic layer was dried over sodium sulfate anhydrate. The solvent was distilled away under reduced pressure, and the residue was purified by silica gel column chromatography (methylene chloride:methanol=100:3) to give a pale yellow foamy substance. This product was suspended in 1N hydrochloric acid (0.3 mL), and the suspension was concentrated under reduced pressure to give the title compound (63 mg).

$^1$H-NMR (DMSO-d$_6$) δ: 1.38-1.50(2H,m), 1.55-1.70(4H,m), 1.86-2.05(2H,m), 2.97(3H,s), 3.02-3.25(2H,m), 3.30-3.60(5H,m), 3.78(1H,br.s), 4.18-4.30(2H,m), 4.45-4.86(2H,m), 7.14(1H,s), 7.16(1H,dd,J=8.8, 2.0 Hz), 7.40(1H,d,J=8.8 Hz), 7.41(1H,br.s), 7.69(1H,d,J=2.0 Hz), 8.09(1H,br.s), 8.43(1H,br.s), 11.18(1H,br.s), 11.82(1H,s).

MS(FAB)m/z: 579(M+H)$^+$.

Example 42

Methyl 2-[2-{[((1R*,2S*)-2-{[(5-chloroindol-2-yl)carbonyl]amino}cyclohexyl)amino]carbonyl}-6,7-dihydrothiazolo[5,4-c]pyridin-5(4H)-yl]ethylcarbamate hydrochloride

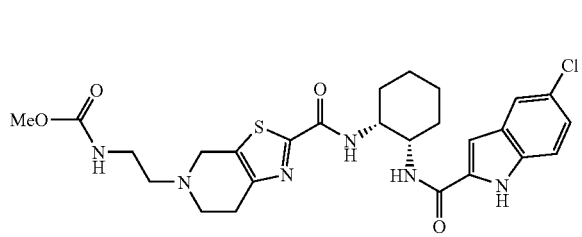

The compound (144 mg) obtained in Example 40 was dissolved in pyridine (3 mL), triethylamine (138 μl) was added, and the mixture was stirred at room temperature for 5 minutes. A solution prepared by adding triphosgene (49 mg) to tetrahydrofuran (1 mL) containing methanol (20 μl) was added dropwise to this solution at room temperature. After stirring for 1 hour, the reaction mixture was concentrated under reduced pressure, and the residue was dissolved in a 9:1 mixture of methylene chloride and methanol. Water was added to the solution for partitioning the mixture. The organic layer was separated and dried over sodium sulfate anhydrate. The solvent was distilled away under reduced pressure, and the residue was purified by silica gel column chromatography (methylene chloride:methanol=100:3) to give a colorless foamy substance. This product was suspended in 1N hydrochloric acid (0.2 mL), and the suspension was concentrated under reduced pressure to give the title compound (60 mg).

$^1$H-NMR (DMSO-d$_6$) δ: 1.38-1.50(2H,m), 1.61(4H,br.s), 1.85-2.04(2H,m), 2.80-3.49(8H,m), 3.52(3H,s), 3.62-4.91(4H,m), 7.14(1H,s), 7.16(1H,dd,J=8.8, 2.0 Hz), 7.37(1H,br.s), 7.40(1H,d,J=8.8 Hz), 7.70(1H,s), 8.11(1H,d,J=6.8 Hz), 8.40(1H,br.s), 11.05(1H,br.s), 11.82(1H,br.s).

MS(FAB)m/z: 559(M+H)$^+$.

Example 43

5-[2-(Acetylamino)ethyl]-N-((1R*,2S*)-2-{[(5-chloroindol-2-yl)carbonyl]amino}cyclohexyl)-4,5,6,7-tetrahydrothiazolo-[5,4-c]pyridine-2-carboxamide hydrochloride

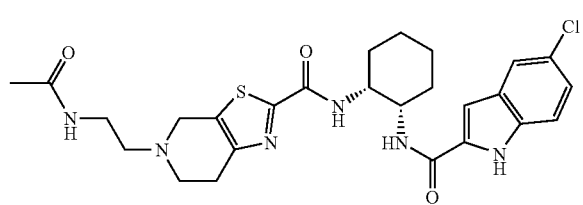

The compound (90 mg) obtained in Example 40 was dissolved in N,N-dimethylformamide (3 mL), triethylamine (65 μl) and acetic anhydride (22 μl) were added, and the mixture was stirred overnight at room temperature. The reaction mixture was concentrated under reduced pressure, and methylene chloride and 0.3N aqueous sodium hydroxide were added to the residue for partitioning the mixture. The resultant organic layer was dried over sodium sulfate anhydrate. The solvent was distilled away under reduced pressure, and the residue was purified by silica gel column chromatography (methylene chloride:methanol=100:3) to give a colorless foamy substance. This product was suspended in 1N hydrochloric acid (0.3 mL), and the suspension was concentrated under reduced pressure to give the title compound (73 mg).

$^1$H-NMR (DMSO-$d_6$) δ: 1.39-1.52(2H,m), 1.54-1.70(4H, m), 1.83(3H,s), 1.84-2.06(2H,m), 3.02-3.87(8H,m), 4.16-4.32(2H,m), 4.40-4.52(1H,m), 4.78-4.88(1H,m), 7.14(1H,s), 7.16(1H,d,J=8.6 Hz), 7.40(1H,d,J=8.6 Hz), 7.70(1H,s), 8.07-8.17(1H,m), 8.22-8.30(1H,m), 8.38-8.52(1H,m), 11.14(1H, br.s), 11.83(1H,s).

MS(FAB)m/z: 543(M+H)$^+$.

Example 44

N-((1R*,2S*)-2-{[(5-Chloroindol-2-yl)carbonyl]amino}cyclohexyl)-5-(2-hydroxyethyl)-4,5,6,7-tetrahydrothiazolo[5,4-c]pyridine-2-carboxamide

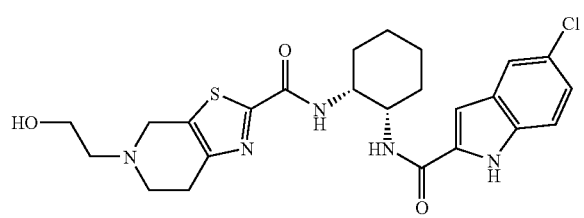

The title compound was obtained from the compound obtained in Example 34 and 2-bromoethanol in a similar manner to Example 25.

$^1$H-NMR (DMSO-$d_6$) δ: 1.37-1.69(6H,m), 1.86-2.03(2H, m), 2.54-2.61(2H,m), 2.75-2.86(4H,m), 3.52-3.59(2H,m), 3.75(2H,s), 4.47(1H,t,J=5.4 Hz), 7.12(1H,s), 7.16(1H,dd, J=8.8, 2.0 Hz), 7.40(1H,d,J=8.8 Hz), 7.70(1H,s), 8.05-8.13 (1H,m), 8.28-8.35(1H,m), 11.78(1H,s).

MS(FAB)m/z: 502(M+H)$^+$.

Example 45

5-Butyl-N-((1R*,2S*)-2-{[(5-chloroindol-2-yl)carbonyl]-amino}cyclohexyl)-4,5,6,7-tetrahydrothiazolo[5,4-c]-pyridine-2-carboxamide hydrochloride

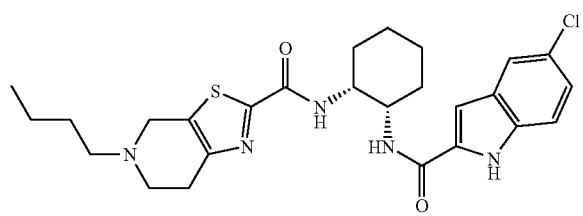

The title compound was obtained from the compound obtained in Example 34 and 1-bromobutane in a similar manner to Example 25.

$^1$H-NMR (DMSO-$d_6$) δ: 0.88(3H,t,J=7.2 Hz), 1.20-1.70 (10H,m), 1.87-2.05(2H,m), 2.55-3.40(8H,m), 4.16-4.30(2H, m), 7.13(1H,s), 7.16(1H,d,J=8.8 Hz), 7.40(1H,d,J=8.8 Hz), 7.69(1H,s), 8.05-8.14(1H,m), 8.35(1H,br.s), 11.81(1H,s).

MS(FAB)m/z: 514(M+H)$^+$.

Example 46

5-Acetyl-N-((1R*,2S)-2-{[(5-chloroindol-2-yl)carbonyl]-amino}cyclohexyl)-4,5,6,7-tetrahydrothiazolo[5,4-c]-pyridine-2-carboxamide

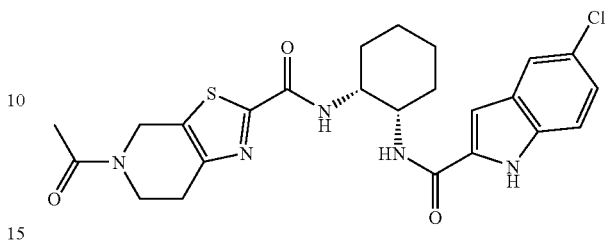

The compound (100 mg) obtained in Example 34 was dissolved in N,N-dimethylformamide (3 mL), triethylamine (84 μl) and acetic anhydride (29 μl) were added, and the mixture was stirred at room temperature for 3 hours. The reaction mixture was concentrated under reduced pressure, and methylene chloride and 1N hydrochloric acid were added to the residue for partitioning the mixture. The resultant organic layer was dried over sodium sulfate anhydrate. The solvent was distilled away under reduced pressure, and the residue was purified by silica gel column chromatography (methylene chloride:methanol=100:3) to give the title compound (86 mg).

$^1$H-NMR (CDCl$_3$) δ: 1.52-1.85(5H,m), 1.91(2H,br.s), 2.10-2.28(4H,m), 2.77-3.00(2H,m), 3.70-4.00(2H,m), 4.19-4.38(1H,m), 4.45(1H,br.s), 4.68-4.99(2H,m), 6.85(1H,s), 7.17-7.22(1H,m), 7.30-7.39(1H,m), 7.50-7.84(3H,m), 9.72-10.05(1H,m).

MS(FAB)m/z: 500(M+H)$^+$.

Example 47

N-((1R*,2S*)-2-{[(5-Chloroindol-2-yl)carbonyl]amino}-cyclohexyl)-5-(methylsulfonyl)-4,5,6,7-tetrahydrothiazolo[5,4-c]pyridine-2-carboxamide

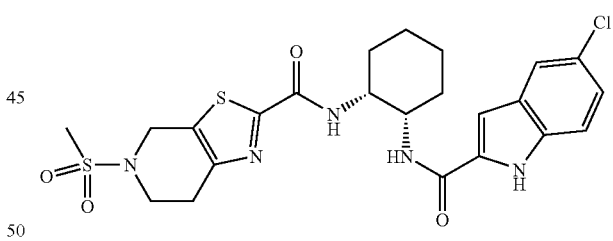

The compound (100 mg) obtained in Example 34 was dissolved in pyridine (3 mL), triethylamine (168 μl) and methanesulfonyl chloride (48 μl) were added, and the mixture was stirred overnight at room temperature. The reaction mixture was concentrated under reduced pressure, and methylene chloride and 1N hydrochloric acid were added to the residue to separate an organic layer. The resultant organic layer was dried over sodium sulfate anhydrate. The solvent was distilled away under reduced pressure, and the residue was purified by silica gel column chromatography (methylene chloride: methanol=100:1) to give the title compound (79 mg).

$^1$H-NMR (CDCl$_3$) δ: 1.50-1.82(5H,m), 1.90(2H,br.s), 2.13 (1H,br.s), 2.89(3H,s), 2.91-2.98(2H,m), 3.60-3.70(2H,m), 4.30(1H,br.s), 4.44(1H,br.s), 4.58(2H,s), 6.87(1H,s), 7.19 (1H,d,J=8.8 Hz), 7.34(1H,d,J=8.8 Hz), 7.61(3H,br.s), 9.91 (1H,br.s).

MS(FAB)m/z: 536(M+H)$^+$.

Example 48

5-Methyl-N-((1R*,2S*)-2-{[(5-methylindol-2-yl)carbonyl]-amino}cyclohexyl)-4,5,6,7-tetrahydrothiazolo[5,4-c]-pyridine-2-carboxamide hydrochloride

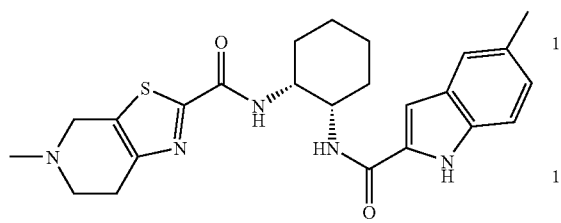

The title compound was obtained from the compound obtained in Referential Example 67 and 5-methylindole-2-carboxylic acid in a similar manner to Example 5.

$^1$H-NMR (DMSO-$d_6$) δ: 1.35-1.50(2H,m), 1.50-1.80(4H,m), 1.85-2.07(2H,m), 2.36(3H,s), 2.88(3H,s), 3.12(2H,br.s), 3.53(2H,br.s), 4.15-4.30(2H,m), 4.30-4.80(2H,br), 7.00(1H,dd,J=8.4, 1.5 Hz), 7.05(1H,d,J=1.5 Hz), 7.30(1H,d,J=8.4 Hz), 7.38(1H,s), 8.00(1H,d,J=7.3 Hz), 8.43(1H,br.s), 11.45(1H,br.s), 11.49(1H,br.s).

MS(FAB)m/z: 452(M+H)$^+$.

Example 49

Ethyl (1R*,3S*,4R*)-4-{[(5-chloroindol-2-yl)carbonyl]amino}-3-{[(5-methyl-4,5,6,7-tetrahydrothiazolo[5,4-c]-pyridin-2-yl)carbonyl]amino}cyclohexanecarboxylate

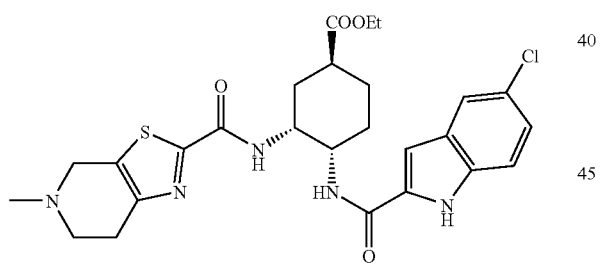

The compound (1.40 g) obtained in Referential Example 91 was suspended in ethanol (8 mL), and HCl in ethanol (10 mL) was added at room temperature, followed by stirring for 12 hours. The solvent was distilled away under reduced pressure to give ethyl (1R*,3S*,4R*)-3-amino-4-{[(5-chloroindol-2-yl)carbonyl]amino}cyclohexanecarboxylate hydrochloride (1.25 g).

The title compound was obtained from the above-described product and the compound obtained in Referential Example 10 in a similar manner to Example 2.

$^1$H-NMR (CDCl$_3$) δ: 1.29(3H,t,J=7.1 Hz), 1.52-1.80(2H,m), 2.03-2.37(4H,m), 2.53(3H,s), 2.57-2.71(1H,m), 3.73 and 3.78(each 1H, each d,J=14.4 Hz), 4.08-4.17(1H,m), 4.18(2H,q,J=7.2 Hz), 4.55-4.65(1H,m), 6.85(1H,br.s), 7.21(1H,dd,J=8.8, 2.0 Hz), 7.33(1H,d,J=8.8 Hz), 7.48(1H,d,J=7.6 Hz), 7.63(1H,d,J=2.0 Hz), 7.98(1H,d,J=7.6 Hz), 9.30(1H,s).

MS(ESI)m/z: 544(M+H)$^+$.

Example 50

Ethyl (1S,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylate

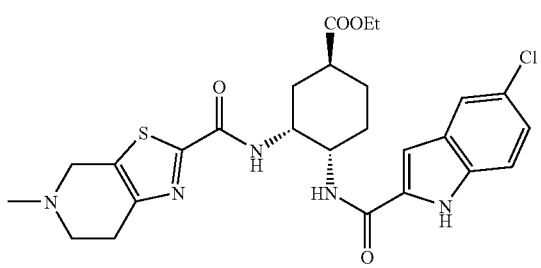

The compound (4.2 g) obtained in Referential Example 97 was suspended in ethanol (25 mL), and HCl in ethanol (55 mL) was added at room temperature, followed by stirring for 11 hours. The solvent was distilled away under reduced pressure to give colorless solids (4.15 g).

This product (4.15 g) was dissolved in N,N-dimethylformamide (40 mL), and the compound (2.86 g) obtained in Referential Example 10, 1-hydroxybenzotriazole monohydrate (1.72 g) and 1-(3-dimethylaminopropyl)-3-ethylcarbodiimide hydrochloride (2.15 g) were added to this solution at room temperature, followed by stirring for 39 hours. The reaction mixture was concentrated under reduced pressure, and water was added to the residue, followed by extraction with chloroform. The resultant organic layer was washed with saturated brine and dried over magnesium sulfate anhydrate. The solvent was distilled away under reduced pressure, and the resultant residue was purified by silica gel column chromatography (chloroform:methanol=100:1) to give the title compound (1.71 g).

[α]$_D$ –94° (C=1.0, chloroform).

Example 51

Methyl (1R*,3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}cyclohexanecarboxylate

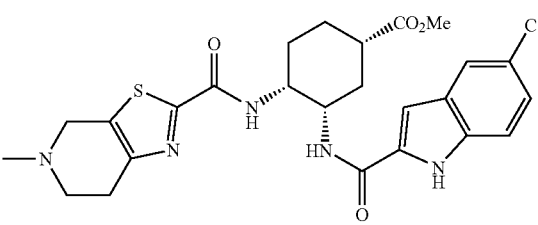

In a manner similar to that employed in Example 49, the compound obtained in Referential Example 107 was treated with HCl in ethanol and then, condensed with the compound obtained in Referential Example 10, to thereby give the title compound.

$^1$H-NMR (DMSO-$d_6$) δ: 1.55-1.80(3H,m), 1.80-2.20(3H,m), 2.60-2.75(1H,m), 2.92(3H,s), 3.15-3.30(1H,m), 3.30-3.50(4H,m), 3.57(3H,s), 3.55-3.70(1H,m), 4.20-4.30(1H,m), 4.30-4.40(1H,m), 7.02(1H,s), 7.17(1H,dd,J=8.5, 2.0 Hz), 7.41(1H,d,J=8.5 Hz), 7.71(1H,s), 8.20-8.35(1H,m), 8.35-8.45(1H,m), 11.82(1H,br).

MS(FAB)m/z: 530(M+H)$^+$.

Example 52

Ethyl (1R*,3S*,4R*)-3-{[(5-chloroindol-2-yl)carbonyl)amino}-4-{[(5-methyl-4,5,6,7-tetrahydrothiazolo[5,4-c]-pyridin-2-yl)carbonyl]amino}cyclohexanecarboxylate

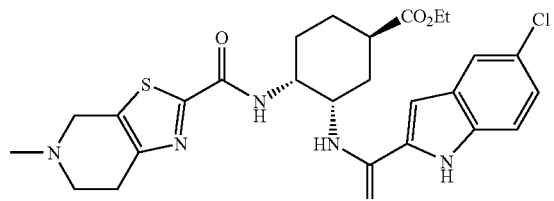

In a manner similar to that employed in Example 49, the compound obtained in Referential Example 98 was treated with HCl in ethanol and then, condensed with 5-chloroindole-2-carboxylic acid, to thereby give the title compound.

$^1$H-NMR (CDCl$_3$) δ: 1.29(3H,t,J=7.1 Hz), 1.82-2.30(6H, m), 2.49(3H,s), 2.62-2.73(1H,m), 3.74-3.85(2H,m), 3.85-3.93(2H,m), 3.71(2H,s), 4.12-4.29(3H,m), 4.49-4.59(1H,m), 6.89(1H,br.s), 7.21(1H,dd,J=8.8, 2.0 Hz), 7.32(1H,d,J=8.8 Hz), 7.33(1H,br.s), 7.41(1H,br.s), 7.62(1H,br.s), 9.37(1H,s).

MS(ESI)m/z: 544(M+H)$^+$.

Example 53

Methyl (1R*,3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}cyclohexanecarboxylate hydrochloride

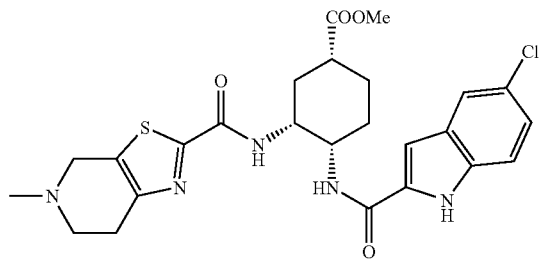

In a manner similar to that employed in Example 49, the compound obtained in Referential Example 106 was treated with 4N HCl-dioxane and then, condensed with 5-chloroindole-2-carboxylic acid, to thereby give the title compound.

$^1$H-NMR (DMSO-d$_6$) δ: 1.65-1.80(3H,m), 1.80-2.10(2H, m), 2.15-2.25(1H,m), 2.55-2.70(1H,m), 2.89(3H,s), 3.05-3.20(1H,m), 3.30-3.50(4H,m), 3.55-3.65(1H,m), 3.62(3H,s), 4.20-4.30(1H,m), 4.35-4.45(1H,m), 7.19(1H,dd,J=8.8, 1.2 Hz), 7.23(1H,s), 7.43(1H,d,J=8.8 Hz), 7.73(1H,s), 8.03(1H, d,J=6.8 Hz), 8.73(1H,d,J=8.5 Hz), 11.15-11.38(1H,br), 11.85(1H,s).

MS(FAB)m/z: 530(M+H)$^+$.

Example 54

Methyl (1R,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylate

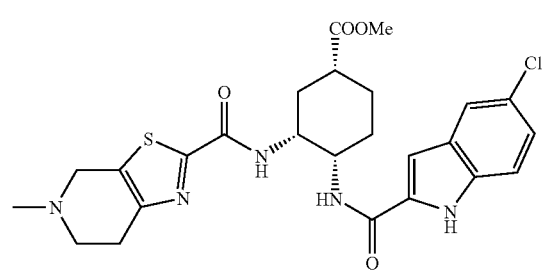

In a manner similar to that employed in Example 49, the compound obtained in Referential Example 112 was treated with 4N HCl-dioxane and then, condensed with 5-chloroindole-2-carboxylic acid, to thereby give the title compound.

$^1$H-NMR (DMSO-d$_6$) δ: 1.67-1.76(3H,m), 1.88-1.91(1H, m), 2.01(1H,br.s), 2.13-2.22(1H,m), 2.52-2.67(4H,m), 2.86 (2H,br.s), 3.04(2H,br.s), 3.33-3.41(1H,m), 3.61(3H,s), 4.22-4.36(3H,m), 7.17-7.22(2H,m), 7.42(1H,d,J=8.8 Hz), 7.72(1H,s), 8.00(1H,d,J=6.9 Hz), 8.68(1H,d,J=8.6 Hz), 11.80(1H,s).

MS(FAB)m/z: 530(M+H)$^+$.

Example 55

N-((1R*,2S*,5S*)-5-(Aminocarbonyl)-2-{(5-chloroindol-2-yl)carbonyl]amino}cyclohexyl)-5-methyl-4,5,6,7-tetrahydrothiazolo[5,4-c]pyridine-2-carboxamide

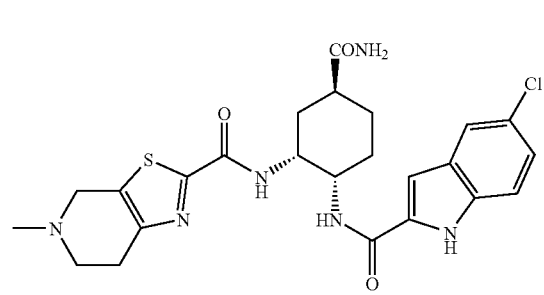

In a manner similar to that employed in Example 49, the compound obtained in Referential Example 113 was treated with 4N HCl-dioxane and then, condensed with the compound obtained in Referential Example 10, to thereby give the title compound.

$^1$H-NMR (CDCl$_3$) δ: 0.78-2.40(7H,m), 2.53(3H,s), 2.80-2.89(1H,m), 2.91-3.00(1H,m), 3.68-3.76(2H,m), 4.08-4.19 (1H,m), 4.54-4.65(1H,m), 6.80(1H,br.s), 7.21(1H,dd,J=8.4, 1.6 Hz), 7.33(1H,d,J=8.4 Hz), 7.38-7.43(1H,m), 7.49-7.55 (1H,m), 7.63(1H,br.s), 9.14(1H,br.s).

MS(ESI)m/z: 515(M+H)$^+$.

Example 56

(1R*,3S*,4R*)-4-{[(5-Chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid

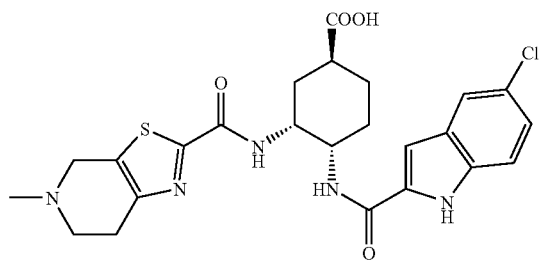

The compound (916 mg) obtained in Example 49 was suspended in a mixture of ethanol (10 mL) and tetrahydrofuran (8 mL), and 1N aqueous sodium hydroxide (3.3 mL) was added at room temperature, followed by stirring for 12 hours at the same temperature. After adding 1N HCl in ethanol (3.3 mL), the solvent was distilled away under reduced pressure, and the residue was washed with water and diethyl ether to give the title compound (712 mg).

Example 57

N-{(1R*,2S*,5S*)-2-{[(5-Chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

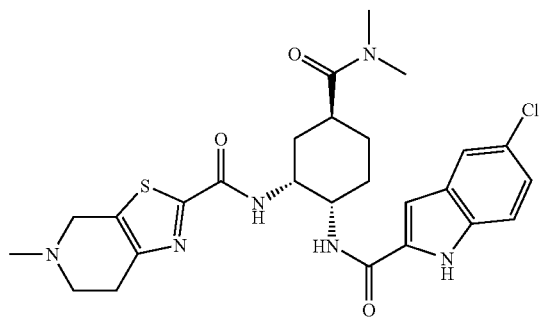

Triethylamine (0.25 mL), dimethylamine hydrochloride (133 mg), 1-hydroxybenzotriazole monohydrate (53 mg) and 1-(3-dimethylaminopropyl)-3-ethylcarbodiimide hydrochloride (75 mg) were added to a chloroform suspension (10 mL) of the compound (168 mg) obtained in Example 56, and the mixture was stirred for 72 hours. The solvent was distilled away under reduced pressure. Water was added to the residue, and the mixture was extracted with chloroform. The resultant organic layer was washed with saturated brine and dried over magnesium sulfate anhydrate. The solvent was distilled away under reduced pressure, and the resultant residue was purified by silica gel column chromatography (methylene chloride:methanol=93:7). The thus-obtained colorless solids (135 mg) were suspended in ethanol (5 mL), and then 1N HCl in ethanol (0.5 mL) was added. The mixture was stirred for 2 hours, and the solvent was distilled away to give the title compound (112 mg).

$^1$H-NMR (DMSO-$d_6$) δ: 1.42-2.07(6H,m), 2.73-3.70(10H,m), 2.88(3H,s), 2.97(3H,s), 4.03-4.20(1H,m), 4.51-4.67(1H,m), 7.04(1H,br.s), 7.16(1H,br,J=8.8 Hz), 7.41(1H,d,J=8.8 Hz), 7.68(1H,br.s), 8.32-8.47(2H,m), 10.76(1H,br.s).

MS(ESI)m/z: 543(M+H)$^+$.

Example 58

(1S,3R,4S)-4-{[(5-Chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid

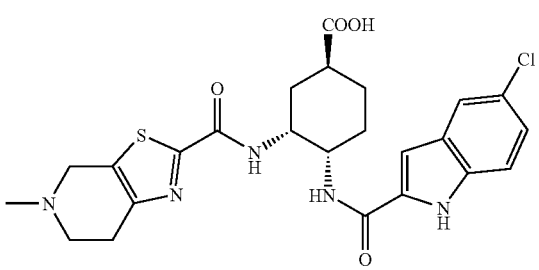

The compound (1.6 g) obtained in Example 50 was suspended in a mixture of ethanol (20 mL) and tetrahydrofuran (15 mL), and 1N aqueous sodium hydroxide (5.9 mL) was added at room temperature, followed by stirring for 12 hours at the same temperature. After adding 1N hydrochloric acid (5.9 mL), the solvent was distilled away under reduced pressure, and the residue was washed with water and diethyl ether to give the title compound (1.19 g).

m.p. 234-236° C.

[α]$_D$ –57° (C=1.0, methanol).

Example 59

N-{(1R,2S,5S)-2-{[(5-Chloroindol-2-yl)carbonyl]amino}-5-[(cyclopropylamino)carbonyl]cyclohexyl}-5-methyl-4,5,6,7-tetrahydrothiazolo[5,4-c]pyridine-2-carboxamide hydrochloride

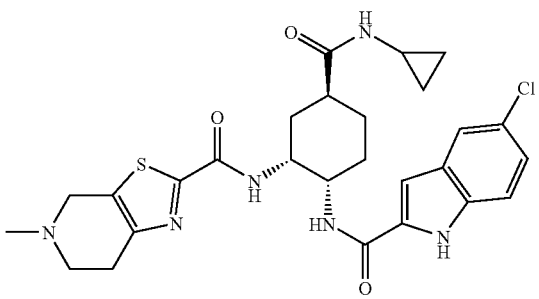

The title compound was obtained from the compound obtained in Example 58 and cyclopropylamine in a similar manner to Example 57.

$^1$H-NMR (DMSO-$d_6$) δ: 0.32-0.40(2H,m), 0.53-0.63(2H,m), 1.50-2.10(6H,m), 2.25-2.40(1H,m), 2.45-2.70(2H,m), 2.91(3H,s), 3.05-3.80(3H,m), 4.05-4.17(1H,m), 4.30-4.55(2H,m), 4.55-4.80(1H,m), 7.03(1H,d,J=1.5 Hz), 7.16(1H,dd,J=8.8, 2.0 Hz), 7.41(1H,d,J=8.8 Hz), 7.68(1H,d,J=2.0 Hz), 7.86(1H,br,J=3.4 Hz), 8.06(1H,br.s), 8.40(1H,br,J=7.6 Hz), 11.20-11.60(1H,br), 11.79(1H,s).

MS(FAB)m/z: 555(M+H)$^+$.

Example 60

N-[(1R,2S,5S)-2-{[(5-Chloroindol-2-yl)carbonyl]amino}-5-(pyrrolidin-1-ylcarbonyl)cyclohexyl]-5-methyl-4,5,6,7-tetrahydrothiazolo[5,4-c]pyridine-2-carboxamide hydrochloride

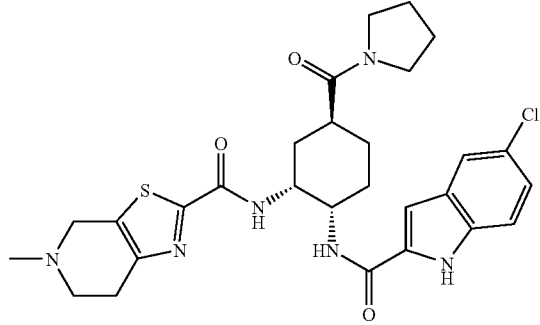

The title compound was obtained from the compound obtained in Example 58 and pyrrolidine in a similar manner to Example 57.

$^1$H-NMR (DMSO-$d_6$) δ: 1.45-2.10(10H,m), 2.75-2.90 (2H,m), 2.90(3H,s), 3.10-3.70(H,m), 4.05-4.20(1H,m), 4.25-4.80(3H,m), 7.05(1H,s), 7.17(1H,d,J=8.7 Hz), 7.41(1H,d, J=8.7 Hz), 7.69(1H,s), 8.32(1H,br,J=7.6 Hz), 8.38(1H,br, J=7.1 Hz), 11.22(1H,br.s), 11.78(1H,s).

MS(FAB)m/z: 569(M+H)$^+$.

Example 61

N-[(1R*,2S*,5S*)-2-{[(5-Chloroindol-2-yl)carbonyl]amino}-5-(4-morpholinylcarbonyl)cyclohexyl]-5-methyl-4,5,6,7-tetrahydrothiazolo[5,4-c]pyridine-2-carboxamide hydrochloride

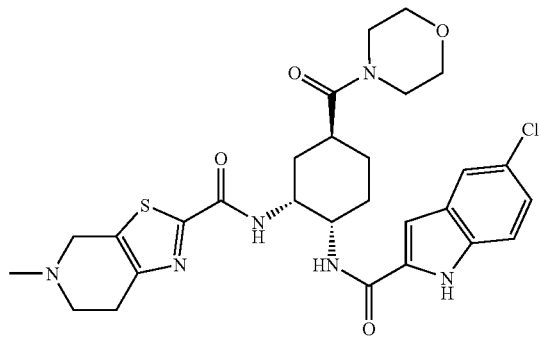

The title compound was obtained from the compound obtained in Example 56 and morpholine in a similar manner to Example 57.

$^1$H-NMR (DMSO-$d_6$) δ: 1.40-2.05(6H,m), 2.75-3.70 (18H,m), 4.02-4.17(1H,m), 4.55-4.69(1H,m), 7.05(1H,br.s), 7.17(1H,br,J=8.8 Hz), 7.41(1H,d,J=8.8 Hz), 7.67(1H,br.s), 8.35(1H,d,J=7.6 Hz), 8.40(1H,d,J=7.6 Hz), 10.79(1H,br.s).

MS(ESI)m/z: 585(M+H)$^+$.

Example 62

N-{(1R,2S,5S)-2-{[(5-Chloroindol-2-yl)carbonyl]amino}-5-[(ethylamino)carbonyl]cyclohexyl}-5-methyl-4,5,6,7-tetrahydrothiazolo[5,4-c]pyridine-2-carboxamide hydrochloride

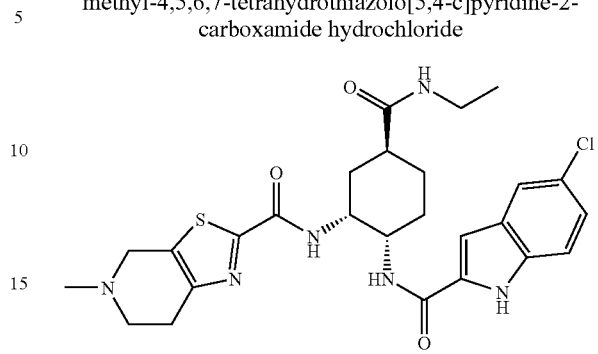

The compound (150 mg) obtained in Example 58 was dissolved in N,N-dimethylformamide (3 mL), and then N-ethylamine hydrochloride (119 mg), 1-hydroxybenzotriazole monohydrate (79 mg), 1-(3-dimethylaminopropyl)-3-ethylcarbodiimide hydrochloride (112 mg) and triethylamine (326 µl) were added, and the mixture was stirred at room temperature for 4 days. The solvent was distilled away under reduced pressure, and saturated aqueous sodium hydrogencarbonate was added to the residue, followed by extraction with methylene chloride. The resultant organic layer was dried over sodium sulfate anhydrate. The solvent was distilled away under reduced pressure, and the resultant residue was purified by silica gel column chromatography (methylene chloride:methanol=47:3). The thus-obtained solid was dissolved in methylene chloride, and then 1N HCl in ethanol (171 µl) was added. The solvent was distilled away under reduced pressure, and methanol and diethyl ether were added to the residue to collect the precipitate formed by filtration to give the title compound (74 mg).

$^1$H-NMR (DMSO-$d_6$) δ: 0.99(3H,t,J=7.2 Hz), 1.57-2.02 (6H,m), 2.33-2.38(1H,m), 2.92(3H,s), 3.01-3.08(2H,m), 3.17-3.20(2H,s), 3.45-3.70(2H,m), 4.10-4.17(1H,m), 4.40-4.69(3H,m), 7.04(1H,d,J=2.0 Hz), 7.17(1H,dd,J=8.8, 2.0 Hz), 7.41(1H,d,J=8.8 Hz), 7.69(1H,d,J=2.0 Hz), 7.78-7.81 (1H,m), 8.08-8.12(1H,m), 8.40(1H,d,J=8.1 Hz), 11.23(1H, br.s), 11.79(1H,br.s).

MS(FAB)m/z: 543(M+H)$^+$.

Example 63

N-{(1R,2S,5S)-2-{[(5-Chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

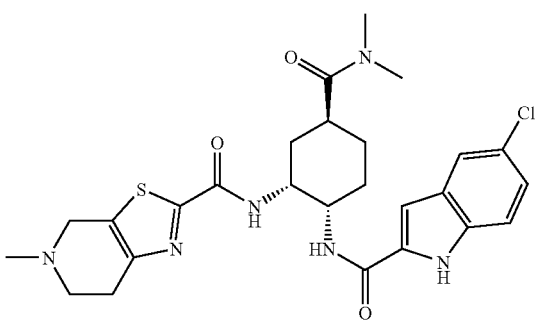

The compound (900 mg) obtained in Example 58 was dissolved in N,N-dimethylformamide (50 mL), and then dim ethylamine hydrochloride (304 mg), 1-hydroxybenzotriazole monohydrate (262 mg), 1-(3-dimethylaminopropyl)-3-ethyl-carbodiimide hydrochloride (369 mg) and diisopropylethylamine (1.83 mL) were added, and the mixture was stirred at room temperature for 12 hours. The solvent was distilled away under reduced pressure, and saturated aqueous sodium hydrogencarbonate was added to the residue, followed by extraction with methylene chloride. The resultant organic layer was dried over sodium sulfate anhydrate. The solvent was distilled away under reduced pressure, and the resultant residue was purified by silica gel column chromatography (methylene chloride:methanol=47:3). The thus-obtained white solids were dissolved in methylene chloride, and then 1N HCl in ethanol (1.49 mL) was added. The solvent was distilled away under reduced pressure, and methanol and diethyl ether were added to the residue to collect the precipitate formed by filtration to give the title compound (777 mg).

$[\alpha]_D$=−53.9° (18° C., c=0.505, methanol)

$^1$H-NMR (DMSO-$d_6$) δ: 1.45-1.60(1H,m), 1.70-1.85(3H, m), 1.90-2.05(2H,m), 2.80(3H,s), 2.91(3H,s), 2.95-3.10(1H, m), 2.97(3H,s), 3.10-3.75(4H,m), 4.05-4.15(1H,m), 4.35-4.75(3H,m), 7.05(1H,s), 7.16(1H,dd,J=8.7, 2.1 Hz), 7.41 (1H,d,J=8.6 Hz), 7.67(1H,s), 8.30-8.45(2H,m), 11.63(1H,br), 11.78(1H,s).

MS(FAB)m/z: 543(M+H)$^+$.

Example 64

N-((1R,2S,5S)-2-{[(5-Chloroindol-2-yl)carbonyl]amino}-5-{[(2-methoxyethyl)(methyl)amino]carbonyl}cyclohexyl)-5-methyl-4,5,6,7-tetrahydrothiazolo[5,4-c]pyridine-2-carboxamide hydrochloride

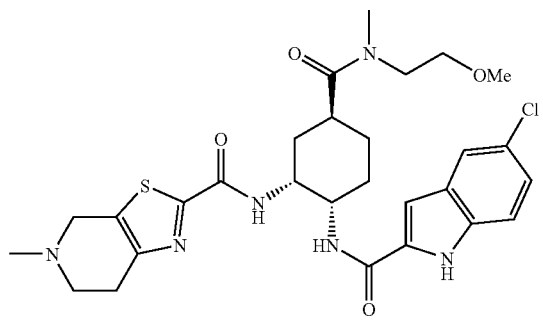

The title compound was obtained from the compound obtained in Example 58 in a similar manner to Example 57.

$^1$H-NMR (DMSO-$d_6$) δ: 1.50-1.99(6H,m), 2.80, 3.01(3H, each s), 2.91(3H,s), 3.03(1H,br.s), 3.16(2H,s), 3.23(3H,s), 3.35-3.67(6H,m), 4.09-4.16(1H,m), 4.43-4.67(3H,m), 7.04-7.06(1H,m), 7.16(1H,dd,J=8.8, 2.0 Hz), 7.42(1H,d,J=8.8 Hz), 7.69(1H,br.s), 8.29-8.41(2H,m), 11.59(1H,br.s), 11.80 (1H,br.s).

MS(FAB)m/z: 587(M+H)$^+$.

Example 65

N-((1R,2S,5S)-2-{[(5-Chloroindol-2-yl)carbonyl]amino}-5-{[(2-hydroxyethyl)(methyl)amino]carbonyl}cyclohexyl)-5-methyl-4,5,6,7-tetrahydrothiazolo[5,4-c]pyridine-2-carboxamide hydrochloride

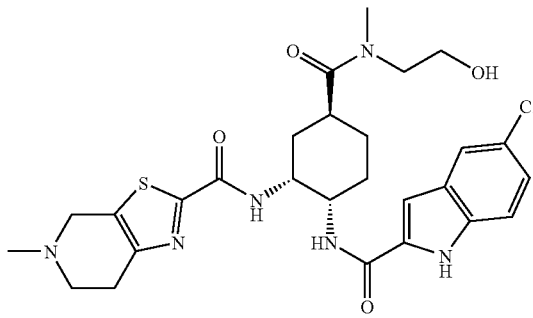

The title compound was obtained from the compound obtained in Example 58 in a similar manner to Example 57.

$^1$H-NMR (DMSO-$d_6$) δ: 1.50-1.55(1H,m), 1.74-1.84(3H, m), 1.94-1.97(2H,m), 2.67, 3.02(3H, each s), 2.91(3H,s), 3.10-3.68(9H,m), 4.11-4.13(1H,m), 4.43-4.66(4H,m), 7.05 (1H,s), 7.16(1H,dd,J=8.7, 2.0 Hz), 7.41(1H,d,J=8.7 Hz), 7.68 (1H,s), 8.34-8.40(2H,m), 11.47(1H,br.s), 11.79(1H,s).

MS(FAB)m/z: 573(M+H)$^+$.

Example 66

N-((1R,2S,5S)-5-(1-Azetidinylcarbonyl)-2-{[(5-chloroindol-2-yl)carbonyl]amino}cyclohexyl)-5-methyl-4,5,6,7-tetrahydrothiazolo[5,4-c]pyridine-2-carboxamide hydrochloride

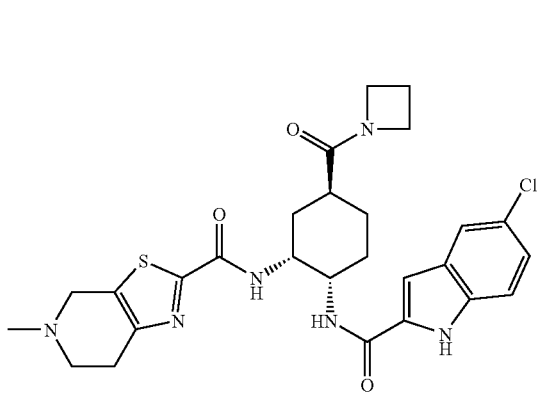

The title compound was obtained from the compound obtained in Example 58 and azetidine hydrochloride in a similar manner to Example 57.

$^1$H-NMR (DMSO-$d_6$)δ: 1.47-1.55(1H,m), 1.65-1.82(3H, m), 1.88-2.01(2H,m), 2.16(2H,quint.,J=7.6 Hz), 3.17-3.67 (5H,m), 3.82(2H,t,J=7.6 Hz), 4.02-4.14(3H,m), 4.43-4.67 (3H,m), 7.06(1H,s), 7.17(1H,dd,J=8.7, 1.7 Hz), 7.41(1H,d, J=8.7 Hz), 7.69(1H,br.s), 8.31(1H,d,J=7.6 Hz), 8.38(1H,d, J=7.6 Hz), 11.41(1H,br.s), 11.80(1H,s).

MS(FAB)m/z: 555(M+H)$^+$.

Example 67

N-((1R,2S,5S)-2-{[(5-Chloroindol-2-yl)carbonyl]amino}-5-{[(3S)-3-fluoropyrrolidinyl]carbonyl}cyclohexyl)-5-methyl-4,5,6,7-tetrahydrothiazolo[5,4-c]pyridine-2-carboxamide hydrochloride

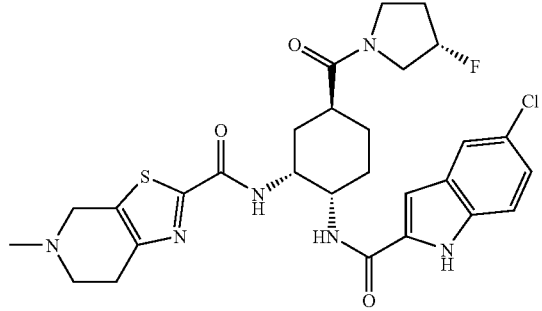

The title compound was obtained from the compound obtained in Example 58 and (S)-3-fluoropyrrolidine (Synlett., 1995, p. 55) in a similar manner to Example 57.

$^1$H-NMR (DMSO-$d_6$) δ: 1.23-3.77(22H,m), 4.11-4.16 (1H,m), 4.58-4.51(1H,m), 5.23-5.42(1H,m), 7.05(1H,s), 7.16(1H,d,J=8.3 Hz), 7.42(1H,d,J=8.3 Hz), 7.68(1H,s), 8.34-8.37(2H,m), 11.78(1H,s).

MS(FAB)m/z: 587(M+H)$^+$.

Example 68

Lithium (1R*,3R*,4S*)-3-{[(5-Chloroindol-2-yl)carbonyl]-amino}-4-{[(5-methyl-4,5,6,7-tetrahydrothiazolo[5,4-c]-pyridin-2-yl)carbonyl]amino}cyclohexanecarboxylate

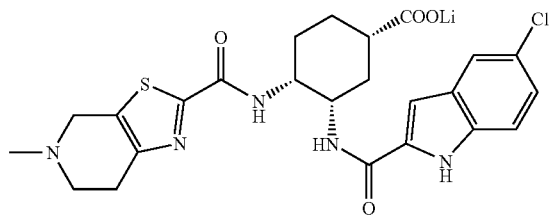

The compound (1.20 g) obtained in Example 51 was dissolved in tetrahydrofuran (32 mL), and lithium hydroxide (60.8 mg) and water (4 mL) were successively added under ice cooling, followed by stirring at room temperature for 14 hours. The solvent was distilled away under reduced pressure to give the title compound (1.12 g).

$^1$H-NMR (DMSO-$d_6$) δ: 1.55-1.70(2H,m), 1.70-2.05(4H, m), 2.10-2.20(1H,m), 2.25-2.40(4H,m), 2.50-2.80(4H,m), 3.45-3.65(3H,m), 4.10-4.30(2H,m), 7.00-7.20(2H,m), 7.50-7.65(2H,m).

Example 69

N-{(1R*,2S*,4S*)-2-{[(5-Chloroindol-2-yl)carbonyl]amino}-4-[(dimethylamino)carbonyl]cyclohexyl}-5-methyl-4,5,6,7-tetrahydrothiazolo[5,4-c]pyridine-2-carboxamide hydrochloride

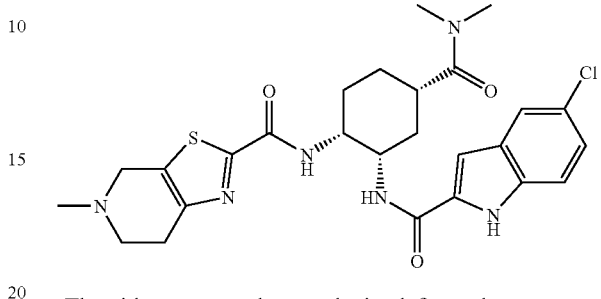

The title compound was obtained from the compound obtained in Example 68 and dimethylamine hydrochloride in a similar manner to Example 57.

$^1$H-NMR (DMSO-$d_6$) δ: 1.40-1.60(2H,m), 1.65-1.80(2H, m), 1.95-2.10(2H,m), 2.84(3H,s), 2.90-3.05(1H,m), 2.92(3H,s), 3.06(3H,s), 3.15-3.75(4H,m), 4.25-4.75(4H,m), 7.02(1H,d,J=1.5 Hz), 7.15(1H,dd,J=8.8, 2.1 Hz), 7.41(1H,d, J=8.8 Hz), 7.69(1H,d,J=2.1 Hz), 8.05(1H,d,J=7.7 Hz), 8.63 (1H,d,J=7.7 Hz), 11.20(1H,br), 11.79(1H,s).

MS(FAB)m/z: 543(M+H)$^+$.

Example 70

N-((1R,2S,5S)-2-{[(5-Chloroindol-2-yl)carbonyl]amino}-5-{[(3R)-3-hydroxypyrrolidinyl]carbonyl}cyclohexyl-5-methyl-4,5,6,7-tetrahydrothiazolo[5,4-c]pyridine-2-carboxamide hydrochloride

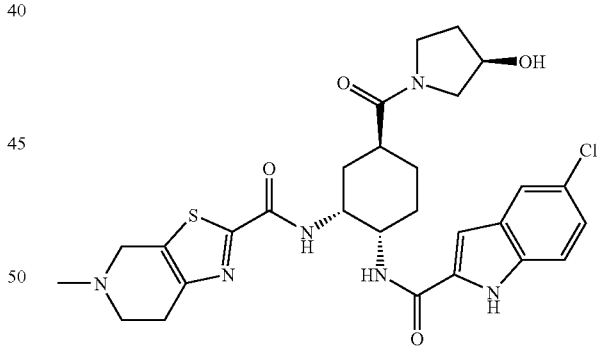

1) The compound (1.18 g) obtained in Referential Example 58 was dissolved in methanol (12 mL), 1N hydrochloric acid (240 μl) and palladium hydroxide (221 mg) were added, and hydrogen was introduced to conduct catalytic reduction under normal pressure at room temperature for 4.5 hours. The catalyst was removed by filtration, and the filtrate was concentrated to solid under reduced pressure to give crude (3R)-3-{[tert-butyl(diphenyl)silyl]oxy}pyrrolidine hydrochloride (984 mg). The thus-obtained product (249 mg), the product (295 mg) obtained in Example 58, 1-(3-dimethylaminopropyl)-3-ethylcarbodiimide hydrochloride (126 mg) and 1-hydroxybenzotriazole monohydrate (87 mg) were dissolved in N,N-dimethylformamide (10 mL). Diisopropylethylamine (450 μl) was added dropwise to the solution under ice cooling, and the mixture was stirred at room temperature for 12 hours. The solvent was distilled away under reduced pressure, methylene chloride and saturated aqueous sodium hydrogencarbonate were added to the residue for partitioning the mixture. The resultant organic layer was dried over sodium sulfate anhydrate, and the solvent was distilled away under reduced pressure. The residue was subjected to silica gel column chromatography (methanol:methylene chloride=3:97) to give N-((1R,2S,5S)-5-[((3R)-3-{[tert-butyl(diphenyl)silyl]oxy}pyrrolidinyl)carbonyl]-2-{[(5-chloroindol-2-yl)carbonyl]amino}cyclohexyl)-5-methyl-4,5,6,7-tetrahydrothiazolo[5,4-c]pyridine-2-carboxamide (248 mg).

$^1$H-NMR (CDCl$_3$) δ: 1.06(9H,s), 1.50-1.60(1H,m), 1.75-2.10(5H,m), 2.20-2.50(2H,m), 2.54(3H,d,J=2.8 Hz), 2.60-3.00(5H,m), 3.30-3.80(6H,m), 4.10-4.20(1H,m), 4.40-4.70(2H,m), 6.85(1H,s), 7.15-7.25(1H,m), 7.30-7.50(8H,m), 7.60-7.70(5H,m), 7.90-8.00(1H,m), 9.38(1H,s).

MS(FAB)m/z: 823(M+H)$^+$.

2) The above product (240 mg) was dissolved in pyridine (10 mL), and hydrogen fluoride-pyridine (3.0 mL) was added dropwise under ice cooling, followed by stirring at 0° C. for 4.5 hours. Ethyl acetate (80 mL) was added to the reaction mixture under ice cooling for dilution. The diluted reaction mixture was poured into ice. After sodium hydrogencarbonate was added to this solution to make the mixture alkaline, liquid partition was conducted. The resultant organic layer was dried over sodium sulfate anhydrate. The solvent was distilled away under reduced pressure, and the residue was subjected to silica gel column chromatography (methanol:methylene chloride=1:19→1:9). The resultant crude purified product was dissolved in methylene chloride and methanol, and then 1N HCl in ethanol (225 μl) was added to dry it once. Methanol and diethyl ether were added to the residue for solidification to give the title compound (114 mg).

$^1$H-NMR (DMSO-d$_6$) δ: 1.50-1.60(1H,m), 1.70-2.10(6H,m), 2.75-2.85(1H,m), 2.92(3H,s), 3.10-3.80(8H,m), 4.10-5.10(6H,m), 7.05(1H,d,J=1.7 Hz), 7.16(1H,dd,J=8.8, 1.7 Hz), 7.42(1H,d,J=8.8 Hz), 7.68(1H,s), 8.30-8.45(2H,m), 11.10-11.40(1H,m), 11.78(1H,s).

MS(FAB)m/z: 585(M+H)$^+$.

Example 71

N-((1R*,2S*)-2-{[(5-Chloroindol-2-yl)carbonyl]amino}-5,5-dimethoxycyclohexyl)-5-methyl-4,5,6,7-tetrahydrothiazolo-[5,4-c]pyridine-2-carboxamide or N-((1R*,2S*)-2-{[(5-chloroindol-2-yl)carbonyl]amino}-4,4-dimethoxycyclohexyl)-5-methyl-4,5,6,7-tetrahydrothiazolo[5,4-c]pyridine-2-carboxamide The title compound was obtained from the compound obtained in Referential Example 118 and the compound obtained in Referential Example 10 in a similar manner to Example 2.

$^1$H-NMR (CDCl$_3$) δ: 2.11-2.15(1H,m), 2.21-2.25(1H,m), 2.41-2.43(1H,m), 2.46(3H,s), 2.70-2.75(1H,m), 2.81-2.88(1H,m), 3.21(3H,s), 3.24(3H,s), 3.49(1H,s), 3.58(1H,d,J=15.6 Hz), 3.71(1H,d,J=15.6 Hz), 3.87-3.93(1H,m), 4.26-4.29(1H,m), 6.85(1H,d,J=2.0 Hz), 7.19(1H,dd,J=8.5, 2.0 Hz), 7.30(1H,d,J=8.5 Hz), 7.62(1H,s), 9.21(1H,s).

Example 72

N-((1R*,2S*)-2-{[(5-Chloroindol-2-yl)carbonyl]amino}-5-oxocyclohexyl)-5-methyl-4,5,6,7-tetrahydrothiazolo[5,4-c]-pyridine-2-carboxamide or N-((1R*,2S*)-2-{[(5-chloroindol-2-yl)carbonyl]amino}-4-oxocyclohexyl)-5-methyl-4,5,6,7-tetrahydrothiazolo[5,4-c]pyridine-2-carboxamide The compound (100 mg) obtained in Example 71 was dissolved in chloroform (2 mL), and trifluoroacetic acid (0.5 mL) and water (0.5 mL) were added, followed by stirring at room temperature for 3.5 hours. Saturated aqueous sodium hydrogencarbonate was added to the reaction mixture, and the mixture was extracted with ethyl acetate. The resultant organic layer was washed with saturated brine and dried over sodium sulfate anhydrate. The solvent was distilled away under reduced pressure, and the resultant residue was purified by silica gel thin layer chromatography (methylene chloride:methanol=19:1). The thus-obtained white solids were dissolved in methanol (4 mL), and then 1N HCl in ethanol (0.38 mL) was added. The solvent was distilled away under reduced pressure to give the title compound (35 mg).

$^1$H-NMR (DMSO-d$_6$) δ: 1.83-1.90(1H,m), 2.08-2.10(1H,m), 2.28-2.32(1H,m), 2.50-2.59(1H,m), 2.87(3H,s), 2.96(1H,t,J=13.0 Hz), 3.06-3.10(2H,m), 3.33-3.36(3H,m), 4.02-4.04(2H,m), 4.55-4.57(2H,m), 7.03(1H,s), 7.15(1H,d,J=8.8 Hz), 7.38(1H,d,J=8.8 Hz), 7.69(1H,s), 8.43(1H,d,J=8.8 Hz), 8.91(1H,d,J=8.8 Hz), 11.75(1H,s).

Example 73

N-[(1R*,2S*)-2-{[(5-Chloroindol-2-yl)carbonyl]amino}-5-(hydroxyimino)cyclohexyl]-5-methyl-4,5,6,7-tetrahydrothiazolo[5,4-c]pyridine-2-carboxamide or N-[(1R*,2S*)-2-[(5-chloroindol-2-yl)carbonyl]amino}-4-(hydroxyimino)cyclohexyl]-5-methyl-4,5,6,7-tetrahydrothiazolo[5,4-c]pyridine-2-carboxamide The compound (133 mg) obtained in Example 72 was dissolved in a mixture of pyridine (8 mL) and methanol (8 mL), and hydroxylamine hydrochloride (30 mg) was added, followed by stirring at room temperature for 3 days. The reaction mixture was concentrated, and water was added to the residue, followed by extraction with ethyl acetate. The resultant organic layer was washed with saturated brine and dried over sodium sulfate anhydrate. The solvent was distilled away under reduced pressure, and the resultant residue was purified by silica gel column chromatography (methylene chloride:methanol=97:3→17:3) to give the title compound (131 mg).

$^1$H-NMR (CDCl$_3$) δ: 1.43-1.86(3H,m), 1.98-2.03(1H,m), 2.26-2.30(1H,m), 2.45(3H,s), 2.47-2.51(1H,m), 2.67-2.71(1H,m), 2.78-2.86(3H,m), 3.86-3.43(2H,m), 4.16-4.24(2H,m), 6.85(1H,s), 7.13-7.16(1H,m), 7.20-7.24(1H,m), 7.46, 7.50(total 1H,s), 7.56-7.64(2H,m), 9.59, 9.62(total 1H,s).

Example 74

N-((7R*,8S*)-8-{[(5-Chloroindol-2-yl)carbonyl]amino}-1,4-dioxaspiro[4.5]dec-7-yl)-5-methyl-4,5,6,7-tetrahydrothiazolo[5,4-c]pyridine-2-carboxamide or N-((7R*,8S*)-7-{[(5-chloroindol-2-yl)carbonyl]amino}-1,4-dioxaspiro-[4.5]dec-8-yl)-5-methyl-4,5,6,7-tetrahydrothiazolo[5,4-c]pyridine-2-carboxamide The title compound was obtained from the compound obtained in Referential Example 120 and the compound obtained in Referential Example 10 in a similar manner to Example 2.

$^1$H-NMR (CDCl$_3$) δ: 1.69-1.87(6H,m), 2.14-2.17(1H,m), 2.30-2.32(1H,m), 2.47(3H,s), 2.70-2.75(1H,m), 2.81-2.89(2H,m), 3.58(1H,d,J=15.4 Hz), 3.72(1H,d,J=15.4 Hz), 3.89-3.91(1H,m), 3.99(4H,s), 4.37-4.40(1H,m), 6.86(1H,d,J=2.0 Hz), 7.19(1H,dd,J=8.8, 2.0 Hz), 7.30(1H,d,J=8.8 Hz), 7.38(1H,d,J=7.3 Hz), 7.62(1H,d,J=2.0 Hz), 9.15(1H,s).

Example 75

N-[(1R*,2S*)-2-{[(5-Chloroindol-2-yl)carbonyl]amino}-5-(methoxyimino)cyclohexyl]-5-methyl-4,5,6,7-tetrahydrothiazolo[5,4-c]pyridine-2-carboxamide or N-[(1R*,2S*)-2-{[(5-chloroindol-2-yl)carbonyl]amino}-4-(methoxyimino)cyclohexyl]-5-methyl-4,5,6,7-tetrahydrothiazolo[5,4-c]-pyridine-2-carboxamide 1) The compound (2.21 g) obtained in Referential Example 124 was dissolved in methylene chloride (30 mL), and trifluoroacetic acid (6 mL) was added, followed by stirring at room temperature for 1.5 hours. The reaction mixture was concentrated, dried with a vacuum pump and then dissolved in N,N-dimethylformamide (20 mL), and then 5-chloroindole-2-carboxylic acid (500 mg), 1-(3-dimethylaminopropyl)-3-ethylcarbodiimide hydrochloride (593 mg), 1-hydroxybenzotriazole monohydrate (473 mg), and N-methylmorpholine (2.8 mL) were added. The mixture was stirred at room temperature for 10 hours. Additionally, 5-chloroindole-2-carboxylic acid (242 mg), 1-(3-dimethylaminopropyl)-3-ethylcarbodiimide hydrochloride (237 mg), and 1-hydroxybenzotriazole monohydrate (189 mg) were added, followed by stirring for 4 hours. Saturated aqueous sodium hydrogencarbonate was added to the reaction mixture, and the mixture was extracted with ethyl acetate and with a mixture of ethyl acetate and tetrahydrofuran. The resultant organic layers were washed with saturated brine and dried over sodium sulfate anhydrate. The solvent was distilled away under reduced pressure, and the resultant residue was purified by silica gel column chromatography (methylene chloride:methanol=97:3→4:1) to give N-[(1R*,2S*)-2-amino-5-(methoxyimino)cyclohexyl]-5-chloroindole-2-carboxamide (368 mg) and N-[(1R*,2S*)-2-amino-4-(methoxyimino)cyclohexyl]-5-chloroindole-2-carboxamide (300 mg).

2) The title compound (mixture of syn and anti isomers in terms of the methoxyimino group) was obtained from one of the above-obtained N-[(1R*,2S*)-2-amino-5-(methoxyimino)cyclohexyl]-5-chloroindole-2-carboxamide and N-[(1R*,2S*)-2-amino-4-(methoxyimino)cyclohexyl]-5-chloroindole-2-carboxamide and the compound obtained in Referential Example 10 in a similar manner to Example 2.

$^1$H-NMR (CDCl$_3$) δ: 1.84-2.00(3H,m), 2.26-2.56(3H,m), 2.46(3H,s), 2.80-2.83(4H,m), 3.57(1H,q,J=15.4 Hz), 3.70 (1H,q,J=15.4 Hz), 3.84, 3.85(total 3H,s), 4.08-4.14(1H,m), 4.26-4.30(1H,m), 6.84(1H,s), 7.17(1H,d,J=8.8 Hz), 7.27(1H,d,J=8.8 Hz), 7.46-7.48(2H,m), 7.56(1H,m), 9.42, 9.55(total 1H,s).

Example 76

N-((1R*,2S*)-2-{[(5-Chloroindol-2-yl)carbonyl]amino}-5-hydroxycyclohexyl)-5-methyl-4,5,6,7-tetrahydrothiazolo-[5,4-c]pyridine-2-carboxamide (Stereoisomer A) or N-((1R*,2S*)-2-{[(5-chloroindol-2-yl)carbonyl]amino}-4-hydroxycyclohexyl)-5-methyl-4,5,6,7-tetrahydrothiazolo[5,4-c]pyridine-2-carboxamide (Stereoisomer A)

1) In a manner similar to that employed in Example 49, the compound obtained in Referential Example 113 was treated with 4N HCl-dioxane and then, condensed with the compound obtained in Referential Example 10, to thereby give the title compound.

2) In a manner similar to that employed in Example 2, N-((1R*,2S*)-5-{[tert-butyl(diphenyl)silyl]oxy}-2-{[(5-chloroindol-2-yl)carbonyl]amino}cyclohexyl)-5-methyl-4,5,6,7-tetrahydrothiazolo[5,4-c]pyridine-2-carboxamide (Stereoisomer A) or N-((1R*,2S*)-4-{[tert-butyl(diphenyl)silyl]oxy}-2-{[(5-chloroindol-2-yl)carbonyl]amino}cyclohexyl)-5-methyl-4,5,6,7-tetrahydrothiazolo[5,4-c]pyridine-2-carboxamide (Stereoisomer A) was obtained from the above product and the product obtained in Referential Example 10.

$^1$H-NMR (CDCl$_3$) δ: 1.06(9H,s), 1.55-1.61(1H,m), 1.85-1.90(1H,m), 2.18-2.25(1H,m), 2.46(3H,s), 2.51(2H,d,J=7.6 Hz), 2.68-2.76(1H,m), 3.56(1H,s), 3.57(1H,d,J=15.3 Hz), 3.72(1H,d,J=15.3 Hz), 3.71-3.81(1H,m), 3.88-3.95(1H,m), 6.78(1H,s), 7.17(1H,dd,J=2.0, 8.8 Hz), 7.37-7.44(7H,m), 7.59(1H,s), 7.65-7.68(6H,m), 9.30(1H,s).

3) In a manner similar to that employed in the steps 3) of Example 28, the title compound was obtained from the above reaction product.

$^1$H-NMR (DMSO-d$_6$) δ: 1.25-1.30(2H,m), 1.45-1.64(2H, m), 1.86(1H,d,J=9.0 Hz), 1.98-2.03(1H,m), 2.33(3H,s), 2.66-2.73(2H,m), 2.75-2.79(2H,m), 3.54(1H,d,J=15.6 Hz), 3.62 (1H,d,J=15.6 Hz), 3.96-4.02(2H,m), 4.78(1H,d,J=4.2 Hz), 7.00(1H,s), 7.14(1H,dd,J=2.0, 8.8 Hz), 7.38(1H,d,J=8.8 Hz), 7.66(1H,s), 8.20(1H,d,J=7.8 Hz), 8.54(1H,d,J=7.8 Hz), 11.69(1H,s).

Example 77

N-((1R*,2S*)-2-{[(5-Chloroindol-2-yl)carbonyl]amino}-5-hydroxy-5-methylcyclohexyl)-5-methyl-4,5,6,7-tetrahydrothiazolo[5,4-c]pyridine-2-carboxamide (Stereoisomer A1) or N-((1R*,2S*)-2-{[(5-chloroindol-2-yl)carbonyl]amino}-4-hydroxy-4-methylcyclohexyl)-5-methyl-4,5,6,7-tetrahydrothiazolo[5,4-c]pyridine-2-carboxamide (Stereoisomer A2)

In a manner similar to that employed in Example 2, the compound obtained in Referential Example 10 was reacted with the compound obtained in Referential Example 128, to thereby give the title compound.

Stereoisomer A1:

$^1$H-NMR (DMSO-d$_6$) δ: 1.24(3H,s), 1.33-1.82(4H,m), 2.34(3H,s), 2.67-3.64(8H,m), 4.02-4.10(2H,m), 4.67(1H,br.s), 7.02(1H,s), 7.13(1H,d,J=8.6 Hz), 7.38(1H,d, J=8.6 Hz), 7.66(1H,d,J=2.0 Hz), 8.21-8.26(1H,m), 8.59(1H, d,J=8.1 Hz), 11.73(1H,br.s)

MS(FAB)m/z: 502(M+H)$^+$.

Stereoisomer A2:

$^1$H-NMR (DMSO-d$_6$) δ: 1.25(3H,s), 1.33-1.79(4H,m), 2.33(3H,s), 2.65-3.63(8H,m), 3.88-3.94(1H,m), 4.20-4.25 (1H,m), 4.59(1H,br), 7.01(1H,s), 7.13(1H,d,J=7.8 Hz), 7.38 (1H,d,J=8.6 Hz), 7.67(1H,s), 8.29(1H,br), 8.43(1H,d,J=9.3 Hz), 11.67(1H,br)

MS(FAB)m/z: 502(M+H)$^+$.

Example 78

N-[(1R*,2R*,5S*)-2-{[(5-Chloroindol-2-yl)carbonyl]amino}-5-(hydroxymethyl)cyclohexyl]-5-methyl-4,5,6,7-tetrahydrothiazolo[5,4-c]pyridine-2-carboxamide

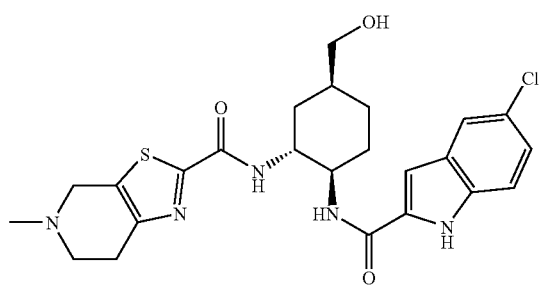

In a manner similar to that employed in Example 49, the compound obtained in Referential Example 129 was treated with HCl in ethanol and then, condensed with the compound obtained in Referential Example 10, to thereby give the title compound.

$^1$H-NMR (DMSO-$d_6$) δ: 1.42-1.90(5H,m), 2.07-2.26(3H,m), 2.46(3H,s), 2.67-2.95(4H,m), 3.55-3.80(4H,m), 3.80-3.95(1H,m), 4.13-4.25(1H,m), 6.84(1H,br.s), 7.17(1H,dd, J=8.8, 2.0 Hz), 7.23-7.35(2H,m), 7.43(1H,d,J=7.2 Hz), 7.58 (1H,br.s), 9.29(1H,s).

MS(ESI)m/z: 502(M+H)$^+$.

Example 79

N-[(1R*,2S*,5S*)-2-{[(5-Chloroindol-2-yl)carbonyl]amino}-5-(methoxymethyl)cyclohexyl]-5-methyl-4,5,6,7-tetrahydrothiazolo[5,4-c]pyridine-2-carboxamide

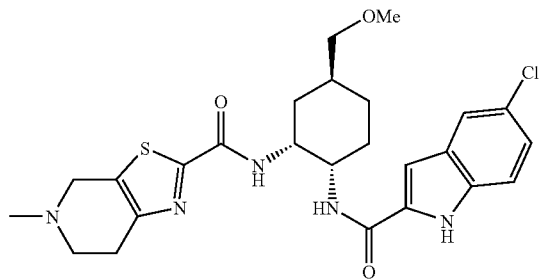

In a manner similar to that employed in Example 49, the compound obtained in Referential Example 135 was treated with HCl in ethanol and then, condensed with the compound obtained in Referential Example 10, to thereby give the title compound.

$^1$H-NMR (CDCl$_3$) δ: 1.20-1.38(1H,m), 1.50-1.67(2H,m), 1.88-2.03(2H,m), 2.03-2.14(1H,m), 2.21-2.32(1H,m), 2.53 (3H,s), 2.75-2.95(2H,m), 3.20-3.35(2H,m), 3.37(3H,s), 3.73 (1H, d,J=16.0 Hz), 3.76(1H,d,J=16.0 Hz), 4.04-4.13(1H,m), 4.53-4.62(1H,m), 6.85(1H,d,J=2.0 Hz), 7.19(1H,dd,J=8.8, 2.0 Hz), 7.33(1H,d,J=8.8 Hz), 7.54(1H,d,J=7.2 Hz), 7.63(1H, d,J=2.0 Hz), 8.07(1H,d,J=5.6 Hz), 9.49(1H,br.s).

Example 80

N-((1R*,2S*,5S*)-2-{[(5-Chloroindol-2-yl)carbonyl]amino}-5-{[(methylsulfonyl)amino]methyl}cyclohexyl)-5-methyl-4,5,6,7-tetrahydrothiazolo[5,4-c]pyridine-2-carboxamide

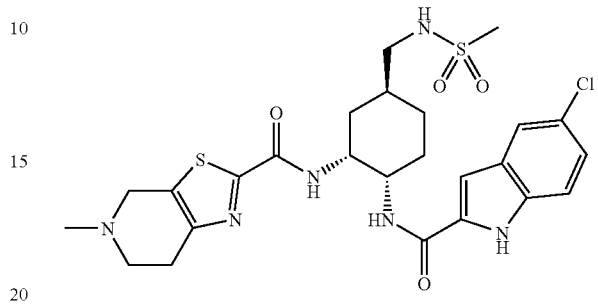

1) The compound (437 mg) obtained in Referential Example 137 was dissolved in ethanol (5 mL), and 4N Hcl-dioxane (5 mL) was added at room temperature, followed by stirring for 13 hours. The solvent was distilled away, and the residue was dissolved in N,N-dimethylformamide (10 mL), and then triethylamine (0.7 mL), the compound (300 mg) obtained in Referential Example 10, 1-hydroxybenzotriazole monohydrate (162 mg) and 1-(3-dimethylaminopropyl)-3-ethylcarbodiimide hydrochloride (230 mg) were added. The mixture was stirred for 13 hours. The solvent was removed under reduced pressure, and water was added to the reaction mixture, followed by extraction with chloroform. The resultant organic layer was washed with saturated aqueous sodium hydrogencarbonate and saturated brine and dried over magnesium sulfate anhydrate. The solvent was distilled away under reduced pressure, and the resultant residue was purified by silica gel column chromatography (methylene chloride:methanol=97:3) to give N-((1R*,2S*,5S*)-5-(azidomethyl)-2-{[(5-chloroindol-2-yl)carbonyl]amino}cyclohexyl)-5-methyl-4,5,6,7-tetrahydrothiazolo[5,4-c]pyridine-2-carboxamide (330 mg).

$^1$H-NMR (DMSO-$d_6$) δ: 1.15-2.08(7H,m), 2.33(3H,s), 2.34-2.95(6H,m), 3.64(2H,s), 4.05-4.17(1H,m), 4.36-4.47 (1H,m), 7.02(1H,s), 7.15(1H,dd,J=8.8, 2.0 Hz), 7.40(1H,d, J=8.8 Hz), 7.67(1H,d,J=2.0 Hz), 8.02(1H,d,J=7.6 Hz), 8.44 (1H,d,J=7.6 Hz), 11.8(1H,s).

2) The compound (300 mg) obtained by the above reaction was dissolved in ethanol (8 mL), and a catalytic amount of 10% palladium on carbon was added, followed by stirring at room temperature for 168 hours in a hydrogen atmosphere. Insoluble matter was filtered, and the solvent was distilled away. The thus-obtained crude N-((1R*,2S*,5S*)-5-(aminomethyl)-2-{[(5-chloroindol-2-yl)carbonyl]amino}cyclohexyl)-5-methyl-4,5,6,7-tetrahydrothiazolo[5,4-c]pyridine-2-carboxamide (150 mg) was dissolved in chloroform (6 mL), and triethylamine (0.2 mL) and methanesulfonyl chloride (0.035 mL) were added under ice cooling, followed by stirring for 13 hours. The solvent was distilled away under reduced pressure, and water was added to the residue, followed by extraction with chloroform. The resultant organic layer was washed with saturated aqueous sodium hydrogencarbonate and saturated brine and dried over magnesium sulfate anhydrate. The solvent was distilled away under reduced pressure, and the resultant residue was purified by silica gel column chromatography (methylene chloride:methanol=24:1) to give the title compound (56 mg).

$^1$H-NMR (CDCl$_3$) δ: 1.18-1.34(2H,m), 1.50-1.75(4H,m), 1.90-2.30(4H,m), 2.53(3H,s), 2.78-2.90(2H,m), 2.90-3.05

(6H,m), 3.20-3.30(1H,m), 3.68-3.81(2H,m), 3.98-4.08(1H, m), 4.54-4.62(1H,m), 6.10-6.19(1H,m), 6.86(1H,s), 7.19 (1H,dd,J=8.8, 2.0 Hz), 7.35(1H,d,J=8.8 Hz), 7.52(1H,d, J=7.6 Hz), 7.62(1H,d,J=2.0 Hz), 8.21(1H,d,J=5.6 Hz), 9.89 (1H,s).

MS(ESI)m/z: 579(M+H)+.

Example 81

N-{(1R*,2S*,5S*)-2-{[(5-Chloroindol-2-yl)carbonyl]amino}-5-[(dimethylamino)methyl]cyclohexyl}-5-methyl-4,5,6,7-tetrahydrothiazolo[5,4-c]pyridine-2-carboxamide trifluoroacetate

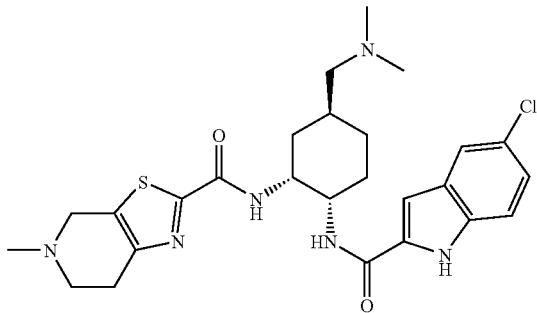

The title compound was obtained from the amine obtained in the step 2) of Example 80 in a similar manner to Example 24.

$^1$H-NMR (DMSO-d$_6$) δ: 1.15-2.22(7H,m), 2.40-2.65(2H, m), 2.68-2.85(6H,m), 2.92-3.08(5H,m), 3.10-3.18(2H,m), 4.08-4.20(1H,m), 4.35-4.51(2H,m), 7.04(1H,s), 7.14-7.20 (1H,m), 7.41(1H,d,J=8.8 Hz), 7.67(1H,s), 8.25-8.42(2H,m), 9.11(1H,br.s), 9.89(1H,s).

MS(ESI)m/z: 529(M+H)+.

Example 82 tert-Butyl (3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}cyclohexylcarbamate (Isomer B) and tert-butyl (3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}cyclohexylcarbamate (Isomer B)

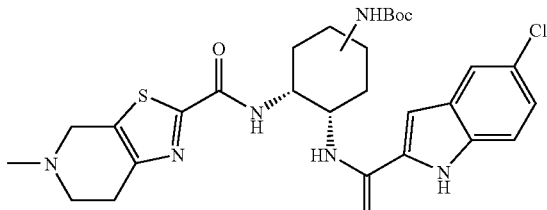

The compound (Stereoisomer B) (1.79 g) obtained in Referential Example 140 was dissolved in tetrahydrofuran (36 mL), and 10% palladium on carbon (0.40 g) was added, followed by stirring at room temperature for 20 hours in a hydrogen atmosphere. After the catalyst was removed by filtration, the filtrate was concentrated under reduced pressure, and the residue was dissolved in N,N-dimethylformamide (36 mL), and then p-nitrophenyl 5-chloroindole-2-carboxylate (2.02 g) was added, followed by stirring for 16 hours. The reaction mixture was concentrated under reduced pressure, and ethyl acetate and water were added to the residue to collect insoluble matter by filtration. The product was washed with ethyl acetate to give crude tert-butyl (3R*,4S*)-3-amino-4-{[(5-chloroindol-2-yl)carbonyl]amino}cyclohexylcarbamate (or (3R*,4S*)-4-amino-3-{[(5-chloroindol-2-yl)carbonyl]amino}cyclohexylcarbamate) (Isomer B1) (1.49 g). The organic layer of the filtrate was washed with water and dried over sodium sulfate anhydrate. The solvent was distilled away under reduced pressure, and the residue was purified by silica gel column chromatography (methylene chloride:methanol=30:1->10:1) to give tert-butyl (3R*,4S*)-4-amino-3-{[(5-chloroindol-2-yl)carbonyl]amino}cyclohexylcarbamate (or tert-butyl (3R*,4S*)-3-amino-4-{[(5-chloroindol-2-yl)carbonyl]amino}cyclohexylcarbamate) (Isomer B2) (0.37 g). One of the title compounds was obtained from the Isomer B1 and the compound obtained in Referential Example 10 in a similar manner to Example 2.

$^1$H-NMR (DMSO-d$_6$) δ: 1.25-1.50(1H,m), 1.37(9H,s), 1.50-1.65(1H,m), 1.75-2.20(4H,m), 2.37(3H,s), 2.70-3.00 (4H,m), 3.60-3.80(3H,m), 4.13(1H,br.a), 4.43(1H,br.s), 6.92 (1H,d,J=7.1 Hz), 7.05(1H,s), 7.17(1H,dd,J=8.8, 2.2 Hz), 7.41 (1H,d,J=8.8 Hz), 7.69(1H,s), 8.15(1H,d,J=7.8 Hz), 8.37(1H, d,J=7.1 Hz), 11.78(1H,s).

MS(FAB)m/z: 587(M+H)+.

The other title compound was obtained from the Isomer B2 in the same manner.

$^1$H-NMR (DMSO-d$_6$) δ: 1.15-1.30(1H,m), 1.35(9H,s), 1.45-1.60(1H,m), 1.65-1.75(1H,m), 1.85-1.95(1H,m), 2.05-2.20(2H,m), 2.34(3H,s), 2.65-2.85(4H,m), 3.55-3.70(3H,m), 4.05-4.14(1H,m), 4.40(1H,br.s), 6.80(1H,d,J=7.3 Hz), 7.15-7.25(2H,m), 7.43(1H,d,J=8.8 Hz), 7.73(1H,d,J=2.0 Hz), 8.05 (1H,d,J=6.6 Hz), 8.51(1H,d,J=8.8 Hz), 11.82(1H,s).

MS(FAB)m/z: 587(M+H)+.

Example 83

N-((1R*,2S*)-5-Amino-2-{[(5-chloroindol-2-yl)carbonyl]-amino}cyclohexyl)-5-methyl-4,5,6,7-tetrahydrothiazolo-[5,4-c]pyridine-2-carboxamide (or N-((1R*,2S*)-4-amino-2-{[(5-chloroindol-2-yl)carbonyl)amino}cyclohexyl)-5-methyl-4,5,6,7-tetrahydrothiazolo[5,4-c]pyridine-2-carboxamide) hydrochloride (Stereoisomer B)

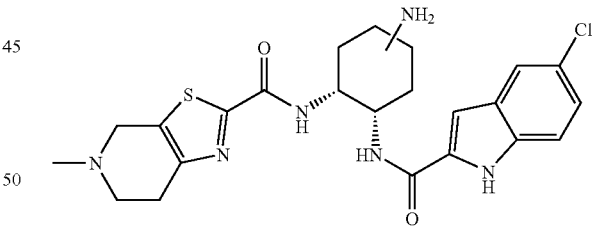

The compound (Stereoisomer B) (1.11 g) synthesized from Isomer B1 in Example 82 was suspended in methylene chloride (20 mL), and HCl in ethanol (20 mL) was added, followed by stirring at room temperature for 2 hours. The solvent was distilled away under reduced pressure, and the residue was purified by gel filtration (Sephadex LH-20, methanol) to give the title compound (1.05 g).

$^1$H-NMR (DMSO-d$_6$) δ: 1.55-1.65(1H,m), 1.75-1.90(2H, m), 1.95-2.20(2H,m), 2.20-2.40(1H,m), 2.90(3H,s), 3.10-3.20(1H,m), 3.20-3.50(3H,m), 3.65-3.75(1H,m), 4.10-4.20 (1H,m), 4.35-4.50(1H,m), 4.55-4.65(1H,m), 4.65-4.75(1H, m), 7.07(1H,s), 7.17(1H,dd,J=8.8, 2.0 Hz), 7.42(1H,d,J=8.8 Hz), 7.69(1H,s), 8.05-8.30(3H,br), 8.40-8.50(2H,m), 11.70-11.90(2H,m).

MS(FAB)m/z: 487(M+H)+.

Example 84

N-{(1R*,2S*)-2-{[(5-Chloroindol-2-yl)carbonyl]amino}-5-[(methylsulfonyl)amino]cyclohexyl}-5-methyl-4,5,6,7-tetrahydrothiazolo[5,4-c]pyridine-2-carboxamide or N-{(1R*,2S*)-2-{[(5-Chloroindol-2-yl)carbonyl]amino}-4-[(methylsulfonyl)amino]cyclohexyl}-5-methyl-4,5,6,7-tetrahydrothiazolo[5,4-c]pyridine-2-carboxamide (Stereoisomer B)

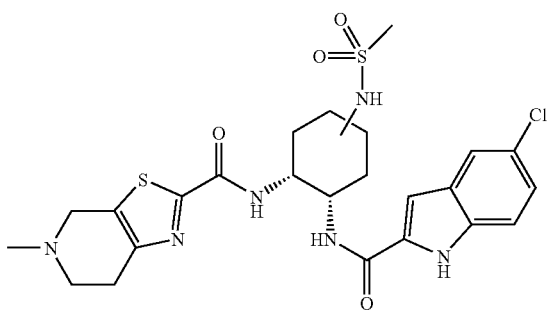

The compound (0.20 g) obtained in Example 83 was suspended in methylene chloride (7 mL), and triethylamine (0.16 mL) and methanesulfonyl chloride (28 µl) were added, followed by stirring at room temperature for 20 hours. After the reaction mixture was diluted with methylene chloride, it was washed with aqueous sodium hydroxide and dried over sodium sulfate anhydrate. The solvent was distilled away under reduced pressure, and the residue was purified by silica gel column chromatography (methylene chloride:methanol=30:1→15:1) to give the title compound (67.9 mg).

$^1$H-NMR (DMSO-d$_6$) δ: 1.40-1.55(1H,m), 1.65-1.85(2H, m), 1.90-2.05(2H,m), 2.15-2.25(1H,m), 2.41(3H,s), 2.75-2.95(4H,m), 2.92(3H,s), 3.55-3.80(3H,m), 4.10-4.20(1H,m), 4.45-4.55(1H,m), 7.08(1H,s), 7.15-7.20(2H,m), 7.41(1H,d,J=8.8 Hz), 7.69(1H,s), 8.27(1H,d,J=7.3 Hz), 8.33(1H,d,J=8.1 Hz), 11.77(1H,s).

MS(FAB)m/z: 565 (M+H)$^+$.

Example 85

N-((1R*,2S*)-5-(Acetylamino)-2-{[(5-chloroindol-2-yl)carbonyl]amino}cyclohexyl)-5-methyl-4,5,6,7-tetrahydrothiazolo[5,4-c]pyridine-2-carboxamide or N-((1R*,2S*)-4-(acetylamino)-2-{[(5-chloroindol-2-yl)carbonyl]amino}cyclohexyl)-5-methyl-4,5,6,7-tetrahydrothiazolo[5,4-c]pyridine-2-carboxamide (Stereoisomer B)

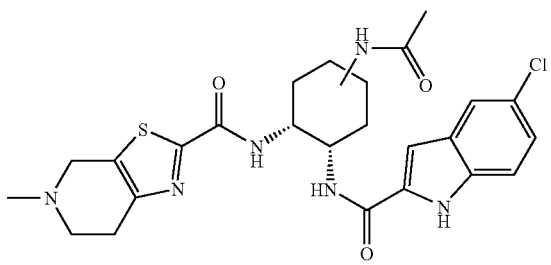

The compound (Stereoisomer B) (0.20 g) obtained in Example 83 was suspended in methylene chloride (7 mL), and triethylamine (0.16 mL) and acetic anhydride (34 µl) were added, followed by stirring at room temperature for 20 hours. Methylene chloride and aqueous sodium hydroxide were added to the reaction mixture to separate insoluble matter by filtration. The organic layer of the filtrate was separated and dried over sodium sulfate anhydrate, and the solvent was then distilled away under reduced pressure. The residue was purified by silica gel column chromatography (methylene chloride:methanol=15:1→10:1) to give the title compound (0.12 g).

$^1$H-NMR (DMSO-d$_6$) δ: 1.35-1.50(1H,m), 1.55-1.70(1H, m), 1.80(3H,s), 1.80-2.05(3H,m), 2.05-2.20(1H,m), 2.47(3H,s), 2.80-3.00(4H,m), 3.75-4.00(3H,m), 4.15-4.30 (1H,m), 4.45-4.55(1H,m), 7.07(1H,s), 7.17(1H,dd,J=8.8, 1.0 Hz), 7.41(1H,d,J=8.8 Hz), 7.69(1H,s), 7.89(1H,d,J=7.3 Hz), 8.24(1H,d,J=8.1 Hz), 8.31(1H,d,J=7.3 Hz), 11.77(1H,s).

MS(FAB)m/z: 528(M+H)$^+$.

Example 86

N-((1R,2S,5S)-2-{[(5-Chloroindol-2-yl)carbonyl]amino}-5-{[methoxy(methyl)amino]carbonyl}cyclohexyl)-5-methyl-4,5,6,7-tetrahydrothiazolo[5,4-c]pyridine-2-carboxamide hydrochloride

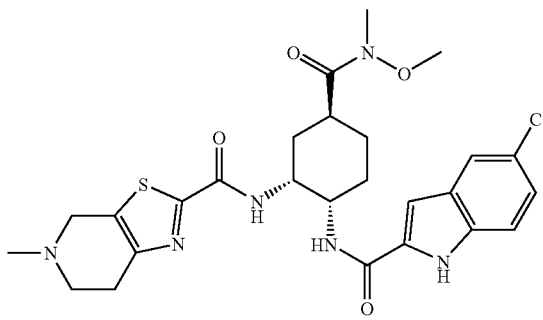

The compound (250 mg) obtained in Example 58 was dissolved in N,N-dimethylformamide (5 mL), and N,O-dimethylhydroxylamine hydrochloride (142 mg), 1-(3-dimethylaminopropyl)-3-ethylcarbodiimide hydrochloride (111 mg), 1-hydroxybenzotriazole monohydrate (89 mg), and N-methylmorpholine (213 mL) were added, followed by stirring at room temperature for 19 hours. After the reaction mixture was concentrated, an aqueous solution of sodium hydrogencarbonate was added to the residue, and the mixture was extracted with ethyl acetate. After the resultant organic layer was washed with saturated brine and dried over sodium sulfate anhydrate, the solvent was distilled away under reduced pressure. The residue was purified by silica gel column chromatography (methylene chloride:methanol=47:3->23:2) to give a colorless amorphous solid (179 mg). This prodcut was dissolved in methanol-tetrahydrofuran, and 1N HCl in ethanol (960 mL) was added to give the title compound.

$^1$H-NMR (DMSO-d$_6$) δ: 1.57-1.91(4H,m), 1.96-2.00(1H, m), 2.10-2.21(1H,m), 2.92(3H,s), 2.93-3.03(2H,m), 3.08(3H,s), 3.10-3.28(2H,m), 4.16-4.19(1H,m), 4.50-4.52 (1H,m), 4.69(1H,br.s), 7.06(1H,s), 7.17(1H,dd,J=8.8, 1.5 Hz), 7.42(1H,d,J=8.8 Hz), 7.70(1H,s), 8.33(1H,br.s), 8.41 (1H,d,J=7.8 Hz), 11.81(1H,br.s).

MS(ESI)m/z: 559(M+H)$^+$.

Example 87

N-{(1R,2S,5S)-2-{[(5-Chloroindol-2-yl)carbonyl]amino}-5-[(2,2-dimethylhydrazino)carbonyl]cyclohexyl}-5-methyl-4,5,6,7-tetrahydrothiazolo[5,4-c]pyridine-2-carboxamide hydrochloride

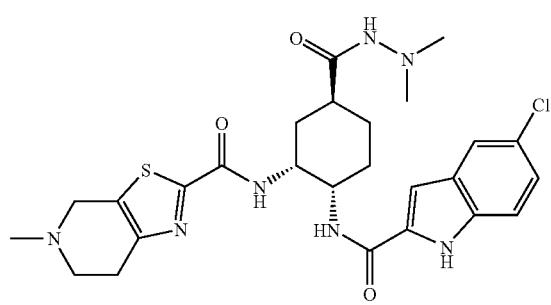

The title compound was obtained from the compound obtained in Example 58 and N,N-dimethylhydrazine in a similar manner to Example 57.

$^1$H-NMR (DMSO-d$_6$) δ: 1.49-1.54(1H,m), 1.76-1.81(2H, m), 1.89-1.93(2H,m), 2.07-2.17(1H,m), 2.33-3.60(14H,m), 4.15-4.19(1H,m), 4.40-4.47(2H,m), 4.70-4.72(1H,m), 7.04 (1H,s), 7.17(1H,dd,J=8.5, 2.0 Hz), 7.42(1H,d,J=8.5 Hz), 7.70 (1H,s), 8.17-8.22(1H,m), 8.41-8.43(1H,m), 11.80(1H,br.s).

MS(ESI)m/z: 558(M+H)$^+$.

Example 88

6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-2-quinolinecarboxamide hydrochloride

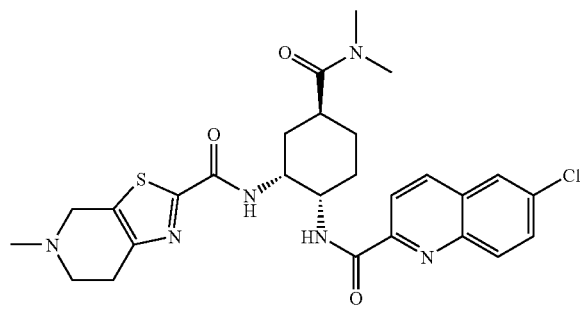

In a manner similar to that employed in Example 49, the compound obtained in Referential Example 145 was treated with HCl in ethanol and then, condensed with the compound obtained in Referential Example 10, to thereby give the title compound.

$^1$H-NMR (DMSO-d$_6$) δ: 1.45-1.60(1H,m), 1.75-1.90(3H, m), 1.90-2.00(1H,m), 2.00-2.20(1H,m), 2.80(3H,s), 2.90(3H,s), 2.99(3H,s), 3.10-3.30(5H,m), 3.56(1H,br), 4.10-4.20(1H,m), 4.40-4.70(2H,m), 7.88(2H,s), 8.15(1H,d,J=8.6 Hz), 8.22(1H,s), 8.52(1H,d,J=8.6 Hz), 8.72(1H,d,J=8.3 Hz), 8.89(1H,d,J=8.3 Hz).

MS(FAB)m/z: 555(M+H)$^+$.

Example 89

N-{(1R,2S,5S)-2-{[(5-Chloro-4-fluoroindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

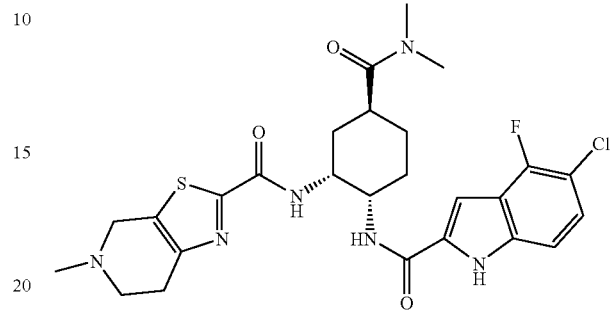

In a manner similar to that employed in Referential Example 91, the compound obtained in Referential Example 144 was condensed with the compound obtained in Referential Example 274. The thus-obtained compound was treated with 4N HCl-dioxane, followed by condensation with the compound obtained in Referential Example 10, to thereby give the title compound.

$^1$H-NMR (DMSO-d$_6$) δ: 1.24-1.98(6H,m), 2.33-3.33(6H, m), 2.81(3H,s), 2.90(3H,s), 2.99(3H,s), 4.12(1H,br.s), 4.30-4.70(1H,m), 4.60(1H,br.s), 7.21(1H,s), 7.27(2H,br.s), 8.37 (1H,d,J=8.1 Hz), 8.43(1H,d,J=7.6 Hz), 12.11(1H,s).

MS(FAB)m/z: 561(M+H)$^+$.

Example 90

7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)isoquinoline-3-carboxamide hydrochloride

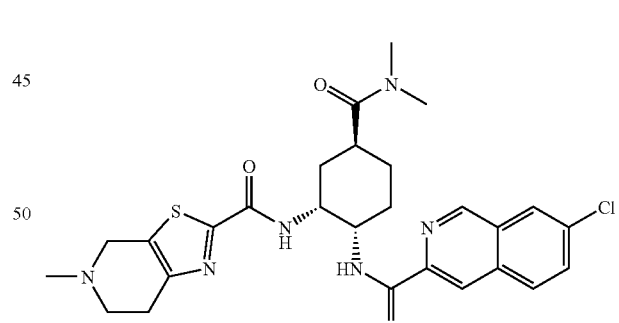

In a manner similar to that employed in Example 49, the compound obtained in Referential Example 146 was treated with HCl in ethanol and then, condensed with the compound obtained in Referential Example 10, to thereby give the title compound.

$^1$H-NMR (DMSO-d$_6$) δ: 1.45-1.65(1H,m), 1.70-1.85(3H, m), 1.95-2.10(1H,m), 2.10-2.20(1H,m), 2.80(3H,s), 2.92(3H,s), 2.96(3H,s), 2.95-3.10(1H,m), 3.10-3.40(3H,m), 3.70-3.80(1H,m), 4.20-4.30(1H,m), 4.40-4.60(2H,m), 4.65-4.80(1H,m), 7.83-7.93(1H,m), 8.26(1H,d,J=8.8 Hz), 8.38(1H,s), 8.60(1H,s), 8.85-9.00(2H,m), 9.30-9.40(1H,m).

MS(FAB)m/z: 555(M+H)$^+$.

Example 91

N-((3R*,4S*)-4-{[(5-Chloroindol-2-yl)carbonyl]amino}-tetrahydrofuran-3-yl)-5-methyl-4,5,6,7-tetrahydrothiazolo-[5,4-c]pyridine-2-carboxamide hydrochloride

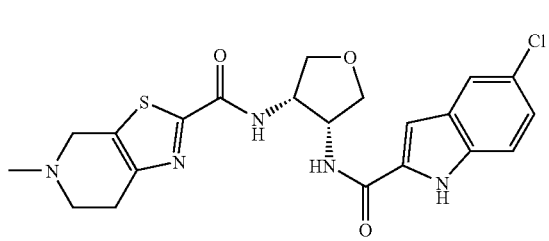

The compound (0.1 g) obtained in Referential Example 10, 1-hydroxybenzotriazole monohydrate (78 mg), and 1-(3-dimethylaminopropyl)-3-ethylcarbodiimide hydrochloride (0.2 g) were successively added to a solution of the compound (0.12 g) obtained in Referential Example 172 in N,N-dimethylformamide (20 mL), and the mixture was stirred at room temperature for 1 day. After the reaction mixture was concentrated, and the resultant residue was diluted with chloroform-methanol (9:1) and washed with saturated aqueous sodium hydrogencarbonate and saturated brine, the resultant organic layer was dried over sodium sulfate anhydrate, and the solvent was distilled away under reduced pressure. The residue was purified by silica gel column chromatography (chloroform:methanol=95:5) to give a free base of the title compound. This product was treated with HCl in ethanol to give the title compound (0.1 g).

$^1$H-NMR (CDCl$_3$) δ: 2.50(3H,s), 2.70-2.90(4H,m), 3.67 (1H,s), 3.70(1H,s), 3.86(1H,dd,J=9.2, 6.3 Hz), 3.97(1H,dd, J=9.7, 4.1 Hz), 4.15(1H,dd,J=9.7, 5.8 Hz), 4.24(1H,dd,J=9.2, 7.0 Hz), 4.75-4.89(1H,m), 4.92-5.03(1H,m), 6.88(1H,s), 7.20(1H,dd,J=8.8, 2.0 Hz), 7.33(1H,d,J=8.8 Hz), 7.35-7.43 (1H,m), 7.58(1H,d,J=2.0 Hz), 7.64(1H,d,J=7.1 Hz), 9.38(1H, s).

MS(FAB)m/z: 460(M+H$^+$)

Example 92

N-((3S,4S)-4-{[(5-Chloroindol-2-yl)carbonyl]amino}-tetrahydrofuran-3-yl)-5-methyl-4,5,6,7-tetrahydrothiazolo-[5,4-c]pyridine-2-carboxamide

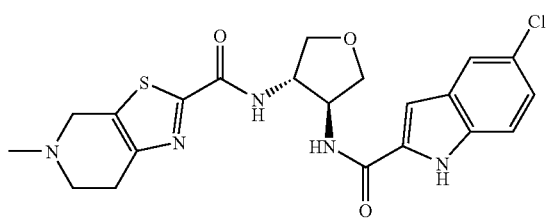

The title compound was obtained from the compound obtained in Referential Example 183 in accordance with the processes of Referential Example 172 and Example 91.

$^1$H-NMR (CDCl$_3$) δ: 2.51(3H,s), 2.83(2H,t,J=5.3 Hz), 2.93(2H,t,J=5.3 Hz), 3.72(2H,s), 3.78-3.89(2H,m), 4.31(1H, dd,J=9.2, 7.3 Hz), 4.41-4.56(2H,m), 4.63-4.75(1H,m), 6.88 (1H,s), 7.22(1H,dd,J=8.8, 2.0 Hz), 7.32(1H,d,J=8.8 Hz), 7.35-7.46(1H,m), 7.55(1H,d,J=7.1 Hz), 7.60(1H,d,J=2.0 Hz), 9.38(1H,s).

MS(FAB)m/z: 460(M+H$^+$).

Example 93

N-((3R,4R)-4-{[(5-Chloroindol-2-yl)carbonyl]amino}-tetrahydrofuran-3-yl)-5-methyl-4,5,6,7-tetrahydrothiazolo-[5,4-c]pyridine-2-carboxamide hydrochloride

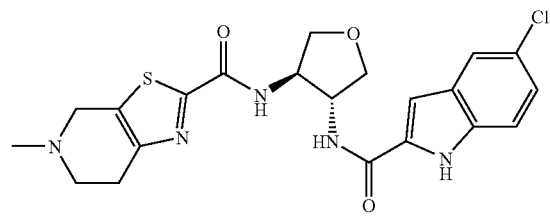

The title compound was obtained from the compound obtained in Referential Example 187 in accordance with the processes of Referential Example 172 and Example 91.

$^1$H-NMR and MS (FAB): The same as those of the enantiomer in Example 92.

Example 94 tert-Butyl (3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidine-1-carboxylate

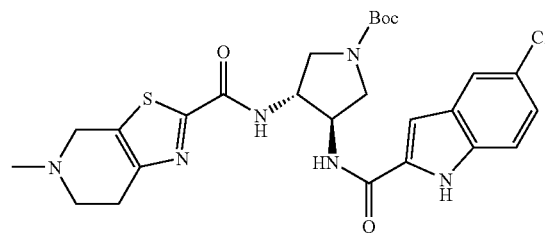

The title compound was obtained from the compound obtained in Referential Example 193 and the compound obtained in Referential Example 10 in accordance with the process of Example 91.

Melting point: 190-192° C.

$^1$H-NMR (CDCl$_3$) δ: 1.45(9H,s), 2.46(3H,s), 2.74-2.81 (4H,m), 3.24-3.37(2H,m), 3.54-3.70(2H,m), 3.96-4.00(1H, m), 4.15-4.23(1H,m), 4.50-4.65(1H,m), 4.77-4.82(1H,m), 6.79, 6.87(total 1H, each s), 7.12-7.95(5H,m), 9.91, 9.97 (total 1H, each s).

MS(FAB)m/z: 559(M+H$^+$).

Example 95

N-((3R,4R)-4-{[(5-Chloroindol-2-yl)carbonyl]amino}-pyrrolidin-3-yl)-5-methyl-4,5,6,7-tetrahydrothiazolo-[5,4-c]pyridine-2-carboxamide hydrochloride

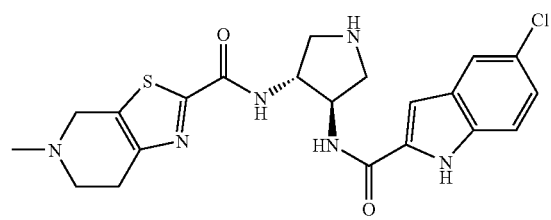

The compound (170 mg) obtained in Example 94 was dissolved in methylene chloride (3 mL), and trifluoroacetic acid (2 mL) was added at room temperature, followed by stirring for 1 hour. After concentrating the reaction mixture, chloroform and saturated aqueous sodium hydrogencarbonate were added. The resultant organic layer was dried over sodium sulfate anhydrate, and the solvent was distilled away under reduced pressure. The resultant residue was purified by silica gel thin layer chromatography (chloroform:methanol:water=7:3:1, under layer). HCl in methanol was added to the resultant product to give the title compound (90 mg) as a hydrochloride (NMR was measured in the form of a free base).

Melting point: 248-250° C. (decomposed)

$^1$H-NMR (CDCl$_3$) δ: 2.44(3H,s), 2.70-2.80(4H,m), 2.97-3.05(2H,m), 3.46-3.68(4H,m), 4.49-4.52(1H,m), 4.60-4.65(1H,m), 6.86(1H,s), 7.05-7.08(1H,m), 7.20(1H,d,J=8.5 Hz), 7.44(1H,s), 7.89(2H,br), 10.51(1H,br).

MS(FAB)m/z: 459(M+H$^+$).

Example 96

N-((3S,4S)-4-{[(5-Chloroindol-2-yl)carbonyl]amino}-5-oxotetrahydrofuran-3-yl)-5-methyl-4,5,6,7-tetrahydrothiazolo[5,4-c]pyridine-2-carboxamide hydrochloride

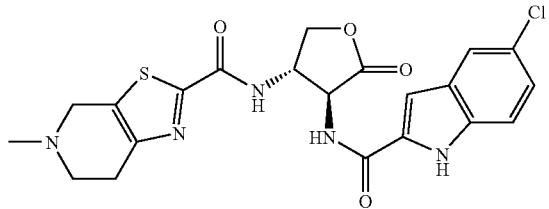

In a manner similar to that employed in Referential Example 69, the tert-butoxycarbonyl group of the compound obtained in Referential Example 196 was removed. Subsequently, in a manner similar to that employed in Example 91, the thus-obtained compound was reacted with the compound obtained in Referential Example 10, to thereby give the title compound.

$^1$H-NMR (DMSO-d$_6$) δ: 2.90(3H,s), 3.02-3.17(2H,m), 3.23-3.34(4H,m), 4.20(1H,t,J=8.6 Hz), 4.61(1H,t,J=8.6 Hz), 4.92-5.01(1H,m), 5.14-5.26(1H,m), 7.09(1H,s), 7.19(1H,dd, J=8.8, 2.0 Hz), 7.41(1H,d,J=8.8 Hz), 7.73(1H,d,J=2.0 Hz), 9.27(1H,d,J=6.8 Hz), 9.35(1H,d,J=6.8 Hz), 11.22-11.33(1H,m), 11.89(1H,s).

MS(FAB)m/z: 474(M+H$^+$).

Example 97

N-((3S,4S)-4-{[(5-Chloroindol-2-yl)carbonyl]amino}-2-oxotetrahydrofuran-3-yl)-5-methyl-4,5,6,7-tetrahydrothiazolo[5,4-c]pyridine-2-carboxamide hydrochloride

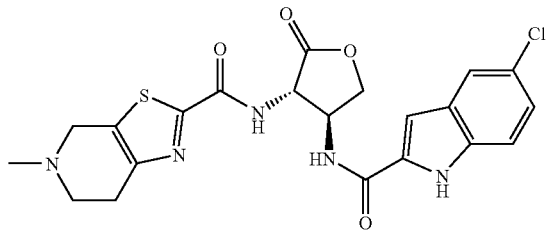

In a manner similar to that employed in Referential Example 69, the tert-butoxycarbonyl group of the compound obtained in Referential Example 197 was removed. Subsequently, in a manner similar to that employed in Example 91, the thus-obtained compound was reacted with 5-chloroindole-2-carboxylic acid, to thereby give the title compound.

$^1$H-NMR (DMSO-d$_6$) δ: 2.52(3H,s), 2.83(2H,t,J=5.9 Hz), 2.91-3.00(2H,m), 3.73(2H,s), 4.23(1H,t,J=8.6 Hz), 4.40-4.53(1H,m), 4.96(1H,dd,J=10.8, 5.2 Hz), 5.16(1H,dd,J=9.2, 7.3 Hz), 7.01(1H,s), 7.25(1H,dd,J=8.8, 2.0 Hz), 7.34(1H,d,J=8.8 Hz), 7.52(1H,d,J=2.0 Hz), 8.01(1H,d,J=5.4 Hz), 8.51-8.63(1H,m), 9.22(1H,s).

MS(FAB)m/z: 474(M+H$^+$).

Example 98

Ethyl (3S,4R)-2-(3-{[(5-chloroindol-2-yl)carbonyl]amino}-4-{[(5-methyl-4,5,6,7-tetrahydrothiazolo[5,4-c]pyridin-2-yl)carbonyl]amino}-2-oxopyrrolidin-1-yl)acetate hydrochloride

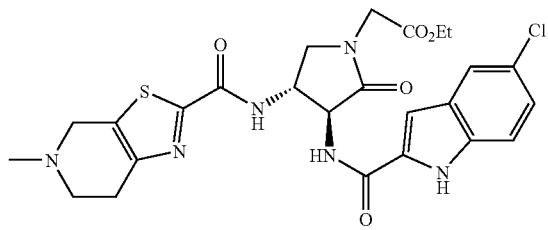

The title compound was obtained from the compound obtained in Referential Example 199 and the compound obtained in Referential Example 10 in a similar manner to Example 91. NMR was measured in the form of a free base.

$^1$H-NMR (DMSO-d$_6$) δ: 1.19(3H,t,J=7.1 Hz), 2.35(3H,s), 2.71-2.84(2H,m), 2.80-2.90(2H,m), 3.40(1H,d,J=10.3 Hz), 3.61(2H,d,J=10.8 Hz), 3.84(1H,dd,J=10.3, 5.6 Hz), 4.01-4.23(4H,m), 4.80-4.94(1H,m), 5.04(1H,t,J=8.6 Hz), 7.01(1H,s), 7.16(1H,dd,J=8.8, 2.0 Hz), 7.40(1H,d,J=8.8 Hz), 7.69(1H,d,J=2.0 Hz), 8.73(1H,d,J=8.6 Hz), 8.90(1H,d,J=8.8 Hz), 11.86(1H,s).

MS(FAB)m/z: 559(M+H$^+$).

Example 99

N-((3R,4S)-4-{[(5-Chloroindol-2-yl)carbonyl]amino}-1-methyl-5-oxopyrrolidin-3-yl)-5-methyl-4,5,6,7-tetrahydrothiazolo[5,4-c]pyridine-2-carboxamide

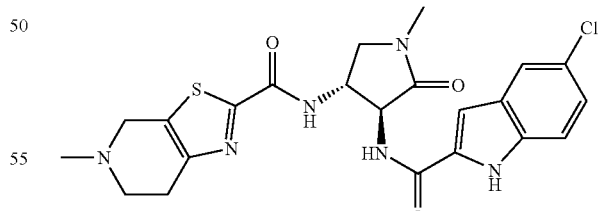

The title compound was obtained from the compound obtained in Referential Example 201 and the compound obtained in Referential Example 10 in a similar manner to Example 91.

$^1$H-NMR (CDCl$_3$) δ: 2.49(3H,s), 2.77-2.82(2H,m), 2.86-2.91(5H,m), 3.69(2H,d,J=1.2 Hz), 4.39-4.54(3H,m), 4.93-4.98(1H,m), 6.98(1H,d,J=1.2 Hz), 7.05-7.34(3H,m), 7.63(1H,d,J=2.0 Hz), 8.11(1H,d,J=7.8 Hz), 9.00(1H,s)

MS(FAB)m/z: 487(M+H$^+$).

Example 100

Methyl 2-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)sulfonyl]acetate

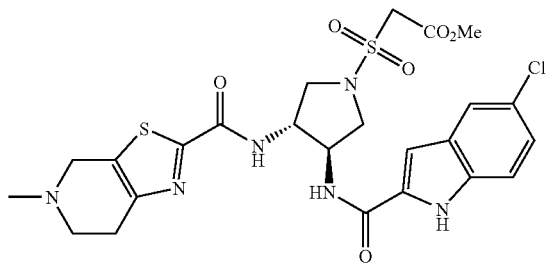

The compound (230 mg) obtained in Example 95 and triethylamine (0.10 mL) were dissolved in methylene chloride (6.9 mL), and the mixture was cooled with ice. Methoxycarbonylmethanesulfonyl chloride (Synthesis, p. 321, 1975) (105 mg) was added. The temperature of the resultant mixture was returned to room temperature, and the mixture was stirred overnight. The reaction mixture was diluted with chloroform, washed with water and saturated brine and then dried over sodium sulfate anhydrate, and the solvent was distilled away under reduced pressure. The resultant residue was purified by silica gel thin layer chromatography (chloroform:methanol=20:1) and powdered with methanol-water to give the title compound (150 mg).

$^1$H-NMR (CDCl$_3$) δ: 2.48(3H,s), 2.76-2.86(4H,m), 3.49-3.73(4H,m), 3.87(3H,s), 3.94-3.98(1H,m), 4.08-4.11(1H,m), 4.13(2H,s), 4.69-4.72(1H,m), 4.88-4.91(1H,m), 6.89(1H,s), 7.12-7.15(1H,m), 7.27-7.28(1H,m), 7.50(1H,s), 7.81-7.86 (2H,m), 9.92(1H,s).

MS(FAB)m/z: 595(M+H$^+$).

Example 101

2-[((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)sulfonyl]acetic acid

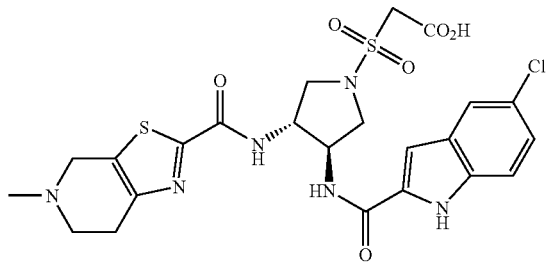

The compound (100 mg) obtained in Example 100 was dissolved in tetrahydrofuran (4 mL)-water (1 mL), and the mixture was cooled with ice. Lithium hydroxide monohydrate (7.8 mg) was added thereto. The temperature of the resultant mixture was returned to room temperature, and the mixture was stirred for 4 hours. After the reaction mixture was neutralized with 1N hydrochloric acid, it was concentrated. Precipitates were collected by filtration, washed with water and 50% ethanol and dried overnight at 50° C. under reduced pressure to give the title compound (87 mg).

$^1$H-NMR (DMSO-d$_6$) δ: 2.50(3H,s), 2.92(4H,s), 3.34-3.43 (4H,m), 3.76-3.85(2H,m), 4.27(each 1H,AB type d,J=14.5 Hz), 4.65-4.71(1H,m), 4.78-4.84(1H,m), 7.14(1H,s), 7.18 (1H,d,J=8.8 Hz), 7.40(1H,d,J=8.8 Hz), 7.72(1H,s), 8.87(1H, d,J=7.8 Hz), 9.12(1H,d,J=8.2 Hz), 11.83(1H,s).

Example 102

Methyl 2-((3R,4R)-3-{[(5-chloroindol-2-yl)carbonyl]amino}-4-{[(5-methyl-4,5,6,7-tetrahydrothiazolo[5,4-c]-pyridin-2-yl)carbonyl]amino}pyrrolidin-1-yl)acetate

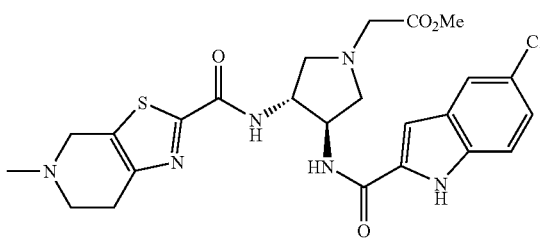

The compound (230 mg) obtained in Example 95 and potassium carbonate (90 mg) were dissolved in N,N-dimethylformamide (4.6 mL), and the mixture was cooled with ice. Methyl bromoacetate (0.062 mL) was added, and the resultant mixture was stirred for 45 minutes. The reaction mixture was diluted with ethyl acetate, washed with water and saturated brine and then dried over sodium sulfate anhydrate, and the solvent was distilled away under reduced pressure. The resultant residue was purified by silica gel thin layer chromatography (chloroform:methanol=10:1) and powdered with methanol-water to give the title compound (190 mg).

$^1$H-NMR (CDCl$_3$) δ: 2.35(2H,s), 2.48(3H,s), 2.73-2.95 (4H,m), 3.34-3.42(2H,m), 3.46(2H,q,J=6.5 Hz), 3.67(2H,q, J=6.5 Hz), 3.75(3H,s), 4.57-4.71(2H,m), 6.91(1H,s), 7.10-7.13(1H,m), 7.31(1H,d,J=9.0 Hz), 7.53(1H,s), 7.77(1H,d, J=8.0 Hz), 7.87(1H,d,J=6.8 Hz), 10.22(1H,s).

MS(FAB)m/z: 531(M+H$^+$).

Example 103

2-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)acetic acid

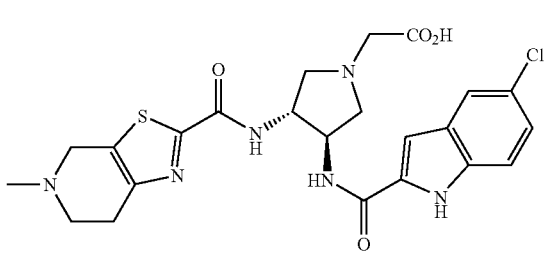

The title compound was obtained from the compound obtained in Example 102 in a similar manner to Example 101.

$^1$H-NMR (DMSO-d$_6$) δ: 2.42(3H,s), 2.69-2.87(6H,m), 3.13(1H,t,J=9.0 Hz), 3.22(1H,t,J=9.0 Hz), 3.33(each 1H,AB type d,J=6.8 Hz), 3.72(2H,s), 4.53-4.60(1H,m), 4.65-4.72 (1H,m), 7.16-7.20(2H,m), 7.42(1H,d,J=8.8 Hz), 7.70(1H,s), 8.85(1H,d,J=7.5 Hz), 9.00(1H,d,J=8.3 Hz), 11.79(1H,s).

Example 104

Methyl 3-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl) propionate

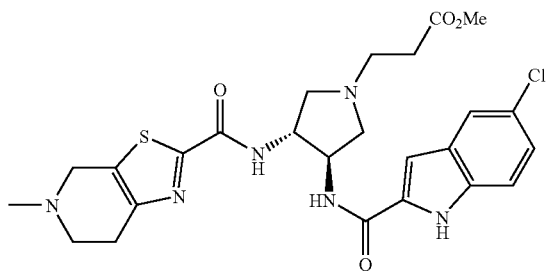

The title compound was obtained from the compound obtained in Example 95 and methyl 3-bromopropionate in a similar manner to Example 102.

$^1$H-NMR (CDCl$_3$) δ: 1.96-2.20(2H,m), 2.49(3H,s), 2.61-2.96(8H,m), 3.17-3.21(2H,m), 3.62-3.72(2H,m), 3.69(3H,s), 4.46-4.49(1H,m), 4.56-4.61(1H,m), 6.87(1H,s), 7.05-7.14(1H,m), 7.32(1H,d,J=9.2 Hz), 7.53(1H,s), 7.65-7.71(2H,m), 10.02(1H,s).
MS(FAB)m/z: 545(M+H$^+$).

Example 105

3-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl) propionic acid

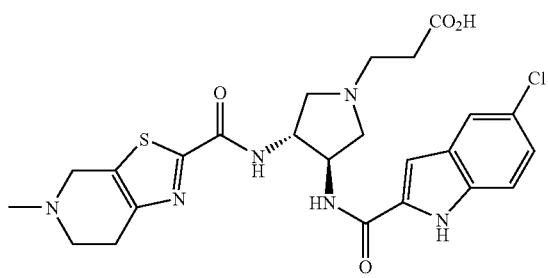

The title compound was obtained from the compound obtained in Example 104 in a similar manner to Example 101.

$^1$H-NMR (DMSO-d$_6$) δ: 2.38(3H,s), 2.39-2.84(10H,m), 2.93(1H,t,J=8.8 Hz), 3.05(1H,t,J=8.8 Hz), 3.65(2H,s), 4.51-4.56(1H,m), 4.63-4.68(1H,m), 7.16-7.19(2H,m), 7.41(1H,d,J=8.8 Hz), 7.69(1H,s), 8.81(1H,d,J=7.8 Hz), 8.97(1H,d,J=8.3 Hz), 11.75(1H,s).

Example 106

Ethyl 3-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionate

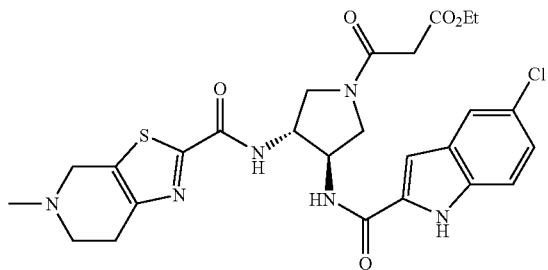

The title compound was obtained from the compound obtained in Example 95 and ethylmalonyl chloride in a similar manner to Example 100.

$^1$H-NMR (DMSO-d$_6$) δ: 1.20(3H,t,J=7.0 Hz), 2.37(3H,s), 2.73-2.75(2H,m), 2.82-2.84(2H,m), 3.35-3.38(2H,m), 3.64(2H,s), 3.68-3.83(2H,m), 3.91-4.00(2H,m), 4.10(2H,q,J=7.0 Hz), 4.61-4.84(2H,m), 7.13(1H,s), 7.18(1H,dd,J=8.5, 2.0 Hz), 7.41(1H,d,J=8.5 Hz), 7.72(1H,s), 8.73(1H,t,J=9.0 Hz), 9.10(1H,d,J=9.0 Hz), 11.79(1H,s).

Example 107

3-((3R,4R)-3-{[(5-Chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionic acid

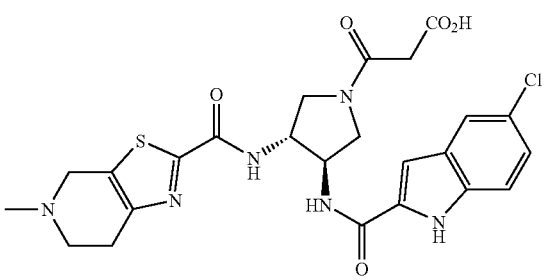

The title compound was obtained from the compound obtained in Example 106 in a similar manner to Example 101.

$^1$H-NMR (DMSO-d$_6$) δ: 2.39(3H,s), 2.77(2H,s), 2.85(2H,s), 3.29-3.55(4H,m), 3.68(2H,s), 3.82-4.01(2H,m), 4.62-4.68(1H,m), 4.77-4.86(1H,m), 7.14(1H,s), 7.18(1H,d,J=8.8 Hz), 7.41(1H,d,J=8.8 Hz), 7.72(1H,s), 8.75(1H,t,J=8.8 Hz), 9.12(1H,d,J=7.8 Hz), 11.81(1H,s).

Example 108

Methyl 1-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)methyl]-cyclopropanecarboxylate

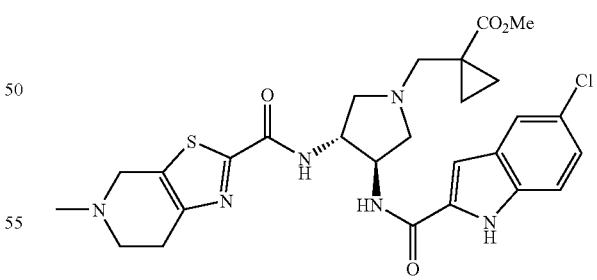

The title compound was obtained from the compound obtained in Example 95 and methyl 1-(bromomethyl)cyclopropanecarboxylate in a similar manner to Example 102.

$^1$H-NMR (CDCl$_3$) δ: 0.78-0.79(2H,m), 1.24-1.26(2H,m), 2.49(3H,s), 2.62-2.88(6H,m), 3.20-3.28(2H,m), 3.66(3H,s), 3.61-3.75(4H,m), 4.45-4.62(2H,m), 6.86(1H,s), 7.12-7.15(1H,m), 7.24-7.28(1H,m), 7.52(1H,d,J=8.5 Hz), 7.54(1H,s), 7.69(1H,d,J=8.0 Hz), 10.00(1H,s).
MS(ESI)m/z: 571(M+H$^+$).

Example 109

1-[((3R,4R)-3-{[(5-Chloroindol-2-yl)carbonyl]amino}-4-{[(5-methyl-4,5,6,7-tetrahydrothiazolo[5,4-c]pyridin-2-yl)carbonyl)amino}pyrrolidin-1-yl)methyl]-cyclopropanecarboxylic acid

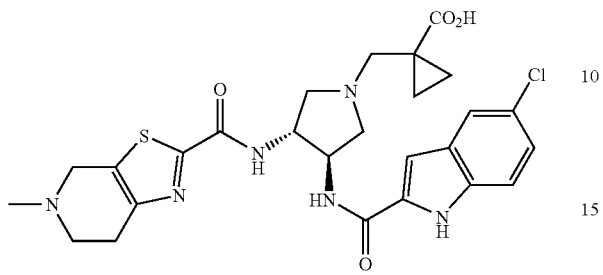

The title compound was obtained from the compound obtained in Example 108 in a similar manner to Example 101.

¹H-NMR (DMSO-d₆) δ: 0.73-0.78(2H,m), 1.04-1.07(2H,m), 2.37(3H,s), 2.65-2.84(6H,m), 3.11-3.20(4H,m), 3.64(2H,s), 4.59-4.74(2H,m), 7.16(1H,s), 7.17(1H,d,J=8.5 Hz), 7.40(1H,d,J=8.5 Hz), 7.70(1H,s), 8.84(1H,d,J=7.5 Hz), 9.12(1H,d,J=7.5 Hz), 11.77(1H,s).

Example 110 tert-Butyl (3R,4R)-3-{[(5-chloroindol-2-yl)carbonyl]amino}-4-{[(5-isopropyl-4,5,6,7-tetrahydrothiazolo[5,4-c]pyridin-2-yl)carbonyl]amino}pyrrolidine-1-carboxylate

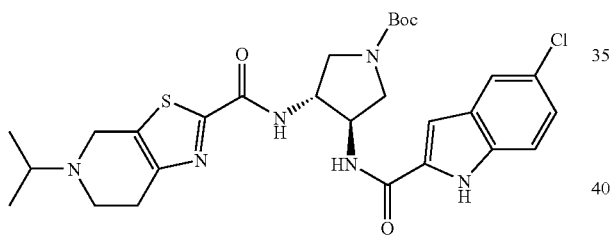

The title compound was obtained from the compound obtained in Referential Example 193 and the compound obtained in Referential Example 148 in a similar manner to Example 91.

¹H-NMR (CDCl₃) δ: 1.12(6H,d,J=6.6 Hz), 1.47(9H,s), 2.83-2.88(4H,m), 2.94-2.99(1H,m), 3.20-3.29(1H,m), 3.31-3.42(1H,m), 3.75-3.81(2H,m), 3.98(1H,t,J=8.5 Hz), 4.15-4.35(2H,m), 4.50-4.65(1H,m), 6.85, 6.91(total 1H, each s), 7.15-7.90(5H,m), 9.41, 9.50(total 1H, each s).

Example 111

N-((3R,4R)-4-{[(5-chloroindol-2-yl)carbonyl]amino}pyrrolidin-3-yl)-5-isopropyl-4,5,6,7-tetrahydrothiazolo[5,4-c]pyridine-2-carboxamide

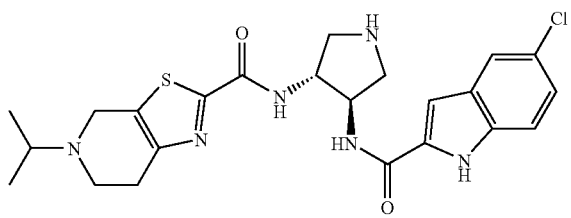

The title compound was obtained from the compound obtained in Example 110 in a similar manner to Example 95.

¹H-NMR (CDCl₃) δ: 1.13(6H,d,J=6.3 Hz), 2.85(4H,br.s), 2.96-3.05(3H,m), 4.51-4.52(1H,m), 4.76-4.80(2H,m), 5.36-5.39(2H,m), 5.53-5.58(1H,m), 7.17-7.19(1H,m), 7.27-7.31(2H,m), 7.57(1H,s), 7.64(2H,br), 9.82(1H,br).

Example 112

Ethyl 3-((3R,4R)-3-{[(5-chloroindol-2-yl)carbonyl]amino}-4-{[(5-isopropyl-4,5,6,7-tetrahydrothiazolo[5,4-c]pyridin-2-yl)carbonyl]amino}pyrrolidin-1-yl)propionate

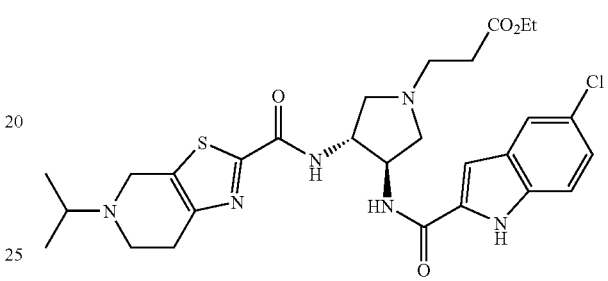

The title compound was obtained from the compound obtained in Example 111 and ethyl 3-bromopropionate in a similar manner to Example 102.

¹-NMR (CDCl₃) δ: 1.14(6H,d,J=6.5 Hz), 1.26(3H,t,J=7.0 Hz), 2.51(3H,t,J=7.0 Hz), 2.63(1H,dd,J=9.5, 6.5 Hz), 2.73-2.91(6H,m), 2.95-3.02(1H,m), 3.22(2H,q,J=7.0 Hz), 3.81(each 1H,AB type d,J=14.5 Hz), 4.16(2H,q,J=7.0 Hz), 4.40-4.45(1H,m), 4.52-4.59(1H,m), 6.88(1H,d,J=2.0 Hz), 7.17-7.19(1H,m), 7.30-7.32(2H,m), 7.59(1H,s), 7.62(1H,s), 9.56(1H,s).

MS(FAB)m/z: 587(M+H⁺).

Example 113

3-((3R,4R)-3-{[(5-Chloroindol-2-yl)carbonyl]amino}-4-{[(5-isopropyl-4,5,6,7-tetrahydrothiazolo[5,4-c]pyridin-2-yl)carbonyl]amino}pyrrolidin-1-yl)propionic acid

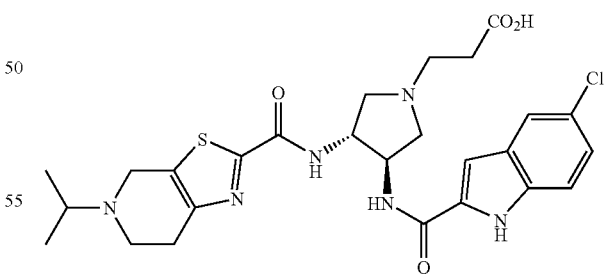

The title compound was obtained from the compound obtained in Example 112 in a similar manner to Example 101.

¹H-NMR (DMSO-d₆) δ: 1.04(6H,d,J=6.6 Hz), 2.40(2H,q,J=7.0 Hz), 2.50(4H,s), 2.60-2.74(4H,m), 2.90-2.94(2H,m), 3.02-3.06(1H,m), 3.20-3.35(2H,m), 4.50-4.53(1H,m), 4.61-4.65(1H,m), 7.15-7.18(2H,m), 7.41(1H,d,J=8.8 Hz), 7.68(1H,s), 8.78(1H,d,J=7.5 Hz), 8.90(1H,d,J=8.0 Hz), 11.73(1H,s).

Example 114

N-((3R,4R)-1-Acetyl-4-{[(5-chloroindol-2-yl)carbonyl]-amino}pyrrolidin-3-yl)-5-isopropyl-4,5,6,7-tetrahydrothiazolo[5,4-c]pyridine-2-carboxamide hydrochloride

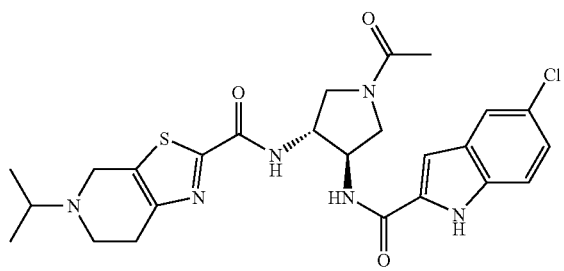

The title compound was obtained from the compound obtained in Example 111 and acetic anhydride in a similar manner to Example 100.

Melting point: 254-258° C. (decomposed).

$^1$H-NMR (DMSO-d$_6$) δ: 1.34-1.37(6H,m), 1.96(3H,s), 3.30-3.55(5H,m), 3.66-3.82(3H,m), 3.95(1H,q,J=8.3 Hz), 4.45-4.82(4H,m), 7.15(1H,s), 7.18(1H,d,J=9.0 Hz), 7.41(1H,d,J=9.0 Hz), 7.71(1H,s), 8.75-8.81(1H,m), 9.21(1H,d,J=8.0 Hz), 11.32(1H,br), 11.83(1H,d,J=7.3 Hz).

MS(FAB)m/z: 529(M+H$^+$).

Example 115

N-[(3R,4R)-4-{[(5-Chloroindol-2-yl)carbonyl]amino}-1-(methylsulfonyl)pyrrolidin-3-yl]-5-isopropyl-4,5,6,7-tetrahydrothiazolo[5,4-c]pyridine-2-carboxamide hydrochloride

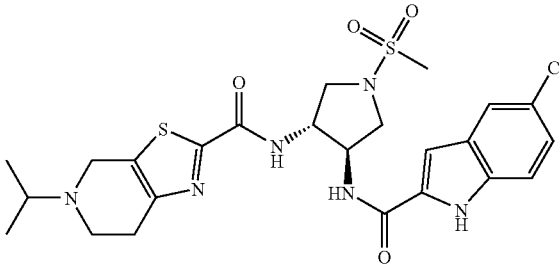

The title compound was obtained from the compound obtained in Example 111 and methanesulfonyl chloride in a similar manner to Example 100.

Melting point: 230-235° C. (decomposed)

$^1$H-NMR (DMSO-d$_6$) δ: 1.32-1.36(6H,m), 3.32(3H,s), 3.43-3.46(5H,m), 3.68-3.75(4H,m), 4.48(1H,m), 4.62-4.72(2H,m), 4.83(1H,t,J=5.5 Hz), 7.14(1H,s), 7.18(1H,d,J=8.6 Hz), 7.40(1H,d,J=8.6 Hz), 7.72(1H,s), 8.82(1H,br), 9.20(1H,d,J=8.3 Hz), 11.30(1H,br), 11.86(1H,d,J=7.5 Hz).

MS(FAB)m/z: 565(M+H$^+$).

Example 116

Ethyl (3R,4R)-3-{[(5-chloroindol-2-yl)carbonyl]amino}-4-{[(5-isopropyl-4,5,6,7-tetrahydrothiazolo[5,4-c]pyridin-2-yl)carbonyl]amino}pyrrolidine-1-carboxylate hydrochloride

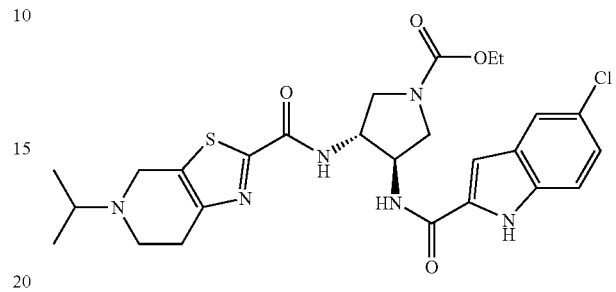

The title compound was obtained from the compound obtained in Example 111 and ethyl chloroformate in a similar manner to Example 100.

Melting point: 225-228° C. (decomposed)

$^1$H-NMR (DMSO-d$_6$) δ: 1.20(3H,t,J=7.0 Hz), 1.31-1.37(6H,m), 3.33-3.45(5H,m), 3.66-3.75(4H,m), 4.05(2H,q,J=7.0 Hz), 4.45-4.77(4H,m), 7.15(1H,s), 7.17(1H,dd,J=8.8, 2.0 Hz), 7.41(1H,d,J=8.8 Hz), 7.71(1H,d,J=2.0 Hz), 8.77(1H,d,J=7.0 Hz), 9.20(1H,d,J=8.0 Hz), 11.30(1H,br), 11.83(1H,d,J=7.5 Hz).

MS(FAB)m/z: 559(M+H$^+$).

Example 117 tert-Butyl (3R*,4S*)-4-{[(5-chloroindol-2-yl)carbonyl]-amino}-3-{[(5-methyl-4,5,6,7-tetrahydrothiazolo[5,4-c]-pyridin-2-yl)carbonyl]amino}piperidine-1-carboxylate

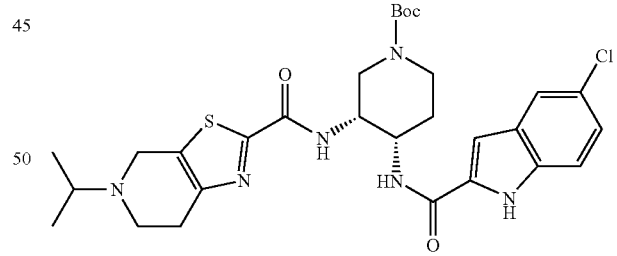

The title compound was obtained from the compound obtained in Referential Example 207 and the compound obtained in Referential Example 10 in a similar manner to Example 91.

Melting point: 152-154° C. (decomposed)

$^1$H-NMR (CDCl$_3$) δ: 1.53(9H,s), 1.62-1.80(1H,m), 2.23-2.30(1H,m), 2.52(3H,s), 2.75-3.05(5H,m), 3.10-3.25(1H,m), 3.68-3.82(2H,m), 4.15-4.45(4H,m), 6.89(1H,s), 7.19(1H,dd,J=8.8, 1.8 Hz), 7.32(1H,d,J=8.8 Hz), 7.92(1H,d,J=1.8 Hz), 7.75(1H,br.s), 8.21(1H,br.s), 9.39(1H,s).

MS(ESI)m/z: 573(M+H)$^+$.

Example 118

N-((3R*,4S*)-4-{[(5-Chloroindol-2-yl)carbonyl]amino}-piperidin-3-yl)-5-methyl-4,5,6,7-tetrahydrothiazolo[5,4-c]pyridine-2-carboxamide dihydrochloride

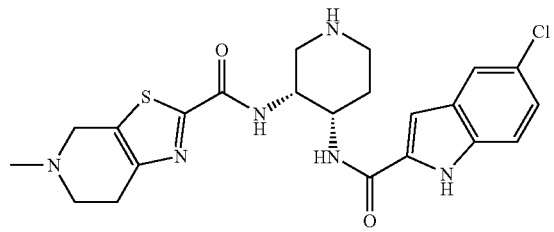

The title compound was obtained from the compound obtained in Example 117 in a similar manner to Example 95.

Melting point: 240-258° C. (decomposed).

$^1$H-NMR (DMSO-$d_6$) δ: 1.85-2.00(1H,m), 2.05-2.20(2H,m), 2.93(3H,s), 3.05-3.60(7H,m), 3.65-3.75(1H,m), 4.10-4.52(2H,m), 4.60-4.75(2H,m), 7.10-7.21(2H,m), 7.43(1H,d,J=8.6 Hz), 7.70(1H,s), 8.50(1H,br.d,J=7.8 Hz), 8.90-9.05 (2H,m), 9.27(1H,br.s), 11.9(1H,br.d,J=13.4 Hz).

MS(ESI)m/z: 473(M+H)$^+$.

Example 119 tert-Butyl (3R*,4S*)-3-{[(5-chloroindol-2-yl)carbonyl]-amino}-4-{[(5-methyl-4,5,6,7-tetrahydrothiazolo[5,4-c]-pyridin-2-yl)carbonyl]amino}piperidine-1-carboxylate

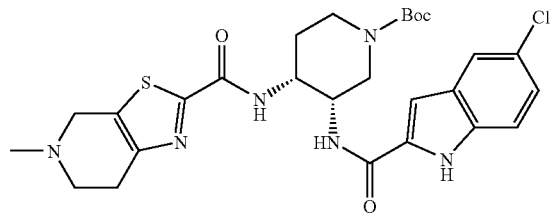

The title compound was obtained from the compound obtained in Referential Example 208 and 5-chloroindole-2-carboxylic acid in a similar manner to Example 91.

Melting point: 187-189° C. (decomposed).

$^1$H-NMR (CDCl$_3$) δ: 1.48(9H,s), 1.72-1.90(1H,m), 2.00 (1H,br.s), 2.00-2.10(1H,m), 2.45(3H,s), 2.60-2.70(2H,m), 2.70-2.80(2H,m), 3.23(1H,t,J=10.8 Hz), 3.35-3.50(1H,m), 3.50-3.72(2H,m), 3.90-4.20(2H,m), 4.30-4.40(1H,m), 4.45-4.55(1H,m), 6.85(1H,d,J=1.5 Hz), 7.17(1H,dd,J=8.8, 1.9 Hz), 7.20-7.30(1H,m), 7.33(1H,d,J=8.8 Hz), 7.58(1H,d, J=1.9 Hz), 10.17(1H,s).

MS(ESI)m/z: 573(M+H$^+$).

Example 120

N-((3R*,4S*)-3-{[(5-Chloroindol-2-yl)carbonyl]amino}-piperidin-4-yl)-5-methyl-4,5,6,7-tetrahydrothiazolo-[5,4-c]pyridine-2-carboxamide dihydrochloride

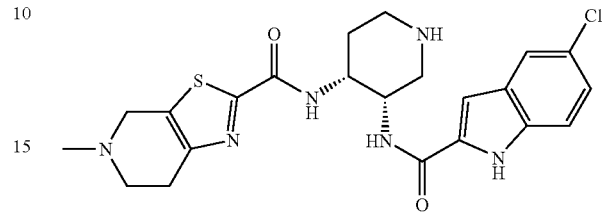

The title compound was obtained from the compound obtained in Example 119 in a similar manner to Example 95.

Melting point: 276-278° C. (decomposed).

$^1$H-NMR (DMSO-$d_6$) δ: 1.77-1.88(1H,m), 2.40-2.50(2H, m), 2.89(3H,s), 2.90-3.20(4H,m), 3.30-3.50(2H,m), 3.63(1H,br.s), 4.33-4.47(2H,m), 4.62-4.75(2H,m), 7.18(1H, dd,J=8.8, 1.9 Hz), 7.42(1H,d,J=8.8 Hz), 7.48(1H,br.s), 7.71 (1H,d,J=1.9 Hz), 8.66(1H,br.s), 8.95(1H,d,J=8.1 Hz), 9.20-9.30(1H,m), 9.45-9.70(1H,m), 11.61(1H,s), 11.90(1H,s).

MS(ESI)m/z: 473(M+H)$^+$.

Example 121 tert-Butyl (3R*,4S*)-4-{[(5-fluoroindol-2-yl)carbonyl]-amino}-3-{[(5-methyl-4,5,6,7-tetrahydrothiazolo[5,4-c]-pyridin-2-yl)carbonyl]amino}piperidine-1-carboxylate

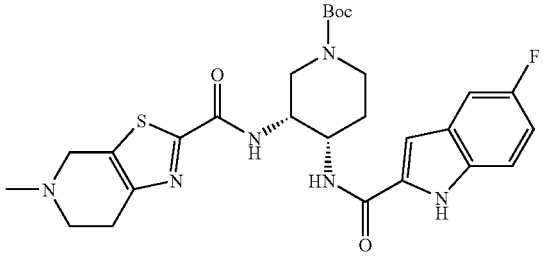

The title compound was obtained from the compound obtained in Referential Example 209 and the compound obtained in Referential Example 10 in a similar manner to Example 91.

$^1$H-NMR (CDCl$_3$) δ: 1.53(9H,s), 1.65-1.78(1H,m), 2.23-2.32(1H,br), 2.52(3H,s), 2.78-3.03(5H,m), 3.15-3.24(1H,br), 3.68-3.82(2H,br), 4.16-4.45(4H,br), 6.91(1H,s), 7.02(1H,td, J=9.0, 2.7 Hz), 7.30(1H,dd,J=9.0, 2.7 Hz), 7.34(1H,dd,J=9.0, 4.4 Hz), 7.65-7.90(1H,br), 8.10-8.40(1H,br), 9.31-9.41(1H, br).

MS(ESI)m/z: 557(M+H$^+$).

Example 122

N-((3R*,4S*)-4-{[(5-Fluoroindol-2-yl)carbonyl]amino}-piperidin-3-yl)-5-methyl-4,5,6,7-tetrahydrothiazolo[5,4-c]pyridine-2-carboxamide dihydrochloride

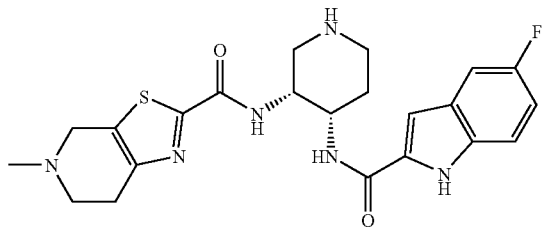

The title compound was obtained from the compound obtained in Example 121 in a similar manner to Example 95.

Melting point: 236-245° C. (decomposed).

$^1$H-NMR (DMSO-d$_6$) δ: 1.85-1.98(1H,br), 2.06-2.18(1H,br), 2.89(3H,s), 3.05-3.75(8H,s), 4.34-4.54(2H,br), 4.60-4.75(2H,br), 7.04(1H,td,J=9.3, 2.4 Hz), 7.15(1H,br.s), 7.37-7.44(2H,m), 8.46(1H,d,J=7.8 Hz), 8.88-9.00(1H,br), 9.09-9.27(2H,br), 11.55-11.75(1H,br), 11.76-11.84(1H,br).

MS(FAB)m/z: 457(M+H$^+$).

Example 123

N-((3R*,4S*)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

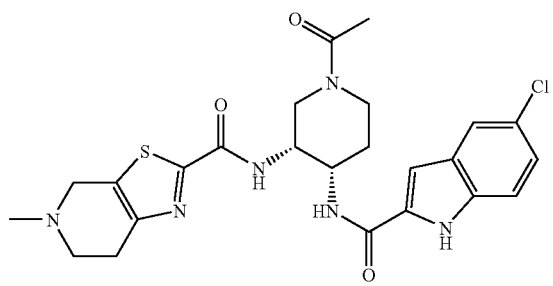

The title compound was obtained from the compound obtained in Example 118 and acetic anhydride in a similar manner to Example 100.

Melting point: 215-225° C. (decomposed)

$^1$H-NMR (DMSO-d$_6$) δ: 1.65-1.85(1H,m), 1.88, 2.06(total 3H, each s), 1.90-2.10(1H,m), 2.91(3H,s), 3.00-3.30(2H,m), 3.30-3.55(2H,m), 3.60-3.90(3H,m), 3.98-4.50(4H,m), 4.65-4.75(1H,m), 7.09(1H,d,J=15.6 Hz), 7.17(1H,d,J=8.8 Hz), 7.41(1H,d,J=8.8 Hz), 7.71(1H,s), 8.23-8.53(2H,m), 11.20-11.55(1H,m), 11.85(1H,br.d,J=5.4 Hz).

MS(ESI)m/z: 515(M+H$^+$).

Example 124

N-((3R*,4S*)-1-Acetyl-3-{[(5-chloroindol-2-yl)carbonyl]-amino}piperidin-4-yl)-5-methyl-4,5,6,7-tetrahydrothiazolo[5,4-c]pyridine-2-carboxamide hydrochloride

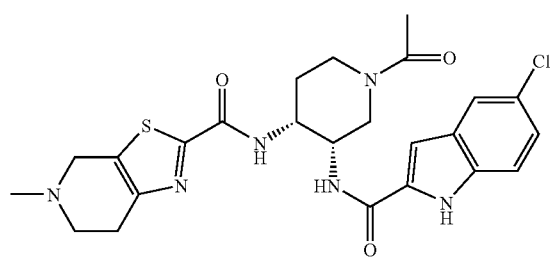

The title compound was obtained from the compound obtained in Example 120 and acetic anhydride in a similar manner in Example 100.

$^1$H-NMR (DMSO-d$_6$) δ: 1.65-1.80(1H,m), 1.81, 2.05(total 3H, each s), 2.00-2.20(1H,m), 2.70-2.85(1H,m), 2.89(3H,s), 3.00-3.20(2H,m), 3.20-3.50(2H,m), 3.64(1H,br.s), 3.78-4.30(2H,m), 4.30-4.50(3H,m), 4.55-4.75(1H,m), 7.05-7.23(2H,m), 7.38-7.48(1H,m), 7.70-7.80(1H,m), 7.79, 8.12(total 1H, each d,J=6.8 Hz), 8.73, 8.83(total 1H, each d,J=8.3 Hz), 11.20-11.50(1H,m), 11.89, 11.92(total 1H, each s).

MS(FAB)m/z: 515(M+H$^+$).

Example 125

N-((3R*,4S*)-1-Acetyl-4-{[(5-fluoroindol-2-yl)carbonyl]-amino}piperidin-3-yl)-5-methyl-4,5,6,7-tetrahydrothiazolo[5,4-c]pyridine-2-carboxamide hydrochloride

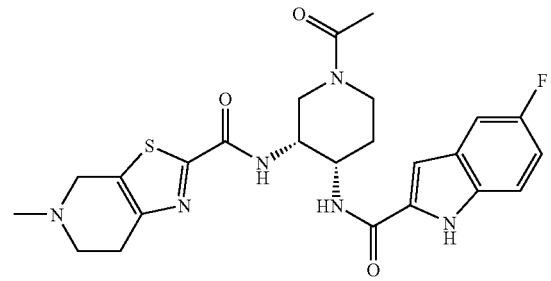

The title compound was obtained from the compound obtained in Example 122 and acetic anhydride in a similar manner to Example 100.

Melting point: 202° C. (decomposed).

$^1$H-NMR (DMSO-d$_6$) δ: 1.67-1.85(1H,m), 1.87(1.5H,s), 1.87-2.10(1H,m), 2.06(1.5H,s), 2.88-2.96(3H,br.s), 3.05-3.30(2H,m), 3.32-3.83(5H,br), 3.97-4.33(2H,m), 4.35-4.50(2H,br), 4.67-4.78(1H,br), 7.01-7.14(2H,m), 7.38-7.44(2H,m), 8.25-8.50(2H,m), 10.85-11.15(1H,br), 11.72-11.80(1H,br).

MS(FAB)m/z: 499(M+H$^+$).

Example 126

N-[(3R*,4S*)-4-{[(5-Chloroindol-2-yl)carbonyl]amino}-1-(methylsulfonyl)piperidin-3-yl]-5-methyl-4,5,6,7-tetrahydrothiazolo[5,4-c]pyridine-2-carboxamide hydrochloride

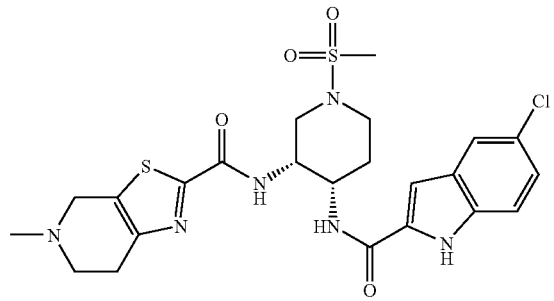

The title compound was obtained from the compound obtained in Example 118 and methanesulfonyl chloride in a similar manner to Example 100.

Melting point: 225-230° C. (decomposed)

$^1$H-NMR (DMSO-d$_6$) δ: 1.80-1.90(1H,m), 2.05-2.15(1H,m), 2.30-2.80(5H,m), 2.85-3.80(9H,m), 4.20-4.90(4H,m), 7.08(1H,d,J=1.7 Hz), 7.18(1H,dd,J=8.7, 1.7 Hz), 7.42(1H,d,J=8.7 Hz), 7.77(1H,s), 8.02-8.20(1H,m), 8.40-8.50(1H,m), 11.00-11.60(1H,m), 11.87(1H,s).

MS(ESI)m/z: 551(M+H$^+$).

Example 127

N-[(3R*,4S*)-3-{[(5-Chloroindol-2-yl)carbonyl]amino}-1-(methylsulfonyl)piperidin-4-yl]-5-methyl-4,5,6,7-tetrahydrothiazolo[5,4-c]pyridine-2-carboxamide hydrochloride

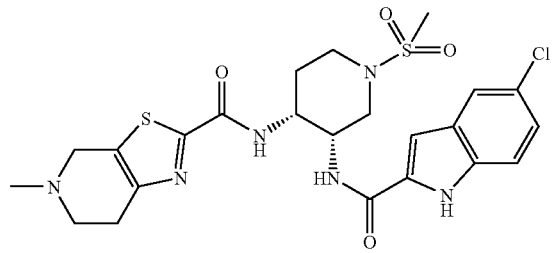

The title compound was obtained from the compound obtained in Example 120 and methanesulfonyl chloride in a similar manner to Example 100.

Melting point: 228-245° C. (decomposed)

$^1$H-NMR (DMSO-d$_6$) δ: 1.75-1.85(1H,m), 2.25-2.40(1H,m), 2.40-2.60(2H,m), 2.76(3H,br.s), 2.90(3H,s), 2.93-3.05(3H,m), 3.12(1H,d,J=10.6 Hz), 3.55-3.80(2H,m), 4.25-4.40(4H,m), 7.17(1H,d,J=1.7 Hz), 7.19(1H,dd,J=8.7, 2.0 Hz), 7.43(1H,d,J=8.7 Hz), 7.74(1H,d,J=2.0 Hz), 8.03(1H,d,J=6.6 Hz), 8.78(1H,d,J=7.4 Hz), 10.90-11.20(1H,br.s), 11.89(1H,s).

MS(ESI)m/z: 551(M+H$^+$).

Example 128

N-[(3R*,4S*)-4-{[(5-Fluoroindol-2-yl)carbonyl]amino}-1-(methylsulfonyl)piperazin-3-yl]-5-methyl-4,5,6,7-tetrahydrothiazolo[5,4-c]pyridine-2-carboxamide hydrochloride

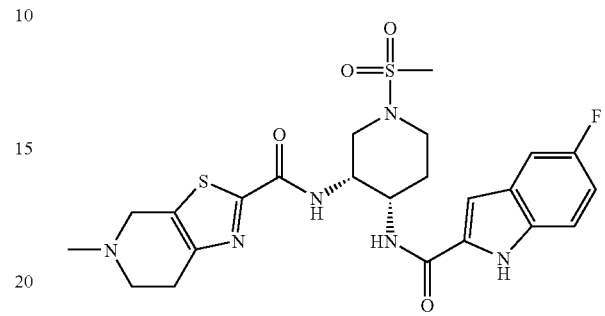

The title compound was obtained from the compound obtained in Example 122 and methanesulfonyl chloride in a similar manner to Example 100.

Melting point: 216-250° C. (decomposed)

$^1$H-NMR (DMSO-d$_6$) δ: 1.80-1.90(1H,m), 2.01-2.12(1H,m), 2.92(3H,s), 2.94(3H,s), 3.00-3.80(8H,m), 4.28-4.53(3H,m), 4.60-4.80(1H,br), 7.01-7.12(2H,m), 7.37-7.44(2H,m), 8.00-8.18(1H,br), 8.39-8.50(1H,br), 11.00-11.60(1H,br), 11.72-11.80(1H,br).

MS(FAB)m/z: 535(M+H$^+$).

Example 129

Methyl (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylate hydrochloride

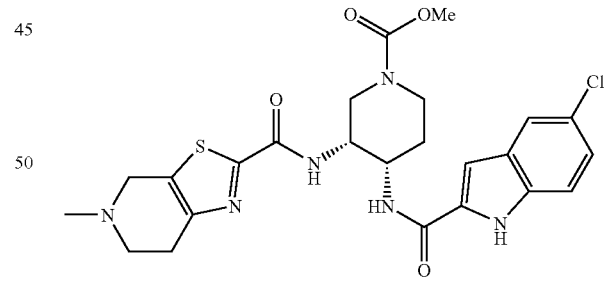

The title compound was obtained from the compound obtained in Example 118 and methyl chloroformate in a similar manner to Example 100.

Melting point: 248-253° C. (decomposed)

$^1$H-NMR (DMSO-d$_6$) δ: 1.65-1.78(1H,m), 1.88-2.03(1H,m), 2.90(3H,s), 3.00-3.80(9H,m), 3.80-3.90(1H,m), 3.95-4.08(1H,m), 4.20-4.70(4H,m), 7.10(1H,s), 7.17(1H,dd,J=8.8, 1.8 Hz), 7.42(1H,d,J=8.8 Hz), 7.71(1H,d,J=1.8 Hz), 8.29(1H,br.s), 8.41(1H,d,J=8.1 Hz), 11.29(1H,br.s), 11.85(1H,s).

MS(ESI)m/z: 531(M+H$^+$).

Example 130

Ethyl (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylate hydrochloride

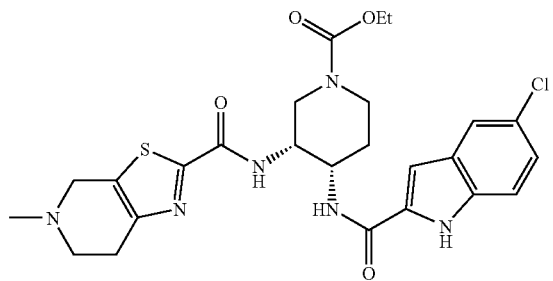

The title compound was obtained from the compound obtained in Example 118 and ethyl chloroformate in a similar manner to Example 100.

Melting point: 215-225° C. (decomposed).

$^1$H-NMR (DMSO-$d_6$) δ: 0.85-1.30(3H,m), 1.65-1.78(1H,m), 1.90-2.03(1H,m), 2.90(3H,s), 3.10-3.40(4H,m), 3.48(1H,br.s), 3.65(1H,br.s), 3.75-4.15(4H,m), 4.25(1H,br.s), 4.32-4.50(2H,m), 4.66(1H,br.s), 7.09(1H,s), 7.18(1H,dd,J=8.8, 2.0 Hz), 7.41(1H,d,J=8.8 Hz), 7.71(1H,d,J=2.0 Hz), 8.23(1H,br.s), 8.45(1H,br.d,J=8.1 Hz), 11.50(1H,br.s), 11.86(1H,s).

MS(ESI)m/z: 545(M+H$^+$).

Example 131

2-Methoxyethyl (3R*,4S*)-4-{[(5-chloroindol-2-yl)carbonyl]amino]-3-{[(5-methyl-4,5,6,7-tetrahydrothiazolo-[5,4-c]pyridin-2-yl)carbonyl]amino}piperidine-1-carboxylate hydrochloride

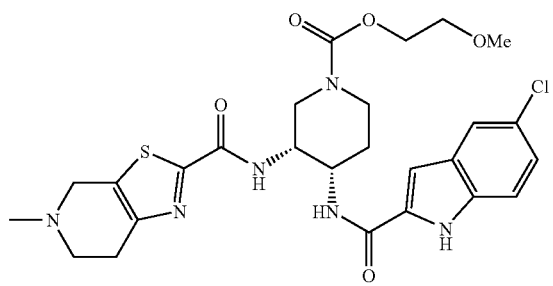

The title compound was obtained from the compound obtained in Example 118 and 2-methoxyethyl chloroformate in a similar manner to Example 100.

Melting point: 224-226° C. (decomposed).

$^1$H-NMR (DMSO-$d_6$) δ: 1.68-1.78(1H,m), 1.90-2.03(1H,m), 2.89(3H,s), 3.00-3.75(11H,m), 3.80-3.90(1H,m), 3.95-4.18(3H,m), 4.20-4.70(4H,m), 7.10(1H,s), 7.17(1H,dd,J=8.8, 2.0 Hz), 7.41(1H,d,J=8.8 Hz), 7.71(1H,d,J=2.0 Hz), 8.26(1H,br.s), 8.42(1H,d,J=7.8 Hz), 11.30(1H,br.s), 11.86(1H,s).

MS(ESI)m/z: 575(M+H$^+$).

Example 132

Ethyl (3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}piperidine-1-carboxylate hydrochloride

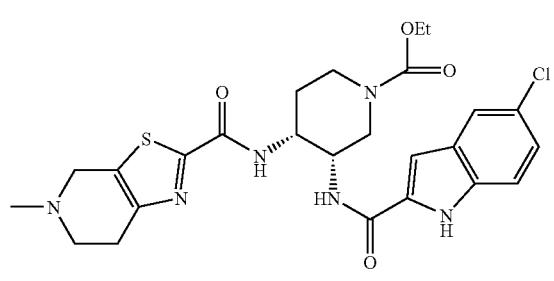

The title compound was obtained from the compound obtained in Example 120 and ethyl chloroformate in a similar manner to Example 100.

Melting point: 213-225° C. (decomposed).

$^1$H-NMR (DMSO-$d_6$) δ: 0.75-1.30(3H,m), 1.60-1.72(1H,m), 2.12-2.25(1H,m), 2.89(3H,s), 2.95-3.20(4H,m), 3.40-3.88(4H,m), 3.90-4.10(2H,m), 4.10-4.30(2H,m), 4.30-4.40(1H,m), 4.40-4.80(1H,m), 7.10(1H,s), 7.18(1H,dd,J=8.8, 2.0 Hz), 7.43(1H,d,J=8.8 Hz), 7.74(1H,s), 8.03(1H,d,J=5.6 Hz), 8.79(1H,s), 11.37(1H,s), 11.88(1H,s).

MS(ESI)m/z: 545(M+H$^+$).

Example 133

N-((3R*,4S*)-4-{[(5-Chloroindol-2-yl)carbonyl]amino}-1-propionylpiperidin-3-yl)-5-methyl-4,5,6,7-tetrahydrothiazolo[5,4-c]pyridine-2-carboxamide hydrochloride

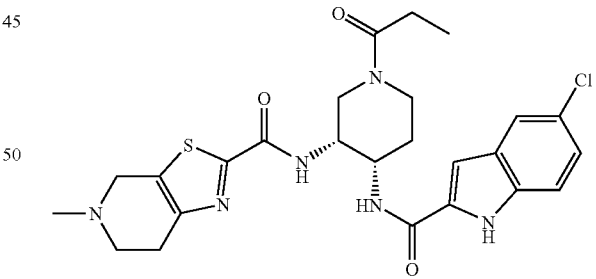

The title compound was obtained from the compound obtained in Example 118 and propionyl chloride in a similar manner to Example 100.

Melting point: 214-228° C. (decomposed).

$^1$H-NMR (DMSO-$d_6$) δ: 0.88-1.10(3H,m), 1.70-2.05(2H,m), 2.06-2.60(2H,m), 2.91(3H,s), 3.14(2H,br.s), 3.20-3.90(5H,m), 3.95-4.80(5H,m), 7.09(1H,d,J=11.0 Hz), 7.17(1H,dd,J=8.8, 1.2 Hz), 7.41(1H,d,J=8.8 Hz), 7.71(1H,s), 8.20-8.50(2H,m), 11.00-11.40(1H,m), 11.86(1H,s).

MS(ESI)m/z: 529(M+H$^+$).

Example 134

N-((3R*,4S*)-4-{[(5-Chloroindol-2-yl)carbonyl]amino}-1-isobutyrylpiperidin-3-yl)-5-methyl-4,5,6,7-tetrahydrothiazolo[5,4-c]pyridine-2-carboxamide hydrochloride

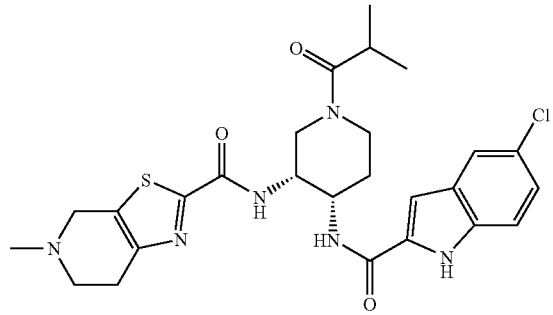

The title compound was obtained from the compound obtained in Example 118 and isobutyryl chloride in a similar manner to Example 100.

Melting point: 266-272° C. (decomposed)

$^1$H-NMR (DMSO-d$_6$) δ: 0.80-1.15(6H,m), 1.70-2.05(2H,m), 2.65-2.80(1H,m), 2.90(3H,s), 2.90-4.80(12H,m), 7.09 (1H,d,J=11.0 Hz), 7.17(1H,dd,J=8.8, 2.0 Hz), 7.41(1H,d,J=8.8 Hz), 7.71(1H,s), 8.00-8.30(1H,m), 8.30-8.50(1H,m), 10.95-11.50(1H,m), 11.86(1H,s).

MS(ESI)m/z: 543(M+H$^+$).

Example 135

N-[(3R*,4S*)-4-{[(5-Chloroindol-2-yl)carbonyl]amino}-1-(2,2-dimethylpropanoyl)piperidin-3-yl]-5-methyl-4,5,6,7-tetrahydrothiazolo[5,4-c]pyridine-2-carboxamide hydrochloride

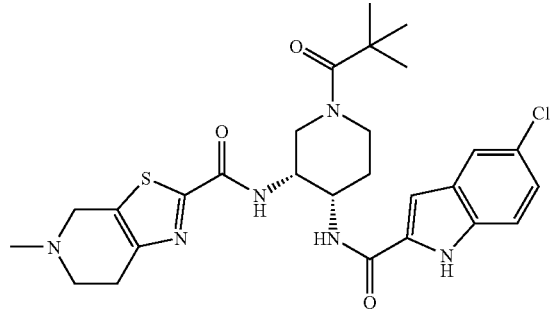

The title compound was obtained from the compound obtained in Example 118 and pivaloyl chloride in a similar manner to Example 100.

Melting point: 250-255° C. (decomposed).

$^1$H-NMR (DMSO-d$_6$) δ: 1.20(9H,s), 1.70-1.81(1H,m), 1.90-2.00(1H,m), 2.88(3H,s), 3.10(2H,br.s), 3.20-3.70(4H,m), 3.95-4.08(1H,m), 4.10-4.20(1H,m), 4.25-4.35(1H,m), 4.35-4.80(3H,m), 7.10(1H,s), 7.16(1H,dd,J=8.8, 1.9 Hz), 7.41(1H,d,J=8.8 Hz), 7.69(1H,d,J=1.9 Hz), 8.06(1H,br.s), 8.38(1H,d,J=7.8 Hz), 11.31(1H,br.s), 11.84(1H,s).

MS(ESI)m/z: 557(M+H$^+$).

Example 136

N-[(3R*,4S*)-4-{[(5-Chloroindol-2-yl)carbonyl]amino}-1-(3,3-dimethylbutanoyl)piperidin-3-yl]-5-methyl-4,5,6,7-tetrahydrothiazolo[5,4-c]pyridine-2-carboxamide hydrochloride

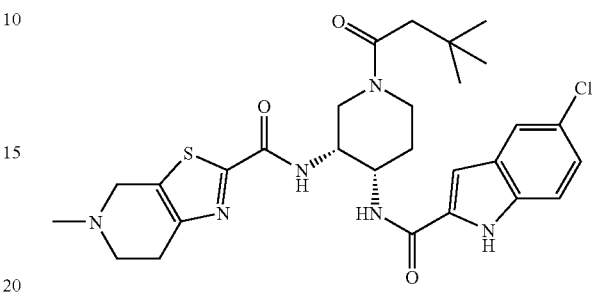

The title compound was obtained from the compound obtained in Example 0.118 and tert-butylacetyl chloride in a similar manner to Example 100.

Melting point: 260-265° C. (decomposed)

$^1$H-NMR (DMSO-d$_6$) δ: 0.91, 1.04(total 9H, each s), 1.68-1.82(1H,m), 1.93-2.40(3H,m), 2.91(3H,s), 3.00-3.20(2H,m), 3.20-4.80(10H,m), 7.08(1H,s), 7.17(1H,dd,J=8.7, 1.2 Hz), 7.41(1H,d,J=8.7 Hz), 7.69(1H,d,J=7.6 Hz), 7.93-8.18(1H,m), 8.38-8.45(1H,m), 10.95-11.30(1H,m), 11.80-11.90(1H,m).

MS(ESI)m/z: 571(M+H$^+$).

Example 137

N-[(3R*,4S*)-4-[(5-Chloroindol-2-yl)carbonyl]amino}-1-(2,2,2-trifluoroacetyl)piperidin-3-yl]-5-methyl-4,5,6,7-tetrahydrothiazolo[5,4-c]pyridine-2-carboxamide hydrochloride

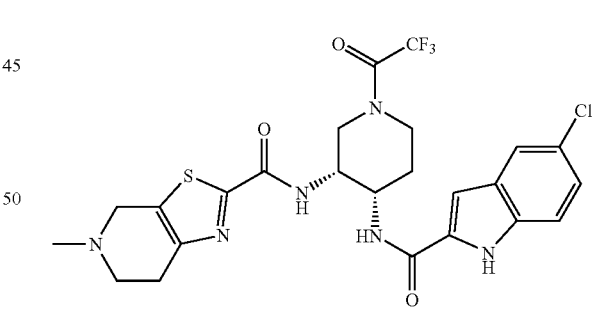

The title compound was obtained from the compound obtained in Example 118 and trifluoroacetic anhydride in a similar manner to Example 100.

Melting point: 262-267° C. (decomposed)

$^1$H-NMR (DMSO-d$_6$) δ: 1.82-1.98(1H,m), 2.05-2.21(1H,m), 2.89(3H,s), 3.05-3.20(2H,m), 3.40-3.75(4H,m), 3.85-3.95(1H,m), 4.00-4.07(1H,m), 4.20-4.70(4H,m), 7.10(1H,s), 7.18(1H,dd,J=8.6, 1.9 Hz), 7.41(1H,d,J=8.6 Hz), 7.72(1H,s), 8.47(1H,dd,J=22.4, 7.9 Hz), 8.60(1H,br), 11.08(1H,br.s), 11.87(1H,s).

MS(ESI)m/z: 569(M+H$^+$).

Example 138

N-[(3R*,4S*)-4-{[(5-Chloroindol-2-yl)carbonyl]amino}-1-(cyclopropylcarbonyl)piperidin-3-yl]-5-methyl-4,5,6,7-tetrahydrothiazolo[5,4-c]pyridine-2-carboxamide hydrochloride

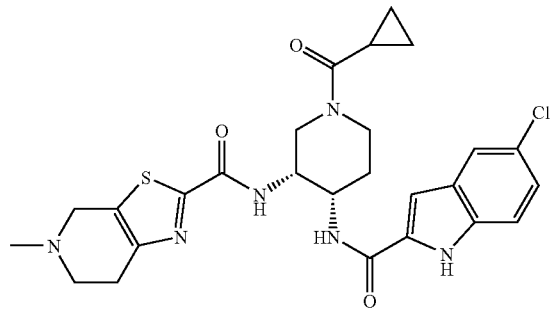

The title compound was obtained from the compound obtained in Example 118 and cyclopropanecarbonyl chloride in a similar manner to Example 100.

Melting point: 280-286° C. (decomposed)

$^1$H-NMR (DMSO-d$_6$) δ: 0.25-0.80(4H,m), 1.65-2.15(4H,m), 2.91(3H,s), 2.90-3.20(3H,m), 3.35-3.70(2H,m), 4.00-4.80(6H,m), 7.06(1H,s), 7.18(1H,d,J=8.8 Hz), 7.42(1H,d,J=8.7 Hz), 7.71(1H,s), 8.18(1H,br.s), 8.40, 8.48(total 1H, each br.s), 11.11(1H,br.s), 11.85(1H,s).

MS(ESI)m/z: 542(M+H$^+$).

Example 139

N-((3R*,4S*)-4-{[(5-Chloroindol-2-yl)carbonyl]amino}-1-(cyclobutylcarbonyl)piperidin-3-yl]-5-methyl-4,5,6,7-tetrahydrothiazolo[5,4-c]pyridine-2-carboxamide hydrochloride

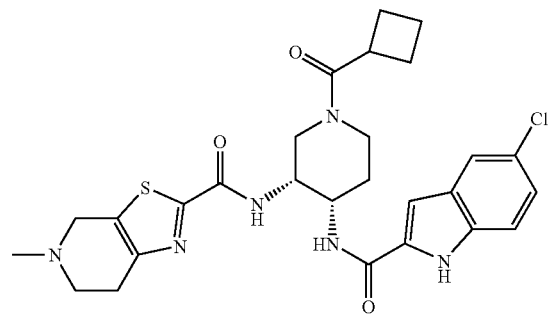

The title compound was obtained from the compound obtained in Example 118 and cyclobutanecarbonyl chloride in a similar manner to Example 100.

Melting point: 271-275° C. (decomposed)

$^1$H-NMR (DMSO-d$_6$) δ: 1.60-2.30(8H,m), 2.89(3H,s), 3.12(2H,br.s), 3.20-3.75(6H,m), 3.75-3.90(1H,m), 4.05-4.80(4H,m), 7.08(1H,s), 7.15(1H,dd,J=9.0, 2.0 Hz), 7.39(1H,d,J=9.0 Hz), 7.68(1H,d,J=2.0 Hz), 8.15(1H,br.s), 8.39(1H,br), 11.19(1H,br.s), 11.84(1H,s).

MS(ESI)m/z: 555(M+H$^+$).

Example 140

N-[(3R*,4S*)-4-{[(5-Chloroindol-2-yl)carbonyl]amino}-1-(cyclopentylcarbonyl)piperidin-3-yl]-5-methyl-4,5,6,7-tetrahydrothiazolo[5,4-c]pyridine-2-carboxamide hydrochloride

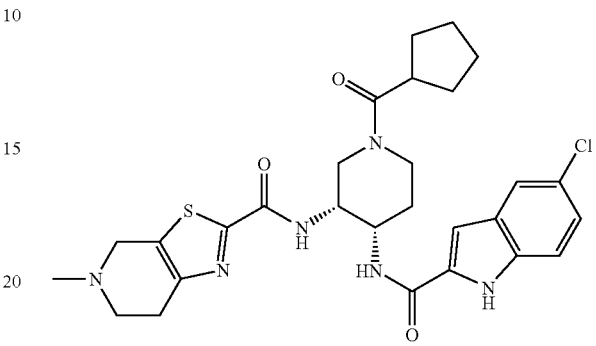

The title compound was obtained from the compound obtained in Example 118 and cyclopentanecarbonyl chloride in a similar manner to Example 100.

Melting point: 254-260° C. (decomposed).

$^1$H-NMR (DMSO-d$_6$) δ: 1.30-2.10(10H,m), 2.90(3H,s), 3.00-3.20(2H,m), 3.20-3.75(5H,m), 3.80-4.80(6H,m), 7.09(1H,s), 7.17(1H,dd,J=8.7, 2.0 Hz), 7.42(1H,d,J=8.7 Hz), 7.71(1H,s), 7.95-8.30(1H,m), 8.35-8.50(1H,m), 11.23(1H,br.s), 11.85(1H,s).

MS(ESI)m/z: 569(M+H$^+$).

Example 141

2-((3R*,4S*)-4-{[(5-Chloroindol-2-yl)carbonyl]amino}-3-{[(5-methyl-4,5,6,7-tetrahydrothiazolo[5,4-c]pyridin-2-yl)carbonyl]amino}piperidin-1-yl)-2-oxoethyl acetate

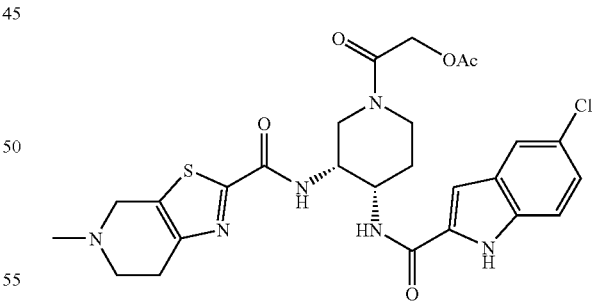

The title compound was obtained from the compound obtained in Example 118 and acetoxyacetyl chloride in a similar manner to Example 100.

$^1$H-NMR (CDCl$_3$) δ: 1.70-2.00(1H,m), 2.05-2.48(3H,m), 2.51(3H,s), 2.70-3.05(4H,m), 3.05-4.10(5H,m), 4.20-4.48(1H,m), 4.50-5.10(4H,m), 6.87(1H,br.s), 7.10-7.82(4H,m), 7.32(1H,d,J=8.8 Hz), 8.35(1H,br.s), 9.34, 9.45(total 1H, each br.s).

MS(ESI)m/z: 573(M+H$^+$).

Example 142

N-((3R*,4S*)-4-{[(5-Chloroindol-2-yl)carbonyl]amino}-1-glycoloylpiperidin-3-yl)-5-methyl-4,5,6,7-tetrahydrothiazolo[5,4-c]pyridine-2-carboxamide hydrochloride

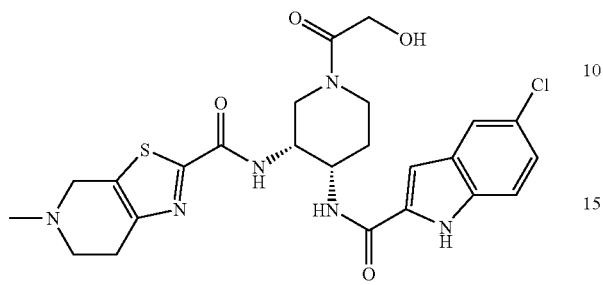

The compound (301.8 mg) obtained in Example 141 was dissolved in tetrahydrofuran (10 mL), and 1N aqueous sodium hydroxide (0.53 mL) was added, followed by stirring at room temperature for 18 hours. Water was added to the reaction mixture, and the mixture was extracted with methylene chloride. The resultant organic layer was successively washed with water and saturated brine and dried over sodium sulfate anhydrate. The solvent was distilled away under reduced pressure, the residue was purified by silica gel column chromatography (methylene chloride:methanol=20:1-10:1), and the solvent was distilled away under reduced pressure. The thus-obtained purified product was dissolved in ethanol (3 mL) and methylene chloride (2 mL), and 1N HCl in ethanol (0.40 mL) was added thereto, followed by stirring for 30 minutes. The solvent was distilled away under reduced pressure, and the residue was solidified with diethyl ether to give the title compound (195 mg).

Melting point: 216-230° C. (decomposed)

$^1$H-NMR (DMSO-d$_6$) δ: 1.70-1.80(1H,m), 1.88-2.10(2H,m), 2.68(3H,s), 3.18(2H,s), 3.08-3.70(5H,m), 3.80-3.95(1H,m), 4.00-4.25(3H,m), 4.25-4.50(2H,m), 4.50-4.65(1H,m), 7.09(1H,d,J=11.0 Hz), 7.17(1H,dd,J=8.8, 2.0 Hz), 7.42(1H,d,J=8.8 Hz), 7.71(1H,s), 8.33(1H,br.s), 8.35-8.50(1H,m), 10.80-11.30(1H,br.s), 11.84(1H,br.s).

Example 143

N-[(3R*,4S*)-4-{[(5-Chloroindol-2-yl)carbonyl]amino}-1-(2-methoxyacetyl)piperidin-3-yl]-5-methyl-4,5,6,7-tetrahydrothiazolo[5,4-c]pyridine-2-carboxamide hydrochloride

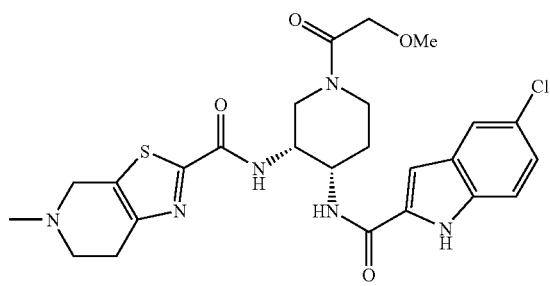

The title compound was obtained from the compound obtained in Example 118 in a similar manner to Example 100.

Melting point: 214-228° C. (decomposed).

$^1$H-NMR (DMSO-d$_6$) δ: 1.70-1.80(1H,m), 1.85-2.05(1H,m), 2.90(3H,s), 3.00-3.20(2H,m), 3.16(3H,s), 3.22-3.82(7H,m), 3.88-4.80(5H,m), 7.09(1H,d,J=9.0 Hz), 7.17(1H,dd, J=8.8, 1.9 Hz), 7.42(1H,d,J=8.8 Hz), 7.70(1H,d,J=1.9 Hz), 8.29(1H,br.s), 8.40-8.50(1H,m), 11.34(1H,br.s), 11.86(1H,s).

MS(ESI)m/z: 545(M+H)$^+$.

Example 144

N-[(3R*,4S*)-4-{[(5-Fluoroindol-2-yl)carbonyl]amino}-1-(2-methoxyacetyl)piperidin-3-yl]-5-methyl-4,5,6,7-tetrahydrothiazolo[5,4-c]pyridine-2-carboxamide hydrochloride

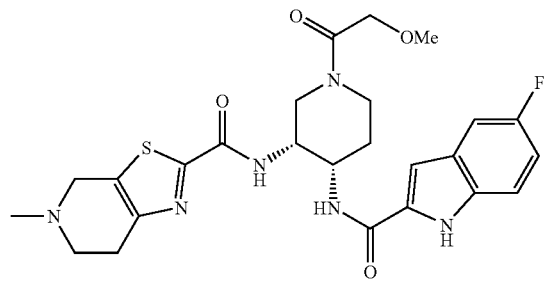

The title compound was obtained from the compound obtained in Example 122 and methoxyacetyl chloride in a similar manner to Example 100.

Melting point: 190-208° C. (decomposed)

$^1$H-NMR (DMSO-d$_6$) δ: 1.70-1.83(1H,br), 1.85-2.10(1H,m), 2.91(3H,s), 3.00-3.55(10H,m), 3.62-3.85(1H,m), 3.90-4.50(6H,m), 4.63-4.78(1H,br), 7.04(1H,td,J=9.4, 2.4 Hz), 7.07-7.13(1H,br), 7.37-7.44(1H,m), 8.16-8.49(2H,m), 11.30-11.70(1H,br), 11.72-11.80(1H,br).

MS(FAB)m/z: 529(M+H$^+$).

Example 145

N-((3R*,4S*)-1-(3-{tert-butyl(diphenyl)silyl}oxy)-2,2-dimethylpropanoyl)-4-{[(5-chloroindol-2-yl)carbonyl]-amino}piperidin-3-yl)-5-methyl-4,5,6,7-tetrahydrothiazolo[5,4-c]pyridine-2-carboxamide

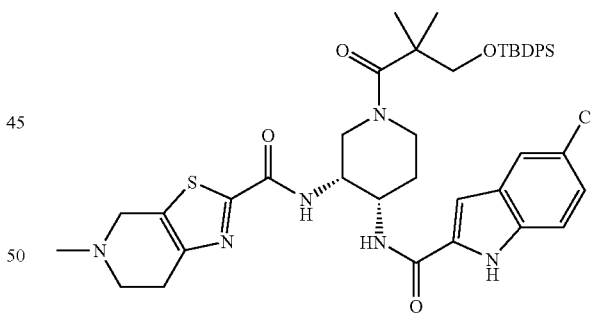

Thionyl chloride (3.0 mL) and a catalytic amount of dimethylformamide were added to a solution of the compound (261 mg) obtained in Referential Example 158 in chloroform (10 mL), and the mixture was stirred overnight at 60° C. The reaction mixture was concentrated under reduced pressure, thereby giving a yellow oil. The title compound (241 mL) was obtained from this product and the compound (200 mg) obtained in Example 118 in a similar manner to Example 100.

Melting point: 153° C.

$^1$H-NMR (CDCl$_3$) δ: 1.07(9H,s), 1.39(6H,d,J=3.9 Hz), 1.57(1H,br.s), 2.26(1H,d,J=10.7 Hz), 2.57(3H,s), 2.86(4H,s), 2.97-3.01(2H,m), 3.78(4H,s), 4.20(1H,br.s), 4.33(1H,d,J=13 Hz), 4.42(1H,br.s), 4.67(1H,d,J=13 Hz), 6.88(1H,s), 7.20-7.23(1H,m), 7.32-7.46(7H,m), 7.64-7.65(6H,m), 7.86(1H,d,J=6.8 Hz), 8.23(1H,s), 9.10(1H,s).

Example 146

N-[(3R*,4S*)-4-{[(5-chloroindol-2-yl)carbonyl]amino}-1-(3-hydroxy-2,2-dimethylpropanoyl)piperidin-3-yl)-5-methyl-4,5,6,7-tetrahydrothiazolo[5,4-c]pyridine-2-carboxamide

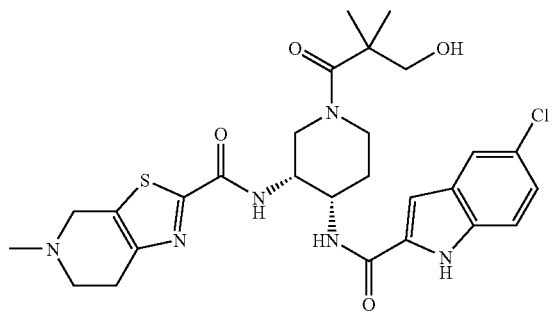

Tetrabutylammonium fluoride (1 M tetrahydrofuran solution, 0.594 mL) was added to a solution of the compound (241 mg) obtained in Example 145 in tetrahydrofuran (30 mL) under ice cooling, and the mixture was stirred overnight at room temperature. The reaction mixture was concentrated under reduced pressure, and the resultant residue was dissolved in methylene chloride. The solution was washed with water and saturated brine and then dried over sodium sulfate anhydrate, and the solvent was distilled away under reduced pressure. The resultant residue was purified by silica gel thin layer chromatography (methylene chloride:methanol=9:1) to give the title compound (116 mg).

Melting point: 220° C. (decomposed).

$^1$H-NMR (DMSO-$d_6$) δ: 1.17(6H,d,J=8.3 Hz), 1.79(1H, br.s), 1.91-1.97(1H,m), 2.49(3H,s), 2.87(4H,s), 3.35-3.50 (4H,m), 3.81(1H,br.s), 3.97(1H,m), 4.10-4.15(1H,m), 4.32 (1H,br.s), 4.42(1H,br.s), 4.52(1H,t,J=5.7 Hz), 7.10(1H,s), 7.16-7.19(1H,m), 7.42(1H,d,J=8.8 Hz), 7.69(1H,s), 8.11(1H, d,J=8.8 Hz), 8.37(1H,d,J=7.3 Hz), 11.8(1H,s).

MS(FAB)m/z: 573(M+H$^+$).

Example 147

N-[(3R*,4S*)-4-{[(5-chloroindol-2-yl)carbonyl]amino}-1-(3-methoxy-2,2-dimethylpropanoyl)piperidin-3-yl)-5-methyl-4,5,6,7-tetrahydrothiazolo[5,4-c]pyridine-2-carboxamide

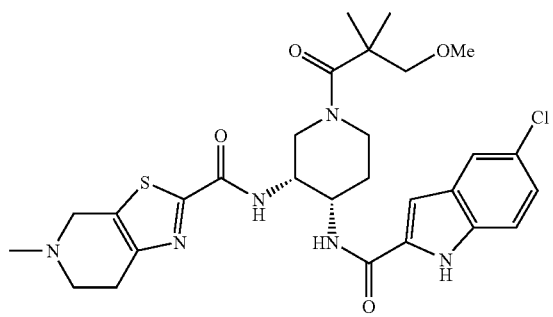

The title compound was obtained from the compound obtained in Example 118 and the compound obtained in Referential Example 160 in a similar manner to Example 145.

Melting point: 240° C. (decomposed).

$^1$H-NMR (CDCl$_3$) δ: 1.34(3H,s), 1.37(3H,s), 1.65-1.77 (1H,m), 2.33-2.37(1H,m), 2.53(3H,s), 2.82-3.29(6H,m), 3.34(3H,s), 3.41(1H,d,J=9.3 Hz), 3.56(1H,d,J=9.3 Hz), 3.76 (2H,d,J=5.9 Hz), 4.26(1H,m), 4.44-4.53(2H,m), 4.82(1H, d,J=13.7 Hz), 6.88(1H,d,J=1.5 Hz), 7.20-7.23(1H,m), 7.33 (1H,d,J=8.8 Hz), 7.64(1H,d,J=1.5 Hz), 7.90(1H,d,J=7.1 Hz), 8.22(1H,d,J=5.1 Hz), 9.18(1H,s).

MS(FAB)m/z: 587(M+H$^+$).

Example 148

2-((3R*,4S*)-4-{[(5-Chloroindol-2-yl)carbonyl]amino}-3-{[(5-methyl-4,5,6,7-tetrahydrothiazolo[5,4-c]pyridin-2-yl)carbonyl]amino}piperidin-1-yl)-1,1-dimethyl-2-oxoethyl acetate

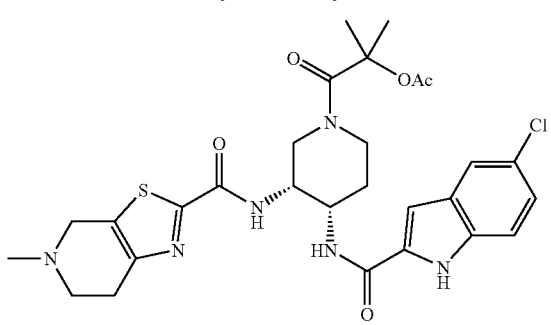

The title compound was obtained from the compound obtained in Example 118 and 2-acetoxyisobutyryl chloride in a similar manner to Example 100.

Melting point: 190° C. (decomposed).

$^1$H-NMR (CDCl$_3$) δ: 1.56-1.67(8H,m), 2.08(3H,s), 2.35 (1H,d,J=10.5 Hz), 2.52(3H,s), 2.82-2.84(2H,m), 2.90-2.96 (2H,m), 3.14(1H,br.s), 3.75(2H,s), 4.25(1H,br.s), 4.40-4.47 (1H,m), 4.54(1H,br.s), 4.80(1H,br.s), 6.86(1H,s), 7.20-7.33 (3H,m), 7.64(1H,d,J=1.7 Hz), 7.76(1H,d,J=7.3 Hz), 9.11(1H, s).

MS(FAB)m/z: 601(M+H$^+$).

Example 149

N-[(3R*,4S*)-4-{[(5-Chloroindol-2-yl)carbonyl]amino}-1-(2-hydroxy-2-methylpropanoyl)piperidin-3-yl]-5-methyl-4,5,6,7-tetrahydrothiazolo[5,4-c]pyridine-2-carboxamide

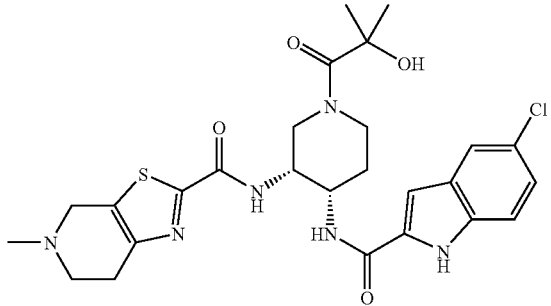

Sodium methoxide (76.8 mg) was added to a solution of the compound (190 mg) obtained in Example 148 in methanol (50 mL), and the mixture was stirred overnight at room temperature. After the reaction mixture was concentrated under reduced pressure, the resultant residue was purified by silica gel thin layer chromatography (methylene chloride:methanol=9:1) to give the title compound (130 mg).

Melting point: 190° C. (decomposed).

$^1$H-NMR (CDCl$_3$) δ: 1.53(3H,s), 1.56-1.78(5H,m), 2.34 (1H,d,J=10.5 Hz), 2.53(3H,s), 2.83-2.86(2H,m), 2.91-2.93 (2H,m), 3.30(1H,d,J=12.5 Hz), 3.75(2H,s), 4.28(1H,d,J=5.6 Hz), 4.43(1H,s), 4.65(1H,d,J=13.5 Hz), 4.95(1H,d,J=13.5 Hz), 6.92(1H,d,J=1.5 Hz), 7.20-7.23(1H,m), 7.33(1H,d, J=8.6 Hz), 7.65(1H,d,J=2.0 Hz), 8.43(1H,d,J=5.6 Hz), 9.14 (1H,s).

MS(FAB)m/z: 559(M+H$^+$).

Example 150

N-{(3R*,4S*)-4-{[(5-Chloroindol-2-yl)carbonyl]amino}-1-[(3-hydroxycyclobutyl)carbonyl]piperidin-3-yl}-5-methyl-4,5,6,7-tetrahydrothiazolo[5,4-c]pyridine-2-carboxamide hydrochloride

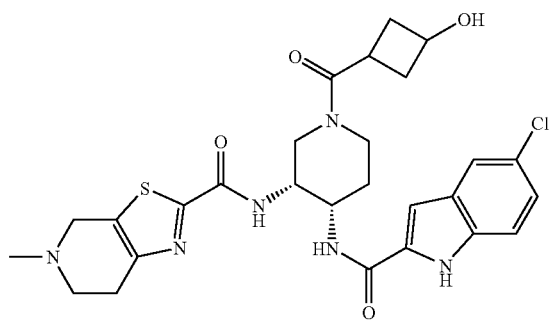

The compound (306 mg) obtained in Example 118, N-methylmorpholine (200 μl), 1-hydroxybenzotriazole monohydrate (87 mg), and 1-(3-dimethylaminopropyl)-3-ethylcarbodiimide hydrochloride (197 mg) were added to a solution of the compound (117 mg) obtained Referential Example 152 in a mixture of tetrahydrofuran (20 mL), methylene chloride (3.0 mL) and, N,N-dimethylformamide (2.0 mL), and the mixture was stirred at room temperature for 3 days. The reaction mixture was diluted with methylene chloride, and saturated aqueous sodium hydrogencarbonate was added for partitioning the mixture into two layers. The resultant organic layer was washed with saturated brine, dried over sodium sulfate anhydrate and then concentrated under reduced pressure. The resultant residue was purified by silica gel column chromatography (methylene chloride:methanol=10:1) to give a free base (207 mg) of the title compound. The free base was treated with 1N HCl in ethanol to give the title compound.

Melting point: 200° C. (decomposed).
$^1$H-NMR (DMSO-$d_6$) δ: 1.78-2.10(4H,m), 2.24-2.68(3H,m), 2.75-5.20(14H,m), 2.91(3H,s), 7.08(0.5H,s), 7.09(0.5H,s), 7.18(1H,dd,J=8.8, 2.0 Hz), 7.42(1H,d,J=8.8 Hz), 7.70(1H,d,J=2.0 Hz), 8.05-8.28(1H,br), 8.38(0.5H,br.d,J=7.3 Hz), 8.43(0.5H,br.d,J=8.3 Hz), 10.80-11.25(1H,br), 11.84(1H,br.s).
MS(ESI)m/z: 571(M+H$^+$).

Example 151

N-{(3R*,4S*)-4-{[(5-Chloroindol-2-yl)carbonyl]amino}-1-[(methoxycyclobutyl)carbonyl]piperidin-3-yl]-5-methyl-4,5,6,7-tetrahydrothiazolo[5,4-c]pyridine-2-carboxamide hydrochloride

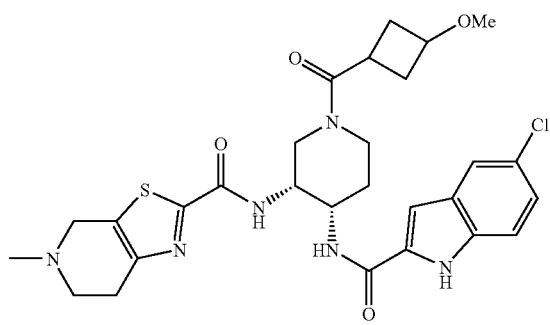

The title compound was obtained from the compound obtained in Example 118 and the compound obtained in Referential Example 154 in a similar manner to Example 150.

Melting point: 191° C. (decomposed)
$^1$H-NMR (DMSO-$d_6$) δ: 1.69-2.23(4H,m), 2.25-2.40(1H,m), 2.71-2.84(0.5H,m), 2.89-3.93(9.5H,m), 2.91(3H,s), 3.01(1H,s), 3.14(2H,s), 4.05-4.80(5H,m), 7.09(1H,s), 7.18(1H,d, J=8.4 Hz), 7.42(1H,d,J=8.4 Hz), 7.70(1H,s), 8.00-8.30(1H,br), 8.36-8.53(1H,m), 11.25-11.75(1H,br), 11.85(1H,br.s).
MS(ESI)m/z: 585(M+H$^+$).

Example 152

N-{(3R*,4S*)-4-{[(5-Chloroindol-2-yl)carbonyl]amino}-1-[3-methoxy-2-(methoxymethyl)propanoyl]piperidin-3-yl]-5-methyl-4,5,6,7-tetrahydrothiazolo[5,4-c]pyridine-2-carboxamide hydrochloride

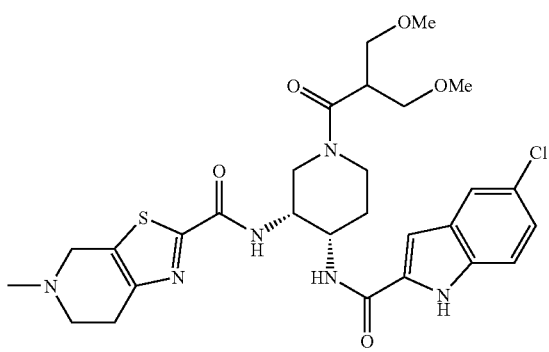

In a manner similar to that employed in Example 150, the compound obtained in Example 118 was condensed with the carboxylic acid obtained through hydrolysis of the compound obtained in Referential Example 155, to thereby give the title compound.

Melting point: 178-184° C. (decomposed).
$^1$H-NMR (DMSO-$d_6$) δ: 1.69-1.82(1H,m), 1.84-2.04(1H,m), 2.91(3H,s), 3.00-3.75(17H,m), 3.95-4.55(5H,m), 4.60-4.80(1H,m), 7.10(1H,br.s), 7.18(1H,dd,J=8.8, 2.0 Hz), 7.42(1H,d,J=8.8 Hz), 7.69(0.5H,br.s), 7.71(1H,br.s), 8.18-8.28(1H,br), 8.35-8.50(1H,br), 11.83(1H,br.s).
MS(ESI)m/z: 603(M+H$^+$).

Example 153

N-((3R*,4S*)-4-{[(5-Chloroindol-2-yl)carbonyl]amino}-1-(tetrahydro-2H-pyran-4-ylcarbonyl)piperidin-3-yl]-5-methyl-4,5,6,7-tetrahydrothiazolo[5,4-c]pyridine-2-carboxamide hydrochloride

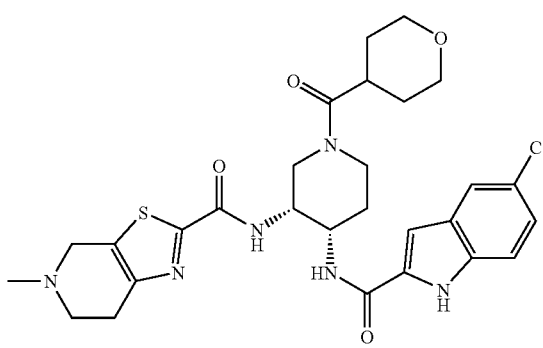

The title compound was obtained from the compound obtained in Example 118 and the compound obtained in Referential Example 156 in a similar manner to Example 150.

Melting point: 225-248° C. (decomposed).

$^1$H-NMR (DMSO-$d_6$) δ: 1.55-1.68(4H,m), 1.70-1.85(1H, m), 1.85-2.05(1H,m), 2.60-2.95(1H,m), 2.89(3H,s), 2.95-3.20(3H,m), 3.20-4.00(9H,m), 4.00-4.80(4H,m), 7.08(1H,s), 7.17(1H,dd,J=8.8, 2.0 Hz), 7.42(1H,d,J=8.8 Hz), 7.71(1H,s), 8.00-8.30(1H,m), 8.35-8.50(1H,m), 11.16(1H,br.s), 11.85(1H,s).

MS(ESI)m/z: 585(M+H$^+$).

Example 154

N-((3R*,4S*)-1-benzoyl-4-{[(5-Chloroindol-2-yl)carbonyl]amino}piperidin-3-yl]-5-methyl-4,5,6,7-tetrahydrothiazolo[5,4-c]pyridine-2-carboxamide hydrochloride

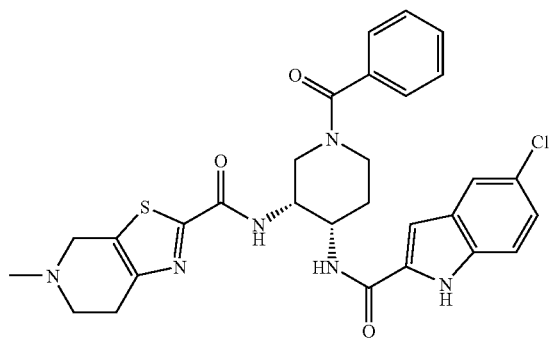

The title compound was obtained from the compound obtained in Example 118 and benzoyl chloride in a similar manner to Example 100.

Melting point: 215-225° C. (decomposed)

$^1$H-NMR (DMSO-$d_6$) δ: 1.75-1.90(1H,m), 1.90-2.20(1H, m), 2.93(3H,s), 3.10-4.00(8H,m), 4.05-4.80(4H,m), 7.00-7.60(5H,m), 7.08(1H,s), 7.16(1H,dd,J=8.8, 1.6 Hz), 7.40 (1H,d,J=8.8 Hz), 7.71(1H,d,J=1.6 Hz), 8.31(1H,br.s), 8.46 (1H,br.s), 11.39(1H,br.s), 11.86(1H,s).

MS(FAB)m/z: 577(M+H$^+$).

Example 155 tert-Butyl (3R*,4S*)-3-({[5-(2-{[tert-butyl(diphenyl) silyl]oxy}-1,1-dimethylethyl)-4,5,6,7-tetrahydrothiazolo-[5,4-c]pyridin-2-yl]carbonyl}amino)-4-{[(5-chloroindol-2-yl)carbonyl]amino}piperidine-1-carboxylate

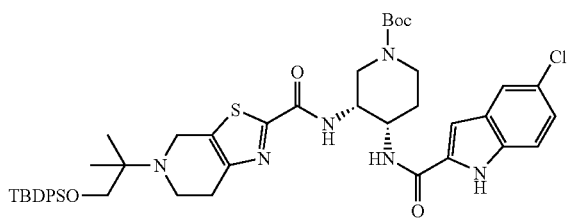

The title compound was obtained from the compound obtained in Referential Example 207 and the compound obtained in Referential Example 42 in a similar manner to Example 91.

$^1$H-NMR (DMSO-$d_6$) δ: 1.00(9H,s), 1.12(6H,s), 1.15-1.50 (9H,m), 1.63-1.75(1H,m), 1.82-2.00(1H,m), 2.60-2.80(3H, m), 2.83-2.95(2H,m), 3.12-3.30(1H,m), 3.30(2H,s), 3.58(2H,s), 3.85-4.10(2H,m), 4.19(1H,br.s), 4.37(1H,br.s), 7.04(1H,s), 7.16(1H,d,J=9.0 Hz), 7.30-7.50(7H,m), 7.50-7.65(4H,m), 7.70(1H,s), 7.99(1H,d,J=6.8 Hz), 8.45(1H,br.s), 11.82(1H,s).

MS(ESI)m/z: 869(M+H)+

Example 156

5-(2-{[tert-Butyl(diphenyl)silyl]oxy}-1,1-dimethylethyl)-N-((3R*,4S*)-4-{[(5-chloroindol-2-yl)carbonyl]amino}piperidin-3-yl)-4,5,6,7-tetrahydrothiazolo[5,4-c]pyridine-2-carboxamide dihydrochloride

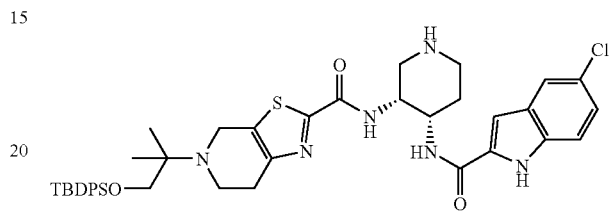

The compound obtained in Example 155 was treated in a manner similar to that employed in Example 95, to thereby give the title compound.

$^1$H-NMR (DMSO-$d_6$) δ: 1.04(9H,s), 1.43, 1.48(total 6H, each s), 1.85-2.00(1H,m), 2.05-2.20(1H,m), 2.95-3.20(2H, m), 3.25-3.60(6H,m), 3.80-3.90(1H,m), 3.95-4.05(1H,m), 4.45-4.55(1H,m), 4.60-4.85(3H,m), 7.10-7.20(2H,m), 7.35-7.55(7H,m), 7.55-7.75(5H,m), 8.52(1H,dd,J=14.4, 7.8 Hz), 8.93(1H,br), 9.20-9.40(2H,m), 11.30-11.50(1H,m), 11.87, 11.92(total 1H, each s).

MS(ESI)m/z: 769(M+H$^+$).

Example 157

5-(2-{[tert-Butyl(diphenyl)silyl]oxy}-1,1-dimethylethyl)-N-[(3R*,4S*)-4-{[(5-chloroindol-2-yl)carbonyl]amino}-1-(2-methoxyacetyl)piperidin-3-yl]-4,5,6,7-tetrahydrothiazolo-[5,4-c]pyridine-2-carboxamide

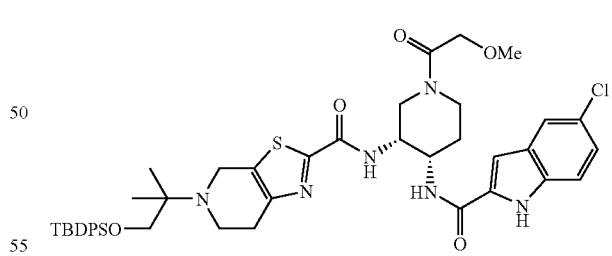

The title compound was obtained from the compound obtained in Example 156 and methoxyacetyl chloride in a similar manner to Example 100.

$^1$H-NMR (CDCl$_3$) δ: 1.07(9H,s), 1.20(6H,s), 1.60-1.85 (1H,m), 2.25-2.40(1H,m), 2.36(2H,s), 2.70-3.20(4H,m), 3.20-3.55(4H,m), 3.55-3.70(2H,m), 3.95-4.10(3H,m), 4.10-4.90(4H,m), 6.90(1H,d,J=1.5 Hz), 7.15-7.30(2H,m), 7.30-7.50(6H,m), 7.60-7.70(5H,m), 8.15-8.22(1H,m), 8.46(1H,d, J=5.1 Hz), 9.28(1H,s).

MS(ESI)m/z: 842(M+H$^+$).

Example 158

N-[(3R*,4S*)-4-{[(5-Chloroindol-2-yl)carbonyl]
amino}-1-(2-methoxyacetyl)piperidin-3-yl]-5-(2-
hydroxy-1,1-dimethylethyl)-4,5,6,7-tetrahydrothia-
zolo[5,4-c]pyridine-2-carboxamide hydrochloride

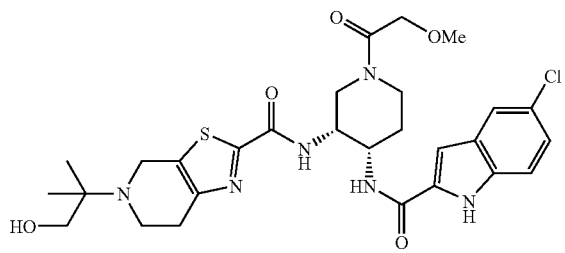

The title compound was obtained from the compound obtained in Example 157 in a similar manner to Example 146.

Melting point: 221-232° C. (decomposed).

$^1$H-NMR (DMSO-$d_6$) δ: 1.32(3H,s), 1.40(3H,s), 1.70-1.85 (1H,m), 1.85-2.10(1H,m), 2.60-3.35(8H,m), 3.40-3.82(3H, m), 3.85-4.05(3H,m), 4.05-4.35(2H,m), 4.50-4.60(1H,m), 4.55-4.80(2H,m), 5.75-5.85(1H,m), 7.08(1H,br.s), 7.17(1H, d,J=8.8 Hz), 7.41(1H,d,J=8.8 Hz), 7.71(1H,s), 8.20-8.35(1H, m), 8.40-8.55(1H,m), 10.00-10.35(1H,m), 11.87(1H,s).

MS(ESI)m/z: 603(M+H$^+$).

Example 159 tert-Butyl (3R*,4S*)-4-{[(5-fluoroindol-2-yl)carbo-
nyl]-amino}-3-{[(5-isopropyl-4,5,6,7-tetrahydrothia-
zolo[5,4-c]-pyridin-2-yl)carbonyl]amino}piperidine-
1-carboxylate

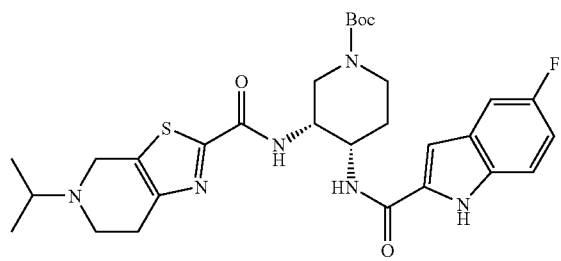

The title compound was obtained from the compound obtained in Referential Example 209 and the compound obtained in Referential Example 148 in a similar manner to Example 91.

$^1$H-NMR (CDCl$_3$) δ: 1.16(6H,d,J=6.6 Hz), 1.53(9H,s), 1.65-1.80(1H,m), 2.23-2.32(1H,m), 2.80-3.10(6H,m), 3.10-3.25(1H,m), 3.80-3.90(2H,m), 4.00-4.50(4H,m), 6.91(1H,s), 6.95-7.05(1H,m), 7.25-7.40(2H,m), 7.74(1H,br.s), 8.21(1H, br.s), 9.30(1H,s).

MS(ESI)m/z: 585(M+H$^+$).

Example 160

N-((3R*,4S*)-4-{[(5-Fluoroindol-2-yl)carbonyl]
amino}-piperidin-3-yl)-5-isopropyl-4,5,6,7-tetrahy-
drothiazolo-[5,4-c]pyridine-2-carboxamide dihydro-
chloride

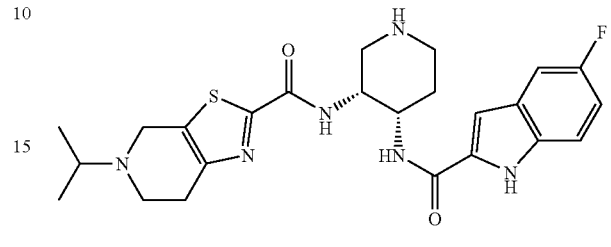

The compound obtained in Example 159 was treated in a manner similar to that employed in Example 95, to thereby give the title compound.

$^1$H-NMR (DMSO-$d_6$) δ: 1.28-1.40(6H,m), 1.85-2.00(1H, m), 2.05-2.20(1H,m), 2.40-2.60(1H,m), 2.95-3.90(8H,m), 4.40-4.55(2H,m), 4.60-4.75(2H,m), 7.00-7.20(2H,m), 7.30-7.50(2H,m), 8.45-8.60(1H,m), 8.85-9.05(1H,m), 9.05-9.50 (2H,m), 11.60-11.90(2H,m).

MS(ESI)m/z: 485(M+H$^+$).

Example 161

N-[(3R*,4S*)-4-{[(5-Fluoroindol-2-yl)carbonyl]
amino}-1-(2-methoxyacetyl)piperidin-3-yl]-5-iso-
propyl-4,5,6,7-tetrahydrothiazolo[5,4-c]pyridine-2-
carboxamide hydrochloride

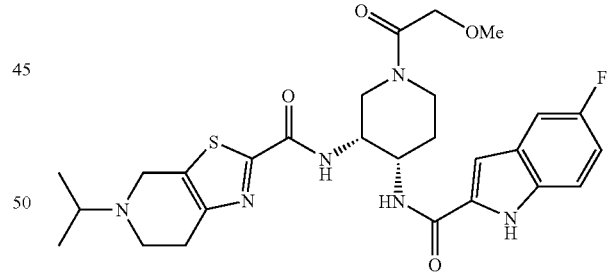

The title compound was obtained from the compound obtained in Example 160 and methoxyacetyl chloride in a similar manner to Example 100.

Melting point: 214-228° C. (decomposed).

$^1$H-NMR (DMSO-$d_6$) δ: 1.25-1.40(6H,m), 1.68-1.82(1H, m), 1.85-2.10(1H,m), 2.90-3.60(8H,m), 3.60-3.85(2H,m), 3.85-4.40(5H,m), 4.40-4.55(2H,m), 4.60-4.75(1H,m), 7.00-7.15(2H,m), 7.35-7.50(2H,m), 8.15-8.50(2H,m), 10.80-11.30(1H,m), 11.73(1H,d,J=6.6 Hz).

MS(ESI)m/z: 557(M+H$^+$).

Example 162

N-{(3R*,4S*)-4-{[(5-Chloroindol-2-yl)carbonyl]amino}-1-[(dimethylamino)carbonyl]piperidin-3-yl}-5-methyl-4,5,6,7-tetrahydrothiazolo[5,4-c]pyridine-2-carboxamide hydrochloride

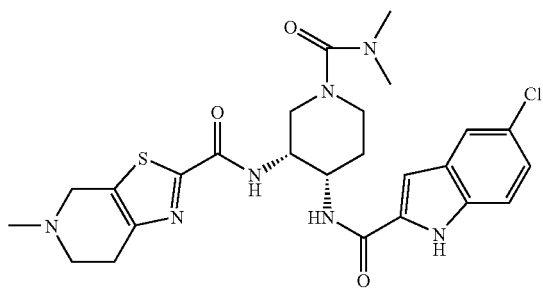

The title compound was obtained from the compound obtained in Example 118 and N,N-dimethylcarbamoyl chloride in a similar manner to Example 100.

Melting point: 267-270° C. (decomposed)

$^1$H-NMR (DMSO-d$_6$) δ: 1.65-1.78(1H,m), 1.97-2.10(1H,m), 2.70(6H,s), 2.90(3H,s), 2.95-3.80(8H,m), 4.25-4.80(4H,m), 7.08(1H,s), 7.16(1H,dd,J=8.8, 1.8 Hz), 7.41(1H,d,J=8.8 Hz), 7.70(1H,s), 8.31(1H,br.s), 8.40(1H,d,J=7.3 Hz), 11.15-11.60(1H,m), 11.82(1H,s).

MS(ESI)m/z: 544(M+H$^+$).

Example 163

N-{(3R*,4S*)-4{[(5-Chloroindol-2-yl)carbonyl]amino}-1-[(ethylamino)carbonyl]piperidin-3-yl}-5-methyl-4,5,6,7-tetrahydrothiazolo[5,4-c]pyridine-2-carboxamide hydrochloride

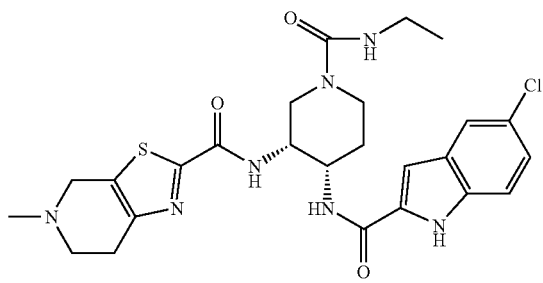

The title compound was obtained from the compound obtained in Example 118 and ethyl isocyanate in a similar manner to Example 100.

Melting point: 221-235° C. (decomposed)

$^1$H-NMR (DMSO-d$_6$) δ: 0.98(3H,t,J=7.1 Hz), 1.60-1.70(1H,m), 1.80-1.95(1H,m), 2.90(3H,s), 2.95-3.40(6H,m), 3.40-4.00(4H,m), 4.25-4.80(4H,m), 6.60-6.80(1H,m), 7.09(1H,s), 7.16(1H,dd,J=8.8, 1.9 Hz), 7.41(1H,d,J=8.8 Hz), 7.68(1H,d,J=1.9 Hz), 8.02(1H,br.s), 8.35(1H,d,J=7.1 Hz), 11.20-11.70(1H,m), 11.82(1H,s).

MS(FAB)m/z: 544(M+H$^+$)

Example 164

N-((3R*,4S*)-1-[(tert-Butylamino)carbonyl]-4-{[(5-chloroindol-2-yl)carbonyl]amino}piperidin-3-yl)-5-methyl-4,5,6,7-tetrahydrothiazolo[5,4-c]pyridine-2-carboxamide hydrochloride

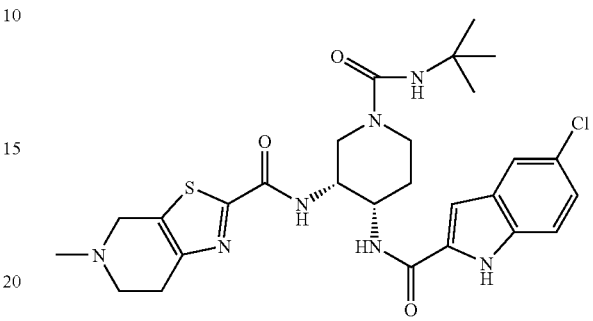

The title compound was obtained from the compound obtained in Example 118 and tert-butyl isocyanate in a similar manner to Example 100.

Melting point: 236-238° C. (decomposed)

$^1$H-NMR (DMSO-d$_6$) δ: 1.21(9H,s), 1.60-1.70(1H,m), 1.80-1.90(1H,m), 2.87(3H,s), 3.00-3.40(6H,m), 3.49(1H,br.s), 3.80-3.90(1H,m), 3.90-4.00(1H,m), 4.20-4.35(2H,m), 4.47(1H,br.s), 5.90(1H,s), 7.06(1H,s), 7.16(1H,dd,J=8.8, 1.9 Hz), 7.41(1H,d,J=8.8 Hz), 7.67(1H,d,J=1.9 Hz), 8.04(1H,d,J=6.8 Hz), 8.34(1H,d,J=7.3 Hz), 11.22(1H,br.s), 11.79(1H,s).

MS(FAB)m/z: 572(M+H$^+$).

Example 165

Methyl 2-((3R*,4S*)-4-{[(5-chloroindol-2-yl)carbonyl]amino}-3-{[(5-methyl-4,5,6,7-tetrahydrothiazolo[5,4-c]-pyridin-2-yl)carbonyl]amino}piperidin-3-yl)acetate dihydrochloride

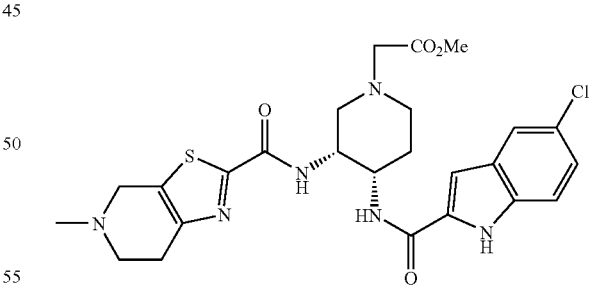

The title compound was obtained from the compound obtained in Example 118 and methyl bromoacetate in a similar manner to Example 102.

Melting point: 253-255° C. (decomposed).

$^1$H-NMR (DMSO-d$_6$, 80° C.) δ: 1.95-2.10(1H,m), 2.10-2.25(1H,m), 2.88(3H,s), 3.00-3.73(8H,m), 3.75(3H,s), 3.97-4.15(2H,m), 4.30-4.80(4H,m), 7.08-7.20(2H,m), 7.44(1H,d,J=8.6 Hz), 7.63(1H,d,J=2.0 Hz), 8.42(1H,d,J=7.3 Hz), 8.62(1H,br.s), 11.82(1H,br.s).

MS(ESI)m/z: 545(M+H$^+$).

Example 166

2-((3R*,4S*)-4-{[(5-Chloroindol-2-yl)carbonyl]amino}-3-{[(5-methyl-4,5,6,7-tetrahydrothiazolo[5,4-c]pyridin-2-yl)carbonyl]amino}piperidin-3-yl)acetic acid hydrochloride

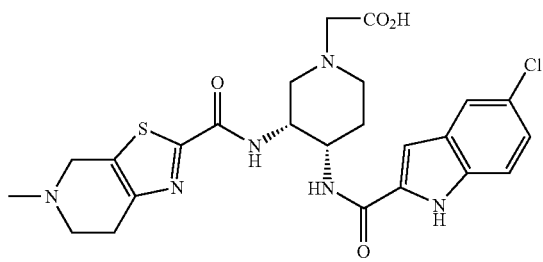

The compound obtained in Example 165 was treated in a manner similar to that employed in Example 101, to thereby give the title compound.

Melting point: 234-240° C. (decomposed)

$^1$H-NMR (DMSO-d$_6$) δ: 1.75-1.95(1H,m), 2.05-2.20(1H,m), 2.88(3H,s), 2.95-3.90(10H,m), 4.20-4.70(4H,m), 7.11(1H,s), 7.16(1H,dd,J=8.8, 2.0 Hz), 7.41(1H,d,J=8.8 Hz), 7.66(1H,d,J=2.0 Hz), 8.46(1H,br.d,J=7.8 Hz), 8.65(1H,br.s), 11.60-12.70(2H,br.s), 11.91(1H,br.s).

Example 167

N-[(3R*,4S*)-4-{[(5-Chloroindol-2-yl)carbonyl]amino}-1-(2-methoxyethyl)piperidin-3-yl]-5-methyl-4,5,6,7-tetrahydrothiazolo[5,4-c]pyridine-2-carboxamide dihydrochloride

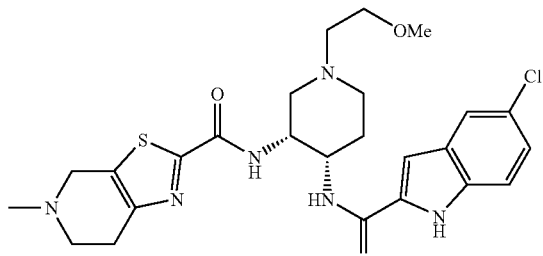

The title compound was obtained from the compound obtained in Example 118 and 2-bromoethyl methyl ether in a similar manner to Example 102 (NMR was measured in the form of a free base).

Melting point: 238-242° C. (decomposed).

$^1$H-NMR (CDCl$_3$) δ: 1.75-1.83(2H,m), 2.27-2.39(2H,m), 2.52(3H,s), 2.60-2.66(1H,m), 2.69-2.75(1H,m), 2.81-2.90 (2H,m), 2.96-3.07(2H,m), 3.41(3H,s), 3.53-3.60(2H,m), 3.75(each 1H,AB type d,J=15.5 Hz), 4.02-4.05(1H,m), 4.40 (1H,br), 6.88(1H,d,J=1.5 Hz), 7.18-7.21(1H,m), 7.31-7.33 (1H,m), 7.63(1H,d,J=1.5 Hz), 8.17(1H,d,J=5.0 Hz), 8.26(1H, d,J=7.0 Hz), 9.30(1H,br.s).

MS(FAB)m/z: 531(M+H$^+$).

Example 168

N-[(3R*,4S*)-4-{[(5-Chloroindol-2-yl)carbonyl]amino}-1-(2-fluoroethyl)piperidin-3-yl]-5-methyl-4,5,6,7-tetrahydrothiazolo[5,4-c]pyridine-2-carboxamide dihydrochloride

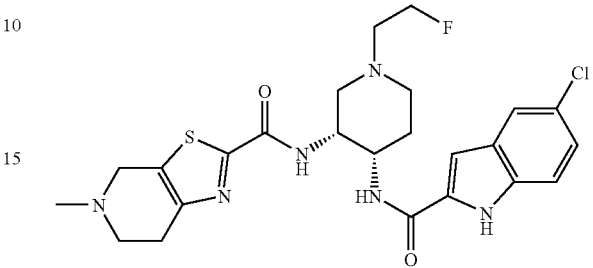

The title compound was obtained from the compound obtained in Example 118 and 2-fluoroethyl bromide in a similar manner to Example 102 (NMR was measured in the form of a free base).

Melting point: 228-233° C. (decomposed)

$^1$H-NMR (CDCl$_3$) δ: 1.77(2H,dq,J=12.5, 4.0 Hz), 2.28-2.32(1H,m), 2.41(1H,t,J=12.5 Hz), 2.52(3H,s), 2.65(1H,d,J=10.5 Hz), 2.76-2.81(1H,m), 2.83-2.86(3H,m), 2.98-3.05 (3H,m), 3.75(each 1H,AB type d,J=15.5 Hz), 4.02-4.08(1H, m), 4.45(1H,br), 4.54-4.59(1H,m), 4.64-4.70(1H,m), 6.87 (1H,d,J=1.5 Hz), 7.19-7.22(1H,m), 7.32(1H,d,J=8.5 Hz), 7.64(1H,d,J=2.0 Hz), 8.11(1H,d,J=5.5 Hz), 8.20(1H,d,J=7.3 Hz), 9.30(1H,br).

MS(FAB)m/z: 519(M+H$^+$).

Example 169

N-((3R,4S)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

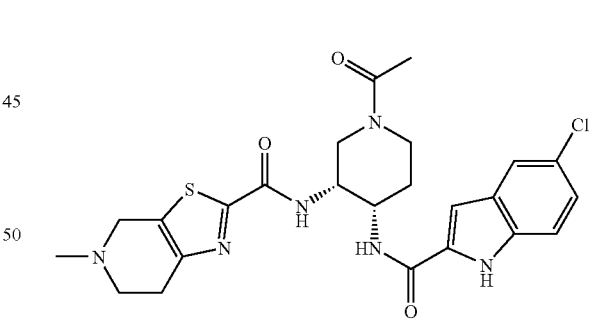

4N HCl-dioxane (7.0 mL) was added to a dioxane solution (15 mL) of the compound (630 mg) obtained in Referential Example 214, and the mixture was stirred at room temperature for 1 hour. The reaction mixture was concentrated under reduced pressure. The thus-obtained yellow solids (590 mg) and the compound (379 mg) obtained in Referential Example 10 were used to give a free base (330 mg) of the title compound in a similar manner to Example 91. This free base was treated with HCl in ethanol to give the title compound (NMR was measured in the form of a free base).

Melting point: 202-222° C. (decomposed).

$^1$H-NMR (DMSO-d$_6$) δ: 1.65-1.85(1H,m), 1.87, 2.06(total 3H, each s), 1.88-2.10(1H,m), 2.37(3H,s), 2.65-2.77(2H,m), 2.79-2.89(2H,m), 2.99-3.09(0.5H,m), 3.30-3.52(2H,m), 3.64

(2H,s), 3.70-3.80(0.5H,m), 3.96-4.21(2H,m), 4.27(1H,br.s), 4.35-4.48(1H,m), 7.07, 7.11(total 1H, each s), 7.18(1H,d, J=8.8 Hz), 7.42(1H,d,J=8.8 Hz), 7.71(1H,s), 8.16-8.22(1H, m), 8.37, 8.46(total 1H, each d,J=7.8 Hz), 11.81, 11.83(total 1H, each s).

MS(ESI)m/z: 515(M+H⁺).

$[\alpha]^{25}_D$=−56.0° (c=0.50, methanol).

Example 170

N-((3R,4R)-1-Acetyl-4-{[(5-chloroindol-2-yl)carbonyl]-amino}piperidin-3-yl)-5-methyl-4,5,6,7-tetrahydrothiazolo[5,4-c]pyridine-2-carboxamide hydrochloride

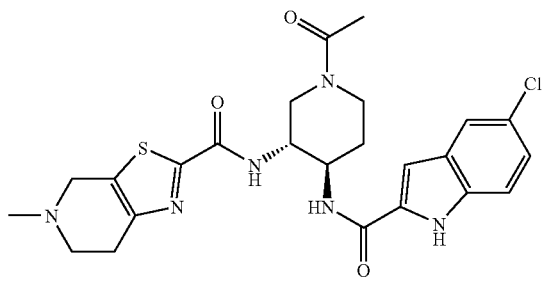

The title compound was obtained from the compound obtained in Referential Example 219 and the compound obtained in Referential Example 10 in a similar manner to Example 169.

Melting point: 221-238° C.

¹H-NMR (DMSO-d₆) δ: 1.45-1.56(0.5H,m), 1.60-1.70 (0.5H,m), 1.89-2.01(1H,m), 2.05(3H,s), 2.51-2.67(1H,m), 2.88(3H,s), 3.00-3.22(3H,m), 3.31-3.40(3H,m), 3.56-3.67 (0.5H,m), 3.78-4.02(1.5H,m), 4.22-4.44(2H,m), 4.56-4.72 (1H,m), 7.02(1H,s), 7.15(1H,dd,J=8.8, 2.0 Hz), 7.37(1H,d, J=8.8 Hz), 7.67(1H,d,J=2.0 Hz), 8.42(1H,d,J=9.8 Hz), 8.67-8.78(1H,m), 11.02-11.14(1H,m), 11.72(0.5H,s), 11.74(0.5H, s).

MS(FAB)m/z: 515(M+H⁺).

$[\alpha]^{25}_D$=−105.4° (c=0.58, methanol)

Example 171

N-[(3R,4S)-4-{[(5-Chloroindol-2-yl)carbonyl] amino}-1-(2-methoxyacetyl)piperidin-3-yl]-5-methyl-4,5,6,7-tetrahydrothiazolo[5,4-c]pyridine-2-carboxamide hydrochloride

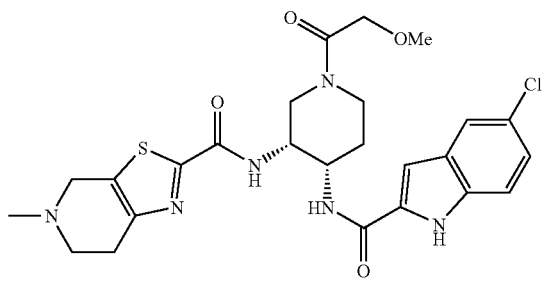

The title compound was obtained from the compound obtained in Referential Example 221 in a similar manner to Example 169.

Melting point: 207-220° C. (decomposed)

¹H-NMR (DMSO-d₆) δ: 1.70-1.80(1H,m), 1.85-2.05(1H, m), 2.90(3H,s), 3.00-3.20(2H,m), 3.16(3H,s), 3.22-3.82(7H, m), 3.88-4.80(5H,m), 7.09(1H,d,J=9.0 Hz), 7.17(1H,dd, J=8.8, 1.9 Hz), 7.42(1H,d,J=8.8 Hz), 7.70(1H,d,J=1.9 Hz), 8.29(1H,br.s), 8.40-8.50(1H,m), 11.20-11.50(1H,m), 11.85 (1H,s).

MS(ESI)m/z: 545(M+H⁺).

$[\alpha]^{25}_D$=−53.4° (c=0.52, methanol).

Example 172

N-[(3R,4R)-4-{[(5-Chloroindol-2-yl)carbonyl] amino}-1-(2-methoxyacetyl)piperidin-3-yl]-5-methyl-4,5,6,7-tetrahydrothiazolo[5,4-c]pyridine-2-carboxamide hydrochloride

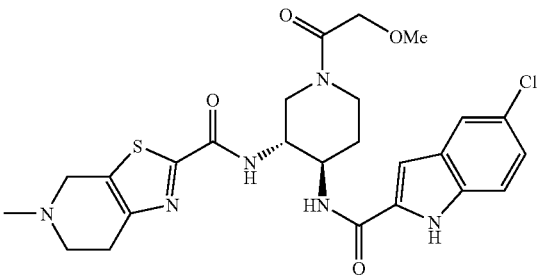

The title compound was obtained from the compound obtained in Referential Example 223 in a similar manner to Example 169.

Melting point: 213-230° C.

¹H-NMR (DMSO-d₆) δ: 1.45-1.56(0.5H,m), 1.61-1.70 (0.5H,m), 1.89-2.00(1H,m), 2.05(3H,s), 2.45-2.67(1H,m), 2.88(3H,s), 3.00-3.21(4H,m), 3.32-3.56(7H,m), 3.78-3.89 (2H,m), 4.00-4.24(2H,m), 4.26-4.43(2H,m), 7.02(1H,s), 7.13(1H,dd,J=8.8, 2.0 Hz), 7.37(1H,d,J=8.8 Hz), 7.67(1H,d, J=2.0 Hz), 8.41(1H,d,J=9.8 Hz), 8.74(1H,d,J=9.8 Hz), 10.80-10.90(1H,m), 11.72(1H,s).

MS(FAB)m/z: 545(M+H⁺).

$[\alpha]^{25}_D$=−100.3° (c=0.51, methanol).

Example 173

N-((3R,4R)-4-{[(5-Chloroindol-2-yl)carbonyl] amino}-6-oxotetrahydro-2H-pyran-3-yl)-5-methyl-4,5,6,7-tetrahydrothiazolo[5,4-c]pyridine-2-carboxamide hydrochloride

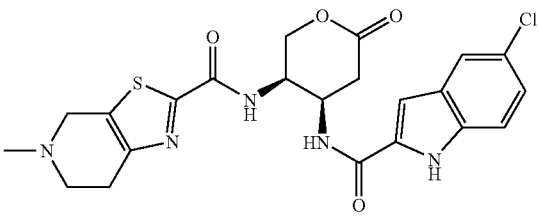

The title compound was obtained from the low-polar compound obtained in Referential Example 176 and the compound obtained in Referential Example 10 in a similar manner to Example 169.

¹H-NMR (DMSO-d₆) δ: 2.41-2.56(2H,m), 2.91(3H,s), 3.01-3.23(1H,m), 3.24-3.56(5H,m), 3.62-3.67(1H,m), 4.21-4.44(1H,m), 4.56-4.78(2H,m), 7.11(1H,s), 7.16(1H,dd,

Example 174

N-((3R,4S)-4-{[(5-Chloroindol-2-yl)carbonyl]amino}-6-oxotetrahydro-2H-pyran-3-yl)-5-methyl-4,5,6,7-tetrahydrothiazolo[5,4-c]pyridine-2-carboxamide hydrochloride

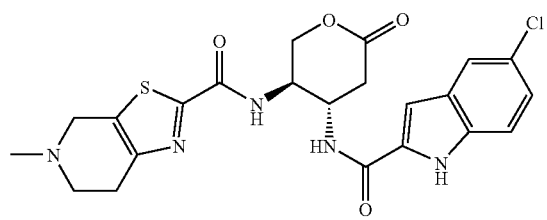

The title compound was obtained from the high-polar compound obtained in Referential Example 176 and the compound obtained in Referential Example 10 in a similar manner to Example 169.

$^1$H-NMR (DMSO-$d_6$) δ: 2.41-2.56(2H,m), 2.91(3H,s), 3.23-3.41(2H,m), 3.43-3.50(2H,m), 3.56-3.67(2H,m), 4.37 (1H,dd,J=13.9, 7.1 Hz), 4.40-4.50(1H,m), 4.56-4.78(2H,m), 7.12(1H,s), 7.17(1H,dd,J=8.8, 2.0 Hz), 7.41(1H,d,J=8.8 Hz), 7.71(1H,d,J=2.0 Hz), 8.44(1H,d,J=8.5 Hz), 8.15(1H,d,J=8.5 Hz), 11.42-11.53(1H,m), 11.79(1H,s).

MS(FAB)m/z: 488(M+H$^+$).

Example 175

Ethyl (3R,4S)-5-{[tert-butyl(diphenyl)silyl]oxy}-3-{[(5-chloroindol-2-yl)carbonyl]amino}-4-{[(5-methyl-4,5,6,7-tetrahydrothiazolo[5,4-c]pyridin-2-yl)carbonyl]amino}-valerate

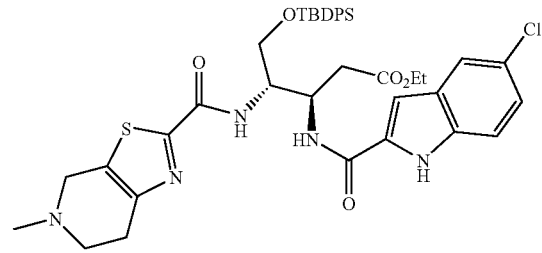

The title compound was obtained from the compound obtained in Referential Example 225 in a similar manner to Example 169.

$^1$H-NMR (CDCl$_3$) δ: 1.09(9H,s), 1.21(3H,t,J=7.4 Hz), 2.49(3H,s), 2.65(1H,dd,J=15.9, 5.4 Hz), 2.67-2.90(5H,m), 3.60(1H,d,J=14.9 Hz), 3.72(1H,d,J=14.9 Hz), 3.78-3.91(2H,m), 4.00-4.21(2H,m), 4.43-4.50(1H,m), 4.78-4.89(1H,m), 6.81(1H,s), 7.20(1H,dd,J=8.8, 2.0 Hz), 7.32-7.52(m,7H), 7.63-7.74(6H,m), 7.89-8.01(1H,m), 9.18(1H,s).

Example 176

Ethyl (3R,4S)-3-{[(5-chloroindol-2-yl)carbonyl]amino}-5-hydroxy-4-{[(5-methyl-4,5,6,7-tetrahydrothiazolo[5,4-c]-pyridin-2-yl)carbonyl]amino}valerate

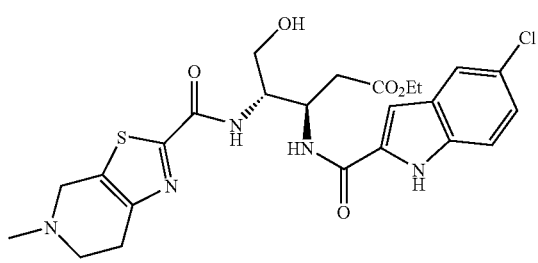

After hydrogen fluoride-pyridine (0.4 mL) was added dropwise to a mixture sulution composed of the compound (0.54 g) obtained in Example 175, pyridine (4.0 mL), and tetrahydrofuran (10 mL) under ice cooling, the reaction mixture was stirred for 18 hours while the temperature thereof was gradually raised to room temperature. The reaction mixture was concentrated, and the resultant residue was purified by silica gel column chromatography (chloroform:methanol=9:1) to give the title compound (0.31 g).

$^1$H-NMR (CDCl$_3$) δ: 1.20(3H,t,J=7.4 Hz), 2.49(3H,s), 2.67-2.90(6H,m), 3.62-3.74(3H,m), 3.78-3.94(1H,m), 4.00-4.20(2H,m), 4.30-4.40(1H,m), 4.80-4.89(1H,m), 6.93(1H,s), 7.23(1H,dd,J=8.8, 2.0 Hz), 7.33(1H,d,J=8.8 Hz), 7.56(1H,d,J=8.5 Hz), 7.61(1H,d,J=2.0 Hz), 7.88(1H,d,J=8.5 Hz), 9.29 (1H,s).

Example 177

N-((3S,4R)-4-{[(5-Chloroindol-2-yl)carbonyl]amino}-6-oxotetrahydro-2H-pyran-3-yl)-5-methyl-4,5,6,7-tetrahydrothiazolo[5,4-c]pyridine-2-carboxamide hydrochloride

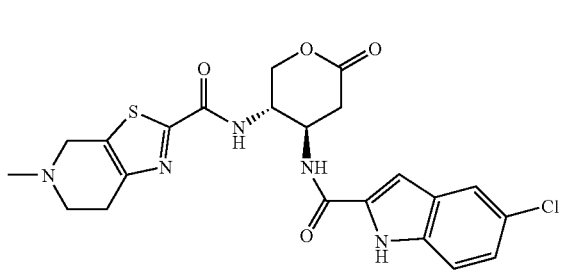

4N HCl-dioxane (20 mL) was added to the compound (0.31 g) obtained in Example 176, and the mixture was heated under reflux for 4 hours. The reaction mixture was concentrated, and the resultant residue was recrystallized from diethyl ether to give the title compound (0.23 g).

Melting point: 221-238° C. (decomposed).

$^1$H-NMR and MS: The same as those of the enantiomer in Example 174.

Example 178

N-((3R*,4R*)-4-{[(5-Chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

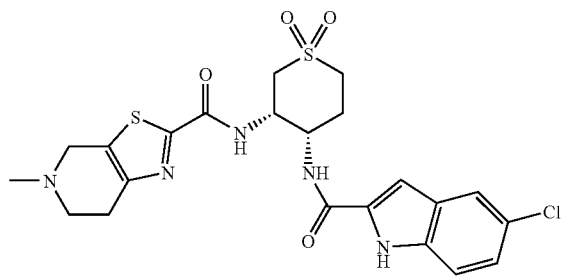

A free base of the title compound was obtained from the compound obtained in Referential Example 227 and 5-chloroindole-2-carboxylic acid in a similar manner to Example 91. This free base was treated with HCl in ethanol to give the title compound.

Melting point: 241-244° C.

$^1$H-NMR (DMSO-d$_6$) δ: 2.14(1H,br), 2.30-2.34(1H,m), 2.92(3H,s), 3.10-3.18(2H,m), 3.41(4H,br), 3.68(2H,br), 4.44(1H,br), 4.63-4.78(3H,m), 7.16-7.18(1H,m), 7.21(1H,s), 7.43(1H,d,J=8.5 Hz), 7.67(1H,d,J=4.6 Hz), 8.39(1H,br), 8.94(1H,br), 11.82(1H,br).

MS(ESI)m/z: 522(M+H$^+$).

Example 179

N-((3R*,4R*)-4-{[(5-Fluoroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

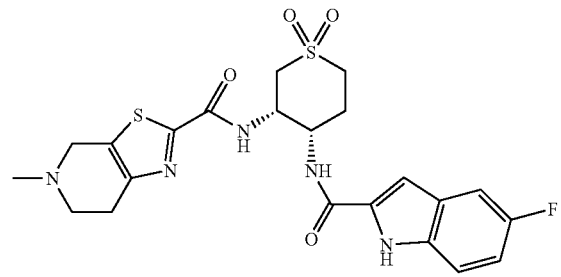

A free base of the title compound was obtained from the compound obtained in Referential Example 227 and 5-fluoroindole-2-carboxylic acid in a similar manner to Example 91. This free base was treated with HCl in ethanol to give the title compound.

Melting point: 243-245° C.

$^1$H-NMR (DMSO-d$_6$) δ: 2.14(1H,br), 2.30-2.33(1H,m), 2.92(3H,s), 3.13(2H,br), 3.51(4H,br), 3.63(2H,br), 4.63(3H,br), 4.78(1H,br), 7.01-7.05(1H,m), 7.21(1H,s), 7.37-7.44(2H,m), 8.36(1H,br), 8.93(1H,d,J=6.8 Hz), 11.72(1H,br).

MS(ESI)m/z: 506(M+H$^+$).

Example 180

N-((3R*,4R*)-3-{[(5-Chloroindol-2-yl)carbonyl]amino}-1,1-dioxohexahydro-1-thiopyran-4-yl)-5-methyl-4,5,6,7-tetrahydrothiazolo[5,4-c]pyridine-2-carboxamide hydrochloride

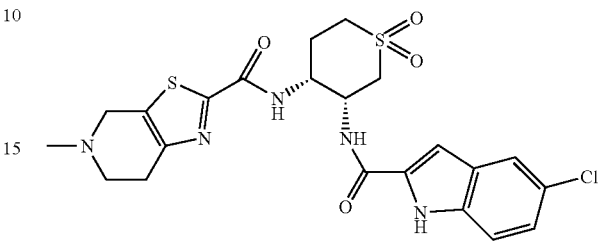

A free base of the title compound was obtained from the compound obtained in Referential Example 229 and the compound obtained in Referential Example 10 in a similar manner to Example 91. This free base was treated with HCl in ethanol to give the title compound.

Melting point: 242-247° C.

$^1$H-NMR (DMSO-d$_6$) δ: 2.16(1H,br), 2.45(1H,br), 2.93(3H,s), 3.13(2H,br), 3.26(4H,br), 3.69(2H,br), 4.45(1H,br), 4.65-4.77(3H,m), 7.01(1H,s), 7.17(1H,dd,J=8.7, 1.4 Hz), 7.43(1H,d,J=8.5 Hz), 7.69(1H,s), 8.35-8.40(1H,m), 9.04(1H,br), 11.86(1H,s).

MS(ESI)m/z: 522(M+H$^+$).

Example 181

N-((3R*,4S*)-4-{[(5-Chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide hydrochloride

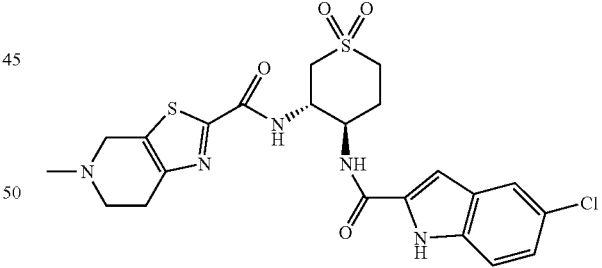

A free base of the title compound was obtained from the compound obtained in Referential Example 231 and 5-chloroindole-2-carboxylic acid in a similar manner to Example 91. This free base was treated with HCl in ethanol to give the title compound.

Melting point: 244-249° C.

$^1$H-NMR (DMSO-d$_6$) δ: 2.17-2.27(2H,m), 2.90(3H,s), 3.09(1H,br), 3.18-3.21(2H,m), 3.31-3.34(2H,m), 3.60-3.67(3H,m), 4.41-4.49(2H,m), 4.54-4.59(2H,m), 7.04(1H,s), 7.09-7.13(1H,m), 7.39(1H,d,J=8.5 Hz), 7.61(1H,d,J=9.9 Hz), 8.52-8.56(1H,m), 8.83-8.85(1H,m), 11.65(1H,d,J=11.9 Hz).

MS(ESI)m/z: 522(M+H$^+$).

Example 182

N-((3R*,4S*)-4-{[(5-Fluoroindol-2-yl)carbonyl]
amino}-1,1-dioxohexahydro-1-thiopyran-3-yl)-5-
methyl-4,5,6,7-tetrahydrothiazolo[5,4-c]pyridine-2-
carboxamide hydrochloride

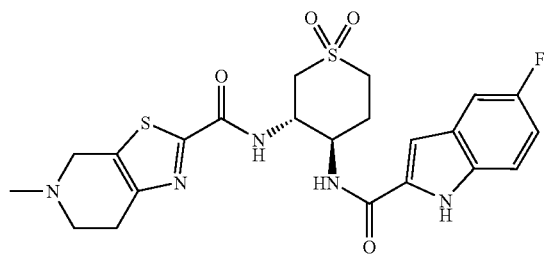

A free base of the title compound was obtained from the compound obtained in Referential Example 231 and 5-fluoroindole-2-carboxylic acid in a similar manner to Example 91. This free base was treated with HCl in ethanol to give the title compound.

Melting point: 236-241° C.

$^1$H-NMR (DMSO-d$_6$) δ: 2.20-2.24(2H,m), 2.89(3H,s), 3.07(1H,br), 3.19-3.22(2H,m), 3.60-3.66(4H,m), 4.43-4.58(5H,m), 6.95-7.00(1H,m), 7.04(1H,s), 7.32-7.38(2H,m), 8.50(1H,d,J=8.5 Hz), 8.83(1H,d,J=8.5 Hz), 11.59(1H,s).

MS(ESI)m/z: 506(M+H$^+$).

Example 183

N-((3R*,4R*)-3-{[(5-Fluoroindol-2-yl)carbonyl]
amino}-1,1-dioxohexahydro-1-thiopyran-4-yl)-5-
methyl-4,5,6,7-tetrahydrothiazolo[5,4-c]pyridine-2-
carboxamide hydrochloride

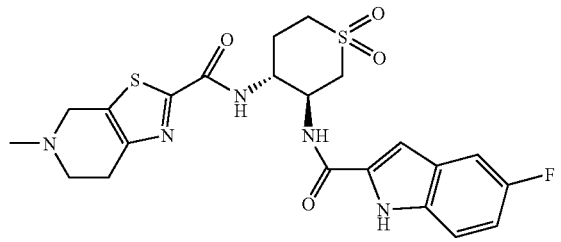

A free base of the title compound was obtained from the compound obtained in Referential Example 233 and the compound obtained in Referential Example 10 in a similar manner to Example 91. This free base was treated with HCl in ethanol to give the title compound.

Melting point: 244-249° C.

$^1$H-NMR (DMSO-d$_6$) δ: 2.12-2.18(1H,m), 2.50(1H,br), 2.92(3H,s), 3.17(3H,br), 3.50-3.61(5H,m), 4.45(1H,br), 4.62-4.78(3H,m), 6.98-7.03(2H,m), 7.36-7.42(2H,m), 8.30(1H,br), 9.00(1H,d,J=8.0 Hz), 11.74(1H,s).

MS(ESI)m/z: 506(M+H$^+$).

Example 184

N-((3S,4R)-4-{[(5-chloroindol-2-yl)carbonyl]
amino}-1-methyl-6-oxopiperidin-3-yl)-5-methyl-4,5,
6,7-tetrahydrothiazolo[5,4-c]pyridine-2-carboxamide
(low-polar compound) and N-((3R,4R)-4-{[(5-chloroindol-2-yl)carbonyl]amino}-1-methyl-6-oxopiperidin-3-yl)-5-methyl-4,5,6,7-tetrahydrothiazolo[5,4-c]
pyridine-2-carboxamide (high-polar compound)

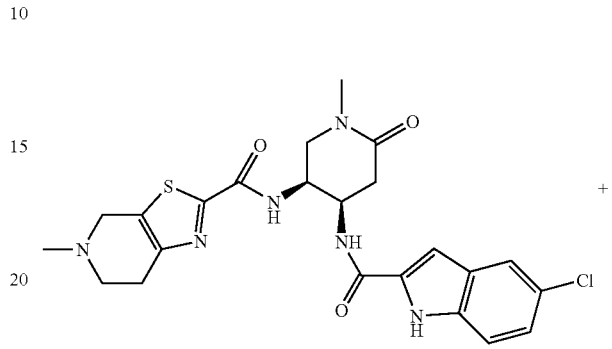

Low-polar compound

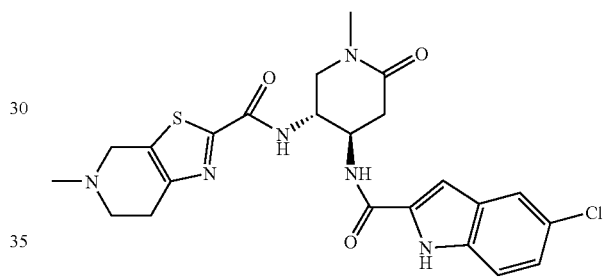

High-polar compound

The title compound was obtained from the compound obtained in Referential Example 236 and the compound obtained in Referential Example 10 in a similar manner to Example 169.

Low-Polar Compound:

Melting poing: 189-203° C. (decomposed)

$^1$H-NMR (CDCl$_3$) δ: 2.52(3H,s), 2.59(1H,q,J=8.8 Hz), 2.71-2.78(2H,m), 2.89-3.00(2H,m), 3.03(3H,s), 3.12(1H,dd,J=17.6, 5.4 Hz), 3.43(1H,dd,J=12.7, 5.1 Hz), 3.70(1H,d,J=15.2 Hz), 3.77(1H,d,J=15.2 Hz), 3.83(1H,dd,J=12.7, 3.9 Hz), 4.55-4.67(2H,m), 6.99(1H,s), 7.23(1H,dd,J=8.8, 2.0 Hz), 7.33(1H,d,J=8.8 Hz), 7.65(1H,d,J=2.0 Hz), 8.07(1H,d,J=5.1 Hz), 8.16(1H,d,J=5.4 Hz), 9.43(1H,s).

MS(FAB)m/z: 501(M+H$^+$).

High-Polar Compound:

Melting point: 183-195° C. (decomposed).

$^1$H-NMR (DMSO-d$_6$) δ: 2.33(3H,s), 2.41-2.50(1H,m), 2.62-2.73(3H,m), 2.75-2.81(1H,m), 2.82(3H,s), 3.21-3.32(2H,m), 3.34-3.50(2H,m), 3.55(1H,d,J=15.4 Hz), 3.63(1H,d,J=15.4 Hz), 4.30-4.40(0.5H,m), 4.50-4.60(0.5H,m), 7.04(1H,s), 7.15(1H,dd,J=8.8, 2.0 Hz), 7.38(1H,d,J=8.8 Hz), 7.67(1H,d,J=2.0 Hz), 8.49(1H,d,J=8.5 Hz), 8.71(1H,d,J=8.5 Hz), 11.74(1H,s).

MS(FAB)m/z: 501(M+H$^+$).

Example 185

5-Chloro-N-((1R*,2S*)-2-{[4-(pyridin-4-yl)benzoyl]-amino}cyclohexyl)indole-2-carboxamide hydrochloride

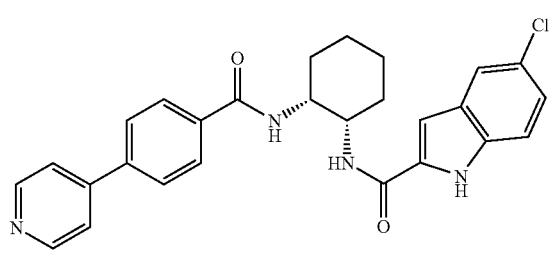

The title compound was obtained from the compound obtained in Referential Example 71 and the compound obtained in Referential Example 237 in a similar manner to the process described in Example 2.

$^1$H-NMR (DMSO-$d_6$) δ: 1.40-1.52(2H,m), 1.60-1.80(4H, m), 1.96-2.10(2H,m), 4.24-4.39(2H,m), 7.15(1H,dd,J=8.8, 2.0 Hz), 7.21(1H,s), 7.40(1H,d,J=8.8 Hz), 7.64(1H,d,J=2.0 Hz), 8.06(4H,s), 8.18(1H,J=7.3 Hz), 8.34-8.42(3H,m), 8.94 (2H,d,J=6.9 Hz), 11.91(1H,s).

MS(FAB)m/z: 473(M+H)$^+$.

Example 186

4-(4-{[((1R*,2S*)-2-{[(5-Chloroindol-2-yl)carbonyl]amino}-cyclohexyl)amino]carbonyl}phenyl) pyridine N-oxide

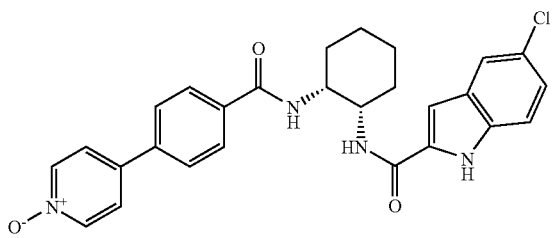

The title compound was obtained from the compound obtained in Referential Example 71 and the compound obtained in Referential Example 240 in a similar manner to the process described in Example 2.

$^1$H-NMR (DMSO-$d_6$) δ: 1.40-1.52(2H,m), 1.60-1.80(4H, m), 1.88-2.00(2H,m), 4.21-4.36(2H,m), 7.12-7.18(2H,m), 7.41(1H,d,J=8.6 Hz), 7.66(1H,s), 7.80-7.87(4H,m), 7.91(2H, d,J=8.3 Hz), 8.01(1H,d,J=7.6 Hz), 8.09(1H,d,J=7.3 Hz), 8.27 (2H,d,J=6.6 Hz), 11.79(1H,s).

MS(FAB)m/z: 489(M+H)$^+$.

Example 187

5-Chloro-N-((1R*,2S*)-2-{[4-(pyridin-2-yl)benzoyl]-amino}cyclohexyl)indole-2-carboxamide hydrochloride

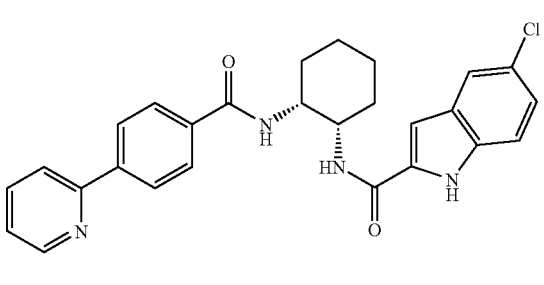

The title compound was obtained from the compound obtained in Referential Example 71 and 4-(2-pyridyl)benzoic acid (Japanese Patent Application Laid-Open (kokai) No. 2000-119253) in a similar manner to the process described in Example 2.

$^1$H-NMR (DMSO-$d_6$) δ: 1.39-1.51(2H,m), 1.60-1.80(4H, m), 1.89-2.00(2H,m), 4.24-4.38(2H,m), 7.12-7.16(2H,m), 7.36-7.39(1H,m), 7.42(1H,d,J=8.8 Hz), 7.66(1H,d,J=2.0 Hz), 7.87-7.90(1H,m), 7.92(2H,d,J=8.3 Hz), 7.98-8.11(3H, m), 8.15(2H,d,J=8.3 Hz), 8.69(1H,d,J=4.6 Hz), 11.80(1H,s).

MS(FAB)m/z: 473(M+H)$^+$.

Example 188

2-(4-{[((1R*,2S*)-2-{[(5-Chloroindol-2-yl)carbonyl]amino}-cyclohexyl)amino]carbonyl}phenyl) pyridine N-oxide

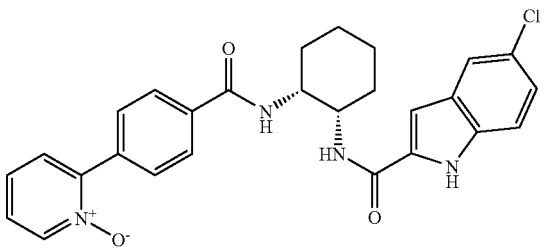

The title compound was obtained from the compound obtained in Referential Example 71 and the compound obtained in Referential Example 241 in a similar manner to the process described in Example 2.

$^1$H-NMR (DMSO-$d_6$) δ: 1.39-1.51(2H,m), 1.60-1.79(4H, m), 1.89-2.00(2H,m), 4.23-4.37(2H,m), 7.12-7.17(2H,m), 7.39-7.43(3H,m), 7.61-7.64(1H,m), 7.67(1H,d,J=2.0 Hz), 7.89(4H,s), 8.00-8.06(1H.m), 8.08-8.02(1H,m), 8.32-8.35 (1H,m), 11.79(1H,s).

MS(FAB)m/z: 489(M+H)$^+$.

Example 189

5-Chloro-N-[(1R*,2R)-2-({[5-(4-pyridin-2-yl)thiazol-2-yl]carbonyl}amino)cyclohexyl]indole-2-carboxamide hydrochloride

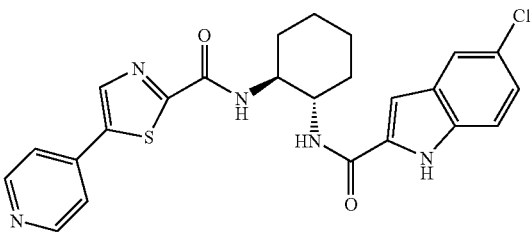

The title compound was obtained from the compound obtained in Referential Example 69 and lithium 5-(4-pyridyl)thiazole-2-carboxylate (Japanese Patent Application Laid-Open (kokai) No. 2000-143623) in a similar manner to the process described in Example 2.

$^1$H-NMR (DMSO-$d_6$) δ: 1.44(2H,br.s), 1.65(4H,br.s), 1.85-2.06(2H,m), 4.23(1H,br.s), 4.30(1H,br.s), 7.14-7.23 (2H,m), 7.41(1H,d,J=8.8 Hz), 7.69(1H,s), 8.04-8.13(2H,m), 8.13(1H,d,J=8.8 Hz), 8.59(1H,d,J=8.0 Hz), 8.75-8.87(3H, m), 11.83(1H,s).

MS(ESI)m/z: 480(M+H)$^+$.

Example 190

5-Chloro-N-[(1R*,2S*)-2-({[1-(pyridin-4-yl)piperidin-4-yl]carbonyl}amino)cyclohexyl]indole-2-carboxamide hydrochloride

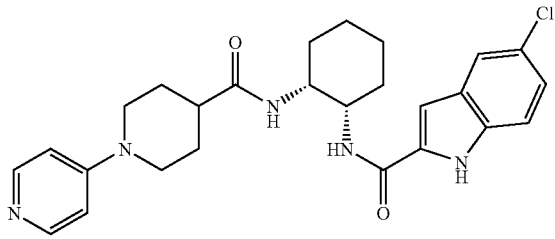

1-(4-Pyridyl)piperidine-4-carboxylic acid (Tetrahedron, 1998, Vol. 44, p. 7095) (206 mg) was suspended in methylene chloride (50 mL), and thionyl chloride (144 μl) was added under ice cooling, followed by stirring for 30 minutes. After triethylamine (969 μl) was added to the reaction mixture, the compound (328 mg) obtained in Referential Example 71 was added, followed by stirring at room temperature for 30 minutes. The reaction mixture was concentrated under reduced pressure, water was added to the residue, the mixture was concentrated under reduced pressure, and precipitate deposited was collected by filtration to give the title compound (310 mg).

$^1$H-NMR (DMSO-$d_6$) δ: 1.30-2.00(10H,m), 2.74(1H,br.s), 3.18(2H,q,J=12.3 Hz), 4.03(1H,br.s), 4.10-4.25(3H,m), 7.15-7.55(4H,m), 7.42(1H,d,J=8.8 Hz), 7.65(1H,s), 7.91(1H,d, J=8.8 Hz), 8.20-8.35(3H,m), 11.91(1H,s), 13.47(1H,br.s).

MS(FAB)m/z: 480(M+H)$^+$.

Example 191

$N^1$-(4-Chlorophenyl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride The compound (288 mg) obtained in Referential Example 242 was dissolved in tetrahydrofuran (8.0 mL), lithium hydroxide (46 mg) and water (1.0 mL) were successively added, and the mixture was stirred at room temperature for 2 hours. The reaction mixture was concentrated under reduced pressure to give a crude product (292 mg) of lithium 2-(4-chloroanilino)-2-oxoacetate as a colorless solid. This crude product and the compound obtained in Referential Example 253 were dissolved in N,N-dimethylformamide (15 mL), and 1-hydroxybenzotriazole monohydrate (164 mg) and 1-(3-dimethylaminopropyl)-3-ethylcarbodiimide hydrochloride (251 mg) were added, followed by stirring at room temperature for 64.5 hours. The solvent was distilled away under reduced pressure, saturated aqueous sodium hydrogencarbonate and methylene chloride were added to the residue for partitioning the mixture, and the resultant organic layer was dried over sodium sulfate anhydrate. After the solvent was distilled away under reduced pressure, the residue was purified by silica gel column chromatography (methylene chloride:methanol=47:3). The thus-obtained pale yellow solids were dissolved in methylene chloride, 1N HCl in ethanol (0.52 mL) was added, and the solvent was distilled away under reduced pressure. Methanol and diethyl ether were added to the residue, and the precipitate formed was collected by filtration to give the title compound (245 mg).

$^1$H-NMR (DMSO-$d_5$) δ: 1.45-1.55(1H,m), 1.60-1.80(3H, m), 1.95-2.10(2H,m), 2.79(3H,s), 2.80-3.00(1H,m), 2.92(3H,s), 2.94(3H,s), 3.10-3.40(2H,m), 3.40-3.80(2H,m), 3.95-4.05(1H,m), 4.40-4.80(3H,m), 7.40(2H,d,J=8.8 Hz), 7.83(2H,d,J=8.8 Hz), 8.75(1H,d,J=7.1 Hz), 9.00-9.10(1H, br), 10.81(1H,s), 11.45-11.75(1H,m).

MS(FAB)m/z: 547(M+H)$^+$.

Example 192

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

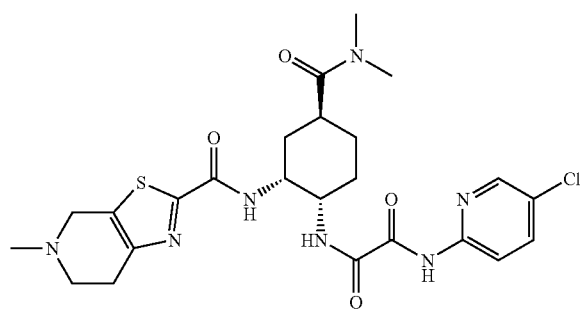

The compound (240 mg) obtained in Referential Example 243 was dissolved in tetrahydrofuran (8.0 mL), lithium hydroxide (41 mg) and water (1.0 mL) were successively added to the solution, and the mixture was stirred at room temperature for 2.5 hours. The reaction mixture was concentrated under reduced pressure to give lithium 2-[(5-chloropyridin-2-yl)amino]-2-oxoacetate (249 mg). Separately, 10% palladium on carbon (200 mg) was added to a solution of the compound (293 mg) obtained in Referential Example 252 in methanol (10 mL), and the mixture was stirred at room temperature for 18 hours in a hydrogen atmosphere. After removing palladium on carbon by filtration, the filtrate was concentrated under reduced pressure to give a crude product (259 mg) of N-{(1R,2S,5S)-2-amino-5-[(dimethylamino)carbonyl]cyclohexyl}-5-methyl-4,5,6,7-tetrahydrothiazolo[5,4-c]-pyridine-2-carboxamide. This crude product (259 mg) and the lithium salt (249 mg) prepared above were added to N,N-dimethylformamide (15 mL), and 1-hydroxybenzotriazole monohydrate (166 mg) and 1-(3-dimethylaminopropyl)-3-ethylcarbodiimide hydrochloride (235 mg) were added, followed by stirring at room temperature for 63.5 hours. The solvent was distilled away under reduced pressure, saturated aqueous sodium hydrogencarbonate and methylene chloride were added to the residue for partitioning the mixture, and the resultant organic layer was dried over sodium sulfate anhydrate. After the solvent was distilled away under reduced pressure, the residue was purified by silica gel column chromatography (methylene chloride:methanol=93:7). The thus-obtained pale yellow solids were dissolved in methylene chloride, 1N HCl in ethanol (0.855 mL) was added to the solution, and the solvent was distilled away under reduced pressure. Methanol and diethyl ether were added to the residue, and the precipitates formed were collected by filtration to give the title compound (209 mg).

¹H-NMR (DMSO-d₆) δ: 1.40-1.57(1H,m), 1.60-1.80(3H, m), 1.95-2.13(2H,m), 2.79(3H,s), 2.80-3.00(1H,m), 2.92(3H,s), 2.94(3H,s), 3.10-3.40(2H,m), 3.40-3.80(2H,m), 3.95-4.05(1H,m), 4.37-4.80(3H,m), 7.90-8.10(2H,m), 8.45(1H,d,J=2.2 Hz), 8.71(1H,d,J=7.6 Hz), 9.10-9.30(1H,br), 10.26(1H,s), 11.30-11.60(1H,br).

MS(FAB)m/z: 548(M+H)⁺.

Example 193

N¹-(3-Chlorophenyl)-N²-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

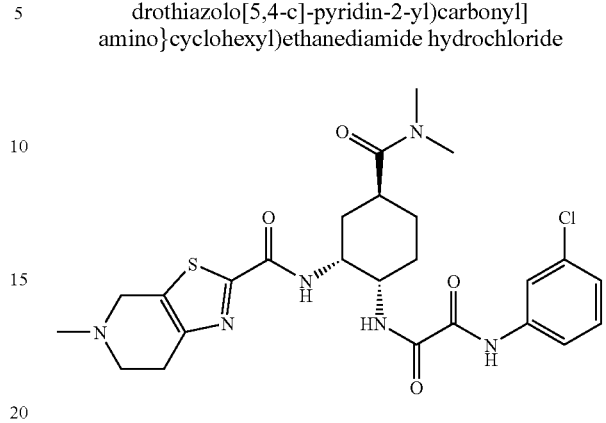

The compound (222 mg) obtained in Referential Example 270 and 3-chloroaniline (63 µl) were dissolved in N,N-dimethylformamide (10 mL), and 1-hydroxybenzotriazole monohydrate (68 mg) and 1-(3-dimethylaminopropyl)-3-ethylcarbodiimide hydrochloride (144 mg) were added, followed by stirring at room temperature for 40 hours. The solvent was distilled away under reduced pressure, saturated aqueous sodium hydrogencarbonate and methylene chloride were added to the residue for partitioning the mixture, and the resultant organic layer was dried over sodium sulfate anhydrate. After the solvent was distilled away under reduced pressure, the residue was purified by silica gel column chromatography (methylene chloride:methanol=30:1). The thus-obtained pale yellow solids were dissolved in methylene chloride, 1N HCl in ethanol (0.50 mL) was added, and the solvent was distilled away under reduced pressure. Diethyl ether was added to the residue, and the precipitate formed was collected by filtration to give the title compound (174 mg).

¹H-NMR (DMSO-d₆) δ: 1.45-1.62(1H,m), 1.65-1.90(3H, m), 1.98-2.20(2H,m), 2.79(3H,s), 2.88-3.10(1H,m), 2.93(3H,s), 2.94(3H,s), 3.15-3.40(2H,m), 3.40-3.90(2H,m), 3.95-4.10(1H,m), 4.40-4.80(3H,m), 7.19(1H,dd,J=9.3, 2.0 Hz), 7.37(1H,d,J=8.2 Hz), 7.77(1H,d,J=8.3 Hz), 7.92-8.05(1H,m), 8.75(1H,d,J=7.3 Hz), 8.95-9.20(1H,br), 10.87(1H, s), 11.25-11.45(1H,br).

Example 194

N¹-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-N²-(4-fluorophenyl)ethanediamide hydrochloride

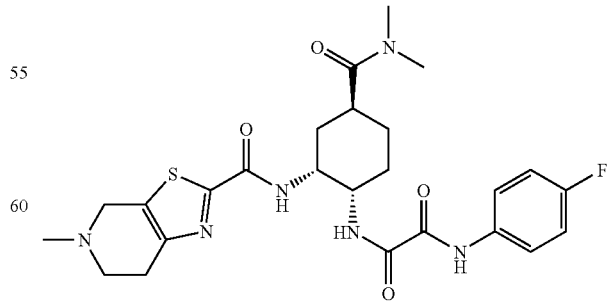

In a manner similar to that described in Example 191, the compound obtained in Referential Example 254 was hydrolyzed and then, condensed with the compound obtained in Referential Example 253, followed by treatment with hydrochloric acid, to thereby give the title compound.

¹H-NMR (DMSO-d$_6$) δ: 1.40-2.13(6H,m), 2.77(3H,s), 2.93(3H,s), 2.97(3H,s), 3.12-3.82(7H,m), 3.93-4.04(1H,m), 4.38-4.46(1H,m), 4.35-4.75(1H,m), 7.11-7.21(2H,m), 7.72-7.84(2H,m), 8.73(1H,d,J=7.6 Hz), 8.93-9.02(1H,m), 10.70 (1H,s).

MS(FAB)m/z: 531(M+H)$^+$.

Example 195

N$^1$-(4-Bromophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

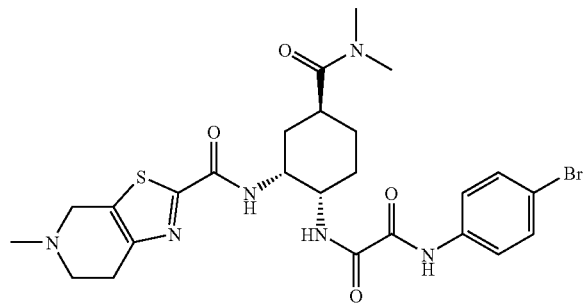

The compound (152 mg) obtained in Referential Example 255 was dissolved in tetrahydrofuran (5.0 mL), 1N aqueous sodium hydroxide (1.20 mL) and methanol (5.0 mL) were successively added, and the mixture was stirred at room temperature for 2.5 hours. The reaction mixture was concentrated under reduced pressure, and methylene chloride (10 mL) and 1N hydrochloric acid (2.0 mL) were added to the residue for partitioning the mixture. The resultant organic layer was dried over sodium sulfate anhydrate, and the solvent was distilled away under reduced pressure to give a crude product (280 mg) of 2-(4-bromoanilino)-2-oxoacetic acid as a colorless solid. This crude product and the compound (280 mg) obtained in Referential Example 253 were dissolved in N,N-dimethylformamide (30 mL), and 1-hydroxybenzotriazole monohydrate (90 mg) and 1-(3-dimethylaminopropyl)-3-ethylcarbodiimide hydrochloride (226 mg) were added, followed by stirring at room temperature overnight. The solvent was distilled away under reduced pressure, saturated aqueous sodium hydrogencarbonate and methylene chloride were added to the residue for partitioning the mixture, and the resultant organic layer was dried over sodium sulfate anhydrate. After the solvent was distilled away under reduced pressure, the residue was purified by silica gel column chromatography (methylene chloride:methanol=97:3). The thus-obtained pale yellow solids were dissolved in methylene chloride, 1N HCl in ethanol (191 µl) was added, and the solvent was distilled away under reduced pressure. Methanol and diethyl ether were added to the residue, and the precipitate formed was collected by filtration to give the title compound (103 mg).

¹H-NMR (DMSO-d$_6$) δ: 1.43-1.57(1H,m), 1.59-1.80(3H, m), 1.97-2.10(2H,m), 2.79(3H,s), 2.84-2.98(7H,m), 3.18(2H,br.s), 3.39-3.72(2H,m), 3.95-4.05(1H,m), 4.20-4.80 (3H,m), 7.53(2H,d,J=8.8 Hz), 7.77(2H,d,J=8.8 Hz), 8.75(1H, d,J=7.3 Hz), 8.97-9.09(1H,m), 10.82(1H,s), 11.11(1H,br.s).

MS(FAB)m/z: 591(M+H)$^+$.

Example 196

N$^1$-(4-Chloro-2-methylphenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

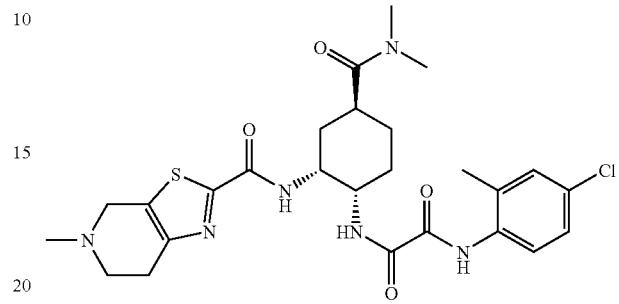

In a manner similar to that described in Example 191, the compound obtained in Referential Example 256 was hydrolyzed and then, condensed with the compound obtained in Referential Example 253, followed by treatment with hydrochloric acid, to thereby give the title compound.

¹H-NMR (DMSO-d$_6$) δ: 1.45-1.55(1H,m), 1.60-1.80(3H, m), 2.00-2.10(2H,m), 2.19(3H,s), 2.79(3H,s), 2.80-3.00(7H, m), 3.31(2H,br.s), 3.40-3.70(2H,br), 3.95-4.05(1H,m), 4.35-4.70(3H,m), 7.20-7.30(1H,m), 7.35(1H,d,J=2.5 Hz), 7.43 (1H,d,J=8.6 Hz), 8.76(1H,d,J=6.6 Hz), 9.00-9.15(1H,br), 10.19(1H,s).

MS(FAB)m/z: 561(M+H)$^+$.

Example 197

N$^1$-(4-Chloro-3-methylphenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

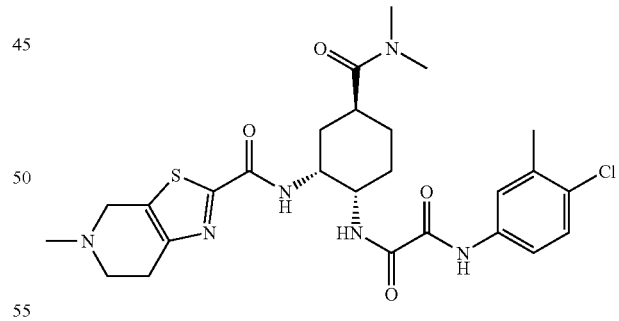

In a manner similar to that described in Example 191, the compound obtained in Referential Example 257 was hydrolyzed and then, condensed with the compound obtained in Referential Example 253, followed by treatment with hydrochloric acid, to thereby give the title compound.

¹H-NMR (DMSO-d$_6$) δ: 1.47-1.53(1H,m), 1.68-1.80(3H, m), 1.98-2.09(2H,m), 2.29(3H,s), 2.79(3H,s), 2.80-3.00(1H, m), 2.95(6H,s), 3.17-3.19(3H,m), 3.40-3.80(1H,m), 3.93-4.02(1H,m), 4.44-4.56(3H,m), 7.38(1H,d,J=8.8 Hz), 7.65 (1H,d,J=8.8 Hz), 7.74(1H,s), 8.75(1H,d,J=7.8 Hz), 8.96(1H, d,J=8.0 Hz), 10.69(1H,s).

MS(FAB)m/z: 561(M+H)$^+$.

Example 198

N$^1$-(4-Chloro-2-fluorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]-amino}cyclohexyl)ethanediamide hydrochloride

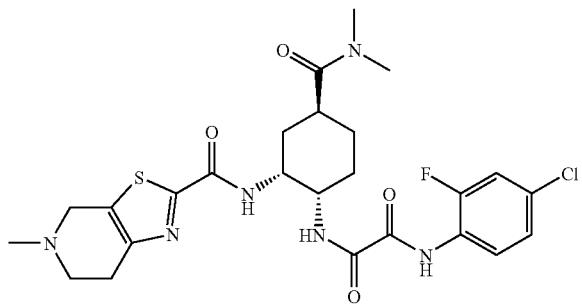

In a manner similar to that described in Example 191, the compound obtained in Referential Example 258 was hydrolyzed and then, condensed with the compound obtained in Referential Example 253, followed by treatment with hydrochloric acid, to thereby give the title compound.

$^1$H-NMR (DMSO-d$_6$) δ: 1.40-1.55(1H,m), 1.58-1.80(3H, m), 1.95-2.12(2H,m), 2.77(3H,s), 2.80-3.00(1H,m), 2.91(3H,s), 2.92(3H,s), 3.10-3.40(2H,m), 3.40-3.80(2H,m), 3.95-4.05(1H,m), 4.30-4.80(3H,m), 7.29(1H,d,J=8.5 Hz), 7.52(1H,dd,J=10.3, 2.0 Hz), 7.61(1H,t,J=8.4 Hz), 8.72(1H,d, J=6.8 Hz), 9.00-9.20(1H,br), 10.38(1H,s), 11.20-11.45(1H, br).

MS(FAB)m/z: 565(M+H)$^+$.

Example 199

N$^1$-(2,4-Dichlorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

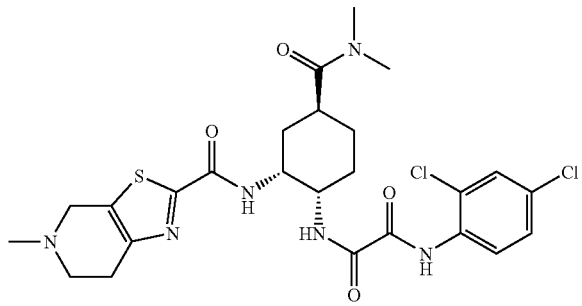

The compound (300 mg) obtained in Referential Example 270 was dissolved in N,N-dimethylformamide (5 mL), and 2,4-dichloroaniline (165 mg), 1-(3-dimethylaminopropyl)-3-ethylcarbodiimide hydrochloride (260 mg), and 1-hydroxybenzotriazole monohydrate (91 mg) were added, followed by stirring at room temperature for 2 days. The solvent was distilled away under reduced pressure, saturated aqueous sodium hydrogencarbonate and methylene chloride were added to the residue for partitioning the mixture, and the resultant organic layer was dried over sodium sulfate anhydrate. After the solvent was distilled away under reduced pressure, the residue was purified by silica gel column chromatography (methylene chloride:methanol=47:3) to give a free base of the title compound. This product was dissolved in methylene chloride, 1N HCl in ethanol (108 μl) was added, and the solvent was distilled away under reduced pressure. A small amount of methanol was added to the residue, and diethyl ether was added dropwise while irradiating with ultrasonic waves to collect the precipitate formed by filtration. This product was washed with diethyl ether to give the title compound (60 mg).

$^1$H-NMR (DMSO-d$_6$) δ: 1.45-1.77(4H,m), 2.03-2.12(2H, m), 2.79(3H,s), 2.92-2.96(7H,m), 3.25(2H,br.s), 3.49(1H,br.s), 3.69(1H,br.s), 3.98-4.04(1H,m), 4.40-4.43 (1H,m), 4.45(1H,br.s), 4.69(1H,br.s), 7.48(1H,dd,J=8.5, 2.4 Hz), 7.75(1H,d,J=2.4 Hz), 7.89(1H,d,J=8.5 Hz), 8.75(1H,d, J=6.8 Hz), 9.21(1H,br.s), 10.25(1H,s), 11.55(1H,br.s).

MS(FAB)m/z: 581(M+H)$^+$.

Example 200

N$^1$-(3,4-Dichlorophenyl)-N$^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

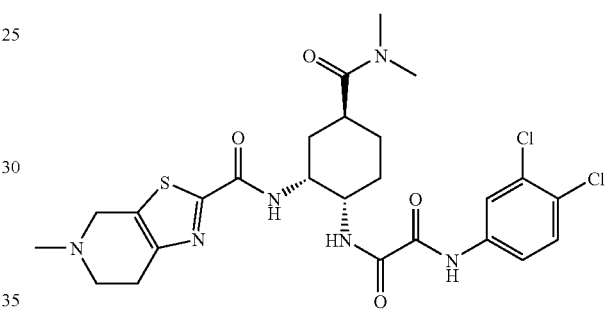

3,4-Dichloroaniline (1.62 g) was dissolved in methylene chloride (20 mL), and triethylamine (1.67 mL) and methyl chlorooxoacetate (1.01 mL) were successively added under ice cooling, and the mixture was stirred at room temperature for 21 hours. Water and methylene chloride were added to the reaction mixture for partitioning the mixture. The resultant aqueous layer was extracted with methylene chloride. Organic layers were combined and dried over magnesium sulfate anhydrate, and the solvent was distilled away under reduced pressure. The resultant residue was dissolved in ethanol (50 mL), and water (25 mL) and lithium hydroxide monohydrate (629 mg) were successively added, followed by stirring at room temperature for 12.5 hours. Lithium hydroxide monohydrate (629 mg) was additionally added, followed by stirring at room temperature for 5.5 hours. The reaction mixture was concentrated to solid under reduced pressur. Water and diethyl ether were added to the residue for partitioning the mixture. Hydrochloric acid was added to the resultant aqueous layer for acidification. The Solid formed was collected by filtration to give a crude product (1.62 g) of 2-(3,4-dichloroanilino)-2-oxoacetic acid as a colorless solid. This crude product (191 mg) and the compound (250 mg) obtained in Referential Example 253 were dissolved in N,N-dimethylformamide (10 mL), and 1-hydroxybenzotriazole monohydrate (110 mg) and 1-(3-dimethylaminopropyl)-3-ethylcarbodiimide hydrochloride (157 mg) were added, followed by stirring at room temperature for 67 hours. The solvent was distilled away under reduced pressure, saturated aqueous sodium hydrogencarbonate and ethyl acetate were added to the residue for partitioning the mixture, and the resultant aqueous layer was extracted 3 times with methylene chloride. Organic layers were combined and dried over sodium sulfate anhydrate. After the solvent was distilled away under reduced pressure, the residue was purified by silica gel column chromatography (methylene chloride:methanol=95:5) to give the title compound (154 mg).

$^1$H-NMR (CDCl$_3$) δ: 1.77-1.88(1H,m), 1.91-1.95(1H,m), 2.05-2.10(3H,m), 2.51(3H,s), 2.77-2.99(6H,m), 2.95(3H,s), 3.05(3H,s), 3.68(1H,d,J=15.5 Hz), 3.74(1H,d,J=15.5 Hz), 4.08-4.13(1H,m), 4.69-4.72(1H,m), 7.40(2H,s), 7.41(1H,d, J=7.7 Hz), 7.90(1H,s), 8.01(1H,d,J=7.7 Hz), 9.27(1H,s).

MS(ESI)m/z: 581(M+H)$^+$.

Example 201

$N^1$-(2,4-Difluorophenyl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

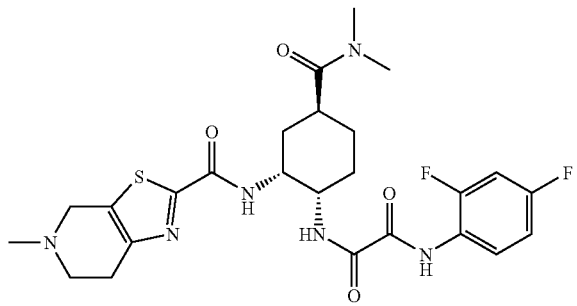

In a manner similar to that described in Example 191, the compound obtained in Referential Example 259 was hydrolyzed, followed by condensation with the compound obtained in Referential Example 253, to thereby give the title compound.

$^1$H-NMR (CDCl$_3$) δ: 1.55-1.62(1H,m), 1.67-1.98(2H,m), 2.01-2.18(4H,m), 2.52(3H,s), 2.77-3.00(4H,m), 2.95(3H,s), 2.99(3H,s), 3.65-3.78(2H,m), 4.06-4.15(1H,m), 4.66-4.73(1H,m), 6.85-6.94(2H,m), 7.38(1H,d,J=8.5 Hz), 7.96(1H,d, J=7.3 Hz), 8.22-8.29(1H,m), 9.36(1H,br).

Example 202

$N^1$-(3,4-Difluorophenyl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

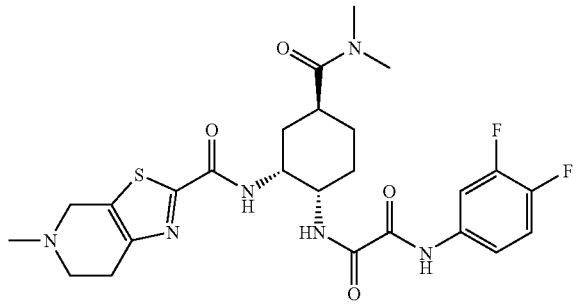

In a manner similar to that described in Example 191, the compound obtained in Referential Example 260 was hydrolyzed, followed by condensation with the compound obtained in Referential Example 253, to thereby give the title compound.

$^1$H-NMR (CDCl$_3$) δ: 1.56-1.73(1H,m), 1.77-1.99(2H,m), 2.00-2.18(4H,m), 2.52(3H,s), 2.75-3.00(4H,m), 2.95(3H,s), 3.06(3H,s), 3.64-3.79(2H,m), 4.05-4.14(1H,m), 4.68-4.75(1H,m), 7.09-7.21(2H,m), 7.38(1H,d,J=8.8 Hz), 7.72(1H, ddd,J=12.0, 7.1, 2.6 Hz), 7.95(1H,d,J=7.8 Hz), 9.22(1H,br).

Example 203

$N^1$-((1S,2R,4S)-4-[(Dimethylamino)carbonyl]-2-{[(5-methyl-4,5,6,7-tetrahydrothiazolo[5,4-c]pyridin-2-yl)carbonyl]-amino}cyclohexyl)-$N^2$-(pyridin-4-yl)ethanediamide hydrochloride

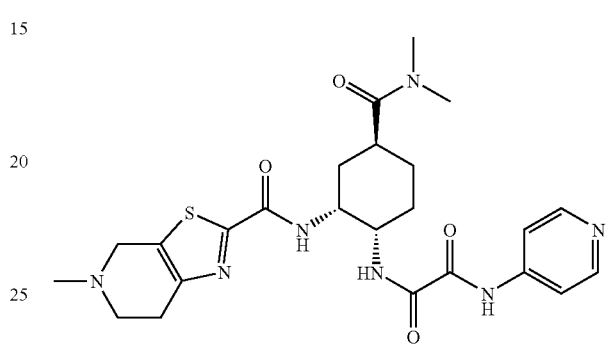

In a manner similar to that described in Example 191, the compound obtained in Referential Example 261 was hydrolyzed and then, condensed with the compound obtained in Referential Example 253, followed by treatment with hydrochloric acid, to thereby give the title compound.

$^1$H-NMR (DMSO-d$_6$) δ: 1.40-2.10(6H,m), 2.77(3H,s), 2.927(3H,s), 2.933(3H,s), 3.05-4.20(8H,m), 4.40-4.55(1H, m), 8.27(2H,d,J=6.8 Hz), 8.67(1H,d,J=8.0 Hz), 8.71(2H,d, J=6.8 Hz), 9.10-9.30(1H,br), 11.81(1H,s).

MS(FAB)m/z: 514(M+H)$^+$.

Example 204

$N^1$-(5-Bromopyridin-2-yl)-$N^2$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide hydrochloride

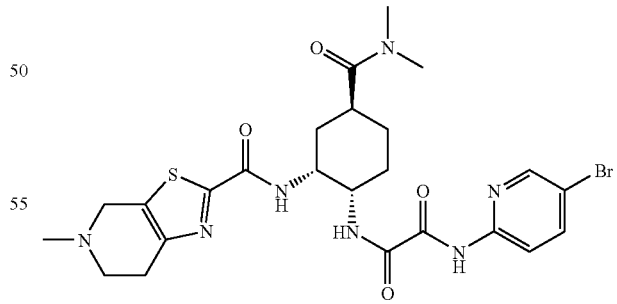

In a manner similar to that described in Example 195, the compound obtained in Referential Example 262 was hydrolyzed and then, condensed with the compound obtained in Referential Example 253, followed by treatment hydrochloric acid, to thereby give the title compound.

$^1$H-NMR (DMSO-d$_6$) δ: 1.43-1.57(1H,m), 1.61-1.81(3H, m), 1.98-2.15(2H,m), 2.79(3H,s), 2.86(3H,s), 2.89-3.01(4H, m), 3.18(2H,br.s), 3.50(2H,br.s), 3.95-4.05(1H,m), 4.35-4.62

(3H,m), 7.97(1H,d,J=9.0 Hz), 8.12(1H,dd,J=9.0, 2.4 Hz), 8.52(1H,d,J=2.4 Hz), 8.70(1H,d,J=7.5 Hz), 9.18(1H,d,J=7.5 Hz), 10.25(1H,br.s).

MS(FAB)m/z: 592(M+H)$^+$.

Example 205

N$^1$-(6-Chloropyridin-3-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

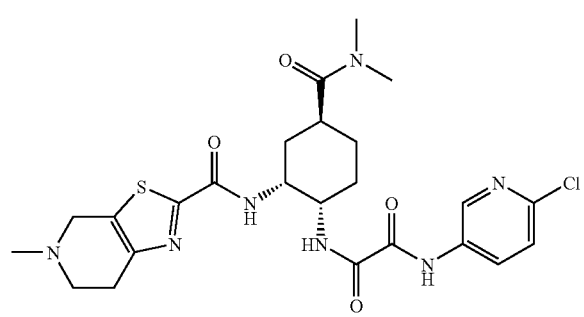

The compound (200 mg) obtained in Referential Example 263, which was a crude product, was dissolved in methanol (10 mL) to heat the solution to 50° C., and 1N aqueous sodium hydroxide (3 mL) was added thereto, followed by stirring for 5 minutes. To this mixture was added 1N hydrochloric acid to adjust the pH to a weak acidity. The solvent was distilled away under reduced pressure to give residue containing 2-[(2-chloropyridin-5-yl)amino]-2-oxoacetic acid. This residue and the compound (250 mg) obtained in Referential Example 253 were added to N,N-dimethylformamide (5 mL), and 1-(3-dimethylaminopropyl)-3-ethylcarbodiimide hydrochloride (328 mg) and 1-hydroxybenzotriazole monohydrate (46 mg) were added, followed by stirring at room temperature for 3 days. The solvent was distilled away under reduced pressure, and saturated aqueous sodium hydrogencarbonate and methylene chloride were added to the residue for partitioning the mixture. The resultant organic layer was dried over sodium sulfate anhydrate, the solvent was distilled away under reduced pressure, and the residue was purified by silica gel column chromatography (methylene chloride:methanol=47:3) to give a free base of the title compound as a pale yellow solid. This product was dissolved in methylene chloride, 1N HCl in ethanol (862 μl) was added, and the solvent was distilled away under reduced pressure. A small amount of methanol was added to the residue, and ethyl acetate and diethyl ether were added dropwise while irradiating with ultrasonic waves to collect the precipitate formed by filtration. This product was washed with diethyl ether to give the title compound (229 mg).

$^1$H-NMR (DMSO-d$_6$) δ: 1.46-1.75(4H,m), 1.99-2.09(2H, m), 2.79(3H,s), 2.92-2.95(7H,m), 3.12-3.53(3H,m), 3.70(1H,br.s), 3.99-4.06(1H,m), 4.44(2H,br.s), 4.69, 4.73(1H, each s), 7.53(1H,d,J=8.5 Hz), 8.23-8.25(1H,m), 8.72-8.77(1H,m), 8.85(1H,s), 9.07, 9.16(1H, each d,J=8.1 Hz), 11.09(1H,d,J=8.1 Hz), 11.78(1H,br.s).

MS(FAB)m/z: 548(M+H)$^+$.

Example 206

N$^1$-(6-Chloropyridazin-3-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

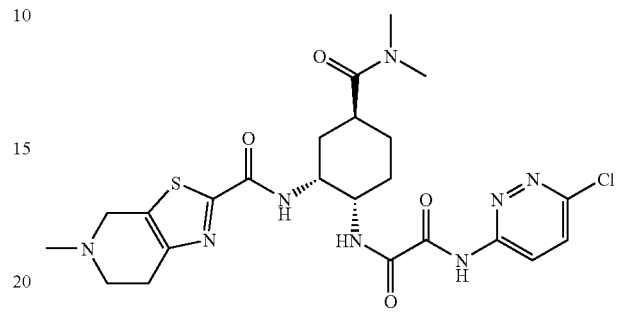

In a manner similar to that described in Example 191, the compound obtained in Referential Example 264 was hydrolyzed and then, condensed with the compound obtained in Referential Example 253, followed by treatment with hydrochloric acid, to thereby give the title compound.

$^1$H-NMR (DMSO-d$_6$) δ: 1.44-1.57(1H,m), 1.62-1.80(3H, m), 2.00-2.10(2H,m), 2.79(3H,s), 2.86(3H,br.s), 2.94(3H,s), 2.95-3.01(1H,m), 3.14-3.23(2H,m), 3.45-3.63(2H,m), 3.96-4.08(1H,m), 4.40-4.60(3H,m), 7.97(1H,d,J=9.3 Hz), 8.26 (1H,d,J=9.3 Hz), 8.69(1H,d,J=7.6 Hz), 9.20(1H,d,J=7.6 Hz), 11.06(1H,s).

MS(FAB)m/z: 549(M+H)$^+$.

Example 207

N$^1$-(5-Chlorothiazol-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride In a manner similar to that described in Example 191, the compound obtained in Referential Example 265 was hydrolyzed and then, condensed with the compound obtained in Referential Example 253, followed by treatment with hydrochloric acid, to thereby give the title compound.

$^1$H-NMR (DMSO-d$_6$) δ: 1.35-2.10(6H,m), 2.77(3H,s), 2.92(3H,s), 2.93(3H,s), 3.05-4.23(8H,m), 4.32-4.80(2H,m), 7.59(1H,s), 8.63(1H,d,J=7.6 Hz), 9.14(1H,d,J=7.6 Hz).

MS(FAB)m/z: 554(M+H)$^+$.

Example 208

N[1]-(5-Chloropyridin-2-yl)-N[2]-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)ethanediamide hydrochloride

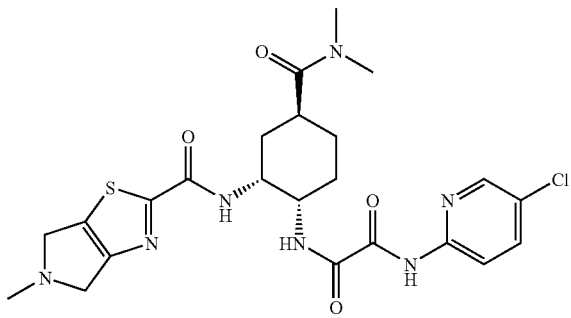

The compound (210 mg) obtained in Referential Example 266 and the compound (350 mg) obtained in Referential Example 272 were dissolved in N,N-dimethylformamide (15 mL), and 1-hydroxybenzotriazole monohydrate (205 mg) and 1-(3-dimethylaminopropyl)-3-ethylcarbodiimide hydrochloride (290 mg) were added, followed by stirring at room temperature for 20 hours. The solvent was distilled away under reduced pressure, and saturated aqueous sodium hydrogencarbonate and methylene chloride were added to the residue for partitioning the mixture. The resultant organic layer was dried over sodium sulfate anhydrate, the solvent was distilled away under reduced pressure, and the residue was purified by silica gel column chromatography (methylene chloride:methanol=20:1). The thus-obtained pale yellow solids were dissolved in methylene chloride, 1N HCl in ethanol (0.46 mL) was added, and the solvent was distilled away under reduced pressure. Methanol and diethyl ether were added to the residue, and the precipitate formed was collected by filtration to give the title compound (248 mg).

$^1$H-NMR (DMSO-d$_6$) δ: 1.47-1.50(1H,m), 1.69-1.76(3H,m), 1.98-2.06(2H,m), 2.79(3H,s), 2.95(3H,s), 2.98-3.05(1H,m), 3.10(3H,s), 3.49-4.62(6H,m), 7.98-8.03(2H,m), 8.45(1H,s), 8.73(1H,d,J=7.6 Hz), 9.10(1H,d,J=8.0 Hz), 10.30(1H,s).

MS(FAB)m/z: 534(M+H)$^+$.

Example 209

N-{(1R,2S,5S)-2-{[2-(4-Chloroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride

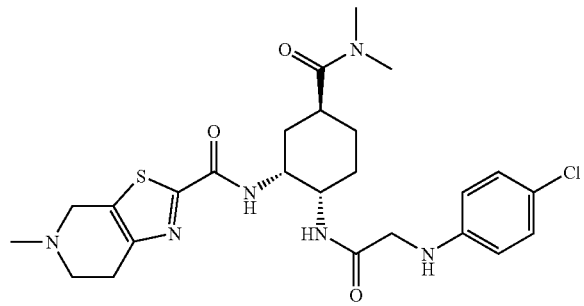

The compound (2.3 g) obtained in Referential Example 267 was dissolved in ethanol (10 mL), and 1N aqueous sodium hydroxide (20 mL) was added, followed by stirring at room temperature for 2 hours. After 1N hydrochloric acid (20 mL) was added to the reaction mixture, the mixture was diluted with water and stirred for 30 minutes. Insoluble matter precipitated was collected by filtration to give 2-(4-chloroanilino)acetic acid (1.05 g) as a colorless solid. This solid and the compound (0.25 g) obtained in Referential Example 253 were dissolved in N,N-dimethylformamide (10 mL), and 1-hydroxybenzotriazole monohydrate (0.11 g) and 1-(3-dimethylaminopropyl)-3-ethylcarbodiimide hydrochloride (0.23 g) were added, followed by stirring at room temperature for 4 days. After the reaction mixture was diluted with chloroform and washed with saturated aqueous sodium hydrogencarbonate and saturated brine, the resultant organic layer was dried over sodium sulfate anhydrate. The solvent was distilled away under reduced pressure, and the residue was purified by silica gel column chromatography (chloroform:methanol=97:3). The thus-obtained pale yellow solid was dissolved in ethanol, 1N HCl in ethanol was added, and the solvent was distilled away under reduced pressure. Methanol and diethyl ether were added to the residue, and the precipitate formed was collected by filtration to give the title compound (0.15 g).

$^1$H-NMR (DMSO-d$_6$) δ: 1.35-1.41(1H,m), 1.59-1.80(3H,m), 1.82-1.95(2H,m), 2.76(3H,s), 2.93(3H,s), 2.94(3H,s), 2.99-3.10(1H,m), 3.10-3.22(2H,m), 3.42-3.60(2H,m), 3.60-3.77(2H,m), 3.80-3.90(1H,m), 4.35-4.48(2H,m), 4.68-4.80(1H,m), 6.40(1H,d,J=6.7 Hz), 6.44(1H,d,J=6.7 Hz), 6.90(1H,d,J=6.7 Hz), 7.00(1H,d,J=6.7 Hz), 7.70-7.89(1H,m), 8.35-8.42(1H,m), 11.05-11.38(1H,m).

Example 210

N-{(1R,2S,5S)-2-{[2-(4-Chloro-2-fluoroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride

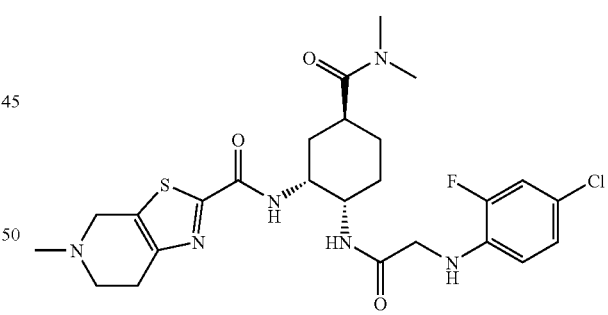

In a manner similar to that described in Example 209, the compound obtained in Referential Example 268 was hydrolyzed and then, condensed with the compound obtained in Referential Example 253, followed by treatment with hydrochloric acid, to thereby give the title compound.

$^1$H-NMR (DMSO-d$_6$) δ: 1.35-1.42(1H,m), 1.55-1.78(3H,m), 1.80-2.00(2H,m), 2.76(3H,s), 2.92(3H,s), 2.94(3H,s), 2.99-3.10(1H,m), 3.10-3.22(2H,m), 3.42-3.60(2H,m), 3.60-3.77(2H,m), 3.85-4.00(1H,m), 4.33-4.48(2H,m), 4.65-4.80(1H,m), 6.41(1H,t,J=8.8 Hz), 6.73(1H,dt,J=8.8, 1.2 Hz), 7.08(1H,dd,J=11.7, 1.2 Hz), 7.78-7.92(1H,m), 8.35-8.42(1H,m), 11.18-11.50(1H,m).

Example 211

N-{(1R,2S,5S)-2-{[(5-Chloroindol-2-yl)carbonyl]amino}-5-[(dimethylamino)carbonyl]cyclohexyl}-4,5,6,7-tetrahydrothiazolo[5,4-c]pyridine-2-carboxamide hydrochloride

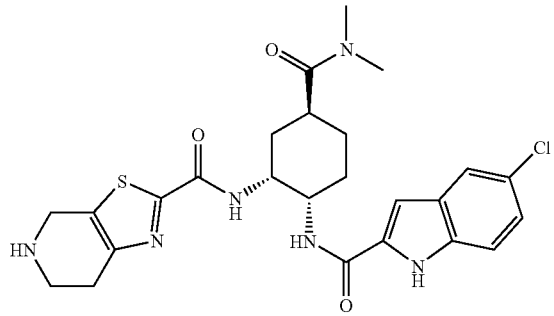

In a manner similar to that employed in Example 2, the compound obtained in Referential Example 432 was condensed with the compound obtained in Referential Example 34, followed by treatment with hydrochloric acid, to thereby give the title compound.

$^1$H-NMR (DMSO-$d_6$) δ: 1.45-1.60(1H,m), 1.70-2.15(6H,m), 2.80(3H,s), 2.97(3H,s), 2.95-3.15(2H,m), 3.35-3.55(2H,m), 4.05-4.20(1H,m), 4.46(2H,s), 4.50-4.65(1H,m), 7.05(1H,s), 7.16(1H,dd,J=8.8, 2.2 Hz), 7.41(1H,d,J=8.8 Hz), 7.68(1H,s), 8.30-8.45(1H,br), 9.30-9.50(1H,br), 11.78(1H,s).

MS(ESI)m/z: 529(M+H)$^+$.

Example 212

N-{(1R,2S,5S)-2-{[(5-Chloroindol-2-yl)carbonyl]amino}-5-[(dimethylamino)carbonyl]cyclohexyl}-5-(4,5-dihydrooxazol-2-yl)-4,5,6,7-tetrahydrothiazolo[5,4-c]pyridine-2-carboxamide

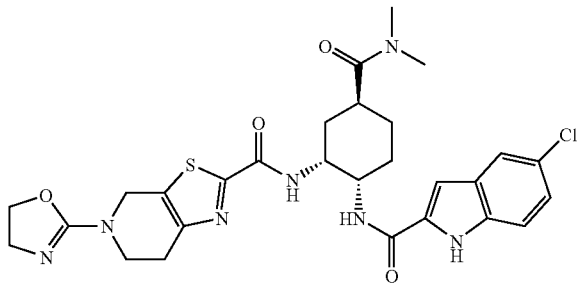

The compound (250 mg) obtained in Example 211 was suspended in methylene chloride, and saturated aqueous sodium hydrogencarbonate was added, followed by fully stirring the mixture. The resultant organic layer was separated and dried over magnesium sulfate anhydrate. Triethylamine (0.5 mL) and bromoethyl isocyanate (43 μl) were then added, followed by stirring at room temperature for 20 hours. Saturated aqueous sodium hydrogencarbonate was added to the reaction mixture to separate an organic layer. The organic layer was dried over magnesium sulfate anhydrate. The solvent was distilled away under reduced pressure, and the residue was purified by silica gel column chromatography (methylene chloride:methanol=22:3) to give the title compound (227 mg).

$^1$H-NMR (CDCl$_3$) δ: 1.50-2.15(4H,m), 2.15-2.40(2H,m), 2.80-3.00(1H,m), 2.97(3H,s), 3.11(3H,s), 3.70-3.95(4H,m), 4.10-4.30(1H,m), 4.30-4.50(2H,m), 4.60-4.70(1H,m), 4.74(2H,s), 6.85(1H,s), 7.21(1H,dd,J=8.8, 2.2 Hz), 7.34(1H,d, J=8.8 Hz), 7.50(1H,br.s), 7.62(1H,s), 7.87(1H,br.s), 9.48(1H, br.s).

MS(ESI)m/z: 598(M+H)$^+$.

Example 213

N-{(1R,2S,5S)-2-{[(5-Chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

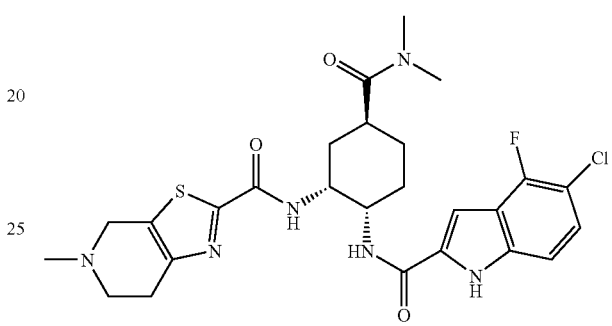

The compound (140 mg) obtained in Referential Example 144 was dissolved in N,N-dimethylformamide (10 mL), and the compound (100 mg) obtained in Referential Example 274, 1-(3-dimethylaminopropyl)-3-ethylcarbodiimide hydrochloride (140 mg), and 1-hydroxybenzotriazole monohydrate (110 mg) were added, followed by stirring at room temperature for 18 hours. The solvent was distilled away under reduced pressure, and the residue was partitioned in water-ethyl acetate, and an aqueous layer was extracted with ethyl acetate. The resultant organic layers were combined, washed with saturated brine and then dried over sodium sulfate anhydrate. The solvent was distilled away under reduced pressure, and the residue was purified by silica gel column chromatography (methanol:methylene chloride=1:19) to give tert-butyl (1R,2S,5S)-2-{[(5-chloro-4-fluoroindol-2-yl)carbonyl]amino}-5-[(dimethylamino)carbonyl]cyclohexyl-carbamate (260 mg). The thus-obtained powder was dissolved in methylene chloride (5 mL), and 4N HCl-dioxane (1.2 mL) was added. After the reaction mixture was stirred at room temperature for 3.5 hours, the solvent was distilled away under reduced pressure. Methylene chloride (10 mL) was added to the residue, and the mixture was concentrated. After this process was repeated 3 times, the residue was dried under reduced pressure to give crude N-{(1S,2R,4S)-2-amino-4-[(dimethylamino)carbonyl]cyclohexyl}-5-chloro-4-fluoroindole-2-carboxamide. This product was dissolved in N,N-dimethylformamide (50 mL), and the compound (150 mg) obtained in Referential Example 10, 1-(3-dimethylaminopropyl)-3-ethylcarbodiimide hydrochloride (140 mg) and 1-hydroxybenzotriazole monohydrate (110 mg) were added, followed by stirring at room temperature for 18 hours. The solvent was distilled away under reduced pressure, and the residue was partitioned in a mixture of water-ethyl acetate-tetrahydrofuran, and an aqueous layer was extracted with ethyl acetate. The resultant organic layers were combined, washed with saturated brine and then dried over sodium sulfate anhydrate. The solvent was distilled away under reduced pressure, and the residue was purified by silica gel column chromatography (methanol:methylene chloride=1:19) to give a free base of the title compound (270 mg). This product was dissolved in methylene chloride (10 mL), and 1N HCl in ethanol (0.72 mL) was added, followed by stirring at room temperature for 30 minutes. Crystals precipitated were collected by filtration to give the title compound (200 mg).

$^1$H-NMR (DMSO-$d_6$) δ: 1.24-1.98(6H,m), 2.33-3.33(6H, m), 2.81(3H,s), 2.90(3H,s), 2.99(3H,s), 4.12(1H, br.s), 4.30-4.70(1H,m), 4.60(1H,br.s), 7.21(1H,s), 7.27(2H,br.s), 8.37 (1H,d,J=8.1 Hz), 8.43(1H,d,J=7.6 Hz), 12.11(1H,s).

MS(FAB)m/z: 561(M+H)$^+$.

Example 214

N-{(1R,2S,5S)-2-{[(5-Chloro-3-fluoroindol-2-yl) carbonyl]amino}-5-[(dimethylamino)carbonyl]cyclohexyl}-5-methyl-4,5,6,7-tetrahydrothiazolo[5,4-c]pyridine-2-carboxamide hydrochloride

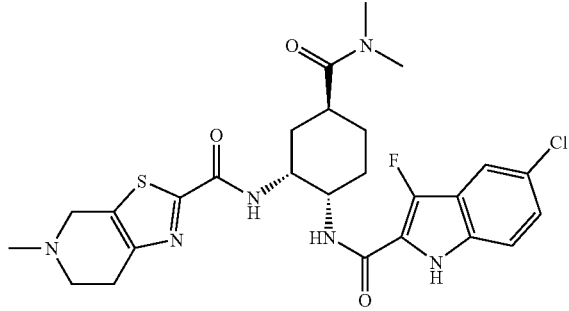

The compound (250 mg) obtained in Referential Example 279 was dissolved in methylene chloride (60 mL), and 4N HCl-dioxane (1.3 mL) was added. After the reaction mixture was stirred at room temperature for 5.5 hours, 4N HCl-dioxane (0.65 mL) was additionally added, and the mixture was stirred at room temperature for 1 hour. The solvent was distilled away under reduced pressure, methylene chloride (10 mL) was added to the residue, and the mixture was concentrated. This process was repeated 3 times. The residue was dried under reduced pressure, and the thus-obtained crude product was dissolved in N,N-dimethylformamide (50 mL), and the compound (160 mg) obtained in Referential Example 10, 1-(3-dimethylamino-propyl)-3-ethylcarbodiimide hydrochloride (150 mg) and 1-hydroxybenzotriazole monohydrate (120 mg) were added, followed by stirring at room temperature for 18 hours. The solvent was distilled away under reduced pressure, and the residue was partitioned in a mixture of water-ethyl acetate, and an aqueous layer was extracted with ethyl acetate. The resultant organic layers were combined, washed with saturated brine and then dried over sodium sulfate anhydrate. The solvent was distilled away under reduced pressure, and the residue was purified twice by silica gel column chromatography (methanol:methylene chloride=2:23→1:9) to give a free base (260 mg) of the title compound. This product was dissolved in methylene chloride, and 1N HCl in ethanol (0.69 mL) was added, followed by stirring at room temperature for 30 minutes. The solvent was distilled away. The residue was dissolved in methanol, and diethyl ether and hexane were added. The thus-obtained crystals were collected by filtration to give the title compound (230 mg).

$^1$H-NMR (DMSO-$d_6$) δ: 1.50-1.56(1H,m), 1.73-1.78(3H, m), 1.94-2.02(2H,m), 2.33-3.55(6H,m), 2.80(3H,s), 2.92(3H,s), 2.98(3H,s), 4.17(1H,br.s), 4.30-4.80(1H,br), 4.62(1H,br.s), 7.25(1H,d,J=8.8, 1.7 Hz), 7.40(1H,d,J=8.8, 1.7 Hz), 7.65(1H,d,J=1.7 Hz), 7.72(1H,d,J=5.9 Hz), 8.74(1H, d,J=8.0 Hz), 10.85-11.35(1H,br), 11.71(1H,s).

MS(FAB)m/z: 561(M+H)$^+$.

Example 215

N-{(1R,2S,5S)-2-{[(3-Bromo-5-chloroindol-2-yl) carbonyl]-amino}-5-[(dimethylamino)carbonyl]cyclohexyl}-5-methyl-4,5,6,7-tetrahydrothiazolo[5,4-c]pyridine-2-carboxamide hydrochloride

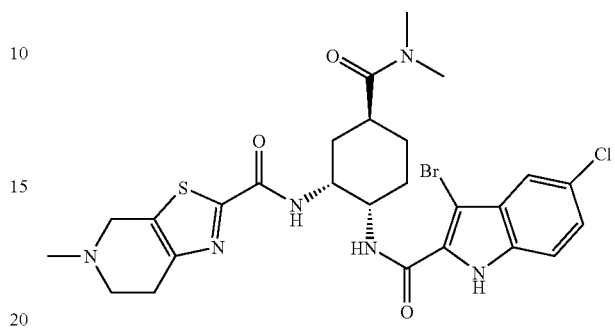

In a manner similar to that employed in Example 214, the compound obtained in Referential Example 282 was treated with 4N HCl-dioxane, followed by condensation with the compound obtained in Referential Example 10, to thereby give the title compound.

$^1$H-NMR (DMSO-$d_6$) δ: 1.51-2.01(6H,m), 2.33-3.29(7H, m), 2.81(3H,s), 2.88(3H,s), 3.01(3H,s), 4.20(1H,br.s), 4.48 (1H,br), 4.70-4.73(1H,m), 7.29(1H,dd,J=8.9, 1.8 Hz), 7.45-7.49(2H,m), 7.80(1H,d,J=7.6 Hz), 8.76(1H,d,J=8.8 Hz), 12.31(1H,s).

MS(FAB)m/z: 622(M+H)$^+$.

Example 216

N-{(1R,2S,5S)-2-{[(3-Chloro-5-fluoroindol-2-yl) carbonyl]-amino}-5-[(dimethylamino)carbonyl]cyclohexyl}-5-methyl-4,5,6,7-tetrahydrothiazolo[5,4-c]pyridine-2-carboxamide hydrochloride

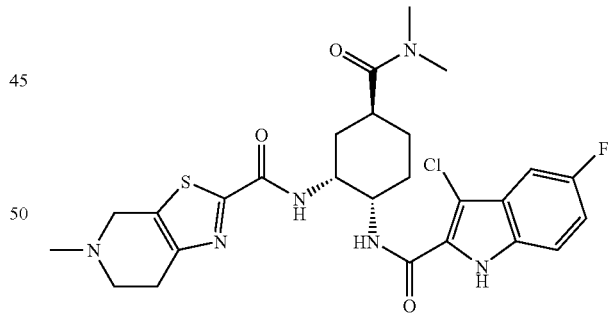

The title compound was obtained from the compound obtained in Referential Example 253 and the compound obtained in Referential Example 284 in a similar manner to the process described in Example 5.

$^1$H-NMR (DMSO-$d_6$) δ: 1.40-1.51(1H,m), 1.75-2.00(5H, m), 2.79(3H,s), 2.92(3H,s), 2.99(3H,s), 3.10-3.21(3H,m), 3.29-3.41(4H,m), 4.11-4.21(1H,m), 4.62-4.75(1H,m), 7.14 (1H,dt,J=8.8, 2.4 Hz), 7.24(1H,dd,J=8.8, 2.4 Hz), 7.45(1H, dd,J=8.8, 4.4 Hz), 7.69(1H,d,J=2.5 Hz), 8.79(1H,d,J=2.5 Hz), 12.10(1H,s).

MS(FAB)m/z: 561(M+H)$^+$.

Example 217

N-{(1R,2S,5S)-2-{[(5-Chloro-3-formylindol-2-yl)carbonyl]-amino}-5-[(dimethylamino)carbonyl]cyclohexyl}-5-methyl-4,5,6,7-tetrahydrothiazolo[5,4-c]pyridine-2-carboxamide hydrochloride

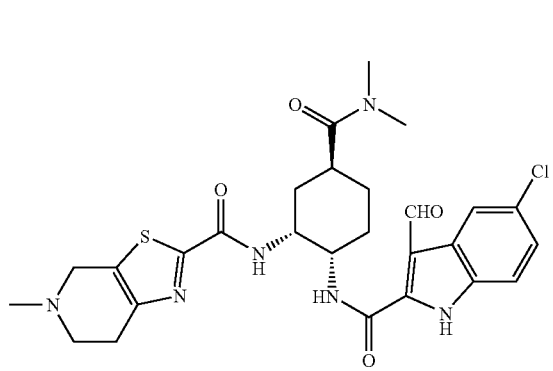

The title compound was obtained from the compound obtained in Referential Example 253 and the compound obtained in Referential Example 286 in a similar manner to the process described in Example 5.

$^1$H-NMR (DMSO-d$_6$) δ: 1.40-1.51(1H,m), 1.75-1.89(4H, m), 1.90-2.01(1H,m), 2.80(3H,s), 2.91(3H,s), 3.03(3H,s), 3.05-3.33(3H,m), 3.60-3.71(1H,m), 4.11-4.21(1H,m), 4.32-4.44(1H,m), 4.62-4.75(2H,m), 7.35(1H,dd,J=8.0, 1.4 Hz), 7.56(1H,d,J=8.0 Hz), 8.21(1H,d,J=1.4 Hz), 8.65(1H,t,J=7.4 Hz), 9.92(1H,d,J=6.8 Hz), 10.15(1H,t,J=9.1 Hz), 13.00(1H, dt,J=6.4).

MS(FAB)m/z: 571(M+H)$^+$.

Example 218

5-Chloro-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl-N$^3$,N$^3$-dimethylindole-2,3-dicarboxamide hydrochloride

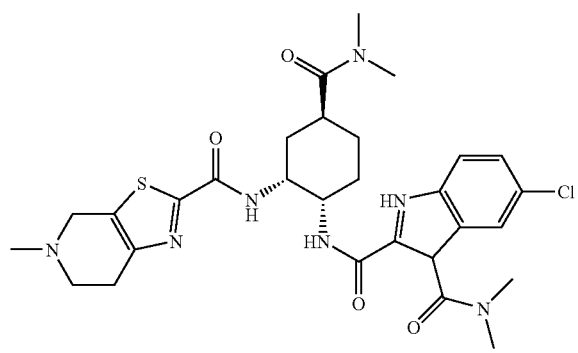

The title compound was obtained from the compound obtained in Referential Example 253 and the compound obtained in Referential Example 289 in a similar manner to the process described in Example 5.

$^1$H-NMR (DMSO-d$_6$) δ: 1.40-1.51(1H,m), 1.75-2.01(5H, m), 2.78(9H,s), 2.93(3H,s), 3.01(3H,s), 3.10-3.33(3H,m), 3.40-3.50(1H,m), 3.65-3.75(1H,m), 4.01-4.09(1H,m), 4.32-4.44(1H,m), 4.62-4.75(2H,m), 7.25(1H,d,J=8.0 Hz), 7.40-7.50(2H,m), 8.62(1H,br), 9.08(1H,br), 12.28(1H,br).

MS(FAB)m/z: 614(M+H)$^+$.

Example 219

N-{(1R,2S,5S)-2-[(6-Chloro-2-naphthoyl)amino]-5-[(dimethylamino)carbonyl]cyclohexyl}-5-methyl-4,5,6,7-tetrahydrothiazolo[5,4-c]pyridine-2-carboxamide hydrochloride

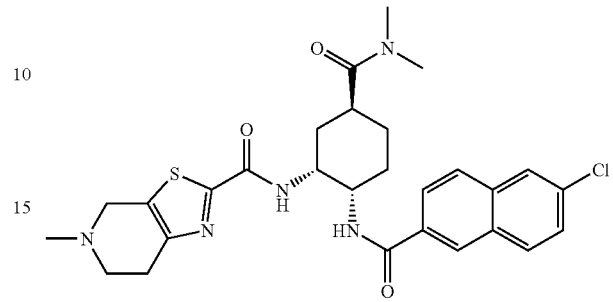

The compound (270 mg) obtained in Referential Example 294 was dissolved in methylene chloride (10 mL), and 1N HCl in ethanol (10 mL) was added, followed by stirring for 90 minutes. The solvent was distilled away under reduced pressure, and the resultant residue was dissolved in N,N-dimethylformamide (7 mL). The compound (110 mg) obtained in Referential Example 10, 1-(3-dimethylaminopropyl)-3-ethylcarbodiimide hydrochloride (100 mg) and 1-hydroxybenzotriazole monohydrate (70 mg) were added, followed by stirring at room temperature for 23 hours. The reaction mixture was concentrated under reduced pressure, and water was added, followed by extraction with ethyl acetate. The resultant organic layer was dried over sodium sulfate anhydrate. The solvent was distilled away under reduced pressure, and the residue was purified twice by silica gel column chromatography (methylene chloride:methanol=20:1→10:1). The thus-obtained free base was dissolved in methanol, and 1N HCl in ethanol (0.30 mL) was added. The solvent was distilled away under reduced pressure, and the residue was washed with ethyl acetate to give the title compound (130 mg).

$^1$H-NMR (DMSO-d$_6$) δ: 1.45-1.60(1H,m), 1.70-1.90(3H, m), 1.90-2.10(2H,m), 2.81(3H,s), 2.91(3H,s), 3.00(3H,s), 3.00-3.22(3H,m), 3.53(2H,br), 4.10-4.20(1H,m), 4.30-4.70 (3H,m), 7.59(1H,dd,J=8.8, 2.2 Hz), 7.87(1H,d,J=8.5 Hz), 7.96(1H,d,J=8.5 Hz), 8.02(1H,d,J=8.8 Hz), 8.10(1H,d,J=2.2 Hz), 8.33(1H,s), 8.43(1H,d,J=8.1 Hz), 8.52(1H,d,J=7.3 Hz).

MS(FAB)m/z: 554 (M+H)$^+$.

Example 220

7-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)cinnoline-3-carboxamide hydrochloride

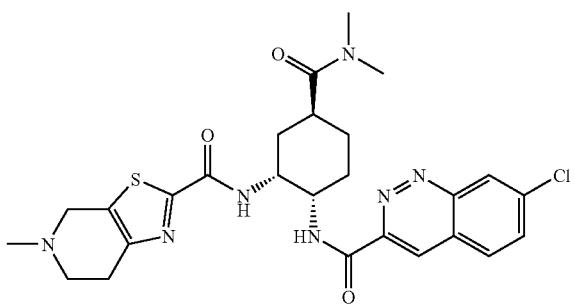

In a manner similar to that employed in Example 219, the compound obtained in Referential Example 299 was treated with HCl in ethanol, followed by condensation with the compound obtained in Referential Example 10, to thereby give the title compound.

¹H-NMR (CDCl₃) δ: 1.50-1.65(1H,m), 1.70-1.90(3H,m), 2.05-2.15(1H,m), 2.15-2.30(1H,m), 2.81(3H,s), 2.85-3.05 (8H,m), 3.15-3.25(2H,m), 3.40-3.80(1H,m), 4.25-4.80(4H,m), 8.02(1H,dd,J=8.8, 2.0 Hz), 8.38(1H,d,J=8.8 Hz), 8.66 (1H,s), 8.91(1H,s), 8.96(1H,d,J=7.3 Hz), 9.53(1H,br).

MS(FAB)m/z: 556(M+H)⁺.

Example 221

N-{(1R,2S,5S)-2-{[(5-Chlorobenzimidazol-2-yl) carbonyl]amino}-5-[(dimethylamino)carbonyl]cyclohexyl}-5-methyl-4,5,6,7-tetrahydrothiazolo[5,4-c] pyridine-2-carboxamide hydrochloride

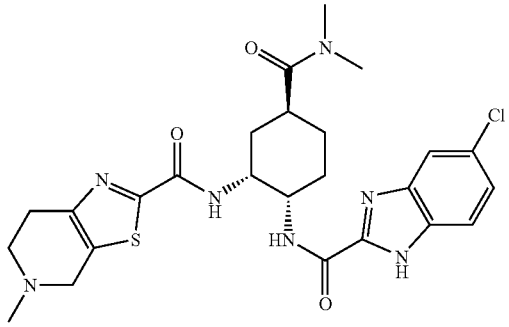

In a manner similar to that employed in Example 219, the compound obtained in Referential Example 300 was treated with HCl in ethanol, followed by condensation with the compound obtained in Referential Example 10, to thereby give the title compound.

¹H-NMR (DMSO-d₆) δ: 1.45-1.60(1H,m), 1.60-1.83(3H, m), 2.00-2.20(2H,m), 2.78(3H,s), 2.92(6H,s), 3.00-3.30(3H, m), 3.47(2H,br.s), 4.10-4.75(4H,m), 7.30(1H,d,J=8.8 Hz), 7.62(1H,d,J=12.5 Hz), 7.63(1H,s), 8.75-8.87(1H,m), 9.09 (1H,dd,J=12.5, 8.8 Hz), 11.20-11.40(1H,m).

MS(FAB)m/z: 546(M+H)⁺.

Example 222

N-((1S,2R,4S)-4-[(Dimethylamino)carbonyl]-2-{[(5-methyl-4,5,6,7-tetrahydrothiazolo[5,4-c]pyridin-2-yl)carbonyl]amino}cyclohexyl)-7-fluoroisoquinoline-3-carboxamide hydrochloride

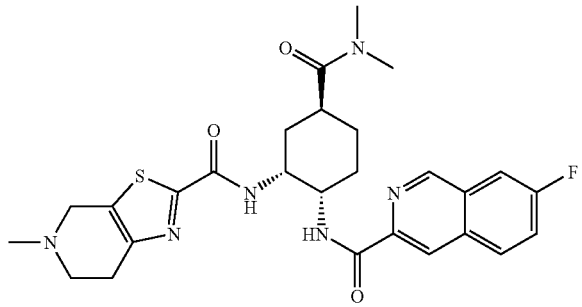

The title compound was obtained from the compound obtained in Referential Example 253 and the compound obtained in Referential Example 304 in a similar manner to the process described in Example 5.

¹H-NMR (DMSO-d₆) δ: 1.50-1.60(1H,m), 1.70-1.85(3H, m), 1.95-2.05(1H,m), 2.10-2.20(1H,m), 2.80(3H,s), 2.90-3.90(5H,m), 2.93(3H,s), 2.96(3H,s), 4.10-4.75(4H,m), 7.75-7.85(1H,m), 8.00-8.05(1H,m), 8.30-8.35(1H,m), 8.61(1H,s), 8.93(2H,d,J=7.3 Hz), 9.31(1H,s).

MS(FAB)m/z: 539(M+H)⁺.

Example 223

N-{(1R,2S,5S)-2-{[(7-Chloro-2H-chromen-3-yl) carbonyl]amino}-5-[(dimethylamino)carbonyl]cyclohexyl}-5-methyl-4,5,6,7-tetrahydrothiazolo[5,4-c] pyridine-2-carboxamide hydrochloride

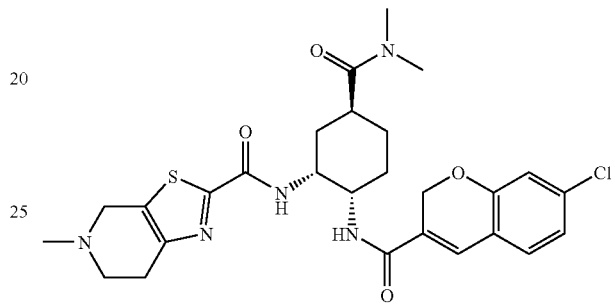

The compound (220 mg) obtained in Referential Example 252 was dissolved in methanol (10 mL), and 10% palladium on carbon (180 mg) was added, followed by stirring at room temperature for 4 hours in a hydrogen atmosphere. After the reaction mixture was filtered, the filtrate was concentrated under reduced pressure, and the residue was dissolved in N,N-dimethylformamide (30 mL). The compound (108 mg) obtained in Referential Example 306, 1-hydroxybenzotriazole monohydrate (78 mg) and 1-(3-dimethylaminopropyl)-3-ethylcarbodiimide hydrochloride (196 mg) were added, followed by stirring at room temperature overnight. The reaction mixture was concentrated under reduced pressure, and methylene chloride and saturated aqueous sodium hydrogencarbonate were added to the residue for partitioning the mixture. The resultant organic layer was dried over sodium sulfate anhydrate. The solvent was distilled away under reduced pressure, and the residue was purified by silica gel column chromatography (methylene chloride:methanol=100:3) to give a pale yellow foamy substance. This foamy substance was dissolved in methylene chloride (2 mL), 1N HCL in ethanol (363 μl) was added, and the solvent was distilled away under reduced pressure. Diethyl ether was added to the residue. The the precipitate formed was collected by filtration to give the title compound (175 mg).

¹H-NMR (DMSO-d₆) δ: 1.40-1.52(1H,m), 1.55-1.96(5H, m), 2.78(3H,s), 2.90(3H,s), 2.98(3H,s), 3.01-3.12(1H,m), 3.13-3.28(2H,m), 3.40-3.85(2H,m), 3.92-4.00(1H,m), 4.35-4.80(3H,m), 4.84(1H,d,J=14.5 Hz), 4.89(1H,d,J=14.5 Hz), 6.92(1H,s), 6.98(1H,dd,J=8.1, 1.7 Hz), 7.08(1H,s), 7.17(1H, d,J=8.3 Hz), 8.12(1H,d,J=8.1 Hz), 8.34(1H,d,J=8.1 Hz).

MS(FAB)m/z: 558(M+H)⁺.

Example 224

N-{(1R,2S,5S)-2-{[(E)-3-(4-Chlorophenyl)-2-propenoyl]amino}-5-[(dimethylamino)carbonyl]cyclohexyl}-5-methyl-4,5,6,7-tetrahydrothiazolo[5,4-c]pyridine-2-carboxamide hydrochloride

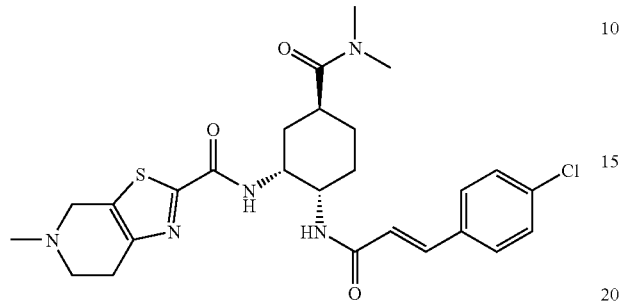

In a manner similar to that employed in Example 219, the compound obtained in Referential Example 307 was treated with HCl in ethanol, followed by condensation with the compound obtained in Referential Example 10, to thereby give the title compound.

$^1$H-NMR (DMSO-d$_6$) δ: 1.35-1.55(1H,m), 1.55-1.90(4H,m), 2.79(3H,s), 2.92(3H,s), 2.99(3H,s), 3.05-3.30(3H,m), 3.40-3.55(1H,m), 3.60-3.75(1H,m), 3.93-4.03(2H,m), 4.35-4.50(1H,m), 4.50-4.60(1H,m), 4.60-4.75(1H,m), 6.65(1H,d,J=15.7 Hz), 7.35(1H,d,J=15.7 Hz), 7.44(1H,d,J=8.6 Hz), 7.55(1H,d,J=8.6 Hz), 8.03(1H,d,J=8.1 Hz), 8.34(1H,br.s), 11.25-11.70(1H,br).

MS(ESI)m/z: 530(M+H)$^+$.

Example 225

6-Chloro-N-((1S,2R,4S)-4-[(dimethylamino)carbonyl]-2-{[(5-methyl-4,5,6,7-tetrahydrothiazolo[5,4-c]pyridin-2-yl)-carbonyl]amino}cyclohexyl)-4-oxo-1,4-dihydroquinoline-2-carboxamide hydrochloride

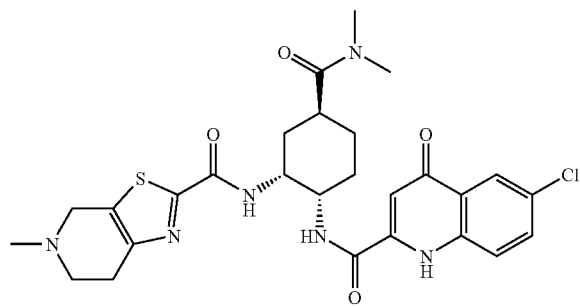

The title compound was obtained from the compound obtained in Referential Example 253 and the compound obtained in Referential Example 309 in a similar manner to the process described in Example 5.

$^1$H-NMR (DMSO-d$_6$) δ: 1.43-1.60(1H,m), 1.65-2.10(3H,m), 2.79(3H,s), 2.92(3H,s), 2.99(3H,s), 3.05-3.20(2H,m), 3.20-3.80(5H,m), 4.08-4.20(1H,m), 4.35-4.50(1H,m), 4.60-4.70(1H,m), 4.70(1H,d,J=15.6 Hz), 6.77(1H,br.s), 7.73(1H,d,J=8.9 Hz), 7.94(1H,d,J=8.9 Hz), 7.97(1H,d,J=2.2 Hz), 8.54(1H,br.s), 8.80-9.00(1H,m), 11.18-11.42 (1H,br), 11.70-12.50(1H,br).

MS(ESI)m/z: 571(M+H)$^+$.

Example 226 tert-Butyl 2-[({(1R,2S,5S)-2-{[(5-chloroindol-2-yl)carbonyl]amino}-5-[(dimethylamino)carbonyl]cyclohexyl}-amino)carbonyl]-4,6-dihydro-5H-pyrrolo[3,4-d]thiazole-5-carboxylate

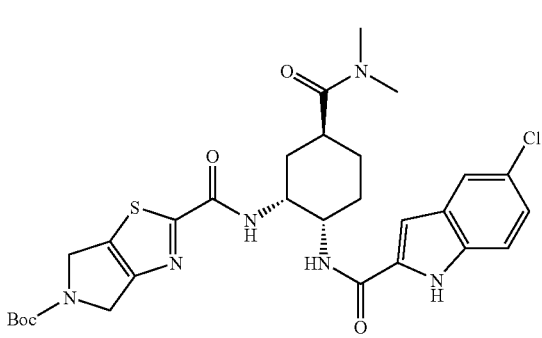

1) The compound (1.46 g) obtained in Referential Example 310 was dissolved in methylene chloride (10 mL), and HCl in ethanol (10 mL) was added at room temperature, followed by stirring for 1 hour. After completion of the reaction, the solvent was distilled away, ethanol was added, the mixture was concentrated, and diisopropyl ether was added to the residue for solidification. The resultant solids were collected by filtration to give N-{(1S,2R,4S)-2-amino-4-[(dimethylamino)carbonyl]cyclohexyl}-5-chloroindole-2-carboxamide hydrochloride.

2) This product was dissolved in N,N-dimethylformamide (5 mL), and the compound (1.31 g) obtained in Referential Example 406, 1-hydroxybenzotriazole monohydrate (640 mg), and 1-(3-dimethylaminopropyl)-3-ethylcarbodiimide hydrochloride (1.36 g) were added, followed by stirring at room temperature for 3 days. The reaction mixture was concentrated, and methylene chloride and saturated aqueous sodium hydrogencarbonate were added to the residue for partitioning the mixture. The resultant organic layer was dried over sodium sulfate anhydrate. After the solvent was distilled away under reduced pressure, the residue was purified by silica gel column chromatography (methanol:methylene chloride=1:19) to give the title compound (1.22 g).

$^1$H-NMR (CDCl$_3$) δ: 1.53(9H,s), 1.70-2.40(6H,m), 2.80-3.20(7H,m), 4.15-4.25(1H,m), 4.55-4.80(5H,m), 6.83(1H,d,J=1.5 Hz), 7.20(1H,dd,J=8.8, 2.0 Hz), 7.33(1H,d,J=8.8 Hz), 7.40-7.50(1H,m), 7.61(1H,br.s), 7.72-7.80(1H,m), 9.41(1H,br.s).

MS(ESI)m/z: 615(M+H)$^+$.

Example 227

5-Chloro-N-{(1S,2R,4S)-2-[[(5,6-dihydro-4H-pyrrolo[3,4-d]-thiazol-2-yl)carbonyl]amino]-4-[(dimethylamino)carbonyl]-cyclohexyl}indole-2-carboxamide hydrochloride

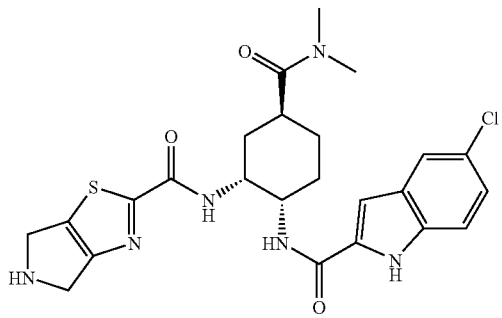

The compound (1.22 g) obtained in Example 226 was dissolved in methylene chloride (5 mL), and, at room temperature, HCl in ethanol (10 mL) was added, followed by stirring for 1 hour. After the reaction mixture was concentrated, saturated aqueous sodium hydrogencarbonate and methylene chloride were added for partitioning the mixture, and the resultant organic layer was dried over sodium sulfate anhydrate. The solvent was distilled away, and the residue was purified by silica gel column chromatography (methanol:methylene chloride=1:9) to give a free base (636 mg) of the title compound as a colorless glassy solid. The free base (200 mg) was dissolved in 1N HCl in ethanol (1 mL). After the solution was concentrated, ethyl acetate was added to solidfy the residue. The thus-obtained colorless powder was collected by filtration and dried to give the title compound (195 mg).

$^1$H-NMR (DMSO-d$_6$) δ: 1.45-1.60(1H,m), 1.70-1.90(3H,m), 1.90-2.05(2H,m), 2.80(3H,s), 2.98(3H,s), 2.98-3.15(1H,m), 4.05-4.20(1H,m), 4.44(2H,br.s), 4.58(3H,br.s), 7.05(1H,d,J=1.5 Hz), 7.16(1H,dd, J=8.7, 1.8 Hz), 7.42(1H,d,J=8.7 Hz), 7.68(1H,d,J=1.8 Hz), 8.38(1H,d,J=7.8 Hz), 8.42(1H,d,J=7.8 Hz), 10.45-10.65(2H,br), 11.78(1H,br.s).

MS(FAB)m/z: 515(M+H)$^+$.

Example 228

5-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)indole-2-carboxamide hydrochloride

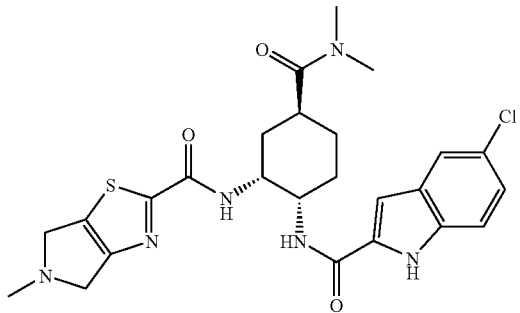

The title compound was obtained from the compound obtained in Example 227 and formalin in a similar manner to the process described in Example 18.

$^1$H-NMR (DMSO-d$_6$) δ: 1.45-1.60(1H,m), 1.65-1.90(3H,m), 1.90-2.05(2H,m), 2.80(3H,s), 2.98(3H,s), 2.98-3.06(1H,m), 3.06(3H,s), 4.05-4.20(1H,m), 4.30-5.00(5H,br.s), 7.04 (1H,d,J=1.7 Hz), 7.17(1H,dd,J=8.8, 2.1 Hz), 7.41(1H,d, J=8.8 Hz) 7.68(1H,d,J=2.1 Hz) 8.36(1H,d,J=7.8 Hz), 8.42 (1H,d,J=8.1 Hz), 11.78(1H,br.s), 12.14(1H,br.s).

MS(FAB)m/z: 529(M+H)$^+$.

Example 229 tert-Butyl 2-{[(((1R,2S,5S)-5-[(dimethylamino)carbonyl]-2-{[(5-fluoroindol-2-yl)carbonyl]amino}cyclohexyl)amino]-carbonyl}-4,6-dihydro-5H-pyrrolo[3,4-d]thiazole-5-carboxylate

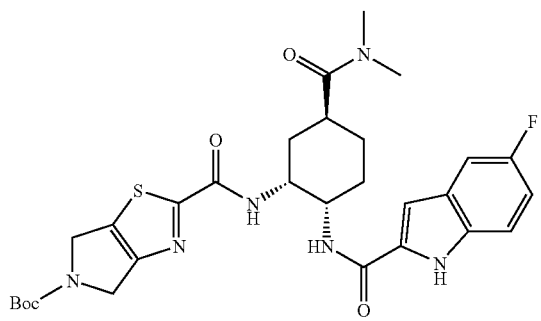

The title compound was obtained from the compound obtained in Referential Example 311 and the compound obtained in Referential Example 406 in a similar manner to the process described in Example 226.

$^1$H-NMR (CDCl$_3$) δ: 1.53(9H,s), 1.60-2.40(6H,m), 2.80-3.20(7H,m), 4.15-4.25(1H,m), 4.55-4.80(5H,m), 6.84-6.87 (1H,m), 7.01(1H,dt,J=2.4, 9.1 Hz), 7.25-7.30(1H,m), 7.34 (1H,dd,J=9.1, 4.3 Hz), 7.42-7.49(1H,m), 7.70-7.80(1H,m), 9.37-9.45(1H,m).

MS(ESI)m/z: 599(M+H)$^+$.

Example 230

N-{(1S,2R,4S)-2-[[(5,6-Dihydro-4H-pyrrolo[3,4-d]thiazol-2-yl)carbonyl]amino}-4-[(dimethylamino)carbonyl]cyclohexyl}-5-fluoroindole-2-carboxamide hydrochloride

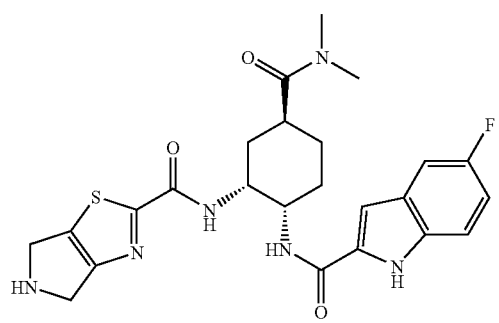

The title compound was obtained from the compound obtained in Example 229 in a similar manner to the process described in Example 227.

$^1$H-NMR (DMSO-d$_6$) δ: 1.45-1.60(1H,m), 1.65-1.90(3H,m), 1.90-2.10(2H,m), 2.80(3H,s), 2.97(3H,s), 2.98-3.15(1H,m), 4.05-4.20(1H,m), 4.35-4.50(2H,m), 4.58(3H,br.s), 6.97-7.10(2H,m), 7.35-7.47(2H,m), 8.34(1H,d,J=7.8 Hz), 8.41 (1H,d,J=8.1 Hz), 10.53(2H,br.s), 11.68(1H,br.s).

MS(FAB)m/z: 499(M+H)$^+$.

Example 231

N-((1S,2R,4S)-4-[(Dimethylamino)carbonyl]-2-{[(5-methyl-5,6-dihydro-4H-pyrrolo[3,4-d]thiazol-2-yl)carbonyl]amino}-cyclohexyl)-5-fluoroindole-2-carboxamide hydrochloride

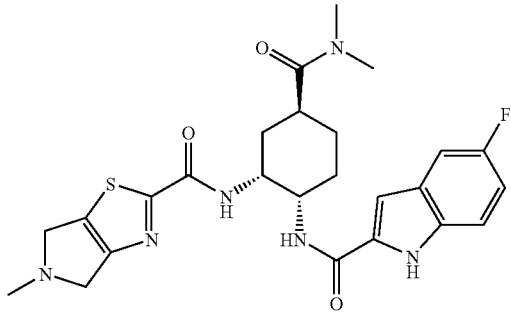

The title compound was obtained from the compound obtained in Example 230 and formalin in a similar manner to the process described in Example 18.

$^1$H-NMR (DMSO-$d_6$) δ: 1.45-1.60(1H,m), 1.65-1.90(3H, m), 1.90-2.10(2H,m), 2.80(3H,s), 2.90-3.20(7H,m), 4.05-4.20(1H, m), 4.30-5.00(5H,br.s), 6.95-7.10(2H,m), 7.35-7.50 (2H,m), 8.33(1H,d,J=7.6 Hz), 8.41(1H,d,J=8.1 Hz), 11.67 (1H,br.s), 12.37(1H,br.s).

MS(FAB)m/z: 513(M+H)$^+$.

Example 232

N-{(1R,2S,5S)-2-[(6-Chloro-2-naphthoyl)amino]-5-[(dimethylamino)carbonyl]cyclohexyl}-5-methyl-5,6-dihydro-4H-pyrrolo[3,4-d]thiazole-2-carboxamide hydrochloride

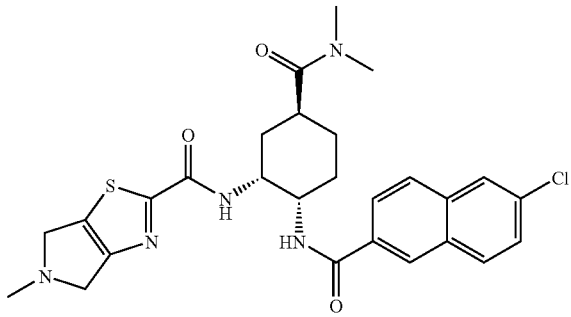

The title compound was obtained from the compound obtained in Referential Example 294 and the compound obtained in Referential Example 293 in a similar manner to the process described in Example 226.

$^1$H-NMR (DMSO-$d_6$) δ: 1.48-1.56(1H,m), 1.71-1.84(3H, m), 1.95-2.04(2H,m), 2.81(3H,s), 3.00(3H,s), 3.02(3H,s), 3.06-3.15(2H,m), 4.13-4.14(1H,m), 4.52-4.63(4H,m), 7.60 (1H,d,J=8.5 Hz), 7.87(1H,d,J=8.8 Hz), 7.96(1H,d,J=8.5 Hz), 8.01(1H,d,J=8.8 Hz), 8.10(1H,s), 8.32(1H,s), 8.45(1H,d, J=8.1 Hz), 8.51(1H,d,J=7.3 Hz).

MS(FAB)m/z: 540(M+H)$^+$.

Example 233

7-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)cinnoline-3-carboxamide hydrochloride and 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)cinnoline-3-carboxamide

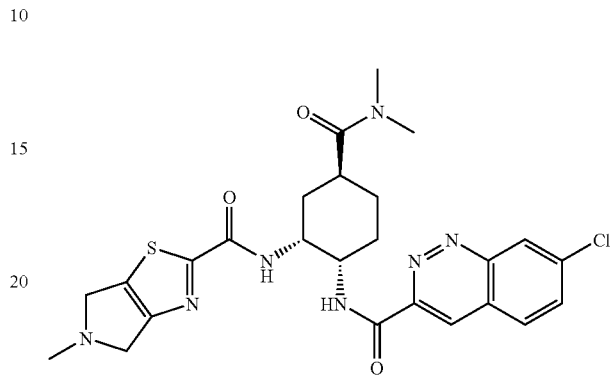

4N HCl-dioxane (3.0 mL) was added to a suspension of the compound (330 mg) obtained in Referential Example 299 in a mixture of dioxane (3.0 mL) and methylene chloride (3.0 mL), and the mixture was stirred at room temperature for 30 minutes. The solvent was distilled away under reduced pressure, and the thus-obtained white powder was dissolved in N,N-dimethylformamide (5.0 mL), and the compound (172 mg) obtained in Referential Example 293, 1-hydroxy-benzotriazole monohydrate (130 mg), and 1-(3-dimethylaminopropyl)-3-ethylcarbodiimide hydrochloride (192 mg) were added, followed by stirring at room temperature for 15 hours. The solvent was distilled away under reduced pressure, methylene chloride and saturated aqueous sodium hydrogencarbonate were added to the residue. The resultant organic layer was washed with saturated saline and then dried over sodium sulfate anhydrate. The solvent was distilled away under reduced pressure, and the residue was purified by silica gel column chromatography (methylene chloride:methanol=20:1). 1N HCl in ethanol (0.35 mL) was added to an ethanol solution (4.0 mL) of the thus-obtained primary product of a high-polar compound, and the solvent was distilled away under reduced pressure. Ethanol and diethyl ether were added to the residue, and the precipitate formed was collected by filtration to give 7-chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)cinnoline-3-carboxamide hydrochloride (184 mg).

$^1$H-NMR (DMSO-$d_6$) δ: 1.50-1.65(1H,m), 1.70-1.90(3H, m), 2.03-2.12(1H, m), 2.15-2.30(1H,m), 2.81(3H,s), 2.90-3.05(1H,m), 2.96(3H,s), 3.07(3H,s), 4.28-4.37(1H, m), 4.40-4.95(5H,br), 8.02(1H,d,J=8.8 Hz), 8.38(1H,d,J=8.8 Hz), 8.66 (1H,s), 8.91(1H,s), 8.97(1H,d,J=7.1 Hz), 9.43-9.57(1H,br), 11.75-11.95(0.5H,br), 12.35-11.55(0.5H,br).

MS(FAB)m/z: 542(M+H)$^+$.

In the purification by the silica gel-column chromatography, low-polar 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)cinnoline-3-carboxamide (98 mg) was also obtained as a by-product.

$^1$H-NMR (CDCl$_3$) δ: 1.90-2.25(6H,m), 2.85-3.00(1H,m), 2.95(3H,s), 3.05(3H,s), 3.91(3H,s), 4.43-4.54(1H,m), 4.86-4.95(1H,m), 6.70(1H,d,J=1.5 Hz), 7.19(1H,d,J=1.5 Hz), 7.59 (1H,d,J=8.8 Hz), 7.76(1H,d,J=8.8 Hz), 7.95(1H,d,J=8.8 Hz), 8.53(1H,s), 8.64(1H,d,J=8.0 Hz), 8.73(1H,s).

MS(FAB)m/z: 540(M+H)$^+$.

Example 234

7-Chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)isoquinoline-3-carboxamide hydrochloride

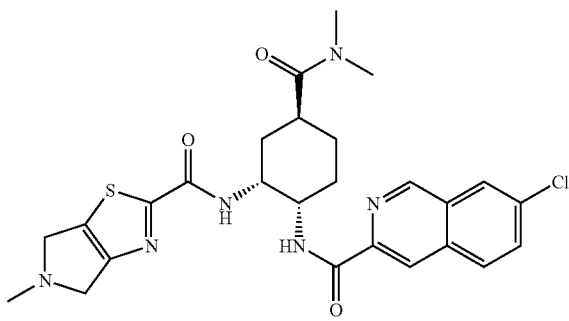

The compound (500 mg) obtained in Referential Example 146 was dissolved in HCl in ethanol (5 mL), and the mixture was stirred at room temperature for 30 minutes. The solvent was distilled away under reduced pressure, and the residue was dissolved in N,N-dimethylformamide (7 mL), and the compound (299 mg) obtained in Referential Example 293, 1-hydroxybenzotriazole monohydrate (71 mg), and 1-(3-dimethylaminopropyl)-3-ethylcarbodiimide hydrochloride (403 mg) were added to the solution, followed by stirring at room temperature overnight. The solvent was distilled away under reduced pressure, saturated aqueous sodium hydrogencarbonate and methylene chloride were added to the residue for partitioning the mixture. The resultant aqueous layer was extracted with methylene chloride. Organic layers were combined and dried over sodium sulfate anhydrate. The solvent was distilled away under reduced pressure, and the residue was purified by silica gel column chromatography (methylene chloride:methanol=93:7) to give a free base (260 mg) of the title compound as a pale yellow solid. This product was dissolved in methylene chloride, 1N HCl in ethanol (961 µl) was added, and the solvent was distilled away under reduced pressure. A small amount of methanol was added to the residue, and diethyl ether was added dropwise to collect the precipitate formed by filtration. This product was washed with diethyl ether to give the title compound (260 mg).

$^1$H-NMR (DMSO-$d_6$) δ: 1.47-1.56(1H,m), 1.71-1.75(3H,m), 1.95-1.99(1H,m), 2.12-2.15(1H,m), 2.78(3H,s), 2.95(3H,s), 2.98(1H,br.s), 3.05(3H,s), 4.19-4.22(1H,m), 4.44-4.52(3H,m), 4.74-4.88(2H,m), 7.87(1H,dd,J=8.8, 1.7 Hz), 8.24(1H,d,J=8.8 Hz), 8.36(1H,d,J=1.7 Hz), 8.58(1H,s), 8.90-8.92(2H,m), 9.30(1H,s), 12.65-12.75(1H,m).

MS(FAB)m/z: 541(M+H)$^+$.

Example 235 tert-Butyl 2-[({(1R,2S,5S)-2-{[(5-chloroindol-2-yl)carbonyl]amino}-5-[(dimethylamino)carbonyl]cyclohexyl}-amino)carbonyl]-6,6-dimethyl-6,7-dihydrothiazolo[4,5-c]pyridine-5(4H)-carboxylate

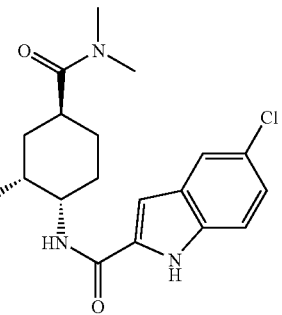

The compound (95.4 mg) obtained in Referential Example 316 was dissolved in diethyl ether (1 mL) in an argon atmosphere, and tert-butyllithium (1.60N pentane solution, 244 µl) was added dropwise at −78° C. After the mixture was stirred for 1 hour at −78° C., carbon dioxide was blown into the reaction mixture for 10 minutes. The reaction mixture was heated to room temperature. After the reaction mixture was concentrated under reduced pressure, the residue was dissolved in N,N-dimethylformamide (5 mL). To the solution, were successively added the compound (178 mg) obtained in Referential Example 432, 1-hydroxybenzotriazole monohydrate (48.0 mg) and 1-(3-dimethylaminopropyl)-3-ethylcarbodiimide hydrochloride (136 mg). The resultant mixture was stirred overnight at room temperature. The reaction mixture was concentrated, and the residue was partitioned between methylene chloride and saturated aqueous sodium hydrogencarbonate. The organic layer was dried over sodium sulfate anhydrate, and the solvent was then distilled away under reduced pressure. The resultant residue was purified by silica gel column chromatography (methanol:methylene chloride=1:19) to give the title compound (140 mg).

$^1$H-NMR (CDCl$_3$) δ: 1.50(9H,s), 1.52(3H,s), 1.54(3H,s), 1.70-2.10(4H,m), 2.15-2.45(2H,m), 2.80-3.20(9H,m), 4.10-4.25(1H,br), 4.60-4.75(3H,m), 6.85(1H,br.s), 7.21(1H,dd, J=8.8, 1.8 Hz), 7.34(1H,d,J=8.8 Hz), 7.48(1H,d,J=7.3 Hz), 7.61-7.63(1H,m), 7.89(1H,br.s), 9.27(1H,br.s).

MS(ESI)m/z: 657(M+H)$^+$.

Example 236

N-{(1R,2S,5S)-2-{[(5-Chloroindol-2-yl)carbonyl]amino}-5-[(dimethylamino)carbonyl]cyclohexyl}-6,6-dimethyl-4,5,6,7-tetrahydrothiazolo[4,5-c]pyridine-2-carboxamide hydrochloride

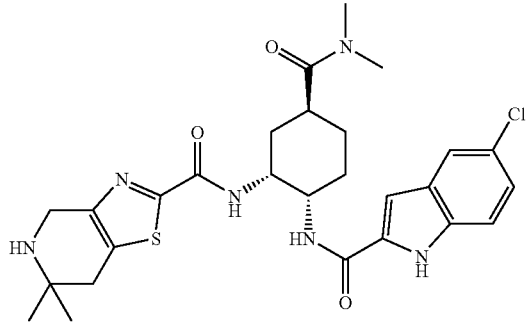

The title compound was obtained from the compound obtained in Example 235 in a similar manner to the process described in Example 227.

¹H-NMR (DMSO-d₆) δ: 1.40(6H,s), 1.45-1.60(1H,m), 1.70-2.05(5H,m), 2.81(3H,s), 2.95-3.15(6H,m), 4.05-4.20(1H,br), 4.25-4.45(2H,m), 4.55-4.65(1H,m), 7.06(1H,d, J=1.7 Hz), 7.17(1H,dd,J=8.8, 2.0 Hz), 7.42(1H,d,J=8.8 Hz), 7.68(1H,d,J=2.0 Hz), 8.34-8.39(2H,m), 9.77(1H,br.s), 9.84(1H,br.s), 11.79(1H,br.s).

MS(ESI)m/z: 557(M+H)⁺.

Example 237 tert-Butyl 2-[({(1R,2S,5S)-2-{[(5-chloroindol-2-yl)carbonyl]amino}-5-[(dimethylamino)carbonyl]cyclohexyl}-amino)carbonyl]-5,7-dihydro-6H-pyrrolo[3,4-d]pyrimidine-6-carboxylate

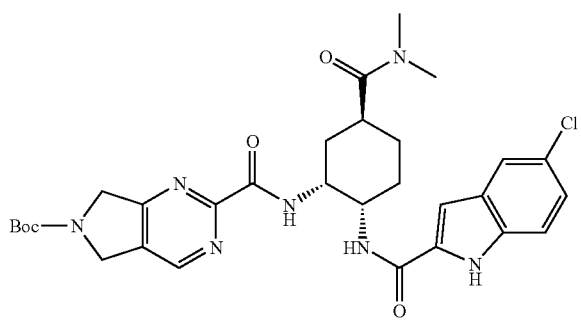

The compound (1.27 g) obtained in Referential Example 50 was dissolved in tetrahydrofuran (48 mL), and lithium hydroxide (117 mg) and water (6.0 mL) were added, followed by stirring at room temperature for 4.5 hours. The reaction mixture was dried to solid under reduced pressure to give a crude carboxylic acid lithim salt (1.24 g). This product was condensed with the compound obtained in Referential Example 432 in a similar manner to the process described in the step 2) of Example 226 to give the title compound.

¹H-NMR (CDCl₃) δ: 1.50-1.70(1H,m), 1.54(9H,s), 1.80-2.10(3H,m), 2.25-2.50(2H,m), 2.85-2.95(1H,m), 2.99(3H,s), 3.14(3H,s), 4.15-4.25(1H,m), 4.65-4.75(1H,m), 4.80-4.90(4H,m), 6.97(1H,s), 7.15-7.25(1H,m), 7.30-7.40(1H,m), 7.60-7.65(1H,m), 8.15-8.25(1H,m), 8.40-8.45(1H,m), 8.75-8.85(1H,m), 9.40-9.45(1H,m).

MS(ESI)m/z: 611(M+H)⁺.

Example 238

N-{(1R,2S,5S)-2-{[(5-Chloroindol-2-yl)carbonyl]amino}-5-[(dimethylamino)carbonyl]cyclohexyl}-6-methyl-6,7-dihydro-5H-pyrrolo[3,4-d]pyrimidine-2-carboxamide hydrochloride

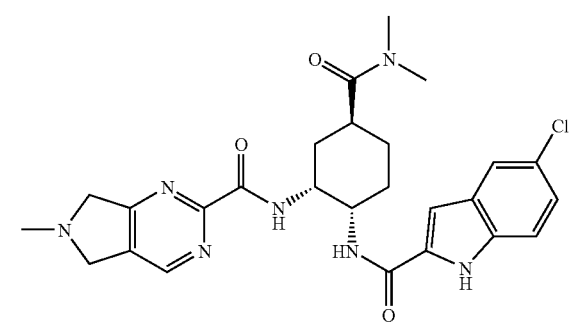

The compound (367 mg) obtained in Example 237 was dissolved in methylene chloride (10 mL), and trifluoroacetic acid (10 mL) was added, followed by stirring at room temperature for 2 hours. The reaction mixture was dried to solid under reduced pressure. The title compound was obtained from the thus-obtained crude product and formalin in a similar manner to the process described in Example 18.

¹H-NMR (DMSO-d₆) δ: 1.50-1.60(1H,m), 1.65-2.10(5H, m), 2.81(3H,s), 2.90-3.00(1H,m), 2.96(3H,s), 3.05(3H,s), 4.10-4.20(1H,m), 4.55-4.65(1H,m), 4.65-4.90(4H,br), 7.06(1H,s), 7.15(1H,dd,J=8.7, 2.1 Hz), 7.41(1H,d,J=8.8 Hz), 7.66(1H,d,J=1.7 Hz), 8.35-8.45(1H,m), 8.57(1H,d,J=8.1 Hz), 9.00(1H,s), 11.80(1H,s), 11.90-12.20(1H,m).

MS(FAB)m/z: 524(M+H)⁺.

Example 239

7-Chloro-N-((1S,2R,4S)-4-[(dimethylamino)carbonyl]-2-{[(6-methyl-6,7-dihydrothiazolo[4,5-d]pyrimidin-2-yl)carbonyl]amino}cyclohexyl)isoquinoline-3-carboxamide hydrochloride

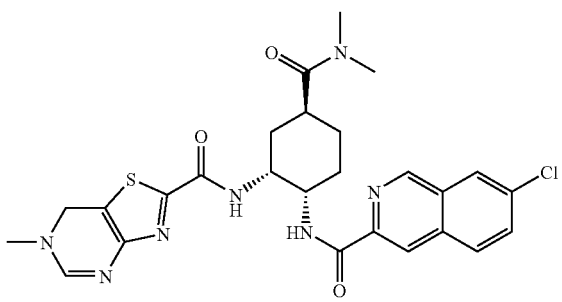

In a manner similar to that employed in Example 49, the compound obtained in Referential Example 146 was treated with HCl in ethanol and condensed with the compound obtained in Referential Example 322, to thereby give the title compound.

¹H-NMR (DMSO-d₆) δ: 1.50-1.60(1H,m), 1.70-1.90(3H, m), 1.90-2.15(2H,m), 2.81(3H,s), 2.95(3H,s), 2.90-3.05(1H, m), 3.26(3H,s), 4.20-4.55(2H,m), 5.00(2H,s), 7.91(1H,d, J=8.8 Hz), 8.27 (1H,d,J=8.8 Hz), 8.37(1H,s), 8.54(1H,s), 8.62(1H,s), 8.79(1H,d,J=8.3 Hz), 8.94(1H,d,J=8.1 Hz), 9.32(1H,s).

MS(ESI)m/z: 554(M+H)⁺.

Example 240

7-Chloro-N-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)isoquinoline-3-carboxamide hydrochloride

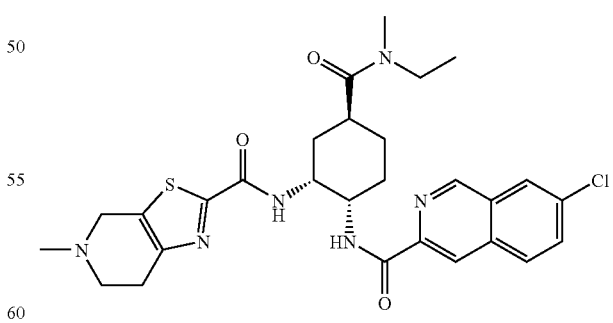

The title compound was obtained from the compound obtained in Referential Example 325 and the compound obtained in Referential Example 10 in a similar manner to the process described in Example 2.

¹H-NMR (DMSO-d₆) δ: 0.98, 1.04(3H, each t,J=7.1 Hz), 1.52-1.60(1H,m), 1.74-1.77(3H,m), 1.96-2.05(1H,m), 2.15-2.18(1H,m), 2.77-2.93(8H,m), 3.17-3.32(3H,m), 3.49(1H,br.s), 4.22(1H,br.s), 4.41-4.45(1H,m), 4.51(1H,br.s), 4.69-4.72(1H,m), 7.89(1H,d,J=8.7 Hz), 8.26 (1H,d,J=8.7 Hz), 8.37(1H,s), 8.60(1H,s), 8.91-8.98(2H,m), 9.32(1H,d,J=6.6 Hz), 11.39, 11.53(1H, each m).
MS(FAB)m/z: 569(M+H)$^+$.

Example 241

N-{(1R*,2S*,5S*)-2-{[(5-Chloroindol-2-yl)carbonyl]amino}-5-[2-(dimethylamino)-2-oxoethyl]cyclohexyl}-5-methyl-4,5,6,7-tetrahydrothiazolo[5,4-c]pyridine-2-carboxamide hydrochloride

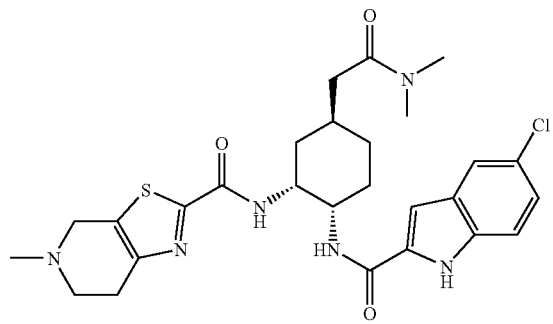

The title compound was obtained from the compound obtained in Referential Example 336 and the compound obtained in Referential Example 10 in a similar manner to the process described in Example 2.

$^1$H-NMR (DMSO-d$_6$) δ: 1.13-1.22(1H,m), 1.40-1.46(1H, m), 1.68-1.99(5H,m), 2.18-2.29(2H,m), 2.80(3H,s), 2.92(3H,s), 2.96(3H,s), 3.22(2H,br.s), 3.49(1H,br.s), 3.70(1H,br.s), 4.09-4.16(1H,m), 4.42-4.46(2H,m), 4.67(1H, br.s), 7.03(1H,s), 7.16(1H,dd,J=8.5, 1.5 Hz), 7.42(1H,d, J=8.5 Hz), 7.67(1H,s), 8.01(1H,d,J=8.5 Hz), 8.40(1H,d,J=7.8 Hz), 11.35-11.58(1H,m), 11.76(1H,br.s).
MS(FAB)m/z: 557(M+H)$^+$.

Example 242

N-{(1R,2S,5S)-2-{[(5-Chloroindol-2-yl)carbonyl]amino}-5-[(methylsulfonyl)methyl]cyclohexyl}-5-methyl-4,5,6,7-tetrahydrothiazolo[5,4-c]pyridine-2-carboxamide hydrochloride

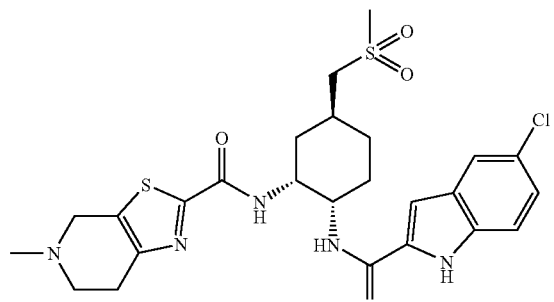

In a manner similar to that employed in Example 219, the compound obtained in Referential Example 340 was treated with HCl in ethanol, followed by condensation with the compound obtained in Referential Example 10, to thereby give the title compound.

$^1$H-NMR (DMSO-d$_6$) δ: 1.35-1.40(1H,m), 1.55-1.62(1H, m), 1.70-1.76(1H,m), 1.88-1.94(1H,m), 2.03-2.07(1H,m), 2.13-2.17(1H,m), 2.30-2.33(4H,m), 2.43-3.48(10H,m), 3.60-3.73(2H,m), 4.11-4.16(1H,m), 4.40-4.42(2H,m), 4.68-4.73(1H,m), 7.05(1H,s), 7.16(1H,dd,J=2.0, 8.8 Hz), 7.41 (1H,d,J=8.8 Hz), 7.68(1H,s), 8.26(1H,d,J=7.8 Hz), 8.39(1H, d,J=7.8 Hz), 11.78(1H,br.s).
MS(ESI)m/z: 564(M+H)$^+$.

Example 243

N-{(1R,2S,5S)-2-{[(2-Chloro-6H-thieno[2,3-b]pyrrol-5-yl)carbonyl]amino}-5-[(dimethylamino)carbonyl]cyclohexyl}-5-methyl-4,5,6,7-tetrahydrothiazolo[5,4-c]pyridine-2-carboxamide

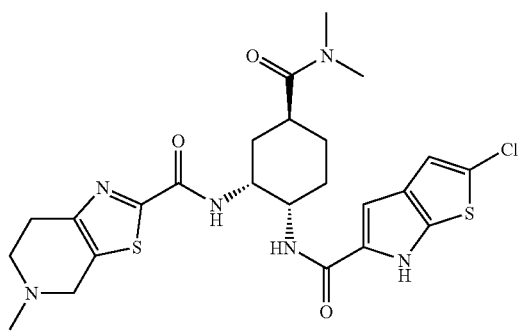

In a manner similar to that employed in Example 223, the compound obtained in Referential Example 252 was subjected to catalytic reduction, followed by condensation with the compound obtained in Referential Example 345, to thereby give the title compound.

$^1$H-NMR (CDCl$_3$) δ: 1.56-1.66(1H,m), 1.76-1.93(2H,m), 2.02-2.06(1H,m), 2.19-2.26(1H,m), 2.30-2.34(1H,m), 2.52 (3H,s), 2.79-2.88(3H,m), 2.91-2.94(2H,m), 2.96(3H,s), 3.09 (3H,s), 3.69-3.77(2H,m), 4.13-4.19(1H,m), 4.58-4.61(1H, m), 6.72(1H,s), 6.84(1H,s), 7.50(1H,d,J=7.3 Hz), 7.60(1H,d, J=5.8 Hz), 10.54(1H,br).
MS(ESI)m/z: 549(M+H)$^+$.

Example 244

N-{(1R,2S,5S)-2-{[3-(4-Chlorophenyl)-2-propynoyl]amino}-5-[(dimethylamino)carbonyl]cyclohexyl}-5-methyl-4,5,6,7-tetrahydrothiazolo[5,4-c]pyridine-2-carboxamide hydrochloride

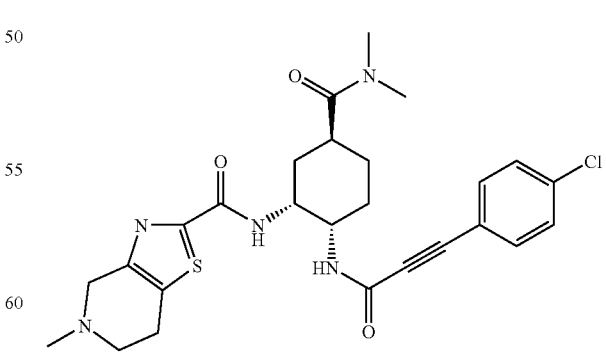

In a manner similar to that employed in Example 223, the compound obtained in Referential Example 252 was subjected to catalytic reduction, followed by condensation with the compound obtained in Referential Example 347, to thereby give the title compound.

¹H-NMR (DMSO-d₆) δ: 1.38-1.50(1H,m), 1.58-1.92(4H,m), 2.78(3H,s), 2.90(3H,s), 2.97(3H,s), 3.01-3.24(3H,m), 3.26-3.80(2H,m), 3.90-3.98(1H,m), 4.30-4.78(3H,m), 7.51(1H,d,J=8.8 Hz), 7.57(1H,d,J=8.8 Hz), 8.34(1H,d,J=8.8 Hz), 8.83(1H,d,J=7.8 Hz).

MS(FAB)m/z: 528(M+H)⁺.

Example 245

6-Chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinazoline-2-carboxamide hydrochloride

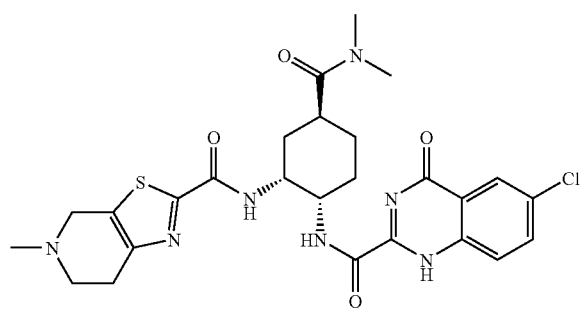

In a manner similar to that employed in Example 223, the compound obtained in Referential Example 252 was subjected to catalytic reduction, followed by condensation with the compound obtained in Referential Example 349, to thereby give the title compound.

¹H-NMR (DMSO-d₆) δ: 1.45-1.60(1H,m), 1.70-1.90(3H,m), 1.90-2.20(3H,m), 2.80(3H,s), 2.93(3H,s), 2.97(3H,s), 2.98-3.80(4H,m), 4.05-4.20(2H,m), 4.35-4.80(3H,m), 7.63(1H,d,J=8.3 Hz), 7.90(1H,d,J=7.3 Hz), 8.75-9.00(2H,m), 11.00-11.50(1H,br), 12.53(1H,br.s).

MS(ESI)m/z: 573(M+H)⁺.

Example 246

N-{(1R,2S,5S)-2-{[2-(4-Chloroanilino)-2-oxoethanethioyl]amino)-5-[(dimethylamino)carbonyl]cyclohexyl}-5-methyl-4,5,6,7-tetrahydrothiazolo[5,4-c]pyridine-2-carboxamide

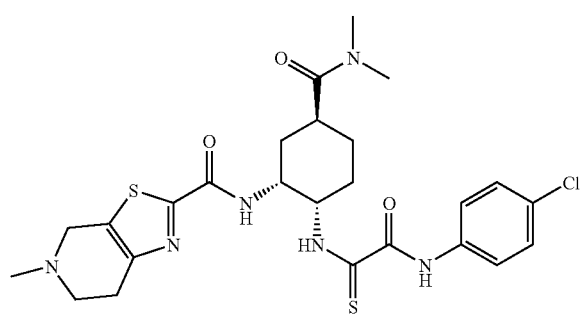

The compound (184 mg) obtained in Referential Example 253 and the compound (150 mg) obtained in Referential Example 351 were dissolved in a mixture of methanol (1 mL)-methylene chloride (4 mL), the solution was stirred under heating at 150° C., to thereby evaporate the solvent, and the heating was continued for 5 minutes. After the reaction mixture was allowed to cool, the formed product was purified by silica gel column chromatography (methylene chloride:methanol=24:1) to give the title compound (59 mg).

¹H-NMR (CDCl₃) δ: 1.65-1.90(2H,m), 1.90-2.00(1H,m), 2.00-2.15(2H,m), 2.20-2.30(1H,m), 2.52(3H,s), 2.75-2.95(5H,m), 2.96(3H,s), 3.07(3H,s), 3.68(1H,d,J=15.2 Hz), 3.75(1H,d,J=15.7 Hz), 4.45-4.60(1H,m), 4.80-4.85(1H,m), 7.31(2H,d,J=8.8 Hz), 7.44(1H,d,J=8.6 Hz), 7.60(2H,d,J=8.8 Hz), 9.99(1H,d,J=7.6 Hz), 10.15(1H,s).

MS(ESI)m/z: 563(M+H)⁺.

Example 247

N-{(1R,2S,5S)-2-({2-[(5-Chloropyridin-2-yl)amino]-2-oxoethanethioyl}amino)-5-[(dimethylamino)carbonyl]-cyclohexyl}-5-methyl-4,5,6,7-tetrahydrothiazolo[5,4-c]-pyridine-2-carboxamide

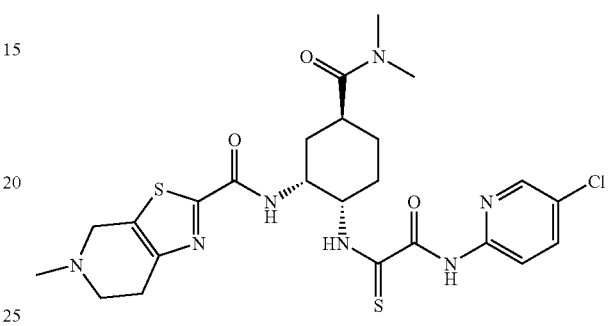

The compound (184 mg) obtained in Referential Example 253 and the compound (150 mg) obtained in Referential Example 353 were dissolved in a mixture of methanol (0.3 mL)-methylene chloride (0.3 mL). The solution was stirred under heating at 150° C., to thereby evaporate the solvent, and the heating was continued for 5 minutes. The reaction mixture was allowed to cool, the formed product was purified by silica gel column chromatography (methylene chloride:methanol=24:1) to give the title compound (52 mg).

¹H-NMR (CDCl₃) δ: 1.60-2.00(3H,m), 2.00-2.20(2H,m), 2.25-2.40(1H,m), 2.53(3H,s), 2.80-2.95(5H,m), 2.96(3H,s), 3.08(3H,s), 3.70(1H,d,J=15.4 Hz), 3.75(1H,d,J=15.4 Hz), 4.45-4.60(1H,m), 4.75-4.85(1H,m), 7.45(1H,d,J=8.3 Hz), 7.67(1H,dd,J=8.8, 2.5 Hz), 8.18(1H,d,J=8.8 Hz), 8.31(1H,d,J=2.0 Hz), 10.06(1H,d,J=6.3 Hz), 10.56(1H,s).

MS(ESI)m/z: 564(M+H)⁺.

Example 248

N-{(1R,2S,5S)-2-({2-[(5-Chloropyridin-2-yl)amino]-2-thioxoacetyl}amino)-5-[(dimethylamino)carbonyl]cyclohexyl}-5-methyl-4,5,6,7-tetrahydrothiazolo[5,4-c]-pyridine-2-carboxamide

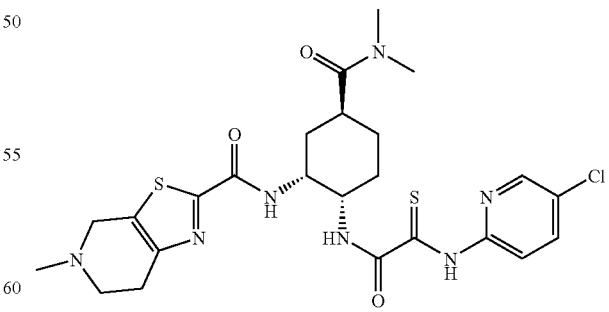

The compound (72 mg) obtained in Referential Example 355 and 2-amino-5-chloropyridine (100 mg) were dissolved in a mixture of methanol (0.2 mL)-methylene chloride (0.2 mL), the solution was stirred under heating at 150° C., and the heating was continued for 8 minutes after distilling off the solvent. After the reaction mixture was allowed to cool, the formed product was purified by silica gel thin layer chromatography (methylene chloride:methanol=23:2) to give the title compound (4 mg).

$^1$H-NMR (CDCl$_3$) δ: 1.60-2.00(3H,m), 2.00-2.20(3H,m), 2.53(3H,s), 2.75-3.00(5H,m), 2.95(3H,s), 3.05(3H,s), 3.65-3.80(2H,m), 4.05-4.15(1H,m), 4.70-4.80(1H,m), 7.28(1H,d), 7.43(1H,d,J=9.3 Hz), 7.75(1H,dd,J=8.8, 2.7 Hz), 8.41(1H,d, J=2.7 Hz), 9.05(1H,d,J=8.8 Hz), 11.56(1H,s).

MS(ESI)m/z: 564(M+H)$^+$.

Example 249

N$^1$-(5-Chloro-2-thienyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

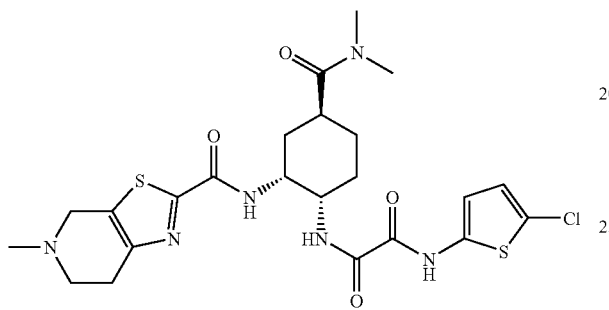

In a manner similar to that described in Example 191, the compound obtained in Referential Example 356 was hydrolyzed and then, condensed with the compound obtained in Referential Example 253, followed by treatment with hydrochloric acid, to thereby give the title compound.

$^1$H-NMR (DMSO-d$_6$) δ: 1.40-1.55(1H,m), 1.60-1.85(3H, m), 1.90-2.15(2H,m), 2.79(3H,s), 2.90-3.15(1H,m), 2.92(3H,s), 2.94(3H,s), 3.15-3.30(2H,m), 3.50-3.80(2H,m), 3.95-4.05(1H,m), 4.35-4.90(3H,m), 6.90(1H,d,J=4.2 Hz), 6.94(1H,d,J=4.2 Hz), 8.72(1H,d,J=7.3 Hz), 9.13(1H,br.s), 11.21(1H,br.s), 12.32(1H,br.s).

MS(ESI)m/z: 553(M+H)$^+$.

Example 250

N-{(1R,2S,5S)-2-{[(4-Chloroanilino)carbonyl]amino}-5-[(dimethylamino)carbonyl]cyclohexyl)-5-methyl-4,5,6,7-tetrahydrothiazolo[5,4-c]pyridine-2-carboxamide hydrochloride

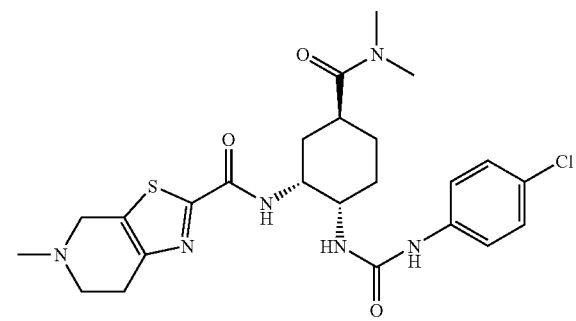

4-Chlorophenyl isocyanate (76.8 mg) was added to a solution of the compound (183 mg) obtained in Referential Example 253 in methylene chloride (20 mL), and the mixture was stirred at room temperature for 24 hours. The solvent was distilled away under reduced pressure, and the residue was purified by silica gel column chromatography (methylene chloride:methanol=20:1→10:1) to evaporate the solvent. The residue was dissolved in ethanol (2 mL) and methylene chloride (2 mL), 1N HCl in ethanol (0.4 mL) was added, followed by stirring at room temperature for 30 minutes. The reaction mixture was concentrated under reduced pressure, and the residue was solidified with diethyl ether to give the title compound (160 mg).

$^1$H-NMR (DMSO-d$_6$) δ: 1.35-1.50(1H,m), 1.60-1.90(5H, m), 2.79(3H,s), 2.92(3H,s), 3.00(3H,s), 3.10-3.60(4H,m), 3.60-3.90(2H,m), 4.35-4.80(3H,m), 6.26(1H,br.s), 7.23(2H, d,J=9.0 Hz), 7.37(2H,d,J=9.0 Hz), 8.53(1H,br.s), 8.72(1H, br.s), 11.35, 11.67(total 1H, each s).

MS(ESI)m/z: 519(M+H)$^+$.

Example 251

N$^1$-((1S,2R,4S)-4-[(Dimethylamino)carbonyl]-2-{[(5-methyl-4,5,6,7-tetrahydrothiazolo[5,4-c]-pyridin-2-yl)carbonyl]-amino}cyclohexyl)-N$^2$-(5-fluoropyridin-2-yl)ethanediamide hydrochloride

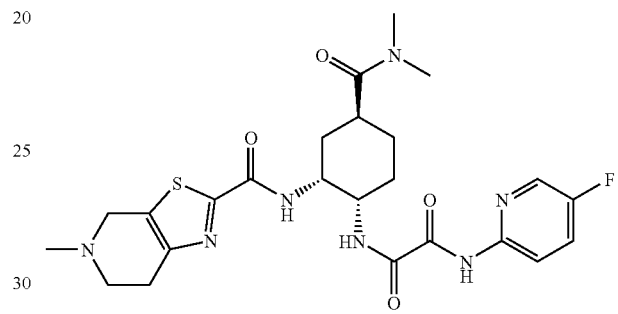

In a manner similar to that described in Example 191, the compound obtained in Referential Example 357 was hydrolyzed and then, condensed with the compound obtained in Referential Example 253, followed by treatment with hydrochloric acid, to thereby give the title compound.

$^1$H-NMR (DMSO-d$_6$) δ: 1.47-1.53(1H,m), 1.68-1.75(3H, m), 1.99-2.10(2H,m), 2.80(3H,s), 2.80-3.00(1H,m), 2.95(6H,s), 3.18-3.21(2H,m), 3.40-3.80(2H,m), 3.87-4.82 (4H,m), 7.82-7.85(1H,m), 8.01-8.05(1H,m), 8.40(1H,d, J=2.9 Hz), 8.71(1H,d,J=7.7 Hz), 9.13(1H,d,J=7.3 Hz), 10.27 (1H,s).

MS(FAB)m/z: 532(M+H)$^+$.

Example 252

N$^1$-(4-Chlorophenyl)-N-((1S,2R,4S)-4-[(dimethylamino)carbonyl]-2-{[(5-methyl-5,6-dihydro-4H-pyrrolo[3,4-d]-thiazol-2-yl)carbonyl]amino}cyclohexyl)ethanediamide hydrochloride

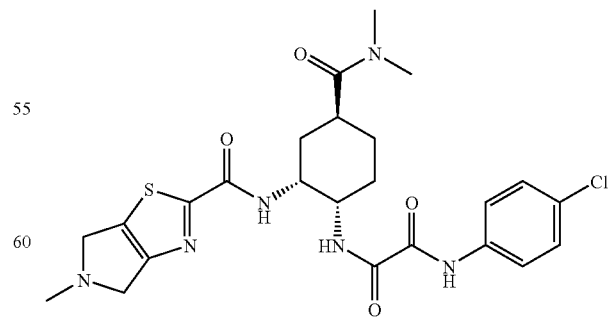

The title compound was obtained from the compound obtained in Referential Example 242 and the compound obtained in Referential Example 272 in a similar manner to the process described in Example 191.

$^1$H-NMR (DMSO-d$_6$) δ: 1.47-1.51(1H,m), 1.69-1.75(3H, m), 1.98-2.05(2H,m), 2.80(3H,s), 2.95(3H,s), 2.98-3.04(1H, m), 3.10(3H,s), 3.40-4.61(6H,m), 7.41(2H,d,J=8.8 Hz), 7.81 (2H,d,J=8.8 Hz), 8.76(1H,d,J=7.6 Hz), 8.95(1H,d,J=8.3 Hz), 10.79(1H,s).

MS(FAB)m/z: 533(M+H)$^+$.

Example 253

N$^1$-[4-Chloro-2-(trifluoromethyl)phenyl]-N$^2$-((1S, 2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

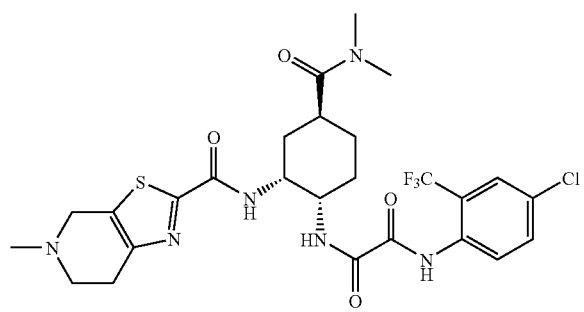

Thionyl chloride (1 mL) was added to a chloroform solution (10 mL) of the compound (269 mg) obtained in Referential Example 359, and the mixture was stirred at 75° C. for 30 minutes. The solvent was distilled away under reduced pressure, and the residue was dried. To the residue were added a methylene chloride solution (7 mL) of the compound (286 mg) obtained in Referential Example 253 and pyridine (3 mL) under ice cooling. The mixture was stirred for 2 hours while the temperature of the system was raised to room temperature. Saturated aqueous sodium hydrogencarbonate (10 mL) was added to the reaction mixture for partitioning the mixture. The resultant organic layer was dried over sodium sulfate anhydrate. The solvent was distilled away under reduced pressure, and the resultant residue was subjected to silica gel column chromatography (methylene chloride:methanol=20: 1) and column chromatography on LH-20 (molecular sieve, methanol) to give a free base (90 mg) of the title compound as a pale yellow amorphous solid. Methylene chloride (5 mL), ethanol (5 mL) and 1N HCl in ethanol (1 mL) were added to this product. Under reduced pressure, the solvent was distilled away, followed by drying to give the title compound.

$^1$H-NMR (DMSO-d$_6$) δ: 1.41-1.55(1H,m), 1.59-1.80(3H, m), 1.98-2.13(2H,m), 2.77(3H,s), 2.91(6H,s), 3.12-3.26(2H, m), 3.30-3.58(2H,m), 3.60-3.78(1H,m), 3.94-4.04(1H,m), 4.35-4.63(2H,m), 4.64-4.80(1H,m), 7.73-7.82(2H,m), 7.85 (1H,s), 8.68-8.73(1H,m), 9.18(1H,br.s), 10.31(1H,s).

MS(ESI)m/z: 615(M+H).

Example 254

N$^1$-{4-Chloro-2-[(dimethylamino)carbonyl]phenyl}-N$^2$ ((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

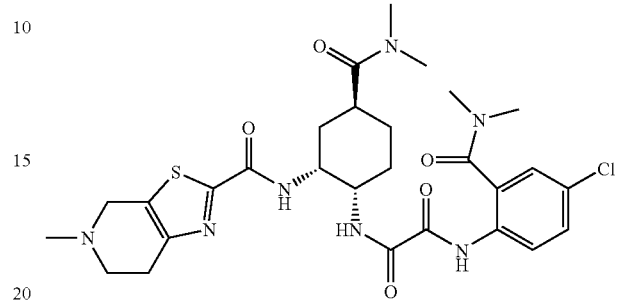

In a manner similar to that described in Example 191, the compound obtained in Referential Example 362 was hydrolyzed and then, condensed with the compound obtained in Referential Example 253, followed by treatment with hydrochloric acid, to thereby give the title compound.

$^1$H-NMR (DMSO-d$_6$) δ: 1.42-1.56(1H,m), 1.59-1.82(3H, m), 1.98-2.14(2H,m), 2.79(3H,s), 2.91(3H,s), 2.93(3H,s), 2.95(3H,s), 2.98(3H,s), 3.10-3.30(4H,m), 3.62-3.79(1H,m), 3.92-4.01(1H,m), 4.34-4.50(2H,m), 4.66-4.79(1H,m), 7.52 (1H,d,J=2.4 Hz), 7.55(1H,dd,J=2.4, 8.5 Hz), 8.05(1H,d, J=8.5 Hz), 8.75(1H,br), 9.10-9.24(1H,m), 10.52(1H,s).

MS(ESI)m/z: 618(M+H)$^+$.

Example 255

N$^1$-[4-Chloro-2-(hydroxymethyl)phenyl]-N$^2$-((1S, 2R,4S)-4-[(dimethylamino)carbonyl]-2-{[(5-methyl-4,5,6,7-tetrahydrothiazolo[5,4-c]pyridin-2-yl)carbonyl]-amino}-cyclohexyl)ethanediamide hydrochloride

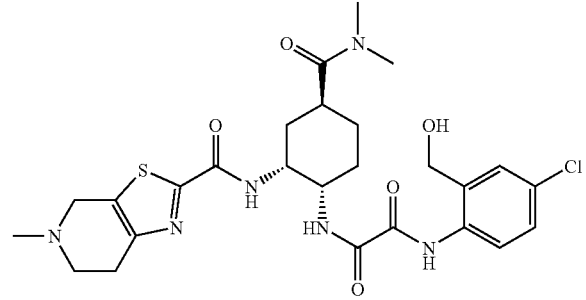

In a manner similar to that described in Example 199, the compound obtained in Referential Example 270 was condensed with 4-chloro-2-hydroxymethylaniline, followed by treatment with hydrochloric acid, to thereby give the title compound.

$^1$H-NMR (DMSO-d$_6$) δ: 1.42-1.57(1H,m), 1.58-1.81(3H, m), 1.98-2.14(2H,m), 2.79(3H,s), 2.93(6H,s), 3.12-3.58(4H, m), 3.67-3.80(1H,m), 3.94-4.04(1H,m), 4.37-4.50(1.5H,m), 4.55(2H,s), 4.67-4.80(1H,m), 5.77-5.92(0.5H,m), 7.37(1H, dd,J=2.4, 8.6 Hz), 7.42(1H,d,J=2.4 Hz), 7.91(1H,d,J=8.6 Hz), 8.74-8.81(1H,m), 9.03-9.19(1H,m), 10.79(1H,s).

MS(ESI)m/z: 577(M+H)$^+$.

Example 256

N[1]-(4-Chloro-2-methoxyphenyl)-N[2]-((1S,2R,4S)-4-[(dimethylamino)carbonyl]-2-{[(5-methyl-4,5,6,7-tetrahydrothiazolo[5,4-c]pyridin-2-yl)carbonyl]amino}-cyclohexyl)ethanediamide hydrochloride

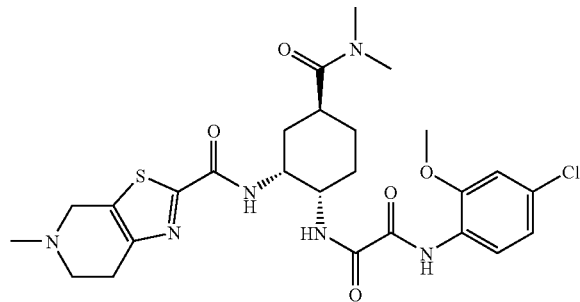

In a manner similar to that described in Example 191, the compound obtained in Referential Example 364 was hydrolyzed and then, condensed with the compound obtained in Referential Example 253, followed by treatment with hydrochloric acid, to thereby give the title compound.

$^1$H-NMR (DMSO-d$_6$) δ: 1.40-1.55(1H,m), 1.58-1.79(3H,m), 1.94-2.11(2H,m), 2.77(3H,s), 2.92(6H,s), 3.05-3.55(4H,m), 3.65-3.75(1H,br), 3.90(3H,s), 3.91-4.00(1H,m), 4.36-4.47(2H,br), 4.65-4.77(1H, br), 7.04(1H,dd,J=8.5, 2.0 Hz), 7.20(1H,d,J=2.0 Hz), 8.06(1H,d,J=8.5 Hz), 8.65-8.80(1H,br), 9.10-9.25(1H,br), 9.74(1H,s), 11.10-11.35(1H,br).

MS(ESI)m/z: 577(M+H)$^+$.

Example 257

N-{(1R,2S,5S)-2-{[2-(4-Chloroanilino)-2-(hydroxyimino)acetyl]amino}-5-[(dimethylamino)carbonyl]-cyclohexyl}-5-methyl-4,5,6,7-tetrahydrothiazolo[5,4-c]-pyridine-2-carboxamide hydrochloride

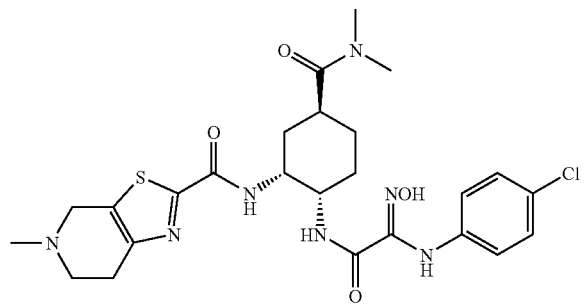

In a manner similar to that described in Example 214, the compound obtained in Referential Example 366 was treated with hydrochloric acid for deprotection, followed by condensation with the compound obtained in Referential Example 10 and treatment with hydrochloric acid, to thereby give the title compound.

$^1$H-NMR (DMSO-d$_6$) δ: 1.41-1.53(1H,m), 1.57-1.77(3H,m), 1.88-2.04(2H,m), 2.77(3H,s), 2.91(6H,s), 3.00-3.60(4H,m), 3.65-3.74(1H,br), 3.87-3.96(1H,m), 4.37-4.48(2H,m), 4.66-4.76(1H,m), 6.70(2H,d,J=8.8 Hz), 7.04(1H,d,J=8.8 Hz), 7.10(1H,d,J=8.8 Hz), 8.40-8.53(2H,m), 8.57-8.66(1H,m), 10.30-10.47(1H,br), 10.66-10.76(1H,br).

MS(ESI)m/z: 562(M+H)$^+$.

Example 258

N[1]-(4-Chlorophenyl)-N[2]-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

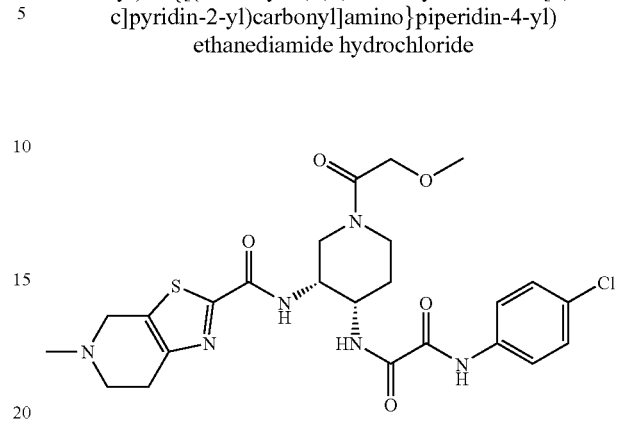

In a manner similar to that described in Example 214, the compound obtained in Referential Example 367 was treated with hydrochloric acid for deprotection, followed by condensation with the compound obtained in Referential Example 10 and treatment with hydrochloric acid, to thereby give the title compound.

$^1$H-NMR (DMSO-d$_6$) δ: 1.60-1.72(1H,m), 1.99-2.22(1H,m), 2.90(3H,s), 3.03-4.80(17H,m), 7.40(2H,d,J=8.8 Hz), 7.83(2H,d,J=8.8 Hz), 8.56-8.73(1H,br), 9.14-9.33(1H,br), 10.83(1H,s), 11.20-11.55(1H,br).

MS(ESI)m/z: 549(M+H)$^+$.

Example 259

N[1]-(5-Chloropyridin-2-yl)-N[2]-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

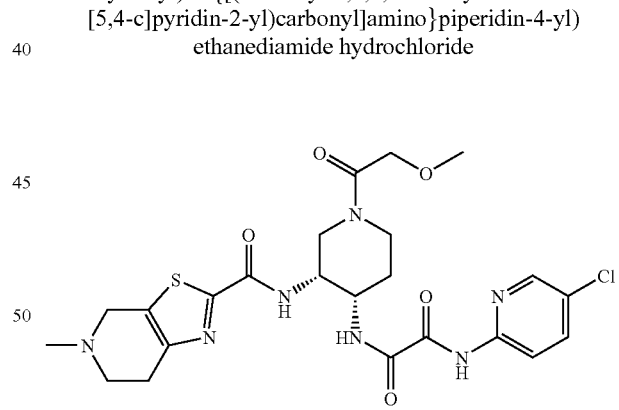

In a manner similar to that described in Example 214, the compound obtained in Referential Example 368 was treated with hydrochloric acid for deprotection, followed by condensation with the compound obtained in Referential Example 10 and treatment with hydrochloric acid, to thereby give the title compound.

$^1$H-NMR (DMSO-d$_6$) δ: 1.60-1.72(1H,m), 1.98-2.20(1H,m), 2.90(3H,s), 3.00-4.77(17H,m), 7.20-7.35(0.8H,br), 7.48-7.56(0.2H,br), 7.94-8.07(1H,br), 8.40-8.70(1H,br), 8.48-8.70(1H,br), 9.23-9.45(1H,br), 10.21-10.35(1H,br), 11.30-11.70(1H,br).

MS(ESI)m/z: 550(M+H)$^+$.

Example 260

N$^1$-(5-Bromopyridin-2-yl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

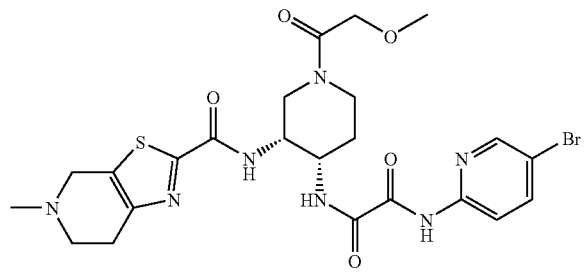

In a manner similar to that described in Example 214, the compound obtained in Referential Example 369 was treated with hydrochloric acid for deprotection, followed by condensation with the compound obtained in Referential Example 10 and treatment with hydrochloric acid, to thereby give the title compound.

$^1$H-NMR (DMSO-d$_6$) δ: 1.60-1.73(1H,m), 1.97-2.20(1H, m), 2.90(3H,s), 3.03-3.52(7H,m), 3.64-4.07(5H,m), 4.10-4.50(4H,m), 4.65-4.78(1H,m), 7.28-7.35(0.2H,m), 7.97(1H, d,J=8.8 Hz), 8.11(1H,dd,J=8.8, 2.2 Hz), 8.51(1H,d,J=2.2 Hz), 8.55-8.67(1H,m), 9.22-9.41(1H,m), 10.20-10.31(0.8H, m), 11.25-11.70(1H,br).

MS(ESI)m/z: 594(M+H)$^+$.

Example 261

N$^1$-(4-Chlorophenyl)-N$^3$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)malonamide hydrochloride

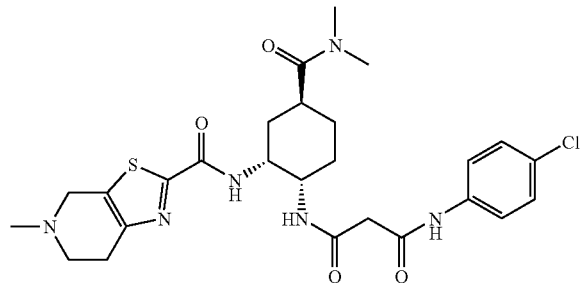

In a manner similar to that described in Example 5, the compound obtained in Referential Example 371 was condensed with the compound obtained in Referential Example 253, followed by treatment with hydrochloric acid, to thereby give the title compound.

$^1$H-NMR (DMSO-d$_6$) δ: 1.32-1.50(1H,m), 1.55-1.87(5H, m), 2.78(3H,m), 2.92(3H,s), 2.98(3H,s), 2.99-3.00(1H,m), 3.05-3.50(5H,m), 3.65-3.75(1H,m), 3.80-3.92(1H,m), 4.35-4.45(1H,m), 4.45-4.55(1H,m), 4.65-4.80(1H,m), 7.34(2H,d, J=8.8 Hz), 7.58(2H,d,J=8.8 Hz), 8.00-8.10(1H,m), 8.30-8.40 (1H,m), 10.29(1H,d,J=12.5 Hz), 12.40(1H,br.s)

MS(FAB)m/z: 561(M+H)$^+$.

Example 262

N$^1$-(3-Chlorophenyl)-N$^3$-((1S,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)malonamide hydrochloride

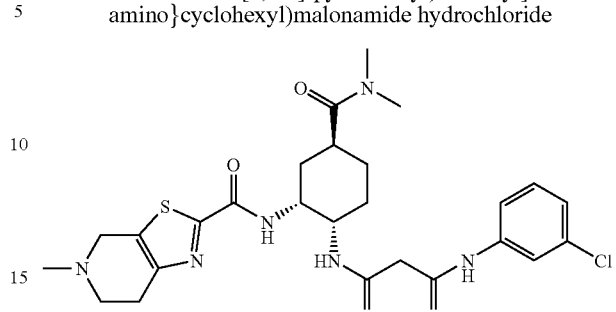

In a manner similar to that described in Example 5, the compound obtained in Referential Example 373 was condensed with the compound obtained in Referential Example 253, followed by treatment with hydrochloric acid, to thereby give the title compound.

$^1$H-NMR (DMSO-d$_6$) δ: 1.32-1.50(1H,m), 1.55-1.90(5H, m), 2.77(3H,s), 2.91(3H,s), 2.98(3H,s), 2.99-3.00(1H,m), 3.05-3.50(5H,m), 3.65-3.80(1H,m), 3.80-3.90(1H,m), 4.35-4.50(1H,m), 4.50-4.60(1H,m), 4.65-4.80(1H,m), 7.09(1H,d, J=8.8 Hz), 7.31(1H,d,J=8.8 Hz), 7.38(1H,t,J=8.8 Hz), 7.79 (1H,s), 8.00-8.10(1H,m), 8.30-8.40(1H,m), 10.28(1H,d, J=12.5 Hz), 11.67(1H,br.s).

MS(FAB)m/z: 561(M+H)$^+$.

Example 263

N$^1$-(5-Chloropyridin-2-yl)-N$^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]-amino}cyclohexyl)ethanediamide hydrochloride

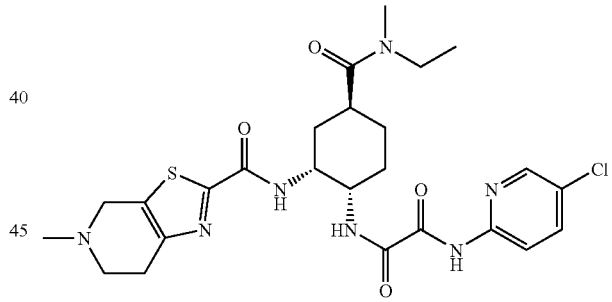

10% Palladium on carbon (0.3 g) was added to a solution of the compound (0.33 g) obtained in Referential Example 404 in ethanol (20 mL), and the mixture was stirred at room temperature for 24 hours in a hydrogen atmosphere. After removing insoluble matter by filtration through Celite pad, the filtrate was concentrated under reduced pressure. The resultant residue (0.37 g) was dissolved in N,N-dimethylformamide (20 mL), and the compound (0.3 g) obtained in Referential Example 266, 1-hydroxybenzotriazole monohydrate (0.2 g) and 1-(3-dimethylaminopropyl)-3-ethylcarbodiimide hydrochloride (0.37 g) were successively added, followed by stirring at room temperature for 18 hours. The reaction mixture was concentrated under reduced pressure, and the resultant residue was diluted with a mixture of chloroform-methanol (9:1) and washed with saturated aqueous sodium hydrogencarbonate and saturated brine. After the resultant organic layer was dried over sodium sulfate anhydrate, and the solvent was distilled away under reduced pressure, the resultant residue was subjected to saparation and purification by silica gel column chromatography (chloroform:methanol=95:5). The fraction of interest was concentrated. A 1N HCl in ethanol was added to form a hydrochloride. This salt was recrystallized from a mixture of methanol and diethyl ether to give the title compound (0.28 g).

$^1$H-NMR (DMSO-d$_6$) δ: 0.95(1.5H,t,J=6.9 Hz), 1.42 (1.5H,t,J=6.9 Hz), 1.40-1.52(1H,m), 1.60-1.78(3H,m), 1.92-2.11(2H,m), 2.74(3H,s), 2.90(3H,s), 3.10-3.38(5H,m), 3.40-3.52(1H,m), 3.68-3.70(1H,m), 3.96-4.05(1H,m), 4.41(2H,s), 4.70(1H,d,J=15.9 Hz), 8.00-8.01(2H,m), 8.44(1H,s), 8.71 (1H,dd,J=10.1, 2.2 Hz), 9.14(0.5H,d,J=7.8 Hz), 9.22(0.5H,d, J=8.3 Hz), 10.24(0.5H,s), 10.28(0.5H,s), 11.48(1H,br.s), 11.61(1H,br.s).

MS(FAB)m/z: 562(M+H)$^+$.

Example 264

N$^1$-(4-Chlorophenyl)-N$^2$-((1S,2R,4S)-4-{[ethyl(methyl)amino]-carbonyl}-2-{[(5-methyl-4,5,6,7-tetrahydrothiazolo[5,4-c]-pyridin-2-yl)carbonyl]amino}cyclohexyl)ethanediamide hydrochloride

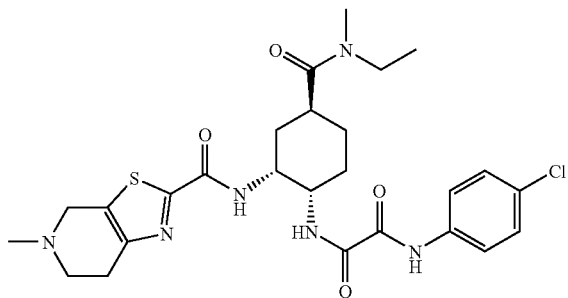

In a manner similar to that described in Example 263, the compound obtained in Referential Example 404 was converted to the corresponding amine, followed by condensation with the compound obtained in Referential Example 374 and treatment with hydrochloric acid, to thereby give the title compound.

$^1$H-NMR (DMSO-d$_6$) δ: 0.97(1.5H,t,J=6.9 Hz), 1.04 (1.5H,t,J=6.9 Hz), 1.40-1.60(1H,m), 1.60-1.80(3H,m), 1.92-2.11(2H,m), 2.74(3H,s), 2.89(3H,s), 3.10-3.32(5H,m), 3.40-3.52(1H,m), 3.65-3.80(1H,m), 3.90-4.05(1H,m), 4.40(2H,s), 4.70(1H,d,J=15.9 Hz), 7.39(2H,d,J=8.8 Hz), 7.82(2H,d, J=8.8 Hz), 8.75(1H,dd,J=10.1, 2.2 Hz), 9.00(0.5H,d,J=7.8 Hz), 9.08(0.5H,d,J=8.3 Hz), 10.81(1H,d,J=4.9 Hz), 11.45 (1H,br.s).

MS(FAB)m/z: 561(M+H)$^+$.

Example 265

N$^1$-(5-Bromopyridin-2-yl)-N$^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide hydrochloride

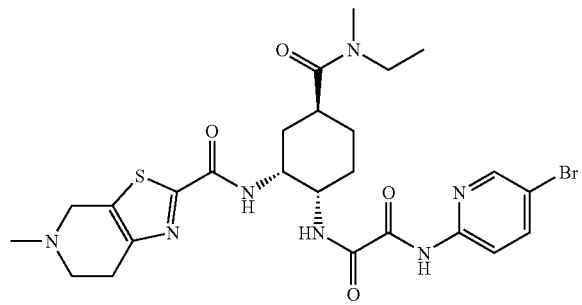

In a manner similar to that described in Example 263, the compound obtained in Referential Example 404 was converted to the corresponding amine, followed by condensation with the compound obtained in Referential Example 375 and treatment with hydrochloric acid, to thereby give the title compound.

$^1$H-NMR (DMSO-d$_6$) δ: 1.02(1.5H,t,J=6.9 Hz), 1.08 (1.5H,t,J=6.9 Hz), 1.49-1.60(1H,m), 1.60-1.86(3H,m), 2.00-2.20(2H,m), 2.81(3H,s), 2.97(3H,s), 3.15-3.42(6H,m), 3.50-3.60(1H,m), 3.70-3.82(1H,m), 4.48(2H,s), 4.77(1H,d,J=15.9 Hz), 8.04(1H,d,J=8.8 Hz), 8.17(1H,d,J=8.8 Hz), 8.58(1H,s), 8.78(1H,dd,J=10.1, 2.2 Hz), 9.21(0.5H,d,J=7.8 Hz), 9.29 (0.5H,d,J=8.3 Hz), 10.29(0.5H,s), 10.33(0.5H,s), 11.53(0.5H,br.s), 11.65(0.5H,br.s).

MS(FAB)m/z: 607(M+H)$^+$.

Example 266

N$^1$-(4-Chlroro-3-fluorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

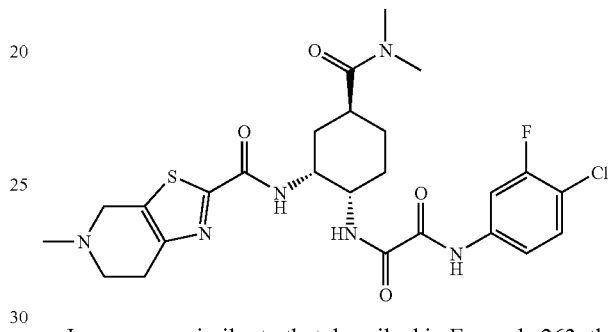

In a manner similar to that described in Example 263, the compound obtained in Referential Example 252 was converted to the corresponding amine, followed by condensation with the compound obtained in Referential Example 378 and treatment with hydrochloric acid, to thereby give the title compound.

$^1$H-NMR (DMSO-d$_6$) δ: 1.44-1.52(1H,m), 1.65-1.76(3H, m), 2.01-2.07(2H,m), 2.77(3H,s), 2.93(6H,s), 2.94-3.00(1H, m), 3.10-3.38(3H,m), 3.68-3.70(1H,m), 3.96-4.05(1H,m), 4.42(2H,s), 4.70(1H,d,J=15.9 Hz), 7.56(1H,t,J=8.8 Hz), 7.68 (1H,d,J=8.8 Hz), 7.90(1H,dd,J=11.7, 1.5 Hz), 8.73(1H,dd, J=12.5, 7.3 Hz), 9.06(1H,dd,J=12.5, 8.1 Hz), 11.01(1H,d, J=5.8 Hz), 11.30-11.42(1H,m).

MS(FAB)m/z: 565(M+H)$^+$.

Example 267

N-{(1R,2S,5S)-2-{[3-(4-Chlorophenyl)-3-oxopropanoyl]amino}-5-[(dimethylamino)carbonyl]cyclohexyl}-5-methyl-4,5,6,7-tetrahydrothiazolo[5,4-c]-pyridine-2-carboxamide

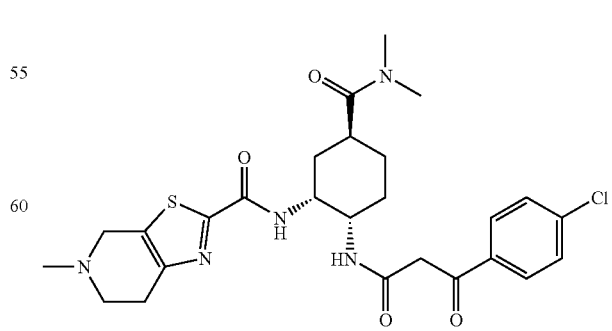

In a manner similar to that described in Example 214, the compound obtained in Referential Example 383 was treated with hydrochloric acid for deprotection, followed by condensation with the compound obtained in Referential Example 10 and treatment with hydrochloric acid, to thereby give the title compound.

$^1$H-NMR (CDCl$_3$) (free base) δ: 1.22-1.32(1H,m), 1.49-1.92(3H,m), 1.95-2.10(2H,m), 2.53(3H,s), 2.70-2.79(1H,m), 2.80-2.90(2H,m), 2.93(6H,s), 2.95-3.09(2H,m), 3.72(2H,s), 3.87(2H,s), 4.05-4.19(1H,m), 4.60-4.70(1H,m), 7.20-7.40 (2H,m), 7.42(2H,d,J=8.3 Hz), 7.87(2H,d,J=8.3 Hz).

MS(FAB)m/z: 546(M+H)$^+$.

Example 268

N$^1$-(5-Chloropyridin-2-yl)-N$^2$-((1R,2R,4S)-4-[(dimethylamino)carbonyl]-2-{[(5-methyl-5H-pyrrolo[3,4-d]-thiazol-2-yl)carbonyl]amino}cyclohexyl)ethanediamide

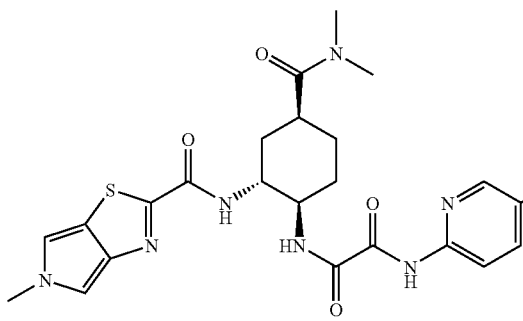

In a manner similar to that described in Example 214, the compound obtained in Referential Example 386 was treated with hydrochloric acid for deprotection, followed by condensation with the compound obtained in Referential Example 293, to thereby give the title compound.

$^1$H-NMR (DMSO-d$_6$) δ: 1.00-2.35(7H,m), 2.96(3H,s), 3.04(3H,s), 3.85-3.95(1H,m), 3.88(3H,s), 4.60-4.75(1H,m), 6.68(1H,d,J=2.0 Hz), 7.17(1H,d,J=2.0 Hz), 7.20-7.32(1H,m), 7.67(1H,dd,J=8.8, 2.8 Hz), 7.99(1H,d,J=8.4 Hz), 8.21 (1H,d,J=8.8 Hz), 8.25(1H,d,J=2.8 Hz), 9.64(1H,s).

HRMS (FAB)m/z: 532.1520(M+H)$^+$.

(Calculated; C$_{23}$H$_{27}$ClN$_7$O$_4$S: 532.1534).

Example 269

N$^1$-[(5-Chloropyridin-2-yl)amino]-N$^2$-((1R,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

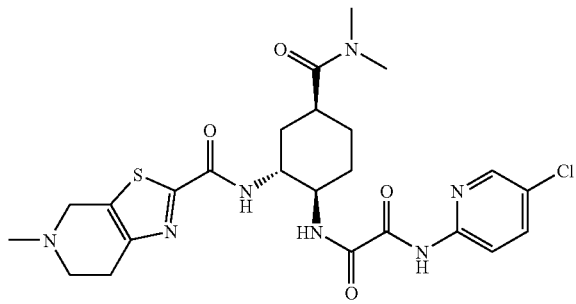

In a manner similar to that described in Referential Example 253, the compound obtained in Referential Example 387 was reduced. In a manner similar to that described in Example 208, the thus-obtained compound was condensed with the compound obtained in Referential Example 266, followed by treatment with hydrochloric acid, to thereby give the title compound.

$^1$H-NMR (DMSO-d$_6$) δ: 1.50-1.98(6H,m), 2.82(3H,s), 2.91(3H,s), 2.95(3H,s), 2.86-3.92(7H,m), 4.30-4.81(2H,m), 7.92-8.09(2H,m), 8.39-8.47(1H,m), 8.56-8.72(2H,m), 10.17 (1H,s).

MS(ESI)m/z: 548(M+H)$^+$.

Example 270

N$^1$-(4-Chlorophenyl)-N$^2$-((1R,2R,4S)-4-[(dimethylamino)carbonyl]-2-{[(5-methyl-4,5,6,7-tetrahydrothiazolo[5,4-c]-pyridin-2-yl)carbonyl]amino}cyclohexyl)ethanediamide

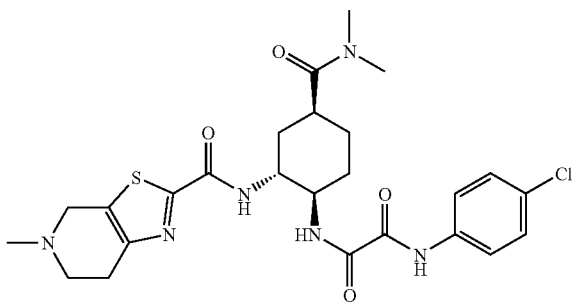

In a manner similar to that described in Referential Example 253, the compound obtained in Referential Example 387 was reduced. In a manner similar to that described in Example 191, the compound obtained in Referential Example 242 was hydrolyzed to form a lithium salt, and the thus-reduced compound was condensed with the lithium salt, followed by treatment with hydrochloric acid, to thereby give the title compound.

$^1$H-NMR (DMSO-d$_6$) δ: 1.50-1.97(6H,m), 2.82(3H,s), 2.91(3H,s), 2.98(3H,s), 2.83-3.88(7H,m), 4.30-4.79(2H,m), 7.37(2H,d,J=8.8 Hz), 7.89(2H,d,J=8.8 Hz), 8.34(1H,d,J=8.4 Hz), 8.63(1H,d,J=8.8 Hz), 10.72(1H,s).

MS(ESI)m/z: 547(M+H)$^+$.

Example 271

N$^1$-{(1R,2S,5S)-2-{[(5-Chloroindol-2-yl)carbonyl]amino}-5-[(dimethylamino)carbonyl]cyclohexyl}-N$^2$-(pyridin-4-yl)ethanediamide hydrochloride

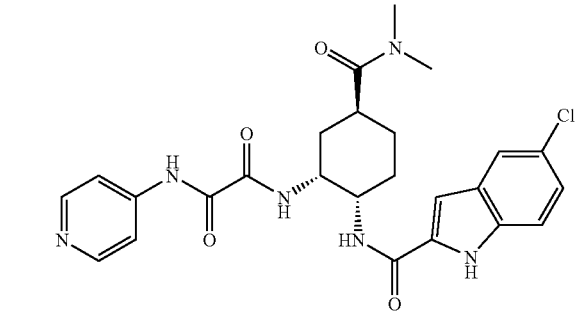

The compound obtained in Referential Example 310 was treated with hydrochloric acid for deprotection. In a manner similar to that described in Example 191, the compound obtained in Referential Example 261 was hydrolyzed to form lithium 2-[(pyridin-4-yl)amino]-2-oxoacetate, and the thus-deprotected compound was condensed with the lithium salt, followed by treatment with hydrochloric acid, to thereby give the title compound.

¹H-NMR (DMSO-d₆) δ: 1.40-2.01(6H,m), 2.79(3H,s), 3.01(3H,s), 3.00-3.18(1H,m), 4.02-4.19(1H,m), 4.45-4.55 (1H,m), 7.09(1H,s), 7.13-7.22(1H,m), 7.41(1H,d,J=8.4 Hz), 7.64(1H,br.s), 8.28(2H,d,J=6.8 Hz), 8.36(1H,d,J=8.0 Hz), 8.62(1H,d,J=8.8 Hz), 8.72(2H,d,J=6.8 Hz), 11.74(1H,s), 11.83(1H,s).

MS(FAB)m/z: 511(M+H)⁺.

Example 272

N¹-{(1R,2S,5S)-2-{[(5-Chloroindol-2-yl)carbonyl]amino}-5-[(dimethylamino)carbonyl]cyclohexyl}-N²-(pyridin-3-yl)ethanediamide hydrochloride

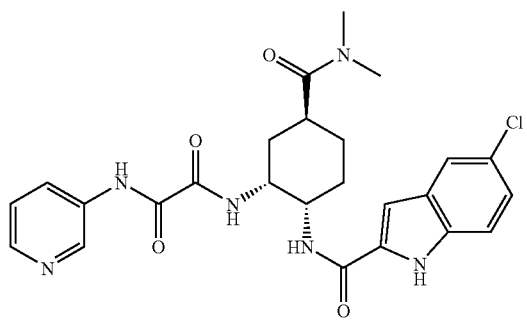

In a manner similar to that described in Referential Example 242, 3-aminopyridine was condensed with methyl 2-chloro-2-oxoacetate to form methyl 2-[(pyridin-3-yl)amino]-2-oxoacetate. In a manner similar to that described in Example 271, the title compound was obtained from the thus-condensed ester product and the compound obtained in Referential Example 310.

¹H-NMR (DMSO-d₆) δ: 1.40-2.05(6H,m), 2.80(3H,s), 3.02(3H,s), 2.92-3.15(1H,m), 4.02-4.17(1H,m), 4.42-4.58 (1H,m), 7.10(1H,s), 7.12-7.19(1H,m), 7.40(1H,d,J=8.4 Hz), 7.62-7.87(2H,m), 8.36-8.64(4H,m), 9.18(1H,s), 11.39(1H,s), 11.79(1H,s).

MS(FAB)m/z: 511(M+H)⁺.

Example 27

N¹-{(1R,2S,5S)-2-{[(5-Chloroindol-2-yl)carbonyl]amino}-5-[(dimethylamino)carbonyl]cyclohexyl}-N-(piperidin-4-yl)ethanediamide hydrochloride

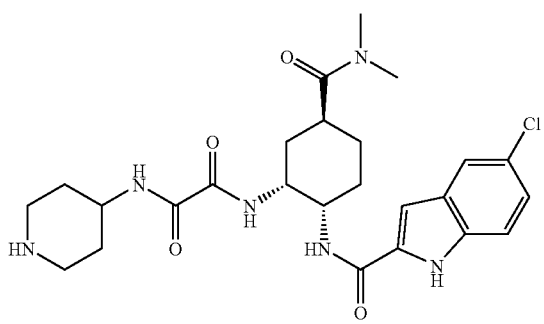

4N HCl-dioxane (8.0 mL) was added to a solution of the compound (400 mg) obtained in Referential Example 389 in ethanol (5.0 mL) at room temperature, and the mixture was stirred at the same temperature for 5 hours. The solvent was distilled away under reduced pressure, the residue was washed with methylene chloride, and insoluble matter was filterred and washed to give the title compound (320 mg).

¹H-NMR (DMSO-d₆) δ: 1.38-1.92(10H,m), 2.77(3H,s), 2.96(3H,s), 2.82-3.35(6H,m), 3.88-4.10(2H,m), 4.34-4.43 (1H,m), 7.05(1H,s), 7.11-7.17(1H,m), 7.38(1H,d,J=8.8 Hz), 7.65(1H,s), 8.25(1H,d,J=8.0 Hz), 8.34(1H,d,J=7.6 Hz), 8.89 (1H,d,J=8.4 Hz), 11.75(1H,s).

MS(ESI)m/z: 517(M+H)⁺.

Example 274

N¹-{(1R,2S,5S)-2-{[(5-Chloroindol-2-yl)carbonyl]amino}-5-[(dimethylamino)carbonyl]cyclohexyl}-N²-(1-methylpiperidin-4-yl)ethanediamide hydrochloride

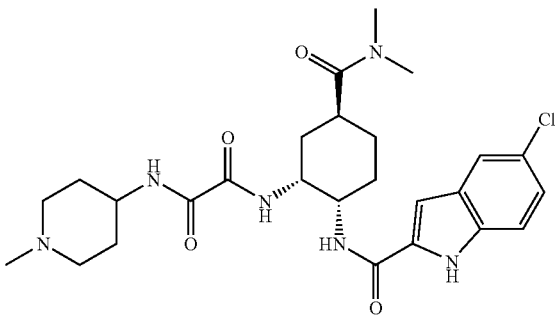

In a manner similar to that described in Referential Example 9, the compound obtained in Example 273 was methylated. The thus-methylated product was treated with hydrochloric acid, to thereby give the title compound.

¹H-NMR (DMSO-d₆) δ: 1.40-2.01(11H,m), 2.67(3H,s), 2.79(3H,s), 2.98(3H,s), 2.85-4.48(7H,m), 7.07(1H,s), 7.16 (1H,dd,J=8.8, 2.0 Hz), 7.40(1H,d,J=8.8 Hz), 7.68(1H,d,J=2.0 Hz), 8.25-8.35(1H,m), 8.37(1H,d,J=7.6 Hz), 8.90-9.02 (1H,m), 9.82(1H,br.s), 11.78(1H,s).

MS(ESI)m/z: 531(M+H)⁺.

Example 275

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N¹-methylethanediamide hydrochloride

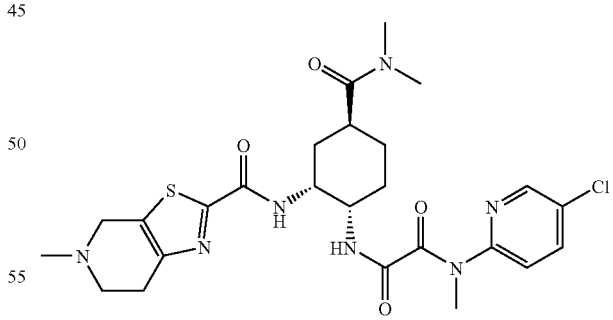

In a manner similar to that described in Example 191, the compound obtained in Referential Example 390 was hydrolyzed and then, condensed with the compound obtained in Referential Example 253, followed by treatment with hydrochloric acid, to thereby give the title compound.

¹H-NMR (DMSO-d₆) δ: 1.32-1.97(6H,m), 2.42-2.51(1H, m), 2.76(3H,s), 2.91(3H,s), 2.93(3H,s), 3.27(3H,s), 3.00-4.80(8H,m), 7.45(1H,br.s), 7.88-7.97(1H,m), 8.25-8.41(2H, m), 8.7.8-8.91(1H,m).

MS(FAB)m/z: 562(M+H)⁺.

Example 276

N$^1$-(5-Chloropyrimidin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

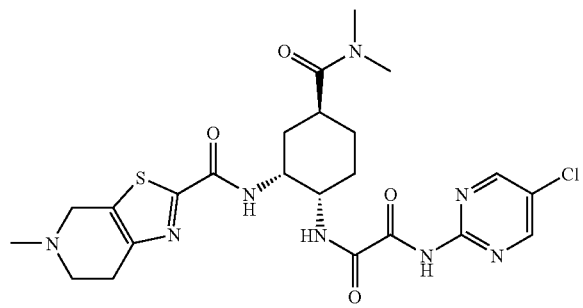

In a manner similar to that described in Example 191, the compound obtained in Referential Example 391 was hydrolyzed and then, condensed with the compound obtained in Referential Example 253, followed by treatment with hydrochloric acid, to thereby give the title compound.

$^1$H-NMR (DMSO-d$_6$) δ: 1.38-2.10(7H,m), 2.77(3H,s), 2.90(3H,s), 2.93(3H,s), 3.04-4.80(8H,m), 8.60-8.70(2H,m), 8.82(2H,s), 9.08(1H,br.s), 10.64(1H,s), 11.57(1H,br.s).

MS(FAB)m/z: 549(M+H)$^+$.

Example 277

N$^1$-(4-Chlorophenyl)-N$^2$-((1S,2R,4S)-4-{[ethyl(methyl)amino]-carbonyl}-2-{[(5-methyl-5,6-dihydro-4H-pyrrolo[3,4-d]-thiazol-2-yl)carbonyl]amino}cyclohexyl)ethanediamide hydrochloride

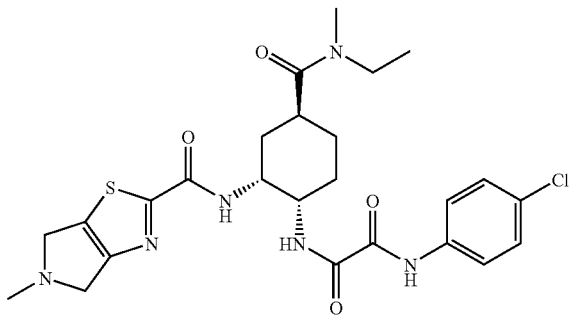

The compound obtained in Referential Example 392 was reduced in a manner similar to that described in Referential Example 253. In a manner similar to that described in Example 195, the compound obtained in Referential Example 242 was hydrolyzed to form the carboxylic acid, and the thus-reduced compound was condensed with the carboxylic acid, followed by treatment with hydrochloric acid, to thereby give the title compound.

$^1$H-NMR (DMSO-d$_6$) δ: 0.96, 1.02(3H, each t,J=7.0 Hz), 1.47-1.58(1H,m), 1.65-1.77(3H,m), 1.98-2.08(2H,m), 2.76-2.91(4H,m), 3.07(3H,s), 3.19-3.41(2H,m), 3.98-4.04(1H,m), 4.42(1H,br.s), 4.46-4.94(4H,m), 7.41(2H,d,J=8.8 Hz), 7.83(2H,d,J=8.8 Hz), 8.74-8.80(1H,m), 9.02(1H,d,J=7.3 Hz), 10.82(1H,s), 12.41(1H,br.s).

MS(FAB)m/z: 547(M+H)$^+$.

Example 278

N$^1$-(5-Bromopyridin-2-yl)-N$^2$-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride

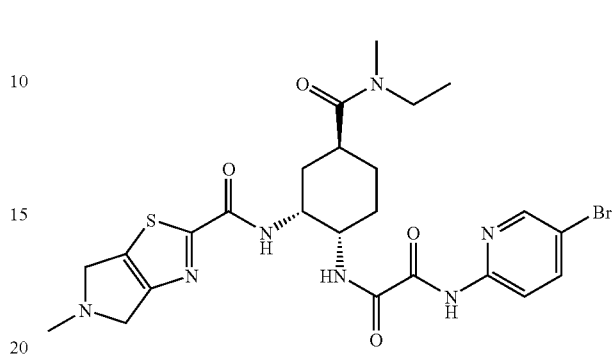

The title compound was obtained from the compound obtained in Referential Example 392 and the compound obtained in Referential Example 262 in a similar manner to the process described in Example 277.

$^1$H-NMR (DMSO-d$_6$) δ: 0.90-1.08(3H,m), 1.40-2.13(6H,m), 2.70-3.53(13H,m), 3.92-4.08(1H,m), 4.35-4.47(1H,m), 7.95(1H,d,J=8.8 Hz), 8.10(1H,dd,J=8.8, 2.4 Hz), 8.50-8.55(1H,m), 8.68-8.78(1H,m), 9.12-9.18(1H,m), 10.26(1H,s).

MS(FAB)m/z: 592(M+H)$^+$.

Example 279

N$^1$-(5-Chloropyridin-2-yl)-N$^2$-(1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride

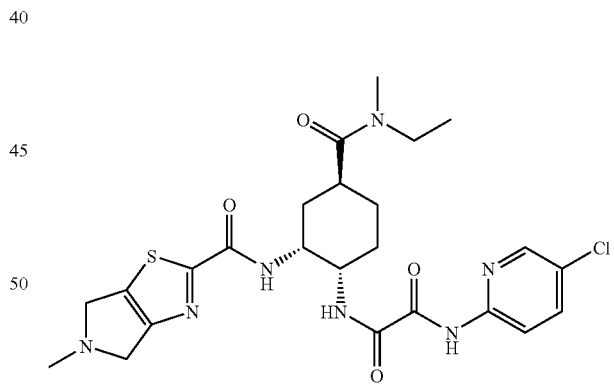

The title compound was obtained from the compound obtained in Referential Example 392 and the compound obtained in Referential Example 243 in a similar manner to the process described in Example 277.

$^1$H-NMR (DMSO-d$_6$) δ: [0.95(t,J=7.0 Hz), 1.01(t,J=6.8 Hz), 3H], 1.45-1.72(4H,m), 1.96-2.07(2H,m), 2.74-2.90(4H,m), 3.06(3H,s), 3.18-3.40(2H,m), 3.95-4.02(1H,m), 4.41(1H,br.s), 4.54-4.90(4H,m), 8.00(2H,br.s), 8.45(1H,s), 8.70-8.75(1H,m), 9.15(1H,br.s), 10.27(1H,br.s), 12.29(1H,br.s).

MS(ESI)m/z: 548(M+H)$^+$.

Example 280

$N^1$-(4-Chloro-3-methoxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride

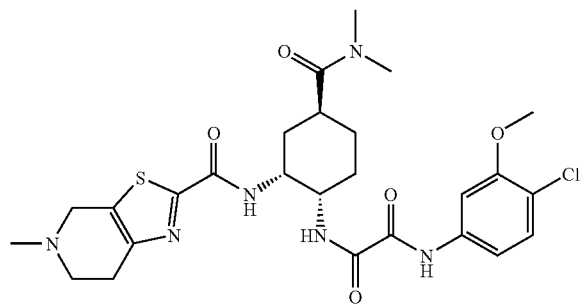

In a manner similar to that described in Example 2, the compound obtained in Referential Example 395 was condensed with the compound obtained in Referential Example 10, followed by treatment with hydrochloric acid, to thereby give the title compound.

$^1$H-NMR (DMSO-$d_6$) δ: 1.46-1.54(1H,m), 1.67-1.77(3H,m), 2.01-2.10(2H,m), 2.79(3H,s), 2.92-2.98(7H,m), 3.21(2H,br.s), 3.49(1H,br.s), 3.69(1H,br.s), 3.80(3H,s), 3.98-4.03(1H,m), 4.42-4.50(2H,m), 4.69(1H,br.s), 7.37(1H,d, J=8.7 Hz), 7.48(1H,dd,J=8.7, 2.2 Hz), 7.72(1H,d,J=2.2 Hz), 8.75(1H,d,J=7.3 Hz), 9.06(1H,br.s), 10.77(1H,s), 11.44(1H,br.s).

MS(FAB)m/z: 577(M+H)$^+$.

Example 281

$N^1$-(4-Chlorophenyl)-$N^2$-((1R*,2R*)-2-[(5-methyl-4,5,6,7-tetrahydrothiazolo[5,4-c]pyridin-2-yl)carbonyl]-amino}cyclopentyl)ethanediamide hydrochloride

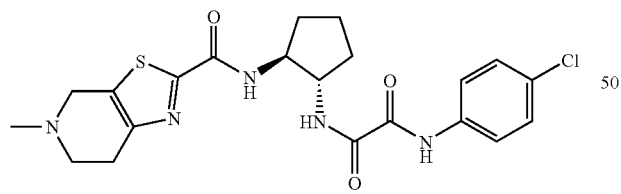

In a manner similar to that described in Example 195, the compound obtained in Referential Example 242 was hydrolyzed, followed by condensation with the compound obtained in Referential Example 62 and treatment with hydrochloric acid, to thereby give the title compound.

$^1$H-NMR (DMSO-$d_6$) δ: 1.65-1.73(4H,m), 1.91-1.96(2H,m), 2.91(3H,s), 3.15(2H,br.s), 3.49(1H,br.s), 3.66(1H,br.s), 4.32-4.42(3H,m), 4.66(1H,br.s), 7.40(2H,d,J=8.9 Hz), 7.84(2H,d,J=8.9 Hz), 8.92(1H,d,J=8.5 Hz), 9.03(1H,d,J=8.3 Hz), 10.76(1H,s), 11.32(1H,br.s).

MS(FAB)m/z: 462(M+H)$^+$.

Example 282

$N^1$-(5-Chloropyridin-2-yl)-$N^2$-((1R*,2R*)-2-{[(5-methyl-4,5,6,7-tetrahydrothiazolo[5,4-c]pyridin-2-yl)carbonyl]-amino}cyclopentyl)ethanediamide hydrochloride

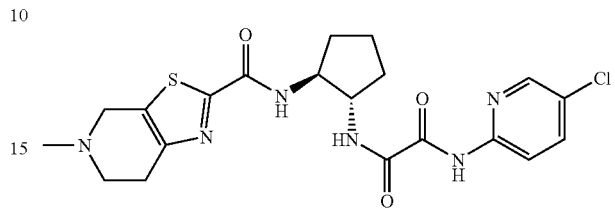

In a manner similar to that described in Example 208, the compound obtained in Referential Example 62 was condensed with the compound obtained in Referential Example 266, followed by treatment with hydrochloric acid, to thereby give the title compound.

$^1$H-NMR (DMSO-$d_6$) δ: 1.71(4H,br.s), 1.96(2H,br.s), 2.90(3H,s), 3.14(1H,br.s), 3.21(1H,br.s), 3.47(1H,br.s), 3.68(1H,br.s), 4.34-4.45(3H,m), 4.66(1H,br.s), 7.99-8.06(2H,m), 8.43-8.44(1H,m), 8.94(1H,d,J=8.3 Hz), 9.20(1H,d,J=8.5 Hz), 10.20(1H,br.s), 11.78(1.1H,br.s).

MS(FAB)m/z: 463(M+H)$^+$.

Example 283

$N^1$-((1S,2R,4S)-4-[(Dimethylamino)carbonyl]-2-{[(5-methyl-4,5,6,7-tetrahydrothiazolo[5,4-c]pyridin-2-yl)carbonyl]-amino}cyclohexyl)-$N^2$-(4-ethynylphenyl)ethanediamide

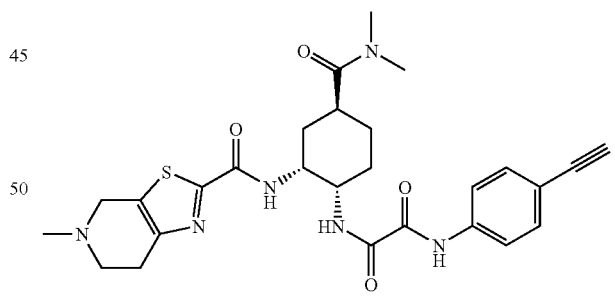

In a manner similar to that described in Example 263, the compound obtained in Referential Example 252 was condensed with the compound obtained in Referential Example 397, to thereby give the title compound.

$^1$H-NMR (CDCl$_3$) δ: 1.67-2.16(6H,m), 2.51(3H,s), 2.76-2.91(5H,m), 2.94(3H,s), 3.04(3H,s), 3.07(1H,s), [3.65(1H,d, J=15.5 Hz), 3.73(1H,d,J=15.5 Hz)AB pattern], 4.09-4.16(1H,m), 4.72-4.75(1H,m), 7.42-7.46(3H,m), 7.58(2H,d, J=8.5 Hz), 8.02(1H,d,J=8.1 Hz), 9.36(1H,s).

MS(FAB)m/z: 537(M+H)$^+$.

Example 284

N$^1$-(5-Chloropyrazin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

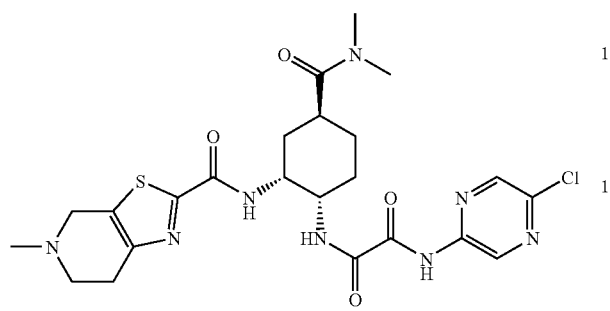

In a manner similar to that described in Referential Example 97, the compound obtained in Referential Example 253 was condensed with the compound obtained in Referential Example 399, followed by treatment with hydrochloric acid, to thereby give the title compound.

$^1$H-NMR (DMSO-d$_6$) δ: 1.44-1.52(1H,m), 1.65-1.77(3H, m), 2.00-2.10(2H,m), 2.77(3H,s), 2.91-2.97(7H,m), 3.20(2H,br.s), 3.48(1H,br.s), 3.68(1H,br.s), 3.97-4.02(1H, m), 4.40-4.46(2H,m), 4.68(1H,br.s), 8.64(1H,d,J=1.2 Hz), 8.70(1H,d,J=7.3 Hz), 9.02(1H,s), 9.21(1H,br.s), 10.91(1H, br.s), 11.50(1H,br.s).

MS(FAB)m/z: 549(M+H)$^+$.

Example 285

N$^1$-(4-Chloro-3-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

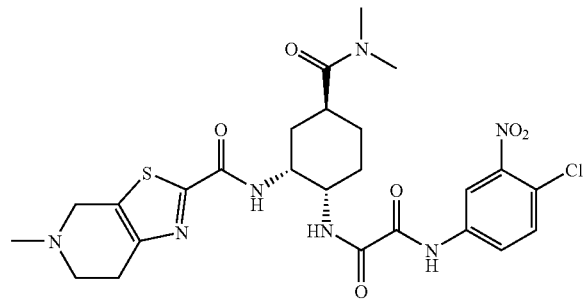

In a manner similar to that described in Referential Example 97, the compound obtained in Referential Example 253 was condensed with the compound obtained in Referential Example 400, followed by treatment with hydrochloric acid, to thereby give the title compound.

$^1$H-NMR (DMSO-d$_6$) δ: 1.44-1.53(1H,m), 1.66-1.73(3H, m), 1.97-2.07(2H,m), 2.77(3H,s), 2.89-3.05(7H,m), 3.20(2H,br.s), 3.55(2H,br.s), 4.00(1H,br.s), 4.44(1H,br.s), 4.52(2H,br.s), 7.75(1H,d,J=8.8 Hz), 8.08(1H,d,J=8.8 Hz), 8.59(1H,s), 8.71(1H,d,J=7.3 Hz), 9.07(1H,d,J=8.0 Hz), 11.24(1H,s), 11.58 (1H,br.s).

MS(FAB)m/z: 592(M+H)$^+$.

Example 286

N$^1$-(4-Chloro-2-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

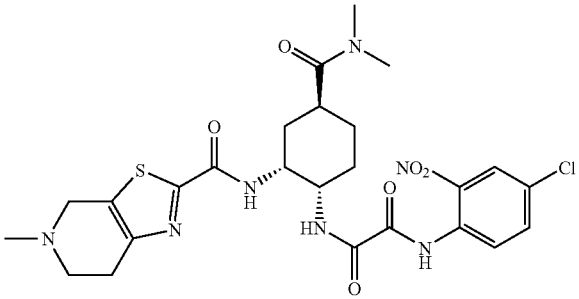

In a manner similar to that described in Example 208, the compound obtained in Referential Example 253 was condensed with the compound obtained in Referential Example 401, followed by treatment with hydrochloric acid, to thereby give the title compound.

$^1$H-NMR (DMSO-d$_6$) δ: 1.46-1.54(1H,m), 1.66-1.77(3H, m), 2.03-2.10(2H,m), 2.79(3H,s), 2.90-2.93(7H,m), 3.17-3.28(2H,m), 3.49(1H,br.s), 3.68(1H,br.s), 3.99-4.04(1H,m), 4.41(1H,br.s), 4.46(1H,br.s), 4.68(1H,br.s), 7.89(1H,d,J=9.0 Hz), 8.20-8.21(2H,m), 8.73(1H,d,J=6.4 Hz), 9.28(1H,br.s), 11.49(1H,br.s), 11.56(1H,s).

MS(FAB)m/z: 592(M+H)$^+$.

Example 287

N$^1$-(3-Amino-4-chlorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

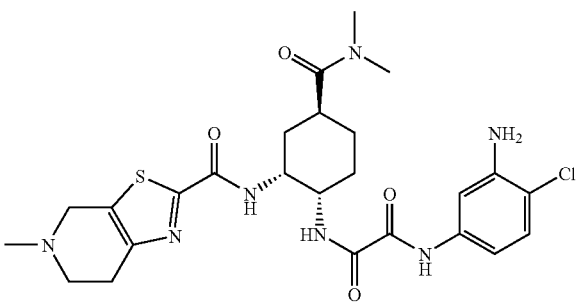

The compound (236 mg) obtained in Example 285 was dissolved in ethanol (25 mL), and a catalytic amount of Raney nickel was added, followed by stirring at room temperature for 17 hours in a hydrogen atmosphere. Thereafter, a catalytic amount of Raney nickel was additionally added, followed by stirring for additional 7 hours. The catalyst was removed by filtration, and the solvent was distilled away under reduced pressure. The residue was purified by silica gel column chromatography (methylene chloride:methanol=23:2) to give a pale yellow solid (101 mg). This product was dissolved in methylene chloride, and 1N HCl in ethanol (360 μl) was added thereto. The solvent was distilled away under reduced pressure, a small amount of methanol was added to the residue, and diethyl ether was added dropwise while irradiating with ultrasonic waves to collect the precipitate formed. This product was washed with diethyl ether to give the title compound (95 mg).

$^1$H-NMR (DMSO-$d_6$) δ: 1.45-1.53(1H,m), 1.66-1.73(3H, m), 1.97-2.10(2H,m), 2.78(3H,s), 2.91-2.94(7H,br.s), 3.11-3.19(1H,m), 3.29(1H,br.s), 3.48(1H,br.s), 3.69(1H,br.s), 3.95-4.02(1H,m), 4.44(2H,br.s), 4.68, 4.72(1H, each br.s), 4.86(2.5H,br.s), 6.98(1H,dd,J=8.5, 1.9 Hz), 7.14(1H,d,J=8.5 Hz), 7.35, 7.38(1H, each br.s), 8.72-8.77(1H,m), [8.91(d, J=7.8 Hz), 8.99(d,J=8.5 Hz), 1H], 10.45, 10.47(1H, each br.s), 11.74(1H,br.s).

MS(FAB)m/z: 562(M+H)$^+$.

Example 288

N$^1$-(2-Amino-4-chlorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]-amino}cyclohexyl)ethanediamide hydrochloride

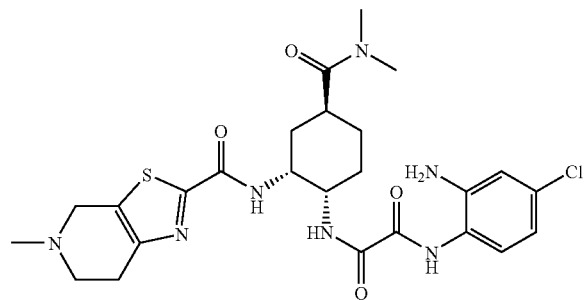

The title compound was obtained from the compound obtained in Example 286 in a similar manner to the process described in Example 287.

$^1$H-NMR (DMSO-$d_6$) δ: 1.45-1.77(4H,m), 2.06-2.09(2H, m), 2.78(3H,s), 2.92(7H,br.s), 3.12-3.19(1H,m), 3.26-3.28 (1H,m), 3.48(1H,br.s), 3.70(1H,br.s), 4.00-4.44(5.7H,m), 4.70, 4.74(1H, each br.s), 6.63-6.66(1H,m), 6.85(1H,br.s), 7.18-7.21(1H,m), 8.77-8.81(1H,m), [8.97(d,J=7.8 Hz), 9.06 (d,J=8.1 Hz), 1H], 9.98(1H,s), 11.60(1H,br.s).

MS(FAB)m/z: 562(M+H)$^+$.

Example 289

N$^1$-(6-Chloro-4-methylpyridin-3-yl)-N$^2$-((1S,2R, 4S)-4-[(dimethylamino)carbonyl]-2-{[(5-methyl-4,5, 6,7-tetrahydrothiazolo[5,4-c]pyridin-2-yl)carbonyl]-amino}cyclohexyl)ethanediamide hydrochloride

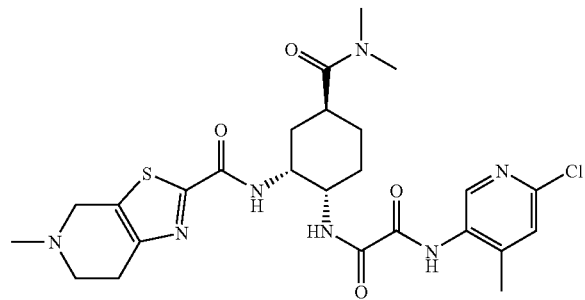

In a manner similar to that described in Example 199, the compound obtained in Referential Example 270 was condensed with the compound obtained in Referential Example 402, followed by treatment with hydrochloric acid, to thereby give the title compound.

$^1$H-NMR (DMSO-$d_6$) δ: 1.45-1.54(1H,m), 1.65-1.77(3H, m), 2.02-2.08(2H,m), 2.22(3H,s), 2.79(3H,s), 2.89-2.93(7H, m), 3.19(2H,br.s), 3.54(2H,br.s), 3.99-4.04(1H,m), 4.40-4.42 (1H,m), 4.50(2H,br.s), 7.49(1H,s), 8.32(1H,s), 8.75(1H,d, J=7.1 Hz), 9.09(1H,d,J=7.3 Hz), 10.48(1H,s), 11.40(0.9H, br.s).

MS(FAB)m/z: 562(M+H)$^+$.

Example 290

N-((1R,2S,5S)-2-({[(E)-2-(4-Chlorophenyl)diazenyl]-carbonyl}amino)-5-[(dimethylamino)carbonyl] cyclohexyl}-5-methyl-4,5,6,7-tetrahydrothiazolo[5, 4-c]pyridine-2-carboxamide hydrochloride

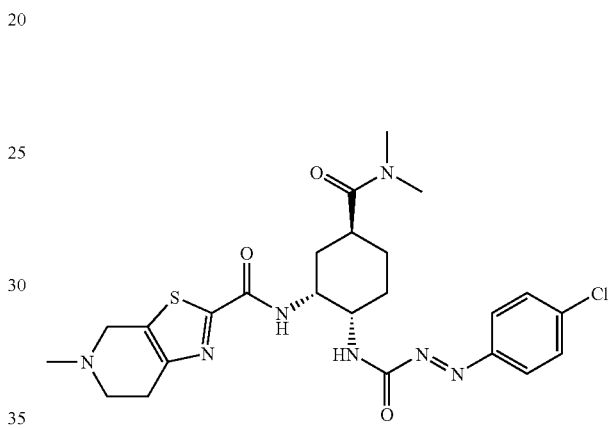

After 10% Palladium on carbon (200 mg) was added to a solution of the compound (700 mg) obtained in Referential Example 252 in tetrahydrofuran (10 mL), and the mixture was stirred at room temperature for 2 days in a hydrogen atmosphere at a pressure of 1 atm, the reaction mixture was filtered, and the compound obtained in Referential Example 405 (470 mg) was added to a solution of an amine obtained by concentrating the filtrate in N,N-dimethylformamide (5.0 mL), followed by stirring at 95° C. for 18 hours. After the reaction mixture was concentrated, and saturated aqueous sodium hydrogencarbonate (50 mL), water (50 mL), and methylene chloride (30 mL) were added for partitioning the mixture, the resultant aqueous layer was extracted with methylene chloride (2×20 mL). Organic layers were combined, dried over sodium sulfate anhydrate, concentrated and purified by silica gel column chromatography (methylene chloride:methanol=12:1). This purified product was treated with 1N HCl in ethanol to give the title compound (100 mg).

$^1$H-NMR (DMSO-$d_6$) δ: 1.40-1.60(1H,m), 1.65-2.05(5H, m), 2.80(3H,s), 2.91(3H,s), 2.99(3H,s), 3.00-3.20(2H,m), 3.20-3.32(1H,m), 3.43(1H,br.s), 3.69(1H,br.s), 3.95(1H,br.s), 4.45(1H,br.s), 4.60-4.80(2H,m), 7.68(2H,d, J=8.7 Hz), 7.83(2H,d,J=8.7 Hz), 8.41(1H,br.s), 8.68(1H,d, J=7.6 Hz), 11.40-11.80(1H,br).

MS(ESI)m/z: 532(M+H)$^+$.

Example 291

N-{(1R,2S,5S)-2-({[2-(4-Chlorophenyl)hydrazino]-carbonyl}amino)-5-[(dimethylamino)carbonyl]cyclohexyl}-5-methyl-4,5,6,7-tetrahydrothiazolo[5,4-c]pyridine-2-carboxamide hydrochloride

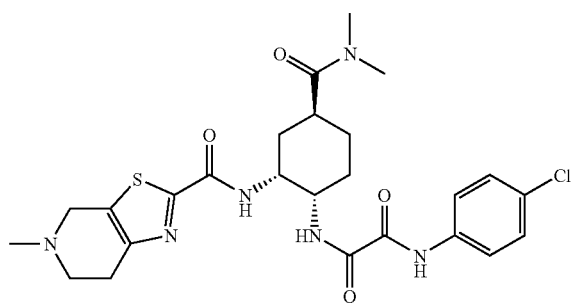

The procedure described in Example 290 was repeated, except that reaction was performed at 40° C. for 3 days under stirring, to thereby give the title compound.

¹H-NMR (DMSO-d₆) δ: 1.30-1.50(1H,m), 1.50-1.80(3H, m), 1.80-1.97(2H,m), 2.76(3H,s), 2.80-3.05(2H,m), 2.91(6H,s), 3.05-3.30(2H,m), 3.47(2H,br.s), 4.30-4.50(2H, m), 4.72(1H,t,J=12.8 Hz), 6.40-6.60(2H,m), 6.55-6.70(2H, m), 6.95-7.20(2H,m), 7.88(1H,d,J=11.3 Hz), 8.48-8.65(1H, m), 11.48-11.80(1H,br).

MS(ESI)m/z: 534(M+H)⁺.

Example 292

N¹-(5-Chloropyridin-2-yl)-N²-((1S,2R,4S)-4-[(dimethylamino)carbonyl]-2-{[(4,5,6,7-tetrahydrothiazolo[5,4-c]pyridin-2-yl)carbonyl]-amino}cyclohexyl)ethanediamide hydrochloride

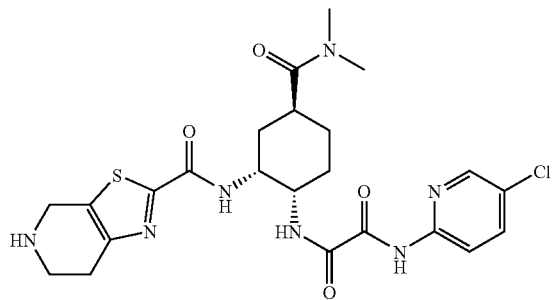

In a manner similar to that described in Example 17, the compound obtained in Referential Example 34 was condensed with the compound obtained in Referential Example 420, followed by treatment with hydrochloric acid, to thereby give the title compound.

¹H-NMR (DMSO-d₆) δ: 1.45-1.55(1H,m), 1.60-1.80(3H, m), 1.95-2.10(2H,m), 2.78(3H,s), 2.85-3.00(4H,m), 3.11(2H,br s), 3.40-3.55(2H,m), 3.95-4.07(1H,m), 4.37-4.45 (1H,m), 4.48(2H,br s), 8.00-8.01(2H,m), 8.10(1H,d,J=7.1 Hz), 8.43-8.47(1H,m), 9.16(1H,d,J=7.8 Hz), 9.43(2H,br s), 10.27(1H,s).

MS(FAB)m/z: 534(M+H)⁺.

Example 293

N-((3R*,4S*)-4-{[(5-Chloroindol-2-yl)carbonyl]amino}-1-[(1-hydroxycyclopropyl)carbonyl]piperidin-3-yl)-5-methyl-4,5,6,7-tetrahydrothiazolo[5,4-c]pyridine-2-carboxamide hydrochloride

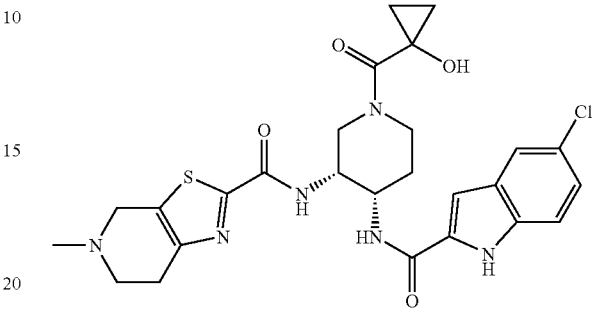

In a manner similar to that described in Example 150, the compound obtained in Example 118 was condensed with 1-hydroxy-1-cyclopropanecarboxylic acid, followed by treatment with hydrochloric acid, to thereby give the title compound.

¹H-NMR (DMSO-d₆) δ: 0.60-0.90(3H,br), 0.92-1.03(1H, m), 1.71-1.84(1H,m), 1.85-2.03(1H,m), 2.91(3H,s), 3.00-3.80(7H,m), 4.05-4.80(5H,m), 6.28-6.42(1H,br), 7.09(1H,s), 7.18(1H,dd,J=8.8, 1.5 Hz), 7.42(1H,d,J=8.8 Hz), 7.70(1H,d, J=1.5 Hz), 8.14-8.29(1H,br), 8.41(1H,br d,J=7.6 Hz), 11.83 (1H,s).

MS(ESI)m/z: 557(M+H)⁺.

Example 294

N-((3R*,4S*)-4-{[(5-Chloroindol-2-yl)carbonyl]amino}-1-[(1-methoxycyclopropyl)carbonyl]piperidin-3-yl)-5-methyl-4,5,6,7-tetrahydrothiazolo[5,4-c]pyridine-2-carboxamide hydrochloride

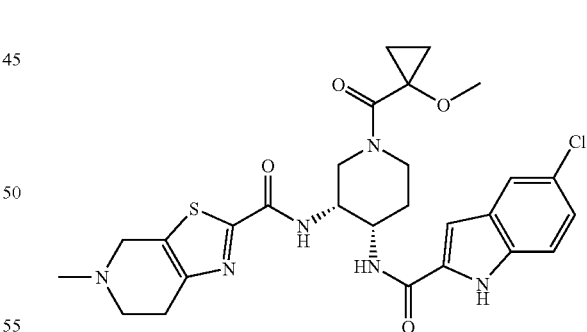

In a manner similar to that described in Example 150, the compound obtained in Example 118 was condensed with the compound obtained in Referential Example 409, followed by treatment with hydrochloric acid, to thereby give the title compound.

¹H-NMR (DMSO-d₆) δ: 0.65-1.05(4H,m), 1.74-1.88(1H, m), 1.92-2.10(1H,m), 2.91(3H,s), 3.00-3.80(10H,m), 4.05-4.83(6H,m), 7.08(1H,s), 7.18(1H,dd,J=8.6, 2.0 Hz), 7.42 (1H,d,J=8.6 Hz), 7.71(1H,d,J=2.0 Hz), 8.08-8.30(1H,br), 8.41(1H,br d,J=7.8 Hz), 10.60-10.80(0.5H,br), 10.85-11.05 (0.5H,br), 11.84(1H,s).

Example 295

7-Chloro-N-((3R,4S)-1-(2-methoxyacetyl)-3-{[(5-methyl-4,5,6,7-tetrahydrothiazolo[5,4-c]pyridin-2-yl)carbonyl]-amino}piperidin-4-yl)-3-isoquinolinecarboxamide hydrochloride

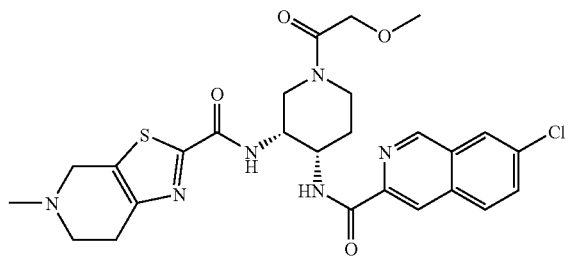

In a manner similar to that described in Example 219, the compound obtained in Referential Example 410 was treated with 4N HCl-dioxane for deprotection, followed by condensation with the compound obtained in Referential Example 10 and treatment with hydrochloric acid, to thereby give the title compound.

$^1$H-NMR (DMSO-$d_6$) δ: 1.60-1.80(1H,m), 2.13-2.38(1H, m), 2.90(3H,s), 3.00-3.87(10H,m), 3.89-4.10(2H,m), 4.15-4.58(4H,m), 4.60-4.78(1H,m), 7.89(1H,d,J=8.8 Hz), 8.25 (1H,d,J=8.8 Hz), 8.37(1H,s), 8.61(1H,s), 8.70-8.95(1H,m), 9.05-9.29(1H,m), 9.36(1H,s), 11.20-11.40(0.5H,br), 11.45-11.65(0.5H,br).

MS(ESI)m/z: 557(M+H)$^+$.

Example 296

$N^1$-(4-chloro-3-fluorophenyl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

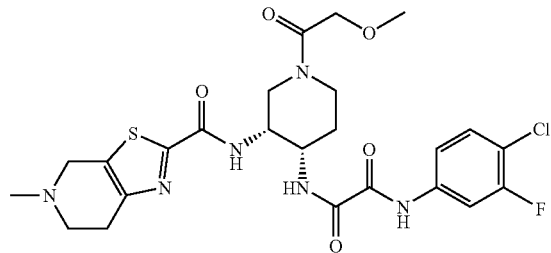

In a manner similar to that described in Example 219, the compound obtained in Referential Example 411 was treated with 4N HCl-dioxane for deprotection, followed by condensation with the compound obtained in Referential Example 10 and treatment with hydrochloric acid, to thereby give the title compound.

$^1$H-NMR (DMSO-$d_6$) δ: 1.60-1.72(1H,m), 1.98-2.21(1H, m), 2.91(3H,s), 3.00-3.52(9H,m), 3.56-4.05(3H,m), 4.08-4.50(4H,m), 4.60-4.78(1H,br), 7.56(1H,t,J=8.8 Hz), 7.70 (1H,d,J=9.0 Hz), 7.91(1H,dd,J=8.8, 2.3 Hz), 8.50-8.72(1H, m), 9.15-9.35(1H,m), 11.02(1H,s), 11.15-11.33(0.5H,br), 11.35-11.50(0.5H,br).

MS(FAB)m/z: 567(M+H)$^+$.

Example 297

$N^1$-(5-chloro-2-thienyl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride

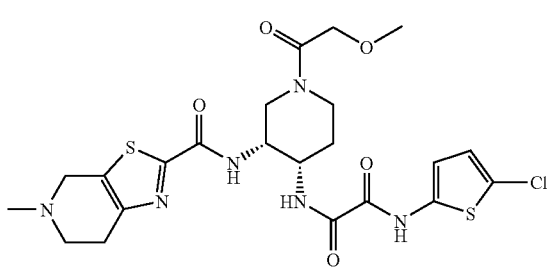

In a manner similar to that described in Example 219, the compound obtained in Referential Example 412 was treated with 4N HCl-dioxane for deprotection, followed by condensation with the compound obtained in Referential Example 10 and treatment with hydrochloric acid, to thereby give the title compound.

$^1$H-NMR (DMSO-$d_6$) δ: 1.60-1.73(1H,m), 1.96-2.19(1H, m), 2.91(3H,s), 3.04-3.54(9H,m), 3.60-4.05(3H,m), 4.07-4.34(3H,m), 4.35-4.54(1H,br), 4.60-4.80(1H,br), 6.89(1H,d, J=4.2 Hz), 6.93(1H,d,J=4.2 Hz), 8.48-8.70(1H,m), 9.18-9.40 (1H,m), 12.31(1H,s).

MS(ESI)m/z: 555(M+H)$^+$.

Example 298

N-{(1R,2S,5S)-2-{[2-(4-Chlorophenoxy)acetyl]amino}-5-[(dimethylamino)carbonyl]cyclohexyl}-5-methyl-4,5,6,7-tetrahydrothiazolo[5,4-c]pyridine-2-carboxamide hydrochloride

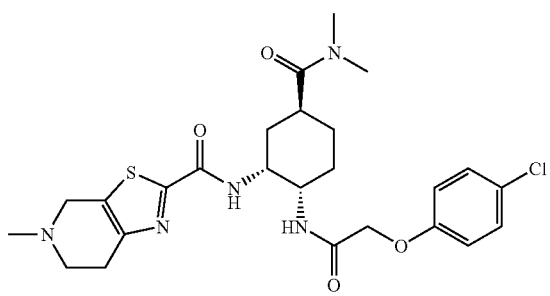

In a manner similar to that described in Example 223, the compound obtained in Referential Example 252 was reduced, followed by condensation with p-chlorophenoxyacetic acid and treatment with hydrochloric acid, to thereby give the title compound.

$^1$H-NMR (DMSO-$d_6$) δ: 1.35-1.47(1H,m), 1.55-1.90(5H, m), 2.77(3H,s), 2.92(3H,s), 2.96(3H,s), 2.98-3.10(1H,m), 3.10-3.80(3H,m), 3.85-3.95(1H,m), 4.35-4.50(4H,m), 4.50-4.80(1H,br), 6.85(2H,d,J=8.5 Hz), 7.15-7.35(1H,br), 7.88-8.03(1H,br), 8.46(1H,d,J=8.8 Hz), 11.30-11.65(1H,br).

MS(FAB)m/z: 534(M+H)$^+$.

Example 299

7-Chloro-N-((1S,2R,4S)-4-[(dimethylamino)carbonyl]-2-{[(5-methyl-5H-pyrrolo[3,4-d]thiazol-2-yl)carbonyl]amino}cyclohexyl)-3-isoquinolinecarboxamide hydrochloride

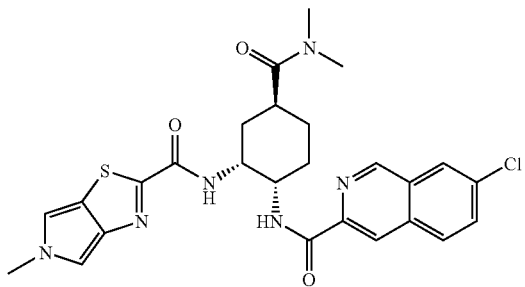

The compound obtained in Referential Example 413 was hydrolyzed to form the carboxylic acid lithium salt. The compound obtained in Referential Example 146 was treated with acid for deprotection, and the thus-deprotected compound was condensed with the lithium salt, followed by treatment with hydrochloric acid, to thereby give the title compound.

$^1$H-NMR (DMSO-$d_6$) δ: 1.00-1.11(2H,m), 1.45-1.60(1H, m), 1.65-1.85(1H,m), 1.95-2.06(1H,m), 2.10-2.24(1H,m), 2.78(3H,s), 2.87-3.02(1H,m), 2.94(3H,s), 3.88(3H,s), 4.16-4.27(1H,m), 4.45-4.56(1H,m), 7.03(1H,s), 7.55(1H,s), 7.87(1H,br d,J=8.3 Hz), 8.24(1H,br d,J=8.8 Hz), 8.33(1H,s), 8.59(1H,s), 8.85(1H,br d,J=7.6 Hz), 9.01(1H,br d,J=7.8 Hz), 9.28(1H,s).

MS(ESI)m/z: 539(M+H)$^+$.

Example 300

N-{(1R,2S,5S)-2-{[(6-Chloro-4-oxo-4H-chromen-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride

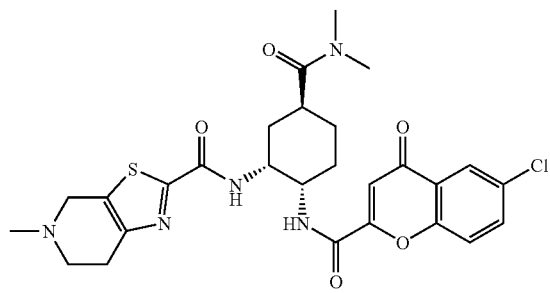

In a manner similar to that described in Example 219, the compound obtained in Referential Example 417 was treated with 4N HCl-dioxane, and the thus-obtained compound was condensed with the compound obtained in Referential Example 10, followed by treatment with hydrochloric acid, to thereby give the title compound.

$^1$H-NMR (DMSO-$d_6$) δ: 1.40-1.53(1H,m), 1.67-2.04(5H, m), 2.40-2.53(1H,m), 2.80(3H,s), 2.92(3H,s), 3.01(3H,s), 3.09-3.22(3H,m), 3.66-3.77(1H,m), 4.01-4.10(1H,m), 4.34-4.49(1H,m), 4.58-4.76(2H,m), 6.80(1H,d,J=4.9 Hz), 7.59-7.70(1H,m), 7.90-8.00(1H,m), 7.96(1H,s), 8.52-8.60(1H,m), 8.80-8.90(1H,m), 11.10-11.25(0.5H,br), 11.40-11.55(0.5H, br).

MS(ESI)m/z: 572(M+H)$^+$.

Example 301

7-Chloro-N-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)-3-cinnolinecarboxamide hydrochloride

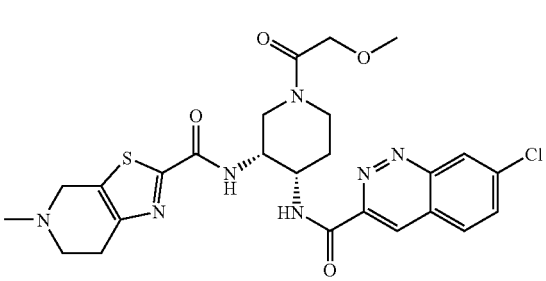

In a manner similar to that described in Example 219, the compound obtained in Referential Example 418 was treated with 4N HCl-dioxane, and the thus-obtained compound was condensed with the compound obtained in Referential Example 10, followed by treatment with hydrochloric acid, to thereby give the title compound.

$^1$H-NMR (DMSO-$d_6$) δ: 1.70-1.80(1H,m), 1.85-2.05(1H, m), 2.90(3H,s), 3.00-3.20(2H,m), 3.16(3H,s), 3.22-3.82(7H, m), 3.88-4.80(5H,m), 7.09(1H,d,J=9.0 Hz), 7.17(1H,dd, J=8.8, 1.9 Hz), 7.42(1H,d,J=8.8 Hz), 7.70(1H,d,J=1.9 Hz), 8.29(1H,br s), 8.40-8.50(1H,m), 11.20-11.50(1H,br m), 11.85(1H,s).

MS(ESI)m/z: 558(M+H)$^+$.

Example 302

N$^1$-(5-Chloropyridin-2-yl)-N$^2$-((1S,2R,4S)-4-[(dimethylamino)carbonyl]-2-{[(5-methyl-4,5,6,7-tetrahydrothieno[3,2-c]pyridin-2-yl)carbonyl]amino}-cyclohexyl)ethanediamide hydrochloride

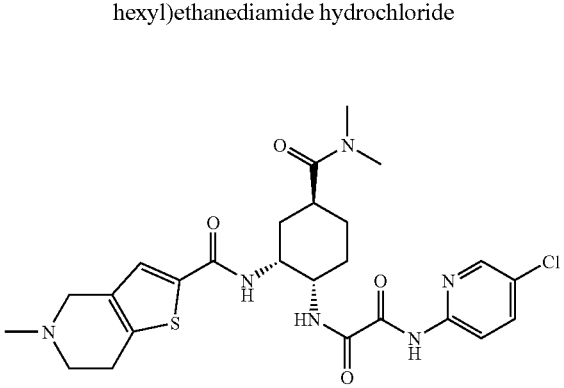

The compound obtained in Referential Example 421 was deprotected by use of hydrochloric acid. In a manner similar to that described in Example 18, the thus-deprotected compound was methylated, followed by treatment with hydrochloric acid, to thereby give the title compound.

$^1$H-NMR (DMSO-$d_6$) δ: 1.42-1.58(1H,m), 1.59-1.80(3H, m), 1.83-1.95(1H,m), 1.97-2.10(1H,m), 2.78(3H,s), 2.89(3H,s), 2.96(3H,s), 3.00-3.10(1H,m), 3.10-3.20(2H, m), 3.45-3.80(1H, m), 3.90-4.00(2H,m), 4.00-4.50(3H,m), 7.77(1H,s), 7.95-8.05(3H,m), 8.44(1H,t,J=1.6 Hz), 8.90(1H,d, J=8.6 Hz), 10.25(1H,s), 11.12(1H,br s).

MS(ESI)m/z: 547(M+H)$^+$.

Example 303

N[1]-(5-Chloropyridin-2-yl)-N[2]-((1S,2R,4S)-4-[(dimethylamino)carbonyl]-2-{[(5-isopropyl-4,5,6,7-tetrahydrothiazolo[5,4-c]pyridin-2-yl)carbonyl]aminocyclohexyl)ethanediamide hydrochloride

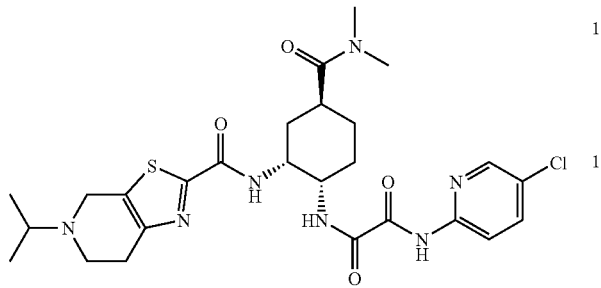

In a manner similar to that described in Example 2, the compound obtained in Referential Example 148 was condensed with the compound obtained in Referential Example 420, followed by treatment with hydrochloric acid, to thereby give the title compound.

$^1$H-NMR (DMSO-$d_6$) δ: 1.30-1.40(6H,m), 1.38-1.58(1H, M), 1.59-1.82(3H,m), 1.95-2.13(2H,m), 2.40-2.65(1H,m), 2.49(3H,s), 2.87-3.55(4H,m), 2.49(3H,s), 3.60-3.82(2H,m), 3.93-4.04(1H,m), 4.37-4.55(2H,M), 4.55-4.72(1H,m), 7.94-8.10(2H,m), 8.43(1H,s), 8.64-8.77(1H,m), 9.12(½H,d,J=7.8 Hz), 9.24(½H,d,J=7.8 Hz), 10.22(½H,s), 10.26(½H,s), 11.25(½H,br s), 11.44(½H,br s).

MS(FAB)m/z: 578(M+H)+.

Example 304

N-((1R,2S,5S)-5-[(Dimethylamino)carbonyl]-2-{[2-(4-fluoroanilino)-2-oxoethanethioyl]amino}cyclohexyl)-5-methyl-4,5,6,7-tetrahydrothiazolo[5,4-c]pyridine-2-carboxamide hydrochloride

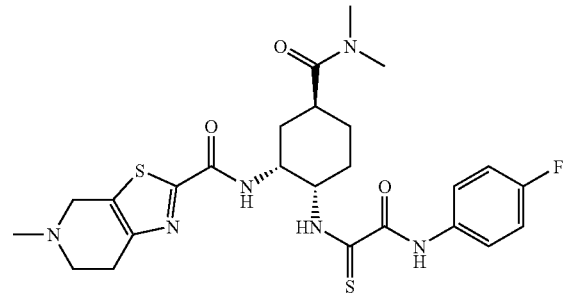

In a manner similar to that described in Example 219, the compound obtained in Referential Example 424 was treated with hydrochloric acid for deprotection, followed by condensation with the compound obtained in Referential Example 10 and treatment with hydrochloric acid, to thereby give the title compound.

$^1$H-NMR (DMSO-$d_6$) δ: 1.45-1.60(1H,m), 1.60-1.80(3H, m), 2.00-2.10(1H,m), 2.20-2.35(1H,m), 2.79(3H,s), 2.93(3H,s), 2.95(3H,s), 2.95-3.10(1H,m), 3.10-3.30(2H,m), 3.40-3.60(1H,m), 3.60-3.80(1H,m), 4.35-4.50(1H,m), 4.50-4.60(1H,m), 4.60-4.80(2H,m), 7.20(2H,t,J=8.8 Hz), 7.77 (2H,dd,J=9.0, 5.1 Hz), 8.80(1H,br), 10.42(1H,s), 10.93(1H, br), 11.28(1H,br).

MS(ESI)m/z: 547(M+H)+.

Example 305

N-[(1R,2S,5S)-5-[(Dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]-pyridine-2-carboxamide hydrochloride

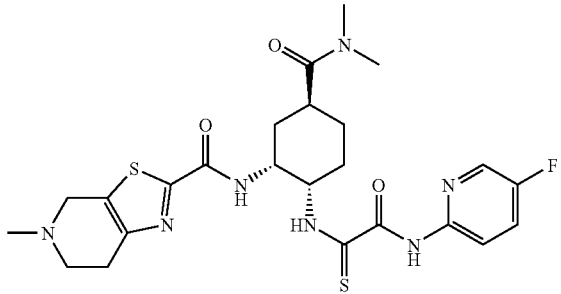

In a manner similar to that described in Example 219, the compound obtained in Referential Example 427 was treated with hydrochloric acid for deprotection, followed by condensation with the compound obtained in Referential Example 10 and treatment with hydrochloric acid, to thereby give the title compound.

$^1$H-NMR (DMSO-$d_6$) δ: 1.43-1.57(1H,m), 1.64-1.87(3H, m), 2.00(1H,br s), 2.17-2.34(1H,m), 2.78(3H,s), 2.90(3H,s), 2.95(3H,s), 2.95-3.10(1H,m), 3.10-3.30(2H,m), 3.40-3.60 (1H,m), 3.68(1H,br s), 4.44(1H,br s), 4.45-4.56(1H,m), 4.60-4.73(2H,m), 7.80-7.90(1H,m), 8.08(1H,dd,J=9.1, 3.9 Hz), 8.41(1H,d,J=2.9 Hz), 8.79(1H,d,J=6.6 Hz), 10.49(1H,s), 11.07(1H,br s), 11.69(1H,br).

MS(ESI)m/z: 548(M+H)+.

Example 306

N-{(1R,2S,5S)-2-({2-[(5-Chloropyridin-2-yl)amino]-2-oxoethanethioyl}amino)-5-[(dimethylamino)carbonyl]-cyclohexyl}-5-methyl-5H-pyrrolo[3,4-d]thiazole-2-carboxamide

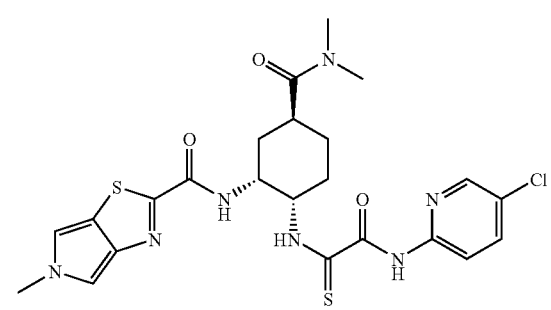

In a manner similar to that described in Example 219, the compound obtained in Referential Example 428 was treated with hydrochloric acid for deprotection, followed by condensation with the compound obtained in Referential Example 293, to thereby give the title compound.

$^1$H-NMR (DMSO-$d_6$) δ: 1.45-1.58(1H,m), 1.63-1.73(2H, m), 1.73-1.87(2H,m), 2.00-2.10(1H,m), 2.20-2.35(1H,m), 2.79(3H,s), 2.95(3H,s), 2.96-3.10(1H,m), 3.89(3H,s), 4.48-4.58(1H,m), 4.60-4.70(1H,m), 7.05(1H,d,J=1.7 Hz), 7.55 (1H,d,J=1.7 Hz), 8.00(1H,dd,J=8.9, 2.4 Hz), 8.05(1H,d, J=8.9 Hz), 8.44(1H,d,J=2.4 Hz), 8.71(1H,d,J=7.3 Hz), 10.57 (1H,s), 11.13(1H,d,J=7.8 Hz).

MS(FAB)m/z: 548(M+H)+.

Example 307

N-{(1R,2S,5S)-2-({2-[(5-Chloropyridin-2-yl)amino]-2-oxoethanethioyl]amino}-5-[(dimethylamino)carbonyl]-cyclohexyl}-5-methyl-5,6-dihydro-4H-pyrrolo[3,4-d]thiazole-2-carboxamide hydrochloride

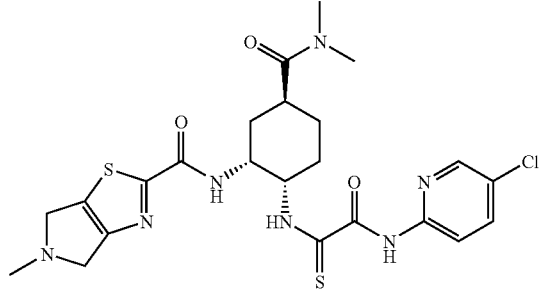

in a manner similar to that described in Example 219, the compound obtained in Referential Example 428 was treated with hydrochloric acid for deprotection, followed by condensation with the compound obtained in Referential Example 293 in an argon atmosphere and treatment with hydrochloric acid, to thereby give the title compound.

$^1$H-NMR (DMSO-$d_6$) δ: 1.42-1.58(1H,m), 1.65-1.87(3H, m), 1.97-2.10(1H,m), 2.17-2.30(1H,m), 2.80(3H,s), 2.96(3H,s), 2.98-3.10(1H,m), 3.07(3H,s), 4.30-5.00(6H,m), 8.00-8.10(1H,m), 8.46(1H,d,J=2.4 Hz), 8.79(1H,t,J=7.3 Hz), 10.54(1H,s), 11.04(1H,d,J=7.8 Hz), 12.24(1H,br s).

MS(ESI)m/z: 550(M+H)$^+$.

Example 308

$N^1$-(5-Chloropyridin-2-yl)-$N^2$-[(1S,2R,4S)-4-[(dimethylamino)carbonyl]-2-({[6-(dimethylamino)-4,5,6,7-tetrahydrobenzothiazol-2-yl]carbonyl}amino)cyclohexyl]-ethanediamide

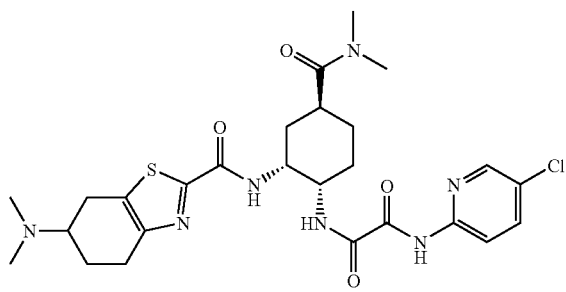

The compound obtained in Referential Example 431 was treated with hydrochloric acid for deprotection. In a manner similar to that described in Example 18, the thus-deprotected product was methylated, followed by treatment with hydrochloric acid, to thereby give the title compound.

$^1$H-NMR (DMSO-$d_6$) δ: 1.42-1.58(1H,m), 1.59-1.80(3H, m), 1.90-2.12(3H,m), 2.30-2.45(1H,m), 2.70-3.00(11H,m), 2.92(3H,s), 3.00-3.20(2H,m), 3.25-3.45(1H,m), 3.63-3.80 (1H,m), 3.88-4.02(1H,m), 4.35-4.47(1H,m), 8.02(1H,s), 8.42-8.55(1H,m), 8.60-8.68(1H,m), 8.93(1H,dd,J=14.5, 8.2 Hz), 9.19(1H,dd,J=17.7, 8.2 Hz), 10.28(1H,s), 10.91(1H,br s).

MS(ESI)m/z: 576(M+H)$^+$.

Example 309

N-{(1R,2S,5S)-2-[({[(4-Chlorophenyl)sulfonyl]amino}-carbonyl)amino]-5-[(dimethylamino)carbonyl]cyclohexyl}-5-methyl-4,5,6,7-tetrahydrothiazolo[5,4-c]pyridine-2-carboxamide hydrochloride

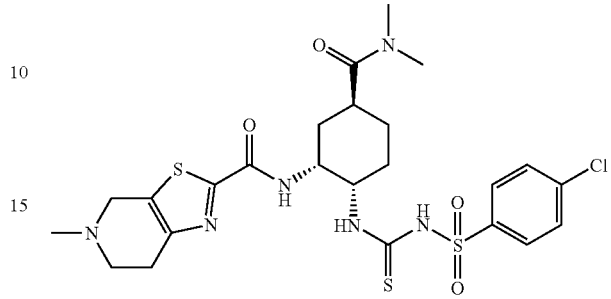

4-Chlorophenylsulfonyl isocyanate (148 μl) was added to a solution of the compound (328.0 mg) obtained in Referential Example 253 in methylene chloride (10 mL), and the mixture was stirred at room temperature for 24 hours. The solvent was distilled away under reduced pressure, and residue was purified by preparative thin-layer silica gel column chromatography (methylene chloride:methanol=9:1). The thus-obtained product was dissolved in ethanol (2 mL) and methylene chloride (2 mL), and 1N HCl in (0.25 mL) was added, followed by stirring at room temperature for 30 minutes. The reaction mixture was concentrated under reduced pressure, and the residue was solidified with diethyl ether to give the title compound (104.3 mg).

$^1$H-NMR (DMSO-$d_6$) δ: 1.25-1.45(1H,m), 1.45-1.80(5H, m), 2.76(3H,s), 2.94(3H,s), 2.97(3H,s), 3.00-3.80(6H,m), 4.35-4.85(3H,m), 6.53(1H,brs), 7.66(2H,d,J=8.5 Hz), 7.86 (2H,d,J=8.5 Hz), 8.50-8.82(1H,m), 10.64(1H,br s), 11.10-11.80(1H,br).

MS(ESI)m/z: 583(M+H)$^+$.

Example 310

$N^1$-(5-Chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide

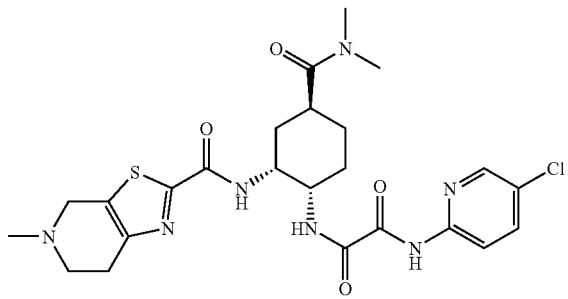

The title compound was obtained from the compound obtained in Referential Example 435 and the compound obtained in Referential Example 10 in a similar manner to Example 2.

$^1$H-NMR (CDCl$_3$) δ: 1.60-1.98(3H,m), 2.00-2.16(3H,m), 2.52(3H,s), 2.78-2.90(3H,m), 2.92-2.98(2H,m), 2.95(3H,s), 3.06(3H,s), 3.69(1H,d,J=15.4 Hz), 3.75(1H,d,J=15.4 Hz), 4.07-4.15(1H,m), 4.66-4.72(1H,m), 7.40(1H,d,J=8.8, 0.6 Hz), 7.68(1H,dd,J=8.8, 2.4 Hz), 8.03(1H,d,J=7.8 Hz), 8.16 (1H,dd,J=8.8, 0.6 Hz), 8.30(1H,dd,J=2.4, 0.6 Hz), 9.72(1H, s).

MS(ESI)m/z: 548(M+H)$^+$.

Example 311

N[1]-(5-Chloropyridin-2-yl)-N[2]-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate

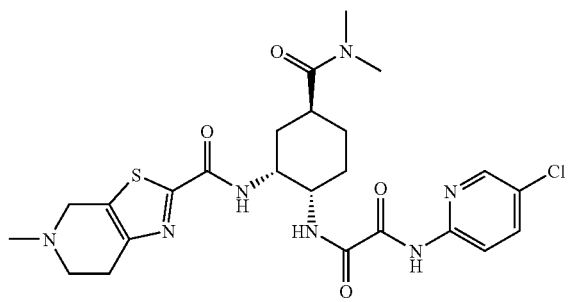

The compound (6.2 g) obtained in Example 310 is dissolved in methylene chloride (120 mL), a 1 mol/L ethanol solution (11.28 mL) of p-toluenesulfonic acid was added to the solution, and the solvent was distilled away. Ethanol (95 mL) containing 15% water was added to the residue, and the mixture was stirred at 60° C. to dissolve it. The solution was then cooled to room temperature and stirred for a day. Crystals precipitated were collected by filtration, washed with ethanol and dried at room temperature for 2 hours under reduced pressure to give the title compound (7.4 g).

$^1$H-NMR (DMSO-$d_6$) δ: 1.45-1.54(1H,m), 1.66-1.78(3H, m), 2.03-2.10(2H,m), 2.28(3H,s), 2.79(3H,s), 2.91-3.02(1H, m), 2.93(3H,s), 2.99(3H,s), 3.13-3.24(2H,m), 3.46-3.82(2H, m), 3.98-4.04(1H,m), 4.43-4.80(3H,m), 7.11(2H,d,J=7.8 Hz), 7.46(2H,d,J=8.2 Hz), 8.01(2H,d,J=1.8 Hz), 8.46(1H,t, J=1.8 Hz), 8.75(1H,d,J=6.9 Hz), 9.10-9.28(1H,br), 10.18(1H,br), 10.29(1H,s).

MS(ESI)m/z: 548(M+H)$^+$.

Elemental analysis: $C_{24}H_{30}ClN_7O_4S \cdot C_7H_8O_3S \cdot H_2O$. Calculated: C, 50.43; H, 5.46; N, 13.28; Cl, 4.80; S, 8.69. Found: C, 50.25; H, 5.36; N, 13.32; Cl, 4.93; S, 8.79.

mp(decomposed): 245-248° C.

Example 312

N[1]-(5-Chloropyridin-2-yl)-N[2]-((1S,2R,4S)-4-[(methylamino)carbonyl]-2-{[(5-methyl-4,5,6,7-tetrahydrothiazoro[5,4-c]-pyridin-2-yl)carbonyl]amino}cyclohexyl)ethanediamide hydrochloride

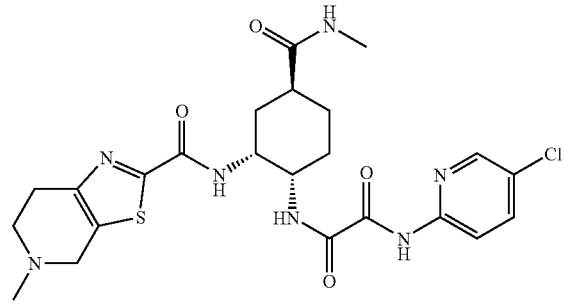

In a manner similar to that described in Example 219, the compound obtained in Referential Example 437 was treated with hydrochloric acid for deprotection, followed by condensation with the compound obtained in Referential Example 10 and treatment with hydrochloric acid, to thereby give the title compound.

$^1$H-NMR (DMSO-$d_6$) δ: 1.48-1.61(1H,m), 1.61-1.74(2H, m), 1.74-1.82(1H,m), 1.98-2.12(2H,m), 2.29-2.38(1H,m), 2.53(3H,d,J=4.2 Hz), 2.92(3H,s), 3.10-3.40(4H,br), 3.40-3.80(1H,br), 3.97-4.05(1H,m), 4.28-4.34(1H,m), 4.34-4.80 (1H,br), 7.70-7.78(1H,m), 7.97-8.07(2H,m), 8.43-8.50(1H, m), 8.49(1H,br.s), 9.27(1H,d,J=7.8 Hz), 10.26(1H,br.s), 11.48(1H,br.s).

MS(ESI)m/z: 534[(M+H)$^+$, Cl$^{35}$], 535[(M+H)$^+$, Cl$^{37}$].

Example 313

N[1]-(5-Chloropyridin-2-yl)-N[2]-((3R,4S)-1-(2-methoxyacetyl)-3-{[4-(pyridin-4-yl)benzoyl]amino}piperidin-4-yl)ethanediamide hydrochloride

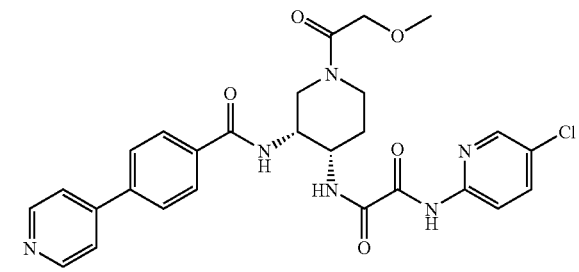

In a manner similar to that described in Example 219, the compound obtained in Referential Example 368 was treated with 4N HCl-dioxane for deprotetcion, followed by condensation with the compound obtained in Referential Example 237 and treatment with hydrochloric acid, to thereby give the title compound.

$^1$H-NMR (DMSO-$d_6$) δ: 1.62-1.75(1H,m), 2.00-2.20(1H, m), 2.80-4.40(11H,m), 7.90-8.00(4H,m), 8.05-8.13(2H,m), 8.14-8.43(3H,m), 8.40-8.45(1H,m), 8.87-9.04(3H,m), 10.20-10.50(2H,br).

MS(FAB)m/z: 551[(M+H)$^+$, Cl$^{35}$], 553[(M+H)$^+$, Cl$^{37}$].

Example 314

N-{(1R,2S,5S)-5-[(Dimethyamino)carbonyl]-2-({2-[(5-methylpyridin-2-yl)amino]-2-oxoethanethioyl}amino)cyclohexyl}-5-methyl-4,5,6,7-tetrahydrothiazolo[5,4-c]pyridin-2-carboxamide hydrochloride

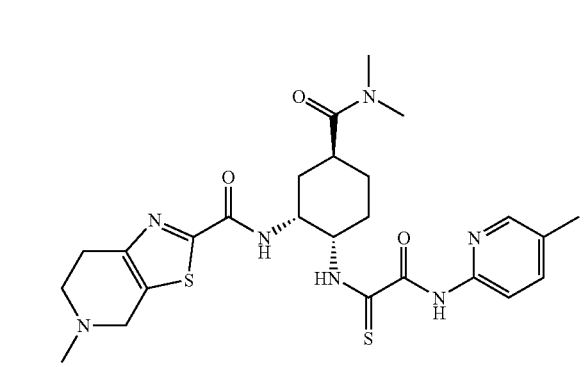

In a manner similar to that described in Example 219, the compound obtained in Referential Example 440 was treated with hydrochloric acid for deprotection, followed by condensation with the compound obtained in Referential Example 10 and treatment with hydrochloric acid, to thereby give the title compound.

$^1$H-NMR (DMSO-$d_6$) δ: 1.45-1.60(1H,m), 1.65-1.90(3H, m), 2.00-2.10(1H,m), 2.20-2.40(1H,m), 2.28(3H,s), 2.80(3H,s), 2.91(3H,s), 2.95-3.10(1H,m), 2.96(3H,s), 3.15-3.30(1H,m), 3.32(2H,s), 3.50-3.80(1H,m), 4.45-4.60(2H,m), 4.60-4.80(2H,m), 7.72(1H,d,J=8.5 Hz), 7.97(1H,d,J=8.5 Hz), 8.23(1H,s), 8.83(1H,d,J=7.3 Hz), 10.38(1H,s), 11.06 (1H,d,J=7.6 Hz), 11.49(1H,br.s).

MS(ESI)m/z: 544(M+H)+.

Example 315

N-[(3R,4S)-4-{[2-(4-Chloroanilino)-2-oxoethanethioyl]-amino}-1-(2-methoxyacetyl)pyperidin-3-yl]-5-methyl-4,5,6,7-tetrahydrothiazolo[5,4-c]pyridin-2-carboxamide hydrochloride

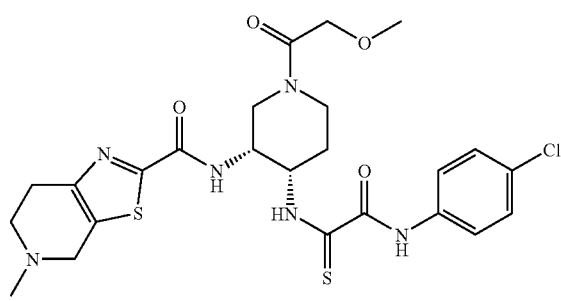

In a manner similar to that described in Example 219, the compound obtained in Referential Example 441 was treated with hydrochloric acid for deprotection, followed by condensation with the compound obtained in Referential Example 10 and treatment with hydrochloric acid, to thereby give the title compound.

$^1$H-NMR (DMSO-d$_6$) δ: 1.71-1.82(1H,m), 2.18-2.44(1H, m), 2.89(3H,s), 3.00-4.85(17H,m), 7.41(2H,d,J=8.8 Hz), 7.77(2H,d,J=8.8 Hz), 8.48-8.73(1H,m), 10.48(1H,br.s), 10.90-11.06(1H,m), 11.45-11.90(1H,br).

MS(ESI)m/z: 565[(M+H)+, Cl$^{35}$], 567[(M+H)+, Cl$^{37}$].

Example 316

N$^1$-(5-Chloropyridin-2-yl)-N$^2$-((1S,2R,4S)-4-[(dimethylamino)carbothioyl]-2-{[(5-methyl-4,5,6,7-tetrahydrothiazolo[5,4-c]pyridin-2-yl)carbonyl]amino}-cyclohexyl)ethanediamide hydrochloride

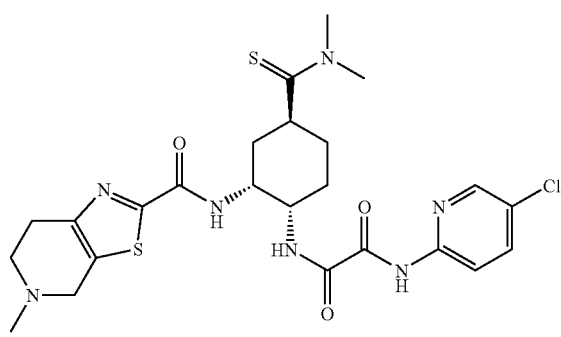

In a manner similar to that described in Example 3, the compound obtained in Referential Example 445 was condensed with the compound obtained in Referential Example 10, followed by treatment with hydrochloric acid, to thereby give the title compound.

$^1$H-NMR (DMSO-d$_6$) δ: 1.66-2.15(6H,m), 2.93(3H,s), 3.15-3.40(9H,m), 3.49(1H,br.s), 3.71(1H,br.s), 3.97-4.01 (1H,m), 4.42(2H,br.s), 4.70(1H,br.s), 8.01(2H,br.s), 8.46(1H, br.s), 8.78(1H,d,J=6.8 Hz), 9.24(1H,br.s), 10.28(1H,s), 11.29 (1H,br.s).

MS(FAB)m/z: 564[(M+H)+, Cl$^{35}$], 566[(M+H)+, Cl$^{37}$].

Example 317

N$^1$-(5-Chloropyridin-2-yl)-N$^2$-((3R,4S)-1-(2-methoxyethanethioyl)-3-{[(5-methyl-4,5,6,7-tetrahydrothiazolo[5,4-c]pyridin-2-yl)carbonyl]amino}-piperidin-4-yl)ethanediamide hydrochloride

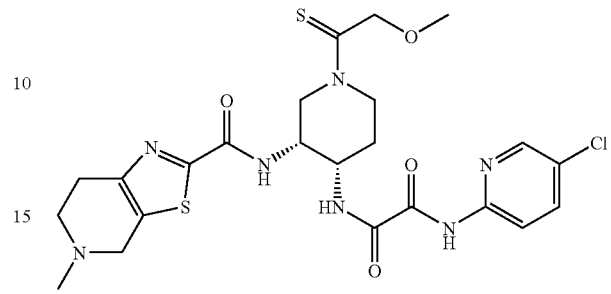

In a manner similar to that described in Example 219, the compound obtained in Referential Example 448 was treated with hydrochloric acid for deprotection, followed by condensation with the compound obtained in Referential Example 10 and treatment hydrochloric acid, to thereby give the title compound.

$^1$H-NMR (DMSO-d$_6$) δ: 1.74-1.85(1H,m), 2.13-2.35(1H, m), 2.89(3H,s), 2.95-3.98(9H,m), 4.05-5.33(8H,m), 7.95-8.06(2H,m), 8.43(1H,s), 8.48-8.73(1H,br), 9.29-9.45(1H,br), 10.21-10.34(1H,br), 11.45-11.90(1H,br).

MS(ESI)m/z: 566[(M+H)+, Cl$^{35}$], 568[(M+H)+, Cl$^{37}$].

Example 318

2,2,2-Trichloroethyl (1S,3R,4S)-4-({2-[(5-Chloropyridin-2-yl)amino]-2-oxoacetyl}amino)-3-{[(5-methyl-4,5,6,7-tetrahydrothiazolo[5,4-c]pyridin-2-yl) carbonyl]amino}-cyclohexanecarboxylate

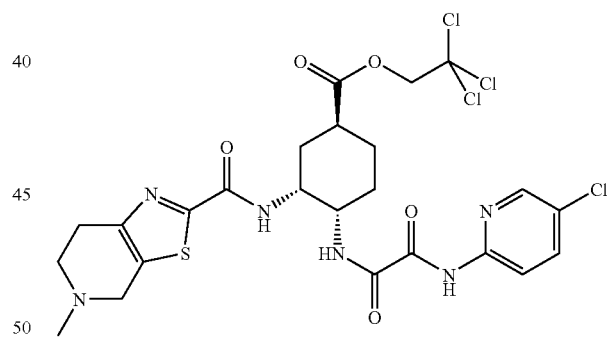

In a manner similar to that described in Example 219, the compound obtained in Referential Example 453 was treated with hydrochloric acid for deprotection, followed by condensation with the compound obtained in Referential Example 10 and treatment with hydrochloric acid, to thereby give the title compound.

$^1$H-NMR (CDCl$_3$) δ: 1.60-1.87(2H,m), 2.04-2.15(2H,m), 2.21-2.32(2H,m), 2.52(3H,s), 2.73-2.89(3H,m), 2.92-2.98 (2H,m), 3.71(1H,d,J=15.4 Hz), 3.73(1H,d,J=15.4 Hz), 4.08-4.16(1H,m), 4.66-4.71(1H,m), 4.72(1H,d,J=12.0 Hz), 4.82 (1H,d,J=12.0 Hz), 7.37(1H,d,J=8.8 Hz), 7.69(1H,dd,J=8.8, 2.4 Hz), 8.05(1H,d,J=8.1 Hz), 8.16(1H,d,J=8.8 Hz), 8.30(1H, d,J=2.4 Hz), 9.69(1H,s).

MS(ESI)m/z: 651[(M+H)$^{+,3}$×Cl$^{35}$], 653[(M+H)$^{+,2}$×Cl$^{35}$, Cl$^{37}$], 655[(M+H)+, Cl$^{35,2}$×Cl$^{37}$].

Example 319

(1S,3R,4S)-4-({2-[5-Chloropyridin-2-yl]amino}-2-oxoacetyl)amino)-3-{[(5-methyl-4,5,6,7-tetrahydrothiazolo[5,4-c]pyridin-2-yl)carbonyl]amino}-cyclohexane carboxylic acid

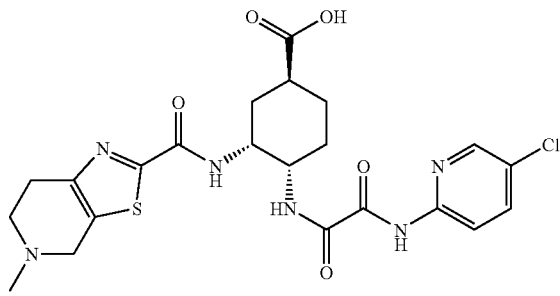

The compound (475 mg) obtained in Example 318 was dissolved in tetrahydrofuran (50 mL), zinc (2.85 g) and acetic acid (5.7 mL) were successively added to the solution, and the mixture was stirred at room temperature for 3 hours. Celite 545 (2.85 g) was added to the reaction mixture to remove insoluble matter by filtration. After the filtrate was concentrated under reduced pressure, methylene chloride was added to the resultant residue, and 1N aqueous sodium hydroxide was added with stirring to adjust the pH of the reaction mixture to 7. After an organic layer was separated, saturated brine (50 mL) was added to an aqueous layer, and the mixture was extracted with methylene chloride (10×50 mL). The resultant organic layers were combined and dried over magnesium sulfate anhydrate. The solvent was distilled away under reduced pressure, and the resultant residue was purified by silica gel column chromatography (methylene chloride:methanol=95:5->9:1→4:1) to give the title compound (140 mg).

$^1$H-NMR (DMSO-$d_6$) δ: 1.50-1.80(3H,m), 1.84-1.95(1H,m), 1.95-2.10(1H,m), 2.15-2.30(1H,m), 2.38(3H,s), 2.40-2.50(1H,m), 2.67-2.80(2H,m), 2.80-2.95(2H,m), 3.66(2H,m), 4.03(1H,br.s), 4.33(1H,br.s), 7.97-8.10(2H,m), 8.45(1H,s), 8.53(1H,d,J=6.8 Hz), 9.19(1H,d,J=8.3 Hz), 10.27(1H,br.s).

MS(FAB)m/z: 521[(M+H)$^+$,$^{35}$Cl], 523[(M+H)$^+$,$^{37}$Cl].

Example 320

N-{(1R,2S,5S)-2-{[2-(4-Chloroanilino)-1-methoxy-imino-2-oxoethyl]amino}-5-[(dimethylamino)carbonyl]cyclohexyl}-5-methyl-4,5,6,7-tetrahydrothiazolo[5,4-c]pyridin-2-carboxamide hydrochloride

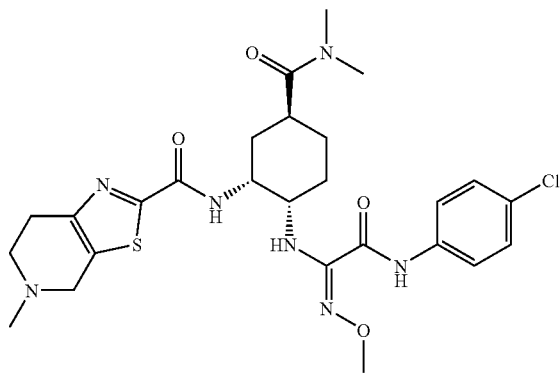

In a manner similar to that described in Referential Example 142, the ester compound obtained in Referential Example 454 was hydrolyzed. In a manner similar to that described in Referential Example 143, the resultant product was condensed with 4-chloroaniline, followed by treatment with hydrochloric acid, to thereby give the title compound.

$^1$H-NMR (DMSO-$d_6$) δ: 1.30-1.17(1H,m), 1.50-1.62(1H,m), 1.62-1.75(2H,m), 1.85-2.00(2H,m), 2.76(3H,s), 2.93(6H,br.s), 3.00-3.10(1H,m), 3.18(1H,br.s), 3.27(1H,br.s), 3.49(1H,br.s), 3.71(1H,br.s), 3.76(3H,s), 3.93(1H,br.s), 4.35-4.50(2H,m), 4.66-4.77(1H,m), 6.09(0.5H,d,J=7.8 Hz), 6.19(0.5H,d,J=7.8 Hz), 7.38(2H,d,J=8.8 Hz), 7.71(2H,d,J=8.8 Hz), 8.70-8.79(1H,m), 10.28(1H,d,J=11.0 Hz), 11.53(0.5H,br.s), 11.45(0.5H,br.s).

MS(FAB)m/z: 576[(M+H)$^+$,$^{35}$Cl], 578[(M+H)$^+$,$^{37}$Cl].

Example 321

N$^1$-(5-Chloropyridin-2-yl)-N$^2$-[(1S,2R,4S)-4-[(dimethylamino)carbonyl]-2-({[1-(pyridin-4-yl)piperidin-4-yl]carbonyl}amino)cyclohexyl]ethanediamide hydrochloride

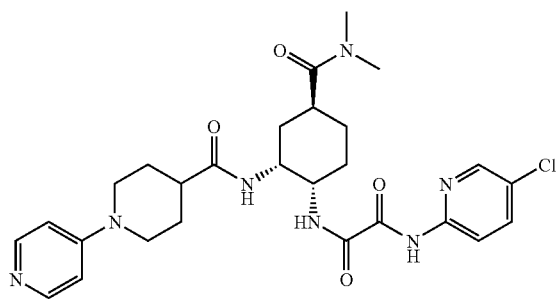

In a manner similar to that described in Example 2, the compound obtained in Referential Example 420 was condensed with 1-(pyridin-4-yl)piperidine-4-carboxylic acid (WO96/10022), followed by treatment with hydrochloric acid, to thereby give the title compound.

$^1$H-NMR (DMSO-$d_6$) δ: 1.35-1.49(1H,m), 1.49-1.78(6H,m), 1.78-1.98(3H,m), 2.75-2.90(1H,m), 2.78(3H,s), 3.02(3H,s), 3.03-3.14(1H,m), 3.14-3.28(2H,m), 3.74-3.85(1H,m), 4.13-4.30(3H,m), 7.18(2H,d,J=7.3 Hz), 7.99(2H,s), 8.10-8.23(3H,m), 8.41(1H,s), 8.50(1H,d,J=8.1 Hz), 10.19(1H,s), 13.73(1H,br.s).

MS(FAB)m/z: 556[(M+H)$^+$,$^{35}$Cl], 558[(M+H)$^+$, $^{37}$Cl].

Example 322

N$^1$-((1S,2R,4S)-4-[(Dimethylamino)carbonyl]-2-{[(5-methyl-4,5,6,7-tetrahydrothiazolo[5,4-c]pyridin-2-yl)carbonyl]-amino}cyclohexyl)-N$^2$-(5-ethynylpyridin-2-yl)ethanediamide

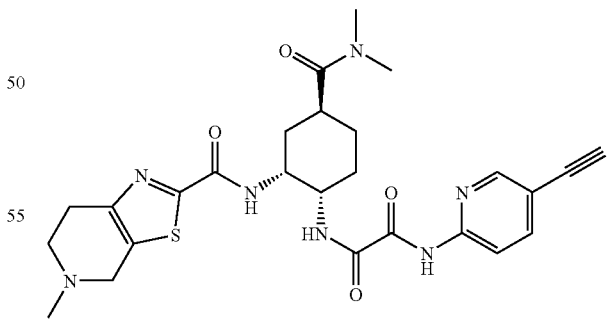

The compound (348 mg) obtained in Referential Example 455 was dissolved in tetrahydrofuran (14 mL), tetrabutylammonium fluoride (1N tetrahydrofuran solution, 628 µl) was added to the solution, and the mixture was stirred at room temperature for 30 minutes. The reaction mixture was decolored with activated carbon (about 1 g) and dried over sodium sulfate anhydrate. After filtration, the solvent was distilled away under reduced pressure, and the residue was purified by silica gel column chromatography (methylene chloride: methanol=93:7) and then dissolved in methylene chloride (about 1 mL). Hexane (about 10 mL) was added to the solution, and the precipitate formed was collected by filtration to give the title compound (116 mg).

$^1$H-NMR (CDCl$_3$) δ: 1.62-2.14(8H,m), 2.52(3H,s), 2.79-2.95(6H,m), 3.05(3H,s), 3.19(1H,s), [AB pattern 3.71(1H,d, J=15.5 Hz), 3.74(1H,d,J=15.5 Hz)], 4.08-4.14(1H,m), 4.66-4.69(1H,m), 7.41(1H,d,J=8.6 Hz), 7.80(1H,dd,J=8.6, 2.2 Hz), 8.03(1H,d,J=7.6 Hz), 8.15(1H,d,J=8.6 Hz), 8.46(1H,d, J=2.2 Hz), 9.75(1H,s).

MS(ESI)m/z: 538(M+H)$^+$.

Example 323

N$^1$-(5-Chloropyridin-2-yl)-N$^2$-((1S,2R,4S)-4-[(dimethylamino)carbonyl]-2-{[(5-methyl-5,6-dihydro-4H-thieno[2,3-c]pyrrol-2-yl)carbonyl]amino}cyclohexyl)ethanediamide

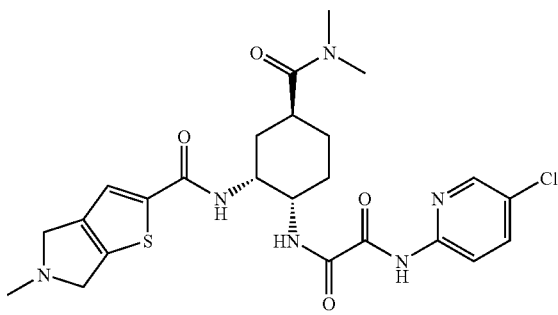

In a manner similar to that described in Example 191, the compound obtained in Referential Example 456 was hydrolyzed, followed by condensation with the compound obtained in Referential Example 420, to thereby give the title compound.

$^1$H-NMR (CDCl$_3$) δ: 1.80-2.15(6H,m), 2.64(3H,s), 2.76-2.79(1H,m), 2.94(3H,s), 3.03(3H,s), 3.84-3.86(2H,m), 3.94-3.99(3H,m), 4.58-4.59(1H,m), 6.70(1H,d,J=6.3 Hz), 7.31(1H,s), 7.70(1H,dd,J=8.8, 2.3 Hz), 8.15-8.18(2H,m), 8.30(1H,d,J=2.3 Hz), 9.72(1H,br.s).

MS(FAB)m/z: 533[(M+H)$^+$, Cl$^{35}$], 535[(M+H)$^+$, Cl$^{37}$].

Example 324

N-{(1R,2S,5S)-2-({2-[6-Chloropyridazin-3-yl]amino}-2-oxoethanethioyl)amino}-5-[(dimethylamino)carbonyl]-cyclohexyl}-5-methyl-4,5,6,7-tetrahydrothiazolo[5,4-c]-pyridin-2-carboxamide hydrochloride

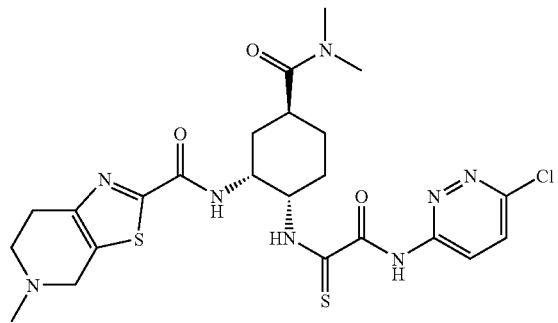

In a manner similar to that described in Example 3, the compound obtained in Referential Example 460 was condensed with the compound obtained in Referential Example 10, followed by treatment with hydrochloric acid, to thereby give the title compound.

$^1$H-NMR (DMSO-d$_6$) δ: 1.48-1.51(1H,m), 1.71-1.79(3H, m), 2.00(1H,br.s), 2.20-2.23(1H,m), 2.78(3H,s), 2.90(3H,s), 2.96(3H,s), 3.05(1H,br.s), 3.16-3.47(3H,m), 3.69(1H,br.s), 4.43(1H,br.s), 4.53(1H,br.s), 4.69(2H,br.s), 7.97(1H,d,J=9.6 Hz), 8.32(1H,d,J=9.6 Hz), 8.73(1H,d,J=7.3 Hz), 11.08(2H, br.s), 11.61-11.75(1H,m).

MS(FAB)m/z: 565[(M+H)$^+$, Cl$^{35}$], 567[(M+H)$^+$, Cl$^{37}$].

Example 325

N-{(1R,2S,5S)-2-({2-[(6-Chloropyridin-3-yl)amino]-2-oxoethanethioyl}amino)-5-[(dimethylamino)carbonyl]-cyclohexyl}-5-methyl-4,5,6,7-tetrahydrothiazolo[5,4-c]pyridin-2-carboxamide hydrochloride

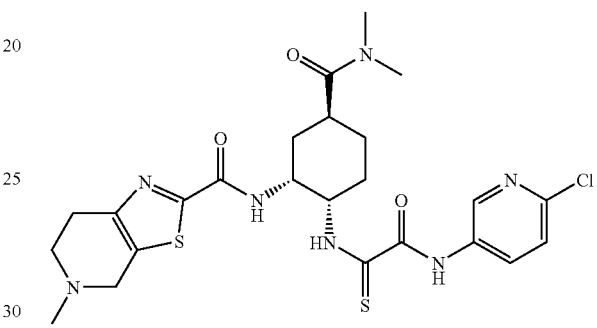

In a manner similar to that described in Example 3, the compound obtained in Referential Example 464 was condensed with the compound obtained in Referential Example 10, followed by treatment with hydrochloric acid, to thereby give the title compound.

$^1$H-NMR (DMSO-d$_6$) δ: 1.47-1.55(1H,m), 1.66-1.78(3H, m), 2.02-2.05(1H,m), 2.21-2.33(1H,m), 2.79(3H,s), 2.91(3H,s), 2.95(3H,s), 2.99-3.04(1H,m), 3.21(2H,br.s), 3.45-3.75(2H,br), 4.40-4.75(4H,m), 7.53(1H,d,J=8.6 Hz), 8.20(1H,dd,J=8.6, 2.6 Hz), 8.77(1H,d,J=7.3 Hz), 8.80(1H,d, J=2.6 Hz), 10.73(1H,s), 10.94(1H,br.d,J=7.6 Hz), 11.37(1H, br.s).

MS(FAB)m/z: 564[(M+H)$^+$, Cl$^{35}$], 566[(M+H)$^+$, Cl$^{37}$].

Example 326

N$^1$-[(3R,4S)-3-({[2'-(Aminosulfonyl)[1,1'-biphenyl]-4-yl]-carbonyl}amino)-1-(2-methoxyacetyl)piperidin-4-yl]-N$^2$-(5-chloropyridin-2-yl)ethanediamide

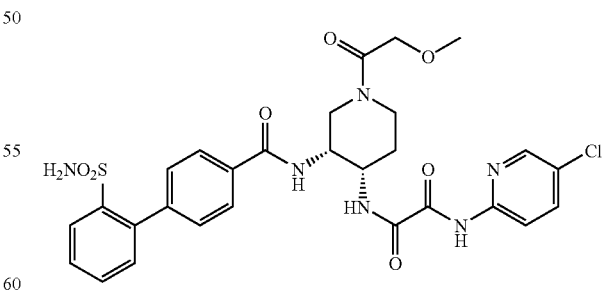

In a manner similar to that described in Example 219, the compound obtained in Referential Example 368 was treated with hydrochloric acid for deprotection, followed by condensation with the compound obtained in Referential Example 465, to thereby give the title compound.

$^1$H-NMR (CDCl$_3$) δ: 1.59-1.85(1H,m), 2.09-2.23(1H,m), 2.88-3.13(1H,m), 3.29-3.51(4H,m), 4.06-4.20(4H,m), 4.51-

4.78(4H,m), 7.09(0.25H,br.s), 7.30(1H,d,J=7.1 Hz), 7.51-7.54(3.75H,m), 7.60(1H,t,J=7.0 Hz), 7.69(1H,dd,J=8.9, 2.2 Hz), 7.94-7.96(2H,m), 8.13-8.22(2H,m), 8.30(1H,d,J=2.2 Hz), 8.91(0.75H,br.d,J=5.9 Hz), 9.18(0.25H,br.s), 9.70(1H, s).

MS(FAB)m/z: 629[(M+H)$^+$, Cl$^{35}$], 631[(M+H)$^+$, Cl$^{37}$].

Example 327

N$^1$-(5-Chloropyridin-2-yl)-N$^2$-{(1S,2R,4S)-4-[(dimethylamino)carbonyl]-2-[(thieno[3,2-b]pyridin-2-ylcarbonyl)amino]cyclohexyl}ethanediamide hydrochloride

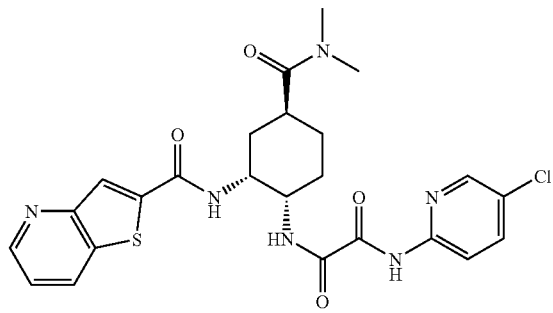

In a manner similar to that described in Example 2, the compound obtained in Referential Example 420 was condensed with lithium thieno[3,2-b]pyridin-2-carboxylate (Japanese Patent Application Laid-Open (kokai) No. 2001-294572), followed by treatment with hydrochloric acid, to thereby give the title compound.

$^1$H-NMR (DMSO-d$_6$) δ: 1.44-1.57(1H,m), 1.62-1.84(3H, m), 1.86-1.98(1H,m), 2.04-2.19(1H,m), 2.78(3H,s), 2.99(3H,s), 3.11-3.25(1H,m), 3.85-4.10(1H,br), 4.44-4.55 (1H,br), 7.51-7.62(1H,m), 7.98(2H,br.s), 8.43(2H,br.s), 8.60 (1H,s), 8.66(1H,br.d,J=8.1 Hz), 8.81(1H,br.d,J=4.2 Hz), 9.05 (1H,br.d,J=7.8 Hz), 10.24(1H,s).

MS(ESI)m/z: 529[(M+H)$^+$, Cl$^{35}$], 531[(M+H)$^+$, Cl$^{37}$].

Example 328

N$^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N$^2$-(5-methylpyridin-2-yl)ethanediamide hydrochloride

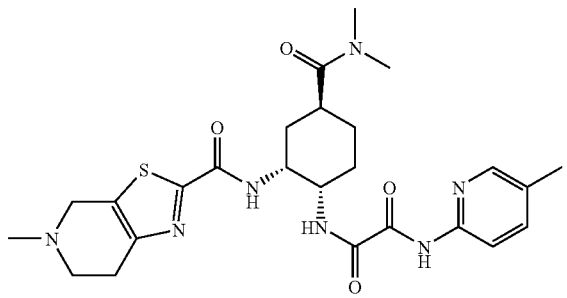

In a manner similar to that employed in Example 208, the title compound was prepared from the compound obtained in Referential Example 467 and the compound obtained in Referential Example 253.

$^1$H-NMR(DMSO-d$_6$)δ: 1.42-1.57(1H, m), 1.60-1.80(3H, m), 1.95-2.15(2H, m), 2.28(3H, s), 2.78(3H, s), 2.90-3.10 (1H, m), 2.92(3H, s), 2.94(3H, s), 3.07-3.38(2H, m), 3.40-3.58(1H, br), 3.60-3.80(1H, m), 3.95-4.05(1H, m), 4.36-4.50 (2H, m), 4.66-4.80(1H, m), 7.73(1H, d, J=8.0 Hz), 7.90-7.94 (1H, m), 8.24(1H, s), 8.70-8.80(1H, m), 9.13(0.5H, d, J=7.3 Hz), 9.21(0.5H, d, J=8.0 Hz), 10.06(1H, s), 11.46(0.5H, br.s), 11.57(0.5H, br.s).

MS(FAB)m/z: 528(M+H)$^+$.

Example 329

N$^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N$^2$-(4-methylphenyl)ethanediamide hydrochloride

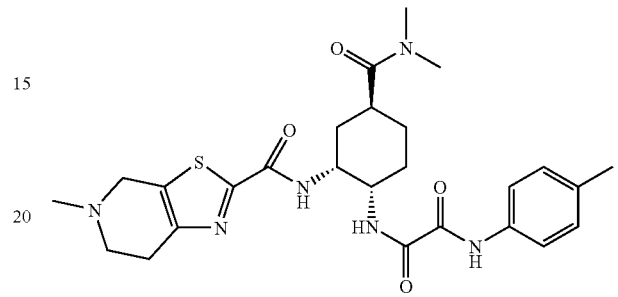

In a manner similar to that described in Example 219, the compound obtained in Referential Example 469 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.42-1.55(1H, m), 1.60-1.80(3H, m), 1.95-2.15(2H, m), 2.26(3H, s), 2.79(3H, s), 2.93(7H, br.s), 3.07-3.35(2H, m), 3.40-3.55(1H, m), 3.65-3.77(1H, m), 3.95-4.06(1H, m), 4.38-4.52(2H, br), 4.67-4.80(1H, m), 7.13 (2H, d, J=8.3 Hz), 7.66(2H, d, J=8.3 Hz), 8.72-8.80(1H, m), 8.96(0.5H, d, J=7.8 Hz), 9.04(0.5H, d, J=8.1 Hz), 10.56(1H, d, J=6.6 Hz), 11.30(1H, br.s).

MS(FAB)m/z: 527(M+H)$^+$.

Example 330

{4-chloro-5-[({(1R,2S,5S)-2-({2-[(5-chloropyridin-2-yl)amino]-2-oxoacetyl}amino)-5-[(dimethylamino)carbonyl]cyclohexyl}amino)carbonyl]-3-thienyl}methyl(methyl)carbamic acid tert-butyl ester

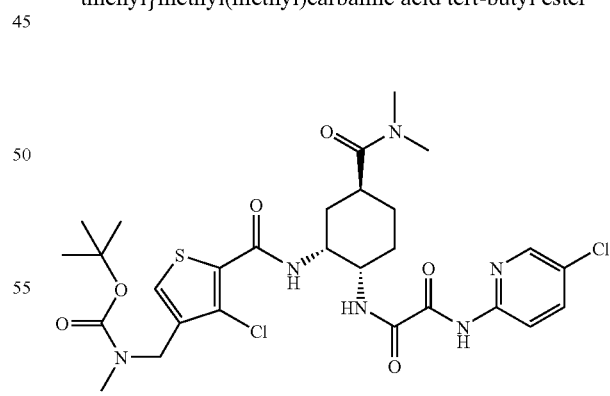

In a manner similar to that employed in Example 2, the compound obtained in Referential Example 471 was condensed with the compound obtained in Referential Example 420, to thereby yield the title compound.

$^1$H-NMR(CDCl$_3$)δ: 1.48(9H, s), 1.50-1.70(1H, m), 1.80-2.00(2H, m), 2.00-2.12(2H, m), 2.14-2.22(1H, m), 2.72-2.83 (1H, m), 2.88, 2.89(total 3H, each s), 2.96(3H, s), 3.04(3H, s), 4.05-4.15(1H, m), 4.32-4.50(1H, m), 4.73-4.80(1H, m), 7.22

(1H, d, J=8.8 Hz), 7.38(1H, br.s), 7.69(1H, dd, J=8.8, 2.6 Hz), 7.99(1H, d, J=7.6 Hz), 8.17(1H, d, J=8.8 Hz), 8.31(1H, d, J=2.6 Hz), 9.70(1H, br.s).
MS(ESI)m/z: 655(M+H)$^+$.

Example 331

N$^1$-{(1S,2R,4S)-2-[({3-chloro-4-[(methylamino) methyl]-2-thienyl}carbonyl)amino]-4-[(dimethylamino)carbonyl]cyclohexyl}-N$^2$-(5-chloropyridin-2-yl)ethanediamide

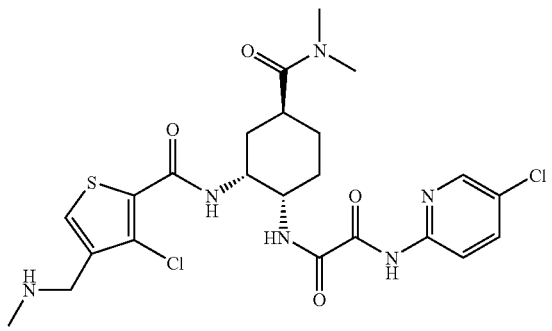

In a manner similar to that employed in Example 227, the title compound was prepared from the compound obtained in Example 330.
$^1$H-NMR(CDCl$_3$)δ: 1.55-1.70(1H, m), 1.75-1.98(2H, m), 2.00-2.22(2H, m), 2.22-2.32(1H, m), 2.52(3H, s), 2.72-2.86(1H, m), 2.96(3H, s), 3.05(3H, s), 3.53-3.82(1H, m), 3.78(2H, s), 4.05-4.16(1H, m), 4.72-4.80(1H, m), 7.27(1H, d, J=7.8 Hz), 7.52(1H, s), 7.67(1H, dd, J=8.8, 2.6 Hz), 8.09(1H, d, J=7.6 Hz), 8.09(1H, d, J=7.6 Hz), 8.13(1H, d, J=8.8 Hz), 8.29(1H, d, J=2.6 Hz), 9.90-11.00(1H, br).
MS(ESI)m/z: 555(M+H)$^+$.

Example 332

N$^1$-{(1S,2R,4S)-2-{[(3-chloro-4-{[4,5-dihydro-1,3-oxazol-2-yl(methyl)amino]methyl}-2-thienyl)carbonyl]amino}-4-[(dimethylamino)carbonyl]cyclohexyl}-N$^2$-(5-chloropyridin-2-yl)ethanediamide hydrochloride

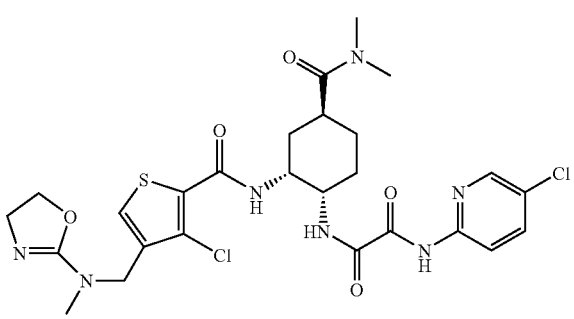

To a suspension of the compound obtained in Example 331 (590 mg) in methylene chloride (20 mL) were added triethylamine (0.735 mL) and 2-bromoethylisocyanate (0.106 mL), and the mixture was stirred for 18 hours at room temperature. The reaction mixture was diluted with methylene chloride, and the diluted solution was washed sequentially with water, 0.5N hydrochloric acid, water, saturated aqueous sodium bicarbonate, and saturated brine. The resultant organic layer was dried over sodium sulfate anhydrate and concentrated under reduced pressure. The residue was purified through silica gel flash column chromatography (methylene chloride: methanol=20:1), and the solvent was removed under reduced pressure. The crude product was dissolved in methylene chloride (2 mL) and ethanol (3 mL), and 1N HCl in ethanol (0.5 mL) was added thereto, followed by stirring for 30 minutes at room temperature and concentration under reduced pressure. Diethyl ether was added to the residue, and the precipitated solid was collected through filtration and washed, to thereby yield the title compound (197 mg) as a colorless powder.
$^1$H-NMR(DMSO-d$_6$)δ: 1.45-1.60(1H, m), 1.60-1.83(3H, m), 1.85-2.02(3H, m), 2.80(3H, s), 2.84(3H, s), 2.90-3.01(1H, m), 2.97(3H, s), 3.25-3.40(2H, m), 3.60(2H, t, J=6.6 Hz), 3.95-4.05(1H, m), 4.30-4.45(3H, m), 6.80(1H, t, J=5.5 Hz), 7.51(1H, s), 7.94-8.06(2H, m), 8.10(1H, d, J=6.8 Hz), 8.42-8.50(1H, m), 8.97(1H, d, J=8.6 Hz), 10.27(1H, s).
MS(ESI)m/z: 624(M+H)$^+$.

Example 333

[4-chloro-5-({[(1R,2S)-2-({2-[(5-chloropyridin-2-yl)amino]-2-oxoacetyl}amino)cyclohexyl]amino}carbonyl)-3-thienyl]methyl(methyl)carbamic acid tert-butyl ester

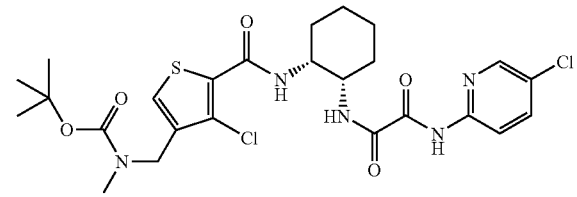

In a manner similar to that described in Example 214, the compound obtained in Referential Example 472 was treated with hydrochloric acid for deprotection. The deprotected compound was condensed with the compound obtained in Referential Example 471, whereby the title compound was obtained.
$^1$H-NMR(CDCl$_3$)δ: 1.15-2.00(6H, m), 1.46(9H, s), 2.87(3H, s), 4.15-4.25(1H, m), 4.30-4.45(2H, m), 4.48-4.56(1H, m), 7.20(1H, d, J=8.1 Hz), 7.27-7.32(1H, m), 7.70(1H, dd, J=8.8, 2.2 Hz), 8.01(1H, d, J=8.3 Hz), 8.18(1H, d, J=8.8 Hz), 8.30(1H, d, J=2.6 Hz), 9.73(1H, br.s).
MS(ESI)m/z: 584(M+H)$^+$.

Example 334

N$^1$-{(1S,2R)-2-[({3-chloro-4-[(methylamino)methyl]-2-thienyl}carbonyl)amino]cyclohexyl}-N$^2$-(5-chloropyridin-2-yl)ethanediamide

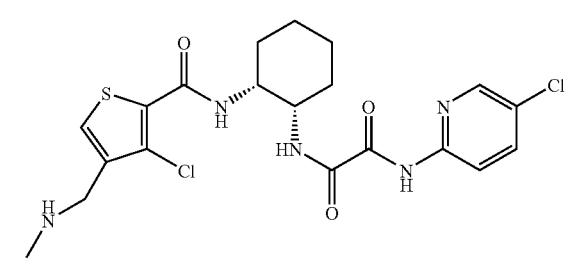

In a manner similar to that employed in Example 227, the title compound was prepared from the compound obtained in Example 333.

¹H-NMR(CDCl₃)δ: 1.48-2.02(8H, m), 2.46(3H, s), 3.72 (2H, s), 4.15-4.25(1H, m), 4.45-4.55(1H, m), 7.22(1H, d, J=8.1 Hz), 7.42(1H, s), 7.71(1H, dd, J=8.8, 2.6 Hz), 8.03(1H, d, J=9.3 Hz), 8.19(1H, dd, J=8.8, 0.73 Hz), 8.31(1H, dd, J=2.6, 0.73 Hz).
MS(ESI)m/z: 484(M+H)⁺.

Example 335

N¹-((1S,2R)-2-{[(3-chloro-4-{[4,5-dihydro-1,3-oxazol-2-yl(methyl)amino]methyl}-2-thienyl)carbonyl]amino}cyclohexyl)-N-(5-chloropyridin-2-yl)ethanediamide

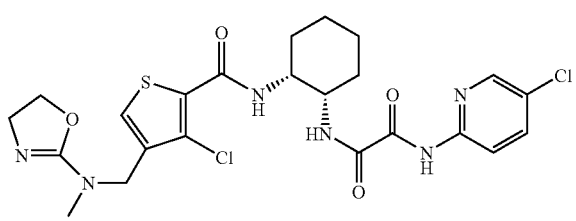

In a manner similar to that employed in Example 332, the title compound was prepared from the compound obtained in Example 334.
¹H-NMR(CDCl₃)δ: 1.50-2.00(8H, m), 2.94(3H, s), 3.80 (2H, t, J=8.5 Hz), 4.17-4.25(1H, m), 4.32(2H, t, J=8.5 Hz), 4.39(1H, d, J=16.5 Hz), 4.41(1H, d, J=16.5 Hz), 4.58-4.67 (1H, m), 7.18(1H, d, J=8.3 Hz), 7.40(1H, s), 7.69(1H, dd, J=8.8, 2.4 Hz), 8.00(1H, d, J=8.1 Hz), 8.17(1H, d, J=8.8 Hz), 8.29(1H, d, J=2.4 Hz), 9.73(1H, br.s).
MS(ESI)m/z: 553(M+H)⁺.

Example 336

N¹-(5-chloropyridin-2-yl)-N²-((1R,2R,4S)-4-[(dimethylamino)carbonyl]-2-{[(5-methyl-5,6,7,8-tetrahydro-4H-thiazolo[5,4-c]azepin-2-yl)carbonyl]amino}cyclohexyl)ethanediamide hydrochloride

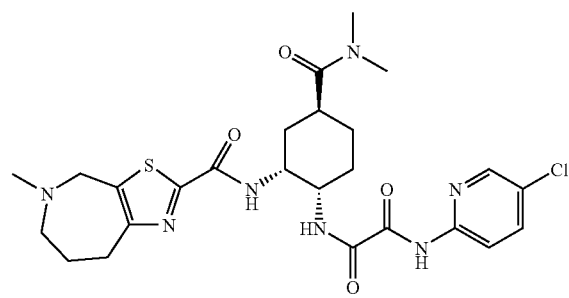

In a manner similar to that employed in Example 2, the compound obtained in Referential Example 477 was condensed with the compound obtained in Referential Example 420, and the product was treated with hydrochloric acid, to thereby yield the title compound.
¹H-NMR(DMSO-d₆)δ: 1.42-1.58(1H,m), 1.60-1.84(3H, m), 1.85-2.15(4H, m), 2.79(6H, br/s), 2.93(4H, br.s), 3.05-3.25(2H, m), 3.49(1H, br.s), 3.63(1H, br.s), 3.95-4.05(1H, m), 4.42(1H, br.s), 4.64(1H, br.s), 4.78(1H, br.s), 8.01(2H, br.s), 8.46(1H, br.s), 8.65(1H, d, J=7.3 Hz), 9.19(1H, d, J=8.1 Hz), 10.29(1H, s), 10.64(1H, br.s).
MS(FAB)m/z: 562(M+H)⁺.

Example 337

N¹-(5-chloropyridin-2-yl)-N²-((1S,2R,4S)-4-[(dimethylamino)carbonyl]-2-{[(4,4,5-trimethyl-5,6-dihydro-4H-pyrrolo[3,4-d]thiazol-2-yl)carbonyl]amino}cyclohexyl)ethanediamide hydrochloride

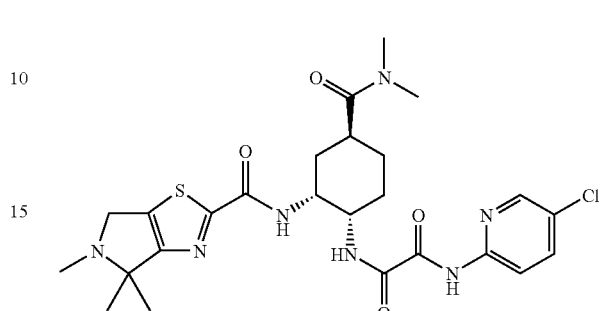

In a manner similar to that employed in Referential Example 10, 4,4,5-trimethyl-5,6-dihydro-4H-pyrrolo[3,4-d]thiazol-2-carboxylic acid lithium salt was prepared from the compound obtained in Referential Example 479. Subsequently, in a manner similar to that employed in Example 2, the lithium salt was condensed with the compound obtained in Referential Example 420, and the product was treated with hydrochloric acid, to thereby give the title compound.
¹H-NMR(DMSO-d₆)δ: 1.45-1.55(4H, m), 1.60-1.85(6H, m), 1.85-2.10(2H, m), 2.78(3H, s), 2.85-3.08(7H, m), 3.93-4.05(1H, br), 4.41-4.53(1H, br), 4.52-4.68(1H, br), 4.70-4.83 (1H, br), 8.01(2H, br.s), 8.45(1H, br.s), 8.63(0.5H, d, J=7.6 Hz), 8.68(0.5H, d, J=7.6 Hz), 9.07-9.20(1H, m), 10.29(0.5H, s), 10.26(0.5H, s), 11.83(0.5H, br.s), 11.76(0.5H, br.s).
MS(FAB)m/z: 562 (M+H)⁺.

Example 338

6-[({(1R,2S,5S)-2-({2-[(5-chloropyridin-2-yl)amino]-2-oxoacetyl}amino)-5-[(dimethylamino)carbonyl]cyclohexyl}amino)carbonyl]-1,3-dihydro-2H-pyrrolo[3,4-c]pyridine-2-carboxylic acid tert-butyl ester

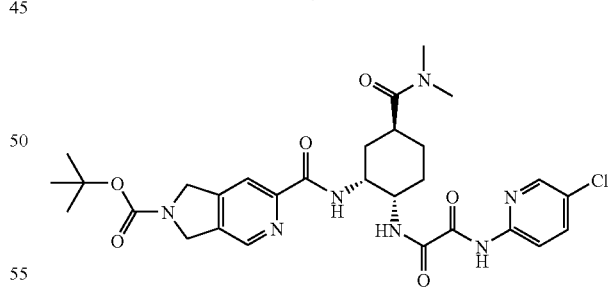

In a manner similar to that employed in Example 2, the compound obtained in Referential Example 481 was condensed with the compound obtained in Referential Example 420, to thereby yield the title compound.
¹H-NMR(CDCl₃)δ: 1.53(4.5H, s), 1.61(4.5H, s), 1.54-2.20(6H, m), 2.76-2.90, (1H, m), 2.96(3H, s), 3.07(3H, s), 4.05-4.15(1H, m), 4.46-4.85(5H, m), 7.67(1H, dd, J=8.8, 2.3 Hz), 8.10-8.23(3H, m), 8.30(1H, d, J=2.3 Hz), 8.30-8.40(1H, m), 8.45(0.5H, br.s), 8.49(0.5H, br.s), 9.72(1H, br.s).
MS(ESI)m/z: 614 (M+H)⁺.

Example 339

N[1]-(5-chloro-2-pyridinyl)-N[2]-{(1S,2R,4S)-2-[(2,3-dihydro-1H-pyrrolo[3,4-c]pyridine-6-ylcarbonyl)amino]-4-[(dimethylamino)carbonyl]cyclohexyl}ethanediamide hydrochloride

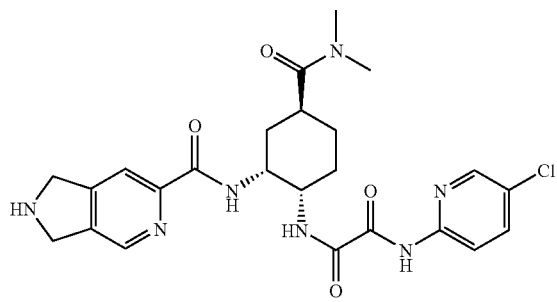

In a manner similar to that employed in Example 227, the title compound was prepared from the compound obtained in Example 338.

$^{1}$H-NMR(DMSO-d$_{6}$)δ: 1.45-1.61(1H, m), 1.62-1.84(3H, m), 1.95-2.10(2H, m), 2.78(3H, s), 2.79-2.90(1H, m), 2.90 (3H, s), 3.90-4.15(1H, m), 4.45-4.53(1H, br), 4.55-4.68(4H, m), 8.00 (2H, br.s), 8.10(1H, s), 8.45(1H, d, J=1.5 Hz), 8.67 (1H, d, J=7.6 Hz), 8.75(1H, s), 9.19(1H, d, J=8.3 Hz), 10.11 (2H, br.s), 10.26(1H, br.s).

MS(FAB)m/z: 514 (M+H)$^{+}$.

Example 340

N[1]-(5-chloro-2-pyridinyl)-N[2]-((1S,2R,4S)-4-[(dimethylamino)carbonyl]-2-{[(2-methyl-2,3-dihydro-1H-pyrrolo[3,4-c]pyridine-6-yl)carbonyl]amino}cyclohexyl)ethanediamide hydrochloride

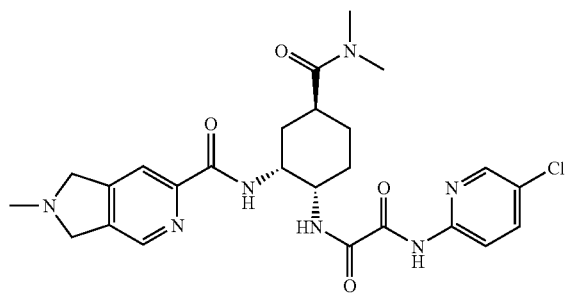

In a manner similar to that employed in Example 18, the title compound was prepared from the compound obtained in Example 339 and formalin.

$^{1}$H-NMR(DMSO-d$_{6}$)δ: 1.45-1.59(1H, m), 1.60-1.85(3H, m), 1.91-2.10(2H, m), 2.78(3H, br.s), 2.80-2.90(1H, m), 2.90 (1.5H, s), 2.92(1.5H, s), 3.01(1.5H, s), 3.02(1.5H, s), 3.90-4.05(1H, m), 4.42-4.60(3H, m), 4.80-5.00(2H, m), 8.00(2H, br.s), 8.11(1H, s), 8.44(1H, d, J=1.5 Hz), 8.60-8.70(1H, m), 8.75(1H, s), 9.18(1H, d, J=7.8 Hz), 10.25(0.5H, s), 10.28 (0.5H, s), 11.95(0.5H, s), 12.02(0.5H, s).

MS(FAB)m/z: 528(M+H)$^{+}$.

Example 341

N[1]-(5-chloropyridin-2-yl)-N[2]-{(1S,2R,4S)-4-[(dimethylamino)carbonyl]-2-[(5,6,7,8-tetrahydro[1,6]naphthyridin-2-ylcarbonyl)amino]cyclohexyl}ethanediamide hydrochloride

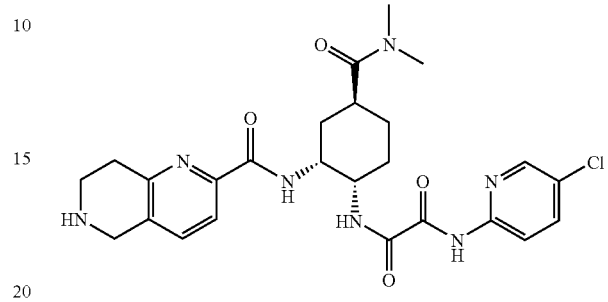

In a manner similar to that employed in Example 2, a lithium salt of a carboxylic acid prepared by hydrolyzing 6-(tert-butoxycarbonyl)-5,6,7,8-tetrahydro[1,6]naphthyridine-2-carboxylic acid methyl ester (Japanese Patent Application Laid-Open (kokai) No. 2000-119253) was condensed with the compound obtained in Referential Example 420, and the product was treated with hydrochloric acid, to thereby give the title compound.

$^{1}$H-NMR(DMSO-d$_{6}$)δ: 1.45-1.62(1H, m), 1.62-1.87(3H, m), 1.89-2.05(2H, m), 2.80(3H, s), 2.81-2.94(1H, m), 2.95 (3H, s), 3.15-3.35(2H, m), 3.51(2H, br.s), 3.90-4.05(1H, m), 4.38(2H, br.s), 4.43-4.55(1H, m), 7.88(2H, br.s), 8.01(2H, br.s), 8.45(1H, d, J=1.5 Hz), 8.51(1H, d, J=8.3 Hz), 9.16(1H, d, J=7.8 Hz), 9.85(1H, br.s), 10.02(1H, br.s), 10.27(1H, br.s).

MS(FAB)m/z: 528(M+H)$^{+}$.

Example 342

N[1]-(5-chloropyridin-2-yl)-N[2]-((1S,2R,4S)-4-[(dimethylamino)carbonyl]-2-{[(6-methyl-5,6,7,8-tetrahydro[1,6]naphthyridin-2-yl)carbonyl]amino}cyclohexyl)ethanediamide hydrochloride

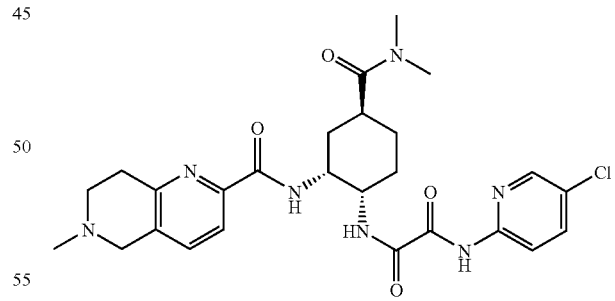

In a manner similar to that employed in Example 18, the title compound was prepared from the compound obtained in Example 341 and formalin.

$^{1}$H-NMR(DMSO-d$_{6}$)δ: 1.45-1.62(1H, m), 1.63-1.80(3H, m), 1.86-2.06(2H, m), 2.80(3H, br.s), 2.81-2.96(7H, m), 3.14-3.27(1H, m), 3.11-3.63(2H, m), 3.76(1H, br.s), 3.99(1H, br.s), 4.35-4.52(2H, m), 4.53-4.65(1H, m), 7.84(1H, J=8.0 Hz), 7.89(1H, J=8.0 Hz), 8.00(2H, br.s), 8.40-8.55(2H, m), 9.07(0.4H, d, J=7.6 Hz), 9.19(0.6H, d, J=8.1 Hz), 10.24(0.6H, s), 10.28(0.4H, s), 11.42-11.80(1H, br).

MS(FAB)m/z: 542(M+H)$^{+}$.

Example 343

N$^1$-(5-chloropyridin-2-yl)-N$^2$-[(1S,2R,4S)-4-[(dimethylamino)carbonyl]L-2-({[5-(pyridin-4-yl)pyrimidin-2-yl]carbonyl}amino)cyclohexyl]ethanediamide hydrochloride

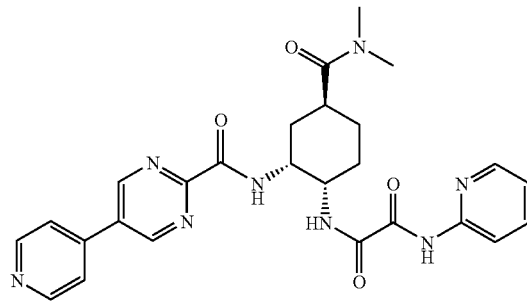

In a manner similar to that employed in Example 2, the compound obtained in Referential Example 420 was condensed with the compound obtained in Referential Example 483, and the product was treated with hydrochloric acid, to thereby yield the title compound.

$^1$H-NMR(DMSO-d$_6$)δ: 1.50-1.63(1H, m), 1.67-1.85(3H, m), 1.95-2.12(2H, m), 2.80(3H, s), 2.86-2.95(1H, m), 2.95 (3H, s), 4.00-4.10(1H, m), 4.45-4.55(1H, m), 8.01(2H, br.s), 8.34(2H, d, J=5.6 Hz), 8.44-8.47(1H, m), 8.79(1H, d, J=7.6 Hz), 8.99(2H, d, J=5.6 Hz), 9.08(1H, d, J=8.3 Hz), 9.54(2H, s), 10.31(1H, s).

MS(FAB)m/z: 551(M+H)$^+$.

Example 344

N$^1$-(5-chloropyridin-2-yl)-N$^2$-{(1S,2R,4S)-4-[(dimethylamino)carbonyl]-2-[({2'-[(dimethylamino)methyl][1,1'-biphenyl]-4-yl}carbonyl)amino]cyclohexyl}ethanediamide hydrochloride

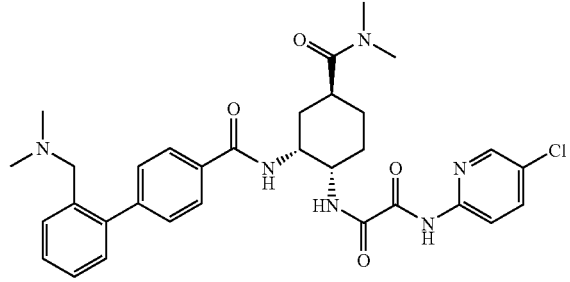

In a manner similar to that described in Example 2, the compound obtained in Referential Example 420 was condensed with the compound obtained in Referential Example 488, and the product was treated with hydrochloric acid, whereby the title compound was obtained.

$^1$H-NMR(DMSO-d$_6$)δ: 1.45-1.56(1H, m), 1.60-1.85(3H, m), 1.85-2.15(2H, m), 2.40-2.55(6H, m), 2.80(3H, s), 2.99 (3H, s), 3.05-3.20(1H, m), 3.93-4.06(1H, m), 4.25-4.33(2H, m), 4.45-4.55(1H, m), 7.30-7.37(1H, m), 7.48(2H, d, J=8.3 Hz), 7.50-7.58(2H, m), 7.84-7.90(1H, m), 7.95-8.05(4H, m), 8.15(1H, d, J=7.3 Hz), 8.46(1H, br.s), 9.20(1H, d, J=8.3 Hz), 10.15-10.29(1H, br), 10.30(1H, br.s).

MS(FAB)m/z: 605 (M+H)$^+$.

Example 345

N$^1$-(5-chloropyridin-2-yl)-N$^2$-[(1S,2R,4S)-4-[(dimethylamino)carbonyl]-2-({4-[2-(hydroxymethyl)pyridin-4-yl]benzoyl}amino)cyclohexyl]ethanediamide hydrochloride

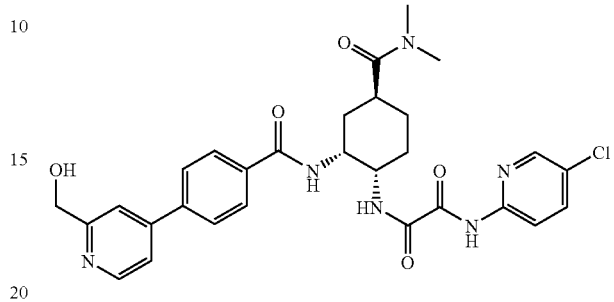

In a manner similar to that employed in Example 2, a lithium salt of a carboxylic acid prepared by hydrolyzing the compound obtained in Referential Example 490 was condensed with the compound obtained in Referential Example 420, and the product was treated with hydrochloric acid, to thereby give the title compound.

$^1$H-NMR(DMSO-d$_6$)δ: 1.44-1.58(1H, m), 1.63-1.81(3H, m), 1.89-1.99(1H, m), 1.99-2.13(1H, m), 2.79(3H, s), 2.97 (3H, s), 3.06-3.17(1H, m), 3.93-4.02(1H, m), 4.44-4.51(1H, m), 4.89(2H, s), 7.99(2H, s), 8.08(4H, m), 8.19(1H, d, J=6.3 Hz), 8.24(1H, d, J=7.3 Hz), 7.29(1H, s), 8.44-8.46(1H, m), 8.80(1H, d, J=5.9 Hz), 9.01(1H, d, J=8.3 Hz), 10.27(1H, s).

MS(ESI)m/z: 579(M+H)$^+$.

Example 346

N$^1$-{(1S,2R,4S)-2-({4-[2-(aminomethyl)pyridin-4-yl]benzoyl}amino)-4-[(dimethylamino)carbonyl]cyclohexyl}-N$^2$-(5-chloropyridin-2-yl)ethanediamide hydrochloride

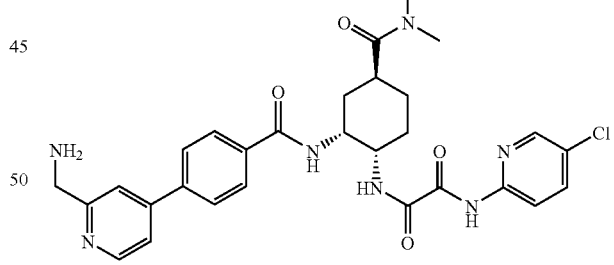

In a manner similar to that employed in Example 2, a lithium salt of a carboxylic acid prepared by hydrolyzing the compound obtained in Referential Example 491 was condensed with the compound obtained in Referential Example 420, and the product was treated with hydrochloric acid, to thereby give the title compound.

$^1$H-NMR(DMSO-d$_6$)δ: 1.40-1.58(1H, m), 1.58-1.83(3H, m), 1.87-1.98(1H, m), 1.98-2.13(1H, m), 2.78(3H, s), 2.97 (3H, s), 3.05-3.17(1H, m), 3.93-4.03(1H, m), 4.17-4.30(2H, m), 4.40-4-50(1H, m), 7.80(1H, dd, J=5.2, 1.6 Hz), 7.90-8.06 (7H, m), 8.18(1H, d, J=7.6 Hz), 8.43-8.46(1H, m), 8.50(3H, br.s), 8.70(1H, d, J=5.2 Hz), 9.01(1H, d, J=8.5 Hz), 10.27(1H, s).

MS(ESI)m/z: 578(M+H)$^+$.

Example 347

N¹-(5-chloropyridin-2-yl)-N²-[(1S,2R,4S)-4-[(dimethylamino)carbonyl]-2-({[1-(phenylsulfonyl)piperidin-4-yl]carbonyl}amino)cyclohexyl]ethanediamide

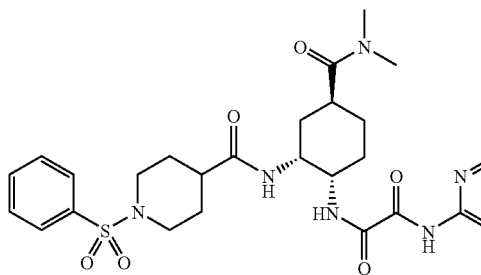

In a manner similar to that employed in Example 2, the compound obtained in Referential Example 420 was condensed with the compound obtained in Referential Example 493, to thereby yield the title compound.

¹H-NMR(CDCl₃)δ: 1.60-2.10(10H, m), 2.12-2.21(1H, m), 2.40(2H, br.t, J=11.2 Hz), 2.65-2.77(1H, m), 2.92(3H, s), 2.99(3H, s), 3.77(2H, br.d, J=11.7 Hz), 3.92-4.05(1H, m), 4.42-4.53(1H, m), 6.31(1H, br.d, J=7.3 Hz), 7.53(2H, t, J=7.3 Hz), 7.62(1H, t, J=7.3 Hz), 7.67-7.78(3H, m), 8.01(1H, brd, J=7.3 Hz), 8.16(1H, d, J=8.8 Hz), 8.31(1H, d, J=2.2 Hz), 9.72(1H, s).

MS(ESI)m/z: 619(M+H)⁺.

Example 348

N¹-(5-chloropyridin-2-yl)-N²-[(1S,2R,4S)-4-[(dimethylamino)carbonyl]-2-({[1-(4-fluorobenzoyl)piperidin-4-yl]carbonyl}amino)cyclohexyl]ethanediamide D22-5792

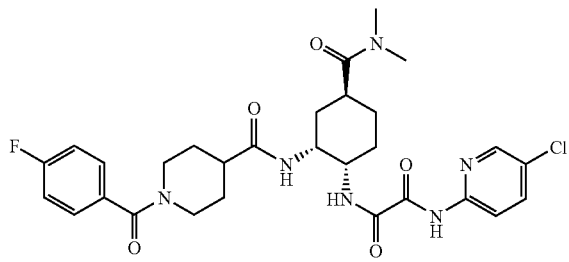

In a manner similar to that employed in Example 2, the compound obtained in Referential Example 420 was condensed with the compound obtained in Referential Example 495, to thereby yield the title compound.

¹H-NMR(CDCl₃)δ: 1.60-2.16(10H, m), 2.37-2.48(1H, m), 2.64-2.78(1H, m), 2.80-3.13(2H, m), 2.94(3H, s), 3.02(3H, s), 3.65-4.18(1H, br), 3.93-4.01(1H, m), 4.43-4.80(2H, br), 6.32(1H, br.d, J=7.1 Hz), 7.09(2H, t, J=8.5 Hz), 7.40(2H, dd, J=8.5, 5.4 Hz), 7.71(1H, dd, J=8.8, 2.4 Hz), 8.04(1H, br.d, J=7.6 Hz), 8.15(1H, d, J=8.8 Hz), 8.30(1H, d, J=2.4 Hz), 9.71(1H, s).

MS(ESI)m/z: 601 (M+H)⁺.

Example 349

N¹-(5-chloropyridin-2-yl)-N²-((1S,2R,4S)-4-[(dimethylamino)carbonyl]-2-{[4-(pyrrolidin-1-ylcarbonyl)benzoyl]amino}cyclohexyl)ethanediamide

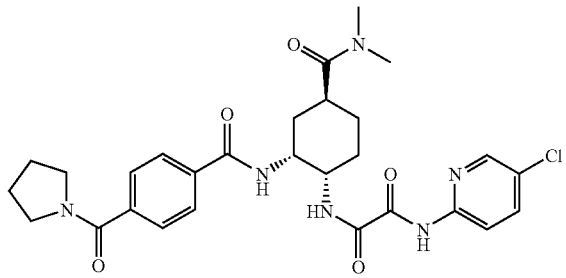

In a manner similar to that employed in Example 2, the compound obtained in Referential Example 420 was condensed with the compound obtained in Referential Example 497, to thereby yield the title compound.

¹H-NMR(CDCl₃)δ: 1.68-2.23(9H, m), 2.33(1H, br.d, J=7.4 Hz), 2.85-3.02(1H, m), 2.92(3H, s), 2.98(3H, s), 3.31(2H, t, J=6.8 Hz), 3.61(2H, t, J=6.8 Hz), 4.13-4.22(1H, m), 4.54-4.63(1H, m), 7.28(2H, d, J=8.1 Hz), 7.63-7.69(1H, m), 7.66(2H, d, J=8.1 Hz), 7.95(1H, br.d, J=5.6 Hz), 8.05(1H, d, J=8.8 Hz), 8.30(1H, d, J=2.4 Hz), 8.54(1H, brd, J=8.3 Hz), 9.76(1H, s).

MS(ESI)m/z: 569(M+H)⁺.

Example 350

N¹-(5-chloropyridin-2-yl)-N²-((1S,2R,4S)-4-[(dimethylamino)carbonyl]-2-{[4-(pyrrolidin-1-ylmethyl)benzoyl]amino}cyclohexyl)ethanediamide hydrochloride

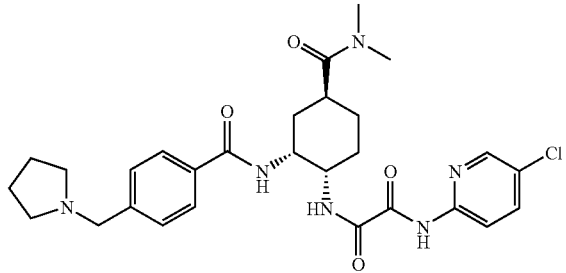

In a manner similar to that employed in Example 2, a lithium salt of a carboxylic acid prepared by hydrolyzing the compound obtained in Referential Example 498 was condensed with the compound obtained in Referential Example 420, and the product was treated with hydrochloric acid, to thereby give the title compound.

¹H-NMR(DMSO-d₆)δ: 1.43-1.57(1H, m), 1.62-2.10(9H, m), 2.78(3H, s), 2.95(3H, s), 2.96-3.12(3H, m), 3.28-3.50(2H, m), 3.92-4.01(1H, m), 4.35-4.48(3H, m), 7.69(2H, d, J=8.1 Hz), 7.92(2H, d, J=8.1 Hz), 7.99(2H, s), 8.09(1H, br.d, J=7.6 Hz), 8.44(1H, s), 8.99(1H, br.d, J=8.3 Hz), 10.27(1H, s), 10.65-10.80(1H, br).

MS(ESI)m/z: 555(M+H)⁺.

Example 351

N[1]-(5-chloropyridin-2-yl)-N[2]-((1S,2R,4S)-4-[(methylamino)carbothioyl]-2-{[(5-methyl-4,5,6,7-tetrahydrothiazolo[5,4-c]pyridin-2-yl)carbonyl]amino}cyclohexyl)ethanediamide hydrochloride

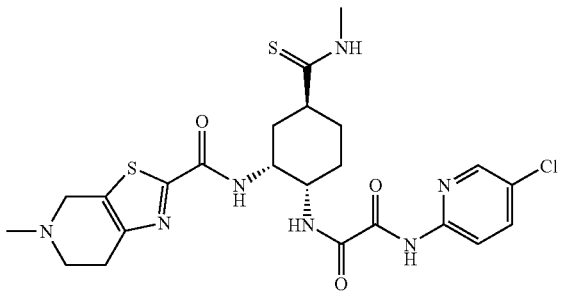

In a manner similar to that described in Example 214, the compound obtained in Referential Example 501 was treated with 4N HCl-dioxane for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.60-2.18(6H, m), 2.70-2.95(4H, m), 2.90(3H, s), 3.06-3.40(2H, m), 3.42-3.54(1H, br), 3.62-3.78(1H, br), 3.96-4.05(1H, m), 4.24-4.34(1H, br), 4.35-4.52(1H, br), 4.60-4.76(1H, m), 7.96-8.04(2H, m), 8.43(1H, s), 8.48-8.60(1H, br), 9.39(1H, br.d, J=7.8 Hz), 9.91-10.03(1H, br), 10.18-10.30(1H, m), 11.72-11.95(1H, br).

MS(ESI)m/z: 550(M+H)$^+$.

Example 352

N-{(1R,2S,5S)-2-{[(4-chloroanilino)sulfonyl]amino}-5-[(dimethylamino)carbonyl]cyclohexyl}-5-methyl-4,5,6,7-tetrahydrothiazolo[5,4-c]pyridine-2-carboxamide hydrochloride

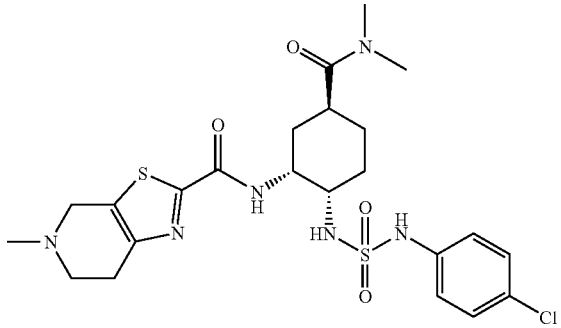

To a solution of 4-chloroaniline (255 mg) in methylene chloride (15 mL), chlorosulfuric acid (146 μL) was added at 0° C. The mixture was stirred for 1 hour at 0° C. and then for 2 hours at room temperature. Phosphorus pentachloride (458 mg) was added to the reaction mixture, followed by heating under reflux for 2 hours. The mixture was cooled to room temperature, and the compound obtained in Referential Example 253 (731 mg) was added thereto. The pH of the mixture was adjusted to be neutral with triethylamine. The resultant mixture was stirred for 17 hours at room temperature, and water was added to the reaction mixture to partition the mixture. The formed aqueous layer was extracted with methylene chloride, and the organic layers were combined together, followed by washing twice with water and drying over sodium sulfate anhydrate. The solvent was removed under reduced pressure, and the residue was purified through silica gel flash column chromatography (methylene chloride:methanol=93:7) and then twice through fractional thin-layer chromatography (methylene chloride:methanol=9:1), to thereby yield a pale yellow solid product (46 mg). The product was dissolved in methylene chloride, and 1N HCl in ethanol (83 μL) was added thereto. The solvent was removed under reduced pressure, and small amounts of methanol and ether were added thereto. The precipitate was collected through filtration, to thereby yield the title compound (34 mg) as a pale yellow solid.

$^1$H-NMR(DMSO-d$_6$)δ: 1.34-1.69(5H, m), 1.98(1H, br.s), 2.75(3H, s), 2.85-2.94(8H, m), 3.17(2H, br.s), 3.50(1H, br.s), 3.69(1H, br.s), 4.39-4.50(2H, m), 4.69(1H, br.s), 7.08-7.15(4H, m), 7.74(1H, br.s), 7.98(1H, br.s), 9.90(1H, s), 11.35(1H, br.s).

MS(FAB)m/z: 555 (M+H)$^+$.

Example 353

N-{(1R,2S,5S)-2-({2-[(5-chloropyrimidin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide hydrochloride

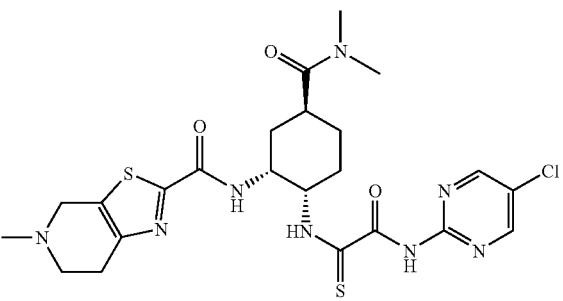

In a manner similar to that described in Example 219, the compound obtained in Referential Example 503 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO)δ: 1.49-1.54(1H, m), 1.68-1.79(3H, m), 1.99-2.02(1H, m), 2.16-2.22(1H, m), 2.80(3H, s), 2.91(3H, s), 2.97(3H, s), 3.06(1H, br.s), 3.20(2H, br.s), 3.49(1H, br.s), 3.64(1H, br.s), 4.40-4.55(2H, m), 4.70(2H, br.s), 8.68(1H, d, J=7.1 Hz), 8.81(2H, s), 10.87(1H, br.s), 10.99(1H, br.s), 11.47(1H, br.s).

MS(FAB)m/z: 565 (M+H)$^+$.

Example 354

N-{(1R,2S,5S)-2-{[2-(4-chloro-3-nitroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide hydrochloride

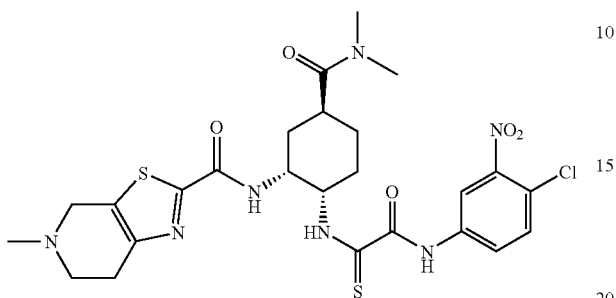

In a manner similar to that described in Example 219, the compound obtained in Referential Example 505 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO)δ: 1.48-1.54(1H, m), 1.67-1.78(3H, m), 1.99-2.03(1H, m), 2.22-2.33(1H, m), 2.79(3H, s), 2.91(3H, s), 2.96(3H, s), 3.01-3.67(5H, m), 4.40-4.80(4H, m), 7.78(1H, d, J=8.8 Hz), 8.05(1H, dd, J=8.8, 1.4 Hz), 8.59(1H, d, J=1.4 Hz), 8.75(1H, d, J=7.6 Hz), 10.89-10.92(2H, m), 11.43(1H, br.s).
MS(ESI)m/z: 608 (M+H)$^+$.

Example 355

N-{(1R,2S,5S)-2-{[2-(3-amino-4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide hydrochloride

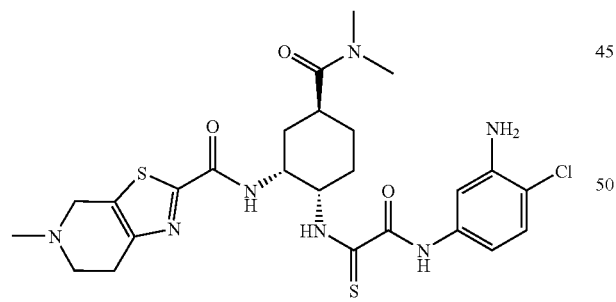

To a solution of the compound Example 354 (45.8 mg) in ethanol (30 mL), 10% palladium carbon (1.00 g) was added, and the mixture was stirred for 3 days at room temperature. The catalyst was removed through filtration, and the solvent was removed under reduced pressure. The residue was purified through silica gel flash column chromatography (methylene chloride:methanol=94:6). The thus-obtained yellow solid (137 mg) was dissolved in methylene chloride (5 mL), and 1N HCl in ethanol (474 μL) was added thereto. Diethyl ether (20 mL) was added to the mixture, and the formed solid was collected through filtration, followed by washing with ether, to thereby yield the title compound (144 mg) as a yellow solid.

$^1$H-NMR(DMSO-d$_6$)δ: 1.46-1.54(1H, m), 1.70-1.78(3H, m), 1.98-2.07(1H, m), 2.21-2.23(1H, m), 2.79(3H, s), 2.91(3H, s), 2.96(3H, s), 3.03(1H, br.s), 3.11-3.19(1H, m), 3.30(1H, br.s), 3.47(1H, br.s), 3.69(1H, br.s), 4.10-4.51(4H, m), 4.68(2H, s), 6.95(1H, dd, J=8.6, 2.3 Hz), 7.18(1H, d, J=8.6 Hz), 7.31(0.5H, s), 7.33(0.5H, s), 8.74-8.80(1H, m), 10.18(1H, d, J=9.8 Hz), 10.83(0.5H, d, J=7.6 Hz), 10.89(0.5H, d, J=8.0 Hz), 11.79(0.5H, br.s), 11.87(0.5H, br.s).
MS(ESI)m/z: 578(M+H)$^+$.

Example 356

6-[({(1R,2S,5S)-2-({2-[(5-chloropyridin-2-yl)amino]-2-oxoacetyl}amino)-5-[(dimethylamino)carbonyl]cyclohexyl}amino)carbonyl]-1,3-dihydro-2H-pyrrolo[3,4-c]pyridine-2-carboxylic acid tert-butyl ester

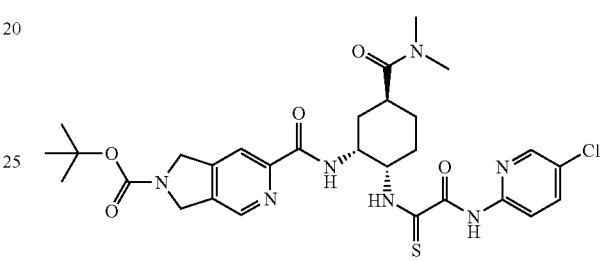

In a manner similar to that described in Example 219, the compound obtained in Referential Example 428 was treated with hydrochloric acid for deprotection. The deprotected compound was condensed with the compound obtained in Referential Example 481, whereby the title compound was obtained.

$^1$H-NMR(CDCl$_3$)δ: 1.53(9H, s), 1.56-2.42(6H, m), 2.85-2.94, (1H, m), 2.98(3H, s), 3.10(3H, s), 4.45-4.52(1H, m), 4.70-4.85(5H, m), 7.67(1H, dd, J=8.8, 2.4 Hz), 8.18(0.5H, br.s), 8.18(1H, d, J=8.8 Hz), 8.23(0.5H, br.s), 8.31(1H, d, J=2.4 Hz), 8.40-8.52(2H, m), 10.29(1H, br.s), 10.60(1H, br.s).
MS(ESI)m/z: 630(M+H)$^+$.

Example 357

N-{(1R,2S,5S)-2-({2-[(5-chloropyridin-2-yl)amino]-2-oxoethanethioyl}amino)-5-[(dimethylamino)carbonyl]cyclohexyl}-2-methyl-2,3-dihydro-1H-pyrrolo[3,4-c]pyridine-6-carboxamide hydrochloride

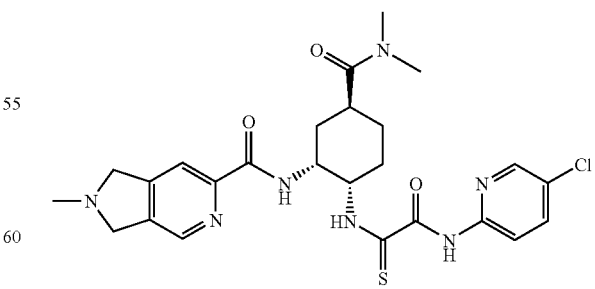

The compound obtained in Example 356 was treated with hydrochloric acid for deprotection. The deprotected compound was methylated in a manner similar to that described in Example 18, and the product was again treated with hydrochloric acid, whereby the title compound was obtained.

¹H-NMR(DMSO-d₆)δ: 1.46-1.61(1H, m), 1.62-1.95(3H, m), 1.95-2.10(1H, m), 2.10-2.30(1H, m), 2.79(3H, br.s), 2.84-2.94(4H, m), 2.95(3H, s), 4.45-4.60(3H, m), 4.75(1H, br.s), 4.80-5.00(2H, m), 7.97-8.13(2H, m), 8.16(1H, br.s), 8.46(1H, br.s), 8.76(2H, br.s), 10.51(0.5H, s), 10.55(0.5H, s), 11.09(1H, br.s), 11.92(0.5H, br.s), 11.99(0.5H, br.s).
MS(FAB)m/z: 544(M+H)⁺.

Example 358

N-{(1R,2S,5S)-2-({2-[(5-chloropyridin-2-yl)amino]-2-oxoethanethioyl}amino)-5-[(dimethylamino)carbonyl]cyclohexyl}-1-(pyridin-4-yl)-4-piperidinecarboxamide hydrochloride

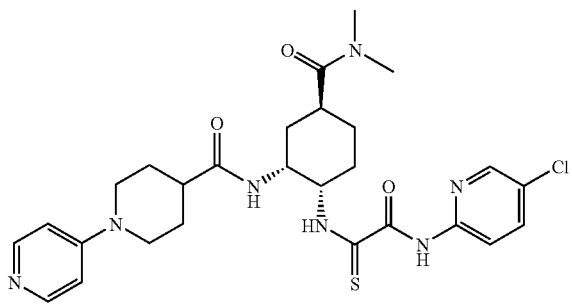

In a manner similar to that described in Example 219, the compound obtained in Referential Example 428 was treated with hydrochloric acid for deprotection. The deprotected compound was condensed with 1-(pyridin-4-yl)-4-puperidinecarboxylic acid (Tetrahedron, 1998, vol. 44, p. 7095), and the product was again treated with hydrochloric acid, whereby the title compound was obtained.
¹H-NMR(DMSO-d₆)δ: 1.38-1.52(1H, m), 1.52-1.73(4H, m), 1.73-1.88(3H, m), 1.88-2.02(2H, m), 2.80(3H, s), 3.04(3H, s), 3.10-3.40(4H, m), 4.14-4.36(3H, m), 4.48-4.57(1H, m), 7.18(2H, d, J=6.8 Hz), 7.90-8.11(2H, m), 8.11-8.30(3H, m), 8.30-8.45(1H, m), 10.33(1H, s), 10.56(1H, d, J=7.3 Hz), 13.48(1H, br.s).
MS(ESI)m/z: 572(M+H)⁺.

Example 359

N-{(1R,2S,5S)-2-{[(7-chlorocinnolin-3-yl)carbothioyl]amino}-5-[(dimethylamino)carbonyl]cyclohexyl}-5-methyl-4,5,6,7-tetrahydrothiazolo[5,4-c]pyridine-2-carboxamide hydrochloride

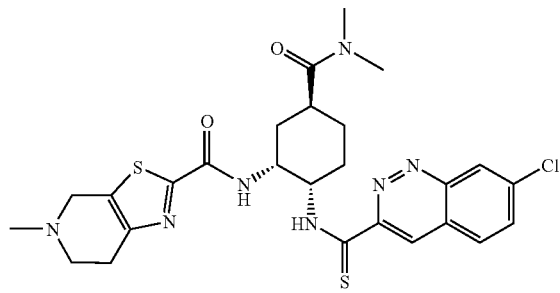

In a manner similar to that employed in Example 2, the compound obtained in Referential Example 509 was condensed with the compound obtained in Referential Example 10, and the product was treated with hydrochloric acid, to thereby give the title compound.

¹H-NMR(DMSO-d₆)δ: 1.55-1.63(1H, m), 1.72-1.78(1H, m), 1.86-1.89(2H, m), 2.10(1H, br.s), 2.40-2.46(1H, m), 2.81(3H, s), 2.91(3H, s), 2.97(3H, s), 3.04(1H, br.s), 3.15-3.20(1H, m), 3.27(1H, br.s), 3.49(1H, br.s), 3.69(1H, br.s), 4.43(1H, br.s), 4.67(1H, br.s), 4.81(1H, br.s), 4.95(1H, br.s), 8.00(1H, d, J=8.8 Hz), 8.41(1H, d, J=8.8 Hz), 8.65(1H, s), 9.06(1H, br.s), 9.20(1H, s), 11.44(1H, br.s), 11.66(1H, br.s).
MS(ESI)m/z: 572(M+H)⁺.

Example 360

N-{(1R,2S,5S)-2-({[(4-chlorobenzoyl)amino]carbonyl}amino)-5-[(dimethylamino)carbonyl]cyclohexyl}-5-methyl-4,5,6,7-tetrahydrothiazolo[5,4-c]pyridine-2-carboxamide hydrochloride

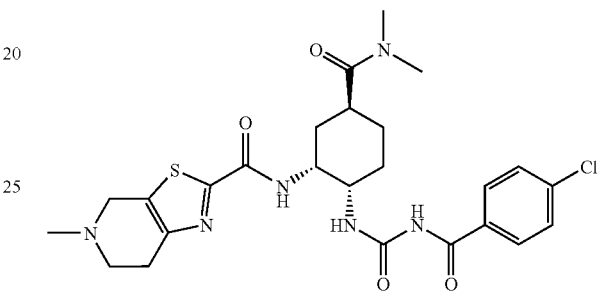

In a manner similar to that employed in Example 2, the compound obtained in Referential Example 511 was condensed with the compound obtained in Referential Example 10, and the product was treated with hydrochloric acid, to thereby give the title compound.
¹H-NMR (DMSO-d₆)δ: 1.45-1.50(1H, m), 1.74-1.84(4H, m), 1.87-1.95(1H, m), 2.80(3H, s), 2.95(3H, s), 3.02(3H, s), 3.13-3.35(3H, m), 3.47(1H, br.s), 3.69(1H, br.s), 3.97(1H, br.s), 4.41-4.44(1H, m), 4.46-4.72(2H, m), 7.56(2H, d, J=8.6 Hz), 7.86-7.88(2H, m), 8.68(1H, br.s), 8.83(1H, br.s).
MS(FAB)m/z: 547(M+H)⁺.

Example 361

N-{(1R,2S,5S)-2-{[(E)-3-(5-chloropyridin-2-yl)acryloyl]amino}-5-[(dimethylamino)carbonyl]cyclohexyl}-5-methyl-4,5,6,7-tetrahydrothiazolo[5,4-c]pyridine-2-carboxamide hydrochloride

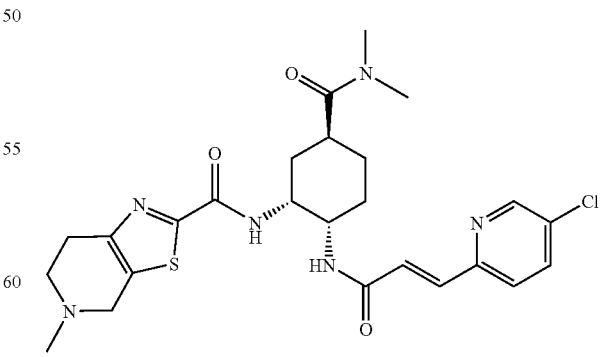

In a manner similar to that described in Example 219, the compound obtained in Referential Example 513 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.37-1.52(1H, m), 1.57-1.92(5H, m), 2.77(3H, s), 2.89(3H, s), 2.99(3H, s), 3.04-3.20(2H, m), 3.20-3.38(1H, m), 3.47(1H, br.s), 3.60-3.90(1H, m), 3.90-4.03(1H, m), 4.36-4.48(1H, m), 4.52-4.62(1H, m), 4.67(1H, br.d, J=16.2 Hz), 7.08(1H, d, J=15.4 Hz), 7.38(1H, dd, J=15.4, 3.9 Hz), 7.60(1H, d, J=8.4 Hz), 7.94(1H, d, J=8.4 Hz), 8.28(1H, d, J=7.1 Hz), 8.35(1H, d, J=9.8 Hz), 8.59(1H, s), 11.72(0.5, br.s), 11.88(0.5H, br.s).

MS(ESI)m/z: 531(M+H)$^+$.

Example 362

N-{(1R,2S,5S)-2-{[(Z)-3-(4-chlorophenyl)-2-fluoro-acryloyl]amino}-5-[(dimethylamino)carbonyl]cyclo-hexyl}-5-methyl-4,5,6,7-tetrahydrothiazolo[5,4-c]pyridine-2-carboxamide hydrochloride

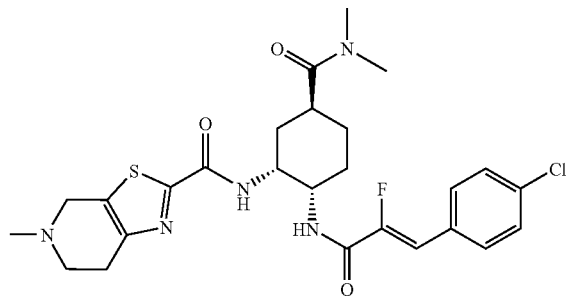

In a manner similar to that described in Example 49, the compound obtained in Referential Example 519 was treated with hydrochloric acid for deprotection. The deprotected compound was condensed with the compound obtained in Referential Example 516, and the product was again treated with hydrochloric acid, whereby the title compound was obtained.

$^1$H-NMR(DMSO-d$_6$)δ: 1.47-1.75(4H, m), 1.97-2.20(2H, m), 2.79(3H, s), 2.92-2.96(7H, m), 3.20(2H, br.s), 3.50(1H, br.s), 3.67(1H, br.s), 4.03(1H, br.s), 4.47(2H, br.s), 4.66(1H, br.s), 6.88(1H, d, J=38.6 Hz), 7.50(2H, d, J=8.4 Hz), 7.66(2H, d, J=8.4 Hz), 8.52-8.56(2H, m), 11.36(1H, br.s).

MS(EI)m/z: 547(M$^+$).

Example 363

N-{(1R,2S,5S)-2-({2-[(5-chloropyridin-2-yl)amino]-2-oxoethanethioyl}amino)-5-[(methylamino)carbo-nyl]cyclohexyl}-5-methyl-4,5,6,7-tetrahydrothiazolo[5,4-c]pyridine-2-carboxamide hydrochloride

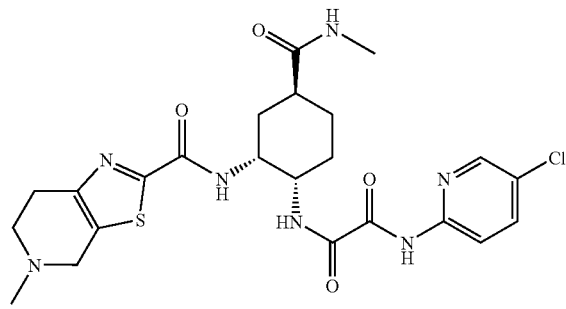

In a manner similar to that described in Example 214, the compound obtained in Referential Example 521 was treated with 4N HCL in dioxane for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.48-1.61(1H, m), 1.61-1.72(1H, m), 1.72-1.87(2H, m), 2.02-2.12(1H, m), 2.15-2.30(1H, m), 2.33-3.43(1H, m), 2.52(3H, d, J=4.4 Hz), 2.86(3H, s), 3.17 (2H, br.s), 3.50(2H, br.s), 4.35-4.60(4H, m), 7.73-7.80(1H, m), 8.00(1H, dd, J=9.0, 2.4 Hz), 8.05(1H, d, J=9.0 Hz), 8.43 (1H, d, J=2.4 Hz), 8.51-8.58(1H, m), 10.55(1H, s), 11.13(1H, d, J=7.8 Hz).

MS(ESI)m/z: 550(M+H)$^+$.

Example 364

N-[(1R,2S,5S)-5-[(dimethylamino)carbonyl]-2-({2-[(5-fluoropyridin-2-yl)amino]-2-oxoethanethioyl}amino)cyclohexyl]-5-methyl-5,6,7,8-tetrahydro-4H-thiazolo[5,4-c]azepine-2-carboxamide hydrochloride

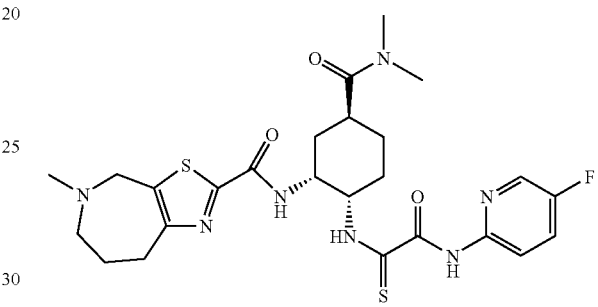

In a manner similar to that employed in Example 2, the compound obtained in Referential Example 522 was condensed with the compound obtained in Referential Example 477, and the product was treated with hydrochloric acid, to thereby give the title compound.

$^1$H-NMR(DMSO-d$_6$)δ: 1.43-1.60(1H, m), 1.61-1.90(3H, m), 1.92-2.18(3H, m), 2.18-2.35(1H, m), 2.70-2.88(6H, m), 2.96(3H, br.s), 2.96-3.00(1H, m), 3.05-3.27(2H, m), 3.40-3.52(1H, br), 3.60-3.80(1H, br), 4.45-4.60(1H, m), 4.60-4.75 (2H, m), 4.75-4.90(1H, m), 7.87(1H, dt, J=2.9, 9.0 Hz), 8.05-8.27(1H, m), 8.43(1H, d, J=2.9 Hz), 8.70-8.82(1H, m), 10.54 (1H, s), 11.05-11.30(2H, m).

MS(FAB)m/z: 562 (M+H)$^+$.

Example 365

(3-{[(((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamic acid tert-butyl ester

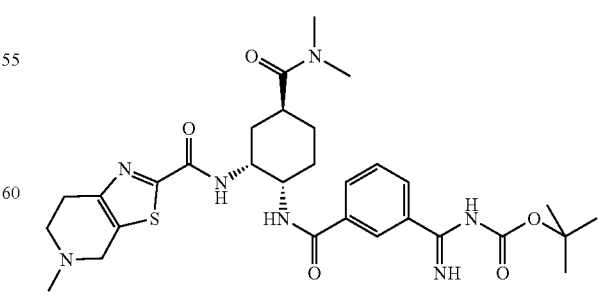

To a solution of the compound obtained in Referential Example 524 (250 mg) in tetrahydrofuran (3.0 mL), were added water (1.0 mL) and lithium hydroxide (20.5 mg) at room temperature. The mixture was stirred for 15 hours and then concentrated under reduced pressure. The thus-obtained solid and the compound obtained in Referential Example 253 (464 mg) were dissolved in N,N-dimethylformamide (5.0 mL), and, at room temperature, 1-hydroxybenzotriazole (140 mg) and 1-[3-(dimethylamino)propyl]-3-ethylcarbodiimide hydrochloride (330 mg) were added to the solution. The resultant mixture was stirred at the same temperature for 21 hours, and the solvent was removed under reduced pressure. Methylene chloride, water, and saturated aqueous sodium hydrogencarbonate were added to the residue to partition the mixture, and the formed aqueous layer was extracted with methylene chloride. The extract was combined with the organic layer, and the mixture was dried over sodium sulfate anhydrate. The solvent was removed under reduced pressure, and the residue was purified through silica gel medium-pressure column chromatography (methylene chloride:methanol=10:1), to thereby yield the title compound (213 mg) as a pale brown foamy solid.

$^1$H-NMR(CDCl$_3$)δ: 1.40-2.32(6H, m), 1.56(9H, s), 2.52 (3H, s), 2.77-2.90(3H, m), 2.90-3.05(2H, m), 2.96(3H, s), 3.11(3H, s), 3.70(1H, d, J=15.5 Hz), 3.73(1H, d, J=15.5 Hz), 4.15-4.23(1H, m), 4.58-4.64(1H, m), 7.43-7.57(2H, m), 7.91 (1H, d, J=6.1 Hz), 7.98(1H, d, J=6.6 Hz), 8.12(1H, d, J=7.8 Hz), 8.23(1H, s), 9.30-10.00(2H, br).

MS(ESI)m/z: 612 (M+H)$^+$.

Example 366

N-{(1R,2S,5S)-2-({3-[amino(imino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride

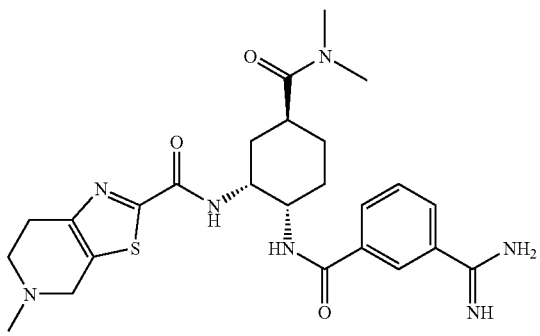

To a solution of the compound obtained in Example 365 (210 mg) in methylene chloride (4.0 mL), was added 4N HCl in dioxane (4.0 mL) at room temperature. The mixture was stirred for 1 hour, and saturated HCl in ethanol (20 mL) was added to the mixture. The resultant mixture was stirred overnight, and the solvent was removed under reduced pressure. Water (4.0 mL) was added to the residue, and the solvent was removed under reduced pressure, followed by drying, to thereby yield the title compound (210 mg) as a pale brown solid.

$^1$H-NMR(DMSO-d$_6$)δ: 1.20-2.10(6H, m), 2.78(3H, s), 2.90-3.20(1H, m), 2.91(3H, s), 2.99(3H, s), 3.20-3.35(1H, m), 3.35-3.80(3H, m), 4.00-4.13(1H, m), 4.35-4.80(3H, m), 7.60-7.75(1H, m), 7.85-8.10(2H, m), 8.10-8.25(1H, m), 8.40-8.53(1H, m), 8.53-8.70(1H, m), 9.25-9.80(4H, m), 11.91(1H, br.s).

MS(ESI)m/z: 512(M+H)$^+$.

Example 367

N-{(1R,2S,5S)-2-[(3-cyanobenzoyl)amino]-5-[(dimethylamino)carbonyl]cyclohexyl}-5-methyl-4,5,6,7-tetrahydrothiazolo[5,4-c]pyridine-2-carboxamide

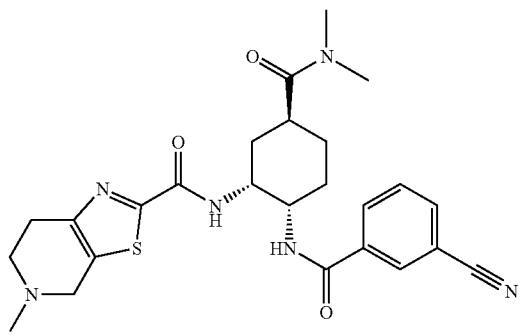

In a manner similar to that described in Example 214, the compound obtained in Referential Example 525 was treated with 4N HCl in dioxane for deprotection. The deprotected compound was condensed with the compound obtained in Referential Example 10, whereby the title compound was obtained.

$^1$H-NMR(CDCl$_3$)δ: 1.50-1.66(1H, m), 1.74-1.88(1H, m), 1.90-2.07(2H, m), 2.22-2.37(2H, m), 2.53(3H, s), 2.79-2.91 (3H, m), 2.91-3.03(2H, m), 2.97(3H, s), 3.13(3H, s), 3.73(1H, d, J=15.4 Hz), 3.74(1H, d, J=15.4 Hz), 4.13-4.21(1H, m), 4.58-4.64(1H, m), 7.47(1H, d, J=7.1 Hz), 7.55(1H, t, J=7.8 Hz), 7.74(1H, d, J=7.8 Hz), 8.03(1H, d, J=5.6 Hz), 8.06(1H, d, J=7.8 Hz), 8.12(1H, s).

MS(ESI)m/z: 494(M$^+$).

Example 368

N-{(1R,2S,5S)-2-({3-[amino(hydroxyimino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride

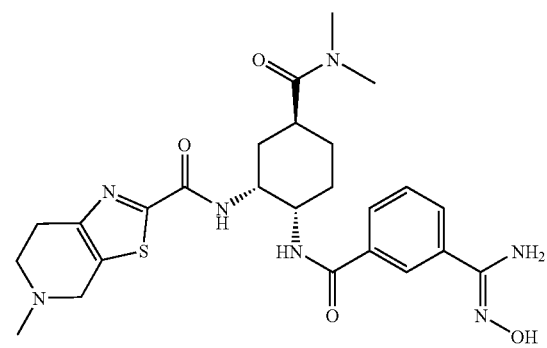

Ethanol (5.0 mL) and tetrahydrofuran (2.0 mL) were added to the compound obtained in Example 367 (270 mg) for dissoltion, and hydroxylamine hydrochloride (114 mg) and triethylamine (230 μL) were added to the solution at room temperature. The mixture was heated under reflux for 3 hours, and saturated aqueous sodium hydrogencarbonate and methylene chloride were added to the reaction mixture to partition the mixture, followed by extracting the formed aqueous layer with methylene chloride. The extract was combined with the organic layer, and the mixture was dried over sodium sulfate anhydrate. The solvent was removed under reduced pressure. The residue was purified through silica gel column chromatography (methylene chloride:methanol=7:1), a sephadex column (methanol), and fractional reversed phase high performance liquid chromatography (acetonitrile-water-formic acid). The product was converted to a hydrochloride with 1N HCl, and subsequently, the salt was purified through use of a sephadex column (methanol), to thereby yield the title compound (175 mg) as a white solid.

$^1$H-NMR(CD$_3$OD)δ: 1.53-1.67(1H, m), 1.78-1.97(5H, m), 2.84(3H, s), 2.96-3.15(2H, m), 3.00(3H, s), 3.03(3H, s), 3.15-3.26(2H, m), 3.64(2H, br.s), 4.09-4.18(1H, m), 4.55(2H, br.s), 7.55(1H, t, J=7.8 Hz), 7.72(1H, d, J=7.8 Hz), 7.94(1H, d, J=7.8 Hz), 8.01(1H, s), 8.08(1H, d, J=9.1 Hz), 8.45(1H, d, J=7.6 Hz).

MS(ESI)m/z: 528(M+H)$^+$.

Example 369

(3-{[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamic acid ethyl ester

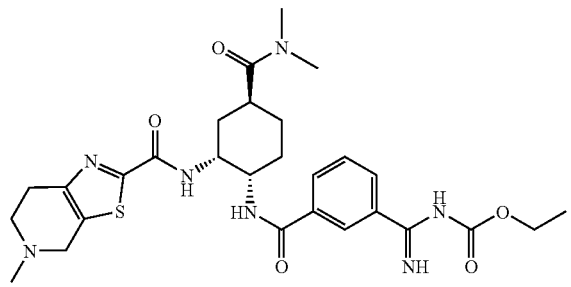

In a manner similar to that described in Example 365, a lithium salt of a carboxylic acid prepared through hydrolyzing the compound obtained in Referential Example 526 was condensed with the compound obtained in Referential Example 253, whereby the title compound was obtained.

$^1$H-NMR(CDCl$_3$)δ: 1.36(3H, t, J=7.1 Hz), 1.55-1.71(1H, m), 1.73-2.05(3H, m), 2.05-2.35(2H, m), 2.52(3H, s), 2.75-3.05(5H, m), 2.97(3H, s), 3.11(3H, s), 3.67-3.80(2H, m), 4.10-4.35(3H, m), 4.55-4.67(1H, m), 7.09(1H, br.s), 7.40-7.60(2H, m), 7.94(1H, d, J=6.1 Hz), 8.03(1H, d, J=7.8 Hz), 8.16(1H, d, J=7.8 Hz), 8.27(1H, s), 9.68(1H, br.s).

MS(ESI)m/z: 584(M+H)$^+$.

Example 370

N-[(1R,2S,5S)-5-[(dimethylamino)carbonyl]-2-({3-[imino(methylamino)methyl]benzoyl}amino)cyclohexyl]-5-methyl-4,5,6,7-tetrahydrothiazolo[5,4-c]pyridine-2-carboxamide formic acid salt D22-9226

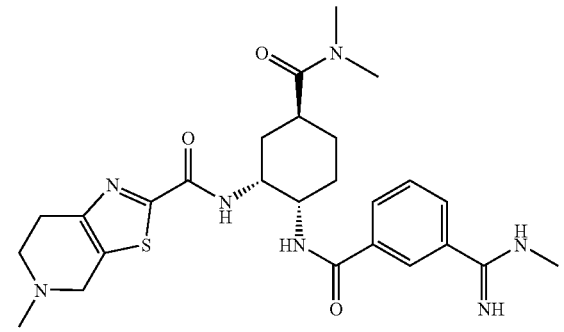

Saturated HCl in ethanol (30 mL) was added to the compound obtained in Example 367 (400 mg) at room temperature. The mixture was stirred for 2 days and then condensed under reduced pressure, thereby yielding a white solid. The solid was dissolved in methanol (10 mL). To the solution, methylamine (2.0M tetrahydrofuran solution) (30 mL) was added at room temperature. The mixture was stirred for 2 hours and then concentrated under reduced pressure, and the residue was purified sequentially through fractional reversed phase high performance liquid chromatography (acetonitrile-water-formic acid) and a sephadex column (methanol), to thereby yield the title compound (152 mg) as a white solid.

$^1$H-NMR(DMSO-d$_6$)δ: 1.40-1.54(1H, m), 1.57-1.71(2H, m), 1.71-1.80(1H, m), 1.90-2.06(2H, m), 2.32(3H, s), 2.45(3H, s), 2.68(2H, d, J=5.6 Hz), 2.75(3H, s), 2.75-2.85(2H, m), 2.91(3H, s), 2.91-3.00(1H, m), 3.42(3H, br.s), 3.59(2H, s), 4.00-4.12(1H, m), 4.43-4.52(1H, m), 7.59(1H, t, J=7.8 Hz), 7.81(1H, d, J=7.8 Hz), 7.96(1H, d, J=7.8 Hz), 8.15(1H, s), 8.34-8.47(2H, m), 8.89(1H, d, J=7.6 Hz).

MS(ESI)m/z: 526(M+H)$^+$.

Example 371

N-{(1R,2S,5S)-2-({3-[amino(methoxyimino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride

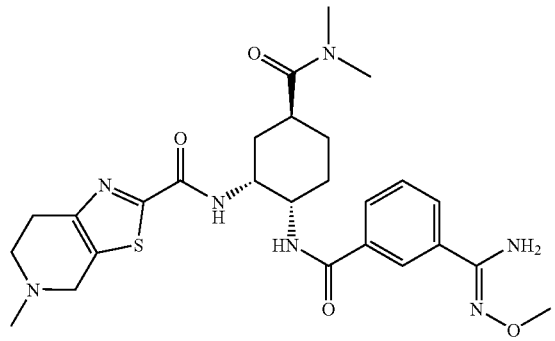

Saturated HCl in ethanol (30 mL) was added to the compound obtained in Example 367 (300 mg) at room temperature. The mixture was stirred for 2 days and then concentrated under reduced pressure, thereby yielding a pale yellow solid. The solid was dissolved in methanol (10 mL). O-Methylhydroxylamine hydrochloride (1.01 g) and triethylamine (1.69 mL) were added to the solution at room temperature. The mixture was stirred for 2 hours, and methylene chloride and saturated aqueous sodium hydrogencarbonate were added to the reaction mixture to partition the mixture, followed by extracting the aqueous layer with methylene chloride. The extract was combined with the organic layer and then dried over sodium sulfate anhydrate, and the solvent was removed under reduced pressure. The residue was purified sequentially through silica gel medium-pressure chromatography (methylene chloride:methanol=20:1→7:1) and fractional reversed phase high performance liquid chromatography (acetonitrile-water-formic acid), and the product was treated with 1N HCl, to thereby yield the title compound (51.8 mg) as a white solid.

$^1$H-NMR(DMSO-d$_6$)δ: 1.44-1.57(1H, m), 1.63-1.88(3H, m), 1.88-2.05(2H, m), 2.79(3H, s), 2.85-3.85(5H, m), 2.90(3H, s), 2.96(3H, s), 3.73(3H, s), 4.04-4.13(1H, m), 4.42(1H, br.s), 4.50-4.60(1H, m), 4.67(1H, br.s), 6.22(2H, br.s), 7.44(1H, t, J=7.8 Hz), 7.75(2H, d, J=7.8 Hz), 7.99(1H, s), 8.33-8.50(2H, m), 11.20-11.60(1H, br).

MS(ESI)m/z: 542(M+H)$^+$.

Example 372

N¹-(5-chloropyridin-2-yl)-N²-((1S,2R,4S)-4-[(dimethylamino)carbonyl]-2-{[4-(3-oxomorpholin-4-yl)benzoyl]amino}cyclohexyl)ethanediamide

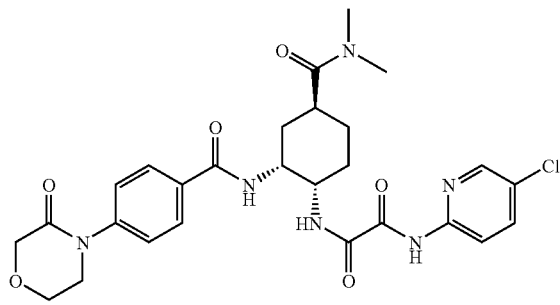

In a manner similar to that employed in Example 2, the compound obtained in Referential Example 531 was condensed with the compound obtained in Referential Example 420, to thereby give the title compound.

¹H-NMR(CDCl₃)δ: 1.72-2.16(6H, m), 2.78-2.88(1H, m), 2.95(3H, s), 3.02(3H, s), 3.76-3.80(2H, m), 4.01-4.08(3H, m), 4.32(2H, s), 4.59-4.65(1H, m), 7.07(1H, d, J=6.9 Hz), 7.38(2H, dt, J=8.6, 2.2 Hz), 7.70(1H, dd, J=8.8, 2.5 Hz), 7.78(2H, dt, J=8.6, 2.2 Hz), 8.16(1H, d, J=8.8 Hz), 8.28-8.31 (2H, m), 9.73(1H, s).

MS(FAB)m/z: 571(M+H)⁺.

Example 373

N-{(1R,2S,5S)-2-{[(Z)-3-(5-chlorothien-2-yl)-2-fluoro-2-propenoyl]amino}-5-[(dimethylamino)carbonyl]cyclohexyl}-5-methyl-4,5,6,7-tetrahydrothiazolo[5,4-c]pyridine-2-carboxamide hydrochloride

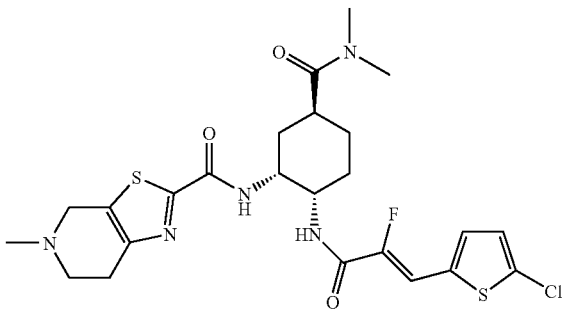

In a manner similar to that described in Example 49, the compound obtained in Referential Example 519 was treated with hydrochloric acid for deprotection. The deprotected compound was condensed with the compound obtained in Referential Example 534, and the product was again treated with hydrochloric acid, whereby the title compound was obtained.

¹H-NMR(DMSO-d₆)δ: 1.42-2.01(6H, m), 2.79(3H, s), 2.91-3.02(7H, m), 3.19(1H, br.s), 3.25(1H, br.s), 3.49(1H, br.s), 3.70(1H, br.s), 3.98-4.05(1H, m), 4.39-4.50(2H, m), 4.70(1H, br.s), 7.19(1H, dd, J=3.9, 1.7 Hz), 7.22(1H, d, J=37.6 Hz), 7.37(1H, d, J=3.9 Hz), 8.50(1H, d, J=7.3 Hz), 8.57(1H, br.s), 11.38-11.53(1H, m).

MS(FAB)m/z: 554 (M+H)⁺.

Example 374

N-{(1R,2S,5S)-2-({2-[(5-chloropyridin-2-yl)amino]-2-oxoethanethioyl}amino)-5-[(dimethylamino)carbonyl]cyclohexyl}-6-methyl-5,6,7,8-tetrahydro-4H-thiazolo[5,4-d]azepine-2-carboxamide hydrochloride

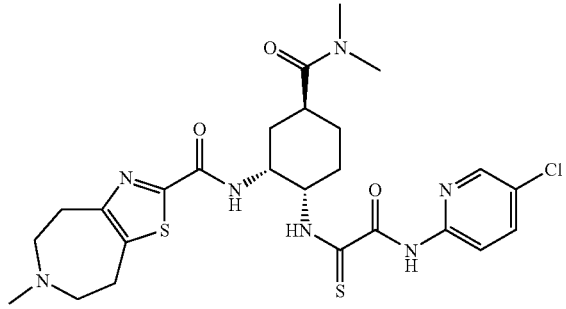

In a manner similar to that described in Example 219, the compound obtained in Referential Example 428 was treated with hydrochloric acid for deprotection. The deprotected compound was condensed with the compound obtained in Referential Example 537, and the product was again treated with hydrochloric acid, whereby the title compound was obtained.

¹H-NMR(DMSO-d₆)δ: 1.44-1.58(1H, m), 1.62-1.74(1H, m), 1.74-1.88(2H, m), 1.95-2.07(1H, m), 2.15-2.30(1H, m), 2.45-2.65(1H, m), 2.79(3H, s), 2.84-3.08(7H, m), 3.16-3.72 (7H, m), 4.45-4.55(1H, m), 4.61-4.70(1H, m), 8.02(1H, dd, J=8.8, 2.4 Hz), 8.07(1H, d, J=8.8 Hz), 8.46(1H, d, J=2.4 Hz), 8.59-8.68(1H, m), 10.56(1H, d, J=4.0 Hz), 10.85(1H, br.s), 11.00-11.09(1H, m).

MSm/z: 578(M+H)⁺.

Example 375

N¹-(5-chloropyridin-2-yl)-N²-{(1S,2R,4S)-2-[(6,7-dihydro-4H-pyrano[4,3-d]thiazol-2-ylcarbonyl)amino]-4-[(dimethylamino)carbonyl]cyclohexyl}ethanediamide

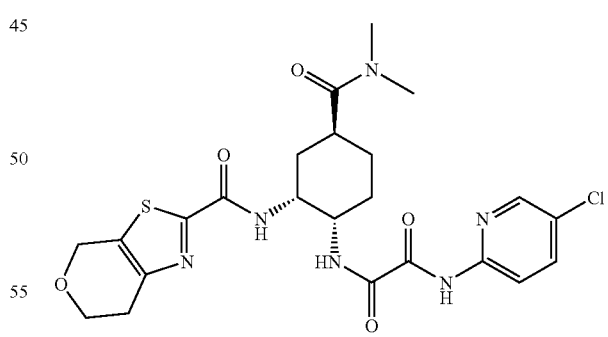

In a manner similar to that employed in Example 2, the compound obtained in Referential Example 26 was condensed with the compound obtained in Referential Example 420, to thereby give the title compound.

¹H-NMR(DMSO-d₆)δ: 1.39-1.56(1H, m), 1.58-1.80(3H, m), 1.97-2.13(2H, m), 2.77(3H, s), 2.92(6H, br.s), 3.90-4.06 (3H, m), 4.35-4.45(1H, m), 4.83(2H, s), 7.96-8.06(2H, m), 8.44(1H, br.s), 8.61(1H, d, J=7.3 Hz), 9.22(1H, d, J=8.1 Hz), 10.25(1H, br.s).

MS(FAB)m/z: 535(M+H)⁺.

Example 376

N-{(1R,2S,5S)-2-({2-[(5-chloropyridin-2-yl)amino]-2-oxoethanethioyl}amino)-5-[(dimethylamino)carbonyl]cyclohexyl}-6-methyl-5,6,7,8-tetrahydro[1,6]naphthyridine-2-carboxamide

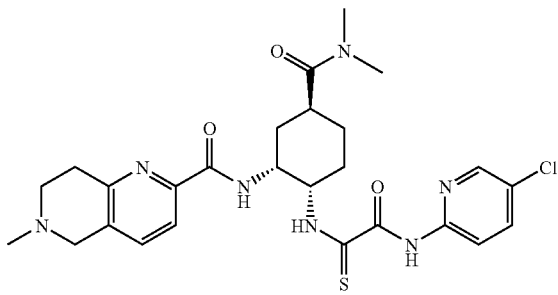

In a manner similar to that described in Example 219, the compound obtained in Referential Example 428 was treated with hydrochloric acid for deprotection. The deprotected compound was condensed with the compound obtained in Referential Example 540, whereby the title compound was obtained.

$^1$H-NMR(CDCl$_3$)δ: 1.50-1.75(2H, m), 1.80-2.10(3H, m), 2.10-2.20(1H, m), 2.30-2.45(1H, m), 2.52(3H, s), 2.75-2.85(2H, m), 2.98(3H, s), 2.95-3.10(2H, m), 3.11(3H, s), 3.66(2H, s), 4.45-4.55(1H, m), 4.65-4.80(1H, m), 7.52(1H, d, J=7.8 Hz), 7.67(1H, dd, J=8.8, 2.4 Hz), 8.05(1H, d, J=7.8 Hz), 8.21(1H, d, J=8.8 Hz), 8.31(1H, d, J=2.7 Hz), 8.50(1H, d, J=7.5 Hz), 10.49(1H, d, J=7.3 Hz), 10.60(1H, s).

MS(ESI)m/z: 558(M+H)$^+$.

Example 377

(1S,3R,4S)-4-({2-[(5-chloropyridin-2-yl)amino]-2-oxoethanethioyl}amino)-3-{[(5-methyl-4,5,6,7-tetrahydrothiazolo[5,4-c]pyridin-2-yl)carbonyl]amino}cyclohexanecarboxylic acid tert-butyl ester

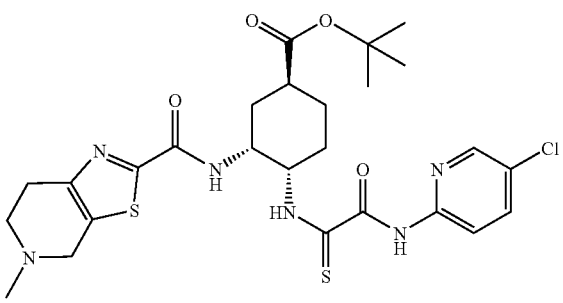

In a manner similar to that employed in Example 2, the compound obtained in Referential Example 543 was condensed with the compound obtained in Referential Example 10, to thereby give the title compound.

$^1$H-NMR(CDCl$_3$)δ: 1.46(9H, s), 1.58-1.78(2H, m), 1.95-2.33(4H, m), 2.49-2.61(1H, m), 2.52(3H, s), 2.80-2.88(2H, m), 2.93-3.00(2H, m), 3.66-3.79(2H, m), 4.40-4.54(1H, m), 4.71-4.84(1H, m), 7.43(1H, d, J=8.3 Hz), 7.68(1H, dd, J=8.8, 2.4 Hz), 8.19(1H, d, J=8.8 Hz), 8.31(1H, d, J=2.4 Hz), 10.13(1H, d, J=7.6 Hz), 10.55(1H, s).

MS(ESI)m/z: 593(M+H)$^+$.

Example 378

(1S,3R,4S)-4-({2-[(5-chloro-2-pyridinyl)amino]-2-oxoethanethioyl}amino)-3-{[(5-methyl-4,5,6,7-tetrahydrothiazolo[5,4-c]pyridin-2-yl)carbonyl]amino}cyclohexanecarboxylic acid hydrochloride

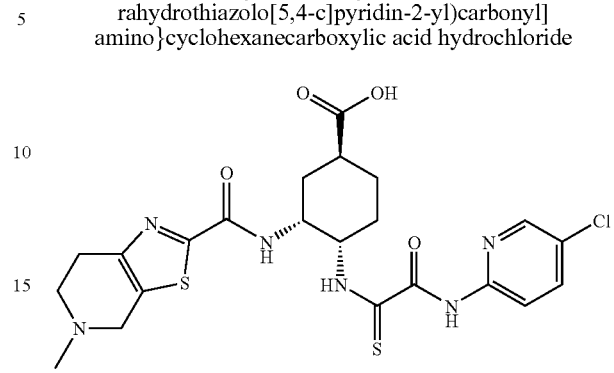

4N HCl in dioxane (10 mL) was added to a solution of the compound obtained in Example 377 (293 mg) in dioxane (8.0 mL), and the mixture was stirred for 16 hours at room temperature. The reaction mixture was concentrated under reduced mixture, and the residue was suspended in diisopropyl ether and then collected through filtration. The collected powder was dissolved in water and then neutralized with saturated aqueous sodium bicarbonate. The aqueous solution was extracted with methylene chloride, and the formed organic layer was washed with saturated brine and dried over sodium sulfate anhydrate, followed by concentration under reduced pressure. 1N HCl in ethanol (0.50 mL) was added to the residue, and the mixture was subjected to concentration under reduced pressure. The residue was dissolved in water, followed by freeze-drying, to thereby yield the title compound (242 mg).

$^1$H-NMR(DMSO-d$_6$)δ: 1.50-1.64(1H, m), 1.66-1.86(2H, m), 1.89-2.04(1H, m), 2.16-2.32(2H, m), 2.51-2.64(1H, m), 2.93(3H, s), 3.12-3.58(3H, m), 3.64-3.80(1H, m), 4.36-4.80(4H, m), 8.03(1H, dd, J=8.8, 2.7 Hz), 8.08(1H, d, J=8.8 Hz), 8.46(1H, d, J=2.7 Hz), 8.73(1H, br.s), 10.57(1H, s), 10.94-11.45(2H, m).

MS(ESI)m/z: 537(M+H)$^+$.

Example 379

(1S,3R,4S)-4-({2-[(5-chloropyridin-2-yl)amino]-2-oxoacetyl}amino)-3-[(6,7-dihydro-4H-pyrano[4,3-d]thiazol-2-ylcarbonyl)amino]cyclohexanecarboxylic acid tert-butyl ester

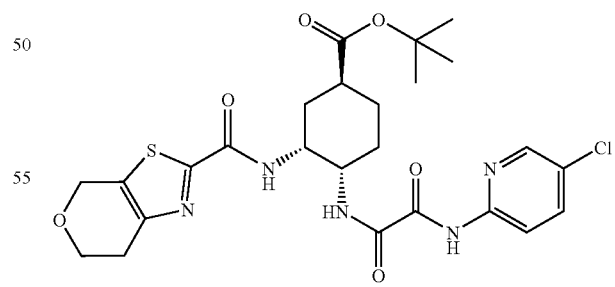

1N HCl-ethyl acetate (3.09 mL) was added to the compound obtained in Referential Example 544 (307 mg), and the resultant suspension was stirred for 7 hours at room temperature. 2N HCl-ethyl acetate (40 mL) was further added to the suspension, and the mixture was stirred for 2 hours at room temperature. The solvent was removed under reduced pressure, and diethyl ether was added to the residue. The precipitated solid was collected through filtration and dried under reduced pressure. The resultant solid was dissolved in N,N-dimethylformamide (10 mL). The compound obtained in Referential Example 26 (191 mg), 1-(3-dimethylaminopropyl)-3-ethylcarbodiimide hydrochloride (288 mg), and 1-hydroxybenzotriazole (135 mg) were added to the solution, and the resultant mixture was stirred for 4 days at room temperature. The solvent was reduced under reduced pressure, methylene chloride and a saturated aqueous solution of sodium hydrogencarbonate were added to the residue to partition the mixture, and the formed organic layer was washed with saturated brine. The organic layer was dried over sodium sulfate anhydrate and then concentrated under reduced pressure, and the residue was purified through silica gel flash column chromatography (methanol:methylene chloride=1:49), to thereby yield the title compound (124 mg).

$^1$H-NMR(CDCl$_3$)δ: 1.46(9H, s), 1.58-1.76(2H, m), 1.90-2.21(4H, m), 2.45-2.55(1H, m), 2.97(2H, t, J=5.6 Hz), 3.99-4.14(3H, m), 4.62-4.71(1H, m), 4.88(2H, br.s), 7.35(1H, d, J=8.8 Hz), 7.69(1H, dd, J=8.8, 2.7 Hz), 7.99(1H, d, J=8.1 Hz), 8.17(1H, d, J=8.8 Hz), 8.30(1H, d, J=2.7 Hz), 9.70(1H, br.s).

MS(ESI)m/z: 564(M+H)$^+$.

Example 380

(1S,3R,4S)-4-({2-[(5-chloropyridin-2-yl)amino]-2-oxoacetyl}amino)-3-[(6,7-dihydro-4H-pyrano[4,3-d]thiazol-2-ylcarbonyl)amino]cyclohexanecarboxylic acid

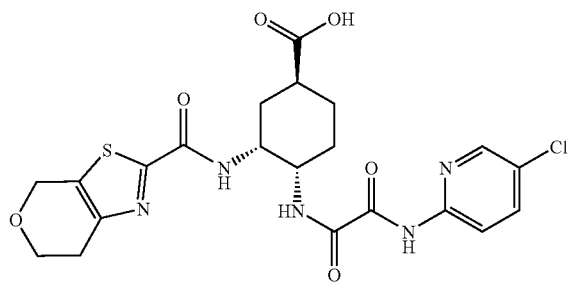

In a manner similar to that employed in Example 378, the title compound was prepared from the compound obtained in Example 379.

$^1$H-NMR(DMSO-d$_6$)δ: 1.44-1.80(3H, m), 1.83-2.11(2H, m), 2.17-2.27(1H, m), 2.45-2.54(1H, m), 2.92(2H, br.s), 3.90-4.10(3H, m), 4.33(1H, br.s), 4.84(2H, br.s), 7.98-8.07 (2H, m), 8.45(1H, d, J=2.2 Hz), 8.59(1H, d, J=7.4 Hz), 9.19 (1H, d, J=8.1 Hz), 10.27(1H, s), 12.23(1H, s).

MS(FAB)m/z: 508(M+H)$^+$.

Example 381

$N^1$-(5-chloropyridin-2-yl)-$N^2$-((1S,2R,4S)-4-[(dimethylamino)carbonyl]-2-{[(2-methyl-1,2,3,4-tetrahydroisoquinolin-6-yl)carbonyl]amino}cyclohexyl)ethanediamide hydrochloride

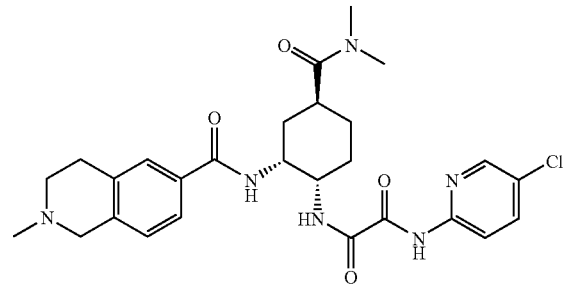

In a manner similar to that described in Example 2, a lithium salt of a carboxylic acid prepared through hydrolyzing the compound obtained in Referential Example 545 was condensed with the compound obtained in Referential Example 420, and the product was treated with hydrochloric acid, whereby the title compound was obtained.

$^1$H-NMR(DMSO-d$_6$)δ: 1.31-1.46(1H, m), 1.49-1.72(3H, m), 1.75-2.01(2H, m), 2.68(3H, s), 2.80(3H, s), 2.86(3H, s), 2.90-3.06(1H, m), 3.05-3.42(3H, m), 3.49-3.61(1H, m), 3.80-3.92(1H, m), 4.13-4.48(3H, m), 7.20(1H, d, J=8.0 Hz), 7.62 (1H, d, J=8.0 Hz), 7.64(1H, s), 7.85-7.95(2H, m), 7.95-8.05 (1H, m), 8.34(1H, s), 8.84-8.96(1H, m), 10.16(1H, s), 11.10 (1H, br.s).

MSm/z: 541 (M+H)$^+$.

Example 382

$N^1$-(5-chloropyridin-2-yl)-$N^2$-[(1S,2R,4R)-2-{[(5-methyl-4,5,6,7-tetrahydrothiazolo[5,4-c]pyridin-2-yl)carbonyl]amino}-4-(thiazol-2-yl)cyclohexyl]ethanediamide hydrochloride and $N^1$-(5-chloropyridin-2-yl)-$N^2$-((1S,2R,4S)-2-{[(5-methyl-4,5,6,7-tetrahydrothiazolo[5,4-c]pyridin-2-yl)carbonyl]amino}-4-(thiazol-2-yl)cyclohexyl]ethanediamide hydrochloride

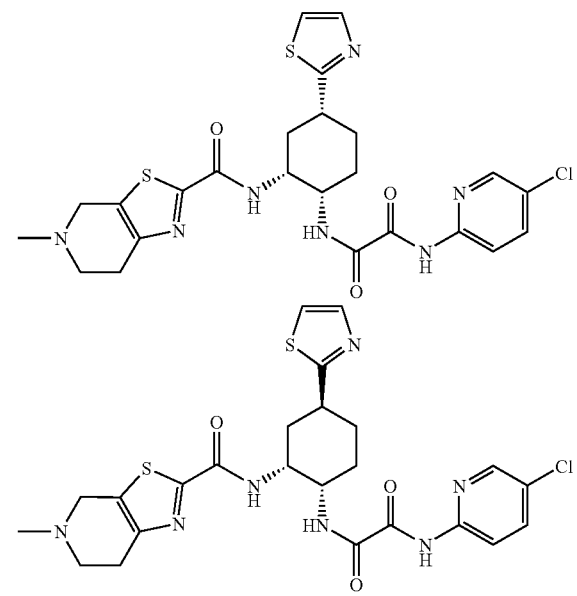

In a manner similar to that described in Example 214, the compound obtained in Referential Example 549 was treated with hydrochloric acid for deprotection. The deprotected compound was condensed with the compound obtained in Referential Example 10, and the resultant two stereoisomers were treated with hydrochloric acid, whereby the title compounds were obtained.

Low-polar compound: $^1$H-NMR(DMSO-d$_6$)δ: 1.60-1.84 (2H, m), 1.86-1.97(1H, m), 2.00-2.14(2H, m), 2.21-2.34(1H, m), 2.89(3H, br.s), 3.01-3.52(4H, m), 3.61-3.74(1H, m), 4.06-4.49(3H, m), 4.63-4.75(1H, m), 7.63(1H, d, J=3.2 Hz), 7.75(1H, d, J=3.2 Hz), 7.98-8.10(2H, m), 8.44(1H, br.s), 8.78-8.87(1H, m), 9.13-9.29(1H, m), 10.34-10.42(1H, m), 11.66(1H, br.s).

MS(FAB)m/z: 560(M+H)$^+$.

High-polar compound: $^1$H-NMR(DMSO-d$_6$)δ: 1.67-1.80 (2H, m), 1.89-1.99(1H, m), 2.10-2.25(2H, m), 2.30-2.46(1H, m), 2.90(3H, br.s), 3.08-3.53(4H, m), 3.65-3.76(1H, m), 4.05-4.53(3H, m), 4.64-4.75(1H, m), 7.62(1H, br.s), 7.73(1H, br.s), 7.97-8.10(2H, m), 8.44(1H, br.s), 8.69-8.81 (1H, m), 9.18-9.34(1H, m), 10.20-10.35(1H, m), 11.48-11.92 (1H, m).

MS(FAB)m/z: 560(M+H)$^+$.

Example 383

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1,2,4-oxadiazol-3-yl)cyclohexyl]ethanediamide hydrochloride

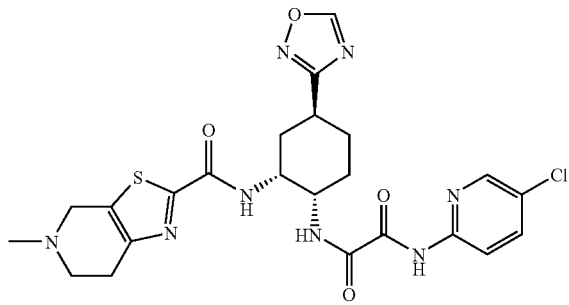

In a manner similar to that described in Example 214, the compound obtained in Referential Example 550 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.64-1.79(2H, m), 1.84-1.95(1H, m), 2.01-2.22(2H, m), 2.30-2.43(1H, m), 2.91(4H, br.s), 3.19 (2H, br.s), 3.34-3.79(2H, m), 4.06-4.17(1H, m), 4.35-4.75 (3H, m), 7.97-8.06(2H, m), 8.42(1H, s), 8.81(1H, d, J=7.1 Hz), 9.21(1H, br.s), 9.51(1H, s), 10.28(1H, s).

MS(FAB)m/z: 545 (M+H)$^+$.

Example 384

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(5-methyl-1,3,4-oxadiazol-2-yl)cyclohexyl]ethanediamide hydrochloride

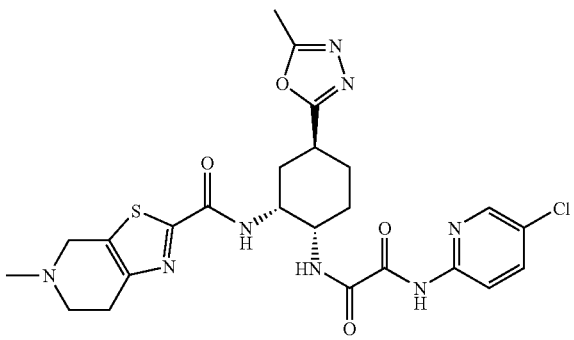

In a manner similar to that described in Example 214, the compound obtained in Referential Example 552 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO-d$_6$)δ: 1.66-1.80(2H, m), 1.87-1.96(1H, m), 2.04-2.20(2H, m), 2.35-2.43(1H, m), 2.45(3H, s), 2.93 (3H, s), 3.16-3.31(2H, m), 3.43-3.57(2H, m), 3.63-3.80(1H, m), 4.08-4.19(1H, m), 4.37-4.52(2H, m), 4.65-4.82(1H, m), 7.99-8.08(2H, m), 8.44-8.48(1H, m), 8.84(1H, d, J=6.8 Hz), 9.22(1H, br.s), 10.30(1H, s), 10.96-11.25(1H, m).

MS(EI)m/z: 558(M$^+$).

Example 385

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1,3,4-oxadiazol-2-yl)cyclohexyl]ethanediamide

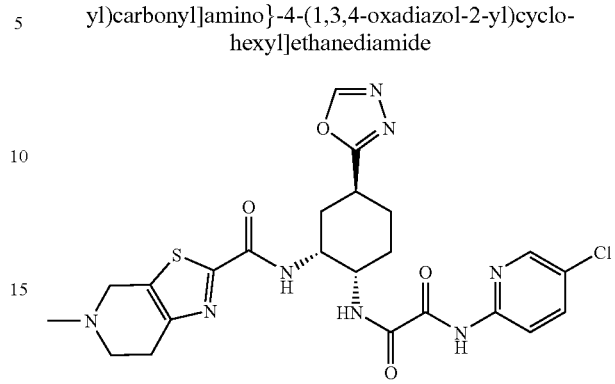

In a manner similar to that described in Example 214, the compound obtained in Referential Example 554 was treated with hydrochloric acid for deprotection. The deprotected compound was condensed with the compound obtained in Referential Example 10, whereby the title compound was obtained.

$^1$H-NMR(CDCl$_3$)δ: 1.72-2.00(2H, m), 2.13-2.23(2H, m), 2.28-2.36(1H, m), 2.39-2.46(1H, m), 2.53(3H, s), 2.80-2.91 (2H, m), 2.93-3.00(2H, m), 3.28-3.38(1H, m), 3.69-3.79(2H, m), 4.14-4.24(1H, m), 4.68-4.77(1H, m), 7.51(1H, d, J=8.3 Hz), 7.70(1H, dd, J=8.8, 2.5 Hz), 8.14(1H, d, J=7.8 Hz), 8.18(1H, d, J=8.8 Hz), 8.31(1H, d, J=2.5 Hz), 8.38(1H, s), 9.72(1H, s).

MS(FAB)m/z: 545 (M+H)$^+$.

Example 386

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1,3-oxazol-2-yl)cyclohexyl]ethanediamide hydrochloride

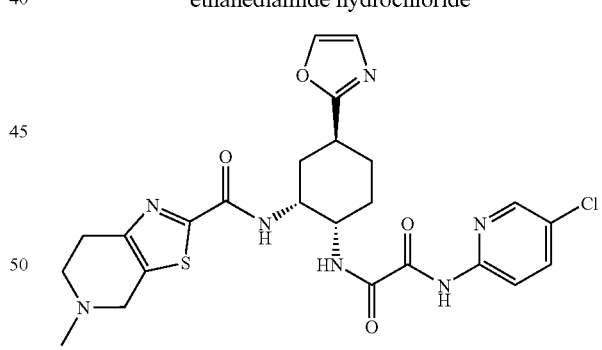

In a manner similar to that described in Example 214, the compound obtained in Referential Example 556 was treated with hydrochloric acid for deprotection. The deprotected compound was condensed with the compound obtained in Referential Example 10, whereby the title compound was obtained.

$^1$H-NMR(DMSO-d$_6$)δ: 1.65-1.82(2H, m), 1.85-2.00(1H, m), 2.01-2.22(2H, m), 2.31-2.48(1H, m), 2.94(3H, s), 3.08-3.74(4H, m), 3.65-3.83(1H, m), 4.06-4.20(1H, m), 4.36-4.55 (2H, m), 4.65-4.82(1H, m), 7.14(1H, s), 8.00-8.17(3H, m), 8.48(1H, s), 8.77-8.90(1H, m), 9.14-9.34(1H, m), 10.25-10.40(1H, m), 11.35-11.68(1H, m).

MSm/z: 544(M+H)$^+$.

Example 387

N¹-(5-chloropyridin-2-yl)-N²-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide hydrochloride

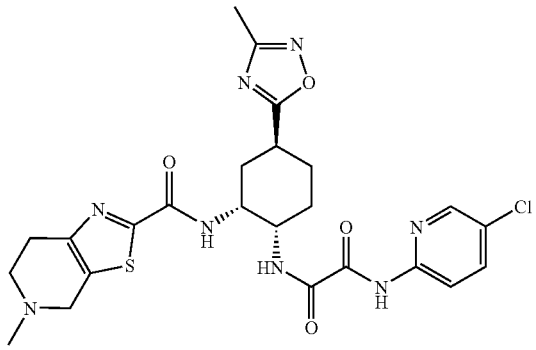

The compound obtained in Referential Example 560 (110 mg) was dissolved in methylene chloride (5 mL), and 4N HCl in dioxane (5 mL) was added to the solution, followed by stirring for 3 hours at room temperature. The solvent was removed under reduced pressure, and the obtained yellow solid was dissolved in N,N-dimethylformamide (5 mL). To the solution, sequentially added were the compound obtained in Referential Example 266 (71.1 mg), 1-hydroxybenzotriazole (42.7 mg), and 1-(dimethylaminopropyl)-3-ethylcarbodiimide hydrochloride (80.9 mg), and the mixture was stirred overnight at room temperature. The reaction mixture was concentrated under reduced pressure, and methylene chloride and aqueous sodium hydrogencarbonate were added to the residue to partition the mixture. The formed organic layer was dried over sodium sulfate anhydrate. The solvent was removed under reduced pressure, and the residue was purified through chromatography (methanol:methylene chloride=1:19). 1N HCl in ethanol was added to the thus-obtained free form, and the mixture was concentrated. Diethyl ether was added to the residue, and the precipitated colorless powder was collected through filtration, to thereby yield the title compound (69.8 mg).

¹H-NMR(DMSO-d$_6$)δ: 1.65-1.85(2H, m), 1.89-1.92(1H, m), 2.05-2.22(2H, m), 2.32(3H, s), 2.35-2.46(1H, m), 2.93 (3H, br.s), 3.05-3.56(4H, m), 3.65-3.78(1H, m), 4.05-4.18 (1H, m), 4.35-4.53(2H, m), 4.65-4.83(1H, m), 7.97-8.10(2H, m), 8.46(1H, br.s), 8.78-8.90(1H, m), 9.15-9.32(1H, m), 10.30(1H, br.s), 10.90-11.30(1H, m). MS(FAB)m/z: 559(M+H)⁺.

Example 388

N¹-(5-chloropyridin-2-yl)-N²-[(1S,2R,4S)-2-{[(5-methyl-4,5,6,7-tetrahydrothiazolo[5,4-c]pyridin-2-yl)carbonyl]amino}-4-(1,3,4-thiadiazol-2-yl)cyclohexyl]ethanediamide hydrochloride

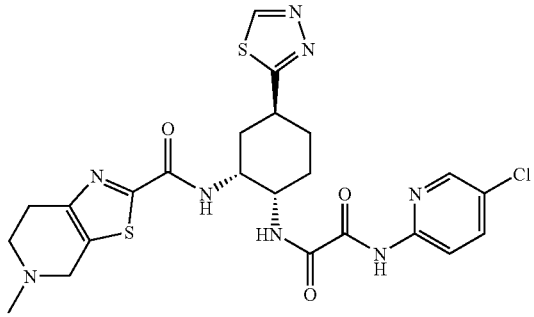

In a manner similar to that described in Example 387, the compound obtained in Referential Example 562 was treated with hydrochloric acid for deprotection. The deprotected compound was condensed with the compound obtained in Referential Example 266, and the product was again treated with hydrochloric acid, whereby the title compound was obtained.

¹H-NMR(DMSO-d$_6$)δ: 1.68-1.86(2H, m), 1.96-2.08(1H, m), 2.11-2.28(2H, m), 2.38-2.47(1H, m), 2.94(3H, s), 3.10-3.30(1H, m), 3.37-3.62(2H, m), 3.63-3.80(1H, m), 4.11-4.23 (1H, m), 4.38-4.51(2H, m), 4.65-4.81(1H, m), 7.99-8.08(2H, m), 8.44-8.48(1H, m), 8.76-8.84(1H, m), 9.20-9.34(1H, m), 9.52(1H, s), 10.29(1H, br.s), 10.99-11.33(1H, m).

MS(ESI)m/z: 561(M+H)⁺.

Example 389

N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide

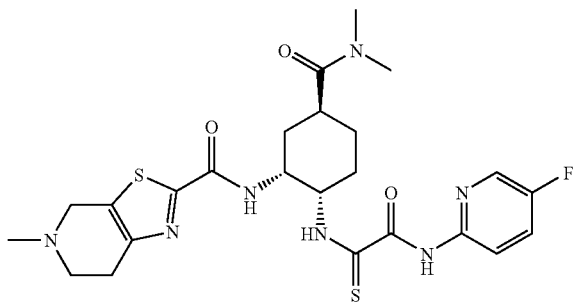

To a solution of the compound obtained in Referential Example 563 (76.3 g) in N,N-dimethylformamide (1.0 L), were added the compound obtained in Referential Example 10 (38.4 g), 1-hydroxybenzotriazole monohydrate (28.8 g), 1-ethyl-3-(3-dimethylaminopropyl)carbodiimide hydrochloride (37.6 g), and diisopropylethylamine (35 mL), and the mixture was stirred for 63 hours at room temperature. The reaction mixture was concentrated under reduced pressure, and methylene chloride (1.2 L) and saturated aqueous sodium hydrogencarbonate (500 mL) were added to the residue. The aqueous layer was extracted with methylene chloride, and the organic layer was washed with saturated aqueous sodium hydrogencarbonate and saturated aqueous sodium chloride and then dried over sodium sulfate anhydrate, followed by concentration under reduced pressure. The residue was purified through silica gel column chromatography (methylene chloride:methanol=50:1→10:1), and the obtained powder (77.2 g) was dissolved in methylene chloride (500 mL). The insoluble substances were removed through filtration, and the filtrate was concentrated under reduced pressure. Methylene chloride (250 mL) was added to the residue, and diethyl ether (1 L) was added dropwise thereto. The mixture was stirred for 30 minutes at 0° C., followed by filtration, to thereby yield the title compound (71.5 g).

¹H-NMR(CDCl$_3$)δ: 1.61-1.75(1H, m), 1.78-2.21(5H, m), 2.19(3H, s), 2.27-2.37(1H, m), 2.52(3H, s), 2.77-2.95(4H, m), 2.96(3H, s), 3.70(1H, d, J=15.4 Hz), 3.75(1H, d, J=15.6 Hz), 4.48-4.57(1H, m), 4.76-4.85(1H, m), 7.40-7.49(2H, m), 8.21(2H, dd, J=8.2, 4.8 Hz), 10.06(1H, br.d, J=7.6 Hz), 10.55 (1H, br.s).

MS(ESI)m/z: 548(M+H)⁺.

Example 390

N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridin-2-carboxamide citric acid monohydrate

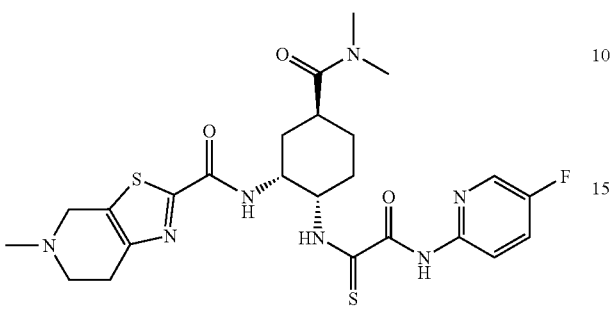

The compound obtained in Example 389 (6.26 g) was suspended in 20% hydrous ethanol (100 mL), and 1M aqueous citric acid (11.4 mL) was added to the suspension. Under stirring at 60° C., 20% hydrous ethanol was gradually added thereto to dissolve the suspension. After filtration with heating, the solution was allowed to cool to room temperature under stirring and then was left to stand for 1 day. The precipitated crystals were collected through filtration and then dried for 2 hours at room temperature under reduced pressure, and the residue was left to stand for 1 day, to thereby yield the title compound (6.95 g).

$^1$H-NMR(DMSO-$d_6$)δ: 1.44-1.56(1H, m), 1.64-1.72(1H, m), 1.74-1.84(2H, m), 2.05(1H, d, J=14.2 Hz), 2.21-2.32(1H, m), 2.47-2.53(1H, m), 2.50(3H, s), 2.71(2H, d, J=15.1 Hz), 2.62(2H, d, J=15.6 Hz), 2.79(3H, s), 2.94-3.01(2H, m), 2.94 (3H, s), 4.48-4.56(1H, m), 4.62-4.68(1H, m), 7.86-7.90(1H, dt, J=8.2 Hz), 8.10(1H, dd, J=9.2, 3.7 Hz), 8.42(1H, d, J=2.7 Hz), 8.72(1H, d, J=6.9 Hz), 10.53(1H, s), 11.11(1H, d, J=7.8 Hz).

Element analysis: $C_{24}H_{30}FN_7O_3S_2 \cdot C_6H_8O_7 \cdot H_2O$ Calculated: C, 47.55; H, 5.32; N, 12.94; F, 2.51; S, 8.46. Found: C, 47.48; H, 5.10; N, 13.05; F, 2.55; S, 8.61.

mp(decomposed): 176 to 179° C.

Example 391

$N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(5-methyl-1,3,4-thisdiazol-2-yl)cyclohexyl]ethanediamide hydrochloride

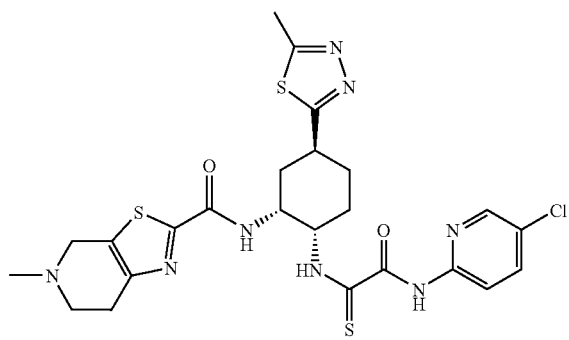

In a manner similar to that described in Example 387, the compound obtained in Referential Example 566 was treated with hydrochloric acid for deprotection. The deprotected compound was condensed with the compound obtained in Referential Example 266, and the product was again treated with hydrochloric acid, whereby the title compound was obtained.

$^1$H-NMR(DMSO-$d_6$)δ: 1.67-1.82(2H, m), 1.92-2.03(1H, m), 2.06-2.26(2H, m), 2.35-2.44(1H, m), 2.68(3H, s), 2.94 (3H, s), 3.13-3.27(2H, m), 3.40-3.56(2H, m), 3.66-3.80(1H, m), 4.09-4.22(1H, m), 4.37-4.51(2H, m), 4.64-4.82(1H, m), 7.98-8.07(2H, m), 8.44-8.48(1H, m), 8.79(1H, br.s), 9.16-9.34(1H, m), 10.29(1H, s).

MS(ESI)m/z: 575(M+H)$^+$.

Example 392

$N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1,3-oxazol-5-yl)cyclohexyl]ethanediamide hydrochloride

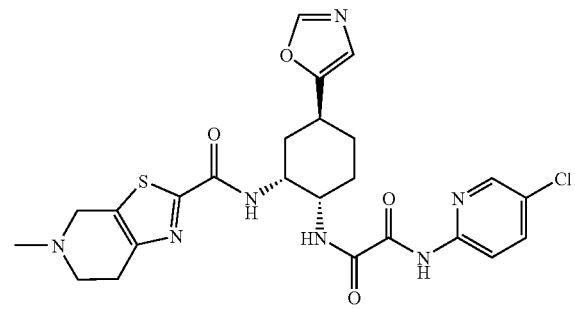

In a manner similar to that described in Example 214, the compound obtained in Referential Example 568 was treated with hydrochloric acid for deprotection. The deprotected compound was condensed with the compound obtained in Referential Example 10, and the product was again treated with hydrochloric acid, whereby the title compound was obtained.

$^1$H-NMR(DMSO-$d_6$)δ: 1.50-1.87(3H, m), 1.97-2.40(3H, m), 2.93(3H, s), 2.96-3.83(5H, m), 4.04-4.16(1H, m), 4.30-4.53(2H, m), 4.62-4.80(1H, m), 6.93(1H, s), 7.96-8.10(2H, m), 8.22(1H, s), 8.45(1H, s), 8.66-8.80(1H, m), 9.17-9.37 (1H, m), 10.24-10.37(1H, m), 11.20-11.54(1H, m).

MS(ESI)m/z: 544(M+H)$^+$.

Example 393

$N^1$-(5-chloropyridin-2-yl)-$N^2$-((1S,2R,4S)-4-(5-methyl-1,2,4-oxadiazol-3-yl)-2-{[(5-methyl-4,5,6,7-tetrahydrothiazolo[5,4-c]pyridin-2-yl)carbonyl]amino}cyclohexyl)ethanediamide hydrochloride

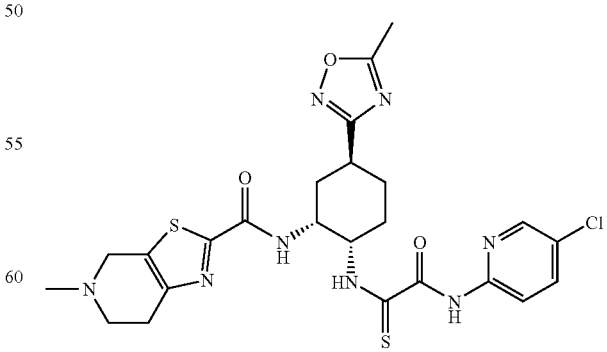

In a manner similar to that described in Example 387, the compound obtained in Referential Example 572 was treated with hydrochloric acid for deprotection. The deprotected compound was condensed with the compound obtained in Referential Example 266, and the product was again treated with hydrochloric acid, whereby the title compound was obtained.

$^1$H-NMR(DMSO-d$_6$)δ: 1.63-1.79(2H, m), 1.80-1.94(1H, m), 1.98-2.24(2H, m), 2.27-2.41(1H, m), 2.56(3H, s), 2.83 (3H, s), 3.04-3.88(6H, m), 4.06-4.18(1H, m), 4.29-4.53(2H, m), 7.98-8.10(2H, m), 8.46(1H, d, J=2.4 Hz), 8.79(1H, d, J=6.8 Hz), 9.23(1H, d, J=8.0 Hz), 10.31(1H, s).

MS(ESI)m/z: 559 (M+H)$^+$.

Example 394

N$^1$-(5-chloropyridin-2-yl)-N$^2$-(1S,2R,4S)-2-{[(5-methyl-4,5,6,7-tetrahydrothiazolo[5,4-c]pyridin-2-yl)carbonyl]amino}-4-(4H-1,2,4-triazol-4-yl)cyclohexyl)ethanediamide hydrochloride

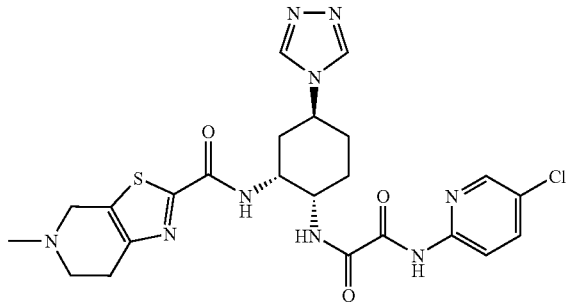

In a manner similar to that described in Example 214, the compound obtained in Referential Example 576 was treated with hydrochloric acid for deprotection. The deprotected compound was condensed with the compound obtained in Referential Example 564, and the product was again treated with hydrochloric acid, whereby the title compound was obtained.

$^1$H-NMR(DMSO-d$_6$)δ: 1.69-1.79(1H, m), 1.87-2.00(1H, m), 2.04-2.14(1H, m), 2.17-2.40(3H, m), 2.92(3H, s), 3.02-3.84(4H, m), 4.13-4.22(1H, m), 4.35-4.83(4H, m), 7.99-8.05 (2H, m), 8.45-8.47(1H, m), 8.65(2H, s), 8.69-8.76(1H, m), 9.39(1H, d, J=8.1 Hz), 10.29(1H, s), 11.49(1H, br.s).

MS(ESI)m/z: 544(M+H)$^+$.

Example 395

N$^1$-(5-chloro-2-thienyl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide citric acid salt

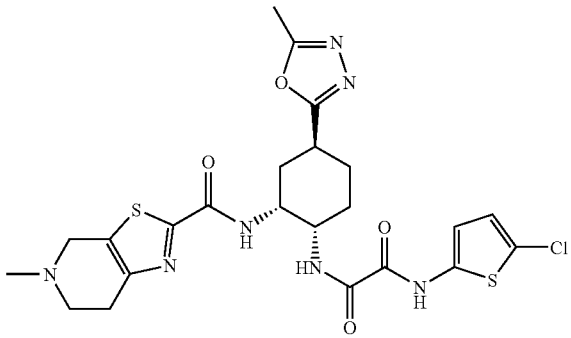

The compound obtained in Referential Example 577 (317 mg) and a lithium salt (249 mg) of a carboxylic acid obtained through hydrolyzing the compound obtained in Referential Example 356 was dissolved in N,N-dimethylformamide (8 mL), and 1-(dimethylaminopropyl)-3-ethylcarbodiimide hydrochloride (308 mg) and 1-hydroxybenzotriazole (159 mg) were added to the solution at 0° C., followed by stirring for 11 hours at room temperature. The reaction mixture was diluted with ethyl acetate, and then washed sequentially with 10% aqueous citric acid, saturated aqueous sodium hydrogencarbonate, and saturated brine, followed by drying over sodium sulfate anhydrate. The residue was concentrated under reduced pressure, and the produced solid was dissolved in methylene chloride (10 mL). 4N HCl in dioxane (10 mL) was added to the solution, and the mixture was stirred for 1 hour at room temperature. The reaction mixture was concentrated under reduced pressure, and the residue was dissolved in N,N-dimethylformamide (8 mL). The compound obtained in Referential Example 10 (262 mg), 1-hydroxybenzotriazole (174 mg), 1-(dimethylaminopropyl)-3-ethylcarbodiimide hydrochloride (308 mg), and triethylamine (149 μL) were added to the solution at room temperature. The reaction mixture was stirred for 19 hours, diluted with methylene chloride, washed with saturated aqueous sodium hydrogencarbonate, and dried over sodium sulfate anhydrate. The residue was concentrated under reduced pressure, and the concentrated product was purified through silica gel thin layer chromatography (methylene chloride:methanol=10:1). The thus-obtained compound was dissolved in ethanol, and hexane was added to the solution, and the precipitated solid was collected through filtration. Ethanol (15 mL) and citric acid monohydrate (138 mg) were added to the solid (371 mg) to dissolve the solid therein, and the solution was concentrated under reduced pressure, followed by co-boiling three times with water and then drying, to thereby yield the title compound (503 mg).

$^1$H-NMR(DMSO-d$_6$)δ: 1.69-1.84(2H, m), 1.87-1.99(1H, m), 2.05-2.22(2H, m), 2.35-2.52(1H, m), 2.48(3H, s), 2.65 (2H, d, J=15.4 Hz), 2.75(2H, d, J=15.4 Hz), 2.98(3H, s), 3.03-3.84(5H, m), 3.84-3.95(2H, m), 4.10-4.21(1H, m), 4.38-4.48(1H, m), 6.93(1H, d, J=4.4 Hz), 6.98(1H, d, J=4.4 Hz), 8.77(1H, d, J=7.6 Hz), 9.22(1H, d, J=8.4 Hz), 12.34(1H, s).

MS(ESI)m/z: 564(M+H)$^+$.

Example 396

N$^1$-(5-bromo-2-pyridinyl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide hydrochloride.

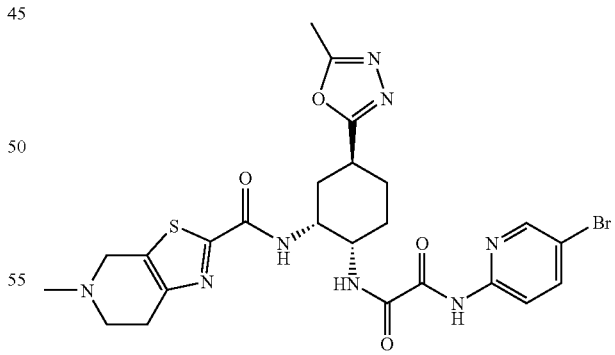

In a manner similar to that described in Example 214, the compound obtained in Referential Example 579 was treated with hydrochloric acid for deprotection. The deprotected compound was condensed with the compound obtained in Referential Example 564, and the product was treated with hydrochloric acid, whereby the title compound was obtained.

$^1$H-NMR(DMSO-d$_6$)δ: 1.70-2.15(5H, m), 2.32-2.43(1H, m), 2.45(3H, s), 2.92(3H, s), 3.10-3.30(3H, m), 3.49(1H, br.s), 3.70(1H, br.s), 4.09-4.17(1H, m), 4.38-4.52(2H, m), 4.69(1H, br.s), 7.99(1H, d, J=8.8 Hz), 8.13(1H, dd, J=8.8, 2.5 Hz), 8.53(1H, d, J=2.5 Hz), 8.83(1H, br.s), 9.22(1H, br.s), 10.28(1H, s), 11.43(1H, br.s).
MS(FAB)m/z: 603(M+H)+.

Example 397

N¹-(4-chlorophenyl)-N²-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide citric acid salt

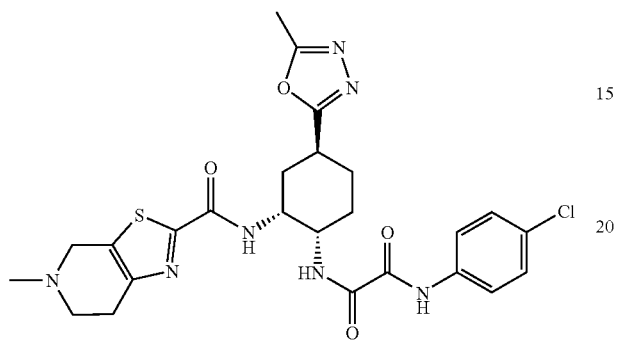

In a manner similar to that described in Example 395, the compound obtained in Referential Example 577 was condensed with the compound obtained in Referential Example 374, and the condensed product was treated with hydrochloric acid for deprotection. The deprotected compound was condensed with the compound obtained in Referential Example 10, and the product was treated with citric acid, whereby the title compound was obtained.
¹H-NMR(DMSO-d₆)δ: 1.66-1.82(2H, m), 1.85-1.97(1H, m), 2.02-2.23(2H, m), 2.34-2.48(1H, m), 2.46(3H, s), 2.63 (2H, d, J=15.4 Hz), 2.72(2H, d, J=15.4 Hz), 2.95(3H, s), 3.03-3.82(5H, m), 3.84-3.92(2H, m), 4.07-4.20(1H, m), 4.37-4.46(1H, m), 7.42(2H, d, J=8.8 Hz), 7.84(2H, d, J=8.8 Hz), 8.78(1H, d, J=7.3 Hz), 9.13(1H, d, J=8.1 Hz), 10.83(1H, s).
MS(ESI)m/z: 558(M+H)+.

Example 398

N¹-(5-chloropyridin-2-yl)-N²-((1S,2R,4S)-4-(5-methyl-1,3,4-oxadiazol-2-yl)-2-{[(6-methyl-5,6,7,8-tetrahydro[1,6]naphthyridin-2-yl)carbonyl]amino}cyclohexyl)ethanediamide citric acid salt

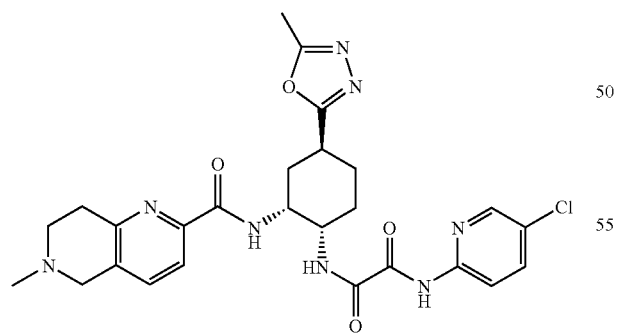

In a manner similar to that described in Example 395, the compound obtained in Referential Example 577 was condensed with the compound obtained in Referential Example 266, and the condensed product was treated with hydrochloric acid for deprotection. The deprotected compound was condensed with the compound obtained in Referential Example 540, and the product was treated with citric acid, whereby the title compound was obtained.

¹H-NMR(DMSO-d₆)δ: 1.70-1.87(2H, m), 1.90-2.21(3H, m), 2.29-2.40(1H, m), 2.47(3H, s), 2.59(3H, s), 2.62(2H, d, J=15.4 Hz), 2.71(2H, d, J=15.4 Hz), 2.90-3.80(5H, m), 3.87-3.95(2H, m), 4.08-4.19(1H, m), 4.48-4.58(1H, m), 7.74(1H, d, J=8.1 Hz), 7.84(1H, d, J=8.1 Hz), 7.98-8.07(2H, m), 8.44-8.48(1H, m), 8.59(1H, d, J=8.1 Hz), 9.21(1H, d, J=7.8 Hz), 10.31(1H, s).
MS(ESI)m/z: 553(M+H)+.

Example 399

N-[(1R,2S,5S)-2-{[(5-chloro-1H-indol-2-yl)carbonyl]amino}-5-(5-methyl-1,3,4-oxadiazol-2-yl)cyclohexyl]-5-methyl-4,5,6,7-tetrahydrothiazolo[5,4-c]pyridine-2-carboxamide citric acid salt

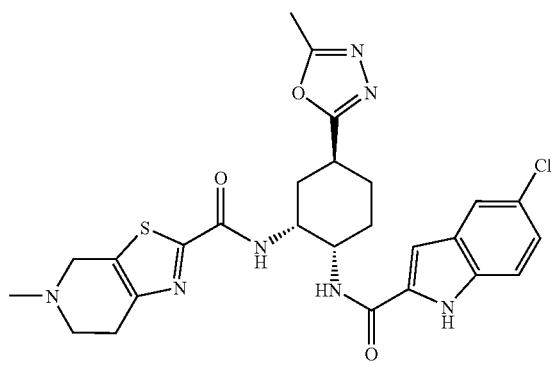

In a manner similar to that described in Example 395, the compound obtained in Referential Example 577 was condensed with 5-chloroindole-2-carboxylic acid, and the condensed product was treated with hydrochloric acid for deprotection. The deprotected compound was condensed with the compound obtained in Referential Example 10, and the product was treated with citric acid, whereby the title compound was obtained.
¹H-NMR(DMSO-d₆)δ: 1.71-1.85(2H, m), 1.90-2.21(3H, m), 2.31-2.43(1H, m), 2.47(3H, s), 2.63(2H, d, J=15.2 Hz), 2.72(2H, d, J=15.2 Hz), 2.94(3H, s), 3.05-3.95(7H, m), 4.20-4.31(1H, m), 4.49-4.58(1H, m), 7.10(1H, d, J=1.6 Hz), 7.19 (1H, dd, J=8.8, 2.0 Hz), 7.44(1H, d, J=8.8 Hz), 7.70(1H, d, J=2.0 Hz), 8.40(1H, d, J=7.6 Hz), 8.44(1H, d, J=7.6 Hz), 11.79(1H, s).
MS(ESI)m/z: 554(M+H)+.

Example 400

N¹-(5-chloro-2-thienyl)-N²-((1S,2R,4S)-4-(5-methyl-1,3,4-oxadiazol-2-yl)-2-{[(6-methyl-5,6,7,8-tetrahydro[1,6]naphthyridin-2-yl)carbonyl]amino}cyclohexyl)ethanediamide citric acid salt

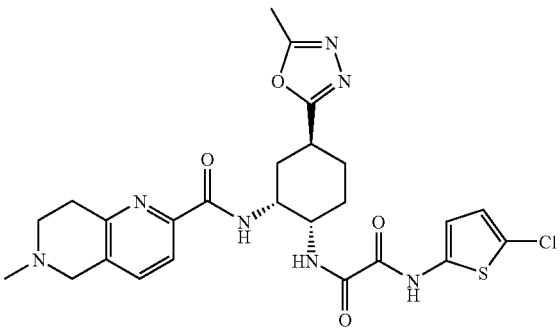

In a manner similar to that described in Example 395, a lithium salt of a carboxylic acid prepared through hydrolyzing the compound obtained in Referential Example 356 was condensed with the compound obtained in Referential Example 577, and the condensed product was treated with hydrochloric acid for deprotection. The deprotected compound was condensed with the compound obtained in Referential Example 540, and the product was treated with citric acid, whereby the title compound was obtained.

$^1$H-NMR(DMSO-d$_6$)δ: 1.70-1.86(2H, m), 1.90-2.21(3H, m), 2.27-2.39(1H, m), 2.46(3H, s), 2.58(3H, s), 2.61(2H, d, J=15.4 Hz), 2.71(2H, d, J=15.4 Hz), 2.98-3.95(7H, m), 4.09-4.19(1H, m), 4.47-4.56(1H, m), 6.90(1H, d, J=4.2 Hz), 6.95 (1H, d, J=4.2 Hz), 7.74(1H, d, J=7.8 Hz), 7.83(1H, d, J=7.8 Hz), 8.58(1H, d, J=8.0 Hz), 9.15(1H, d, J=8.0 Hz), 12.32(1H, s).

MS(ESI)m/z: 558 (M+H)$^+$.

Example 401

N$^1$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-N$^2$-{5-[2-(trimethylsilyl)ethynyl]pyridin-2-yl}ethanediamide

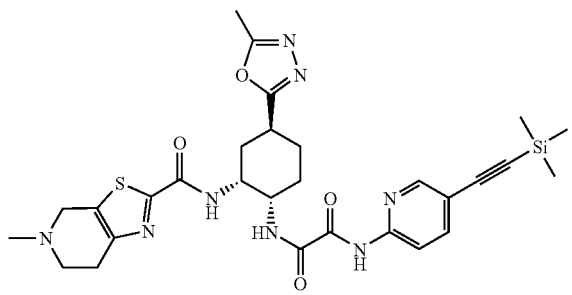

In a manner similar to that employed in Referential Example 455, the title compound was prepared from the compound obtained in Example 396.

$^1$H-NMR(CDCl$_3$)δ: 0.26(9H, s), 1.77-1.92(2H, m), 2.08-2.43(4H, m), 2.52(6H, s), 2.81-2.89(2H, m), 2.93-2.98(2H, m), 3.19-3.28(1H, m), 3.68-3.77(2H, m), 4.13-4.22(1H, m), 4.68-4.74(1H, m), 7.48(1H, d, J=8.4 Hz), 7.78(1H, dd, J=8.4, 2.3 Hz), 8.11-8.17(2H, m), 8.44(1H, d, J=2.3 Hz), 9.73(1H, s).

MS(FAB)m/z: 621(M+H)$^+$.

Example 402

N$^1$-(5-ethynylpyridin-2-yl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl] amino}cyclohexyl)ethanediamide

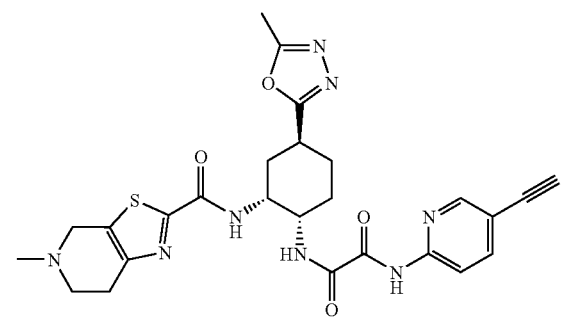

Potassium fluoride (116 mg) was added to a solution of the compound obtained in Example 401 (617 mg) in methanol (30 mL), and the mixture was stirred for 7 hours at room temperature. The solvent was removed under reduced pressure, and methylene chloride and water were added to the residue to partition the mixture. The organic layer was dried over sodium sulfate anhydrate, and the solvent was removed under reduced pressure. The residue was purified through silica gel flash column chromatography (methylene chloride: methanol=93:7). The thus-obtained solid was dissolved in methanol, water was added thereto, and the solvent was removed under reduced pressure, to thereby yield the title compound (287 mg).

$^1$H-NMR(CDCl$_3$)δ: 1.81-1.96(2H, m), 2.07-2.19(2H, m), 2.27(1H, br.s), 2.41(1H, d, J=13.2 Hz), 2.52(3H, s), 2.58(3H, s), 2.88-3.07(4H, m), 3.22(1H, s), 3.27(1H, br.s), 3.76-3.92 (2H, m), 4.20(1H, s), 4.71-4.76(1H, m), 7.60(1H, d, J=8.3 Hz), 7.79(1H, d, J=8.3 Hz), 8.14(1H, d, J=8.3 Hz), 8.23(1H, d, J=7.4 Hz), 8.45(1H, s), 9.81(1H, s).

MS(FAB)m/z: 549(M+H)$^+$.

Example 403

7-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-3-cinnolinecarboxamide citric acid salt

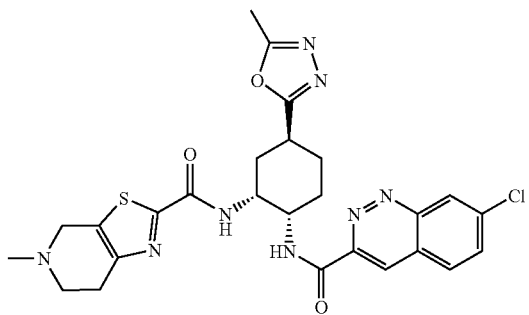

In a manner similar to that described in Example 214, the compound obtained in Referential Example 580 was treated with hydrochloric acid for deprotection. The deprotected compound was condensed with the compound obtained in Referential Example 10, and the product was treated with citric acid, whereby the title compound was obtained.

$^1$H-NMR(DMSO-d$_6$)δ: 1.75-1.90(2H, m), 1.91-2.03(1H, m), 2.10-2.22(1H, m), 2.25-2.52(2H, m), 2.47(3H, s), 2.63 (2H, d, J=15.4 Hz), 2.73(2H, d, J=15.4 Hz), 2.96(3H, s), 3.00-3.95(7H, m), 4.41-4.58(2H, m), 8.02(1H, ddd, J=8.8, 2.0, 2.0 Hz), 8.39(1H, dd, J=8.8, 1.6 Hz), 8.65-8.70(1H, m), 8.90-8.94(1H, m), 9.00(1H, d, J=6.8 Hz), 9.66(1H, d, J=8.4 Hz).

MS(ESI)m/z: 5.67(M+H)$^+$.

Example 404

N-[(1R,2S,5S)-2-{[(Z)-3-(4-chlorophenyl)-2-fluoroacryloyl]amino}-5-(5-methyl-1,3,4-oxadiazol-2-yl) cyclohexyl]-5-methyl-4,5,6,7-tetrahydrothiazolo[5,4-c]pyridine-2-carboxamide citric acid salt

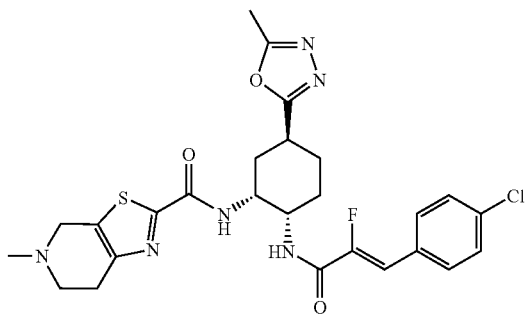

In a manner similar to that described in Example 395, the compound obtained in Referential Example 577 was condensed with the compound obtained in Referential Example 516, and the condensed product was treated with hydrochloric acid for deprotection. The deprotected compound was condensed with the compound obtained in Referential Example 10, and the product was treated with citric acid, whereby the title compound was obtained.

$^1$H-NMR(DMSO-$d_6$)δ: 1.66-1.80(2H, m), 1.85-1.96(1H, m), 2.00-2.16(2H, m), 2.30-2.41(1H, m), 2.46(3H, s), 2.63 (2H, d, J=15.6 Hz), 2.72(2H, d, J=15.6 Hz), 2.96(3H, s), 3.10-3.95(7H, m), 4.11-4.22(1H, m), 4.40-4.50(1H, m), 6.90 (1H, d, J=38.8 Hz), 7.51(2H, d, J=8.4 Hz), 7.68(2H, d, J=8.4 Hz), 8.54(1H, d, J=7.2 Hz), 8.62(1H, d, J=7.6 Hz).

MS(ESI)m/z: 559(M+H)$^+$.

Example 405

7-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-3-isoquinolinecarboxamide citric acid salt

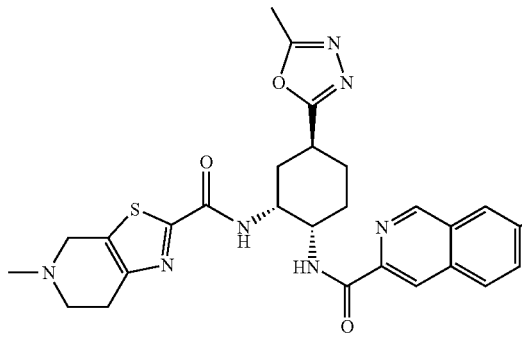

In a manner similar to that described in Example 214, the compound obtained in Referential Example 581 was treated with hydrochloric acid for deprotection. The deprotected compound was condensed with the compound obtained in Referential Example 10, and the product was treated with citric acid, whereby the title compound was obtained.

$^1$H-NMR(DMSO-$d_6$)δ: 1.69-1.86(2H, m), 1.89-2.03(1H, m), 2.05-2.19(1H, m), 2.20-2.34(1H, m), 2.34-2.49(1H, m), 2.47(3H, s), 2.63(2H, d, J=15.4 Hz), 2.72(2H, d, J=15.4 Hz), 2.96(3H, s), 3.00-3.80(5H, m), 3.84-3.91(2H, m), 4.30-4.42 (1H, m), 4.47-4.56(1H, m), 7.91(1H, dd, J=8.8, 2.2 Hz), 8.27(1H, d, J=8.8 Hz), 8.37-8.41(1H, m), 8.61(1H, s), 8.95 (1H, d, J=7.3 Hz), 9.08(1H, d, J=8.3 Hz), 9.36(1H, s).

MS(ESI)m/z: 566(M+H)$^+$.

Example 406

6-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-4-oxo-1,4-dihydro-2-quinazolinecarboxamide citric acid salt

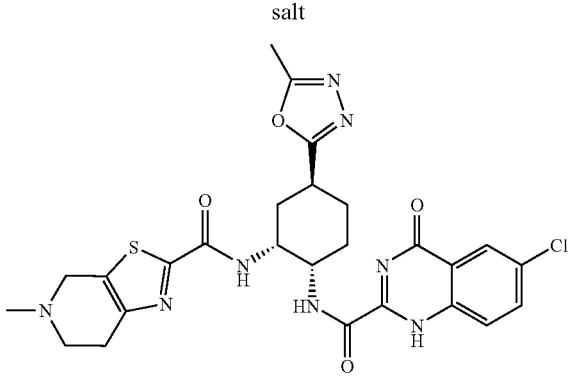

In a manner similar to that described in Example 395, the compound obtained in Referential Example 577 was condensed with the compound obtained in Referential Example 349, and the condensed product was treated with hydrochloric acid for deprotection. The deprotected compound was condensed with the compound obtained in Referential Example 10, and the product was treated with citric acid, whereby the title compound was obtained.

$^1$H-NMR(DMSO-$d_6$)δ: 1.71-1.88(2H, m), 1.90-2.02(1H, m), 2.07-2.26(2H, m), 2.34-2.44(1H, m), 2.47(3H, s), 2.63 (2H, d, J=15.4 Hz), 2.73(2H, d, J=15.4 Hz), 2.95(3H, s), 3.17-3.94(7H, m), 4.18-4.30(1H, m), 4.46-4.56(1H, m), 7.76 (1H, d, J=8.8 Hz), 7.89-7.94(1H, m), 8.08-8.13(1H, m), 8.76-8.85(1H, m), 8.96-9.06(1H, m).

MS(ESI)m/z: 583(M+H)$^+$.

Example 407

N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,2,4-oxadiazol-5-yl)cyclohexyl]ethanediamide hydrochloride

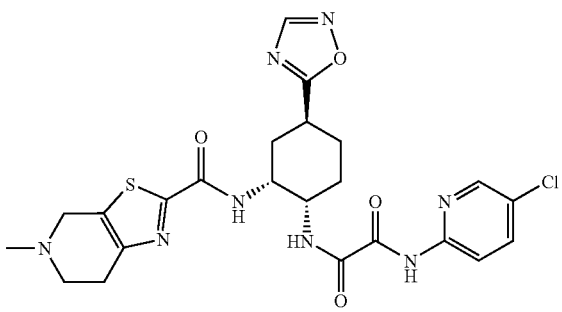

In a manner similar to that described in Example 387, the compound obtained in Referential Example 583 was treated with hydrochloric acid for deprotection. The deprotected compound was condensed with the compound obtained in Referential Example 266, and the product was treated with hydrochloric acid, whereby the title compound was obtained.

$^1$H-NMR(DMSO-$d_6$)δ: 1.65-1.85(2H, m), 1.92-2.05(1H, m), 2.09-2.23(2H, m), 2.37-2.50(1H, m), 2.92(3H, s), 3.11-3.57(4H, m), 3.71(1H, br.s), 4.14(1H, br.s), 4.44(2H, br.s), 4.64-4.79(1H, m), 7.98-8.09(2H, m), 8.46(1H, br.s), 8.84(1H, br.s), 8.91(1H, br.s), 9.15-9.33(1H, m), 10.29(1H, br.s), 11.36-11.67(1H, m).

MS(FAB)m/z: 545(M+H)$^+$.

Example 408

N$^1$-(5-chloropyridin-2-yl)-N$^2$-{(1S,2R,4S)-2-{[(5-methyl-4,5,6,7-tetrahydrothiazolo[5,4-c]pyridin-2-yl)carbonyl]amino}-4-[5-(trifluoromethyl)-1,3,4-oxadiazol-2-yl]cyclohexyl}ethanediamide hydrochloride

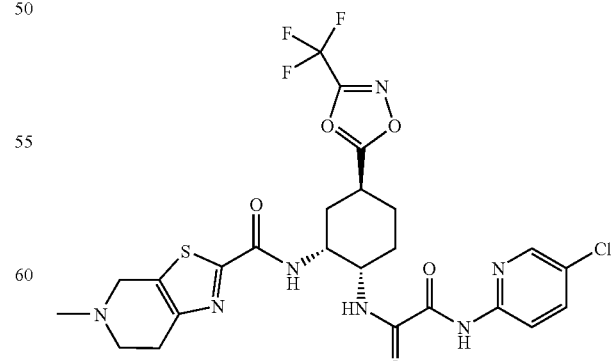

In a manner similar to that described in Example 214, the compound obtained in Referential Example 586 was treated with hydrochloric acid for deprotection. The deprotected compound was condensed with the compound obtained in Referential Example 10, and the product was treated with hydrochloric acid, whereby the title compound was obtained.

$^1$H-NMR(DMSO-$d_6$)δ: 1.70-1.88(2H, m), 1.95-2.06(1H, m), 2.10-2.23(2H, m), 2.42-2.49(1H, m), 2.92(3H, s), 3.09-3.81(5H, m), 4.15(1H, br.s), 4.33-4.56(2H, m), 4.57-4.79(1H, m), 7.99-8.08(2H, m), 8.46(1H, br.s), 8.86(1H, d, J=7.1 Hz), 9.24(1H, br.s), 10.30(1H, s), 11.48(1H, br.s).

MS(ESI)m/z: 613(M+H)$^+$.

Example 409

N$^1$-(5-chloro-2-thienyl)-N$^2$-((1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)ethanediamide hydrochloride

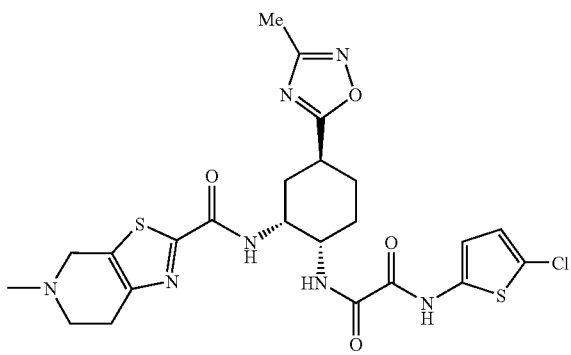

In a manner similar to that described in Example 387, the compound obtained in Referential Example 560 was treated with hydrochloric acid for deprotection. The deprotected compound was condensed with a lithium salt of a carboxylic acid prepared through hydrolyzing the compound obtained in Referential Example 356, and the product was again treated with hydrochloric acid, whereby the title compound was obtained.

$^1$H-NMR(DMSO-$d_6$)δ: 1.65-1.82(2H, m), 1.90-1.99(1H, m), 2.06-2.18(2H, m), 2.31(3H, s), 2.36-2.46(1H, m), 2.92(3H, s), 3.21(2H, br.s), 3.32-3.38(1H, m), 3.50(1H, br.s), 3.68(1H, br.s), 4.08-4.16(1H, m), 4.37-4.74(3H, m), 6.91(1H, d, J=4.2 Hz), 6.94(1H, d, J=4.2 Hz), 8.83(1H, d, J=6.9 Hz), 9.15(1H, br.s), 11.43(1H, br.s), 12.31(1H, s).

MS(FAB)m/z: 564 (M+H)$^+$.

Example 410

N$^1$-(6-chloropyridazin-3-yl)-N$^2$-((1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)ethanediamide hydrochloride

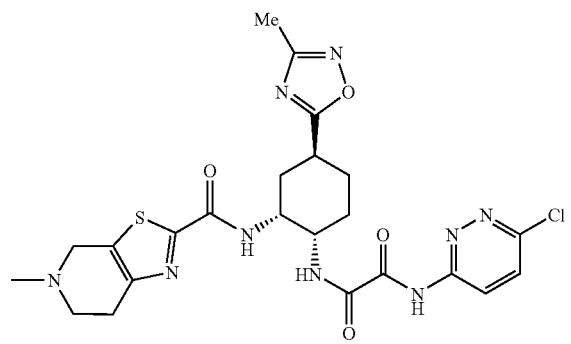

In a manner similar to that described in Example 387, the compound obtained in Referential Example 560 was treated with hydrochloric acid for deprotection. The deprotected compound was condensed with a lithium salt of a carboxylic acid prepared through hydrolyzing the compound obtained in Referential Example 264, and the product was again treated with hydrochloric acid, whereby the title compound was obtained.

$^1$H-NMR(DMSO-$d_6$)δ: 1.69-1.82(2H, m), 1.97-2.03(1H, m), 2.08-2.20(2H, m), 2.32(3H, s), 2.39-2.45(1H, m), 2.81-2.83(4H, m), 3.10-3.53(3H, m), 4.10-4.18(1H, m), 4.36-4.46(4H, m), 7.98(1H, d, J=9.2 Hz), 8.29(1H, d, J=9.2 Hz), 8.79(1H, d, J=7.1 Hz), 9.27(1H, d, J=7.8 Hz), 11.06(1H, s).

MS(FAB)m/z: 560(M+H)$^+$.

Example 411

N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(2-oxo-1,3-oxazolidin-3-yl)cyclohexyl]ethanediamide

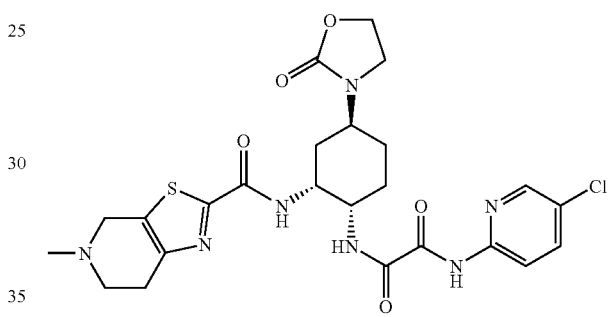

p-Toluenesufonic acid monohydrate (301 mg) was added to a solution of the compound obtained in Referential Example 589 (696 mg) in methanol (70 mL), and the mixture was heated under reflux overnight. p-Toluenesulfonic acid monohydrate (82 mg) was further added to the reaction mixture, and the resultant mixture was heated under reflux for two hours. The solvent was removed under reduced pressure, and the residue was dissolved in N,N-dimethylformamide (50 mL). The compound obtained in Referential Example 564 (338 mg), 3-(3-dimethylaminopropyl)-1-ethylcarbodiimide hydrochloride (552 mg), and 1-hydroxybenzotriazole (97 mg) were added to the solution, and the mixture was stirred overnight at room temperature. Triethylamine (599 μL) was added to the reaction mixture, and the resultant mixture was stirred overnight at 45° C. Water and ethyl acetate were added to the reaction mixture to partition the mixture, and the organic layer was washed with water and saturated brine. The organic layer was dried over sodium sulfate anhydrate, and the solvent was removed under reduced pressure. The residue was purified through silica gel flash column chromatography (methylene chloride:methanol=93:7). A fraction of interest was concentrated, and diethyl ether was added to the residue. The thus-precipitated solid was collected through filtration, to thereby yield the title compound (83 mg).

$^1$H-NMR(CDCl$_3$)δ: 1.46(9H, s), 1.58-1.65(2H, m), 1.79-2.05(4H, m), 3.47-3.55(2H, m), 3.84-3.93(2H, m), 4.29(1H, br.s), 4.33-4.39(2H, m), 5.08(1H, br.s), 7.70(1H, dd, J=8.8, 2.5 Hz), 8.10(1H, br.s), 8.19(1H, dd, J=8.8, 0.7 Hz), 8.31(1H, dd, J=2.5, 0.7 Hz), 9.71(1H, s).

MS(ESI)m/z: 562 (M+H)$^+$.

Example 412

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(tetrazol-1-yl)cyclohexyl]ethanediamide

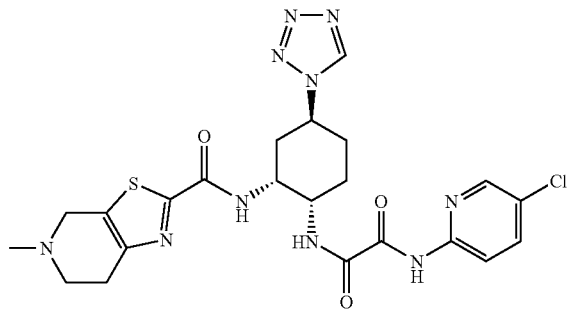

In a manner similar to that described in Example 214, the compound obtained in Referential Example 592 was treated with hydrochloric acid for deprotection. The deprotected compound was condensed with the compound obtained in Referential Example 10, whereby the title compound was obtained.

$^1$H-NMR(CDCl$_3$)δ: 1.90-2.02(1H, m), 2.16-2.29(2H, m), 2.40-2.52(2H, m), 2.52(3H, s), 2.59-2.66(1H, m), 2.80-2.91 (2H, m), 2.94-2.98(2H, m), 3.68-3.78(2H, m), 4.23-4.32(1H, m), 4.78-4.92(2H, m), 7.55(1H, d, J=8.1 Hz), 7.70(1H, dd, J=8.9, 2.6 Hz), 8.05(1H, d, J=7.6 Hz), 8.16(1H, dd, J=8.9, 0.6 Hz), 8.32(1H, dd, J=2.6, 0.6 Hz), 8.72(1H, s), 9.72(1H, s).

MS(ESI)m/z: 545(M+H)$^+$.

Example 413

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1H-pyrrol-1-yl)cyclohexyl]ethanediamide hydrochloride

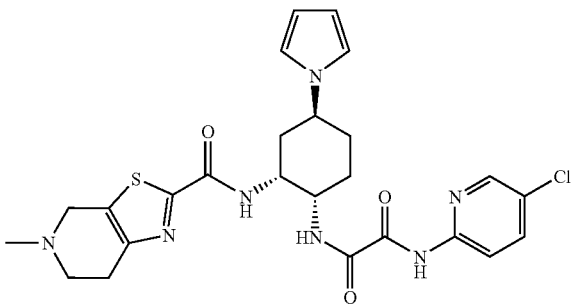

In a manner similar to that described in Example 214, the compound obtained in Referential Example 594 was treated with hydrochloric acid for deprotection. The deprotected compound was condensed with the compound obtained in Referential Example 564, and the product was again treated with hydrochloric acid, whereby the title compound was obtained.

$^1$H-NMR(DMSO-d$_6$)δ: 1.67-1.78(1H, m), 1.82-1.95(1H, m), 1.97-2.06(1H, m), 2.13-2.31(3H, m), 2.94(3H, s), 3.29-3.39(2H, m), 3.51(1H, br.s), 3.73(1H, br.s), 4.12-4.30(2H, m), 4.43(2H, br.s), 4.66-4.80(1H, m), 5.96(2H, br.s), 6.85 (2H, br.s), 7.98-8.06(2H, m), 8.46(1H, br.s), 8.72(1H, br.s), 9.36(1H, br.s), 10.28(1H, br.s), 11.20-11.48(1H, m).

MS(FAB)m/z: 542(M+H)$^+$.

Example 414

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1,2,4-triazol-5-yl)cyclohexyl]ethanediamide hydrochloride

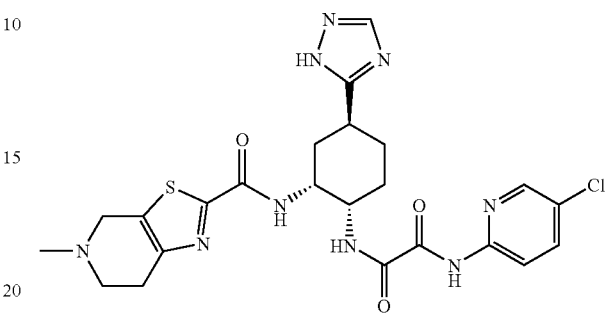

In a manner similar to that described in Example 214, the compound obtained in Referential Example 597 was treated with hydrochloric acid for deprotection. The deprotected compound was condensed with the compound obtained in Referential Example 564, and the product was again treated with hydrochloric acid, whereby the title compound was obtained.

$^1$H-NMR(DMSO-d$_6$)δ: 1.64-1.79(2H, m), 1.83-1.95(1H, m), 1.97-2.08(1H, m), 2.09-2.21(1H, m), 2.28-2.38(1H, m), 2.89(3H, s), 2.97-3.63(5H, m), 4.04-4.16(1H, m), 4.34-4.62 (3H, m), 7.81(1H, br.s), 8.01(1H, dd, J=8.9, 2.3 Hz), 8.05(1H, d, J=8.9 Hz), 8.46(1H, d, J=2.3 Hz), 8.74(1H, d, J=6 Hz), 9.24(1H, br.s), 10.28(1H, s), 13.67(1H, br.s).

MS(FAB)m/z: 544 (M+H)$^+$.

Example 415

N[1]-(5-chloropyridin-2-yl)-N[2]-[(1S,2R,4S)-2-{[(5-methyl-4,5,6,7-tetrahydrothiazolo[5,4-c]pyridin-2-yl)carbonyl]amino}-4-(1-methyl-1H-1,2,4-triazol-5-yl)cyclohexyl]ethanediamide hydrochloride

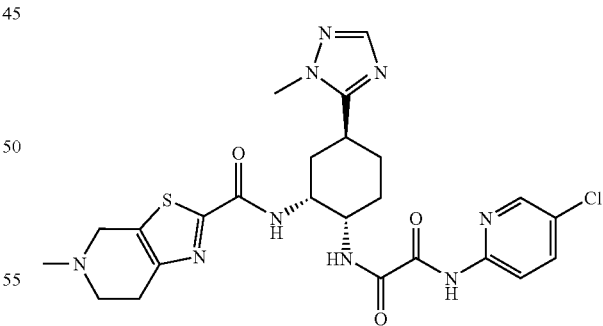

In a manner similar to that described in Example 214, the compound obtained in Referential Example 599 was treated with hydrochloric acid for deprotection. The deprotected compound was condensed with the compound obtained in Referential Example 564, and the product was again treated with hydrochloric acid, whereby the title compound was obtained.

$^1$H-NMR(DMSO-d$_6$)δ: 1.60-1.76(2H, m), 1.77-1.88(1H, m), 1.94-2.04(1H, m), 2.05-2.18(1H, m), 2.25-2.36(1H, m), 2.85-2.98(4H, m), 3.15-3.67(4H, m), 3.78(3H, s), 4.08(1H, br.s), 4.31-4.70(3H, m), 7.97-8.08(2H, m), 8.30(1H, s), 8.44 (1H, br.s), 8.71(1H, d, J=6.8 Hz), 9.14-9.26(1H, m), 10.27 (1H, s).
MS(FAB)m/z: 558 (M+H)+.
MS(FAB)m/z: 544 (M+H)+.

Example 416

7-chloro-N-((1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)-3-cinnolinecarboxamide hydrochloride

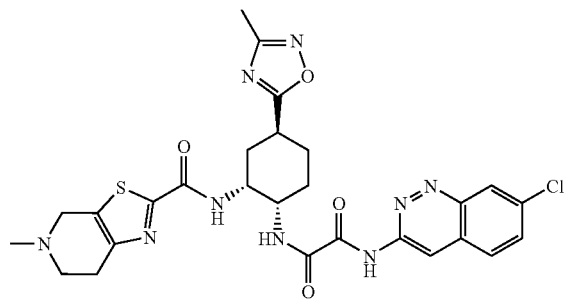

In a manner similar to that described in Example 387, the compound obtained in Referential Example 560 was treated with hydrochloric acid for deprotection. The deprotected compound was condensed with the compound obtained in Referential Example 298, and the product was again treated with hydrochloric acid, whereby the title compound was obtained.

$^1$H-NMR(DMSO-d$_6$)δ: 1.76-1.90(2H, m), 1.97-2.06(1H, m), 2.16-2.23(1H, m), 2.28-2.38(4H, m), 2.44-2.52(1H, m), 2.88(3H, s), 3.21(2H, br.s), 3.27-3.42(1H, m), 3.55(2H, br.s), 4.41-4.56(4H, m), 8.01(1H, dd, J=8.8, 1.7 Hz), 8.38(1H, d, J=9.1 Hz), 8.67(1H, s), 8.91(1H, s), 9.06(1H, d, J=6.9 Hz), 9.64(1H, d, J=7.8 Hz).
MS(ESI)m/z: 567(M+H)+.

Example 417

N$^1$-(5-chloropyridin-2-yl)-N$^2$-((3R,4S)-3-{[(5-methyl-4,5,6,7-tetrahydrothiazolo[5,4-c]pyridin-2-yl)carbonyl]amino}-1-(thiazol-2-yl)piperidin-4-yl)ethanediamide hydrochloride

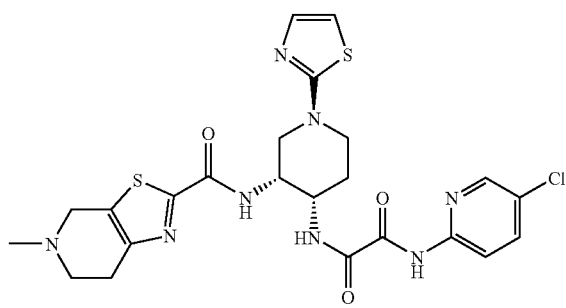

In a manner similar to that described in Example 214, the compound obtained in Referential Example 603 was treated with hydrochloric acid for deprotection. The deprotected compound was condensed with the compound obtained in Referential Example 10, and the product was treated with hydrochloric acid, whereby the title compound was obtained.

$^1$H-NMR(DMSO-d$_6$)δ: 1.73-1.87(1H, m), 2.21-2.37(1H, m), 2.91(3H, s), 3.03-3.29(2H, m), 3.31-3.52(2H, (2H, m), 3.84-4.53(5H, m), 4.64-4.76(1H, m), 6.91(1H, br.s), 7.23(1H, br.s), 8.02(2H, s), 8.46(1H, s), 8.70-8.93(1H, m), 9.28, 9.36(total 1H, each d, J=7.8 Hz), 10.28, 10.33(total 1H, each br.s), 11.30-11.64(1H, br).
MS(ESI)m/z: 561 (M+H)+.

Test Example 1

Determination of Human FXa-Inhibiting Effect (IC$_{50}$ Value):
5% DMSO solutions (10 μl) of each test compound (the concentrations of which were suitably set stepwise), Tris buffer (100 mM Tris, 200 mM potassium chloride, 0.2% BSA, pH 7.4) (40 μl), and 0.0625 U/ml human FXa (Enzyme Research Laboratories, Inc., dissolved and diluted with Tris buffer) (10 μl) were put in respective wells of a 96-well microplate, and a 750 μM aqueous solution (40 μl) of S-2222 (Chromogenix Co.) was added thereto. Absorbance at 405 nm was measured for 10 minutes at room temperature, and an increase in absorbance (ΔOD/min) was calculated. As a control, Tris buffer was used in place of the test compound.
The percent inhibition (%) calculated using the following equation at the final concentration of the test compound and the final concentration of the test compound were plotted on the axis of ordinate and the axis of abscissa of logarithmic normal probability paper, respectively, and the 50% inhibition concentration (IC$_{50}$ value) was calculated.

Percent inhibition (%)=[1−(ΔOD/min of test compound)÷(ΔOD/min of control)]×100

(Result)
As shown in Table 1, the compounds of the present invention were found to have potent FXa-inhibiting effect.

TABLE 1

| Compound | Human FXa-inhibiting effect (IC$_{50}$): nM |
|---|---|
| Ex. 3 | 86 |
| Ex. 7 | 83 |
| Ex. 11 | 92 |
| Ex. 54 | 4.2 |
| Ex. 62 | 3.5 |
| Ex. 63 | 2.5 |
| Ex. 74 | 1.4 |
| Ex. 101 | 26 |
| Ex. 130 | 4.5 |
| Ex. 138 | 4.4 |
| Ex. 143 | 5.8 |
| Ex. 164 | 4.8 |
| Ex. 191 | 1.2 |
| Ex. 192 | 2.0 |
| Ex. 194 | 5.0 |
| Ex. 204 | 1.5 |
| Ex. 246 | 3.1 |
| Ex. 247 | 1.9 |
| Ex. 248 | 5.4 |
| Ex. 384 | 1.0 |
| Ex. 385 | 1.3 |
| Ex. 387 | 1.2 |
| Ex. 394 | 1.1 |
| Ex. 395 | 0.72 |
| Ex. 396 | 1.1 |
| Ex. 402 | 1.1 |
| Ex. 413 | 1.0 |

Test Example 2

Determination of Anti-FXa Activity in Rat Plasma after Oral Administration:

(A) Administration and Blood Collection:

A drug solution (1 mg/ml) obtained by dissolving or suspending a test compound (10 mg) in 0.5% methyl cellulose (MC) was orally administered to rats (10 ml/kg). After 0.5, 1, 2 and 4 hours from the drug administration, the blood (0.5 ml) was collected through the jugular vein using a syringe containing a 3.13% (w/v) aqueous solution (50 µl) of trisodium citrate dihydrate (amount of blood collected: 0.45 ml). For rats of a control group, the same blood collection was conducted after a 0.5% MC solution was administered. Each blood sample was centrifuged at 1500×g for 10 minutes at 4° C. to separate plasma, and the plasma was preserved at −40° C. until it was used in the following determination of anti-FXa activity in plasma.

(B) Determination of FXa-Inhibiting Activity in Plasma:

In the determination of anti-FXa activity in plasma, S-2222 was used as a substrate. Tris buffer (100 mM Tris, 200 mM potassium chloride, 0.2% BSA, pH 7.4) (5456 µl), human FXa (2.5 U/ml, 44 µl), and water (550 µl) were mixed. The resultant human FXa solution was used in the following test.

Rat plasma (5 µl) obtained in accordance with the procedure (A) described above was put in wells of a 96-well microplate, and the above-described human FXa solution (55 µl) and a 750 µM aqueous solution (40 µl) of S-2222 were sequentially added. Immediately after that, absorbance at 405 nm was measured at room temperature and a rate of reaction (ΔOD/min) was calculated with a spectrophotometer SPECTRAmax 340 or 190 (Molecular Devices Co., U.S.A.).

The anti-FXa activity, i.e., percent inhibition (%) was calculated in accordance with the following equation:

Percent inhibition (%)=[1−(ΔOD/min of sample)÷(average value of ΔOD/min of the control group)]×100

(Result)

The compounds described in Examples 63, 191, 192, 194, and 204 exhibited potent FXa-inhibiting activity in plasma (i.e., 62% to 96%) at an oral dose of 10 mg/kg.

The invention claimed is:

1. A compound represented by formula (1):

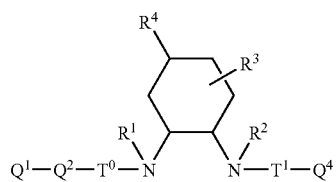

(1)

wherein $R^1$, $R^2$ and $R^3$ are each a hydrogen atom;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$R^4$ represents a substituted or unsubstituted 5-membered heterocyclic group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^0$ represents a carbonyl or thiocarbonyl group; and $T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (wherein R' represents a hydrogen atom, hydroxyl group, alkyl group or alkoxy group), group —C(=O)-$A^1$-N(R")— (wherein $A^1$ represents an alkylene group which has 1 to 5 carbon atoms and may be substituted, and R" represents a hydrogen atom, hydroxyl group, alkyl group or alkoxy group, group), —C(=O)—NH—, group —C(=S)—NH—, group —C(=O)—NH—NH—, group —C(=O)-$A^2$-C(=O)— (wherein $A^2$ represents a single bond or alkylene group having 1 to 5 carbon atoms), group —C(=O)-$A^3$-C(=O)—NH— (wherein $A^3$ represents an alkylene group having 1 to 5 carbon atoms), group —C(=O)—C(=NOR$^a$)—N(R$^b$), group —C(=S)—C(=NOR$^a$)—N(R$^b$)— (wherein R$^a$ represents a hydrogen atom, alkyl group or alkanoyl group, and R$^b$ represents a hydrogen atom, hydroxyl group, alkyl group or alkoxy group), group —C(=O)—N=N—, group —C(=S)—N=N—, group —C(=NOR$^c$)—C(=O)—N(R$^d$)— (wherein R$^c$ represents a hydrogen atom, alkyl group, alkanoyl group, aryl group or aralkyl group, and R$^d$ represents a hydrogen atom, hydroxyl group, alkyl group or alkoxy group), group —C(=N—N(R$^e$)(R$^f$))—C(=O)—N(R$^g$)— (wherein R$^e$ and R$^f$ each independently represent a hydrogen atom, alkyl group, alkanoyl group or alkyl (thiocarbonyl) group, and R$^g$ represents a hydrogen atom, hydroxyl group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)— or thiocarbonyl group; a salt thereof.

2. The compound according to claim 1, a salt thereof, wherein the group $Q^4$ in formula (1) is a group selected from the group consisting of a phenyl group which may be substituted, a naphthyl group which may be substituted, an anthryl group which may be substituted, a phenanthryl group which may be substituted, a styryl group which may be substituted, a phenylethynyl group which may be substituted, a pyridyl group which may be substituted, a pyridazinyl group which may be substituted, a pyradinyl group which may be substituted, a furyl group which may be substituted, a thienyl group which may be substituted, a pyrrolyl group which may be substituted, a thiazolyl group which may be substituted, an oxazolyl group which may be substituted, a pyrimidinyl group which may be substituted, a tetrazolyl group which may be substituted, a thienylethenyl group which may be substituted, a pyridylethenyl group which may be substituted, an indenyl group which may be substituted, an indanyl group which may be substituted, a tetrahydronaphthyl group which may be substituted, a benzofuryl group which may be substituted, an isobenzofuryl group which may be substituted, a benzothienyl group which may be substituted, an indolyl group which may be substituted, an indolinyl group which may be substituted, an isoindolyl group which may be substituted, an isoindolinyl group which may be substituted, an indazolyl group which may be substituted, a quinolyl group which may be substituted, a dihydroquinolyl group which may be substituted, a 4-oxodihydroquinolyl group (dihydroquinolin-4-on) which may be substituted, a tetrahydroquinolyl group which may be substituted, an isoquinolyl group which may be substituted, a tetrahydroisoquinolyl group which may be substituted, a chromenyl group which may be substituted, a chromanyl group which may be substituted, an isochromanyl group which may be substituted, a 4H-4-oxobenzopyranyl group which may be substituted, a 3,4-dihydro-4H-4-oxobenzopyranyl group which may be substituted, a 4H-quinolizinyl group which may be substituted, a quinazolinyl group which may be substituted, a dihydroquinazolinyl group which may be substituted, a tetrahydroquinazolinyl group which may be substituted, a quinoxalinyl group which may be substituted, a tetrahydroquinoxalinyl group which may be substituted, a cinnolinyl group which may be substituted, a tetrahydrocinnolinyl group which may be substituted, an indolizinyl group which may be substituted, a tetrahydroindolizinyl group which may be substituted, a benzothiazolyl group which may be substituted, a tetrahydrobenzothiazolyl group which may be substituted, a benzoxazolyl group which may be substituted, a benzoisothiazolyl group which may be substituted, a benzoisoxazolyl group which may be substituted, a benzimidazolyl group which may be substituted, a naphthyridinyl group which may be substituted, a tetrahydronaphthyridinyl group which may be substituted, a thienopyridyl group which may be substituted, a tetrahydrothienopyridyl group which may be substituted, a thiazolopyridyl group which may be substituted, a tetrahydrothiazolopyridyl group which may be substituted, a thiazolopyridazinyl group which may be substituted, a tetrahydrothiazolopyridazinyl group which may be substituted, a pyrrolopyridyl group which may be substituted, a dihydropyrrolopyridyl group which may be substituted, a tetrahydropyrrolopyridyl group which may be substituted, a pyrrolopyrimidinyl group which may be substituted, a dihydropyrrolopyrimidinyl group which may be substituted, a pyridoquinazolinyl group which may be substituted, a dihydropyridoquinazolinyl group which may be substituted, a pyridopyrimidinyl group which may be substituted, a tetrahydropyridopyrimidinyl group which may be substituted, a pyranothiazolyl group which may be substituted, a dihydropyranothiazolyl group which may be substituted, a furopyridyl group which may be substituted, a tetrahydrofuropyridyl group which may be substituted, an oxazolopyridyl group which may be substituted, a tetrahydrooxazolopyridyl group which may be substituted, an oxazolopyridazinyl group which may be substituted, a tetrahydrooxazolopyridazinyl group which may be substituted, a pyrrolothiazolyl group which may be substituted, a dihydropyrrolothiazolyl group which may be substituted, a pyrroloxazolyl group which may be substituted, a dihydropyrroloxazolyl group which may be substituted, a thienopyrrolyl group which may be substituted, a thiazolopyrimidinyl group which may be substituted, a 4-oxo-tetrahydrocinnolinyl group which may be substituted, a 1,2,4-benzothiadiazinyl group which may be substituted, a 1,1-dioxy-2H-1,2,4-benzothiadiazinyl group which may be substituted, a 1,2,4-benzoxadiazinyl group which may be substituted, a cyclopentapyranyl group which may be substituted, a thienofuranyl group which may be substituted, a furopyranyl group which may be substituted, a pyridoxazinyl group which may be substituted, a pyrazoloxazolyl group which may be substituted, an imidazothiazolyl group which may be substituted, an imidazopyridyl group which may be substituted, a tetrahydroimidazopyridyl group which may be substituted, a pyrazinopyridazinyl group which may be substituted, a benzoisoquinolyl group which may be substituted, a furocinnolyl group which may be substituted, a pyrazolothiazolopyridazinyl group which may be substituted, a tetrahydropyrazolothiazolopyridazinyl group which may be substituted, a hexahydrothiazolopyridazinopyridazinyl group which may be substituted, an imidazotriazinyl group which may be substituted, an oxazolopyridyl group which may be substituted, a benzoxepinyl group which may be substituted, a benzoazcpinyl group which may be substituted, a tetrahydrobenzoazepinyl group which may be substituted, a benzodiazepinyl group which may be substituted, a benzotriazepinyl group which may be substituted, a thienoazepinyl group which may be substituted, a tetrahydrothienoazepinyl group which may be substituted, a thienodiazepinyl group which may be substituted, a thienotriazepinyl group which may be substituted, a thiazoloazepinyl group which may be substituted, a tetrahydrothiazoloazepinyl group which may be substituted, a 4,5,6,7-tetrahydro-5,6-tetramethylenethiazolopyridazinyl group which may be substituted, and a 5,6-trimethylene-4,5,6,7-tetrahydrothiazolopyridazinyl group which may be substituted.

3. The compound according to claim 2, a salt thereof, wherein the substituent(s) on the group $Q^4$ are 1 to 3 substituents selected from the group of substituents consisting of a hydroxyl group, halogen atoms, halogenoalkyl groups, an amino group, a cyano group, aminoalkyl groups, a nitro group, hydroxyalkyl groups, alkoxyalkyl groups, a carboxyl group, carboxyalkyl groups, alkoxycarbonylalkyl groups, acyl groups, an amidino group, a hydroxyamidino group, linear, branched or cyclic alkyl groups having 1 to 6 carbon atoms, linear, branched or cyclic alkoxy groups having 1 to 6 carbon atoms, amidino groups substituted by a linear, branched or cyclic alkyl group having 1 to 6 carbon atoms, amidino groups substituted by a linear, branched or cyclic alkoxy group having 1 to 6 carbon atoms, amidino groups substituted by a linear, branched or cyclic alkoxycarbonyl group having 2 to 7 carbon atoms, linear, branched or cyclic alkenyl groups having 2 to 6 carbon atoms, linear or branched alkynyl groups having 2 to 6 carbon atoms, linear, branched or cyclic alkoxycarbonyl groups having 2 to 6 carbon atoms, a carbamoyl group, mono- or di-alkylcarbamoyl groups having on the nitrogen atom one or two linear, branched or cyclic alkyl groups having 1 to 6 carbon atoms, mono- or di-alkylamino groups having one or two linear, branched or cyclic alkyl groups having 1 to 6 carbon atoms, and 5- or 6-membered nitrogen-containing heterocyclic groups.

4. The compound according to claim 1, a salt thereof, wherein the group $Q^4$ in formula (1) represents one selected from the group consisting of:

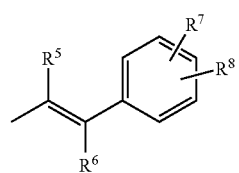

(a)

wherein $R^5$ and $R^6$ each independently represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^7$ and $R^8$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(b)

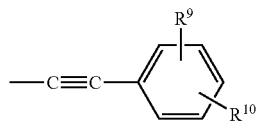

wherein $R^9$ and $R^{10}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(c)

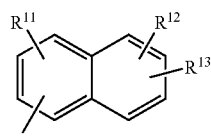

wherein $R^{11}$, $R^{12}$ and $R^{13}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(d)

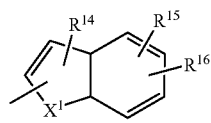

wherein $X^1$ represents $CH_2$, CH, NH, NOH, N, O or S, and $R^{14}$, $R^{15}$ and $R^{16}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(e)

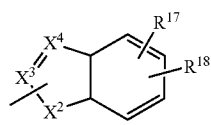

wherein $X^2$ represents NH, N, O or S, $X^3$ represents N, C or CH, $X^4$ represents N, C or CH, and $R^{17}$ and $R^{18}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, excluding the cases where $X^3$ and $X^4$ are a combination of C and CH and are simultaneously C or CH;

(f)

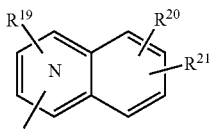

wherein N indicates that 1 or 2 carbon atoms of the ring substituted by $R^{19}$ have been substituted by a nitrogen atom, and $R^{19}$, $R^{20}$ and $R^{21}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(g)

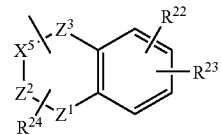

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ and $R^{23}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, and $R^{24}$ represents a hydrogen atom or alkyl group;

(h)

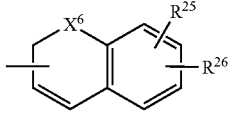

wherein $X^6$ represents O or S, and $R^{25}$ and $R^{26}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(i)

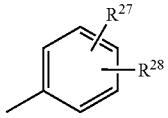

wherein $R^{27}$ and $R^{28}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(j)

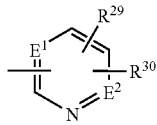

wherein $E^1$ and $E^2$ each independently represent N or CH, and $R^{29}$ and $R^{30}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(k)

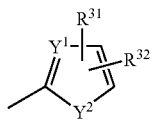

wherein $Y^1$ represents CH or N, $Y^2$ represents —N($R^{33}$)— (in which $R^{33}$ represents a hydrogen atom or alkyl group having 1 to 6 carbon atoms), O or S, and $R^{31}$ and $R^{32}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group; and (l)

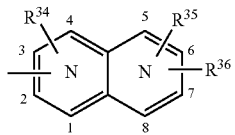

wherein numerals 1 to 8 indicate positions, N indicates that any one of carbon atoms of positions 1 to 4 and any one of carbon atoms of positions 5 to 8 has each been substituted by a nitrogen atom, and $R^{34}$, $R^{35}$ and $R^{36}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group.

5. The compound according to claim 1, a salt thereof, wherein the group $Q^4$ in formula (1) represents one selected from the group consisting of:

(a)

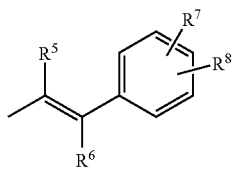

wherein $R^5$ and $R^6$ each independently represent a hydrogen atom or alkyl group, $R^7$ represents a hydrogen atom, and $R^8$ represents a hydrogen atom, halogen atom, alkyl group or alkynyl group;

(b)

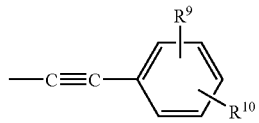

wherein $R^9$ represents a hydrogen atom, and $R^{10}$ represents a hydrogen atom, halogen atom, alkyl group or alkynyl group;

(c)

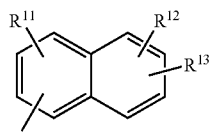

wherein each of $R^{11}$ and $R^{12}$ represents a hydrogen atom, and $R^{13}$ represents a hydrogen atom, halogen atom, alkyl group or alkynyl group;

(d)

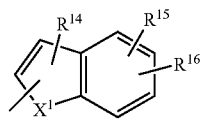

wherein $X^1$ represents NH, NOH, N, O or S, $R^{14}$ represents a hydrogen atom, halogen atom, acyl group, N-alkylcarbamoyl group, N,N-dialkylcarbamoyl group or alkyl group, $R^{15}$ represents a hydrogen atom or halogen atom, and $R^{16}$ represents a hydrogen atom, halogen atom, alkyl group or alkynyl group;

(e)

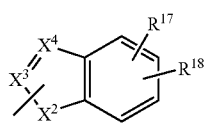

wherein $X^2$ represents NH, O or S, $X^3$ represents N, C or CH, $X^4$ represents N, C or CH, $R^{17}$ represents a hydrogen atom, and $R^{18}$ represents a hydrogen atom, halogen atom, alkyl group or alkynyl group, excluding the cases where $X^3$ and $X^4$ are a combination of C and CH and are simultaneously C or CH;

(f)

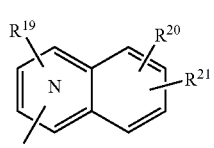

wherein N indicates that 1 or 2 carbon atoms of the ring substituted by $R^{19}$ have been substituted by a nitrogen atom, each of $R^{19}$ and $R^{20}$ represents a hydrogen atom, and $R^{21}$ represents a hydrogen atom, cyano group, halogen atom, alkyl group, alkenyl group, alkynyl group or halogenoalkyl group;

(g)

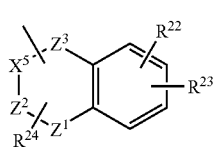

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ represents a hydrogen atom, $R^{23}$ represents a hydrogen atom, halogen atom, alkyl group or alkynyl group, and $R^{24}$ represents a hydrogen atom;

(h)
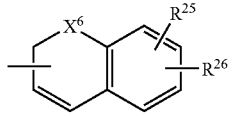

wherein $X^6$ represents O, $R^{25}$ represents a hydrogen atom, and $R^{26}$ represents a hydrogen atom, halogen atom, alkyl group or alkynyl group;

(i)
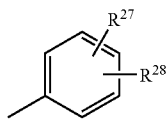

wherein $R^{27}$ represents a hydrogen atom or halogen atom, and $R^{28}$ represents a hydrogen atom, halogen atom, alkyl group or alkynyl group;

(j)
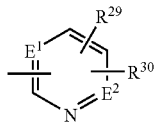

wherein $E^1$ and $E^2$ each independently represent N or CH, $R^{29}$ represents a hydrogen atom or halogen atom, and $R^{30}$ represents a hydrogen atom, halogen atom, alkyl group or alkynyl group;

(k)
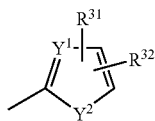

wherein $Y^1$ represents CH or N, $Y^2$ represents —N($R^{33}$)— (in which $R^{33}$ represents a hydrogen atom or alkyl group having 1 to 6 carbon atoms), O or S, $R^{31}$ represents a hydrogen atom or halogen atom, and $R^{32}$ represents a hydrogen atom, halogen atom, alkyl group or alkynyl group; and (l)
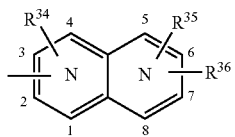

wherein numerals 1 to 8 indicate positions, each N indicates that any one of carbon atoms of positions 1 to 4 and any one of carbon atoms of positions 5 to 8 has each been substituted by a nitrogen atom, $R^{34}$ represents a hydrogen atom or halogen atom, $R^{35}$ represents a hydrogen atom or halogen atom, and $R^{36}$ represents a hydrogen atom, halogen atom, alkyl group or alkynyl group.

6. The compound according to claim 1, a salt thereof, wherein the group $Q^4$ in formula (1) is a group selected from the group consisting of a 4-chlorostyryl, 4-fluorostyryl, 4-bromostyryl, 4-ethynylstyryl, 4-chlorophenylethynyl, 4-fluorophenylethynyl, 4-bromophenylethynyl, 4-ethynylphenylethynyl, 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, 7-ethynyl-2-naphthyl, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzimidazol-2-yl, 5-fluorobenzimidazol-2-yl, 5-bromobenzimidazol-2-yl, 5-ethynylbenzimidazol-2-yl, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, 7-ethynylcinnolin-3-yl, 7-chloro-2H-chromen-3-yl, 7-fluoro-2H-chromen-3-yl, 7-bromo-2H-chromen-3-yl, 7-ethynyl-2H-chromen-3-yl, 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, 6-ethynyl-4-oxo-1,4-dihydroquinazolin-2-yl, phenyl, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl, 3,4-dibromophenyl, 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 6-chloro-3-pyridazinyl, 6-fluoro-3-pyridazinyl, 6-bromo-3-pyridazinyl, 6-ethynyl-3-pyridazinyl, 5-chloro-2-thiazolyl, 5-fluoro-2-thiazolyl, 5-bromo-2-thiazolyl, 5-ethynyl-2-thiazolyl, 2-chlorothieno[2,3-b]pyrrol-5-yl, 2-fluorothieno[2,3-b]pyrrol-5-yl, and 2-bromothieno[2,3-b]pyrrol-5-yl or 2-ethynylthieno[2,3-b]pyrrol-5-yl group.

7. The compound according to claim 1, a salt thereof, wherein the group $Q^1$ in formula (1) is a saturated or unsaturated, bicyclic or tricyclic condensed hydrocarbon group which may be substituted, or a saturated or unsaturated, bicyclic or tricyclic condensed heterocyclic group which may be substituted.

8. The compound according to claim 7, a salt thereof, wherein the group $Q^1$ in formula (1) is one selected from the group consisting of a thienopyridyl group which may be substituted, tetrahydrothienopyridyl group which may be substituted, thiazolopyridyl group which may be substituted, tetrahydrothiazolopyridyl group which may be substituted, thiazolopyridazinyl group which may be substituted, tetrahydrothiazolopyridazinyl group which may be substituted, pyranothiazolyl group which may be substituted, dihydropyranothiazolyl group which may be substituted, furopyridyl group which may be substituted, tetrahydrofuropyridyl group which may be substituted, oxazolopyridyl group which may be substituted, tetrahydrooxazolopyridyl group which may be substituted, pyrrolopyridyl group which may be substituted, dihydropyrrolopyridyl group which may be substituted, tetrahydropyrrolopyridyl group which may be substituted, pyrrolopyrimidinyl group which may be substituted, dihydropyrrolopyrimidinyl group which may be substituted, oxazolopyridazinyl group which may be substituted, tetrahydrooxazolopyridazinyl group which may be substituted, pyrrolothiazolyl group which may be substituted, dihydropyrrolothiazolyl group which may be substituted, pyrrolooxazolyl group which may be substituted, dihydropyrrolooxazolyl group which may be substituted, benzothiazolyl group which may be substituted, tetrahydrobenzothiazolyl group which may be substituted, thiazolopyrimidinyl group which may be substituted, dihydrothiazolopyrimidinyl group which may be substituted, benzoazepinyl group which may be substituted, tetrahydrobenzoazepinyl group which may be substituted, thiazoloazepinyl group which may be substituted, tetrahydrothiazoloazepinyl group which may be substituted, thienoazepinyl group which may be substituted, tetrahydrothienoazepinyl group which may be substituted, 4,5,6,7-tetrahydro-5,6-tetramethylenethiazolopyridazinyl group which may be substituted, and 5,6-trimethylene-4,5,6,7-tetrahydrothiazolopyridazinyl group which may be substituted.

9. The compound according to claim 7, a salt thereof, wherein the substituent(s) on the group $Q^1$ are 1 to 3 substituents selected from the group consisting of a hydroxyl group, halogen atoms, halogenoalkyl groups, an amino group, a cyano group, an amidino group, a hydroxyamidino group, $C_1$-$C_6$ alkyl groups, $C_3$-$C_6$ cycloalkyl $C_1$-$C_6$ alkyl groups, hydroxy $C_1$-$C_6$ alkyl groups, $C_1$-$C_6$ alkoxy groups, $C_1$-$C_6$ alkoxy $C_1$-$C_6$ alkyl group, a carboxyl group, $C_2$-$C_6$ carboxyalkyl groups, $C_2$-$C_6$ alkoxycarbonyl $C_1$-$C_6$ alkyl groups, amidino groups substituted by a $C_2$-$C_6$ alkoxycarbonyl group, $C_2$-$C_6$ alkenyl groups, $C_2$-$C_6$ alkynyl groups, $C_2$-$C_6$ alkoxycarbonyl groups, amino $C_1$-$C_6$ alkyl groups, $C_1$-$C_6$ alkylamino $C_1$-$C_6$ alkyl groups, di($C_1$-$C_6$ alkyl)amino $C_1$-$C_6$ alkyl groups, $C_2$-$C_6$ alkoxycarbonylamino $C_1$-$C_6$ alkyl groups, $C_1$-$C_6$ alkanoyl groups, $C_1$-$C_6$ alkanoylamino $C_1$-$C_6$ alkyl groups, $C_1$-$C_6$ alkylsulfonyl groups, $C_1$-$C_6$ alkylsulfonylamino $C_1$-$C_6$ alkyl groups, a carbamoyl group, $C_1$-$C_6$ alkylcarbamoyl groups, N,N-di($C_1$-$C_6$ alkyl)carbamoyl groups, $C_1$-$C_6$ alkylamino groups, di($C_1$-$C_6$ alkyl)amino groups, aminosulfonyl groups, arylsulfonyl groups, arylcarbonyl groups which may have a substituent such as a halogen atom, $C_2$-$C_6$ alkoxycarbonyl($C_1$-$C_6$ alkyl)amino $C_1$-$C_6$ alkyl groups, $C_1$-$C_6$ alkylsulfonyl $C_1$-$C_6$ alkyl groups, 5- or 6-membered heterocyclic groups containing one of nitrogen, oxygen and sulfur or the same or different two atoms thereof, 5- or 6-membered heterocyclic group $C_1$-$C_4$ alkyl group, 5- to 6-membered heterocyclic group-carbonyl groups, 5- or 6-membered heterocyclic group-amino $C_1$-$C_4$ alkyl groups, 5- or 6-membered heterocyclic group-amino groups, 5- or 6-membered heterocyclic group-oxy groups, 3- to 6-membered heterocyclic group-carbonyl $C_1$-$C_4$ alkyl groups and 5- or 6-membered heterocyclic group-($C_1$-$C_6$ alkyl)amino $C_1$-$C_4$ alkyl groups.

10. The compound according to claim 1, a salt thereof, wherein the group $T^1$ in formula (1) is one selected from the group consisting of a carbonyl group, —C(=O)—C(=O)—

N(R')—, —C(=S)—C(=O)—N(R')—, —C(=O)—C(=S)—N(R')— and —C(=S)—C(=S)—N(R')— wherein R' represents a hydrogen atom, hydroxyl group, alkyl group or alkoxy group.

11. The compound according to claim 10, a salt thereof, wherein the group $T^1$ in formula (1) is selected from the group consisting of —C(=O)—C(=O)—N(R')—, —C(=S)—C(=O)—N(R')—, —C(=O)—C(=S)—N(R')— and —C(=S)—C(=S)—N(R')— wherein R' represents a hydrogen atom, hydroxyl group, alkyl group or alkoxy group.

12. The compound according to claim 1, which is represented by formula (1):

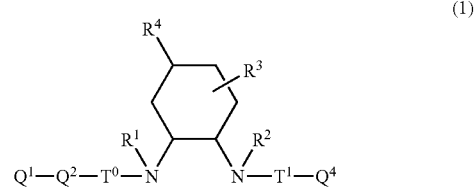

(1)

wherein $R^1$, $R^2$ and $R^3$ represent a hydrogen atom;

$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted; and $R^4$ represents a substituted or unsubstituted 5-membered heterocyclic group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^0$ represents a carbonyl or thiocarbonyl group; and $T^1$ represents a carbonyl group, sulfonyl group or thiocarbonyl group; a salt thereof.

13. The compound according to claim 12, a salt thereof, wherein the group $Q^1$ is a saturated or unsaturated, bicyclic or tricyclic condensed hydrocarbon group which may be substituted, or a saturated or unsaturated, bicyclic or tricyclic condensed heterocyclic group which may be substituted, and $Q^2$ is a single bond.

14. The compound according to claim 13, a salt thereof, wherein the group $Q^1$ is one selected from the group consisting of a thienopyridyl group which may be substituted, tetrahydrothienopyridyl group which may be substituted, thiazolopyridyl group which may be substituted, tetrahydrothiazolopyridyl group which may be substituted, thiazolopyridazinyl group which may be substituted, tetrahydrothiazolopyridazinyl group which may be substituted, pyranothiazolyl group which may be substituted, dihydropyranothiazolyl group which may be substituted, furopyridyl group which may be substituted, tetrahydrofuropyridyl group which may be substituted, oxazolopyridyl group which may be substituted, tetrahydrooxazolopyridyl group which may be substituted, pyrrolopyridyl group which may be substituted, dihydropyrrolopyridyl group which may be substituted, tetrahydropyrrolopyridyl group which may be substituted, pyrrolopyrimidinyl group which may be substituted, dihydropyrrolopyrimidinyl group which may be substituted, oxazolopyridazinyl group which may be substituted, tetrahydrooxazolopyridazinyl group which may be substituted, pyrrolothiazolyl group which may be substituted, dihydropyrrolothiazolyl group which may be substituted, pyrrolooxazolyl group which may be substituted, dihydropyrrolooxazolyl group which may be substituted, benzothiazolyl group which may be substituted, tetrahydrobenzothiazolyl group which may be substituted, thiazolopyrimidinyl group which may be substituted, dihydrothiazolopyrimidinyl group which may be substituted, benzoazepinyl group which may be substituted, tetrahydrobenzoazepinyl group which may be substituted, thiazoloazepinyl group which may be substituted, tetrahydrothiazoloazepinyl group which may be substituted, thienoazepinyl group which may be substituted, tetrahydrothienoazepinyl group which may be substituted, 4,5,6,7-tetrahydro-5,6-tetramethylenethiazolopyridazinyl group which may be substituted, and 5,6-trimethylene-4,5,6,7-tetrahydrothiazolopyridazinyl group which may be substituted.

15. The compound according to claim 12, a salt thereof, wherein the substituent(s) on the group $Q^1$ are 1 to 3 substituent(s) selected from from the group consisting of a hydroxyl group, halogen atoms, halogenoalkyl groups, an amino group, a cyano group, an amidino group, a hydroxyamidino group, $C_1$-$C_6$ alkyl groups, $C_3$-$C_6$ cycloalkyl $C_1$-$C_6$ alkyl groups, hydroxy $C_1$-$C_6$ alkyl groups, $C_1$-$C_6$ alkoxy groups, $C_1$-$C_6$ alkoxy $C_1$-$C_6$ alkyl groups, a carboxyl group; $C_2$-$C_6$ carboxyalkyl groups, $C_2$-$C_6$ alkoxycarbonyl $C_1$-$C_6$ alkyl groups, amidino groups substituted by a $C_2$-$C_6$ alkoxycarbonyl group, $C_2$-$C_6$ alkenyl groups, $C_2$-$C_6$ alkynyl groups, $C_2$-$C_6$ alkoxycarbonyl groups, amino $C_1$-$C_6$ alkyl groups, $C_1$-$C_6$ alkylamino $C_1$-$C_6$ alkyl groups, di($C_1$-$C_6$ alkyl)amino $C_1$-$C_6$ alkyl groups, $C_2$-$C_6$ alkoxycarbonylamino $C_1$-$C_6$ alkyl groups, $C_1$-$C_6$ alkanoyl groups, $C_1$-$C_6$ alkanoylamino $C_1$-$C_6$ alkyl groups, $C_1$-$C_6$ alkylsulfonyl groups, $C_1$-$C_6$ alkylsulfonylamino $C_1$-$C_6$ alkyl groups, a carbamoyl group, $C_1$-$C_6$ alkylcarbamoyl groups, N,N-di($C_1$-$C_6$ alkyl)carbamoyl groups, $C_1$-$C_6$ alkylamino groups, di($C_1$-$C_6$ alkyl)amino groups, aminosulfonyl groups, arylsulfonyl groups, arylcarbonyl groups which may have a substituent such as a halogen atom, $C_2$-$C_6$ alkoxycarbonyl($C_1$-$C_6$ alkyl)amino $C_1$-$C_6$ alkyl groups, $C_1$-$C_6$ alkylsulfonyl $C_1$-$C_6$ alkyl groups, 5- or 6-membered heterocyclic groups containing one of nitrogen, oxygen and sulfur or the same or different two atoms thereof, 5- or 6-membered heterocyclic group $C_1$-$C_4$ alkyl group, 5- to 6-membered heterocyclic group-carbonyl groups, 5- or 6-membered heterocyclic group amino $C_1$-$C_4$ alkyl group, 5- or 6-membered heterocyclic group-amino groups, 5- or 6-membered heterocyclic group-oxy groups, 3- to 6-membered heterocyclic group-carbonyl $C_1$-$C_4$ alkyl groups and 5- or 6-membered heterocyclic group-($C_1$-$C_6$ alkyl)amino $C_1$-$C_4$ alkyl groups.

16. The compound according to claim 12, a salt thereof, wherein the group $Q^4$ is a group selected from the group consisting of a naphthyl group which may be substituted, an anthryl group which may be substituted, a phenanthryl group which may be substituted, a styryl group which may be substituted, a phenylethynyl group which may be substituted, a thienylethenyl group which may be substituted, a pyridylethenyl group which may be substituted, an indenyl group which may be substituted, an indanyl group which may be substituted, a tetrahydronaphthyl group which may be substituted, a benzofuryl group which may be substituted, an isobenzofuryl group which may be substituted, a benzothienyl group which may be substituted, an indolyl group which may be substituted, an indolinyl group which may be substituted, an isoindolyl group which may be substituted, an isoindolinyl group which may be substituted, an indazolyl group which may be substituted, a quinolyl group which may be substituted, a dihydroquinolyl group which may be substituted, a 4-oxodihydroquinolyl group (dihydroquinolin-4-on) which may be substituted, a tetrahydroquinolyl group which may be substituted, an isoquinolyl group which may be substituted, a tetrahydroisoquinolyl group which may be substituted, a chromenyl group which may be substituted, a chromanyl group which may be substituted, an isochromanyl group which may be substituted, a 4H-4-oxobenzopyranyl group which may be substituted, a 3,4-dihydro-4H-4-oxobenzopyranyl group which may be substituted, a 4H-quinolizinyl group which may be substituted, a quinazolinyl group which may be substituted, a dihydroquinazolinyl group which may be substituted, a tetrahydroquinazolinyl group which may be substituted, a quinoxalinyl group which may be substituted, a tetrahydroquinoxalinyl group which may be substituted, a cinnolinyl group which may be substituted, a tetrahydrocinnolinyl group which may be substituted, an indolizinyl group which may be substituted, a tetrahydroindolizinyl group which may be substituted, a benzothiazolyl group which may be substituted, a tetrahydrobenzothiazolyl group which may be substituted, a benzoxazolyl group which may be substituted, a benzoisothiazolyl group which may be substituted, a benzoisoxazolyl group which may be substituted, a benzimidazolyl group which may be substituted, a naphthyridinyl group which may be substituted, a tetrahydronaphthyridinyl group which may be substituted, a thienopyridyl group which may be substituted, a tetrahydrothienopyridyl group which may be substituted, a thiazolopyridyl group which may be substituted, a tetrahydrothiazolopyridyl group which may be substituted, a thiazolopyridazinyl group which may be substituted, a tetrahydrothiazolopyridazinyl group which may be substituted, a pyrrolopyridyl group which may be substituted, a dihydropyrrolopyridyl group which may be substituted, a tetrahydropyrrolopyridyl group which may be substituted, a pyrrolopyrimidinyl group which may be substituted, a dihydropyrrolopyrimidinyl group which may be substituted, a pyridoquinazolinyl group which may be substituted, a dihydropyridoquinazolinyl group which may be substituted, a pyridopyrimidinyl group which may be substituted, a tetrahydropyridopyrimidinyl group which may be substituted, a pyranothiazolyl group which may be substituted, a dihydropyranothiazolyl group which may be substituted, a furopyridyl group which may be substituted, a tetrahydrofuropyridyl group which may be substituted, an oxazolopyridyl group which may be substituted, a tetrahydrooxazolopyridyl group which may be substituted, an oxazolopyridazinyl group which may be substituted, a tetrahydrooxazolopyridazinyl group which may be substituted, a pyrrolothiazolyl group which may be substituted, a dihydropyrrolothiazolyl group which may be substituted, a pyrrolooxazolyl group which may be substituted, a dihydropyrrolooxazolyl group which may be substituted, a thienopyrrolyl group which may be substituted, a thiazolopyrimidinyl group which may be substituted, a 4-oxotetrahydrocinnolinyl group which may be substituted, a 1,2,4-benzothiadiazinyl group which may be substituted, a 1,1-dioxy-2H-1,2,4-benzothiadiazinyl group which may be substituted, a 1,2,4-benzoxadiazinyl group which may be substituted, a cyclopentapyranyl group which may be substituted, a thienofuranyl group which may be substituted, a furopyranyl group which may be substituted, a pyridoxazinyl group which may be substituted, a pyrazoloxazolyl group which may be substituted, an imidazothiazolyl group which may be substituted, an imidazopyridyl group which may be substituted, a tetrahydroimidazopyridyl group which may be substituted, a pyrazinopyridazinyl group which may be substituted, a benzoisoquinolyl group which may be substituted, a furocinnolyl group which may be substituted, a pyrazolothiazolopyridazinyl group which may be substituted, a tetrahydropyrazolothiazolopyridazinyl group which may be substituted, a hexahydrothiazolopyridazinopyridazinyl group which may be substituted, an imidazotriazinyl group which may be substituted, an oxazolopyridyl group which may be substituted, a benzoxepinyl group which may be substituted, a benzoazepinyl group which may be substituted, a tetrahydrobenzoazepinyl group which may be substituted, a benzodiazepinyl group which may be substituted, a benzotriazepinyl group which may be substituted, a thienoazepinyl group which may be substituted, a tetrahydrothienoazepinyl group which may be substituted, a thienodiazepinyl group which may be substituted, a thienotriazepinyl group which may be substituted, a thiazoloazepinyl group which may be substituted, a tetrahydrothiazoloazepinyl group which may be substituted, a 4,5,6,7-tetrahydro-5,6-tetramethylencthiazolopyridazinyl group which may be substituted and a 5,6-trimethylene-4,5,6,7-tetrahydrothiazolopyridazinyl group which may be substituted.

17. The compound according to claim 12, a salt thereof, wherein the substituent(s) on the group $Q^4$ are 1 to 3 substituents selected from the group consisting of a hydroxyl group, halogen atoms, halogenoalkyl groups, an amino group, a cyano group, aminoalkyl groups, a nitro group, hydroxyalkyl groups, alkoxyalkyl groups, a carboxyl group, carboxyalkyl groups, alkoxycarbonylalkyl groups, acyl groups, an amidino group, a hydroxyamidino group, linear, branched or cyclic alkyl groups having 1 to 6 carbon atoms, linear, branched or cyclic alkoxy groups having 1 to 6 carbon atoms, amidino groups substituted by a linear, branched or cyclic alkyl group having 1 to 6 carbon atoms, amidino groups substituted by a linear, branched or cyclic alkoxy group having 1 to 6 carbon atoms, amidino groups substituted by linear, branched or cyclic alkoxycarbonyl group having 2 to 7 carbon atoms, linear, branched or cyclic alkenyl groups having 2 to 6 carbon atoms, linear or branched alkynyl groups having 2 to 6 carbon atoms, linear, branched or cyclic alkoxycarbonyl groups having 2 to 6 carbon atoms, a carbamoyl group, mono- or di-alkylcarbamoyl groups having on the nitrogen atom one or two linear, branched or cyclic alkyl groups having 1 to 6 carbon atoms, mono- or di-alkylamino groups having one or two linear, branched or cyclic alkyl groups having 1 to 6 carbon atoms, and 5- or 6-membered nitrogen-containing heterocyclic groups.

18. The compound according to claim 12, a salt thereof, wherein the group $Q^4$ represents one selected from the group consisting of:

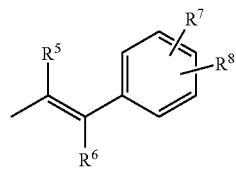

(a)

wherein $R^5$ and $R^6$ each independently represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^7$ and $R^8$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

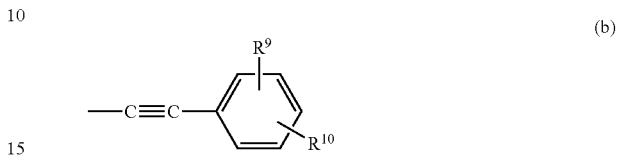

(b)

wherein $R^9$ and $R^{10}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

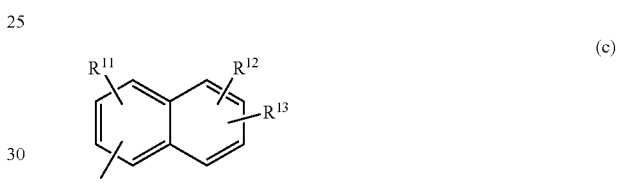

(c)

wherein $R^{11}$ $R^{12}$ and $R^{13}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

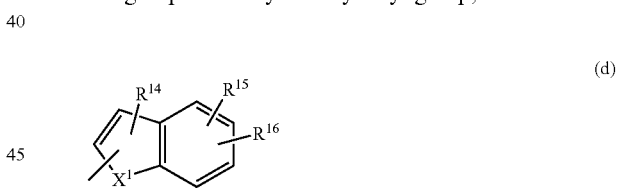

(d)

wherein $X^1$ represents $CH_2$, CH, NH, NOH, N, O or S, and $R^{14}$, $R^{15}$ and $R^{16}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

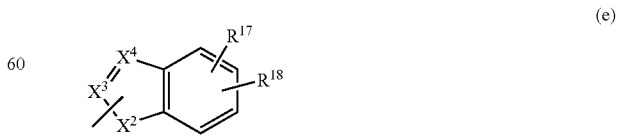

(e)

wherein $X^2$ represents NH, N, O or S, $X^3$ represents N, C or CH, $X^4$ represents N, C or CH, and $R^{17}$ and $R^{18}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, excluding the cases where $X^3$ and $X^4$ are a combination of C and CH and are simultaneously C or CH;

(f)

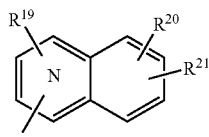

wherein N indicates that 1 or 2 carbon atoms of the ring substituted by $R^{19}$ have been substituted by a nitrogen atom, and $R^{19}$, $R^{20}$ and $R^{21}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

(g)

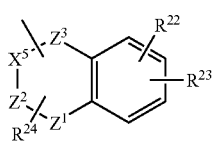

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ and $R^{23}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, and $R^{24}$ represents a hydrogen atom or alkyl group;

(h)

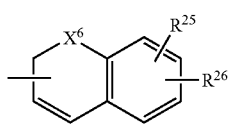

wherein $X^6$ represents O or S, and $R^{25}$ and $R^{26}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group; and (i)

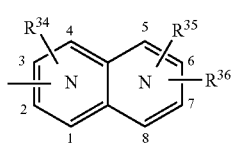

wherein numerals 1 to 8 indicate positions, each N indicates that any one of carbon atoms of positions 1 to 4 and any one of carbon atoms of positions 5 to 8 has each been substituted by a nitrogen atom, and $R^{34}$, $R^{35}$ and $R^{36}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group.

19. The compound according to claim 12, a salt thereof, wherein the group $Q^4$ represents one selected from the group consisting of:

(a)

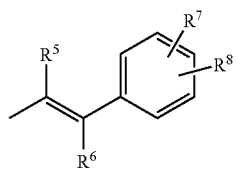

wherein $R^5$ and $R^6$ each independently represent a hydrogen atom or alkyl group, $R^7$ represents a hydrogen atom, and $R^8$ represents a hydrogen atom, halogen atom, alkyl group or alkynyl group;

(b)

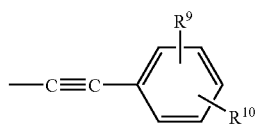

wherein $R^9$ represents a hydrogen atom, and $R^{10}$ represents a hydrogen atom, halogen atom, alkyl group or alkynyl group;

(c)

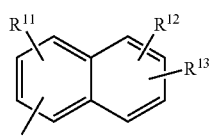

wherein each of $R^{11}$ and $R^{12}$ represents a hydrogen atom, and $R^{13}$ represents a hydrogen atom, halogen atom, alkyl group or alkynyl group;

(d)

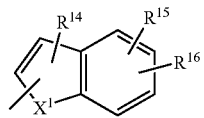

wherein $X^1$ represents NH, NOH, N, O or S, $R^{14}$ represents a hydrogen atom, halogen atom, acyl group, N-alkylcarbamoyl group, N,N-dialkylcarbamoyl group or alkyl group, $R^{15}$ represents a hydrogen atom or halogen atom, and $R^{16}$ represents a hydrogen atom, halogen atom, alkyl group or alkynyl group;

(e)

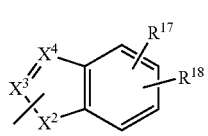

wherein $X^2$ represents NH, O or S, $X^3$ represents N, C or CH, $X^4$ represents N, C or CH, $R^{17}$ represents a hydrogen atom, and $R^{18}$ represents a hydrogen atom, halogen atom, alkyl group or alkynyl group, excluding the cases where $X^3$ and $X^4$ are a combination of C and CH and are simultaneously C or CH;

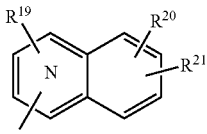
(f)

wherein N indicates that 1 or 2 carbon atoms of the ring substituted by $R^{19}$ have been substituted by a nitrogen atom, each of $R^{19}$ and $R^{20}$ represents a hydrogen atom, and $R^{21}$ represents a hydrogen atom, cyano group, halogen atom, alkyl group, alkenyl group, alkynyl group or halogenoalkyl group;

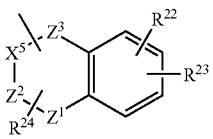
(g)

wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$-$Z^2$ indicates that $X^5$ and $Z^2$ are bonded to each other by a single bond or double bond, $R^{22}$ represents a hydrogen atom, $R^{23}$ represents a hydrogen atom, halogen atom, alkyl group or alkynyl group, and $R^{24}$ represents a hydrogen atom;

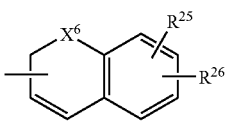
(h)

wherein $X^6$ represents O, $R^{25}$ represents a hydrogen atom, and $R^{26}$ represents a hydrogen atom, halogen atom, alkyl group or alkynyl group; and

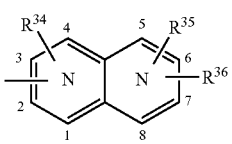
(l)

wherein numerals 1 to 8 indicate positions, each N indicates that any one of carbon atoms of positions 1 to 4 and any one of carbon atoms of positions 5 to 8 has each been substituted by a nitrogen atom, $R^{34}$ represents a hydrogen atom or halogen atom, $R^{35}$ represents a hydrogen atom or halogen atom, and $R^{36}$ represents a hydrogen atom, halogen atom, alkyl group or alkynyl group.

20. The compound according to claim 12, a salt thereof, wherein the group $Q^4$ is one selected from the group consisting of a 4-chlorostyryl, 4-fluorostyryl, 4-bromostyryl, 4-ethynylstyryl, 4-chlorophenylethynyl, 4-fluorophenylethynyl, 4-bromophenylethynyl, 4-ethynylphenylethynyl, 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, 7-ethynyl-2-naphthyl, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzimidazol-2-yl, 5-fluorobenzimidazol-2-yl, 5-bromobenzimidazol-2-yl, 5-ethynylbenzimidazol-2-yl, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, 7-ethynylcinnolin-3-yl, 7-chloro-2H-chromen-3-yl, 7-fluoro-2H-chromen-3-yl, 7-bromo-2H-chromen-3-yl, 7-ethynyl-2H-chromen-3-yl, 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, 6-ethynyl-4-oxo-1,4-dihydroquinazolin-2-yl, 2-chlorothieno[2,3-b]pyrrol-5-yl, 2-fluorothieno[2,3-b]pyrrol-5-yl, 2-bromothieno[2,3-b]pyrrol-5-yl and 2-ethynylthienol[2,3-b]pyrrol-5-yl group.

21. The compound according to claim 12, a salt thereof, wherein $T^1$ is a carbonyl group.

22. The compound according to claim 1, which is represented by formula (1):

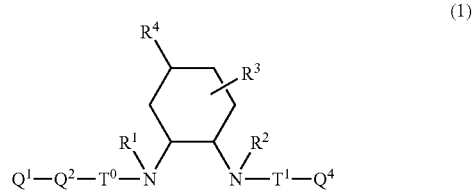
(1)

wherein
$R^1$, $R^2$ and $R^3$ each represent a hydrogen atom;
$Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;
$Q^2$ represents a single bond, a linear or branched alkylene group having 1 to 6 carbon atoms, a linear or branched alkenylene group having 2 to 6 carbon atoms, a linear or branched alkynylene group having 2 to 6 carbon atoms, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$R^4$ represents a substituted or unsubstituted 5-membered heterocyclic group;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^0$ represents a carbonyl or thiocarbonyl group; and $T^1$ represents group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-$A^1$-N(R")— (in which $A^1$ represents an alkylene group which has 1 to 5 carbon atoms and may be substituted, and R" represents a hydrogen atom, hydroxyl group, alkyl group or alkoxy group), group —C(=O)—NH—, group —C(=S)—NH—, group —C(=O)—NH—NH—, group —C(=O)-$A^2$-C(=O)— (in which $A^2$ represents a single bond or alkylene group having 1 to 5 carbon atoms), group —C(=O)-$A^3$-C(=O)—NH— (in which $A^3$ represents an alkylene group having 1 to 5 carbon atoms), group —C(=O)—C(=NOR$^a$)—N(R$^b$)—, group —C(=S)—C(=NOR$^a$)—N(R$^b$)— (in which R$^a$ represents a hydrogen atom, alkyl group or alkanoyl group, and R$^b$ represents a hydrogen atom, hydroxyl group, alkyl group or alkoxy group), group —C(=O)—N=N—, group —C(=S)—N=N—, group —C(=NOR$^c$)—C(=O)—N(R$^d$)— (in which R$^c$ represents a hydrogen atom, alkyl group, alkanoyl group, aryl group or aralkyl group, and R$^d$ represents a hydrogen atom, hydroxyl group, alkyl group or alkoxy group), group —C(=N—N(R$^e$)(R$^f$))—C(=O)—N(R$^g$)— (in which R$^e$ and R$^f$ each independently represent a hydrogen atom, alkyl group, alkanoyl or alkyl(thiocarbonyl) group, and R$^g$ represents a hydrogen atom, hydroxyl group, alkyl group or alkoxy group) group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)— or thiocarbonyl group, a salt thereof.

23. The compound according to claim 22, a salt thereof, wherein the group $Q^1$ is a saturated or unsaturated, bicyclic or tricyclic condensed hydrocarbon group which may be substituted, or a saturated or unsaturated, bicyclic or tricyclic condensed heterocyclic group which may be substituted, and $Q^2$ is a single bond.

24. The compound according to claim 22, a salt thereof, wherein the group $Q^1$ is one selected from the group consisting of a thienopyridyl group which may be substituted, tetrahydrothienopyridyl group which may be substituted, thiazolopyridyl group which may be substituted, tetrahydrothiazolopyridyl group which may be substituted, thiazolopyridazinyl group which may be substituted, tetrahydrothiazolopyridazinyl group which may be substituted, pyranothiazolyl group which may be substituted, dihydropyranothiazolyl group which may be substituted, furopyridyl group which may be substituted, tetrahydrofuropyridyl group which may be substituted, oxazolopyridyl group which may be substituted, tetrahydrooxazolopyridyl group which may be substituted, pyrrolopyridyl group which may be substituted, dihydropyrrolopyridyl group which may be substituted, tetrahydropyrrolopyridyl group which may be substituted, pyrrolopyrimidinyl group which may be substituted, dihydropyrrolopyrimidinyl group which may be substituted, oxazolopyridazinyl group which may be substituted, tetrahydrooxazolopyridazinyl group which may be substituted, pyrrolothiazolyl group which may be substituted, dihydropyrrolothiazolyl group which may be substituted, pyrroloooxazolyl group which may be substituted, dihydropyrroloooxazolyl group which may be substituted, benzothiazolyl group which may be substituted, tetrahydrobenzothiazolyl group which may be substituted, thiazolopyrimidinyl group which may be substituted, dihydrothiazolopyrimidinyl group which may be substituted, benzoazepinyl group which may be substituted, tetrahydrobenzoazepinyl group which may be substituted, thiazoloazepinyl group which may be substituted, tetrahydrothiazoloazepinyl group which may be substituted, thienoazepinyl group which may be substituted, tetrahydrothienoazepinyl group which may be substituted, 4,5,6,7,-tetrahydro-5,6-tetramethylenethiazolopyridazinyl group which may be substituted and 5,6-trimethylene-4,5,6,7-tetrahydrothi azolopyridazinyl group which may be substituted.

25. The compound according to claim 22, a salt thereof, wherein the substituent(s) on the group $Q^1$ are 1 to 3 substituent(s) selected from the group consisting of a hydroxyl group, halogen atoms, halogenoalkyl groups, an amino group, a cyano group, an amidino group, a hydroxyamidino group, $C_1$-$C_6$ alkyl groups, $C_3$-$C_6$ cycloalkyl-$C_1$-$C_6$ alkyl groups, hydroxy-$C_1$-$C_6$ alkyl groups, $C_1$-$C_6$ alkoxy groups, $C_1$-$C_6$ alkoxy-$C_1$-$C_6$ alkyl groups, a carboxyl group, $C_2$-$C_6$ carboxyalkyl groups, $C_2$-$C_6$ alkoxycarbonyl-$C_1$-$C_6$ alkyl groups, amidino groups substituted by a $C_2$-$C_6$ alkoxycarbonyl group, $C_2$-$C_6$ alkenyl groups, $C_2$-$C_6$ alkynyl groups, $C_2$-$C_6$ alkoxycarbonyl groups, amino $C_1$-$C_6$ alkyl groups, $C_1$-$C_6$ alkylamino-$C_1$-$C_6$ alkyl groups, di($C_1$-$C_6$ alkyl)amino-$C_1$-$C_6$ alkyl groups, $C_2$-$C_6$ alkoxycarbonylamino-$C_1$-$C_6$ alkyl groups, $C_1$-$C_6$ alkanoyl groups, $C_1$-$C_6$ alkanoylamino-$C_1$-$C_6$ alkyl groups, $C_1$-$C_6$ alkylsulfonyl groups, $C_1$-$C_6$ alkylsulfonylamino-$C_1$-$C_6$ alkyl groups, a carbamoyl group, $C_1$-$C_6$ alkylcarbamoyl groups, N,N-di($C_1$-$C_6$ alkyl)carbamoyl groups, $C_1$-$C_6$ alkylamino groups, di($C_1$-$C_6$ alkyl)amino groups, aminosulfonyl groups, arylsulfonyl groups, arylcarbonyl groups which may have a substituent such as a halogen atom, $C_2$-$C_6$ alkoxycarbonyl($C_1$-$C_6$ alkyl)amino $C_1$-$C_6$ alkyl groups, $C_1$-$C_6$ alkylsulfonyl $C_1$-$C_6$ alkyl groups, 5- or 6-membered heterocyclic groups containing one of nitrogen, oxygen and sulfur or the same or different two atoms thereof, 5- or 6-membered heterocyclic group-$C_1$-$C_4$ alkyl group, 5- to 6-membered heterocyclic group-carbonyl groups, 5- or 6-membered heterocyclic group-amino-$C_1$-$C_4$ alkyl group, 5- or 6-membered heterocyclic group-amino groups, 5- or 6-membered heterocyclic group-oxy groups, 3- to 6-membered heterocyclic group-carbonyl $C_1$-$C_4$ alkyl groups and 5- or 6-membered heterocyclic group-($C_1$-$C_6$ alkyl)amino $C_1$-$C_4$ alkyl groups.

26. The compound according to claim 22, a salt thereof, wherein the group $Q^4$ is a group selected from the group consisting of a phenyl group which may be substituted, a pyridyl group which may be substituted, a pyridazinyl group which may be substituted, a pyrazinyl group which may be substituted, a furyl group which may be substituted, a thienyl group which may be substituted, a pyrrolyl group which may be substituted, a thiazolyl group which may be substituted, an oxazolyl group which may be substituted, a pyrimidinyl group which may be substituted and a tetrazolyl group which may be substituted.

27. The compound according to claim 22, a salt thereof, wherein the substituent(s) on the group Q⁴ are 1 to 3 substituents selected from the group consisting of a hydroxyl group, halogen atoms, halogenoalkyl groups, an amino group, a cyano group, aminoalkyl groups, a nitro group, hydroxyalkyl groups, alkoxyalkyl groups, a carboxyl group, carboxyalkyl groups, alkoxycarbonylalkyl groups, acyl groups, an amidino group, a hydroxyamidino group, linear, branched or cyclic alkyl groups having 1 to 6 carbon atoms, linear, branched or cyclic alkoxy groups having 1 to 6 carbon atoms, amidino groups substituted by a linear, branched or cyclic alkyl group having 1 to 6 carbon atoms, amidino groups substituted by a linear, branched or cyclic alkoxy group having 1 to 6 carbon atoms, amidino groups substituted by a linear, branched or cyclic alkoxycarbonyl group having 2 to 7 carbon atoms, linear, branched or cyclic alkenyl groups having 2 to 6 carbon atoms, linear or branched alkynyl groups having 2 to 6 carbon atoms, linear, branched or cyclic alkoxycarbonyl groups having 2 to 6 carbon atoms, a carbamoyl group, mono- or di-alkylcarbamoyl groups having on the nitrogen atom one or two linear, branched or cyclic alkyl groups having 1 to 6 carbon atoms, mono- or di-alkylamino groups having one or two linear, branched or cyclic alkyl groups having 1 to 6 carbon atoms, and 5- or 6-membered nitrogen-containing heterocyclic groups.

28. The compound according to claim 22, a salt thereof, wherein the group Q⁴ represents one selected from the group consisting of:

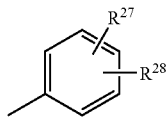

(i)

wherein $R^{27}$ and $R^{28}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group;

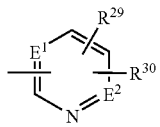

(j)

wherein $E^1$ and $E^2$ each independently represent N or CH, and $R^{29}$ and $R^{30}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group; and

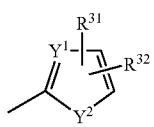

(k)

wherein $Y^1$ represents CH or N, $Y^2$ represents —N($R^{33}$)— (in which $R^{33}$ represents a hydrogen atom or alkyl group having 1 to 6 carbon atoms), O or S, and $R^{31}$ and $R^{32}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group.

29. The compound according to claim 22, a salt thereof, wherein the group Q⁴ represents one selected from the group consisting of:

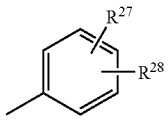

(i)

wherein $R^{27}$ represents a hydrogen atom or halogen atom, and $R^{28}$ represents a hydrogen atom, halogen atom, alkyl group or alkynyl group;

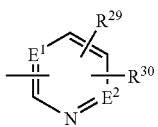

(j)

wherein $E^1$ and $E^2$ each independently represent N or CH, $R^{29}$ represents a hydrogen atom or halogen atom, and $R^{30}$ represents a hydrogen atom, halogen atom, alkyl group or alkynyl group; and

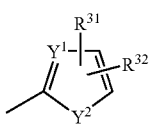

(k)

wherein $Y^1$ is CH or N, $Y^2$ is —N($R^{33}$)— (in which $R^{33}$ represents a hydrogen atom or alkyl group having 1 to 6 carbon atoms), O or S, and $R^{31}$ represents a hydrogen atom or halogen atom, and $R^{32}$ represents a hydrogen atom, halogen atom, alkyl group or alkynyl group.

30. The compound according to claim 22, a salt thereof, wherein the group Q⁴ is one selected from the group consisting of a phenyl, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl, 3,4-dibromophenyl, 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3- pyridyl, 6-chloro-3-pyridazinyl, 6-fluoro-3-pyridazinyl, 6-bromo-3-pyridazinyl, 6-ethynyl-3-pyridazinyl, 5-chloro-2-thiazolyl, 5-fluoro-2-thiazolyl, 5-bromo-2-thiazolyl and 5-ethynyl-2-thiazolyl.

31. The compound according to claim 22, a salt thereof, wherein the group $T^1$ is a group selected from the groups consisting of —C(=O)—C(=O)—N(R')—, —C(=S)—C(=O)—N(R')—, —C(=O)—C(=S)—N(R')— and —C(=S)—C(=S)—N(R')—.

32. A compound represented by the following formula (4):

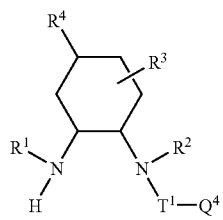

(4)

(wherein $R^1$, $R^2$ and $T^1$ have the same meanings as defined in claim 1, wherein $R^3$ and $R^4$ have the same meanings as defined in claim 1, and $Q^4$ represents one selected from the group consisting of an aryl group which may be substituted, a heteroaryl group which may be substituted, a saturated or unsaturated, bicyclic or tricyclic condensed hydrocarbon group which may be substituted, and a saturated or unsaturated, bicyclic or tricyclic condensed heterocyclic group which may be substituted), a salt thereof.

33. A compound represented by the following formula (9):

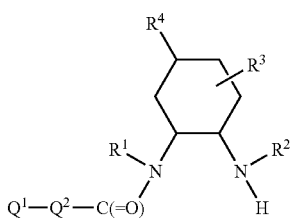

(9)

wherein $Q^2$, $R^1$, $R^2$, $R^3$ and $R^4$ have the same meanings as defined in claim 1, $Q^1$ represents a saturated or unsaturated, bicyclic or tricyclic condensed heterocyclic group which may be substituted, a salt thereof.

34. A compound represented by the following formula (4):

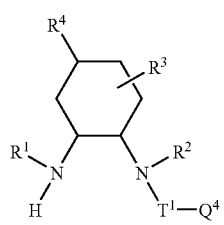

(4)

(wherein $R^1$, $R^2$, $R^3$, $R^4$ and $T^1$ have the same meanings as defined in claim 12, and $Q^4$ represents an aryl group which may be substituted, a heteroaryl group which may be substituted, a saturated or unsaturated, bicyclic or tricyclic condensed hydrocarbon group which may be substituted, or a saturated or unsaturated, bicyclic or tricyclic condensed heterocyclic group which may be substituted), a salt thereof.

35. A compound represented by the following formula (9):

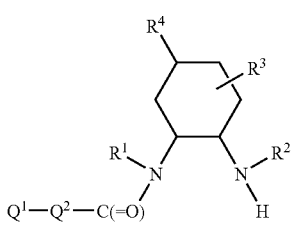

(9)

wherein $Q^2$, $R^1$, $R^2$, $R^3$ and $R^4$ have the same meanings as defined in claim 12, $Q^1$ represents a saturated or unsaturated, bicyclic or tricyclic condensed heterocyclic group which may be substituted, a salt thereof.

36. A compound represented by the following formula (4):

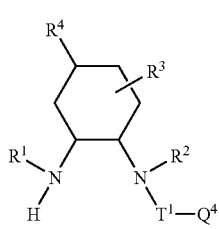

(4)

wherein $R^1$, $R^2 R^3$, $R^4$ and $T^1$ have the same meanings as defined in claim 22, and $Q^4$ represents one selected from the group consisting of an aryl group which may be substituted, a heteroaryl group which may be substituted, a saturated or unsaturated, bicyclic or tricyclic condensed hydrocarbon group which may be substituted, and a saturated or unsaturated, bicyclic or tricyclic condensed heterocyclic group which may be substituted), a salt thereof.

37. A compound represented by the following formula (9):

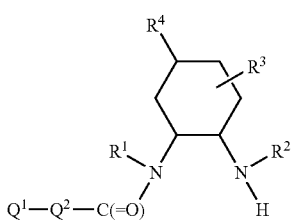

(9)

wherein $Q^2$, $R^1$, $R^2$, $R^3$ and $R^4$ have the same meanings as defined in claim 22, and $Q^1$ represents a saturated or unsaturated, bicyclic or tricyclic condensed heterocyclic group which may be substituted, a salt thereof.

* * * * *

UNITED STATES PATENT AND TRADEMARK OFFICE
CERTIFICATE OF CORRECTION

| | | |
|---|---|---|
| PATENT NO. | : 7,576,135 B2 | Page 1 of 1 |
| APPLICATION NO. | : 10/540259 | |
| DATED | : August 18, 2009 | |
| INVENTOR(S) | : Ohta et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this

Twenty-eighth Day of September, 2010

David J. Kappos
*Director of the United States Patent and Trademark Office*